(12) United States Patent
Kobayashi

(10) Patent No.: US 8,394,294 B2
(45) Date of Patent: *Mar. 12, 2013

(54) FOUR-RING LIQUID CRYSTAL COMPOUND HAVING LATERAL FLUORINE, LIQUID CRYSTAL COMPOSITION AND LIQUID CRYSTAL DISPLAY DEVICE

(75) Inventor: Masahide Kobayashi, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 40 days.

This patent is subject to a terminal disclaimer.

(21) Appl. No.: 12/996,758

(22) PCT Filed: Jun. 2, 2009

(86) PCT No.: PCT/JP2009/060082
§ 371 (c)(1),
(2), (4) Date: Dec. 7, 2010

(87) PCT Pub. No.: WO2009/150966
PCT Pub. Date: Dec. 17, 2009

(65) Prior Publication Data
US 2011/0090450 A1    Apr. 21, 2011

(30) Foreign Application Priority Data
Jun. 9, 2008 (JP) ................. 2008-150972

(51) Int. Cl.
C09K 19/00 (2006.01)
C09K 19/06 (2006.01)
C09K 19/34 (2006.01)
C09K 19/52 (2006.01)
G02F 1/13 (2006.01)

(52) U.S. Cl. ........ 252/299.63; 252/299.01; 252/299.6; 252/299.61; 252/299.62; 252/299.64; 428/1.1; 428/1.3; 349/1; 349/182

(58) Field of Classification Search ............ 252/299.01, 252/299.6, 299.61, 299.62, 299.63, 299.64; 428/1.1, 1.3; 349/1, 182
See application file for complete search history.

(56) References Cited

U.S. PATENT DOCUMENTS 7,081,279 B2 * 7/2006 Kato et al. ............. 428/1.1
2010/0309402 A1 * 12/2010 Kobayashi et al. ...... 349/54

FOREIGN PATENT DOCUMENTS

| EP | 1903090 | 3/2008 |
| EP | 2199270 | 6/2010 |
| GB | 2216523 | 10/1989 |
| JP | 2503441 | 10/1990 |
| JP | 11-116512 | 4/1999 |
| JP | 2007-002132 | 1/2007 |
| WO | 89/02425 | 3/1989 |
| WO | 89/06678 | 7/1989 |
| WO | 98/23564 | 6/1998 |

* cited by examiner

Primary Examiner — Geraldina Visconti
(74) Attorney, Agent, or Firm — J.C. Patents

(57) ABSTRACT

The invention provides a liquid crystal compound which has stability to heat, light and so forth, a nematic phase in a wide temperature range, a small viscosity, a large optical anisotropy, and a suitable elastic constant $K_{33}$, and further has a suitable and negative dielectric anisotropy and an excellent compatibility with other liquid crystal compounds. Moreover, the invention provides a liquid crystal composition comprising this liquid crystal compound and a liquid crystal display device containing this liquid crystal composition.

A liquid crystal compound represented by formula (a):

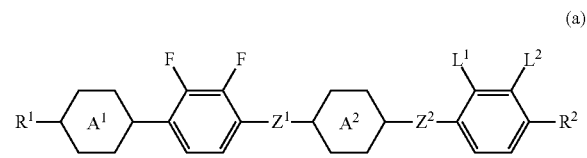

(a)

for example, $R^1$ and $R^2$ are alkyl having 1 to 10 carbons, alkenyl having 2 to 10 carbons or alkoxy having 1 to 9 carbons; ring $A^1$ and ring $A^2$ are 1,4-phenylene or trans-1,4-cyclohexylene; $L^1$ and $L^2$ are hydrogen or fluorine, and at least one of $L^1$ and $L^2$ is fluorine; and $Z^1$ and $Z^2$ are a single bond, —$(CH_2)_2$—, —CH=CH—, —$CH_2O$— or —$OCH_2$—.

26 Claims, No Drawings

FOUR-RING LIQUID CRYSTAL COMPOUND HAVING LATERAL FLUORINE, LIQUID CRYSTAL COMPOSITION AND LIQUID CRYSTAL DISPLAY DEVICE

FIELD OF THE INVENTION

The invention relates to a liquid crystal compound, a liquid crystal composition and a liquid crystal display device. The invention relates more specifically to a fluorobenzene derivative, which is a liquid crystal compound, having fluorine at a lateral position, a liquid crystal composition with a nematic phase comprising this compound, and a liquid crystal display device containing this composition.

BACKGROUND OF THE INVENTION

A liquid crystal display device typified by a liquid crystal display panel, a liquid crystal display module and so forth utilizes optical anisotropy, dielectric anisotropy and so forth which are possessed by a liquid crystal compound (in this invention, a liquid crystal compound means a generic term for a compound having a nematic phase, a smectic phase and so forth, and a compound having no liquid crystal phases but useful as a component of a liquid crystal composition). As operating modes of this liquid crystal display device, a variety of modes are known, such as PC (phase change), TN (twisted nematic), STN (super twisted nematic), BTN (bistable twisted nematic), ECB (electrically controlled birefringence), OCB (optically compensated bend), IPS (in-plane switching), VA (vertical alignment) and PSA (polymer sustained alignment) modes.

It is known that, among these operating modes, the ECB, IPS and VA modes and so forth are utilizing a homeotropic property of liquid crystal molecules, and that a limited-viewing angle which is a disadvantage of conventional display modes such as the TN and STN modes can be improved especially by use of the IPS and VA modes.

A large number of liquid crystal compounds in which hydrogen on the benzene-ring is replaced by fluorine have been studied conventionally as components for a liquid crystal composition having negative dielectric anisotropy which is useable to the liquid crystal display device with these operating modes (for example, refer to the patent documents Nos. 1 to 6.).

For example, the compounds (A) and (B) in which hydrogen on the benzene-ring is replaced by fluorine have been studied (refer to the patent documents Nos. 1 and 2). However, such compounds do not have a large negative dielectric anisotropy.

The terphenyl compound (C) having fluorine at a lateral position has been studied (refer to the patent document No. 3). However, this compound has a high melting point and a poor compatibility.

The compound (D) having an ester bonding group and a lateral fluorine has been studied (refer to the patent document No. 4). However, the compound (D) does not have a large negative dielectric anisotropy.

Moreover, the compounds (E) and (F) having an ethylene bonding group and a lateral fluorine have been studied (refer to the patent documents No. 5 and 6). However, the compound (E) has a poor compatibility and the compound (F) does not have a large negative dielectric anisotropy.

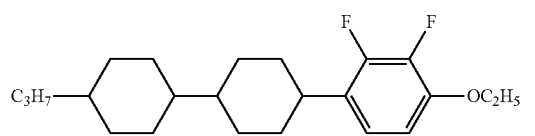

(A)

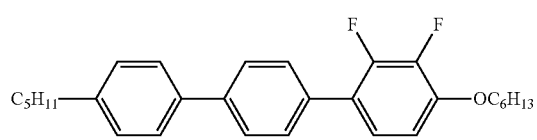

(B)

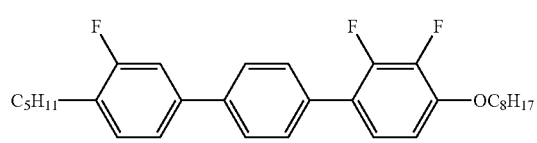

(C)

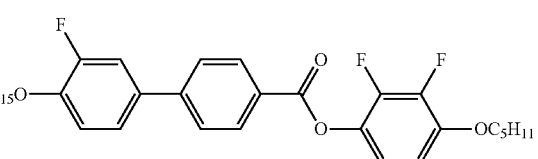

(D)

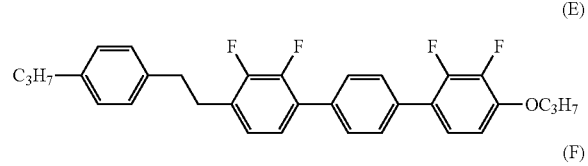

(E)

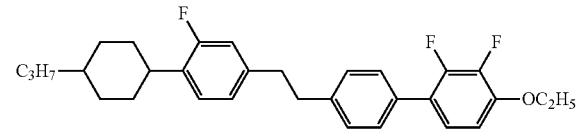

(F)

PRIOR ART DOCUMENTS (PATENT DOCUMENTS)

The patent documents cited herein are No. 1: JP H02-503441 A (1990); No. 2: WO 1989/02425 A; No. 3: JP H11-116512 A (1999); No. 4: WO 1989/06678 A; No. 5: WO 1998/23564 A; and No. 6: JP 2007-002132 A.

DISCLOSURE OF THE INVENTION

Subject to be Solved by the Invention

In view of the circumstances described above, even liquid crystal display devices by means of operating modes such as the IPS and VA modes are more problematic than CRTs for use of display devices, and, for example, an improvement of response speed, an improvement of contrast, and a decrease in driving voltage are required.

The display device operated by means of the IPS mode or the VA mode described above contains a liquid crystal composition having mostly negative dielectric anisotropy. It is required for liquid crystal compounds included in this liquid crystal composition to have characteristics shown in items (1) to (8) below in order to further improve these characteristics and so forth. That is to say:

(1) being chemically stable and physically stable,
(2) having a high clearing point (transition temperature on a liquid crystal phase-an isotropic phase),
(3) being low in the minimum temperature of liquid crystal phases (a nematic phase, a smectic phase and so forth), especially of the nematic phase,
(4) being small in viscosity,
(5) having a suitable optical anisotropy,
(6) having a suitable and negative dielectric anisotropy,
(7) having a suitable elastic constant $K_{33}$ ($K_{33}$: bend elastic constant), and
(8) being excellent in compatibility with other liquid crystal compounds.

A voltage holding ratio can be increased by use of a composition including a chemically and physically stable liquid crystal compound as described in item (1) for a display device. The temperature range of a nematic phase can be increased when a composition includes a liquid crystal compound having a high clearing point or a low minimum temperature of liquid crystal phases as described in items (2) and (3), and thus the display device is usable in a wide temperature range.

Furthermore, the response speed can be improved when a composition including a compound having a small viscosity as described in item (4) and a compound having a large elastic constant $K_{33}$ as described in item (7) is used for a display device, and the contrast of a display device can be improved when a composition that includes a compound having a suitable dielectric anisotropy as described in item (5) is used for the display device. Optical anisotropy is required in a range of small to large values according to the design of a device. Recently, a method for improving the response speed by means of a smaller cell thickness has been investigated, whereby a liquid crystal composition having a large optical anisotropy has also been required.

Moreover, when a liquid crystal compound has a large negative dielectric anisotropy, the threshold voltage of the liquid crystal composition including this compound can be decreased. Hence, the driving voltage of a display device can be decreased and electric power consumption can also be decreased when a composition including a compound having a suitable and negative dielectric anisotropy as described in item (6) is used for the display device. Further, the driving voltage of a display device can be decreased and the electric power consumption can also be decreased when a composition including a compound having a small elastic constant $K_{33}$ as described in item (7) is used for the display device.

The liquid crystal compound is generally used as a composition prepared by being mixed with many other liquid crystal compounds in order to exhibit characteristics which cannot be attained with a single compound. Accordingly, it is desirable that a liquid crystal compound used for a display device has an excellent compatibility with other liquid crystal compounds and so forth, as described in item (8). Since the display device may be used in a wide temperature range including a lower temperature than the freezing point, a compound which exhibits an excellent compatibility even in a low temperature region may be desirable.

The first aim of the invention is to provide a liquid crystal compound having stability to heat, light and so forth, a nematic phase in a wide temperature range, a small viscosity, a large optical anisotropy and a suitable elastic constant $K_{33}$, and further having a suitable and negative dielectric anisotropy and an excellent compatibility with other liquid crystal compounds.

The second aim of the invention is to provide a liquid crystal composition comprising this compound and having stability to heat, light and so forth, a small viscosity, a large optical anisotropy, a suitable and negative dielectric anisotropy, a suitable elastic constant $K_{33}$ and a low threshold voltage, and further having a high maximum temperature of a nematic phase (phase-transition temperature on a nematic phase-an isotropic phase) and a low minimum temperature of the nematic phase.

The third aim of the invention is to provide a liquid crystal display device that contains the composition described above, having a short response time, *a low electric power consumption, a low driving voltage, a large contrast and a wide temperature range in which the device can be used.

Means to Solve the Subjects

The inventors have keenly studied these subjects and thus found that a four-ring liquid crystal compound having fluorine at a lateral position, in a specific structure having phenylene in which hydrogen on the benzene ring is replaced by fluorine, has stability to heat, light and so forth, a nematic phase in a wide temperature range, a small viscosity, a large optical anisotropy and a suitable elastic constant $K_{33}$, and further has a suitable and negative dielectric anisotropy and an excellent compatibility with other liquid crystal compounds. They also found that a liquid crystal composition comprising this compound has stability to heat, light and so forth, a small viscosity, a large optical anisotropy, a suitable elastic constant $K_{33}$, a suitable and negative dielectric anisotropy and a low threshold voltage, and further has a high maximum temperature of a nematic phase and a low minimum temperature of the nematic phase. They further found that a liquid crystal display device containing this composition has a short response time, a low electric power consumption, a small driving voltage, a large contrast ratio, and a wide temperature range in which the device can be used. On the basis of the above findings, the invention has been completed.

The invention includes items 1 to 30 described below.
Item 1. A liquid crystal compound represented by formula (a):

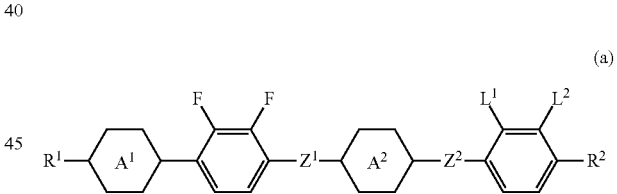

wherein, in formula (a),
$R^1$ and $R^2$ are each independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^1$ and ring $A^2$ are each independently 1,4-phenylene, trans-1,4-cyclohexylene, 1,4-cyclohexenylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl;
$L^1$ and $L^2$ are each independently hydrogen or fluorine, and at least one of $L^1$ and $L^2$ is fluorine; and
$Z^1$ and $Z^2$ are each independently a single bond, —(CH$_2$)$_2$—, —CH=CH—, —C≡C—, —CH$_2$O—, —OCH$_2$—, —COO— or —OCO—.
Item 2. The compound according to item 1, wherein, in formula (a), ring $A^1$ and ring $A^2$ are each independently 1,4-phenylene, trans-1,4-cyclohexylene, tetrahydropyran-2,5-diyl or tetrahydropyran-3,6-diyl.

Item 3. The compound according to item 2, which is represented by formula (a-1) or (a-2):

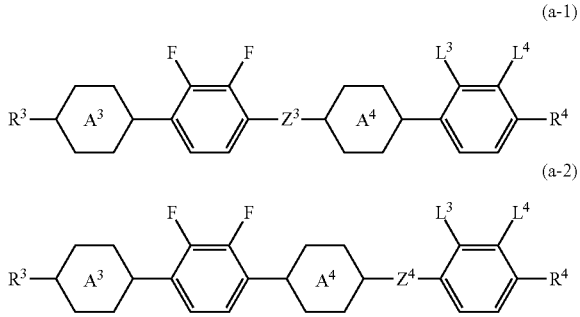

wherein, in formulas (a-1) and (a-2), $R^3$ and $R^4$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^3$ and ring $A^4$ are each independently 1,4-phenylene, trans-1,4-cyclohexylene, tetrahydropyran-2,5-diyl or tetrahydropyran-3,6-diyl;

$L^3$ and $L^4$ are each independently hydrogen or fluorine, and at least one of $L^3$ and $L^4$ is fluorine;

$Z^3$ and $Z^4$ are each independently —$(CH_2)_2$—, —CH=CH—, —$CH_2O$—, —$OCH_2$—, —COO— or —OCO—.

Item 4. The compound according to item 3, which is represented by any one of formulas (a-3) to (a-8):

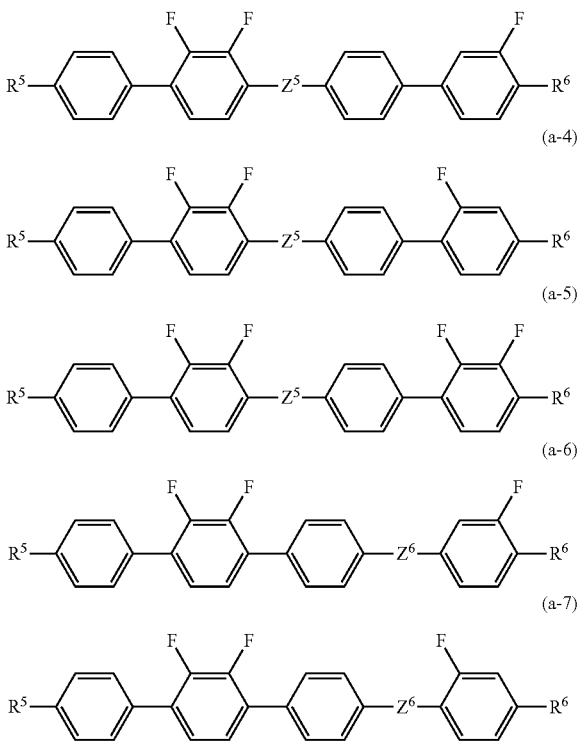

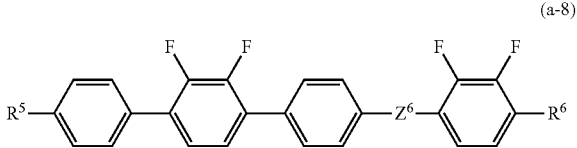

wherein, in formulas (a-3) to (a-8), $R^5$ and $R^6$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^5$ and $Z^6$ are each independently —$(CH_2)_2$—, —CH=CH—, —$CH_2O$—, —$OCH_2$—, —COO— or —OCO—.

Item 5. The compound according to item 3, which is represented by any one of formulas (a-9) to (a-14):


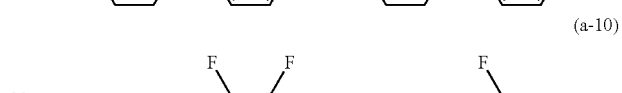


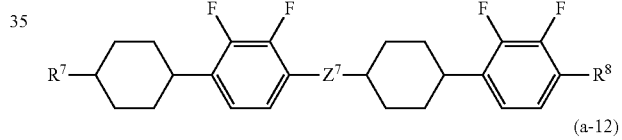


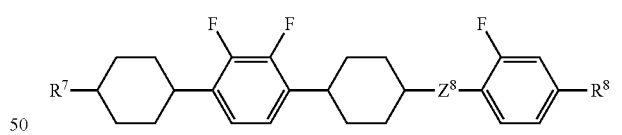

wherein, in formulas (a-9) to (a-14), $R^7$ and $R^8$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^7$ and $Z^8$ are each independently —$(CH_2)_2$—, —CH=CH—, —$CH_2O$—, —$OCH_2$—, —COO— or —OCO—.

Item 6. The compound according to item 3, which is represented by any one of formulas (a-15) to (a-26):

(a-15) 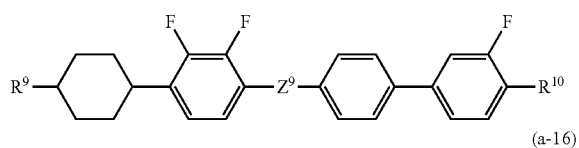

(a-16) 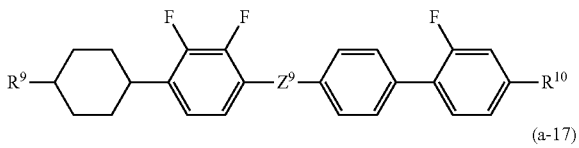

(a-17) 

(a-18) 

(a-19) 

(a-20) 

(a-21) 

(a-22) 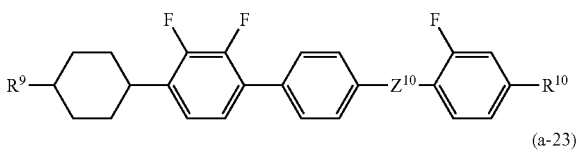

(a-23) 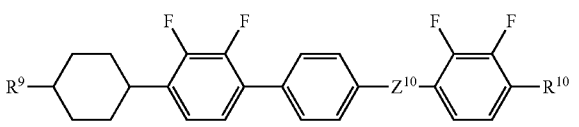

(a-24) 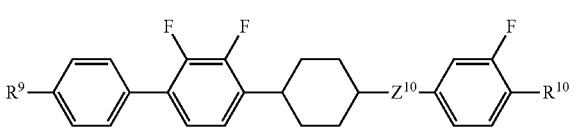

(a-25)

(a-26) 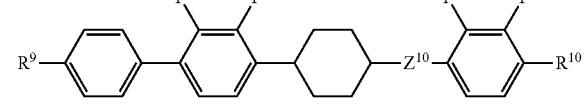

wherein, in formulas (a-15) to (a-26), $R^9$ and $R^{10}$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $Z^9$ and $Z^{10}$ are each independently —(CH$_2$)$_2$—, —CH=CH—, —CH$_2$O—, —OCH$_2$—, —COO— or —OCO—.

Item 7. The compound according to item 4, wherein, in formulas (a-3) to (a-8), $Z^5$ and $Z^6$ are —CH$_2$O—.

Item 8. The compound according to item 4, wherein, in formulas (a-3) to (a-8), $Z^5$ and $Z^6$ are —OCH$_2$—.

Item 9. The compound according to item 4, wherein, in formulas (a-3) to (a-8), $Z^5$ and $Z^6$ are —(CH$_2$)$_2$—.

Item 10. The compound according to item 4, wherein, in formulas (a-3) to (a-8), $Z^5$ and $Z^6$ are —COO—.

Item 11. The compound according to item 4, wherein, in formulas (a-3) to (a-8), $Z^5$ and $Z^6$ are —OCO—.

Item 12. The compound according to item 5, wherein, in formulas (a-9) to (a-14), $Z^7$ and $Z^8$ are —CH$_2$O—.

Item 13. The compound according to item 5, wherein, in formulas (a-9) to (a-14), $Z^7$ and $Z^8$ are —OCH$_2$—.

Item 14. The compound according to item 5, wherein, in formulas (a-9) to (a-14), $Z^7$ and $Z^8$ are —(CH$_2$)$_2$—.

Item 15. The compound according to item 5, wherein, in formulas (a-9) to (a-14), $Z^7$ and $Z^8$ are —COO—.

Item 16. The compound according to item 5, wherein, in formulas (a-9) to (a-14), $Z^7$ and $Z^8$ are —OCO—.

Item 17. The compound according to item 6, wherein, in formulas (a-15) to (a-26), $Z^9$ and $Z^{10}$ are —CH$_2$O—.

Item 18. The compound according to item 6, wherein, in formulas (a-15) to (a-26), $Z^9$ and $Z^{10}$ are —OCH$_2$—.

Item 19. The compound according to item 6, wherein, in formulas (a-15) to (a-26), $Z^9$ and $Z^{10}$ are —(CH$_2$)$_2$—.

Item 20. The compound according to item 6, wherein, in formulas (a-15) to (a-26), $Z^9$ and $Z^{10}$ are —COO—.

Item 21. The compound according to item 6, wherein, in formulas (a-15) to (a-26), $Z^9$ and $Z^{10}$ are —OCO—.

Item 22. A liquid crystal composition which has negative dielectric anisotropy, comprising a first component which is at least one compound selected from compounds according to any one of items 1 to 21, and a second component which is at least one compound selected from the group of compounds represented by formulas (e-1) to (e-3):

(e-1)

$$Ra_{11}\text{—}A^{11}\text{—}Z^{11}\text{—}A^{12}\text{—}Rb_{11}$$

(e-2)

$$Ra_{11}\text{—}A^{11}\text{—}Z^{11}\text{—}A^{12}\text{—}Z^{12}\text{—}A^{13}\text{—}Rb_{11}$$

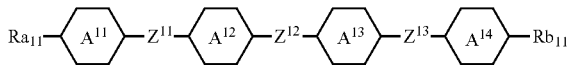

wherein, in formulas (e-1) to (e-3), $Ra_{11}$ and $Rb_{11}$ are each independently alkyl having 1 to 10 carbons, and in this alkyl, —$CH_2$— may be nonadjacently replaced by —O—, and —$(CH_2)_2$— may be nonadjacently replaced by —CH═CH—, and hydrogen may be replaced by fluorine;

ring $A^{11}$, ring $A^{12}$, ring $A^{13}$ and ring $A^{14}$ are each independently trans-1,4-cyclohexylene, 1,4-phenylene, 2-fluoro-1,4-phenylene, 3-fluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl; and $Z^{11}$, $Z^{12}$ and $Z^{13}$ are each independently a single bond, —$CH_2$—$CH_2$—, —CH═CH—, —C≡C—, —COO— or —$CH_2$O—.

Item 23. A liquid crystal composition which has negative dielectric anisotropy, comprising a first component which is at least one compound selected from the group of compounds according to items 3, and a second component which is at least one compound selected from the group of compounds represented by formulas (e-1) to (e-3) according to item 22.

Item 24. The liquid crystal composition according to item 23, wherein the content ratio of the first component is in the range of 5% to 60% by weight and the content ratio of the second component is in the range of 40% to 95% by weight, based on the total weight of the liquid crystal composition.

Item 25. The liquid crystal composition according to item 22 or 23, further comprising a third component which is least one compound selected from the group of compounds represented by formulas (g-1) to (g-6), in addition to the first and second components:

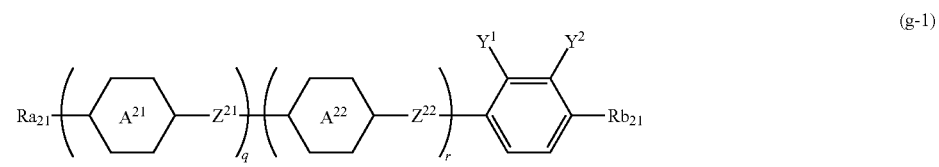

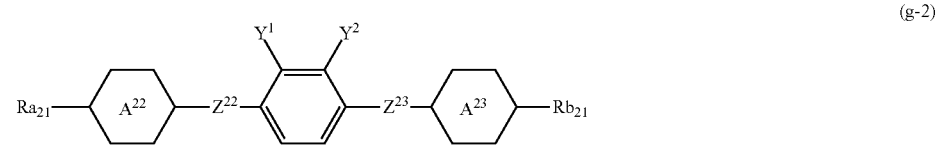

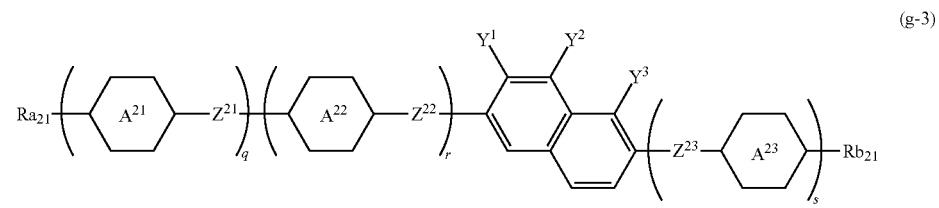

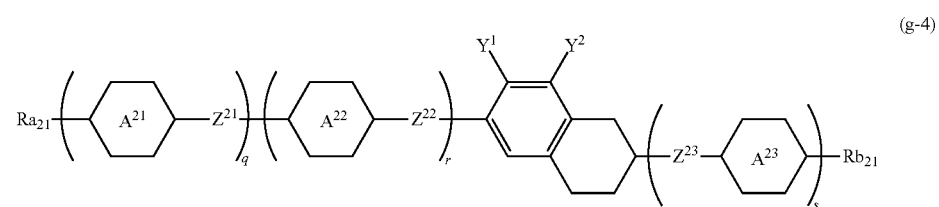

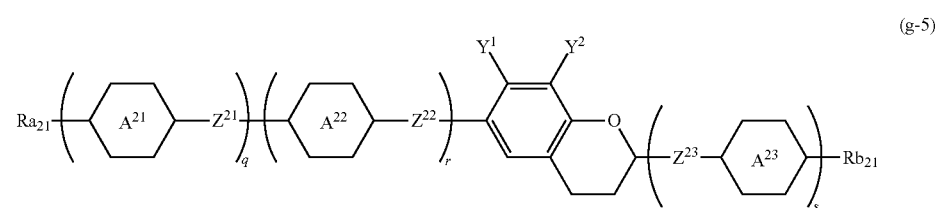

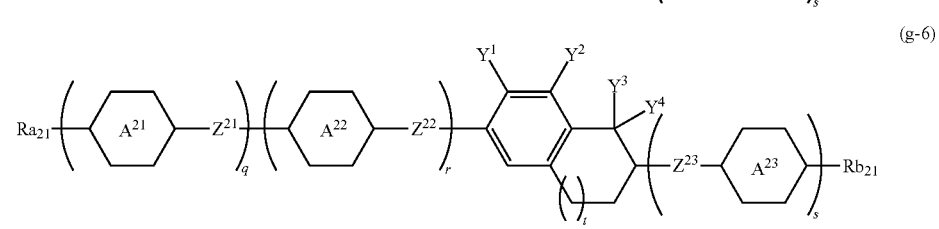

wherein, in formulas (g-1) to (g-6),

Ra$_{21}$ and Rb$_{21}$ are each independently hydrogen or alkyl having 1 to 10 carbons, and in this alkyl, —CH$_2$— may be nonadjacently replaced by —O—, and —(CH$_2$)$_2$— may be nonadjacently replaced by —CH=CH—, and hydrogen may be replaced by fluorine;

ring A$^{21}$, ring A$^{22}$ and ring A$^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl;

Z$^{21}$, Z$^{22}$ and Z$^{23}$ are each independently a single bond, —CH$_2$—CH$_2$—, —CH=CH—, —C≡C—, —OCF$_2$—, —CF$_2$O—, —OCF$_2$CH$_2$—, —CH$_2$CH$_2$CF$_2$O—, —COO—, —OCO—, —OCH$_2$— or —CH$_2$O—;

Y$^1$, Y$^2$, Y$^3$ and Y$^4$ are each independently fluorine or chlorine;

q, r and s are each independently 0, 1 or 2, q+r is 1 or 2, and q+r+s is 1, 2 or 3; and t is 0, 1 or 2.

Item 26. The liquid crystal composition according to item 25, further comprising a third component which is least one compound selected from the group of compounds represented by formulas (h-1) to (h-7), in addition to the first and second components:

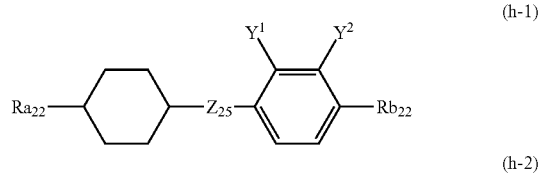
(h-1)

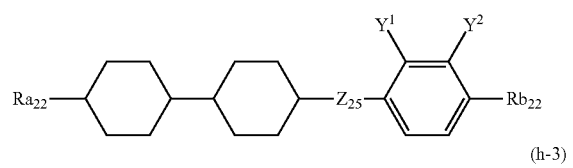
(h-2)

(h-3)

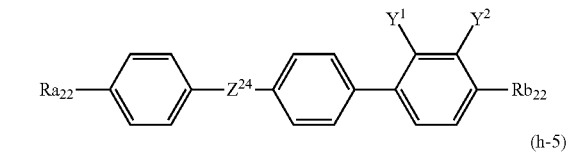
(h-4)

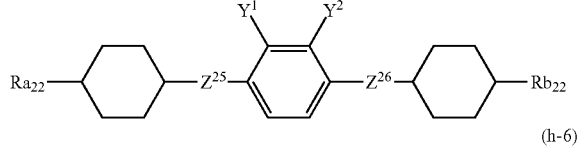
(h-5)

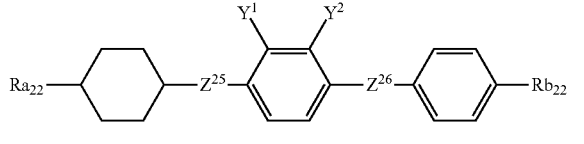
(h-6)

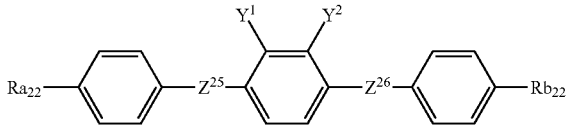
(h-7)

wherein, in formulas (h-1) to (h-7),

Ra$_{22}$ and Rb$_{22}$ are each independently straight-chain alkyl having 1 to 8 carbons, straight-chain alkenyl having 2 to 8 carbons or alkoxy having 1 to 7 carbons;

Z$^{24}$, Z$^{25}$ and Z$^{26}$ are each independently a single bond, —CH$_2$CH$_2$—, —CH$_2$O— or —OCH$_2$—; and Y$^1$ and Y$^2$ are simultaneously fluorine, or one of Y$^1$ and Y$^2$ is fluorine and the other is chlorine.

Item 27. A liquid crystal composition which has negative dielectric anisotropy, comprising a first component which is at least one compound selected from the compounds according to Item 3, a second component which is at least one compound selected from the group of compounds represented by formulas (e-1) to (e-3) according to item 22, and a third component which is at least one compound selected from the group of compounds represented by formulas (h-1) to (h-7) according to item 26.

Item 28. The liquid crystal composition according to anyone of items 25 to 27, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

Item 29. A liquid crystal display device containing the liquid crystal composition according to any one of items 22 to 28.

Item 30: The liquid crystal display device according to item 29, wherein the operating mode thereof is a VA mode, an IPS mode or a PSA mode, and the driving mode thereof is an active matrix mode.

Effect of the Invention

The liquid crystal compound of the invention has stability to heat, light and so forth, a nematic phase in a wide temperature range, a small viscosity, a large optical anisotropy and a suitable elastic constant K$_{33}$ (K$_{33}$: bend elastic constant), and further has a suitable and negative dielectric anisotropy and an excellent compatibility with other liquid crystal compounds. Moreover, the liquid crystal compound of the invention is quite excellent in the increasing tendency of the optical anisotropy without decreasing the maximum temperature of a nematic phase or increasing the viscosity.

The liquid crystal compound of the invention has a small viscosity, a large optical anisotropy, a suitable elastic constant K$_{33}$, a suitable and negative dielectric anisotropy and a low threshold voltage, and further has a high maximum temperature of a nematic phase and a low minimum temperature of the nematic phase. Since the liquid crystal composition of the invention has a large optical anisotropy, it is particularly effective in a device which requires a large optical anisotropy.

The liquid crystal display device of the invention is characterized by comprising this liquid crystal composition, and consequently has a short response time, a low electric power consumption, a small driving voltage, a large contrast ratio and a wide temperature range in which the device can be used, and can be suitably used as a liquid crystal display device with a display mode such as a PC, TN, STN, ECB, OCB, IPS, VA or PSA mode. It can be suitably used especially as a liquid crystal display device with an IPS, VA or PSA mode.

EMBODIMENT TO CARRY OUT THE INVENTION

Hereinafter, the invention is explained in more detail.

In the following description, the amount of a compound which is expressed in percentage means the weight percentage (% by weight) based on the total weight of the composition unless otherwise noted.

[Compound (a)]

The liquid crystal compound of the invention has a structure represented by formula (a). Hereinafter the compound is also referred to as "the compound (a)."

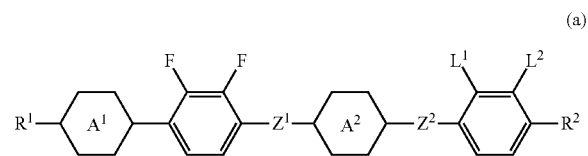

(a)

In formula (a), $R^1$ and $R^2$ are each independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

Ring $A^1$ and ring $A^2$ are each independently 1,4-phenylene, trans-1,4-cyclohexylene, 1,4-cyclohexenylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl.

$L^1$ and $L^2$ are each independently hydrogen or fluorine and at least one of them is fluorine, and $Z^1$ and $Z^2$ are each independently a single bond, —(CH$_2$)$_2$—, —CH═CH—, —C≡C—, —CH$_2$O—, —OCH$_2$—, —COO— or —OCO—.

The compound (a) has 1,4-phenylene in which hydrogen at the 2- or 3-position is replaced by fluorine, and 1,4-phenylene in which hydrogen at the 2- and 3-positions are replaced by fluorine, as described above. The compound (a) exhibits a small viscosity, a suitable optical anisotropy, a suitable elastic constant $K_{33}$, a large negative dielectric anisotropy and an excellent compatibility with other liquid crystal compounds because of having such a structure. In particular, the compound (a) is quite excellent in view of a large negative dielectric anisotropy, without decreasing the maximum temperature of a nematic phase and without increasing the viscosity.

In the formula, $R^1$ and $R^2$ are hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and are, for example, CH$_3$ (CH$_2$)$_3$—, —CH$_2$—, CH$_3$ (CH$_2$)$_2$O—, —CH$_3$—O—(CH$_2$)$_2$—, CH$_3$—O—CH$_2$—O—, H$_2$C═CH—(CH$_2$)$_2$—, CH$_3$—CH═CH—CH$_2$— or CH$_3$—CH═CH—O—.

However, a group such as CH$_3$—O—O—CH$_2$— in which oxygen and another oxygen are adjacent and a group such as CH$_3$—CH═CH—CH═CH— in which double bond parts are adjacent are undesirable in consideration for the stability of the compound.

More specifically, $R^1$ and $R^2$ include hydrogen, alkyl, alkoxy, alkoxyalkyl, alkenyl and alkenyloxy.

It is desirable that the chain of the carbon-carbon bonds in these groups is straight. If the chain of carbon-carbon bonds is straight, the temperature ranges of liquid crystal phases can be increased and viscosity can be decreased. If either $R^1$ or $R^2$ is an optically active group, the compound is useful as a chiral dopant and a reverse twisted domain which will occur in a liquid crystal display device can be prevented by adding the compound to a liquid crystal composition.

$R^1$ and $R^2$ are preferably alkyl, alkoxy, alkoxyalkyl and alkenyl, and more preferably alkyl, alkoxy and alkenyl.

If $R^1$ and $R^2$ are alkyl, alkoxy, and alkenyl, the temperature ranges of liquid crystal phases on the liquid crystal compounds can be increased.

A desirable configuration of —CH═CH— in the alkenyl depends on the position of a double bond.

A trans-configuration is desirable in the alkenyl having a double bond in an odd-numbered position, such as —CH═CHCH$_3$, —CH═CHC$_2$H$_5$, —CH═CHC$_3$H$_7$, —CH═CHC$_4$H$_9$, —C$_2$H$_4$—CH═CHCH$_3$ and —C$_2$H$_4$—CH═CHC$_2$H$_5$.

On the other hand, a cis-configuration is desirable in the alkenyl having a double bond at an even-numbered position, such as —CH$_2$CH═CHCH$_3$, —CH$_2$CH═CHC$_2$H$_5$ and —CH$_2$CH═CHC$_3$H$_7$. The alkenyl compound possessing a desirable configuration described above has a wide temperature range of liquid crystal phases, a large elastic constant ratio $K_{33}/K_{11}$ ($K_{33}$: bend elastic constant, $K_{11}$: spray elastic constant), and a decreased viscosity of the compound. Furthermore, if this liquid crystal compound is added to a liquid crystal composition, the maximum temperature ($T_{NI}$) of a nematic phase can be increased.

Specific examples of the alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$ and —C$_{10}$H$_{21}$;

specific examples of the alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$ and —OC$_9$H$_{19}$;

specific examples of the alkoxyalkyl include —CH$_2$OCH$_3$, —CH$_2$OC$_2$H$_5$, —CH$_2$OC$_3$H$_7$, —(CH$_2$)$_2$OCH$_3$, —(CH$_2$)$_2$OC$_2$H$_5$, —(CH$_2$)$_2$OC$_3$H$_7$, —(CH$_2$)$_3$OCH$_3$, —(CH$_2$)$_4$OCH$_3$ and —(CH$_2$)$_5$OCH$_3$;

specific examples of the alkenyl include —CH═CH$_2$, —CH═CHCH$_3$, —CH$_2$CH═CH$_2$, —CH═CHC$_2$H$_5$, —CH$_2$CH═CHCH$_3$, —(CH$_2$)$_2$CH═CH$_2$, —CH═CHC$_3$H$_7$, —CH$_2$CH═CHC$_2$H$_5$, —(CH$_2$)$_2$CH═CHCH$_3$ and —(CH$_2$)$_3$CH═CH$_2$; and specific examples of the alkenyloxy include —OCH$_2$CH═CH$_2$, —OCH$_2$CH═CHCH$_3$ and —OCH$_2$CH═CHC$_2$H$_5$.

Therefore, among the specific examples of $R^1$ and $R^2$, —CH$_3$, —C$_2$H$_5$, —C$_3$H$_7$, —C$_4$H$_9$, —C$_5$H$_{11}$, —OCH$_3$, —OC$_2$H$_5$, —OC$_3$H$_7$, —OC$_4$H$_9$, —OC$_5$H$_{11}$, —CH$_2$OCH$_3$, —(CH$_2$)$_2$OCH$_3$, —(CH$_2$)$_3$OCH$_3$, —CH$_2$CH═CH$_2$, —CH$_2$CH═CHCH$_3$, —(CH$_2$)$_2$CH═CH$_2$, —CH$_2$CH═CHC$_2$H$_5$, —(CH$_2$)$_2$CH═CHCH$_3$, —(CH$_2$)$_3$CH═CH$_2$, —(CH$_2$)$_3$CH═CHCH$_3$, —(CH$_2$)$_3$CH═CHC$_2$H$_5$, —(CH$_2$)$_3$CH═CHC$_3$H$_7$, —OCH$_2$CH═CH$_2$, —OCH$_2$CH═CHCH$_3$ and —OCH$_2$CH═CHC$_2$H$_5$ are desirable, and —CH$_3$, —C$_2$H$_5$, —C$_3$H$_7$, —OCH$_3$, —OC$_2$H$_5$, —OC$_3$H$_7$, —OC$_4$H$_9$, —(CH$_2$)$_2$ CH═CH$_2$, —(CH$_2$)$_2$CH═CHCH$_3$ and —(CH$_2$)$_2$CH═CHC$_3$H$_7$ are more desirable.

Ring $A^1$ and ring $A^2$ are 1,4-phenylene, trans-1,4-cyclohexylene, cyclohexene-1,4-diyl, trans-1,3-dioxane-2,5-diyl, trans-tetrahydropyran-2,5-diyl, pyrimidine-2,5-diyl and pyridine-2,5-diyl, and in the rings, hydrogen may be replaced by fluorine.

Ring $A^1$ and ring $A^2$ are preferably 1,4-phenylene, trans-1,4-cyclohexylene, cyclohexene-1,4-diyl, trans-1,3-dioxane-2,5-diyl and trans-tetrahydropyran-2,5-diyl.

Among these rings, 1,4-phenylene and trans-1,4-cyclohexylene are more desirable, and trans-1,4-cyclohexylene is most desirable.

In particular, viscosity can be decreased if at least one of these rings is trans-1,4-cyclohexylene, and if this liquid crystal compound is added to a liquid crystal composition, the maximum temperature ($T_{NI}$) of a nematic phase can be increased.

$L^1$ and $L^2$ are each independently a hydrogen atom or a fluorine atom, and at least one of them is a fluorine atom.

It is desirable that one of $L^1$ and $L^2$ is hydrogen and the other is fluorine in order to decrease the melting point of the compound.

It is desirable that both of $L^1$ and $L^2$ are fluorine in order to increase the dielectric anisotropy of the compound negatively.

$Z^1$ and $Z^2$ are a single bond, —$(CH_2)_2$—, —CH=CH—, —C≡C—, —$CH_2O$—, —$OCH_2$—, —COO— or —OCO—.

$Z^1$ and $Z^2$ are preferably a single bond, —$(CH_2)_2$— or —CH=CH— for decreasing the viscosity of the compound. Among these $Z^1$ and $Z^2$, —COO— or —OCO— is more desirable for increasing the maximum temperature ($T_{NI}$) of the nematic phase of the compound. Furthermore, —$CH_2O$— or —$OCH_2$— is more desirable for increasing negatively the dielectric anisotropy of the compound.

A single bond, —$(CH_2)_2$—, —$CH_2O$— and —$OCH_2$— are desirable and a single bond and —$(CH_2)_2$— are more desirable, in consideration of the stability of the compound.

When $Z^1$ and $Z^2$ are —CH=CH—, the configuration of other groups bonded to the double bond is preferably trans. The temperature range of liquid crystal phases of a liquid crystal compound can be increased by the effect of such configuration, and when this liquid crystal compound is added to a liquid crystal composition, the maximum temperature ($T_{NI}$) of a nematic phase can be increased.

If $Z^1$ and/or $Z^2$ is —CH=CH—, the temperature range of liquid crystal phases can be increased, the elastic constant ratio $K_{33}/K_{11}$ ($K_{33}$: bend elastic constant, $K_{11}$: spray elastic constant) can be increased, and the viscosity of the compound can be decreased, and when this liquid crystal compound is added to a liquid crystal composition, the maximum temperature ($T_{NI}$) of a nematic phase can be increased.

Incidentally, the liquid crystal compound (a) may also contain isotopes such as $^2H$ (deuterium), $^{13}C$ and so forth in a larger amount than the amount of the natural abundance, since such isotopes do not cause a large difference in physical properties of the compound.

In this liquid crystal compound (a), it is possible to adjust physical properties such as the dielectric anisotropy, to desired physical properties by suitably selecting $R^1$, $R^2$, ring $A^1$, ring $A^2$, $Z^1$ and $Z^2$.

Examples of desirable compounds of the compound (a) include the compounds (a-1) to (a-26).

(a-3)

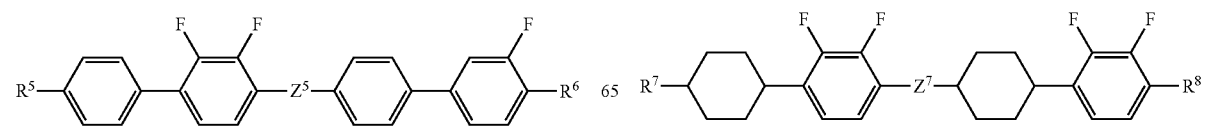

(a-4)

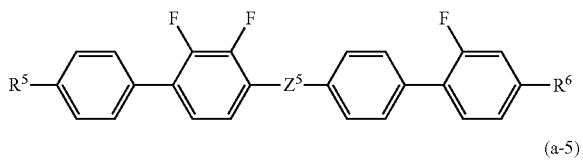

(a-5)

(a-6)

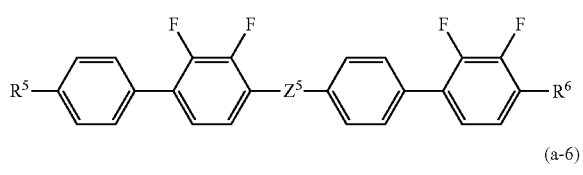

(a-7)


(a-8)

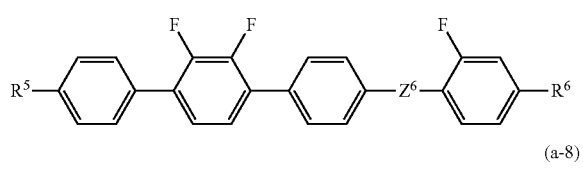

In formulas (a-3) to (a-8), $R^5$ and $R^6$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and $Z^5$ and $Z^6$ are a single bond, —$(CH_2)_2$—, —CH=CH—, —C≡C—, —$CH_2O$—, —$OCH_2$—, —COO— or —OCO—.

Since the compounds (a-3) to (a-8) have a 1,4-phenylene group, they are more desirable in view of stability to heat or light, a higher maximum temperature of a nematic phase and a suitable elastic constant $K_{33}$.

(a-9)

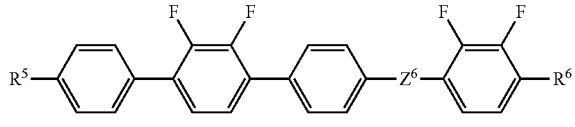

(a-10)

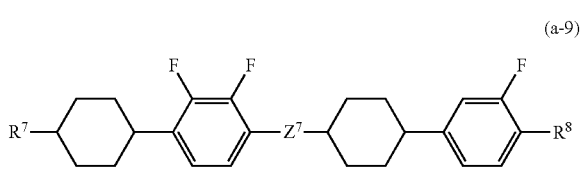

(a-11)

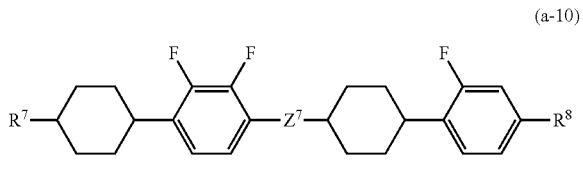

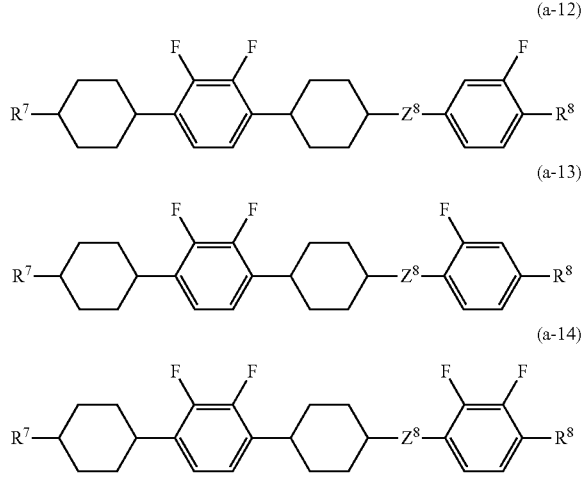

In formulas (a-9) to (a-14), $R^7$ and $R^8$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and $Z^7$ and $Z^8$ are a single bond, —(CH$_2$)$_2$—, —CH=CH—, —C≡C—, —CH$_2$O—, —OCH$_2$—, —COO— or —OCO—.

Since the compounds (a-9) to (a-14) have two 1,4-cyclohexylene groups, they are more desirable in view of stability to heat or light, a lower minimum temperature of liquid crystal phases, a higher maximum temperature of a nematic phase, a suitable optical anisotropy, a suitable elastic constant $K_{33}$ and a smaller viscosity.

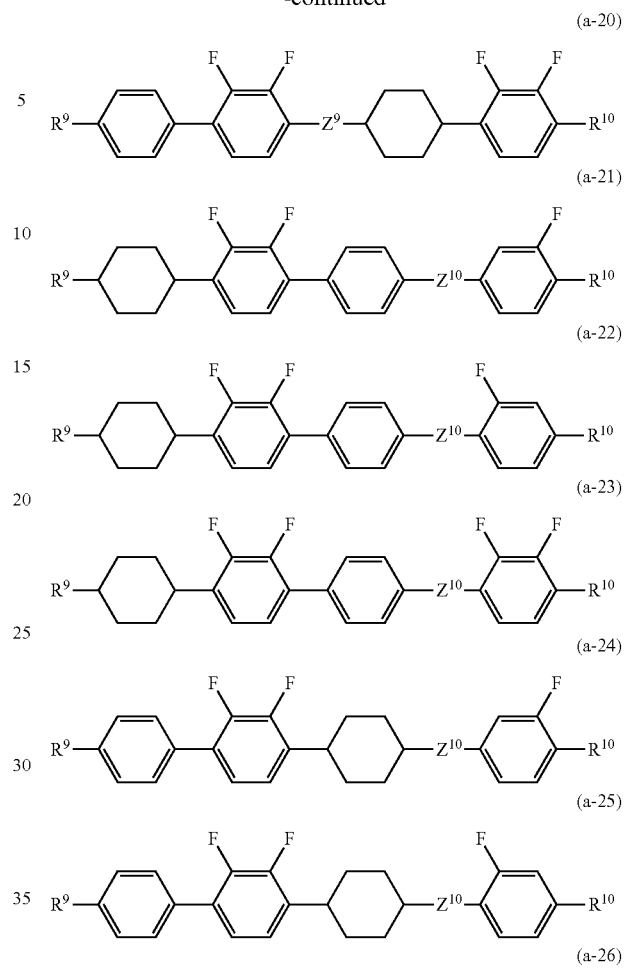

In formulas (a-15) to (a-26), $R^9$ and $R^{10}$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, and $Z^9$ and $Z^{10}$ are a single bond, —(CH$_2$)$_2$—, —CH=CH—, —C≡C—, —CH$_2$O—, —OCH$_2$—, —COO— or —OCO—.

Since the 1,4-cyclohexylene groups are positioned asymmetrically with respect to the entire compound, the compounds are more desirable in view of stability to heat or light, a lower minimum temperature of liquid crystal phases, a suitable elastic constant $K_{33}$ and a smaller viscosity.

The compounds (a-3) to (a-26) have a large negative dielectric anisotropy, stability to heat or light, a nematic phase in a wide temperature range, a suitable optical anisotropy and a suitable elastic constant $K_{33}$. Among these, the compounds where $Z^5$ to $Z^{10}$ are —CH=CH— are desirable in view of a lower minimum temperature of liquid crystal phases, a scarcely decreased maximum temperature of a nematic phase and a smaller viscosity. The compounds where $Z^5$ to $Z^{10}$ are —COO— or —OCO— are more desirable in view of a higher maximum temperature of a nematic phase. Moreover, the compounds where $Z^5$ to $Z^{10}$ are —(CH$_2$)$_2$— are still more desirable in view of a lower minimum temperature of liquid crystal phases, a higher compatibility and a smaller viscosity. Further, the compounds where $Z^5$ to $Z^{10}$ are —$CH_2O$— or —$OCH_2$— are most desirable in view of a larger negative dielectric anisotropy and smaller viscosity.

When liquid crystal compounds are the compounds (a-3) to (a-26), they have a large negative dielectric anisotropy and an excellent compatibility with other liquid crystal compounds. Furthermore, they have stability to heat, light or the like, a small viscosity, a large optical anisotropy and a suitable elastic constant $K_{33}$. A liquid crystal composition comprising this compound (a) is stable under conditions in which a liquid crystal display device is usually used, and this compound does not deposit its crystals (or its smectic phase) even when the composition is kept at low temperature.

Hence, the compound (a) is suitably applied to a liquid crystal composition used for a liquid crystal display device with a display mode such as PC, TN, STN, ECB, OCB, IPS, VA and PSA, and is quite suitably applied to a liquid crystal composition used for a liquid crystal display device with a display mode such as IPS, VA or PSA.

[Synthesis of Compound (a)]

The liquid crystal compound (a) can be synthesized by suitably combining techniques in synthetic organic chemistry. Methods of introducing objective terminal groups, rings and bonding groups into starting materials are described, for example, in Organic Syntheses (John Wiley & Sons, Inc), Organic Reactions (John Wiley & Sons, Inc), Comprehensive Organic Synthesis (Pergamon Press), New Experimental Chemistry Course (Shin Jikken Kagaku Kouza, in Japanese title) (Maruzen Co., LTD.), and so forth.

<Formation of Bonding Group $Z^1$ or $Z^2$>

One example of methods for forming the bonding group $Z^1$ or $Z^2$ (the same applies to $Z^3$ to $Z^{10}$) is shown. Schemes for forming the bonding groups are illustrated as follows. In the schemes, MSG or $MSG^2$ is a monovalent organic group. A plurality of the MSG (or $MSG^2$) used in the schemes may be identical or different. The compounds (1A) to (1H) correspond to the compound (a).

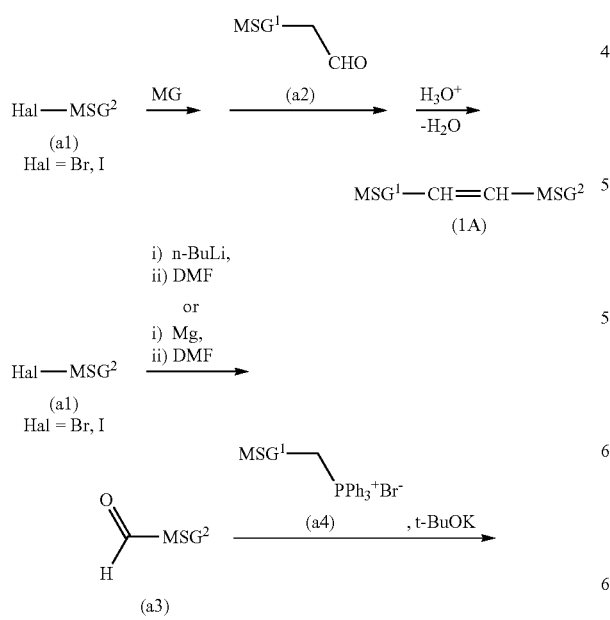

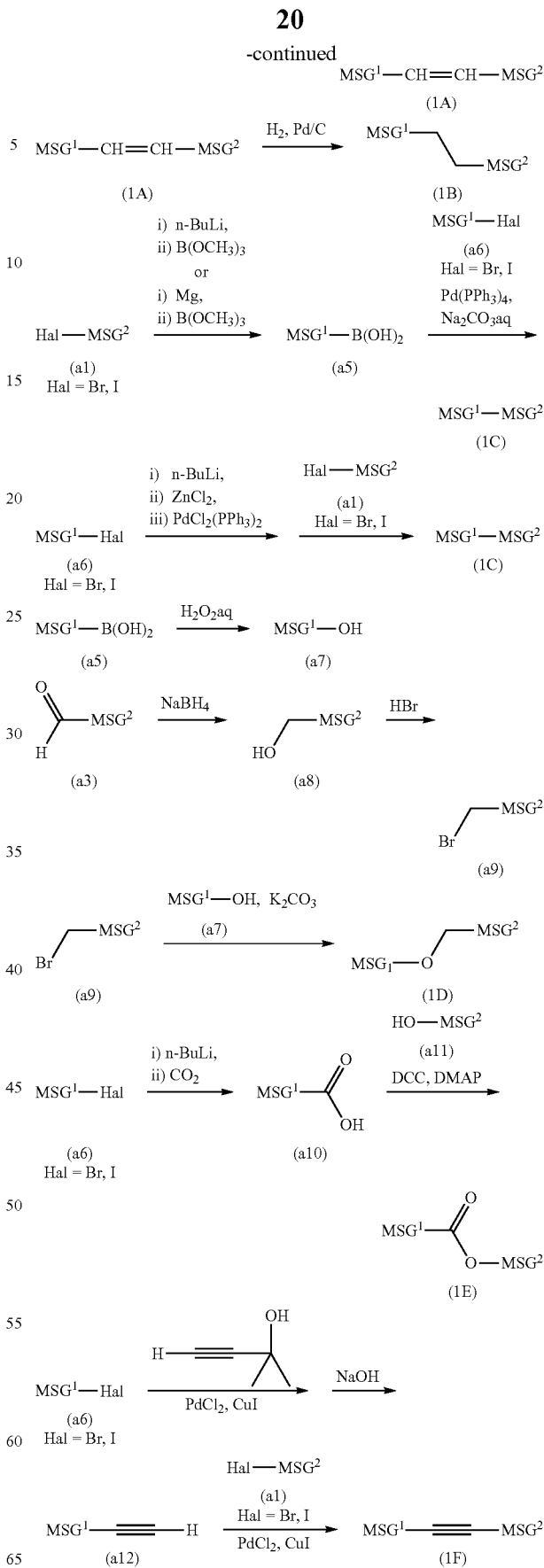

<Formation of Double Bonds>

A Grignard reagent is prepared by reacting the organohalogen compound (a1) having the monovalent organic group MSG², with magnesium. A corresponding alcohol derivative is synthesized by reacting the Grignard reagent thus prepared or a lithium salt with the aldehyde derivative (a2). Then, the corresponding compound (1A) can be synthesized by dehydrating the alcohol derivative obtained, in the presence of an acid catalyst such as p-toluenesulfonic acid.

The organohalogen compound (a1) is treated with butyllithium or magnesium and then reacted with a formamide such as N,N-dimethylformamide (DMF), giving the aldehyde derivative (a3). The compound (1A) having a corresponding double bond can be synthesized by reacting the aldehyde (a3) obtained with phosphorus ylide that is obtained by the treatment of the phosphonium salt (a4) with a base such as potassium t-butoxide. Incidentally, the cis-isomer is isomerized to a trans-isomer according to any known method as required, since in this reaction, a cis-isomer may be formed depending on reaction conditions.

<Formation of —(CH₂)₂—>

The compound (1B) can be synthesized by hydrogenating the compound (1A) in the presence of a catalyst such as palladium on carbon (Pd/C).

<Formation of Single Bonds>

A Grignard reagent or a lithium salt is prepared by reacting the organohalogen compound (a1) with magnesium or butyllithium. The dihydroxyborane derivative (a5) is synthesized by reacting the Grignard reagent or the lithium salt thus prepared with a boric acid ester such as trimethyl borate, and then by hydrolyzing in the presence of an acid such as hydrochloric acid. The compound (1C) can be synthesized by reacting the dihydroxyborane derivative (a5) with the organohalogen compound (a6) in the presence of a catalyst, for example, of an aqueous carbonate solution and tetrakis(triphenylphosphine)palladium (Pd(PPh₃)₄).

The compound (1C) can be synthesized by reacting the organohalogen compound (a6) which has a monovalent organic group MSG¹ with butyl lithium and further with zinc chloride, and then reacting the resultant compound with the compound (a1) in the presence of, for example, a bistriphenylphosphinedichloropalladium (Pd(PPh₃)₂Cl₂) catalyst.

<Formation of —CH₂O— or —OCH₂—>

The alcohol derivative (a7) is obtained by oxidizing the dihydroxyborane derivative (a5) with an oxidizing agent such as hydrogen peroxide. Separately, the alcohol derivative (a8) is obtained by reducing the aldehyde derivative (a3) with a reducing agent such as sodium borohydride. The organohalogen compound (a9) is obtained by halogenating the alcohol derivative (a8) thus obtained with hydrobromic acid or the like. The compound (1D) can be synthesized by reacting the alcohol derivative (a7) thus obtained with the organohalogen compound (a9) in the presence of potassium carbonate or the like.

<Formation of —COO— and —OCO—>

The compound (a6) is reacted with n-butyllithium and then with carbon dioxide, giving the carboxylic acid derivative (a10). The compound (1E) having —COO— can be synthesized by dehydrating the carboxylic acid derivative (a10) and the phenol derivative (a11) in the presence of DCC (1,3-dicyclohexylcarbodiimide) and DMAP (4-dimethylaminopyridine). The compounds having —OCO— can also be synthesized according to this method.

<Formation of —C≡C—>

The compound (a12) is obtained by reacting the compound (a6) with 2-methyl-3-butyn-2-ol in the presence of a catalyst of dichloropalladium and copper halide, and then deprotecting the resulting product under a basic condition. The compound (1F) is synthesized by reacting the compound (a12) with the compound (a1) in the presence of a catalyst of dichloropalladium and copper halide.

<Formation of Ring A¹ or Ring A²>

Starting materials are commercially available or methods for their syntheses are well known with regard to rings, such as 1,4-phenylene, trans-1,4-cyclohexylene, 1,4-cyclohexenylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl and pyridine-3,6-diyl.

[Method of Synthesizing Compound (a)]

Synthetic examples for the liquid crystal compound (a), that is to say, the liquid crystal compound represented by the general formula (a), are shown as follows.

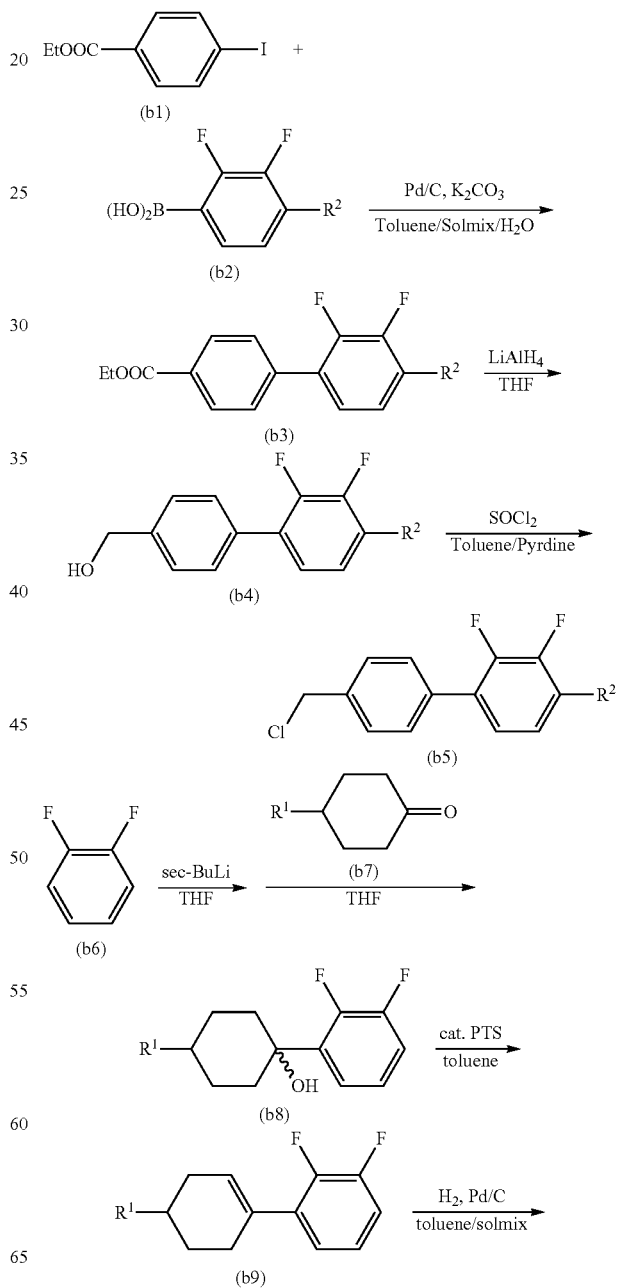

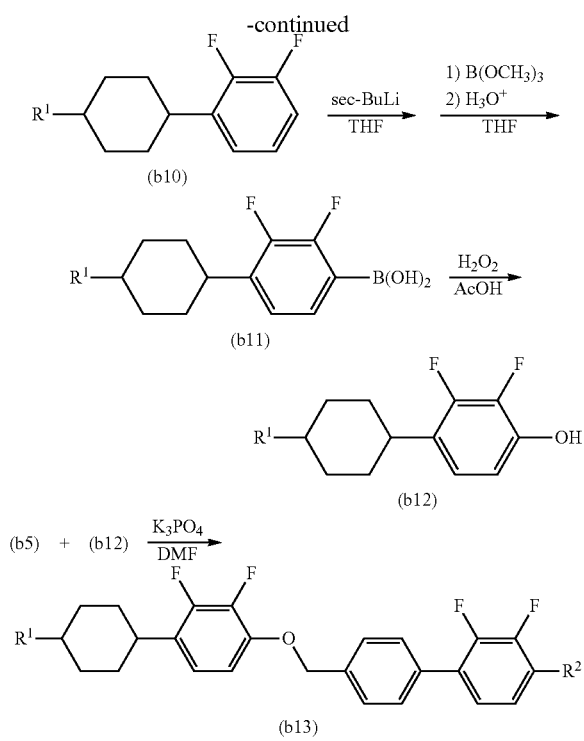

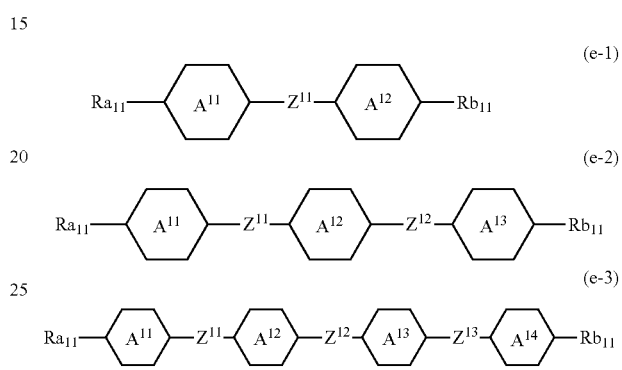

The compound (b3) is obtained by reacting ethyl 4-iodobenzoate (b1) with the dihydroxyborane derivative (b2) in the presence of a catalyst of potassium carbonate, Pd/C, or the like. The compound (b4) is obtained by reducing the compound (b3) with lithium aluminum hydride or the like. Then, the compound (b5) is obtained by chlorinating the compound (b4) with thionyl chloride or the like.

Separately, a lithium salt is prepared by reacting 1,2-difluorobenzene (b6) with sec-BuLi. The alcohol derivative (b8) is obtained by reacting this lithium salt with the carbonyl derivative (b7). The cyclohexene derivative (b9) is obtained by dehydrating the alcohol derivative (b8) obtained in the presence of an acid catalyst of p-toluenesulfonic acid or the like. The compound (b10) is obtained by hydrogenating this compound (b9) in the presence of a catalyst, such as Pd/C. A lithium salt is prepared by reacting the compound (b10) thus obtained with s-butyl lithium. The dihydroxyborane derivative (b11) is obtained by reacting this lithium salt with trimethoxyborane. The phenol derivative (b12) is obtained by reacting the compound (b11) with an aqueous solution of hydrogen peroxide. The compound (b13), which is one example of the compound (a) of the invention, can be synthesized by etherifying the compound (b5) obtained by use of the above procedure with the phenol derivative (b12) in the presence of a base such as potassium carbonate.

[Liquid Crystal Compositions]

The liquid crystal composition of the invention is explained as follows. The components of this liquid crystal composition are characterized by including at least one of the compound (a), and the components may include two or more of the compounds (a), and may be composed of the compound (a) alone. When the liquid crystal composition of the invention is prepared, its components can also be selected, for example, by taking into consideration of the dielectric anisotropy of the compound (a). The liquid crystal composition in which the components are selected has a small viscosity, a suitable and negative dielectric anisotropy, a suitable elastic constant $K_{33}$, a low threshold voltage, a high maximum temperature of a nematic phase (phase-transition temperature on a nematic phase-an isotropic phase), and a low minimum temperature of the nematic phase.

[Liquid Crystal Composition (1)]

In the liquid crystal composition of the invention, a composition that further comprises at least one compound selected from the group of compounds represented by formulas (e-1) to (e-3) as a second component (hereinafter also referred to as the compounds (e-1) to (e-3), respectively) in addition to the compound (a) is desirable. Hereinafter, the composition is also referred to as the liquid crystal composition (1).

In formulas (e-1) to (e-3), $Ra_{11}$ and $Rb_{11}$ are each independently alkyl having 1 to 10 carbons, and in the alkyl, —$CH_2$— may be nonadjacently replaced by —O—, and —$(CH_2)_2$— may be nonadjacently replaced by —CH=CH—, and hydrogen may be replaced by fluorine.

In formulas (e-1) to (e-3), ring $A^{11}$, ring $A^{12}$, ring $A^{13}$ and ring $A^{14}$ are each independently 1,4-phenylene, trans-1,4-cyclohexylene, 1,4-cyclohexenylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl.

In formulas (e-1) to (e-3), $Z^{11}$, $Z^{12}$ and $Z^{13}$ are each independently a single bond, —$CH_2$—$CH_2$—, —CH=CH—, —C≡C—, —COO— or $CH_2O$—.

Viscosity of a liquid crystal composition can be decreased and the minimum temperature of a nematic phase can be decreased by adding a second component to the compound (a). Since the dielectric anisotropy of the compounds (e-1) to (e-3) are nearly 0 (zero), the dielectric anisotropy of the liquid crystal composition including the compounds can be adjusted so as to approach 0 (zero).

The compound (e-1) or (e-2) is effective in decreasing the viscosity and increasing the voltage holding ratio in the liquid crystal composition comprising the compound. The compound (e-3) is effective in increasing the maximum temperature of a nematic phase and increasing the voltage holding ratio in the liquid crystal composition comprising the compound.

If two or more rings are trans-1,4-cyclohexylene in the ring $A^{11}$, ring $A^{12}$, ring $A^{13}$ and ring $A^{14}$, the maximum temperature of a nematic phase in the liquid crystal composition comprising the compound can be increased. If two or more rings are 1,4-phenylene, the optical anisotropy of the liquid crystal composition comprising the compound can be increased.

More desirable compounds for the second components are represented by formulas (2-1) to (2-74) (hereinafter also referred to as the compounds (2-1) to (2-74), respectively). In these compounds, $Ra_{11}$ and $Rb_{11}$ have the meanings identical to those described for the compounds (e-1) to (e-3).
(2-1)
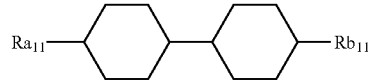
(2-2)
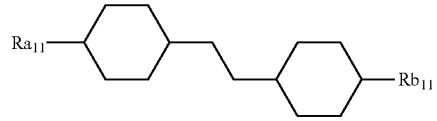
(2-3)
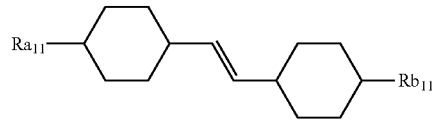
(2-4)
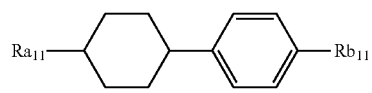
(2-5)
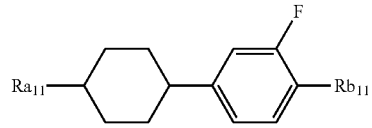
(2-6)
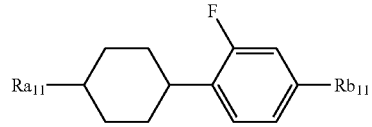
(2-7)
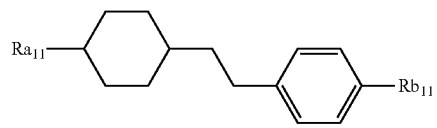
(2-8)
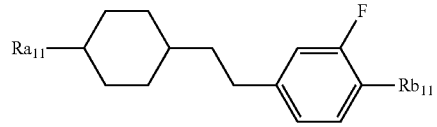
(2-9)
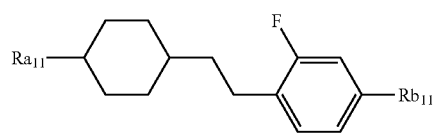
(2-10)
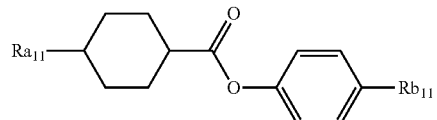
(2-11)
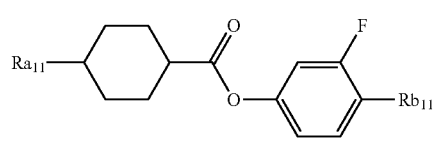
-continued
(2-12)
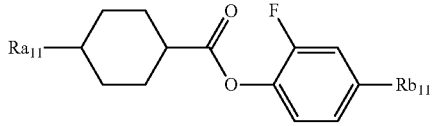
(2-13)
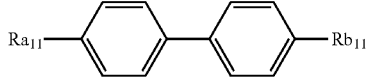
(2-14)
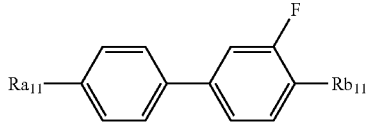
(2-15)
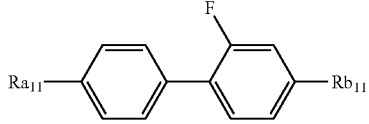
(2-16)
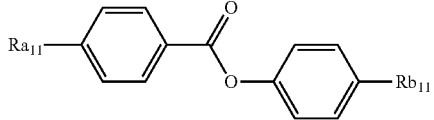
(2-17)
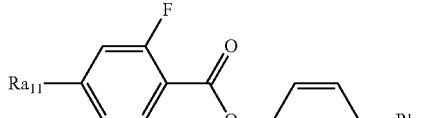
(2-18)
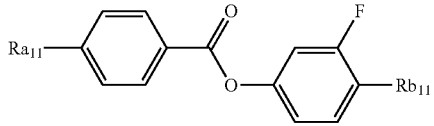
(2-19)
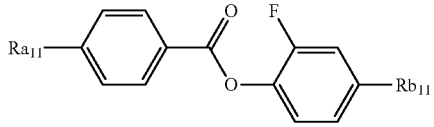
(2-20)
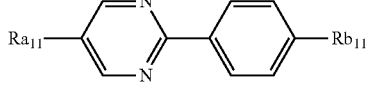
(2-21)
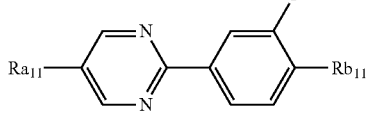
(2-22)
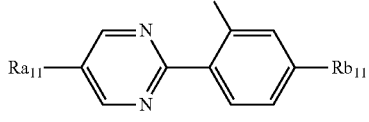

(2-23) 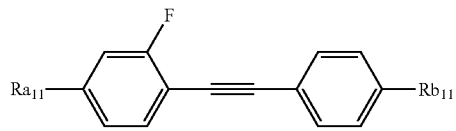
(2-24) 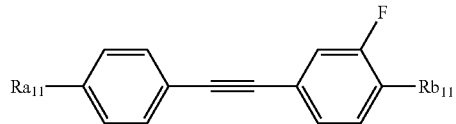
(2-25) 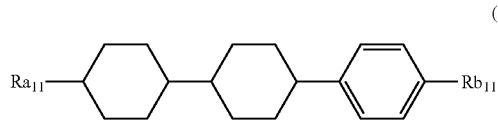
(2-26) 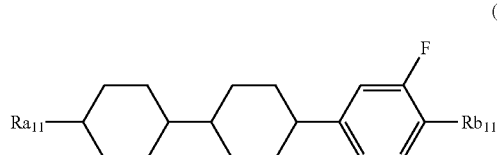
(2-27) 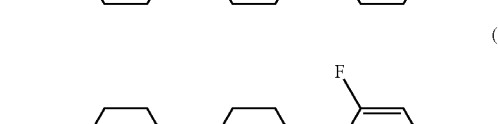
(2-28) 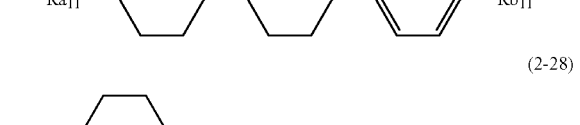
(2-29) 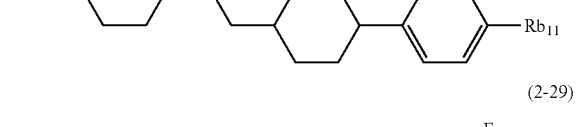
(2-30) 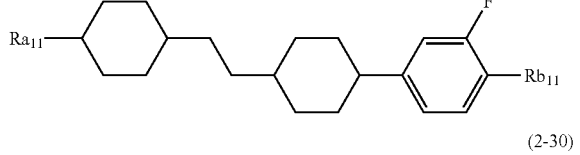
(2-31) 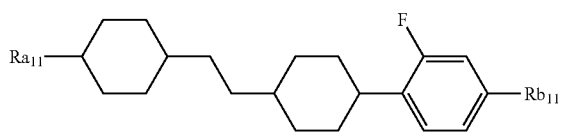
(2-32) 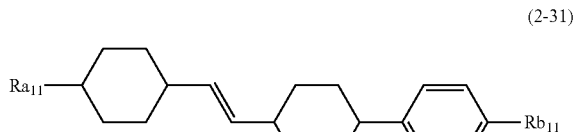
(2-33) 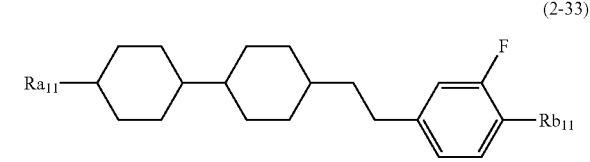
(2-34) 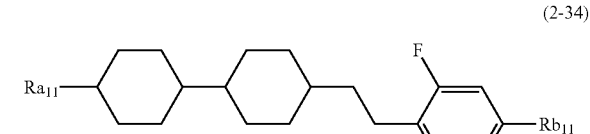
(2-35) 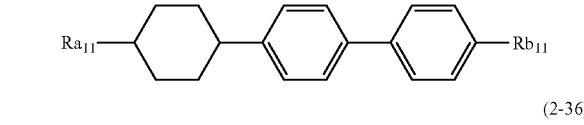
(2-36) 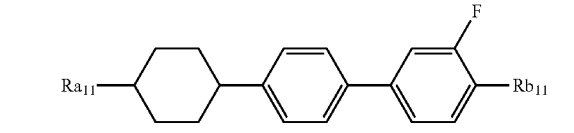
(2-37) 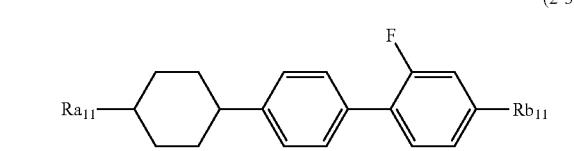
(2-38) 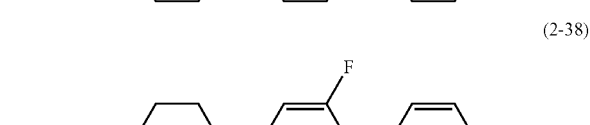
(2-39) 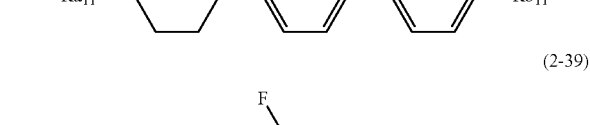
(2-40) 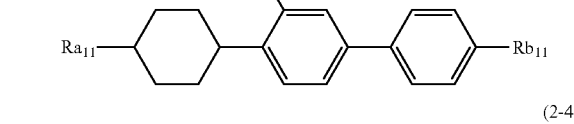
(2-41) 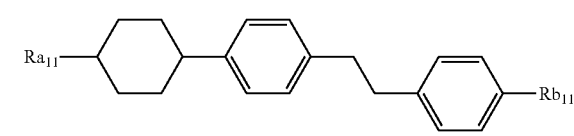
(2-42) 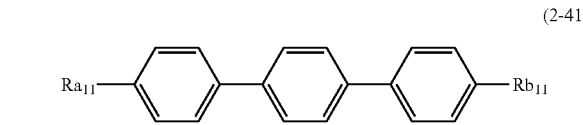
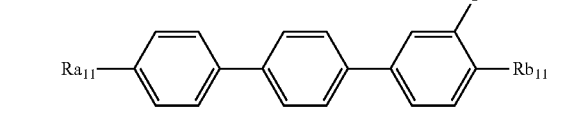

(2-43) 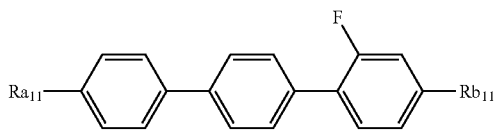
(2-44) 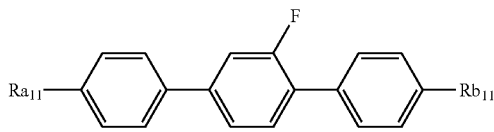
(2-45) 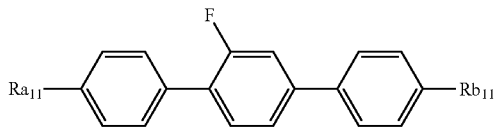
(2-46) 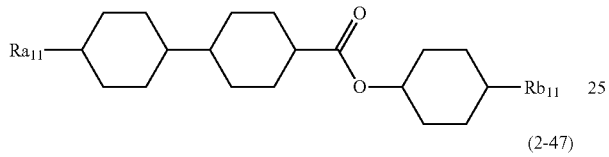
(2-47) 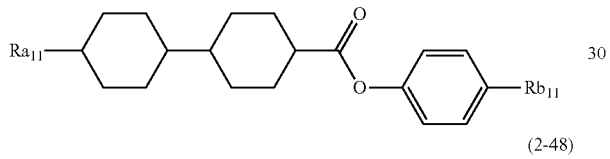
(2-48) 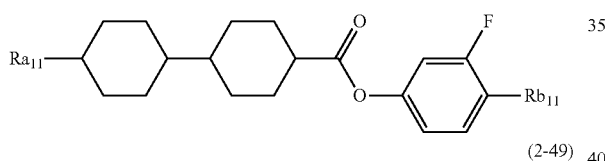
(2-49) 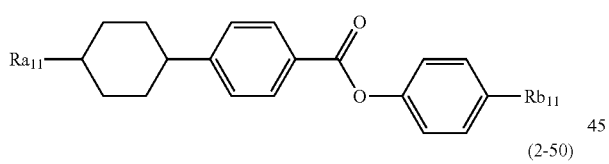
(2-50) 
(2-51) 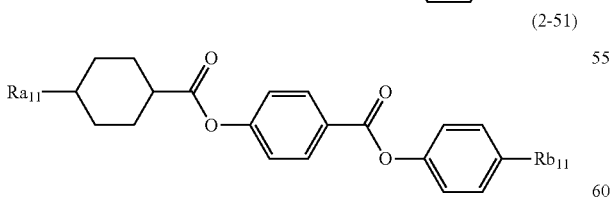
(2-52) 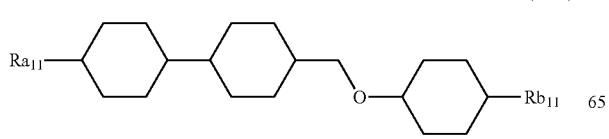
(2-53) 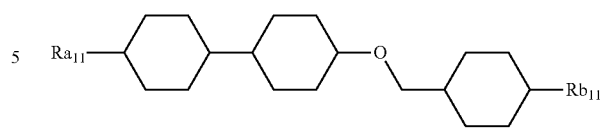
(2-54) 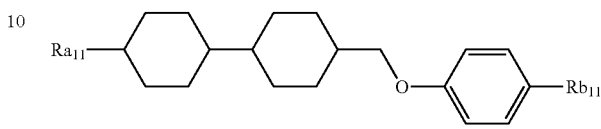
(2-55) 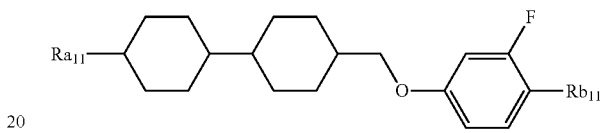
(2-56) 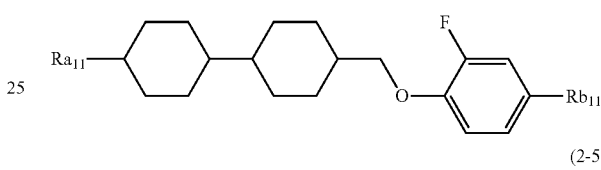
(2-57) 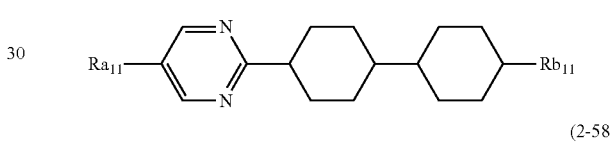
(2-58) 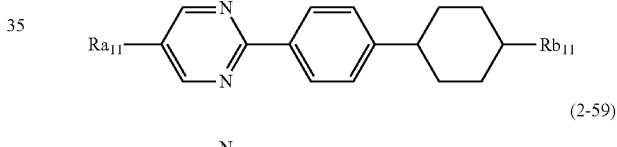
(2-59) 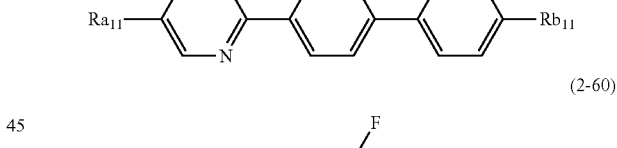
(2-60) 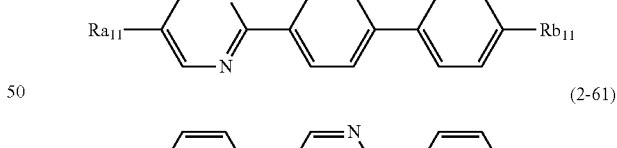
(2-61) 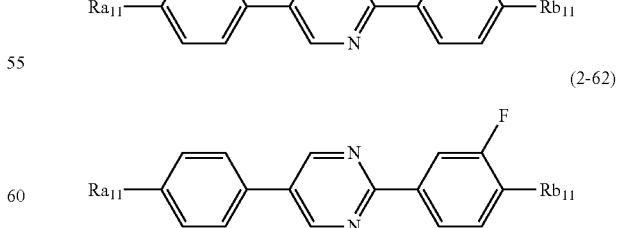
(2-62) 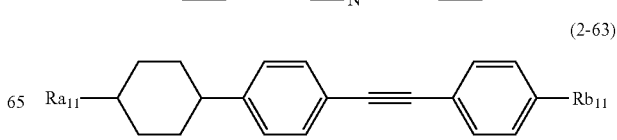
(2-63) 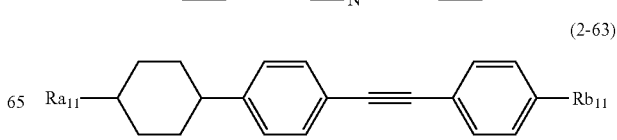

(2-64)
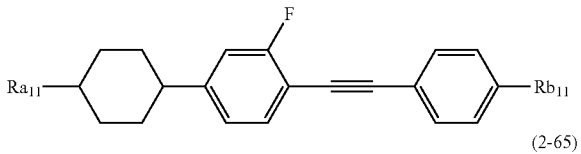

(2-65)
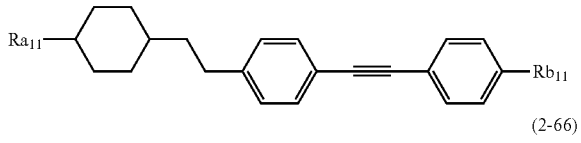

(2-66)

(2-67)
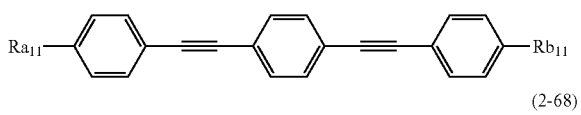

(2-68)
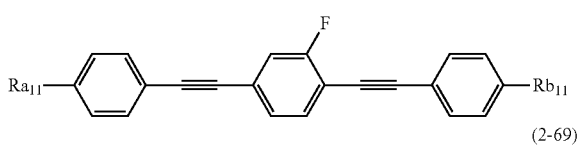

(2-69)
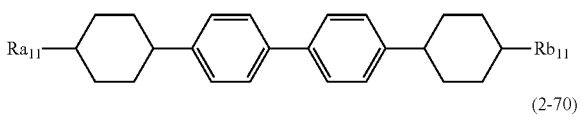

(2-70)
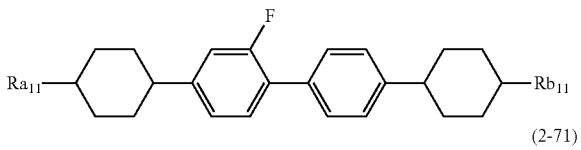

(2-71)
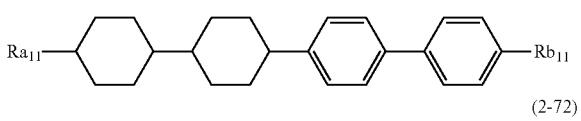

(2-72)
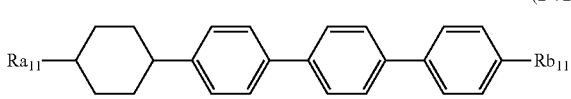

(2-73)

(2-74)
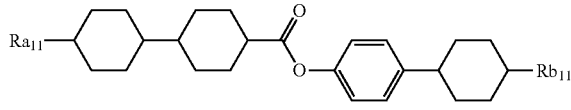

If the second component is the compounds (2-1) to (2-74), the liquid crystal composition having an excellent heat resistance and light resistance, a higher specific resistance-value and a nematic phase in a wide range can be prepared.

In particular, the liquid crystal composition (1), wherein the first component is at least one compound selected from the group of compounds represented by formulas (a-2) to (a-11) and the second component is at least one compound selected from the group of compounds represented by formulas (e-1) to (e-3), has a quite excellent heat resistance and light resistance, a wider range of a nematic phase, a larger voltage holding ratio, a smaller viscosity and a suitable elastic constant $K_{33}$.

Although the content of the second component in the liquid crystal composition (1) of the invention is not limited particularly, it is desirable to increase the content in view of a smaller viscosity. Since the threshold voltage of the liquid crystal composition tends to increase with an increase of the content of the second component, the content of the second component is in the range of 40% to 95% by weight based on the total weight of the liquid crystal compounds included in the liquid crystal composition (1), and the content of the first component is more preferably in the range of 5% to 60% by weight based on the total weight of the liquid crystal compounds included in the liquid crystal composition (1) when the liquid crystal composition of the invention is used, for example, for a liquid crystal device with a VA mode.

[Liquid Crystal Composition (2)]

A liquid crystal composition comprising at least one compound selected from the group of the liquid crystal compounds represented by formulas (g-1) to (g-6) (hereinafter also referred to as the compounds (g-1) to (g-6), respectively) as a third component, in addition to the first component and the second component, is also desirable (hereinafter also referred to as the liquid crystal composition (2)) for the liquid crystal composition of the invention.

(g-1)
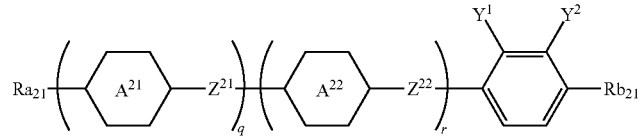

(g-2)
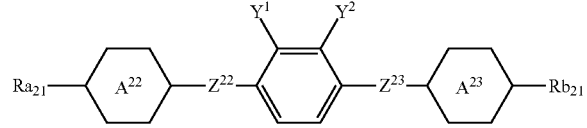

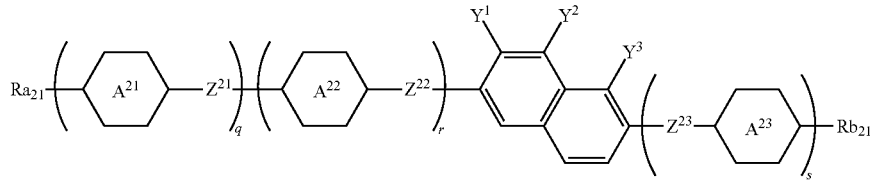

(g-3)

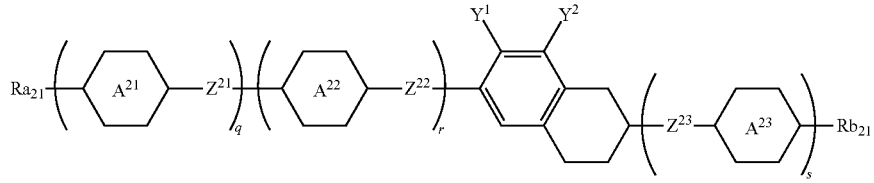

(g-4)

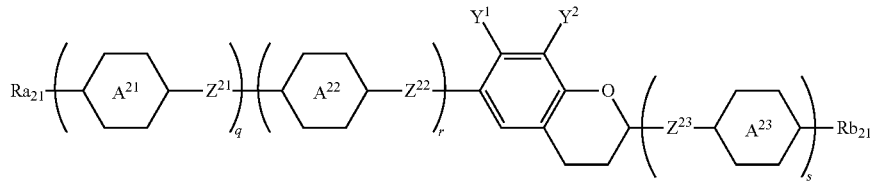

(g-5)

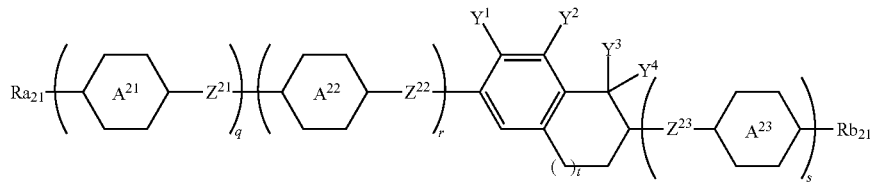

(g-6)

In formulas (g-1) to (g-6), $Ra_{21}$ and $Rb_{21}$ are each independently hydrogen or alkyl having 1 to 10 carbons, and in the alkyl, —$CH_2$— may be nonadjacently replaced by —O—, and —$(CH_2)_2$— may be nonadjacently replaced by —CH=CH—, and hydrogen may be replaced by fluorine.

In formulas (g-1) to (g-6), rings $A^{21}$, $A^{22}$ and $A^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl.

In formulas (g-1) to (g-6), $Z^{21}$, $Z^{22}$ and $Z^{23}$ are each independently a single bond, —$CH_2$—$CH_2$—, —CH=CH—, —C≡C—, —$OCF_2$—, —$CF_2O$—, —$OCF_2CH_2CH_2$—, —$CH_2CH_2CF_2O$—, —COO—, —OCO—, —$OCH_2$— or —$CH_2O$—, and $Y^1$, $Y^2$, $Y^3$ and $Y^4$ are each independently fluorine or chlorine.

In formulas (g-1) to (g-6), q, r and s are each independently 0, 1 or 2, q+r is 1 or 2, q+r+s is 1, 2 or 3, and t is 0, 1 or 2.

When q is 2, two of rings $A^{21}$ may be identical or may be different, and two of $Z^{21}$ may also be identical or may be different.

When r is 2, two of rings $A^{22}$ may be identical or may be different, and two of $Z^{22}$ may also be identical or may be different.

When s is 2, two of rings $A^{23}$ may be identical or may be different, and two of $Z^{23}$ may also be identical or may be different.

The liquid crystal composition (2) which further comprises the third component has a large negative dielectric anisotropy.

Moreover, the liquid crystal composition having a wide temperature range of a nematic phase, a small viscosity, a large negative dielectric anisotropy and a large specific resistance-value can be obtained when the third component is comprised, and the liquid crystal composition in which these physical properties are suitably balanced is obtained.

Among the third components, at least one compound selected from the group of compounds represented by formulas (h-1) to (h-7) (hereinafter also referred to as the compounds (h-1) to (h-7), respectively) is more desirable in view of a small viscosity, heat resistance and light resistance.

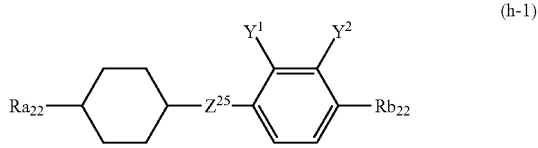

(h-1)

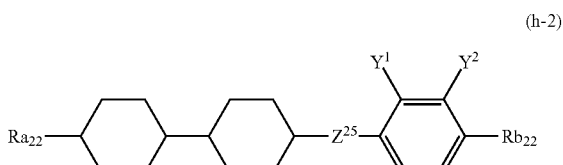

(h-2)

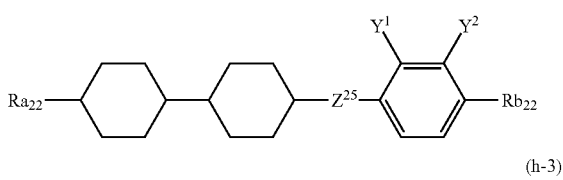

(h-3)

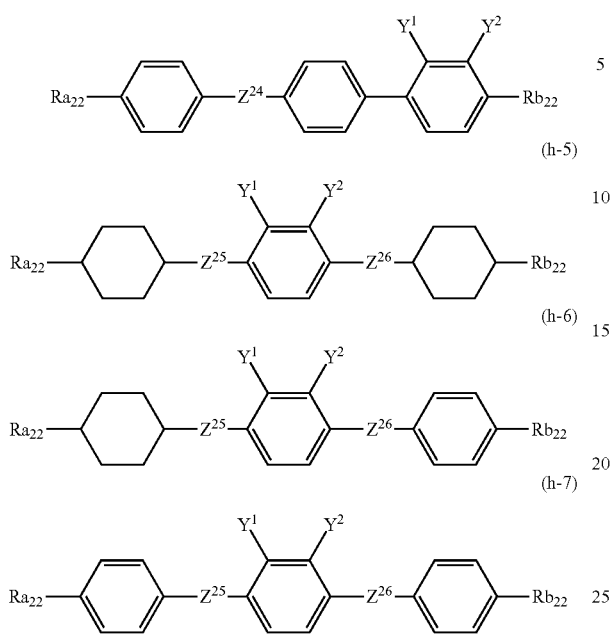

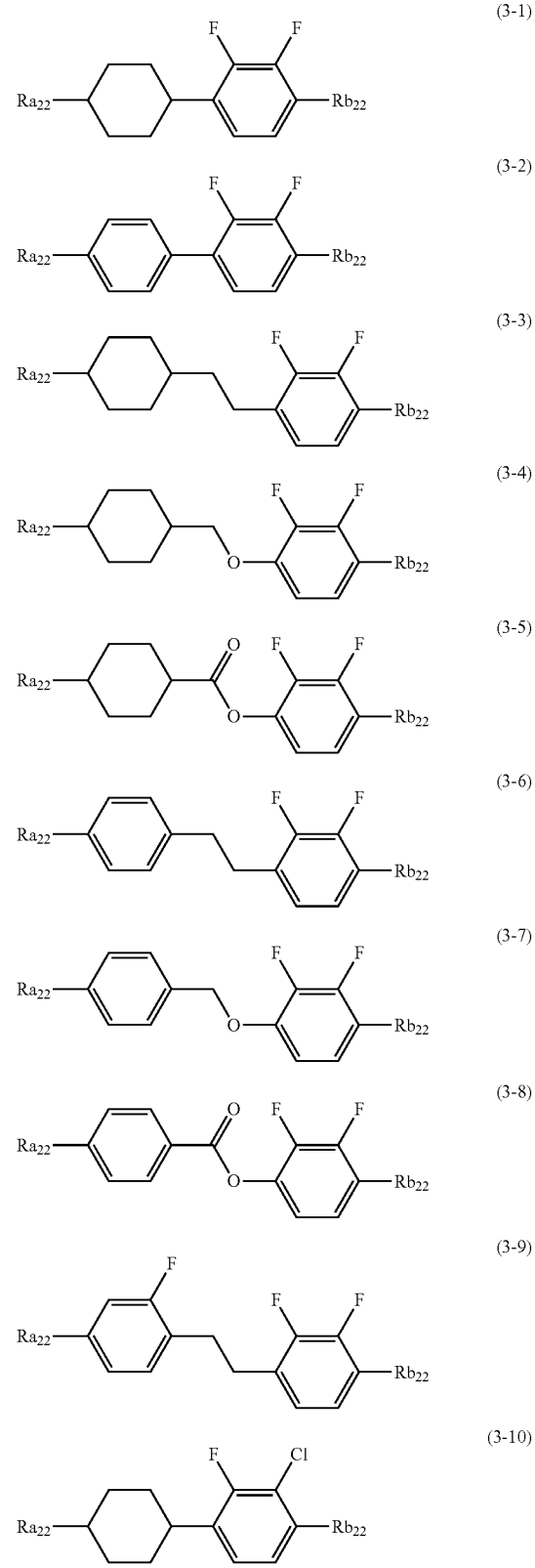

In formulas (h-1) to (h-7), $Ra_{22}$ and $Rb_{22}$ are each independently straight-chain alkyl having 1 to 8 carbons, straight-chain alkenyl having 2 to 8 carbons or alkoxy having 1 to 7 carbons, $Z^{24}$, $Z^{25}$ and $Z^{26}$ are a single bond, —CH$_2$CH$_2$—, —CH$_2$O—, —OCH$_2$—, —COO— or —OCO—, and $Y^1$ and $Y^2$ are simultaneously fluorine, or one of them is fluorine and the other is chlorine.

For example, the compounds (h-1) and (h-2) can decrease viscosity, decrease the threshold voltage-value, and decrease the minimum temperature of a nematic phase in the liquid crystal composition comprising them. The compounds (h-2), (h-3) and (h-4) can decrease the threshold voltage-value without decreasing the maximum temperature of the nematic phase, in the liquid crystal composition comprising them.

The compounds (h-3) and (h-6) can increase optical anisotropy and the compounds (h-4) and (h-7) can further increase optical anisotropy.

The compounds (h-5), (h-6) and (h-7) can decrease the minimum temperature of a nematic phase in the liquid crystal composition comprising them.

Among the liquid crystal compositions (2), in particular, a liquid crystal composition which comprises first, second and third components has an excellent heat resistance and light resistance, a wide temperature range of a nematic phase, a small viscosity, a large voltage holding ratio, a suitable optical anisotropy, a suitable dielectric anisotropy and a suitable elastic constant $K_{33}$, wherein the first component is at least one compound selected from the group of compounds represented by formulas (a-1) to (a-26), the second component is at least one compound selected from the group of compounds represented by formulas (e-1) to (e-3), and the third component is at least one compound selected from the group of compounds represented by formulas (h-1) to (h-7). Furthermore, the liquid crystal composition is desirable in view of these physical properties suitably balanced.

Among the third components, that is, the group of the compounds (g-1) to (g-6), more desirable are the compounds (3-1) to (3-118). In these compounds, $Ra_{22}$ and $Rb_{22}$ are each independently straight-chain alkyl having 1 to 8 carbons, straight-chain alkenyl having 2 to 8 carbons or alkoxy having 1 to 7 carbons.

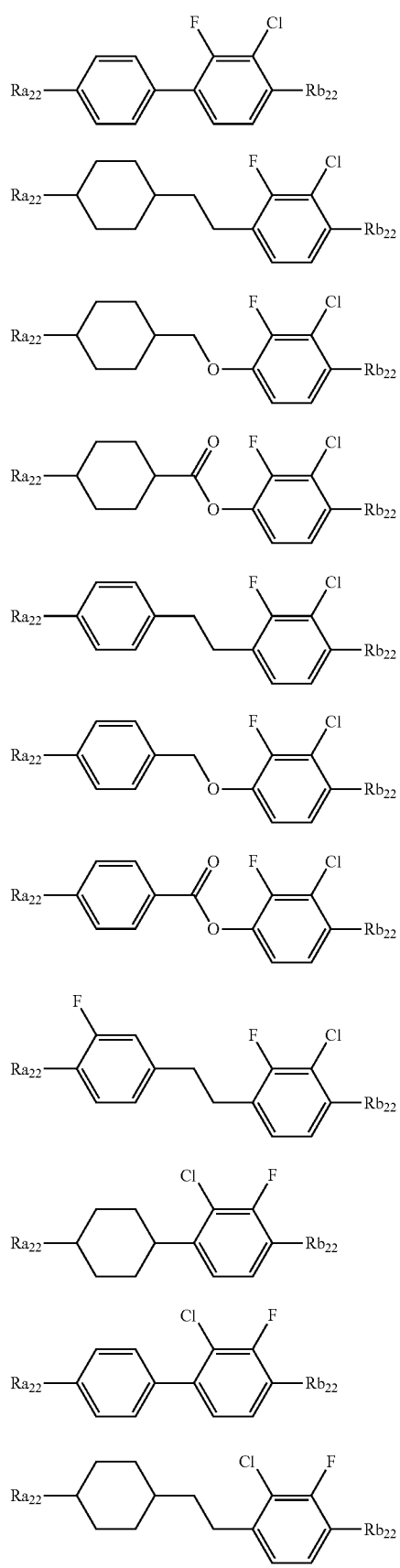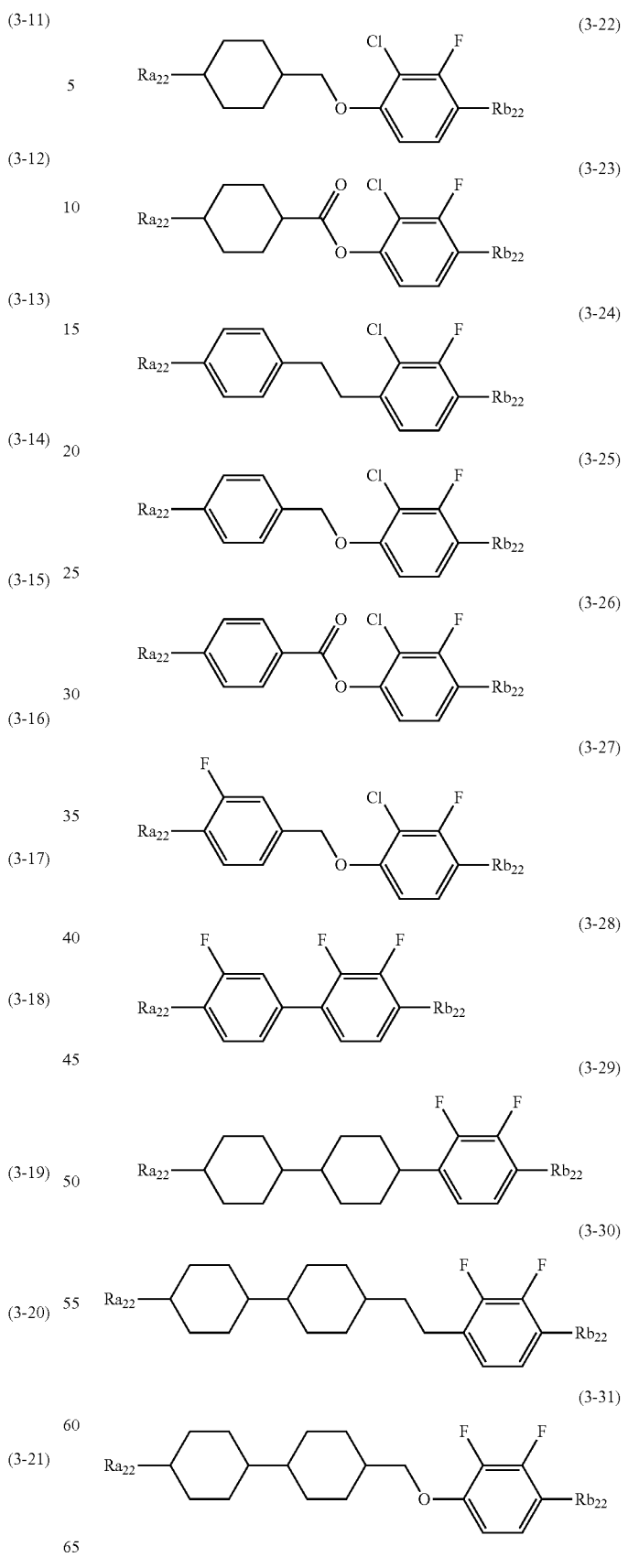

(3-32)
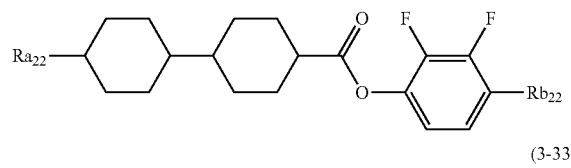
(3-33)
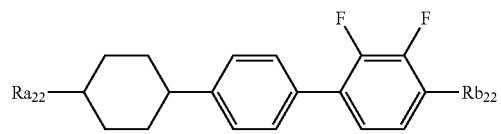
(3-34)
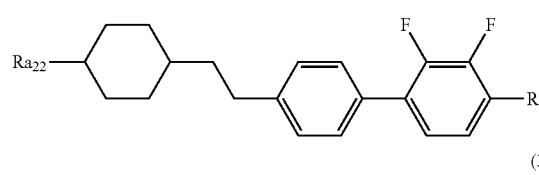
(3-35)
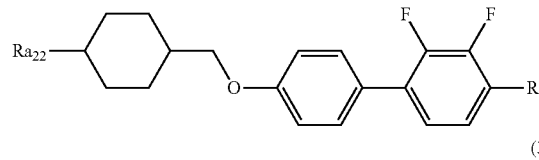
(3-36)
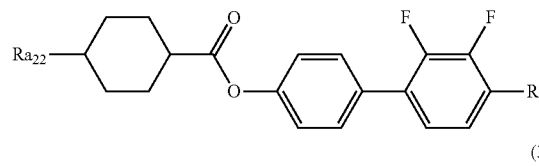
(3-37)
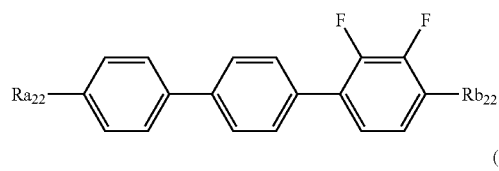
(3-38)
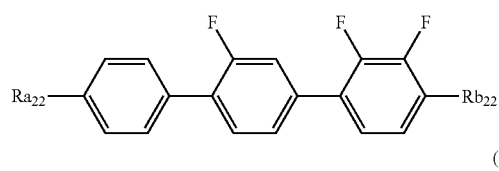
(3-39)
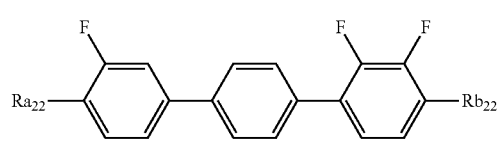
(3-40)
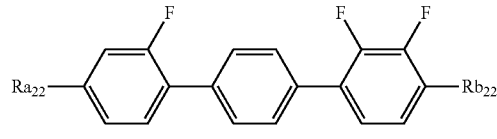
(3-41)
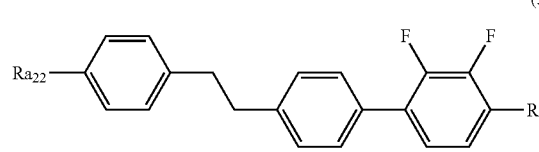
(3-42)
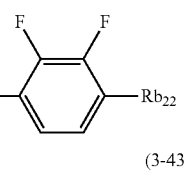
(3-43)
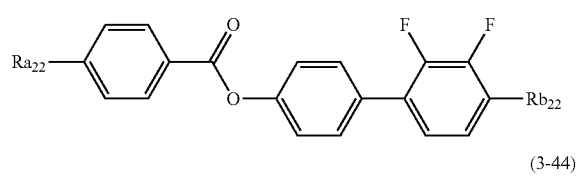
(3-44)
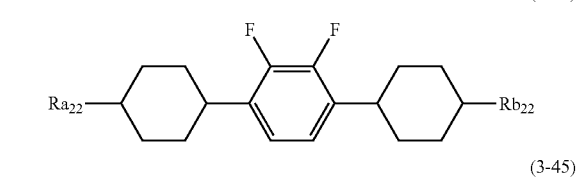
(3-45)
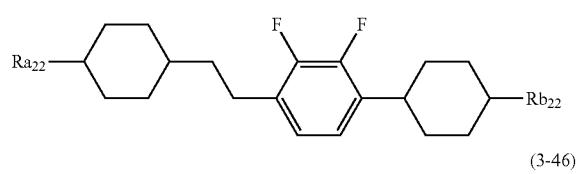
(3-46)
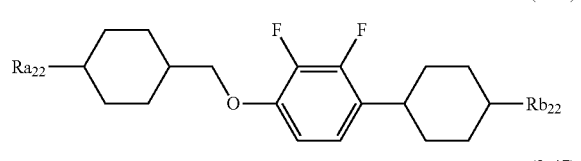
(3-47)
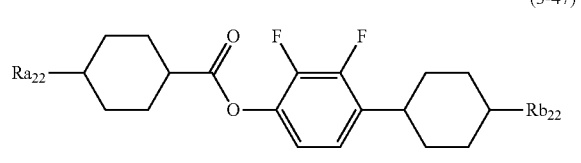
(3-48)
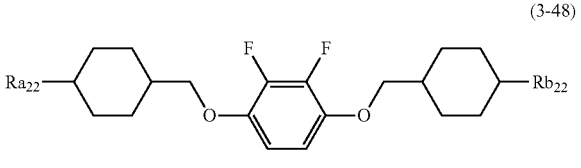
(3-49)
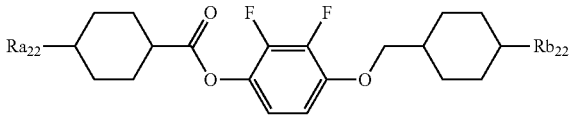
(3-50)
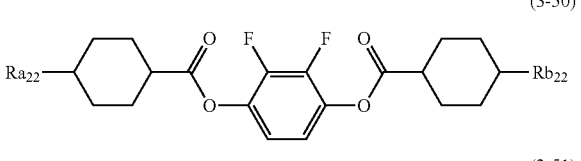
(3-51)
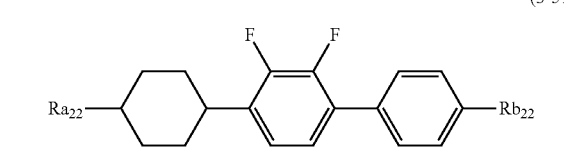

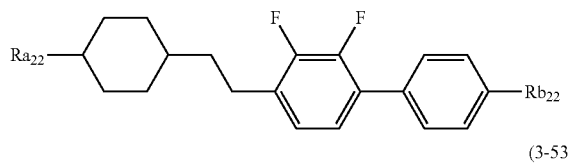
(3-52)
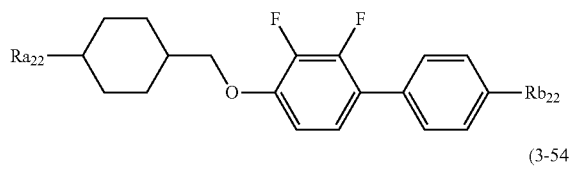
(3-53)
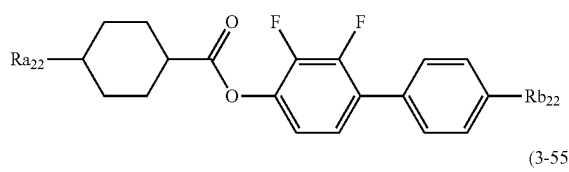
(3-54)
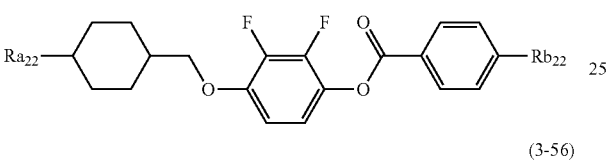
(3-55)
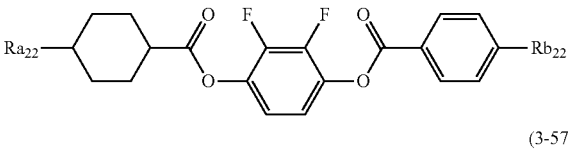
(3-56)
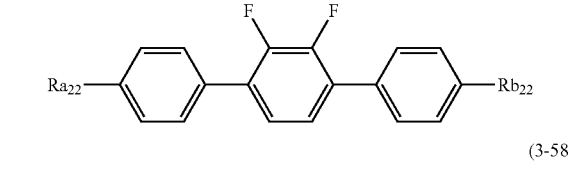
(3-57)
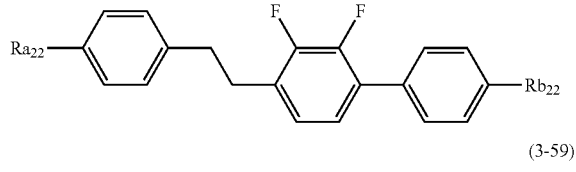
(3-58)

(3-59)
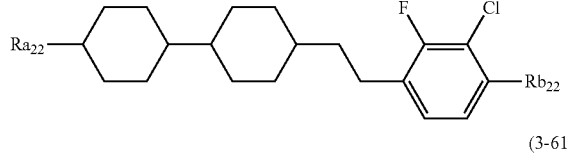
(3-60)
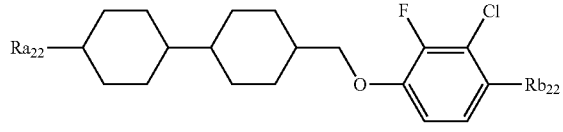
(3-61)
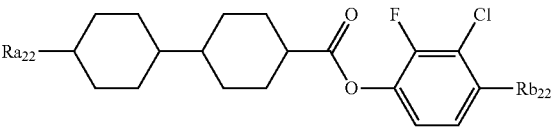
(3-62)
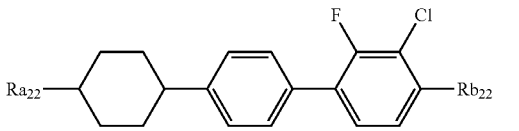
(3-63)
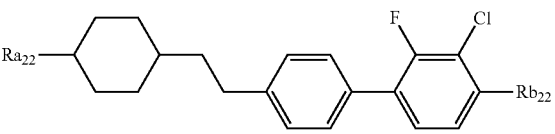
(3-64)
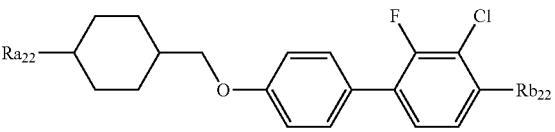
(3-65)
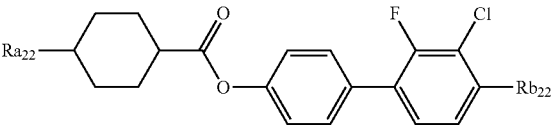
(3-66)
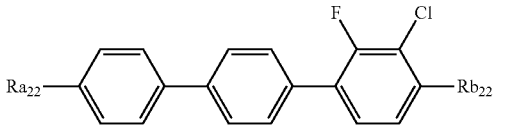
(3-67)
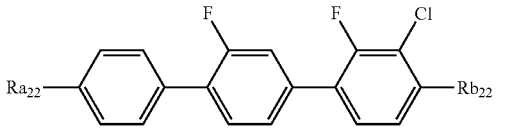
(3-68)
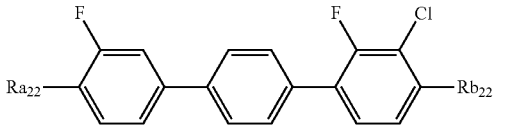
(3-69)
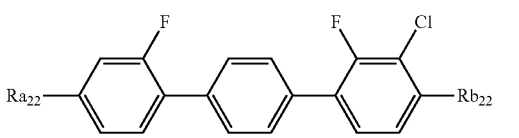
(3-70)
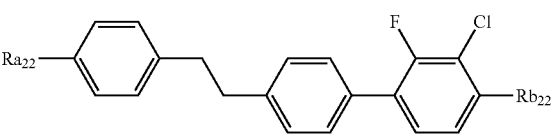
(3-71)

(3-72) 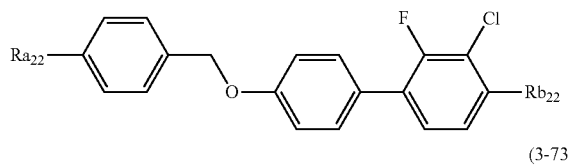
(3-73) 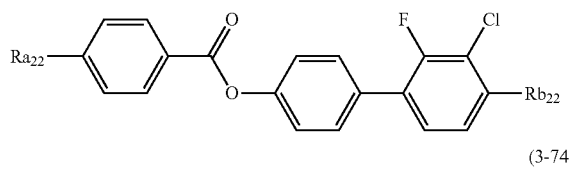
(3-74) 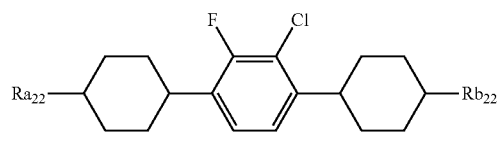
(3-75) 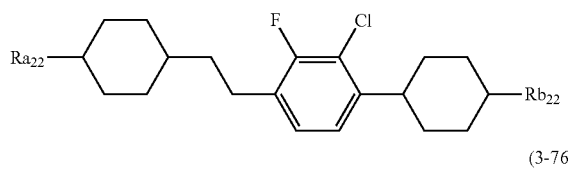
(3-76) 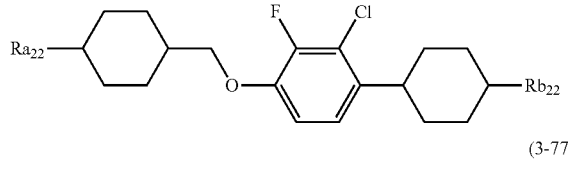
(3-77) 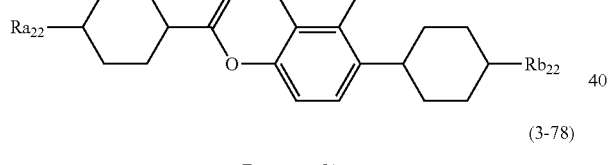
(3-78) 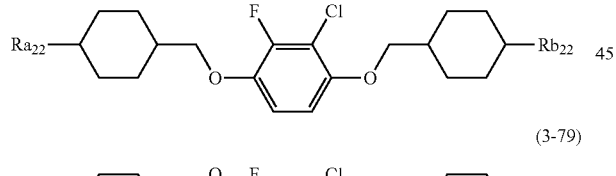
(3-79) 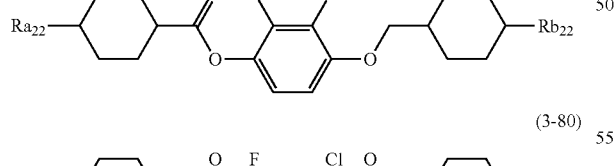
(3-80) 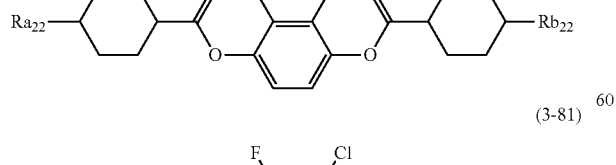
(3-81) 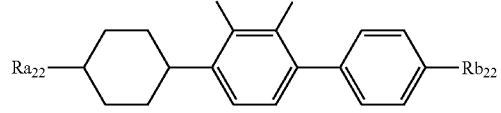
(3-82) 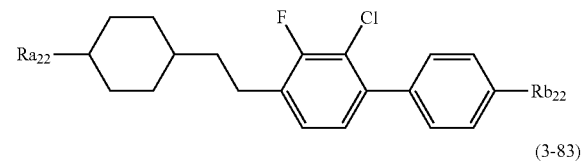
(3-83) 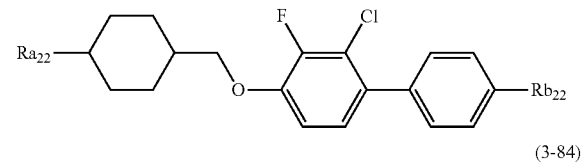
(3-84) 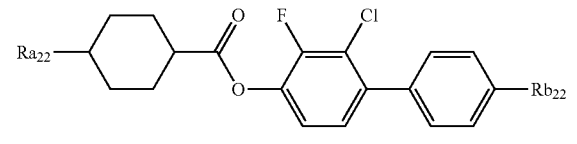
(3-85) 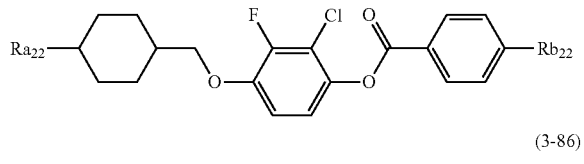
(3-86) 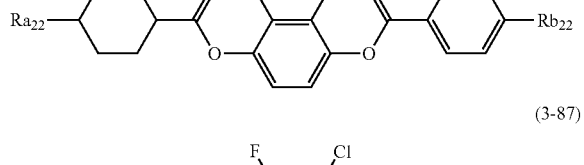
(3-87) 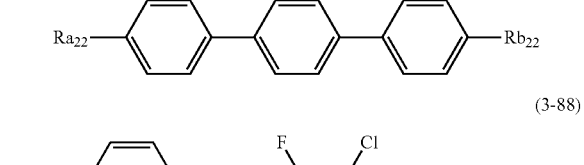
(3-88) 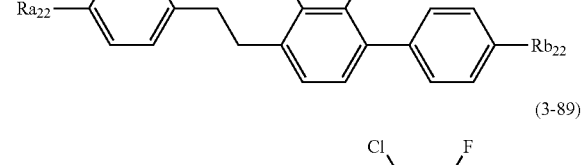
(3-89) 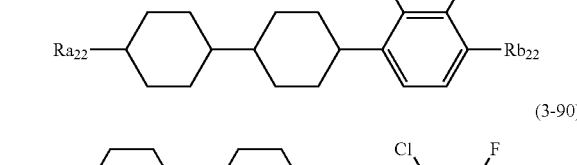
(3-90) 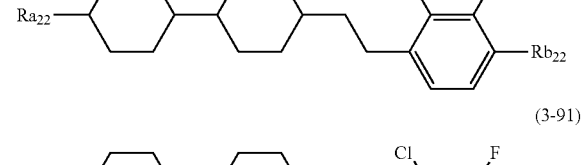
(3-91) 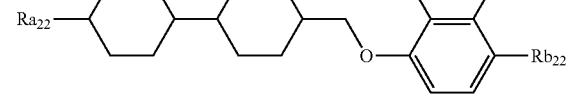

(3-92)
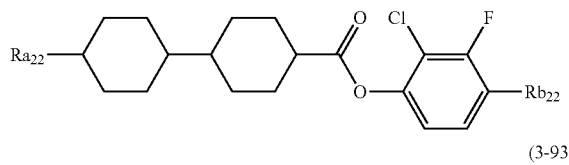
(3-93)
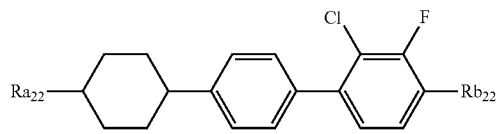
(3-94)

(3-95)

(3-96)
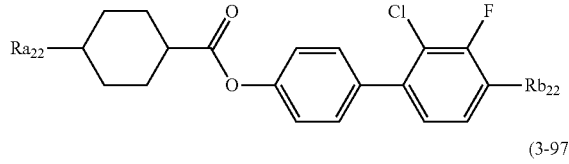
(3-97)
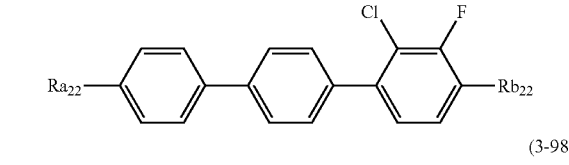
(3-98)
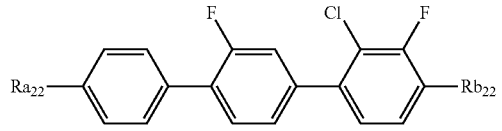
(3-99)

(3-100)
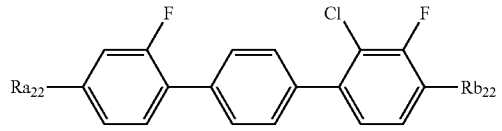
(3-101)
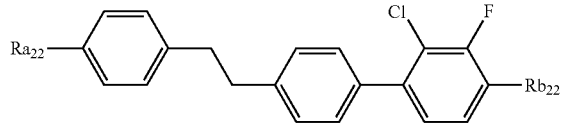
(3-102)
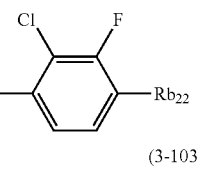
(3-103)
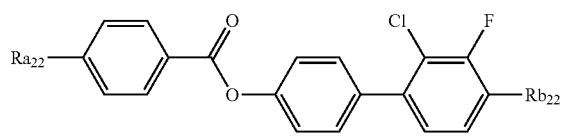
(3-104)
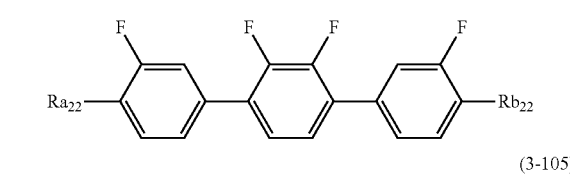
(3-105)
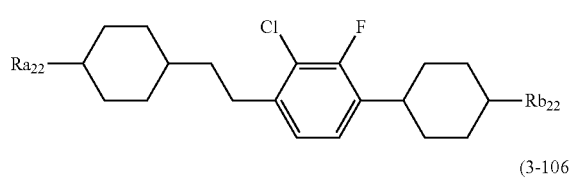
(3-106)
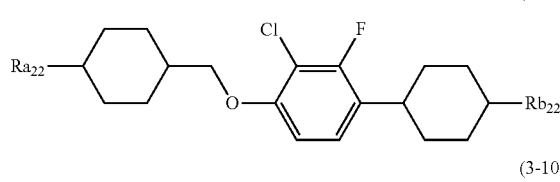
(3-107)
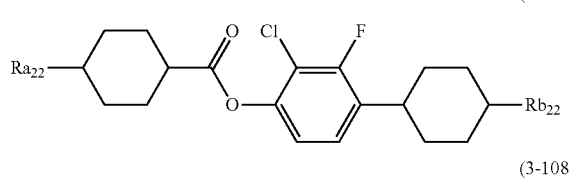
(3-108)
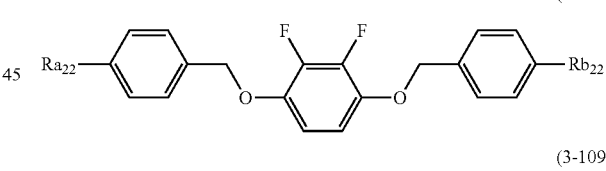
(3-109)
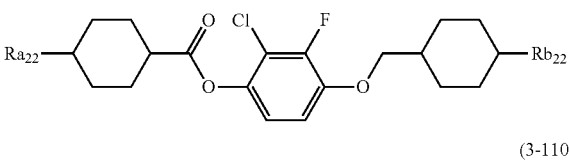
(3-110)
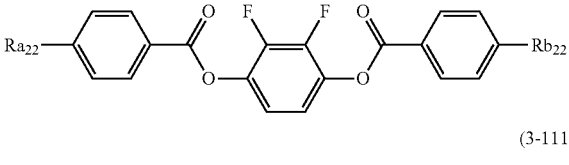
(3-111)
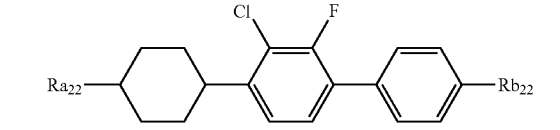

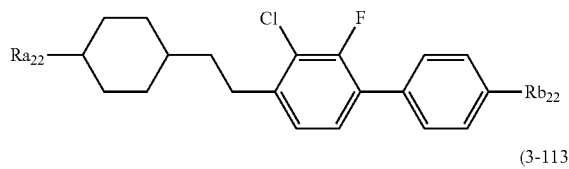
(3-112)
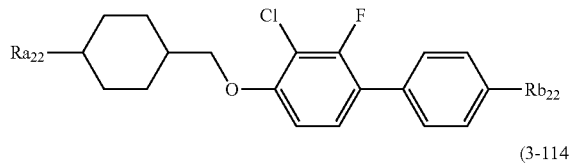
(3-113)
(3-114)
(3-115)
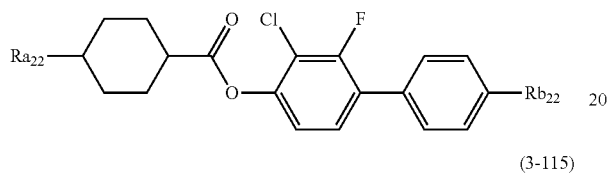
(3-116)
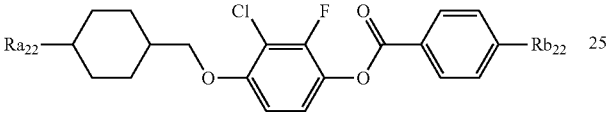
(3-117)
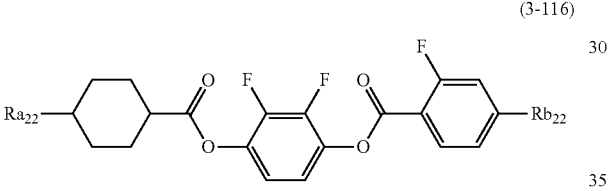
(3-118)
For example, compounds having a condensed ring, such as the compounds (g-3) to (g-6), are desirable in view of decreasing a threshold voltage-value, and the compounds (3-119) to (3-144) are desirable in view of heat resistance or light resistance. In these compounds, $Ra_{22}$ and $Rb_{22}$ have the meanings identical to those described for the compounds (g-3) to (g-6).
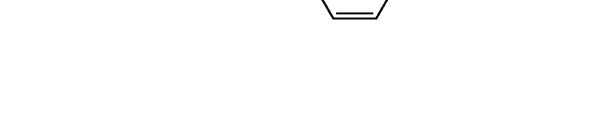
(3-119)
(3-120)
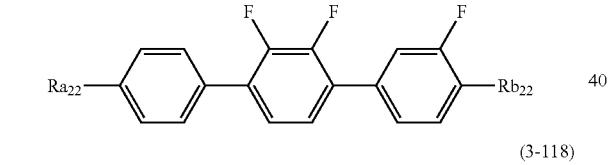
(3-121)
(3-122)

(3-123)
(3-124)
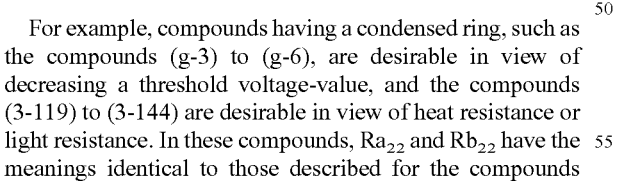
(3-125)
(3-126)
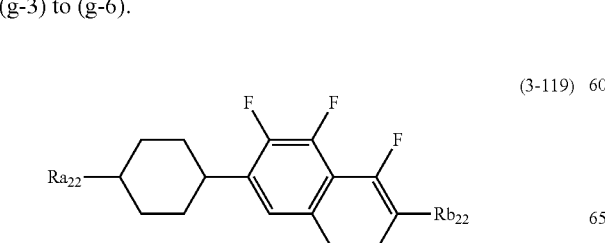
(3-127)

(3-128)
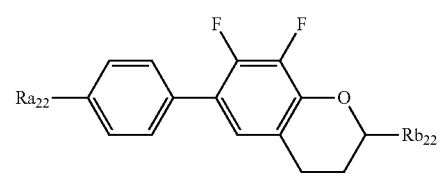
(3-129)
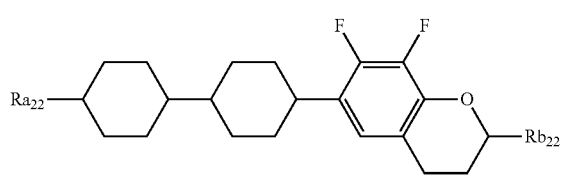
(3-130)
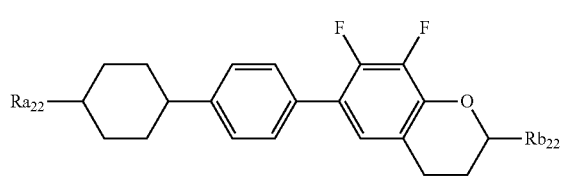
(3-131)
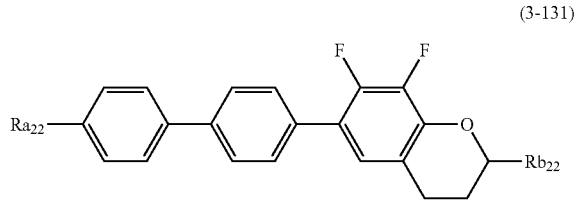
(3-132)
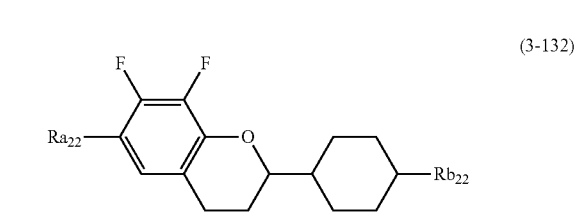
(3-133)
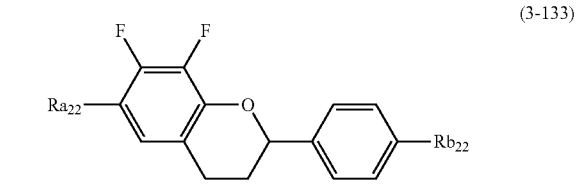
(3-134)
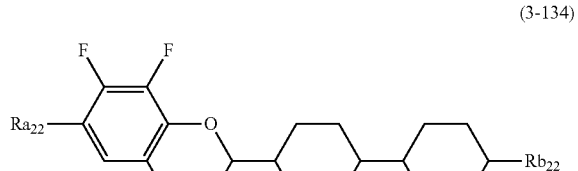
(3-135)
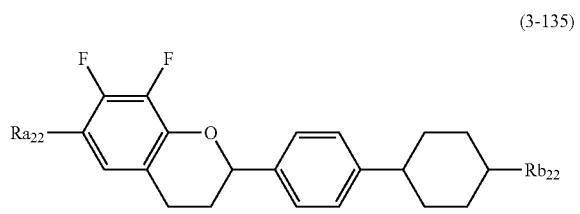
(3-136)
(3-137)
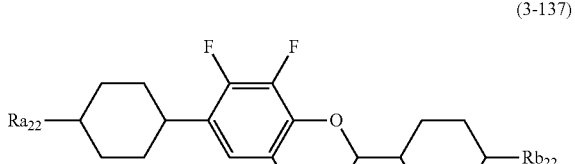
(3-138)
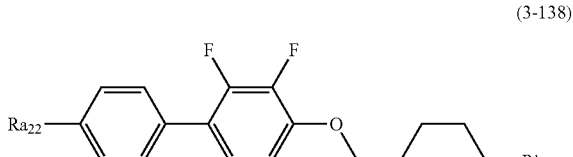
(3-139)
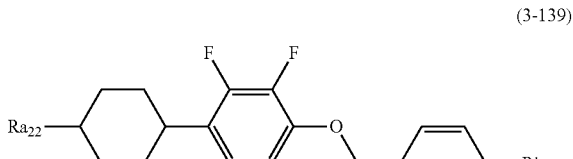
(3-140)
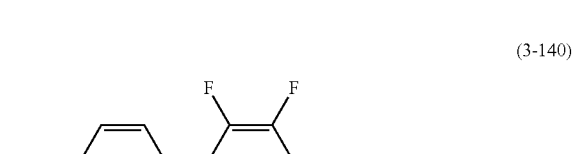
(3-141)
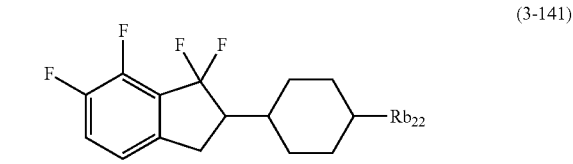
(3-142)
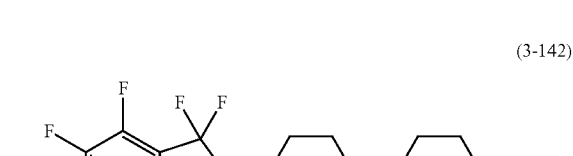
(3-143)
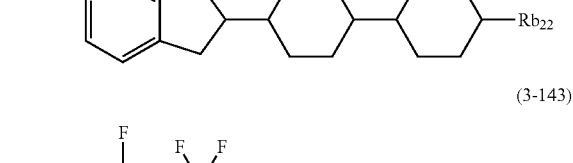

(3-144)

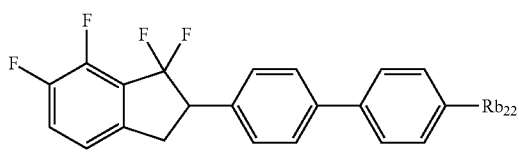

Although the content of the third component in the liquid crystal composition of the invention is not limited particularly, it is desirable to increase the content in view of preventing a decrease in the absolute value of negative dielectric anisotropy.

Although the content ratios of the first component, second component and third component of the liquid crystal composition (2) of the invention are not limited particularly, it is desirable that the content ratio of the liquid crystal compound (a) is in the range of 5% to 60% by weight, the content ratio of the second component is in the range of 20% to 75% by weight, and the content ratio of the third component is in the range of 20% to 75% by weight based on the total weight of the liquid crystal composition (2).

When the ratios of the contents of the first, second and third components of the liquid crystal composition (2) are in these ranges, the composition (2) has an excellent heat resistance and light resistance, a wide temperature range of a nematic phase, a small viscosity, a large voltage holding ratio, a suitable optical anisotropy, a suitable dielectric anisotropy and a suitable elastic constant $K_{33}$. Furthermore, a liquid crystal composition in which these physical properties are more suitably balanced is obtained.

[Aspects and so Forth of Liquid Crystal Composition]

In one aspect on the liquid crystal composition of the invention, other liquid crystal compounds may be added to liquid crystal compounds of the first and second components, and of the third component which is used as required, for the purpose of further adjusting, for example, characteristics of the liquid crystal composition. In another aspect on the liquid crystal composition of the invention, no other liquid crystal compounds may be added to the liquid crystal compounds of the first and second components, and of the third component which is used as required, in view of their cost.

Additives, such as an optically active compound, dye, an antifoaming agent, an ultraviolet absorber, an antioxidant, polymerizable compound and a polymerization initiator, may further be added to the liquid crystal composition of the invention.

When the optically active compound is added to the liquid crystal composition of the invention, it may induce a helical structure in liquid crystals, forming a twist angle and so forth.

A known chiral dopant is added as a optically active compound. The chiral dopant is effective in inducing a helical structure in liquid crystals, adjusting a twist angle required and then preventing a reverse twist. Examples of the chiral dopant includes the following optically active compounds (Op-1) to (Op-13).

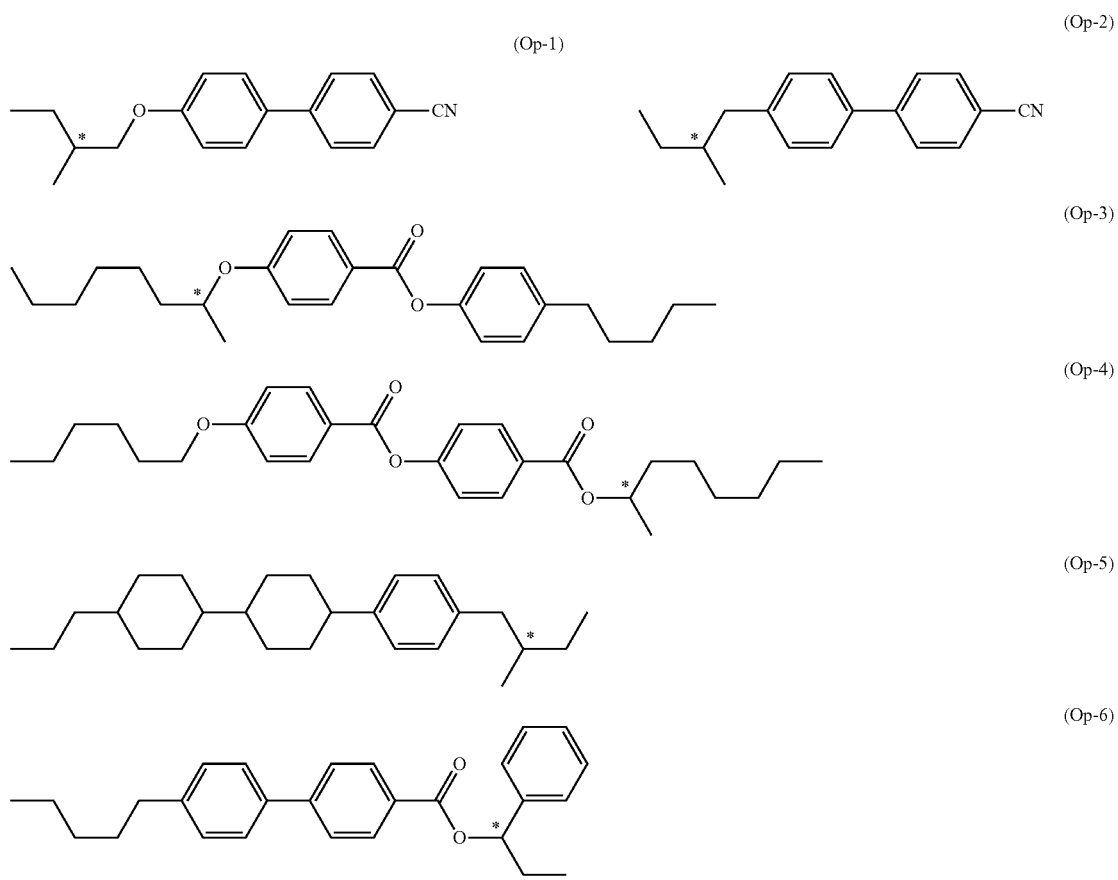

-continued

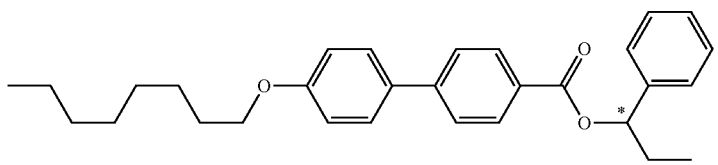
(Op-7)

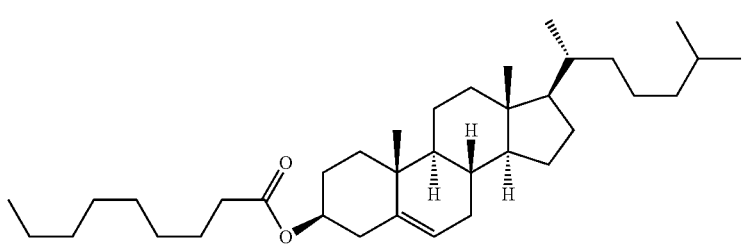
(Op-8)

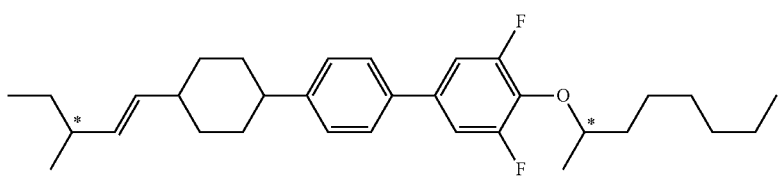
(Op-9)

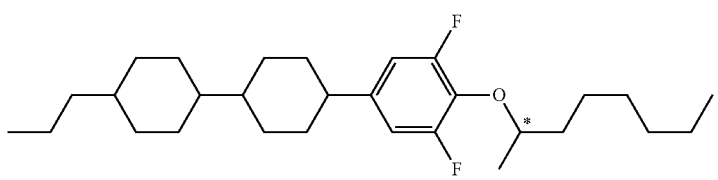
(Op-10)

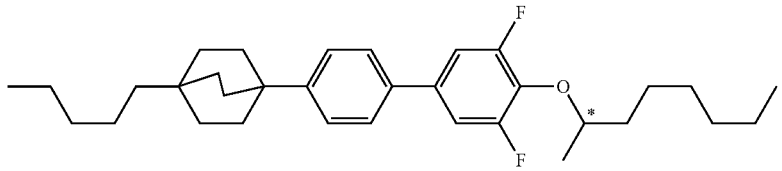
(Op-11)

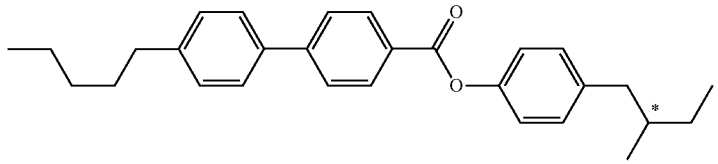
(Op-12)

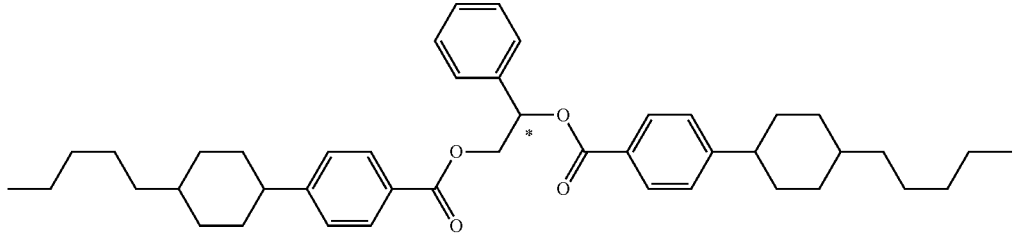
(Op-13)

When a dye is added to the liquid crystal composition of the invention, the liquid crystal composition can be applied to the liquid crystal display device which has a Guest host (GH) mode.

When an antifoaming agent is added to the liquid crystal composition of the invention, it is possible to suppress the formation of foam during the transportation of the liquid crystal composition or in a process of manufacturing liquid crystal display devices using this liquid crystal composition.

When the ultraviolet absorber or the antioxidant is added to the liquid crystal composition of the invention, it is possible to prevent degradation of the liquid crystal composition and of the liquid crystal display device containing the liquid crystal composition. For example, the antioxidant can suppress a decrease in specific resistance, when the liquid crystal composition is heated.

The ultraviolet absorber includes a benzophenone-based ultraviolet absorber, a benzoate-based ultraviolet absorber and a triazole-based ultraviolet absorber. A specific example of the benzophenone-based ultraviolet absorber is 2-hydroxy-4-n-octoxybenzophenone.

A specific example of the benzoate-based ultraviolet absorber is 2,4-di-t-butylphenyl-3,5-di-t-butyl-4-hydroxybenzoate. Specific examples of the triazole-based ultraviolet absorber are 2-(2-hydroxy-5-methylphenyl)benzotriazole, 2-[2-hydroxy-3-(3,4,5,6-tetrahydroxyphthalimido-methyl)-5-methylphenyl]benzotriazole and 2-(3-t-butyl-2-hydroxy-5-methylphenyl)-5-chlorobenzotriazole.

The antioxidant includes a phenol-based antioxidant, an organosulfur-based antioxidant and so forth. An antioxidant represented by formula (I) is desirable especially in view of a large effect on antioxidation without varying the physical properties of the liquid crystal composition.

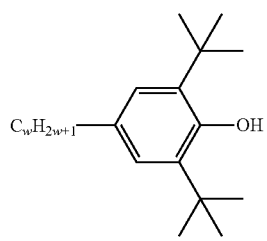

(I)

In formula (I), w is an integer of 1 to 15.

Specific examples of the phenol-based antioxidant are 2,6-di-t-butyl-4-methylphenol, 2,6-di-t-butyl-4-ethylphenol, 2,6-di-t-butyl-4-propylphenol, 2,6-di-t-butyl-4-butylphenol, 2,6-di-t-butyl-4-pentylphenol, 2,6-di-t-butyl-4-hexylphenol, 2,6-di-t-butyl-4-heptylphenol, 2,6-di-t-butyl-4-octylphenol, 2,6-di-t-butyl-4-nonylphenol, 2,6-di-t-butyl-4-decylphenol, 2,6-di-t-butyl-4-undecylphenol, 2,6-di-t-butyl-4-dodecylphenol, 2,6-di-t-butyl-4-tridecylphenol, 2,6-di-t-butyl-4-tetradecylphenol, 2,6-di-t-butyl-4-pentadecylphenol, 2,2'-methylenebis(6-t-butyl-4-methylphenol), 4,4'-butylidenebis(6-t-butyl-3-methylphenol), 2,6-di-t-butyl-4-(2-octadecyloxycarbonyl)ethylphenol and pentaerythritol tetrakis[3-(3,5-di-t-butyl-4-hydroxyphenyl)propionate].

Specific examples of the organosulfur-based antioxidant are dilauryl-3,3'-thiopropionate, dimyristyl-3,3'-thiopropionate, distearyl-3,3'-thiopropionate, pentaerythritol tetrakis (3-laurylthiopropionate) and 2-mercaptobenzimidazole.

Additives typified by an ultraviolet absorber, an antioxidant and so forth may be added and used in the range of amounts which do not prevent the purpose of the invention and can attain the purpose of the addition of the additives.

When the ultraviolet absorber or the antioxidant is added, for example, its content ratio is usually in the range of 10 ppm to 500 ppm, preferably in the range of 30 ppm to 300 ppm, and more preferably in the range of 40 ppm to 200 ppm based on the total weight of the liquid crystal composition of the invention.

Incidentally, in another aspect, the liquid crystal composition of the invention may include impurities of starting materials, by-products, solvents used for reactions, catalysts for syntheses and so forth, which are contaminations in the process such as for synthesizing each compound constituting a liquid crystal composition and for preparing the liquid crystal composition.

The polymerizable compound is mixed into the composition for adjusting to a device having a polymer sustained alignment (PSA) mode. Desirable examples of the polymerizable compound include compounds having a polymerizable group, such as acrylates, methacrylates, vinyl compounds, vinyloxy compounds, propenyl ethers and epoxy compounds (oxiranes, oxetanes). Especially desirable examples of the polymerizable compound are acrylate derivatives or methacrylate derivatives. A desirable ratio of the polymerizable compound is 0.05% by weight or more for achieving its effect and is 10% by weight or less for avoiding a poor display. A more desirable ratio is in the range of 0.1% to 2% by weight. The polymerizable compound is preferably polymerized on irradiation with ultraviolet light or the like in the presence of a suitable initiator such as a photopolymerization initiator. Suitable conditions for polymerization, suitable types of the initiator and suitable amounts thereof are known to a person skilled in the art and are described in the literature. For example, Irgacure 651®, Irgacure 184® or Darocure 1173® (Ciba Geigy AG), which is photo-initiator, is suitable for radical polymerization. The polymerizable compound includes the photopolymerization initiator preferably in the range of 0.1% to 5% by weight, and most preferably in the range of 1% to 3% by weight.

[Method for Preparing Liquid Crystal Compositions]

When each of the compounds of the components in the liquid crystal composition of the invention is a liquid, for example, the composition is prepared by mixing and shaking the compounds. When solids are included, the composition is prepared by mixing the compounds, and then shaking after the compounds have been heated and liquefied. Moreover, the liquid crystal composition of the invention can also be prepared according to other known methods.

[Characteristics of Liquid Crystal Compositions]

Since the maximum temperature of a nematic phase can be adjusted to 70° C. or above and the minimum temperature of the nematic phase can be adjusted to −20° C. or below in the liquid crystal composition of the invention, the temperature range of the nematic phase is wide. Accordingly, the liquid crystal display device containing this liquid crystal composition can be used in a wide temperature range.

In the liquid crystal composition of the invention, the optical anisotropy can be properly adjusted in the range of 0.10 to 0.13, or in the range of 0.05 to 0.18, by suitably adjusting the composition ratio and so forth.

The dielectric anisotropy can be normally adjusted in the range of −5.0 to −2.0, and preferably in the range of −4.5 to −2.5 in the liquid crystal composition of the invention. The liquid crystal composition having the dielectric anisotropy of the range of −4.5 to −2.5 can be suitably used for a liquid crystal display device which operates by means of the IPS and VA modes.

[Liquid Crystal Display Devices]

The liquid crystal composition of the invention can be used not only for the liquid crystal display devices with operating modes such as the PC, TN, STN, OCB and PSA modes which are driven by means of the AM mode, but also for liquid crystal display devices with operating modes such as the PC, TN, STN, OCB, VA and IPS modes which are driven by means of the passive matrix (PM) mode.

The liquid crystal display devices with the AM and PM modes can be applied to liquid crystal displays and so forth having any of a reflection type, a transmission type, and a semi-transmission type.

Moreover, the liquid crystal composition of the invention can also be used for a dynamic scattering (DS) mode-device having the liquid crystal composition to which a conducting agent is added, and a nematic curvilinear aligned phase (NCAP) device having the liquid crystal composition microencapsulated, and a polymer dispersed (PD) device having a three-dimensional network polymer formed in the liquid crystal composition, for example, a polymer network (PN) device.

Since the liquid crystal composition of the invention has the characteristics described above, it can be suitably used for the liquid crystal display device with an AM mode which is driven by means of an operating mode such as the VA, IPS or PSA mode, wherein the liquid crystal composition having negative dielectric anisotropy is used, especially for the liquid crystal display device with the AM mode which is driven by means of the VA mode.

The direction of an electric field is perpendicular to liquid crystal layers in a liquid crystal display device which is driven by means of the TN mode, the VA mode or the like. On the other hand, the direction of an electric field is parallel to liquid crystal layers in a liquid crystal display device which is driven by means of the IPS mode or the like. The structure of the liquid crystal display device which is driven by means of the VA mode is reported by K. Ohmura, S. Kataoka, T. Sasaki and Y. Koike, SID '97 Digest of Technical Papers, 28, 845 (1997), and the structure of the liquid crystal display device which is driven by means of the IPS mode is reported in WO 1991/10936 A (patent family: U.S. Pat. No. 5,576,867).

EXAMPLES

Examples of Compound (a)

The invention will be explained below in more detail based on examples. However, the invention is not limited to the examples. The term "%" means "% by weight", unless otherwise specified.

Since the compounds obtained were identified by means of nuclear magnetic resonance spectra obtained by using $^1$H-NMR analyses, gas chromatograms obtained by using gas chromatography (GC) analyses and so forth, methods for analyses will be explained at first.

$^1$H-NMR Analysis:

A model DRX-500 apparatus (made by Bruker BioSpin Corporation) was used for measurement. Samples prepared in examples and so forth were dissolved in deuterated solvents such as $CDCl_3$, in which the samples were soluble, and measurement was carried out under the conditions of room temperature, thirty two times of accumulation and 500 MHz. In the explanation of the nuclear magnetic resonance spectra obtained, symbols s, d, t, q, m and br stand for singlet, doublet, triplet, quartet, multiplet and broad, respectively. Tetramethylsilane (TMS) was used as a zero-point standard of chemical shifts δ.

GC Analysis:

A Gas Chromatograph Model GC-14B made by Shimadzu Corporation was used for measurement. A capillary column CBP1-M25-025 (length 25 m, bore 0.22 mm, film thickness 0.25 μm; dimethylpolysiloxane as a stationary phase; nonpolar) made by Shimadzu Corporation was used. Helium was used as a carrier gas, and its flow rate was adjusted to 1 ml per minute. The temperature of the sample injector was set at 280° C. and the temperature of the detector (FID) was set at 300° C.

A sample was dissolved in toluene, giving a 1% by weight solution, and then 1 microliter of the solution obtained was injected into the sample injector.

Chromatopac Model C-R6A made by Shimadzu Corporation or its equivalent was used as a recorder. The resulting gas chromatogram indicated the retention time of peaks and the values of peak areas corresponding to component compounds.

Chloroform or hexane, for example, may also be used as a solvent for diluting the sample. The following capillary columns may also be used: DB-1 (length 30 m, bore 0.32 mm, film thickness 0.25 μm) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd, and so forth.

The ratio of peak areas in the gas chromatogram corresponds to the ratio of component compounds. In general, the percentage by weight of each component compound in an analytical sample is not completely the same with the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used. This is because there is no significant difference among the correction coefficients of liquid crystal compounds as components. An internal standard method by use of gas chromatograms is employed in order to determine the composition ratio of the liquid crystal compounds in the liquid crystal composition more accurately by means of gas chromatograms. The component of each liquid crystal compound (test-component) weighed accurately in a fixed amount and a liquid crystal compound serving as a standard (standard reference material) are analyzed simultaneously by means of gas chromatography, and the relative intensity on the ratio of the peak area of the test-component to that of the standard reference material is calculated in advance. Next, the composition ratio of the liquid crystal compounds in the liquid crystal composition can be determined more accurately by means of the gas-chromatographic analysis using the correction based on the relative intensity of the peak area of each component to that of the standard reference material.

[Samples for Measuring Physical Properties of Compounds and so Forth]

Two kinds of samples were used for measuring the physical properties of compounds: one was a compound itself, and the other was a mixture of the compound and mother liquid crystals.

In the latter case using a sample in which a compound is mixed with mother liquid crystals, measurement is carried out according to the following method. First, the sample is prepared by mixing 15% by weight of the liquid crystal compound obtained and 85% by weight of the mother liquid crystals. Then, extrapolated values are calculated from the measured values of the resulting sample by means of an extrapolation method based on the following formula. The extrapolated values are regarded as the physical property-values of the compound.

<Extrapolated value>=(100×<Measured value of sample>−<% by weight of mother liquid crystals>×<Measured value of mother liquid crystals>)/<% by weight of liquid crystal compound>

When a smectic phase or crystals are deposited at even at this ratio of the liquid crystal compound to the mother liquid crystals at 25° C., the ratio of the compound to the mother liquid crystals is changed in the order of 10% by weight: 90% by weight, 5% by weight: 95% by weight, and 1% by weight: 99% by weight. The physical properties of a sample are measured using a composition ratio in which the smectic phase or the crystals are not deposited at 25° C. Extrapolated values are determined according to the above equation, and regarded as the values of the physical properties of the compound.

There are a variety of mother liquid crystals used for the measurement and, for example, the composition ratio of the mother liquid crystals (i) is as shown below.

Mother Liquid Crystals (i):

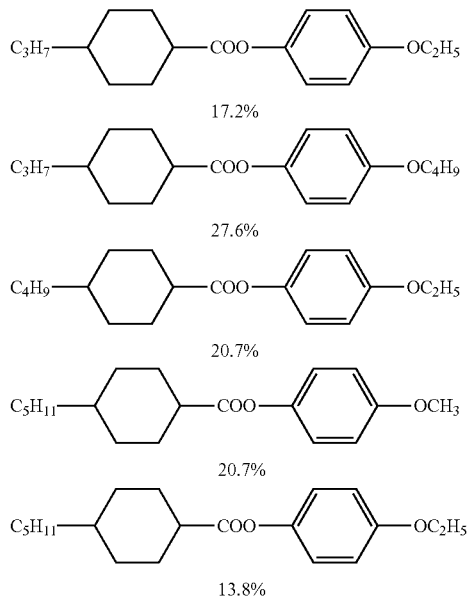

A liquid crystal composition itself was used as a sample for measuring the physical properties of the liquid crystal composition.

[Method for Measuring Physical Properties of Compounds and so Forth]

Physical properties were measured according to the following methods. Most methods are described in the Standards of Electronic Industries Association of Japan, EIAJ•ED 2521 A or those with some modifications. No TFT was attached to a TN device or a VA device used for measurement.

In the measured values, values obtained by use of a sample of a compound itself and values obtained by use of a sample of a liquid crystal composition itself, as they were, were reported herein as experimental data. When a sample in which a compound was mixed with mother liquid crystals was used, values calculated by means of extrapolation were reported herein as physical property values.

Phase Structure and Transition Temperature (° C.):

Measurement was carried out according to the following methods (1) and (2).

(1) A compound was placed on a hot plate of a melting point apparatus (Hot Stage Model FP-52 made by Mettler Toledo International Inc.) equipped with a polarizing microscope, and phase conditions and their changes were observed with the polarizing microscope, specifying the kinds of liquid crystal phases while the compound was heated at the rate of 3° C. per minute.

(2) A sample was heated and then cooled at a rate of 3° C. per minute by use of a Perkin-Elmer differential scanning calorimeter, a DSC-7 System or a Diamond DSC System. A starting point of an endothermic peak or an exothermic peak caused by a phase change of the sample was obtained by means of the extrapolation (on set) and the phase transition temperature was determined.

Hereinafter, the symbol C stood for crystals, which were expressed by $C_1$ or $C_2$ when the kinds of crystals were distinguishable. The symbols S and N stood for a smectic phase and a nematic phase, respectively. The symbol I stood for a liquid (isotropic). When a smectic B phase, or a smectic A phase was distinguishable in the smectic phases, they were expressed as SB, or SA, respectively. Transition temperatures were expressed, for example, as "C 50.0 N 100.0 I", which means that the transition temperature from crystals to a nematic phase (CN) is 50.0° C., and the transition temperature from the nematic phase to a liquid (NI) is 100.0° C. The same applied to other transition temperatures.

Maximum Temperature of Nematic Phase ($T_{NI}$; ° C.)

A sample (a liquid crystal composition, or a mixture of a compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. Maximum temperature meant a temperature measured when part of the sample began to change from a nematic phase to an isotropic liquid. Hereinafter, the maximum temperature of a nematic phase may simply be abbreviated to the "maximum temperature".

Compatibility at Low Temperature

Samples were prepared by mixing a compound with mother liquid crystals so that the amount of the compound became 20% by weight, 15% by weight, 10% by weight, 5% by weight, 3% by weight and 1% by weight, and placed in glass vials. After these glass vials had been kept in a freezer at −10° C. or −20° C. for a certain period, they were observed whether or not crystals or a smectic phase had been deposited.

Viscosity (Bulk Viscosity; η; 20° C. measurement; mPa·s)

Viscosity was measured by use of an E-type viscometer.

Rotational Viscosity (γ1; measured at 25° C.; mPa·s)

Measurement was carried out according to the method described in M. Imai, et al., Molecular Crystals and Liquid Crystals, Vol. 259, 37 (1995). A sample (a liquid crystal composition, or a mixture of a compound and mother liquid crystals) was put in a VA device in which a distance between two glass substrates (cell gap) was 20 μm. Voltage was applied to the device stepwise with an increment of 1 volt in the range of 30 to 50 volts. After 0.2 second of no voltage application, the voltage application was repeated with only one rectangular wave (rectangular pulse; 0.2 second) and no voltage application (2 seconds). The peak current and the peak time of a transient current generated by the voltage applied were measured. The value of rotational viscosity was obtained from the measured values and the calculating equation (8) in page 40 of the paper presented by M. Imai, et al. The value of dielectric anisotropy necessary for the calculation was available from the section on dielectric anisotropy described below.

Optical Anisotropy (Refractive Index Anisotropy; Measured at 25° C.; Δn)

Measurement was carried out by use of an Abbe refractometer with a polarizing plate attached to the ocular, on irradiation with light at a wavelength of 589 nm. The surface of a main prism was rubbed in one direction, and then a sample (a liquid crystal composition, or a mixture of a compound and mother liquid crystals) was dropped onto the main prism. A refractive index (η∥) was measured when the direction of polarized light was parallel to that of the rubbing. A refractive index (n⊥) was measured when the direction of polarized light was perpendicular to that of the rubbing. The value of optical anisotropy was calculated from the equation: Δn=n∥− n⊥.

Dielectric Anisotropy (Δ∈; measured at 25° C.)

Dielectric anisotropy was measured by the following method. A solution of octadecyltriethoxysilane (0.16 mL) in ethanol (20 mL) was applied to a thoroughly cleaned glass substrate. The glass substrate was rotated with a spinner, and then heated at 150° C. for one hour. A VA device in which a distance (cell gap) was 20 μm was assembled from the two glass substrates.

A polyimide alignment film was prepared on glass substrates in a similar manner. After a rubbing-treatment to the alignment film obtained on the glass substrates, a TN device in which a distance between the two glass substrates was 9 μm and the twist angle was 80 degrees was assembled.

A sample (a liquid crystal composition, or a mixture of a compound and mother liquid crystals) was put in the VA device obtained, a voltage of 0.5 V (1 kHz, sine waves) was applied, and then a dielectric constant (∈∥) in a major axis direction of the liquid crystal molecules was measured.

The sample (the liquid crystal composition, or the mixture of the compound and the mother liquid crystals) was put in the TN device obtained, a voltage of 0.5 V (1 kHz, sine waves) was applied, and then the dielectric constant (∈⊥) in a minor axis direction of liquid crystal molecules was measured. The value of dielectric anisotropy was calculated from the equation of Δ∈=∈∥–∈⊥.

Voltage Holding Ratio (VHR; measured at 25° C.; %)

A TN device used for measurement had a polyimide-alignment film and a distance between two glass substrates (cell gap) of 6 μm. A sample (a liquid crystal composition, or a mixture of a compound and mother liquid crystals) was put in the device, and then the device was sealed with an adhesive polymerizable under ultraviolet radiation. The TN device was charged by applying pulse voltage (60 microseconds at 5 V). Decaying voltage was measured for 16.7 milliseconds with a High Speed Voltmeter, and the area A between a voltage curve and a horizontal axis in a unit period was measured. The area B was an area without the decrease. The voltage holding ratio was the percentage of the area A to the area B.

Elastic Constant ($K_{11}$ and $K_{33}$; Measured at 25° C.)

Elastic Constant Measurement System Model EC-1 made by Toyo Corporation was used for measurement. A sample was put in a homeotropic cell in which a distance between two glass substrates (cell gap) was 20 μm. An electric charge of 20 volts to 0 volts was applied to the cell, and electrostatic capacity and applied voltage were measured. The measured values of the electrostatic capacity (C) and the applied voltage (V) were fitted to equation (2.98) and equation (2.101) in page 75 of the "Liquid Crystal Device Handbook" (Nikkan Kogyo Shimbun, Ltd.) and the value of the elastic constant was obtained from equation (2.100).

Example 1

Synthesis of 4-ethoxy-2,3-difluoro-4'-[2,3-difluoro-4-(4-pentylcyclohexyl)phenoxymethyl]-1,1'-biphenyl (No. 1123)

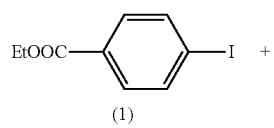

(1)

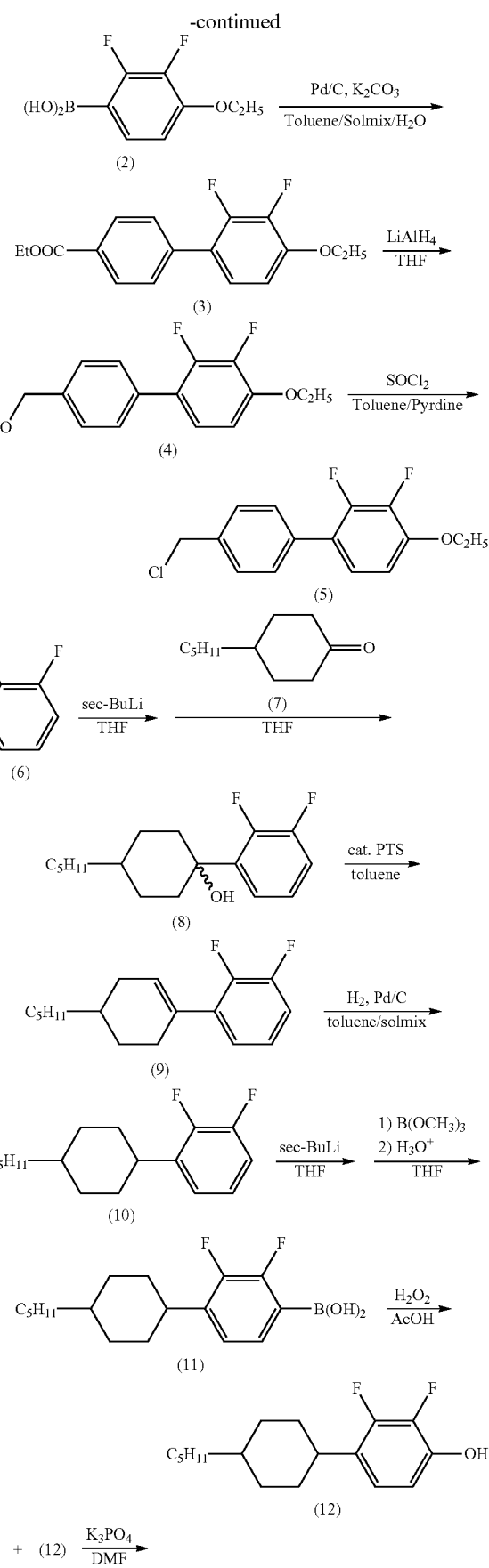

-continued

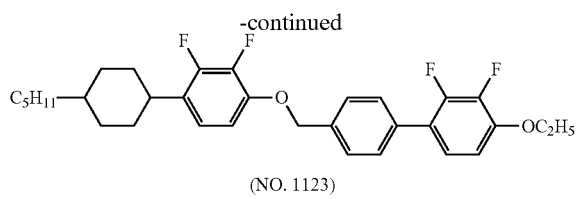

(NO. 1123)

First Step:

4-Iodoethyl benzoate (1) (25.0 g), 4-ethoxy-2,3-difluorophenylboronic acid (2) (20.1 g), potassium carbonate (25.0 g), palladium on carbon (NX type of 5% Pd/C; 50% wet; made by N. E. Chemcat; hereinafter referred to as Pd/C) (0.25 g), toluene (100 ml), ethanol (100 ml) and water (100 ml) were put in a reaction vessel under a nitrogen atmosphere, and heated under reflux for 2 hours. The reaction mixture was cooled to 25° C., and then poured into water (500 ml) and toluene (500 ml), and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The product was further purified by means of recrystallization from ethanol and dried, giving 18.8 g of ethyl 4-ethoxy-2,3-difluoro-4'-biphenylbenzoate (3). The yield based on the compound (1) was 67.9%.

Second Step:

Lithium aluminum hydride (1.4 g) was suspended in THF (100 ml). The compound (3) (18.8 g) was added dropwise to the suspension in the temperature range of −20° C. to −10° C., and the mixture was stirred in the same temperature range for 2 hours. After the termination of the reaction had been confirmed by means of GC analysis, ethyl acetate and a saturated aqueous solution of ammonia were sequentially added to the reaction mixture under ice-cooling, and deposits were removed by filtration through Celite. The filtrate was extracted in ethyl acetate. The obtained organic layer was washed sequentially with water and saturated brine, and then dried over anhydrous magnesium sulfate. The product was purified by means of recrystallization from heptane, dried, and concentrated under reduced pressure, giving 12.0 g of (4-ethoxy-2,3-difluoro-4'-biphenyl)methanol (4). The yield based on the compound (3) was 74.0%.

Third Step:

The compound (4) (12.0 g), toluene (50 ml) and pyridine (0.12 ml) were put in a reaction vessel under a nitrogen atmosphere, and stirred at 45° C. for 1 hour. Then, thionyl chloride (3.6 ml) was added in the temperature range of 45° C. to 55° C., and the mixture was heated under reflux for 2 hours. The reaction mixture was cooled to 25° C., then poured into water (200 ml) and toluene (200 ml), and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate twice and with water three times, and then dried over anhydrous magnesium sulfate. The solution obtained was concentrated under reduced pressure, and the residue obtained was purified with a fractional operation by means of column chromatography using a mixed solvent of toluene and heptane (toluene:heptane=1:1 by volume) as the eluent and silica gel as the stationary phase powder. The product was further purified by means of recrystallization from Solmix A-11 and dried, giving 9.4 g of 4'-chloromethyl-4-ethoxy-2,3-difluoro-biphenyl (5). The yield from the compound (4) was 73.2%.

Fourth Step:

1,2-Difluorobenzene (6) (100.0 g) and THF (500 ml) were put in a reaction vessel under a nitrogen atmosphere, and cooled to −74° C. sec-Butyllithium (1.00 M, in a n-hexane and cyclohexane solution; 876.5 ml) was added dropwise thereto in the temperature range of −74° C. to −70° C., and the mixture was stirred for another 2 hours. Then, 4-pentylcyclohexanone (7) (177.0 g) in a THF (200 ml) solution was added dropwise thereto in the temperature range of −75° C. to −70° C., and the stirring was continued for another 8 hours while the mixture was allowed to return to 25° C. The reaction mixture obtained was poured into a vessel containing an aqueous 1N-HCl solution (500 ml) and ethyl acetate (500 ml), and mixed. The mixture was then allowed to stand until it had separated into two phases of organic and aqueous phases, and extraction was carried out. The organic phase obtained was fractionated, washed sequentially with water, a saturated aqueous solution of sodium hydrogencarbonate and water, and then dried over anhydrous magnesium sulfate. The solvent was then distilled off under reduced pressure, giving 215.1 g of 4-pentyl(2,3-difluorophenyl)cyclohexanol (8). The compound (8) obtained was a yellow oil.

Fifth Step:

The compound (8) (215.1 g), p-toluenesulfonic acid (6.5 g) and toluene (500 ml) were mixed, and the mixture was heated under reflux for 2 hours while water being distilled was removed. The reaction mixture was cooled to 30° C., and then water (500 ml) and toluene (500 ml) were added thereto and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate and water, and then dried over anhydrous magnesium sulfate. The product obtained was purified with a fractional operation by means of column chromatography using heptane as the eluent and silica gel as the stationary phase powder, and dried, giving 186.6 g of 4-pentyl-(2,3-difluorophenyl)-cyclohexene (9). The yield based on the compound (8) was 92.7%.

Sixth Step:

The compound (9) (50.0 g) was dissolved in a mixed solvent of toluene (150 ml) and Solmix A-11 (150 ml), Pd/C (0.5 g) was added thereto, and the mixture was stirred at room temperature under a hydrogen atmosphere until hydrogen absorption had ceased. After the reaction had been completed, Pd/C was removed and then the solvent was distilled off. The residue obtained was purified with a fractional operation by means of column chromatography using heptane as the eluent and silica gel as the stationary phase powder, and further purified by means of recrystallization from Solmix A-11 and dried, giving 47.0 g of 4-pentyl-(2,3-difluorophenyl)cyclohexane (10). The yield based on the compound (9) was 94.0%.

Seventh Step:

4-Pentyl-(2,3-difluorophenyl)cyclohexane (10) (20.0 g) and THF (100 ml) were put in a reaction vessel under a nitrogen atmosphere, and cooled to −74° C. sec-Butyllithium (1.00 M, in a n-hexane and cyclohexane solution; 82.6 ml) was added dropwise thereto in the temperature range of −74° C. to −70° C., and the mixture was stirred for another 2 hours. Then, trimethyl borate (9.4 g) in a THF (50 ml) solution was added dropwise thereto in the temperature range of −74° C. to −65° C., and the stirring was continued for another 8 hours while the mixture was allowed to return to 25° C. Then, the reaction mixture was poured into a vessel containing 1N-hydrochloric acid (100 ml) and ice-water (500 ml), and mixed. Ethyl acetate (300 ml) was added thereto and the mixture was allowed to be separated into organic and aqueous phases, and extraction was carried out. The obtained organic layer was fractionated, washed sequentially with water, a saturated aqueous solution of sodium bicarbonate and brine, and then dried over anhydrous magnesium sulfate. The solvent was then distilled off under reduced pressure, giving 18.7 g of 2,3-difluoro-4-(4-propylcyclohexyl)-boronic acid (11). The yield based on the compound (10) was 80.3%.

Eighth Step:

The compound (11) (18.7 g) and acetic acid (100 ml) were put in a reaction vessel under a nitrogen atmosphere, and hydrogen peroxide (31% aqueous solution; 14.5 ml) was added dropwise in the temperature range of 25° C. to 30° C., and the mixture was stirred for another 2 hours at room temperature. Then, the reaction mixture was poured into a vessel containing an aqueous solution of sodium hydrogensulfite (100 ml) and ethyl acetate (300 ml), and the mixture was mixed. The mixture was then allowed to stand until it had separated into organic and aqueous phases, and extraction was carried out. The organic phase obtained was fractionated, washed sequentially with water and brine, and then dried over anhydrous magnesium sulfate. The solvent was distilled off under reduced pressure, giving 17.4 g of 2,3-difluoro-4-(4-propylcyclohexyl)phenol (12). The yield based on the compound (11) was 99.0%.

Ninth Step:

2,3-Difluoro-4-(4-propylcyclohexyl)phenol (12) (3.0 g) and tripotassium phosphate ($K_3PO_4$; 7.5 g) were added to DMF (100 ml) under a nitrogen atmosphere, and the mixture was stirred at 70° C. The compound (5) (2.0 g) was added thereto, and the mixture was stirred at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase was carried out. The organic phase obtained was fractionated, washed with brine, and then dried over anhydrous magnesium sulfate. The solvent was distilled off under reduced pressure, and the product obtained was purified with a fractional operation by means of column chromatography using a mixed solvent of heptane and toluene (heptane:toluene=1:2 by volume) as the eluent and silica gel as the stationary phase powder. The product was further purified by means of recrystallization from a mixed solvent of Solmix A-11 and heptane (Solmix A-11: heptane=1:2 by volume) and dried, giving 2.2 g of 4-ethoxy-2,3-difluoro-4'-[2,3-difluoro-4-(4-pentylcyclohexyl)phenoxymethyl]-1,1'-biphenyl (No. 1123). The yield based on the compound (5) was 42.5%.

The chemical shift δ (ppm) of $^1$H-NMR analysis was as follows, and the compound obtained was identified as 4-ethoxy-2,3-difluoro-4'-[2,3-difluoro-4-(4-pentylcyclohexyl)phenoxymethyl]-1,1'-biphenyl (No. 1123). The solvent for measurement was $CDCl_3$.

Chemical shift δ (ppm); 7.51 (dd, 4H), 7.09 (td, 1H), 6.84 (td, 1H), 6.80 (td, 1H), 6.73 (td, 1H), 5.15 (s, 2H), 4.16 (q, 2H), 2.74 (td, 1H), 1.88-1.80 (m, 4H), 1.49 (t, 3H), 1.44 (td, 2H), 1.35-1.18 (m, 9H), 1.11-1.01 (m, 2H) and 0.89 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 1123) were as follows.

Transition temperature: C 130.1 N 197.5 I.

$T_{NI}$=192.6° C., Δ∈=−7.40, Δn=0.207.

Example 2

Synthesis of trans-4-(2,3-difluoro-4-ethoxyphenyl)-4-[2,3-difluoro-4-(4-pentylcyclohexyl)phenoxymethyl]cyclohexane (No. 943)

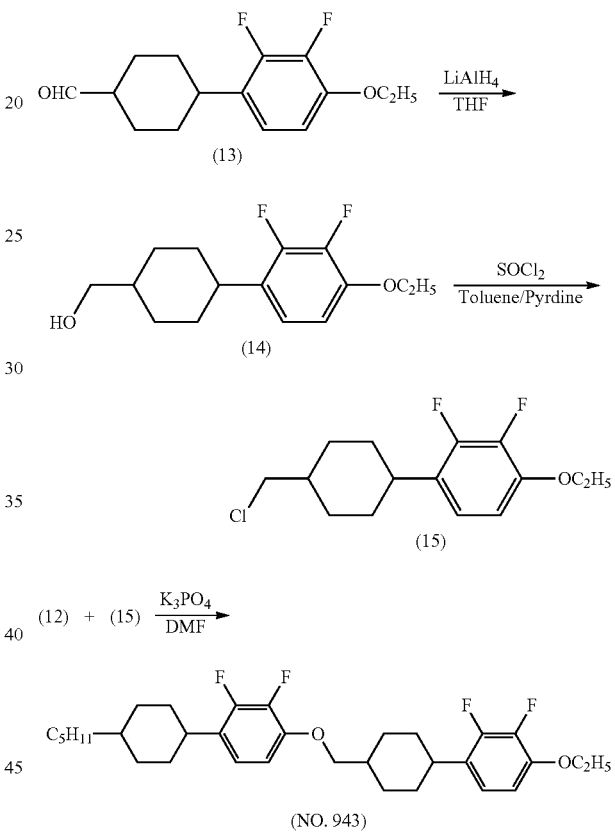

First Step:

Lithium aluminum hydride (4.2 g) was suspended in THF (300 ml). To this suspension, 4-(4-ethoxy-2,3-difluorophenyl)-cyclohexanecarboaldehyde (13) (50.0 g) was added dropwise in the temperature range of −20° C. to −10° C., and the mixture was stirred in this temperature range for another 2 hours. After the termination of the reaction had been confirmed by means of GC analysis, ethyl acetate and a saturated aqueous solution of ammonia were sequentially added to the reaction mixture under ice-cooling, and deposits were removed by filtration through Celite. The filtrate was extracted in ethyl acetate. The organic phase obtained was washed sequentially with water and saturated brine, and then dried over anhydrous magnesium sulfate. The organic phase was purified by means of recrystallization from heptane, dried and concentrated under reduced pressure, giving 47.6 g of 4-hydroxymethyl-(4-ethoxy-2,3-difluoro)cyclohexane (14). The yield based on the compound (13) was 94.5%.

Second Step:

The compound (14) (47.6 g), toluene (300 ml) and pyridine (0.5 ml) were put in a reaction vessel under a nitrogen atmosphere, and stirred at 45° C. for 1 hour. Then, thionyl chloride (14.0 ml) was added thereto in the temperature range of −45° C. to −55° C., and the mixture was heated under reflux for 2 hours. The reaction mixture was cooled to 25° C., and then poured into water (300 ml) and toluene (300 ml), and mixed. The mixture was then allowed to stand until it had separated into two phases of organic and aqueous phases, and extraction into an organic phase carried out. The organic phase obtained was fractionated, washed sequentially with a saturated aqueous solution of sodium hydrogencarbonate twice and with water three times, and then dried over anhydrous magnesium sulfate. The solution obtained was concentrated under reduced pressure, and the residue obtained was purified with a fractional operation by means of column chromatography using a mixed solvent of toluene and heptane (toluene:heptane=1:1 by volume) as the eluent and silica gel as the stationary phase powder, and further purified by means of recrystallization from Solmix A-11 and dried, giving 47.6 g of 4-chloromethyl-(4-ethoxy-2,3-difluorophenyl)-cyclohexane (15). The yield based on the compound (14) was 93.6%.

Third Step:

4-Ethoxy-2,3-difluorophenol (12) (2.4 g) and tripotassium phosphate ($K_3PO_4$; 7.4 g) were added to DMF (100 ml) under a nitrogen atmosphere, and the mixture was stirred at 70° C. Then, the compound (15) (2.0 g) was added thereto, and the mixture was stirred at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using a mixed solvent of heptane and toluene (heptane:toluene=1:2 by volume) as the eluent and silica gel as the stationary phase powder. The product was further purified by means of recrystallization from a mixed solvent of Solmix A-11 and heptane (Solmix A-11: heptane=1:2 by volume) and dried, giving 2.3 g of trans-4-(2,3-difluoro-4-ethoxyphenyl)-4-[2,3-difluoro-4-(4-pentylcyclohexyl)phenoxymethyl]cyclohexane (No. 943). The yield based on the compound (15) was 62.2%

The chemical shift δ (ppm) of $^1$H-NMR analysis was as follows, and the compound obtained was identified as trans-4-(2,3-difluoro-4-ethoxyphenyl)-4-[2,3-difluoro-4-(4-pentylcyclohexyl)phenoxymethyl]cyclohexane (No. 943). The solvent for measurement was $CDCl_3$.

Chemical shift δ (ppm); 6.84 (td, 2H), 6.67 (td, 2H), 4.09 (q, 2H), 3.85 (d, 2H), 2.80 (tt, 1H), 2.74 (tt, 1H), 2.03 (d, 2H), 1.96-1.81 (m, 7H), 1.56-1.38 (m, 7H), 1.36-1.18 (m, 11H), 1.12-1.02 (m, 2H), and 0.89 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 943) were as follows.

Transition temperature: C 101.8 N 204.0 I.
$T_{NI}$=187.3° C., Δ∈=−6.15, Δn=0.134.

Example 3

Synthesis of trans-4-(2,3-difluoro-4-ethoxyphenyl)-4-[2,3-difluoro-4'-butoxy-1,1'-biphenoxymethyl] cyclohexane (No. 1041)

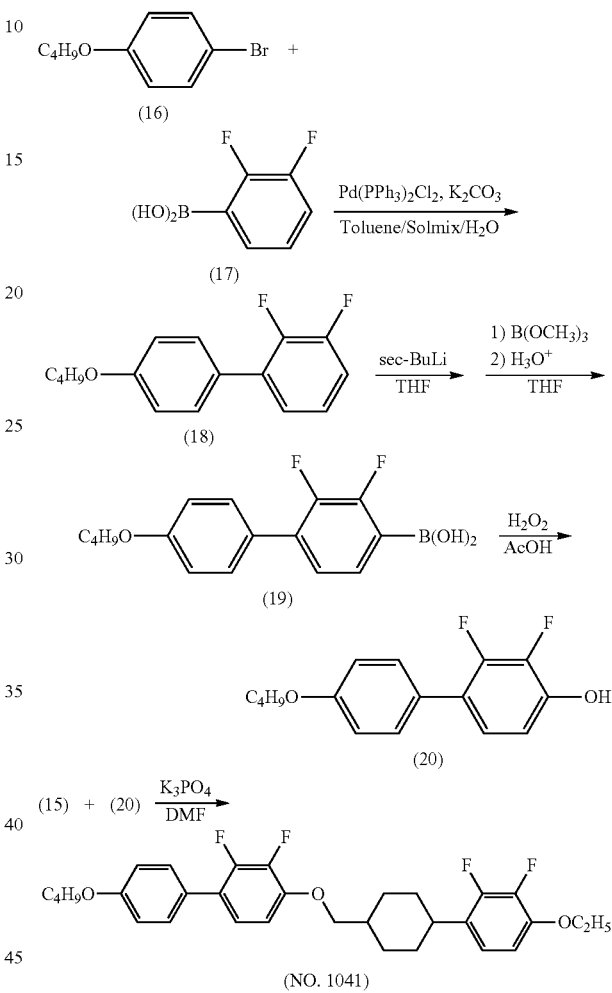

First Step:

4-Bromobutoxybenzene (16) (50.0 g), 2,3-difluorophenylboronic acid (17) (37.9 g), potassium carbonate (90.5 g), $Pd(Ph_3P)_2Cl_2$ (4.6 g), toluene (200 ml), Solmix A-11 (200 ml) and water (200 ml) were put in a reaction vessel under a nitrogen atmosphere, and heated under reflux for 2 hours. The reaction mixture was cooled to 25° C., and then poured into water (500 ml) and toluene (500 ml), and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The product was further purified by means of recrystallization from Solmix A-11 and dried, giving 44.7 g of 4'-butoxy-2,3-difluoro-1,1'-biphenyl (18). The yield based on the compound (16) was 78.1%.

Second Step:

4'-Butoxy-2,3-difluoro-1,1'-biphenyl (18) (20.0 g) and THF (200 ml) were put in a reaction vessel under a nitrogen atmosphere, and cooled to −74° C. sec-Butyllithium (1.00 M, in a n-hexane and cyclohexane solution; 83.9 ml) was added dropwise thereto in the temperature range of −74° C. to −70° C., and the mixture was stirred for another 2 hours. Then, trimethyl borate (9.5 g) in a THF (50 ml) solution was added dropwise thereto in the temperature range of −74° C. to −65° C., and the stirring was continued for another 8 hours while the mixture was allowed to return to 25° C. Then, the reaction mixture was poured into a vessel containing 1N-hydrochloric acid (100 ml) and ice-water (500 ml), and mixed. Ethyl acetate (300 ml) was added thereto and the mixture was allowed to be separated into organic and aqueous phases, and extraction into an organic phase was carried out. The obtained organic layer was fractionated, washed sequentially with water, a saturated aqueous solution of sodium bicarbonate and brine, and then dried over anhydrous magnesium sulfate. Then, the solvent was distilled off under reduced pressure, giving 21.3 g of 4'-butoxy-2,3-difluoro-1,1'-biphenyl-4-boronic acid (19). The yield based on the compound (18) was 91.3%.

Third Step:

The compound (19) (10.0 g) and acetic acid (50 ml) were put in a reaction vessel under a nitrogen atmosphere, hydrogen peroxide (31% aqueous solution; 4.5 ml) was added dropwise thereto in the temperature range of 25° C. to 30° C., and the mixture was stirred for another 2 hours at room temperature. Then, the reaction mixture was poured into a vessel containing an aqueous solution sodium hydrogensulfite (100 ml) and ethyl acetate (200 ml), and mixed. The mixture was then allowed to stand until it had separated into two phases of organic and aqueous phases, and extraction into an organic phase was carried out. The organic phase obtained was fractionated, washed sequentially with water and brine, and then dried over anhydrous magnesium sulfate. The solvent was distilled off under reduced pressure, giving 8.9 g of 4'-butoxy-4-hydroxy-2,3-difluoro-1,1'-biphenyl (20). The yield based on the compound (19) was 97.9%.

Fourth Step:

The compound (20) (2.3 g) and tripotassium phosphate ($K_3PO_4$; 7.4 g) were added to DMF (100 ml) under a nitrogen atmosphere, and the mixture was stirred at 70° C. The compound (15) (2.0 g) was added thereto, and the mixture was stirred at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase an extractive operation into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. The product was further purified by means of recrystallization from a mixed solvent of Solmix A-11 and ethyl acetate (Solmix A-11:ethyl acetate=2:1 by volume) and dried, giving 2.0 g of trans-4-(2,3-difluoro-4-ethoxyphenyl)-4-[2,3-difluoro-4'-butoxy-1,1'-biphenoxymethyl]cyclohexane (No. 1041). The yield based on the compound (15) was 54.4%.

The chemical shift δ (ppm) of $^1$H-NMR analysis was as follows, and the obtained compound was identified as trans-4-(2,3-difluoro-4-ethoxyphenyl)-4-[2,3-difluoro-4'-butoxy-1,1'-biphenoxymethyl]cyclohexane (No. 1041). The solvent for measurement was $CDCl_3$.

Chemical shift δ (ppm); 7.42 (d, 2H), 7.07 (td, 1H), 6.96 (d, 2H), 6.86 (td, 1H), 6.78 (td, 1H), 6.68 (td, 1H), 4.09 (q, 2H), 4.00 (t, 2H), 3.91 (d, 2H), 2.82 (tt, 1H), 2.07 (m, 2H), 1.94 (m, 3H), 1.79 (quint, 2H), 1.55-1.48 (m, 4H), 1.44 (t, 3H), 1.34-1.23 (m, 2H) and 0.99 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 1041) were as follows.

Transition temperature: C 124.4 N 223.8 I.

$T_{NI}$=202.6° C., Δ∈=−6.44, Δn=0.167.

Example 4

Synthesis of trans-4-(2,3-difluoro-4-ethoxyphenyl)-4-[2,3-difluoro-4-(4-butoxycyclohexenyl)phenoxymethyl]cyclohexane (No. 951)

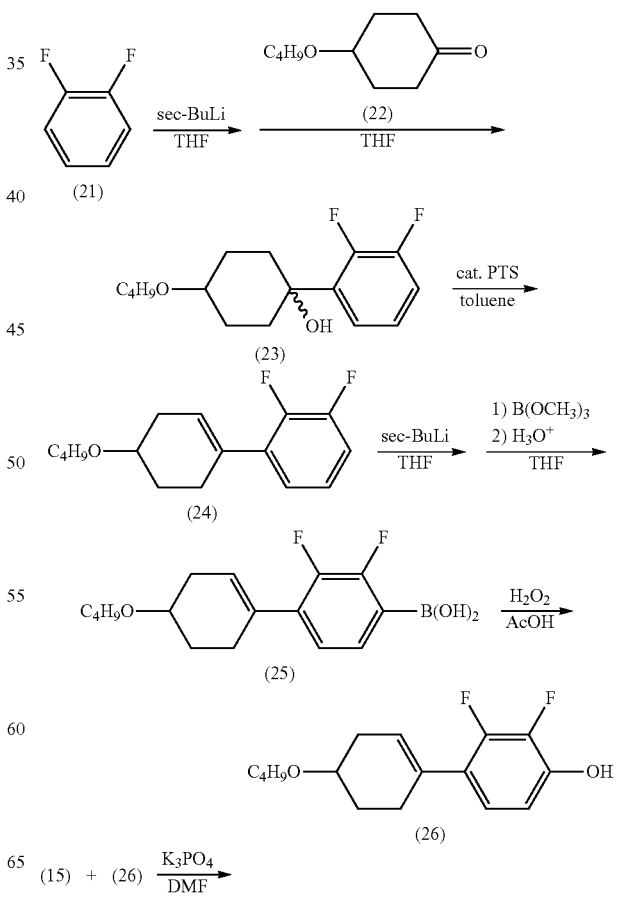

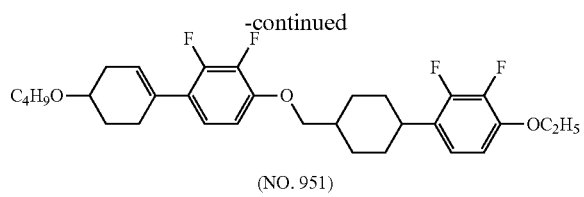

(NO. 951)

First Step:

1,2-Difluorobenzene (21) (57.0 g) and THF (1000 ml) were put in a reaction vessel under a nitrogen atmosphere, and cooled to −74° C. sec-Butyllithium (1.00 M, in a n-hexane and cyclohexane solution; 500.0 ml) was added dropwise thereto in the temperature range of −74° C. to −70° C., and the mixture was stirred for another 2 hours. Then, 4-butoxycyclohexanone (22) (85.1 g) in a THF (200 ml) solution was added dropwise thereto in the temperature range of −75° C. to −70° C., and the stirring was continued for another 8 hours while the mixture was allowed to return to 25° C. The reaction mixture obtained was poured into a vessel containing an aqueous 1N-HCl solution (500 ml) and ethyl acetate (500 ml), and mixed. The mixture was then allowed to stand until it had separated into organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. Then, the solvent was distilled off under reduced pressure, giving 130.1 g of 4-butoxy-(2,3-difluorophenyl)cyclohexanol (23). The obtained compound (23) was a yellow oil.

Second Step:

The compound (23) (130.1 g), p-toluenesulfonic acid (1.3 g) and toluene (500 ml) were mixed, and the mixture was heated under reflux for 2 hours while water being distilled was removed. The reaction mixture was cooled to 30° C., and then water (500 ml) and toluene (500 ml) were added thereto and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate and water, and then dried over anhydrous magnesium sulfate. The solution obtained was purified with a fractional operation by means of column chromatography using toluene as the eluent and silica gel as the stationary phase powder, and dried, giving 71.6 g of 4-butoxy-(2,3-difluorophenyl)cyclohexene (24). The compound (24) obtained was a colorless oil, having the boiling point at 131 to 132° C./3 mmHg, and the yield based on the compound (6) was 66.5%.

Third Step:

4-Butoxy-(2,3-difluorophenyl)cyclohexene (24) (11.0 g) and THF (200 ml) were put in a reaction vessel under a nitrogen atmosphere, and cooled to −74° C. sec-Butyllithium (1.00 M, in a n-hexane and cyclohexane solution; 50.0 ml) was added dropwise thereto in the temperature range of −74° C. to −70° C., and the mixture was stirred for another 2 hours. Then, trimethyl borate (5.2 g) in a THF (50 ml) solution was added dropwise thereto in the temperature range of −74° C. to −65° C., and the stirring was continued for another 8 hours while the mixture was allowed to return to 25° C. Then, the reaction mixture was poured into a vessel containing 1N-hydrochloric acid (100 ml) and ice-water (500 ml), and mixed. Then, ethyl acetate (300 ml) was added thereto and the mixture was allowed to be separated into organic and aqueous phases, and extraction into an organic phase was carried out. The obtained organic layer was fractionated, washed sequentially with water, a saturated aqueous solution of sodium bicarbonate and brine, and then dried over anhydrous magnesium sulfate. Then, the solvent was distilled off under reduced pressure, giving 10.7 g of 4-(4-butoxycyclohexenyl)-2,3-difluorophenylboronic acid (25). The yield based on the compound (24) was 83.6%.

Fourth Step:

The compound (25) (8.5 g) and acetic acid (50 ml) were put in a reaction vessel under a nitrogen atmosphere, hydrogen peroxide (31% aqueous solution; 4.9 ml) was added dropwise thereto in the temperature range of 25° C. to 30° C., and the mixture was stirred for 2 hours at room temperature. Then, the reaction mixture was poured into a vessel containing an aqueous solution of sodium hydrogensulfite (100 ml) and ethyl acetate (200 ml), and mixed. The mixture was then allowed to stand until it had separated into organic and aqueous phases, and extraction into an organic phase was carried out. The organic phase obtained was fractionated, washed sequentially with water and brine, and then dried over anhydrous magnesium sulfate. Then, the solvent is distilled off under reduced pressure, giving 2.8 g of 4-(4-butoxycyclohexenyl)-2,3-difluorophenol (26). The yield based on the compound (25) was 49.1%.

Fifth Step:

The compound (25) (2.8 g) and tripotassium phosphate ($K_3PO_4$; 7.4 g) were added to DMF (100 ml) under a nitrogen atmosphere, and the mixture was stirred at 70° C. The compound (15) (2.6 g) was added thereto, and the mixture was stirred at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. The product was further purified by means of recrystallization from a mixed solvent of Solmix A-11 and ethyl acetate (Solmix A-11:ethyl acetate=2:1 by volume) and dried, giving 1.6 g of trans-4-(2,3-difluoro-4-ethoxyphenyl)-4-[2,3-difluoro-4-(4-butoxycyclohexenyl)phenoxymethyl]cyclohexane (No. 951). The yield based on the compound (15) was 33.4%.

The chemical shift δ (ppm) of $^1$H-NMR analysis was as follows, and the compound obtained was identified as trans-4-(2,3-difluoro-4-ethoxyphenyl)-4-[2,3-difluoro-4-(4-butoxycyclohexenyl)phenoxymethyl]cyclohexane (No. 951). The solvent for measurement was $CDCl_3$.

Chemical shift δ (ppm); 6.89 (td, 1H), 6.85 (td, 1H), 6.68 (td, 1H), 6.67 (td, 1H), 5.82 (m, 1H), 4.09 (q, 2H), 3.86 (d, 2H), 3.62 (m, 1H), 3.51 (m, 2H), 2.81 (tt, 1H), 2.59-2.38 (m, 3H), 2.23-2.14 (m, 1H), 2.08-2.00 (m, 3H), 1.96-1.84 (m, 3H), 1.79-1.70 (m, 1H), 1.62-1.34 (m, 9H), 1.26 (qd, 2H) and 0.93 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 951) were as follows.

Transition temperature: C 96.0 N 158.4 I.

$T_{NI}$=147.9° C., Δ∈=−6.90, Δn=0.154.

Example 5

Synthesis of 2,3-difluoro-4-ethoxy-[trans-4-(4'-butoxy-2,3-difluoro-1,1'-biphenyl)cyclohexylmethyl]benzene (No. 3921)

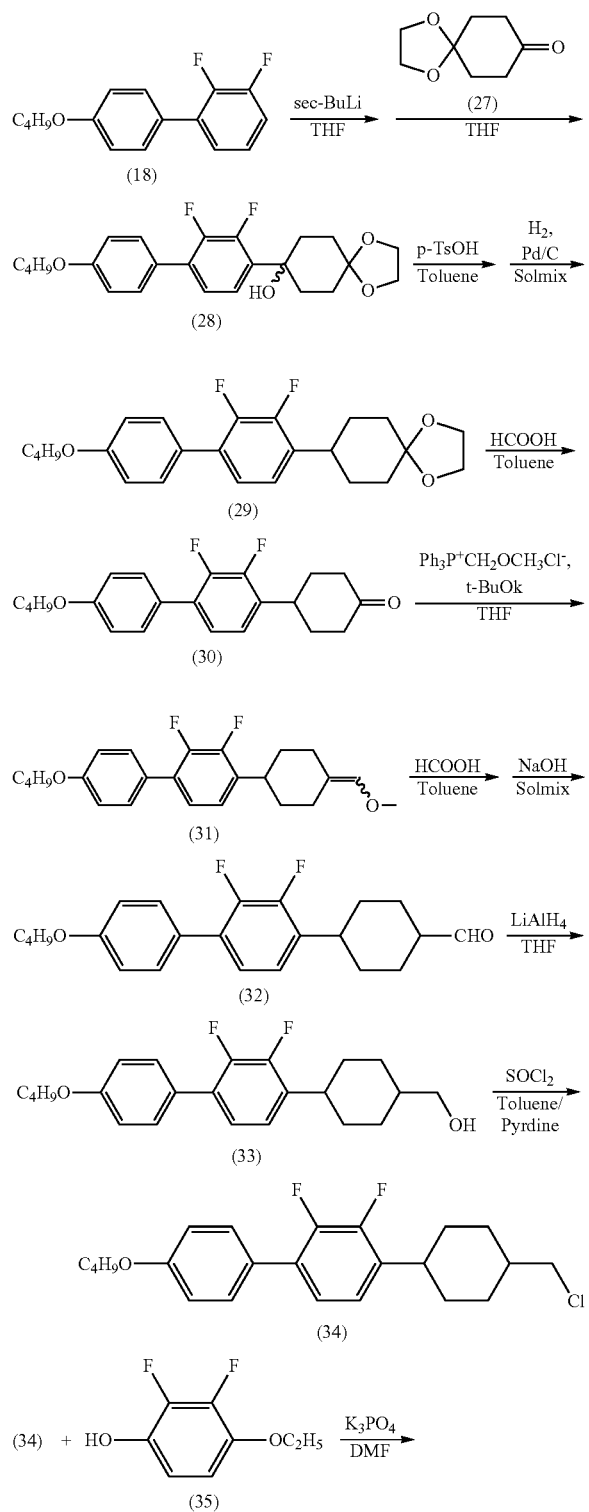

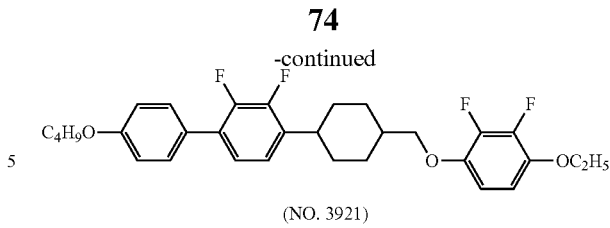

(NO. 3921)

First Step:

4'-Butoxy-2,3-difluoro-1,1'-biphenyl (18) (10.0 g) and THF (100 ml) were put in a reaction vessel under a nitrogen atmosphere, and cooled to −74° C. sec-Butyllithium (1.00 M, in a n-hexane and cyclohexane solution; 46.0 ml) was added dropwise thereto in the temperature range of −74° C. to −70° C., and the mixture was stirred for another 2 hours. 1,4-Dioxaspyro[4.5]decan-8-one (27) (6.0 g) dissolved in THF (150 ml) was slowly added dropwise thereto in the temperature range of −74° C. to −70° C., and the stirring was continued for another 8 hours while the mixture was allowed to return to 25° C. The reaction mixture obtained was poured into a vessel containing an aqueous solution of ammonium chloride (3%; 500 ml) and toluene (300 ml) which had been cooled to 0° C., and mixed. The mixture was then allowed to stand until it had separated into organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. Then, the solvent was distilled off under reduced pressure, giving 15.9 g of 8-(4'-butoxy-2,3-difluoro-1,1'-biphenyl)-1,4-dioxaspyro[4.5]decan-8-ol (28). The obtained compound (28) was a yellow oil.

Second Step:

The compound (28) (15.9 g), p-toluenesulfonic acid (0.49 g), ethylene glycol (0.81 g) and toluene (250 ml) were mixed, and the mixture was heated under reflux for 2 hours while water being distilled was removed. The reaction mixture was cooled to 30° C., and then water (200 ml) and toluene (300 ml) were added thereto, and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate and water, and then dried over anhydrous magnesium sulfate. The solution obtained was purified with a fractional operation by means of column chromatography using toluene as the eluent and silica gel as the stationary phase powder. The product was dissolved in a mixed solvent of toluene (150 ml) and Solmix A-11 (150 ml), Pd/C (0.15 g) was added thereto, and the mixture was stirred at room temperature under a hydrogen atmosphere until hydrogen absorption had ceased. After the reaction had been completed, Pd/C was removed and then the solvent was distilled off. The residue obtained was purified with a fractional operation by means of column chromatography using heptane as the eluent and silica gel as the stationary phase powder, and further purified by means of recrystallization from Solmix A-11, and dried, giving 10.6 g of 8-(4'-butoxy-2,3-difluoro-1,1'-biphenyl)-1,4-dioxaspyro[4.5]decane (29). The obtained compound (29) was a yellow oil.

Third Step:

The compound (29) (10.6 g), formic acid (87%; 20 ml) and toluene (200 ml) were mixed, and the mixture was heated under reflux for 2 hours. The reaction mixture was cooled to 30° C., and then water (200 ml) and toluene (300 ml) were added thereto and mixed. The mixture was then allowed to stand until it had separated into two phases of organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. The solvent was then distilled off under reduced pressure, and the residue obtained was purified with a fractional operation by means of column chromatography using toluene as the eluent and silica gel as the stationary phase powder. The product was further purified by means of recrystallization from heptane and dried, giving 6.6 g of 1-(4'-butoxy-2,3-difluoro-1,1'-biphenyl)-cyclohexan-4-one (30). The yield based on the compound (29) was 69.9%.

Fourth Step:

Well-dried methoxymethyltriphenylphosphonium chloride (7.6 g) and THF (100 ml) were mixed under a nitrogen atmosphere, and cooled to −30° C. Then, potassium t-butoxide (t-BuOK; 2.5 g) was put in thereto in twice in the temperature range of −30° C. to −20° C. After the mixture had been stirred at −20° C. for 30 minutes, the compound (29) (6.6 g) dissolved in THF (100 ml) was added dropwise thereto in the temperature range of −30° C. to −20° C. After the reaction mixture had been stirred at −10° C. for 30 minutes, it was poured into a mixture of water (200 ml) and toluene (200 ml), and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The eluent obtained was concentrated under reduced pressure, giving 6.6 g of 1-(4'-butoxy-2,3-difluoro-1,1'-biphenyl)-4-methoxymethylenecyclohexane (31). The yield based on the compound (30) was 92.7%.

Fifth Step:

The compound (31) (6.6 g), formic acid (87%; 8.0 g), and toluene (100 ml) were mixed, and the mixture was heated under reflux for 2 hours. The reaction mixture was cooled to 30° C., and then water (100 ml) and toluene (200 ml) were added thereto and mixed. The mixture was then allowed to stand until it had separated into two phases of organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. The solvent was distilled off under reduced pressure, giving a light yellow solid (6.3 g). This residue was dissolved in toluene (50 ml). The resultant solution was added to a mixture of sodium hydroxide (95%; 0.5 g) and Solmix A-11 (32 ml) which had been cooled to 7° C., and the mixture was stirred at 10° C. for another 2 hours. Then, an aqueous 2N-sodium hydroxide solution (12.8 ml) was added thereto, and the resultant mixture was stirred at 5° C. for another 2 hours. The reaction mixture obtained was poured into a mixture of water (200 ml) and toluene (200 ml), and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The solvent was distilled off under reduced pressure, and the residue obtained was concentrated. The residue was purified with a fractional operation by means of column chromatography using toluene as the fluent and silica gel as the stationary phase powder, and dried, giving 6.3 g of 1-(4'-butoxy-2,3-difluoro-1,1'-biphenyl)-cyclohexanecarboaldehyde (32). The yield based on the compound (31) was 99.1%.

Sixth Step:

Lithium aluminum hydride (0.4 g) was suspended in THF (300 ml). The compound (32) (6.4 g) was added dropwise to this suspension in the temperature range of −20° C. to −10° C., and the mixture was stirred in this temperature range for another 2 hours. After the termination of the reaction had been confirmed by means of GC analysis, ethyl acetate and a saturated aqueous solution of ammonia were sequentially added to the reaction mixture under ice-cooling, and deposits were removed by filtration through Celite. The filtrate was extracted in ethyl acetate. The organic phase obtained was washed sequentially with water and saturated brine, and then dried over anhydrous magnesium sulfate. The product was purified by means of recrystallization from heptane, dried and concentrated under reduced pressure, giving 5.9 g of 4-hydroxymethyl-(4'-butoxy-2,3-difluoro-1,1'-biphenyl)cyclohexane (33). The yield based on the compound (32) was 91.8%.

Seventh Step:

The compound (33) (5.9 g), toluene (100 ml) and pyridine (0.5 ml) were put in a reaction vessel under a nitrogen atmosphere, and the mixture was stirred at 45° C. for 1 hour. Then, thionyl chloride (1.4 ml) was added in the temperature range of 45° C. to 55° C., and heated under reflux for 2 hours. The reaction mixture was cooled to 25° C., and then poured into water (200 ml) and toluene (200 ml), and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate twice and with water three times, and then dried over anhydrous magnesium sulfate. The solution obtained was concentrated under reduced pressure, and the residue obtained was purified with a fractional operation by means of column chromatography using a mixed solvent of toluene and heptane (toluene:heptane=1:1 by volume) as the eluent and silica gel as the stationary phase powder. The product was further purified by means of recrystallization from Solmix A-11, and dried, giving 4.9 g of 4-chloromethyl-(4'-butoxy-2,3-difluoro-1,1'-biphenyl)-cyclohexane (34). The yield based on the compound (31) was 78.5%.

Eighth Step:

4-Ethoxy-2,3-difluorophenol (35) (0.96 g) and tripotassium phosphate ($K_3PO_4$; 7.4 g) were added to DMF (100 ml) under a nitrogen atmosphere, and the mixture was stirred at 70° C. The compound (34) (2.0 g) was added thereto and the mixture was stirred at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. The product was further purified by means of recrystallization from a mixed solvent of Solmix A-11 and ethyl acetate (Solmix A-11:ethyl acetate=2:1 by volume) and dried, giving 1.4 g of trans-4-(4-ethoxy-2,3- difluorophenyl)-4-[4'-butoxy-2,3-difluoro-1,1'-biphenoxymethyl]cyclohexane (No. 3921). The yield based on the compound (15) was 50.7%.

The chemical shift δ (ppm) of $^1$H-NMR analysis was as follows, and the compound obtained was identified as trans-4-(4-ethoxy-2,3-difluorophenyl)-4-[4'-butoxy-2,3-difluoro-1,1'-biphenoxymethyl]cyclohexane (No. 3921). The solvent for measurement was CDCl$_3$.

Chemical shift δ (ppm); 7.46 (d, 1H), 7.11 (t, 1H), 7.01 (t, 1H), 6.97 (d, 2H), 6.64 (m, 2H), 4.06 (q, 2H), 4.01 (t, 2H), 3.84 (d, 2H), 2.92 (tt, 1H), 2.10-2.03 (m, 2H), 2.03-1.87 (m, 3H), 1.79 (quint, 2H), 1.63-1.46 (m, 5H), 1.43 (t, 3H), 1.29 (qd, 2H) and 0.99 (t, 3H).

Measured values of the compound itself were used for the transition temperature, and values converted from the measured values of the sample, in which the compound was mixed with the mother liquid crystals (i), by means of the extrapolation method described above were used for the maximum temperature (T$_{NI}$), the dielectric anisotropy (Δ∈) and the optical anisotropy (Δn). The physical property values of the compound (No. 3921) were as follows.

Transition temperature: C$_1$ 85.4 C$_2$ 96.2 N 228.4 I.

T$_{NI}$=204.6° C., Δ∈=-6.93, Δn=0.217.

Example 6

Synthesis of 2,3-difluoro-4-ethoxy-[trans-4-{(trans-4-pentylcyclohexyl)-2,3-difluorophenyl}cyclohexylmethyl]benzene (No. 3823)

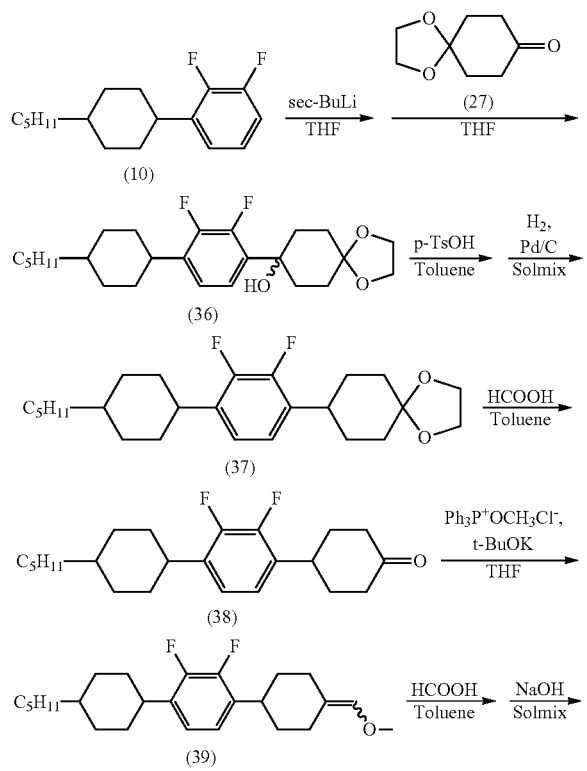

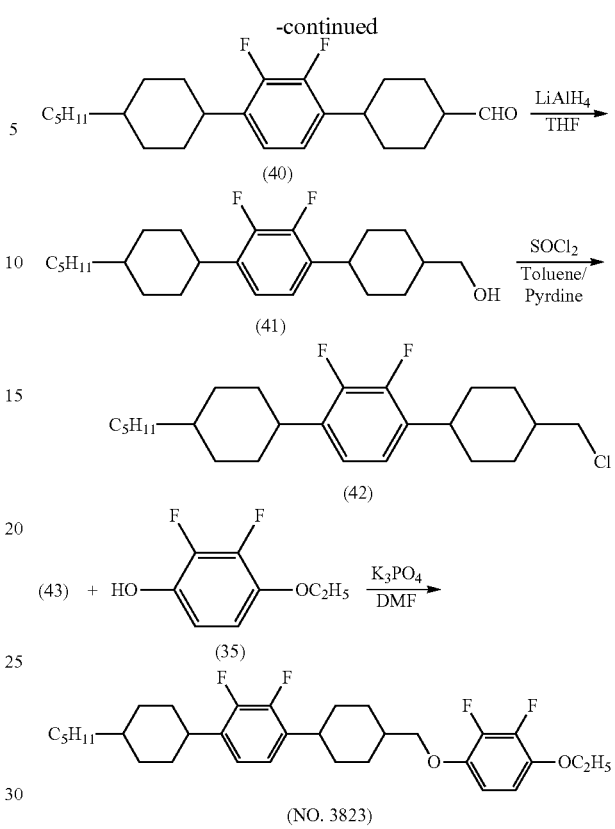

First Step:

4-Pentyl-(2,3-difluorophenyl)cyclohexane (10) (10.0 g) and THF (100 ml) were put in a reaction vessel under a nitrogen atmosphere, and cooled to −74° C. sec-Butyllithium (1.00 M, in a n-hexane and cyclohexane solution; 45.0 ml) was added dropwise thereto in the temperature range of −74° C. to −70° C., and the mixture was stirred for another 2 hours. 1,4-Dioxaspyro[4.5]decan-8-one (26) (5.9 g) dissolved in THF (150 ml) was slowly added dropwise thereto in the temperature range of −74° C. to −70° C., and the stirring was continued for another 8 hours while the mixture was allowed to return to 25° C. The reaction mixture obtained was poured into a vessel containing an aqueous solution of ammonium chloride (3%; 500 ml) and toluene (300 ml) which had been cooled to 0° C., and mixed. The mixture was then allowed to stand until it had separated into organic and aqueous phases, and extraction was carried out. The organic phase obtained was fractionated, washed sequentially with water, a saturated aqueous solution of sodium hydrogencarbonate and water, and then dried over anhydrous magnesium sulfate. Then, the solvent was distilled off under reduced pressure, giving 15.7 g of 8-[4-pentyl-(2,3-difluorophenyl)cyclohexyl]-1,4-dioxaspyro[4.5]decan-8-ol (36). The compound obtained (36) was a yellow oil.

Second Step:

The compound (36) (15.7 g), p-toluenesulfonic acid (0.47 g), ethylene glycol (0.79 g) and toluene (200 ml) were mixed, and the mixture was heated under reflux for 2 hours while water being distilled was removed. The reaction mixture was cooled to 30° C., and then water (200 ml) and toluene (300 ml) were added thereto and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate and water, and then dried over anhydrous magnesium sulfate. The solution obtained was purified with a fractional operation by means of column chromatography using toluene as the eluent and silica gel as the stationary phase powder. The product was dissolved in a mixed solvent of toluene (150 ml) and Solmix A-11 (150 ml), and Pd/C (0.16) was added thereto. The mixture was stirred at room temperature under a hydrogen atmosphere until hydrogen absorption had ceased. After the reaction had been completed, Pd/C was removed and then the solvent was distilled off. The residue obtained was purified with a fractional operation by means of column chromatography using heptane as the eluent and silica gel as the stationary phase powder. The product was further purified by means of recrystallization from Solmix A-11 and dried, giving 13.2 g of 8-[4-pentyl-(2,3-difluorophenyl)cyclohexyl]-1,4-dioxaspyro[4.5]decane (37). The yield based on the compound (36) was 87.8%.

Third Step:

The compound (37) (13.2 g), formic acid (87%; 15 ml) and toluene (100 ml) were mixed, and the mixture was heated under reflux for 2 hours. The reaction mixture was cooled to 30° C., and then water (200 ml) and toluene (300 ml) were added thereto and mixed. The mixture was then allowed to stand until it had separated into two phases of organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. The solvent was then distilled off under reduced pressure, and the residue obtained was purified with a fractional operation by means of column chromatography using toluene as the eluent and silica gel as the stationary phase powder. The product was further purified by means of recrystallization from heptane, giving 7.6 g of 1-[4-pentyl-(2,3-difluorophenyl)cyclohexyl]-cyclohexan-4-one (38). The yield based on the compound (37) was 64.6%.

Fourth Step:

Well-dried methoxymethyltriphenylphosphonium chloride (8.6 g) and THF (100 ml) were mixed under a nitrogen atmosphere, and cooled to −30° C. Then, potassium t-butoxide (t-BuOK; 2.8 g) was put in thereto in twice in the temperature range of −30° C. to −20° C. After the mixture had been stirred at −20° C. for 30 minutes, the compound (38) (7.6 g) dissolved in THF (100 ml) was added dropwise thereto in the temperature range of −30° C. to −20° C. After the reaction mixture had been stirred at −10° C. for 30 minutes, it was poured into a mixture of water (200 ml) and toluene (200 ml), and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The eluent obtained was concentrated under reduced pressure, giving 8.1 g of 1-[4-pentyl-(2,3-difluorophenyl)cyclohexyl]-4-methoxymethylenecyclohexane (39). The yield based on the compound (38) was 99.0%.

Fifth Step:

The compound (39) (8.1 g), formic acid (87%; 9.5 g) and toluene (100 ml) were mixed, and the mixture was heated under reflux for 2 hours. The reaction mixture was cooled to 30° C., and then water (100 ml) and toluene (200 ml) were added thereto and mixed. The mixture was then allowed to stand until it had separated into two phases of organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. The solvent was distilled off under reduced pressure, giving a white solid. This residue was dissolved in toluene (50 ml). The solution was added to a mixture of sodium hydroxide (95%; 0.5 g) and Solmix A-11 (32 ml) which had been cooled to 7° C., and the solution obtained was stirred at 10° C. for 2 hours. Then, an aqueous 2N-sodium hydroxide solution (16 ml) was added thereto, and the mixture was stirred at 5° C. for 2 hours. The reaction mixture obtained was poured into a mixture of water (200 ml) and toluene (200 ml), and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. Then, the solvent was distilled off under reduced pressure, and the residue obtained was concentrated, purified with a fractional operation by means of column chromatography using toluene as the eluent and silica gel as the stationary phase powder and dried, giving 7.5 g of 1-[4-pentyl-(2,3-difluorophenyl)cyclohexyl]-cyclohexanecarboaldehyde (40). The yield based on the compound (39) was 97.1%.

Sixth Step:

Lithium aluminum hydride (0.45 g) was suspended in THF (100 ml). The compound (40) (7.5 g) dissolved in THF (100 ml) was added dropwise to this suspension in the temperature range of −20° C. to −10° C., and the mixture was stirred in this temperature range for another 2 hours. After the termination of the reaction had been confirmed by GC analysis, ethyl acetate and a saturated aqueous solution of ammonia were sequentially added to the reaction mixture under ice-cooling, and deposits were removed by filtration through Celite. The filtrate was extracted in ethyl acetate. The organic phase obtained was washed sequentially with water and saturated brine, and then dried over anhydrous magnesium sulfate. Then, the product was purified by means of recrystallization from heptane, dried and concentrated under reduced pressure, giving 7.4 g of 4-hydroxymethyl-[4-pentyl-(2,3-difluorophenyl)cyclohexyl]-cyclohexane (41). The yield based on the compound (40) was 98.1%.

Seventh Step:

The compound (41) (7.4 g), toluene (100 ml) and pyridine (0.5 ml) were put in a reaction vessel under a nitrogen atmosphere, and the mixture was stirred at 45° C. for 1 hour. Then, thionyl chloride (1.7 ml) was added in the temperature range of 45° C. to 55° C., and the mixture was heated under reflux for 2 hours. The reaction mixture was cooled to 25° C., and then poured into water (200 ml) and toluene (200 ml), and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate twice and with water three times, and then dried over anhydrous magnesium sulfate. The solution obtained was concentrated under reduced pressure, and the residue obtained was purified with a fractional operation by means of column chromatography using heptane as the eluent and silica gel as the stationary phase powder, and dried, giving 7.3 g of 4-chloromethyl-[4-pentyl-(2,3-difluorophenyl)cyclohexyl]-cyclohexane (42). The yield based on the compound (41) was 94.1%.

Eighth Step:

4-Ethoxy-2,3-difluorophenol (34) (0.96 g) and tripotassium phosphate ($K_3PO_4$; 7.4 g) were added to DMF (100 ml) under a nitrogen atmosphere, and the mixture was stirred at 70° C. Then, the compound (41) (2.0 g) was added thereto and the mixture was stirred at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. The product was further purified by means of recrystallization from a mixed solvent of Solmix A-11 and ethyl acetate (Solmix A-11:ethyl acetate=2:1 by volume) and dried, giving 1.8 g of 2,3-difluoro-4-ethoxy-[trans-4-{(trans-4-pentylcyclohexyl)-2,3-difluorophenyl}cyclohexylmethyl]benzene (No. 3823). The yield based on the compound (42) was 65.3%.

The chemical shift δ (ppm) of $^1$H-NMR analysis was as follows, and the obtained compound was identified as 2,3-difluoro-4-ethoxy-[trans-4-{(trans-4-pentylcyclohexyl)-2,3-difluorophenyl}cyclohexylmethyl]benzene (No. 3823). The solvent for measurement was $CDCl_3$.

Chemical shift δ (ppm); 6.88 (m, 2H), 6.62 (m, 2H), 4.06 (q, 2H), 3.83 (d, 2H), 2.86 (tt, 1H), 2.79 (tt, 1H), 2.04 (m, 2H), 1.93 (m, 2H), 1.85 (m, 5H), 1.59-1.38 (m, 7H), 1.36-1.27 (m, 11H), 1.04 (m, 2H) and 0.89 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 3823) were as follows.

Transition temperature: $C_1$ 33.1 $C_2$ 91.5 N 209.3 I.
$T_{NI}$=179.3° C., Δ∈=−6.10, Δn=0.134.

Example 7

Synthesis of 4-ethoxy-2,3-difluoro-1,1'-biphenylbenzoic acid trans-4-pentylcyclohexyl-2,3-difluorophenyl ester (No. 1843)

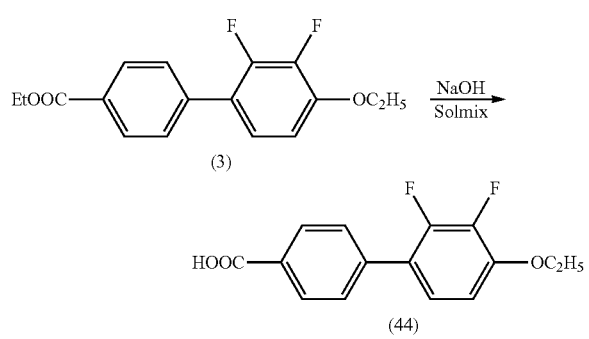

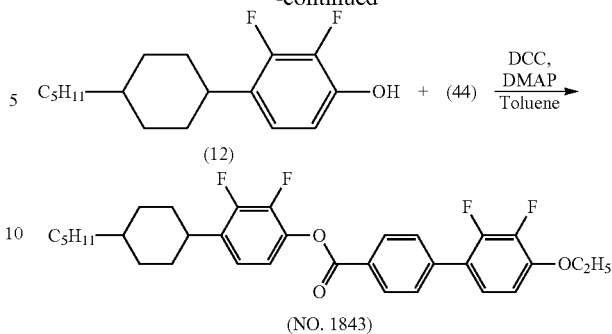

First Step:

The compounds (3) (29.1 g), sodium hydroxide (11.4 g), Solmix A-11 (100 ml) and water (100 ml) were mixed, and the mixture was heated under reflux for 2 hours. The reaction mixture was cooled to 30° C., and then aqueous 6N-hydrochloric acid solution (100 ml) and toluene (200 ml) were added hereto and mixed. The mixture was then allowed to stand until it had separated into two phases of organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate, giving 13.0 g of 4-ethoxy-2,3-difluoro-4'-biphenylbenzoic acid (44). The yield based on the compound (3) was 49.2%.

Second Step:

The compound (44) (1.97 g), 2,3-difluoro-4-(4-propylcyclohexyl)phenol (12) (2.0 g), 1,3-dicyclohexylcarbodiimide (DCC) (1.5 g) and 4-dimethylaminopyridine (DMAP) (0.09 g) were added to toluene (100 ml) under a nitrogen atmosphere, and the mixture was stirred at 25° C. for 20 hours. After the termination of the reaction had been confirmed by GC analysis, toluene (100 ml) and water (100 ml) were added thereto and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder. The product was further purified by means of recrystallization from a mixed solvent of heptane and THF (heptane:THF=2:1 by volume) and dried, giving 2.65 g of 4-ethoxy-2,3-difluoro-1,1'-biphenylbenzoic acid trans-4-pentylcyclohexyl-2,3-difluorophenyl ester (No. 1843). The yield based on the compound (12) was 69.0%.

The chemical shift δ (ppm) of $^1$H-NMR analysis was as follows, and the obtained compound was identified as 4-ethoxy-2,3-difluoro-1,1'-biphenylbenzoic acid trans-4-pentylcyclohexyl-2,3-difluorophenyl ester (No. 1843). The solvent for measurement was $CDCl_3$.

Chemical shift δ (ppm); 8.26 (d, 2H), 7.66 (d, 2H), 7.16 (td, 1H), 7.03 (td, 1H), 6.99 (td, 1H), 6.84 (td, 1H), 4.18 (q, 2H), 2.85 (tt, 1H), 1.89 (m, 4H), 1.53-1.43 (m, 5H), 1.37-1.19 (m, 9H), 1.14-1.04 (m, 2H) and 0.90 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy ($\Delta\varepsilon$) and the optical anisotropy ($\Delta n$). The physical property values of the compound (No. 1843) were as follows.

Transition temperature: C 90.9 N 304.5 I.
$T_{NI}$=247.9° C., $\Delta\varepsilon$=−5.82, $\Delta n$=0.227.

Example 8

Synthesis of trans-(4-ethoxy-2,3-difluorophenyl) cyclohexylbenzoic acid trans-4-pentylcyclohexyl-2,3-difluorophenyl ester (No. 1663)

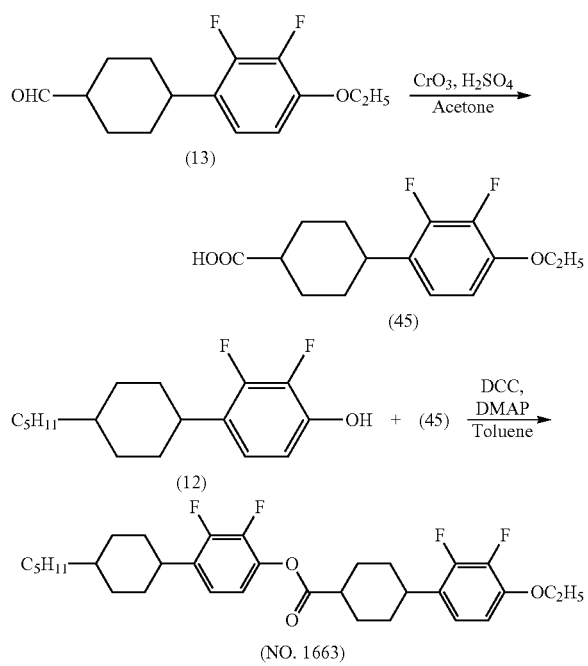

First Step:

The compound (13) (10.0 g) and acetone (50 ml) were mixed, and the mixture was stirred at 35° C. for 30 minutes. After the addition of the Jones reagent (8N, 4.7 ml) to this mixture in the temperature range of 30° C. to 40° C., the stirring was continued at 35° C. for another 2 hours. The reaction mixture was cooled to 30° C., and then toluene (200 ml) and water (200 ml) were added thereto and mixed. The mixture was then allowed to stand until it had separated into two phases of organic and aqueous phases, and extraction into an organic phase was carried out. The organic phase obtained was fractionated, washed sequentially with water, an aqueous solution of sodium thiosulfate and water, and then dried over anhydrous magnesium sulfate, giving 8.8 g of 4-ethoxy-2,3-difluoro-(trans-4-cyclohexyl)-carboxylic acid (45). The yield based on the compound (13) was 83.1%.

Second Step:

The compound (45) (1.0 g), 2,3-difluoro-4-(4-propylcyclohexyl)phenol (12) (1.0 g), 1,3-dicyclohexylcarbodiimide (DCC) (0.75 g) and 4-dimethylaminopyridine (DMAP) (0.04 g) were added to toluene (100 ml) under a nitrogen atmosphere, and the mixture was stirred at 25° C. for 20 hours. After the termination of the reaction had been confirmed by GC analysis, toluene (100 ml) and water (100 ml) were added thereto and mixed. The mixture was then allowed to stand until it had separated into two phases of organic and aqueous phases, and extraction into an organic phase was carried out. The organic phase obtained was fractionated, washed with water, and then dried over anhydrous magnesium sulfate. The obtained solution was concentrated under reduced pressure, and the residue was purified with a fractional operation by means of column chromatography using toluene as the eluent and silica gel as the stationary phase powder. The product was further purified by means of recrystallization from a mixed solvent of heptane and THF (heptane:THF=2:1 by volume) and dried, giving 1.39 g of trans-(4-ethoxy-2,3-difluorophenyl)cyclohexylbenzoic acid trans-4-pentylcyclohexyl-2,3-difluorophenyl ester (No. 1663). The yield based on the compound (12) was 71.5%.

The chemical shift δ (ppm) of $^1$H-NMR analysis was as follows, and the obtained compound was identified as trans-(4-ethoxy-2,3-difluorophenyl)cyclohexylbenzoic acid trans-4-pentylcyclohexyl-2,3-difluorophenyl ester (No. 1663). The solvent for measurement was $CDCl_3$.

Chemical shift δ (ppm); 6.88 (m, 2H), 6.62 (m, 2H), 4.06 (q, 2H), 3.83 (d, 2H), 2.86 (tt, 1H), 2.79 (tt, 1H), 2.04 (m, 2H), 1.93 (m, 2H), 1.85 (m, 5H), 1.59-1.38 (m, 7H), 1.36-1.27 (m, 11H), 1.04 (m, 2H) and 0.89 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy ($\Delta\varepsilon$) and the optical anisotropy ($\Delta n$). The physical property values of the compound (No. 1663) were as follows.

Transition temperature: C 92.6 N 289.4 I.
$T_{NI}$=219.9° C., $\Delta\varepsilon$=−7.37, $\Delta n$=0.140.

Example 9

Synthesis of 2-(4-(trans-4-(4-ethoxy-2,3-difluorophenyl)cyclohexyl)methoxy)-2,3-difluorophenyl)-5-pentyl-1,3-dioxane (No. 940)

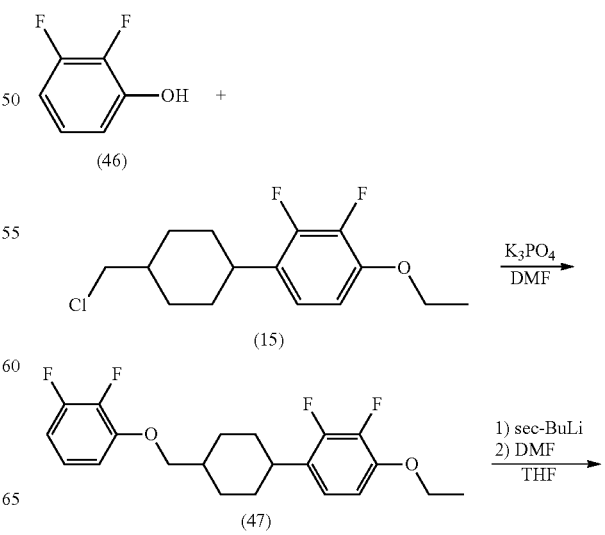

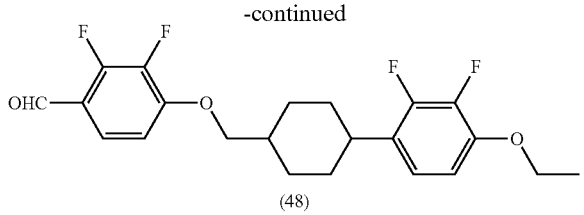

(48)

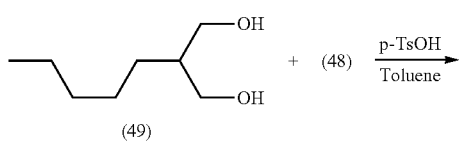

(49)

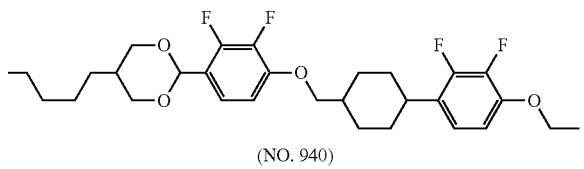

(NO. 940)

First Step:

2,3-Difluorophenol (46) (13.8 g) and tripotassium phosphate ($K_3PO_4$; 73.4 g) were added to DMF (200 ml) under a nitrogen atmosphere, and the mixture was stirred at 70° C. The compound (15) (20.0 g) was added thereto and the stirring was continued at 70° C. for 7 hours. After the reaction mixture obtained had been cooled to 30° C., solids were separated by filtration, and then toluene (100 ml) and water (100 ml) were added to and mixed with the filtrate. The mixture was then allowed to stand until it had separated into two phases of organic and aqueous phases, and extraction into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. The product was further purified by means of recrystallization from a mixed solvent of Solmix A-11 and ethyl acetate (Solmix A-11:ethyl acetate=2:1 by volume) and dried, giving 19.8 g of 2,3-difluoro-4-ethoxy-[trans-4-(2,3-difluorophenoxymethyl)cyclohexyl]benzene (47). The yield based on the compound (15) was 74.8%.

Second Step:

The compound (47) (18.1 g) and THF (200 ml) were put in a reaction vessel under a nitrogen atmosphere, and cooled to −74° C. sec-Butyllithium (1.00 M, in a n-hexane and cyclohexane solution; 52.1 ml) was added dropwise thereto in the temperature range of −74° C. to −70° C., and the mixture was stirred for another 2 hours. Then, DMF (3.8 g) dissolved in THF (150 ml) was slowly added dropwise in the temperature range of −74° C. to −70° C., and the stirring was continued for another 8 hours while the mixture was allowed to return to 25° C. The reaction mixture obtained was poured into a vessel containing an aqueous solution of ammonium chloride (3%; 300 ml) and toluene (200 ml) which had been cooled to 0° C., and mixed. The mixture was then allowed to stand until it had separated into organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. Then, the solvent was distilled off under reduced pressure, and the residue obtained was purified by means of recrystallization from a mixed solvent of THF and heptane (THF:heptane=1:5 by volume) and dried, giving 16.0 g of 2,3-difluoro-4-ethoxy-[trans-4-(2,3-difluorophenoxymethyl)cyclohexyl]benzaldehyde (48). The yield based on the compound (47) was 82.4%.

Third Step:

The compound (48) (3.0 g), 2-pentylpropane-1,3-diol (1.6 g), p-toluenesulfonic acid (0.02 g) and toluene (100 ml) were mixed, and the mixture was heated under reflux for 2 hours. The reaction mixture was cooled to 30° C., and then water (100 ml) and toluene (100 ml) were added thereto and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate and water, and then dried over anhydrous magnesium sulfate. The solution obtained was purified with a fractional operation by means of column chromatography using toluene as the eluent and silica gel as the stationary phase powder. Then, the solvent was distilled off under reduced pressure, and the residue obtained was further purified by means of recrystallization from a mixed solvent of THF and heptane (THF:heptane=1:5 by volume) and dried, giving 1.9 g of 2-(4-((trans-4-(4-ethoxy-2,3-difluorophenyl)cyclohexyl)methoxy)-2,3-difluorophenyl)-5-pentyl-1,3-dioxane (No. 940). The yield based on the compound (48) was 48.3%.

The chemical shift δ (ppm) of $^1$H-NMR analysis was as follows, and the compound obtained was identified as 2-(4-((trans-4-(4-ethoxy-2,3-difluorophenyl)cyclohexyl)methoxy)-2,3-difluorophenyl)-5-pentyl-1,3-dioxane (No. 940). The solvent for measurement was $CDCl_3$.

Chemical shift δ (ppm); 7.28 (m, 2H), 6.84 (t, 1H), 6.74 (t, 1H), 6.67 (t, 1H), 5.63 (s, 1H), 4.21 (dd, 2H), 4.12 (q, 2H), 3.88 (d, 2H), 3.54 (t, 2H), 2.80 (tt, 1H), 2.12 (m, 1H), 2.02 (m, 2H), 1.91 (m, 3H), 1.55-1.48 (m, 2H), 1.44 (t, 3H), 1.36-1.20 (m, 8H), 1.10 (m, 2H) and 0.89 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 940) were as follows.

Transition temperature: C 102.5 N 185.8 I.

$T_{NI}$=174.6° C., Δ∈=−3.69, Δn=0.137.

Example 10

Synthesis of 1-(4-(2,3-difluoro-4-(4-pentylcyclohexyl)phenyl)cyclohex-3-enyl)-4-ethoxy-2,3-difluorobenzene (No. 12)

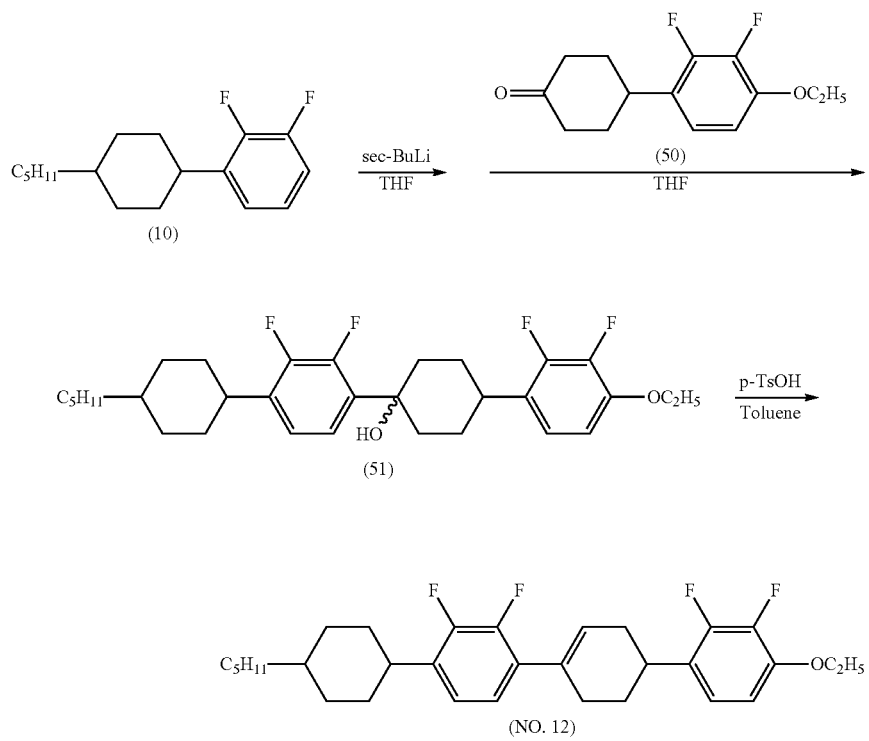

First Step:

4-Pentyl-(2,3-difluorophenyl)cyclohexane (10) (5.0 g) and THF (100 ml) were put in a reaction vessel under a nitrogen atmosphere, and cooled to −74° C. sec-Butyllithium (1.00 M, in a n-hexane and cyclohexane solution; 23.0 ml) was added dropwise thereto in the temperature range of −74° C. to −70° C., and the mixture was stirred for another 2 hours. 1-(4-Ethoxy-2,3-difluorophenyl)-cyclohexan-4-one (50) (4.8 g) dissolved in THF (150 ml) was slowly added dropwise thereto in the temperature range of −74° C. to −70° C., and the stirring was continued for another 8 hours while the mixture was allowed to return to 25° C. The reaction mixture obtained was poured into a vessel containing an aqueous solution of ammonium chloride (3%; 500 ml) and toluene (300 ml) which had been cooled to 0° C., and mixed. The mixture was then allowed to stand until it had separated into organic and aqueous phases, and extraction into an organic phase was carried out. The organic phase obtained was fractionated, washed sequentially with water, a saturated aqueous solution of sodium hydrogencarbonate and water, and then dried over anhydrous magnesium sulfate. Then, the solvent was distilled off under reduced pressure, giving 9.7 g of 1-(2,3-difluoro-4-(4-pentylcyclohexyl)phenyl)-4-(4-ethoxy-2,3-difluorophenyl)cyclohexanol (51). The compound (51) obtained was a yellow solid.

Second Step:

The compound (51) (9.7 g), p-toluenesulfonic acid (0.15 g) and toluene (200 ml) were mixed, and the mixture was heated under reflux for 2 hours while water being distilled was removed. The reaction mixture was cooled to 30° C., and then water (200 ml) and toluene (300 ml) were added thereto and mixed. The mixture was then allowed to stand until it had separated into two phases of organic and aqueous phases, and extraction into an organic phase was carried out. The organic phase obtained was fractionated, washed sequentially with a saturated aqueous solution of sodium hydrogencarbonate and water, and then dried over anhydrous magnesium sulfate. The solution obtained was purified with a fractional operation by means of column chromatography using a mixed solvent of heptane and toluene (heptane:toluene=2:3 by volume) as the eluent and silica gel as the stationary phase powder. The solvent was distilled off, and the residue obtained was purified with a fractional operation by means of column chromatography using toluene as the eluent and silica gel as the stationary phase powder. The product was further purified by means of recrystallization from a mixed solvent of Solmix A-11 and ethyl acetate (Solmix A-11:ethyl acetate=2:1 by volume) and dried, giving 4.7 g of 1-(4-(2,3-difluoro-4-(4-pentylcyclohexyl)phenyl)cyclohex-3-enyl)-4-ethoxy-2,3-difluorobenzene (No. 12). The yield based on the compound (10) was 49.8%.

The chemical shift δ (ppm) of $^1$H-NMR analysis was as follows, and the obtained compound was identified as 1-(4-(2,3-difluoro-4-(4-pentylcyclohexyl)phenyl)cyclohex-3-enyl)-4-ethoxy-2,3-difluorobenzene (No. 12). The solvent for measurement was $CDCl_3$.

Chemical shift δ (ppm); 6.98-6.88 (m, 3H), 6.70 (t, 1H), 6.02 (m, 1H), 4.11 (q, 2H), 3.20 (m, 1H), 2.82 (tt, 1H), 2.65-2.40 (m, 3H), 2.36-2.27 (m, 1H), 2.05-2.00 (m, 1H), 2.00-1.84 (m, 5H), 1.55-1.42 (m, 5H), 1.38-1.20 (m, 9H), 1.14-1.03 (m, 2H) and 0.90 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 12) were as follows.

Transition temperature: C 83.1 N 218.4 I.

$T_{NI}$=184.6° C., Δ∈=−6.46, Δn=0.140.

Example 11

Synthesis of 1-(4-(2,3-difluoro-4-(4-pentylcyclohexyl)phenyl)cyclohexyl)-4-ethoxy-2,3-difluorobenzene (No. 13)

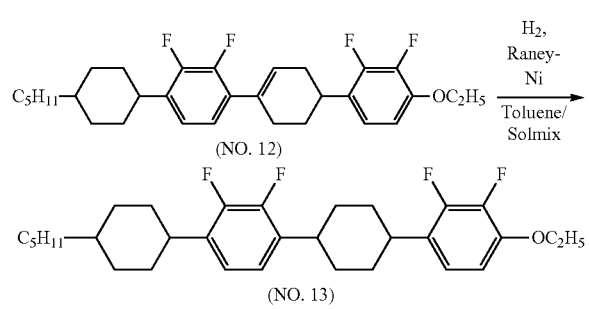

First Step:

The compound (No. 832) (3.5 g) was dissolved in a mixed solvent of toluene (150 ml) and Solmix A-11 (150 ml). Raney nickel (0.35 g) was added thereto, and the mixture was stirred at room temperature under a hydrogen atmosphere until hydrogen absorption had ceased. After the reaction had been completed, Raney nickel was removed and the solvent was distilled off. The residue obtained was purified with a fractional operation by means of column chromatography using a mixed solvent of heptane and toluene (heptane:toluene=2:3 by volume) as the eluent and silica gel as the stationary phase powder, and further purified by means of recrystallization from a mixed solvent of ethyl acetate and Solmix A-11 (ethyl acetate: Solmix A-11=1:2 by volume) and dried, giving 3.1 g of 1-(4-(2,3-difluoro-4-(4-pentylcyclohexyl)phenyl)cyclohexyl)-4-ethoxy-2,3-difluorobenzene (No. 13). The yield based on the compound (No. 12) was 85.4%.

The chemical shift δ (ppm) of $^1$H-NMR analysis was as follows, and the compound obtained was identified as 1-(4-(2,3-difluoro-4-(4-pentylcyclohexyl)phenyl)cyclohexyl)-4-ethoxy-2,3-difluorobenzene (No. 13). The solvent for measurement was $CDCl_3$.

Chemical shift δ (ppm); 6.96-6.86 (m, 3H), 6.70 (t, 1H), 4.10 (q, 2H), 2.97-2.85 (m, 2H), 2.80 (tt, 1H), 1.98 (d, 4H), 1.86 (d, 4H), 1.65 (m, 4H), 1.53-1.41 (m, 5H), 1.36-1.18 (m, 9H), 1.13-1.02 (m, 2H) and 0.89 (t, 3H).

Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). The physical property values of the compound (No. 13) were as follows.

Transition temperature: C 144.9 N 263.2 I.
$T_{NI}$=191.6° C., ∈Δ=−4.22, Δn=0.137

Example 12

The compounds No. 1 to No. 4890 shown below can be synthesized by synthetic methods similar to those described in Examples 1 to 11. Attached data were measured in accordance with the methods described above. Measured values of the compound itself were used for the transition temperature, and values converted from the measured values of the sample, in which the compound was mixed with the mother liquid crystals (i), by means of the extrapolation method described above were used for the maximum temperature ($T_{NI}$), the dielectric anisotropy (Δ∈) and the optical anisotropy (Δn). Incidentally, the values for the compounds No. 940, No. 951, No. 1041 and No. 1123 were obtained by preparing liquid crystal compositions consisting of 95% by weight of the mother liquid crystals and 5% by weight of each of the compounds, and by measuring the physical properties of the compositions obtained and by extrapolating the measured values. The values for the compounds No. 13 and No. 3921 were obtained by preparing liquid crystal compositions consisting of 90% by weight of the mother liquid crystals and 10% by weight of each of the compounds, and by measuring the physical properties of the compositions obtained, and by extrapolating the measured values. The values of the compounds No. 12, No. 943, No. 1663, No. 1843 and No. 3823 were obtained by preparing liquid crystal compositions consisting of 85% by weight of the mother liquid crystals and 15% by weight of each of the compounds, and by measuring the physical properties of the compositions obtained, and by extrapolating the measured values.

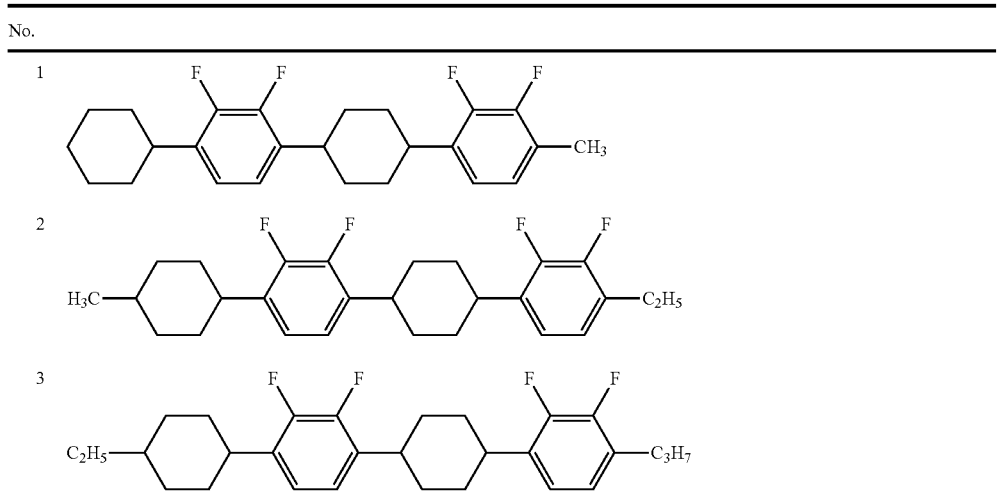

| No. | |
|---|---|
| 4 | 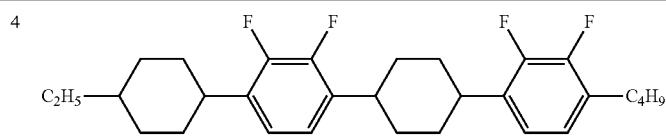 |
| 5 | 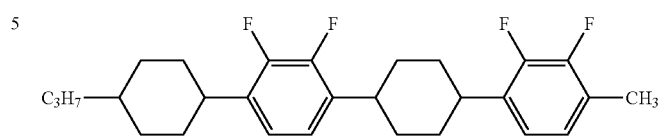 |
| 6 | 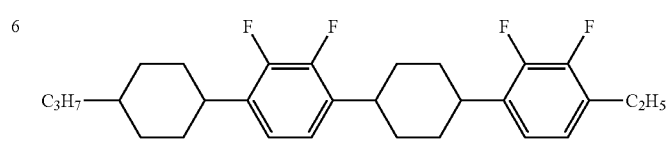 |
| 7 | 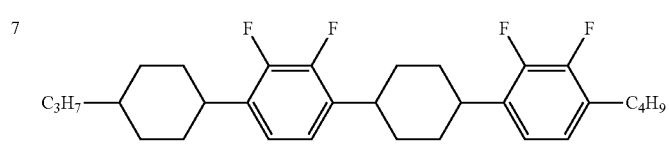 |
| 8 | 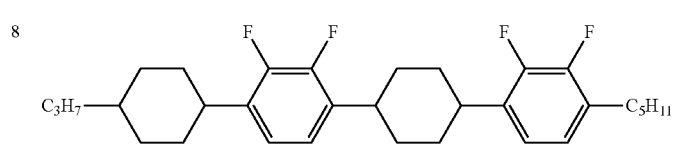 |
| 9 | 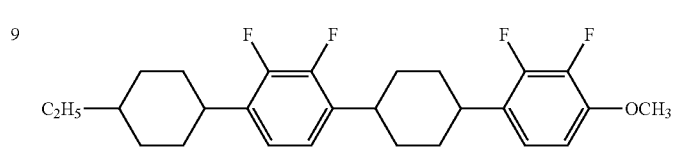 |
| 10 | 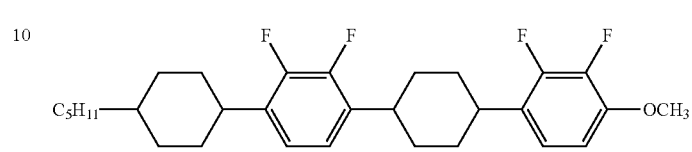 |
| 11 | 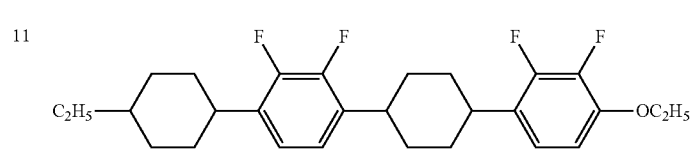 |
| 12 | 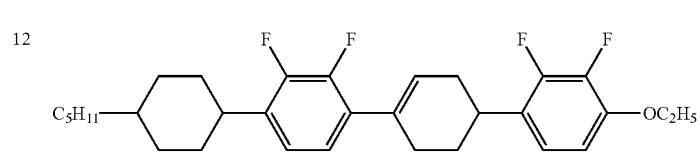 |
| | C 83.1 N 218.4 I<br>$T_{NI}$; 184.6° C., $\Delta\epsilon$; −6.46, $\Delta n$; 0.140 |
| 13 | 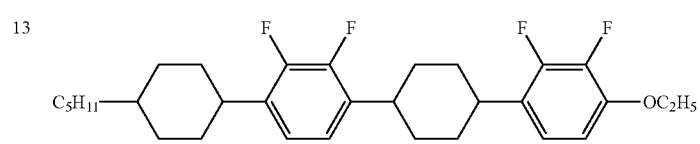 |
| | C 144.9 N 263.2 I<br>$T_{NI}$; 191.6° C., $\Delta\epsilon$; −4.22, $\Delta n$; 0.137 |

| No. | |
|---|---|
| 14 | 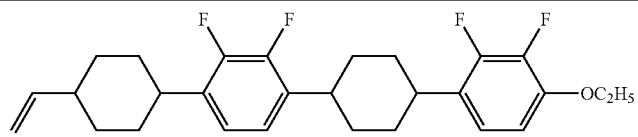 |
| 15 | 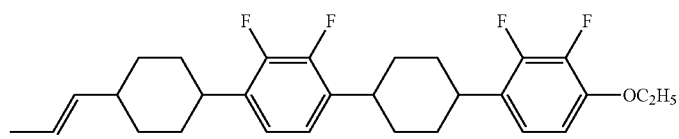 |
| 16 | 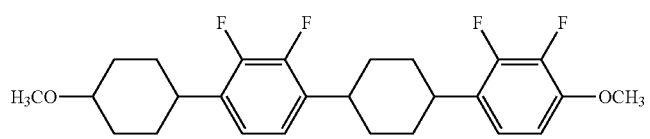 [SMILES: COc1ccc(C2CCC(c3ccc(C4CCC(OC)CC4)c(F)c3F)CC2)c(F)c1F] |
| 17 | 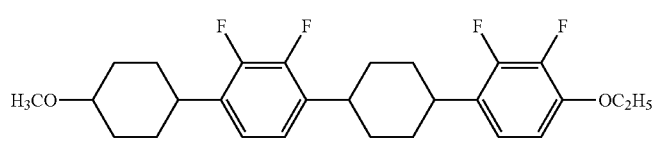 |
| 18 | 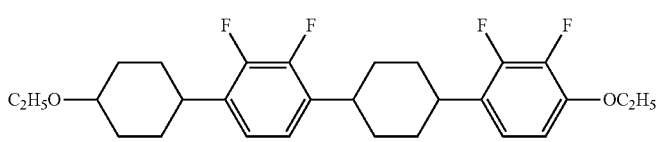 |
| 19 | 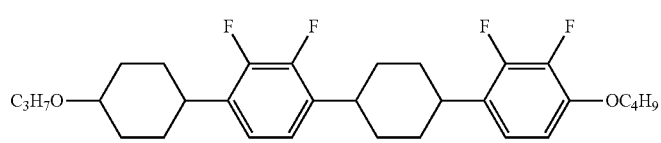 |
| 20 | 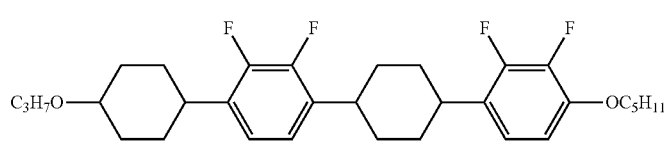 |
| 21 | 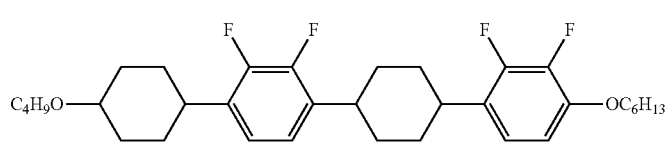 |
| 22 | 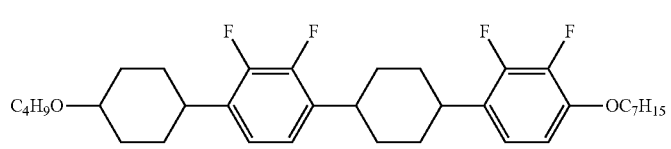 |
| 23 | 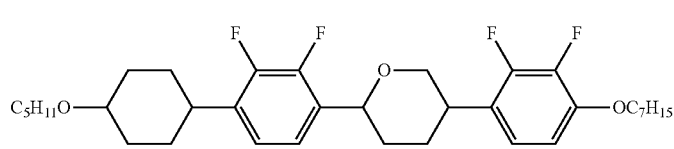 |
| 24 | 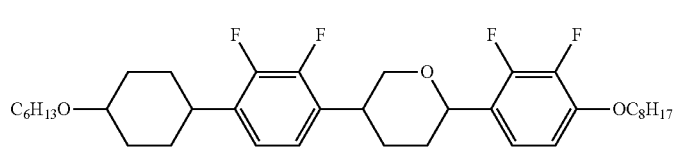 |

| No. | |
|---|---|
| 25 | 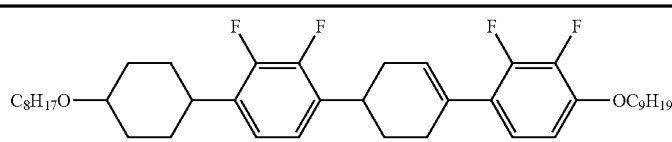 |
| 26 | 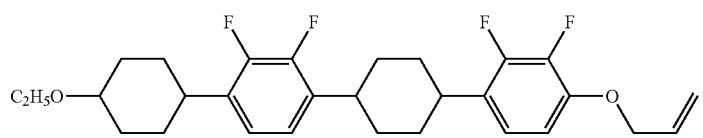 |
| 27 | 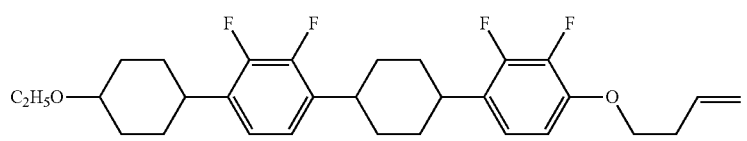 |
| 28 | 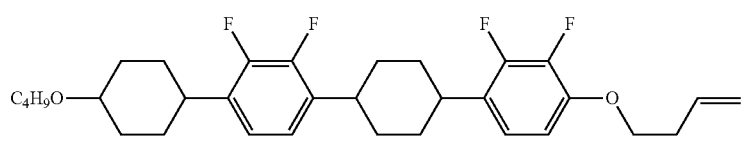 |
| 29 | 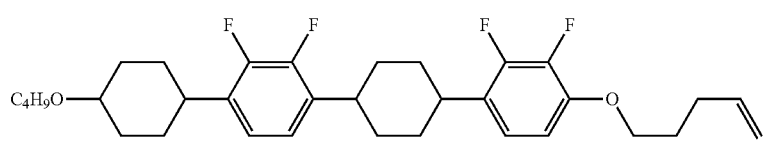 |
| 30 | 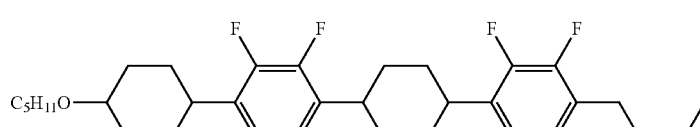 |
| 31 | 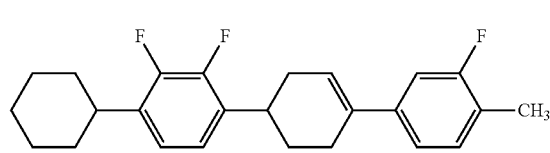 |
| 32 | 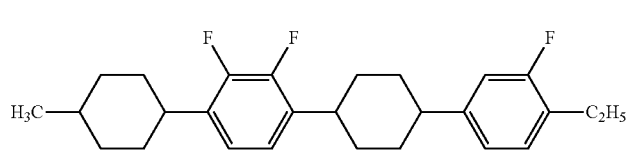 |
| 33 | 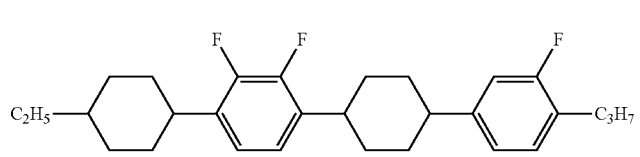 |
| 34 | 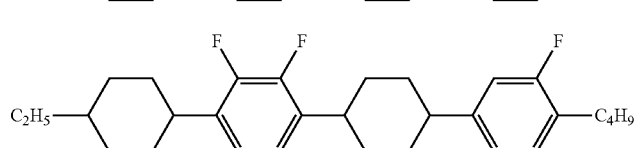 |
| 35 | 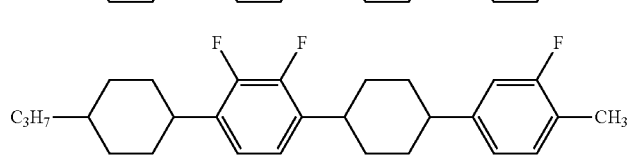 |

| No. | |
|---|---|
| 36 | 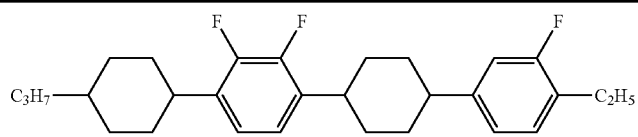 |
| 37 | 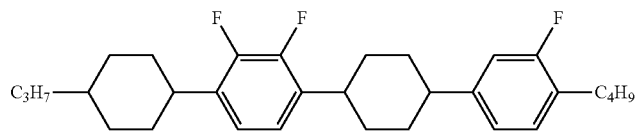 |
| 38 | 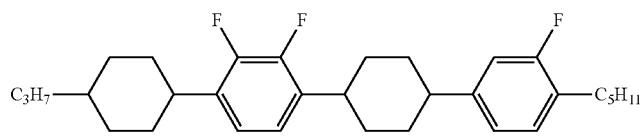 |
| 39 | 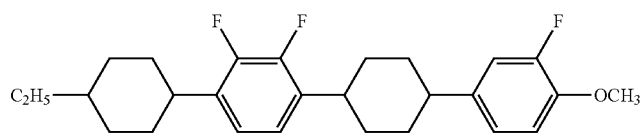 [SMILES: CCC1CCC(c2ccc(C3CCC(c4ccc(OC)c(F)c4)CC3)c(F)c2F)CC1] |
| 40 | 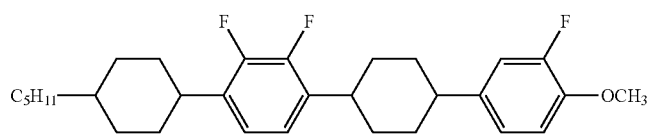 |
| 41 | 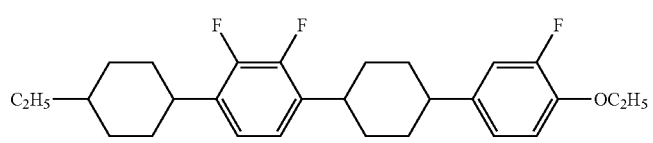 [SMILES: CCOc1ccc(C2CCC(c3ccc(C4CCC(CC)CC4)c(F)c3F)CC2)cc1F] |
| 42 | 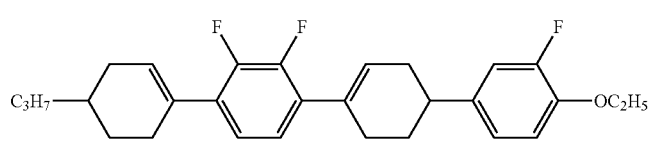 |
| 43 | 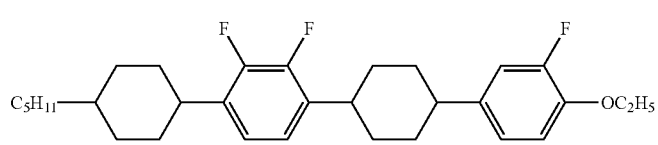 |
| 44 | 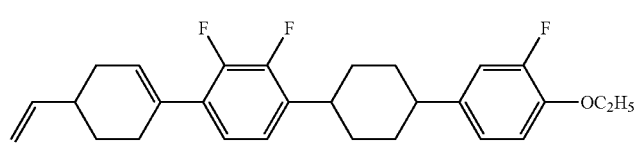 [SMILES: C=CC1CC=C(c2ccc(C3CCC(c4ccc(OCC)c(F)c4)CC3)c(F)c2F)CC1] |
| 45 | 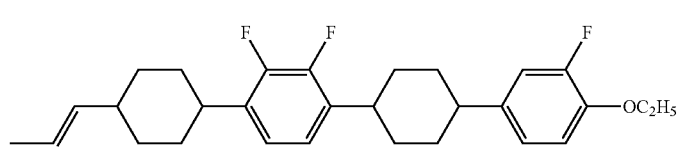 |
| 46 | 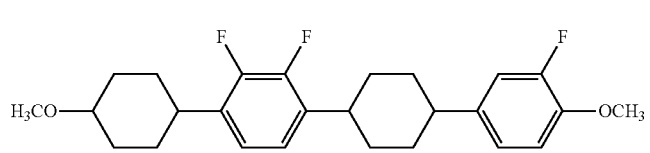 |

| No. |
|---|
| 47 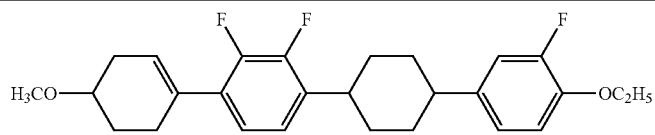 |
| 48 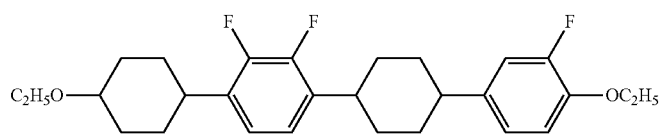 |
| 49 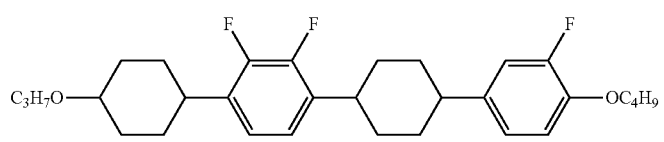 |
| 50 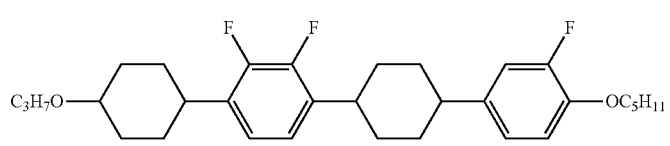 |
| 51 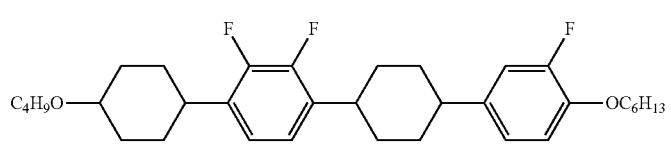 |
| 52 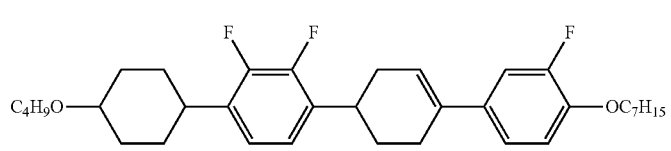 |
| 53 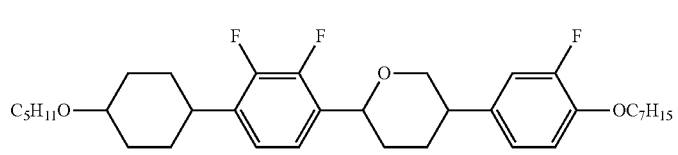 |
| 54 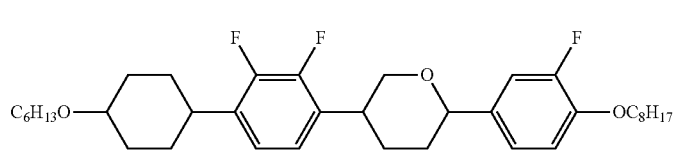 |
| 55 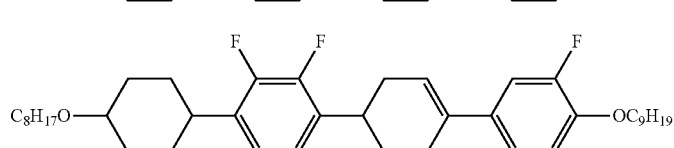 |
| 56 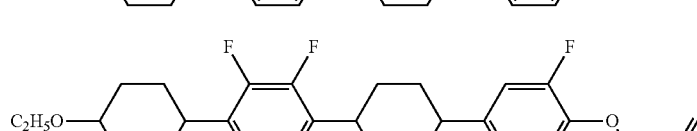 |
| 57 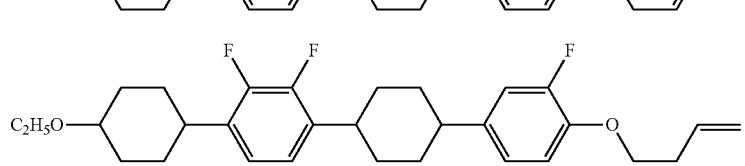 |

| No. |
|---|
| 58 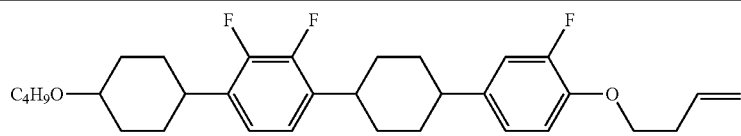 |
| 59 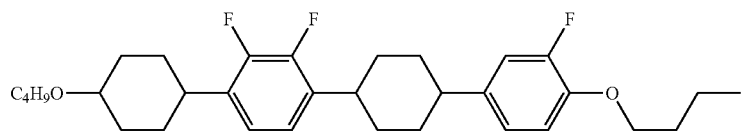 |
| 60 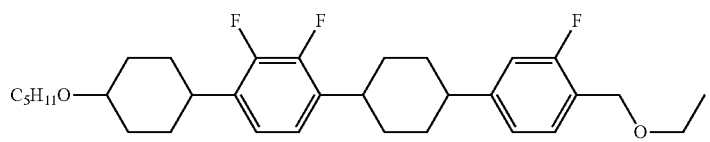 |
| 61 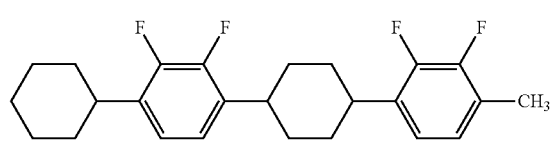 [SMILES: Cc1ccc(C2CCC(c3ccc(C4CCCCC4)c(F)c3F)CC2)c(F)c1F] |
| 62 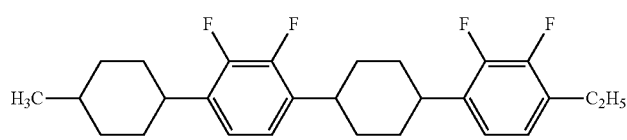 [SMILES: CCc1ccc(C2CCC(c3ccc(C4CCC(C)CC4)c(F)c3F)CC2)c(F)c1F] |
| 63 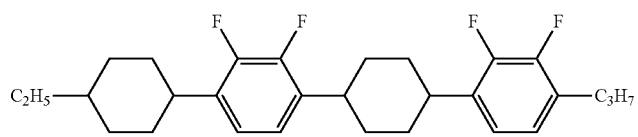 |
| 64 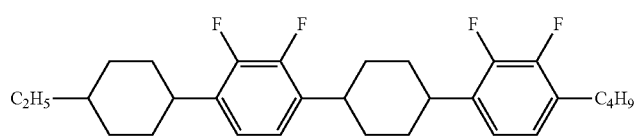 |
| 65 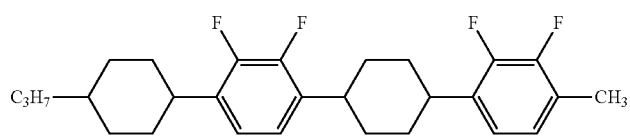 |
| 66 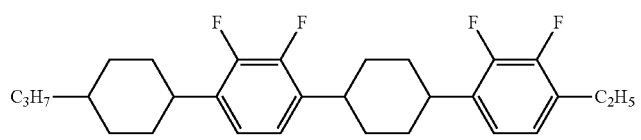 |
| 67 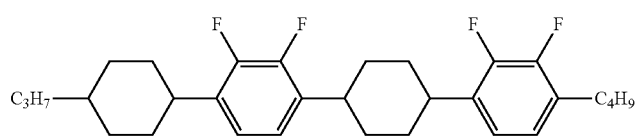 |
| 68 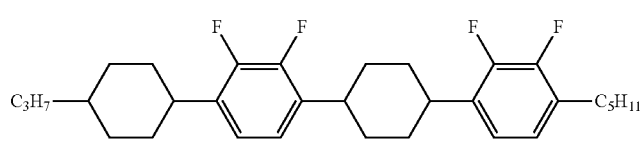 |

-continued
| No. |
|---|
| 69 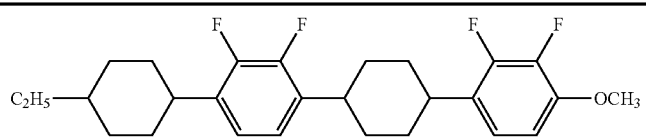 |
| 70 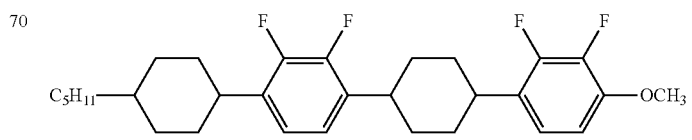 |
| 71 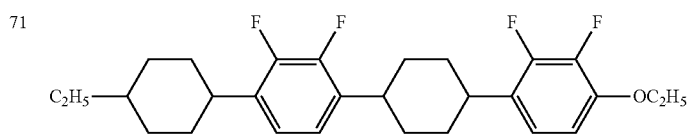 |
| 72 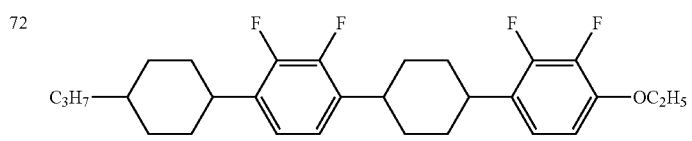 |
| 73 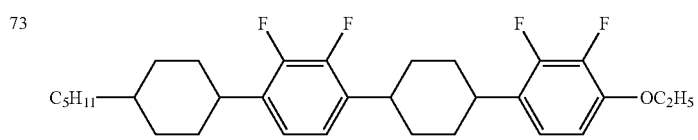 |
| 74 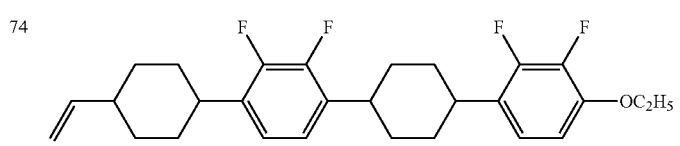 |
| 75 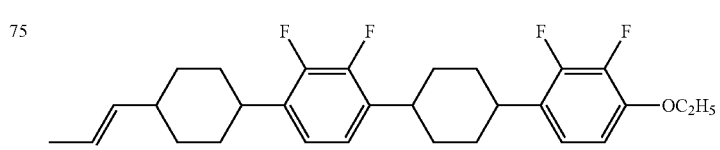 |
| 76 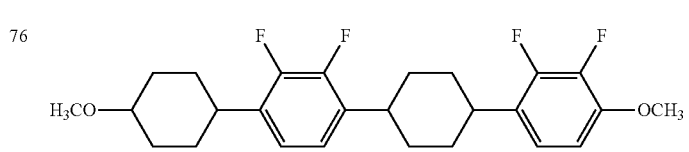 |
| 77 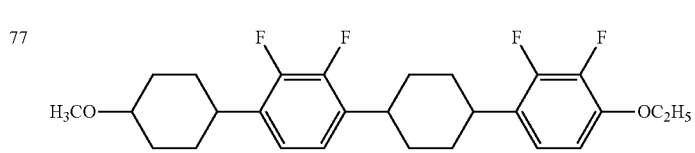 |
| 78 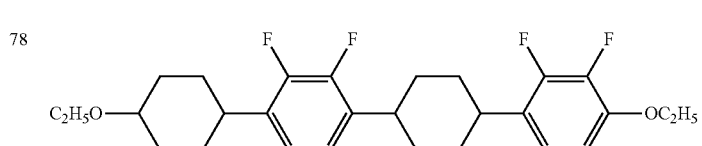 |
| 79 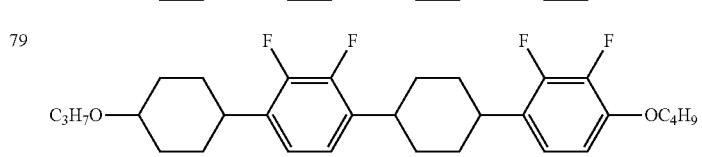 |

| No. | |
|---|---|
| 80 | 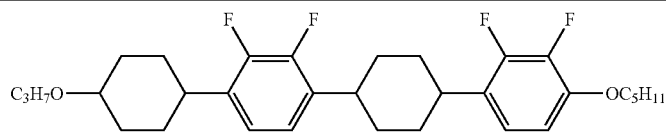 |
| 81 | 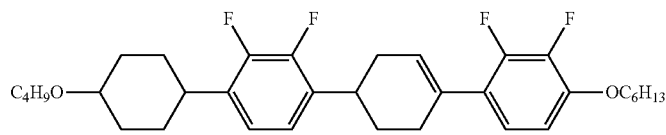 |
| 82 | 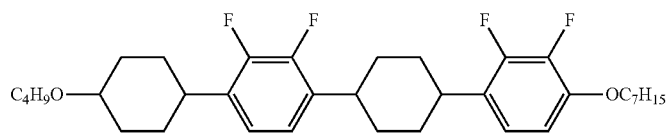 |
| 83 | 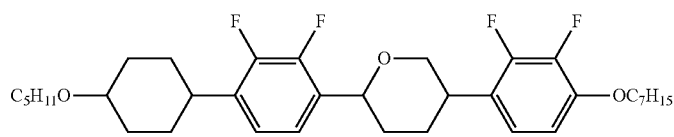 |
| 84 | 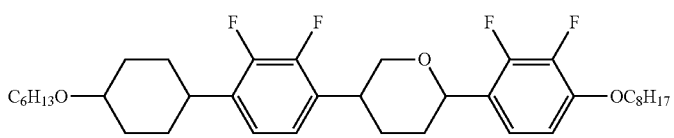 |
| 85 | 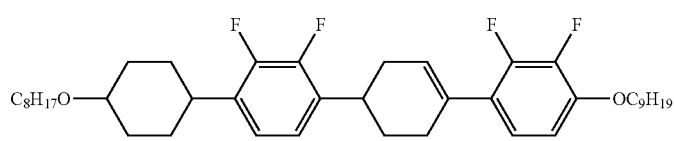 |
| 86 | 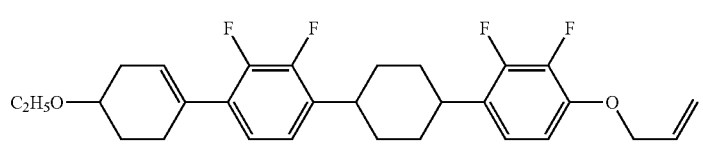 |
| 87 | 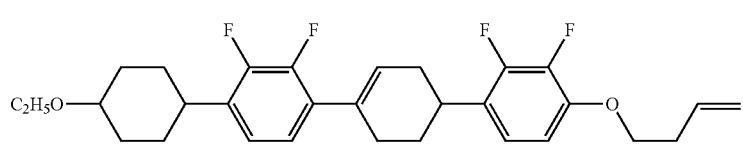 |
| 88 | 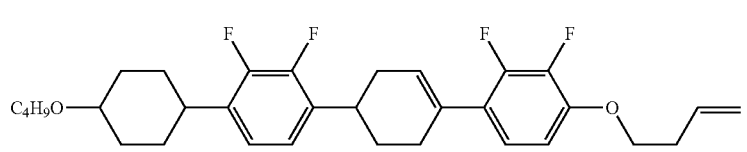 |
| 89 | 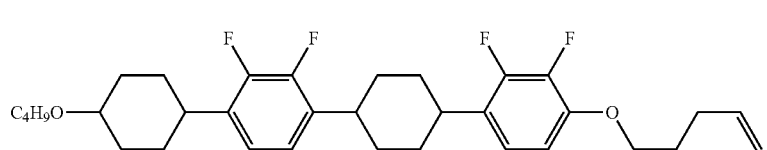 |
| 90 | 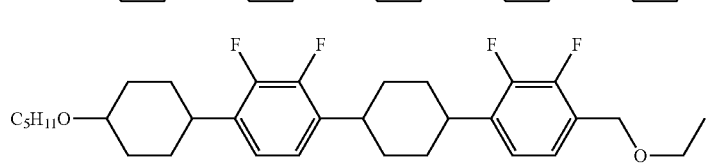 |

| No. | |
|---|---|
| 91 | 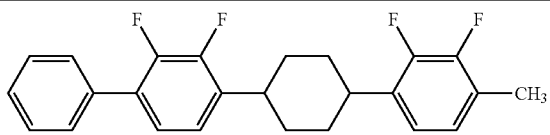 |
| 92 | 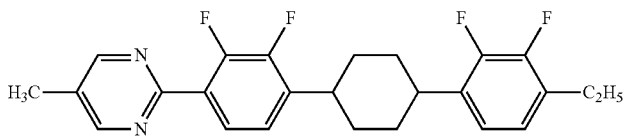 [SMILES: CCc1ccc(C2CCC(c3ccc(-c4ncc(C)cn4)c(F)c3F)CC2)c(F)c1F] |
| 93 | 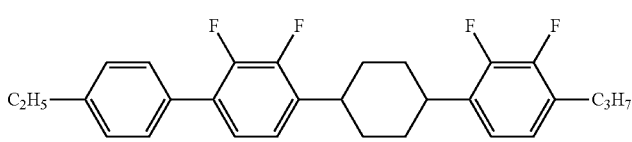 |
| 94 | 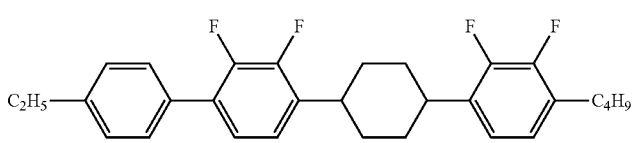 |
| 95 | 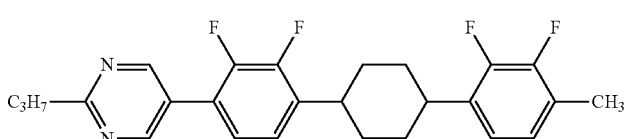 |
| 96 | 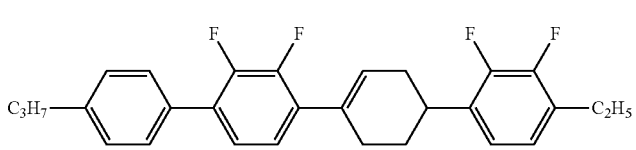 |
| 97 | 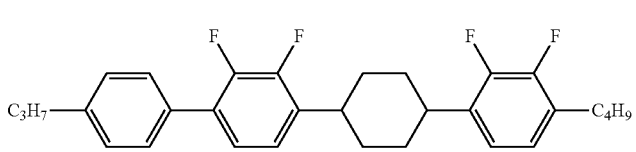 |
| 98 | 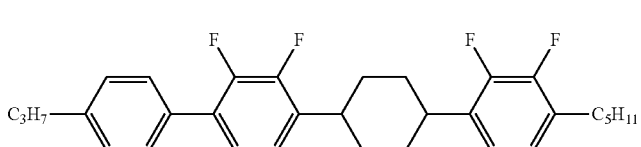 |
| 99 | 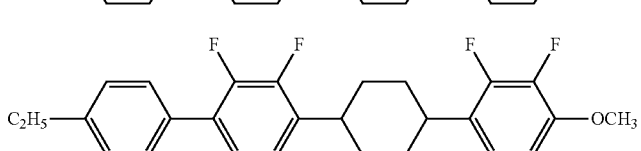 |
| 100 | 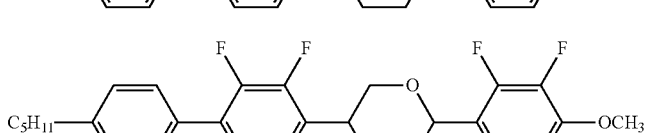 |
| 101 | 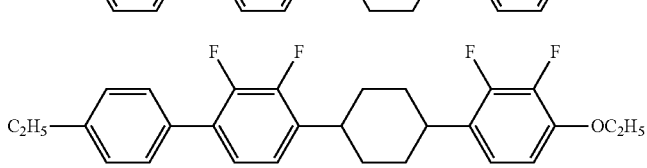 |

| No. | |
|---|---|
| 102 | 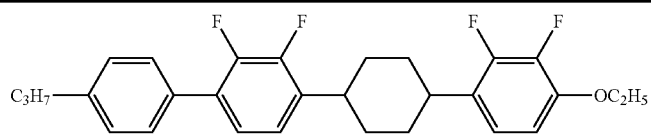 |
| 103 | 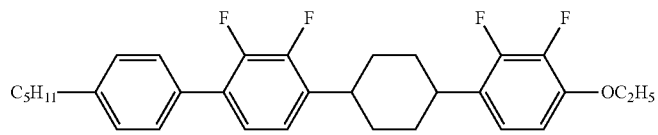 |
| 104 | 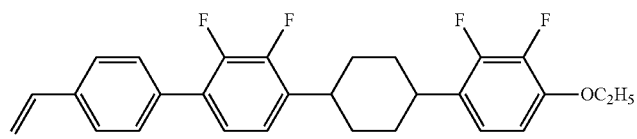 [SMILES: C=Cc1ccc(-c2ccc(C3CCC(c4ccc(OCC)c(F)c4F)CC3)c(F)c2F)cc1] |
| 105 | 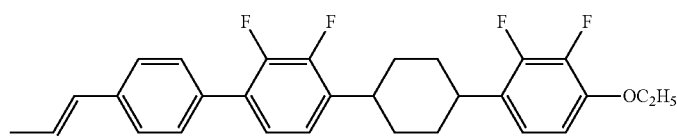 [SMILES: C/C=C/c1ccc(-c2ccc(C3CCC(c4ccc(OCC)c(F)c4F)CC3)c(F)c2F)cc1] |
| 106 | 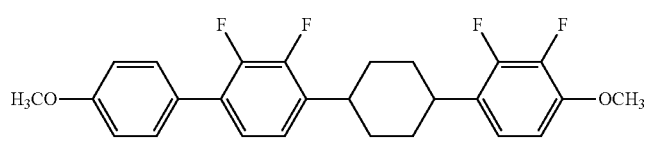 [SMILES: COc1ccc(-c2ccc(C3CCC(c4ccc(OC)c(F)c4F)CC3)c(F)c2F)cc1] |
| 107 | 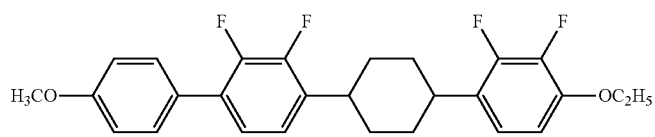 |
| 108 | 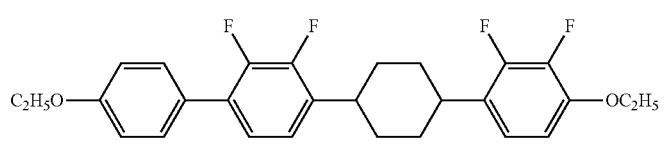 |
| 109 | 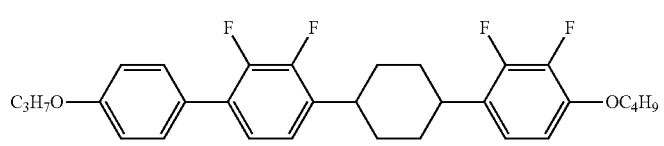 |
| 110 | 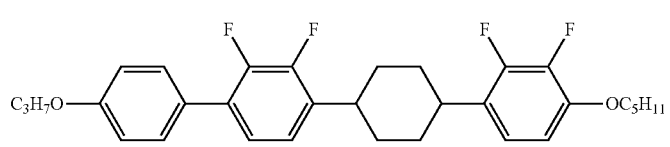 |
| 111 | 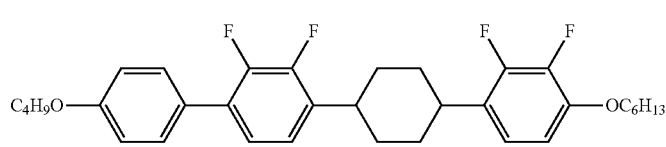 |
| 112 | 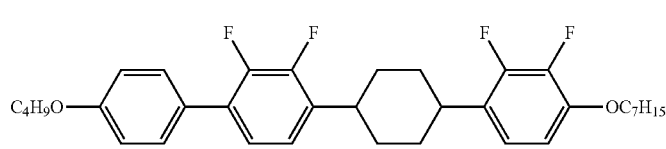 |

| No. | |
|---|---|
| 113 | 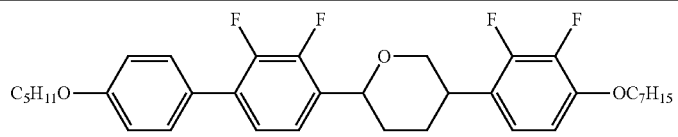 |
| 114 | 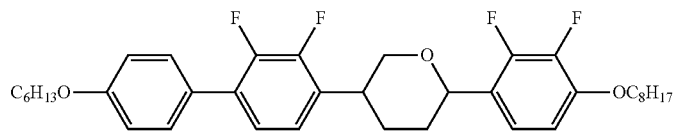 |
| 115 | 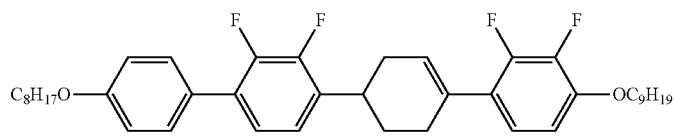 |
| 116 | 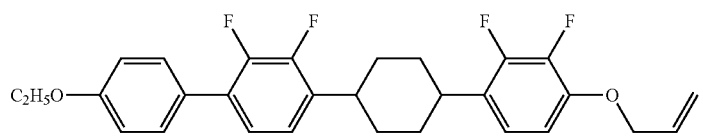 |
| 117 | 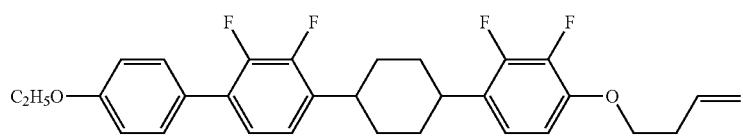 |
| 118 | 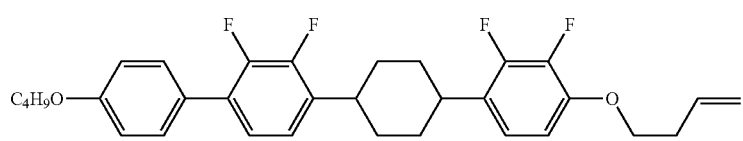 |
| 119 | 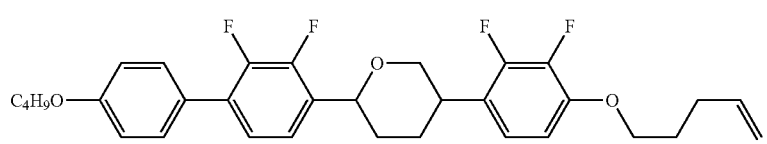 |
| 120 | 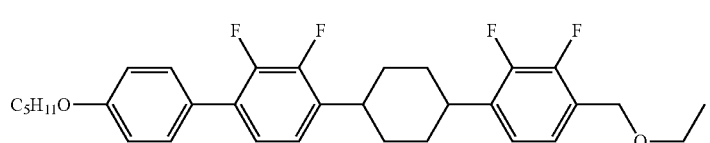 |
| 121 | 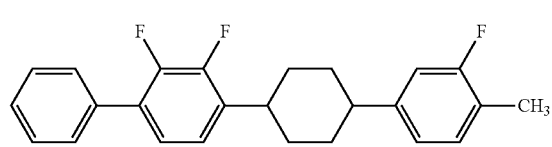 |
| 122 | 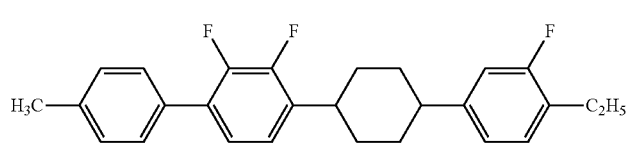 [SMILES: CCc1ccc(C2CCC(c3ccc(-c4ccc(C)cc4)c(F)c3F)CC2)cc1F] |
| 123 | 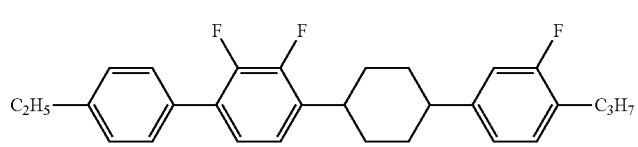 |

-continued
| No. | |
|---|---|
| 124 | 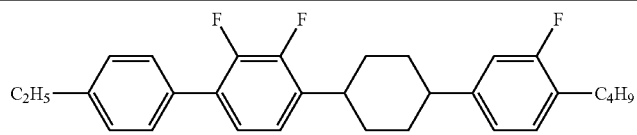 |
| 125 | 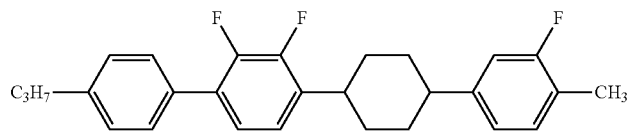 |
| 126 | 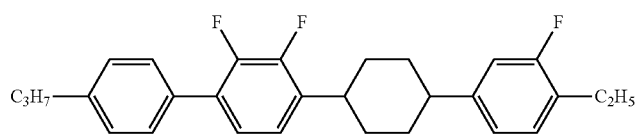 |
| 127 | 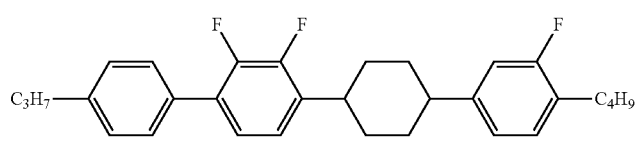 |
| 128 | 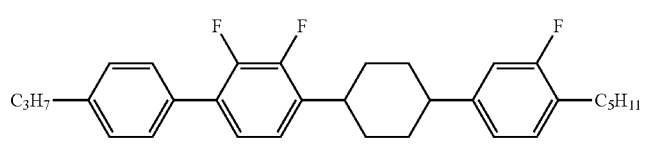 |
| 129 | 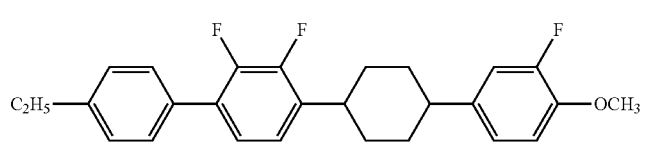 [SMILES: CCc1ccc(-c2ccc(C3CCC(c4ccc(OC)c(F)c4)CC3)c(F)c2F)cc1] |
| 130 | 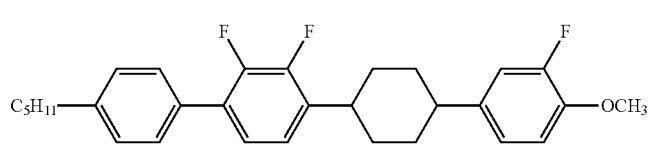 |
| 131 | 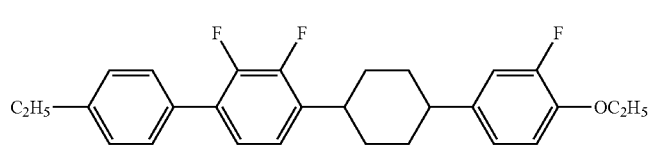 [SMILES: CCOc1ccc(C2CCC(c3ccc(-c4ccc(CC)cc4)c(F)c3F)CC2)cc1F] |
| 132 | 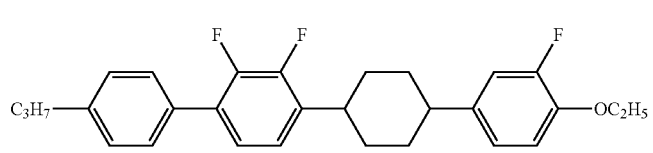 |
| 133 | 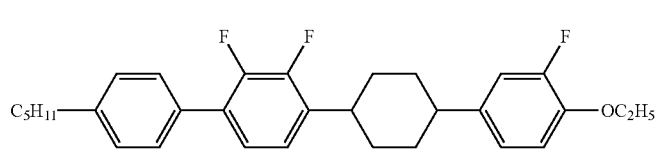 |
| 134 | 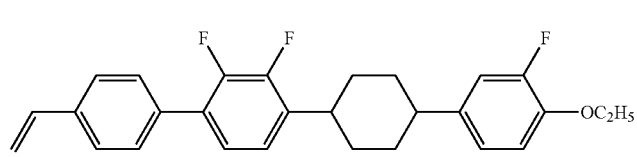 [SMILES: C=Cc1ccc(-c2ccc(C3CCC(c4ccc(OCC)c(F)c4)CC3)c(F)c2F)cc1] |

| No. | |
|---|---|
| 135 | 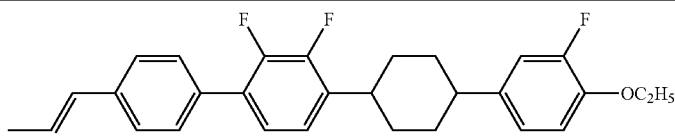 |
| 136 | 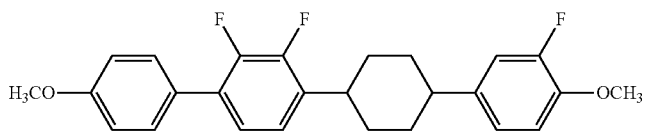 [SMILES: COc1ccc(-c2ccc(C3CCC(c4ccc(OC)c(F)c4)CC3)c(F)c2F)cc1] |
| 137 | 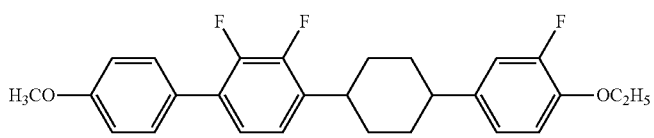 [SMILES: CCOc1ccc(C2CCC(c3ccc(-c4ccc(OC)cc4)c(F)c3F)CC2)cc1F] |
| 138 | 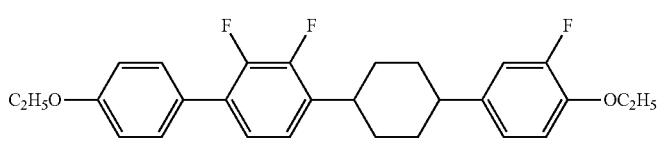 |
| 139 | 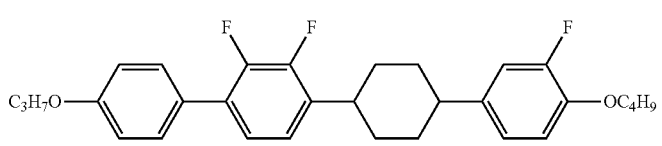 |
| 140 | 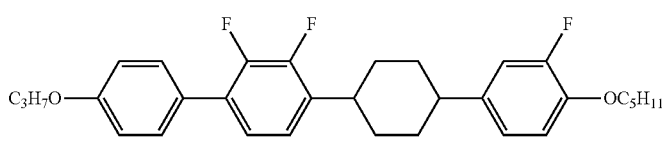 |
| 141 | 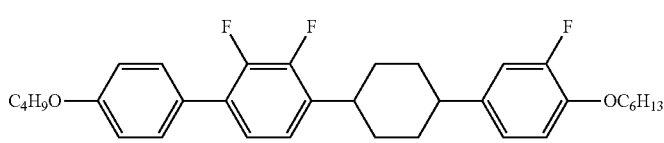 |
| 142 | 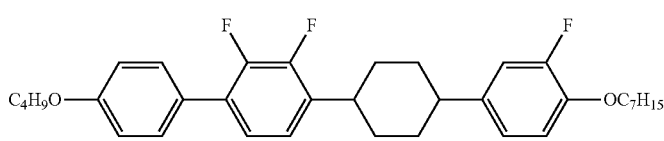 |
| 143 | 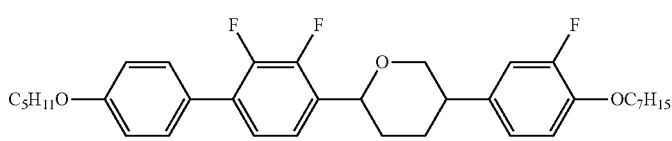 |
| 144 | 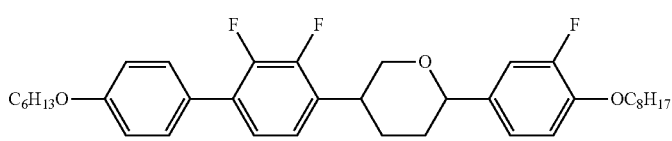 |
| 145 | 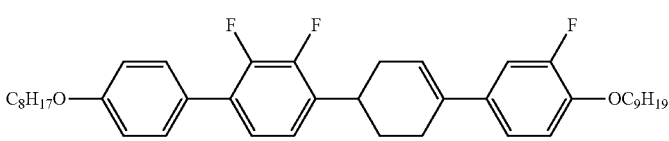 |

| No. |
|---|
| 146 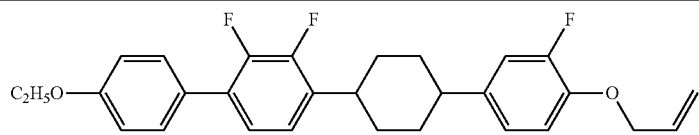 |
| 147 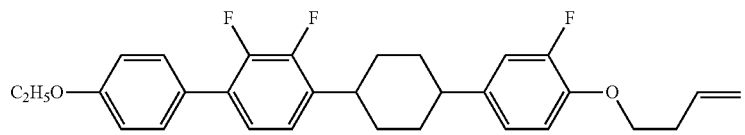 |
| 148 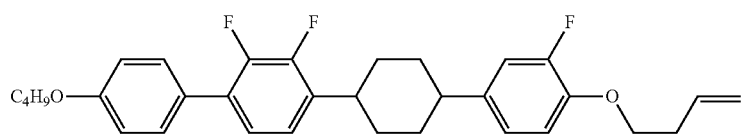 |
| 149 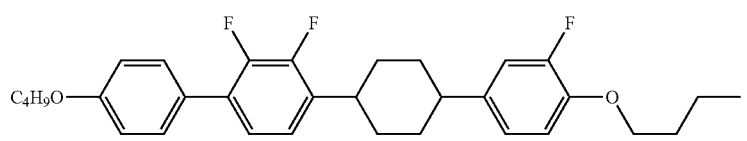 |
| 150 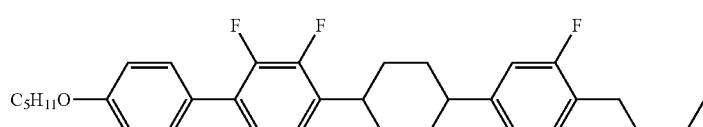 |
| 151 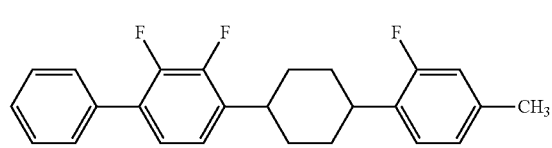 |
| 152 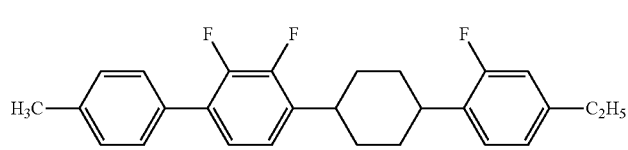 [SMILES: CCc1ccc(C2CCC(c3ccc(-c4ccc(C)cc4)c(F)c3F)CC2)c(F)c1] |
| 153 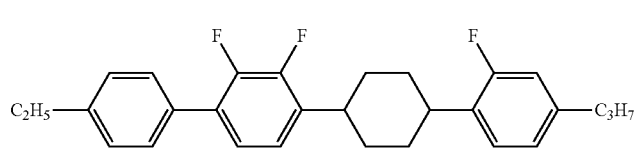 |
| 154 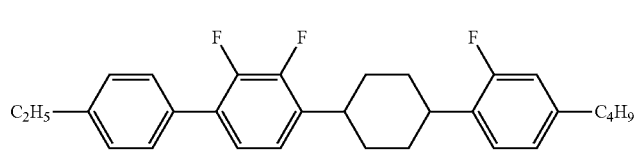 |
| 155 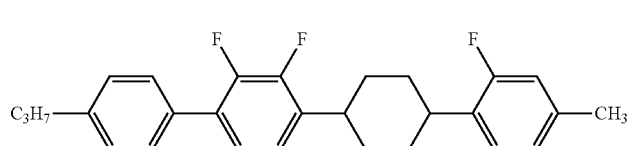 |
| 156 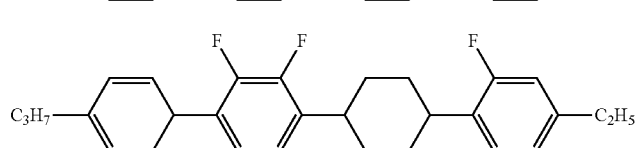 |

| No. | |
|---|---|
| 157 | 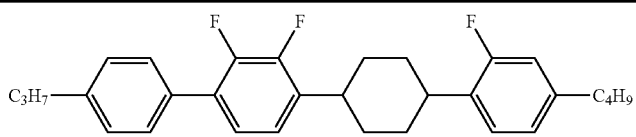 |
| 158 | 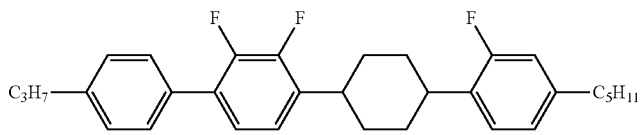 |
| 159 | 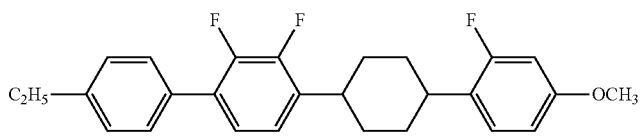 [SMILES: CCc1ccc(-c2ccc(C3CCC(c4ccc(OC)cc4F)CC3)c(F)c2F)cc1] |
| 160 | 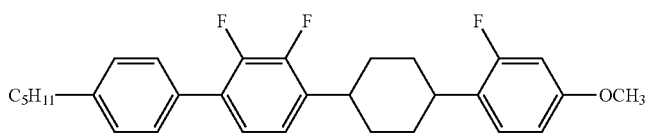 |
| 161 | 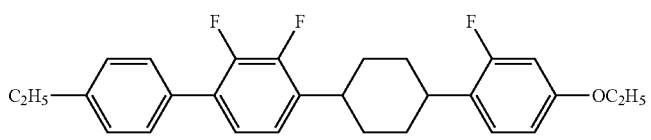 |
| 162 | 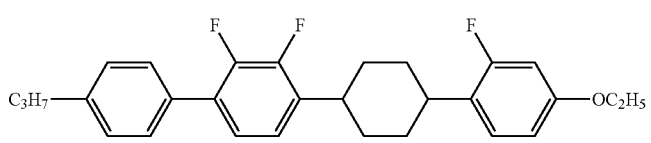 |
| 163 | 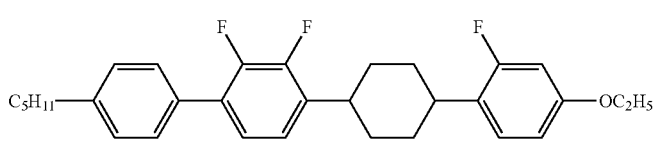 |
| 164 | 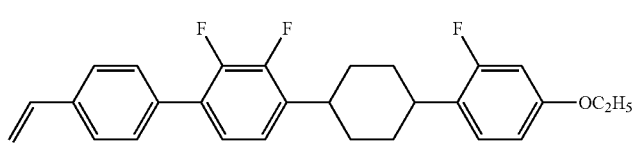 |
| 165 | 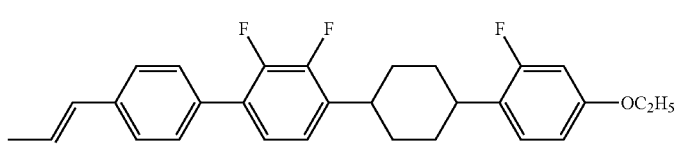 [SMILES: C/C=C/c1ccc(-c2ccc(C3CCC(c4ccc(OCC)cc4F)CC3)c(F)c2F)cc1] |
| 166 | 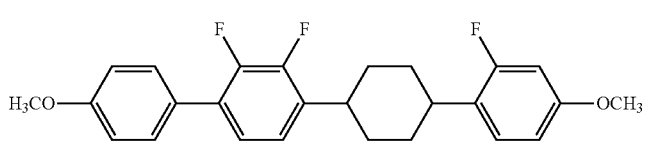 [SMILES: COc1ccc(-c2ccc(C3CCC(c4ccc(OC)cc4F)CC3)c(F)c2F)cc1] |
| 167 | 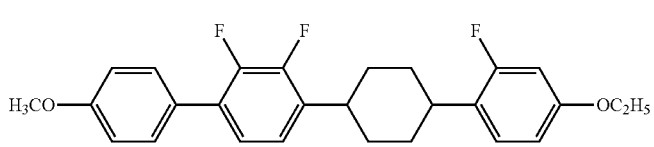 [SMILES: CCOc1ccc(C2CCC(c3ccc(-c4ccc(OC)cc4)c(F)c3F)CC2)c(F)c1] |

| No. | |
|---|---|
| 168 | 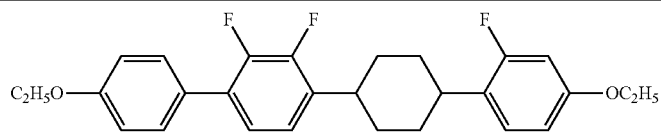 |
| 169 | 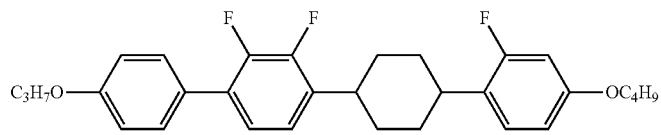 |
| 170 | 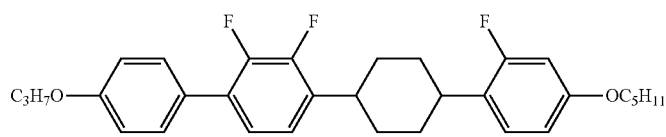 |
| 171 | 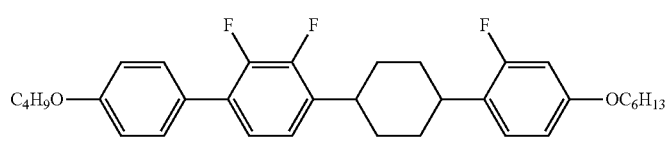 |
| 172 | 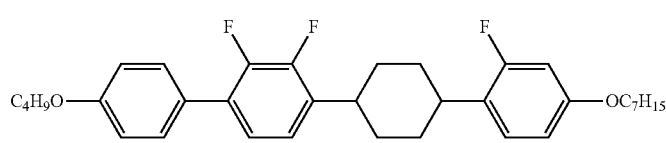 |
| 173 | 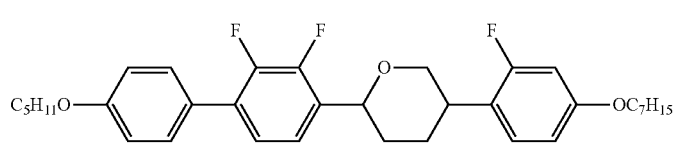 |
| 174 | 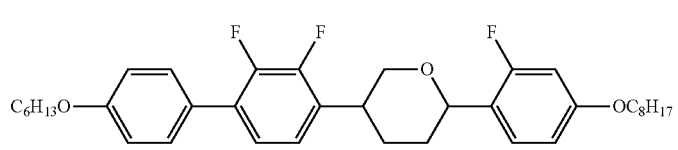 |
| 175 | 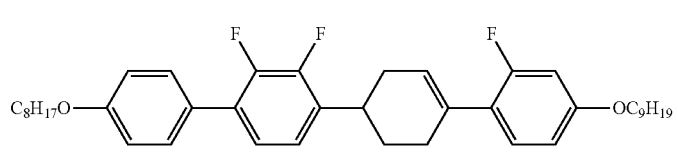 |
| 176 | 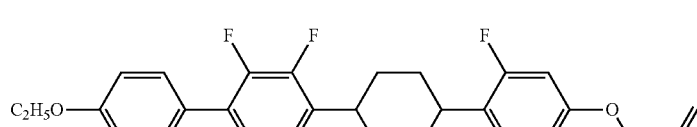 |
| 177 | 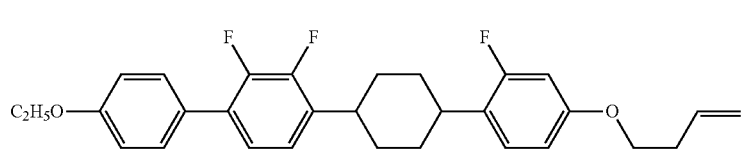 |
| 178 | 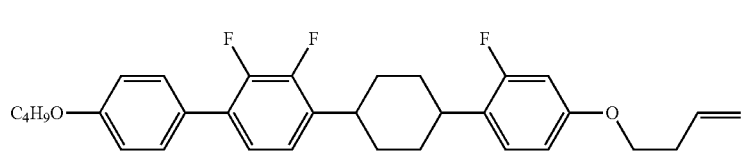 |

| No. | |
|---|---|
| 179 | 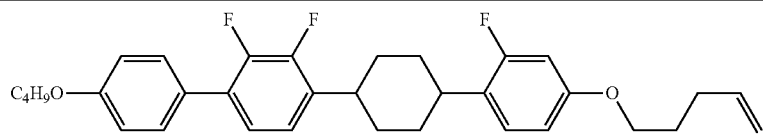 |
| 180 | 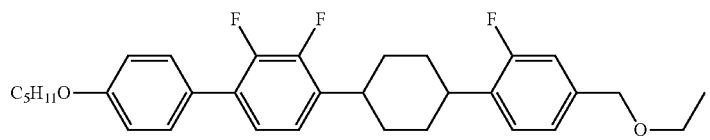 |
| 181 | 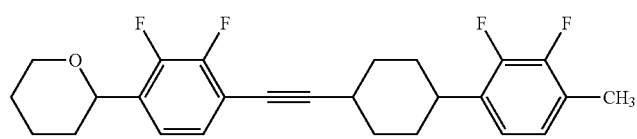 [SMILES: Cc1ccc(C2CCC(C#Cc3ccc(C4CCCCO4)c(F)c3F)CC2)c(F)c1F] |
| 182 | 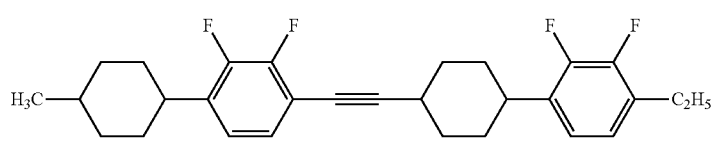 [SMILES: CCc1ccc(C2CCC(C#Cc3ccc(C4CCC(C)CC4)c(F)c3F)CC2)c(F)c1F] |
| 183 | 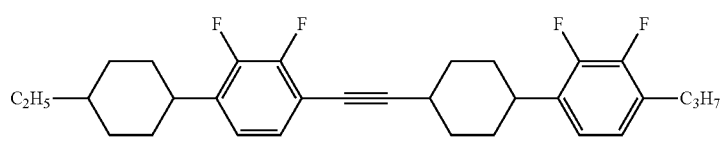 |
| 184 | 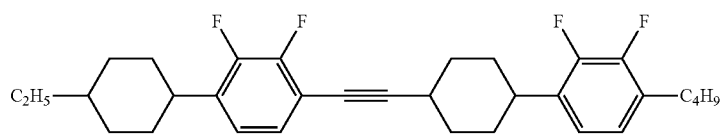 |
| 185 | 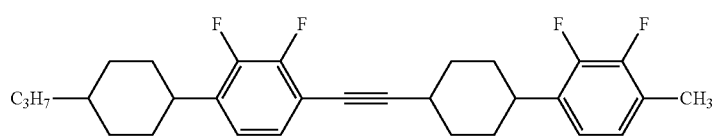 |
| 186 | 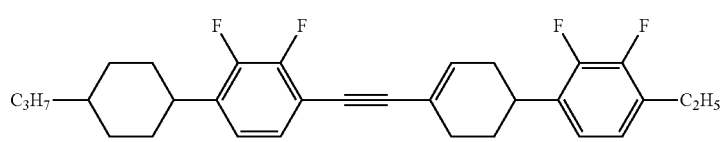 |
| 187 | 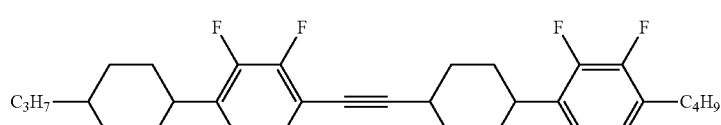 |
| 188 | 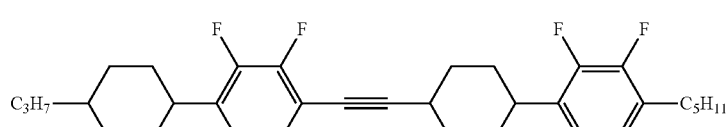 |
| 189 | 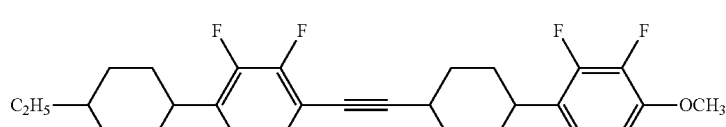 |

| No. | |
|---|---|
| 190 | C₅H₁₁–[Cy]–[Ph(F,F)]–C≡C–[THP-O]–[Ph(F,F)]–OCH₃ |
| 191 | C₂H₅–[Cy]–[Ph(F,F)]–C≡C–[Cy]–[Ph(F,F)]–OC₂H₅ |
| 192 | C₃H₇–[Cy]–[Ph(F,F)]–C≡C–[Cy]–[Ph(F,F)]–OC₂H₅ |
| 193 | C₅H₁₁–[Cy]–[Ph(F,F)]–C≡C–[Cy]–[Ph(F,F)]–OC₂H₅ |
| 194 | CH₂=CH–[Cy]–[Ph(F,F)]–C≡C–[Cy]–[Ph(F,F)]–OC₂H₅ |
| 195 | CH₃–CH=CH–[Cy]–[Ph(F,F)]–C≡C–[Cy]–[Ph(F,F)]–OC₂H₅ |
| 196 | H₃CO–[Cy]–[Ph(F,F)]–[Cy]–C≡C–[Ph(F,F)]–OCH₃ |
| 197 | H₃CO–[Cy]–[Ph(F,F)]–[Cy]–C≡C–[Ph(F,F)]–OC₂H₅ |
| 198 | C₂H₅O–[Cy]–[Ph(F,F)]–[Cy]–C≡C–[Ph(F,F)]–OC₂H₅ |
| 199 | C₃H₇O–[Cy]–[Ph(F,F)]–[Cy]–C≡C–[Ph(F,F)]–OC₄H₉ |
| 200 | C₃H₇O–[Cy]–[Ph(F,F)]–[Cy]–C≡C–[Ph(F,F)]–OC₅H₁₁ |

| No. | |
|---|---|
| 201 | 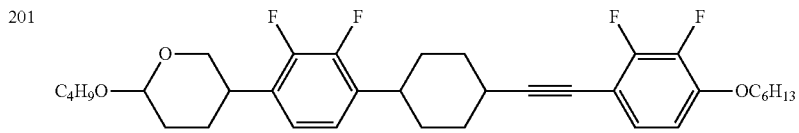 |
| 202 | 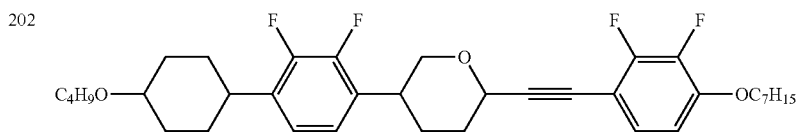 |
| 203 | 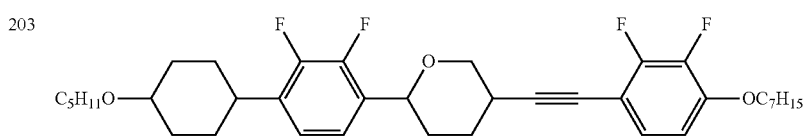 |
| 204 | 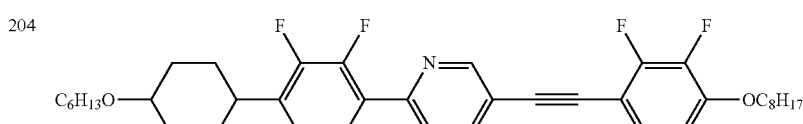 |
| 205 | 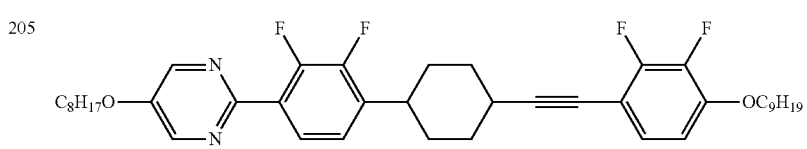 |
| 206 | 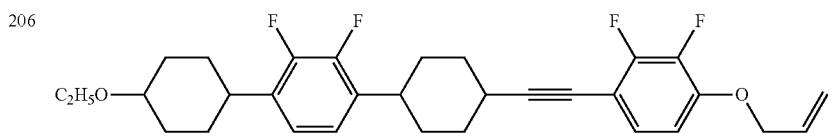 |
| 207 | 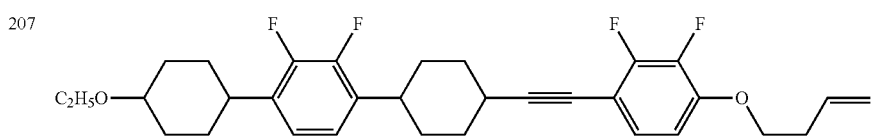 |
| 208 | 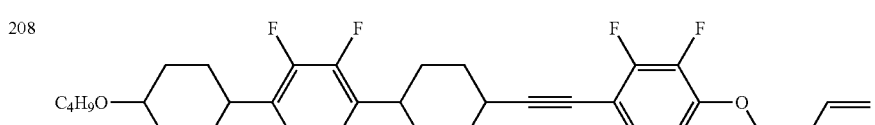 |
| 209 |  |
| 210 | 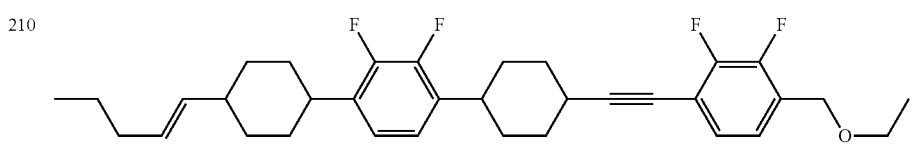 |

-continued
| No. | |
|---|---|
| 211 | 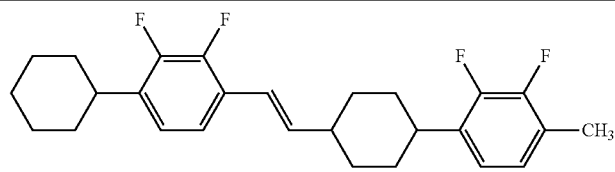 |
| 212 | 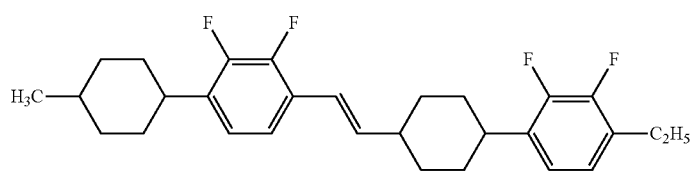 [SMILES: CCc1ccc(C2CCC(/C=C/c3ccc(C4CCC(C)CC4)c(F)c3F)CC2)c(F)c1F] |
| 213 | 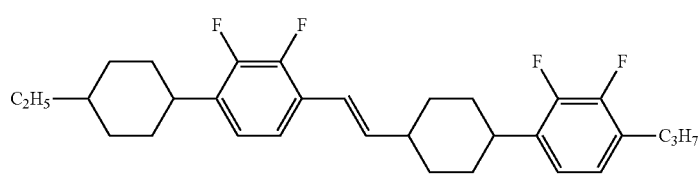 |
| 214 | 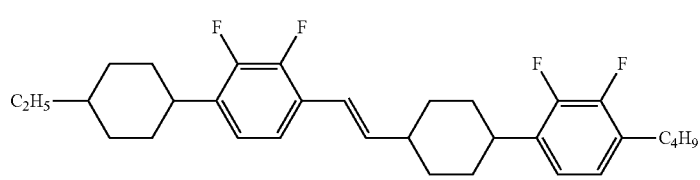 |
| 215 | 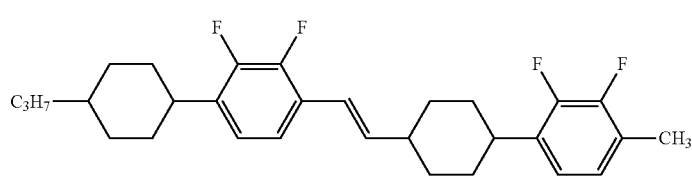 |
| 216 | 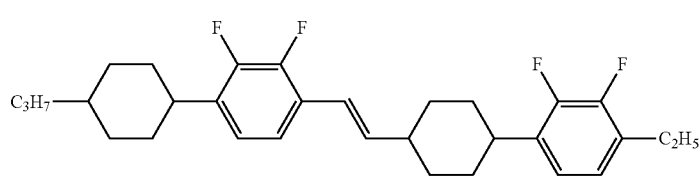 |
| 217 | 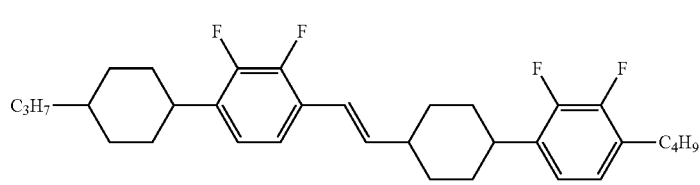 |
| 218 | 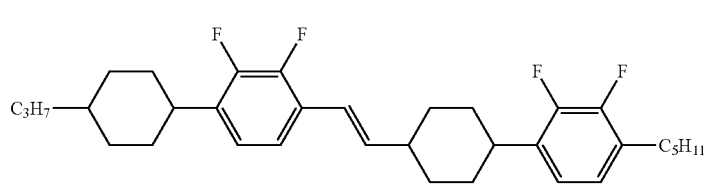 |
| 219 | 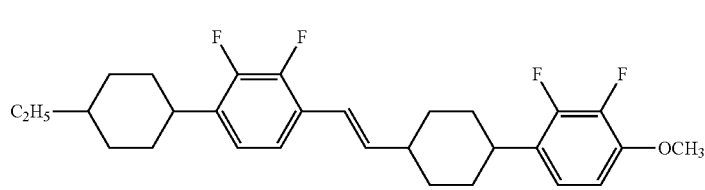 [SMILES: CCC1CCC(c2ccc(/C=C/C3CCC(c4ccc(OC)c(F)c4F)CC3)c(F)c2F)CC1] |

| No. | |
|---|---|
| 220 | 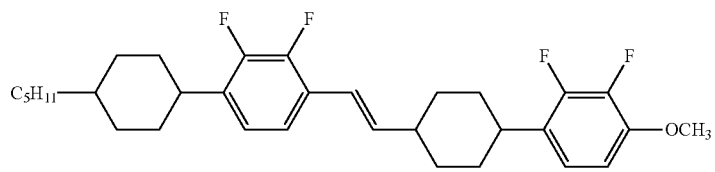 |
| 221 | 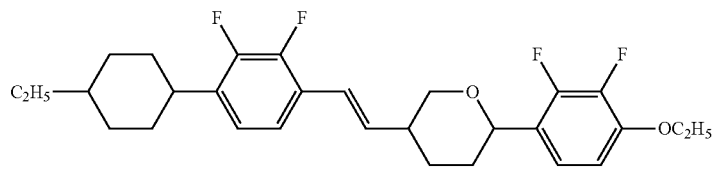 [SMILES: CCOc1ccc(C2CCC(/C=C/c3ccc(C4CCC(CC)CC4)c(F)c3F)CO2)c(F)c1F] |
| 222 | 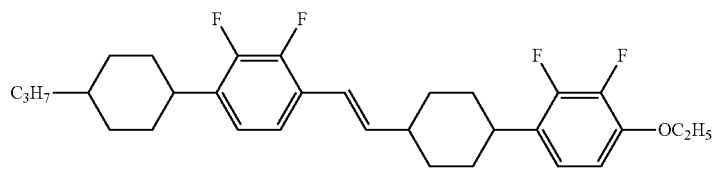 |
| 223 | 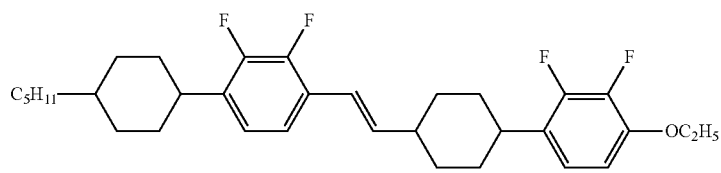 |
| 224 | 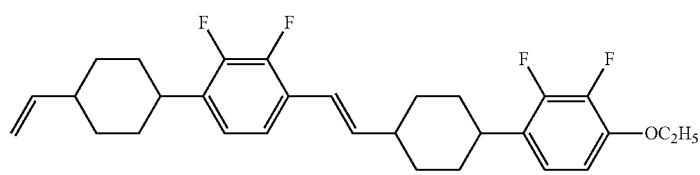 [SMILES: C=CC1CCC(c2ccc(/C=C/C3CCC(c4ccc(OCC)c(F)c4F)CC3)c(F)c2F)CC1] |
| 225 | 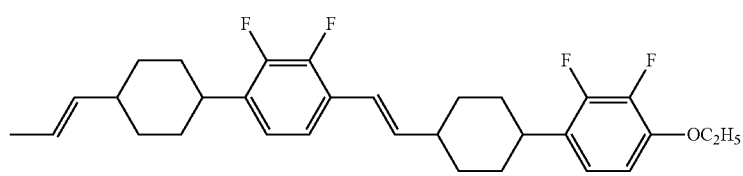 [SMILES: C/C=C/C1CCC(c2ccc(/C=C/C3CCC(c4ccc(OCC)c(F)c4F)CC3)c(F)c2F)CC1] |
| 226 | 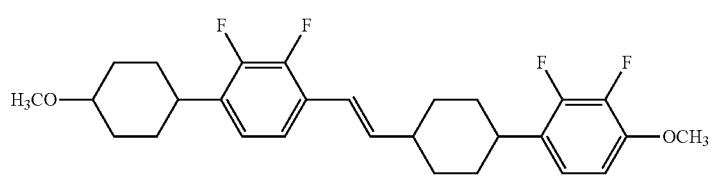 |
| 227 | 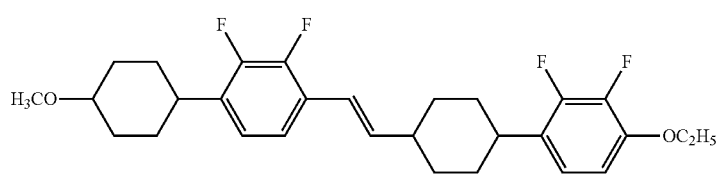 |

| No. | |
|---|---|
| 228 | 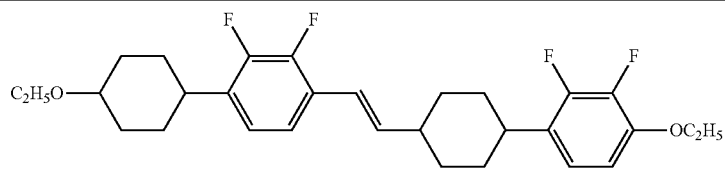 |
| 229 | 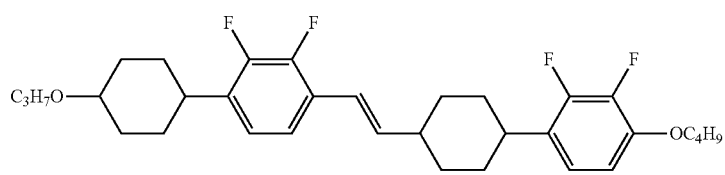 |
| 230 | 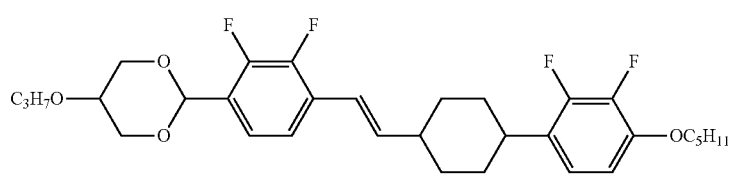 |
| 231 | 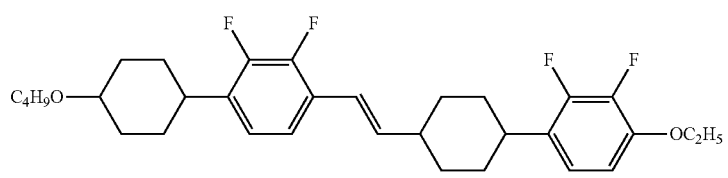 |
| 232 | 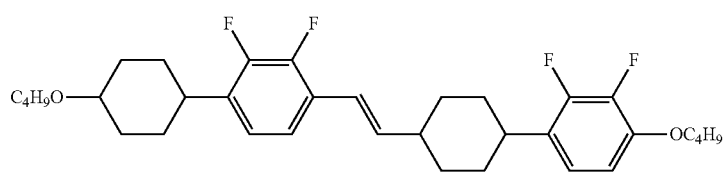 |
| 233 | 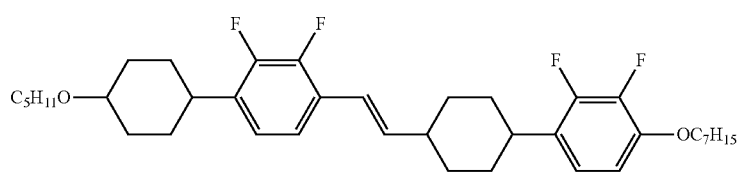 |
| 234 | 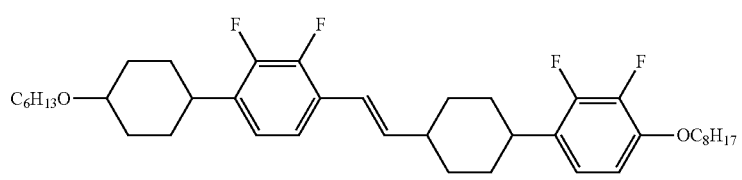 |
| 235 | 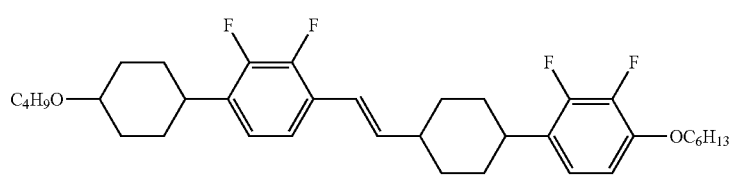 |
| 236 | 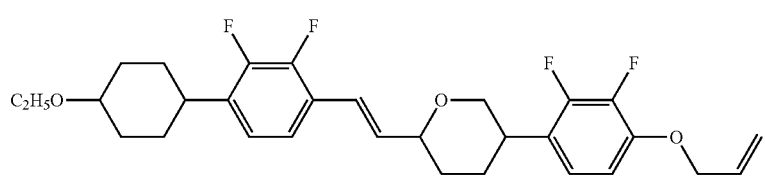 |

| No. |
|---|
237
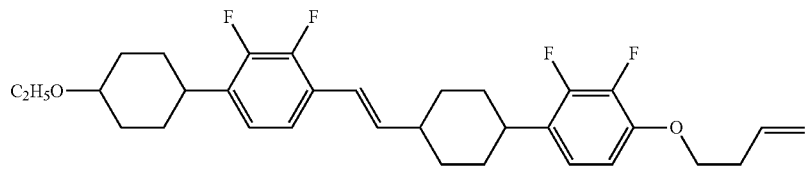
238
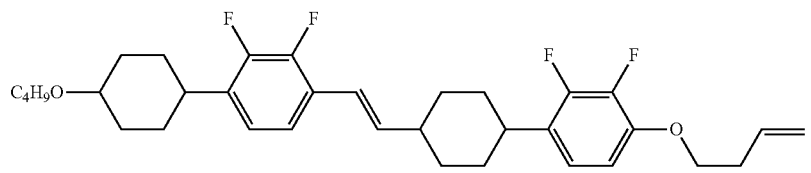
239
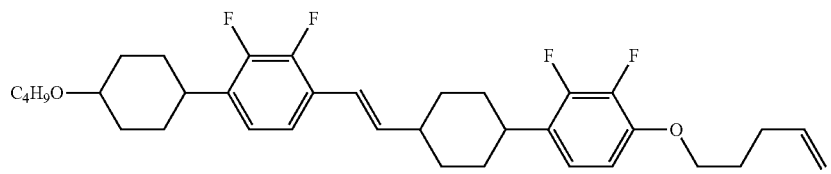
240
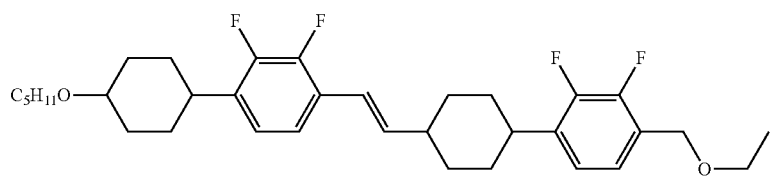
241
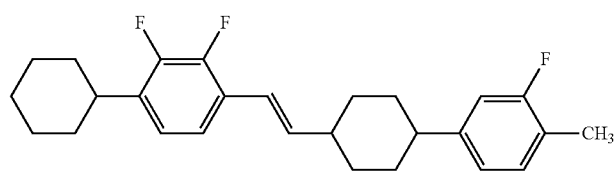 [SMILES: Cc1ccc(C2CCC(/C=C/c3ccc(C4CCCCC4)c(F)c3F)CC2)cc1F]
242
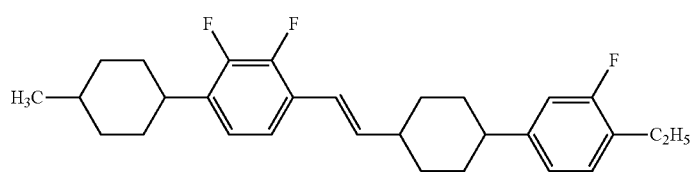 [SMILES: CCc1ccc(C2CCC(/C=C/c3ccc(C4CCC(C)CC4)c(F)c3F)CC2)cc1F]
243
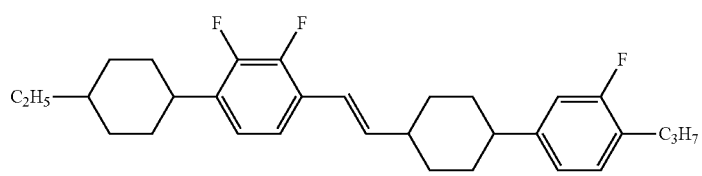
244
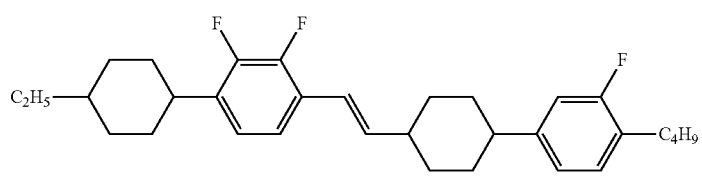

| No. | |
|---|---|
| 245 | 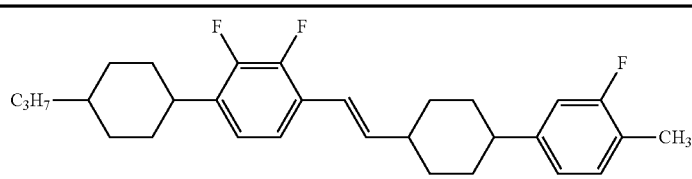 |
| 246 | 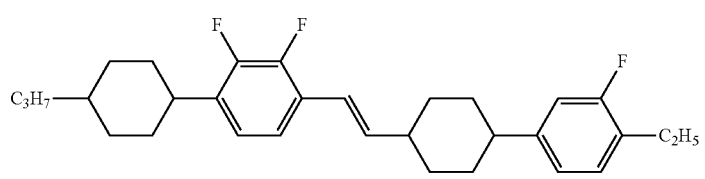 |
| 247 | 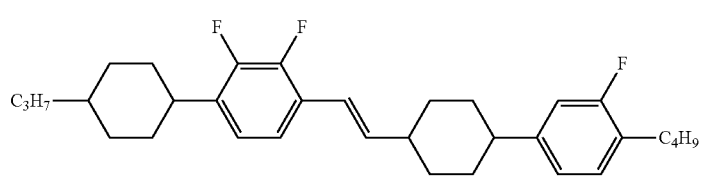 |
| 248 | 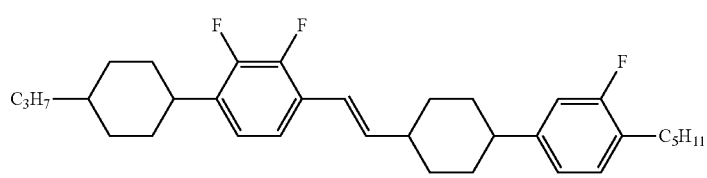 |
| 249 | 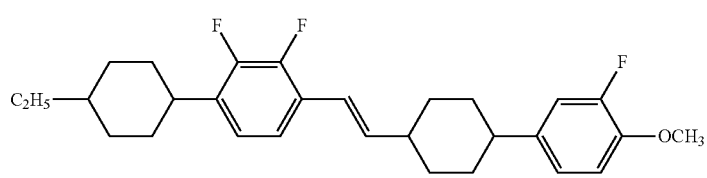 [SMILES: CCC1CCC(c2ccc(/C=C/C3CCC(c4ccc(OC)c(F)c4)CC3)c(F)c2F)CC1] |
| 250 | 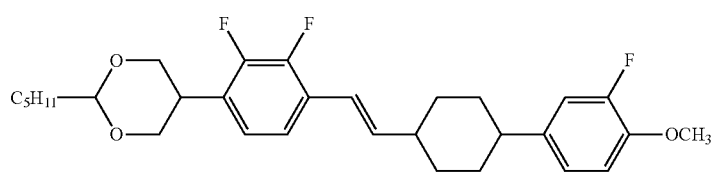 |
| 251 | 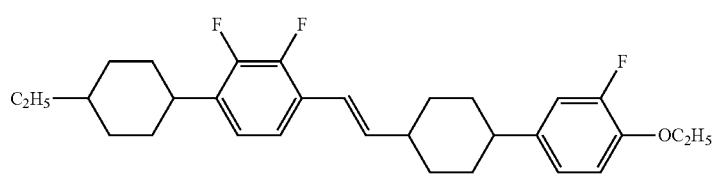 [SMILES: CCOc1ccc(C2CCC(/C=C/c3ccc(C4CCC(CC)CC4)c(F)c3F)CC2)cc1F] |
| 252 | 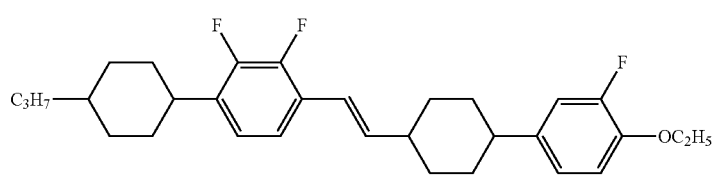 |
| 253 | 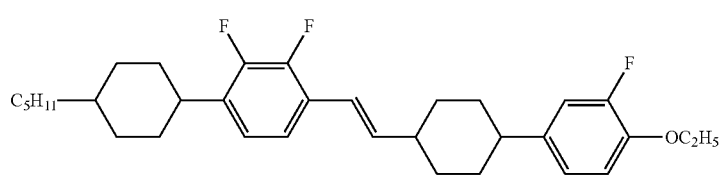 |

-continued
| No. | |
|---|---|
| 254 | 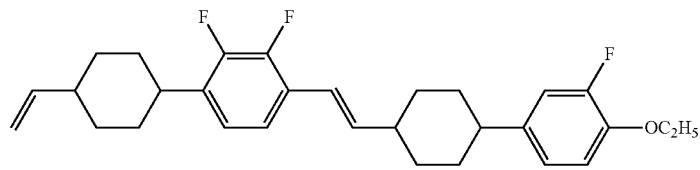 |
| 255 | 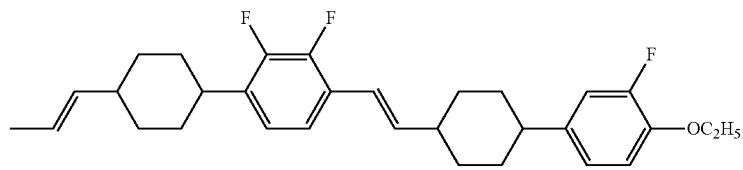 |
| 256 | 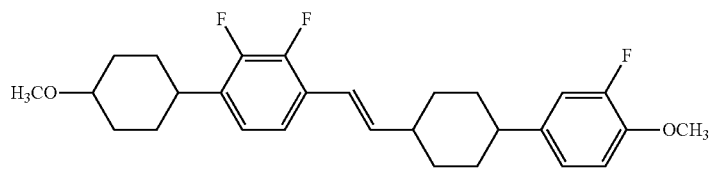 |
| 257 | 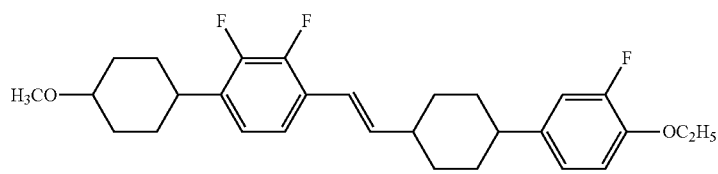 [SMILES: CCOc1ccc(C2CCC(/C=C/c3ccc(C4CCC(OC)CC4)c(F)c3F)CC2)cc1F] |
| 258 | 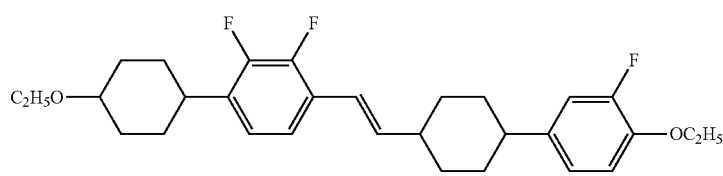 |
| 259 | 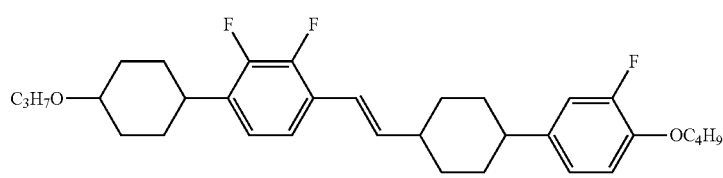 |
| 260 | 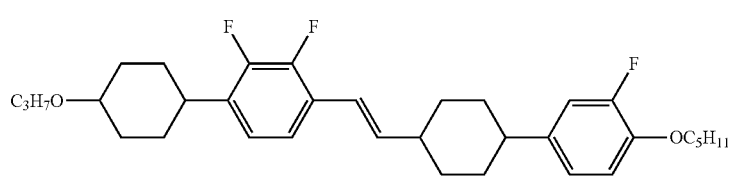 |
| 261 | 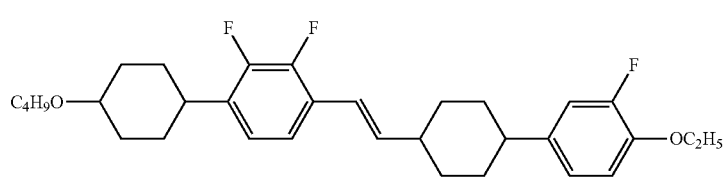 |

| No. | |
|---|---|
| 262 | 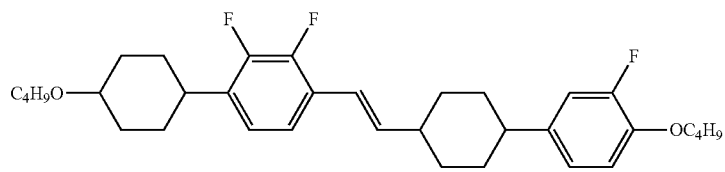 |
| 263 | 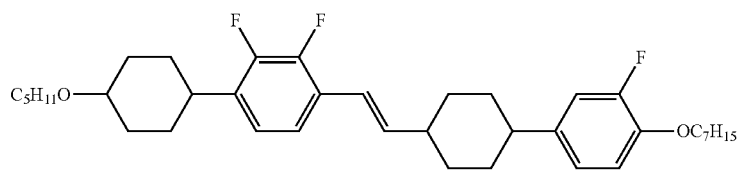 |
| 264 | 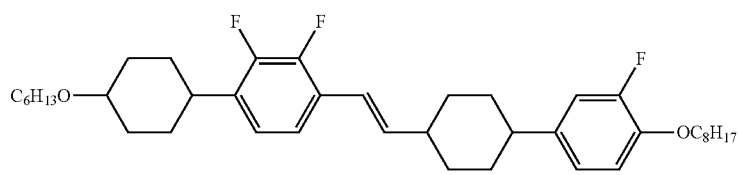 |
| 265 | 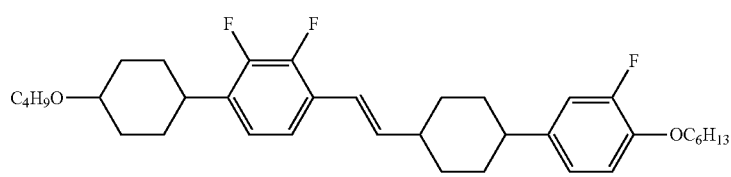 |
| 266 | 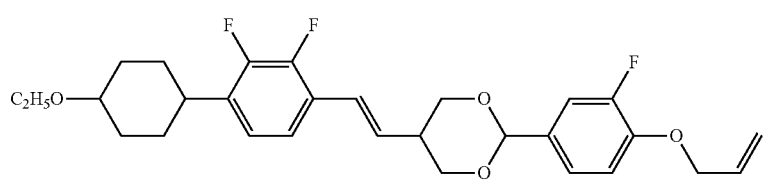 |
| 267 | 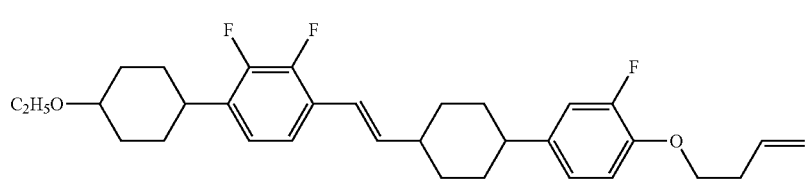 |
| 268 | 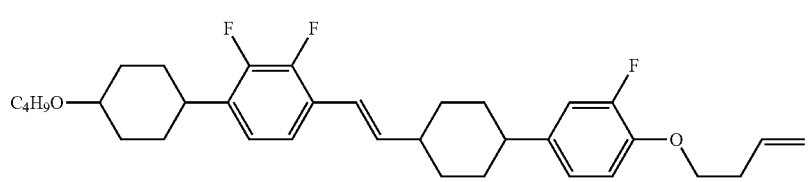 |
| 269 | 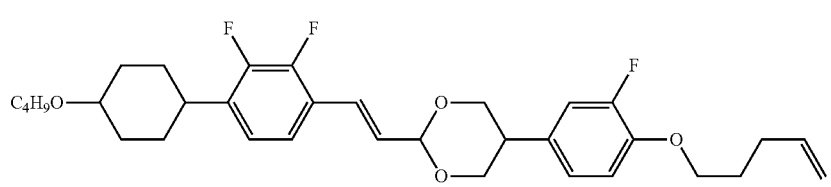 |

| No. |
|---|
| 270 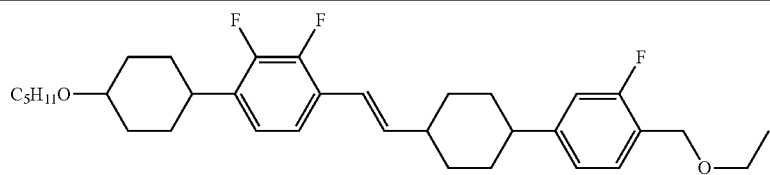 |
| 271 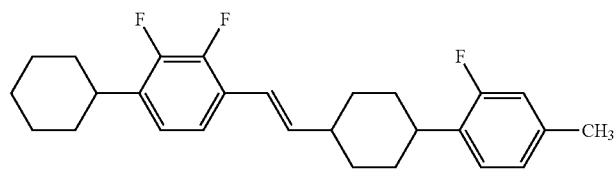 [SMILES: Cc1ccc(C2CCC(/C=C/c3ccc(C4CCCCC4)c(F)c3F)CC2)c(F)c1] |
| 272 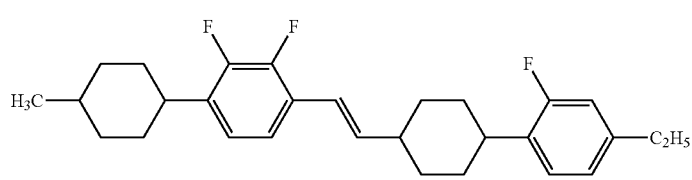 |
| 273 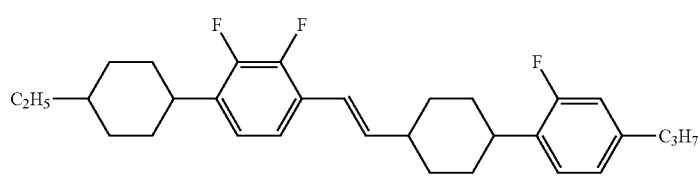 |
| 274 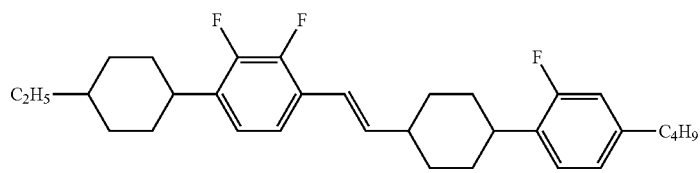 |
| 275 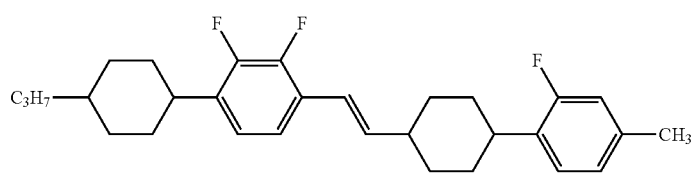 |
| 276 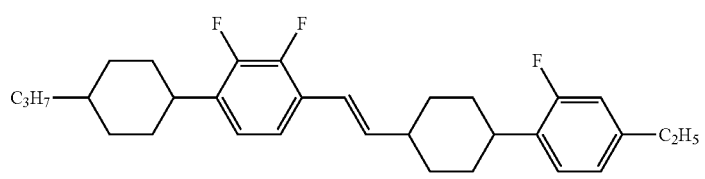 |
| 277 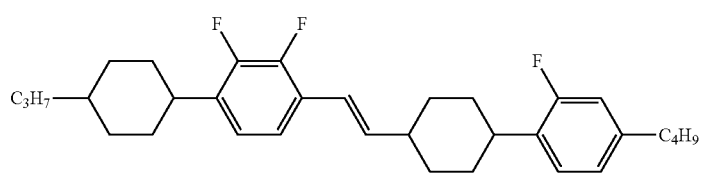 |
| 278 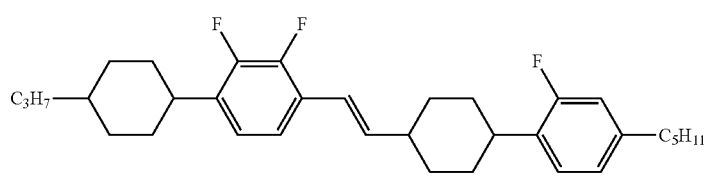 |

| No. | |
|---|---|
| 279 | 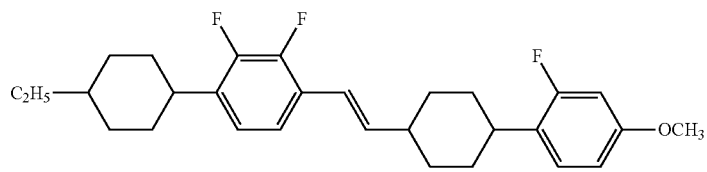 |
| 280 | 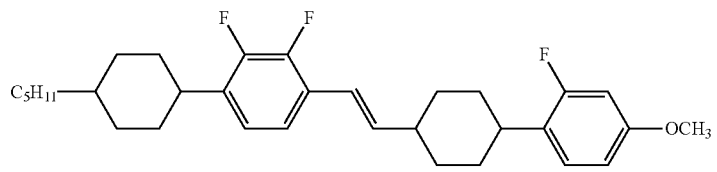 |
| 281 | 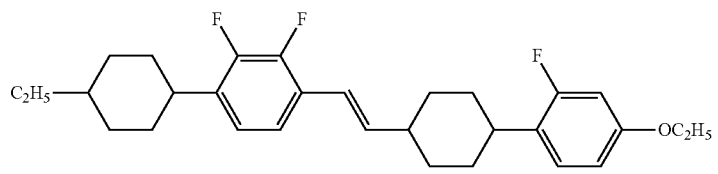 |
| 282 | 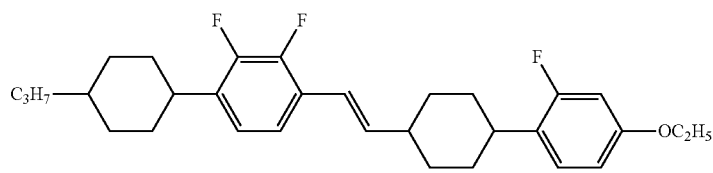 |
| 283 | 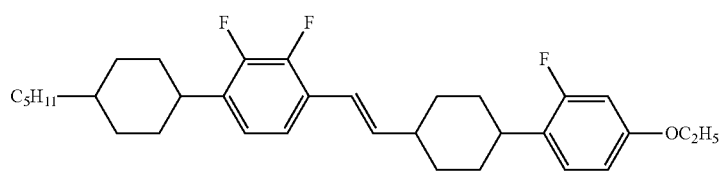 |
| 284 | 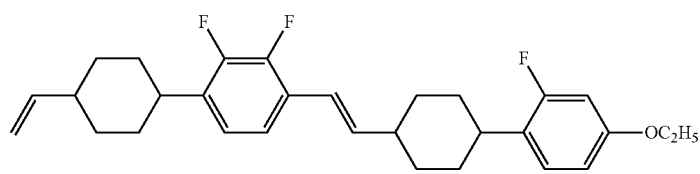 [SMILES: C=CC1CCC(c2ccc(/C=C/C3CCC(c4ccc(OCC)cc4F)CC3)c(F)c2F)CC1] |
| 285 | 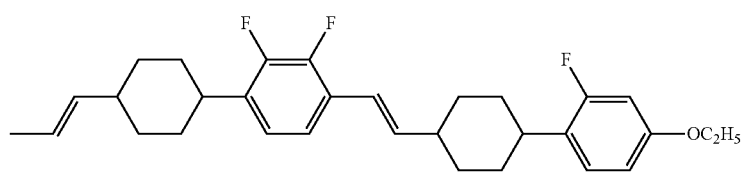 |
| 286 | 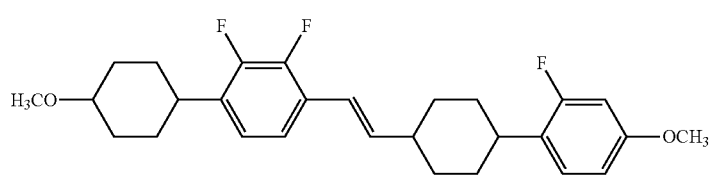 [SMILES: COc1ccc(C2CCC(/C=C/c3ccc(C4CCC(OC)CC4)c(F)c3F)CC2)c(F)c1] |

| No. |
|---|
| 287 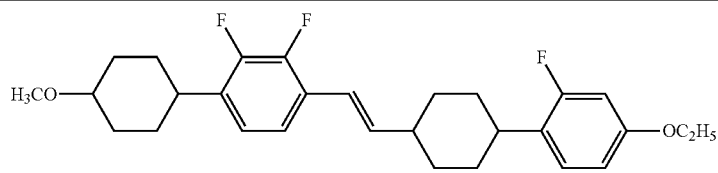 |
| 288 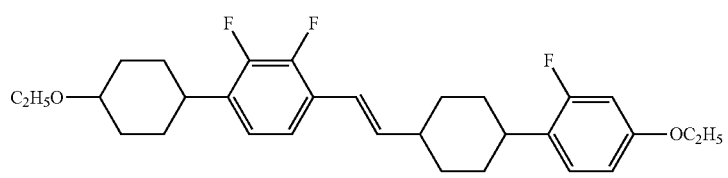 |
| 289 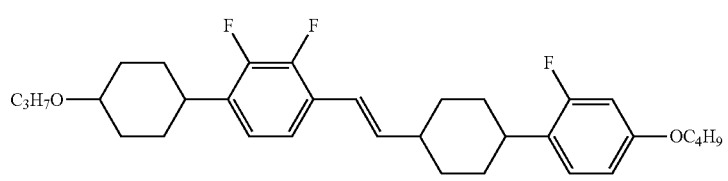 |
| 290 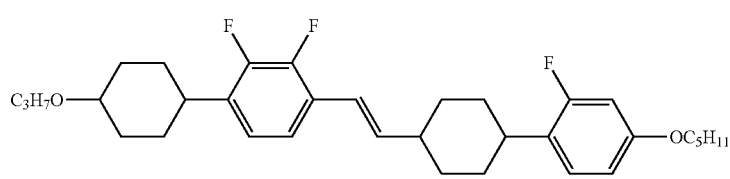 |
| 291 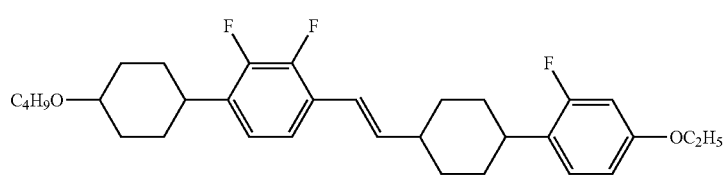 |
| 292 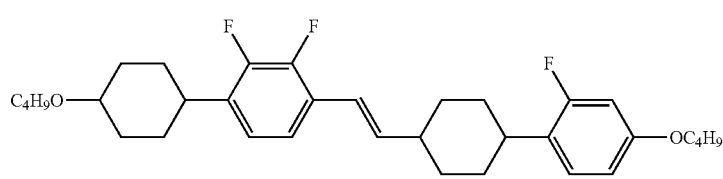 |
| 293 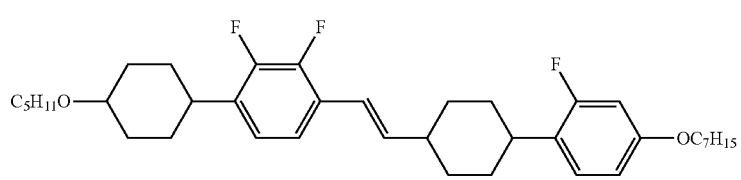 |
| 294 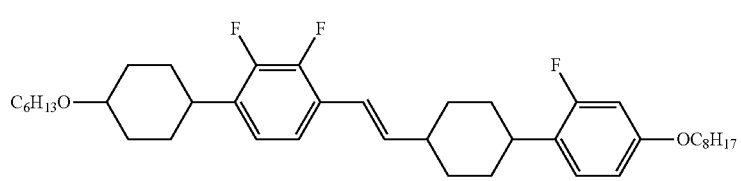 |
| 295 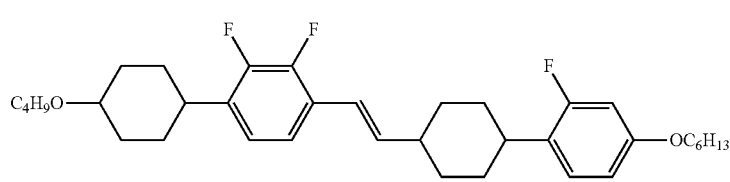 |

| No. | |
|---|---|
| 296 | 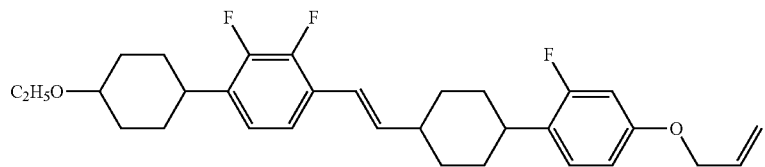 |
| 297 | 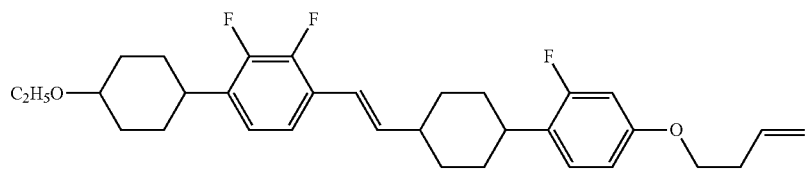 |
| 298 | 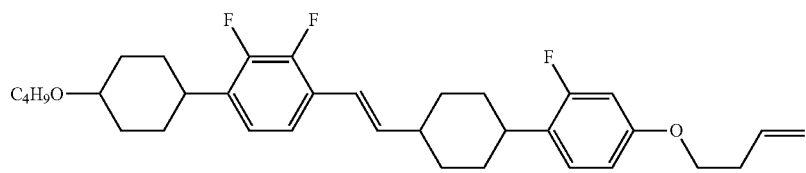 |
| 299 | 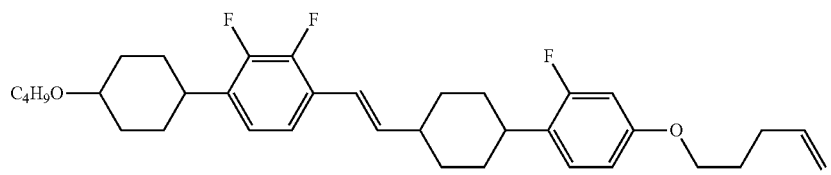 |
| 300 | 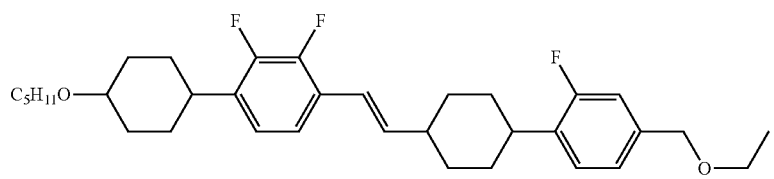 |
| 301 | 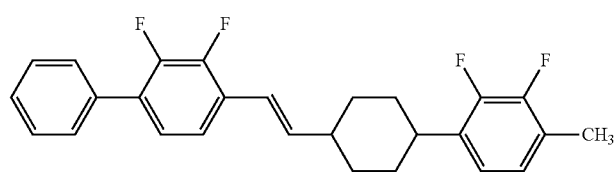 [SMILES: Cc1ccc(C2CCC(/C=C/c3ccc(-c4ccccc4)c(F)c3F)CC2)c(F)c1F] |
| 302 | 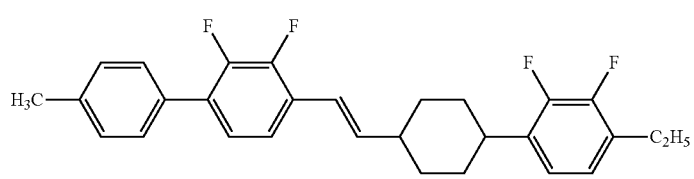 |
| 303 | 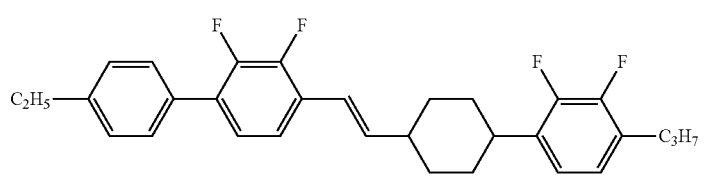 |

| No. | |
|---|---|
| 304 | 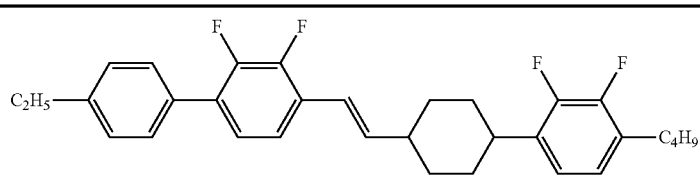 |
| 305 | 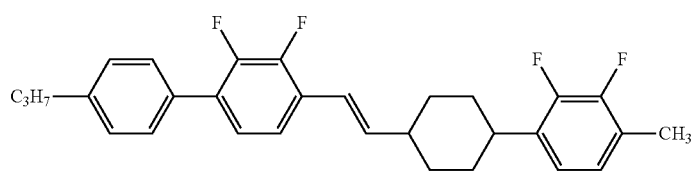 |
| 306 | 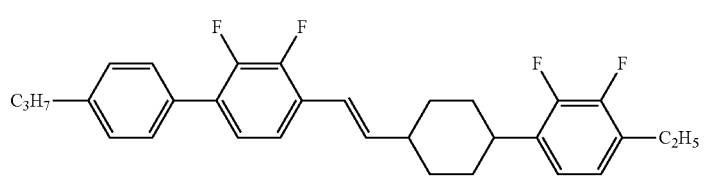 |
| 307 | 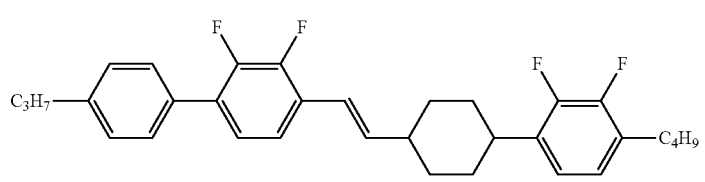 |
| 308 | 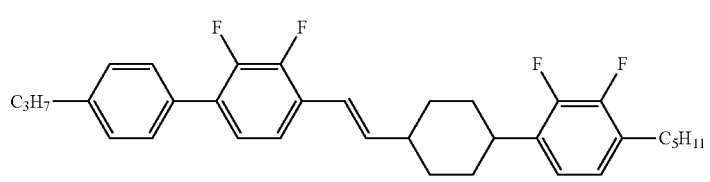 |
| 309 | 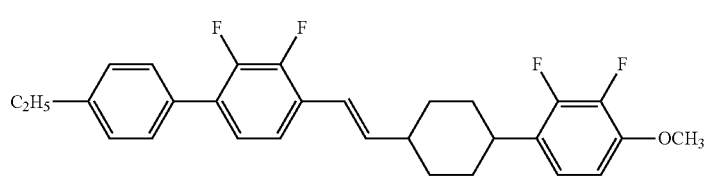 [SMILES: CCc1ccc(-c2ccc(/C=C/C3CCC(c4ccc(OC)c(F)c4F)CC3)c(F)c2F)cc1] |
| 310 | 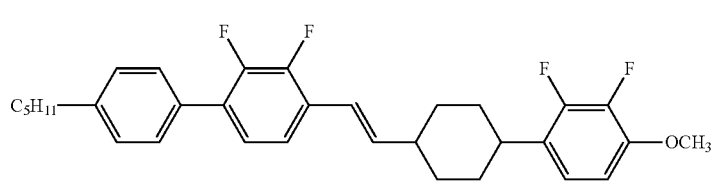 |
| 311 | 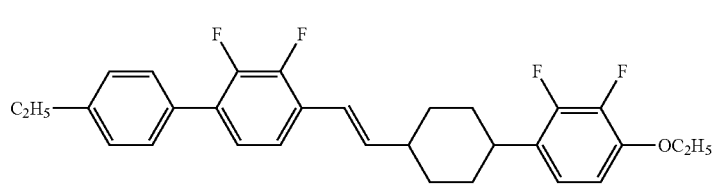 [SMILES: CCOc1ccc(C2CCC(/C=C/c3ccc(-c4ccc(CC)cc4)c(F)c3F)CC2)c(F)c1F] |
| 312 | 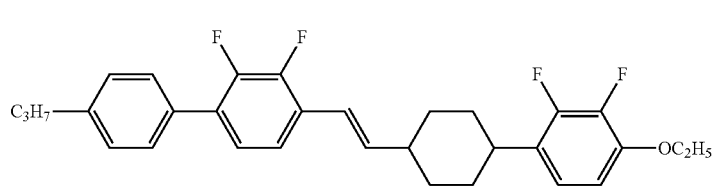 |

-continued
| No. | |
|---|---|
| 313 | 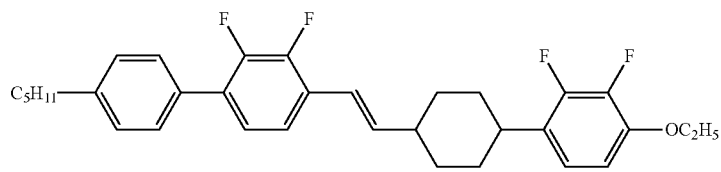 |
| 314 | 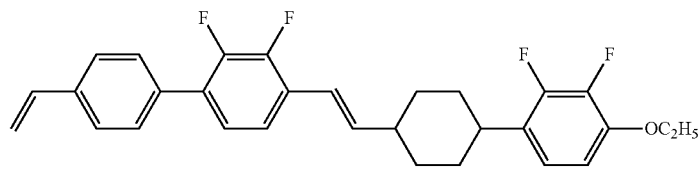 |
| 315 | 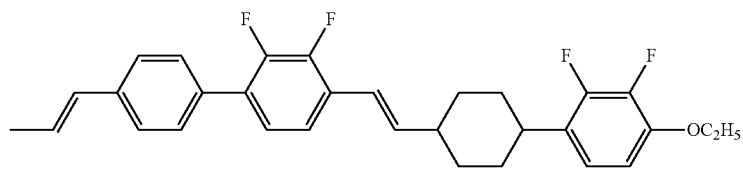 |
| 316 | 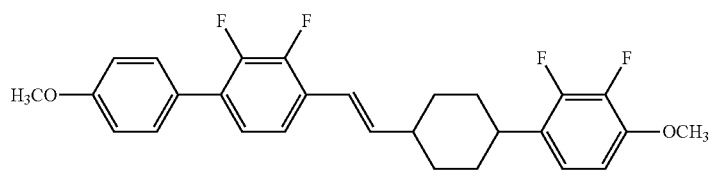 |
| 317 | 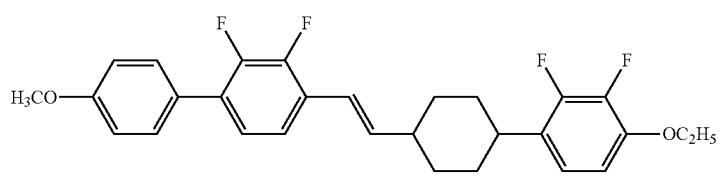 |
| 318 | 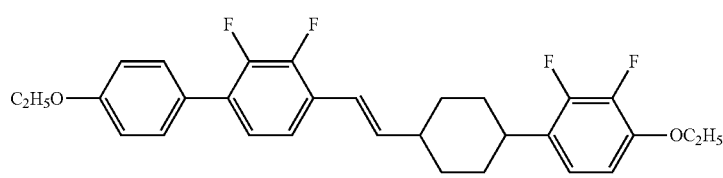 |
| 319 | 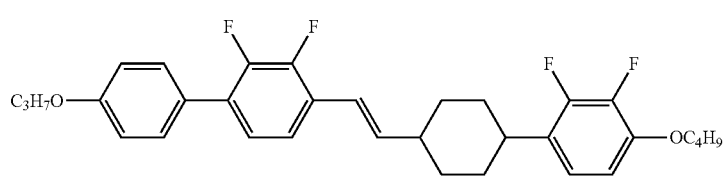 |
| 320 | 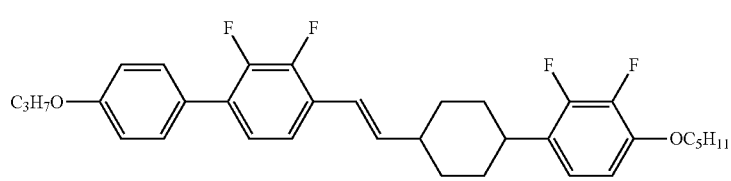 |

| No. | |
|---|---|
| 321 | 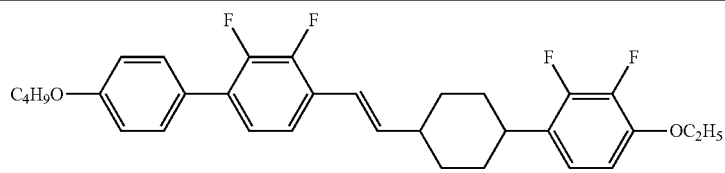 |
| 322 | 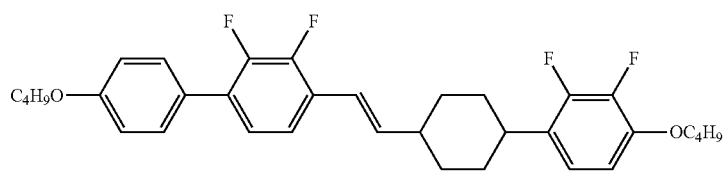 |
| 323 | 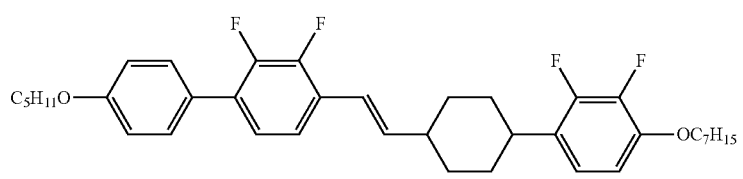 |
| 324 | 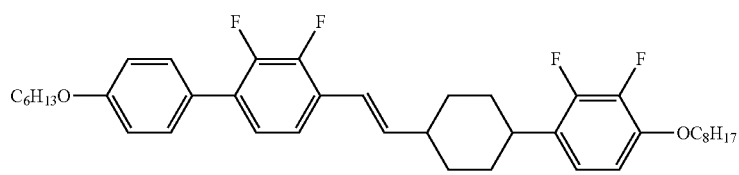 |
| 325 | 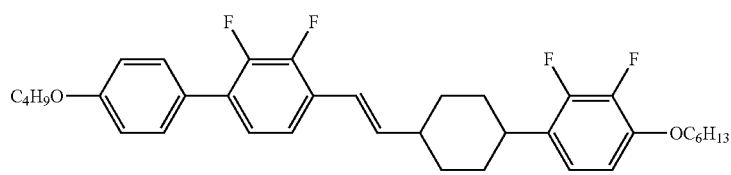 |
| 326 | 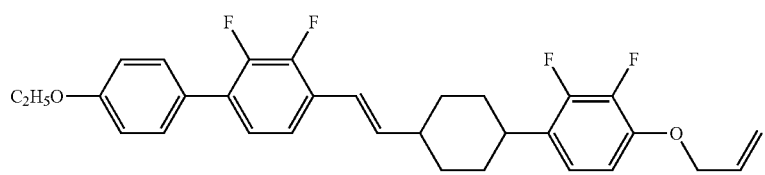 |
| 327 | 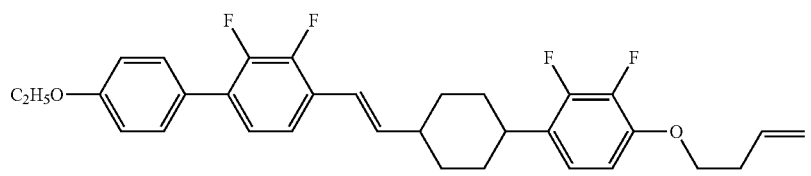 |
| 328 | 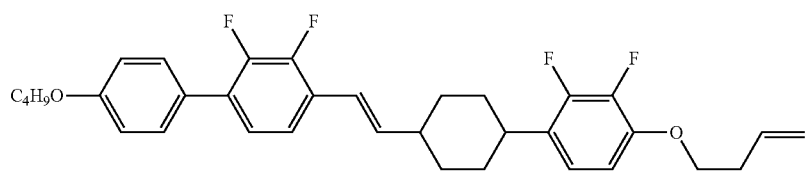 |
| 329 | 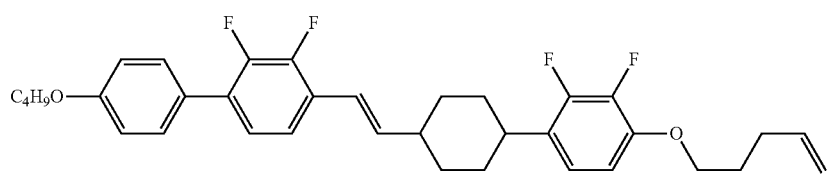 |

| No. | |
|---|---|
| 330 | 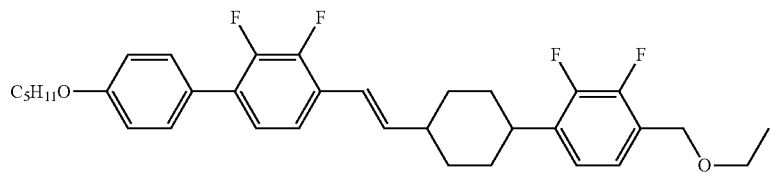 |
| 331 | 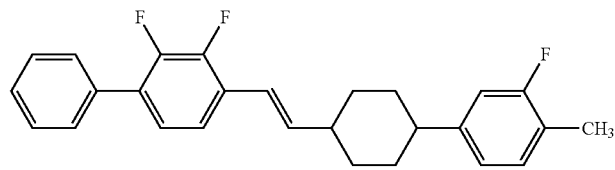 |
| 332 | 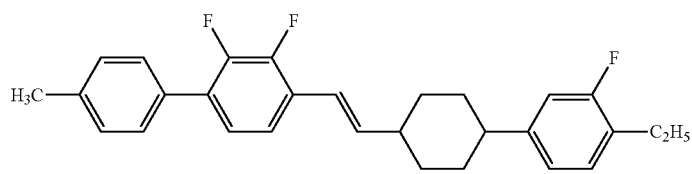 |
| 333 | 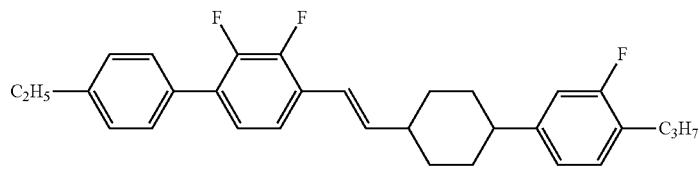 |
| 334 | 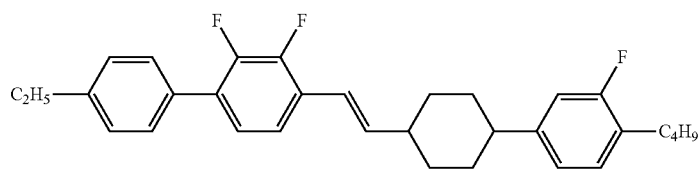 |
| 335 | 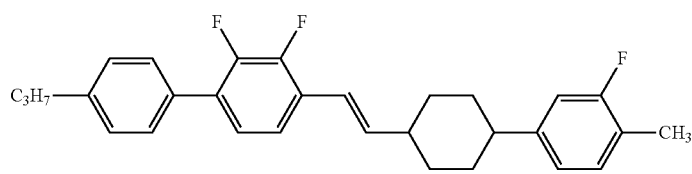 |
| 336 | 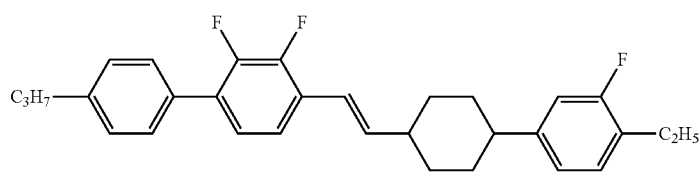 |
| 337 | 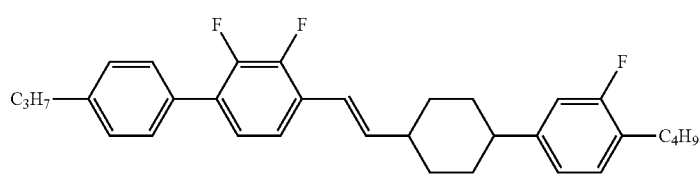 |

-continued
| No. | |
|---|---|
| 338 | 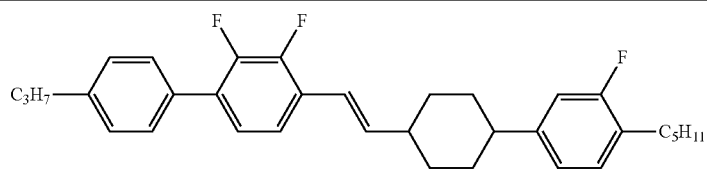 |
| 339 | 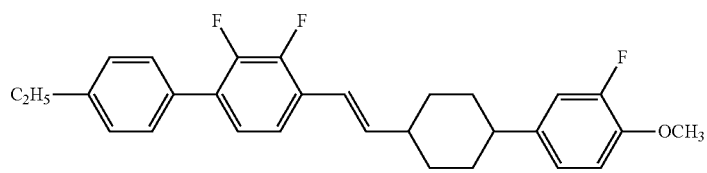 |
| 340 | 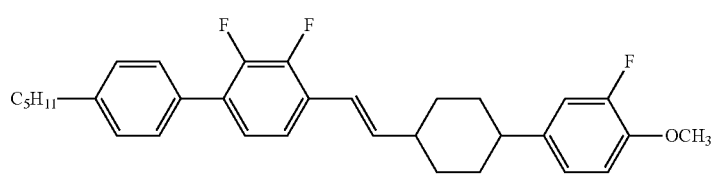 |
| 341 | 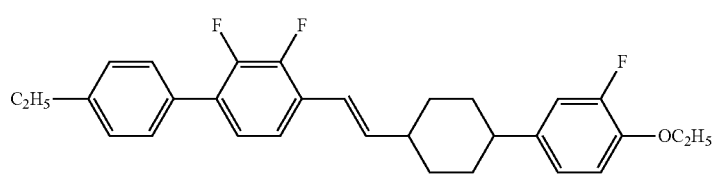 |
| 342 | 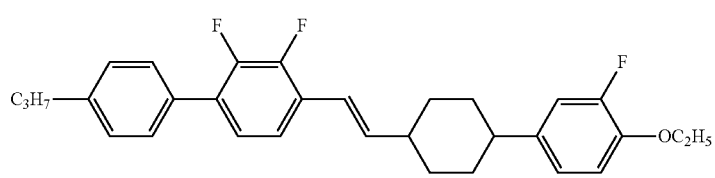 |
| 343 | 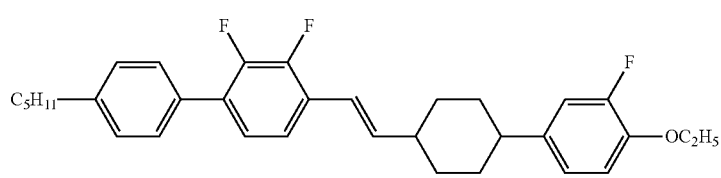 |
| 344 | 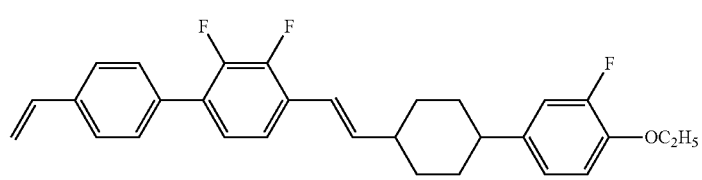 [SMILES: C=Cc1ccc(-c2ccc(/C=C/C3CCC(c4ccc(OCC)c(F)c4F)CC3)c(F)c2F)cc1] |
| 345 | 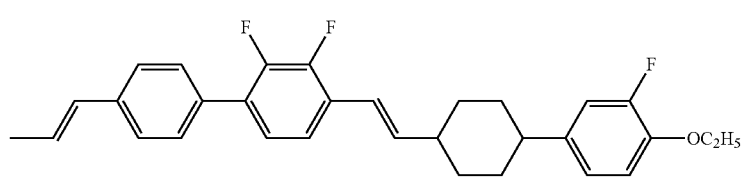 [SMILES: C/C=C/c1ccc(-c2ccc(/C=C/C3CCC(c4ccc(OCC)c(F)c4F)CC3)c(F)c2F)cc1] |
| 346 | 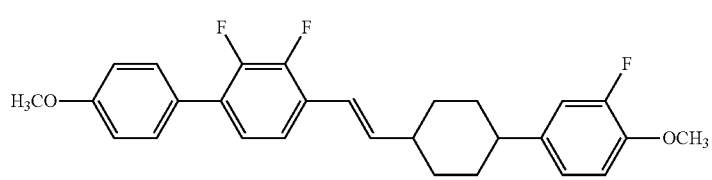 [SMILES: COc1ccc(-c2ccc(/C=C/C3CCC(c4ccc(OC)c(F)c4)CC3)c(F)c2F)cc1] |

| No. | |
|---|---|
| 347 | 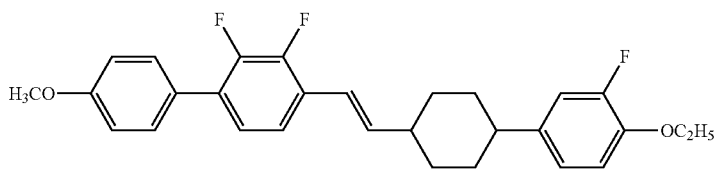 |
| 348 | 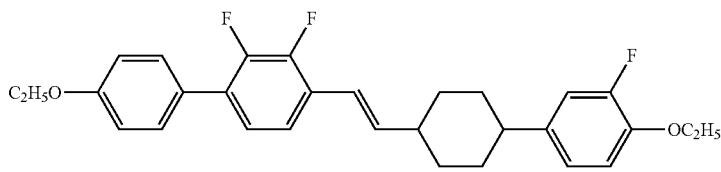 |
| 349 | 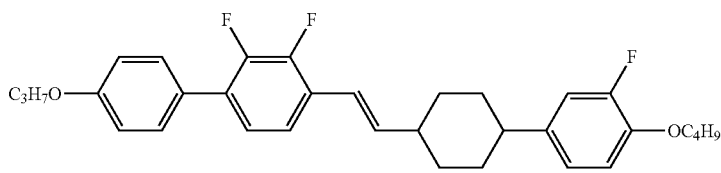 |
| 350 | 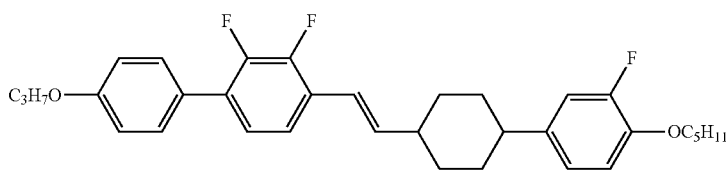 |
| 351 | 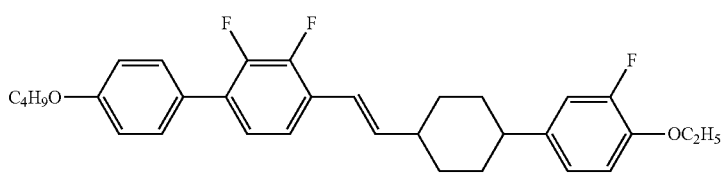 |
| 352 | 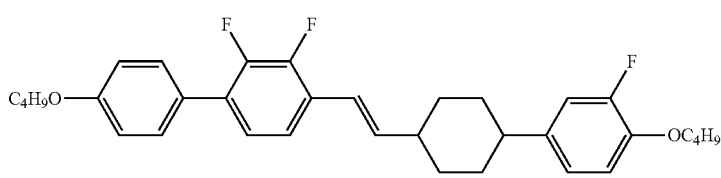 |
| 353 | 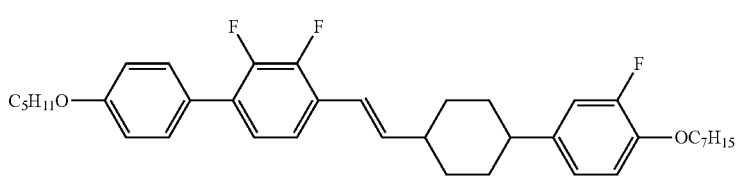 |
| 354 | 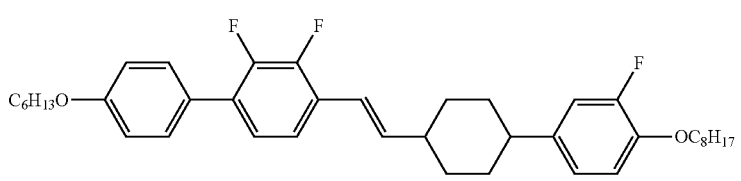 |

| No. | |
|---|---|
| 355 | 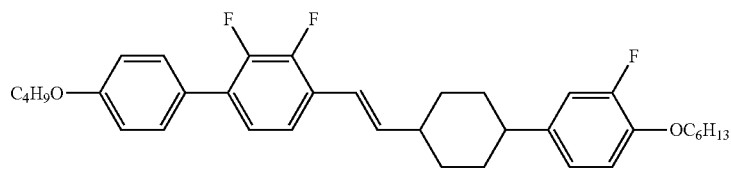 |
| 356 | 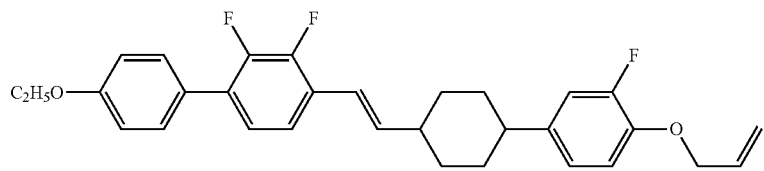 |
| 357 | 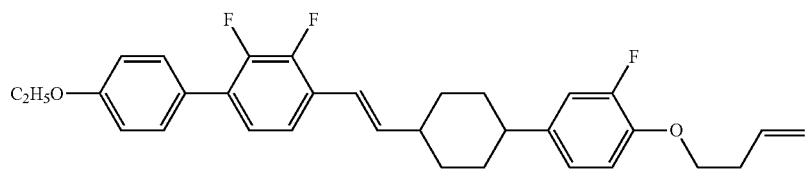 |
| 358 | 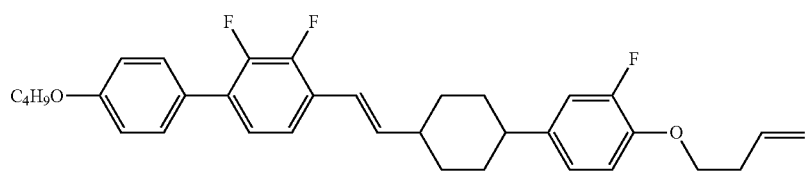 |
| 359 | 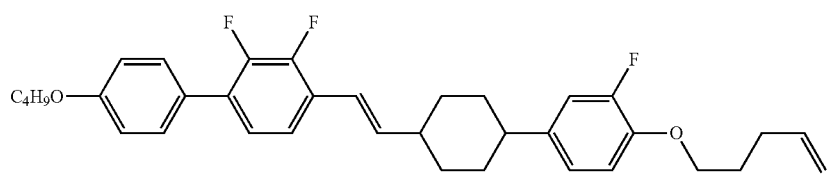 |
| 360 | 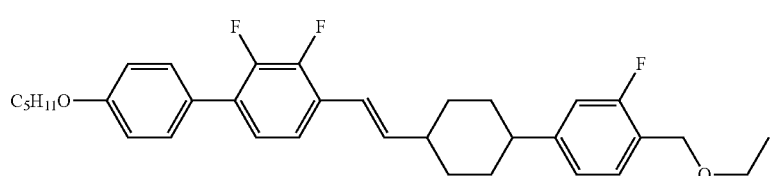 |
| 361 | 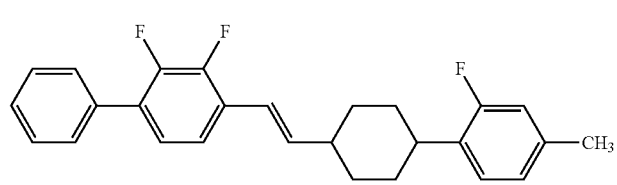 |
| 362 | 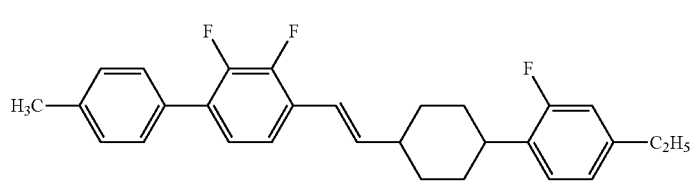 |

| No. |
|---|
| 363 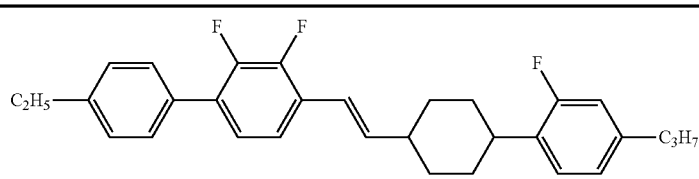 |
| 364 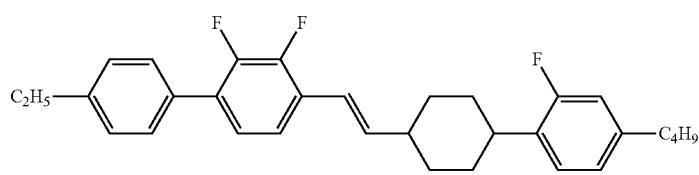 |
| 365 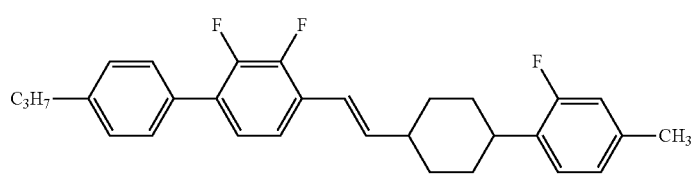 |
| 366 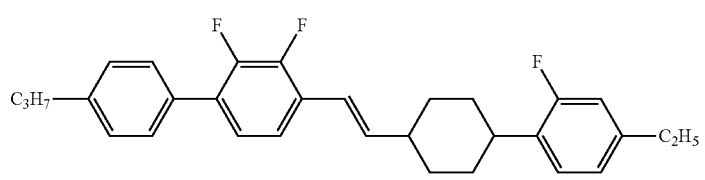 |
| 367 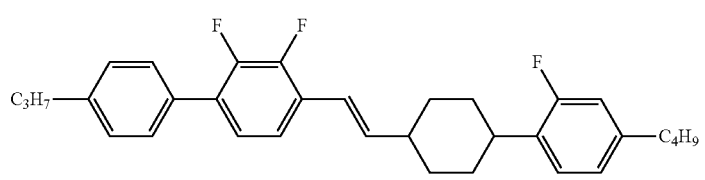 |
| 368 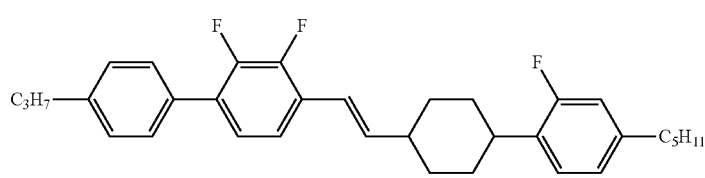 |
| 369 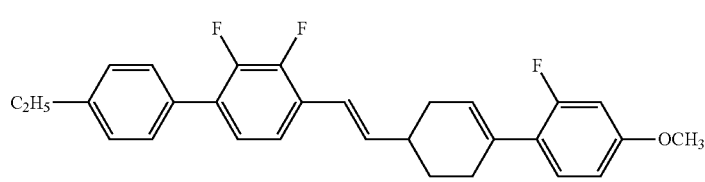 |
| 370 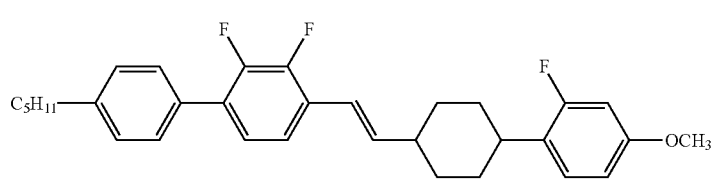 |
| 371 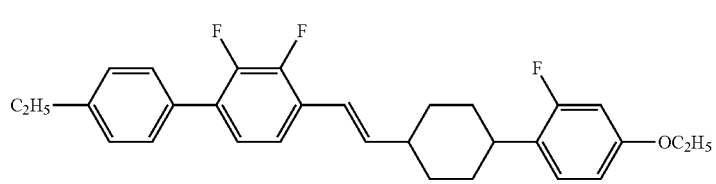 |

| No. | |
|---|---|
| 372 | 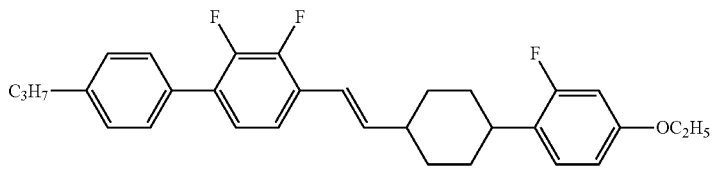 |
| 373 | 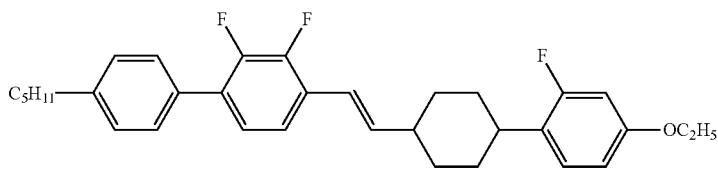 |
| 374 | 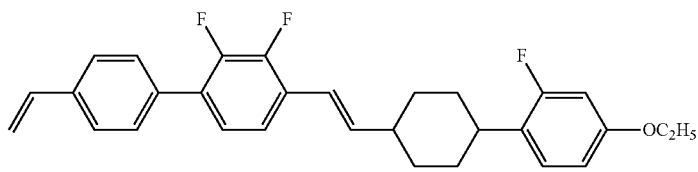 |
| 375 | 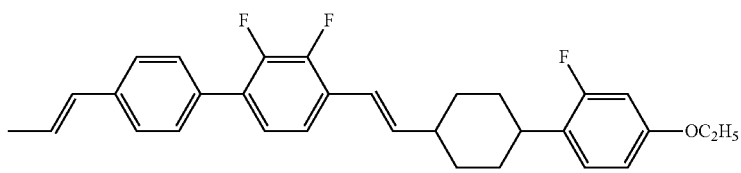 |
| 376 | 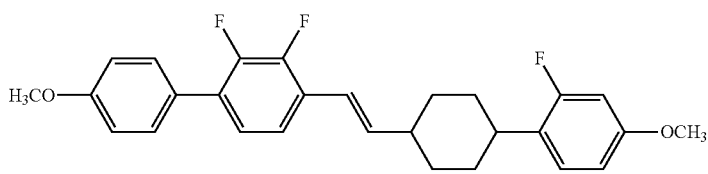 |
| 377 | 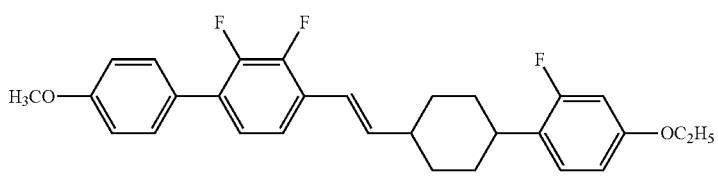 |
| 378 | 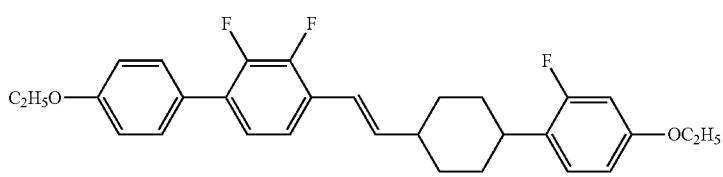 |
| 379 | 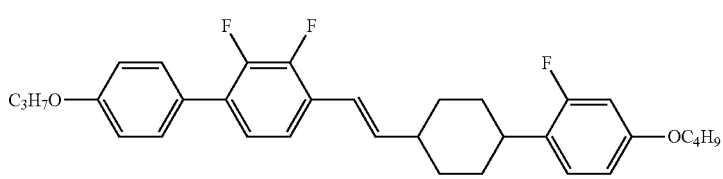 |

-continued
| No. | |
|---|---|
| 380 | 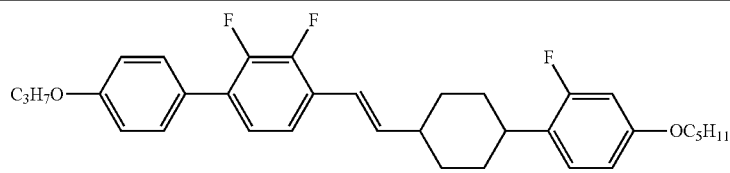 |
| 381 | 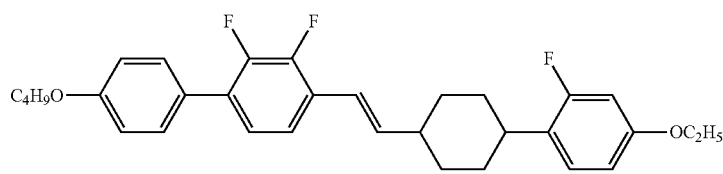 |
| 382 | 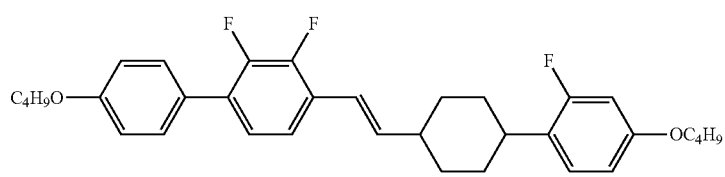 |
| 383 | 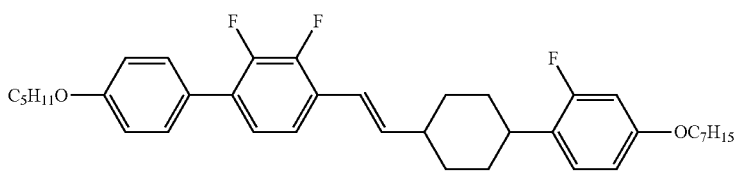 |
| 384 | 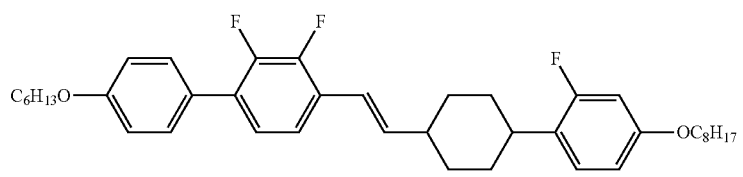 |
| 385 | 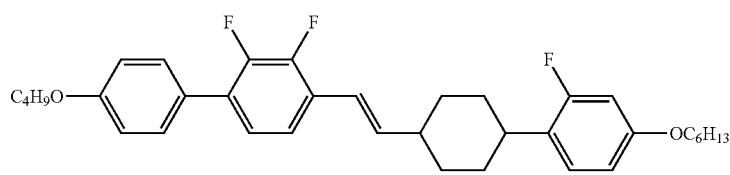 |
| 386 | 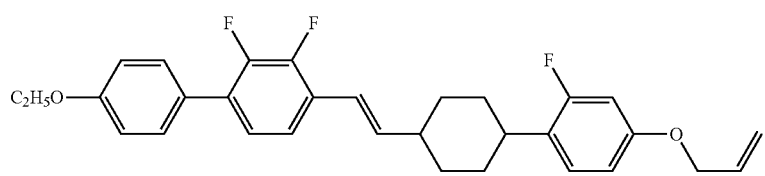 |
| 387 | 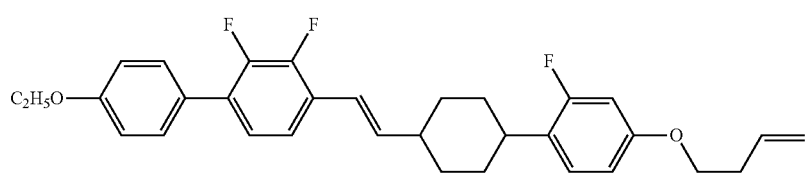 |
| 388 | 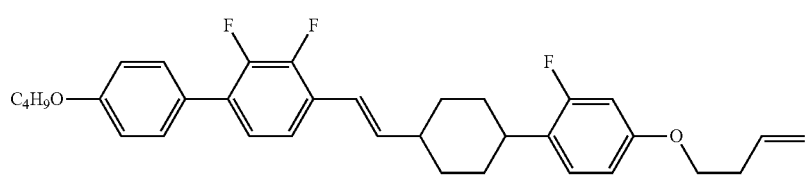 |

| No. | |
|---|---|
| 389 | 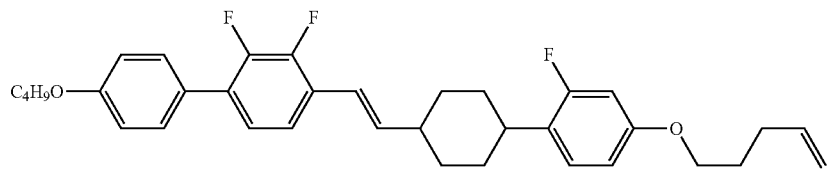 |
| 390 | 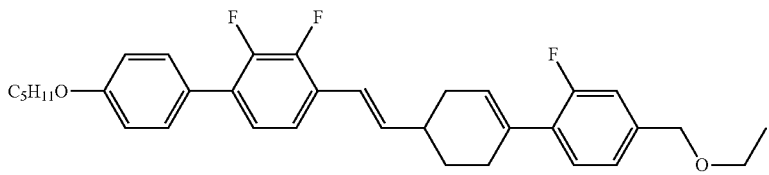 |
| 391 | 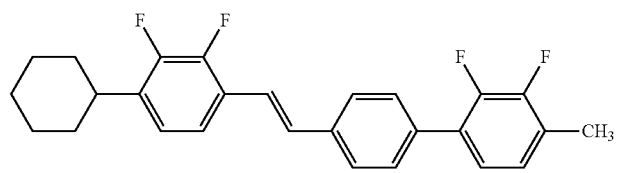 [SMILES: Cc1ccc(-c2ccc(/C=C/c3ccc(C4CCCCC4)c(F)c3F)cc2)c(F)c1F] |
| 392 | 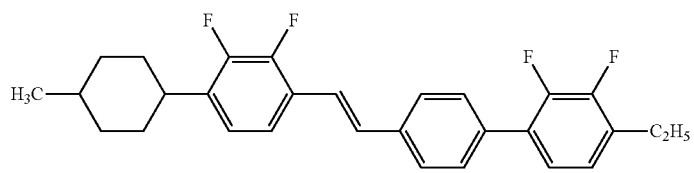 [SMILES: CCc1ccc(-c2ccc(/C=C/c3ccc(C4CCC(C)CC4)c(F)c3F)cc2)c(F)c1F] |
| 393 | 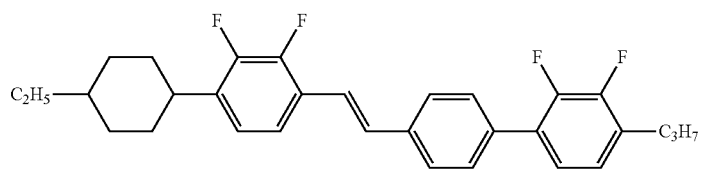 |
| 394 | 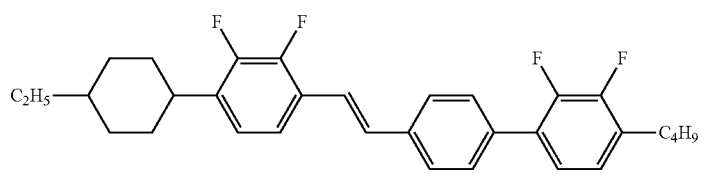 |
| 395 | 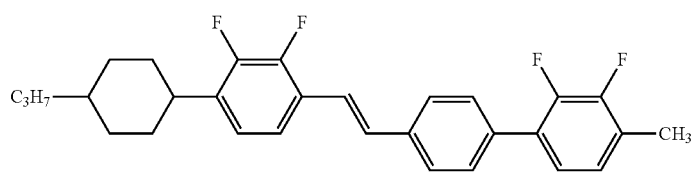 |
| 396 | 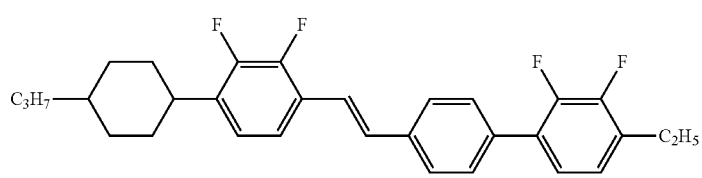 |

| No. | |
|---|---|
| 397 | 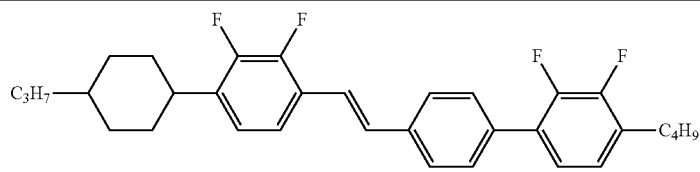 |
| 398 | 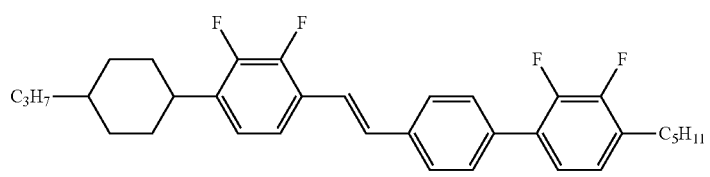 |
| 399 | 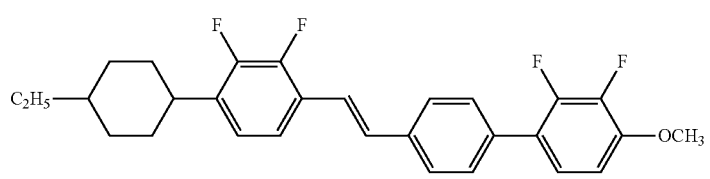 |
| 400 | 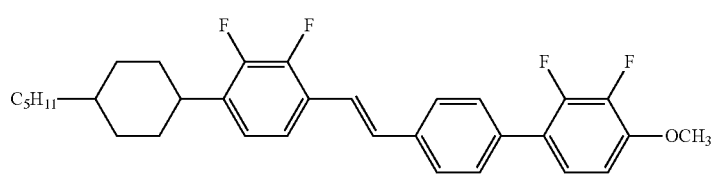 |
| 401 | 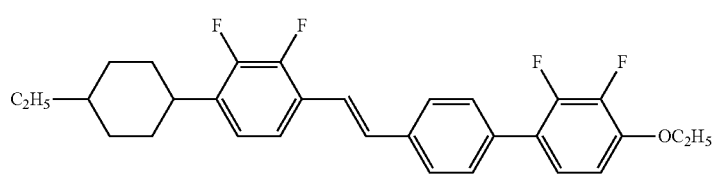 [SMILES: CCOc1ccc(-c2ccc(/C=C/c3ccc(C4CCC(CC)CC4)c(F)c3F)cc2)c(F)c1F] |
| 402 | 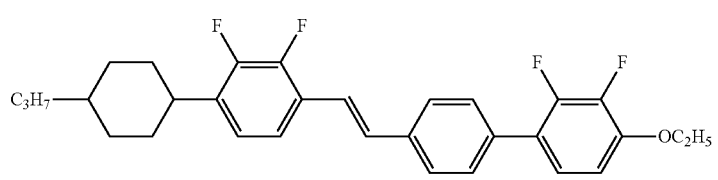 |
| 403 | 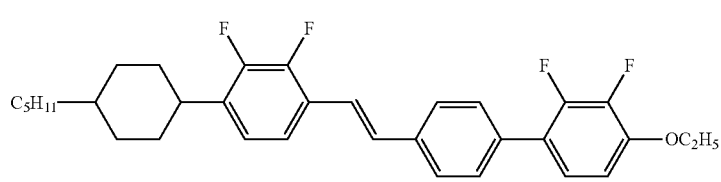 |
| 404 | 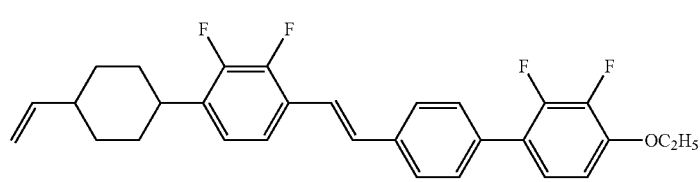 |
| 405 | 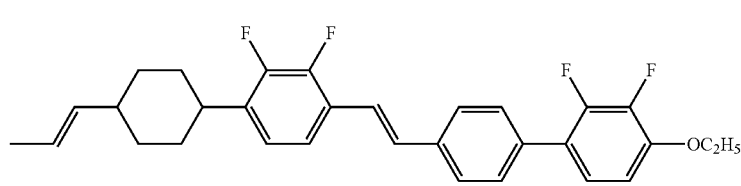 |

| No. | |
|---|---|
| 406 | 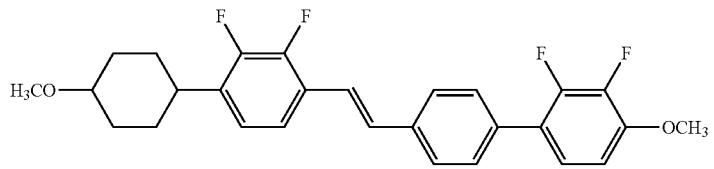 |
| 407 | 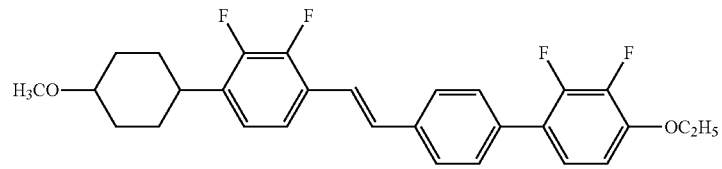 [SMILES: CCOc1ccc(-c2ccc(/C=C/c3ccc(C4CCC(OC)CC4)c(F)c3F)cc2)c(F)c1F] |
| 408 | 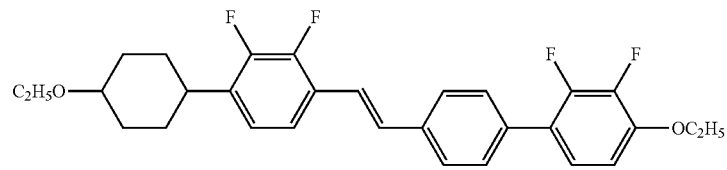 |
| 409 | 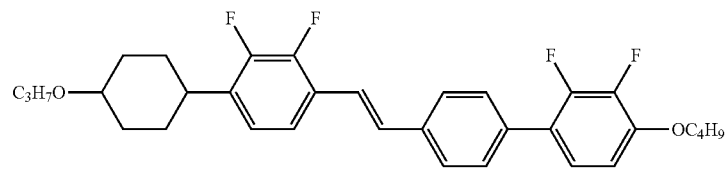 |
| 410 | 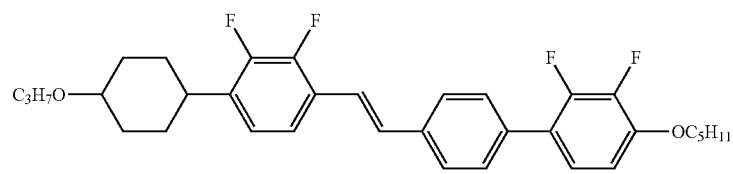 |
| 411 | 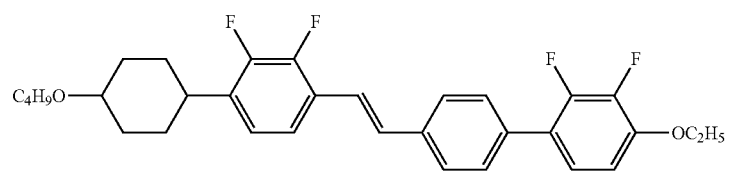 |
| 412 | 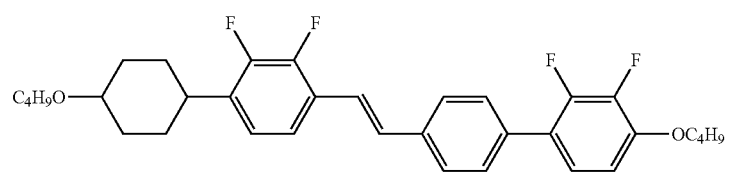 |
| 413 | 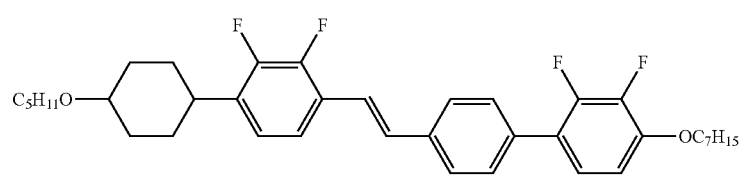 |

| No. | |
|---|---|
| 414 | 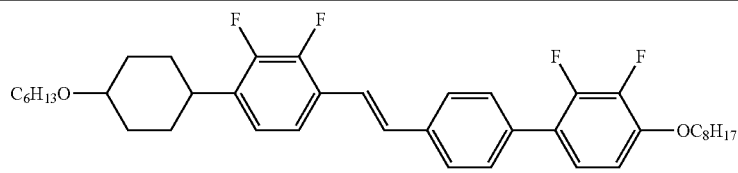 |
| 415 | 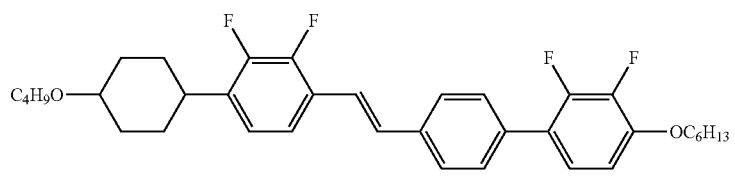 |
| 416 | 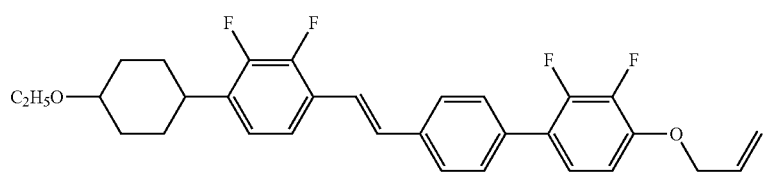 |
| 417 | 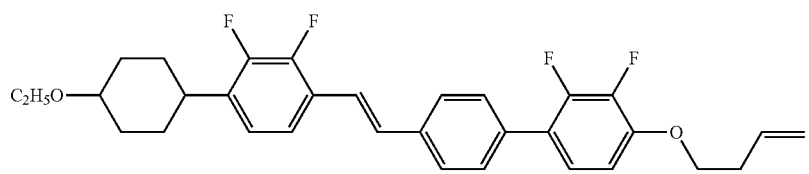 |
| 418 | 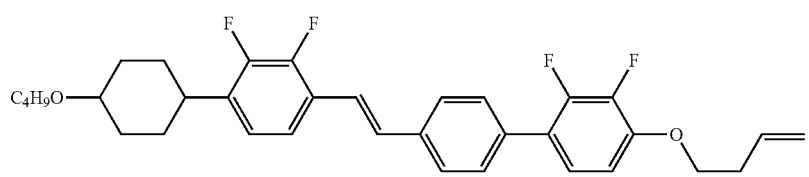 |
| 419 | 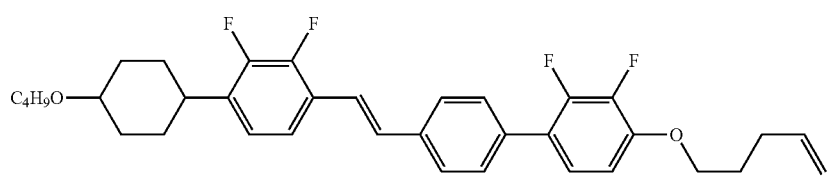 |
| 420 | 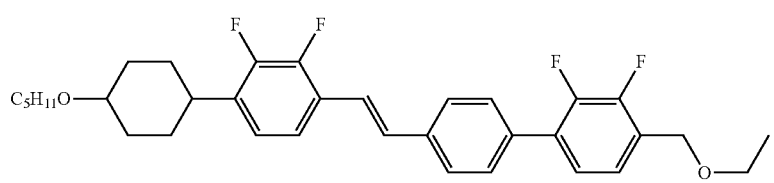 |
| 421 | 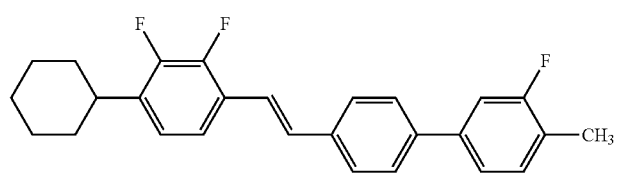 [SMILES: Cc1ccc(-c2ccc(/C=C/c3ccc(C4CCCCC4)c(F)c3F)cc2)cc1F] |
| 422 | 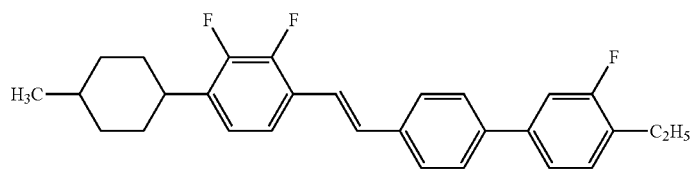 |

-continued
| No. | |
|---|---|
| 423 | 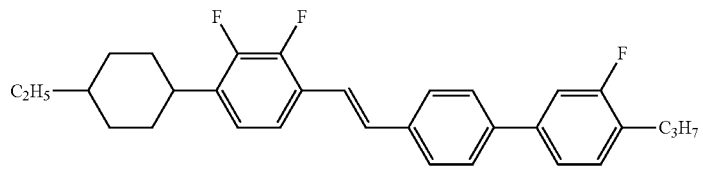 |
| 424 | 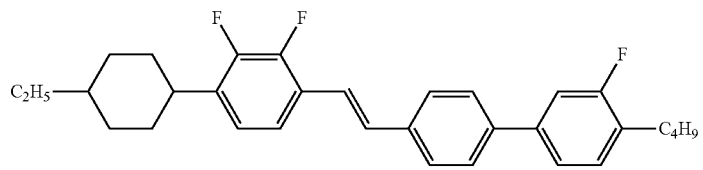 |
| 425 | 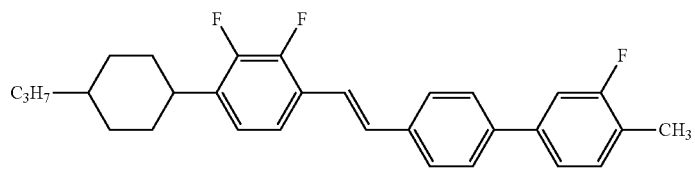 |
| 426 | 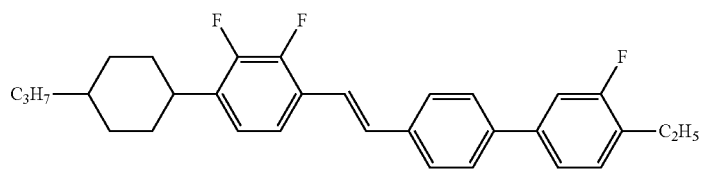 |
| 427 | 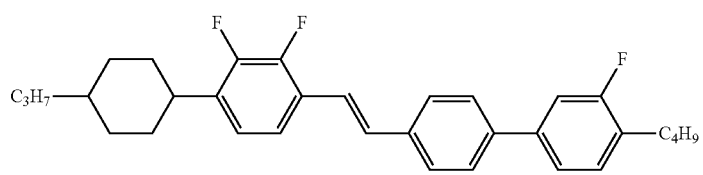 |
| 428 | 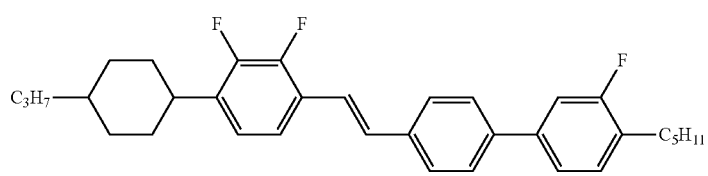 |
| 429 | 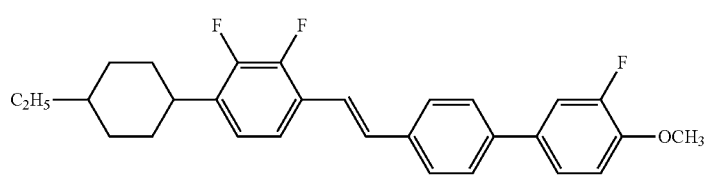 |
| 430 | 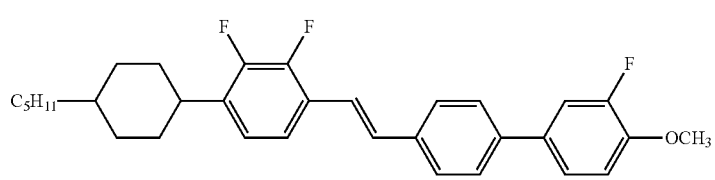 |

| No. | |
|---|---|
| 431 | 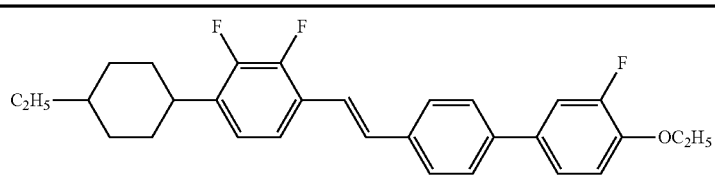 |
| 432 | 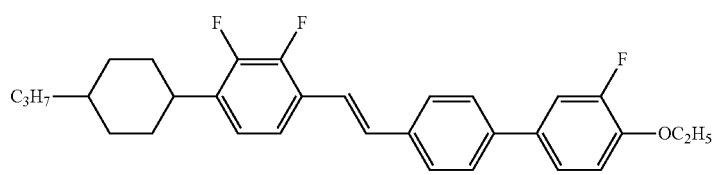 |
| 433 | 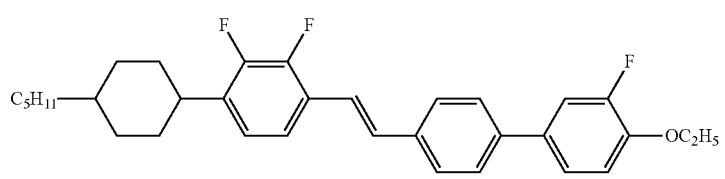 |
| 434 | 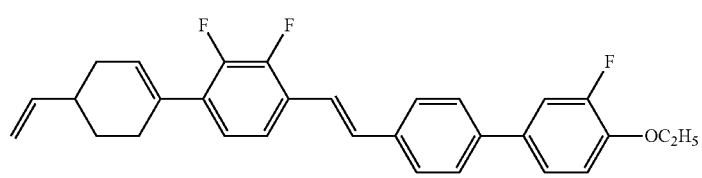 |
| 435 | 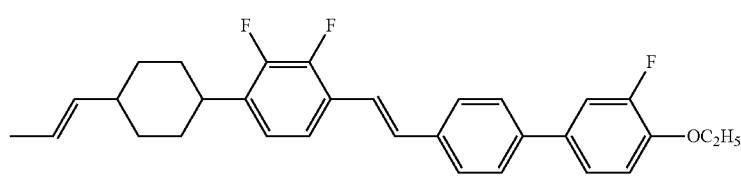 [SMILES: C/C=C/C1CCC(c2ccc(/C=C/c3ccc(-c4ccc(OCC)c(F)c4)cc3)c(F)c2F)CC1] |
| 436 | 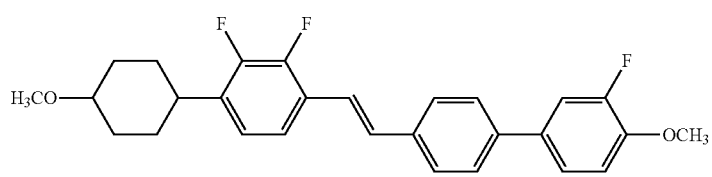 |
| 437 | 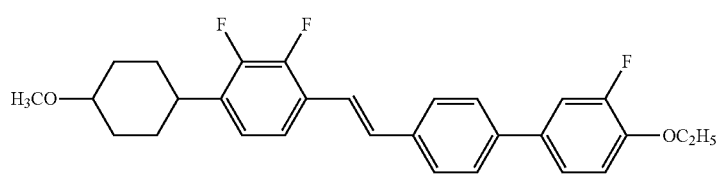 [SMILES: CCOc1ccc(-c2ccc(/C=C/c3ccc(C4CCC(OC)CC4)c(F)c3F)cc2)cc1F] |
| 438 | 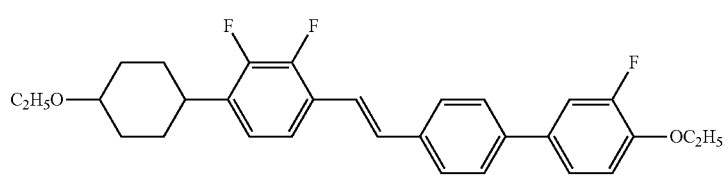 |
| 439 | 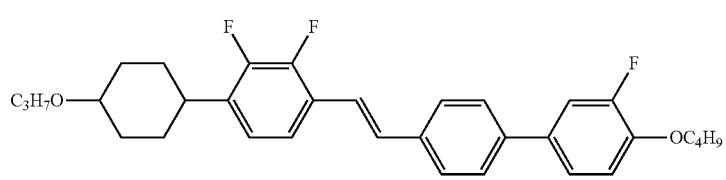 |

-continued
| No. | |
|---|---|
| 440 | 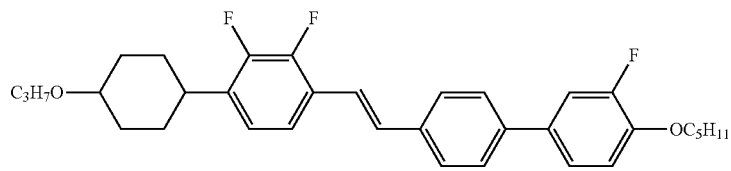 |
| 441 | 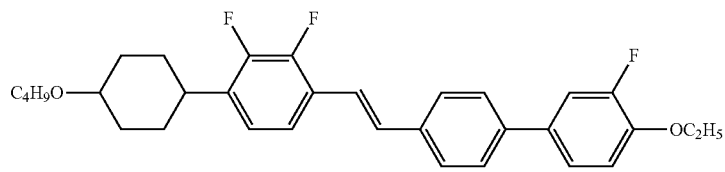 |
| 442 | 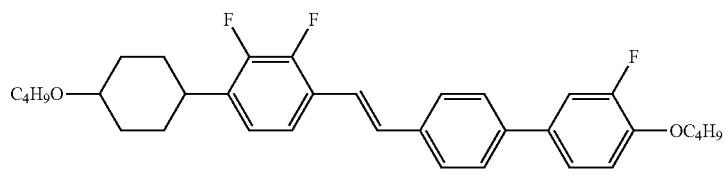 |
| 443 | 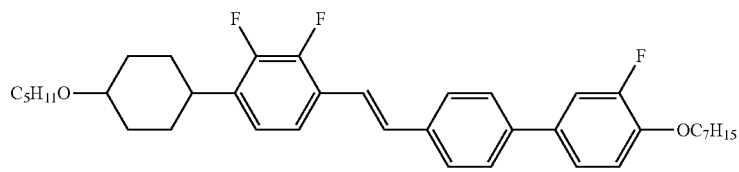 |
| 444 | 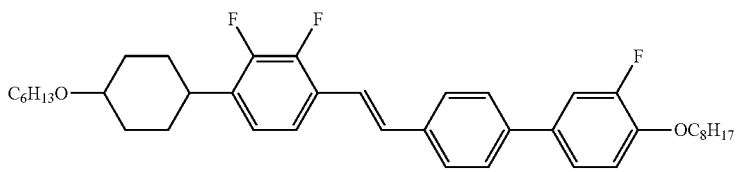 |
| 445 | 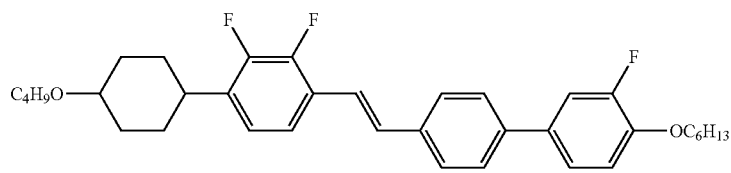 |
| 446 | 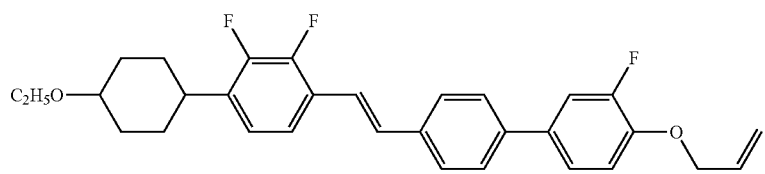 |
| 447 | 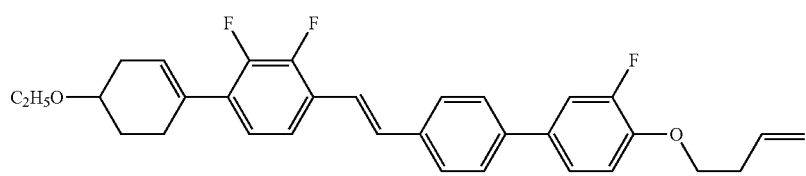 |

| No. | |
|---|---|
| 448 | 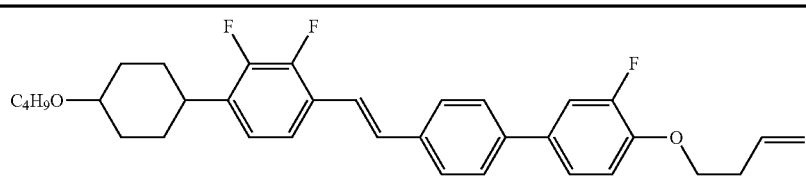 |
| 449 | 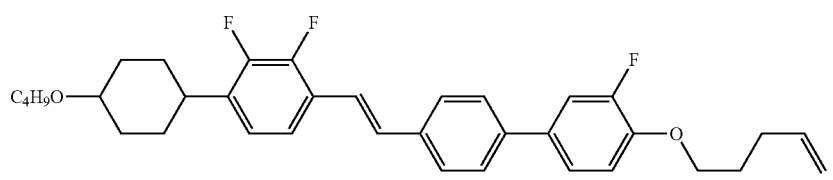 |
| 450 | 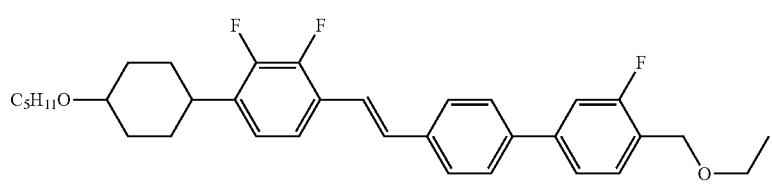 |
| 451 | 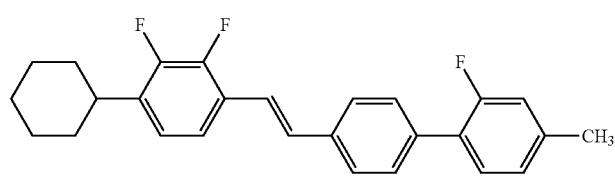 [SMILES: Cc1ccc(-c2ccc(/C=C/c3ccc(C4CCCCC4)c(F)c3F)cc2)c(F)c1] |
| 452 | 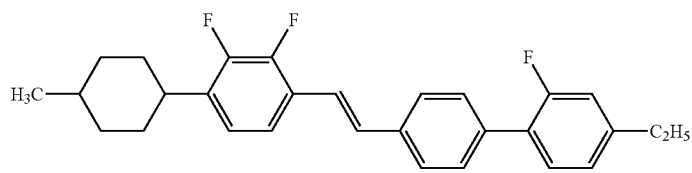 |
| 453 | 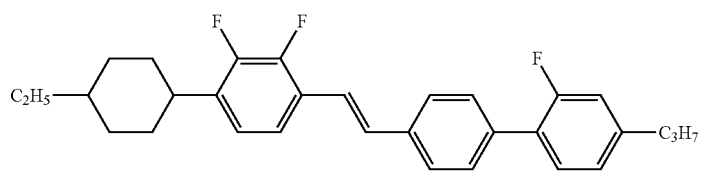 |
| 454 | 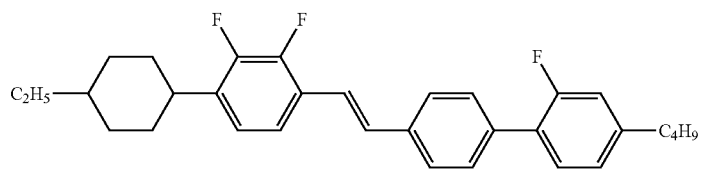 |
| 455 | 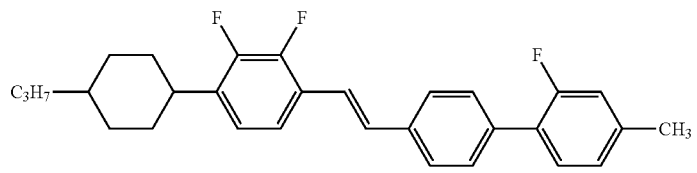 |
| 456 | 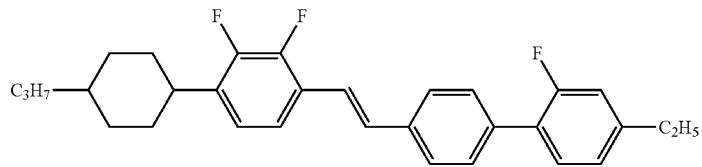 |

-continued
| No. | |
|---|---|
| 457 | 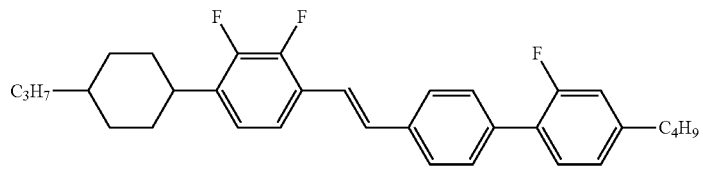 |
| 458 | 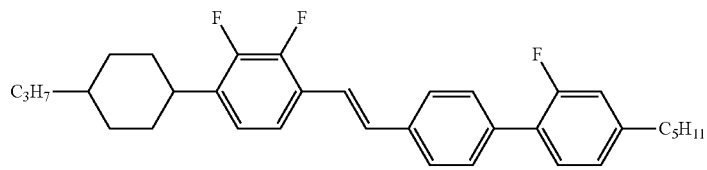 |
| 459 | 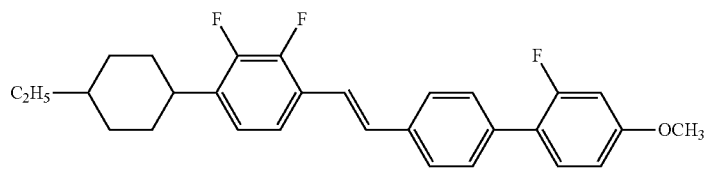 |
| 460 | 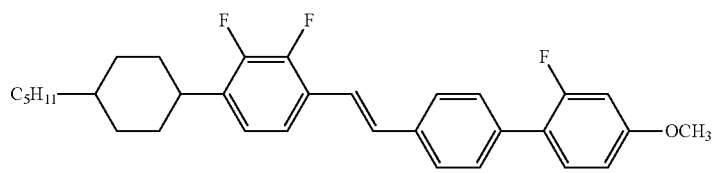 |
| 461 | 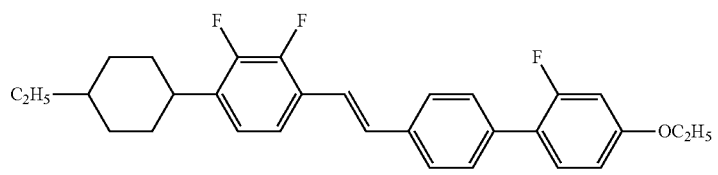 [SMILES: CCOc1ccc(-c2ccc(/C=C/c3ccc(C4CCC(CC)CC4)c(F)c3F)cc2)c(F)c1] |
| 462 | 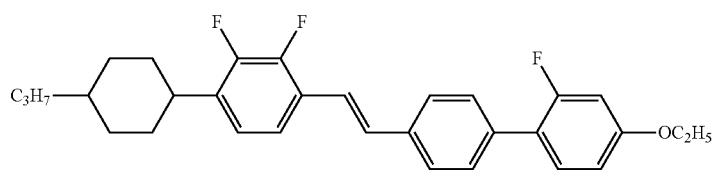 |
| 463 | 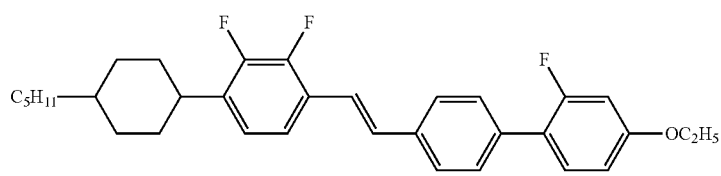 |
| 464 | 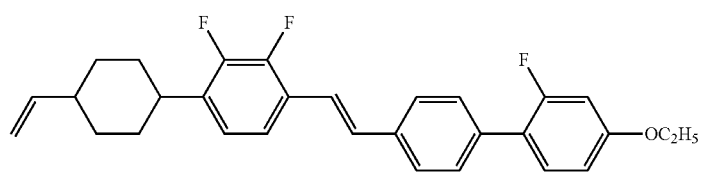 [SMILES: C=CC1CCC(c2ccc(/C=C/c3ccc(-c4ccc(OCC)cc4F)cc3)c(F)c2F)CC1] |

-continued
| No. | |
|---|---|
| 465 | 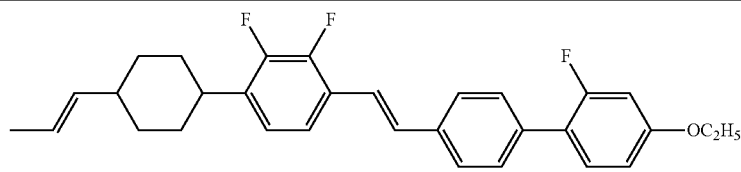 |
| 466 | 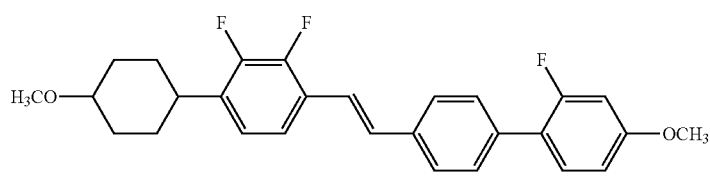 [SMILES: COc1ccc(-c2ccc(/C=C/c3ccc(C4CCC(OC)CC4)c(F)c3F)cc2)c(F)c1] |
| 467 | 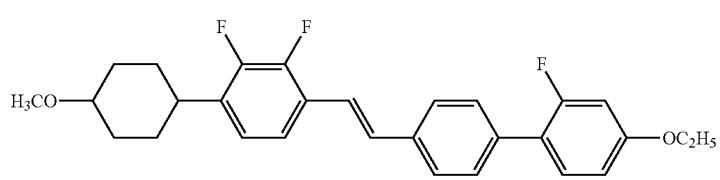 [SMILES: CCOc1ccc(-c2ccc(/C=C/c3ccc(C4CCC(OC)CC4)c(F)c3F)cc2)c(F)c1] |
| 468 | 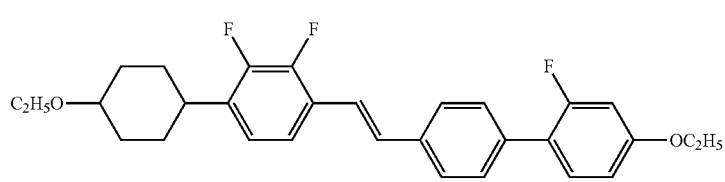 |
| 469 | 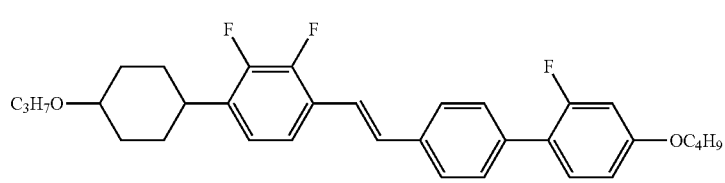 |
| 470 | 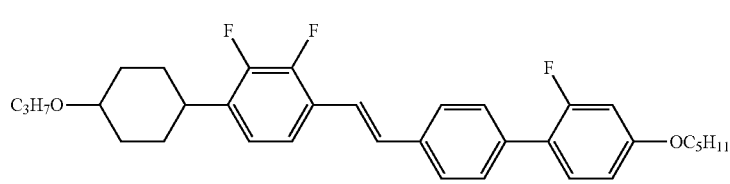 |
| 471 | 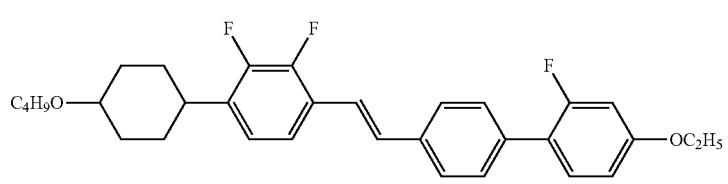 |
| 472 | 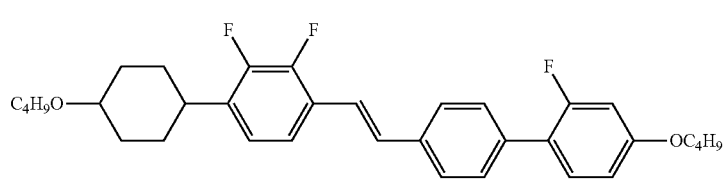 |
| 473 | 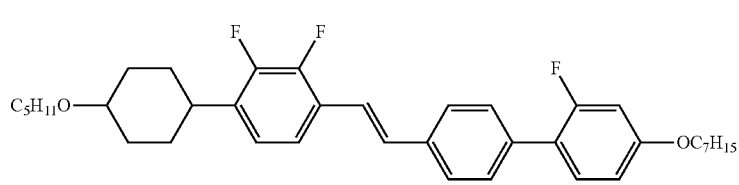 |

| No. | |
|---|---|
| 474 | 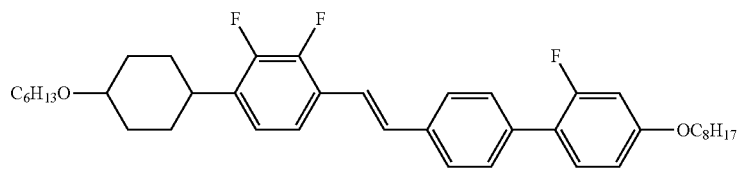 |
| 475 | 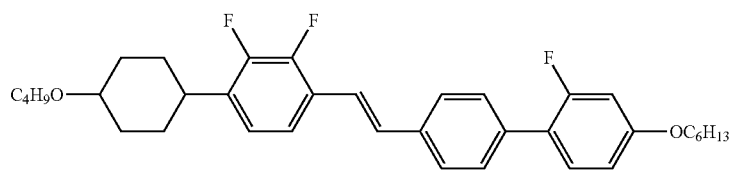 |
| 476 | 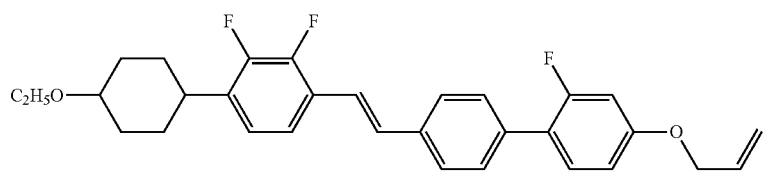 |
| 477 | 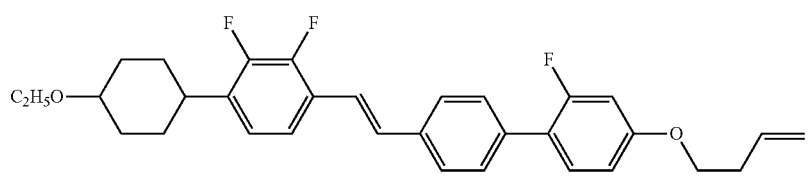 |
| 478 | 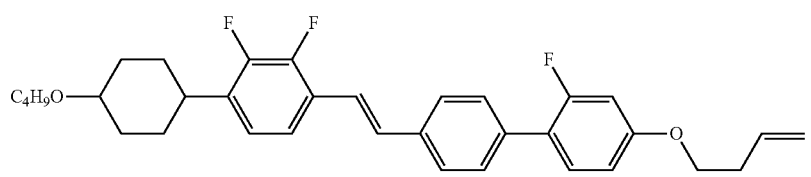 |
| 479 | 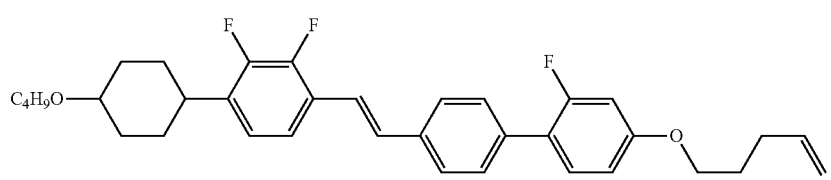 |
| 480 | 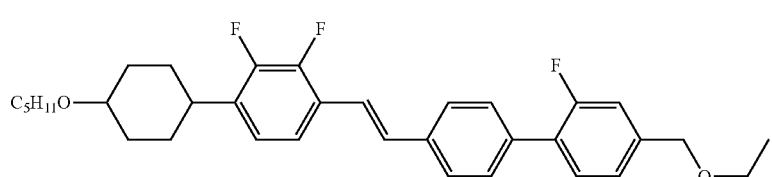 |
| 481 | 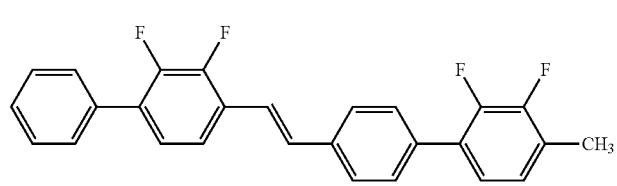 |

-continued
| No. | |
|---|---|
| 482 | 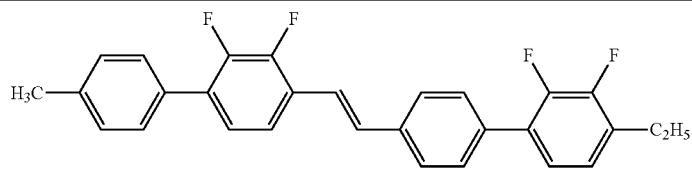 |
| 483 | 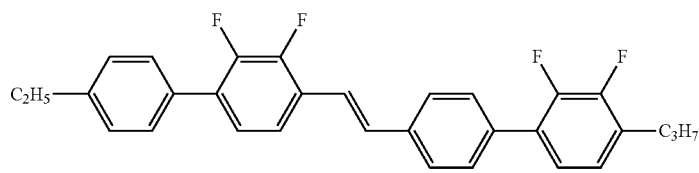 |
| 484 | 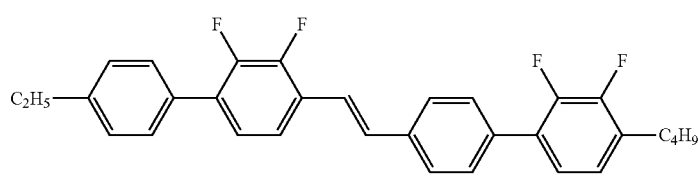 |
| 485 | 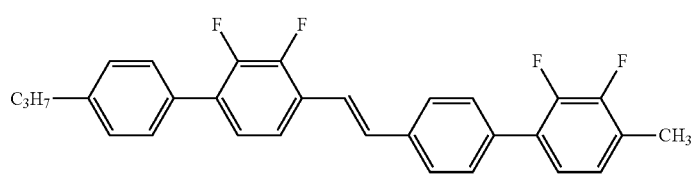 |
| 486 | 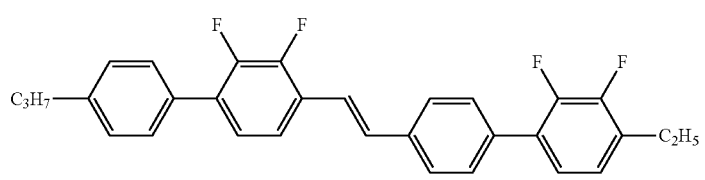 |
| 487 | 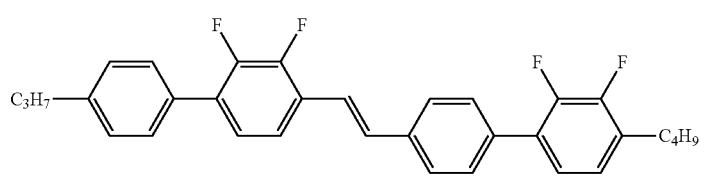 |
| 488 | 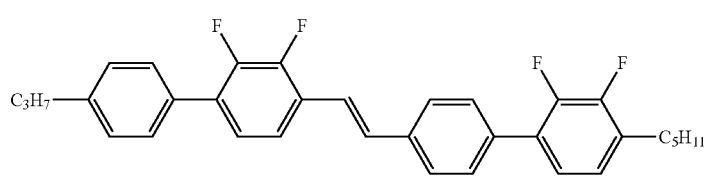 |
| 489 | 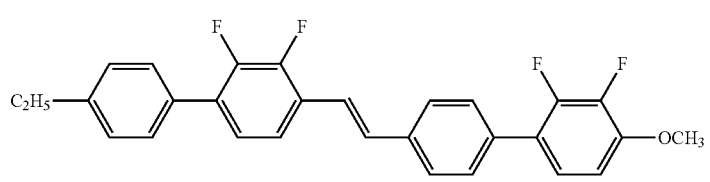 |
| 490 | 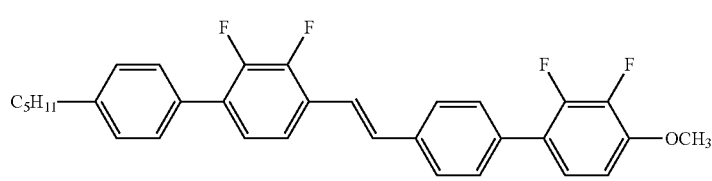 |

| No. | |
|---|---|
| 491 | 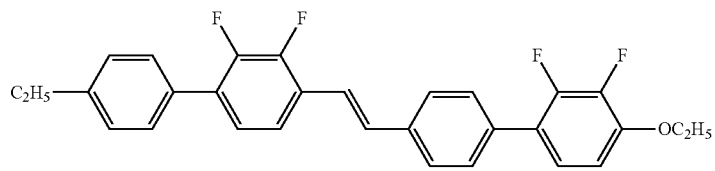 [SMILES: CCOc1ccc(-c2ccc(/C=C/c3ccc(-c4ccc(CC)cc4)c(F)c3F)cc2)c(F)c1F] |
| 492 | 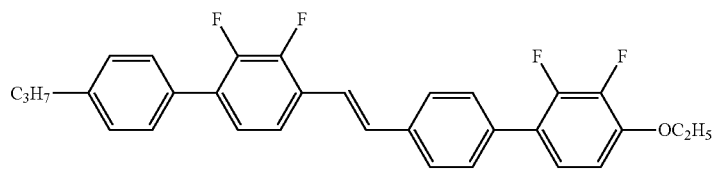 |
| 493 | 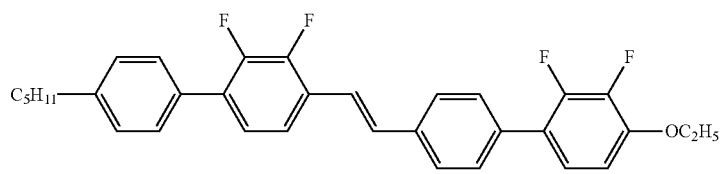 |
| 494 | 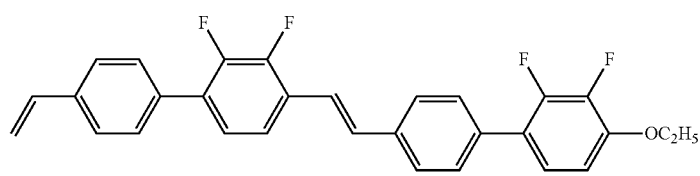 |
| 495 | 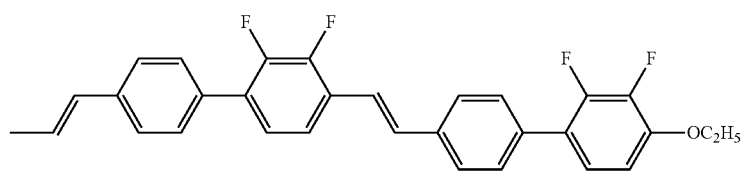 [SMILES: C/C=C/c1ccc(-c2ccc(/C=C/c3ccc(-c4ccc(OCC)c(F)c4F)cc3)c(F)c2F)cc1] |
| 496 | 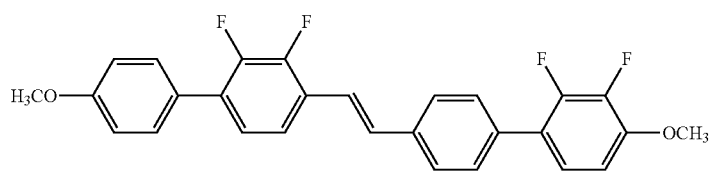 |
| 497 | 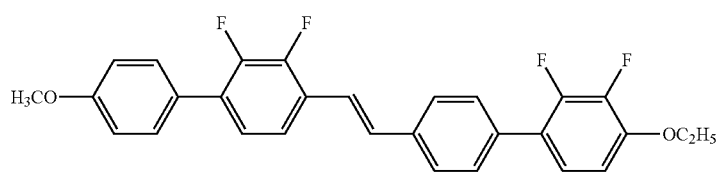 [SMILES: CCOc1ccc(-c2ccc(/C=C/c3ccc(-c4ccc(OC)cc4)c(F)c3F)cc2)c(F)c1F] |
| 498 | 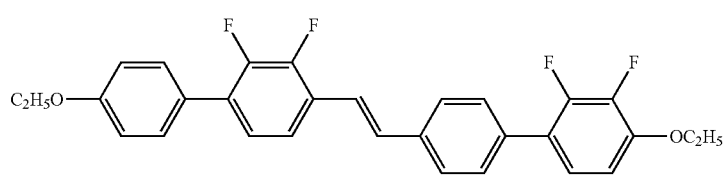 |

| No. | |
|---|---|
| 499 | 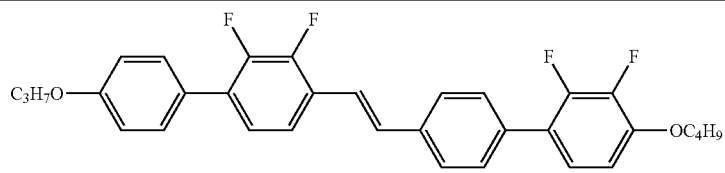 |
| 500 | 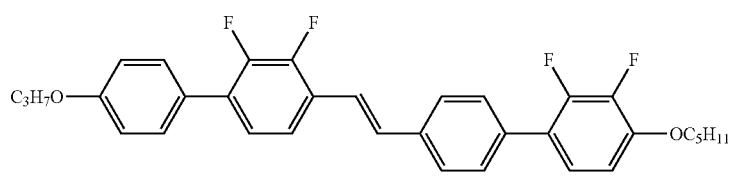 |
| 501 | 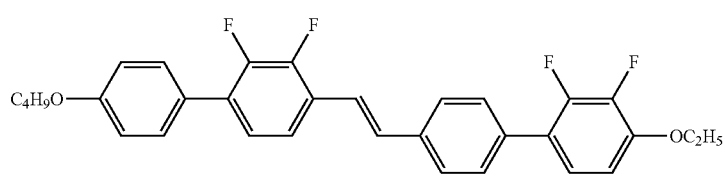 |
| 502 | 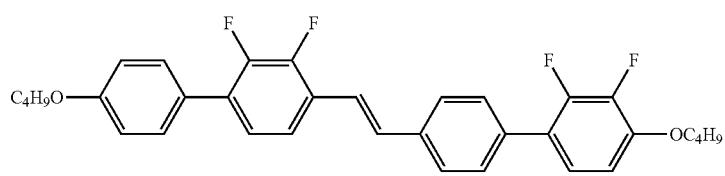 |
| 503 | 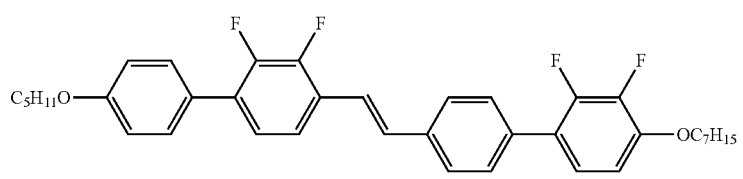 |
| 504 | 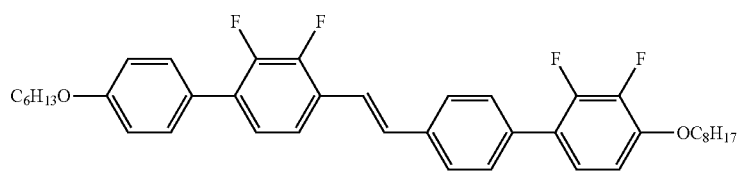 |
| 505 | 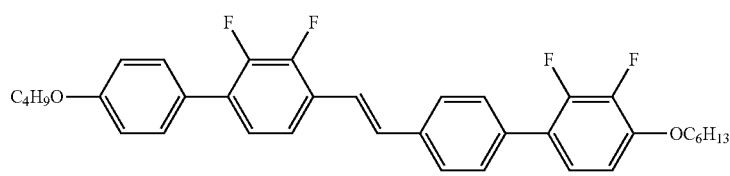 |
| 506 | 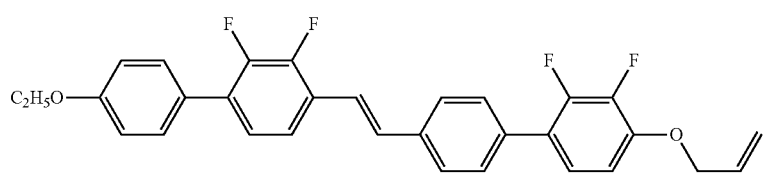 |
| 507 | 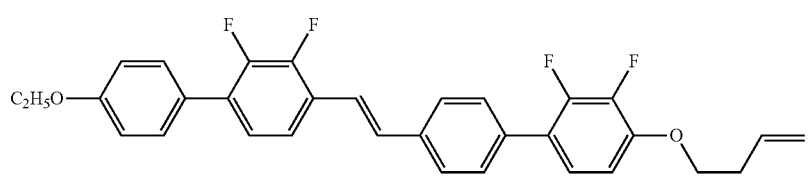 |

| No. | |
|---|---|
| 508 | 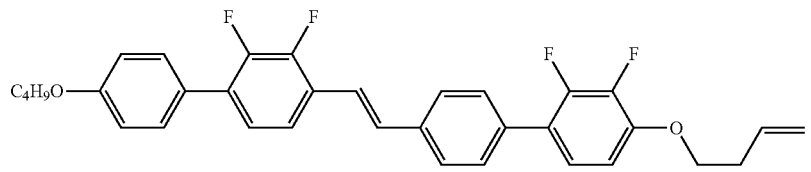 |
| 509 | 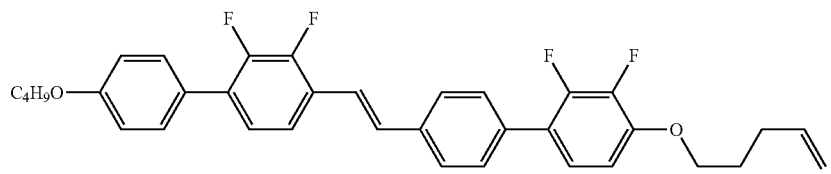 |
| 510 | 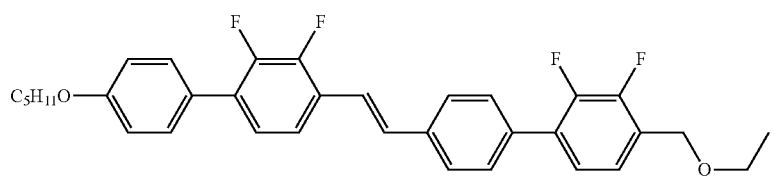 |
| 511 | 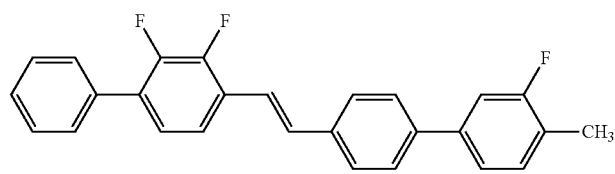 [SMILES: Cc1ccc(-c2ccc(/C=C/c3ccc(-c4ccccc4)c(F)c3F)cc2)cc1F] |
| 512 | 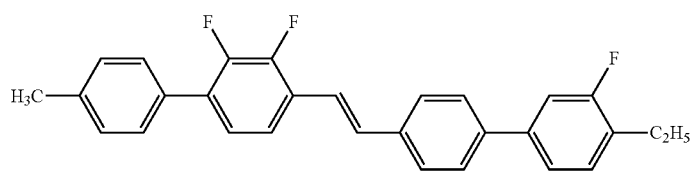 [SMILES: CCc1ccc(-c2ccc(/C=C/c3ccc(-c4ccc(C)cc4)c(F)c3F)cc2)cc1F] |
| 513 | 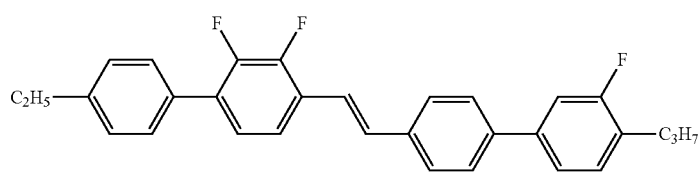 |
| 514 | 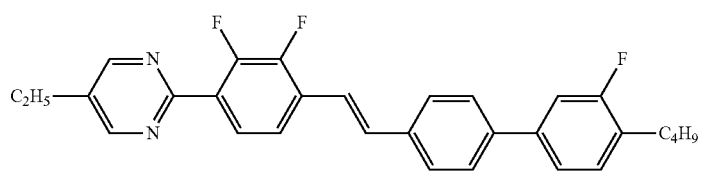 |
| 515 | 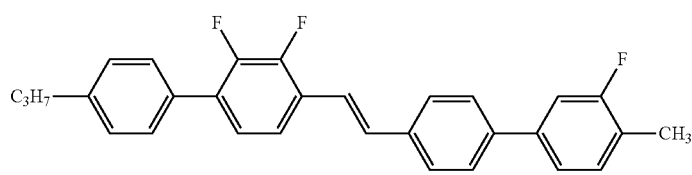 |

| No. | |
|---|---|
| 516 | 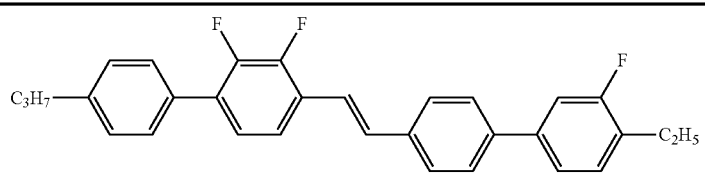 |
| 517 | 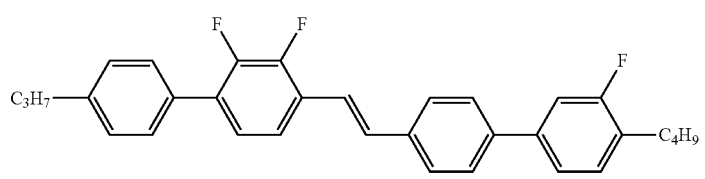 |
| 518 | 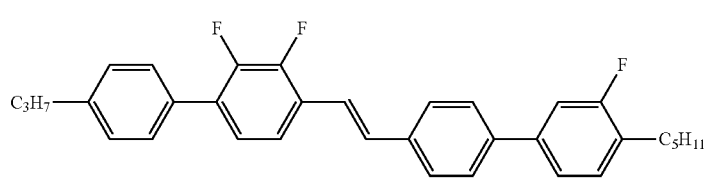 |
| 519 | 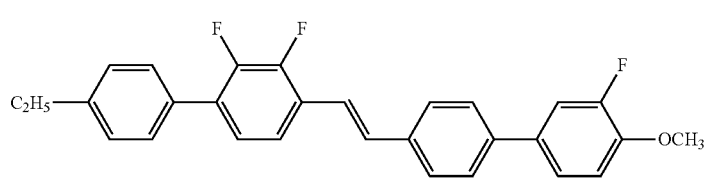 [SMILES: CCc1ccc(-c2ccc(/C=C/c3ccc(-c4ccc(OC)c(F)c4)cc3)c(F)c2F)cc1] |
| 520 | 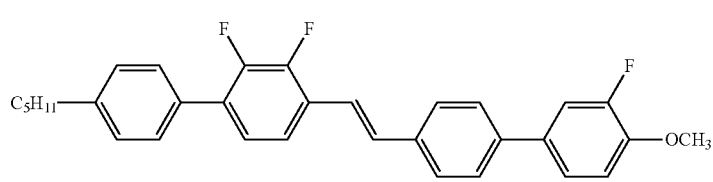 |
| 521 | 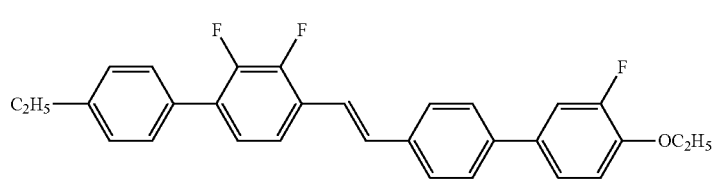 [SMILES: CCOc1ccc(-c2ccc(/C=C/c3ccc(-c4ccc(CC)cc4)c(F)c3F)cc2)cc1F] |
| 522 | 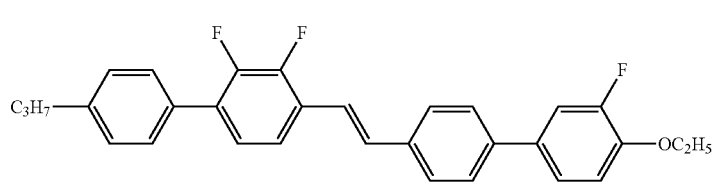 |
| 523 | 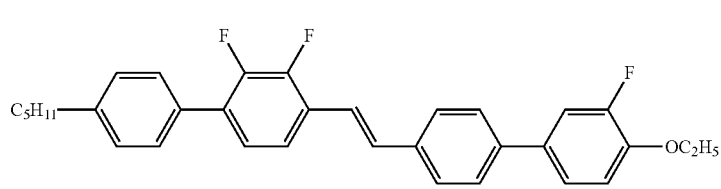 |
| 524 | 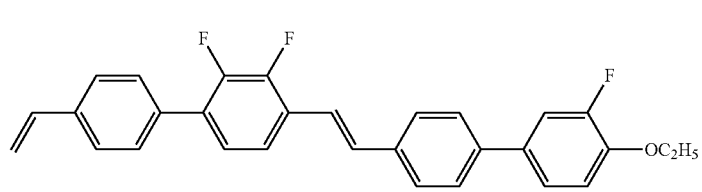 |

| No. | |
|---|---|
| 525 | 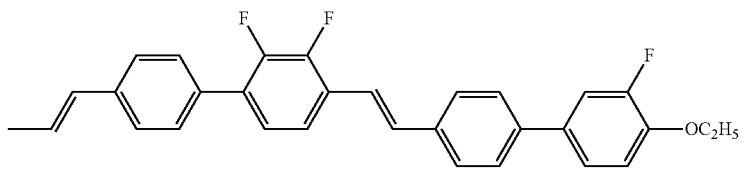 [SMILES: C/C=C/c1ccc(-c2ccc(/C=C/c3ccc(-c4ccc(OCC)c(F)c4)cc3)c(F)c2F)cc1] |
| 526 | 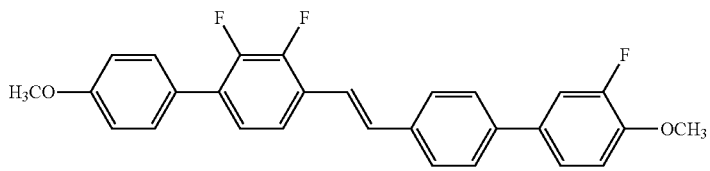 [SMILES: COc1ccc(-c2ccc(/C=C/c3ccc(-c4ccc(OC)c(F)c4)cc3)c(F)c2F)cc1] |
| 527 | 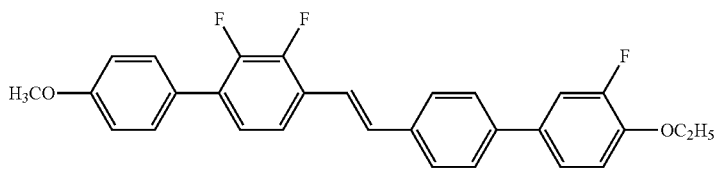 [SMILES: CCOc1ccc(-c2ccc(/C=C/c3ccc(-c4ccc(OC)cc4)c(F)c3F)cc2)cc1F] |
| 528 | 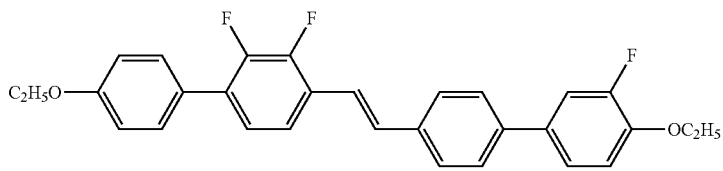 |
| 529 | 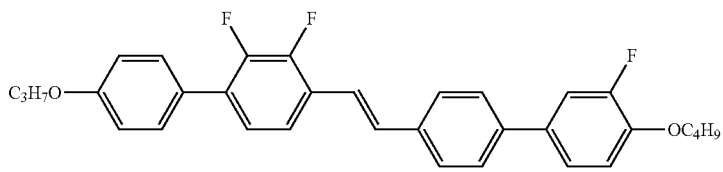 |
| 530 | 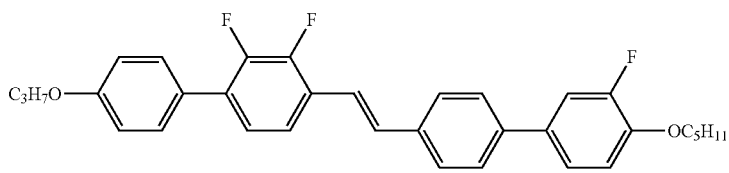 |
| 531 | 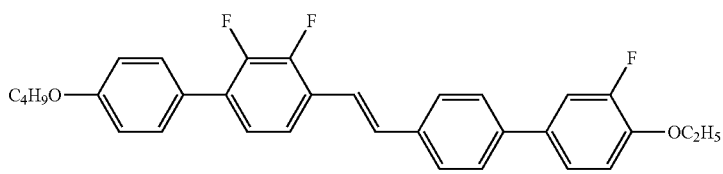 |
| 532 | 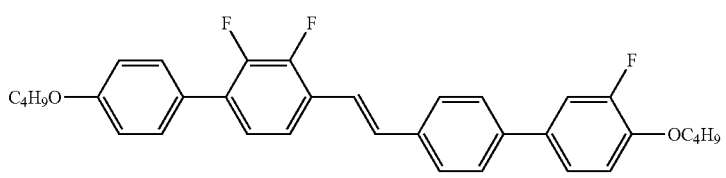 |

| No. | |
|---|---|
| 533 | 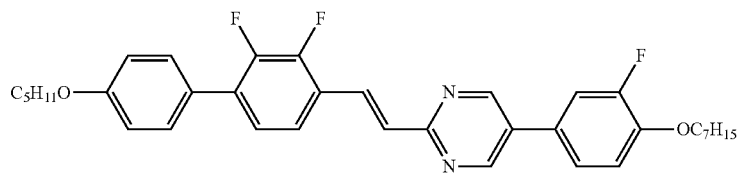 |
| 534 | 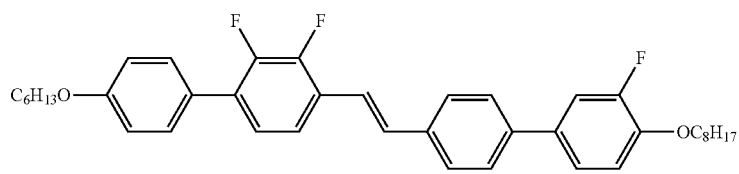 |
| 535 | 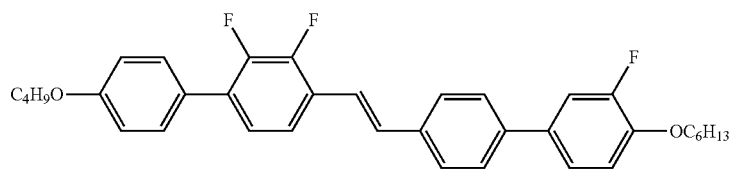 |
| 536 | 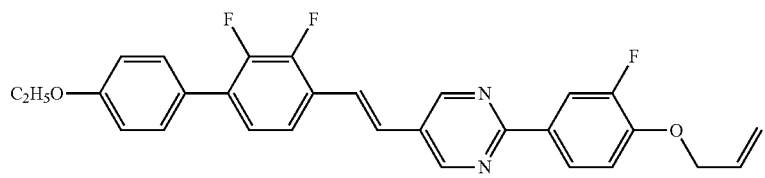 |
| 537 | 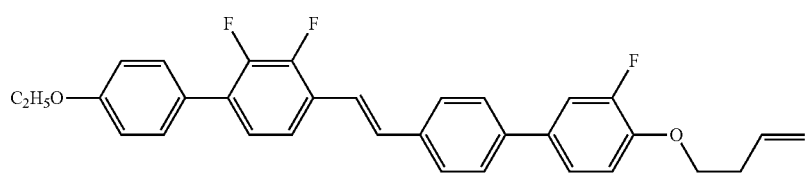 |
| 538 | 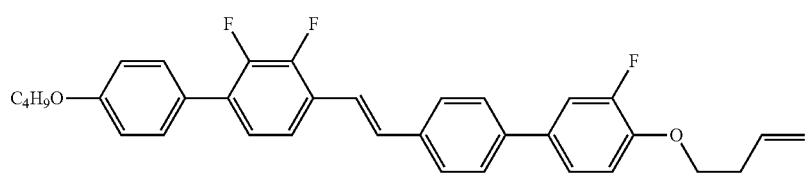 |
| 539 | 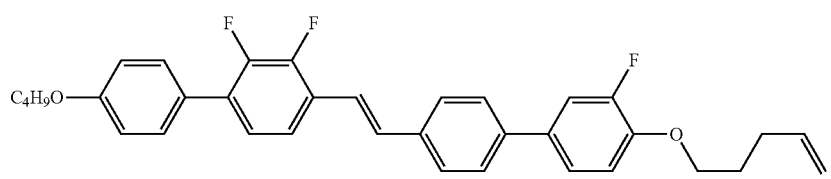 |
| 540 | 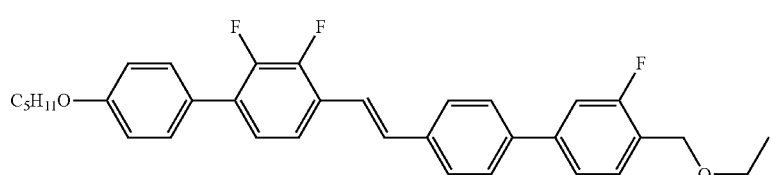 |

| No. | |
|---|---|
| 541 | 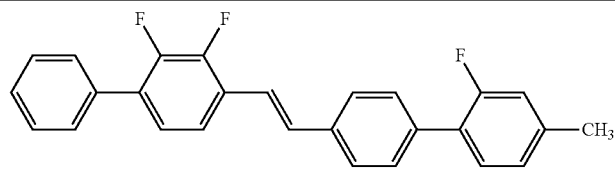 |
| 542 | 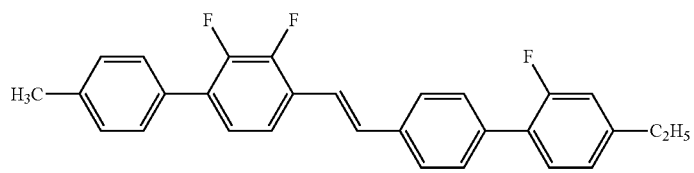 [SMILES: CCc1ccc(-c2ccc(/C=C/c3ccc(-c4ccc(C)cc4)c(F)c3F)cc2)c(F)c1] |
| 543 | 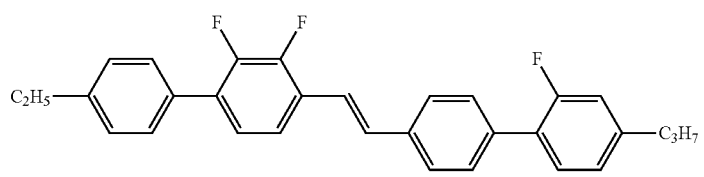 |
| 544 | 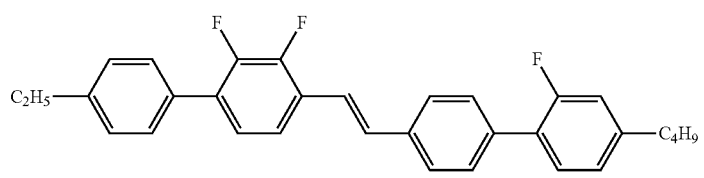 |
| 545 | 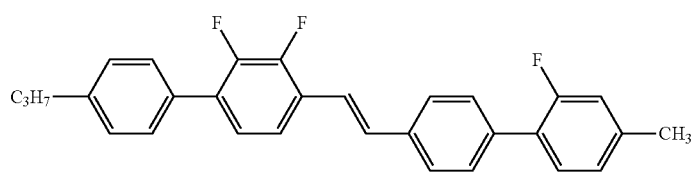 |
| 546 | 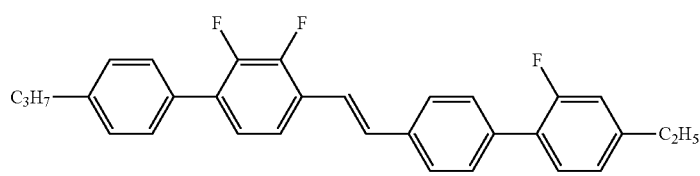 |
| 547 | 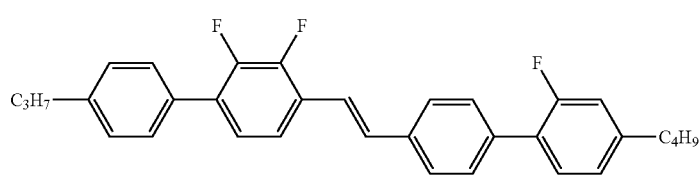 |
| 548 | 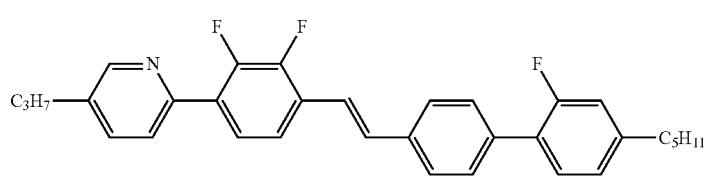 |
| 549 | 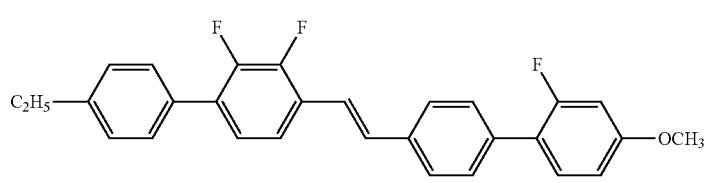 |

-continued
| No. | |
|---|---|
| 550 | 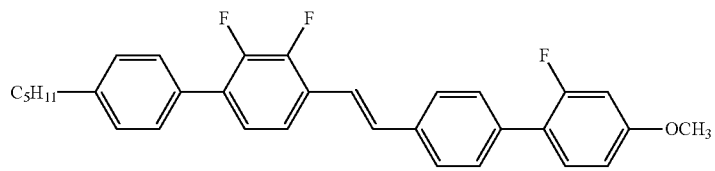 |
| 551 | 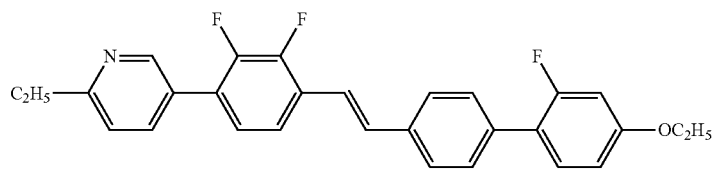 [SMILES: CCOc1ccc(-c2ccc(/C=C/c3ccc(-c4ccc(CC)nc4)c(F)c3F)cc2)c(F)c1] |
| 552 | 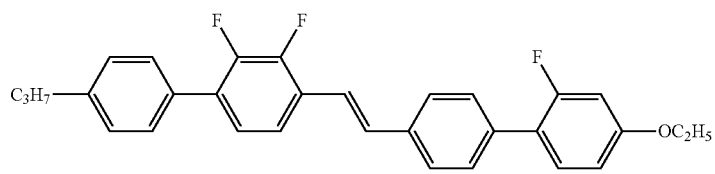 |
| 553 | 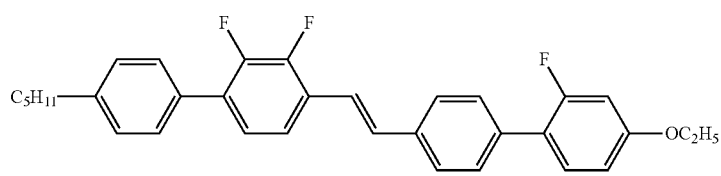 |
| 554 | 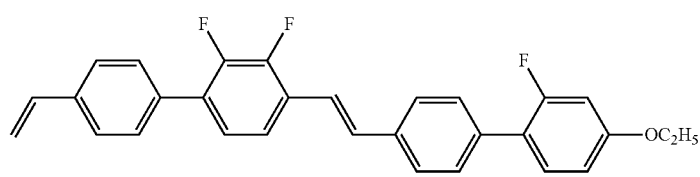 [SMILES: C=Cc1ccc(-c2ccc(/C=C/c3ccc(-c4ccc(OCC)cc4F)cc3)c(F)c2F)cc1] |
| 555 | 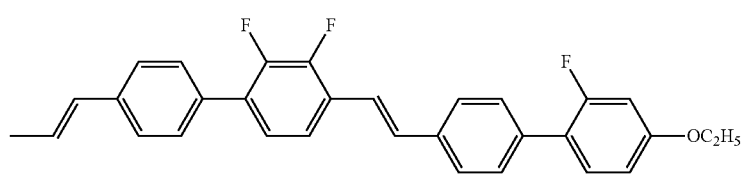 |
| 556 | 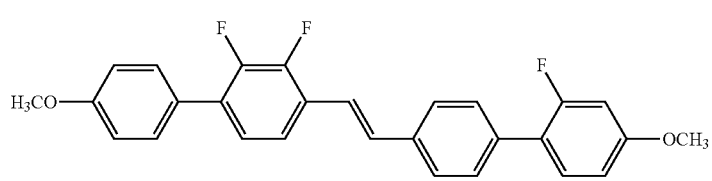 [SMILES: COc1ccc(-c2ccc(/C=C/c3ccc(-c4ccc(OC)cc4F)cc3)c(F)c2F)cc1] |
| 557 | 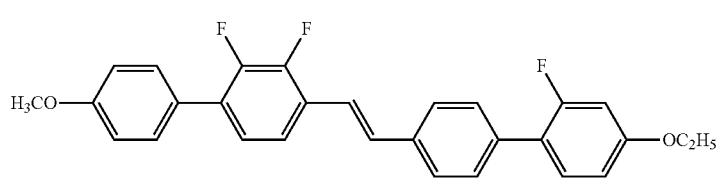 |

| No. | |
|---|---|
| 558 | 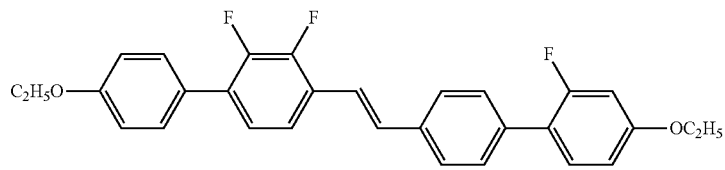 |
| 559 | 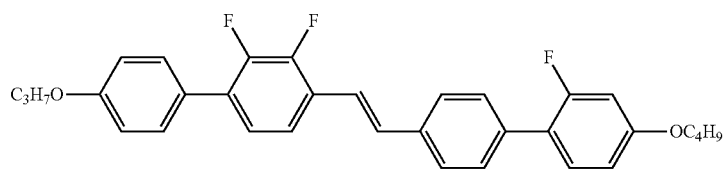 |
| 560 | 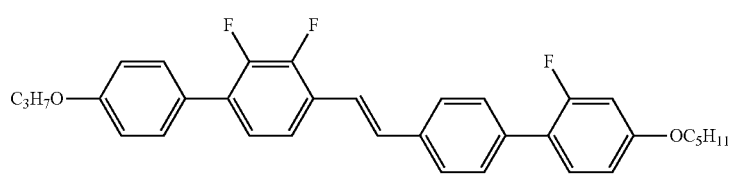 |
| 561 | 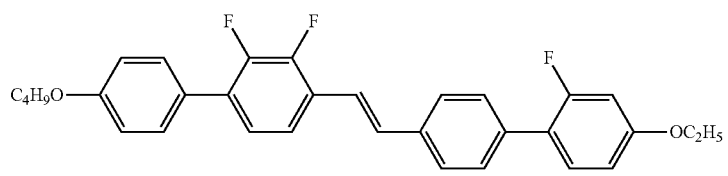 |
| 562 | 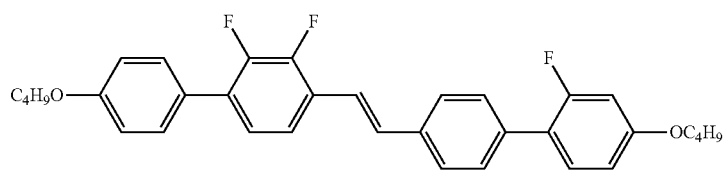 |
| 563 | 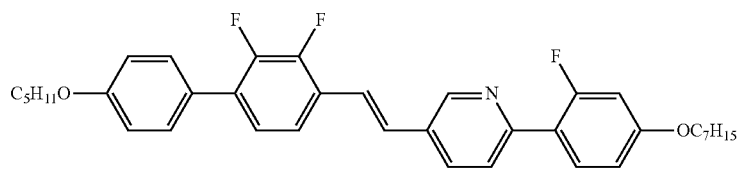 |
| 564 | 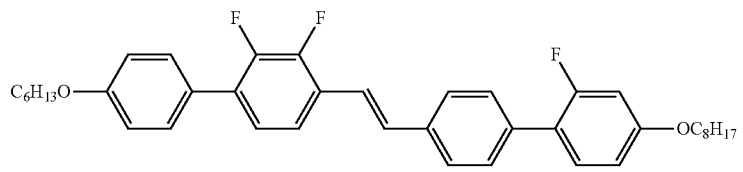 |
| 565 | 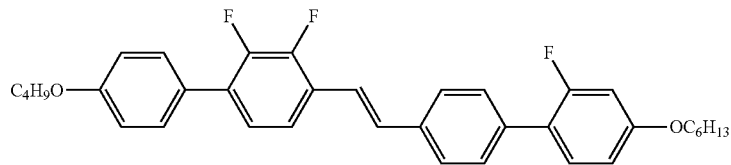 |
| 566 | 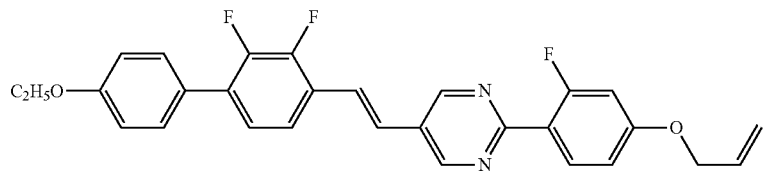 |

-continued
| No. | |
|---|---|
| 567 | 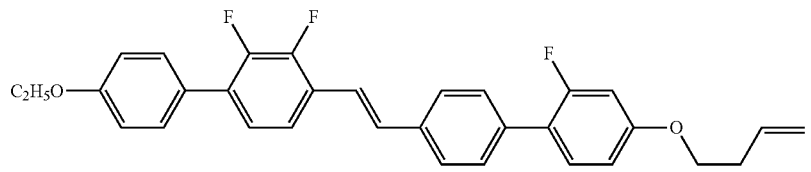 |
| 568 | 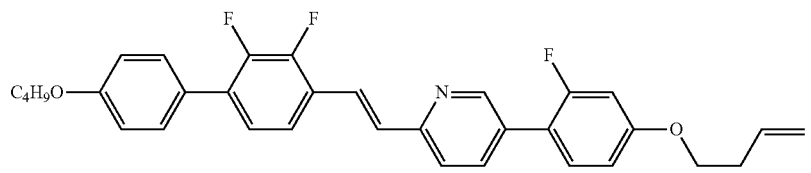 |
| 569 | 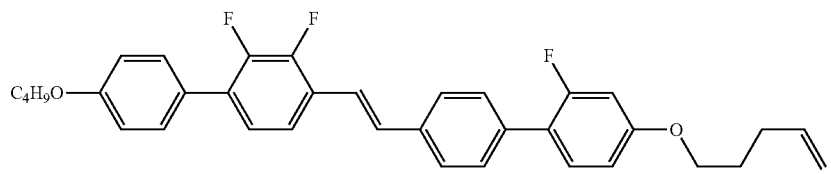 |
| 570 | 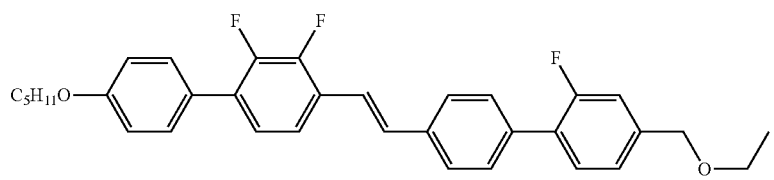 |
| 571 | 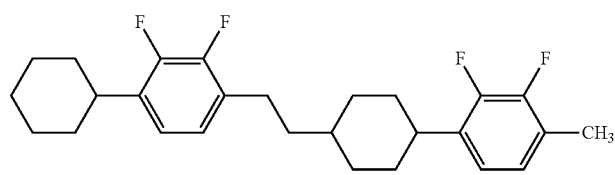 [SMILES: Cc1ccc(C2CCC(CCc3ccc(C4CCCCC4)c(F)c3F)CC2)c(F)c1F] |
| 572 | 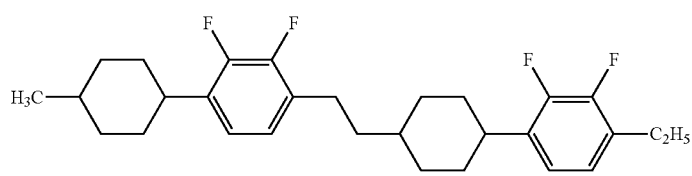 |
| 573 | 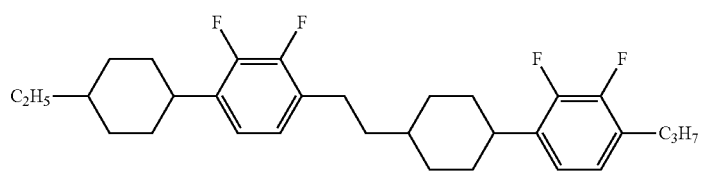 |
| 574 | 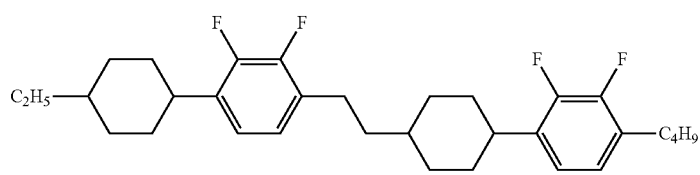 |

| No. | |
|---|---|
| 575 | 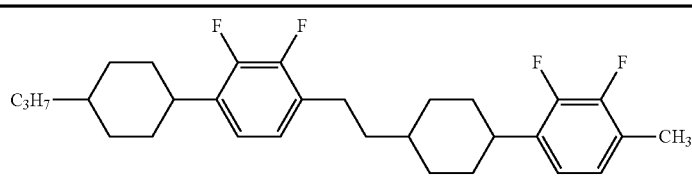 |
| 576 | 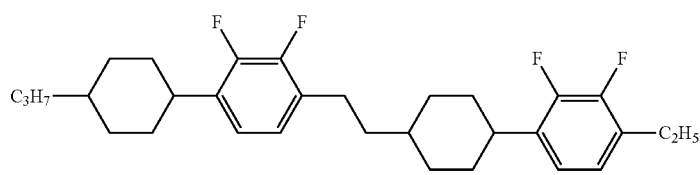 |
| 577 | 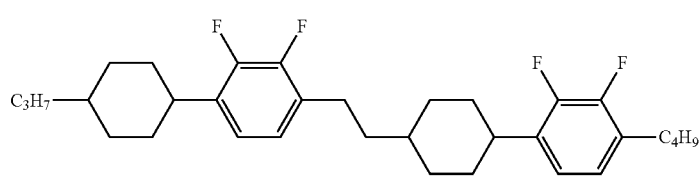 |
| 578 | 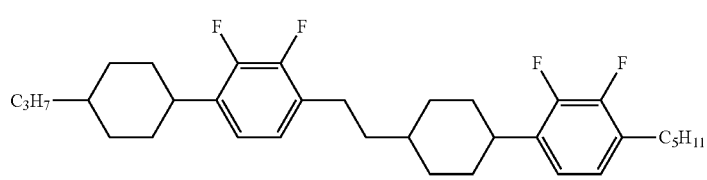 |
| 579 | 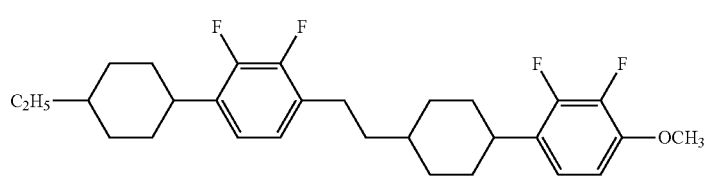 |
| 580 | 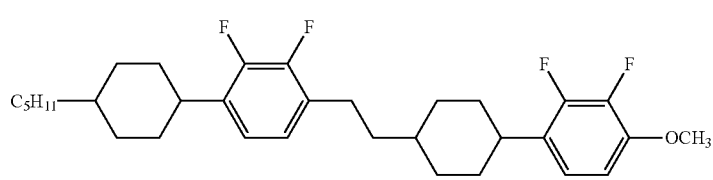 |
| 581 | 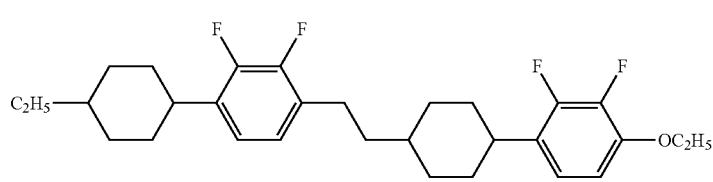 |
| 582 | 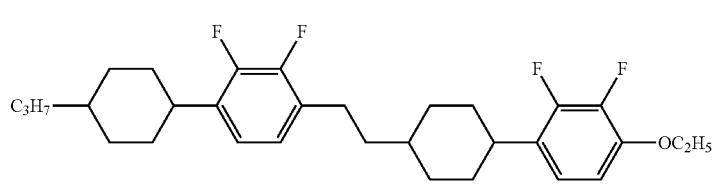 |
| 583 | 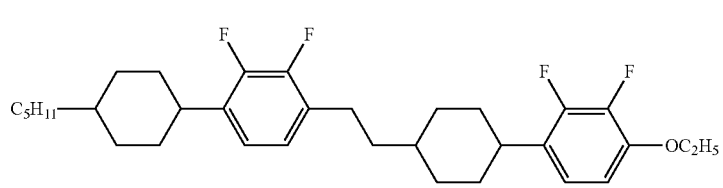 |

| No. | |
|---|---|
| 584 | 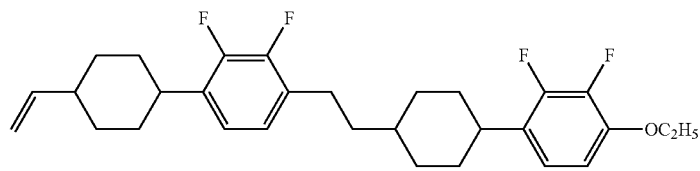 [SMILES: C=CC1CCC(c2ccc(CCC3CCC(c4ccc(OCC)c(F)c4F)CC3)c(F)c2F)CC1] |
| 585 | 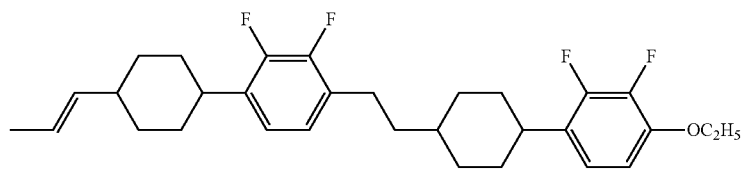 |
| 586 | 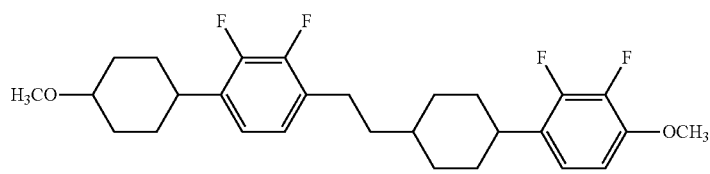 |
| 587 | 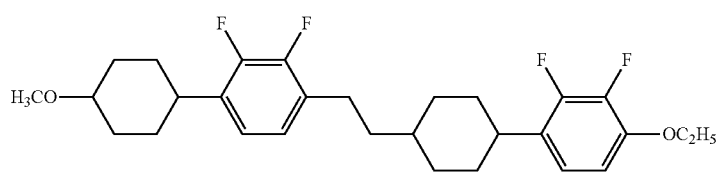 |
| 588 | 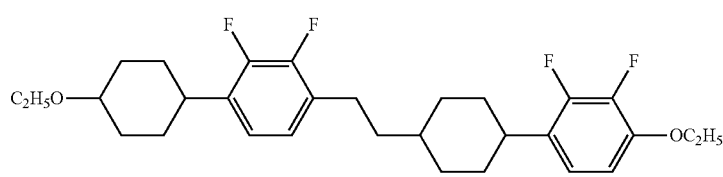 |
| 589 | 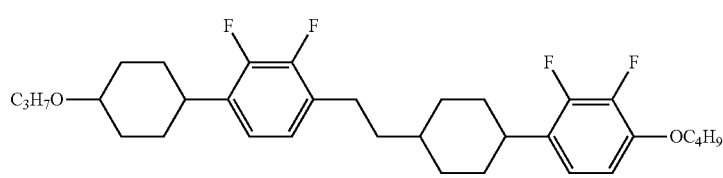 |
| 590 | 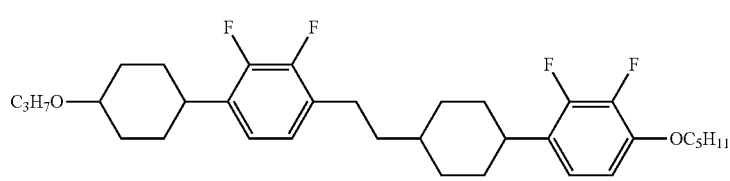 |
| 591 | 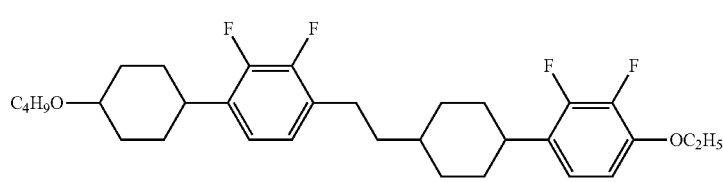 |

| No. | |
|---|---|
| 592 | 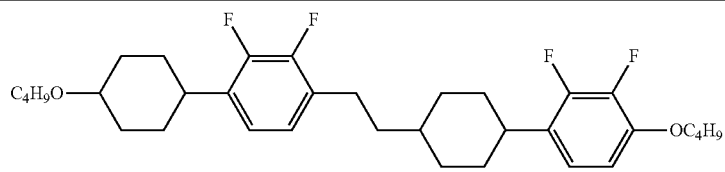 |
| 593 | 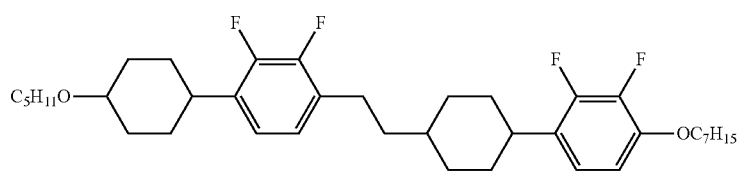 |
| 594 | 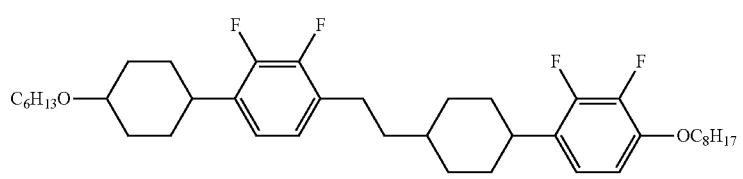 |
| 595 | 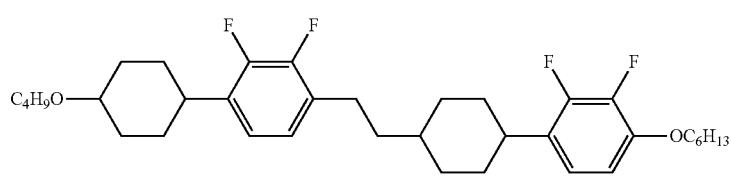 |
| 596 | 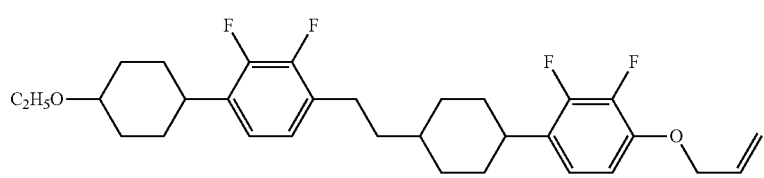 |
| 597 | 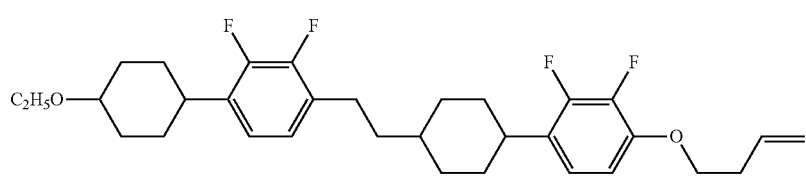 |
| 598 | 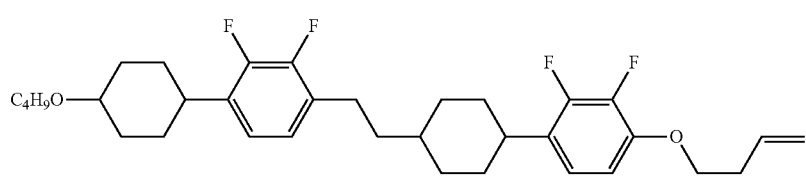 |
| 599 | 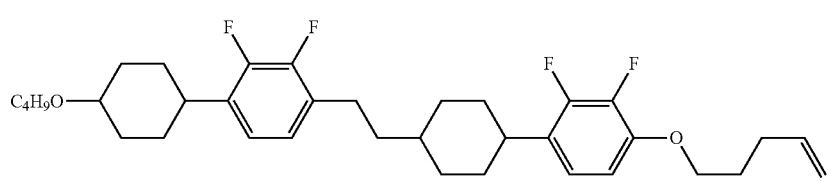 |
| 600 | 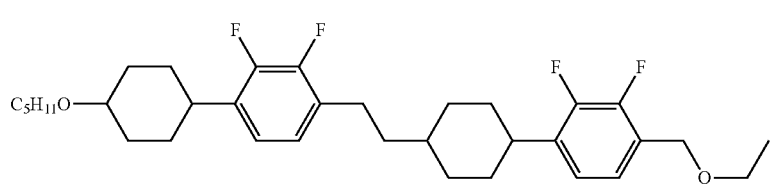 |

| No. | |
|---|---|
| 601 | 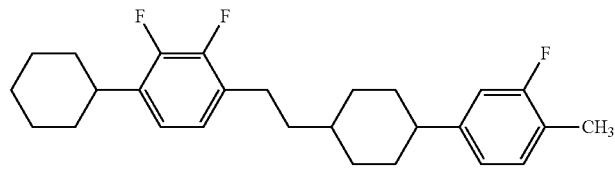 |
| 602 | 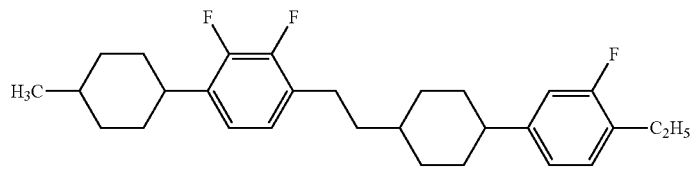 |
| 603 | 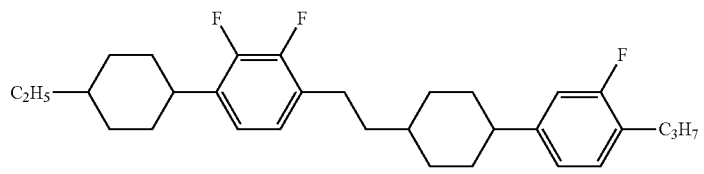 |
| 604 | 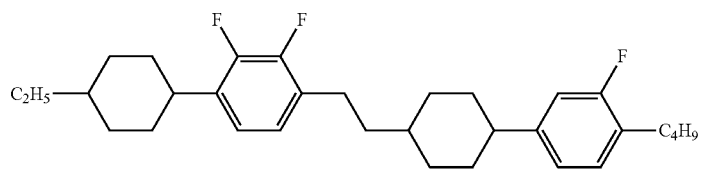 |
| 605 | 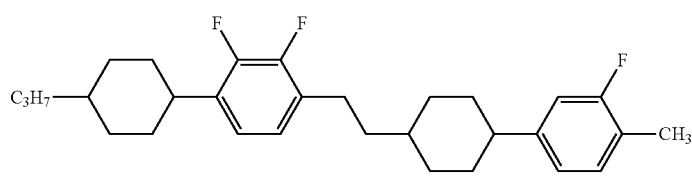 |
| 606 | 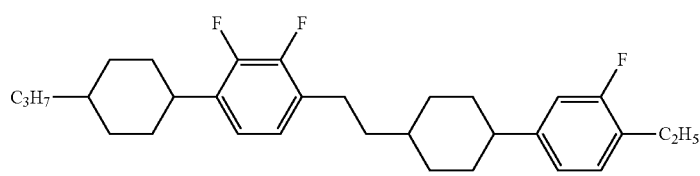 |
| 607 | 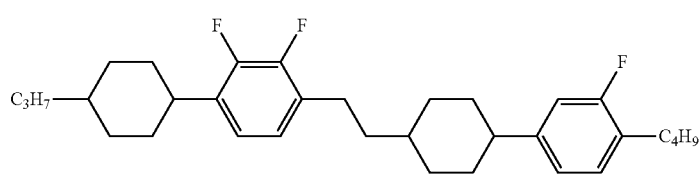 |
| 608 | 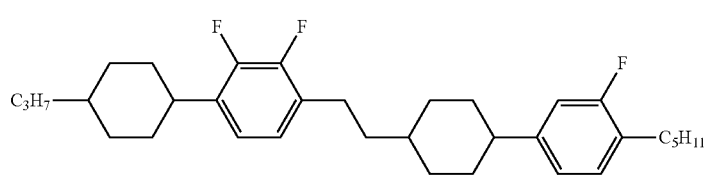 |

| No. | |
|---|---|
| 609 | 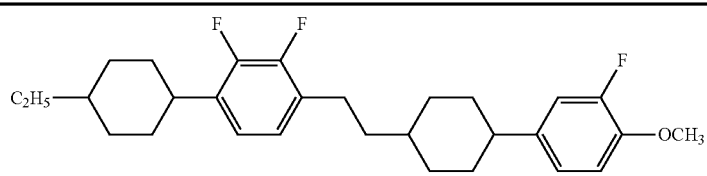 |
| 610 | 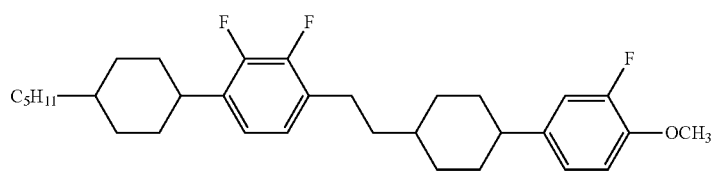 |
| 611 | 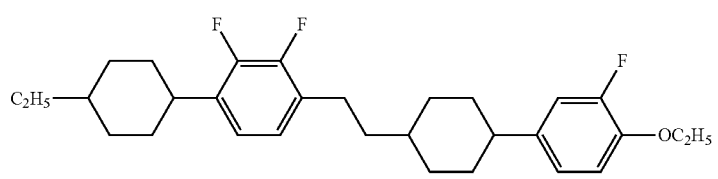 [SMILES: CCOc1ccc(C2CCC(CCc3ccc(C4CCC(CC)CC4)c(F)c3F)CC2)cc1F] |
| 612 | 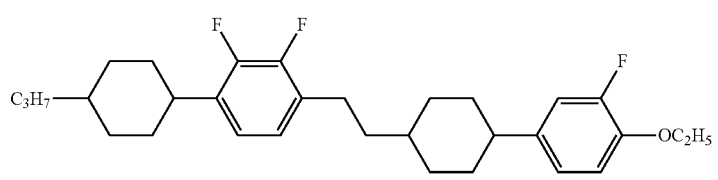 |
| 613 | 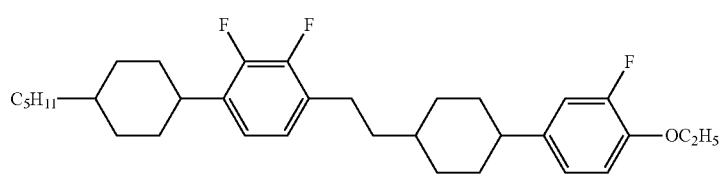 |
| 614 | 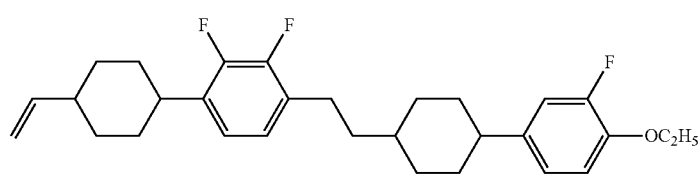 |
| 615 | 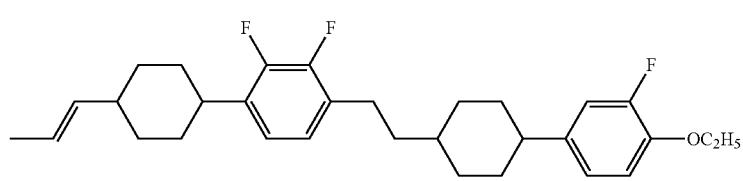 |
| 616 | 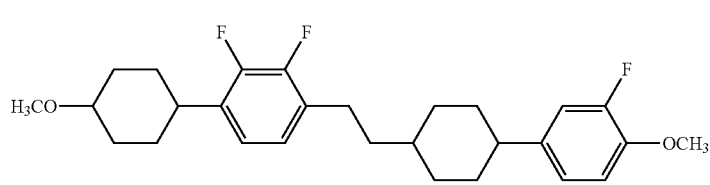 |
| 617 | 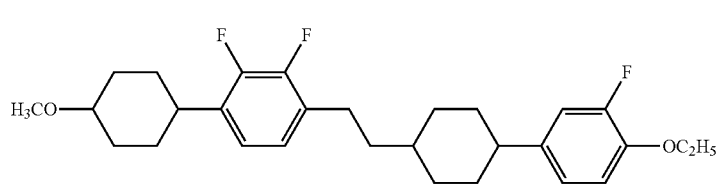 |

| No. | |
|---|---|
| 618 | 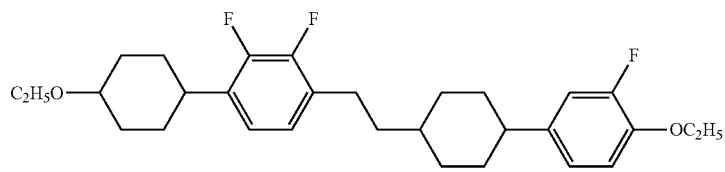 |
| 619 | 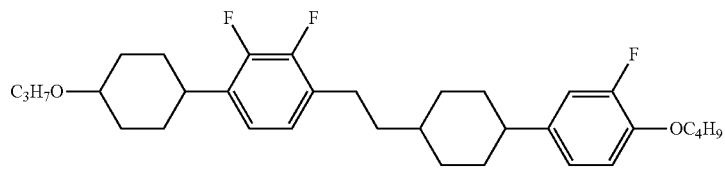 |
| 620 | 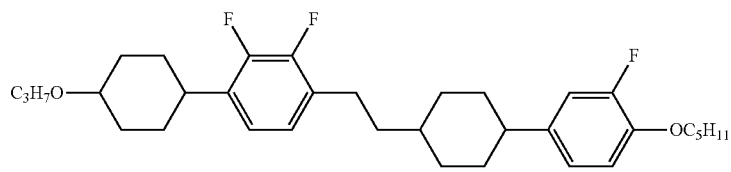 |
| 621 | 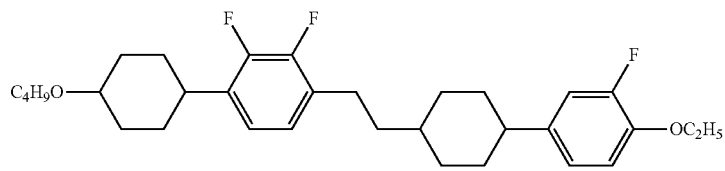 |
| 622 | 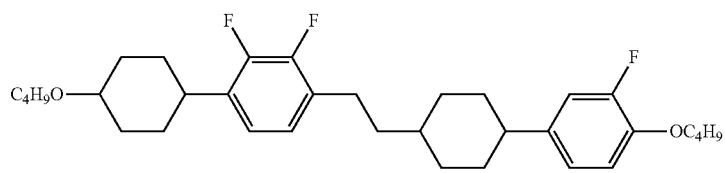 |
| 623 | 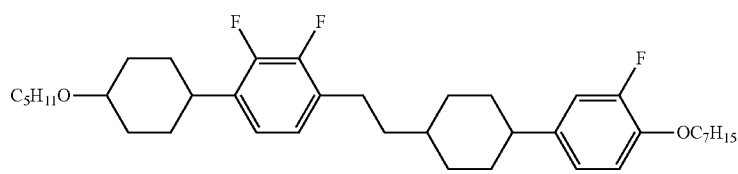 |
| 624 | 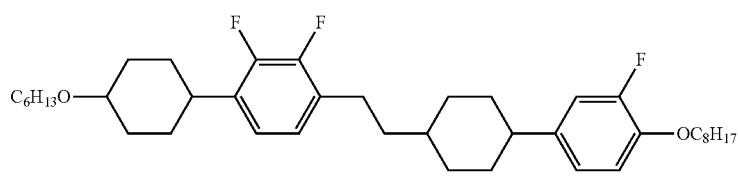 |
| 625 | 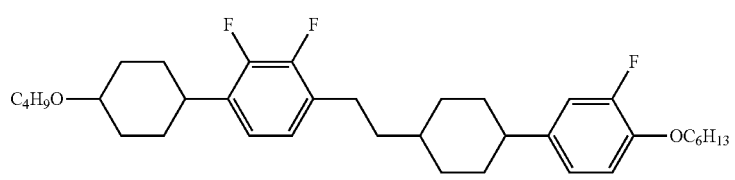 |

| No. |
|---|
| 626 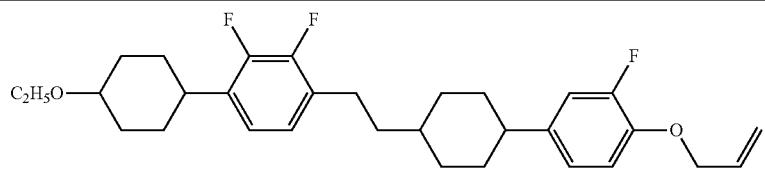 |
| 627 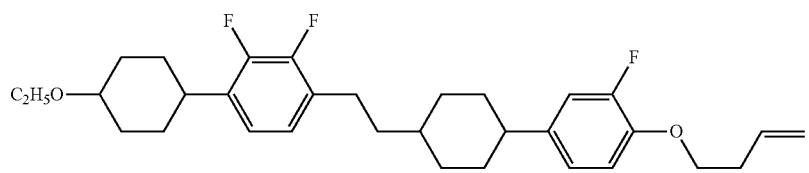 |
| 628 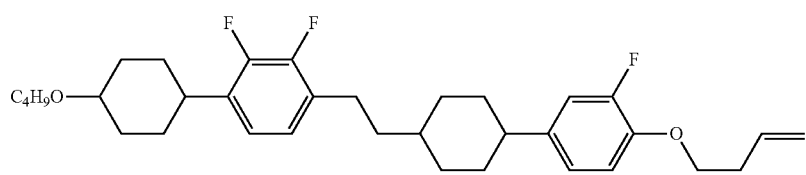 |
| 629 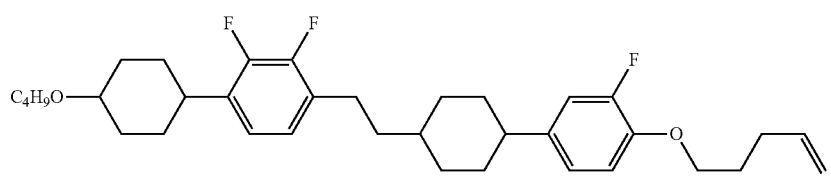 |
| 630 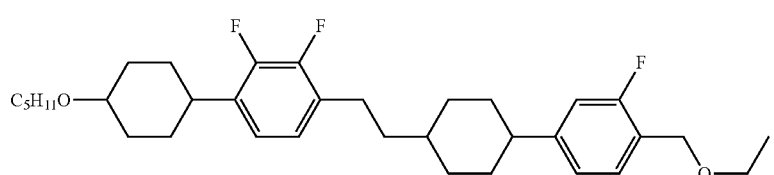 |
| 631 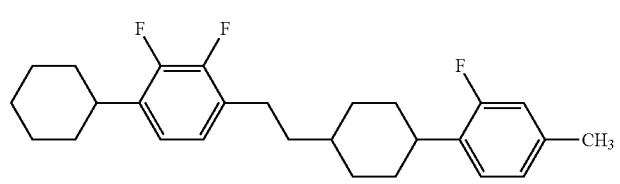 |
| 632 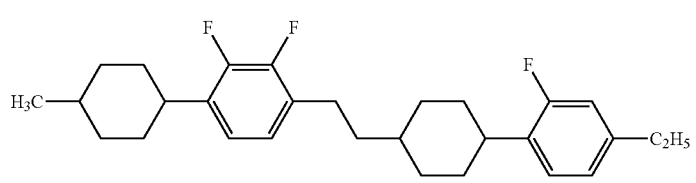 |
| 633 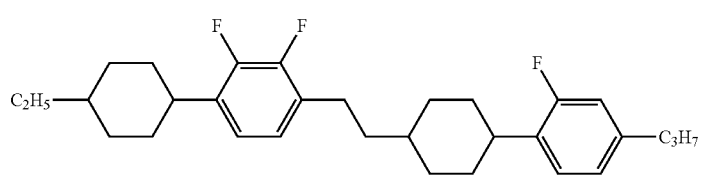 |
| 634 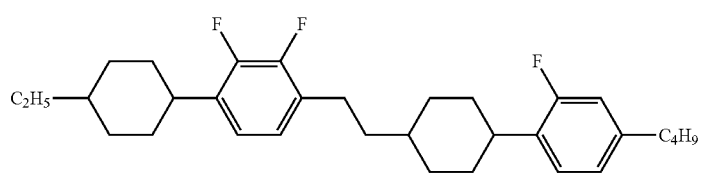 |

| No. | |
|---|---|
| 635 | 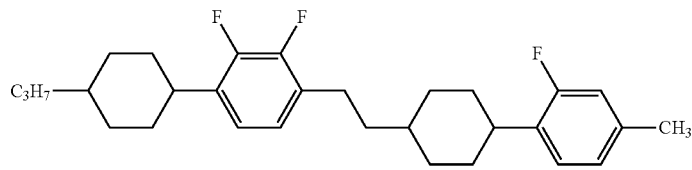 |
| 636 | 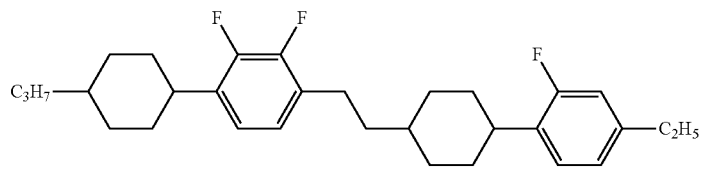 |
| 637 | 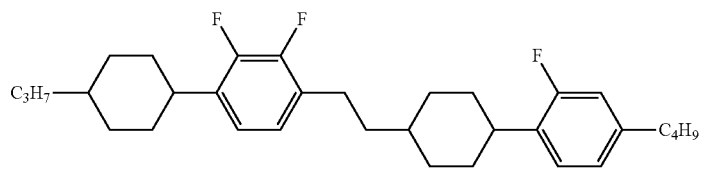 |
| 638 | 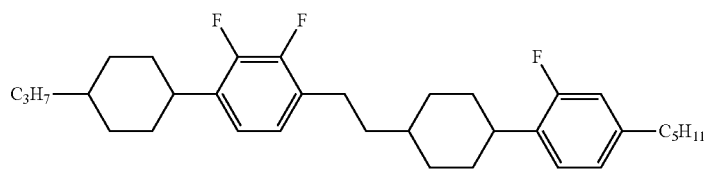 |
| 639 | 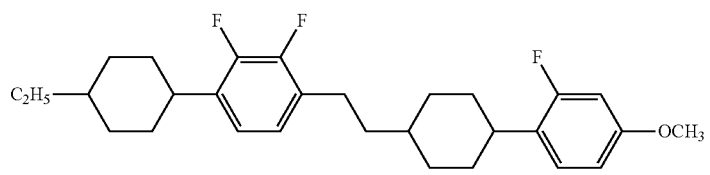 |
| 640 | 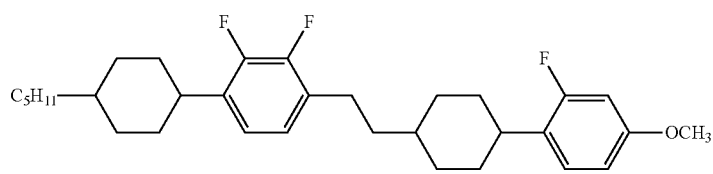 |
| 641 | 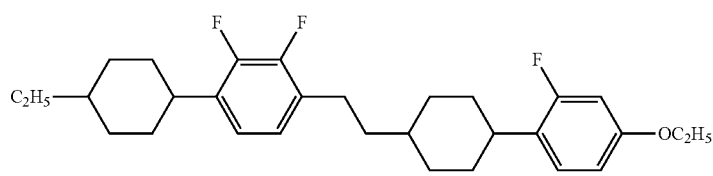 |
| 642 | 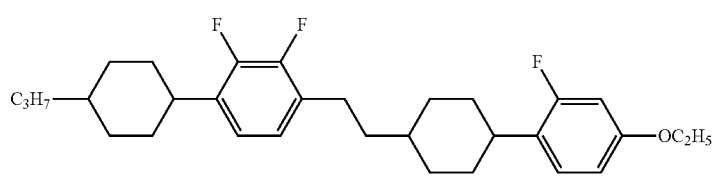 |

| No. | |
|---|---|
| 643 | 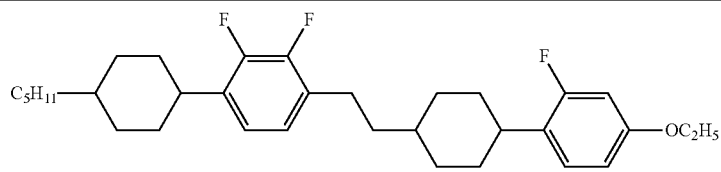 |
| 644 | 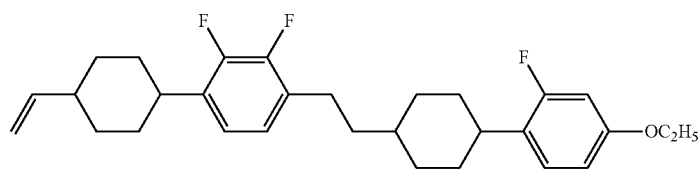 |
| 645 | 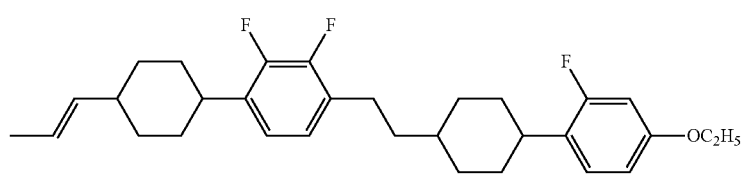 |
| 646 | 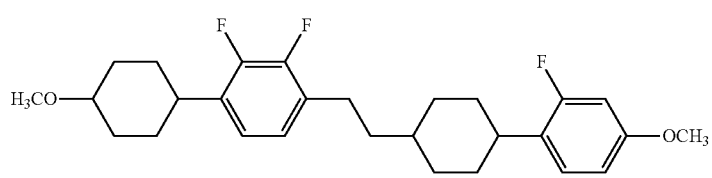 |
| 647 | 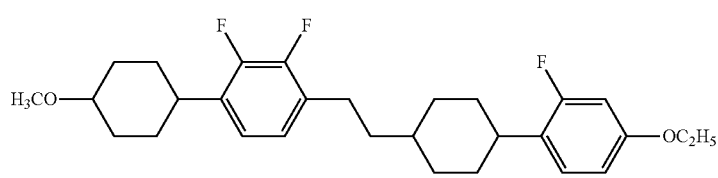 |
| 648 | 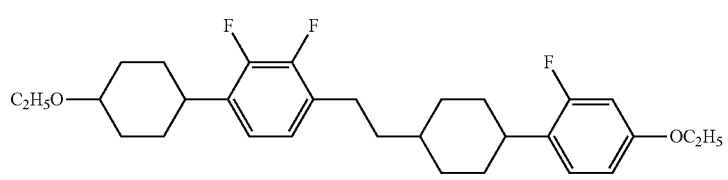 |
| 649 | 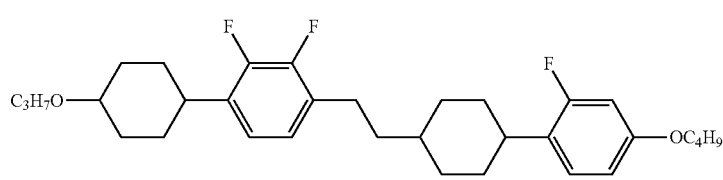 |
| 650 | 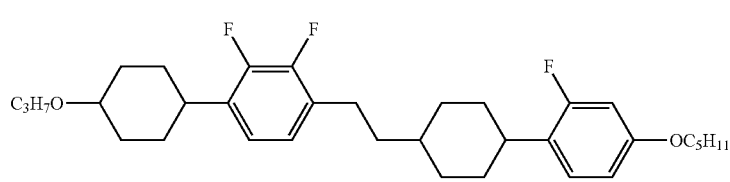 |
| 651 | 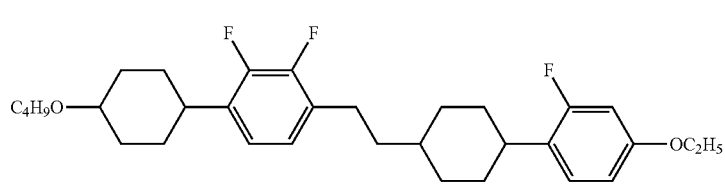 |

| No. | |
|---|---|
| 652 | 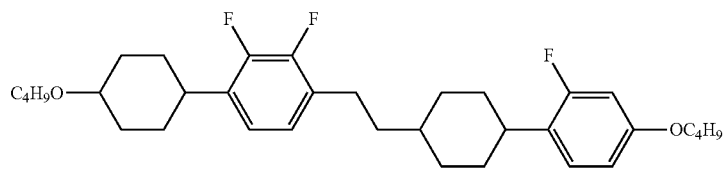 |
| 653 | 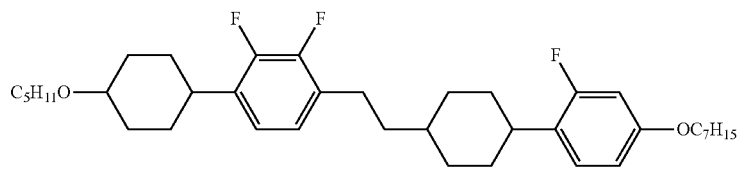 |
| 654 | 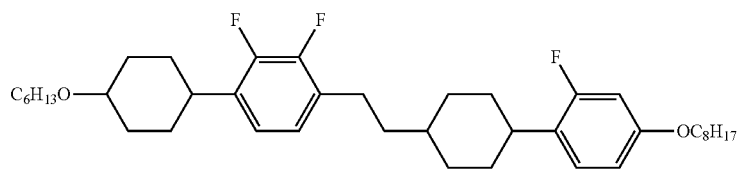 |
| 655 | 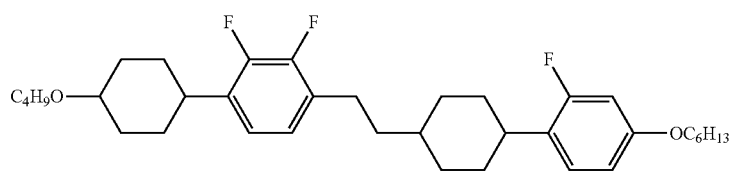 |
| 656 | 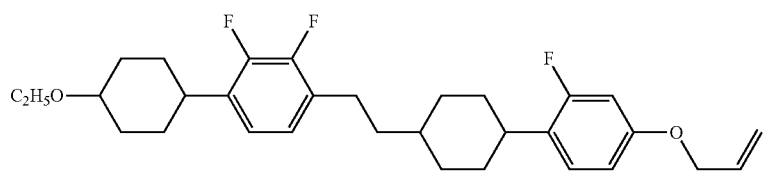 |
| 657 | 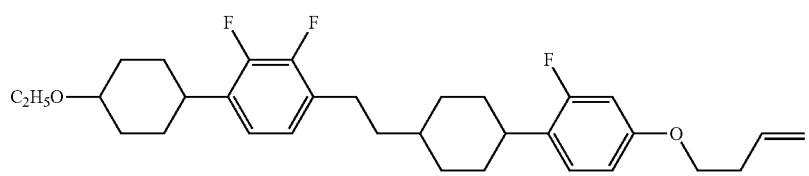 |
| 658 | 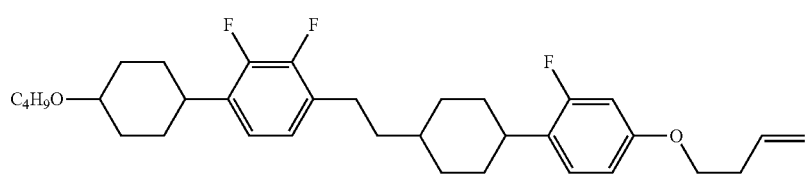 |
| 659 | 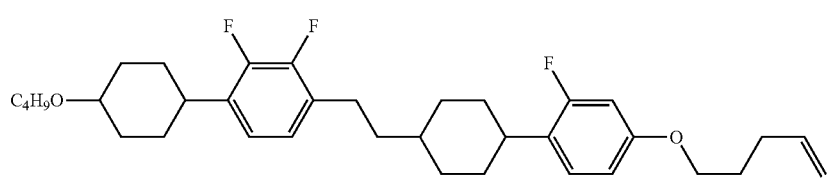 |

| No. |
|---|
| 660 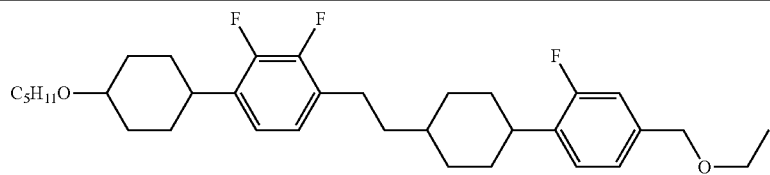 |
| 661 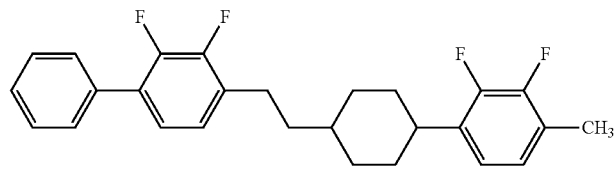 |
| 662 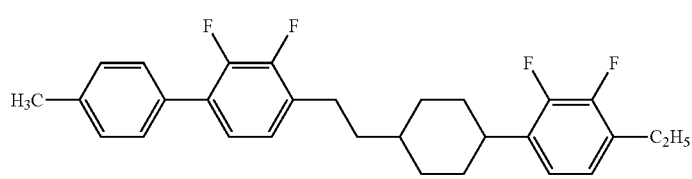 |
| 663 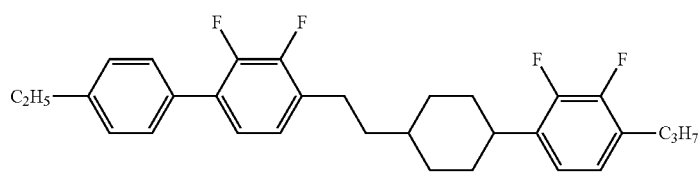 |
| 664 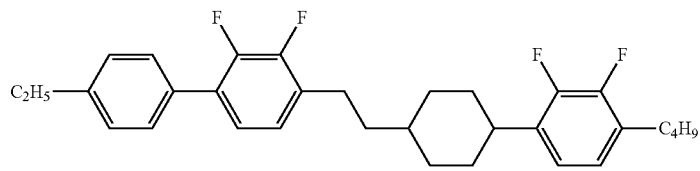 |
| 665 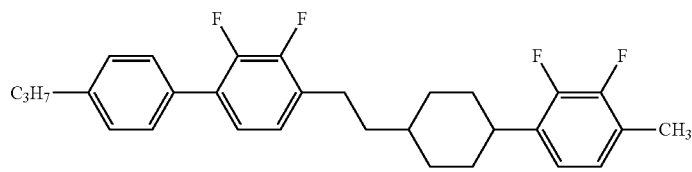 |
| 666 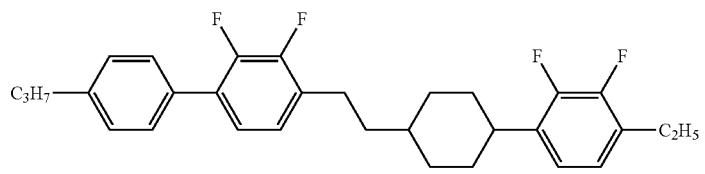 |
| 667 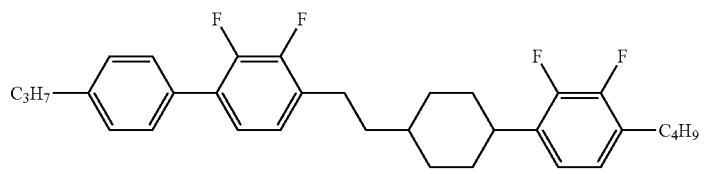 |
| 668 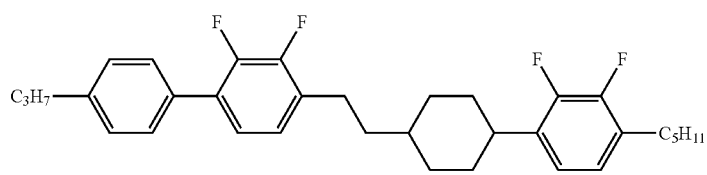 |

| No. | |
|---|---|
| 669 | 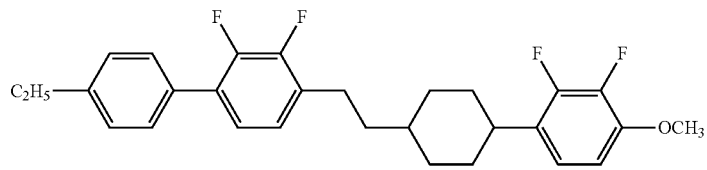 |
| 670 | 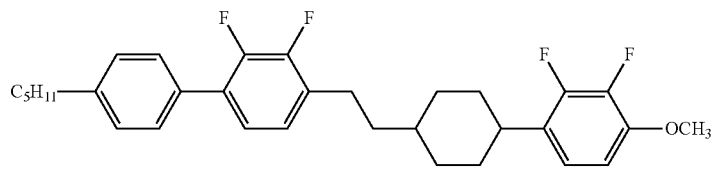 |
| 671 | 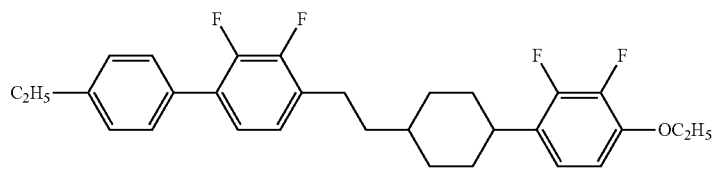 |
| 672 | 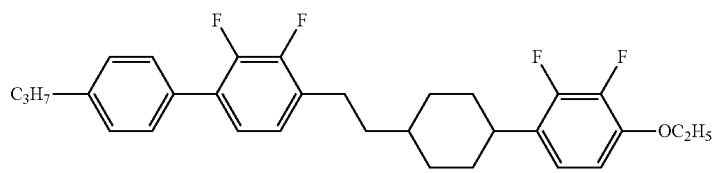 |
| 673 | 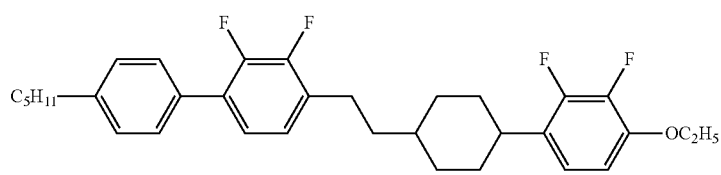 |
| 674 | 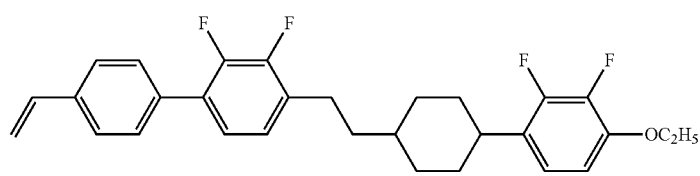 |
| 675 | 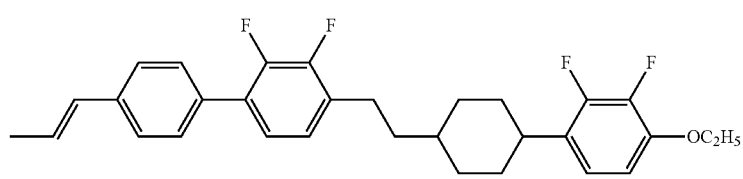 |
| 676 | 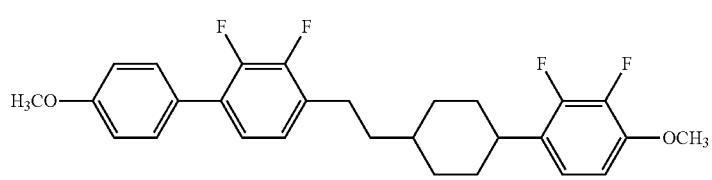 |

-continued
| No. |
|---|
| 677 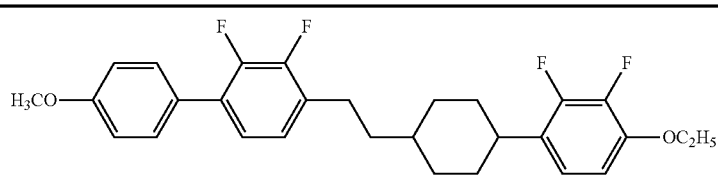 |
| 678 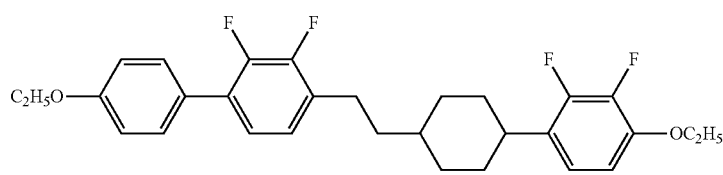 |
| 679 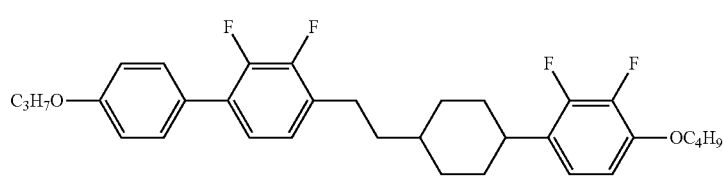 |
| 680 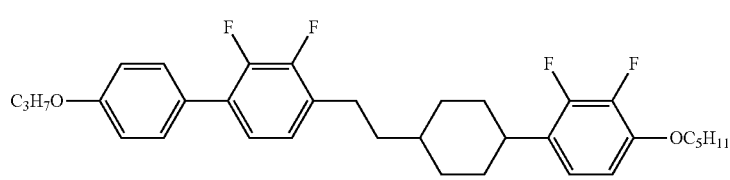 |
| 681 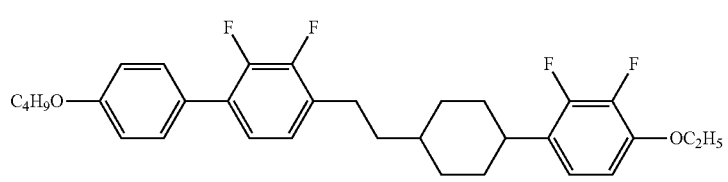 |
| 682 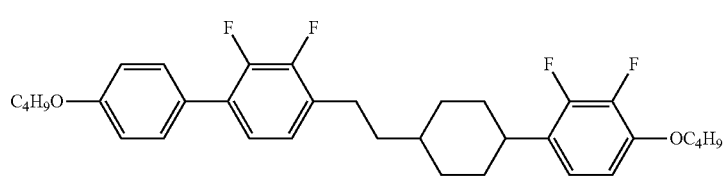 |
| 683 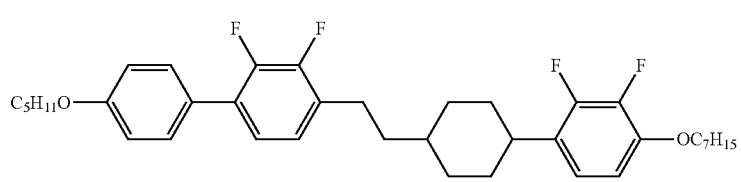 |
| 684 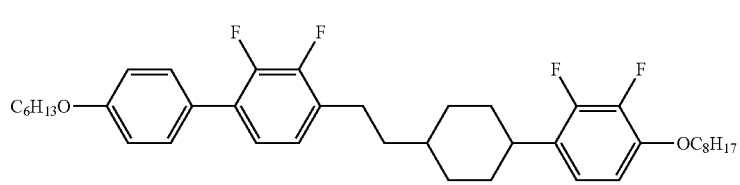 |
| 685 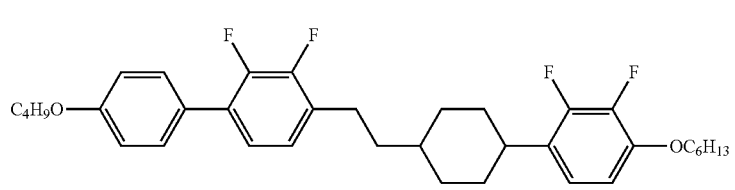 |

| No. |
|---|
| 686 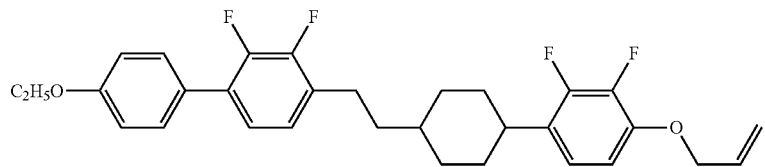 |
| 687 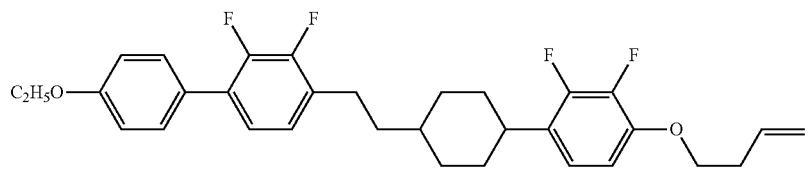 |
| 688 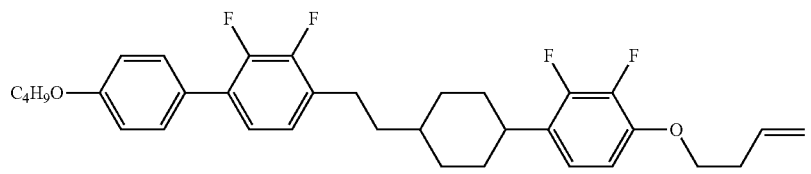 |
| 689 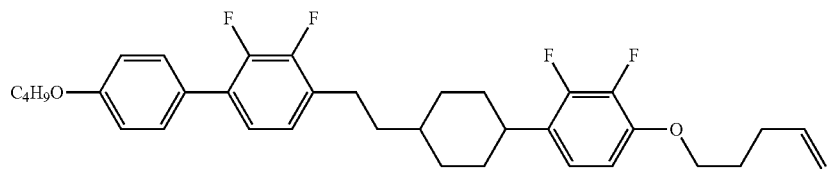 |
| 690 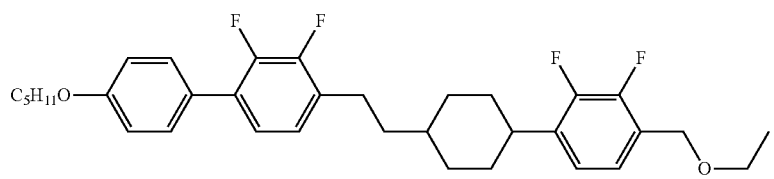 |
| 691 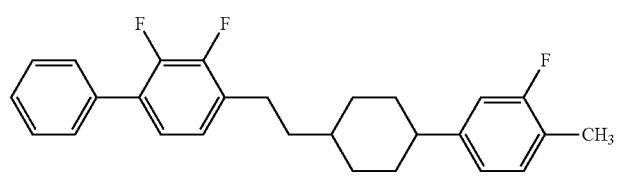 |
| 692 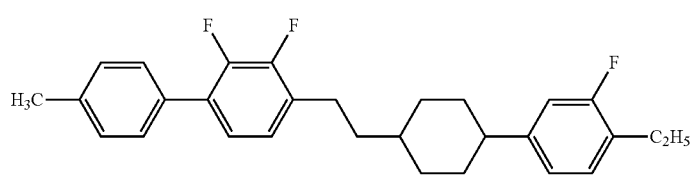 |
| 693 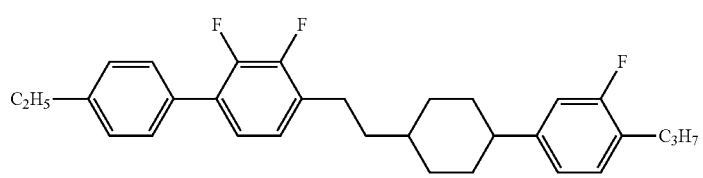 |

-continued
| No. | |
|---|---|
| 694 | 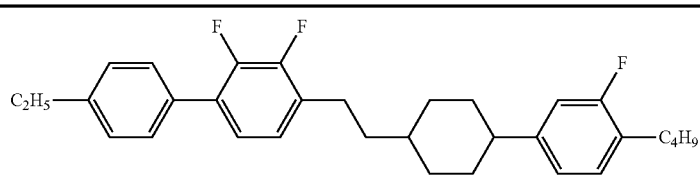 |
| 695 | 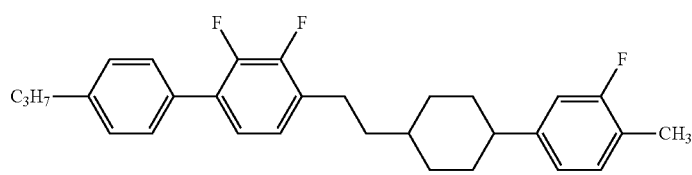 |
| 696 | 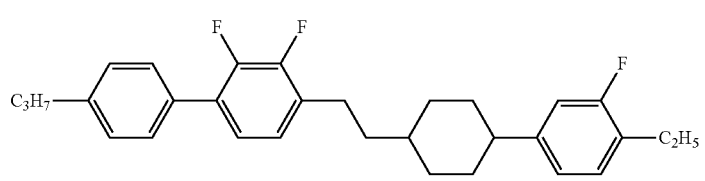 |
| 697 | 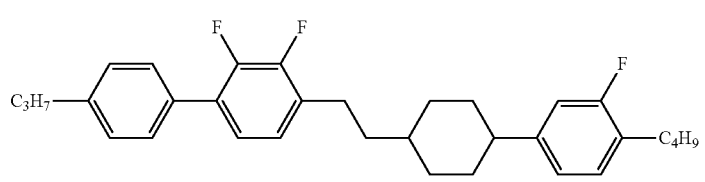 |
| 698 | 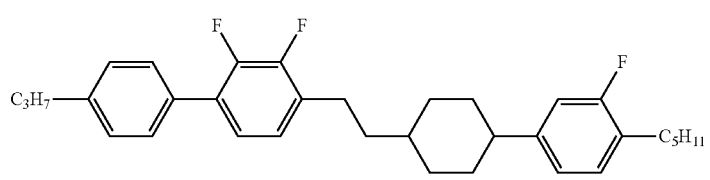 |
| 699 | 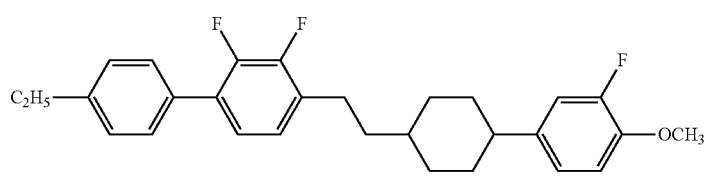 |
| 700 | 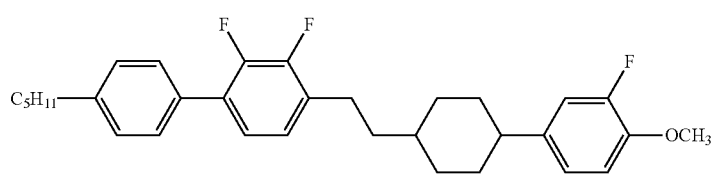 |
| 701 | 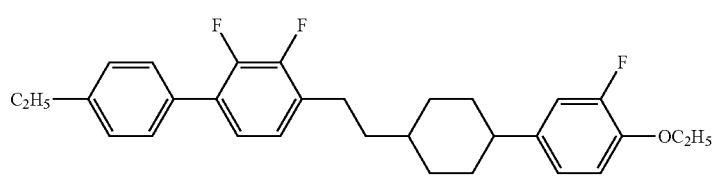 |
| 702 | 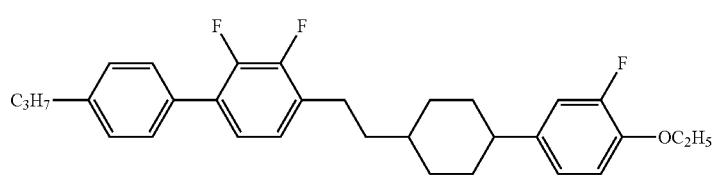 |

| No. | |
|---|---|
| 703 | 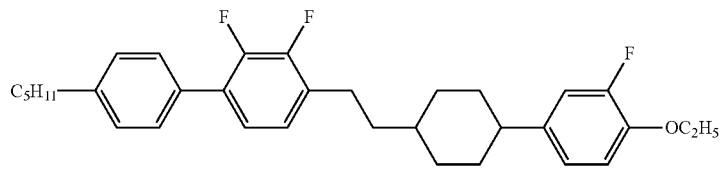 |
| 704 | 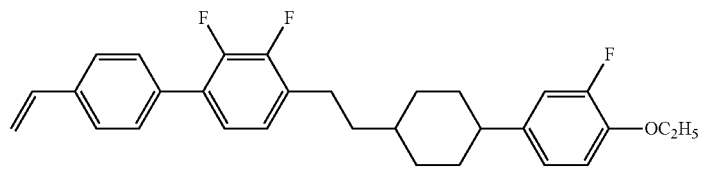 |
| 705 | 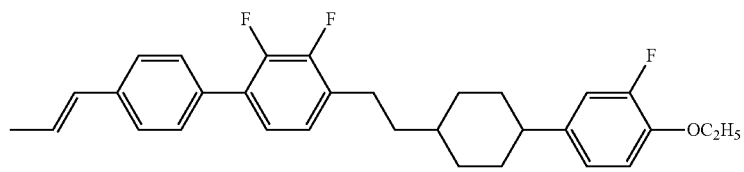 |
| 706 | 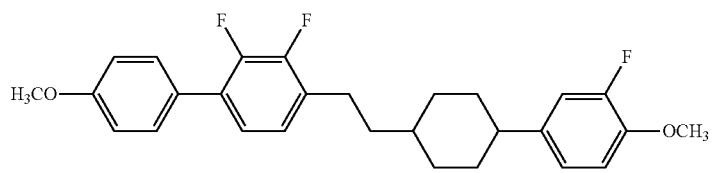 |
| 707 | 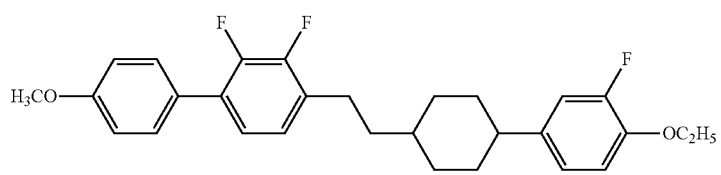 |
| 708 | 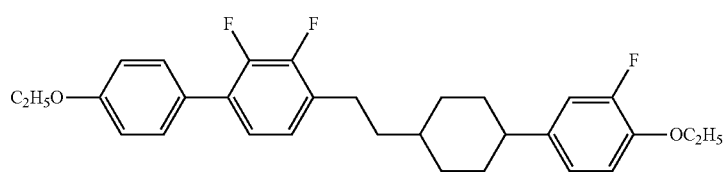 |
| 709 | 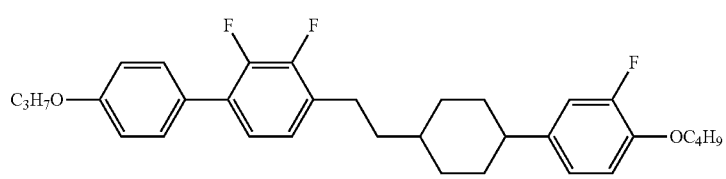 |
| 710 | 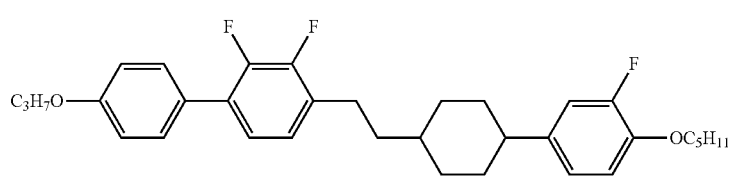 |

-continued
| No. | |
|---|---|
| 711 | 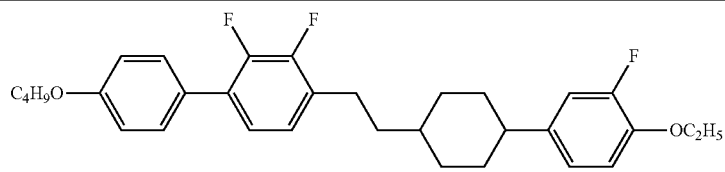 |
| 712 | 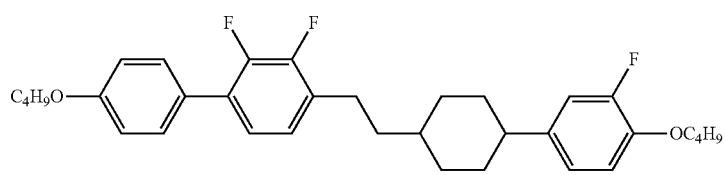 |
| 713 | 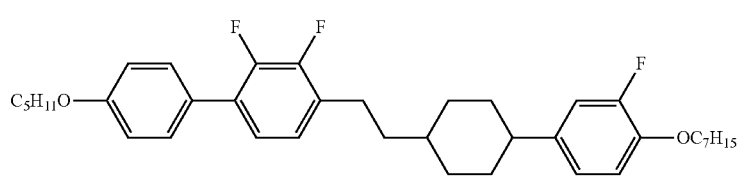 |
| 714 | 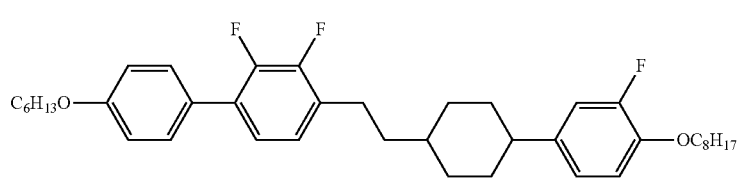 |
| 715 | 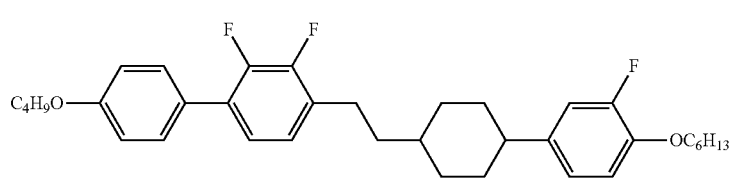 |
| 716 | 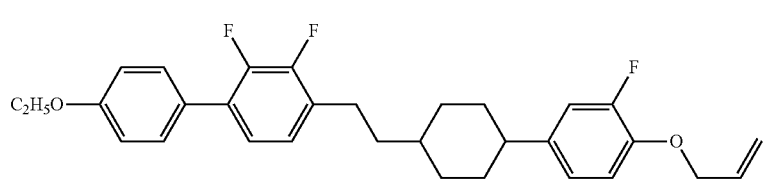 |
| 717 | 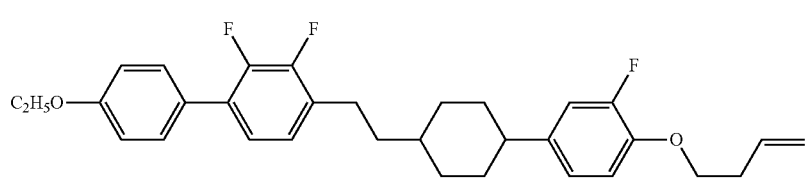 |
| 718 | 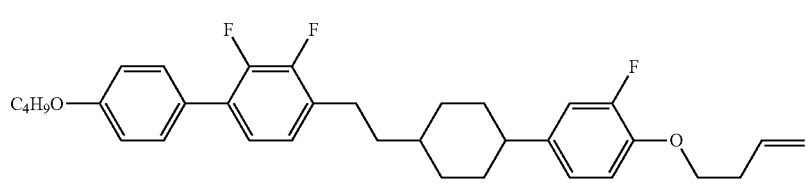 |
| 719 | 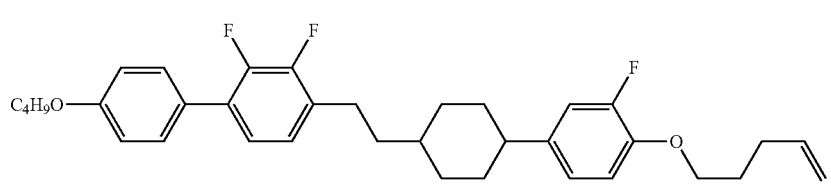 |

| No. | |
|---|---|
| 720 | 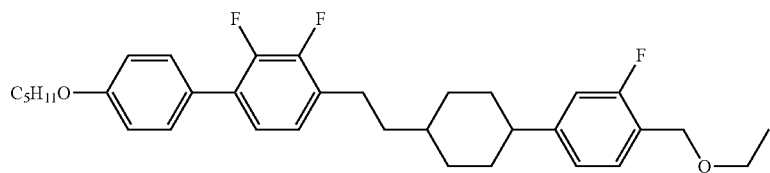 |
| 721 | 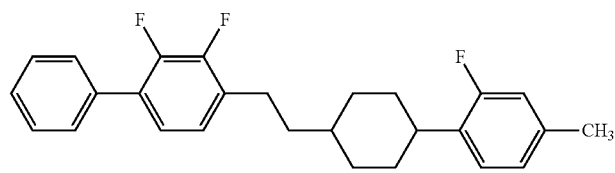 [SMILES: Cc1ccc(C2CCC(CCc3ccc(-c4ccccc4)c(F)c3F)CC2)c(F)c1] |
| 722 | 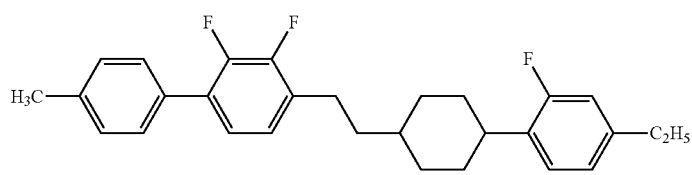 |
| 723 | 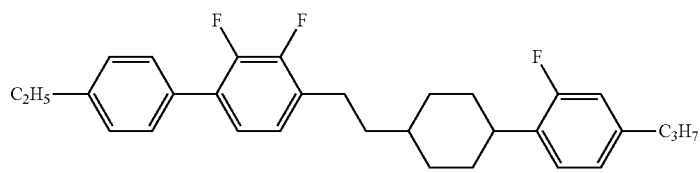 |
| 724 | 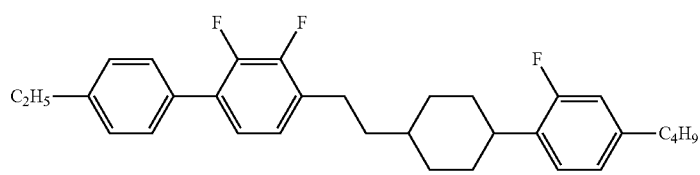 |
| 725 | 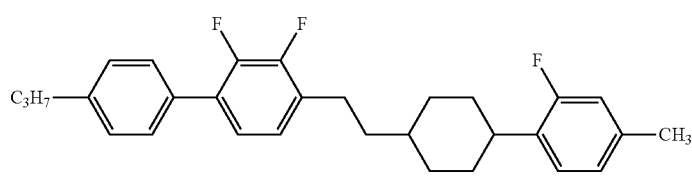 |
| 726 | 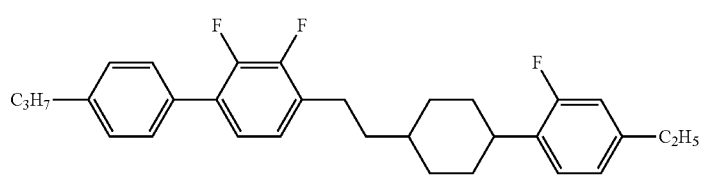 |
| 727 | 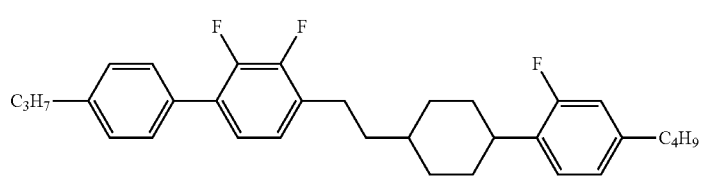 |

| No. | |
|---|---|
| 728 | 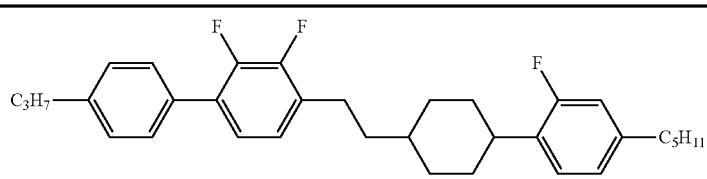 |
| 729 | 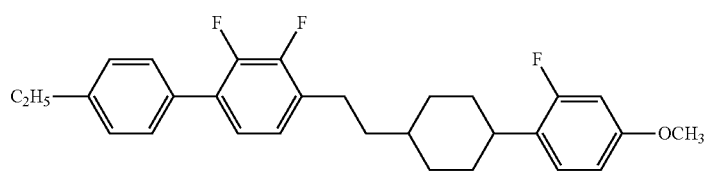 |
| 730 | 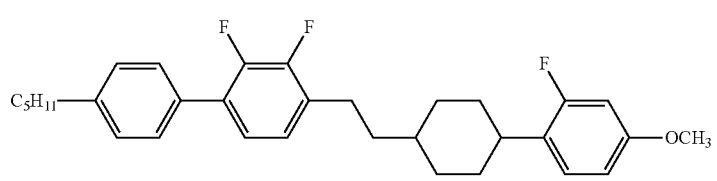 |
| 731 | 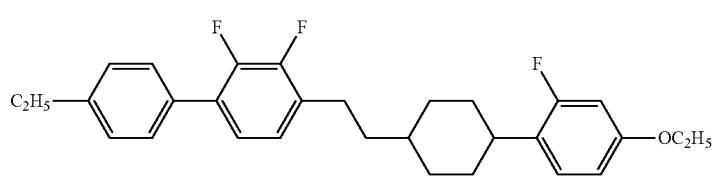 |
| 732 | 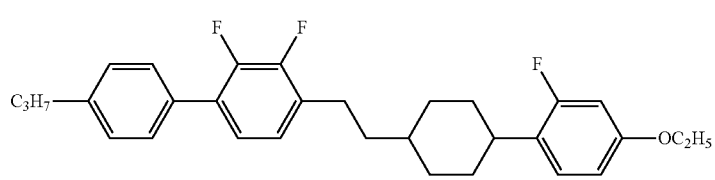 |
| 733 | 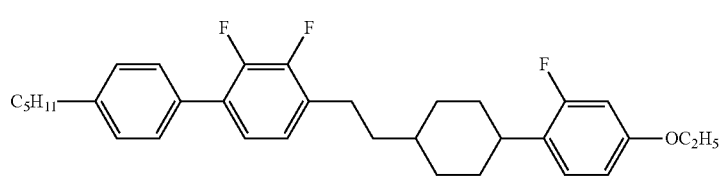 |
| 734 | 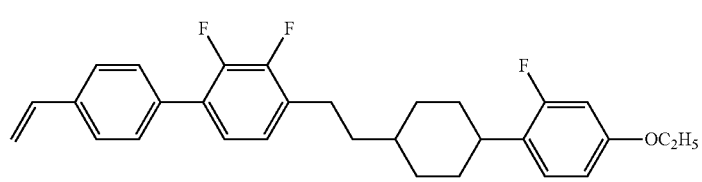 |
| 735 | 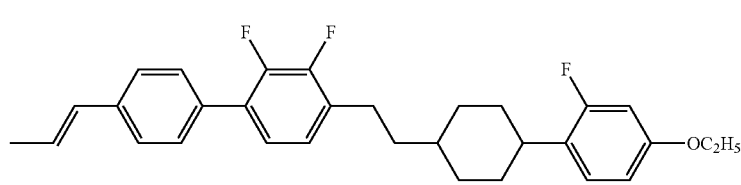 |
| 736 | 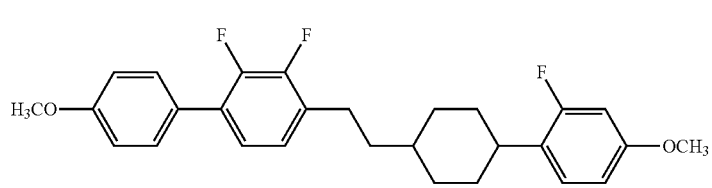 |

| No. | |
|---|---|
| 737 | 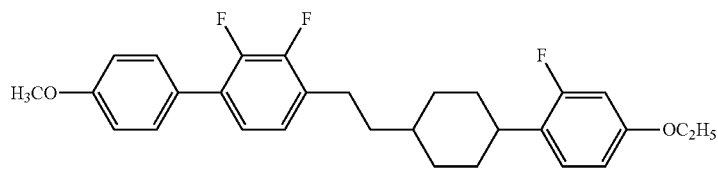 |
| 738 | 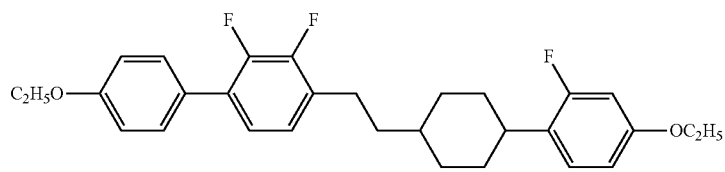 |
| 739 | 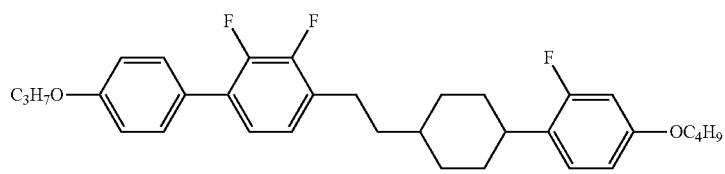 |
| 740 | 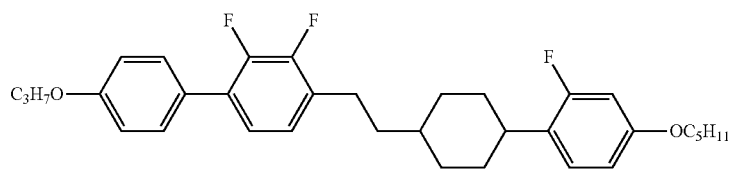 |
| 741 | 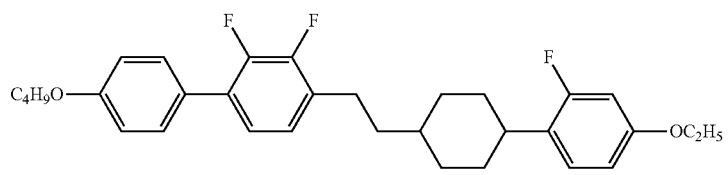 |
| 742 | 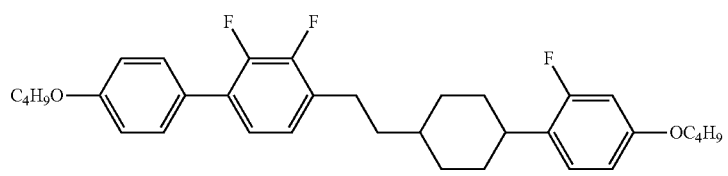 |
| 743 | 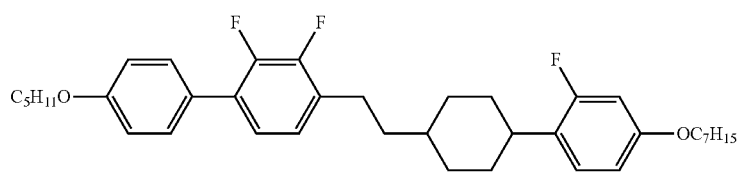 |
| 744 | 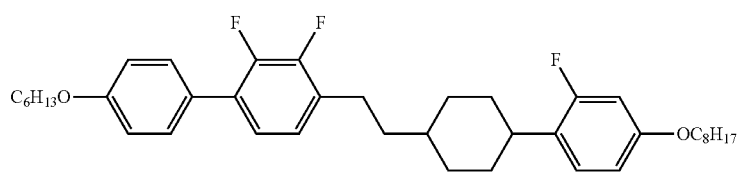 |

-continued
| No. | |
|---|---|
| 745 | 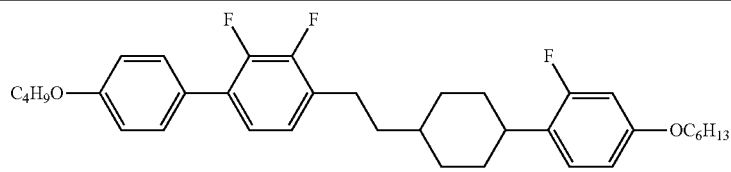 |
| 746 | 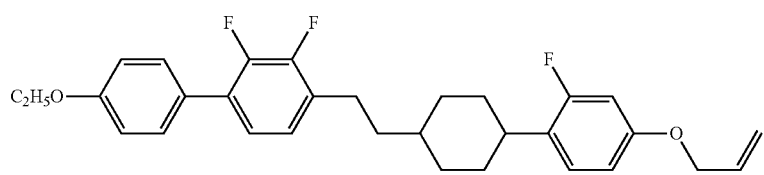 |
| 747 | 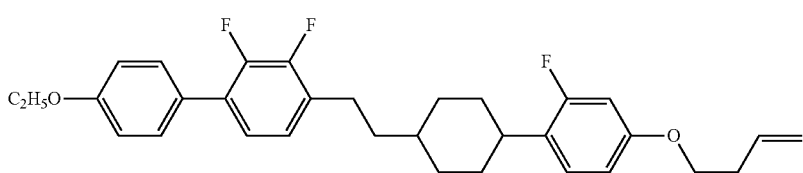 |
| 748 | 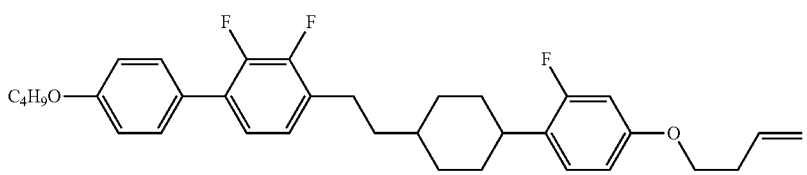 |
| 749 | 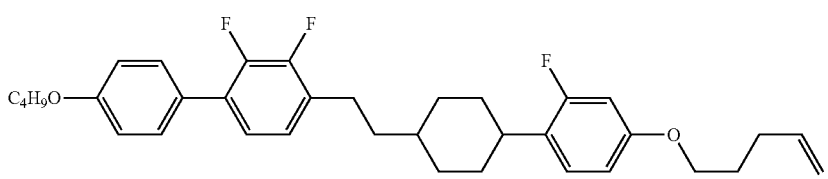 |
| 750 | 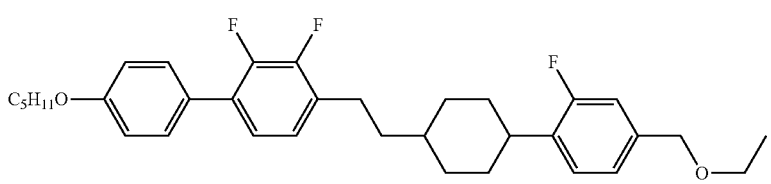 |
| 751 | 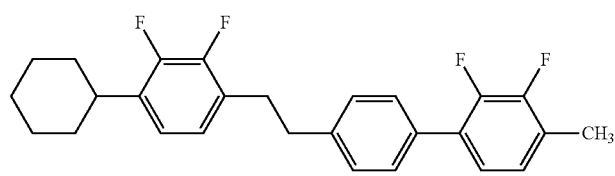 |
| 752 | 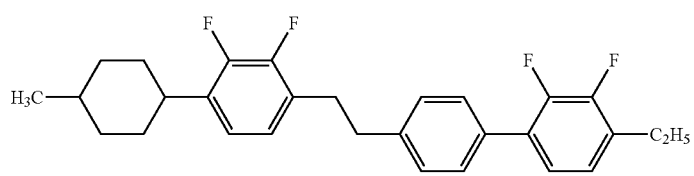 |
| 753 | 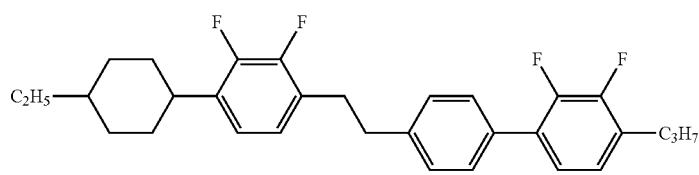 |

-continued
| No. | |
|---|---|
| 754 | 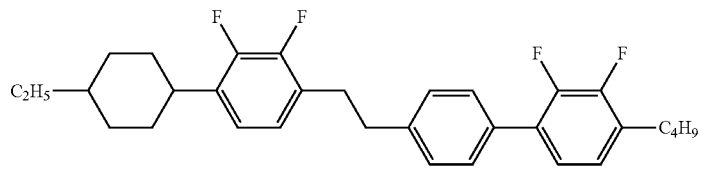 |
| 755 | 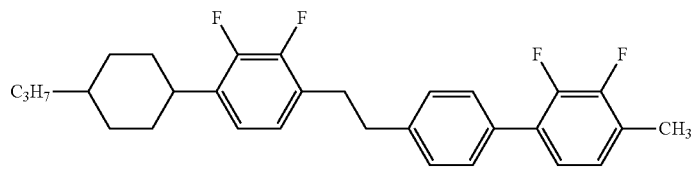 |
| 756 | 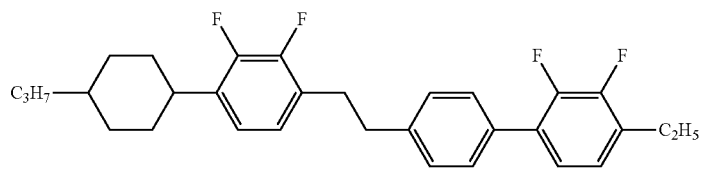 |
| 757 | 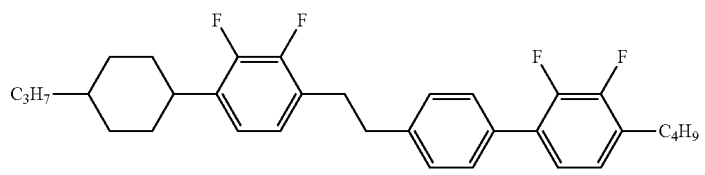 |
| 758 | 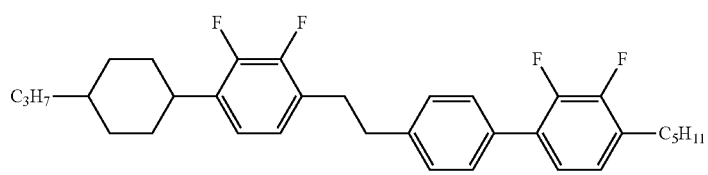 |
| 759 | 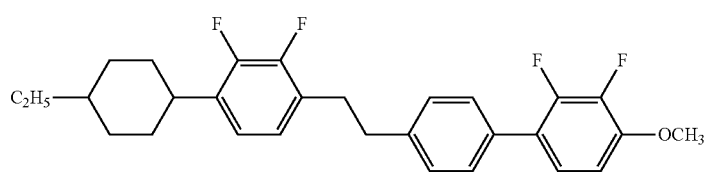 |
| 760 | 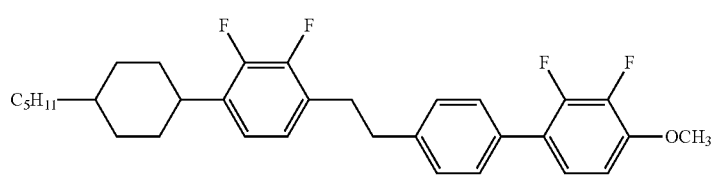 |
| 761 | 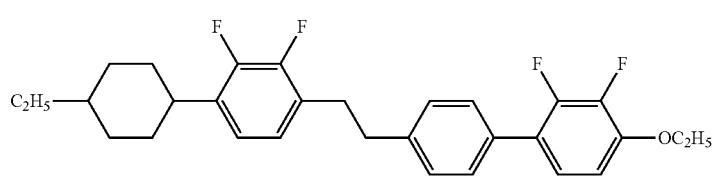 |

| No. | |
|---|---|
| 762 | 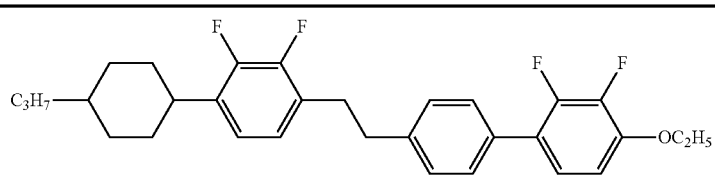 |
| 763 | 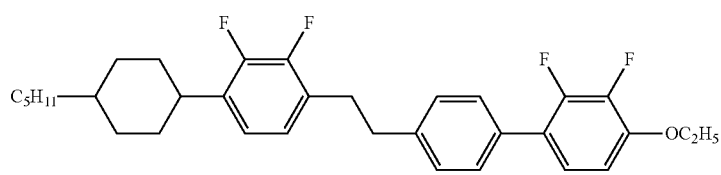 |
| 764 | 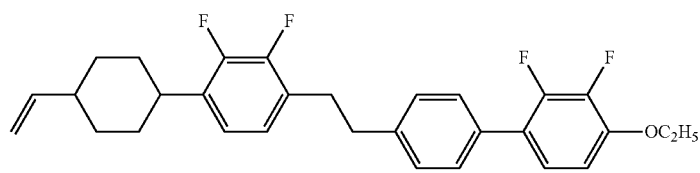 |
| 765 | 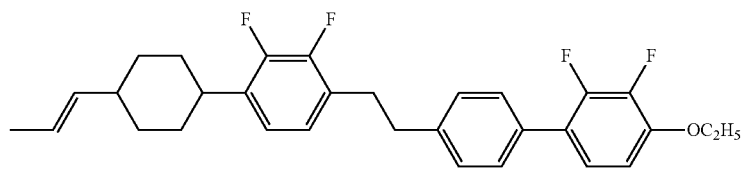 |
| 766 | 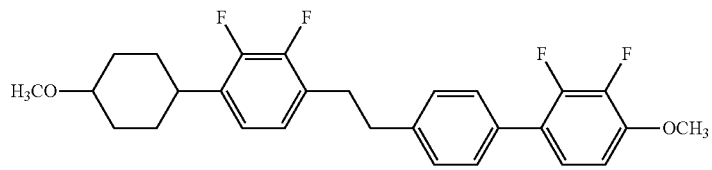 |
| 767 | 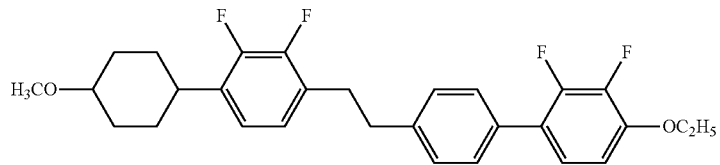 |
| 768 | 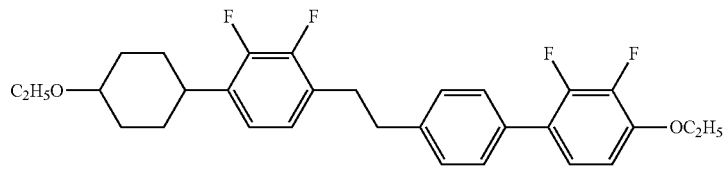 |
| 769 | 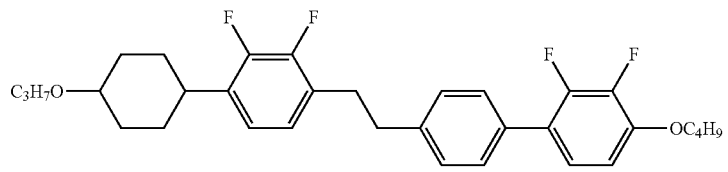 |
| 770 | 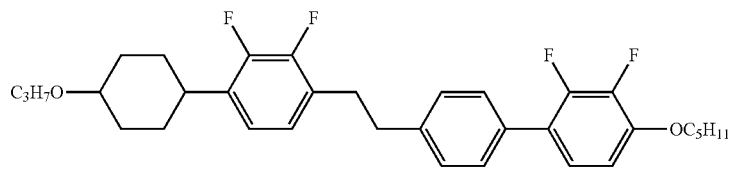 |

| No. | |
|---|---|
| 771 | 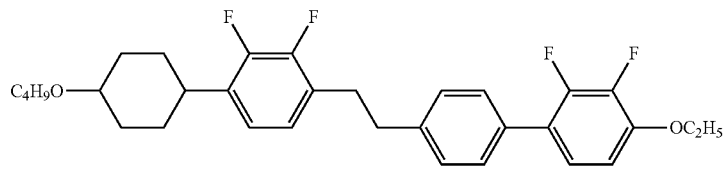 |
| 772 | 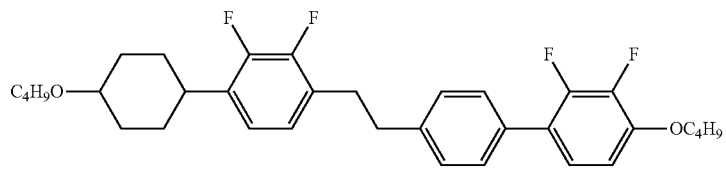 |
| 773 | 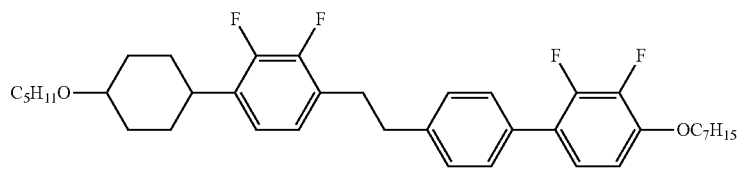 |
| 774 | 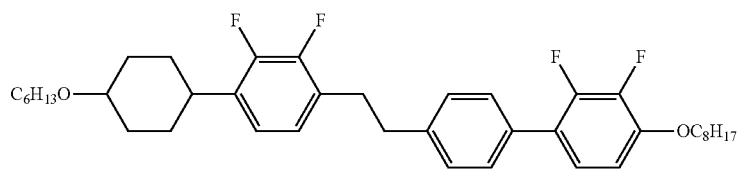 |
| 775 | 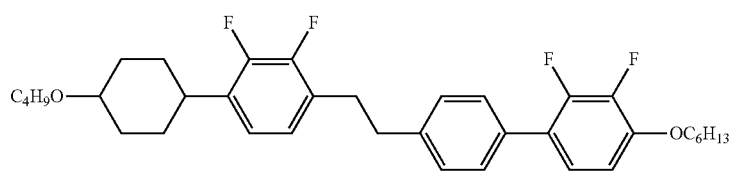 |
| 776 | 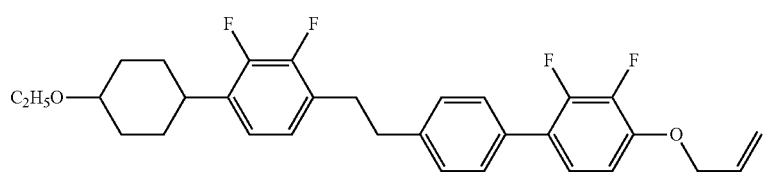 |
| 777 | 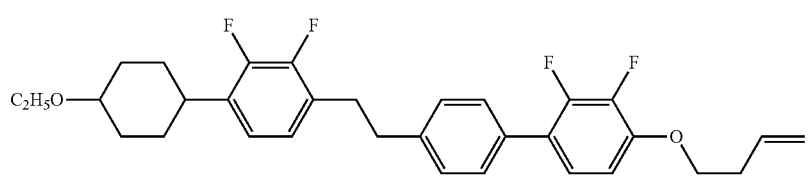 |
| 778 | 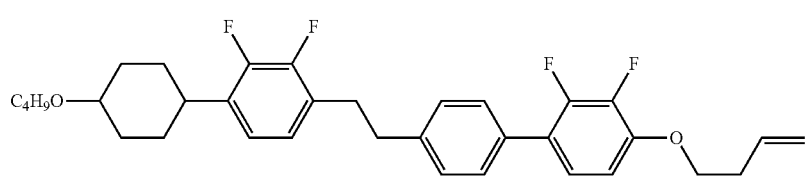 |

| No. | |
|---|---|
| 779 | 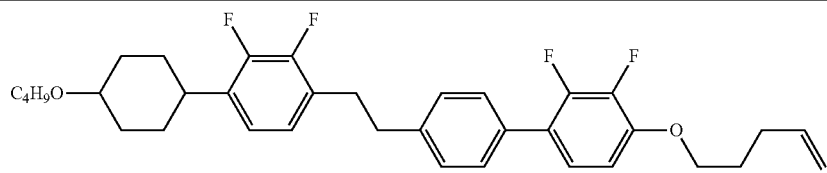 |
| 780 | 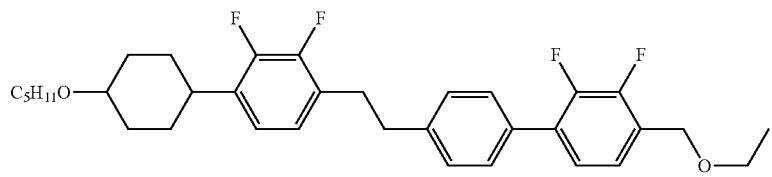 |
| 781 | 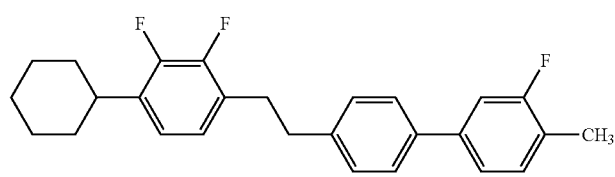 |
| 782 | 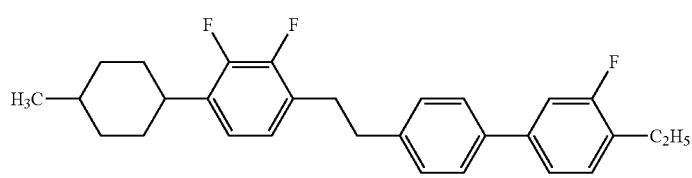 [SMILES: CCc1ccc(-c2ccc(CCc3ccc(C4CCC(C)CC4)c(F)c3F)cc2)cc1F] |
| 783 | 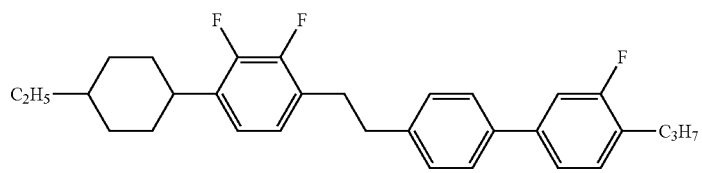 |
| 784 | 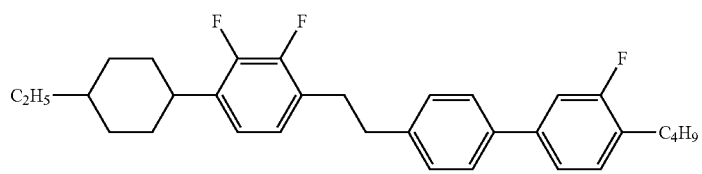 |
| 785 | 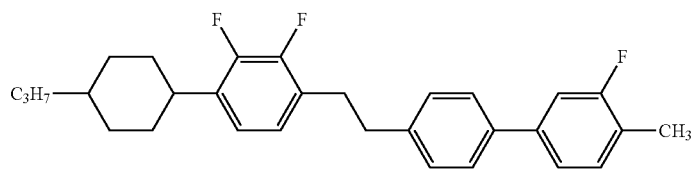 |
| 786 | 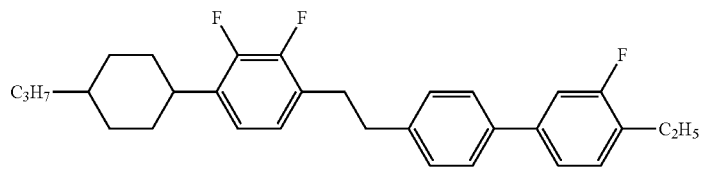 |
| 787 | 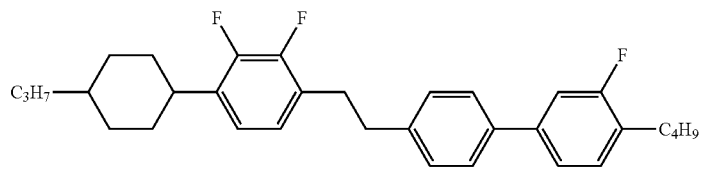 |

| No. | |
|---|---|
| 788 | 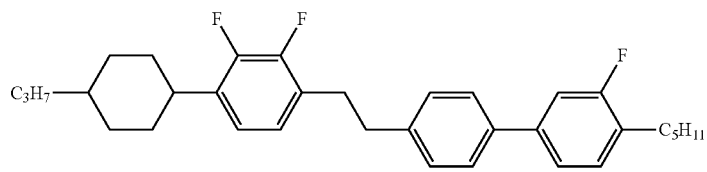 |
| 789 | 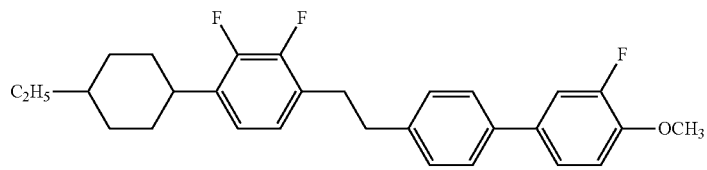 |
| 790 | 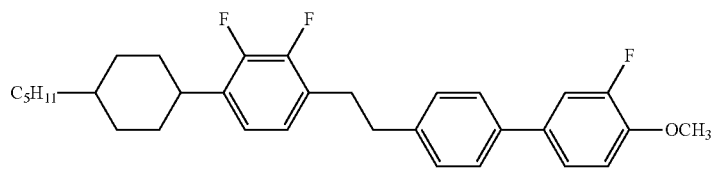 |
| 791 | 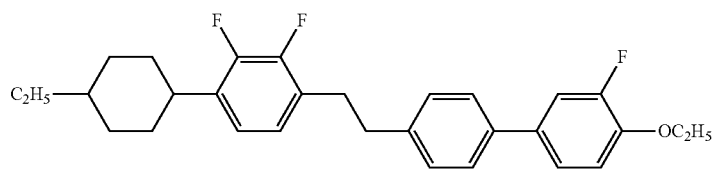 [SMILES: CCOc1ccc(-c2ccc(CCc3ccc(C4CCC(CC)CC4)c(F)c3F)cc2)cc1F] |
| 792 | 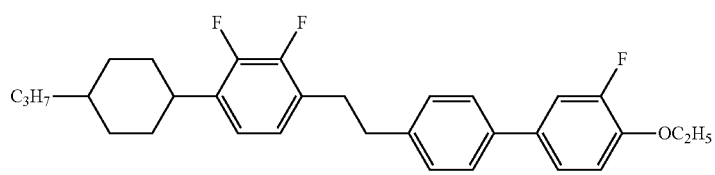 |
| 793 | 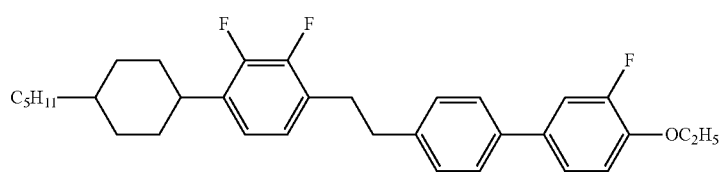 |
| 794 | 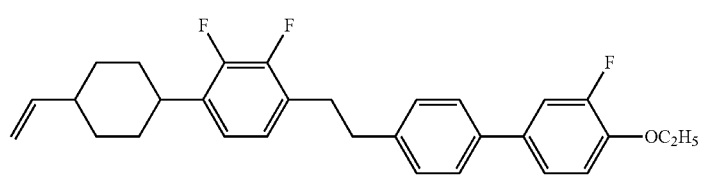 |
| 795 | 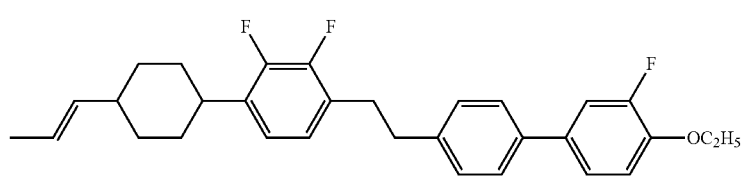 |

| No. | |
|---|---|
| 796 | 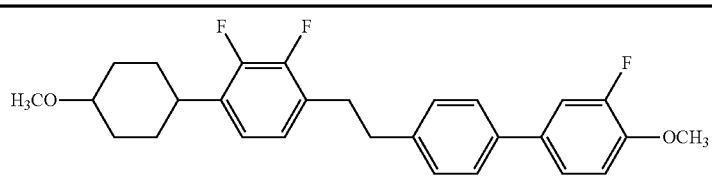 |
| 797 | 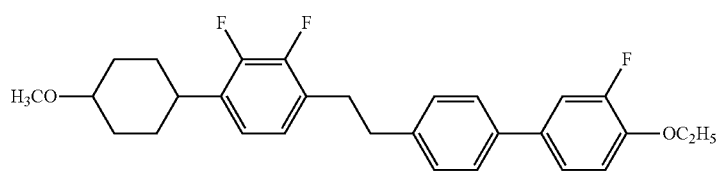 |
| 798 | 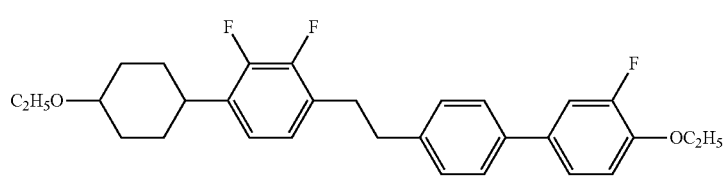 |
| 799 | 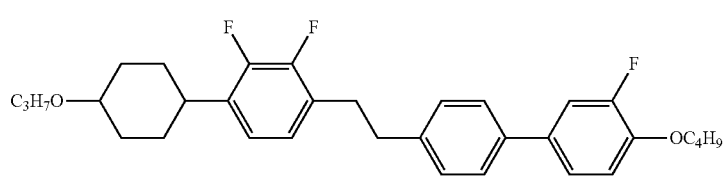 |
| 800 | 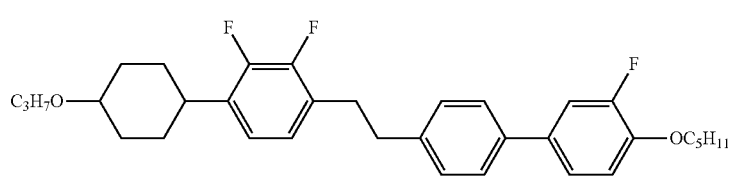 |
| 801 | 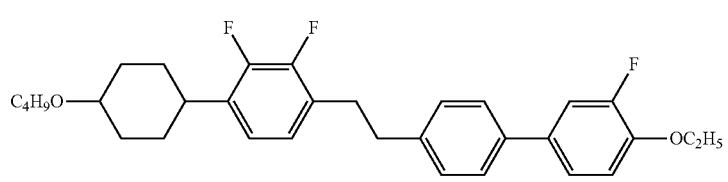 |
| 802 | 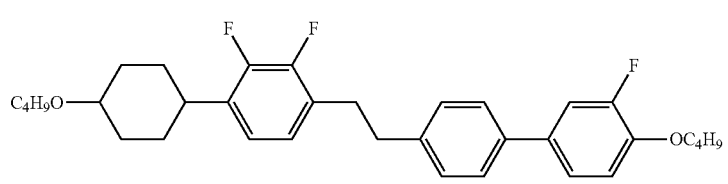 |
| 803 | 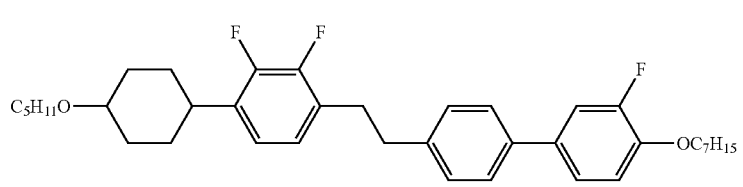 |
| 804 | 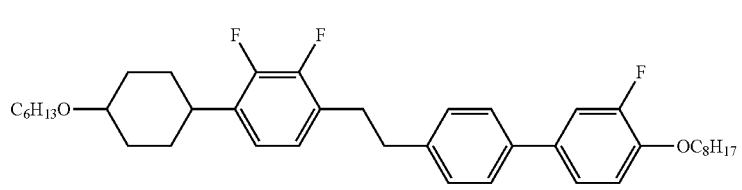 |

| No. |
|---|
| 805 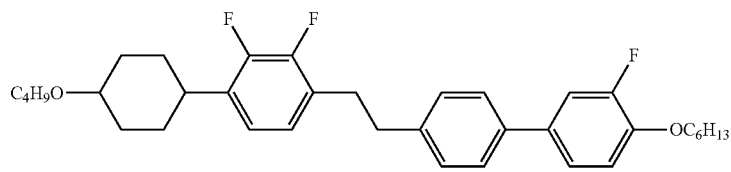 |
| 806 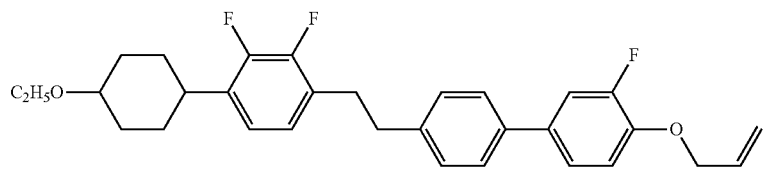 |
| 807 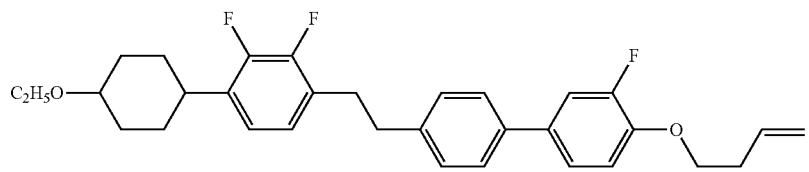 |
| 808 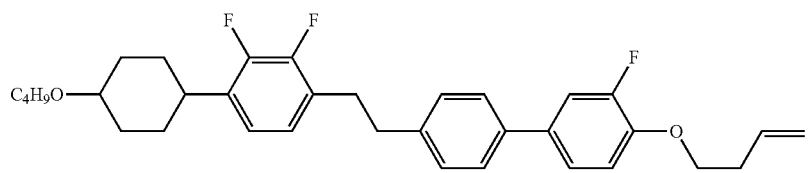 |
| 809 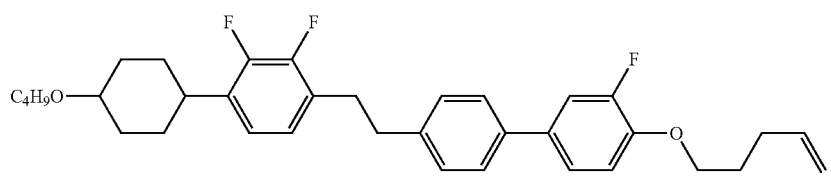 |
| 810 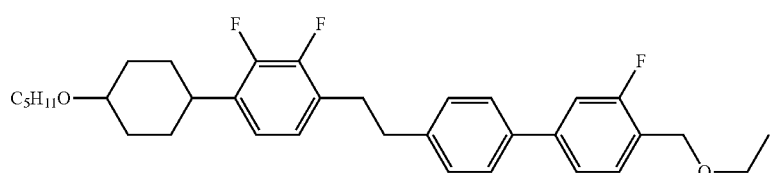 |
| 811 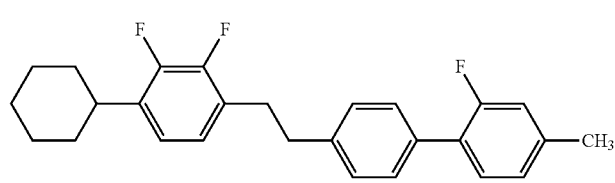 |
| 812 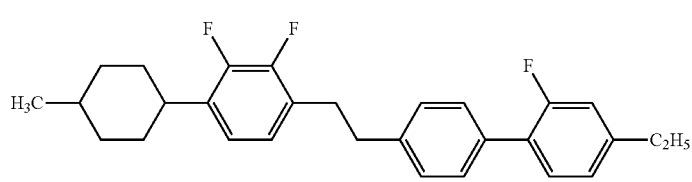 |

-continued
| No. |
|---|
| 813 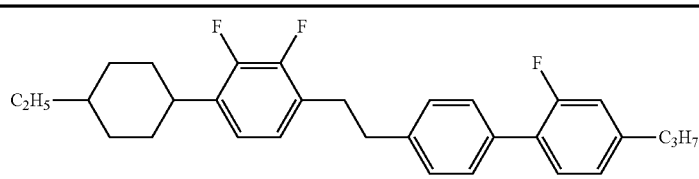 |
| 814 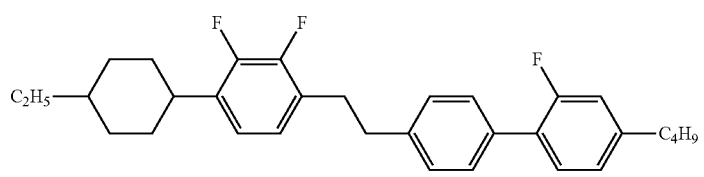 |
| 815 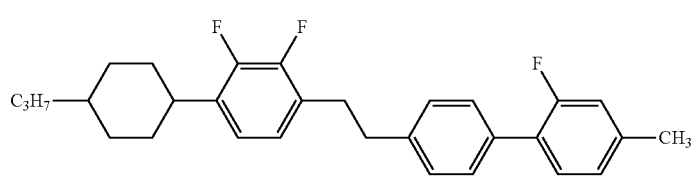 |
| 816 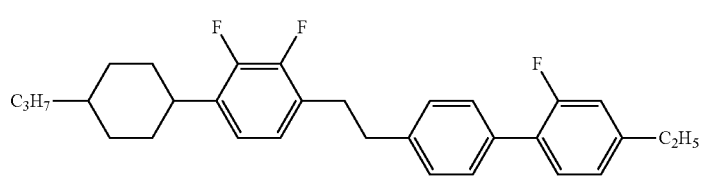 |
| 817 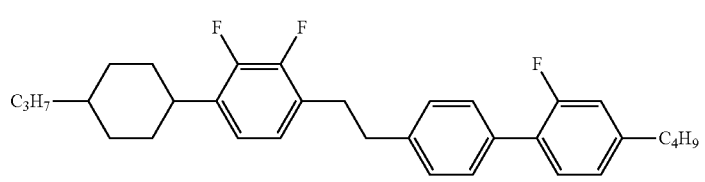 |
| 818 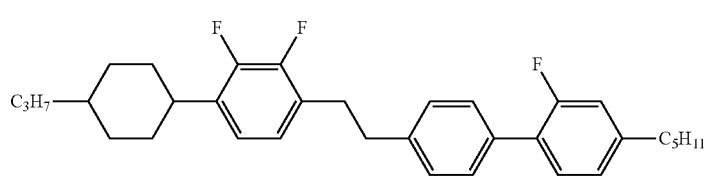 |
| 819 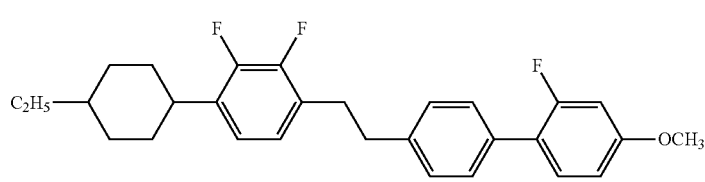 [SMILES: CCC1CCC(c2ccc(CCc3ccc(-c4ccc(OC)cc4F)cc3)c(F)c2F)CC1] |
| 820 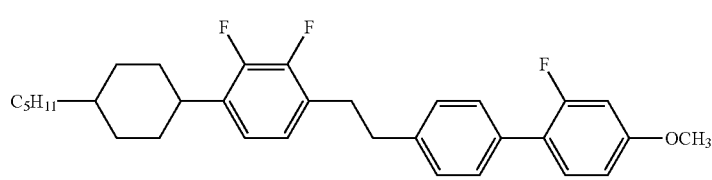 |
| 821 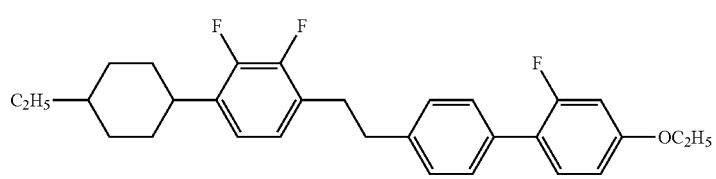 |

| No. | |
|---|---|
| 822 | 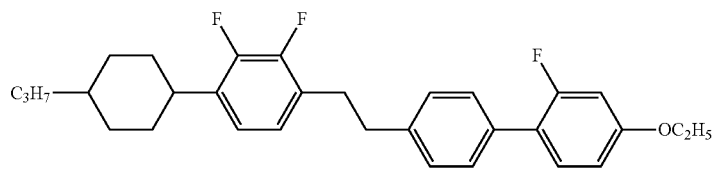 |
| 823 | 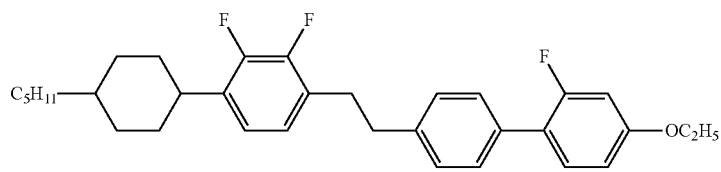 |
| 824 | 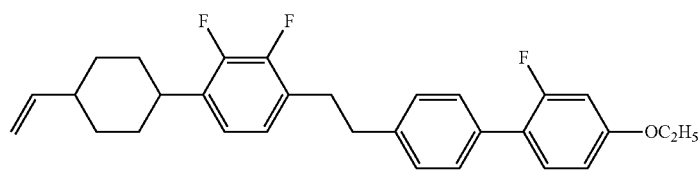 |
| 825 | 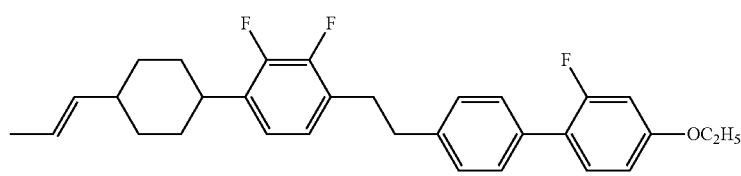 [SMILES: C/C=C/C1CCC(c2ccc(CCc3ccc(-c4ccc(OCC)cc4F)cc3)c(F)c2F)CC1] |
| 826 | 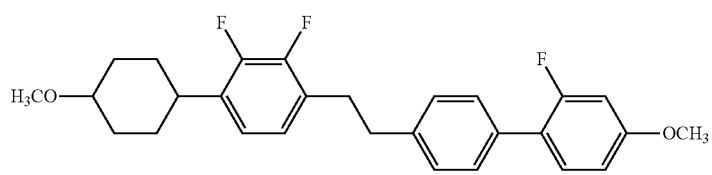 |
| 827 | 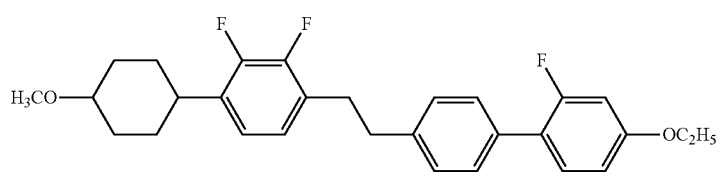 |
| 828 | 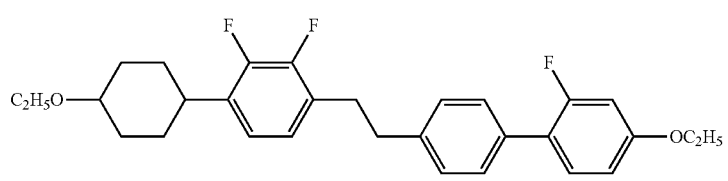 |
| 829 | 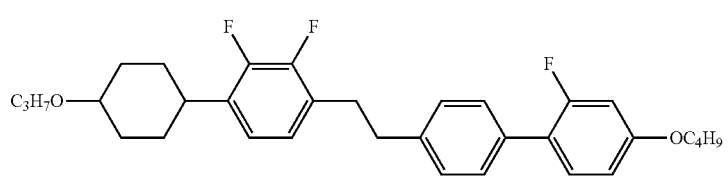 |

| No. | |
|---|---|
| 830 | 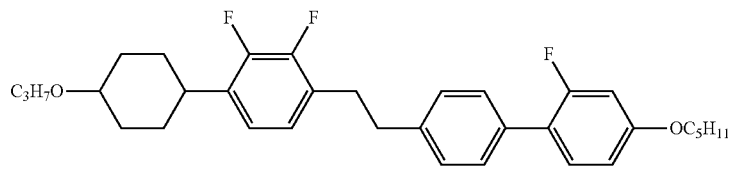 |
| 831 | 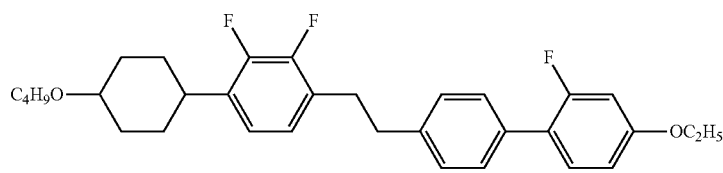 |
| 832 | 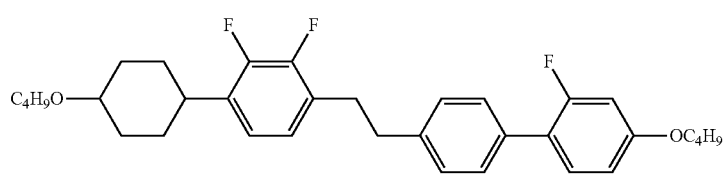 |
| 833 | 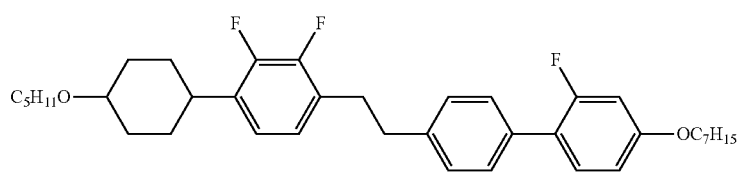 |
| 834 | 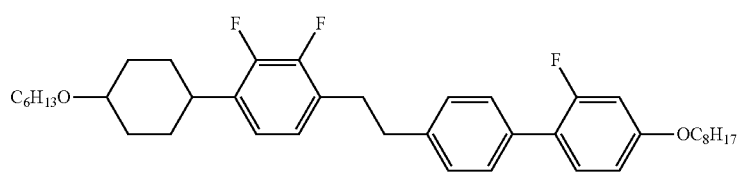 |
| 835 | 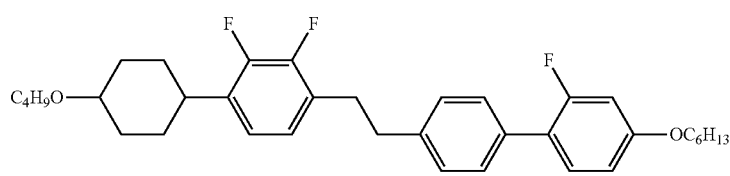 |
| 836 | 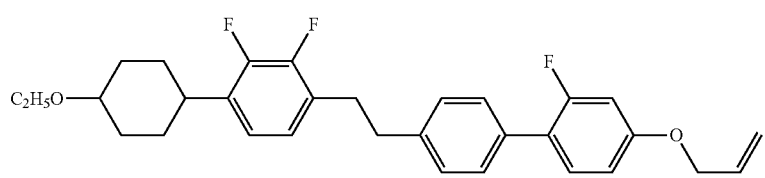 |
| 837 | 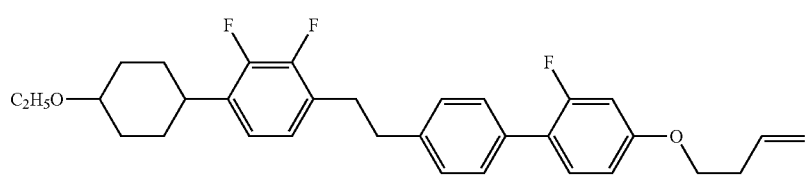 |
| 838 | 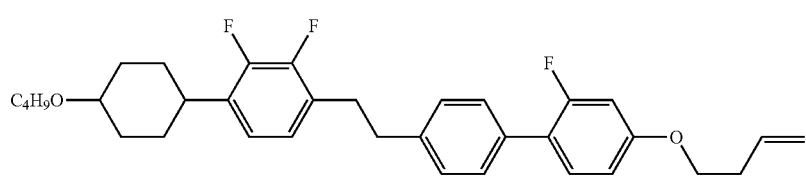 |

| No. | |
|---|---|
| 839 | 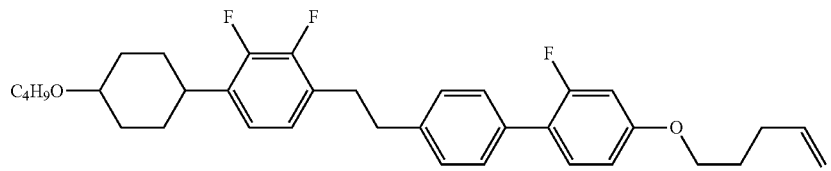 |
| 840 | 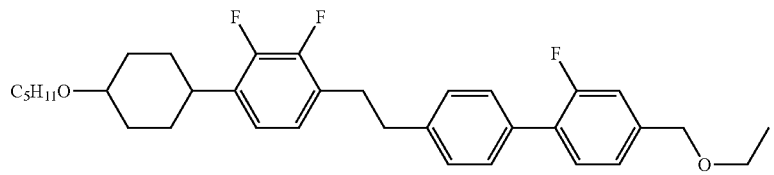 |
| 841 | 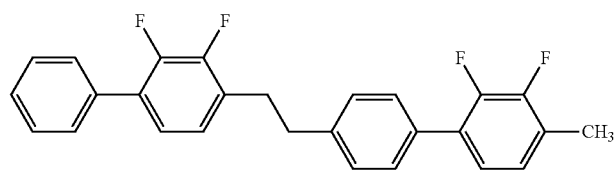 |
| 842 | 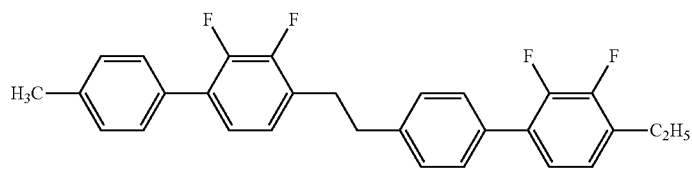 |
| 843 | 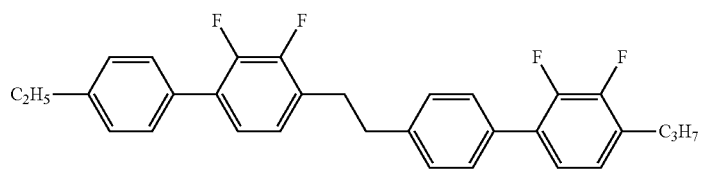 |
| 844 | 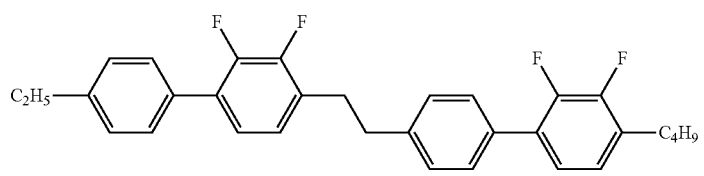 |
| 845 | 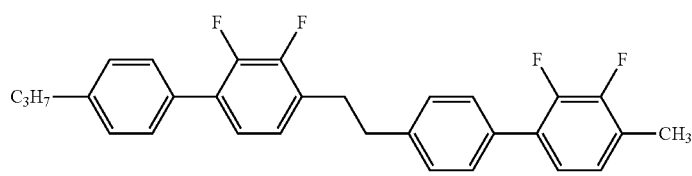 |
| 846 | 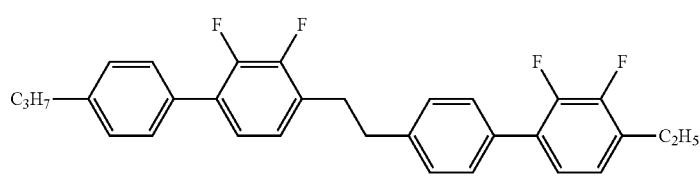 |

| No. | |
|---|---|
| 847 | 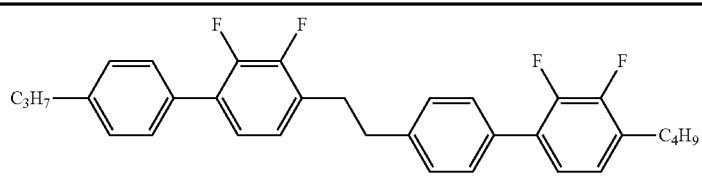 |
| 848 | 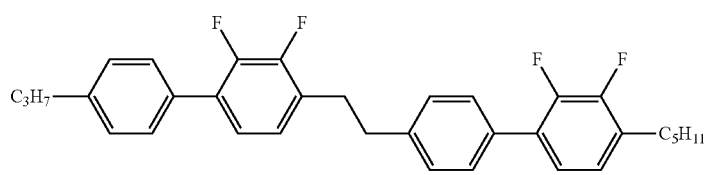 |
| 849 | 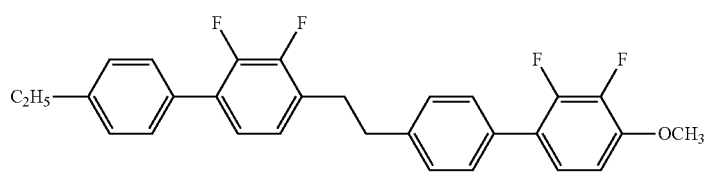 |
| 850 | 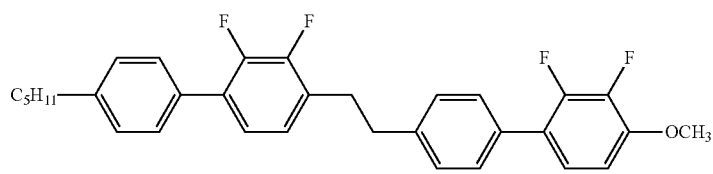 |
| 851 | 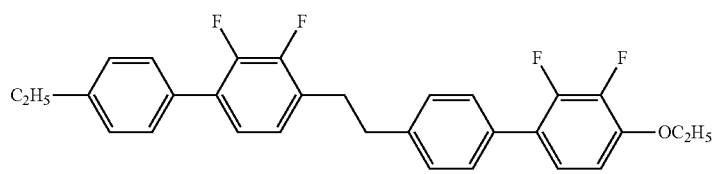 |
| 852 | 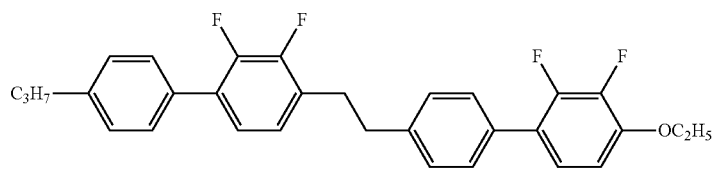 |
| 853 | 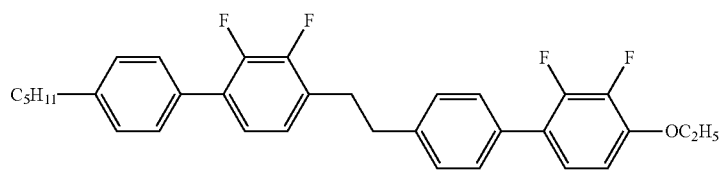 |
| 854 | 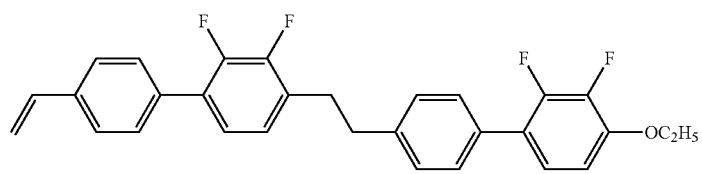 |
| 855 | 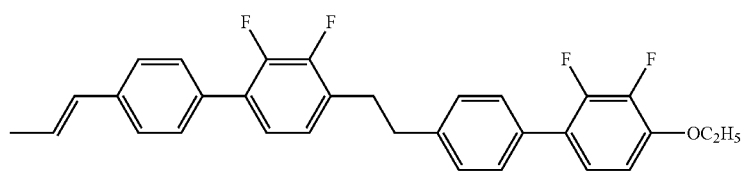 |

| No. |
|---|
| 856 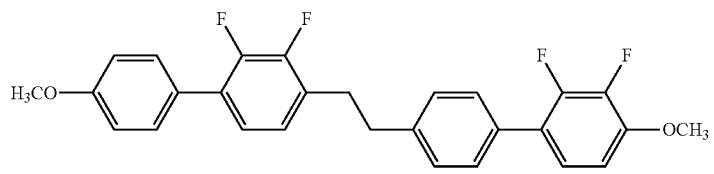 |
| 857 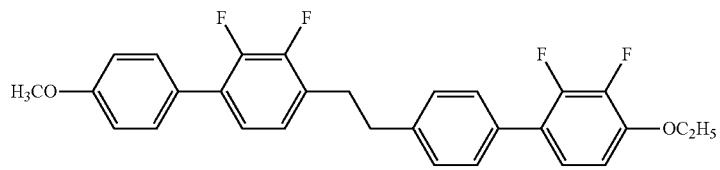 |
| 858 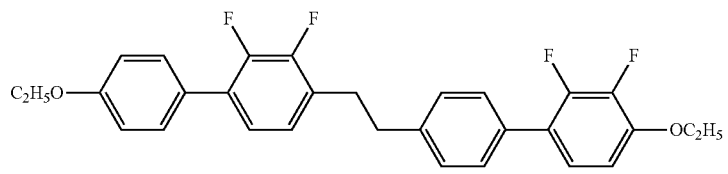 |
| 859 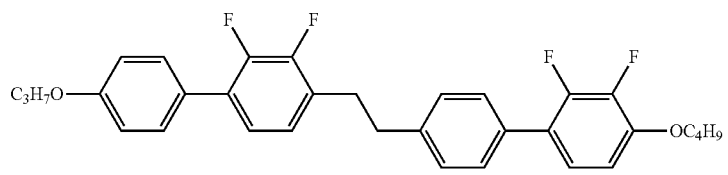 |
| 860 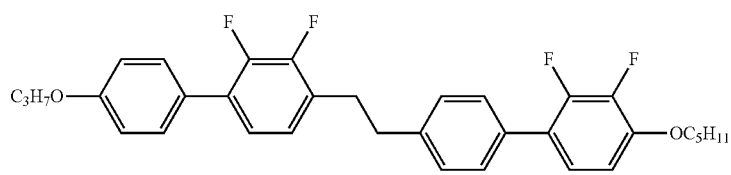 |
| 861 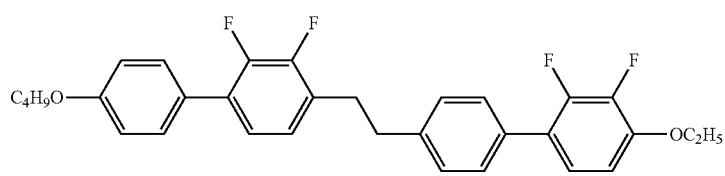 |
| 862 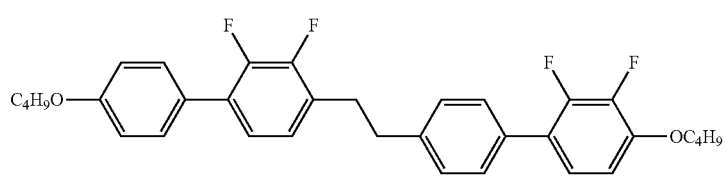 |
| 863 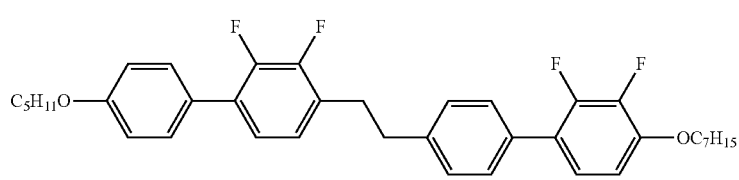 |

-continued
| No. | |
|---|---|
| 864 | 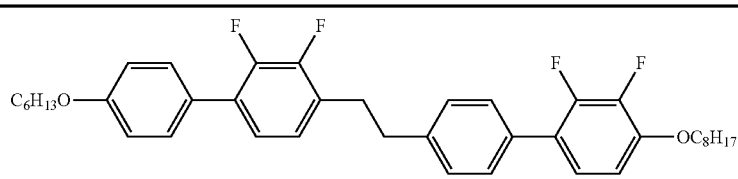 |
| 865 | 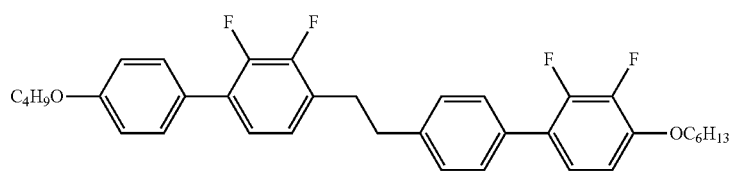 |
| 866 | 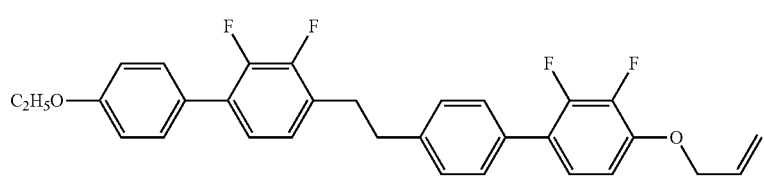 |
| 867 | 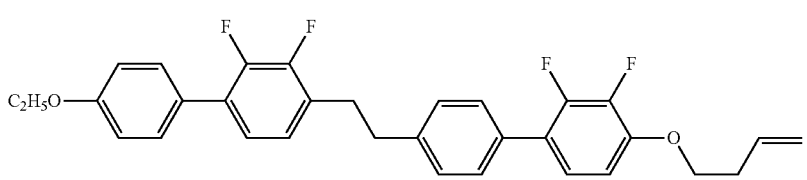 |
| 868 | 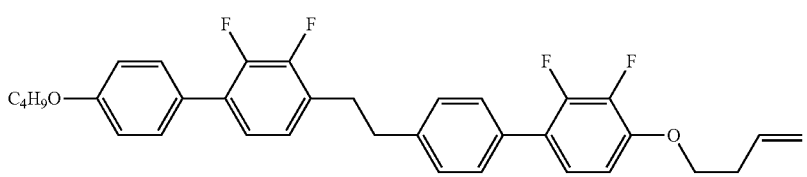 |
| 869 | 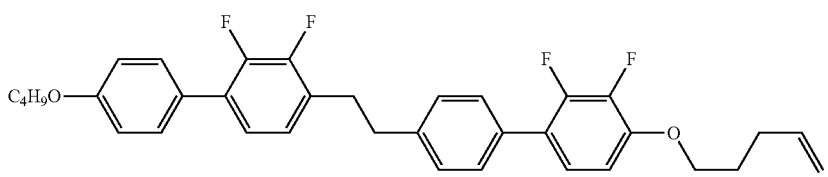 |
| 870 | 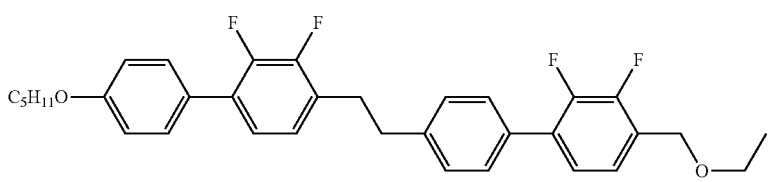 |
| 871 | 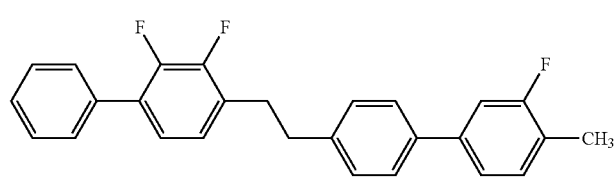 |
| 872 | 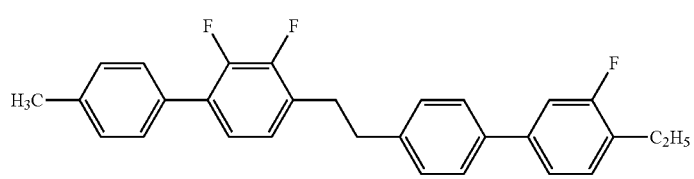 |

-continued
| No. | |
|---|---|
| 873 | 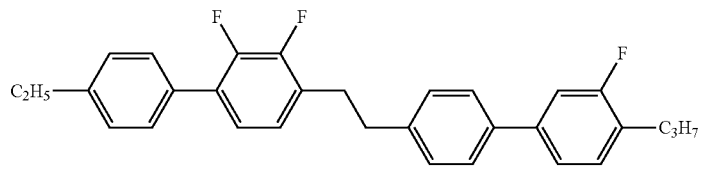 |
| 874 | 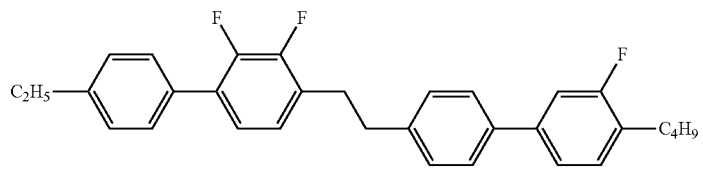 |
| 875 | 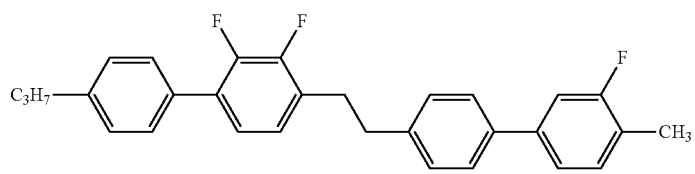 |
| 876 | 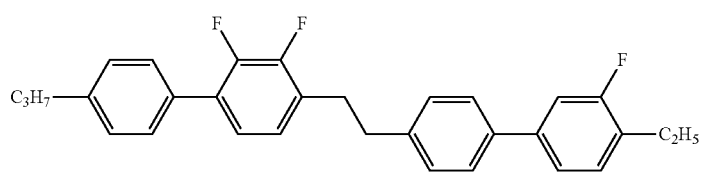 |
| 877 | 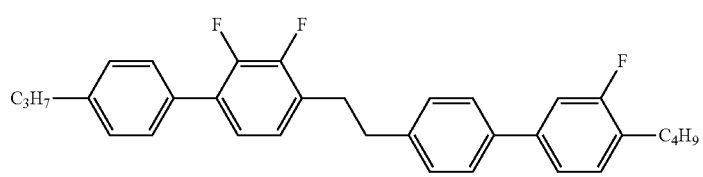 |
| 878 | 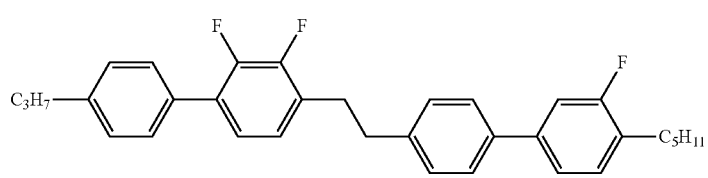 |
| 879 | 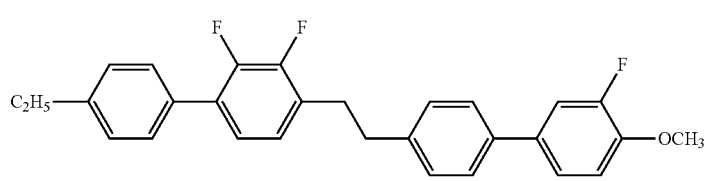 |
| 880 | 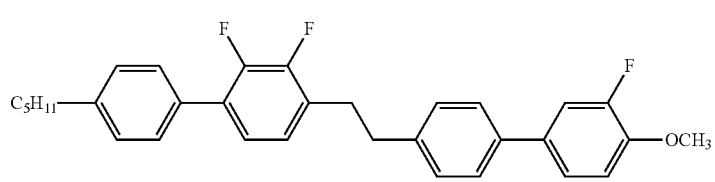 |

-continued
| No. |
|---|
| 881 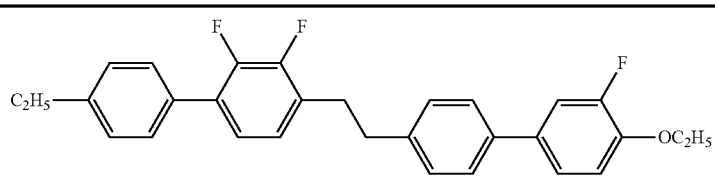 |
| 882 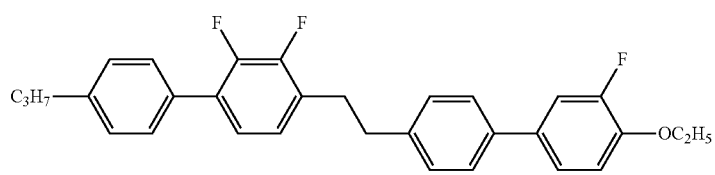 |
| 883 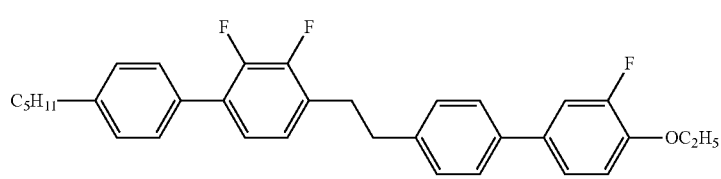 |
| 884 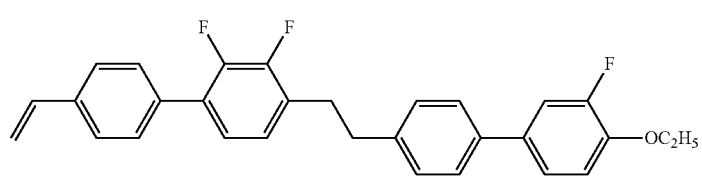 |
| 885 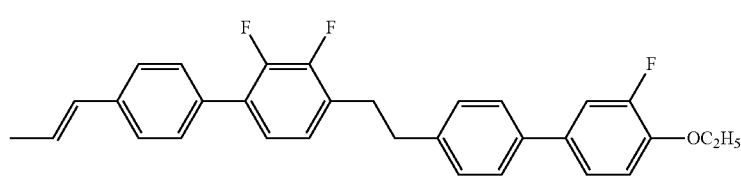 |
| 886 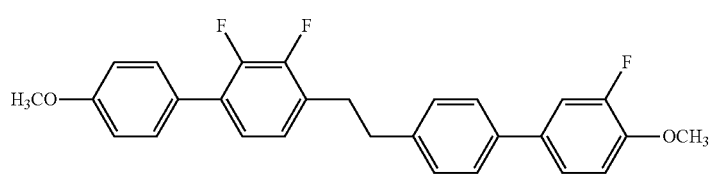 [SMILES: COc1ccc(-c2ccc(CCc3ccc(-c4ccc(OC)c(F)c4)cc3)c(F)c2F)cc1] |
| 887 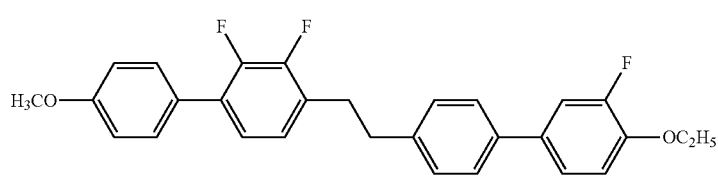 [SMILES: CCOc1ccc(-c2ccc(CCc3ccc(-c4ccc(OC)cc4)c(F)c3F)cc2)cc1F] |
| 888 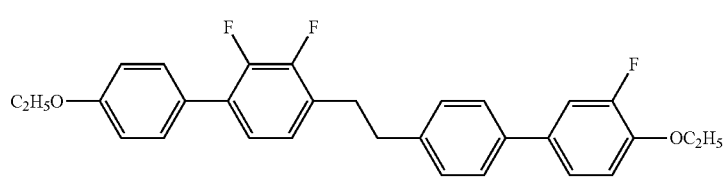 |
| 889 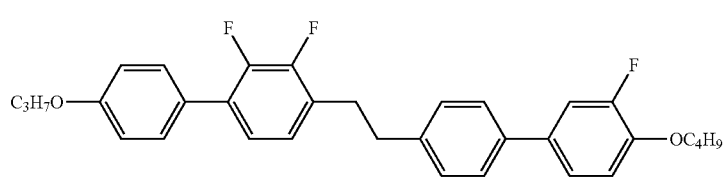 |

| No. | |
|---|---|
| 890 | 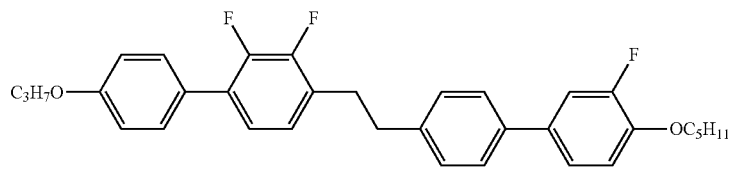 |
| 891 | 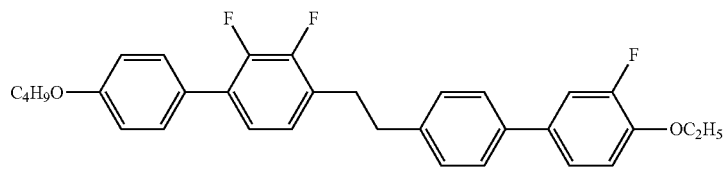 |
| 892 | 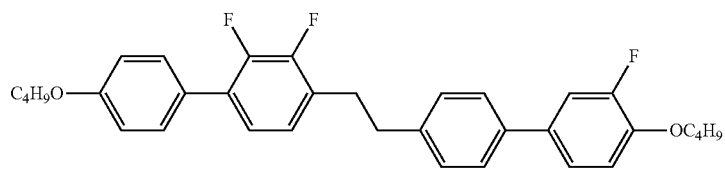 |
| 893 | 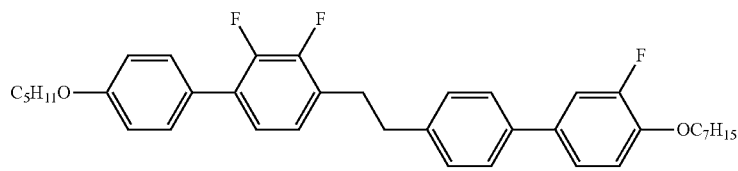 |
| 894 | 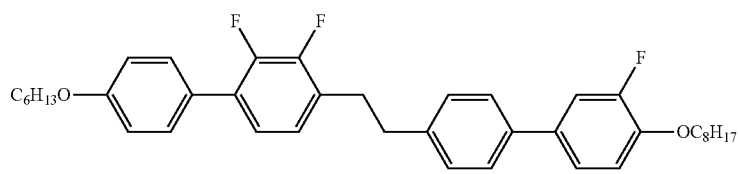 |
| 895 | 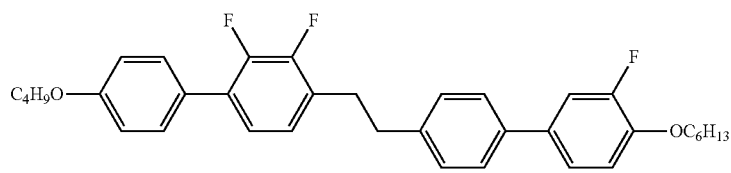 |
| 896 | 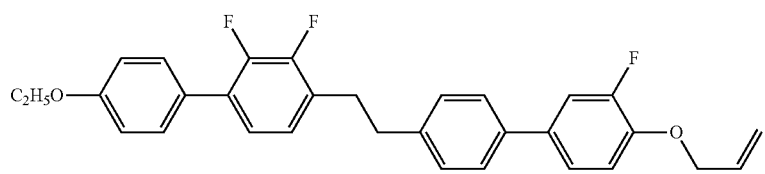 |
| 897 | 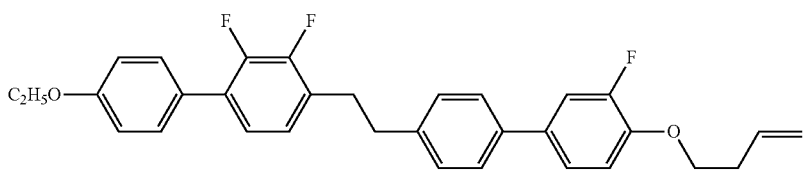 |

| No. |  |
|---|---|
| 898 | 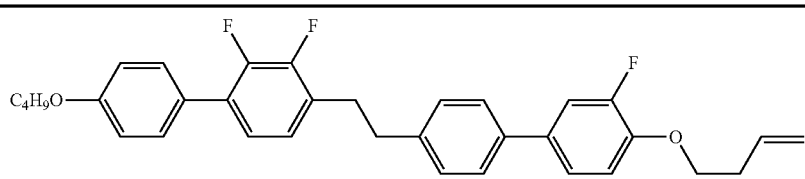 |
| 899 | 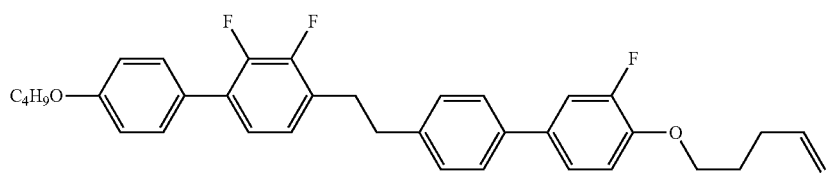 |
| 900 | 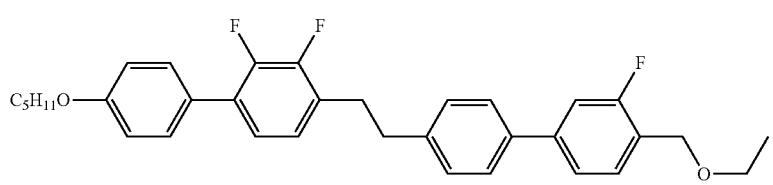 |
| 901 | 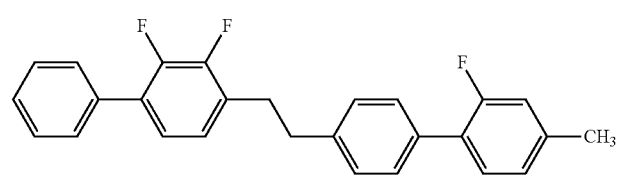 |
| 902 | 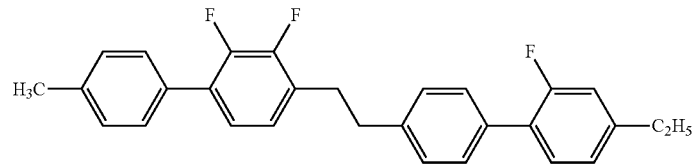 |
| 903 | 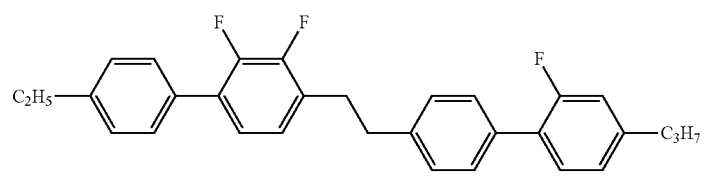 |
| 904 | 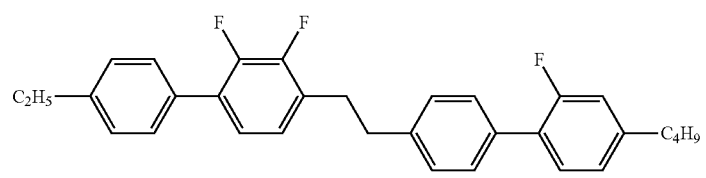 |
| 905 | 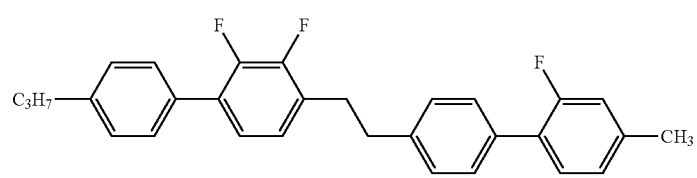 |
| 906 | 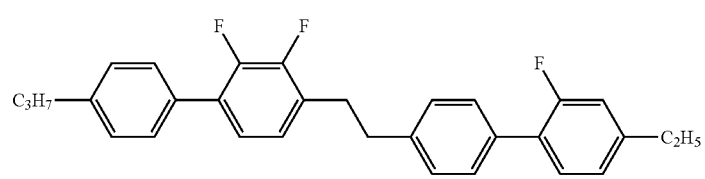 |

| No. |
|---|
| 907 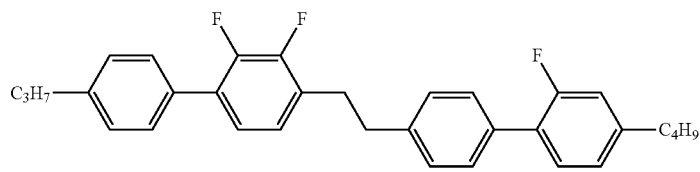 |
| 908 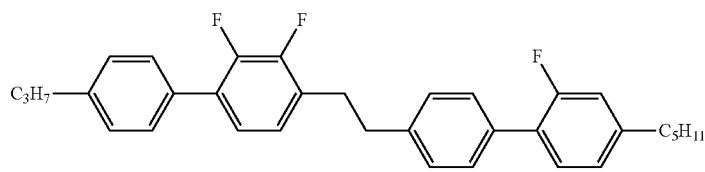 |
| 909 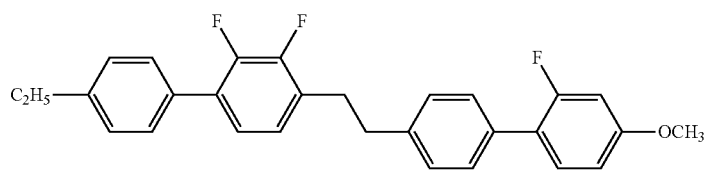 |
| 910 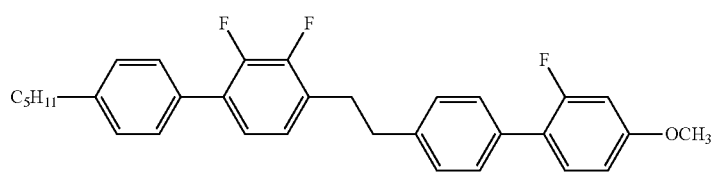 |
| 911 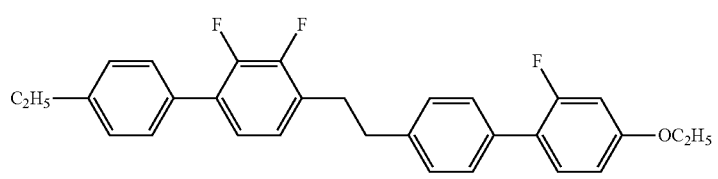 |
| 912 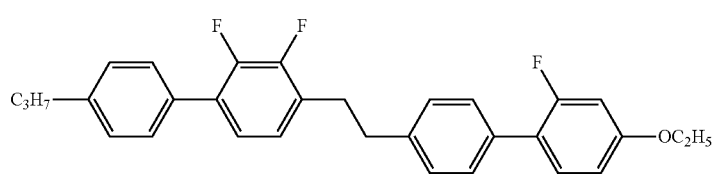 |
| 913 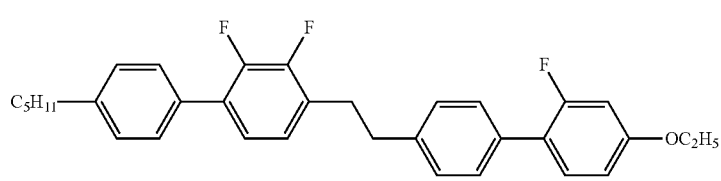 |
| 914 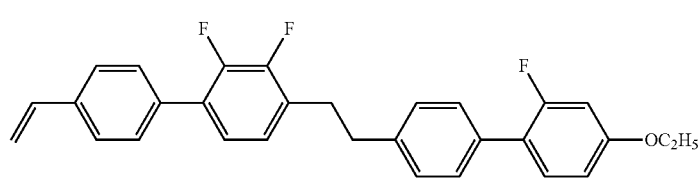 |

| No. |
|---|
| 915 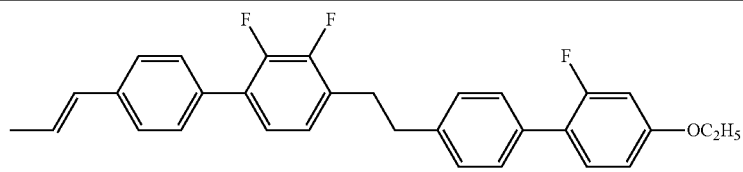 |
| 916 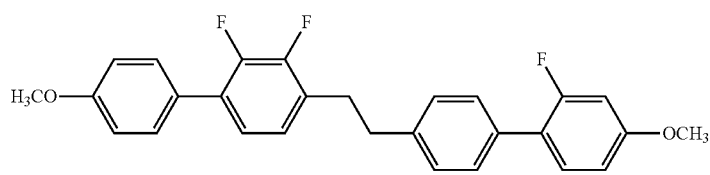 [SMILES: COc1ccc(-c2ccc(CCc3ccc(-c4ccc(OC)cc4F)cc3)c(F)c2F)cc1] |
| 917 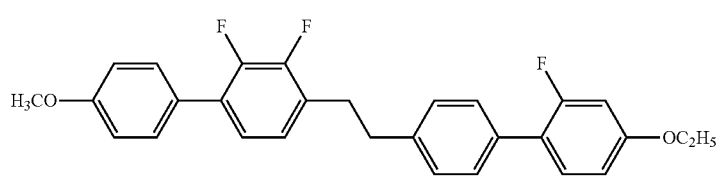 |
| 918 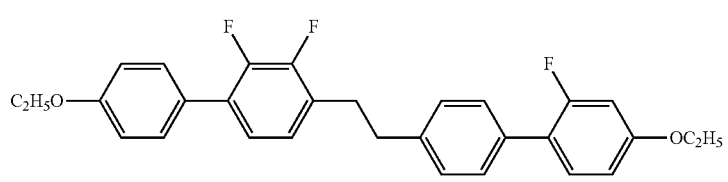 |
| 919 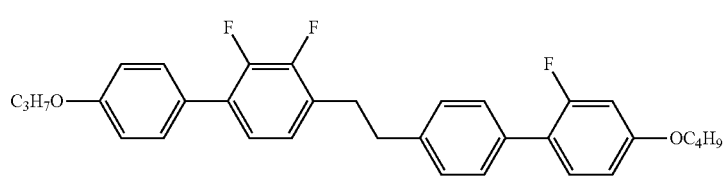 |
| 920 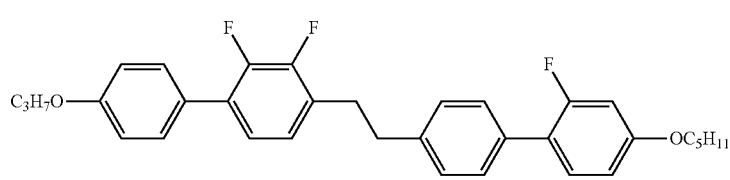 |
| 921 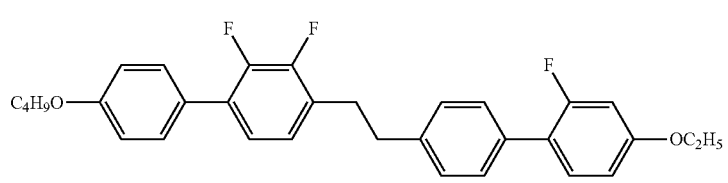 |
| 922 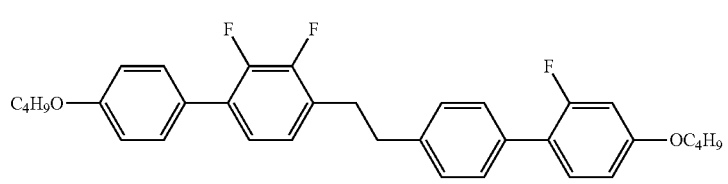 |
| 923 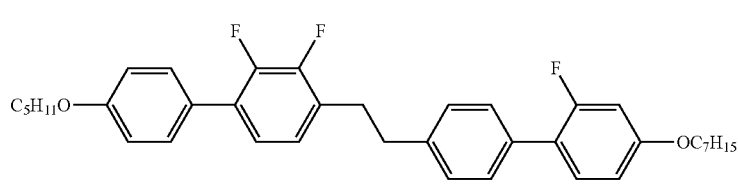 |

| No. | |
|---|---|
| 924 | 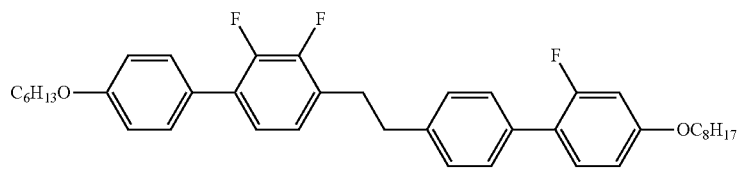 |
| 925 | 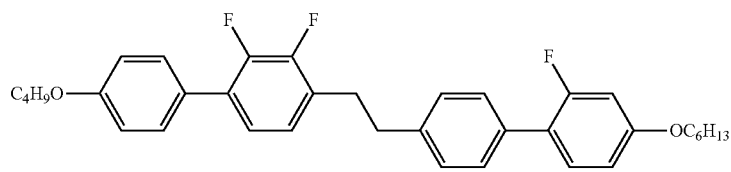 |
| 926 | 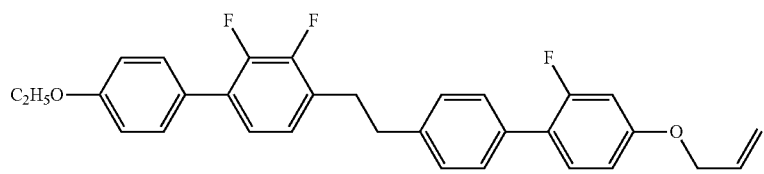 |
| 927 | 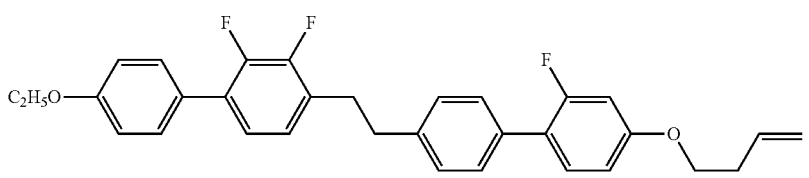 |
| 928 | 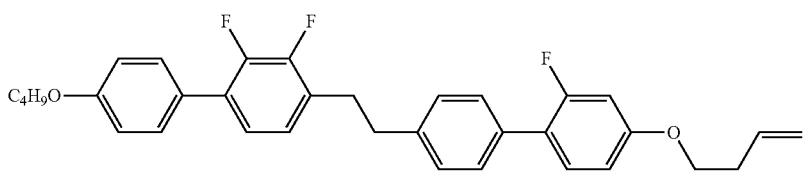 |
| 929 | 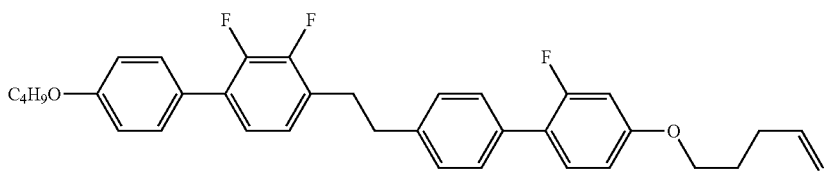 |
| 930 | 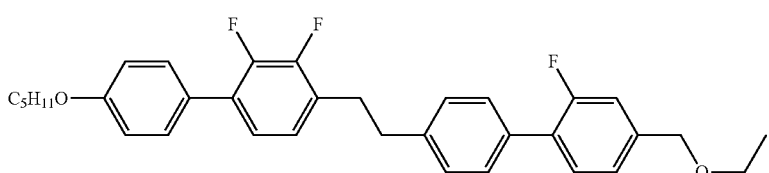 |
| 931 | 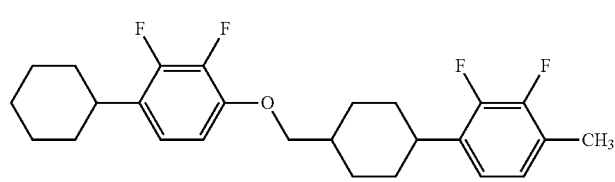 |

| No. | |
|---|---|
| 932 | 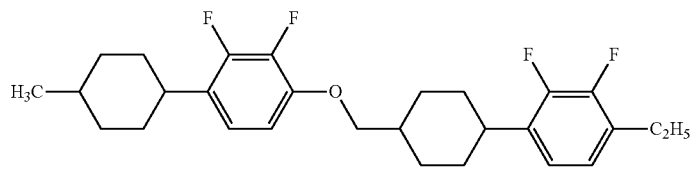 |
| 933 | 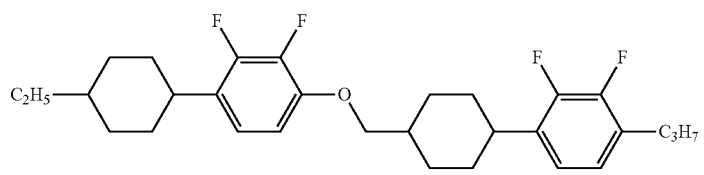 |
| 934 | 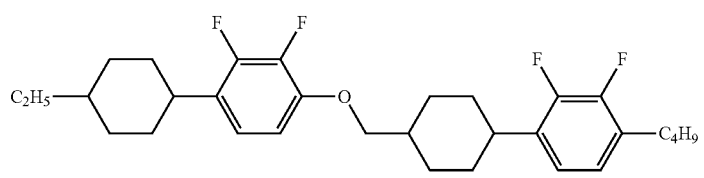 |
| 935 | 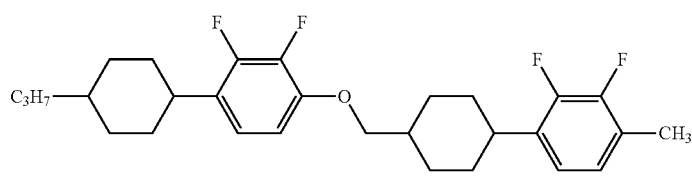 |
| 936 | 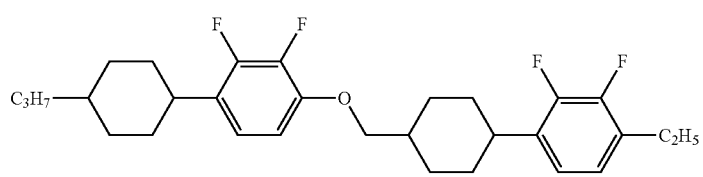 |
| 937 | 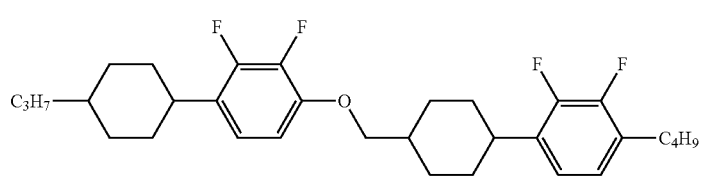 |
| 938 | 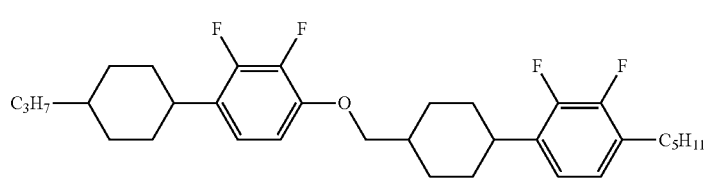 |
| 939 | 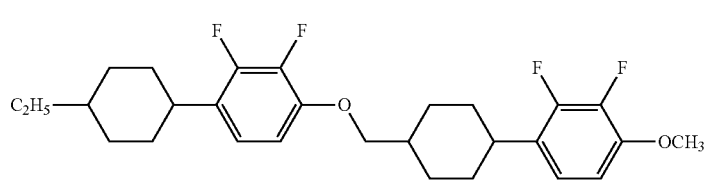 |

| No. | |
|---|---|
| 940 | 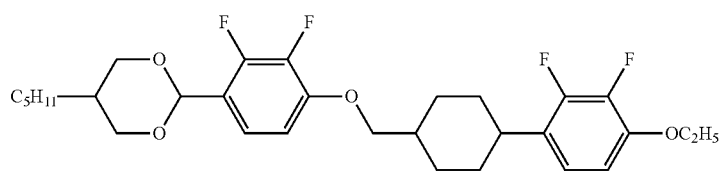<br>C 102.5 N 185.8 I<br>T$_{NI}$; 174.6° C., Δε; −3.69, Δn; 0.137 |
| 941 | 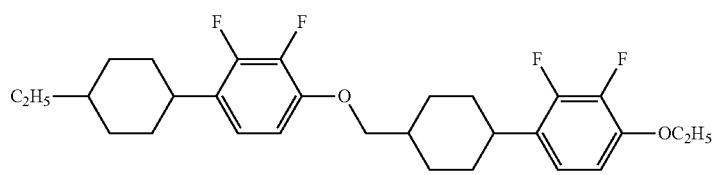 |
| 942 | 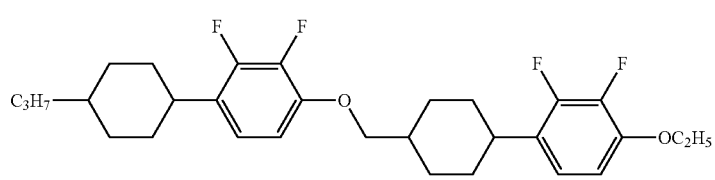 |
| 943 | 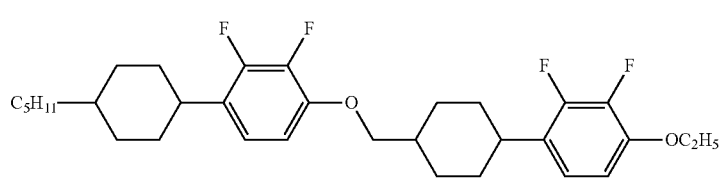<br>C 101.8 N 204.0 I<br>T$_{NI}$; 187.3° C., Δε; −6.15, Δn; 0.134 |
| 944 | 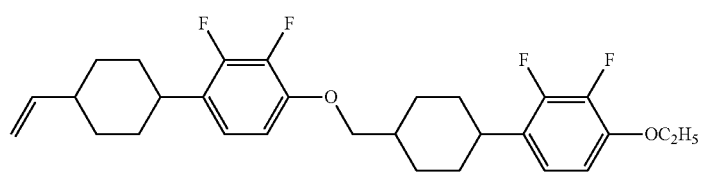 |
| 945 | 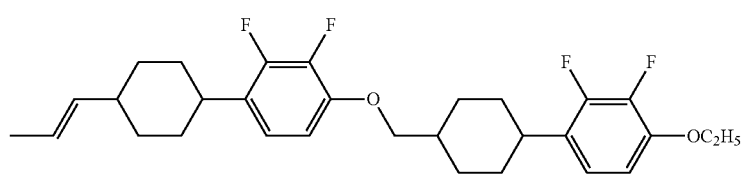 [SMILES: C/C=C/C1CCC(c2ccc(OCC3CCC(c4ccc(OCC)c(F)c4F)CC3)c(F)c2F)CC1] |
| 946 | 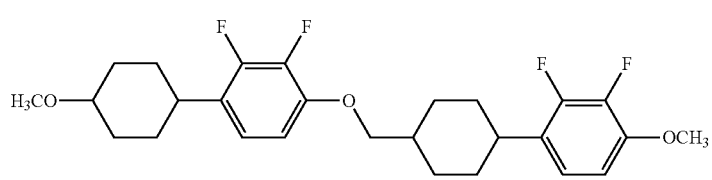 |
| 947 | 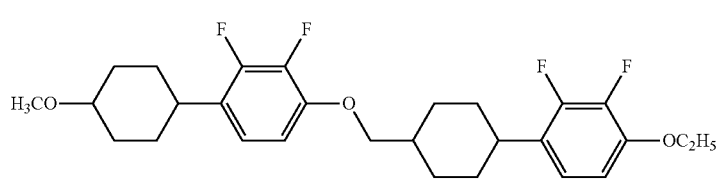 |

| No. | |
|---|---|
| 948 | 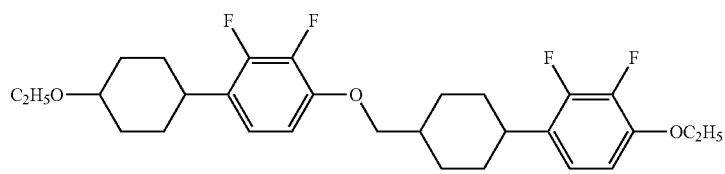 |
| 949 | 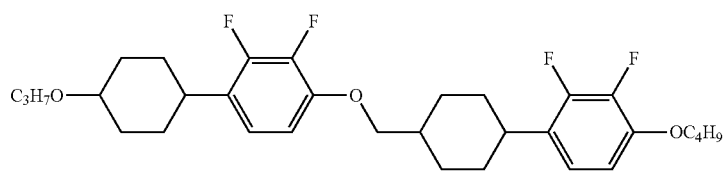 |
| 950 | 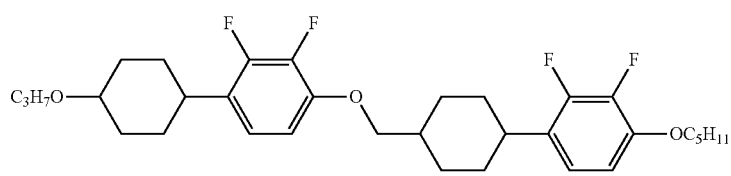 |
| 951 | 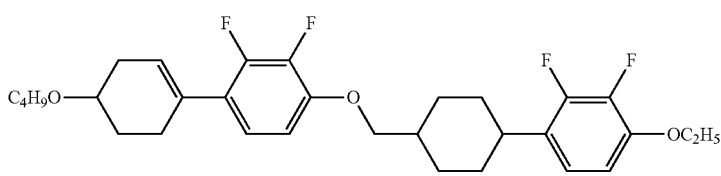<br>C 96.0 N 158.4 I<br>T$_{NI}$; 147.9° C., Δε; −6.90, Δn; 0.154 |
| 952 | 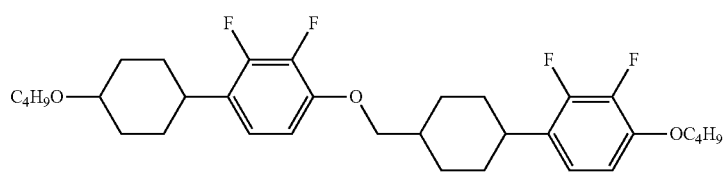 |
| 953 | 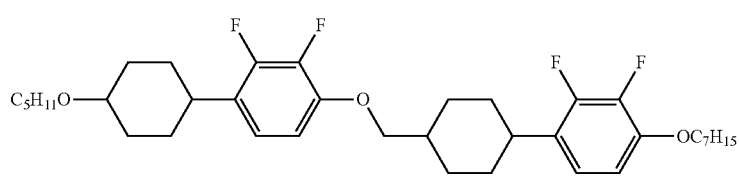 |
| 954 | 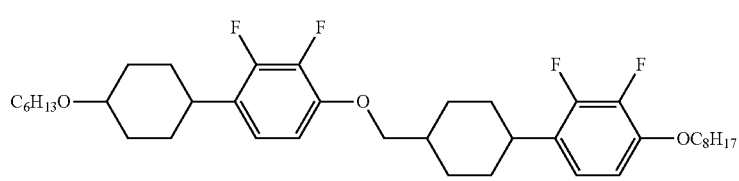 |
| 955 | 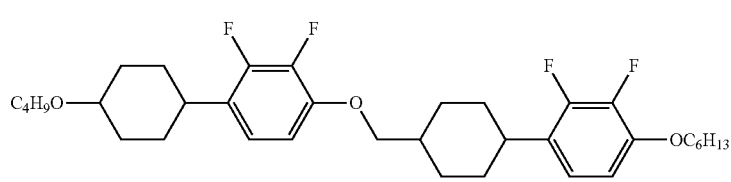 |

| No. | |
|---|---|
| 956 | 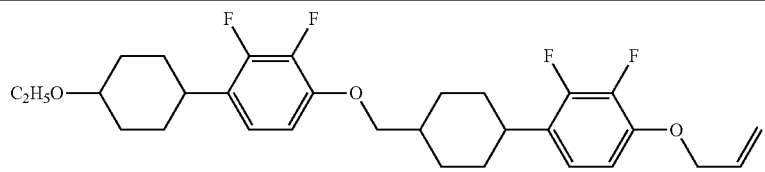 |
| 957 | 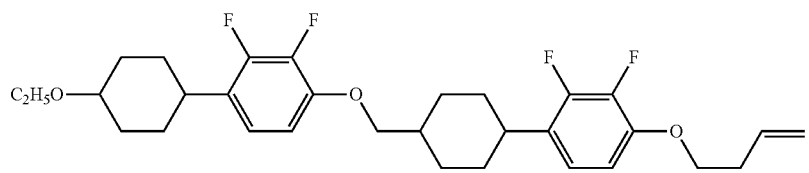 |
| 958 | 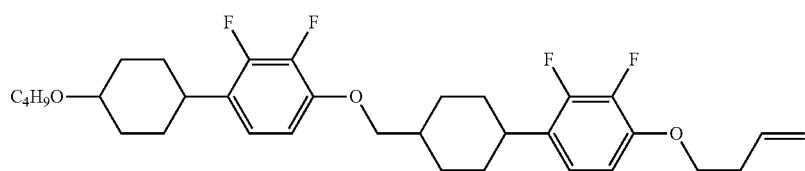 |
| 959 | 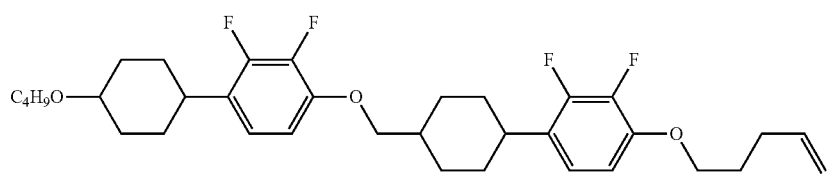 |
| 960 | 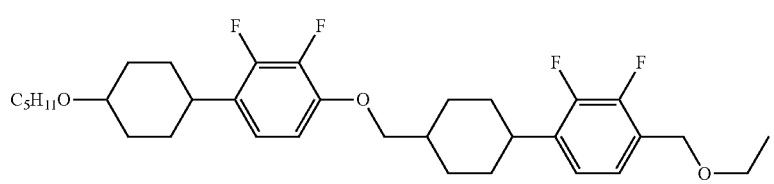 |
| 961 | 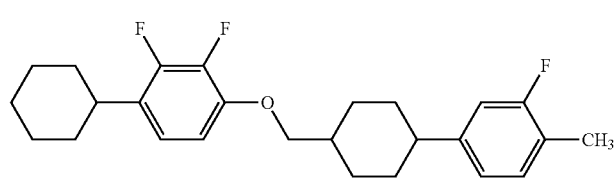 |
| 962 | 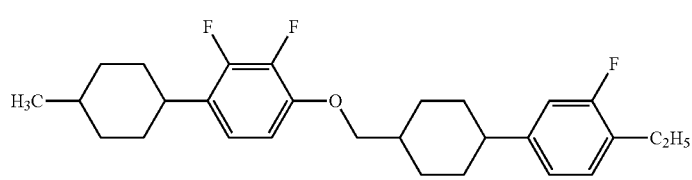 [SMILES: CCc1ccc(C2CCC(COc3ccc(C4CCC(C)CC4)c(F)c3F)CC2)cc1F] |
| 963 | 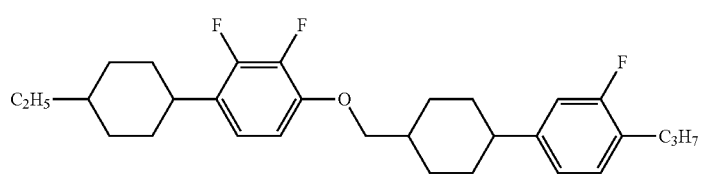 |
| 964 | 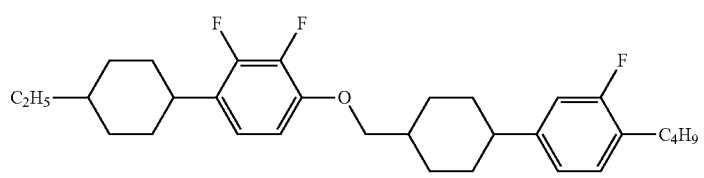 |

| No. |
|---|
| 965 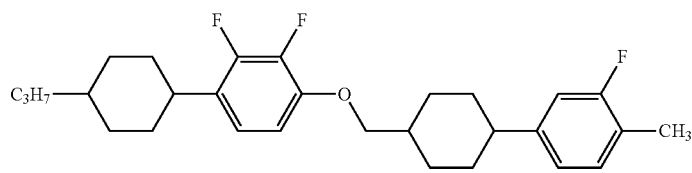 |
| 966 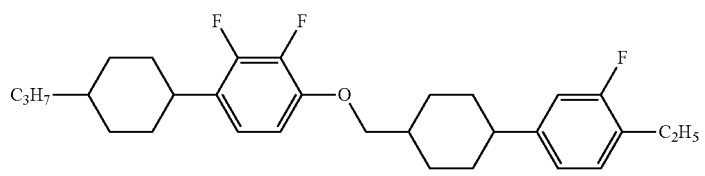 |
| 967 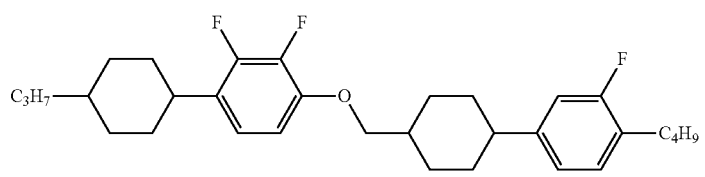 |
| 968 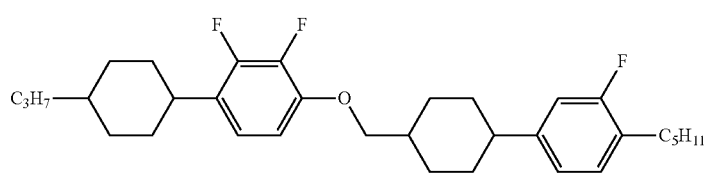 |
| 969 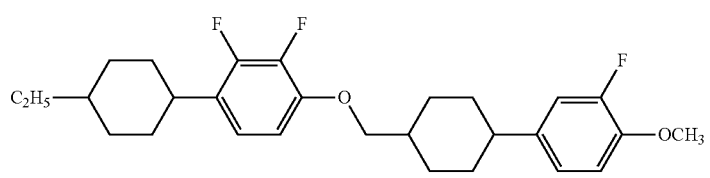 |
| 970 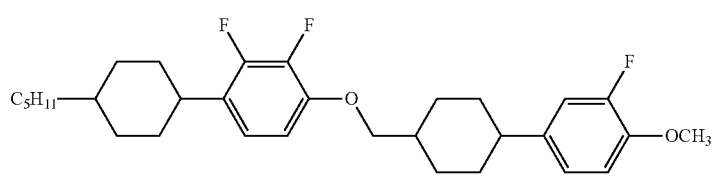 |
| 971 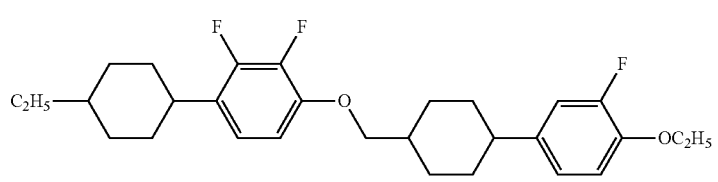 |
| 972 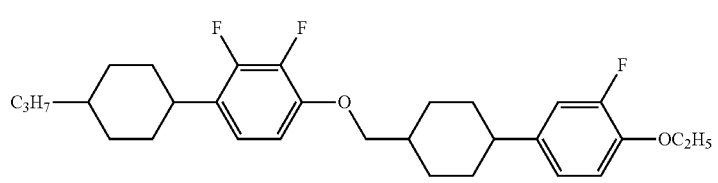 |

| No. | |
|---|---|
| 973 | 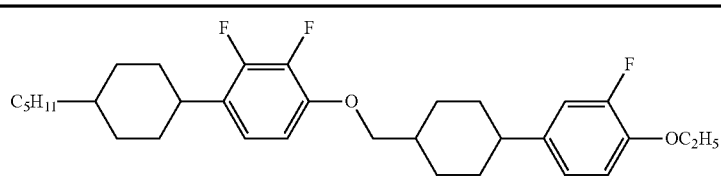 |
| 974 | 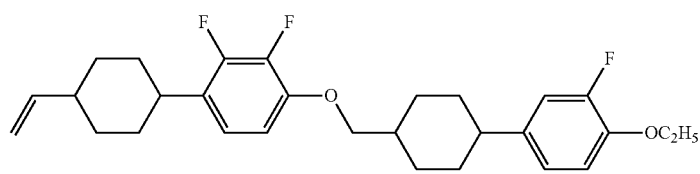 |
| 975 | 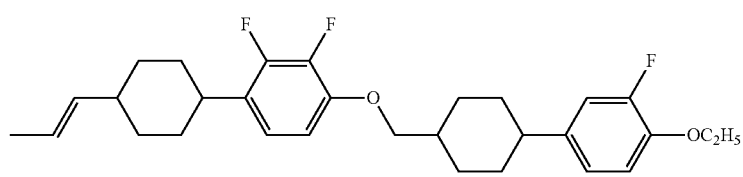 [SMILES: C/C=C/C1CCC(c2ccc(OCC3CCC(c4ccc(OCC)c(F)c4)CC3)c(F)c2F)CC1] |
| 976 | 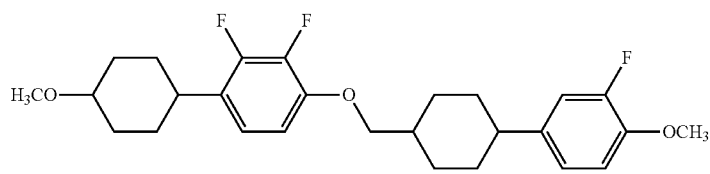 |
| 977 | 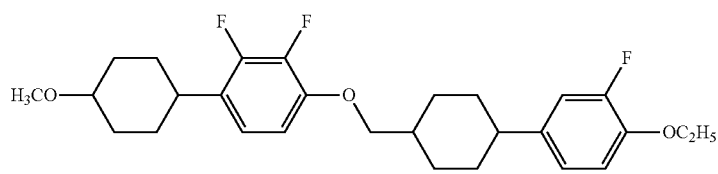 [SMILES: CCOc1ccc(C2CCC(COc3ccc(C4CCC(OC)CC4)c(F)c3F)CC2)cc1F] |
| 978 | 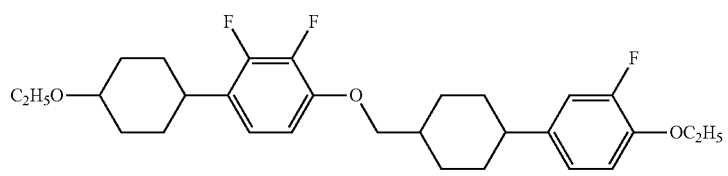 |
| 979 | 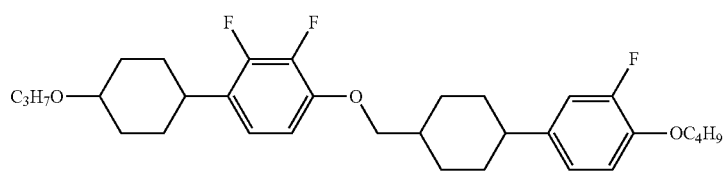 |
| 980 | 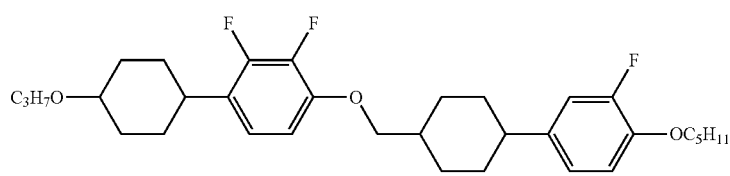 |
| 981 | 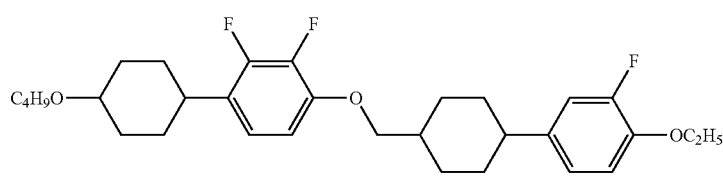 |

| No. | |
|---|---|
| 982 | 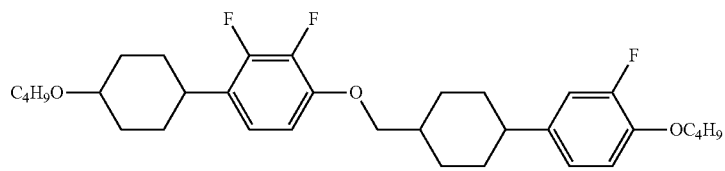 |
| 983 | 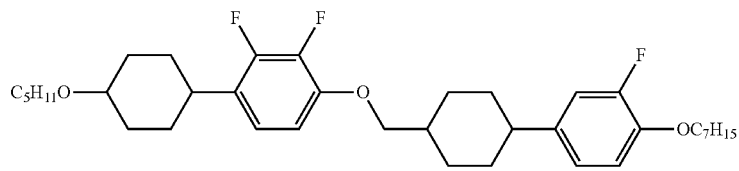 |
| 984 | 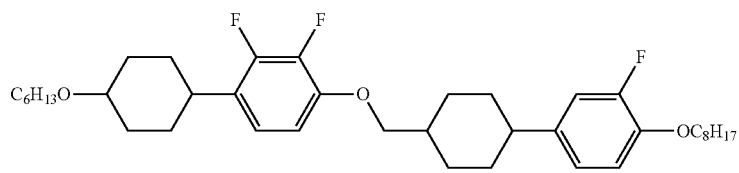 |
| 985 | 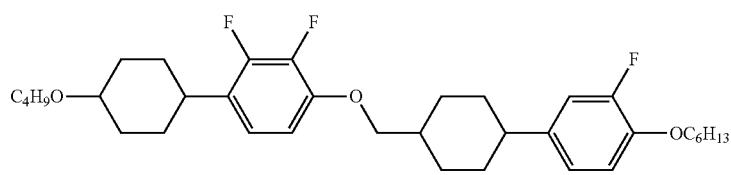 |
| 986 | 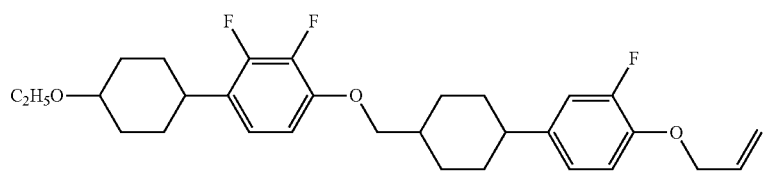 |
| 987 | 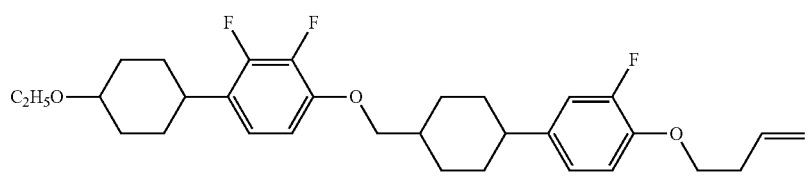 |
| 988 | 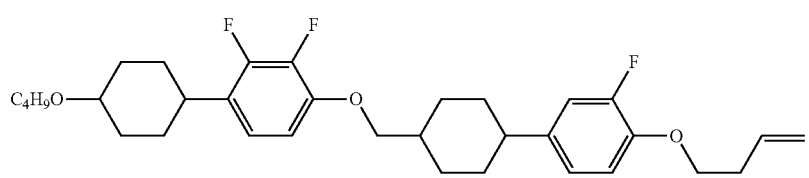 |
| 989 | 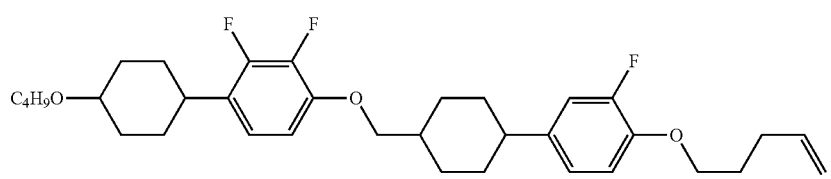 |

-continued
| No. | |
|---|---|
| 990 | 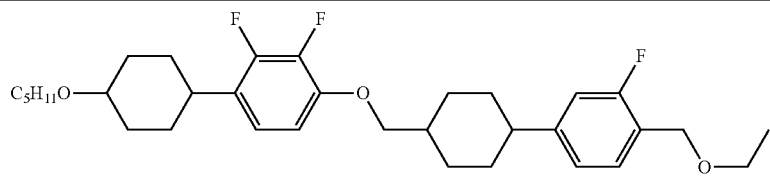 |
| 991 | 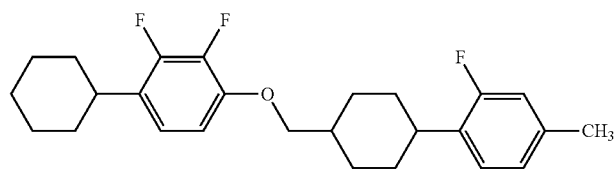 [SMILES: Cc1ccc(C2CCC(COc3ccc(C4CCCCC4)c(F)c3F)CC2)c(F)c1] |
| 992 | 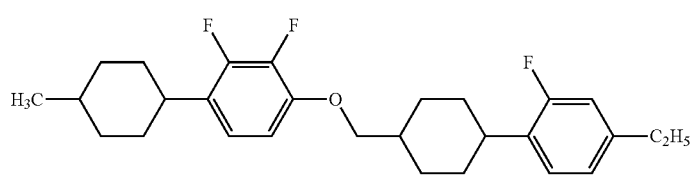 [SMILES: CCc1ccc(C2CCC(COc3ccc(C4CCC(C)CC4)c(F)c3F)CC2)c(F)c1] |
| 993 | 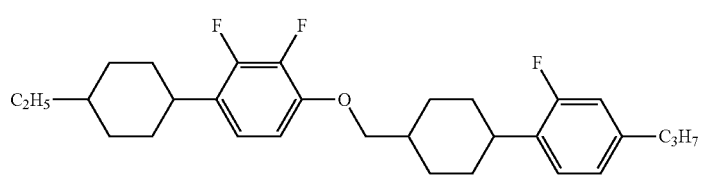 |
| 994 | 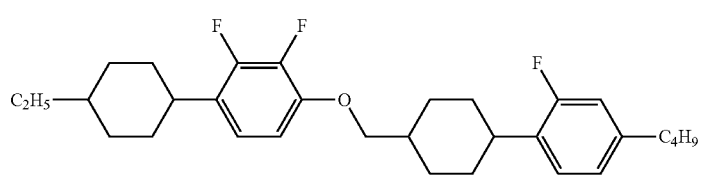 |
| 995 | 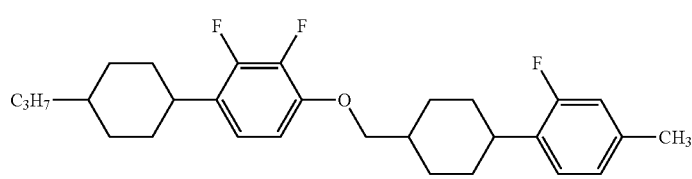 |
| 996 | 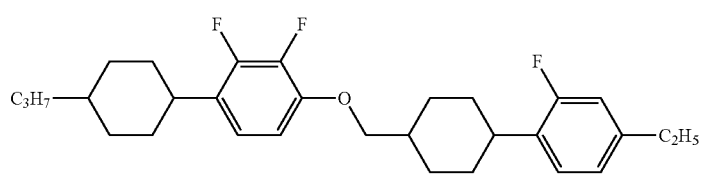 |
| 997 | 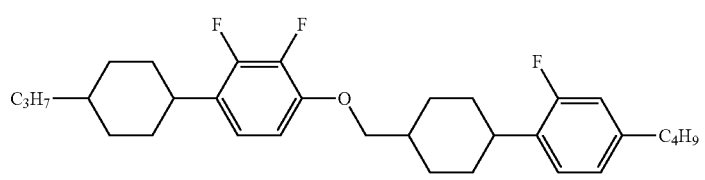 |
| 998 | 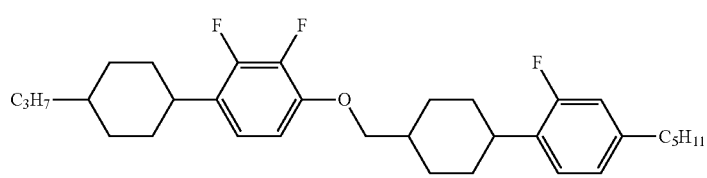 |

| No. |
|---|
| 999 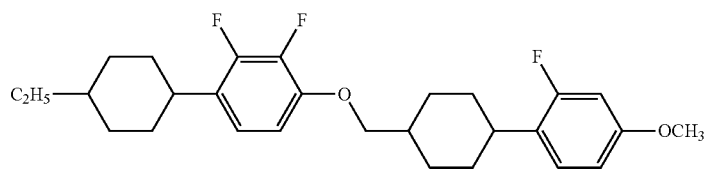 |
| 1000 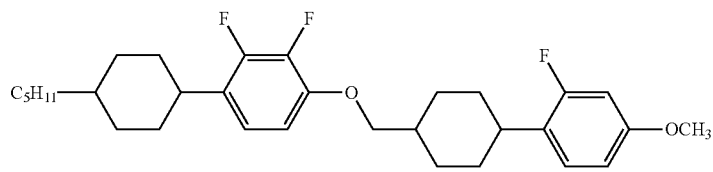 |
| 1001 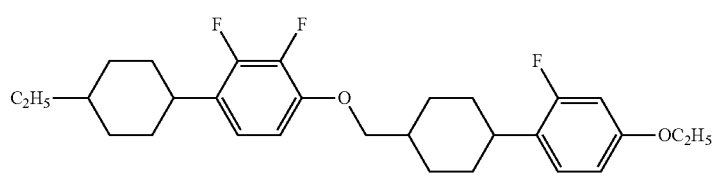 |
| 1002 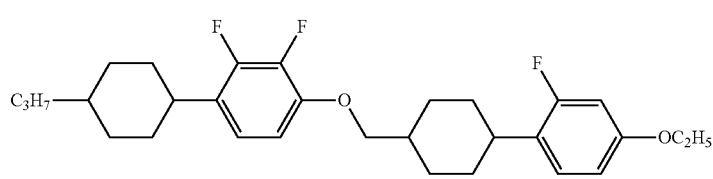 |
| 1003 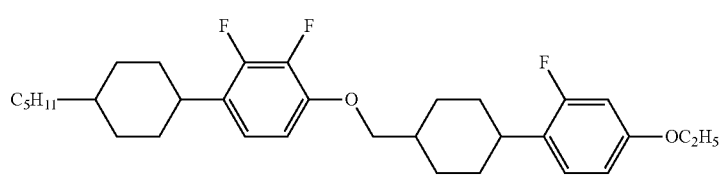 |
| 1004 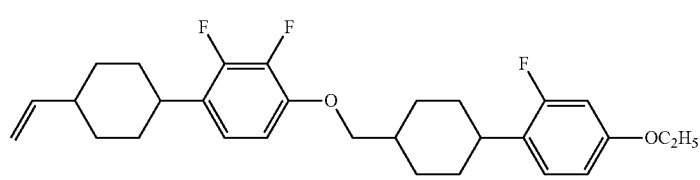 |
| 1005 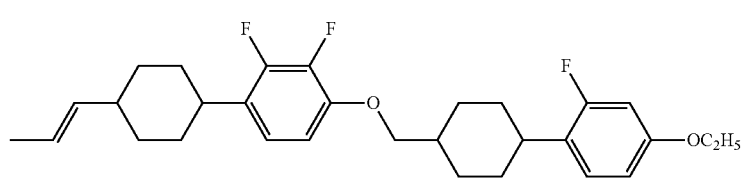 [SMILES: C/C=C/C1CCC(c2ccc(OCC3CCC(c4ccc(OCC)cc4F)CC3)c(F)c2F)CC1] |
| 1006 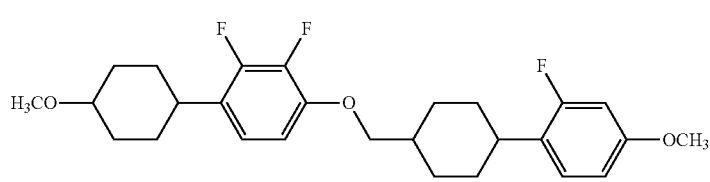 |

| No. |
|---|
| 1007 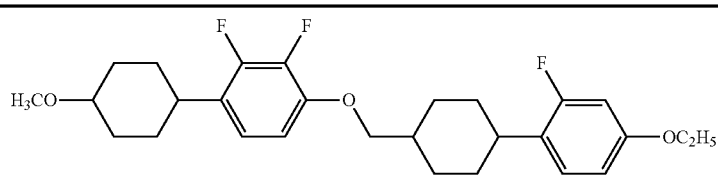 |
| 1008 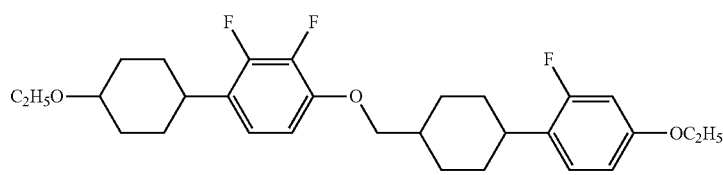 |
| 1009 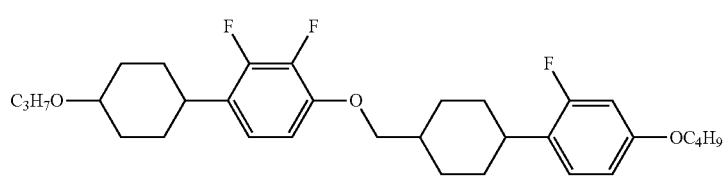 |
| 1010 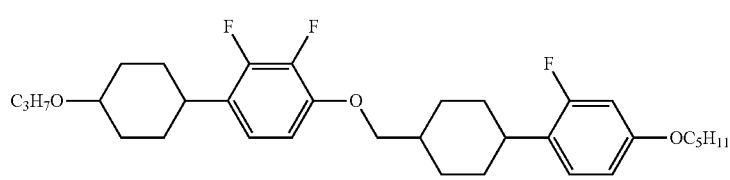 |
| 1011 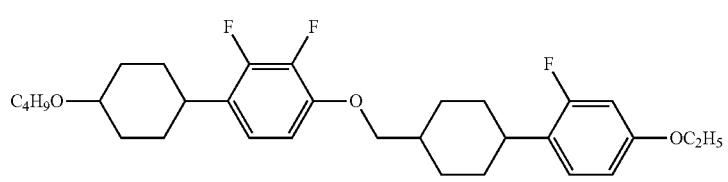 |
| 1012 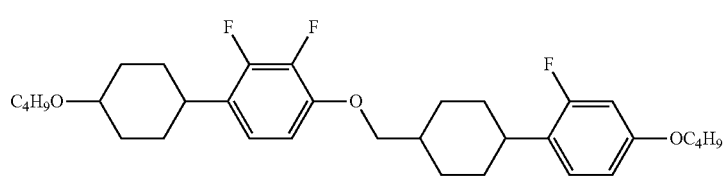 |
| 1013 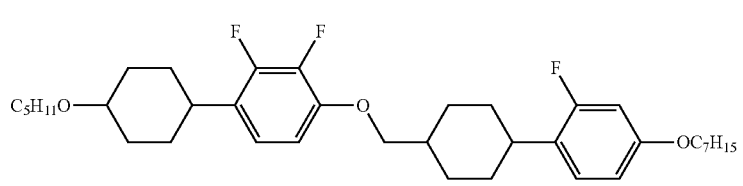 |
| 1014 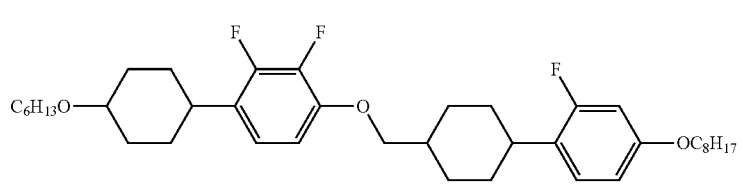 |
| 1015 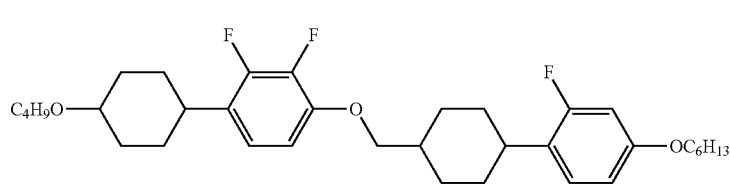 |

| No. | |
|---|---|
| 1016 | 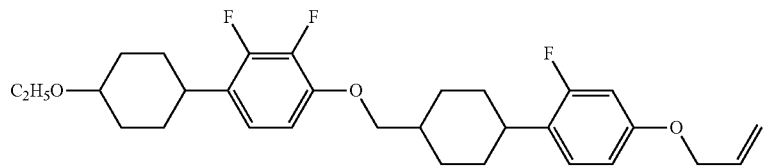 |
| 1017 | 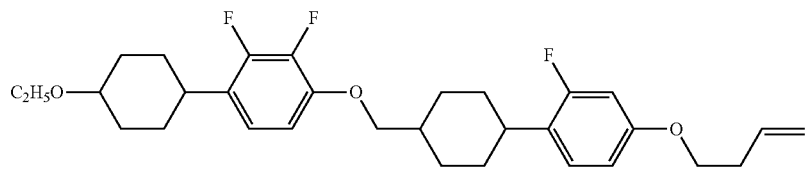 |
| 1018 | 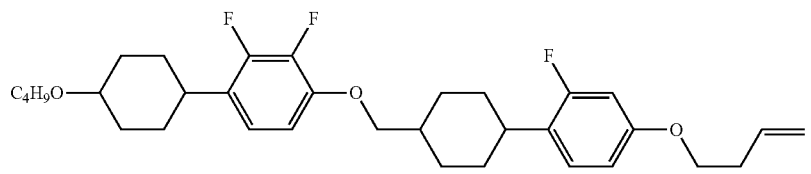 |
| 1019 | 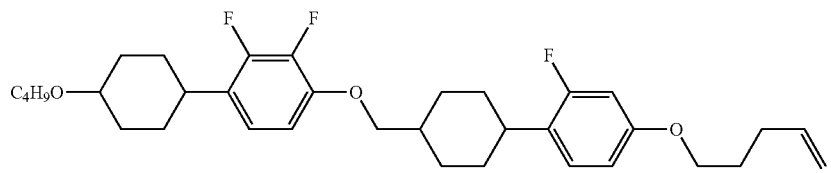 |
| 1020 | 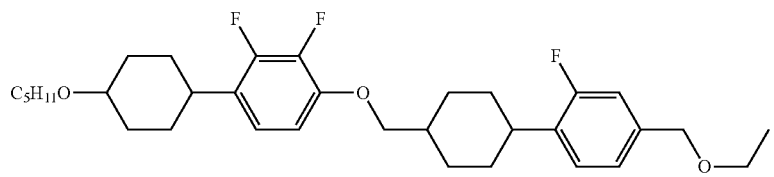 |
| 1021 | 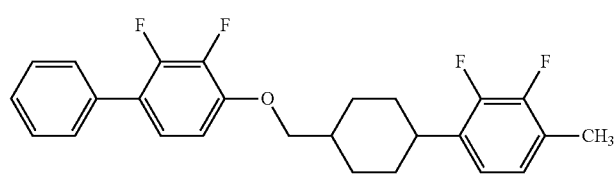 |
| 1022 | 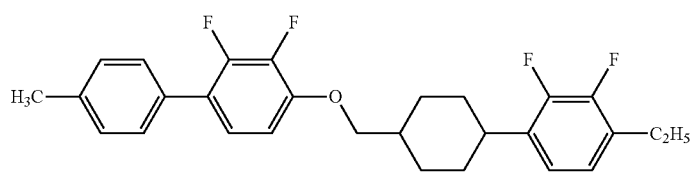 |
| 1023 | 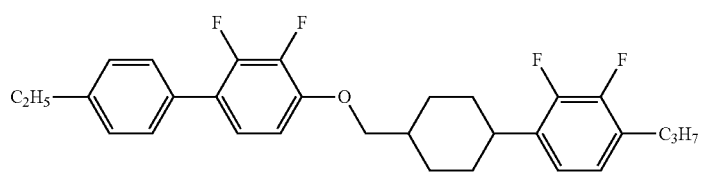 |

-continued
| No. | |
|---|---|
| 1024 | 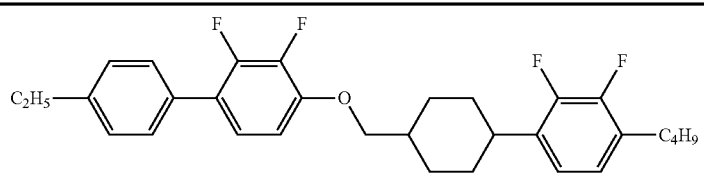 |
| 1025 | 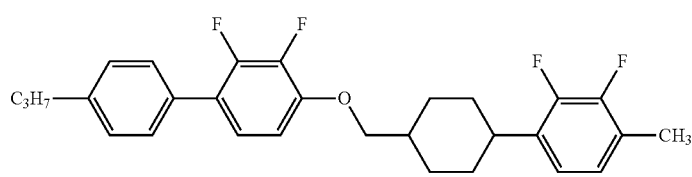 |
| 1026 | 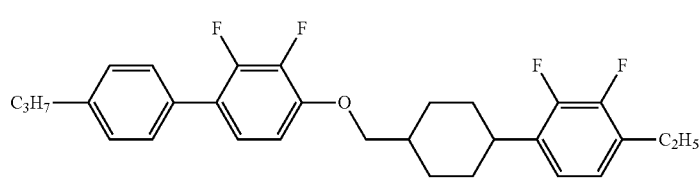 |
| 1027 | 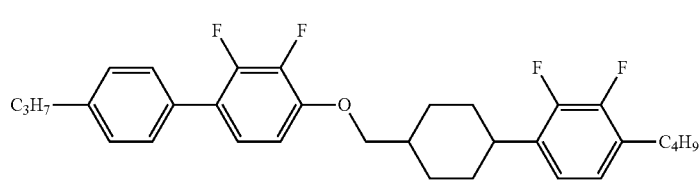 |
| 1028 | 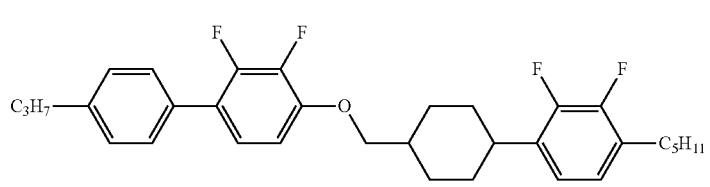 |
| 1029 | 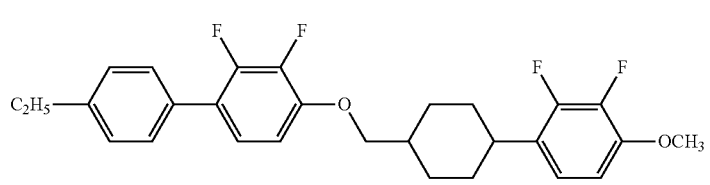 [SMILES: CCc1ccc(-c2ccc(OCC3CCC(c4ccc(OC)c(F)c4F)CC3)c(F)c2F)cc1] |
| 1030 | 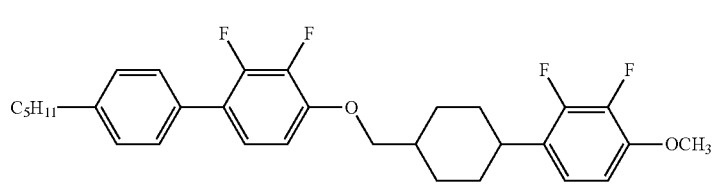 |
| 1031 | 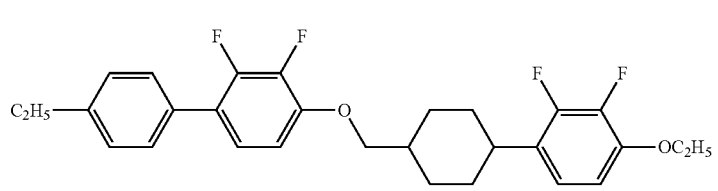 [SMILES: CCOc1ccc(C2CCC(COc3ccc(-c4ccc(CC)cc4)c(F)c3F)CC2)c(F)c1F] |
| 1032 | 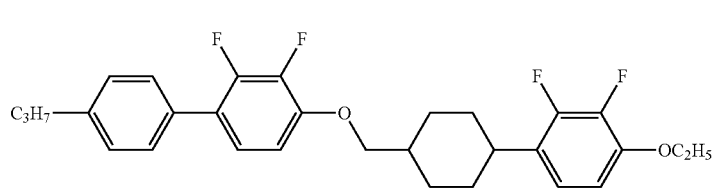 |

| No. |
|---|
| 1033 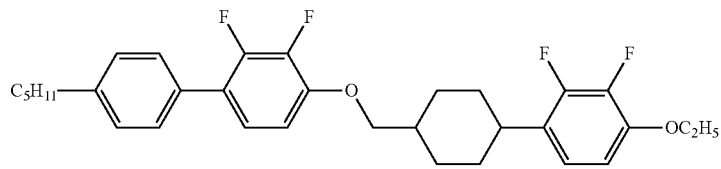 |
| 1034 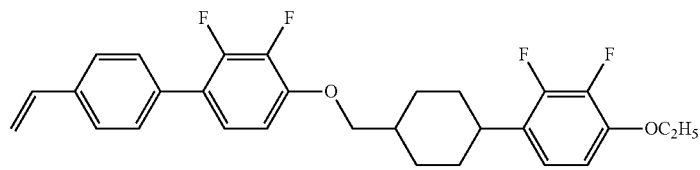 |
| 1035 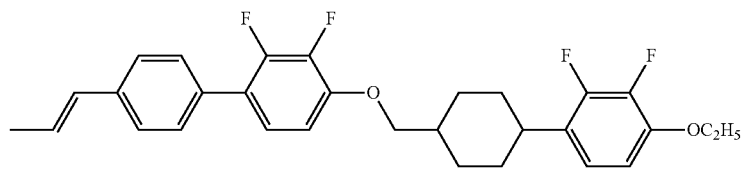 |
| 1036 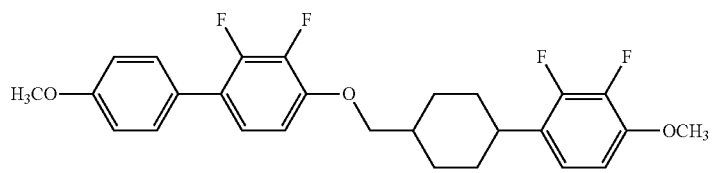 |
| 1037 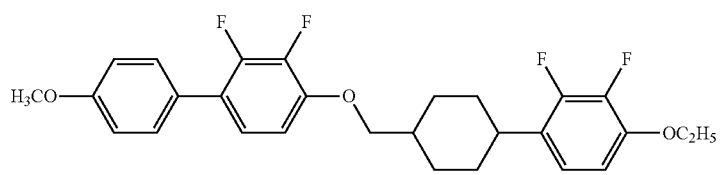 [SMILES: CCOc1ccc(C2CCC(COc3ccc(-c4ccc(OC)cc4)c(F)c3F)CC2)c(F)c1F] |
| 1038 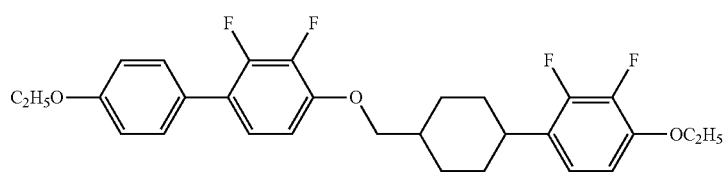 |
| 1039 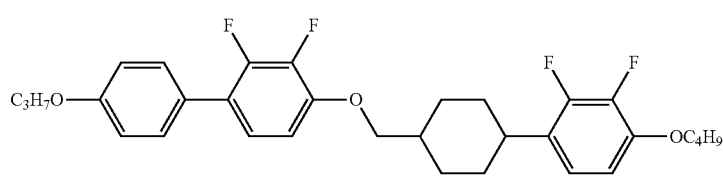 |
| 1040 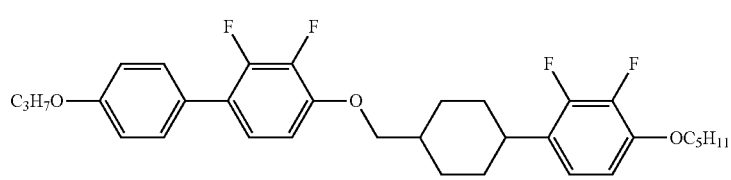 |

| No. |
|---|
| 1041 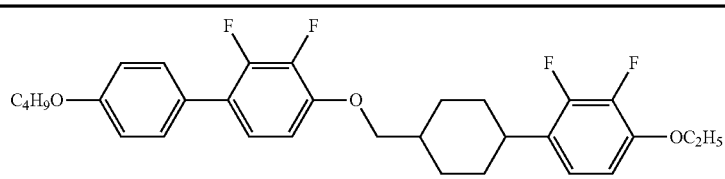 |
| 1042 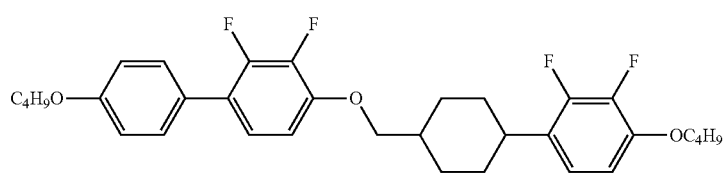 |
| 1043 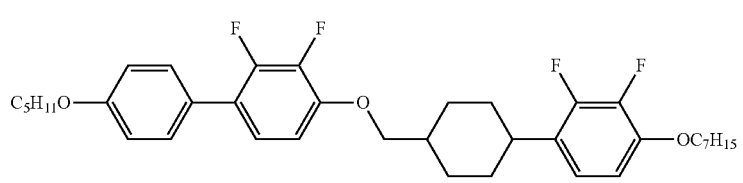 |
| 1044 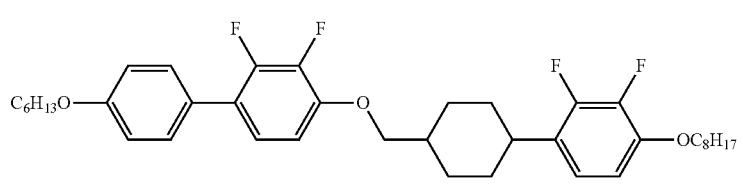 |
| 1045 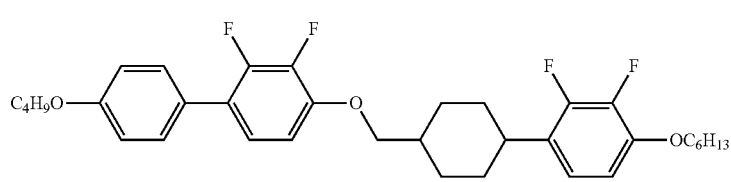 |
| 1046 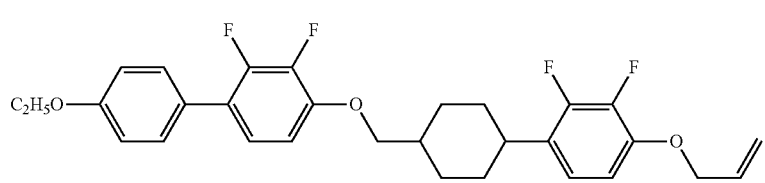 |
| 1047 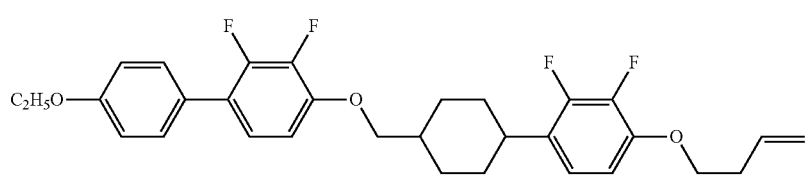 |
| 1048 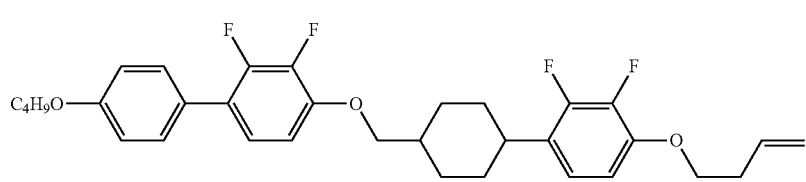 |
| 1049 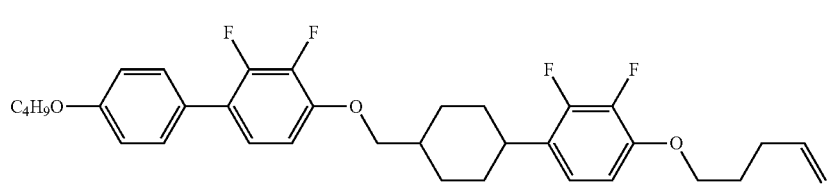 |

| No. | |
|---|---|
| 1050 | 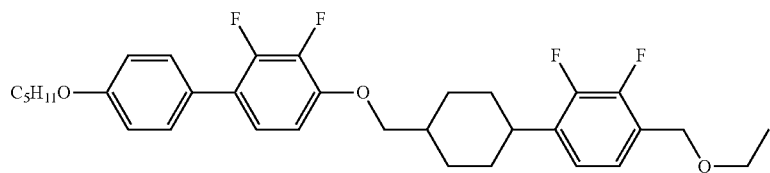 |
| 1051 | 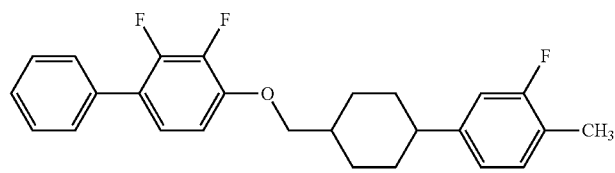 |
| 1052 | 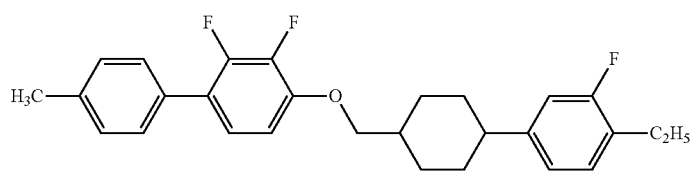 [SMILES: CCc1ccc(C2CCC(COc3ccc(-c4ccc(C)cc4)c(F)c3F)CC2)cc1F] |
| 1053 | 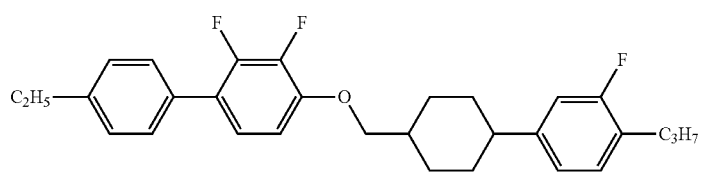 |
| 1054 | 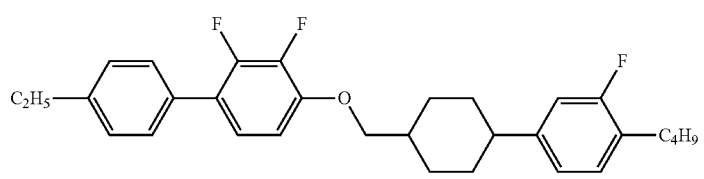 |
| 1055 | 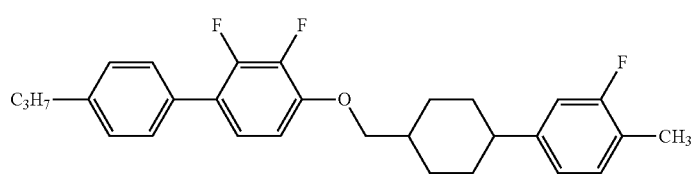 |
| 1056 | 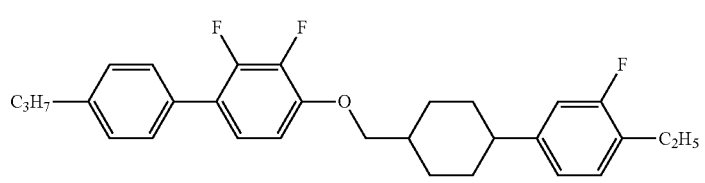 |
| 1057 | 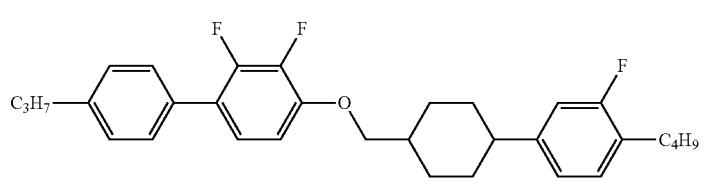 |

| No. | |
|---|---|
| 1058 | 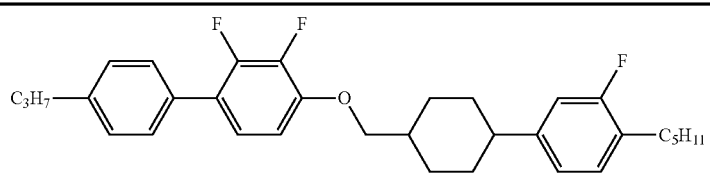 |
| 1059 | 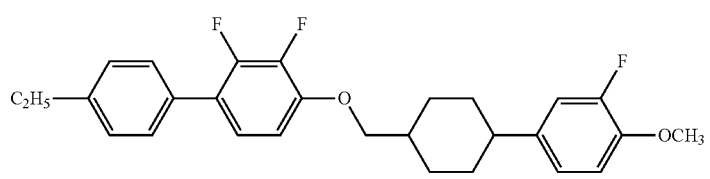 [SMILES: CCc1ccc(-c2ccc(OCC3CCC(c4ccc(OC)c(F)c4)CC3)c(F)c2F)cc1] |
| 1060 | 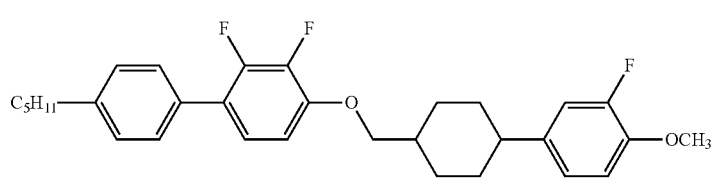 |
| 1061 | 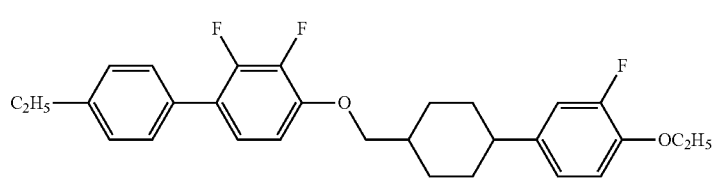 |
| 1062 | 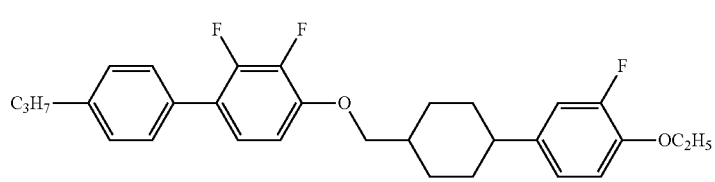 |
| 1063 | 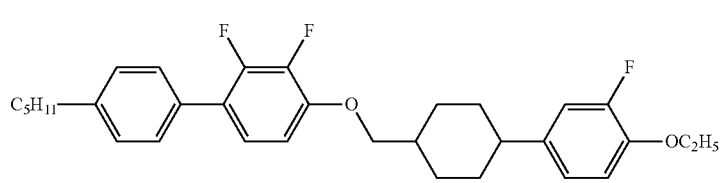 |
| 1064 | 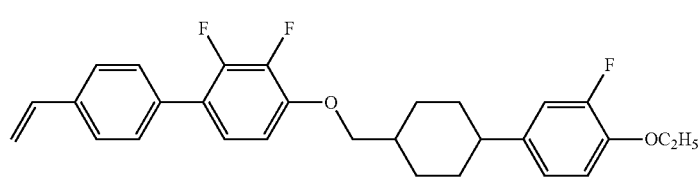 [SMILES: C=Cc1ccc(-c2ccc(OCC3CCC(c4ccc(OCC)c(F)c4)CC3)c(F)c2F)cc1] |
| 1065 | 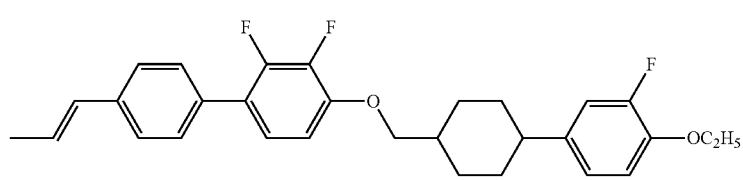 [SMILES: C/C=C/c1ccc(-c2ccc(OCC3CCC(c4ccc(OCC)c(F)c4)CC3)c(F)c2F)cc1] |
| 1066 | 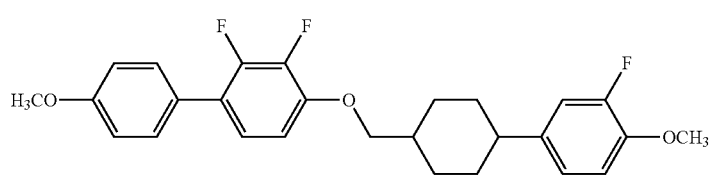 [SMILES: COc1ccc(-c2ccc(OCC3CCC(c4ccc(OC)c(F)c4)CC3)c(F)c2F)cc1] |

| No. | |
|---|---|
| 1067 | 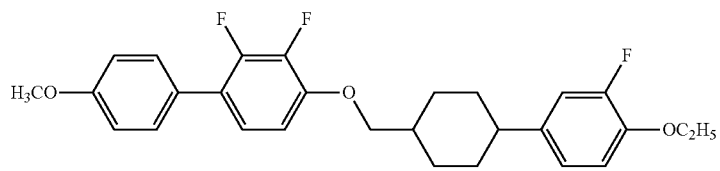 |
| 1068 | 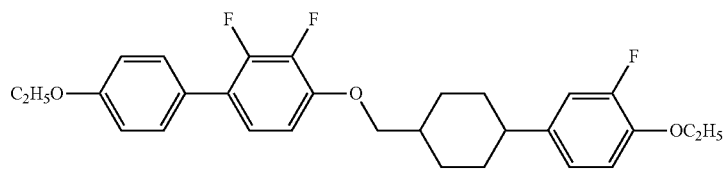 |
| 1069 | 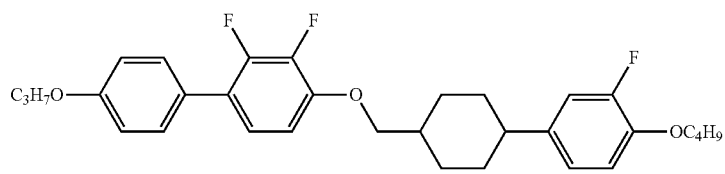 |
| 1070 | 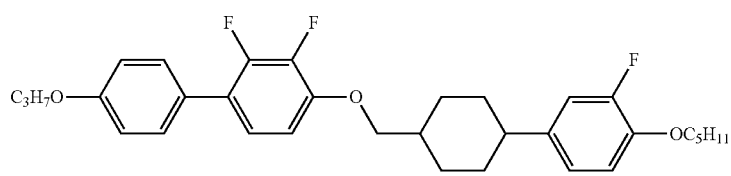 |
| 1071 | 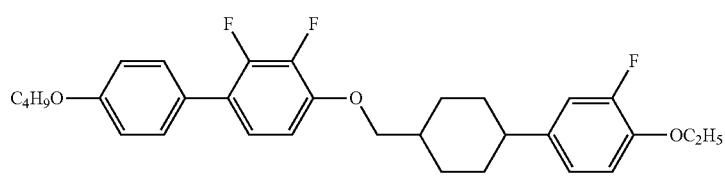 |
| 1072 | 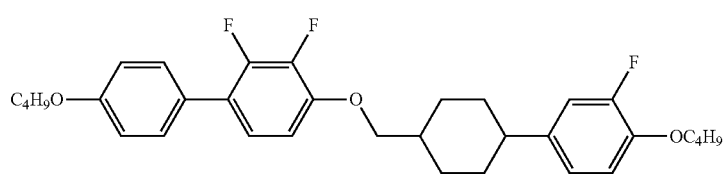 |
| 1073 | 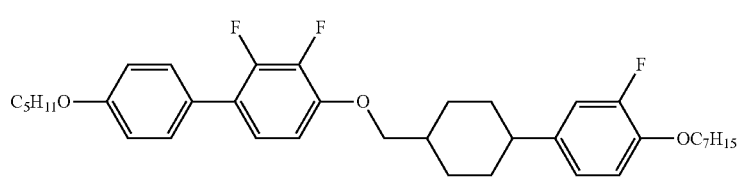 |
| 1074 | 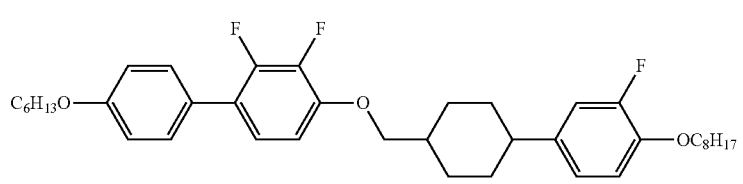 |

| No. |
|---|
| 1075 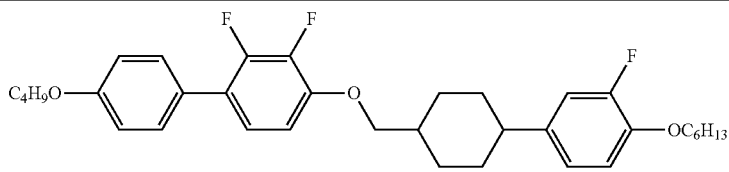 |
| 1076 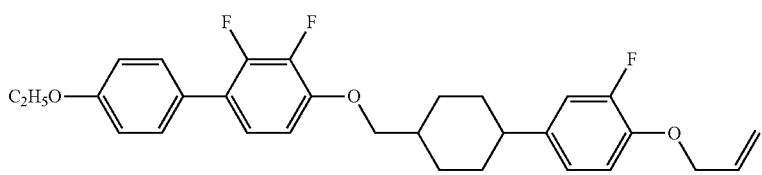 |
| 1077 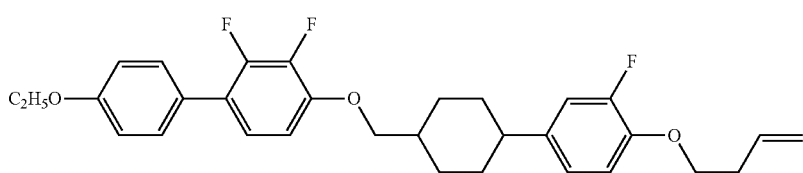 |
| 1078 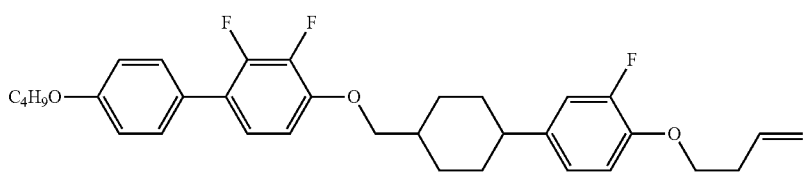 |
| 1079 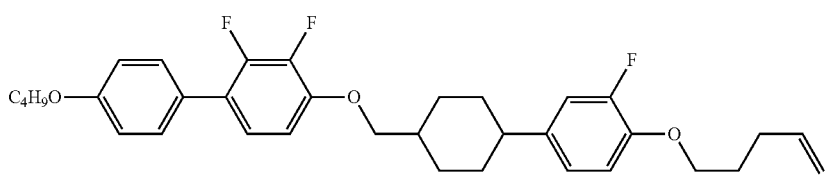 |
| 1080 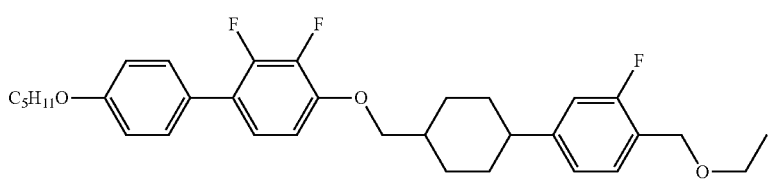 |
| 1081 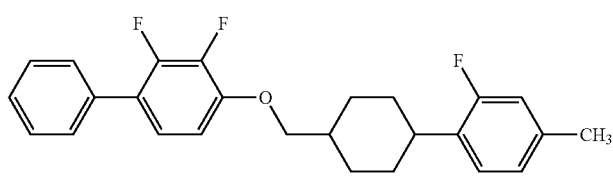 |
| 1082 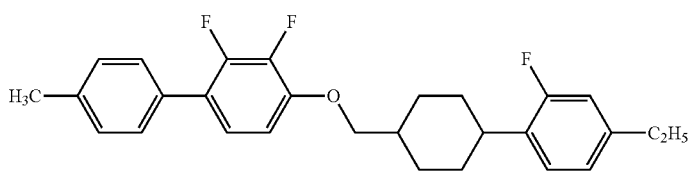 |
| 1083 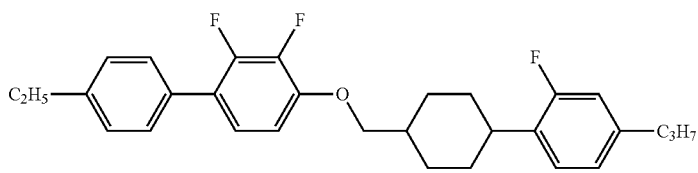 |

| No. | |
|---|---|
| 1084 | 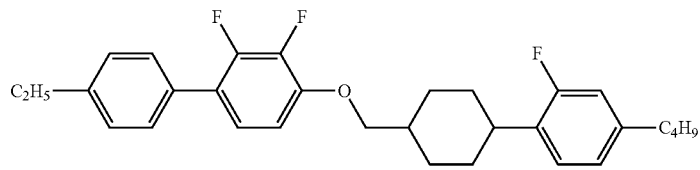 |
| 1085 | 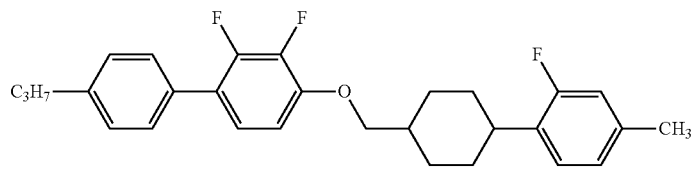 |
| 1086 | 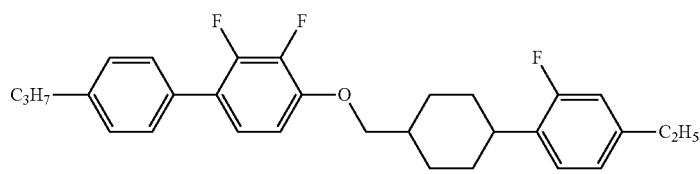 |
| 1087 | 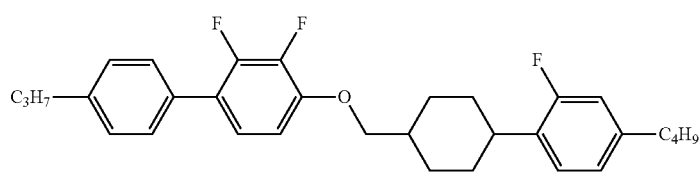 |
| 1088 | 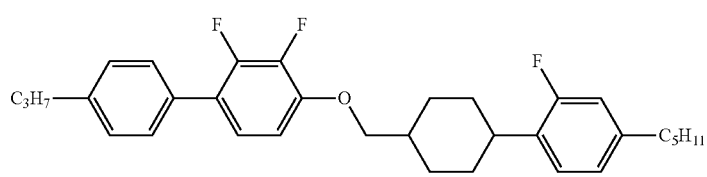 |
| 1089 | 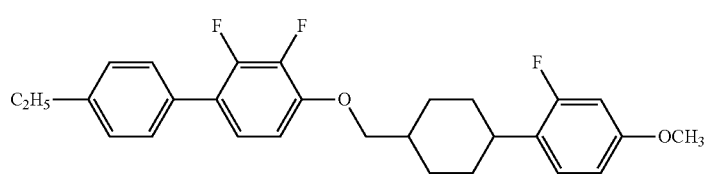 |
| 1090 | 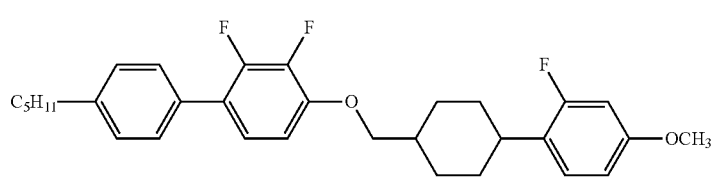 |
| 1091 | 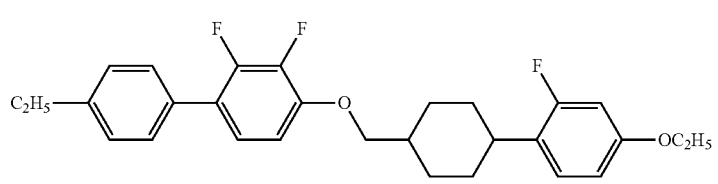 |

| No. |
|---|
| 1092 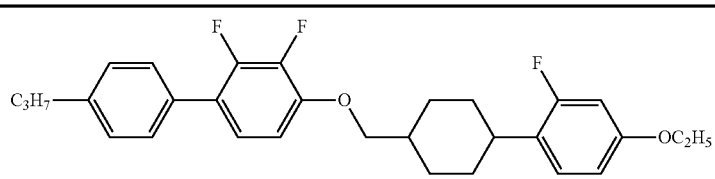 |
| 1093 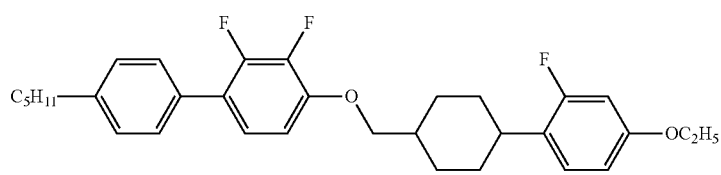 |
| 1094 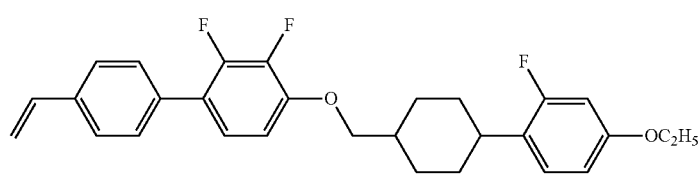 |
| 1095 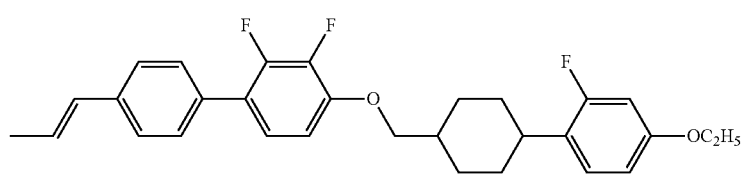 |
| 1096 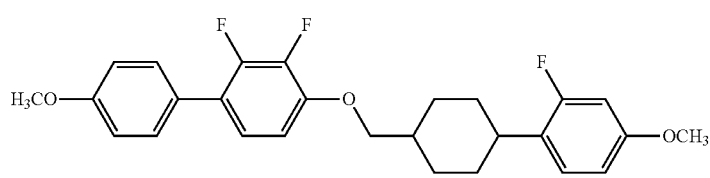 [SMILES: COc1ccc(-c2ccc(OCC3CCC(c4ccc(OC)cc4F)CC3)c(F)c2F)cc1] |
| 1097 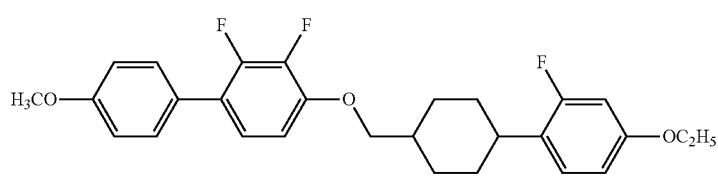 [SMILES: CCOc1ccc(C2CCC(COc3ccc(-c4ccc(OC)cc4)c(F)c3F)CC2)c(F)c1] |
| 1098 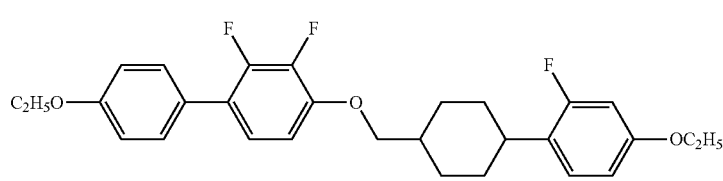 |
| 1099 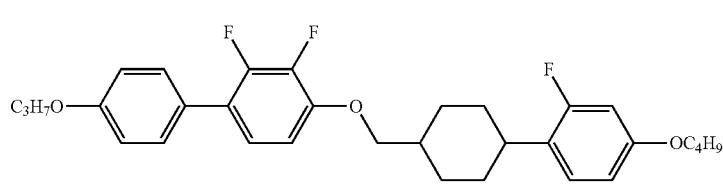 |
| 1100 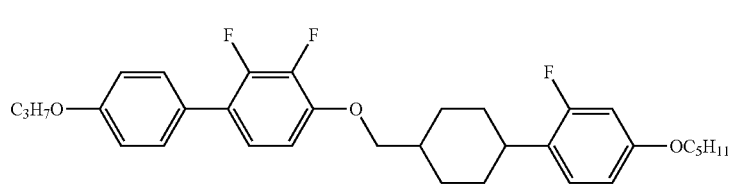 |

| No. | |
|---|---|
| 1101 | 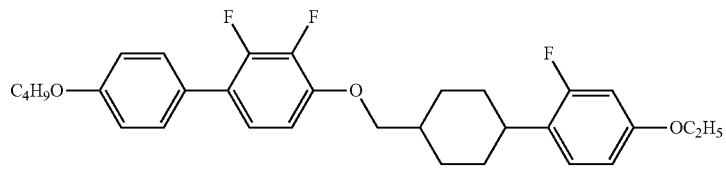 |
| 1102 | 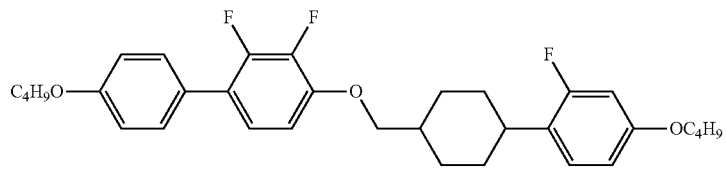 |
| 1103 | 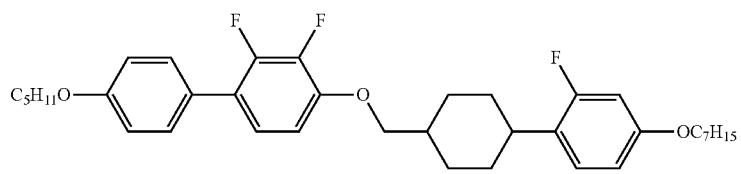 |
| 1104 | 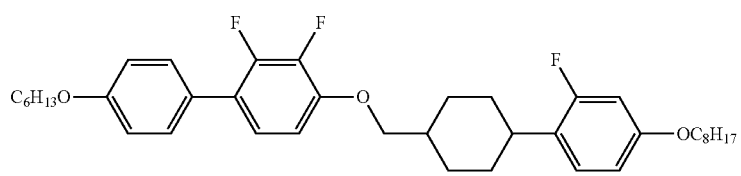 |
| 1105 | 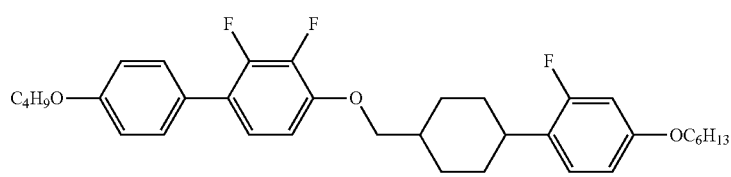 |
| 1106 | 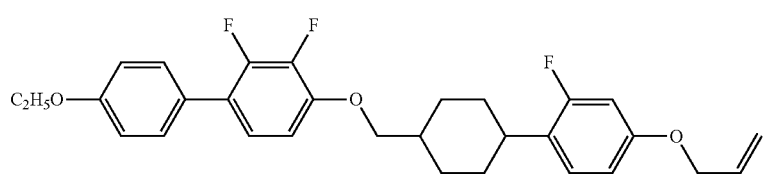 |
| 1107 | 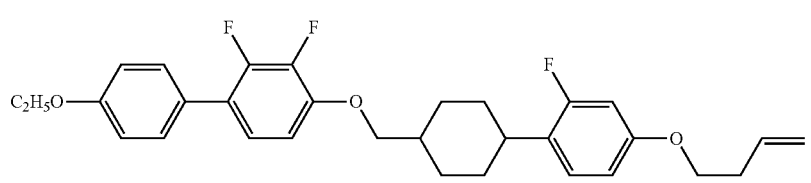 |
| 1108 | 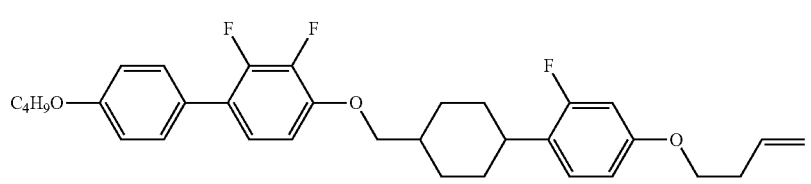 |

-continued
| No. | |
|---|---|
| 1109 | 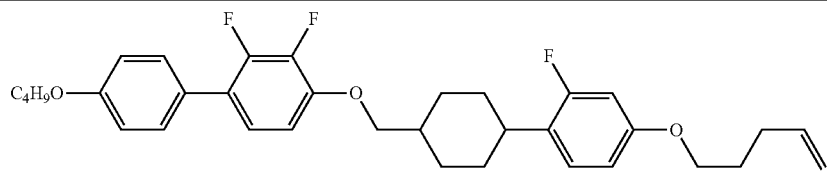 |
| 1110 | 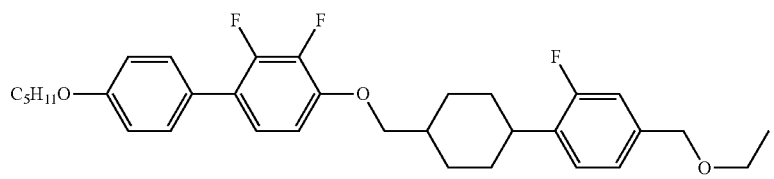 |
| 1111 | 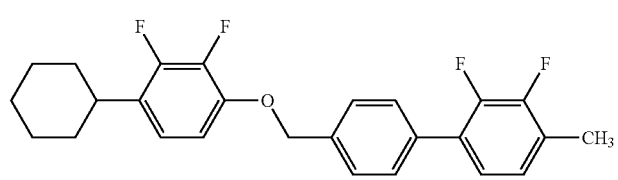 |
| 1112 | 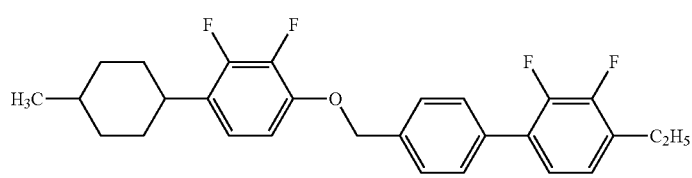 |
| 1113 | 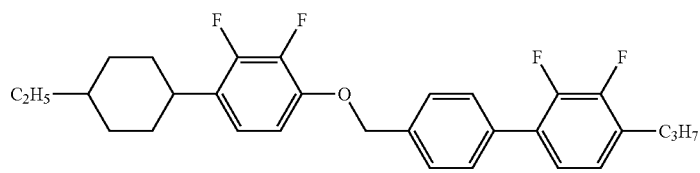 |
| 1114 | 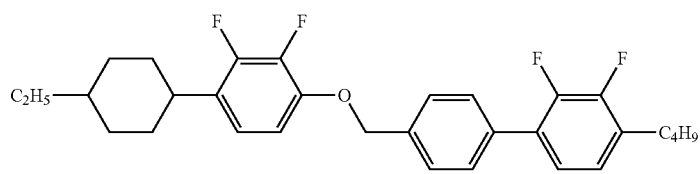 |
| 1115 | 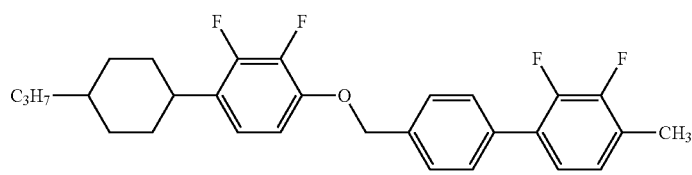 |
| 1116 | 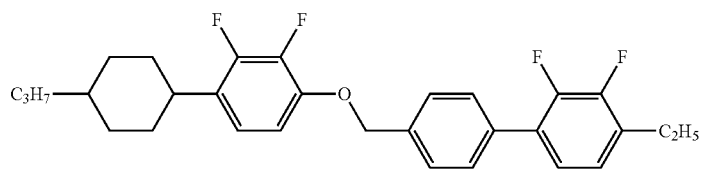 [SMILES: COc1ccc(-c2ccc(COc3ccc(C4CCC(OC)CC4)c(F)c3F)cc2)c(F)c1F] |
| 1117 | 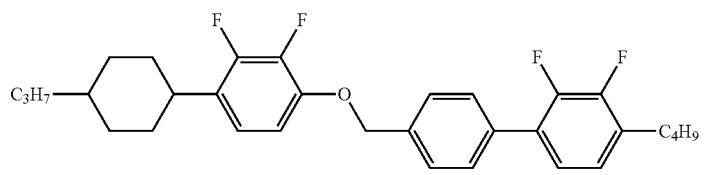 |

-continued

| No. | |
|---|---|
| 1118 | |
| 1119 | |
| 1120 | |
| 1121 | |
| 1122 | |
| 1123 | C 130.1 N 197.5 I<br>T$_{NI}$; 192.6° C., Δε; −7.40, Δn; 0.207 |
| 1124 | |
| 1125 | |

-continued
| No. | |
|---|---|
| 1126 | 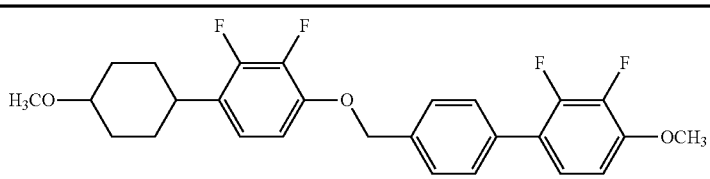 |
| 1127 | 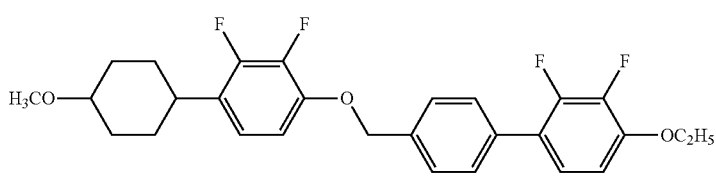 [SMILES: CCOc1ccc(-c2ccc(COc3ccc(C4CCC(OC)CC4)c(F)c3F)cc2)c(F)c1F] |
| 1128 | 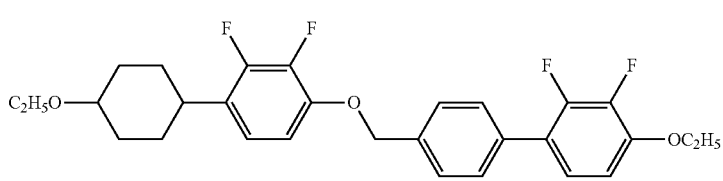 |
| 1129 | 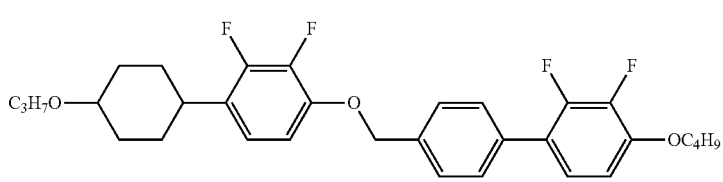 |
| 1130 | 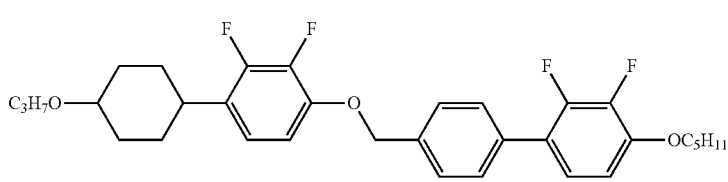 |
| 1131 | 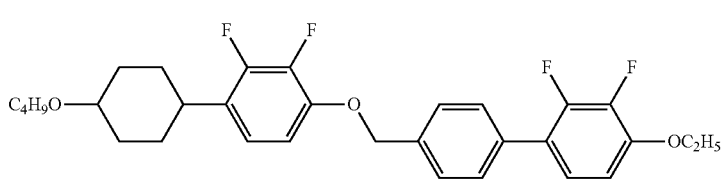 |
| 1132 | 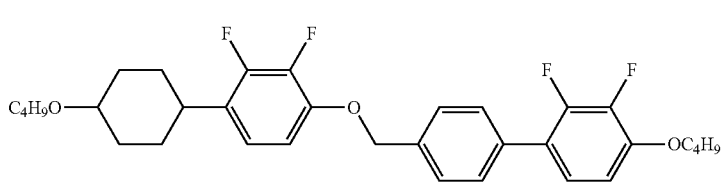 |
| 1133 | 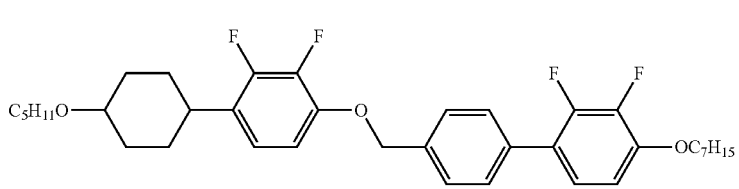 |
| 1134 | 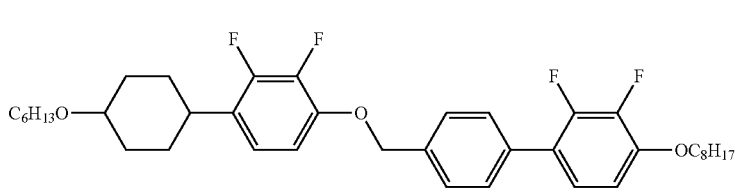 |

| No. | |
|---|---|
| 1135 | 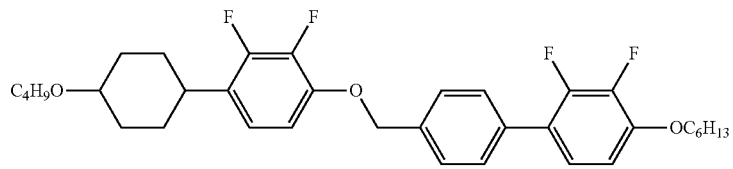 |
| 1136 | 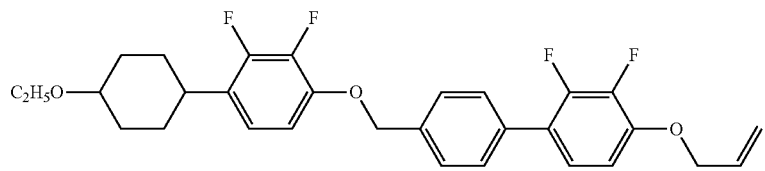 |
| 1137 | 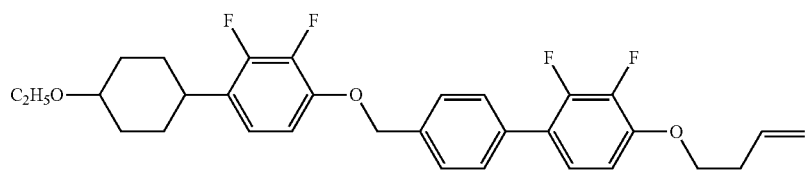 |
| 1138 | 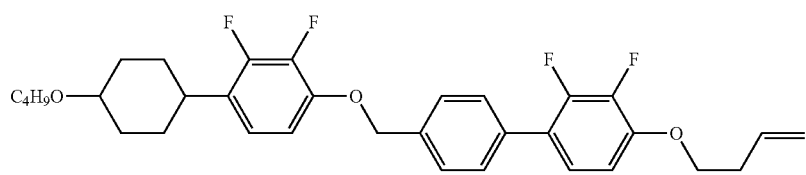 |
| 1139 | 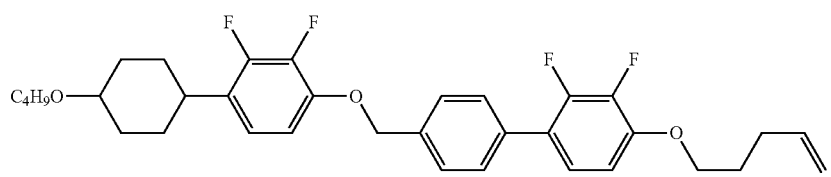 |
| 1140 | 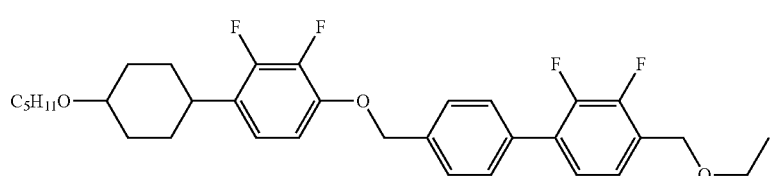 |
| 1141 | 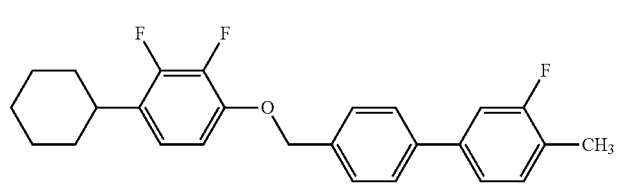 |
| 1142 | 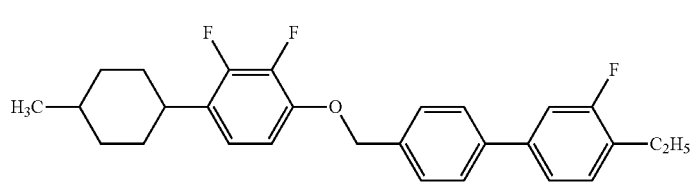 [SMILES: CCc1ccc(-c2ccc(COc3ccc(C4CCC(C)CC4)c(F)c3F)cc2)cc1F] |

| No. | |
|---|---|
| 1143 | 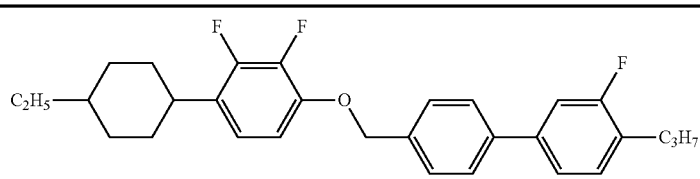 |
| 1144 | 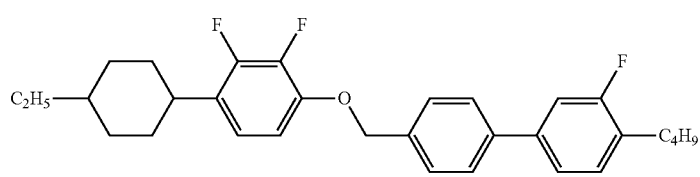 |
| 1145 | 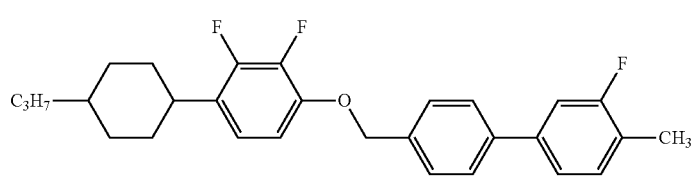 |
| 1146 | 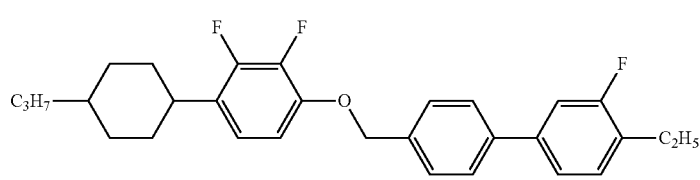 |
| 1147 | 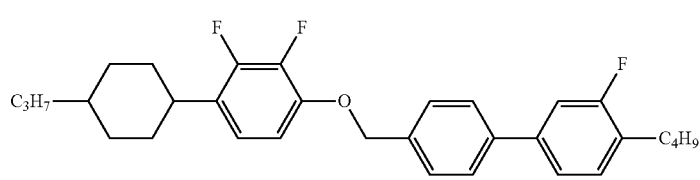 |
| 1148 | 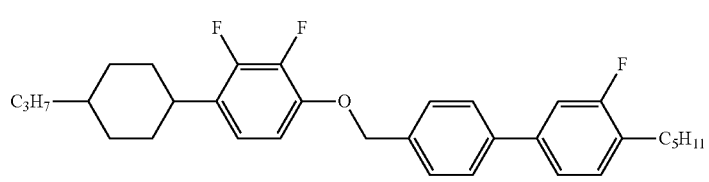 |
| 1149 | 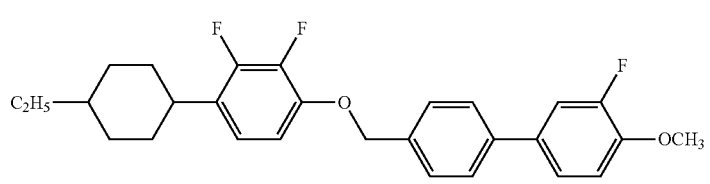 [SMILES: CCC1CCC(c2ccc(OCc3ccc(-c4ccc(OC)c(F)c4)cc3)c(F)c2F)CC1] |
| 1150 | 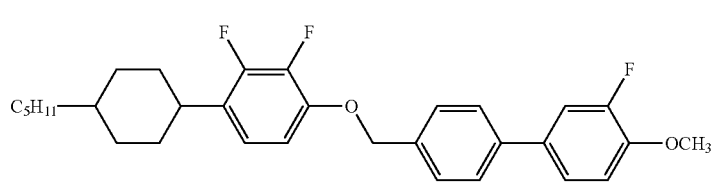 |
| 1151 | 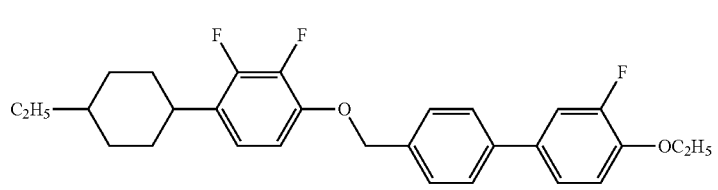 |

| No. | |
|---|---|
| 1152 | 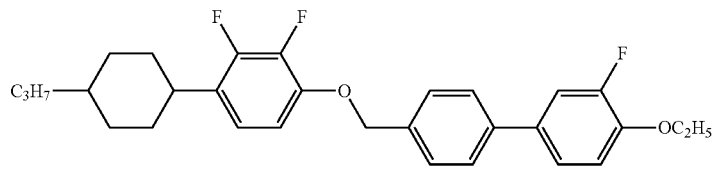 |
| 1153 | 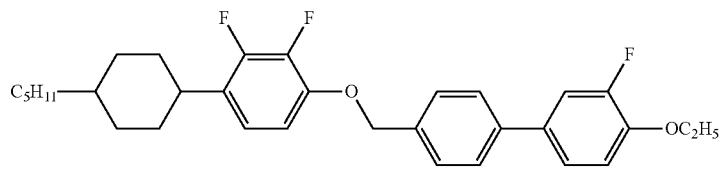 |
| 1154 | 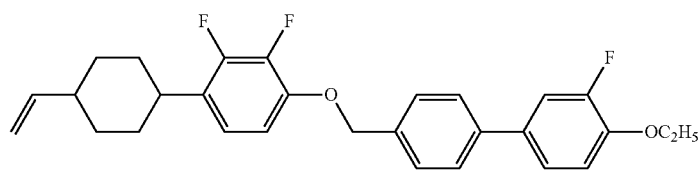 |
| 1155 | 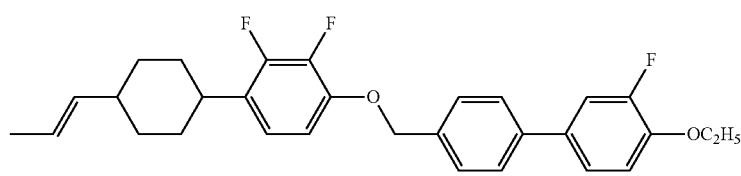 |
| 1156 | 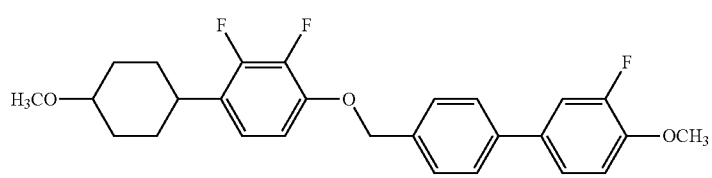 |
| 1157 | 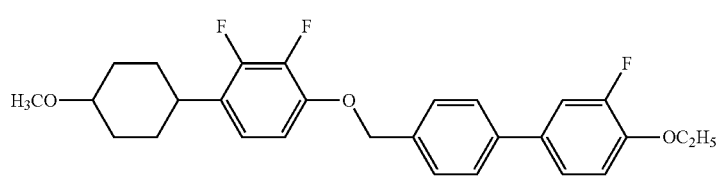 |
| 1158 | 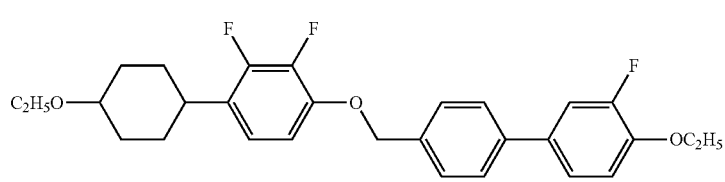 |
| 1159 | 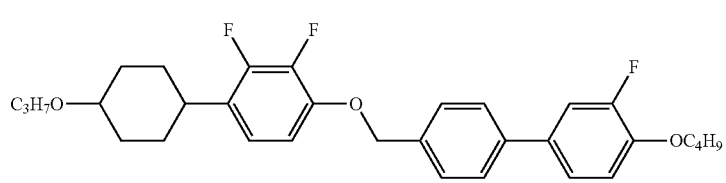 |

| No. | |
|---|---|
| 1160 | 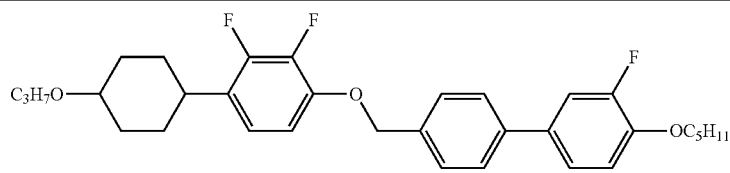 |
| 1161 | 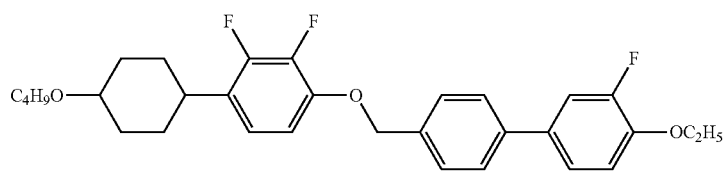 |
| 1162 | 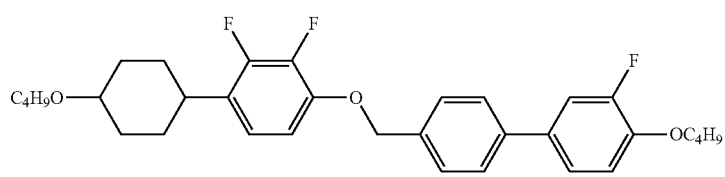 |
| 1163 | 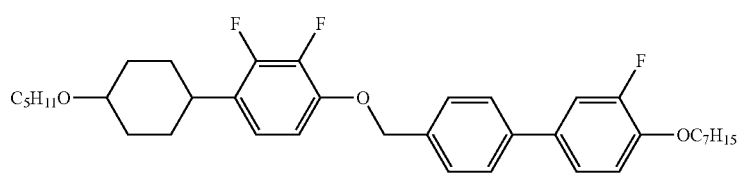 |
| 1164 | 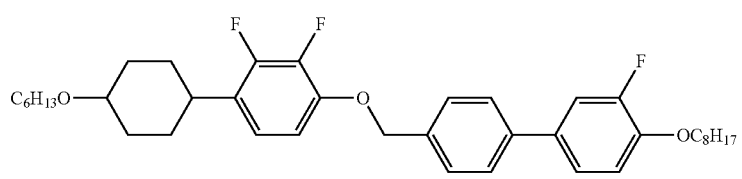 |
| 1165 | 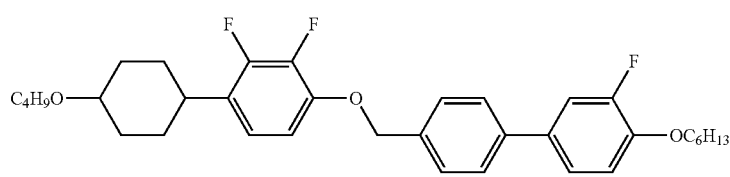 |
| 1166 | 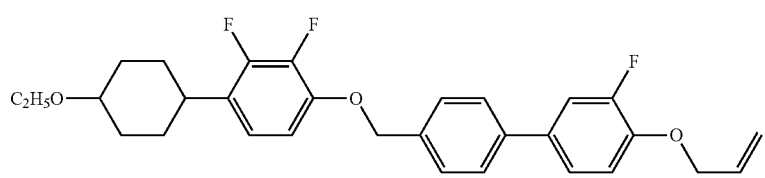 |
| 1167 | 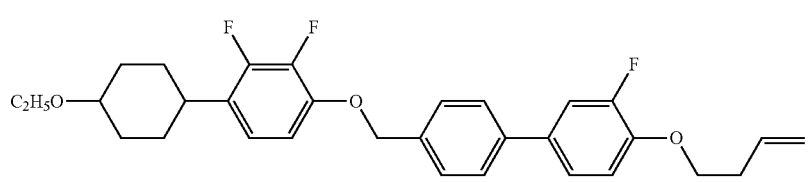 |
| 1168 | 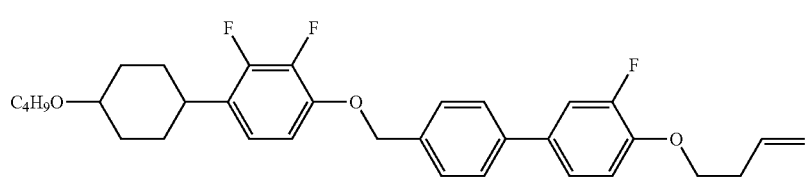 |

| No. |
|---|
| 1169 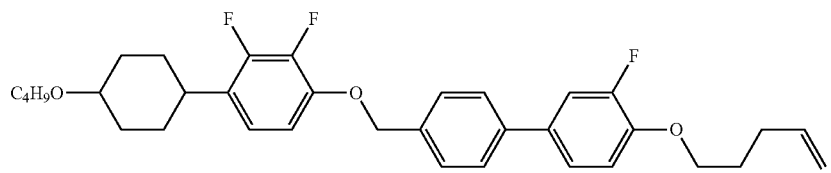 |
| 1170 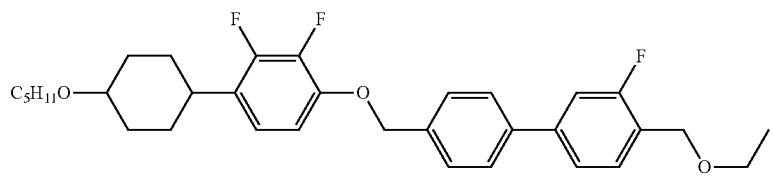 |
| 1171 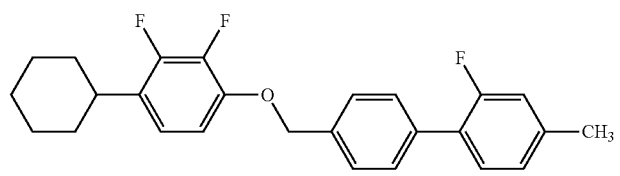 [SMILES: Cc1ccc(-c2ccc(COc3ccc(C4CCCCC4)c(F)c3F)cc2)c(F)c1] |
| 1172 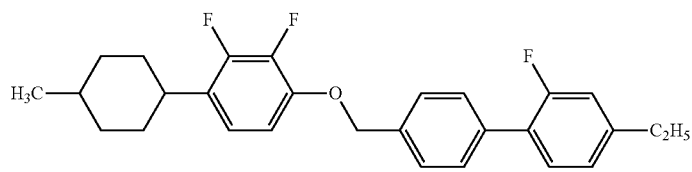 [SMILES: CCc1ccc(-c2ccc(COc3ccc(C4CCC(C)CC4)c(F)c3F)cc2)c(F)c1] |
| 1173 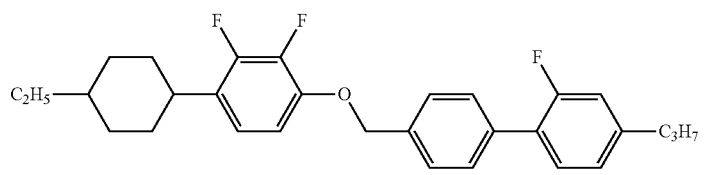 |
| 1174 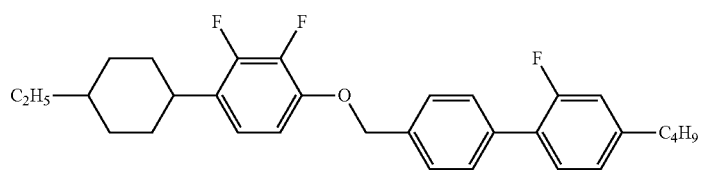 |
| 1175 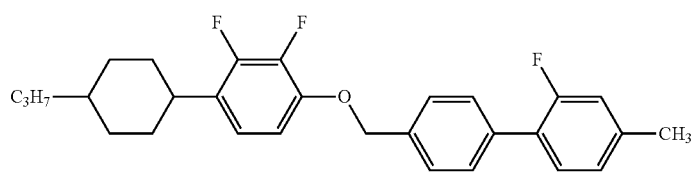 |
| 1176 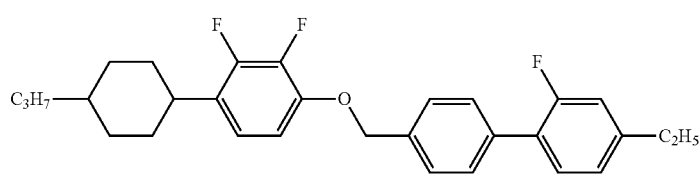 |

-continued
| No. | |
|---|---|
| 1177 | 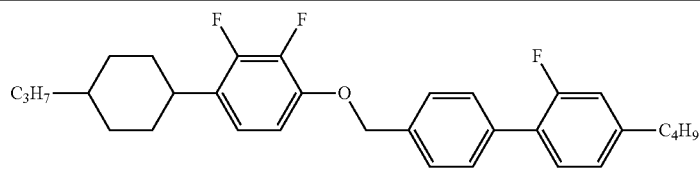 |
| 1178 | 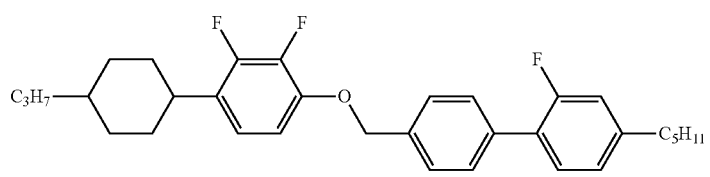 |
| 1179 | 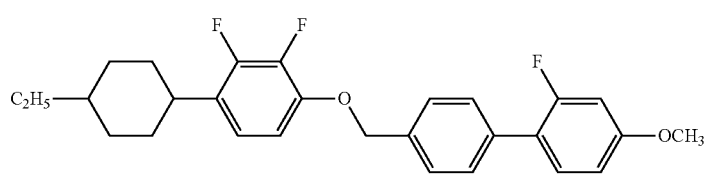 |
| 1180 | 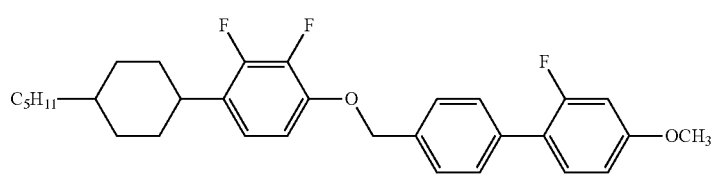 |
| 1181 | 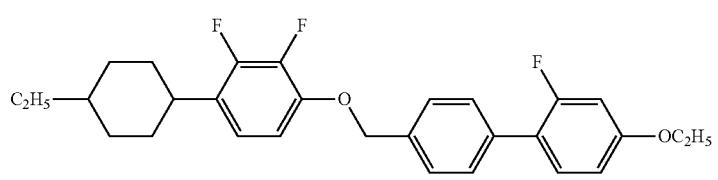 [SMILES: CCOc1ccc(-c2ccc(COc3ccc(C4CCC(CC)CC4)c(F)c3F)cc2)c(F)c1] |
| 1182 | 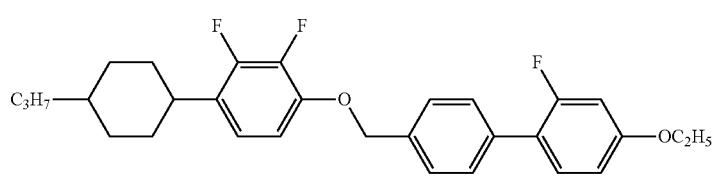 |
| 1183 | 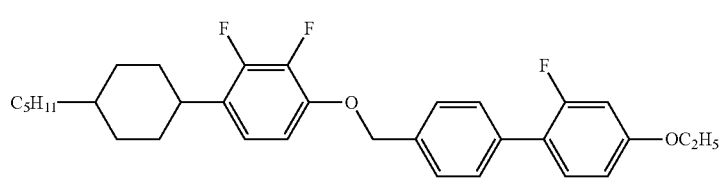 [SMILES: CCOc1ccc(-c2ccc(COc3ccc(C4CCC(OC)CC4)c(F)c3F)cc2)c(F)c1] |
| 1184 | 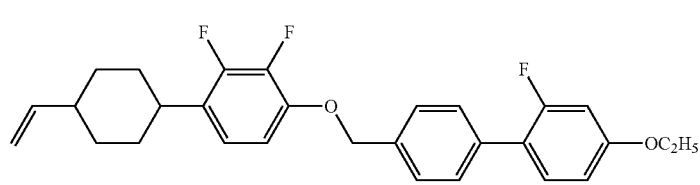 |
| 1185 | 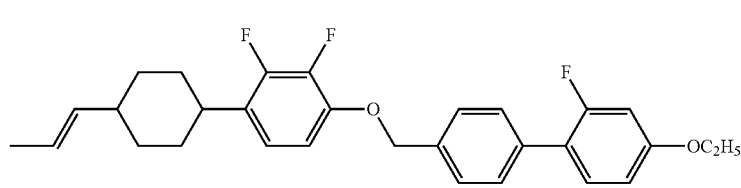 |

| No. | |
|---|---|
| 1186 | 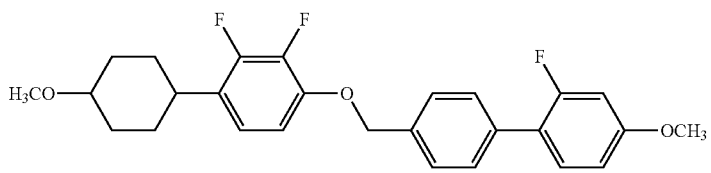 |
| 1187 | 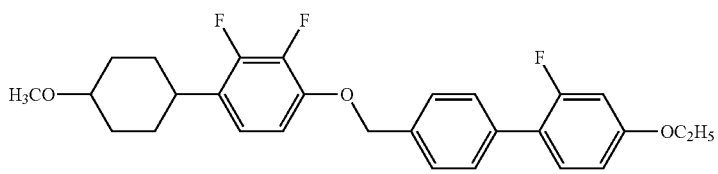 |
| 1188 | 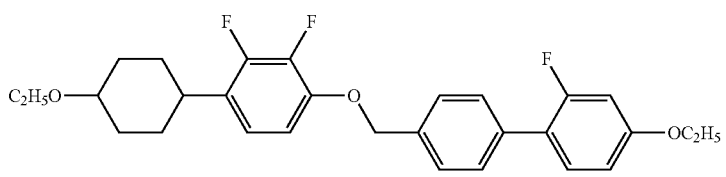 |
| 1189 | 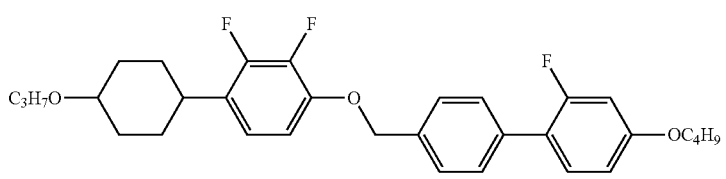 |
| 1190 | 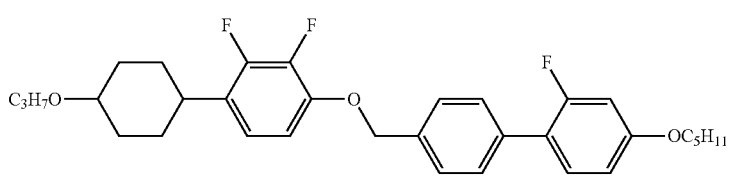 |
| 1191 | 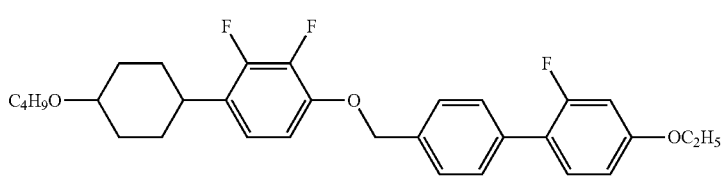 |
| 1192 | 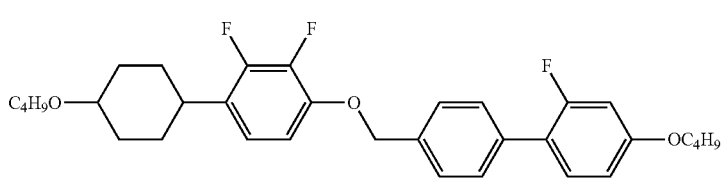 |
| 1193 | 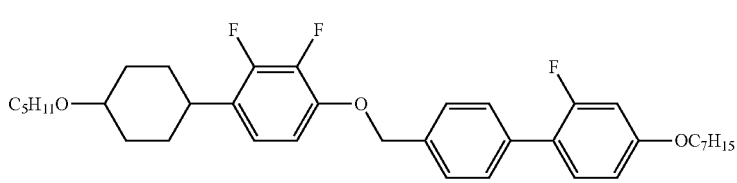 |

-continued
| No. |
|---|
| 1194 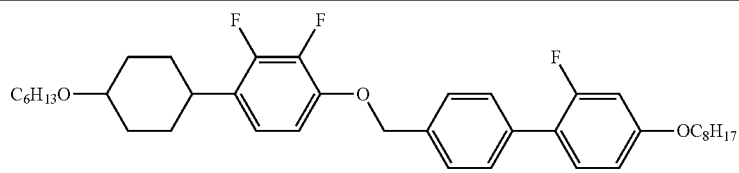 |
| 1195 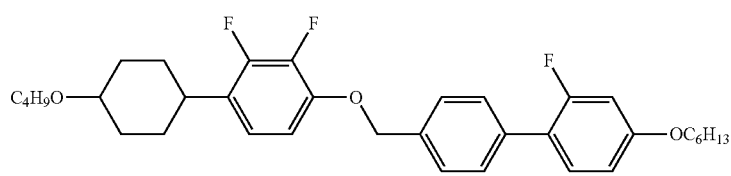 |
| 1196 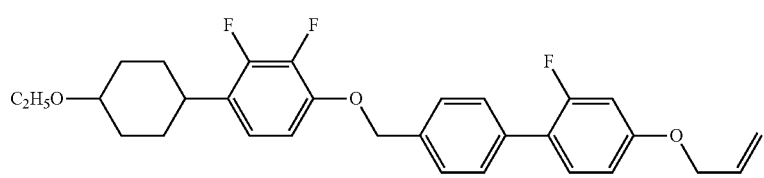 |
| 1197 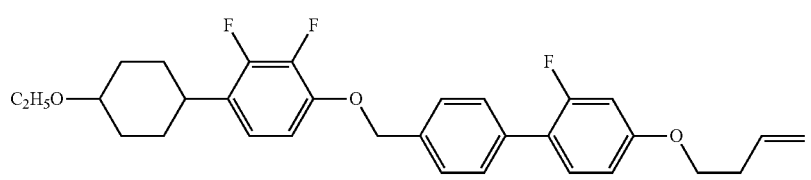 |
| 1198 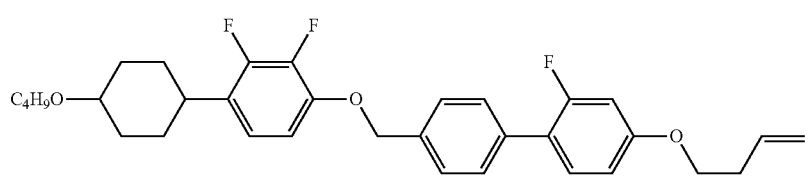 |
| 1199 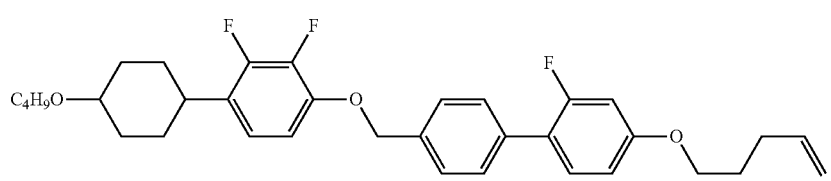 |
| 1200 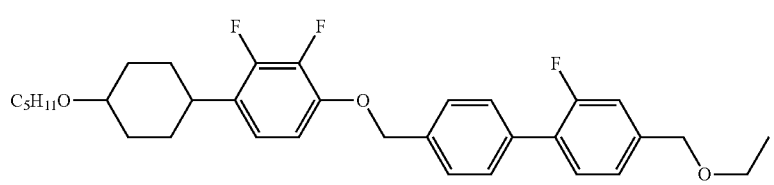 |
| 1201 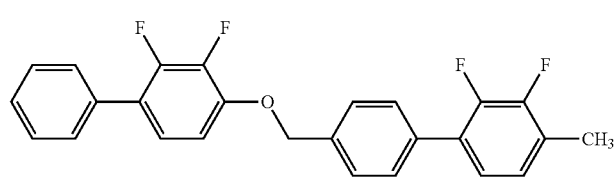 |
| 1202 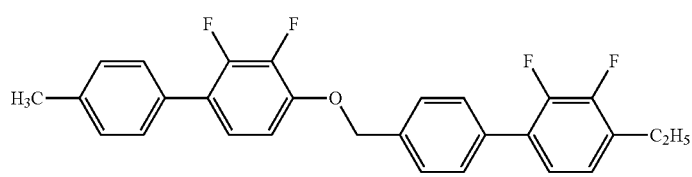 |

| No. | |
|---|---|
| 1203 | 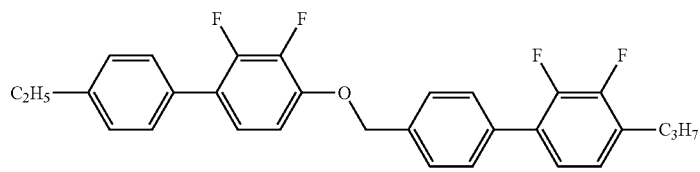 |
| 1204 | 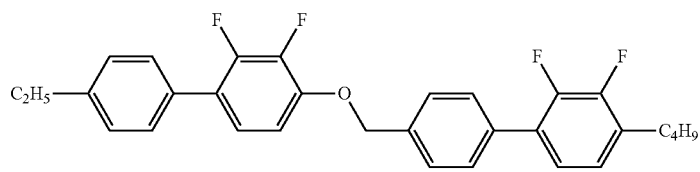 |
| 1205 | 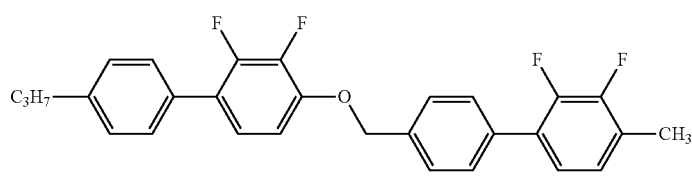 |
| 1206 | 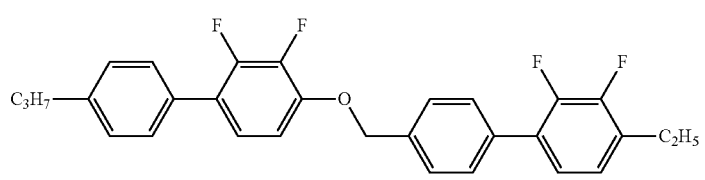 |
| 1207 | 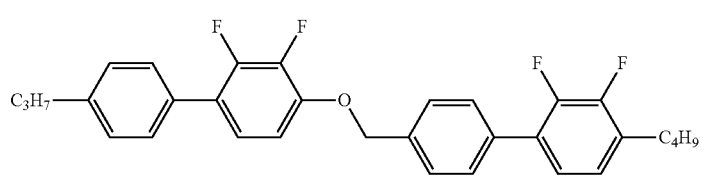 |
| 1208 | 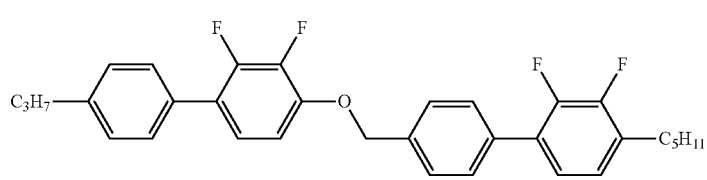 |
| 1209 | 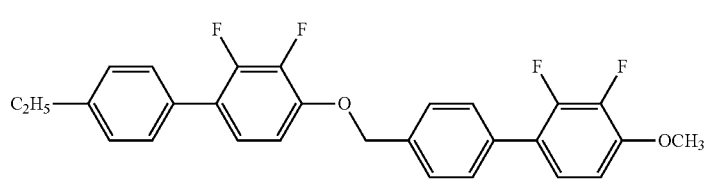 |
| 1210 | 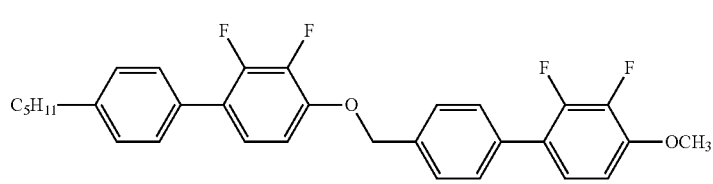 |

| No. | |
|---|---|
| 1211 | 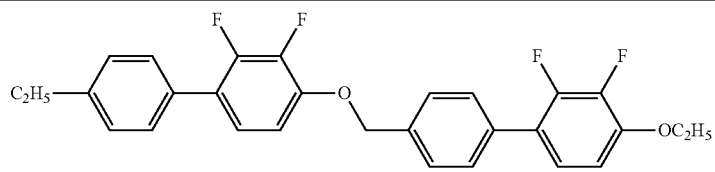 |
| 1212 | 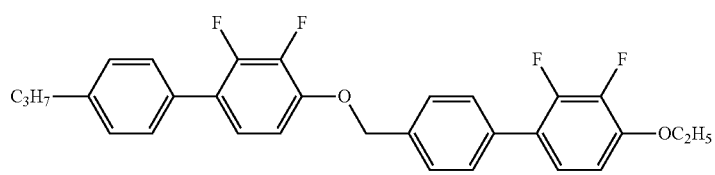 |
| 1213 | 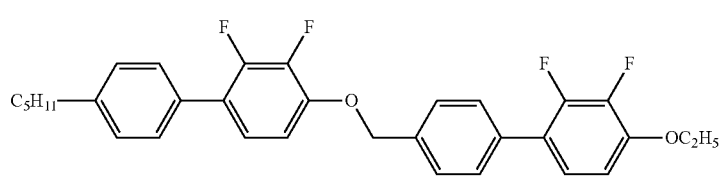 |
| 1214 | 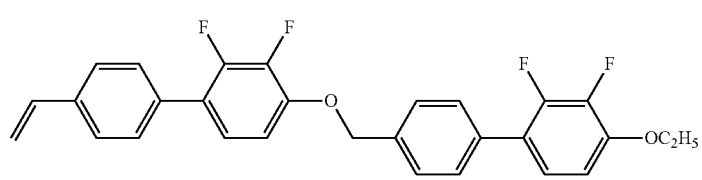 |
| 1215 | 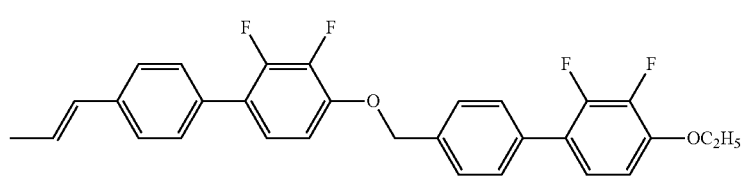 |
| 1216 | 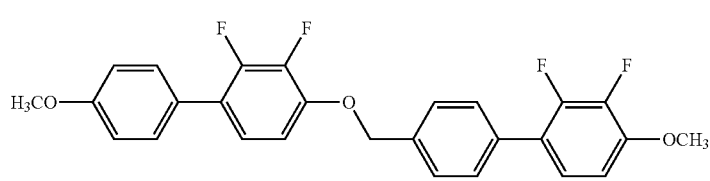 [SMILES: COc1ccc(-c2ccc(OCc3ccc(-c4ccc(OC)c(F)c4F)cc3)c(F)c2F)cc1] |
| 1217 | 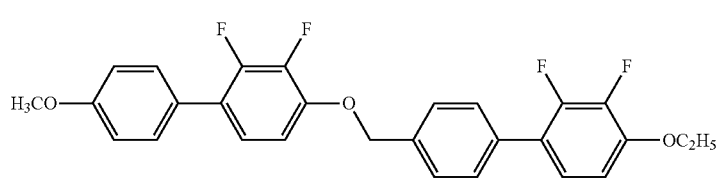 |
| 1218 | 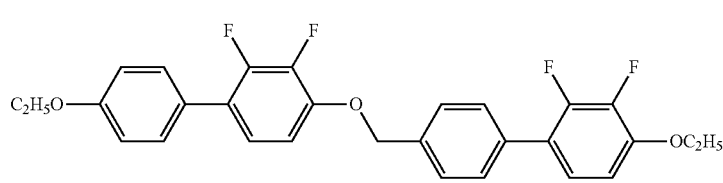 |
| 1219 | 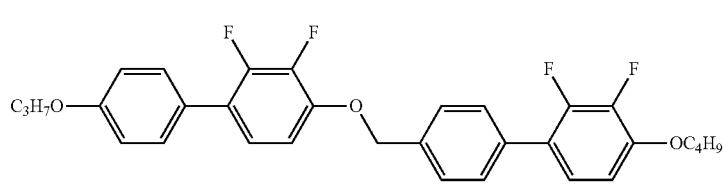 |

| No. |
|---|
| 1220 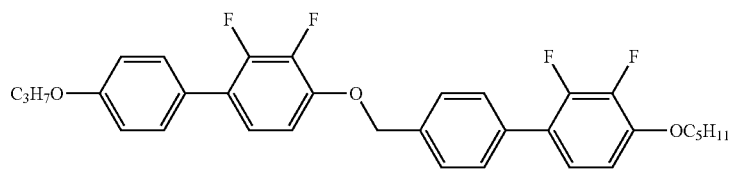 |
| 1221 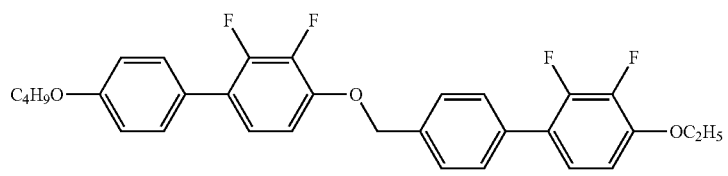 |
| 1222 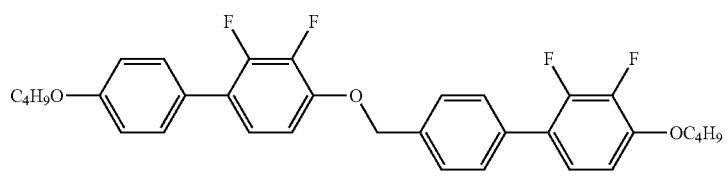 |
| 1223 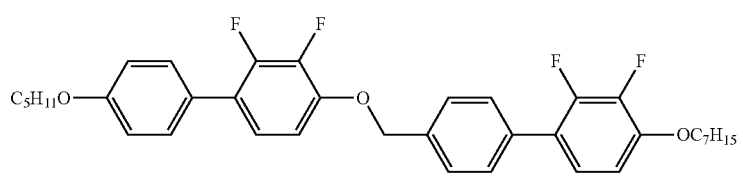 |
| 1224 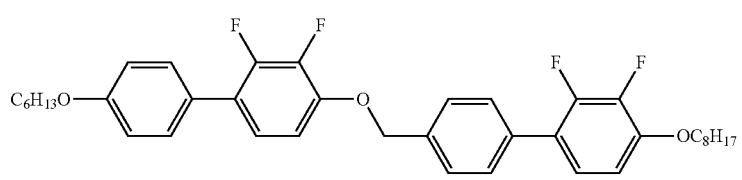 |
| 1225 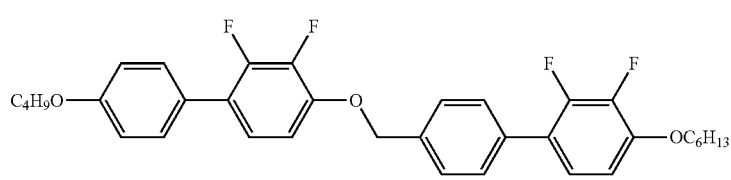 |
| 1226 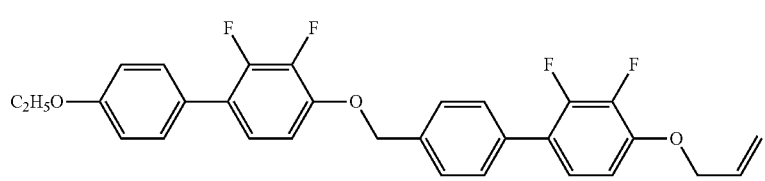 |
| 1227 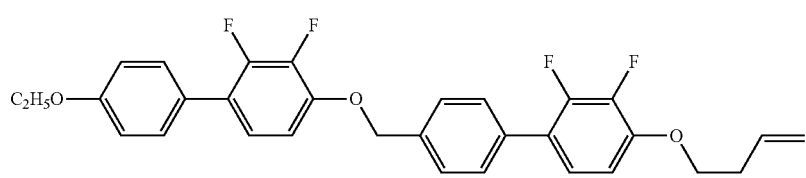 |

| No. | |
|---|---|
| 1228 | 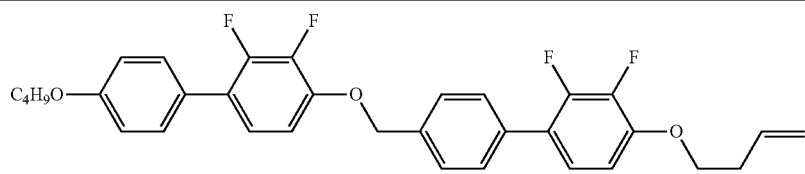 |
| 1229 | 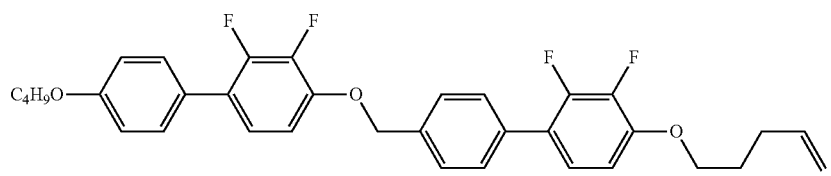 |
| 1230 | 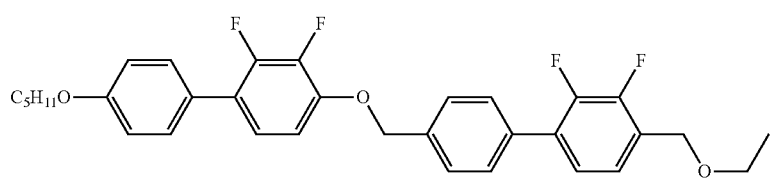 |
| 1231 | 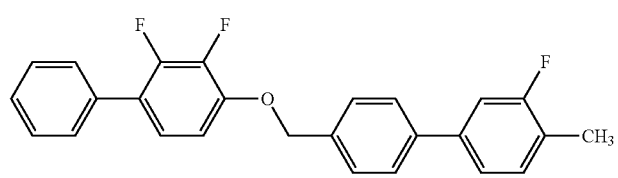 |
| 1232 | 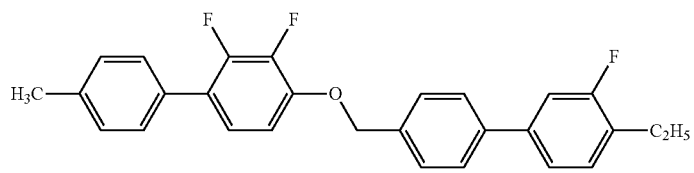 |
| 1233 | 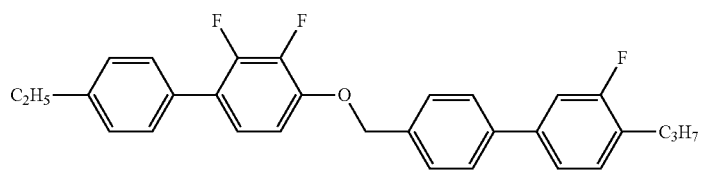 |
| 1234 | 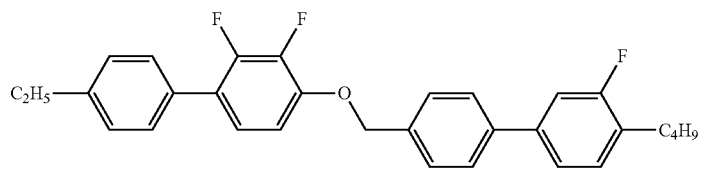 |
| 1235 | 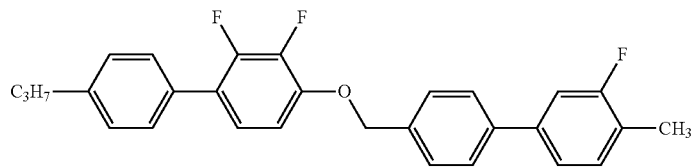 |
| 1236 | 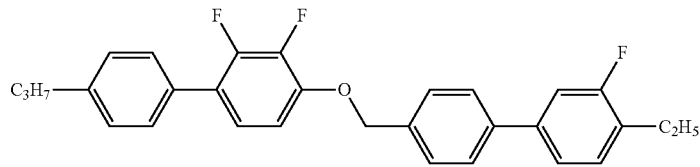 |

-continued
| No. | |
|---|---|
| 1237 | 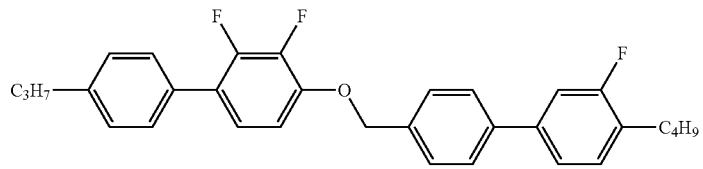 |
| 1238 | 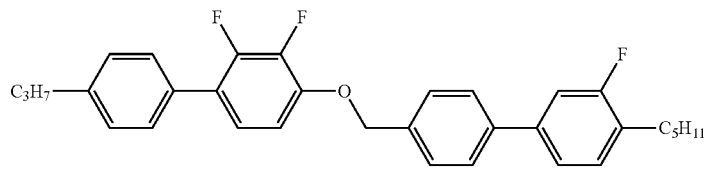 |
| 1239 | 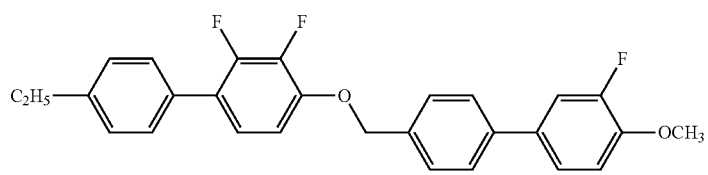 |
| 1240 | 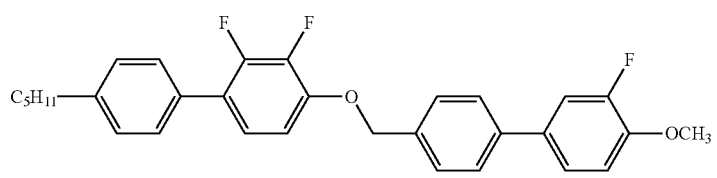 |
| 1241 | 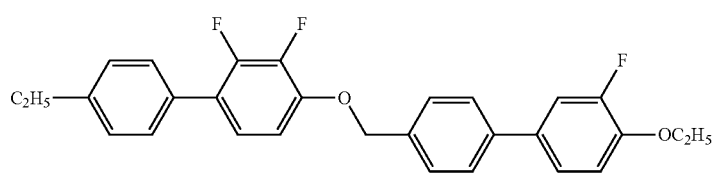 |
| 1242 | 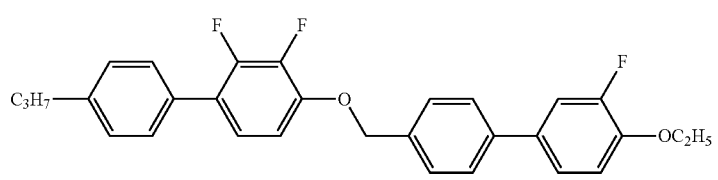 |
| 1243 | 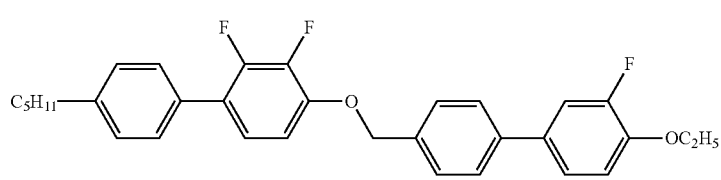 |
| 1244 | 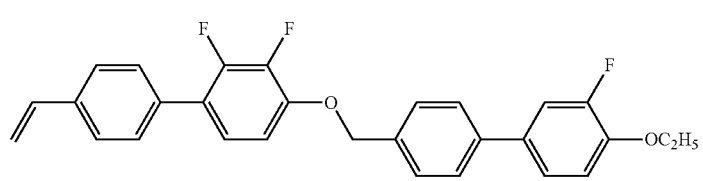 |

| No. | |
|---|---|
| 1245 | 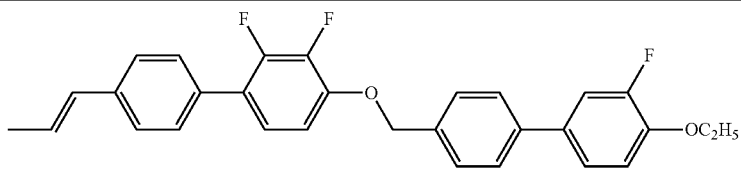 |
| 1246 | 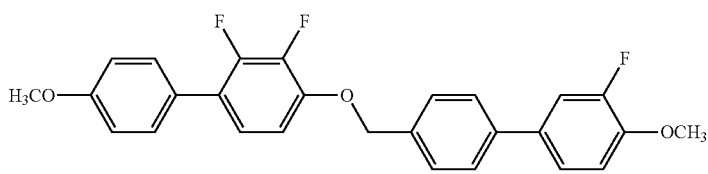 [SMILES: COc1ccc(-c2ccc(OCc3ccc(-c4ccc(OC)c(F)c4)cc3)c(F)c2F)cc1] |
| 1247 | 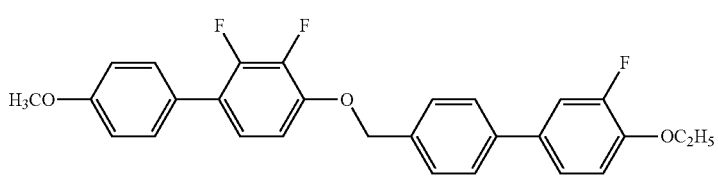 |
| 1248 | 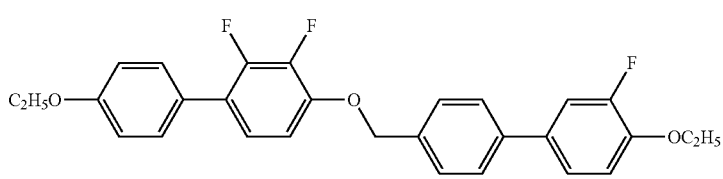 |
| 1249 | 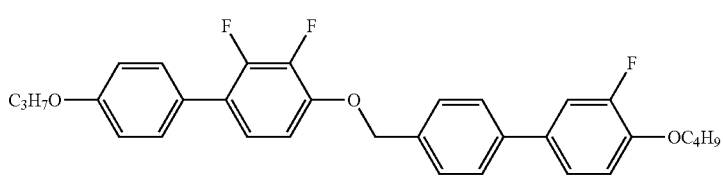 |
| 1250 | 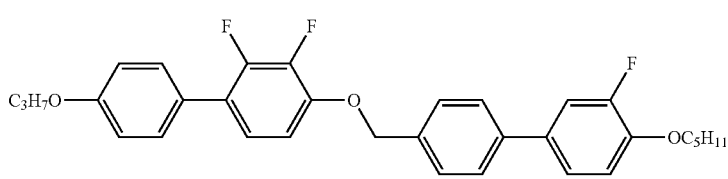 |
| 1251 | 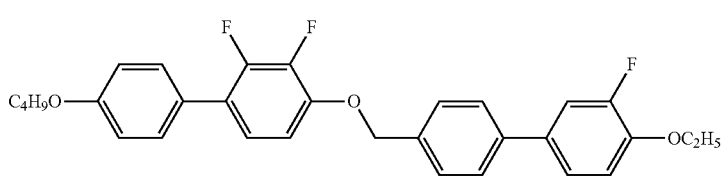 |
| 1252 | 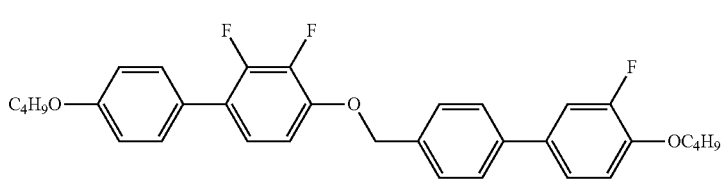 |
| 1253 | 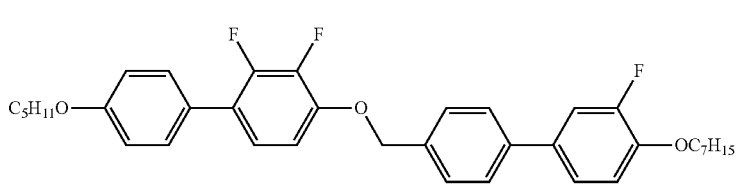 |

| No. | |
|---|---|
| 1254 | 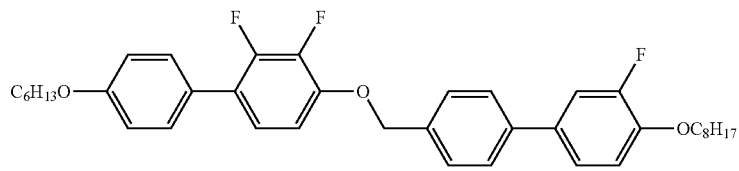 |
| 1255 | 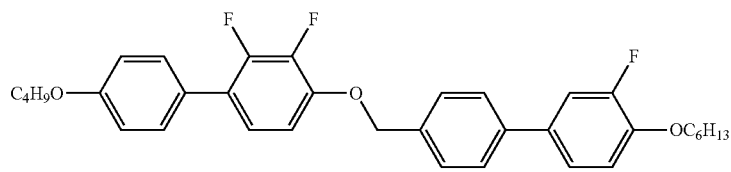 |
| 1256 | 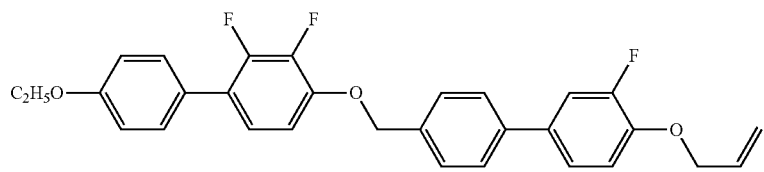 |
| 1257 | 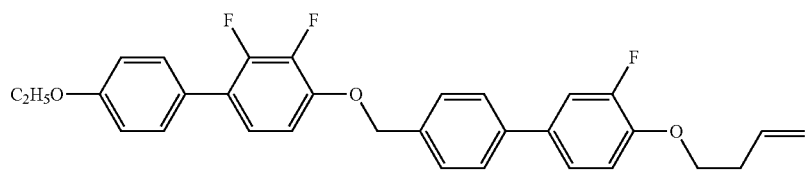 |
| 1258 | 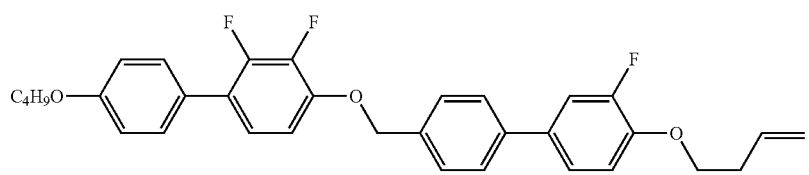 |
| 1259 | 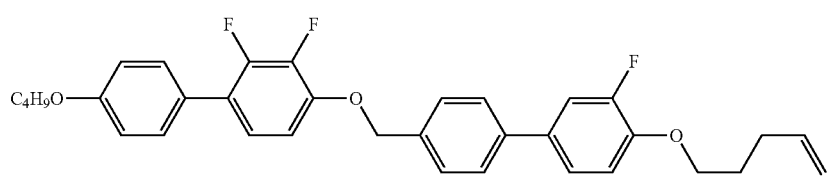 |
| 1260 | 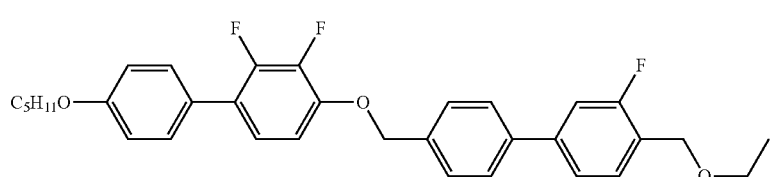 |
| 1261 | 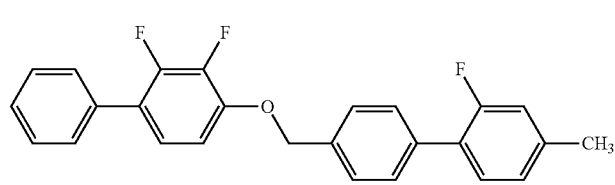 |

| No. |
|---|
| 1262 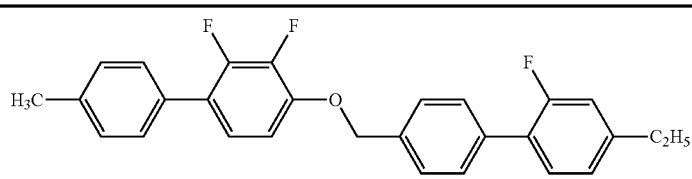 |
| 1263 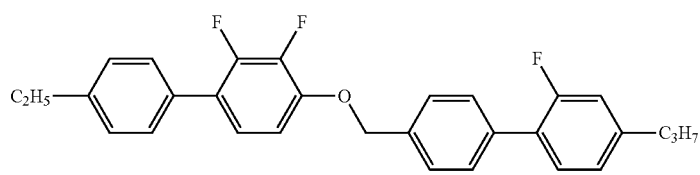 |
| 1264 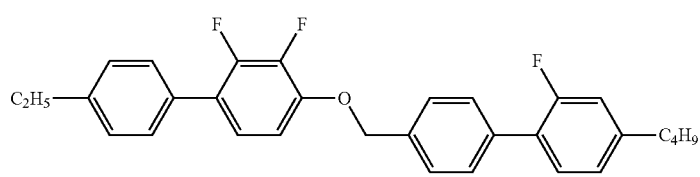 |
| 1265 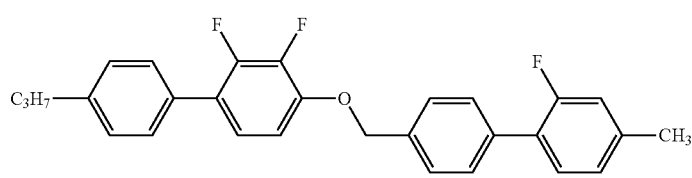 |
| 1266 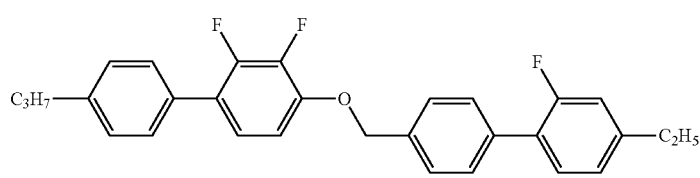 |
| 1267 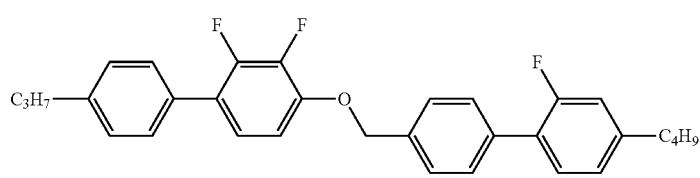 |
| 1268 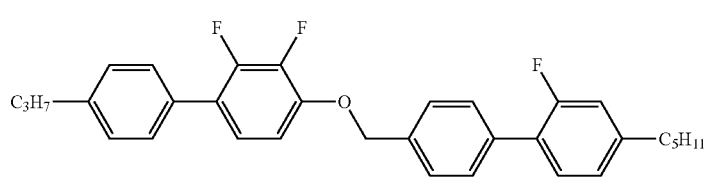 |
| 1269 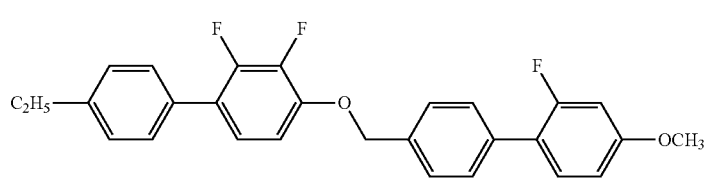 |
| 1270 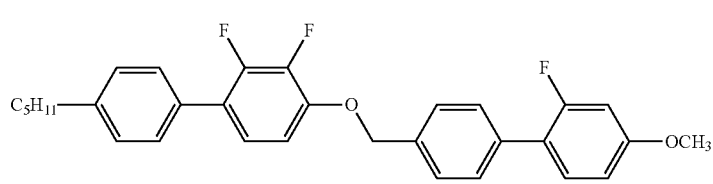 |

-continued
| No. |
|---|
| 1271 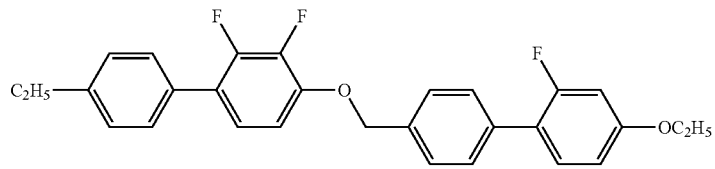 |
| 1272 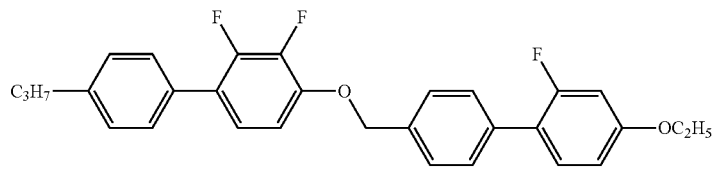 |
| 1273 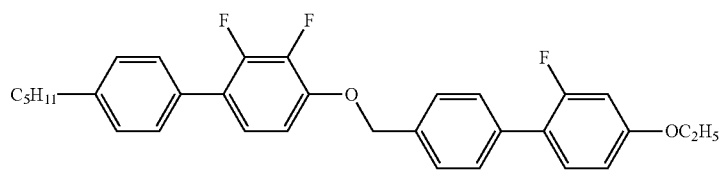 [SMILES: CCOc1ccc(-c2ccc(COc3ccc(-c4ccc(OC)cc4)c(F)c3F)cc2)c(F)c1] |
| 1274 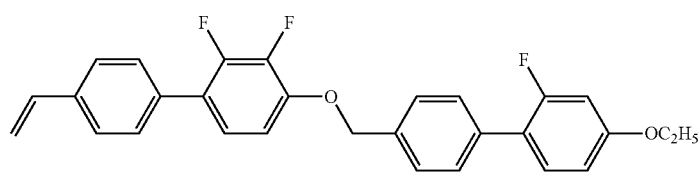 |
| 1275 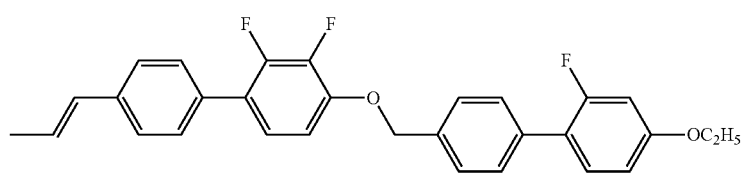 |
| 1276 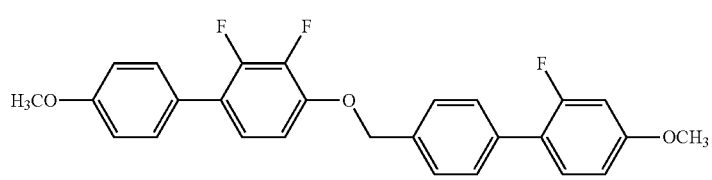 |
| 1277 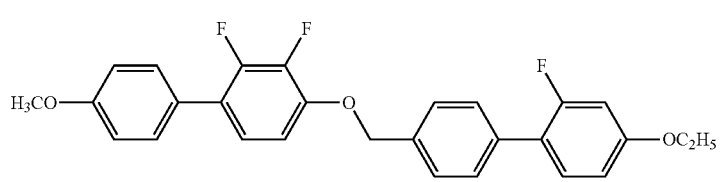 |
| 1278 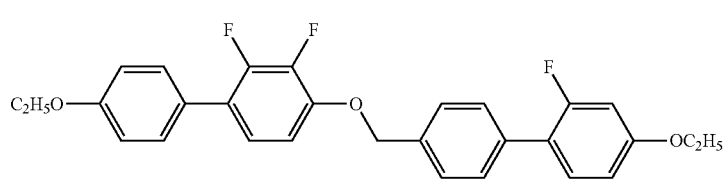 |

-continued
| No. | |
|---|---|
| 1279 | 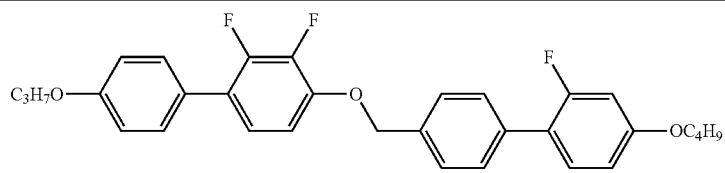 |
| 1280 | 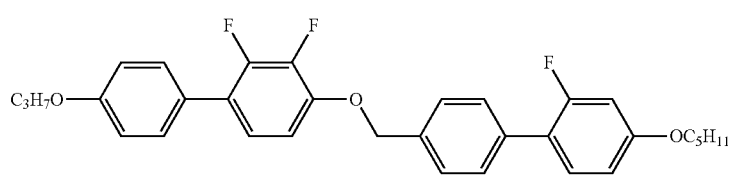 |
| 1281 | 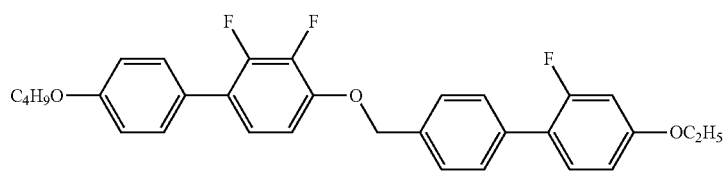 |
| 1282 | 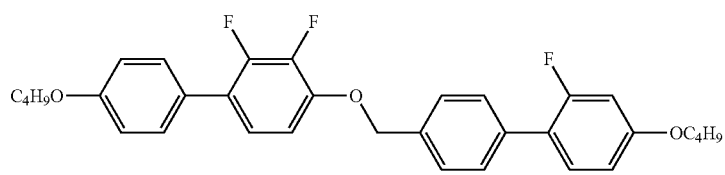 |
| 1283 | 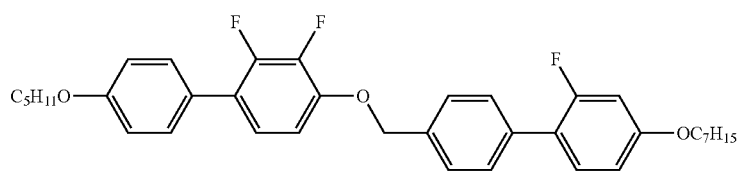 |
| 1284 | 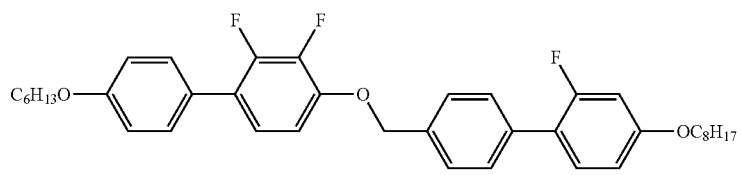 |
| 1285 | 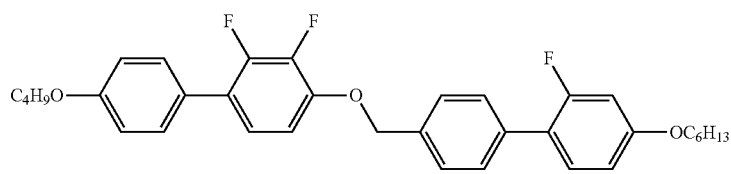 |
| 1286 | 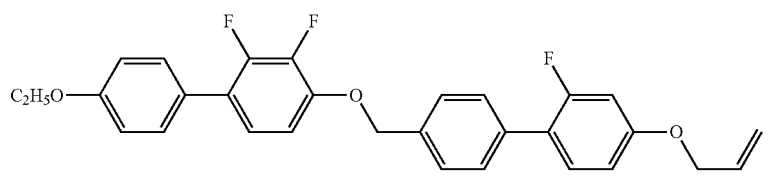 |
| 1287 | 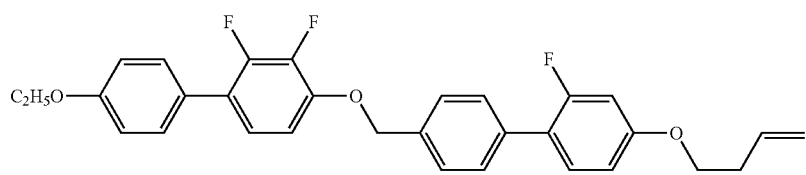 |

| No. | |
|---|---|
| 1288 | 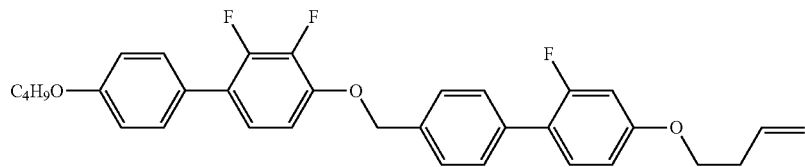 |
| 1289 | 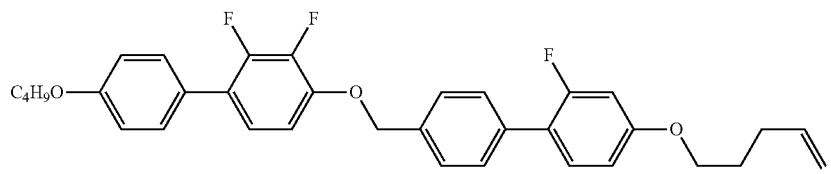 |
| 1290 | 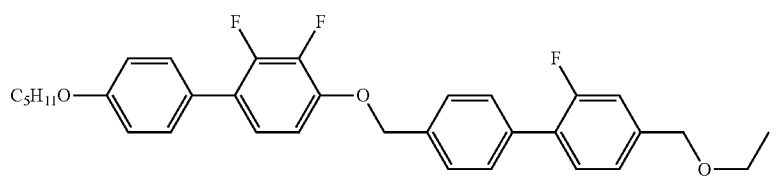 |
| 1291 | 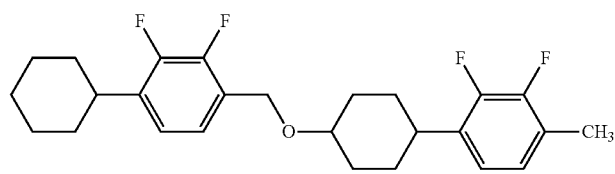 |
| 1292 | 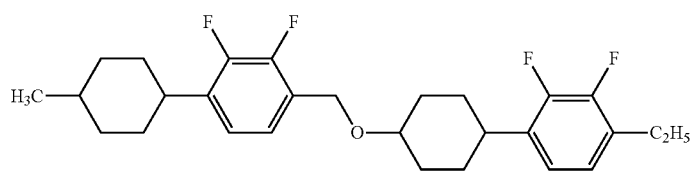 |
| 1293 | 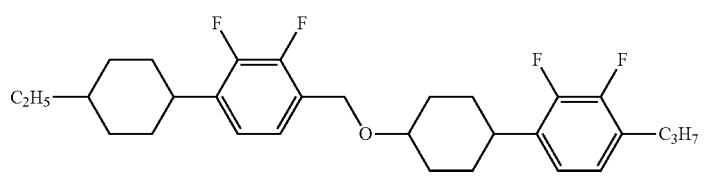 |
| 1294 | 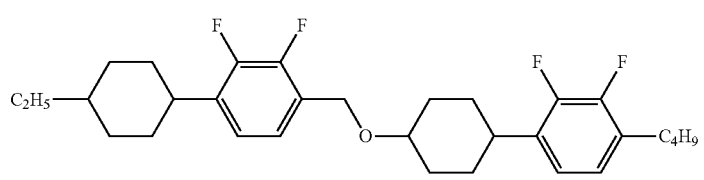 |
| 1295 | 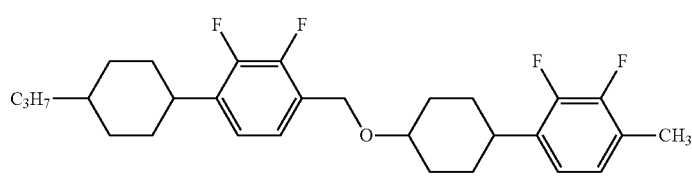 |

-continued
| No. | |
|---|---|
| 1296 | 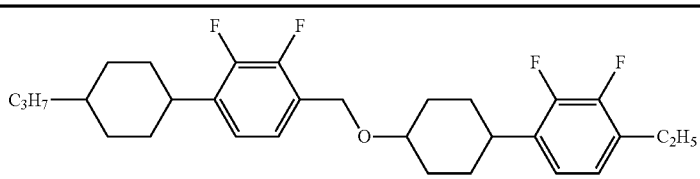 |
| 1297 | 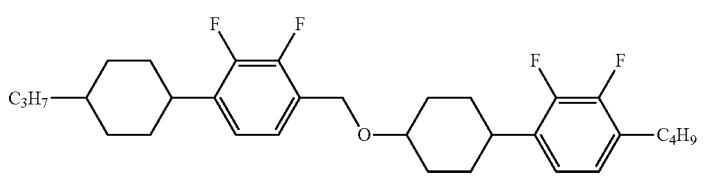 |
| 1298 | 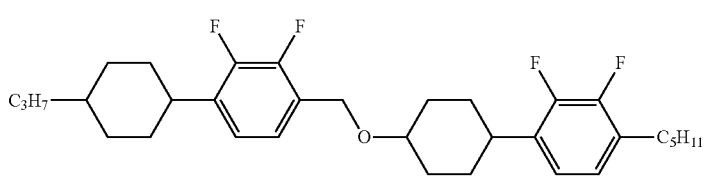 |
| 1299 | 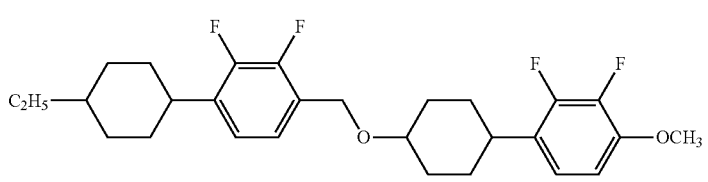 |
| 1300 | 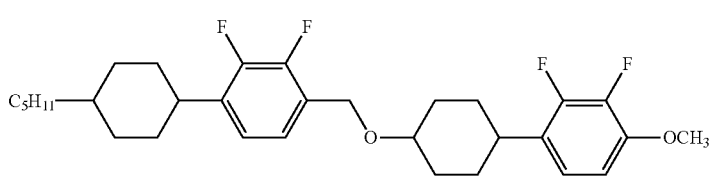 |
| 1301 | 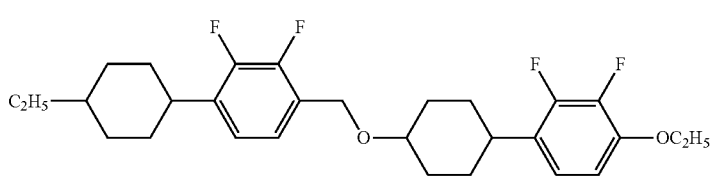 |
| 1302 | 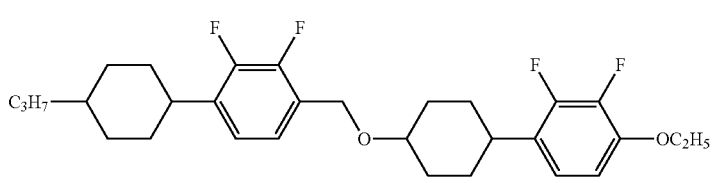 |
| 1303 | 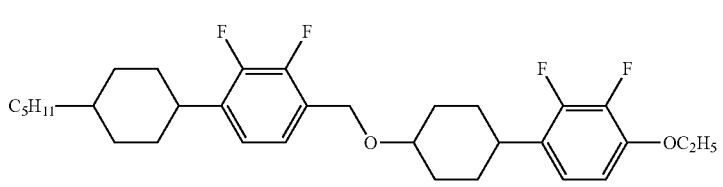 |
| 1304 | 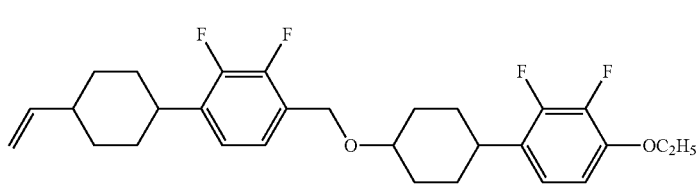 |

| No. |
|---|
| 1305 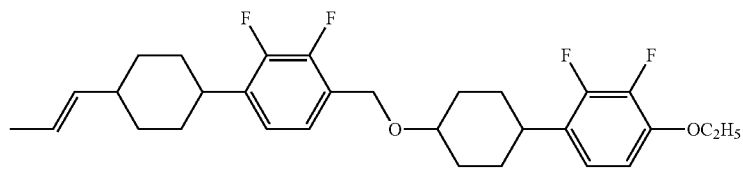 |
| 1306 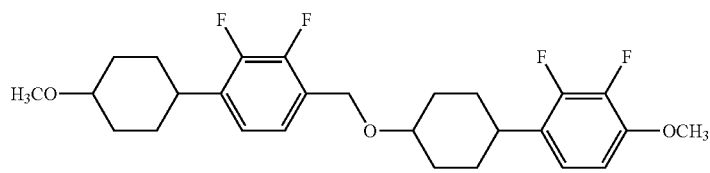 |
| 1307 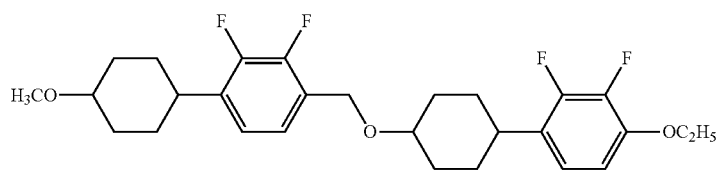 |
| 1308 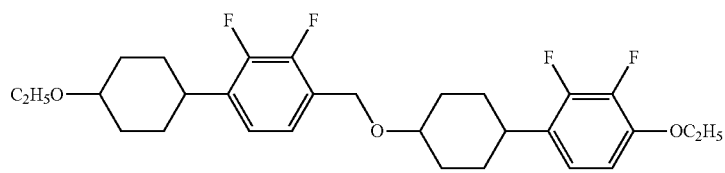 |
| 1309 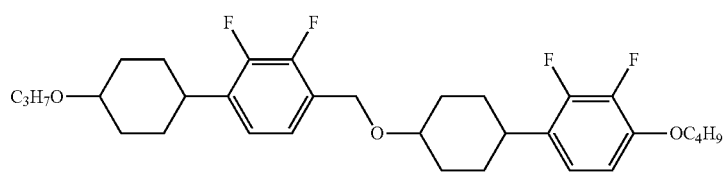 |
| 1310 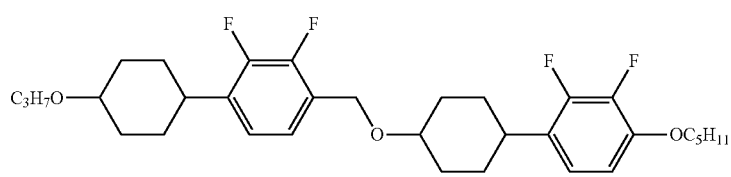 |
| 1311 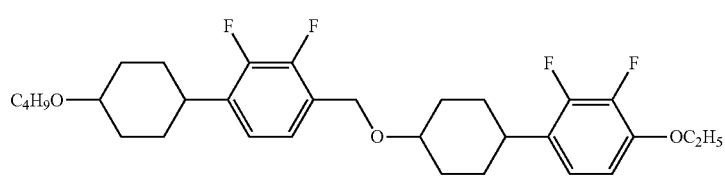 |
| 1312 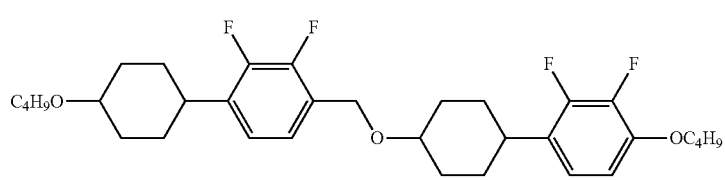 |

| No. |
|---|
| 1313 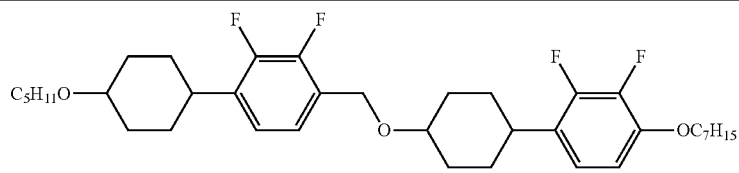 |
| 1314 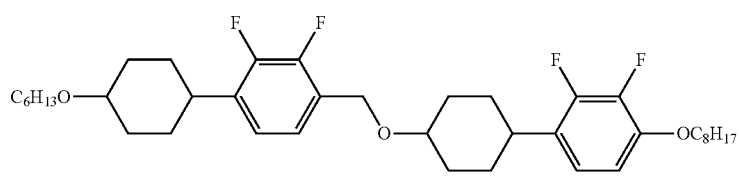 |
| 1315 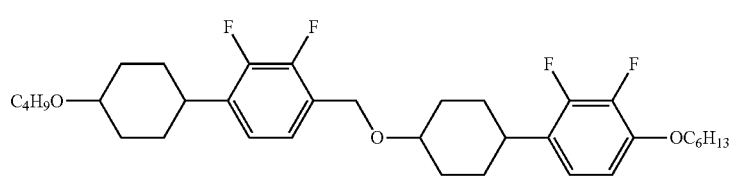 |
| 1316 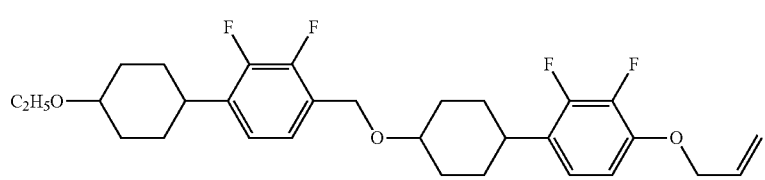 |
| 13171 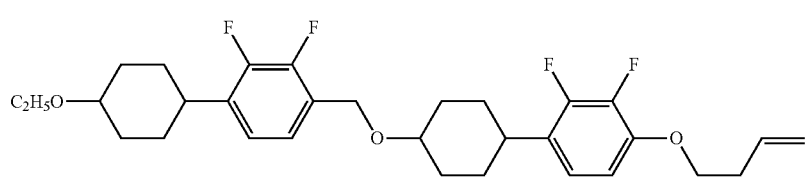 |
| 1318 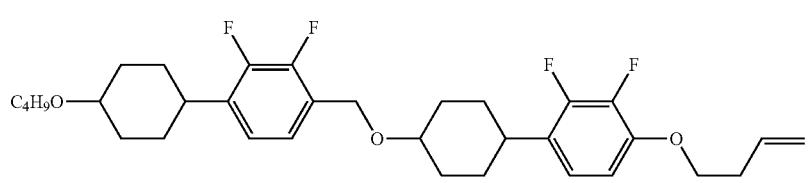 |
| 1319 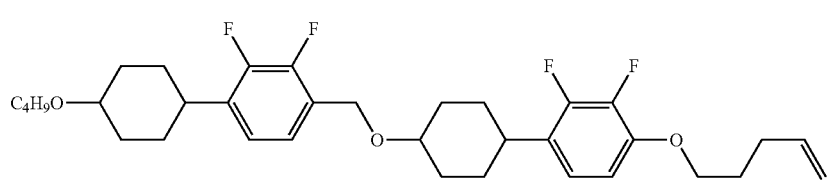 |
| 1320 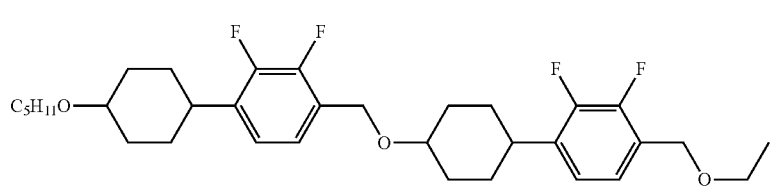 |
| 1321 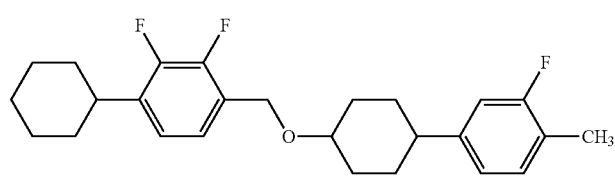 |

| No. | |
|---|---|
| 1322 | 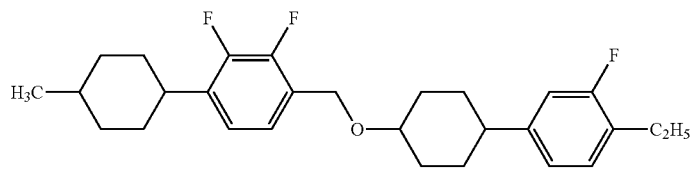 |
| 1323 | 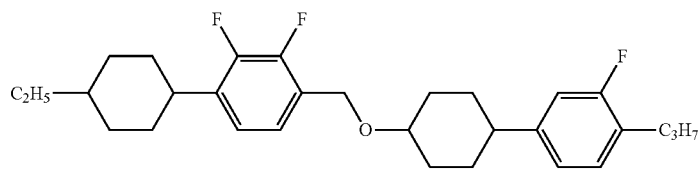 |
| 1324 | 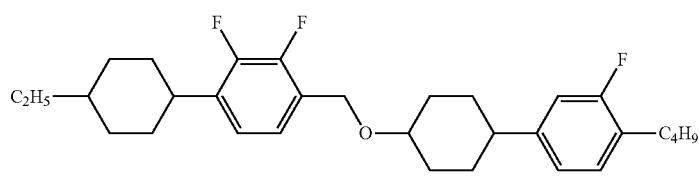 |
| 1325 | 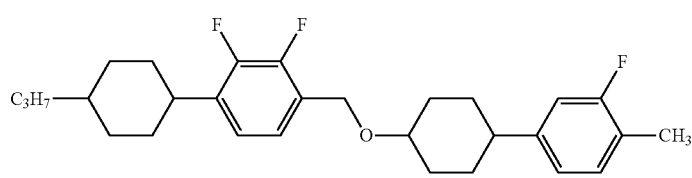 |
| 1326 | 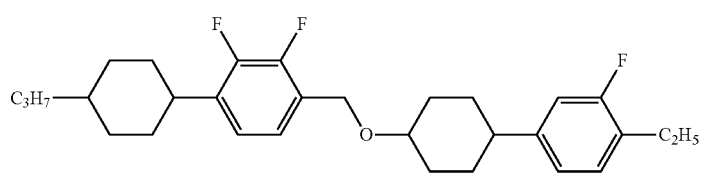 |
| 1327 | 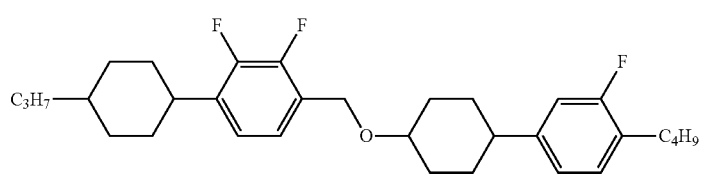 |
| 1328 | 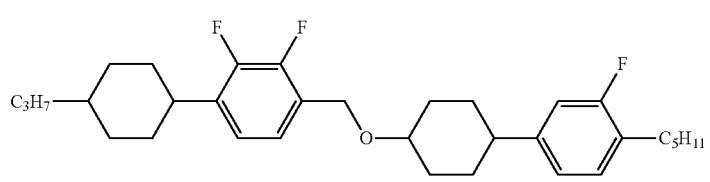 |
| 1329 | 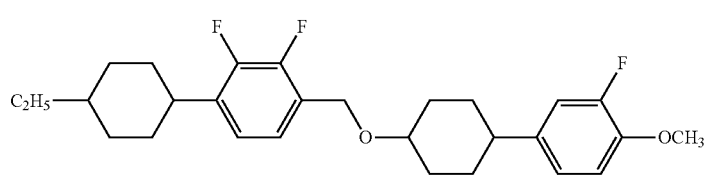 |

| No. | |
|---|---|
| 1330 | 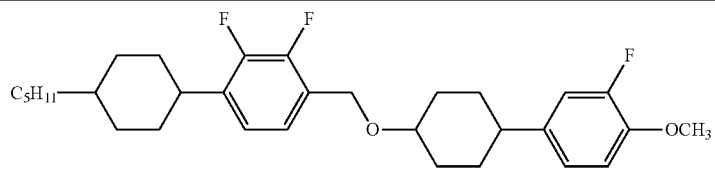 |
| 1331 | 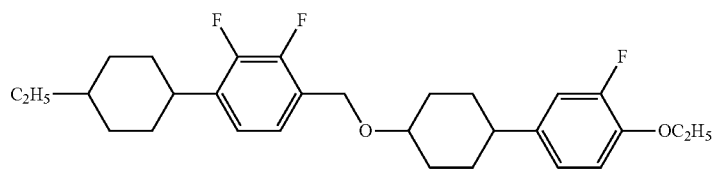 |
| 1332 | 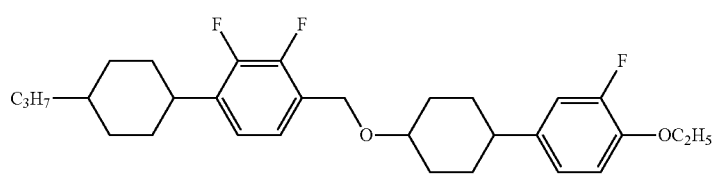 |
| 1333 | 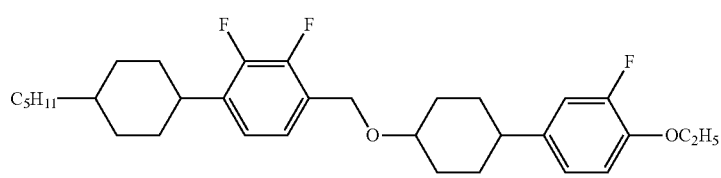 |
| 1334 | 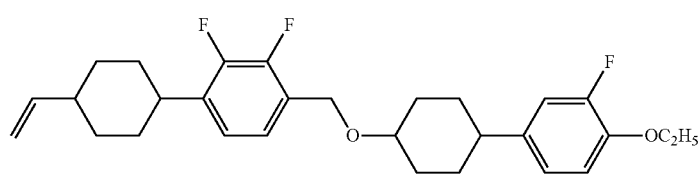 [SMILES: C=CC1CCC(c2ccc(COC3CCC(c4ccc(OCC)c(F)c4)CC3)c(F)c2F)CC1] |
| 1335 | 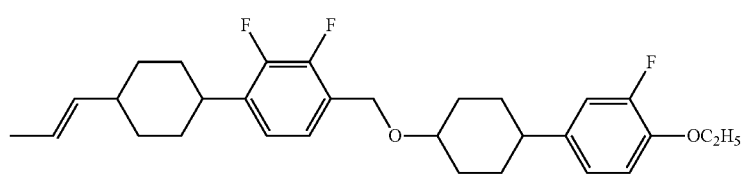 |
| 1336 | 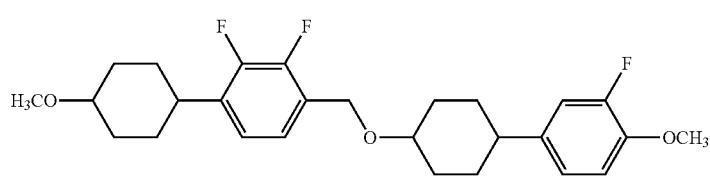 |
| 1337 | 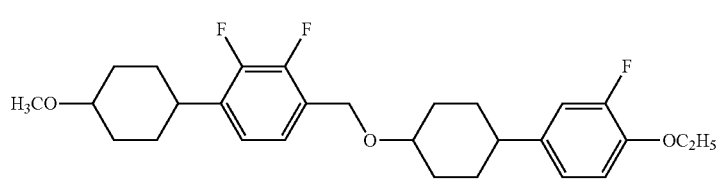 |
| 1338 | 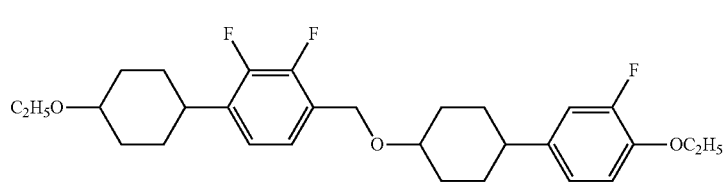 |

| No. | |
|---|---|
| 1339 | 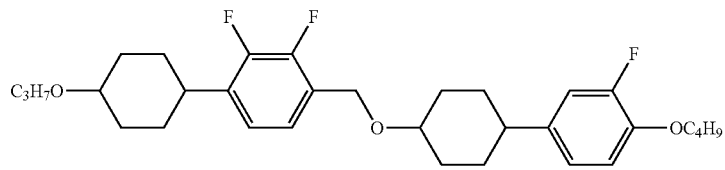 |
| 1340 | 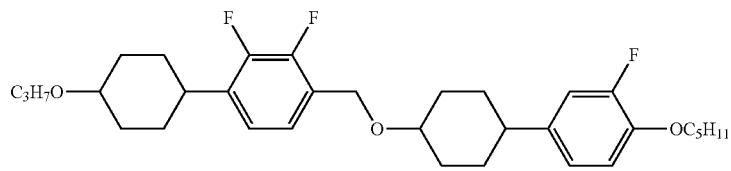 |
| 1341 | 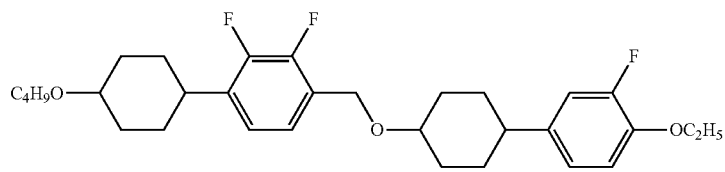 |
| 1342 | 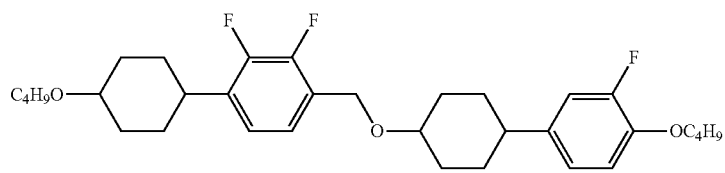 |
| 1343 | 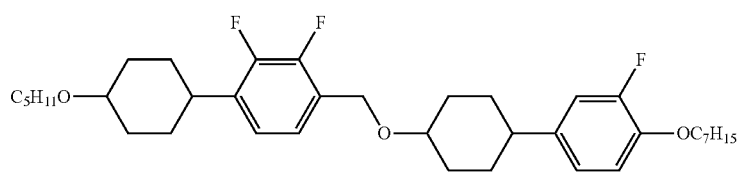 |
| 1344 | 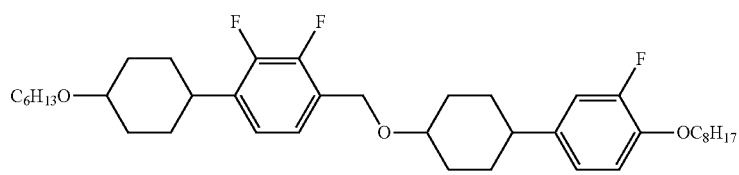 |
| 1345 | 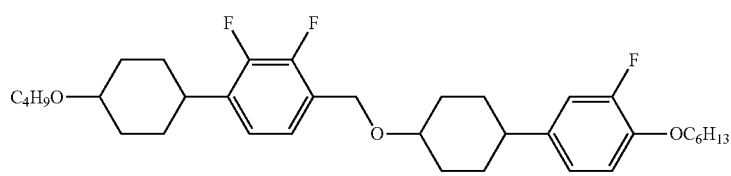 |
| 1346 | 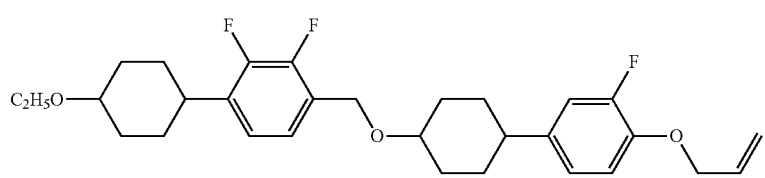 |

| No. |
|---|
| 1347 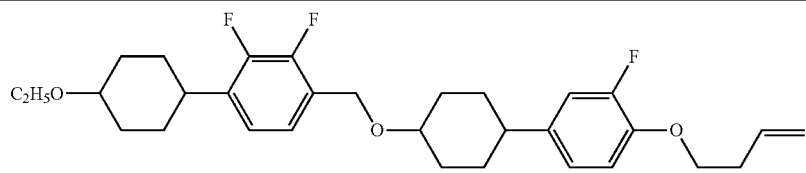 |
| 1348 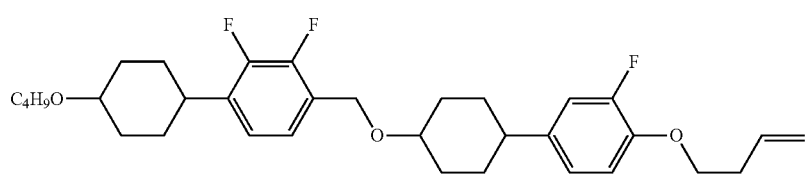 |
| 1349 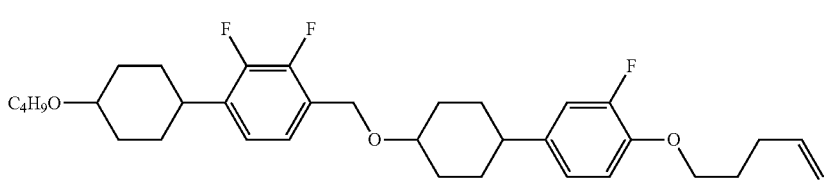 |
| 1350 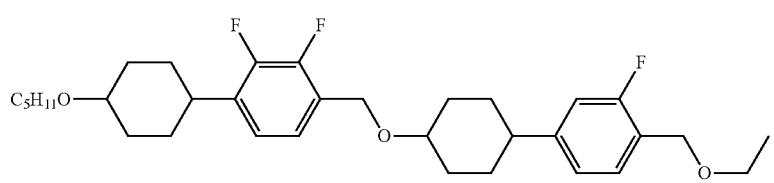 |
| 1351 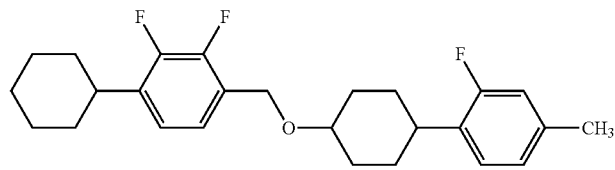 |
| 1352 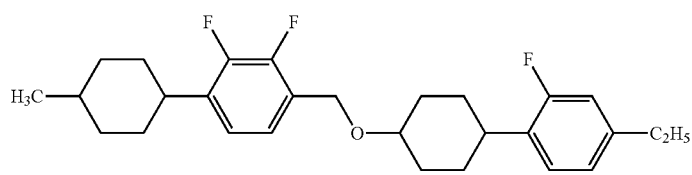 |
| 1353 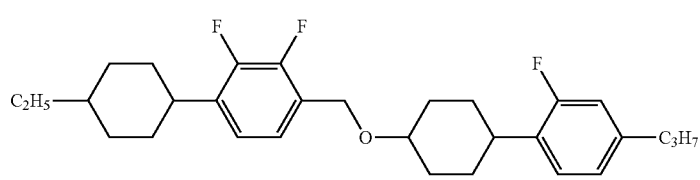 |
| 1354 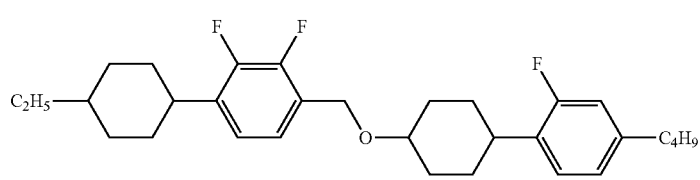 |
| 1355 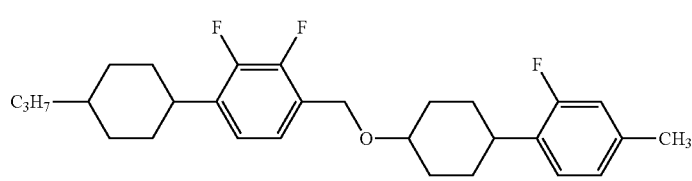 |

| No. | |
|---|---|
| 1356 | 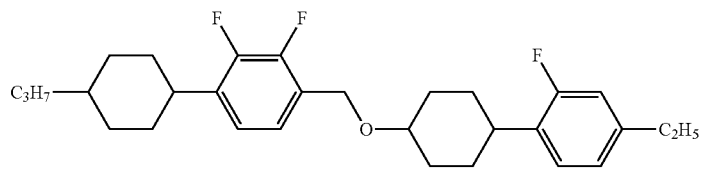 |
| 1357 | 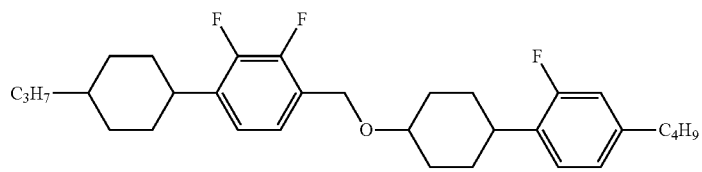 |
| 1358 | 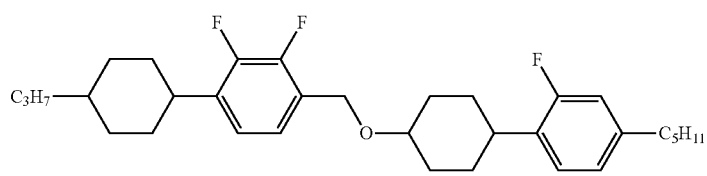 |
| 1359 | 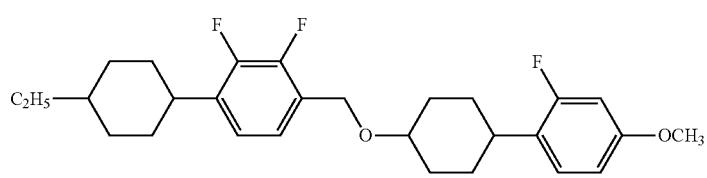 |
| 1360 | 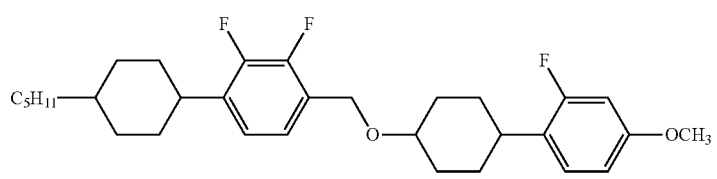 |
| 1361 | 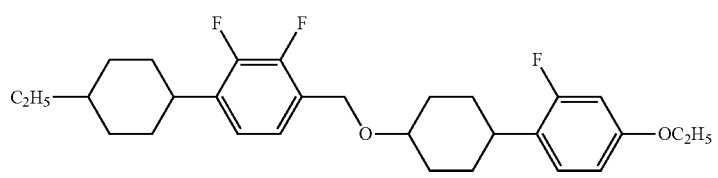 |
| 1362 | 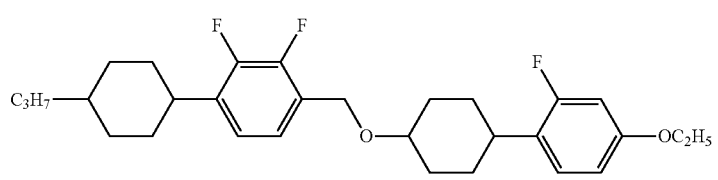 |
| 1363 | 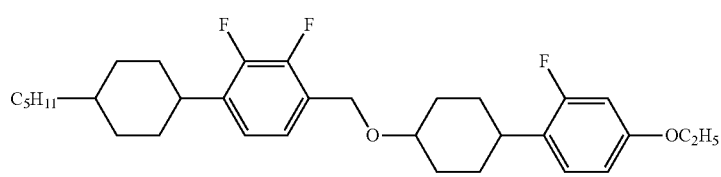 |

| No. |
|---|
| 1364 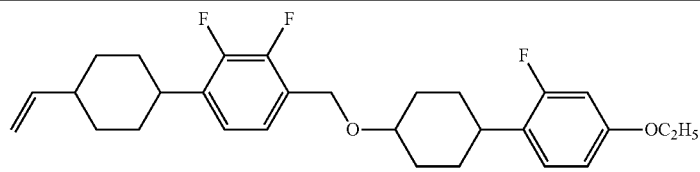 |
| 1365 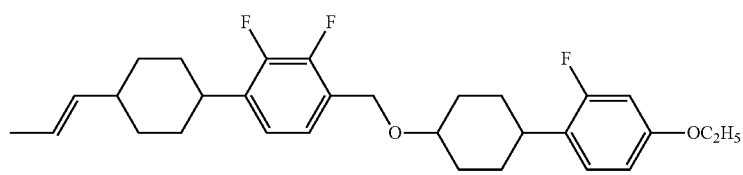 |
| 1366 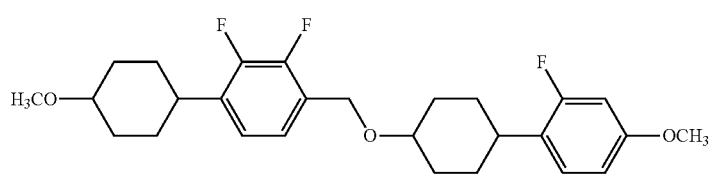 [SMILES: COc1ccc(C2CCC(OCc3ccc(C4CCC(OC)CC4)c(F)c3F)CC2)c(F)c1] |
| 1367 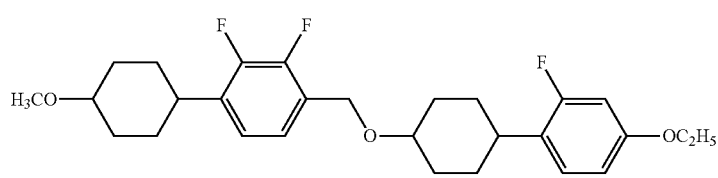 |
| 1368 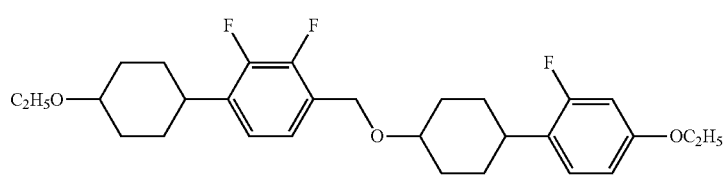 |
| 1369 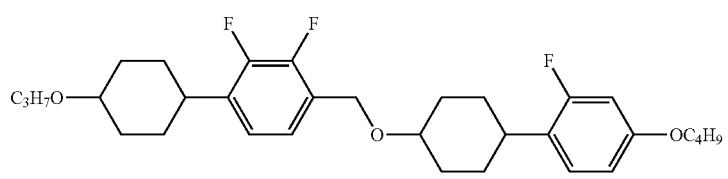 |
| 1370 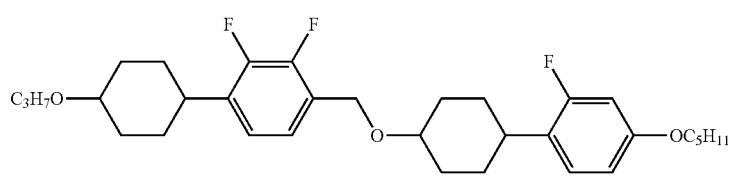 |
| 1371 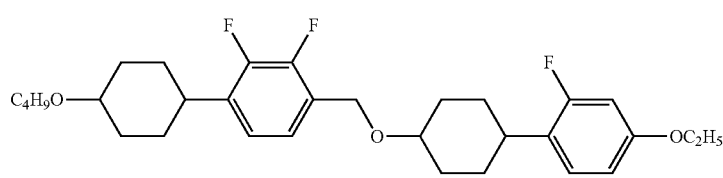 |
| 1372 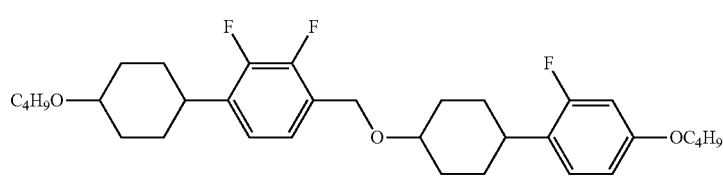 |

-continued
| No. | |
|---|---|
| 1373 | 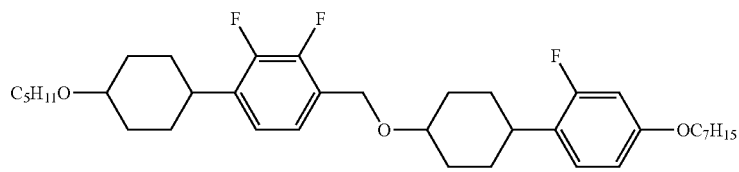 |
| 1374 | 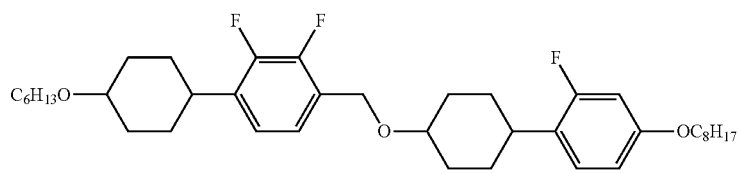 |
| 1375 | 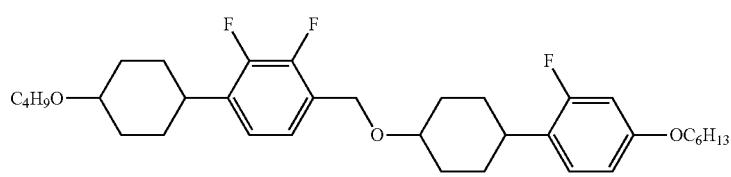 |
| 1376 | 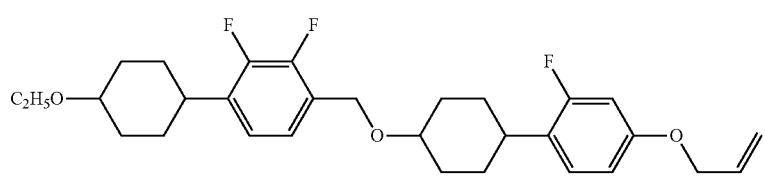 |
| 1377 | 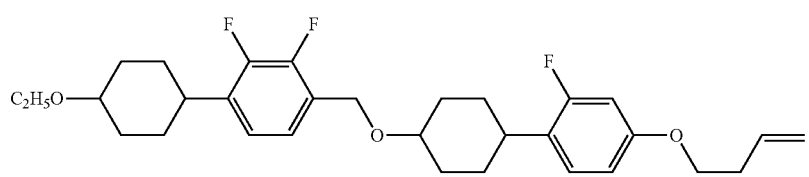 |
| 1378 | 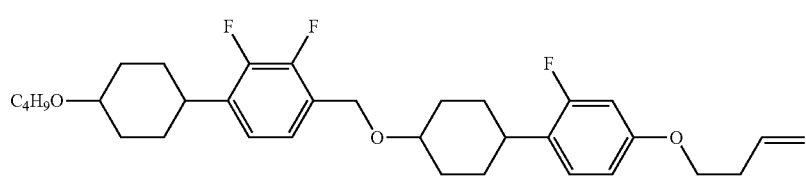 |
| 1379 | 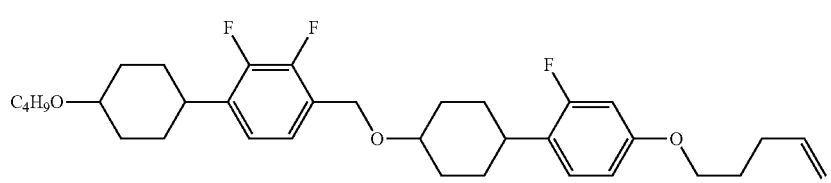 |
| 1380 | 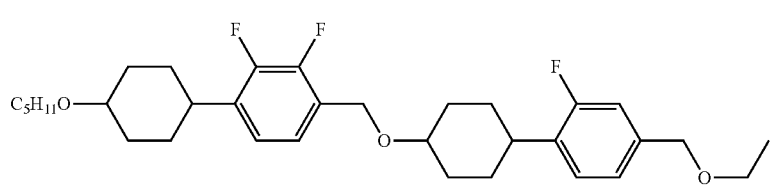 |

| No. | |
|---|---|
| 1381 | 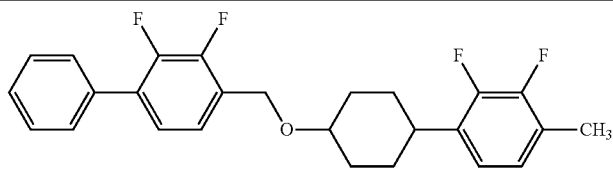 |
| 1382 | 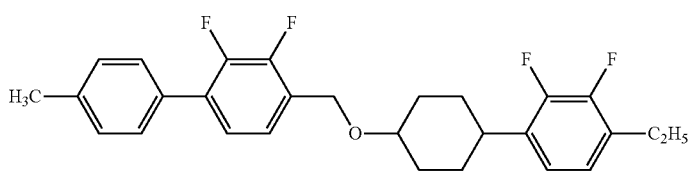 |
| 1383 | 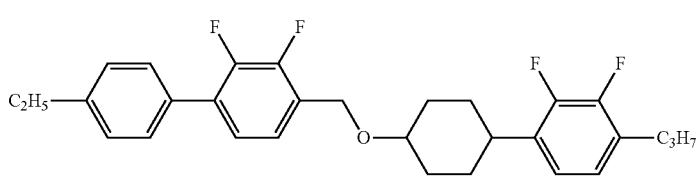 |
| 1384 | 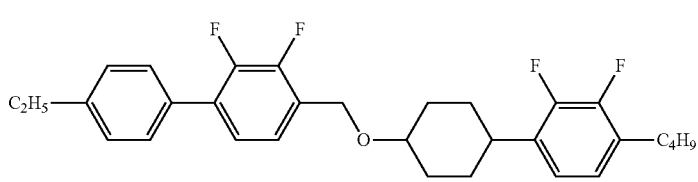 |
| 1385 | 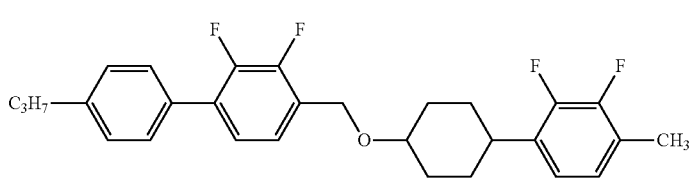 |
| 1386 | 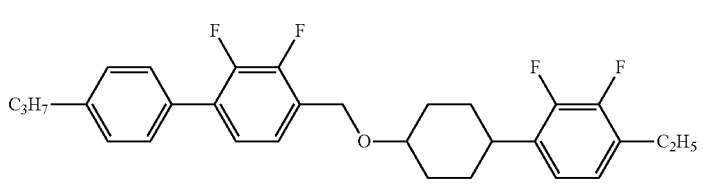 |
| 1387 | 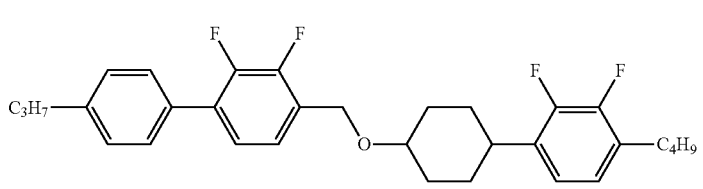 |
| 1388 | 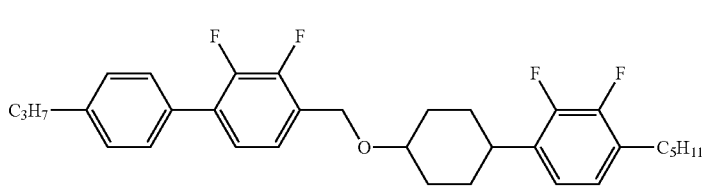 |
| 1389 | 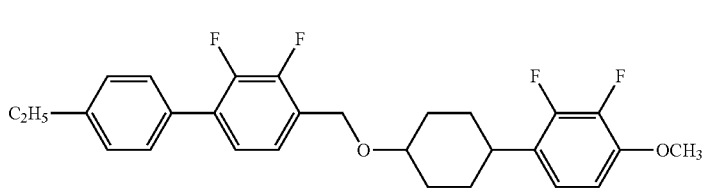 |

-continued
| No. | |
|---|---|
| 1390 | 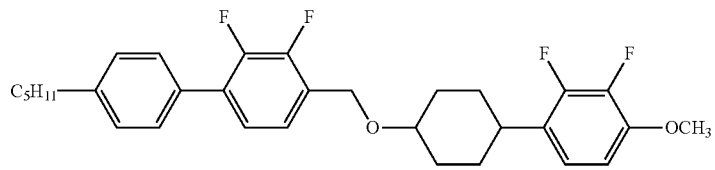 |
| 1391 | 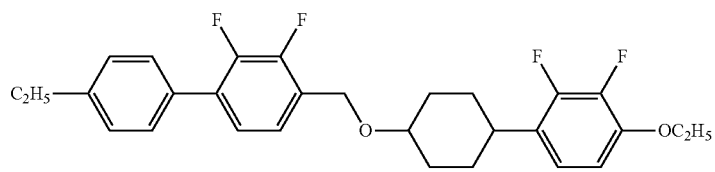 |
| 1392 | 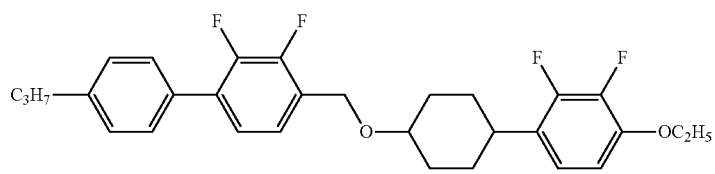 |
| 1393 | 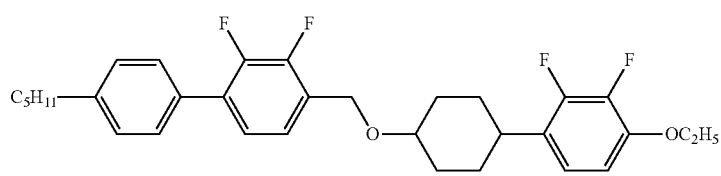 |
| 1394 | 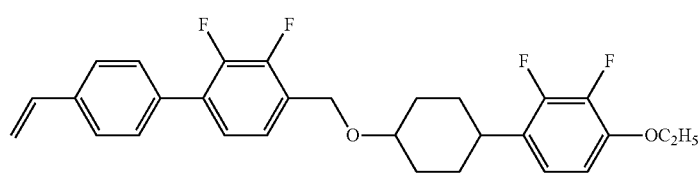 |
| 1395 | 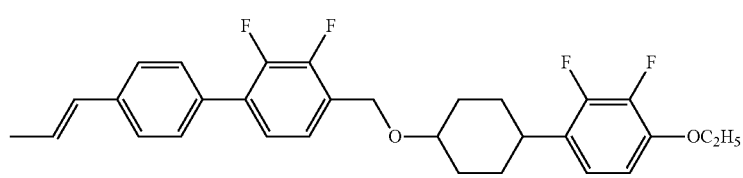 |
| 1396 | 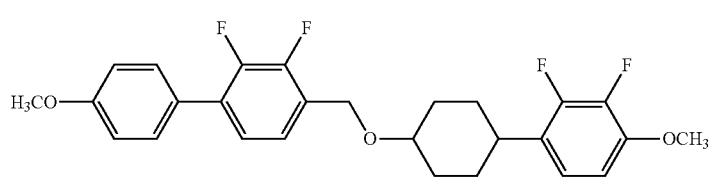 |
| 1397 | 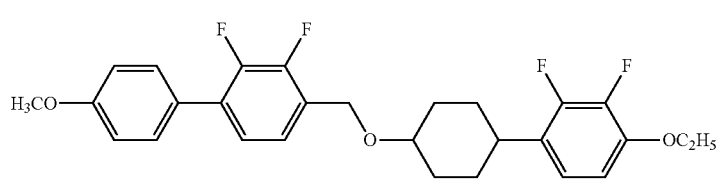 [SMILES: CCOc1ccc(C2CCC(OCc3ccc(-c4ccc(OC)cc4)c(F)c3F)CC2)c(F)c1F] |

| No. |
|---|
| 1398 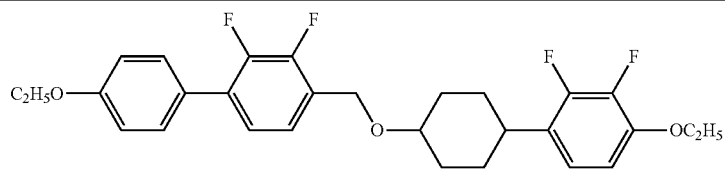 |
| 1399 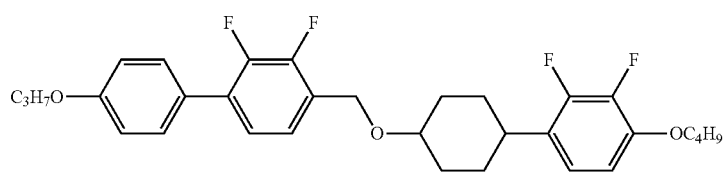 |
| 1400 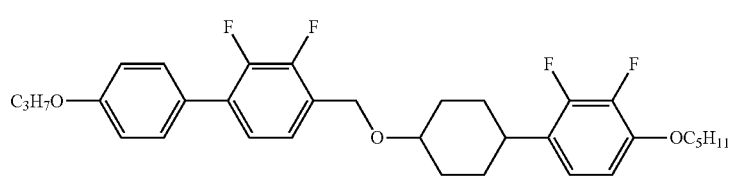 |
| 1401 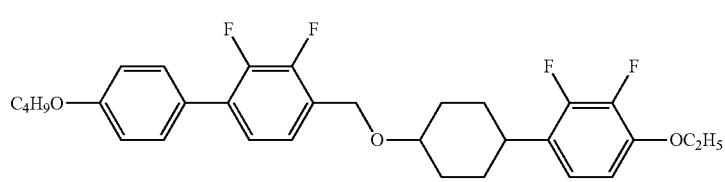 |
| 1402 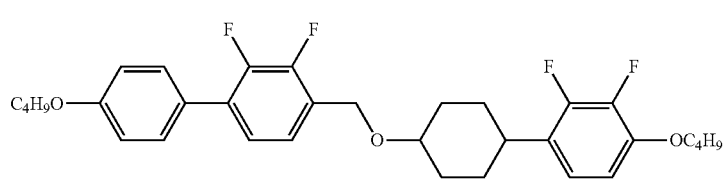 |
| 1403 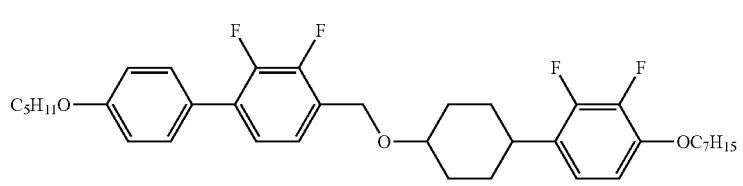 |
| 1404 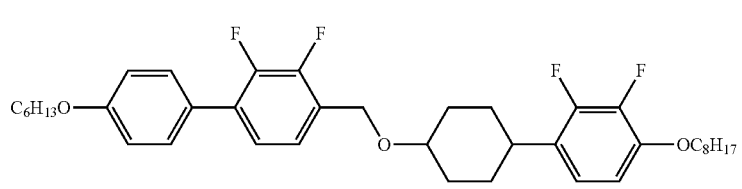 |
| 1405 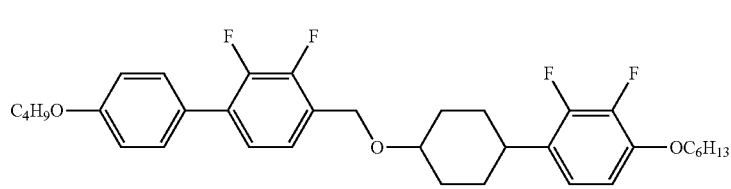 |
| 1406 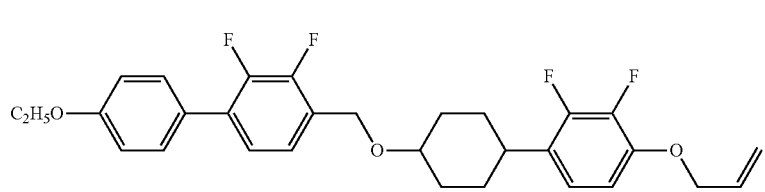 |

| No. |  |
|---|---|
| 1407 | 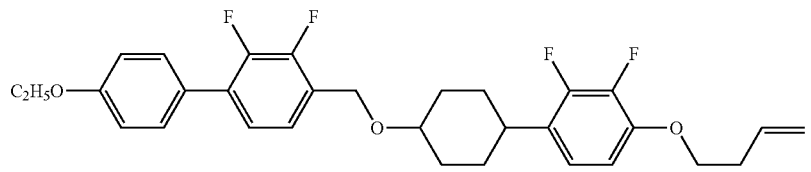 |
| 1408 | 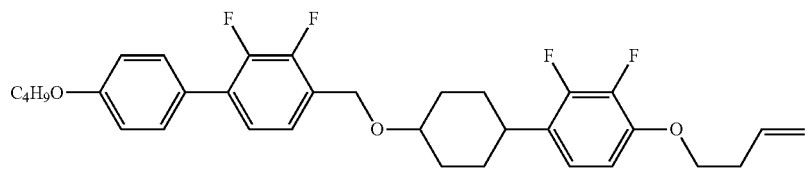 |
| 1409 | 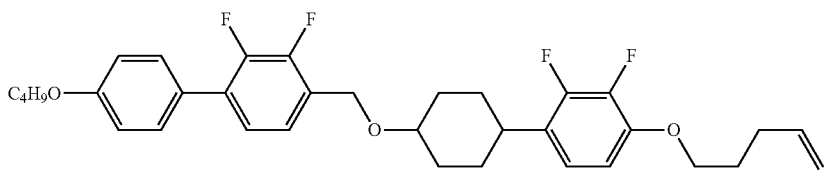 |
| 1410 | 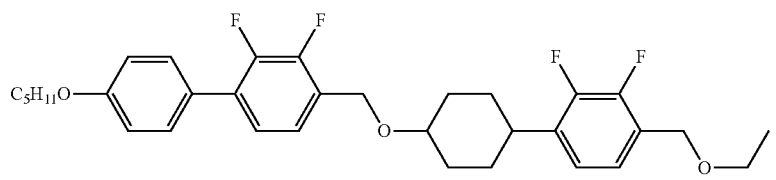 |
| 1411 | 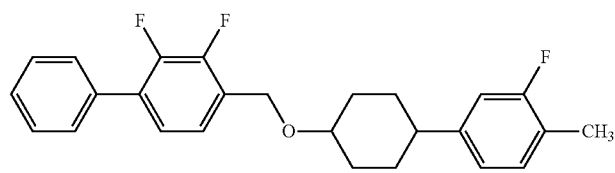 |
| 1412 | 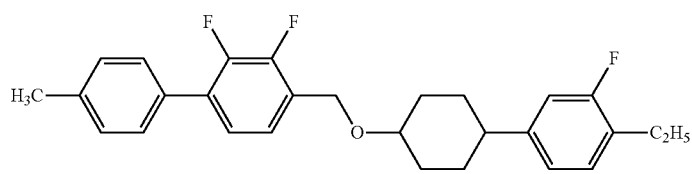 |
| 1413 | 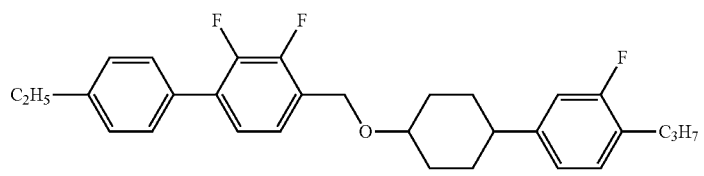 |
| 1414 | 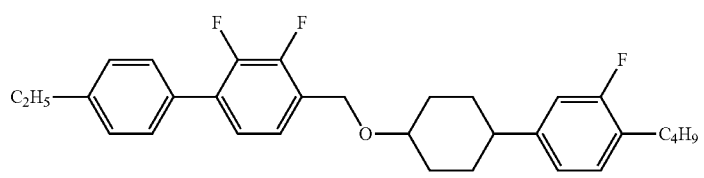 |

-continued
| No. | |
|---|---|
| 1415 | 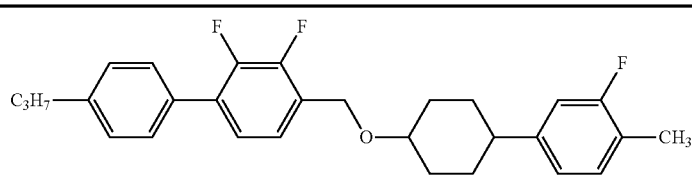 |
| 1416 | 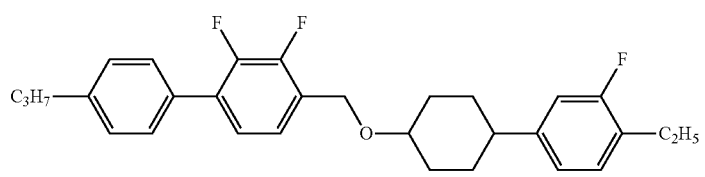 |
| 1417 | 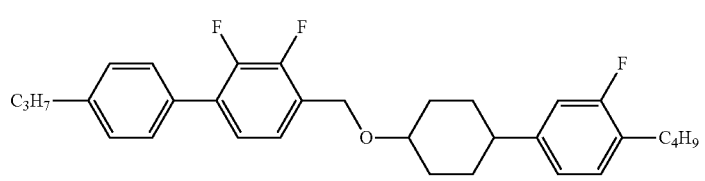 |
| 1418 | 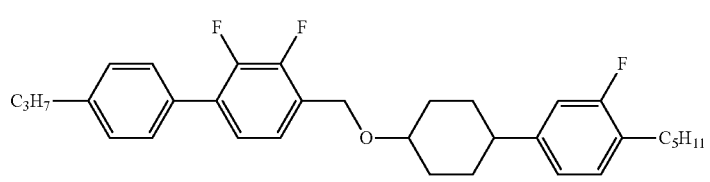 |
| 1419 | 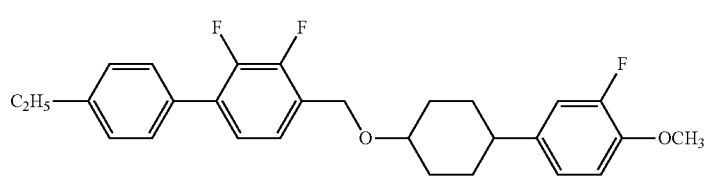 |
| 1420 | 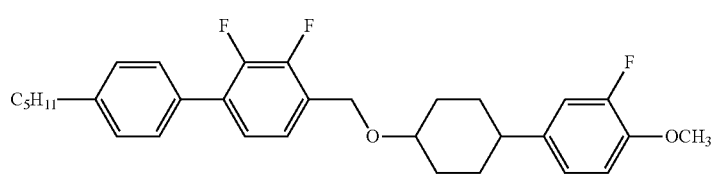 |
| 1421 | 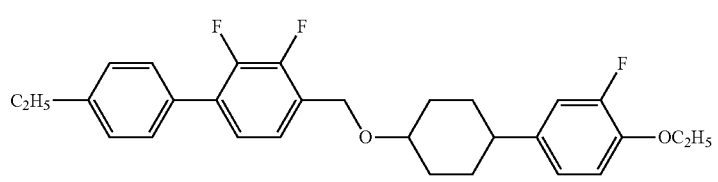 |
| 1422 | 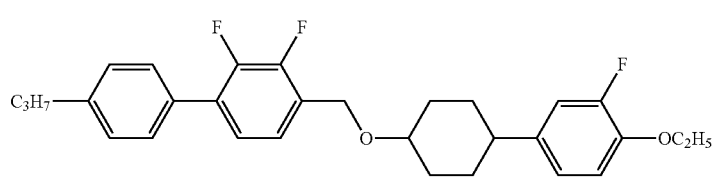 |
| 1423 | 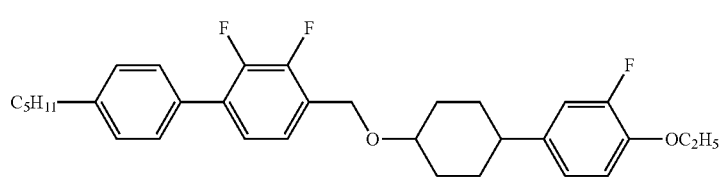 |

| No. | |
|---|---|
| 1424 | 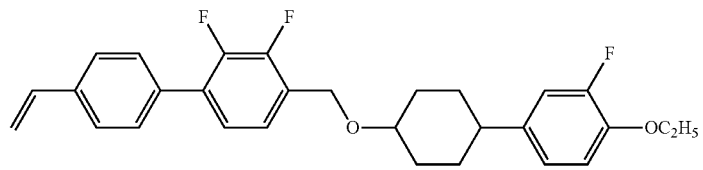 [SMILES: C=Cc1ccc(-c2ccc(COC3CCC(c4ccc(OCC)c(F)c4)CC3)c(F)c2F)cc1] |
| 1425 | 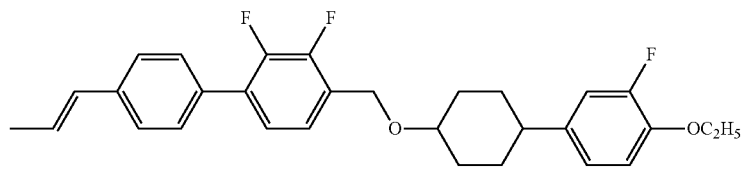 |
| 1426 | 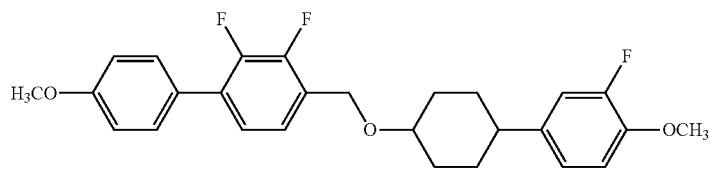 |
| 1427 | 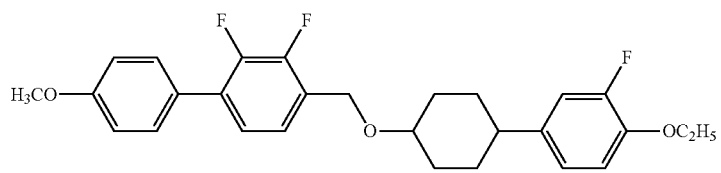 [SMILES: CCOc1ccc(C2CCC(OCc3ccc(-c4ccc(OC)cc4)c(F)c3F)CC2)cc1F] |
| 1428 | 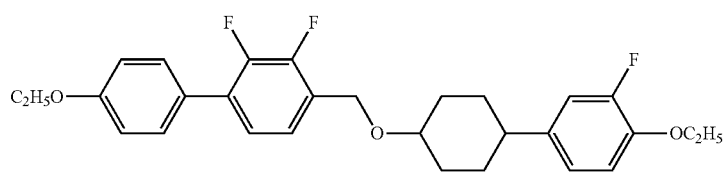 |
| 1429 | 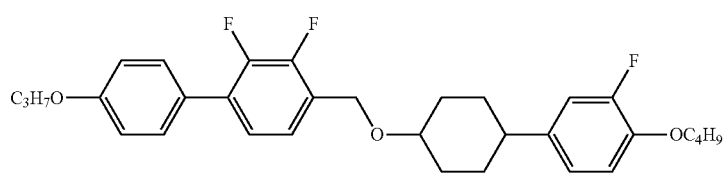 |
| 1430 | 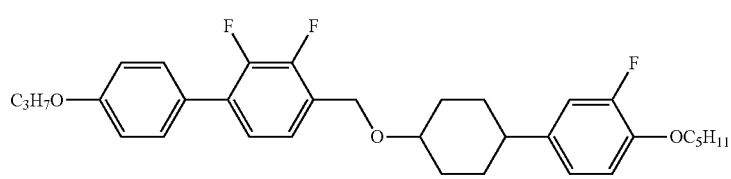 |
| 1431 | 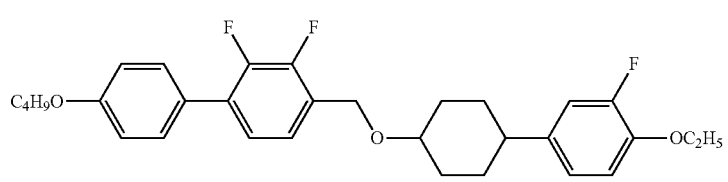 |

| No. | |
|---|---|
| 1432 | 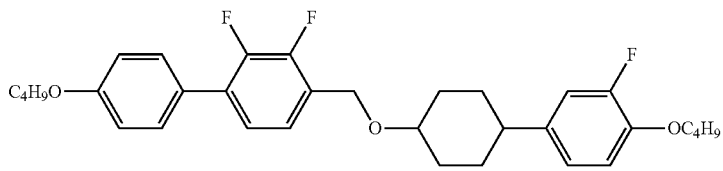 |
| 1433 | 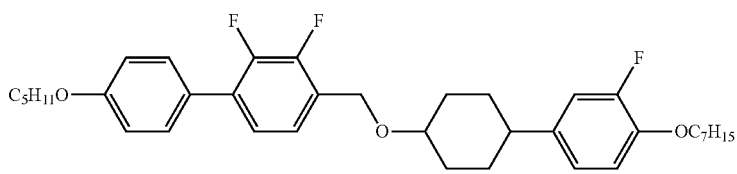 |
| 1434 | 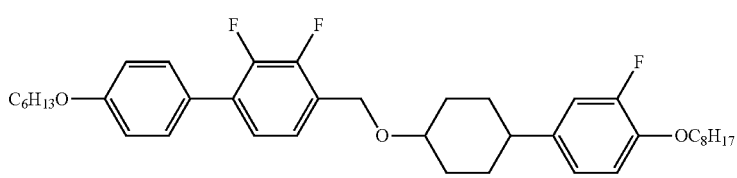 |
| 1435 | 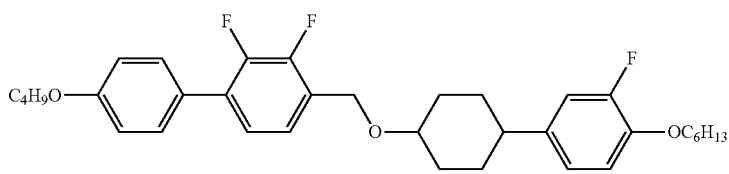 |
| 1436 | 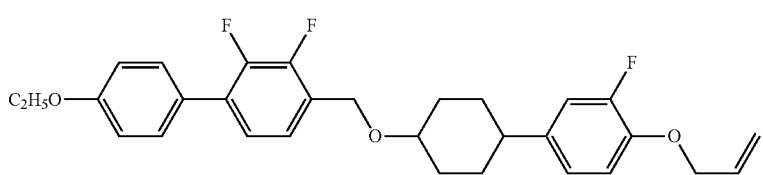 |
| 1437 | 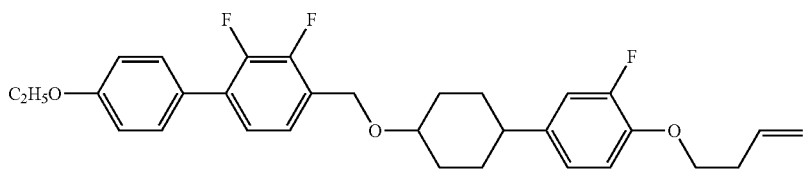 |
| 1438 | 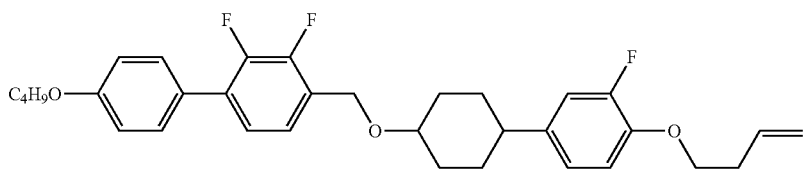 |
| 1439 | 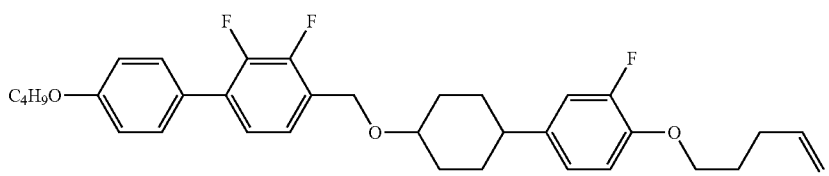 |
| 1440 | 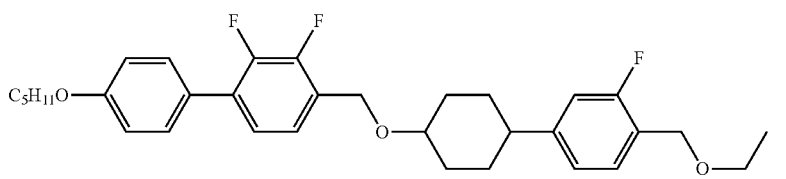 |

| No. | |
|---|---|
| 1441 | 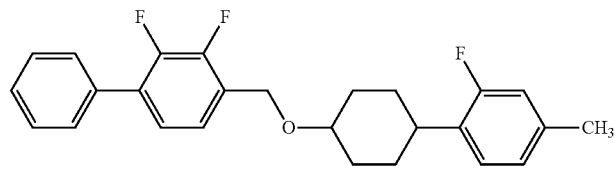 |
| 1442 | 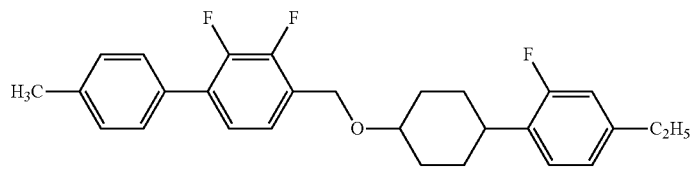 |
| 1443 | 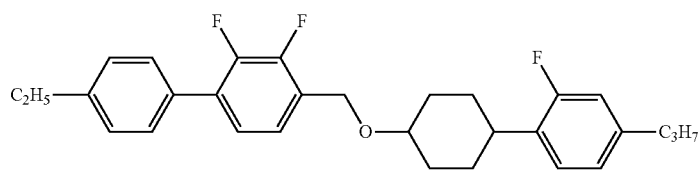 |
| 1444 | 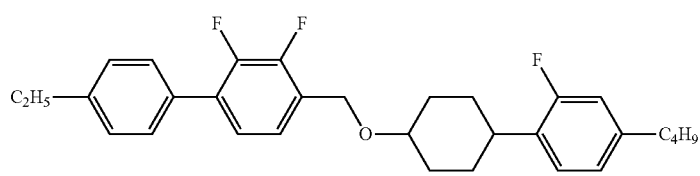 |
| 1445 | 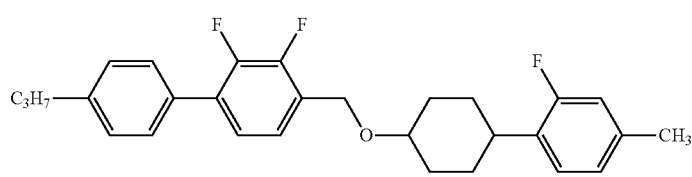 |
| 1446 | 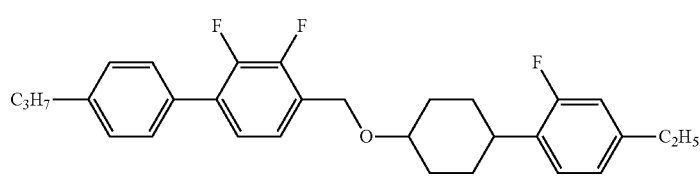 |
| 1447 | 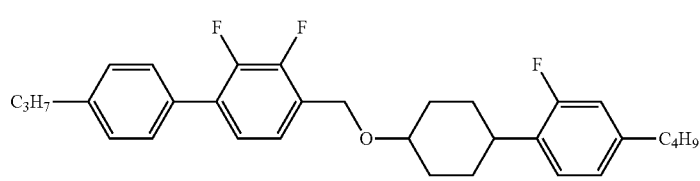 |
| 1448 | 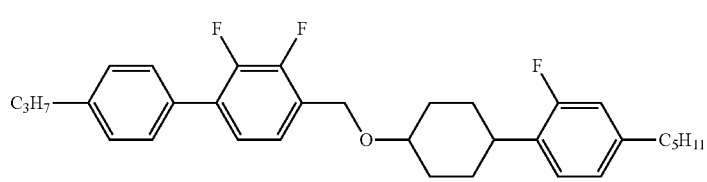 |

-continued
| No. | |
|---|---|
| 1449 | 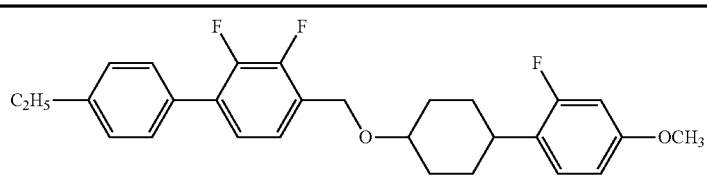 |
| 1450 | 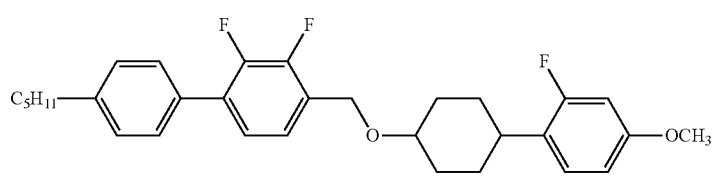 |
| 1451 | 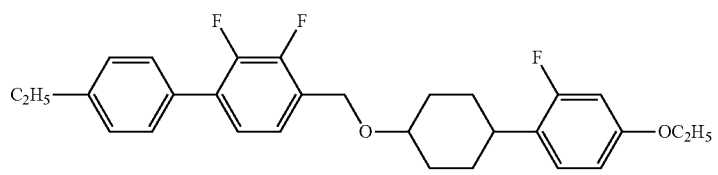 |
| 1452 | 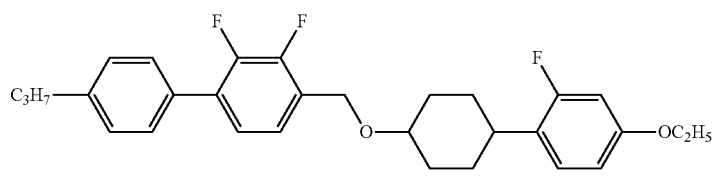 |
| 1453 | 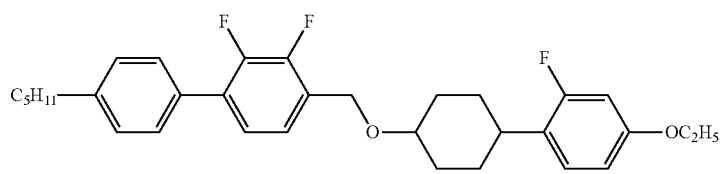 |
| 1454 | 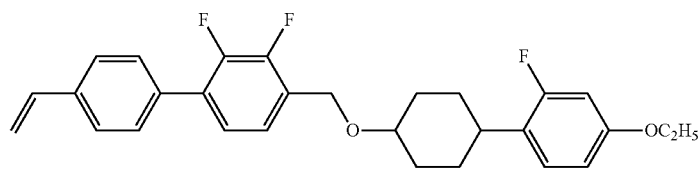 |
| 1455 | 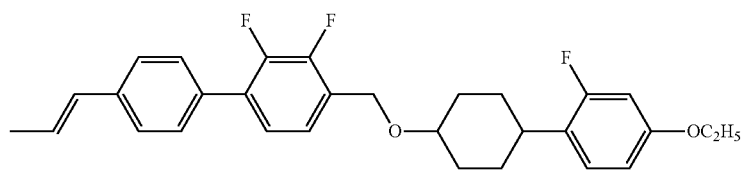 |
| 1456 | 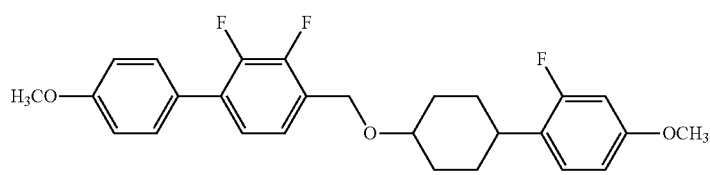 [SMILES: COc1ccc(-c2ccc(COC3CCC(c4ccc(OC)cc4F)CC3)c(F)c2F)cc1] |
| 1457 | 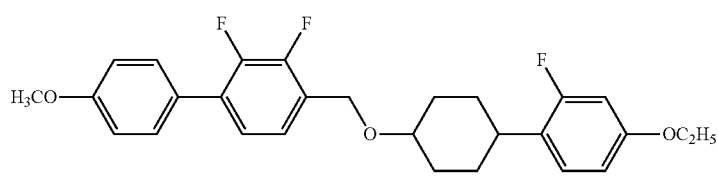 [SMILES: CCOc1ccc(C2CCC(OCc3ccc(-c4ccc(OC)cc4)c(F)c3F)CC2)c(F)c1] |

-continued
| No. | |
|---|---|
| 1458 | 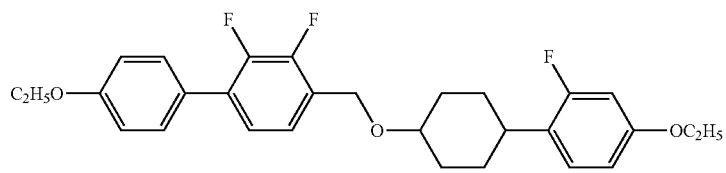 |
| 1459 | 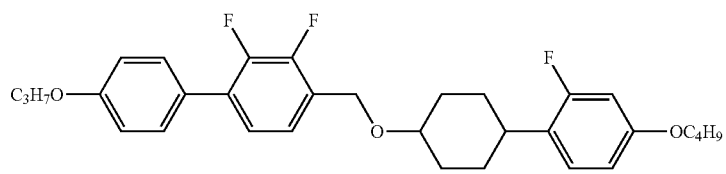 |
| 1460 | 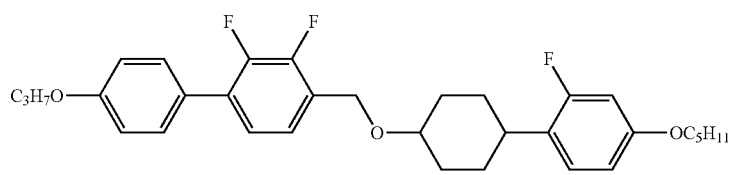 |
| 1461 | 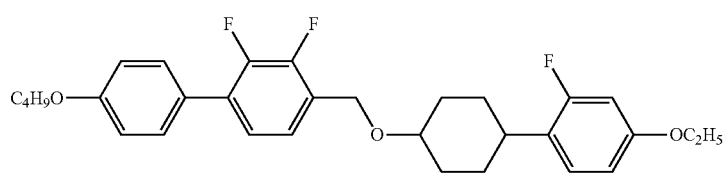 |
| 1462 | 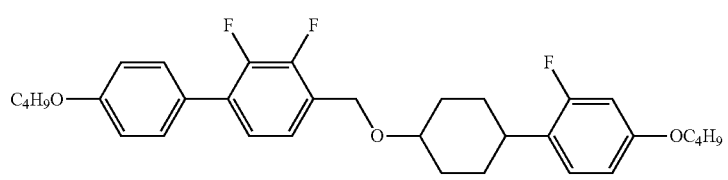 |
| 1463 | 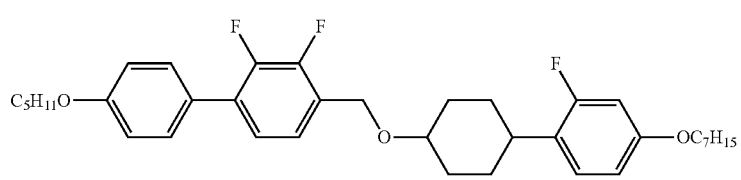 |
| 1464 | 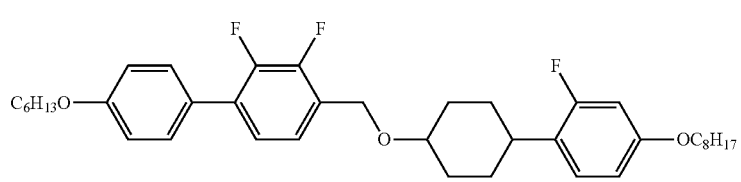 |
| 1465 | 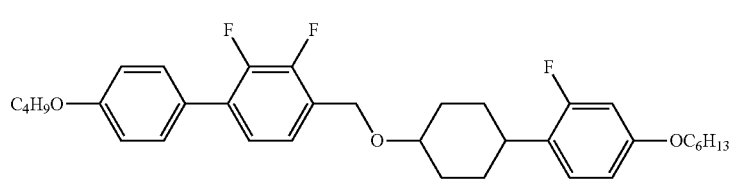 |

| No. | |
|---|---|
| 1466 | 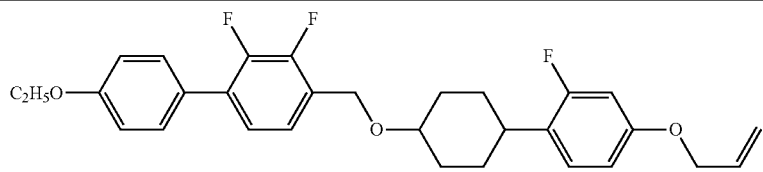 |
| 1467 | 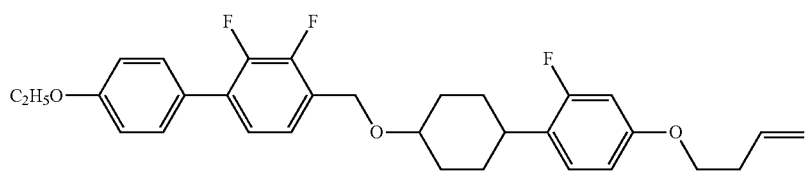 |
| 1468 | 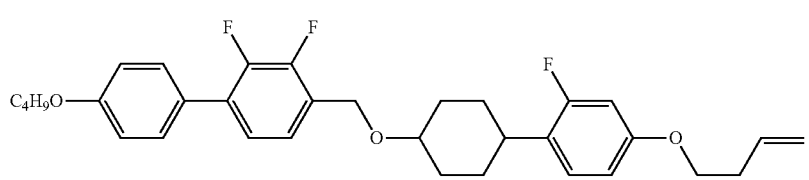 |
| 1469 | 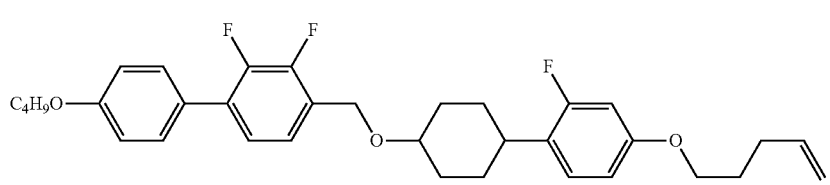 |
| 1470 | 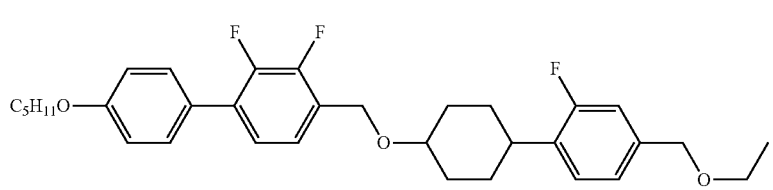 |
| 1471 | 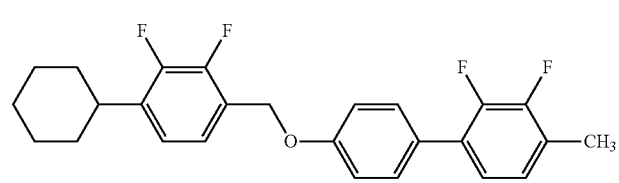 |
| 1472 | 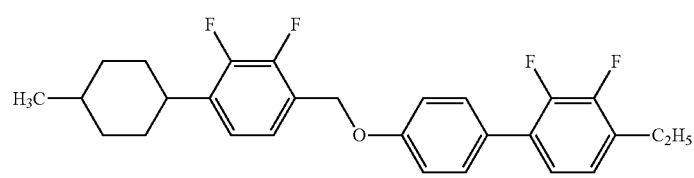 |
| 1473 | 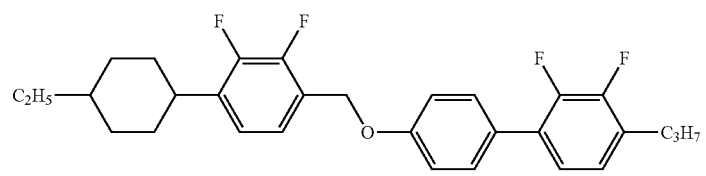 |
| 1474 | 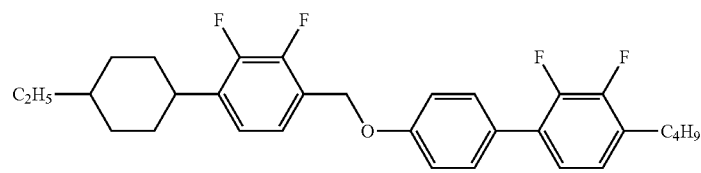 |

| No. | |
|---|---|
| 1475 | 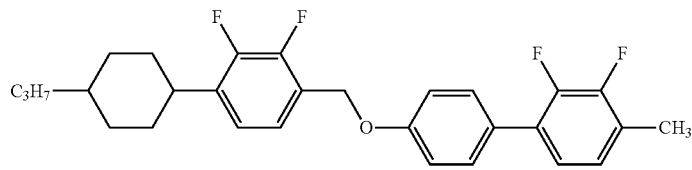 |
| 1476 | 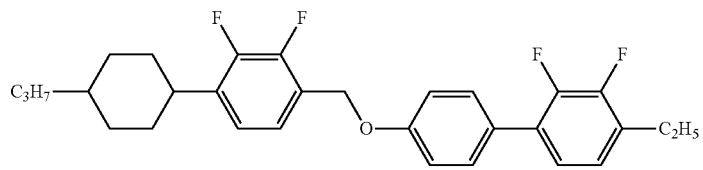 |
| 1477 | 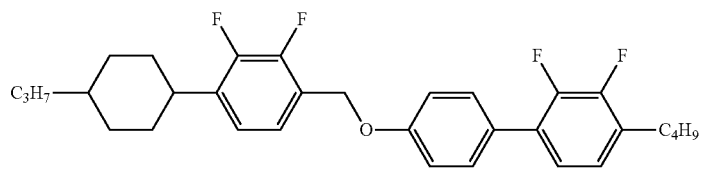 |
| 1478 | 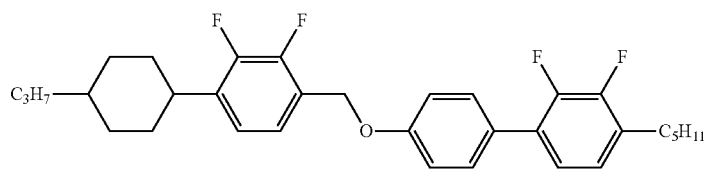 |
| 1479 | 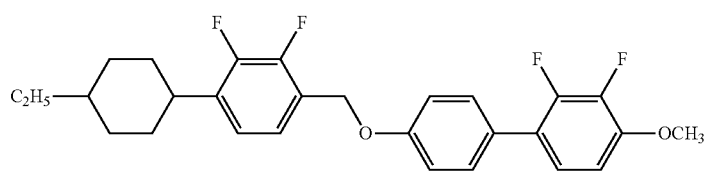 |
| 1480 | 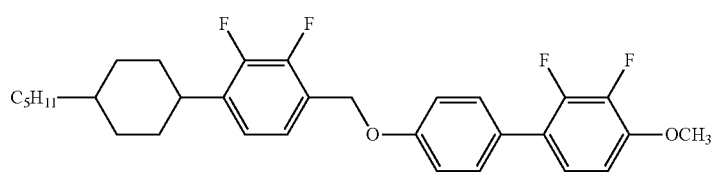 |
| 1481 | 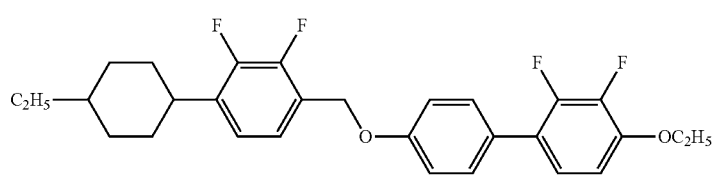 |
| 1482 | 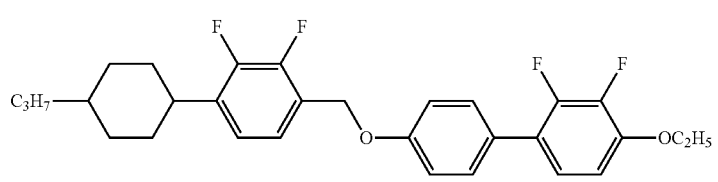 |

| No. | |
|---|---|
| 1483 | 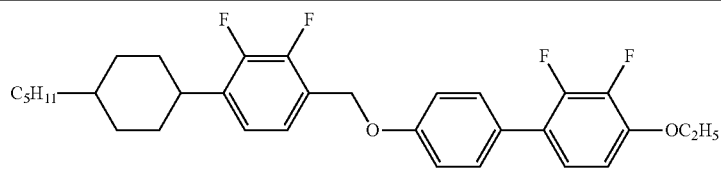 |
| 1484 | 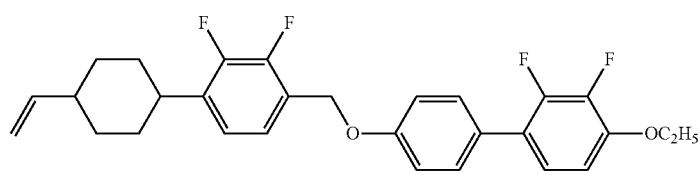 |
| 1485 | 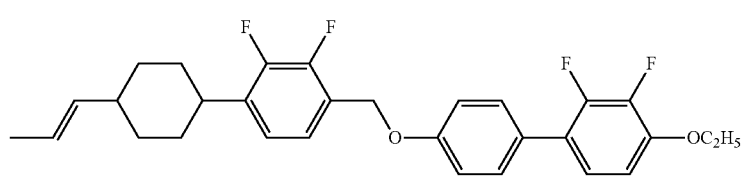 |
| 1486 | 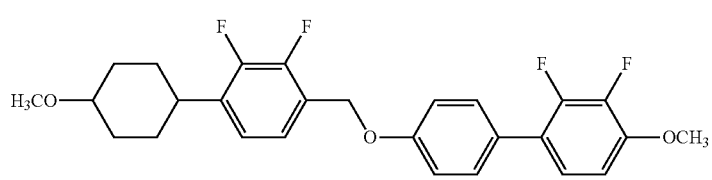 [SMILES: COc1ccc(-c2ccc(OCc3ccc(C4CCC(OC)CC4)c(F)c3F)cc2)c(F)c1F] |
| 1487 | 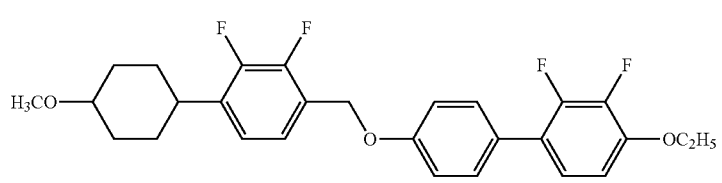 |
| 1488 | 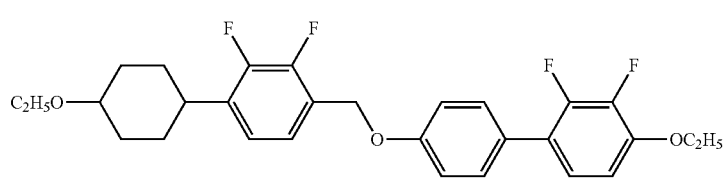 |
| 1489 | 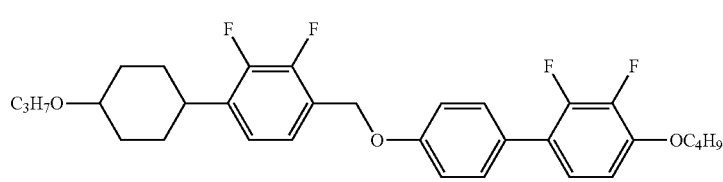 |
| 1490 | 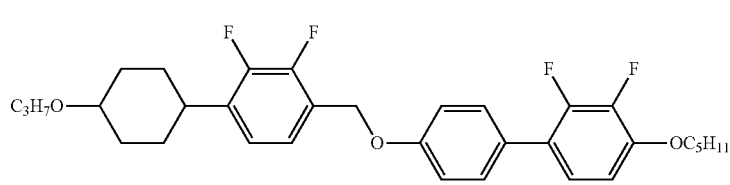 |
| 1491 | 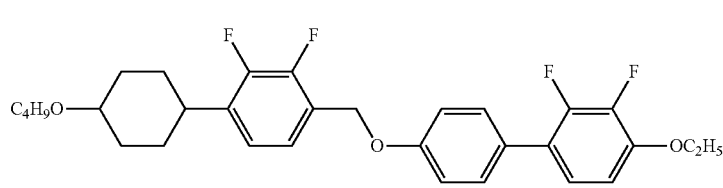 |

| No. | |
|---|---|
| 1492 | 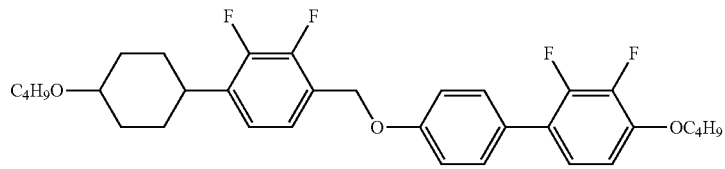 |
| 1493 | 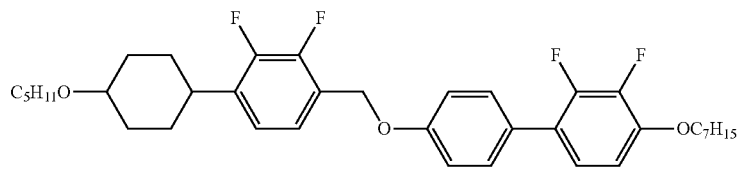 |
| 1494 | 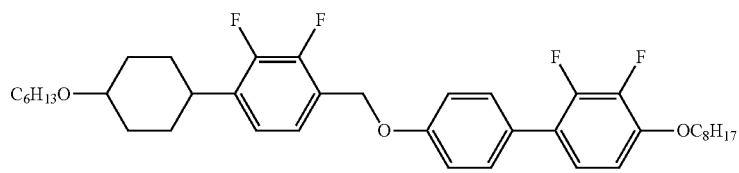 |
| 1495 | 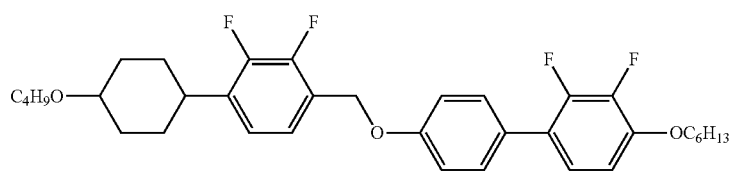 |
| 1496 | 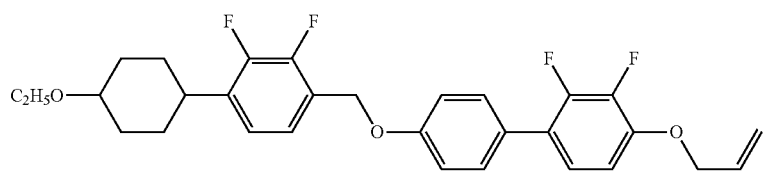 |
| 1497 | 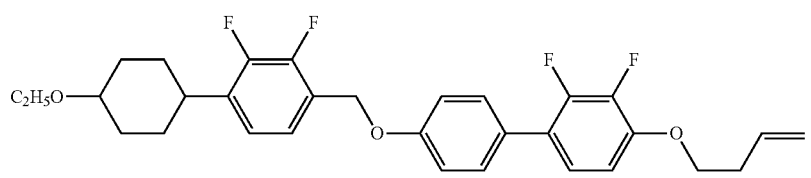 |
| 1498 | 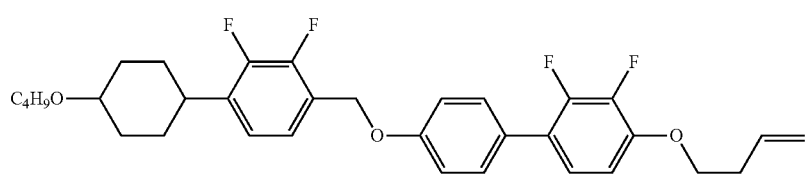 |
| 1499 | 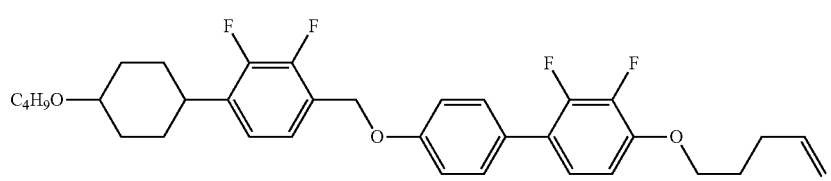 |

-continued
| No. | |
|---|---|
| 1500 | 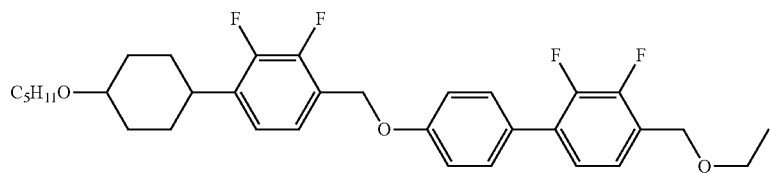 |
| 1501 | 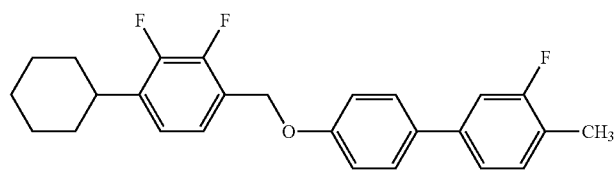 |
| 1502 | 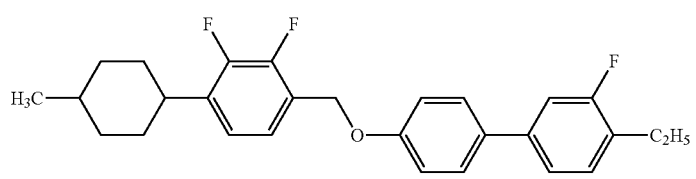 |
| 1503 | 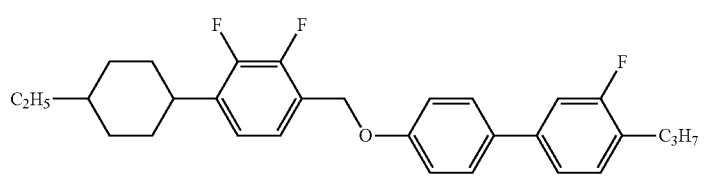 |
| 1504 | 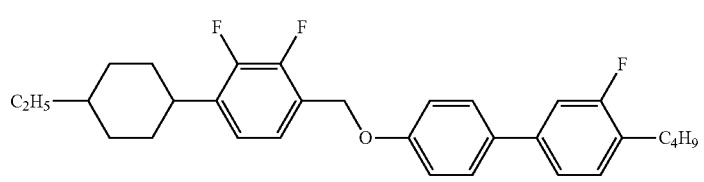 |
| 1505 | 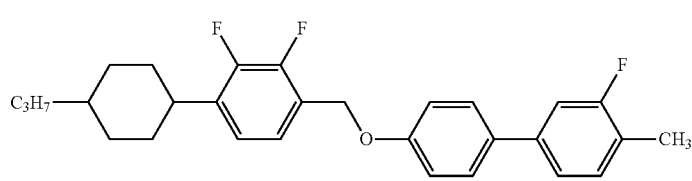 |
| 1506 | 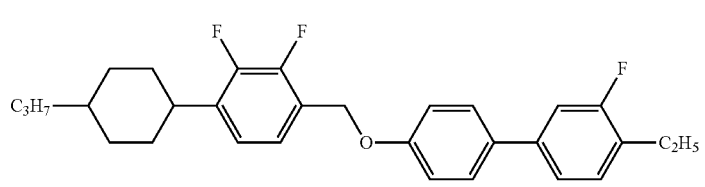 |
| 1507 | 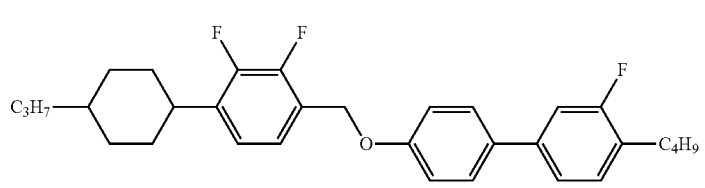 |

| No. |
|---|
| 1508 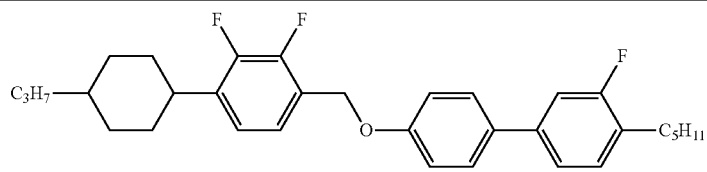 |
| 1509 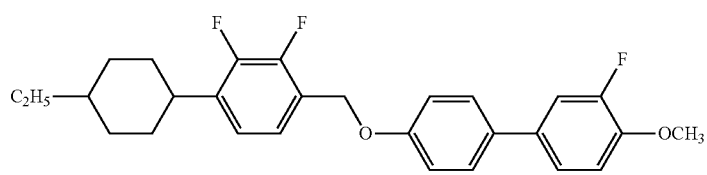 |
| 1510 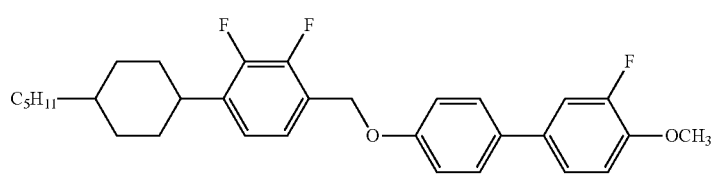 |
| 1511 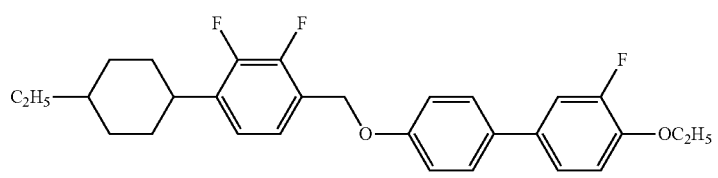 |
| 1512 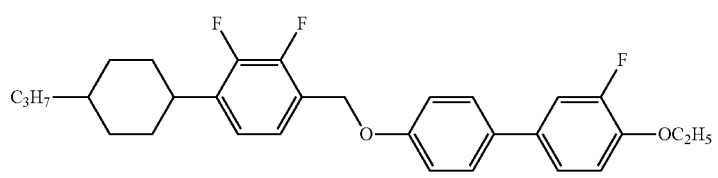 |
| 1513 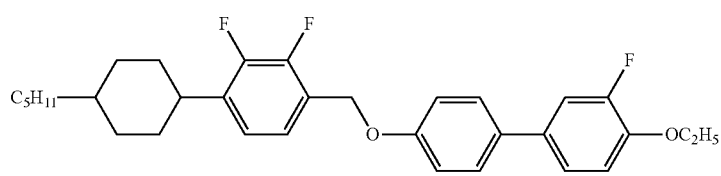 |
| 1514 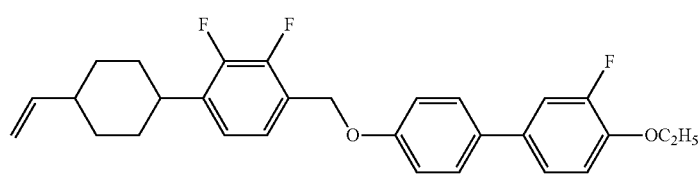 [SMILES: C=CC1CCC(c2ccc(COc3ccc(-c4ccc(OCC)c(F)c4)cc3)c(F)c2F)CC1] |
| 1515 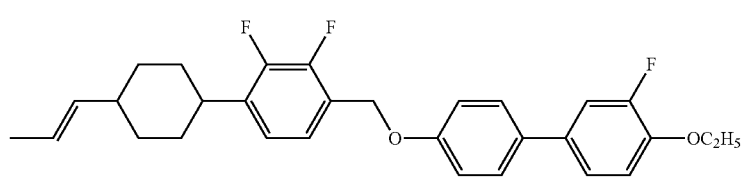 |
| 1516 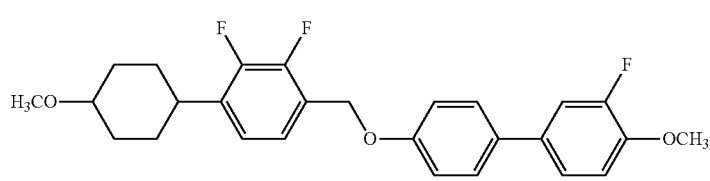 |

| No. | |
|---|---|
| 1517 | 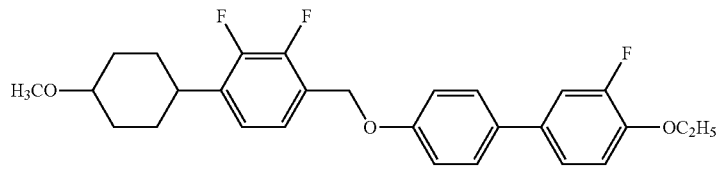 |
| 1518 | 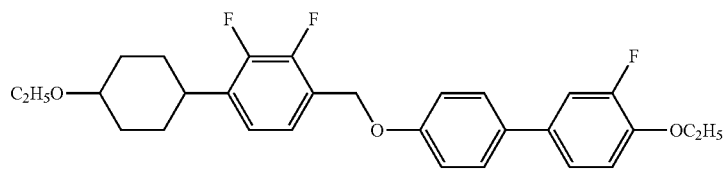 |
| 1519 | 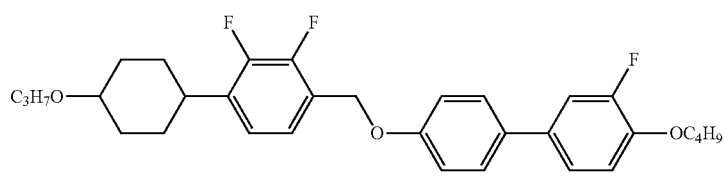 |
| 1520 | 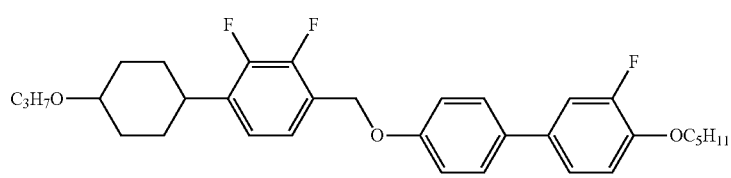 |
| 1521 | 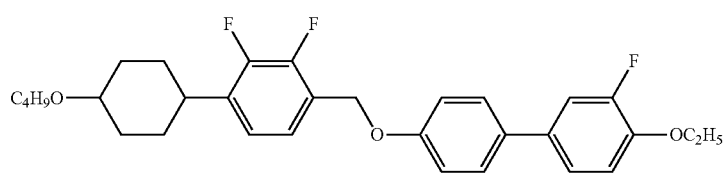 |
| 1522 | 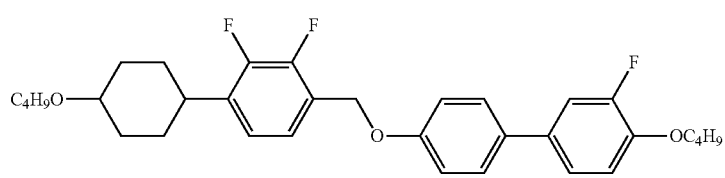 |
| 1523 | 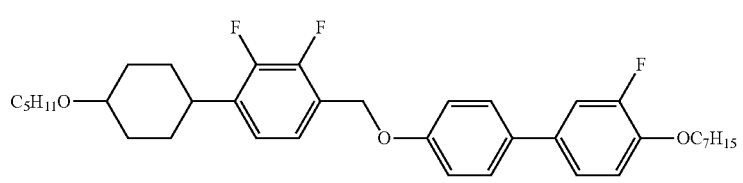 |
| 1524 | 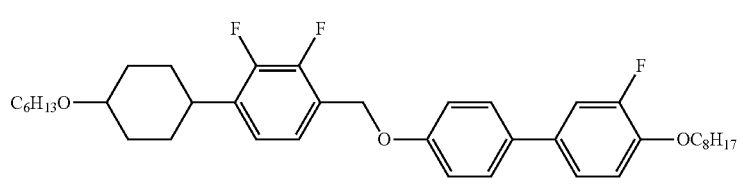 |

| No. | |
|---|---|
| 1525 | 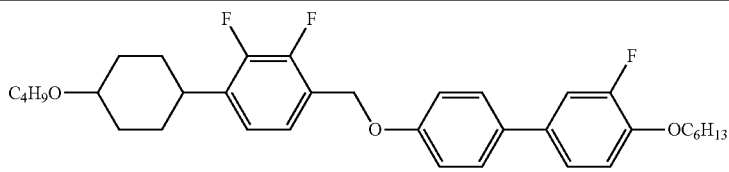 |
| 1526 | 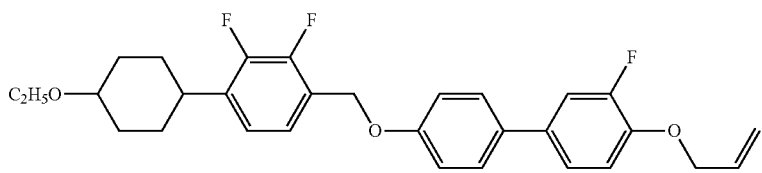 |
| 1527 | 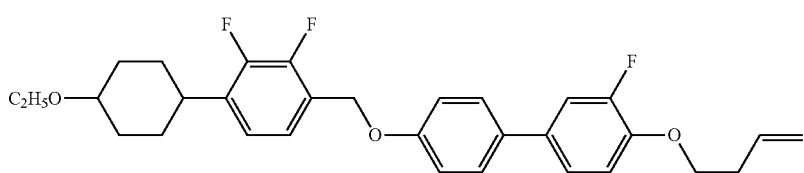 |
| 1528 | 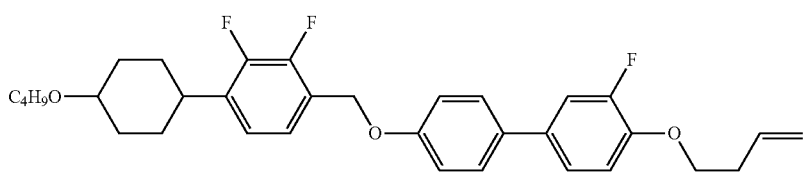 |
| 1529 | 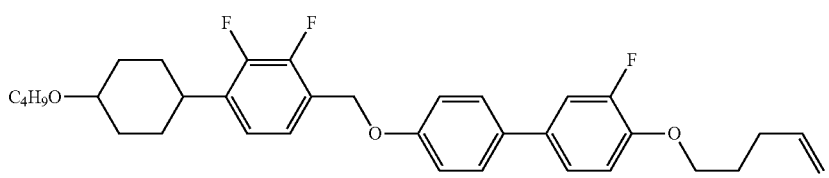 |
| 1530 | 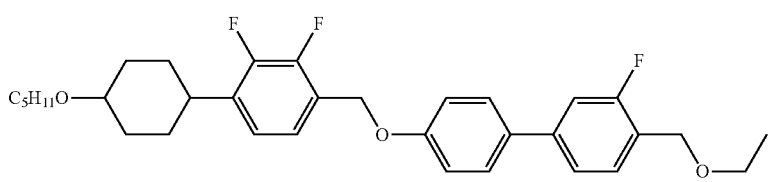 |
| 1531 | 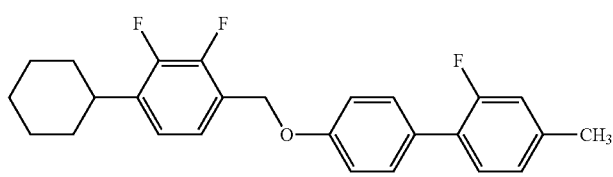 |
| 1532 | 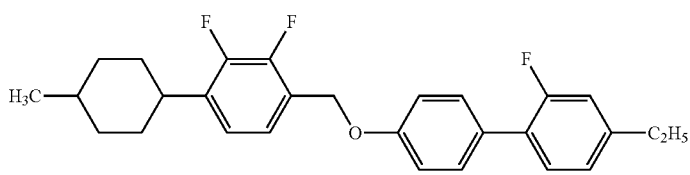 [SMILES: CCc1ccc(-c2ccc(OCc3ccc(C4CCC(C)CC4)c(F)c3F)cc2)c(F)c1] |
| 1533 | 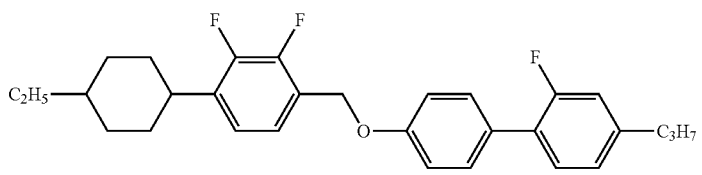 |

| No. | |
|---|---|
| 1534 | 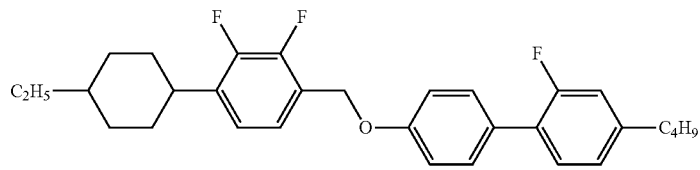 |
| 1535 | 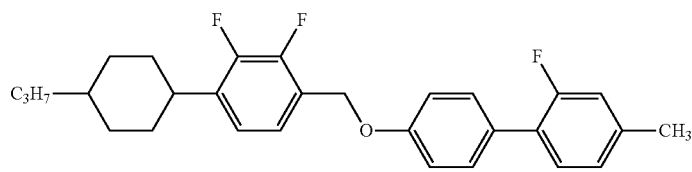 |
| 1536 | 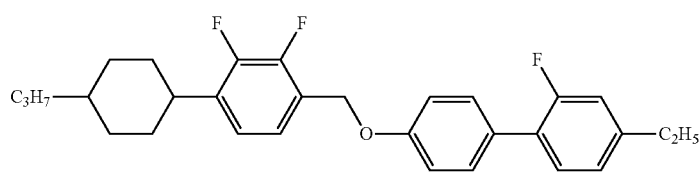 |
| 1537 | 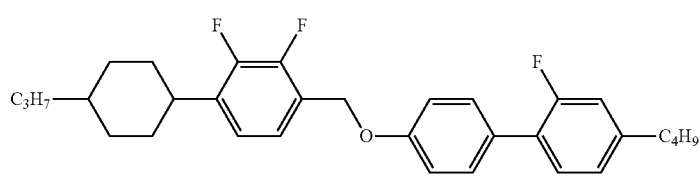 |
| 1538 | 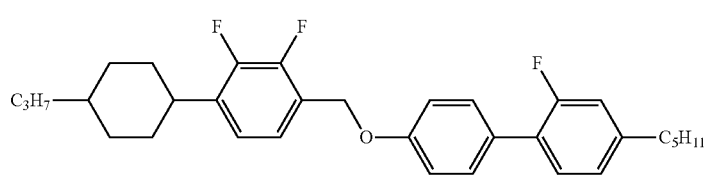 |
| 1539 | 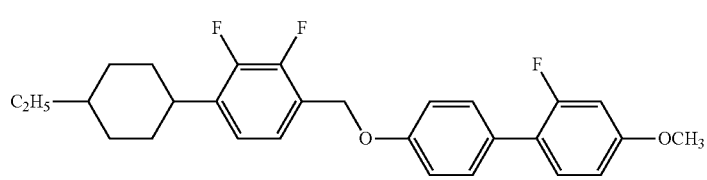 |
| 1540 | 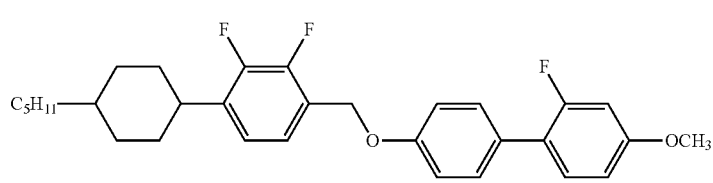 |
| 1541 | 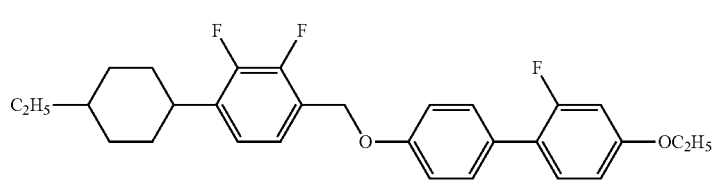 |

| No. | |
|---|---|
| 1542 | 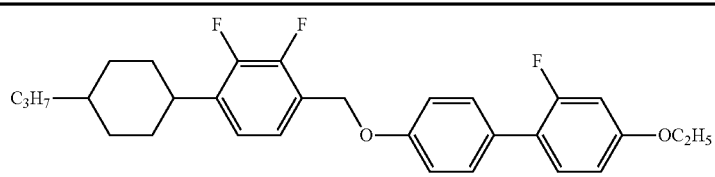 |
| 1543 | 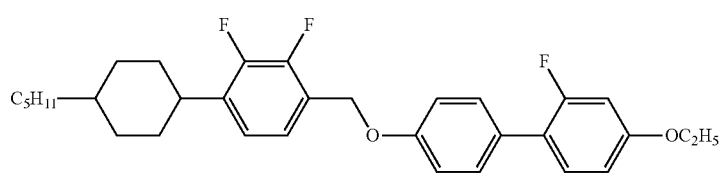 |
| 1544 | 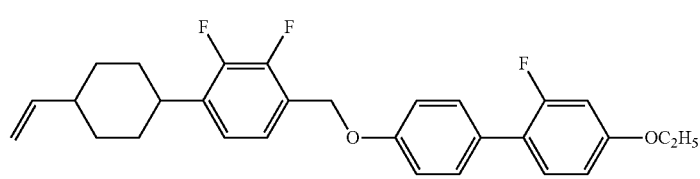 |
| 1545 | 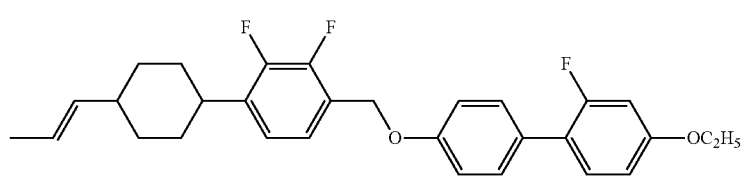 |
| 1546 | 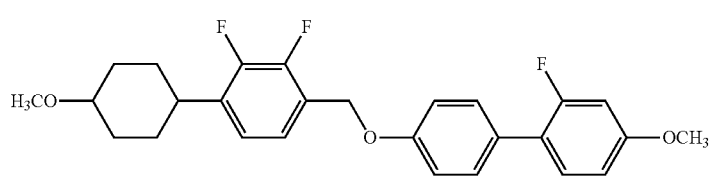 |
| 1547 | 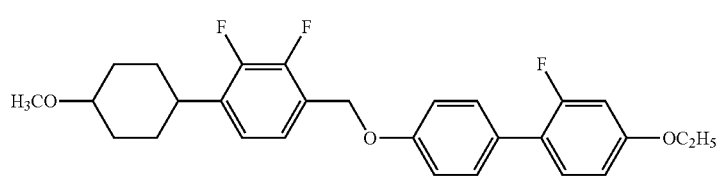 |
| 1548 | 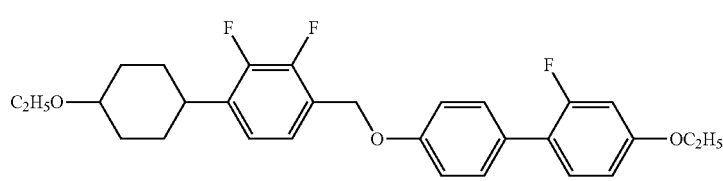 |
| 1549 | 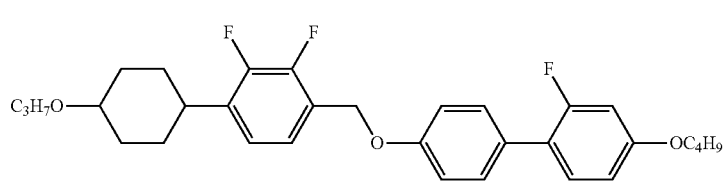 |
| 1550 | 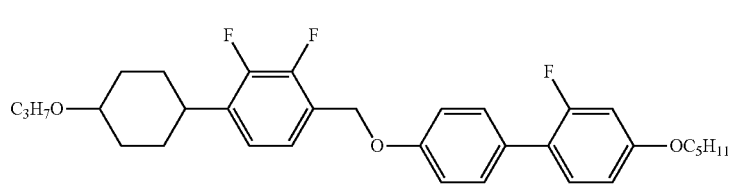 |

| No. | |
|---|---|
| 1551 | 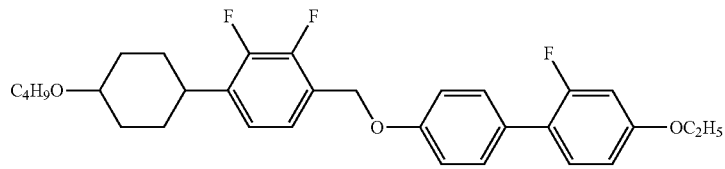 |
| 1552 | 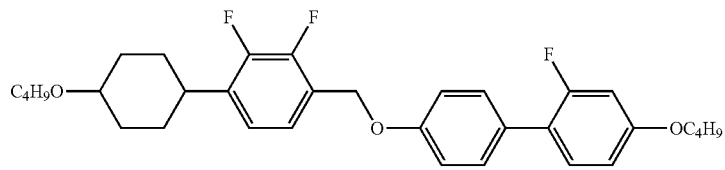 |
| 1553 | 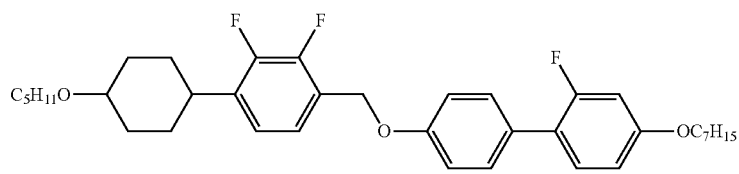 |
| 1554 | 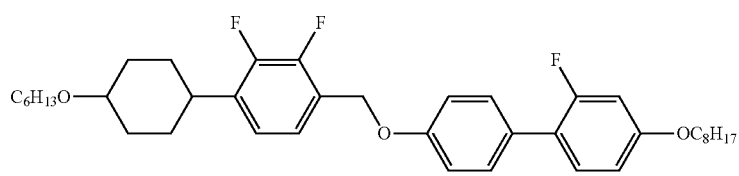 |
| 1555 | 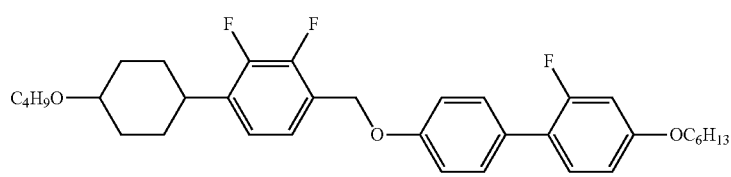 |
| 1556 | 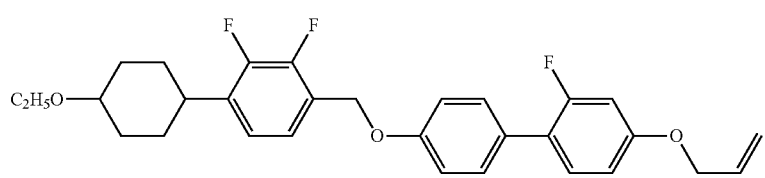 |
| 1557 | 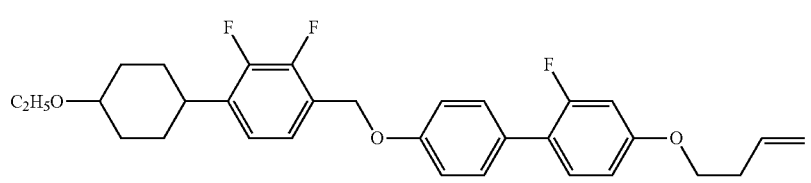 |
| 1558 | 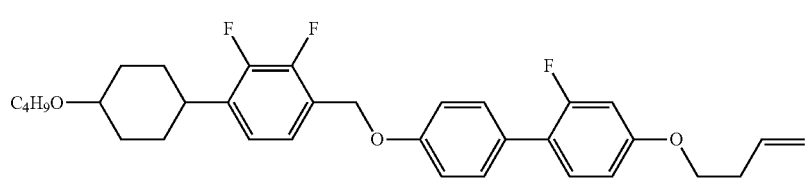 |

-continued
| No. | |
|---|---|
| 1559 | 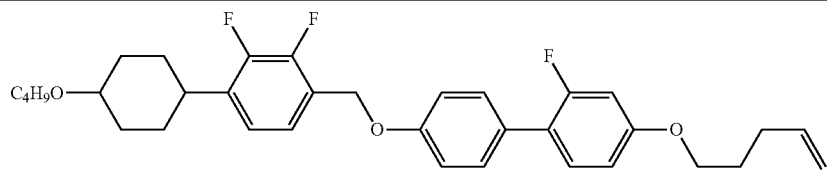 |
| 1560 | 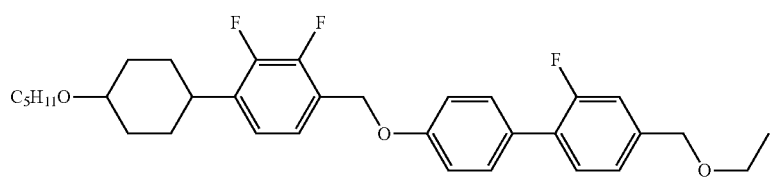 |
| 1561 | 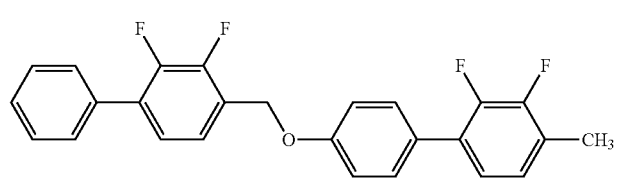 |
| 1662 | 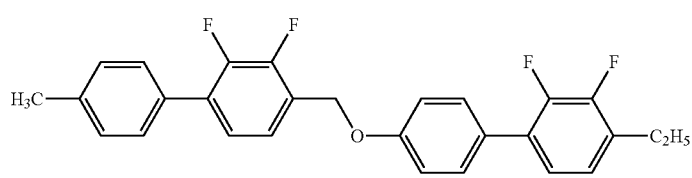 [SMILES: CCc1ccc(-c2ccc(OCc3ccc(-c4ccc(C)cc4)c(F)c3F)cc2)c(F)c1F] |
| 1563 | 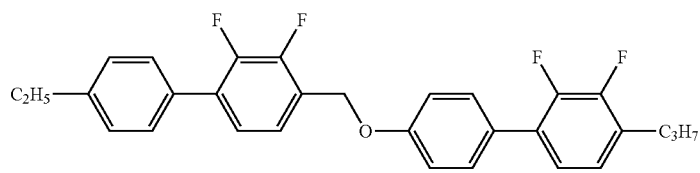 |
| 1564 | 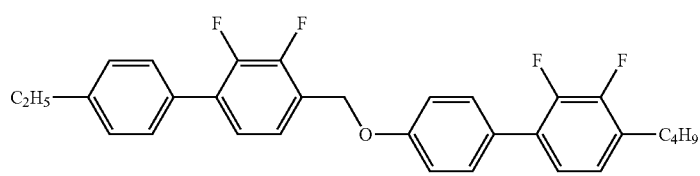 |
| 1565 | 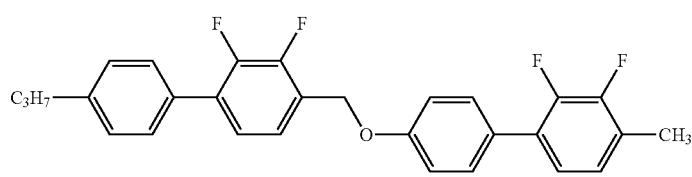 |
| 1566 | 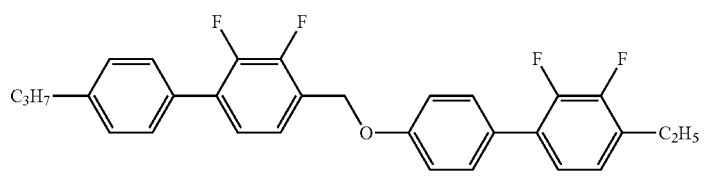 |
| 1567 | 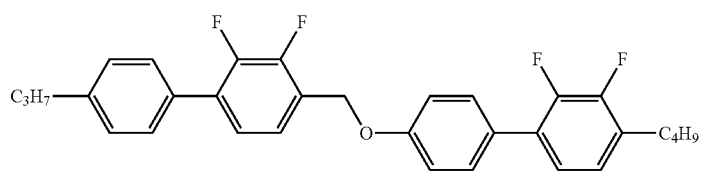 |

| No. | |
|---|---|
| 1568 | 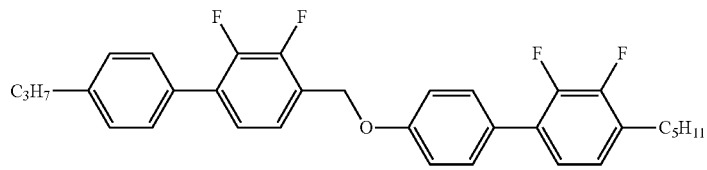 |
| 1569 | 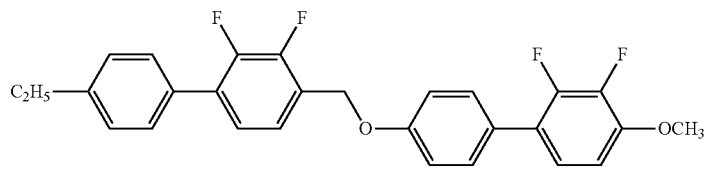 |
| 1570 | 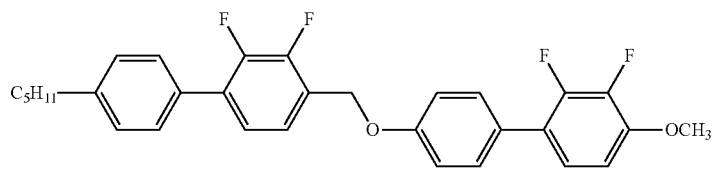 |
| 1571 | 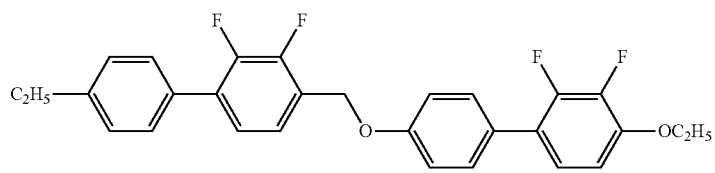 |
| 1572 | 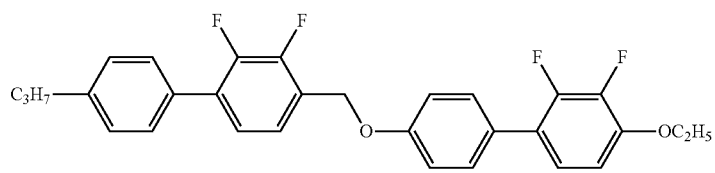 |
| 1573 | 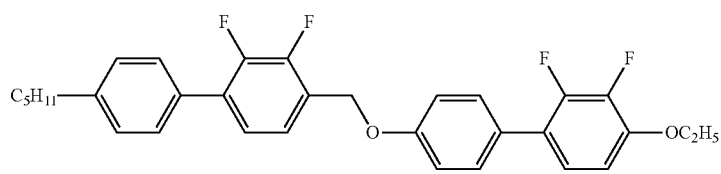 |
| 1574 | 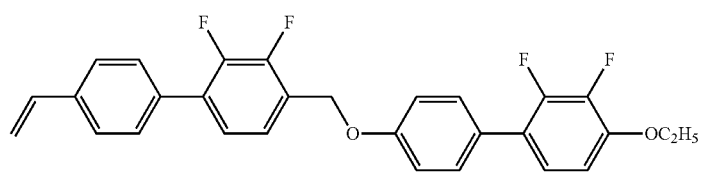 |
| 1575 | 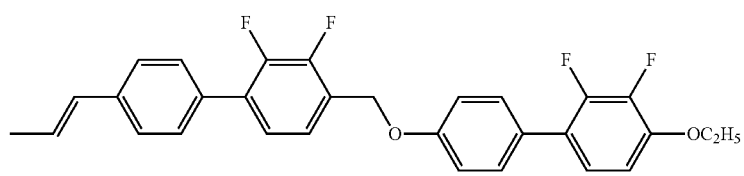 [SMILES: C/C=C/c1ccc(-c2ccc(COc3ccc(-c4ccc(OCC)c(F)c4F)cc3)c(F)c2F)cc1] |

-continued
| No. |
|---|
| 1576 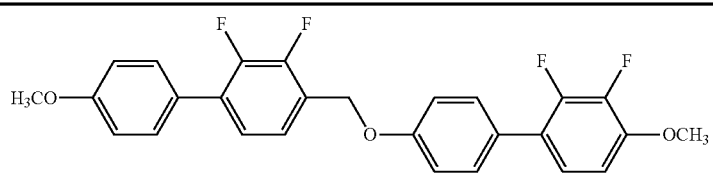 |
| 1577 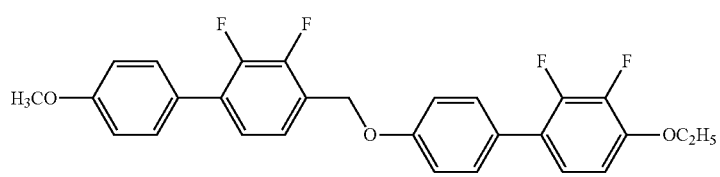 |
| 1578 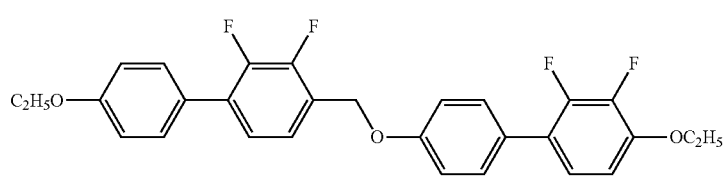 |
| 1579 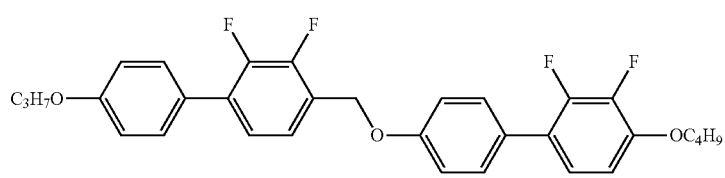 |
| 1580 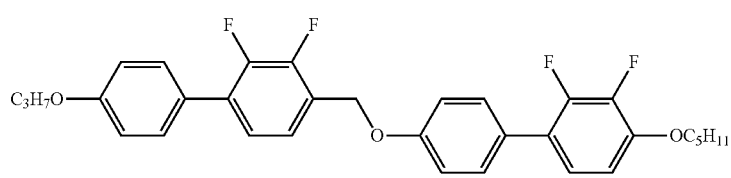 |
| 1581 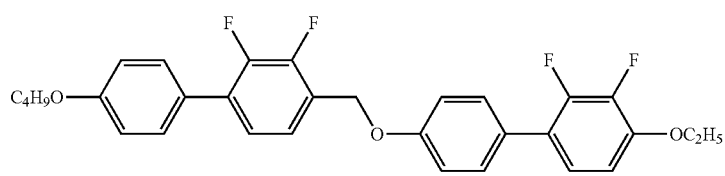 |
| 1582 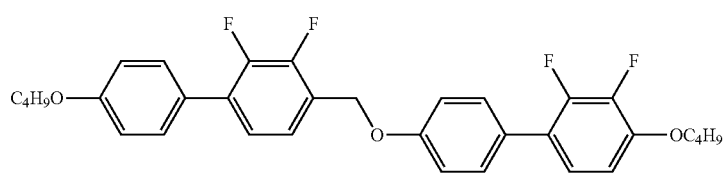 |
| 1583 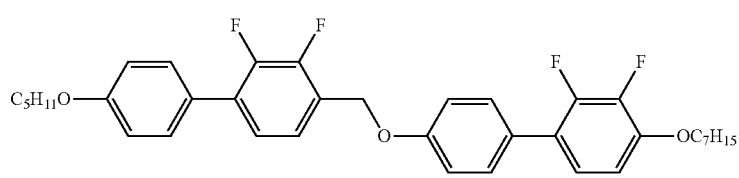 |
| 1584 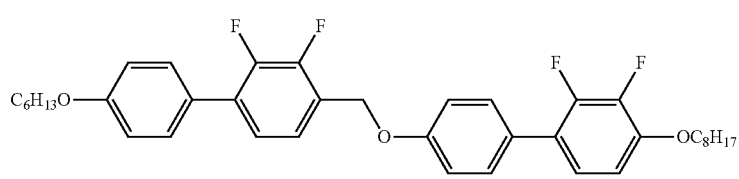 |

-continued
| No. |
|---|
1585 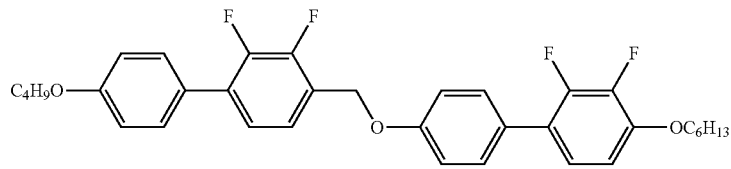
1586 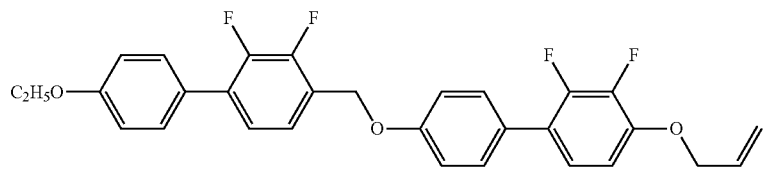
1587 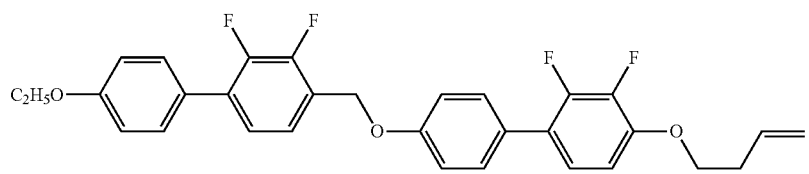
1588 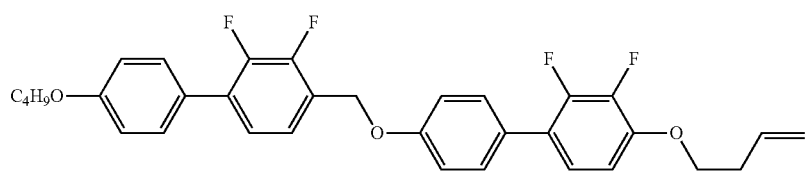
1589 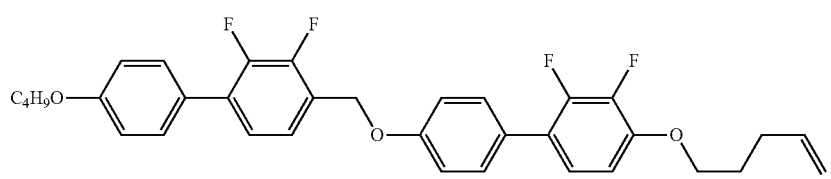
1590 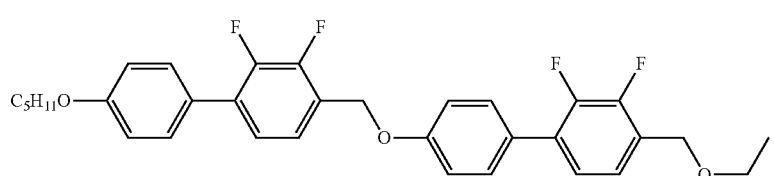
1591 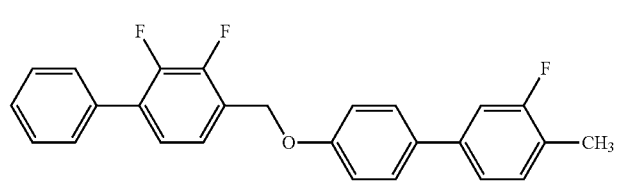
1592 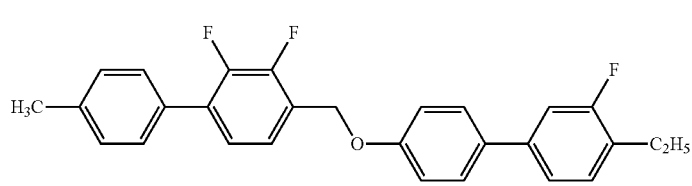 [SMILES: CCc1ccc(-c2ccc(OCc3ccc(-c4ccc(C)cc4)c(F)c3F)cc2)cc1F]

| No. | |
|---|---|
| 1593 | 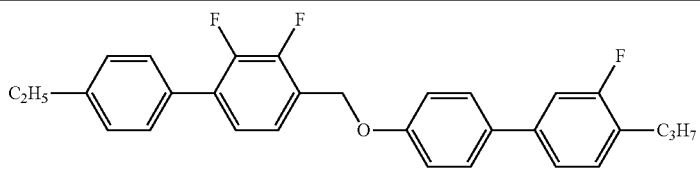 |
| 1594 | 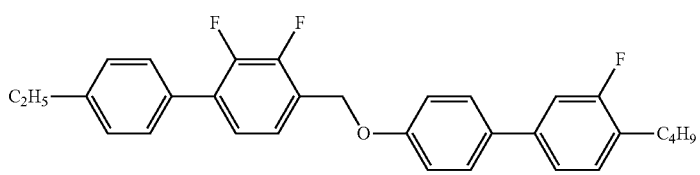 |
| 1595 | 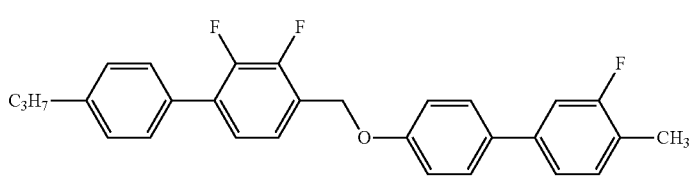 |
| 1596 | 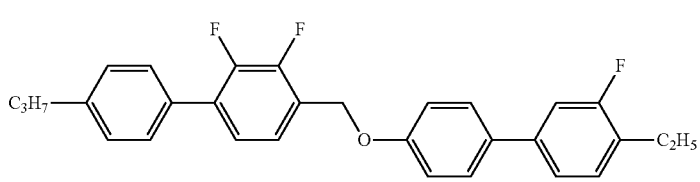 |
| 1597 | 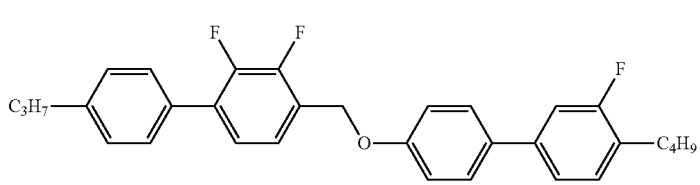 |
| 1598 | 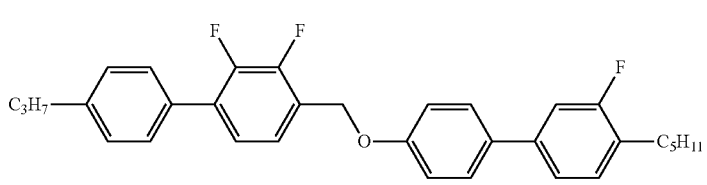 |
| 1599 | 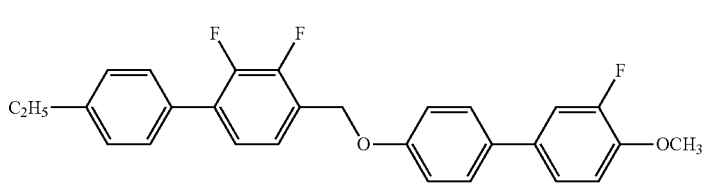 |
| 1600 | 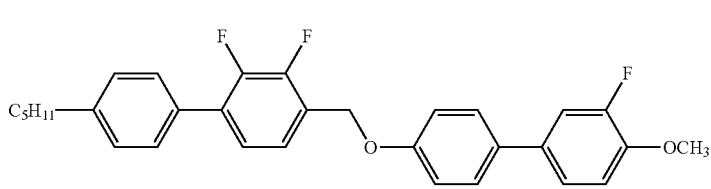 [SMILES: COc1ccc(-c2ccc(COc3ccc(-c4ccc(OC)c(F)c4)cc3)c(F)c2F)cc1] |
| 1601 | 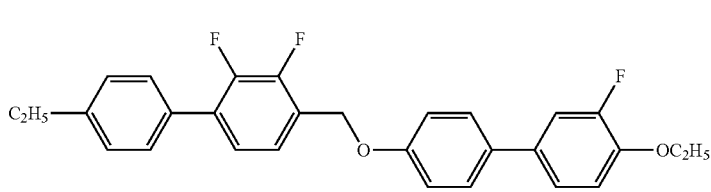 |

-continued
| No. |
|---|
| 1602 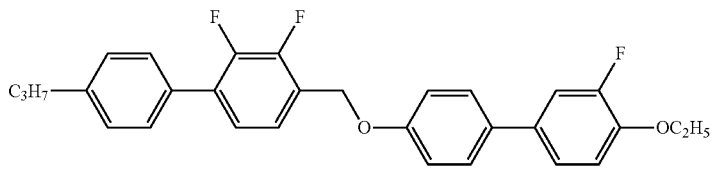 |
| 1603 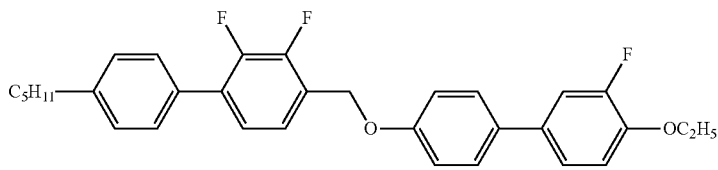 |
| 1604 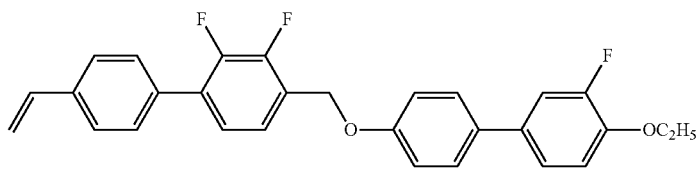 |
| 1605 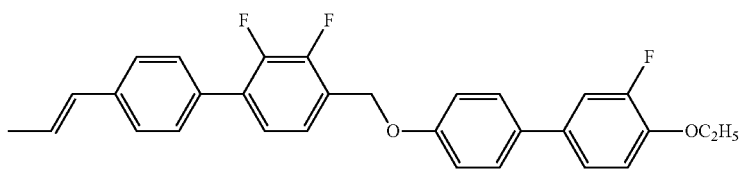 |
| 1606 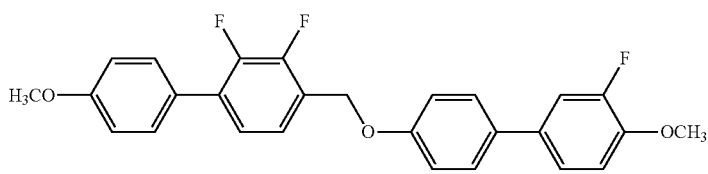 |
| 1607 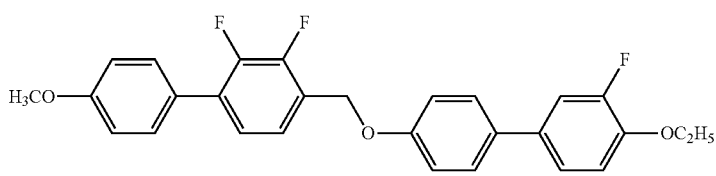 |
| 1608 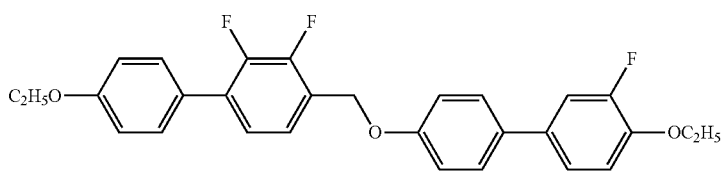 |
| 1609 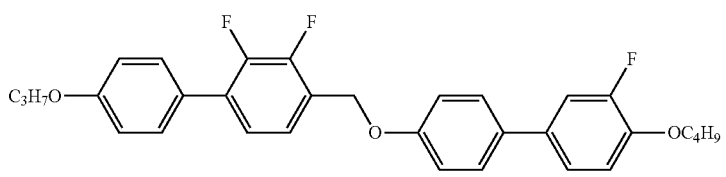 |

| No. | |
|---|---|
| 1610 | 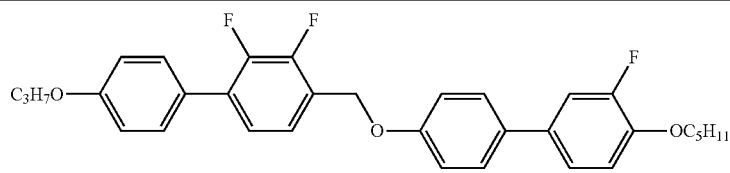 |
| 1611 | 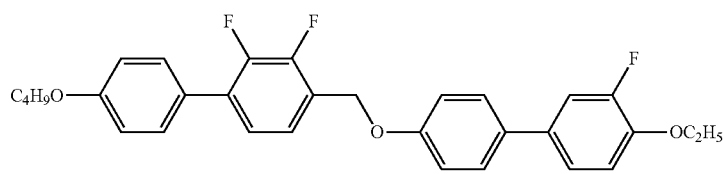 |
| 1612 | 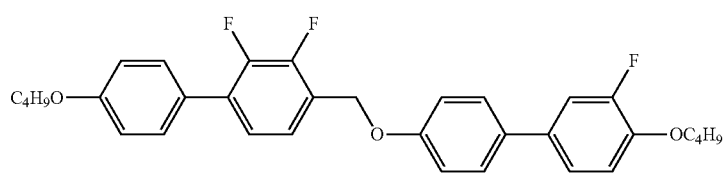 |
| 1613 | 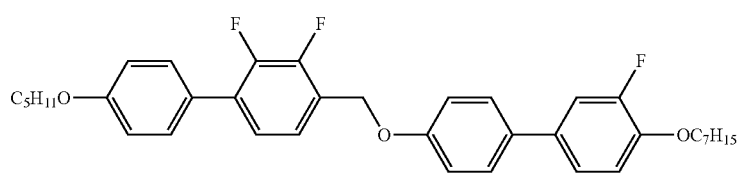 |
| 1614 | 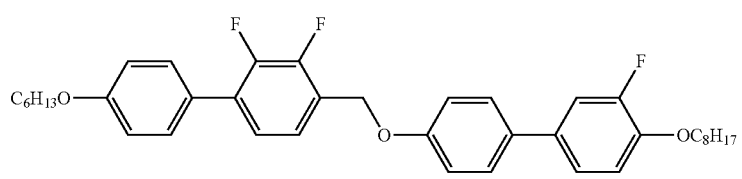 |
| 1615 | 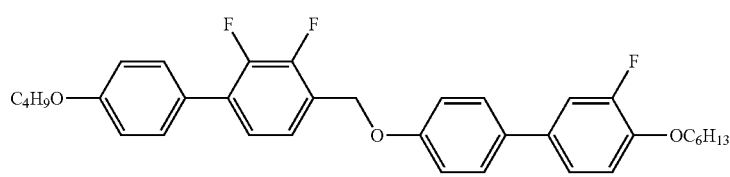 |
| 1616 | 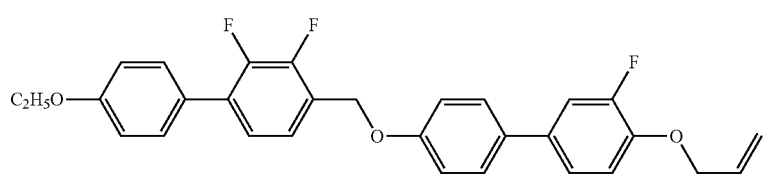 |
| 1617 | 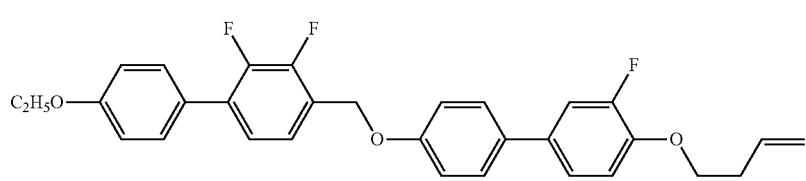 |
| 1618 | 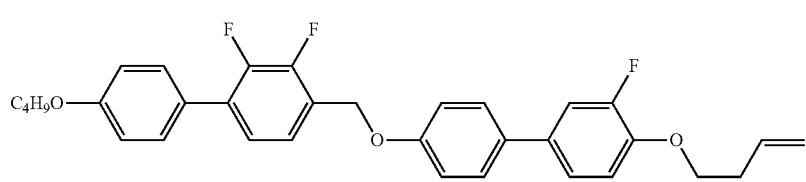 |

| No. | |
|---|---|
| 1619 | 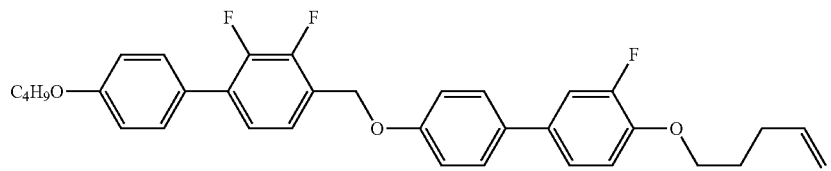 |
| 1620 | 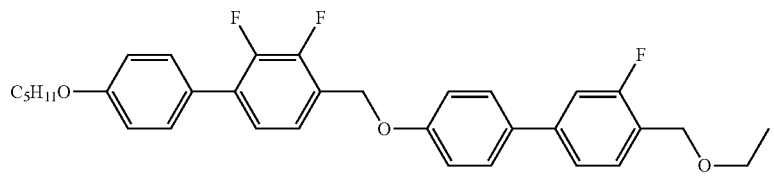 |
| 1621 | 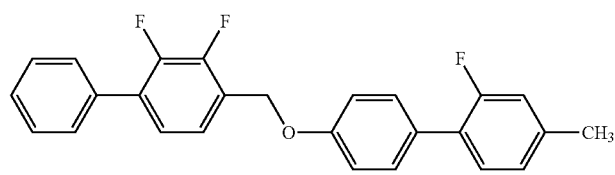 |
| 1622 | 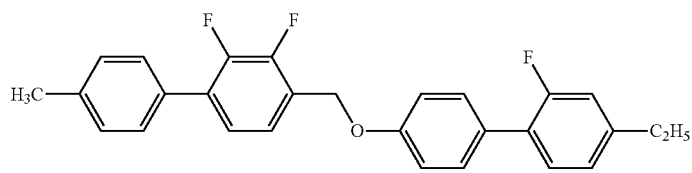 |
| 1623 | 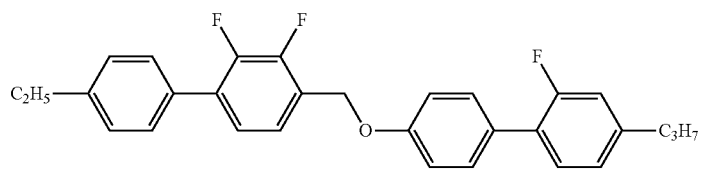 |
| 1624 | 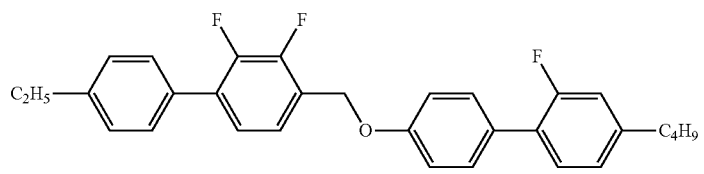 |
| 1625 | 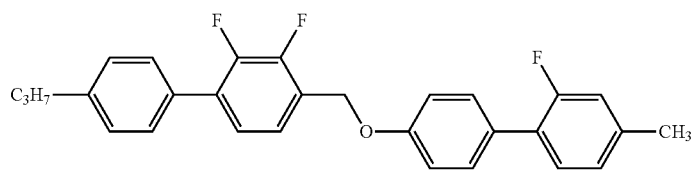 |
| 1626 | 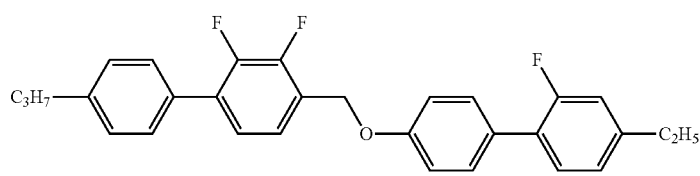 |

| No. | |
|---|---|
| 1627 | 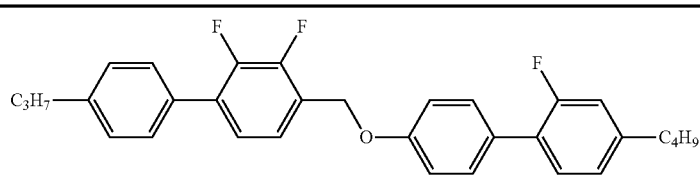 |
| 1628 | 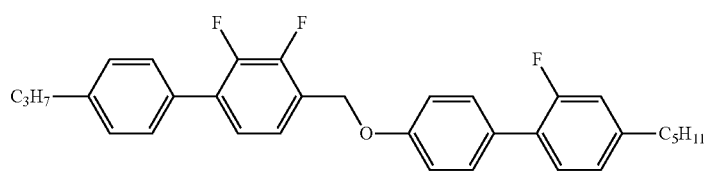 |
| 1629 | 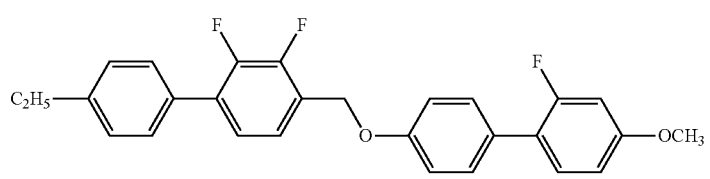 |
| 1630 | 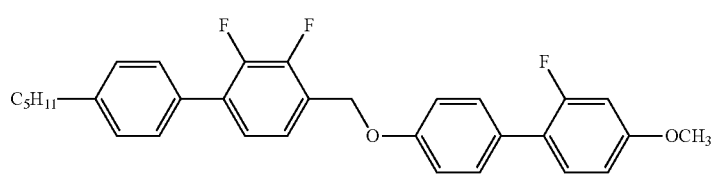 |
| 1631 | 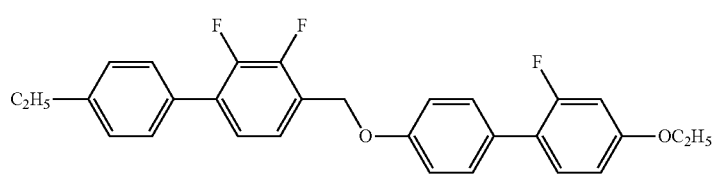 |
| 1632 | 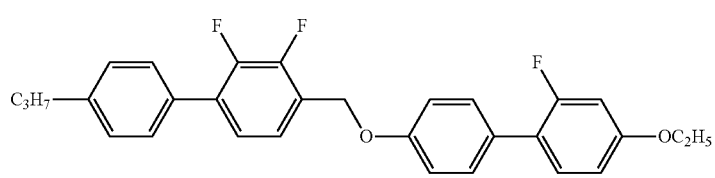 |
| 1633 | 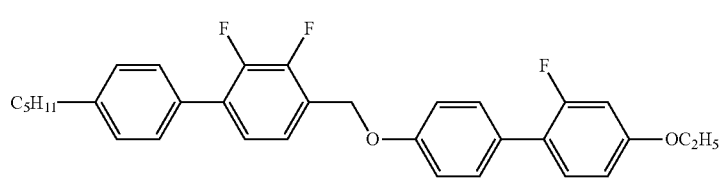 |
| 1634 | 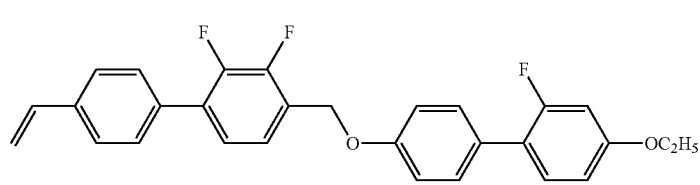 |
| 1635 | 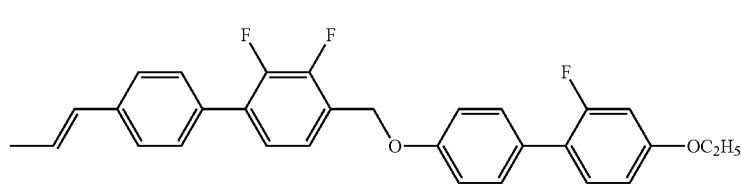 |

| No. |
|---|
| 1636 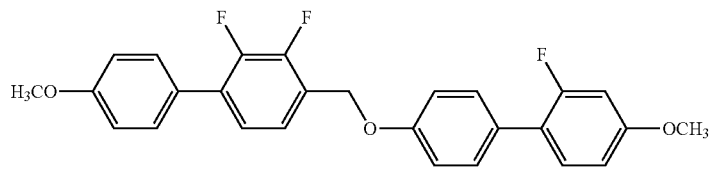 |
| 1637 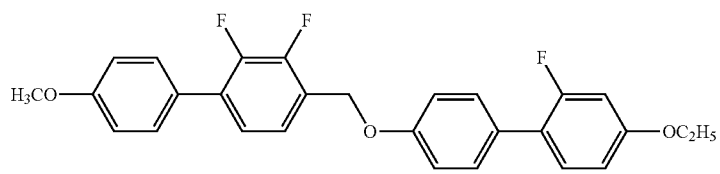 |
| 1638 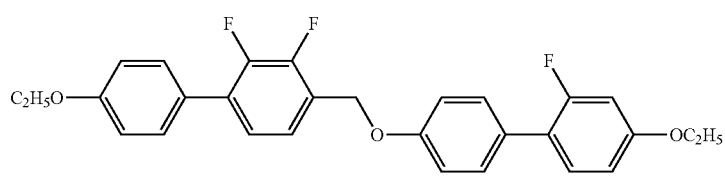 |
| 1639 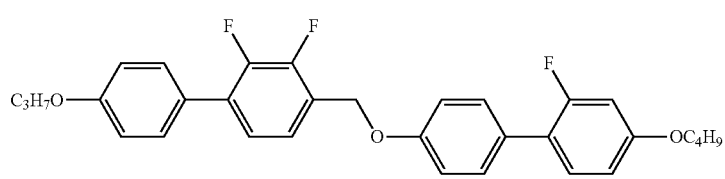 |
| 1640 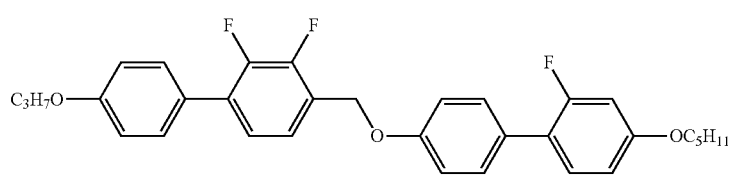 |
| 1641 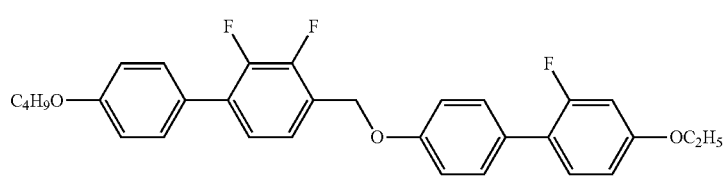 |
| 1642 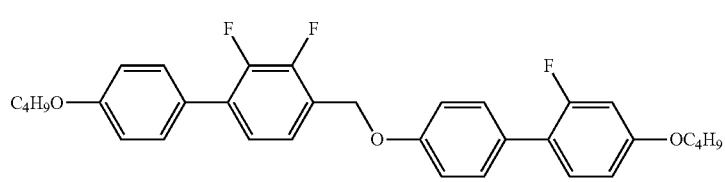 |
| 1643 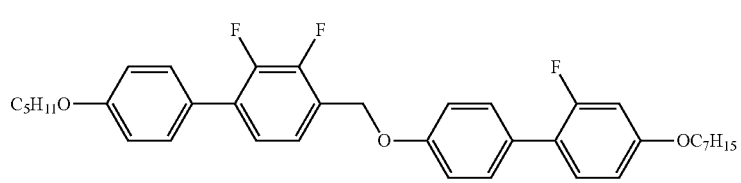 |

| No. | |
|---|---|
| 1644 | 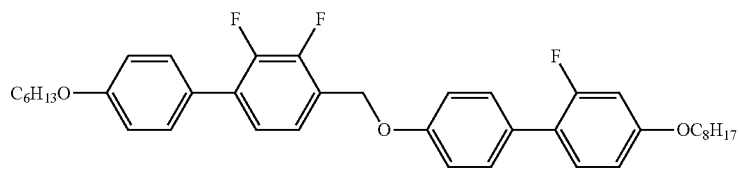 |
| 1645 | 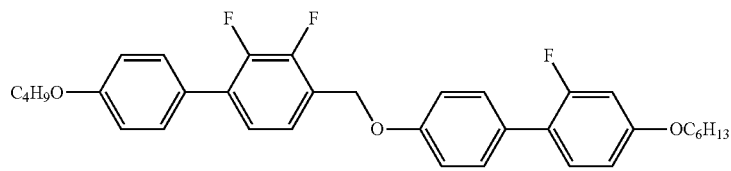 |
| 1646 | 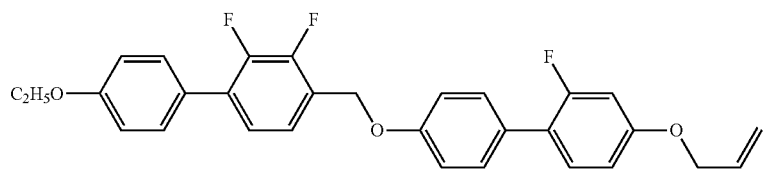 |
| 1647 | 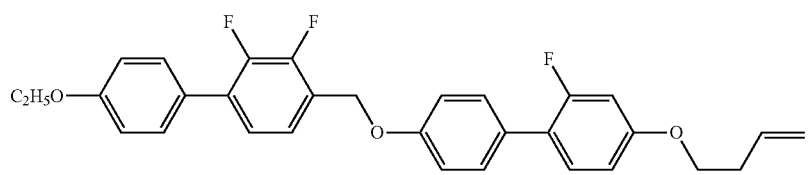 |
| 1648 | 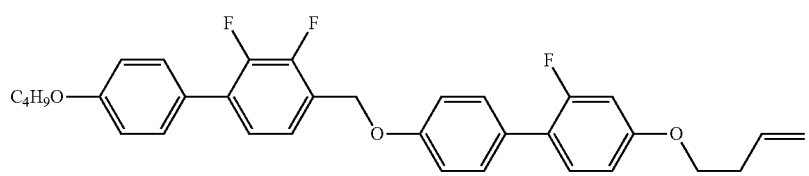 |
| 1649 | 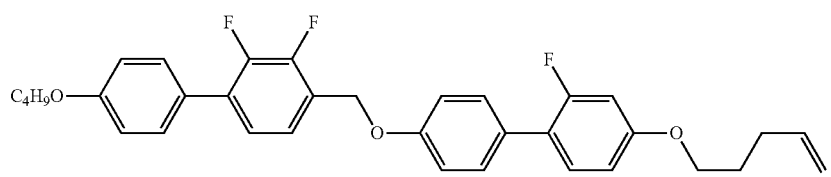 |
| 1650 | 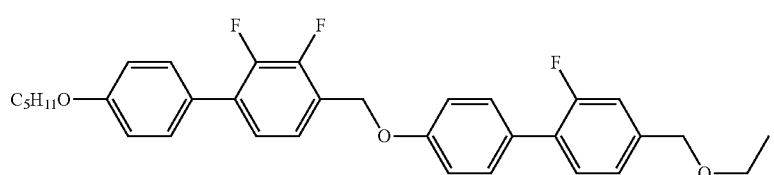 |
| 1651 | 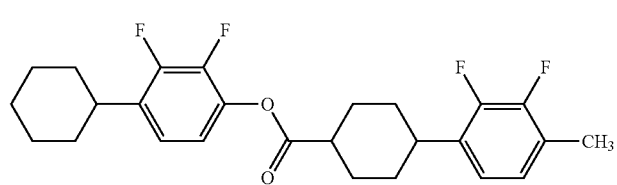 |

| No. | |
|---|---|
| 1652 | 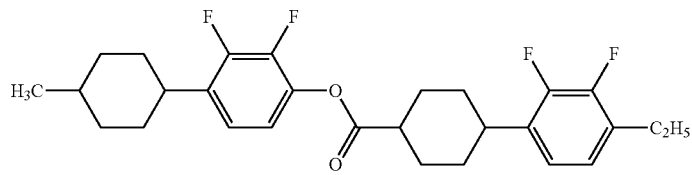 |
| 1653 | 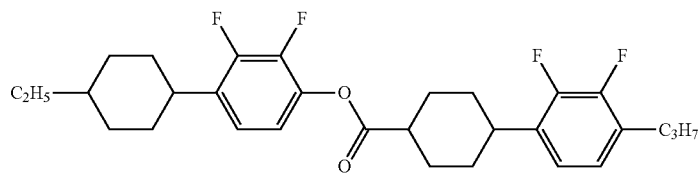 |
| 1654 | 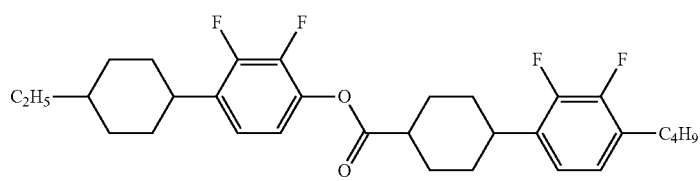 |
| 1655 | 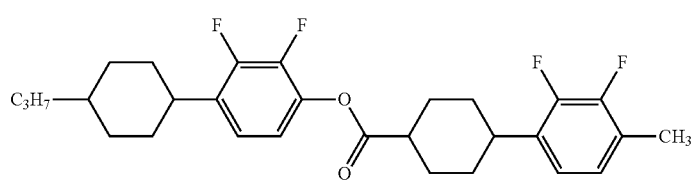 |
| 1656 | 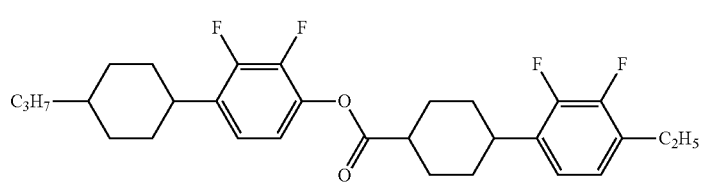 |
| 1657 | 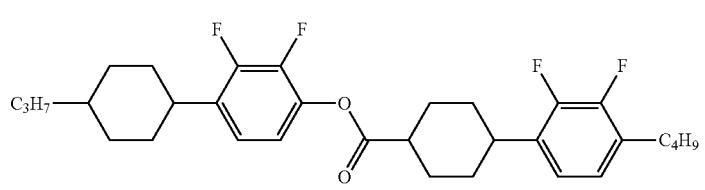 |
| 1658 | 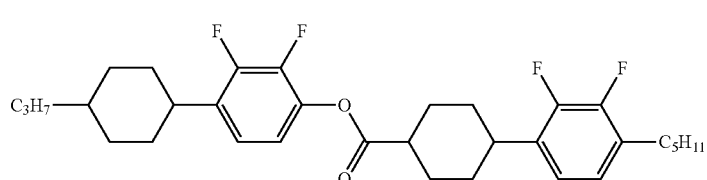 |
| 1659 | 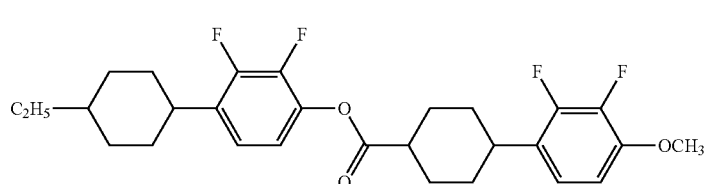 |

-continued
| No. | |
|---|---|
| 1660 | 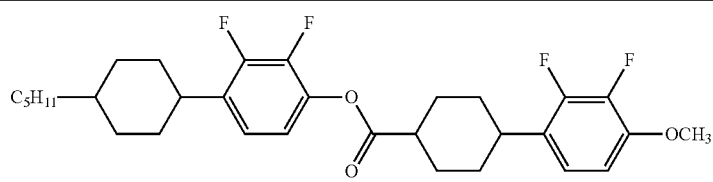 |
| 1661 | 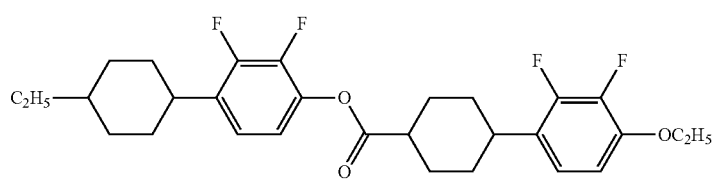 |
| 1662 | 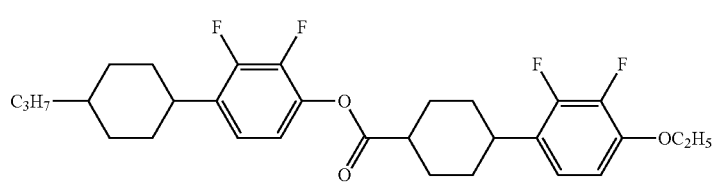 |
| 1663 | 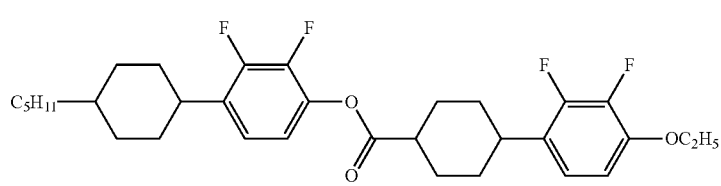<br>C 92.6 N 289.4 I<br>$T_{NI}$; 219.9° C., Δε; −7.37, Δn; 0.140 |
| 1664 | 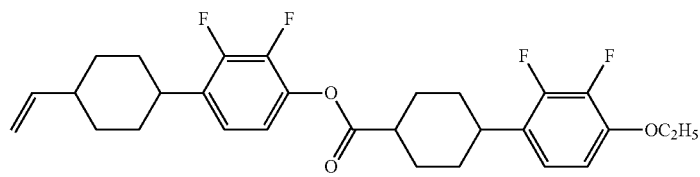 |
| 1665 | 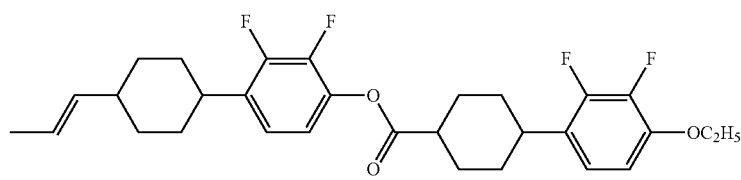 |
| 1666 | 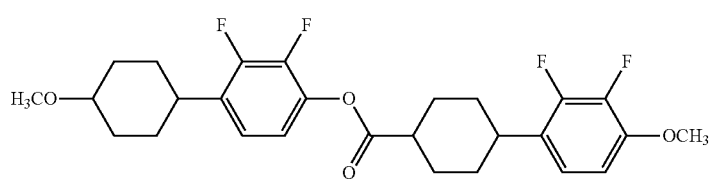 [SMILES: COc1ccc(C2CCC(C(=O)Oc3ccc(C4CCC(OC)CC4)c(F)c3F)CC2)c(F)c1F] |
| 1667 | 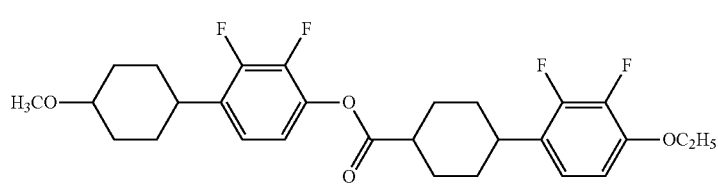 [SMILES: CCOc1ccc(C2CCC(C(=O)Oc3ccc(C4CCC(OC)CC4)c(F)c3F)CC2)c(F)c1F] |

-continued
| No. | |
|---|---|
| 1668 | 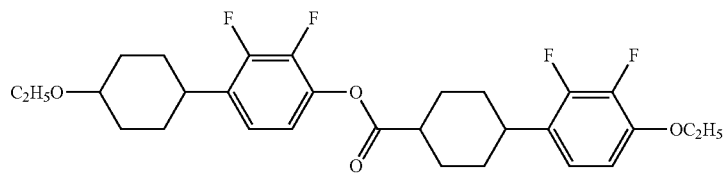 |
| 1669 | 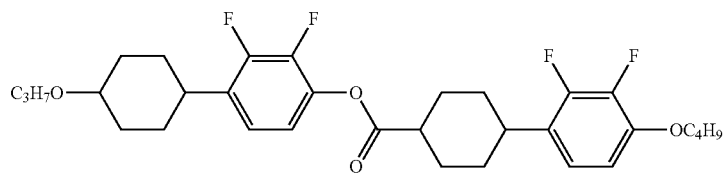 |
| 1670 | 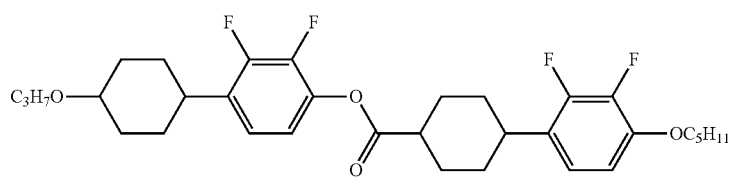 |
| 1671 | 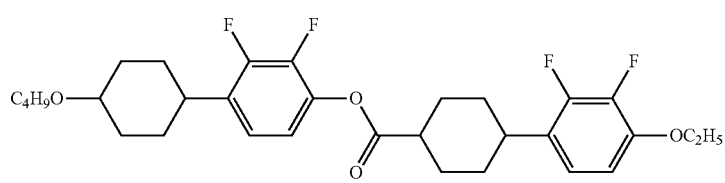 |
| 1672 | 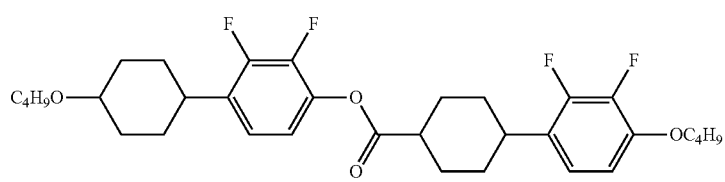 |
| 1673 | 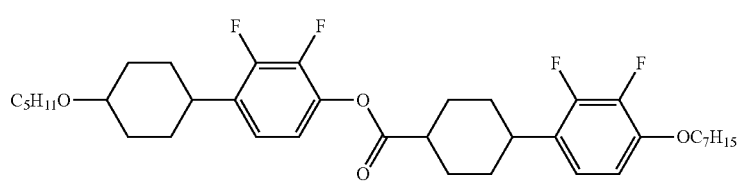 |
| 1674 | 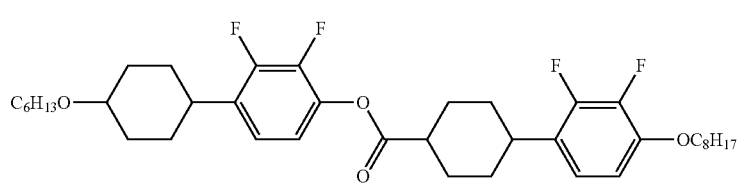 |
| 1675 | 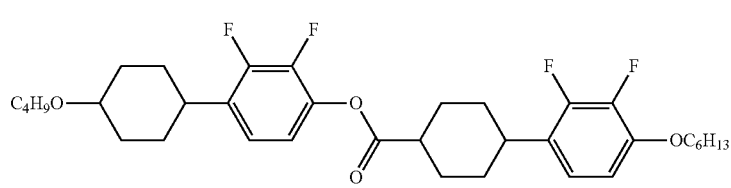 |

| No. | |
|---|---|
| 1676 | 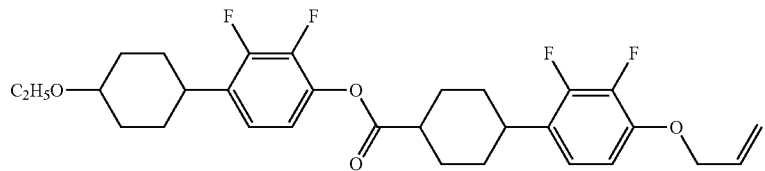 |
| 1677 | 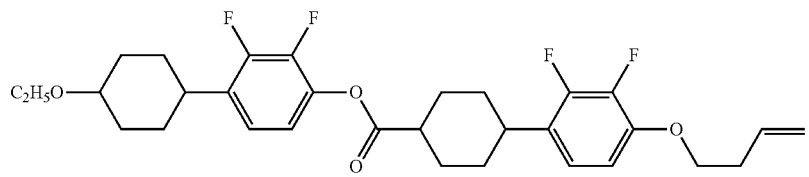 |
| 1678 | 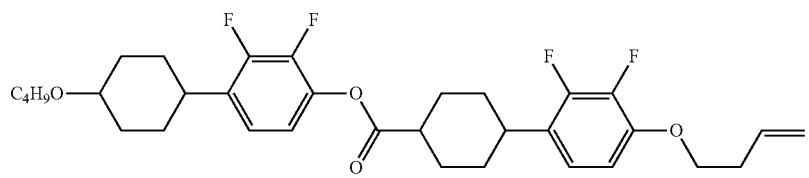 |
| 1679 | 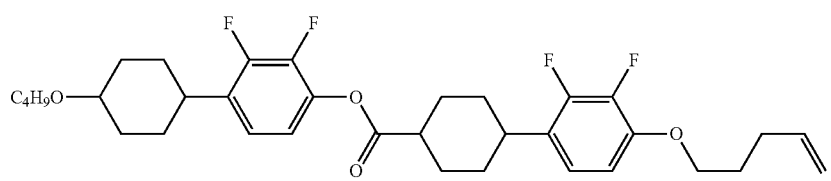 |
| 1680 | 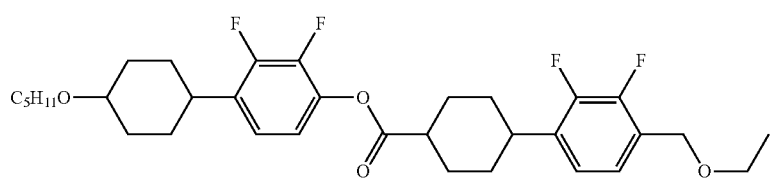 |
| 1681 | 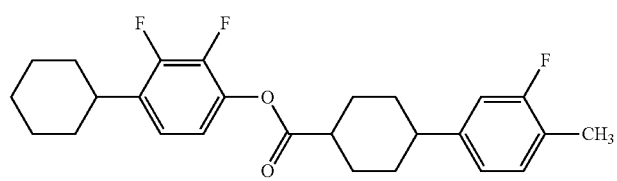 [SMILES: Cc1ccc(C2CCC(C(=O)Oc3ccc(C4CCCCC4)c(F)c3F)CC2)cc1F] |
| 1682 | 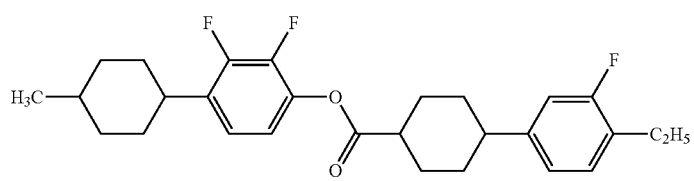 [SMILES: CCc1ccc(C2CCC(C(=O)Oc3ccc(C4CCC(C)CC4)c(F)c3F)CC2)cc1F] |
| 1683 | 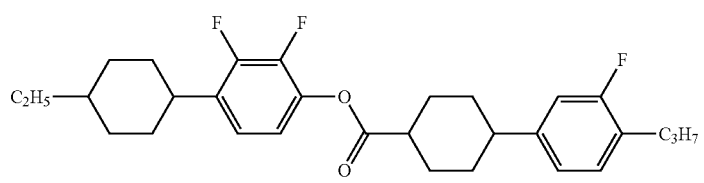 |

| No. | |
|---|---|
| 1684 | 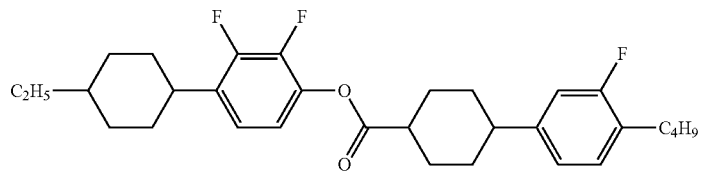 |
| 1685 | 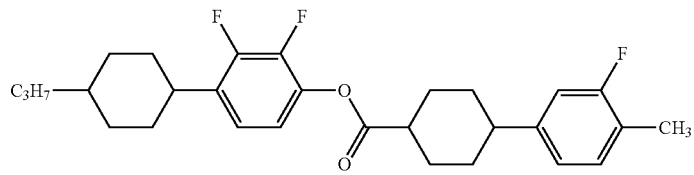 |
| 1686 | 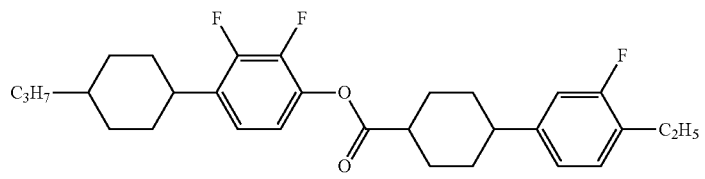 |
| 1687 | 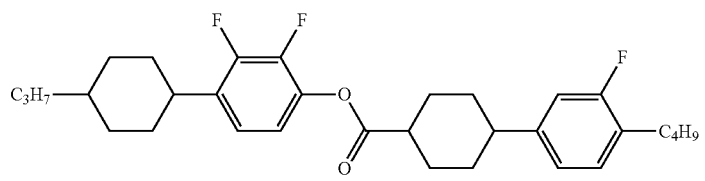 |
| 1688 | 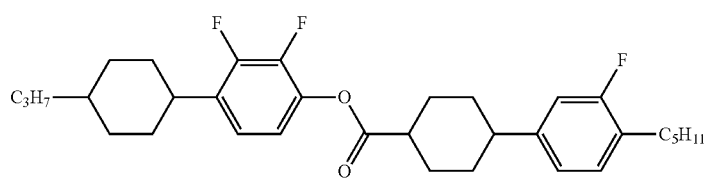 |
| 1689 | 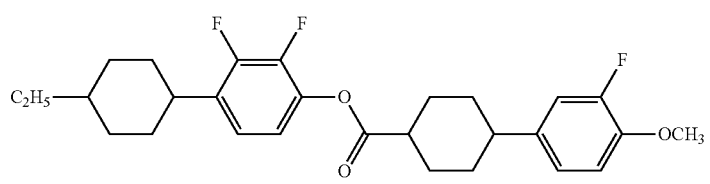 [SMILES: CCC1CCC(c2ccc(OC(=O)C3CCC(c4ccc(OC)c(F)c4)CC3)c(F)c2F)CC1] |
| 1690 | 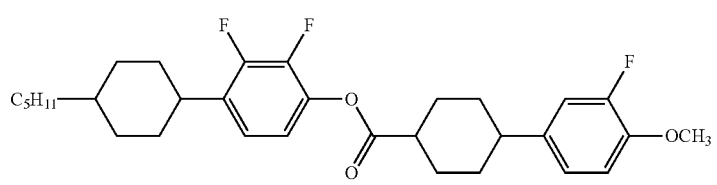 |
| 1691 | 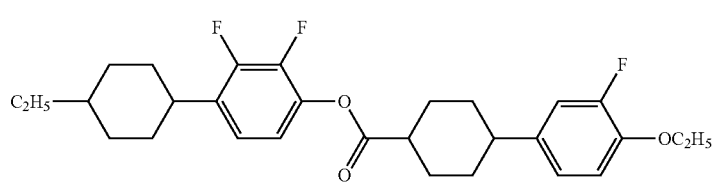 |

| No. | |
|---|---|
| 1692 | 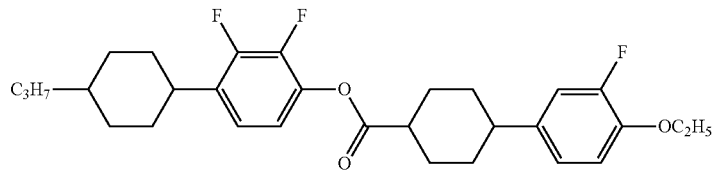 |
| 1693 | 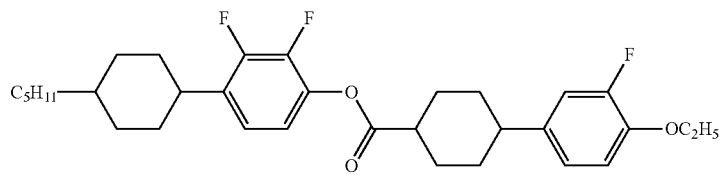 |
| 1694 | 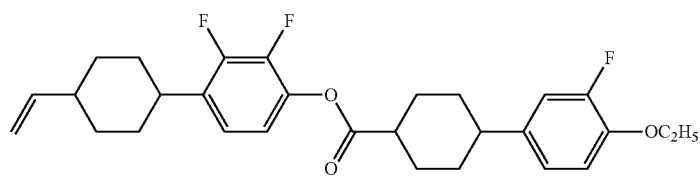 [SMILES: C=CC1CCC(c2ccc(OC(=O)C3CCC(c4ccc(OCC)c(F)c4)CC3)c(F)c2F)CC1] |
| 1695 | 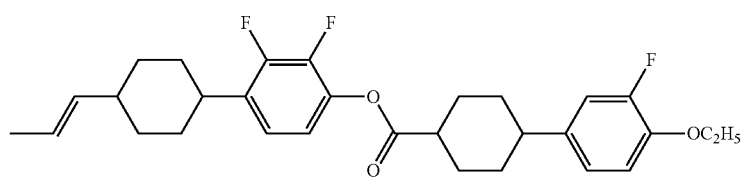 [SMILES: C/C=C/C1CCC(c2ccc(OC(=O)C3CCC(c4ccc(OCC)c(F)c4)CC3)c(F)c2F)CC1] |
| 1696 | 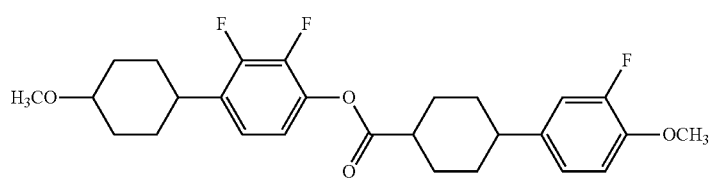 [SMILES: COc1ccc(C2CCC(C(=O)Oc3ccc(C4CCC(OC)CC4)c(F)c3F)CC2)cc1F] |
| 1697 | 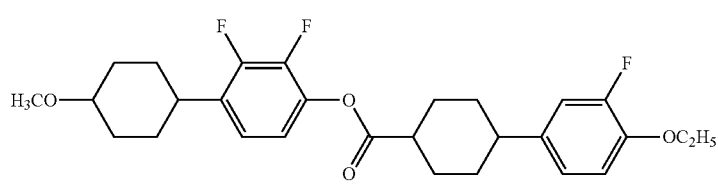 [SMILES: CCOc1ccc(C2CCC(C(=O)Oc3ccc(C4CCC(OC)CC4)c(F)c3F)CC2)cc1F] |
| 1698 | 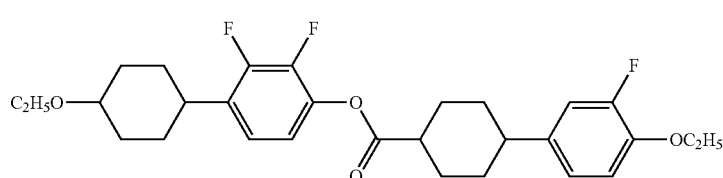 |
| 1699 | 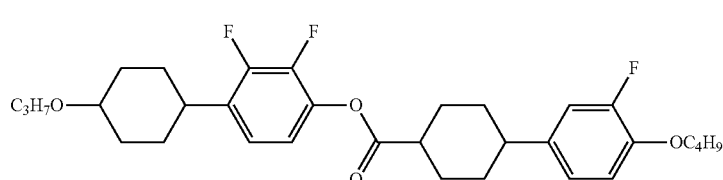 |

| No. | |
|---|---|
| 1700 | 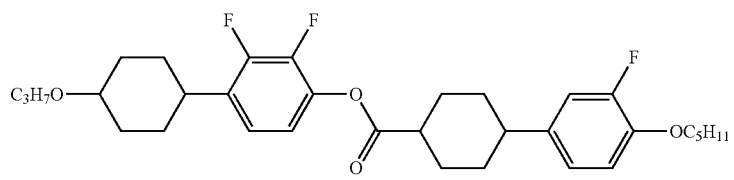 |
| 1701 | 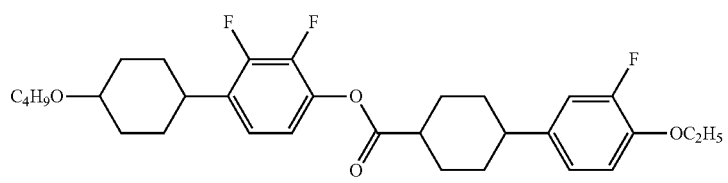 |
| 1702 | 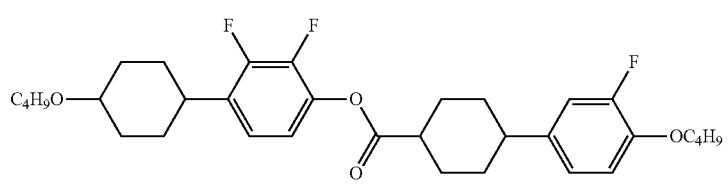 |
| 1703 | 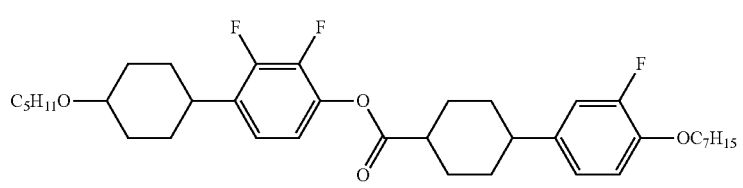 |
| 1704 | 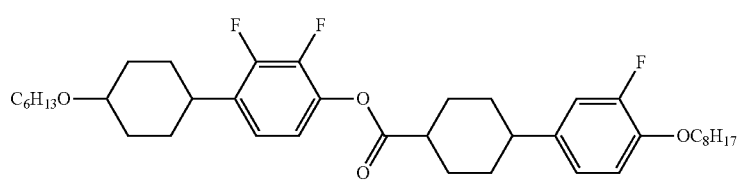 |
| 1705 | 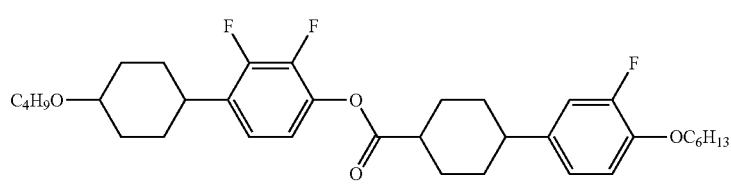 |
| 1706 | 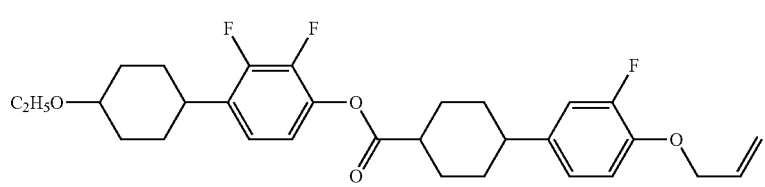 |
| 1707 | 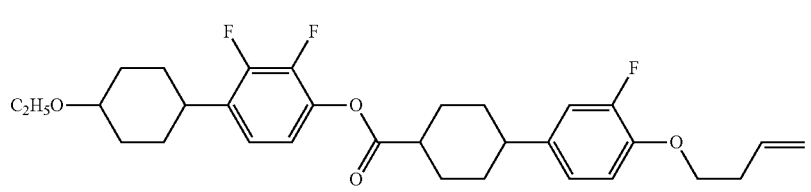 |

| No. |
|---|
| 1708 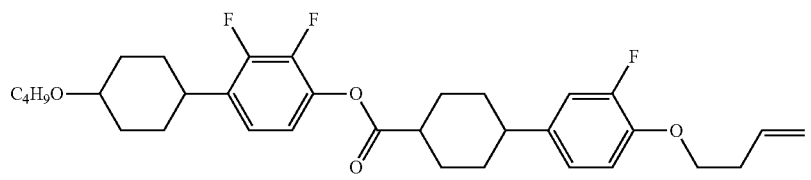 |
| 1709 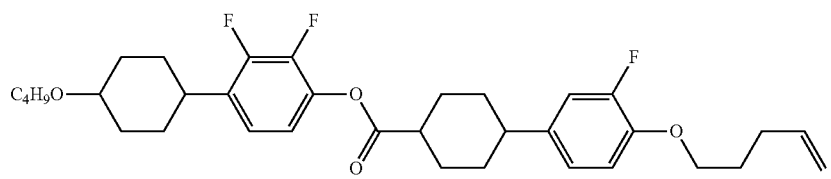 |
| 1710 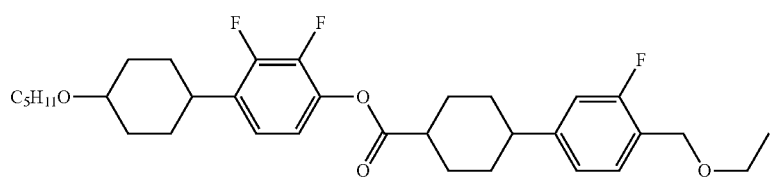 |
| 1711 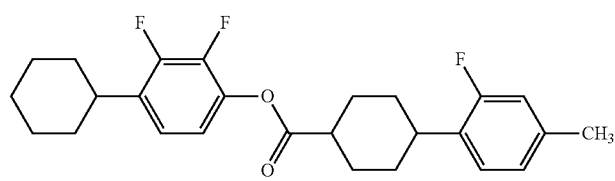 [SMILES: Cc1ccc(C2CCC(C(=O)Oc3ccc(C4CCCCC4)c(F)c3F)CC2)c(F)c1] |
| 1712 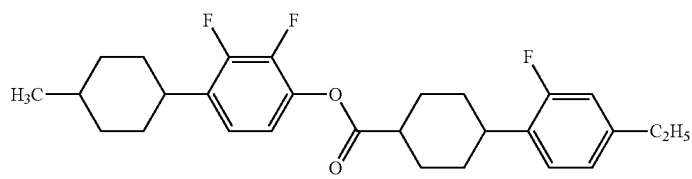 [SMILES: CCc1ccc(C2CCC(C(=O)Oc3ccc(C4CCC(C)CC4)c(F)c3F)CC2)c(F)c1] |
| 1713 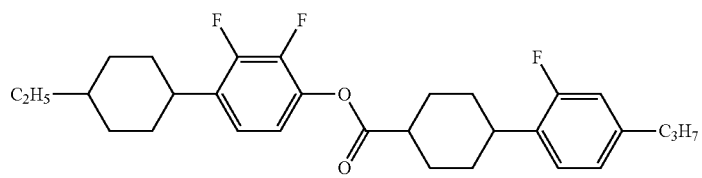 |
| 1714 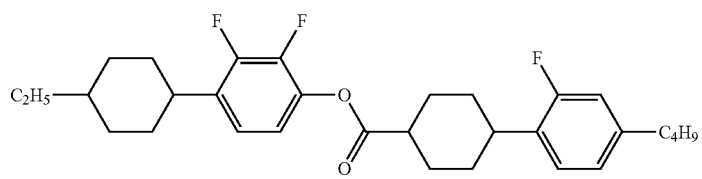 |
| 1715 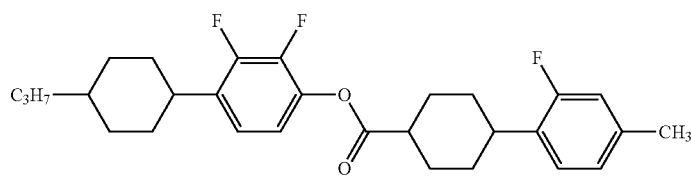 |

| No. | |
|---|---|
| 1716 | 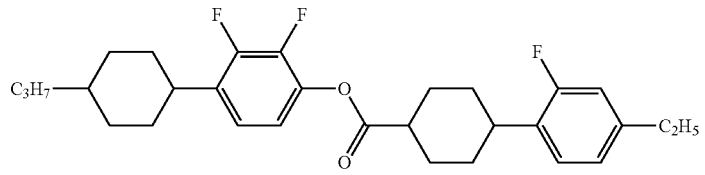 |
| 1717 | 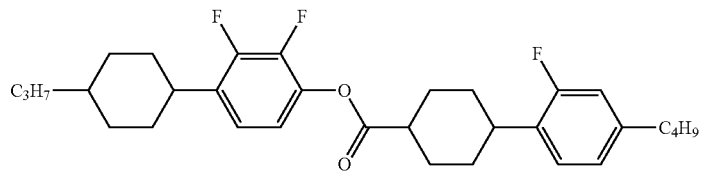 |
| 1718 | 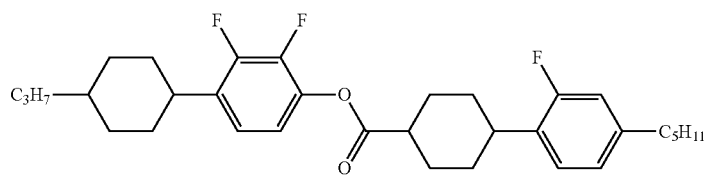 |
| 1719 | 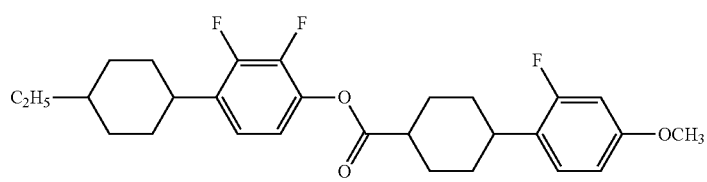 [SMILES: CCC1CCC(c2ccc(OC(=O)C3CCC(c4ccc(OC)cc4F)CC3)c(F)c2F)CC1] |
| 1720 | 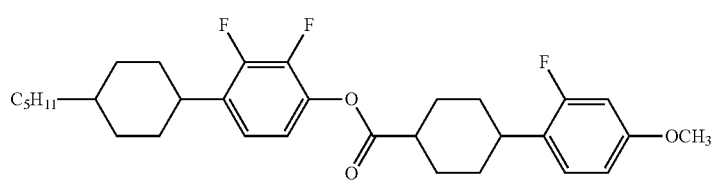 |
| 1721 | 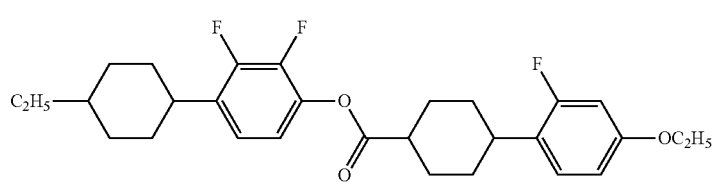 [SMILES: CCOc1ccc(C2CCC(C(=O)Oc3ccc(C4CCC(CC)CC4)c(F)c3F)CC2)c(F)c1] |
| 1722 | 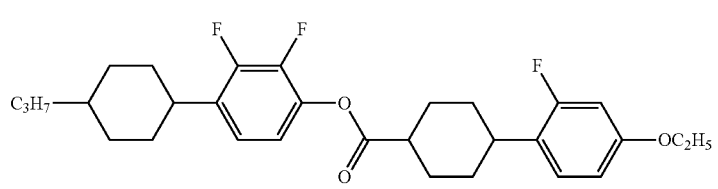 |
| 1723 | 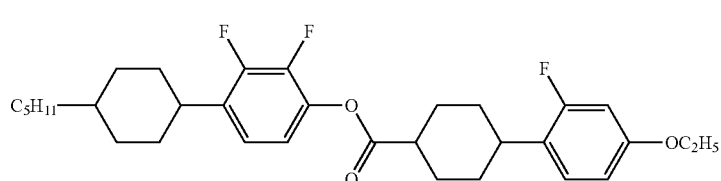 |

-continued
| No. | |
|---|---|
| 1724 | 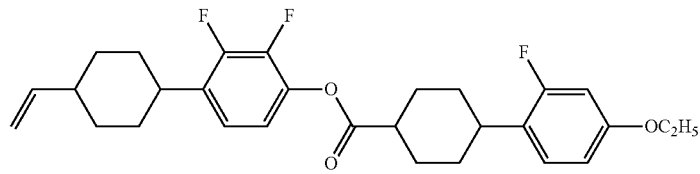 [SMILES: C=CC1CCC(c2ccc(OC(=O)C3CCC(c4ccc(OCC)cc4F)CC3)c(F)c2F)CC1] |
| 1725 | 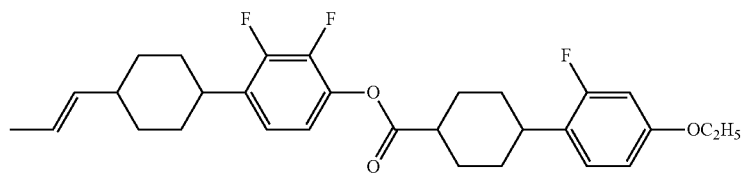 [SMILES: C/C=C/C1CCC(c2ccc(OC(=O)C3CCC(c4ccc(OCC)cc4F)CC3)c(F)c2F)CC1] |
| 1726 | 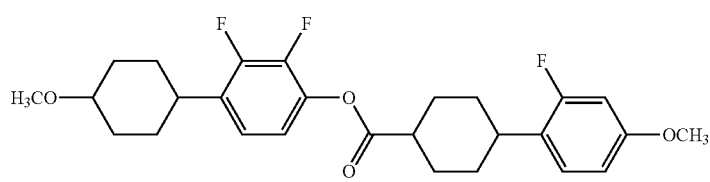 |
| 1727 | 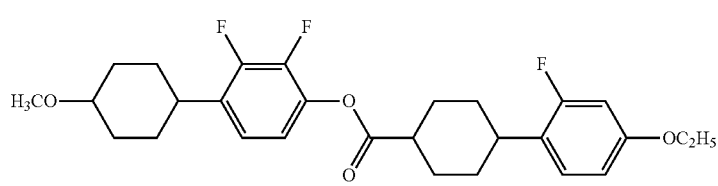 |
| 1728 | 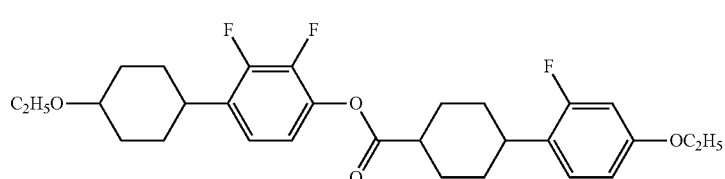 |
| 1729 | 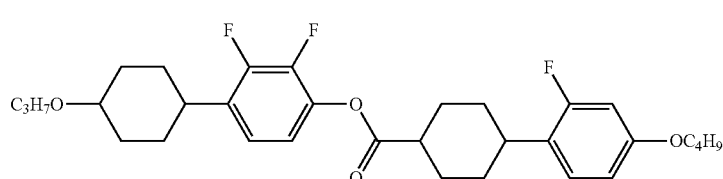 |
| 1730 | 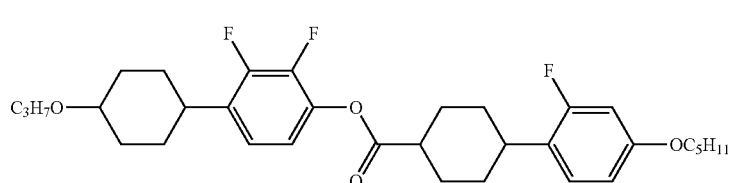 |
| 1731 | 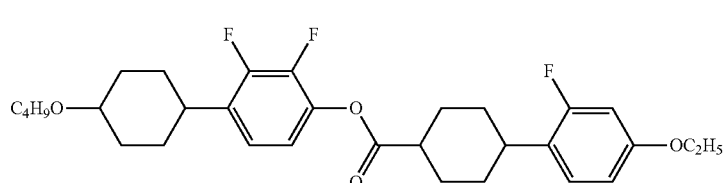 |

| No. | |
|---|---|
| 1732 | 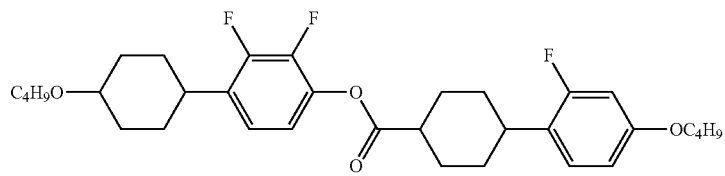 |
| 1733 | 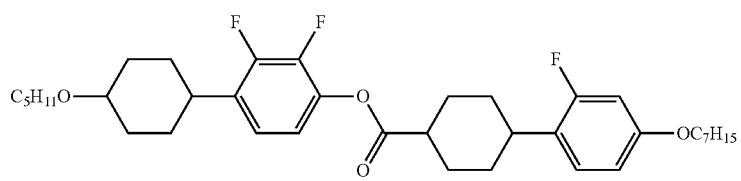 |
| 1734 | 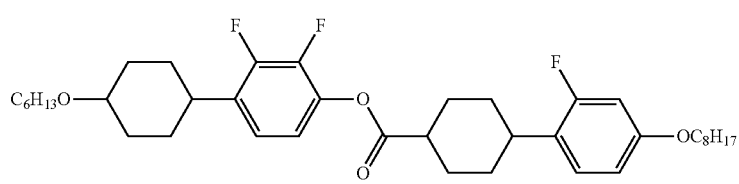 |
| 1735 | 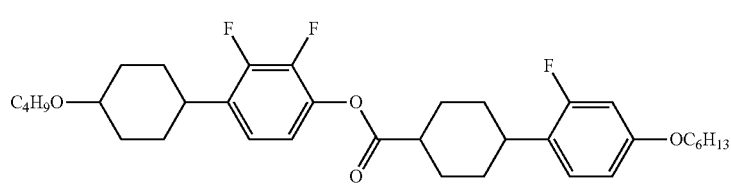 |
| 1736 | 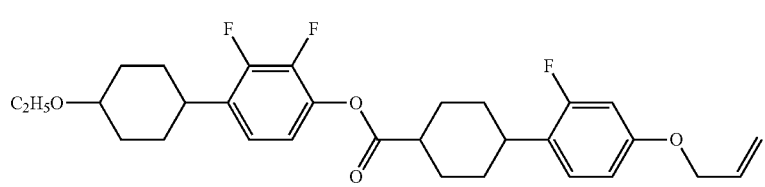 |
| 1737 | 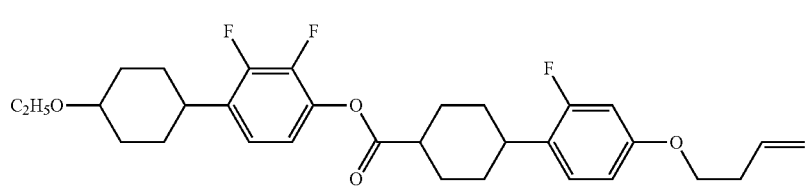 |
| 1738 | 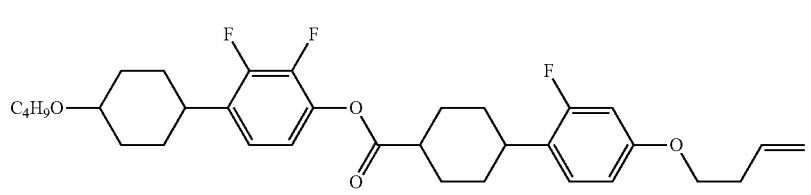 |
| 1739 | 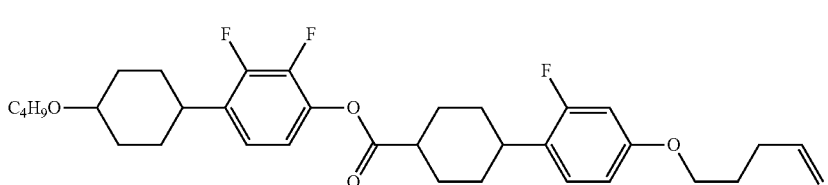 |

| No. | |
|---|---|
| 1740 | 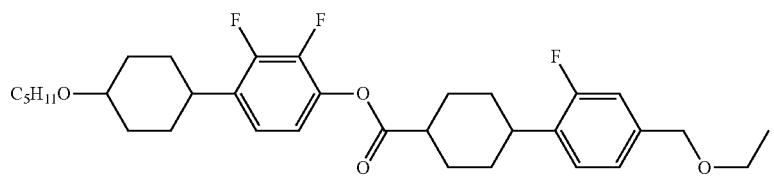 |
| 1741 | 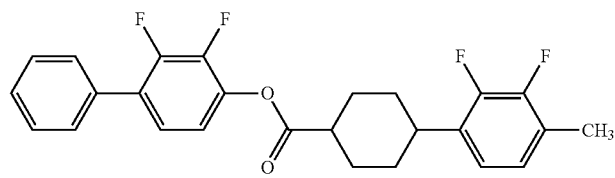 [SMILES: Cc1ccc(C2CCC(C(=O)Oc3ccc(-c4ccccc4)c(F)c3F)CC2)c(F)c1F] |
| 1742 | 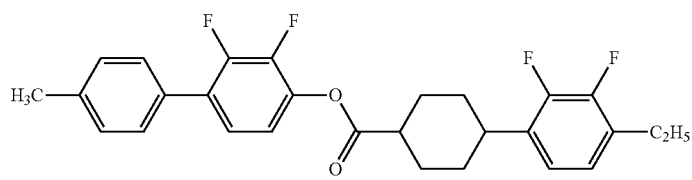 [SMILES: CCc1ccc(C2CCC(C(=O)Oc3ccc(-c4ccc(C)cc4)c(F)c3F)CC2)c(F)c1F] |
| 1743 | 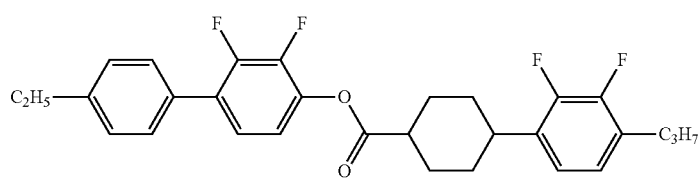 |
| 1744 | 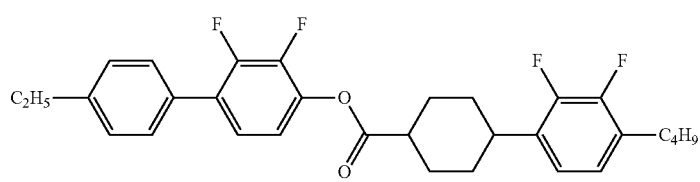 |
| 1745 | 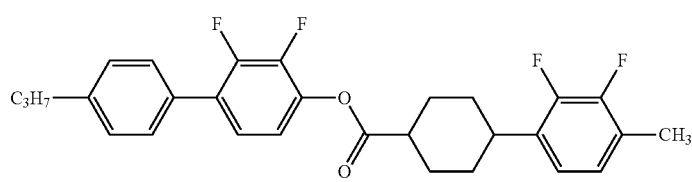 |
| 1746 | 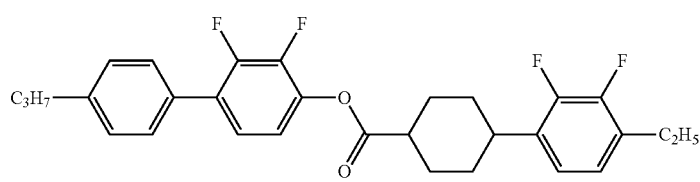 |
| 1747 | 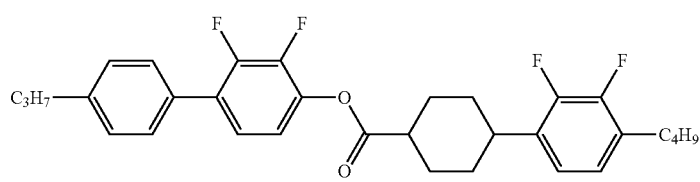 |

| No. | |
|---|---|
| 1748 | 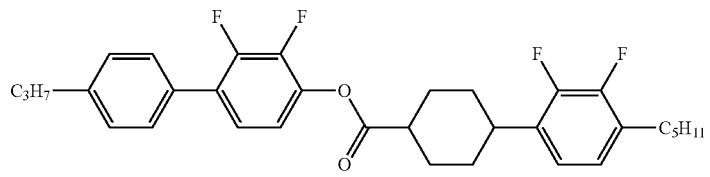 |
| 1749 | 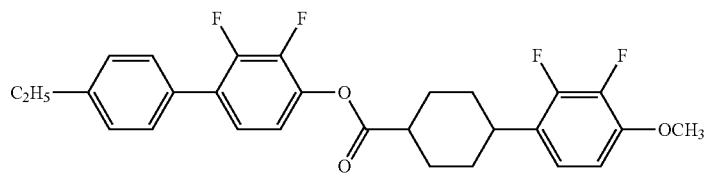 |
| 1750 | 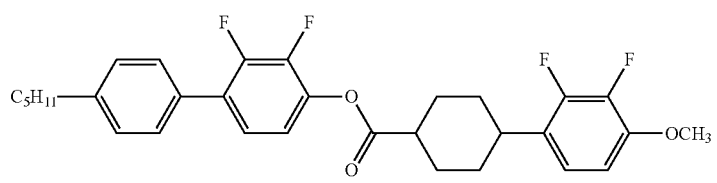 |
| 1751 | 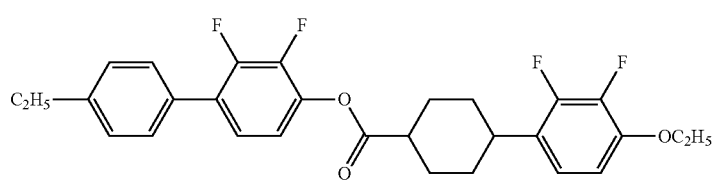 [SMILES: CCOc1ccc(C2CCC(C(=O)Oc3ccc(-c4ccc(CC)cc4)c(F)c3F)CC2)c(F)c1F] |
| 1752 | 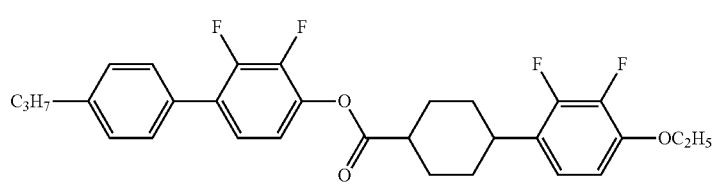 |
| 1753 | 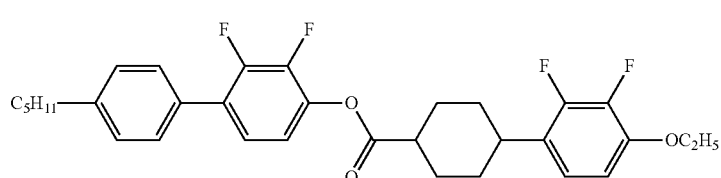 |
| 1754 | 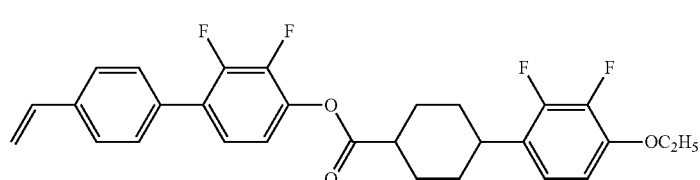 |
| 1755 | 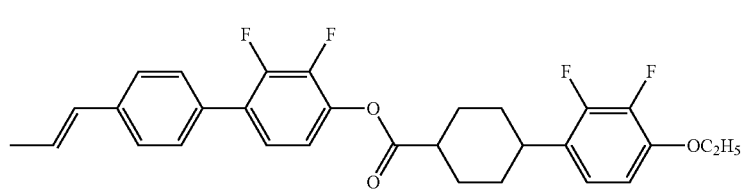 |

-continued
| No. | |
|---|---|
| 1756 | 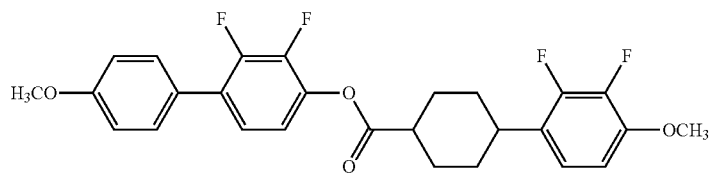 |
| 1757 | 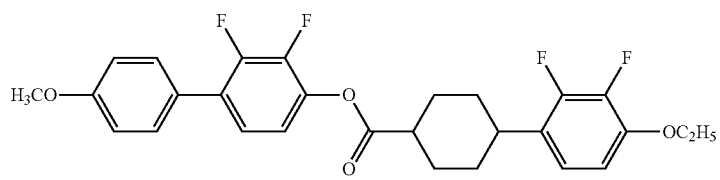 [SMILES: CCOc1ccc(C2CCC(C(=O)Oc3ccc(-c4ccc(OC)cc4)c(F)c3F)CC2)c(F)c1F] |
| 1758 | 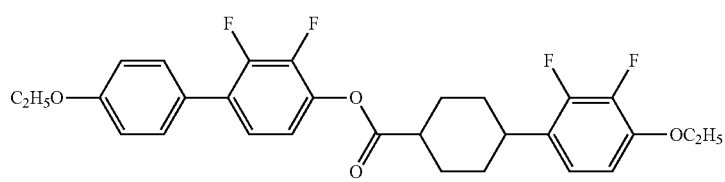 |
| 1759 | 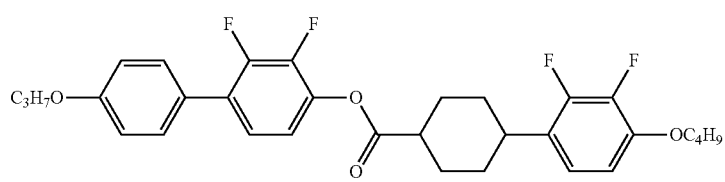 |
| 1760 | 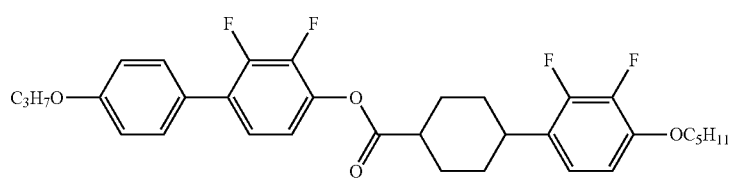 |
| 1761 | 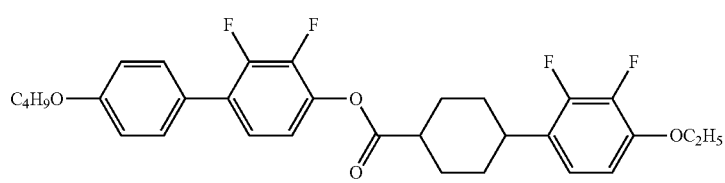 |
| 1762 | 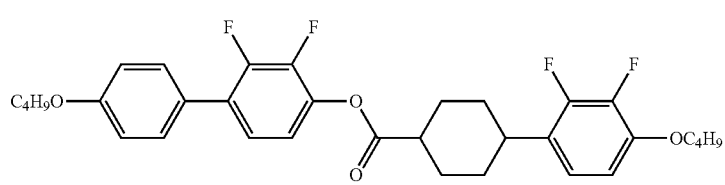 |
| 1763 | 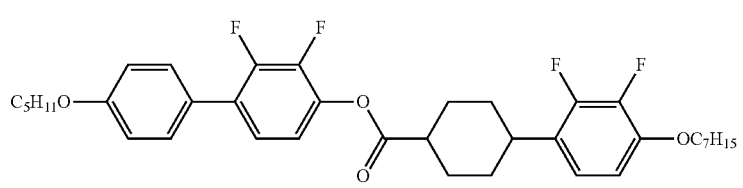 |

-continued
| No. | |
|---|---|
| 1764 | 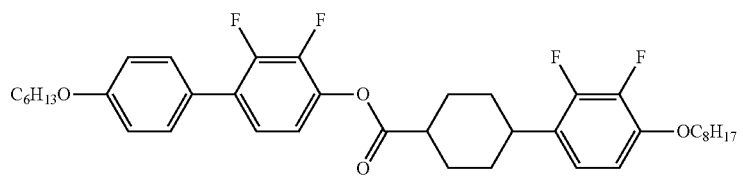 |
| 1765 | 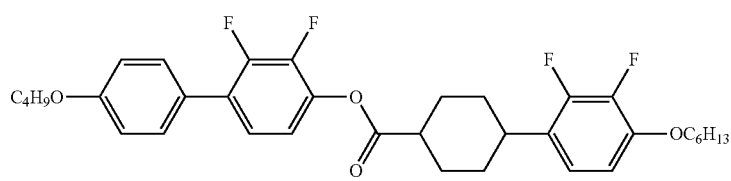 |
| 1766 | 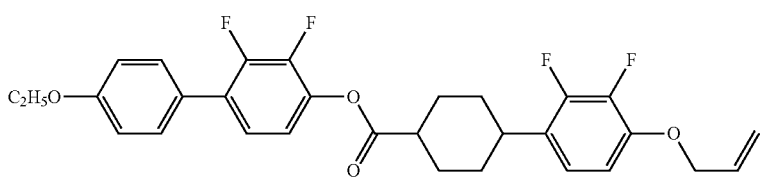 |
| 1767 | 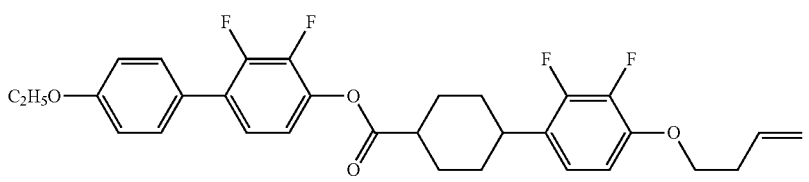 |
| 1768 | 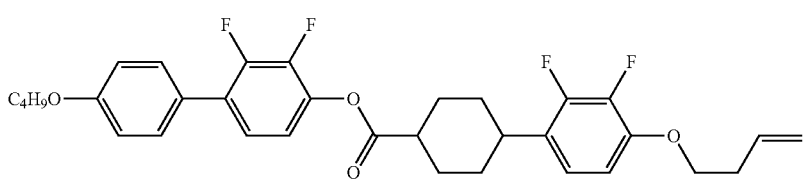 |
| 1769 | 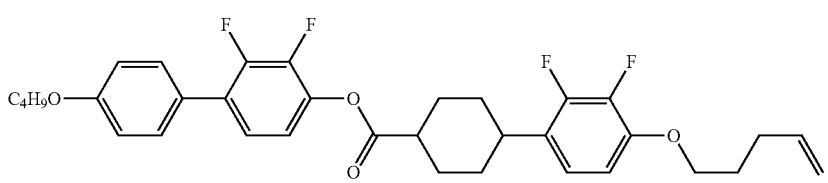 |
| 1770 | 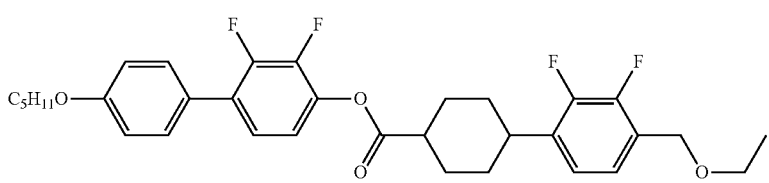 |
| 1771 | 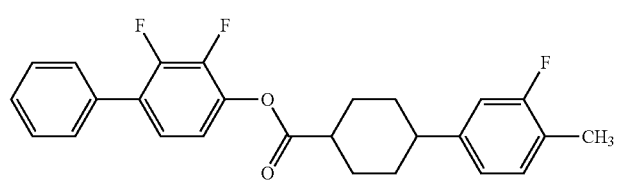 |

-continued
| No. | |
|---|---|
| 1772 | 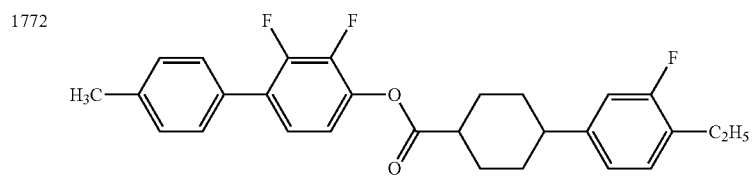 |
| 1773 | 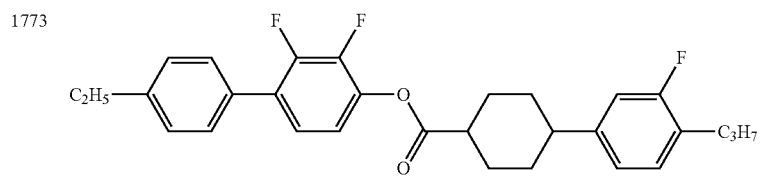 |
| 1774 | 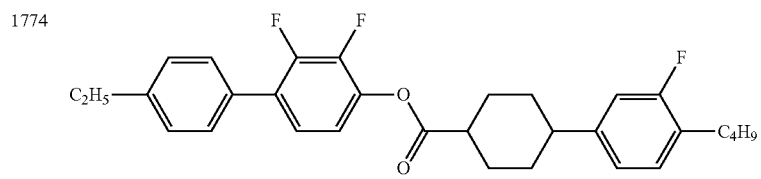 |
| 1775 | 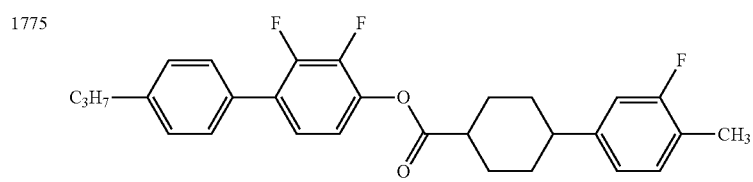 |
| 1776 | 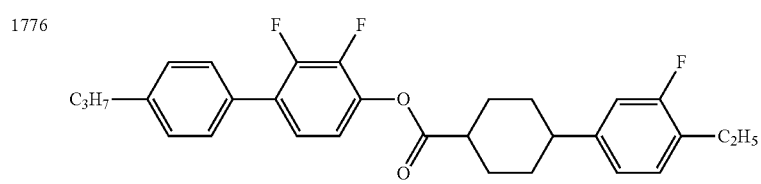 |
| 1777 | 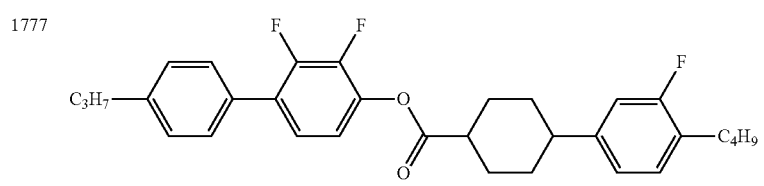 |
| 1778 | 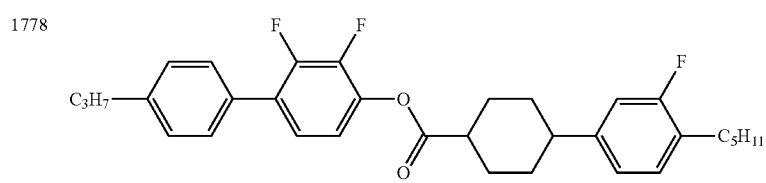 |
| 1779 | 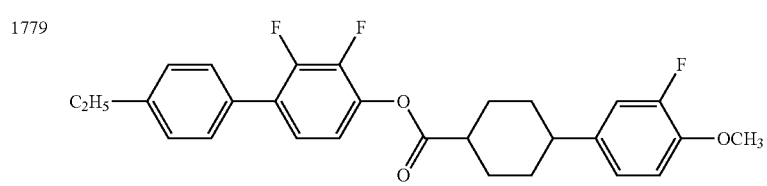 |

| No. | |
|---|---|
| 1780 | 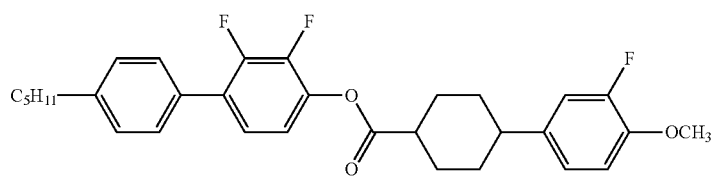 |
| 1781 | 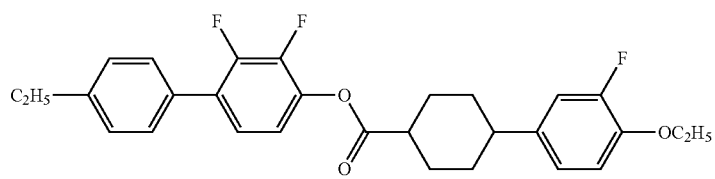 |
| 1782 | 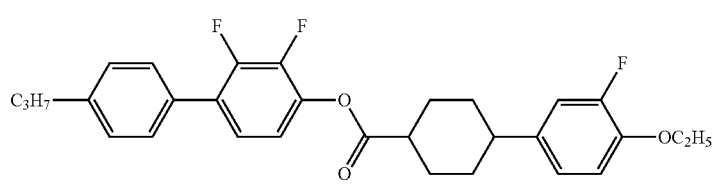 |
| 1783 | 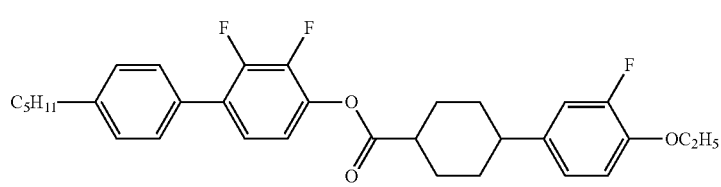 |
| 1784 | 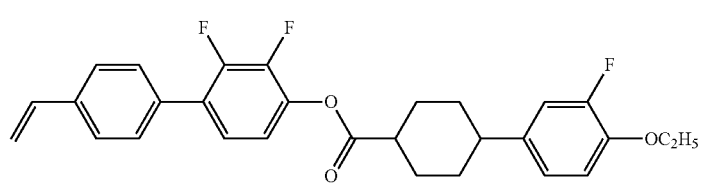 |
| 1785 | 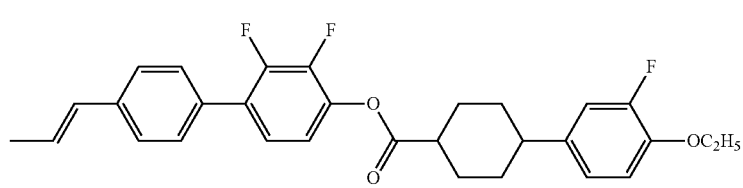 [SMILES: C/C=C/c1ccc(-c2ccc(OC(=O)C3CCC(c4ccc(OCC)c(F)c4)CC3)c(F)c2F)cc1] |
| 1786 | 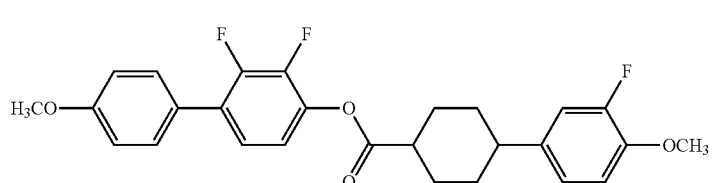 |
| 1787 | 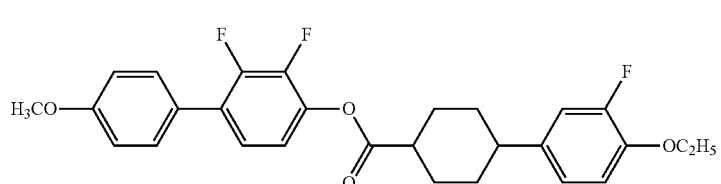 |

| No. |
|---|
| 1788 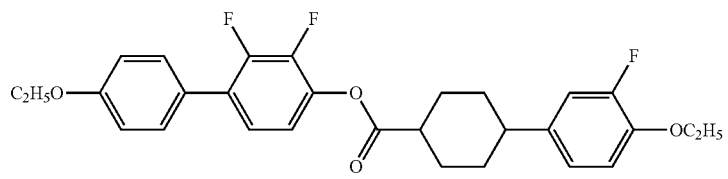 |
| 1789 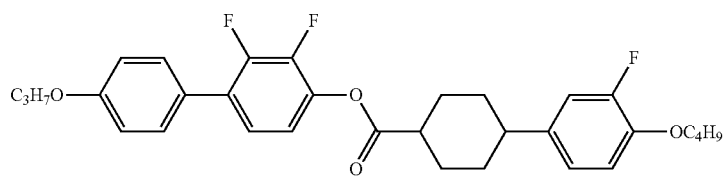 |
| 1790 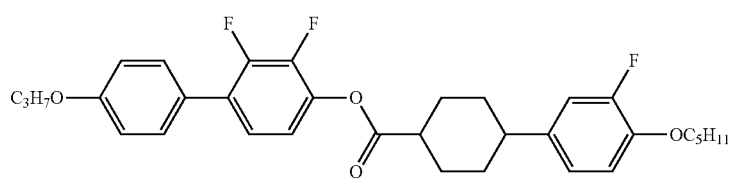 |
| 1791 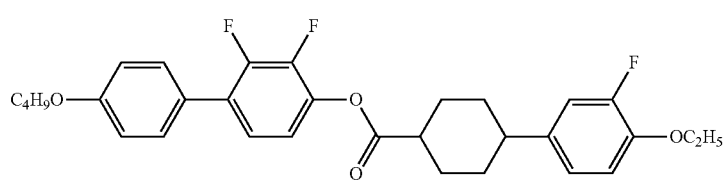 |
| 1792 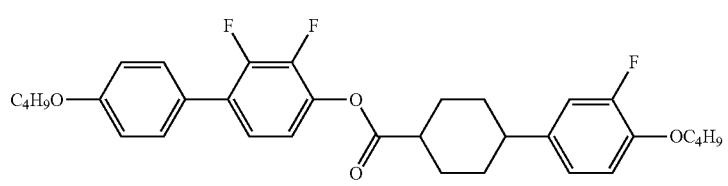 |
| 1793 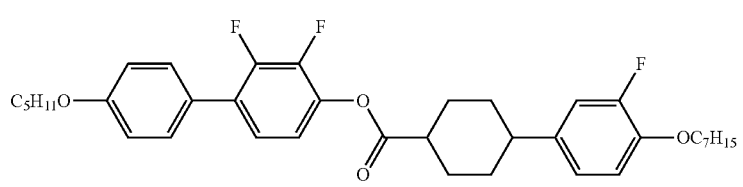 |
| 1794 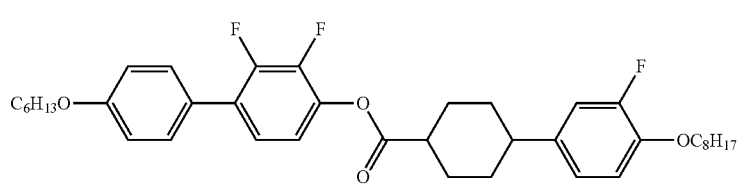 |
| 1795 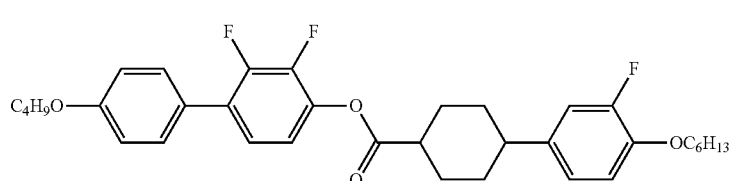 |

| No. | |
|---|---|
| 1796 | 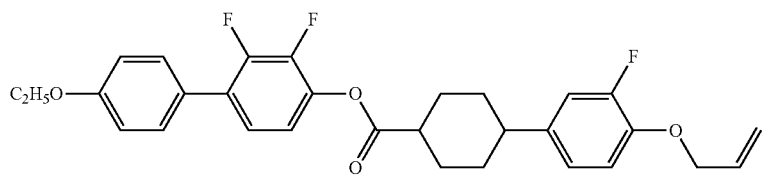 |
| 1797 | 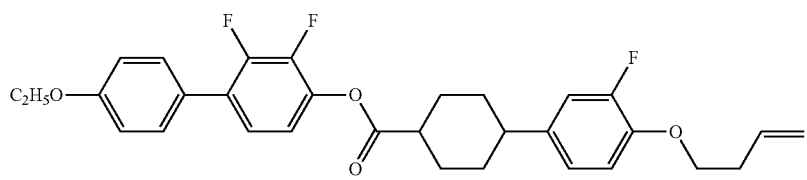 |
| 1798 | 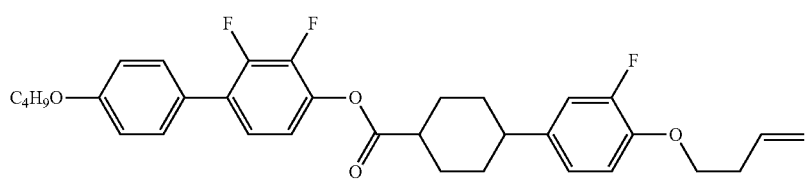 |
| 1799 | 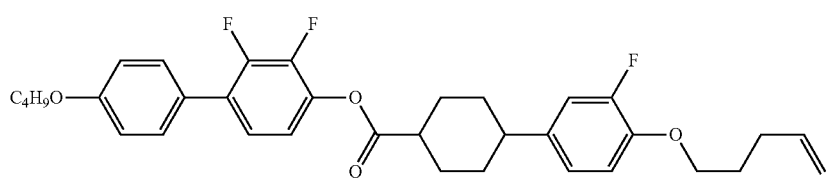 |
| 1800 | 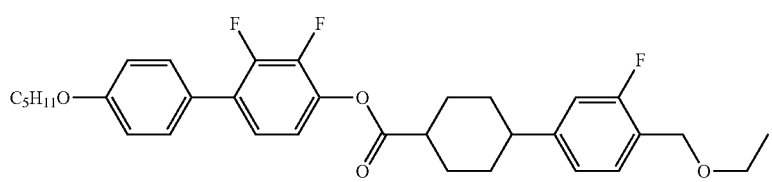 |
| 1801 | 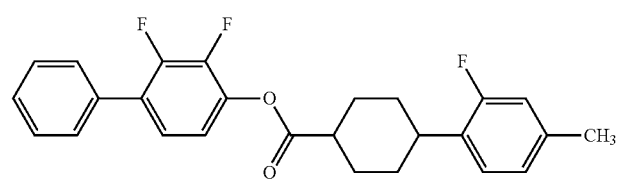 [SMILES: Cc1ccc(C2CCC(C(=O)Oc3ccc(-c4ccccc4)c(F)c3F)CC2)c(F)c1] |
| 1802 | 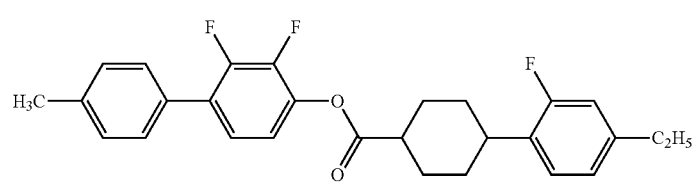 [SMILES: CCc1ccc(C2CCC(C(=O)Oc3ccc(-c4ccc(C)cc4)c(F)c3F)CC2)c(F)c1] |
| 1803 | 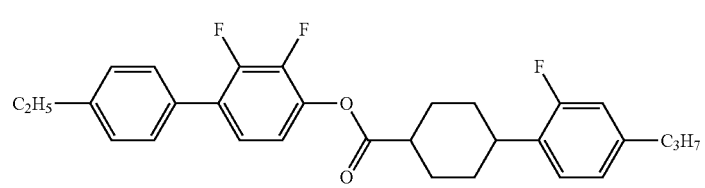 |

| No. |
|---|
| 1804 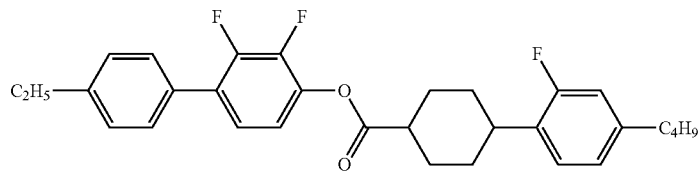 |
| 1805 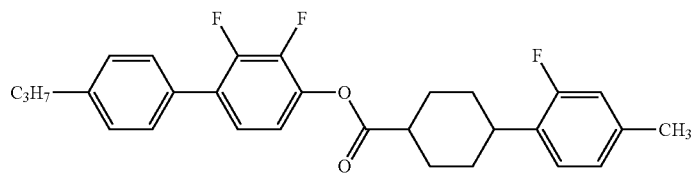 |
| 1806 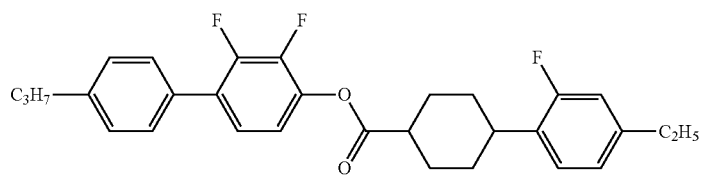 |
| 1807 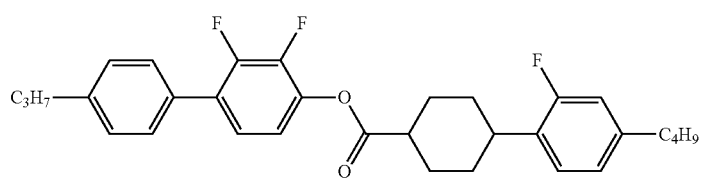 |
| 1808 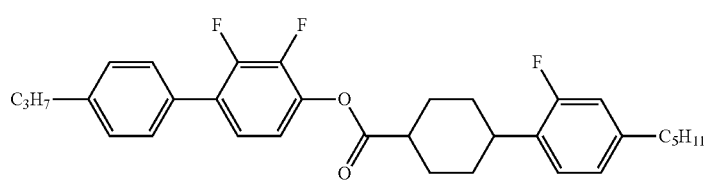 |
| 1809 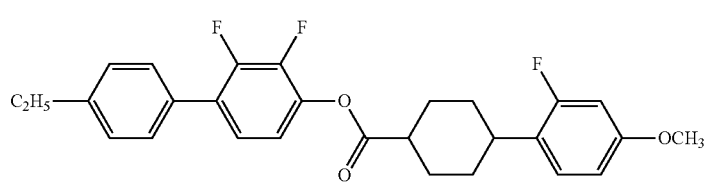 [SMILES: CCc1ccc(-c2ccc(OC(=O)C3CCC(c4ccc(OC)cc4F)CC3)c(F)c2F)cc1] |
| 1810 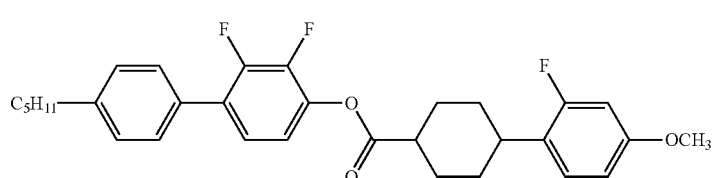 |
| 1811 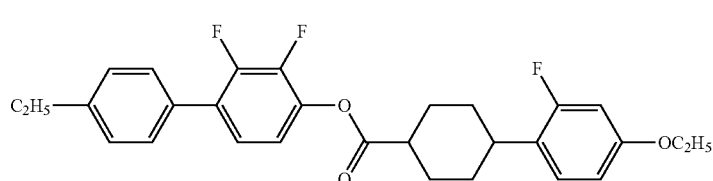 |

-continued
| No. | |
|---|---|
| 1812 | 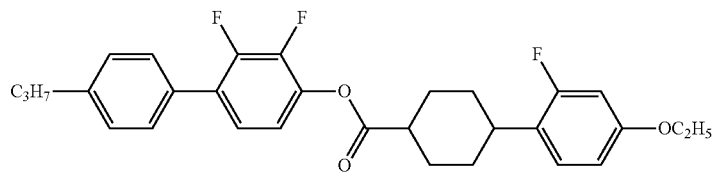 |
| 1813 | 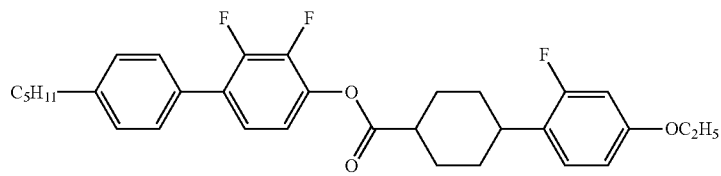 |
| 1814 | 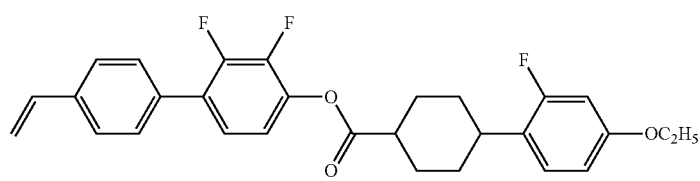 [SMILES: C=Cc1ccc(-c2ccc(OC(=O)C3CCC(c4ccc(OCC)cc4F)CC3)c(F)c2F)cc1] |
| 1815 | 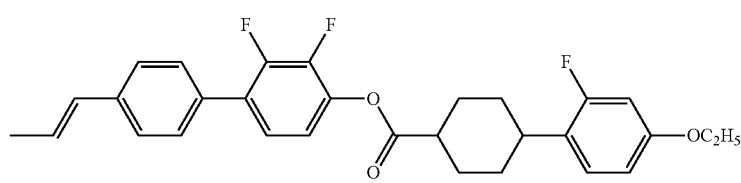 [SMILES: C/C=C/c1ccc(-c2ccc(OC(=O)C3CCC(c4ccc(OCC)cc4F)CC3)c(F)c2F)cc1] |
| 1816 | 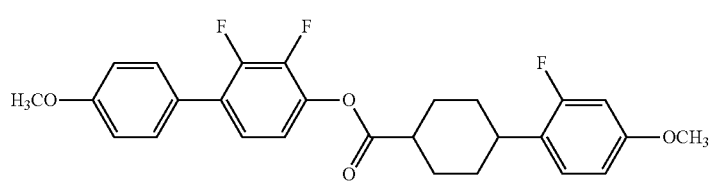 [SMILES: COc1ccc(-c2ccc(OC(=O)C3CCC(c4ccc(OC)cc4F)CC3)c(F)c2F)cc1] |
| 1817 | 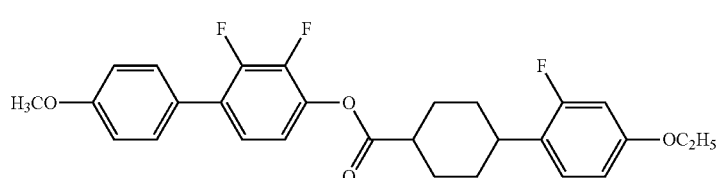 |
| 1818 | 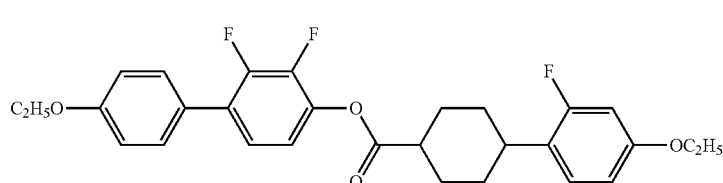 |
| 1819 | 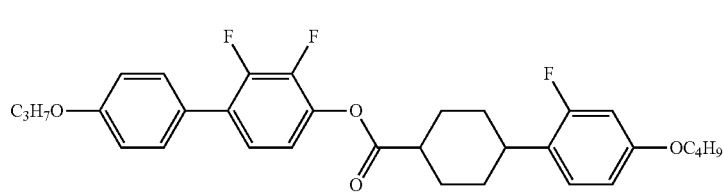 |

| No. | |
|---|---|
| 1820 | 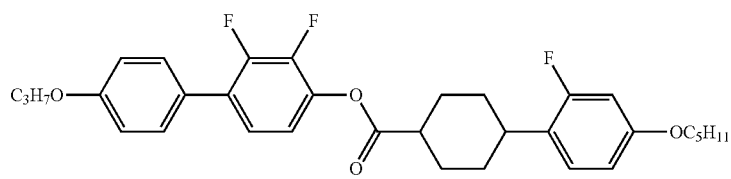 |
| 1821 | 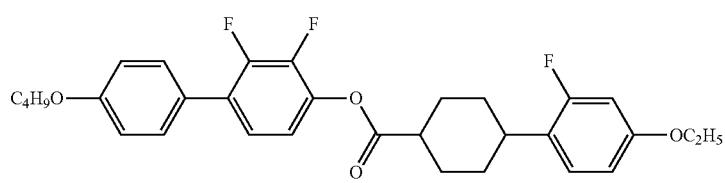 |
| 1822 | 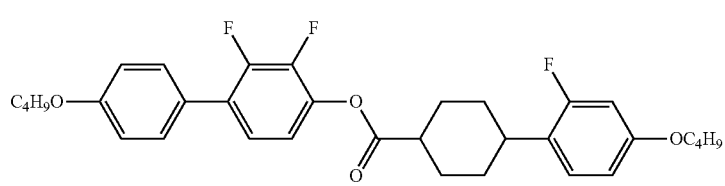 |
| 1823 | 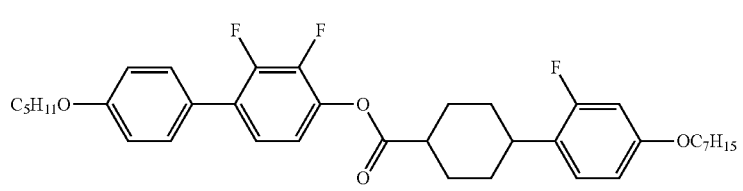 |
| 1824 | 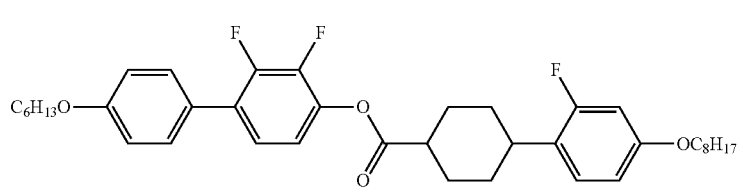 |
| 1825 | 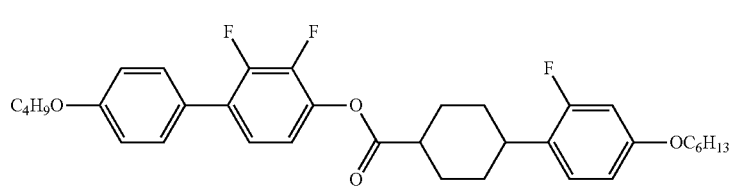 |
| 1826 | 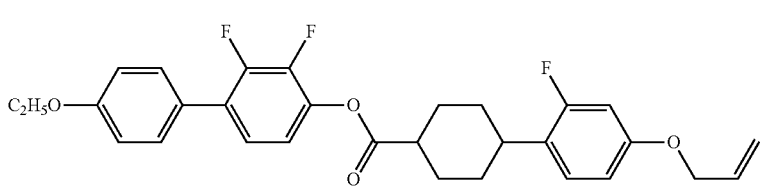 |
| 1827 | 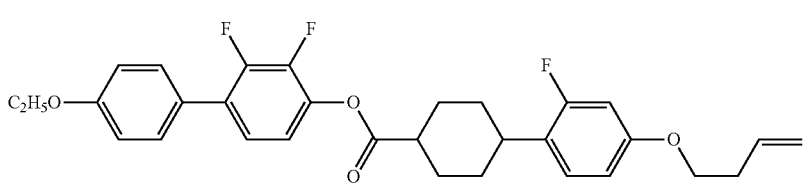 |

-continued
| No. | |
|---|---|
| 1828 | 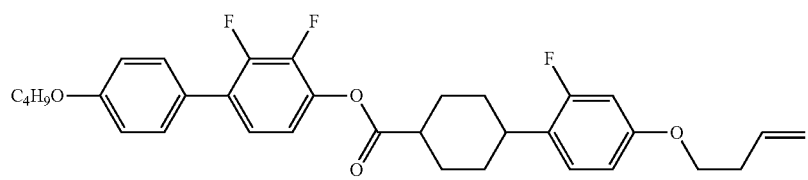 |
| 1829 | 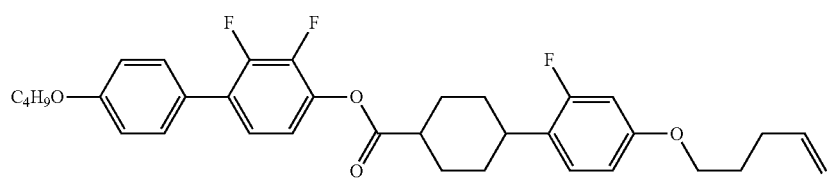 |
| 1830 | 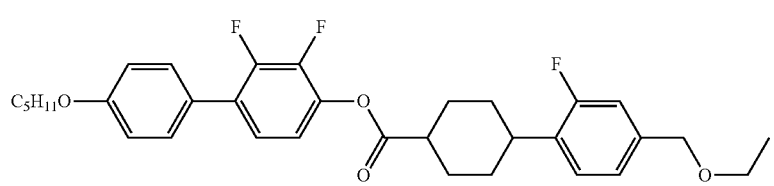 |
| 1831 | 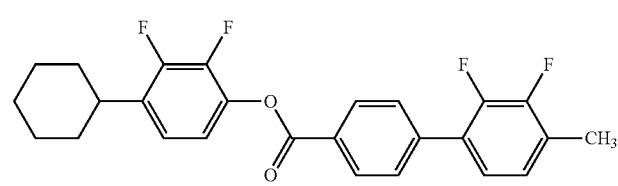 [SMILES: Cc1ccc(-c2ccc(C(=O)Oc3ccc(C4CCCCC4)c(F)c3F)cc2)c(F)c1F] |
| 1832 | 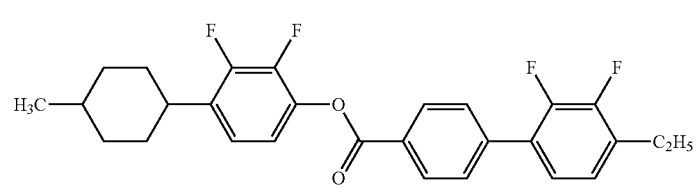 |
| 1833 | 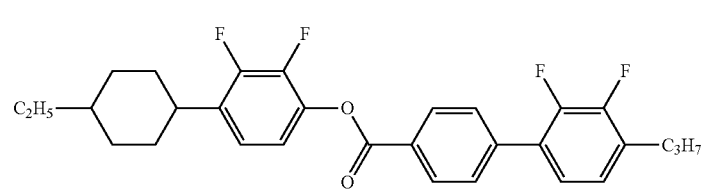 |
| 1834 | 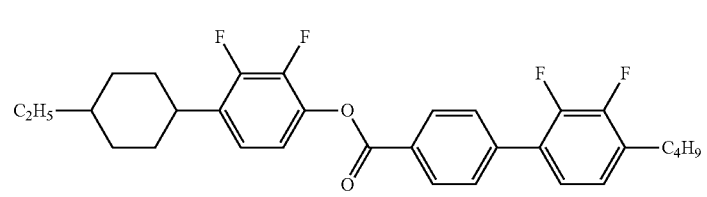 |
| 1835 | 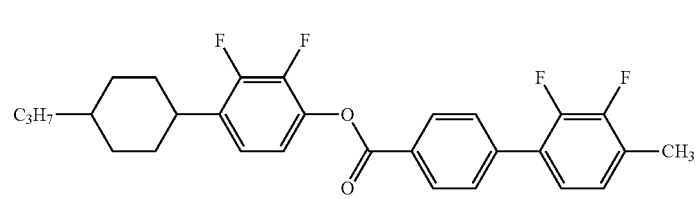 |

| No. | |
|---|---|
| 1836 | 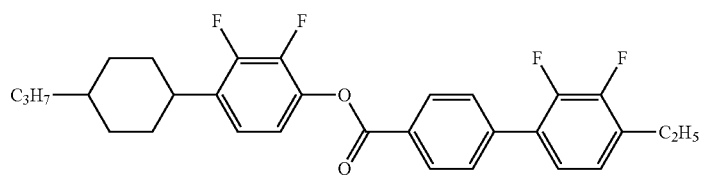 |
| 1837 | 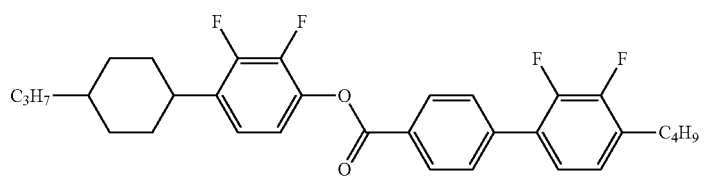 |
| 1838 | 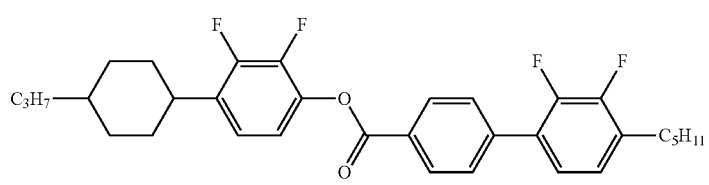 |
| 1839 | 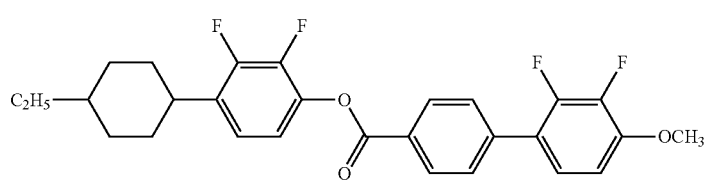 [SMILES: CCC1CCC(c2ccc(OC(=O)c3ccc(-c4ccc(OC)c(F)c4F)cc3)c(F)c2F)CC1] |
| 1840 | 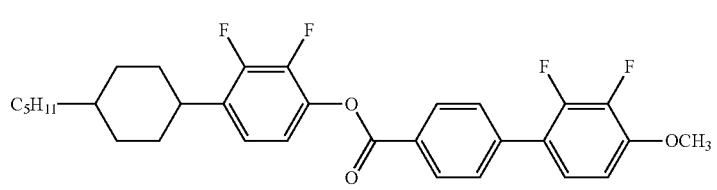 |
| 1841 | 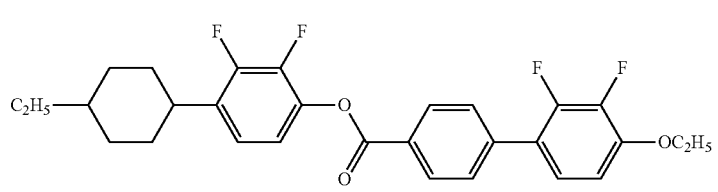 |
| 1842 | 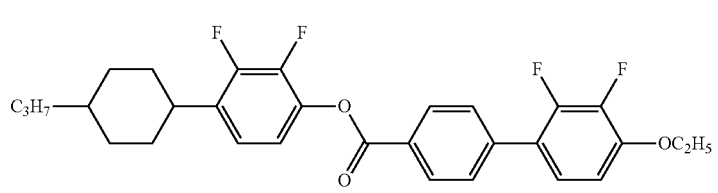 |
| 1843 | 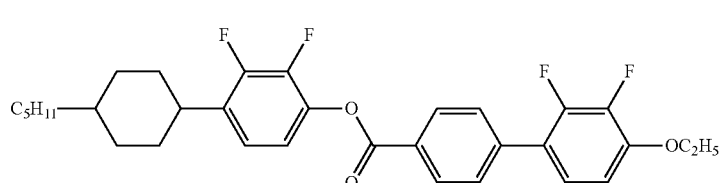 |
C 90.9 N 304.5 I
$T_{NI}$; 247.9° C., Δε; −5.82, Δn; 0.227

| No. | |
|---|---|
| 1844 | 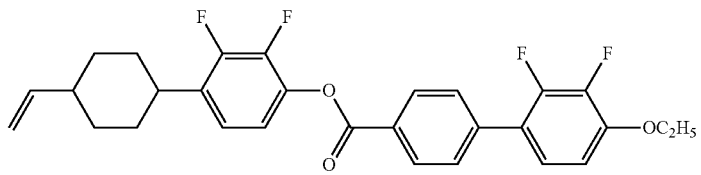 [SMILES: C=CC1CCC(c2ccc(OC(=O)c3ccc(-c4ccc(OCC)c(F)c4F)cc3)c(F)c2F)CC1] |
| 1845 | 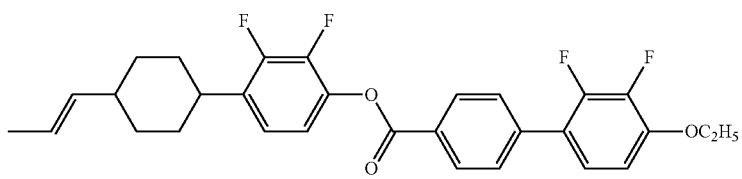 [SMILES: C/C=C/C1CCC(c2ccc(OC(=O)c3ccc(-c4ccc(OCC)c(F)c4F)cc3)c(F)c2F)CC1] |
| 1846 | 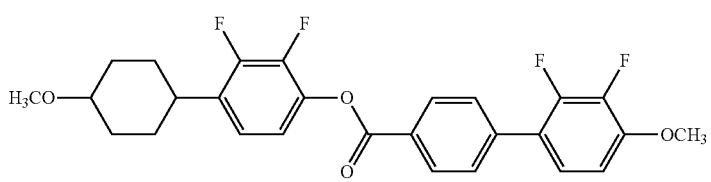 [SMILES: COc1ccc(-c2ccc(C(=O)Oc3ccc(C4CCC(OC)CC4)c(F)c3F)cc2)c(F)c1F] |
| 1847 | 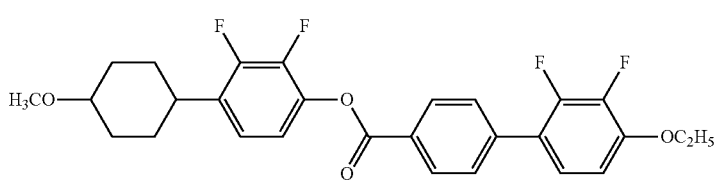 [SMILES: CCOc1ccc(-c2ccc(C(=O)Oc3ccc(C4CCC(OC)CC4)c(F)c3F)cc2)c(F)c1F] |
| 1848 | 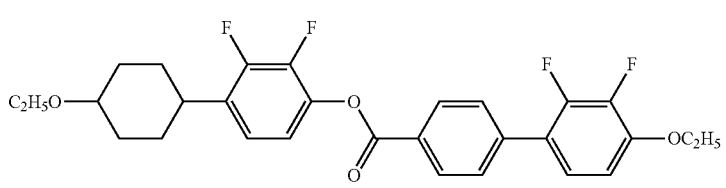 |
| 1849 | 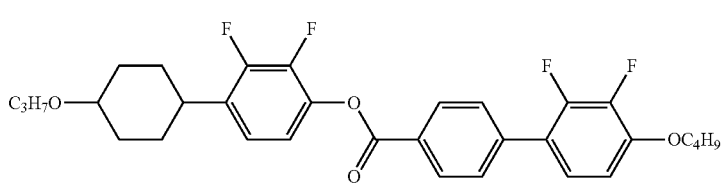 |
| 1850 | 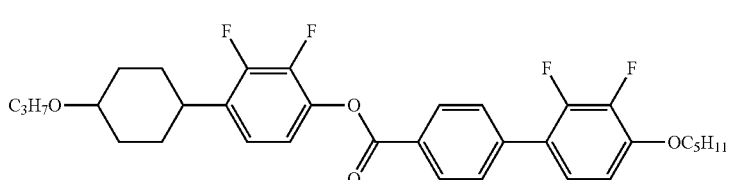 |
| 1851 | 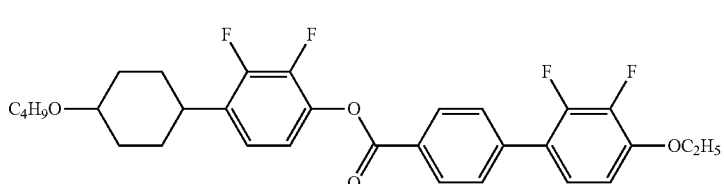 |

| No. |
|---|
| 1852 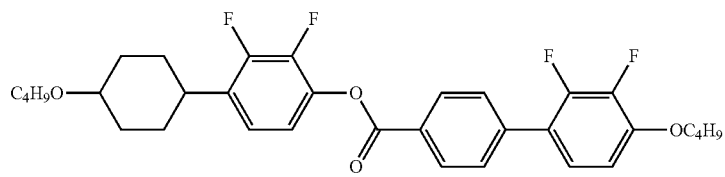 |
| 1853 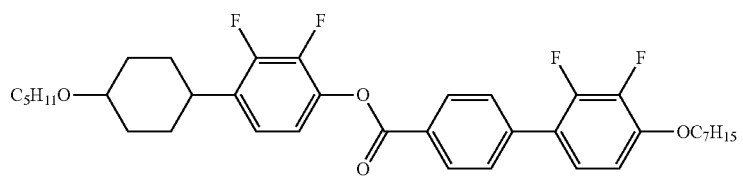 |
| 1854 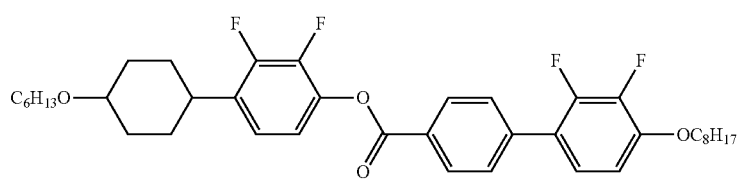 |
| 1855 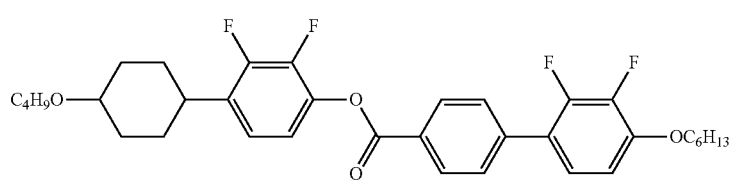 |
| 1856 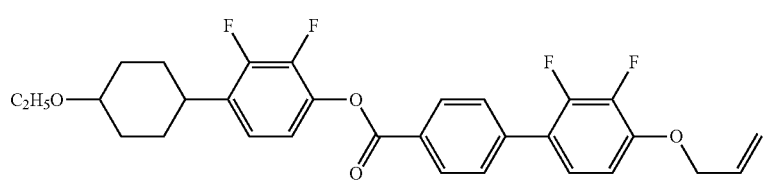 |
| 1857 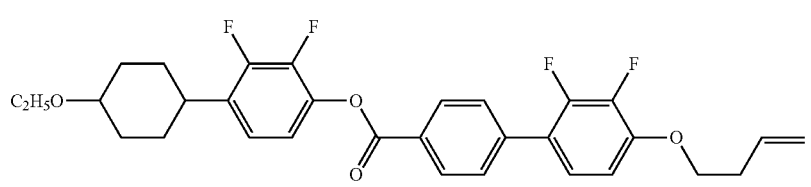 |
| 1858 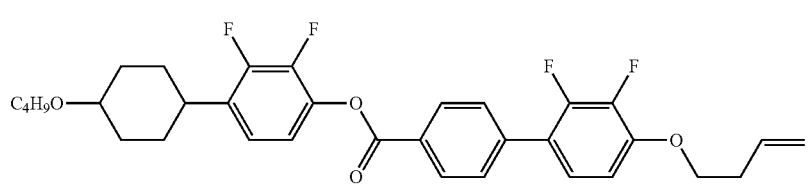 |
| 1859 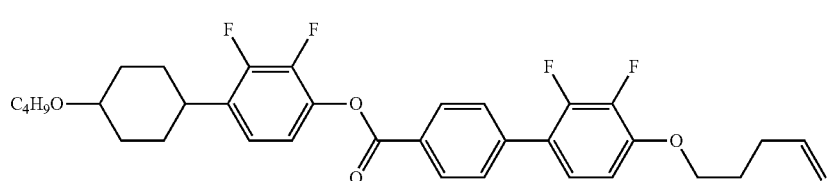 |

| No. | |
|---|---|
| 1860 | 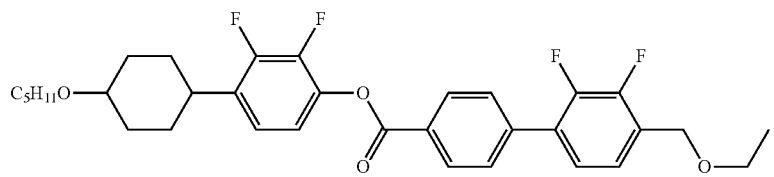 |
| 1861 | 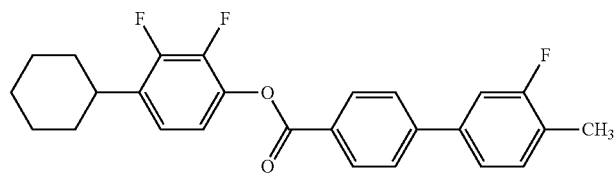 [SMILES: Cc1ccc(-c2ccc(C(=O)Oc3ccc(C4CCCCC4)c(F)c3F)cc2)cc1F] |
| 1862 | 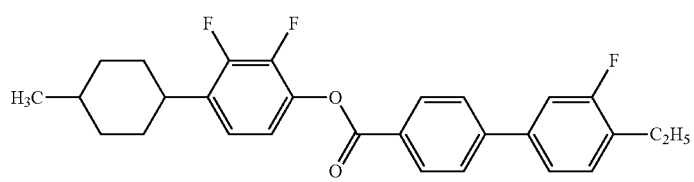 |
| 1863 | 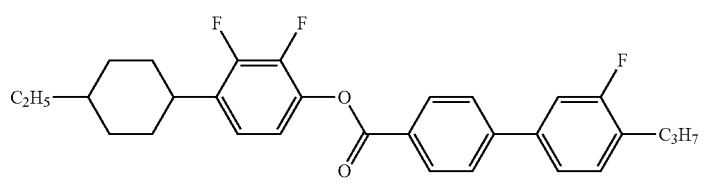 |
| 1864 | 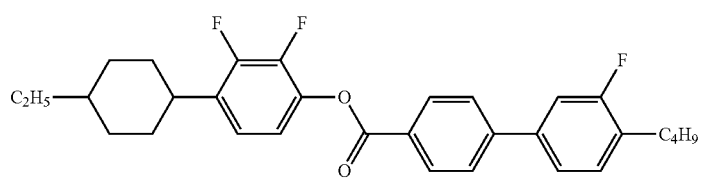 |
| 1865 | 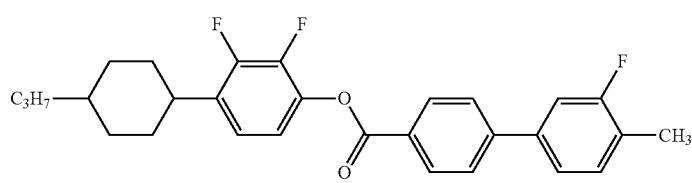 |
| 1866 | 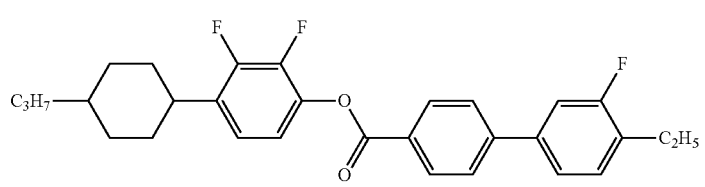 |
| 1867 | 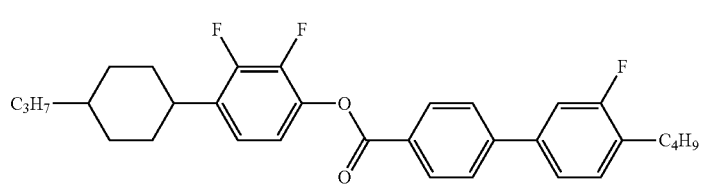 |

| No. | |
|---|---|
| 1868 | 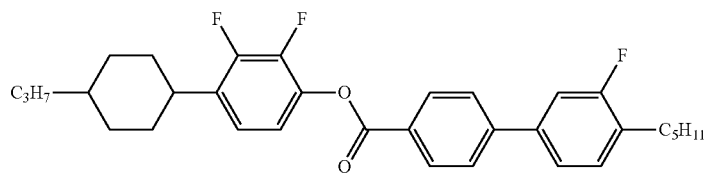 |
| 1869 | 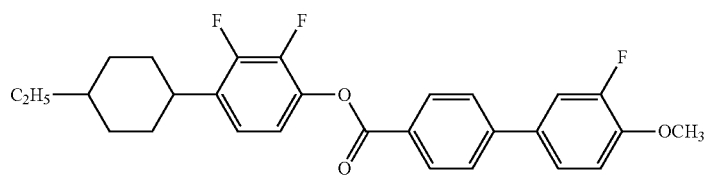 |
| 1870 | 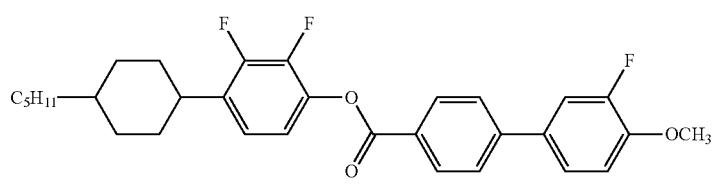 |
| 1871 | 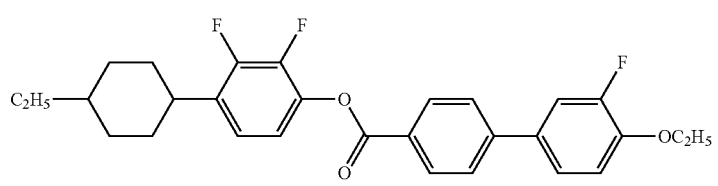 |
| 1872 | 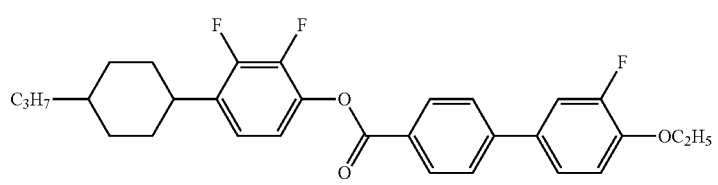 |
| 1873 | 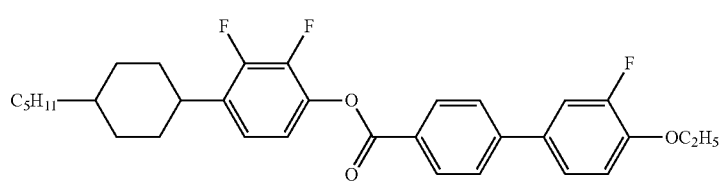 |
| 1874 | 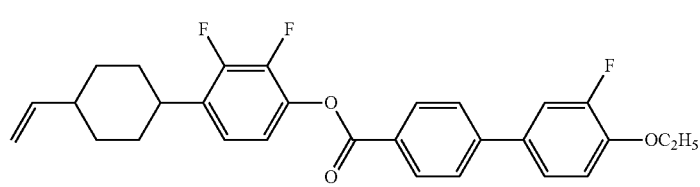 [SMILES: C=CC1CCC(c2ccc(OC(=O)c3ccc(-c4ccc(OCC)c(F)c4)cc3)c(F)c2F)CC1] |
| 1875 | 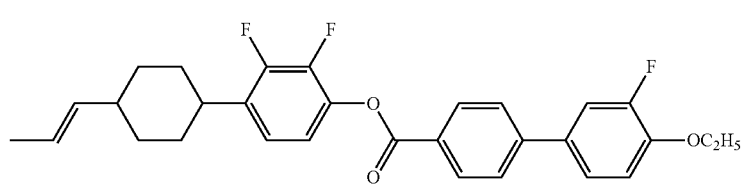 |

| No. | |
|---|---|
| 1876 | 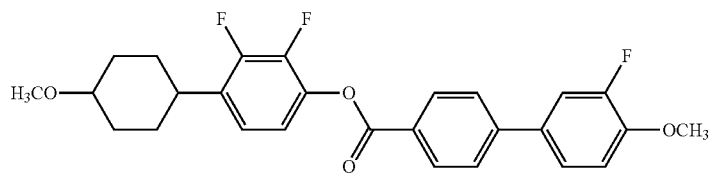 |
| 1877 | 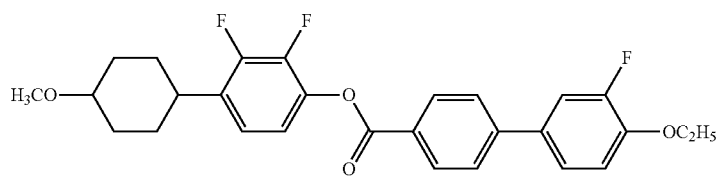 [SMILES: CCOc1ccc(-c2ccc(C(=O)Oc3ccc(C4CCC(OC)CC4)c(F)c3F)cc2)cc1F] |
| 1878 | 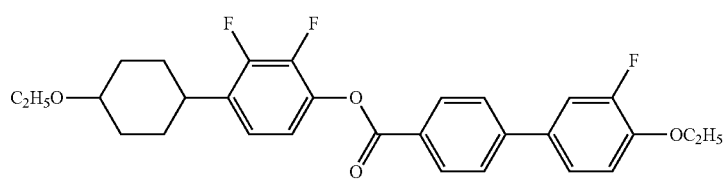 |
| 1879 | 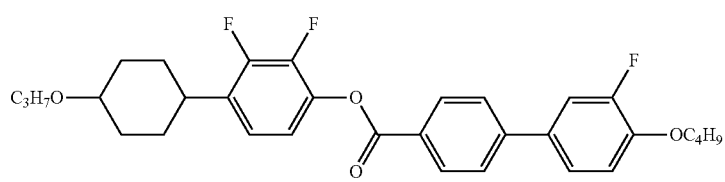 |
| 1880 | 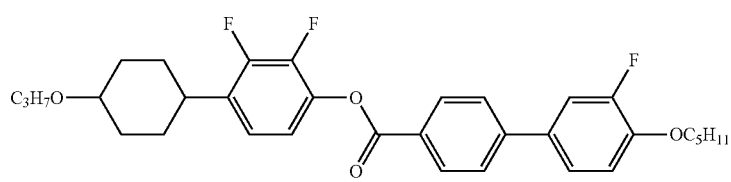 |
| 1881 | 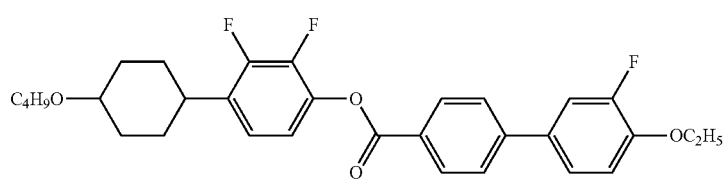 |
| 1882 | 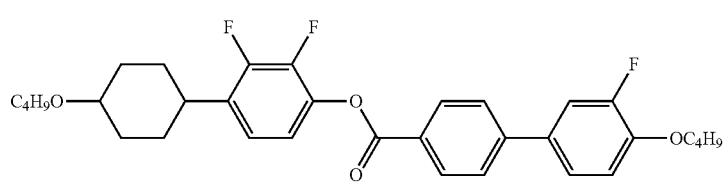 |
| 1883 | 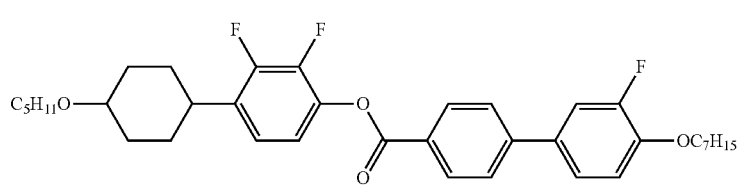 |

| No. | |
|---|---|
| 1884 | 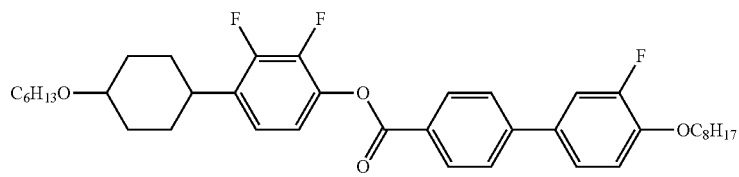 |
| 1885 | 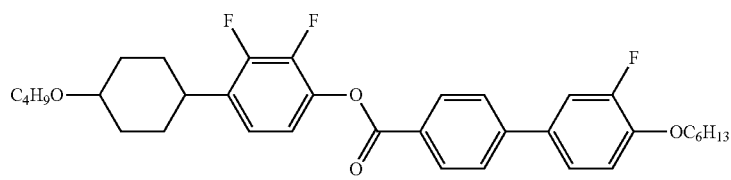 |
| 1886 | 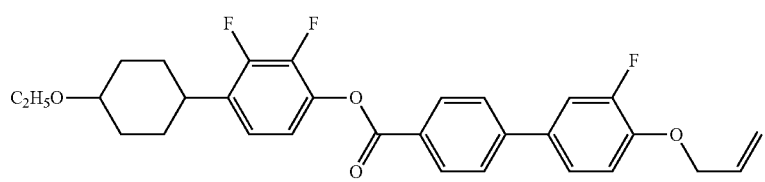 |
| 1887 | 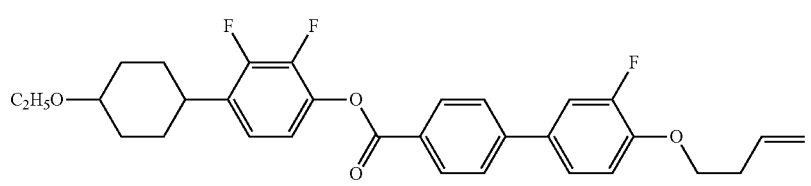 |
| 1888 | 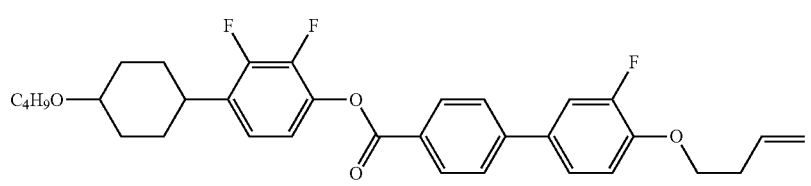 |
| 1889 | 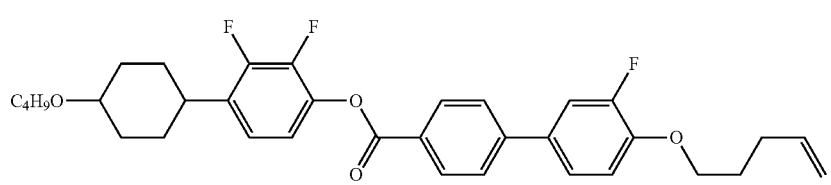 |
| 1890 | 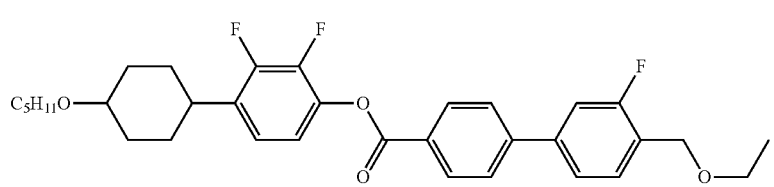 |
| 1891 | 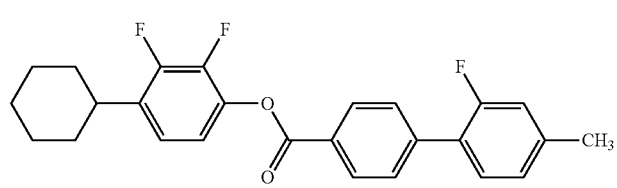 |

-continued
| No. | |
|---|---|
| 1892 | 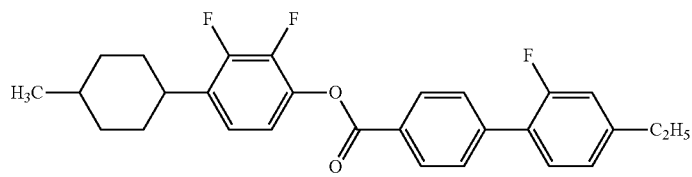 [SMILES: CCc1ccc(-c2ccc(C(=O)Oc3ccc(C4CCC(C)CC4)c(F)c3F)cc2)c(F)c1] |
| 1893 | 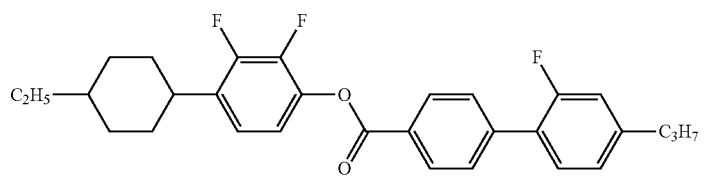 |
| 1894 | 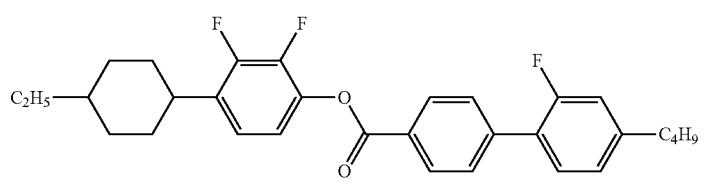 |
| 1895 | 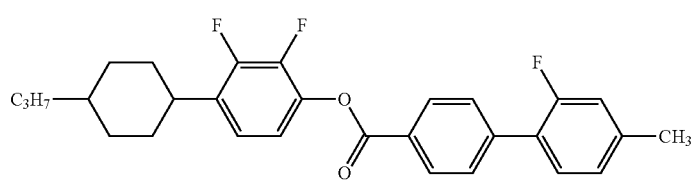 |
| 1896 | 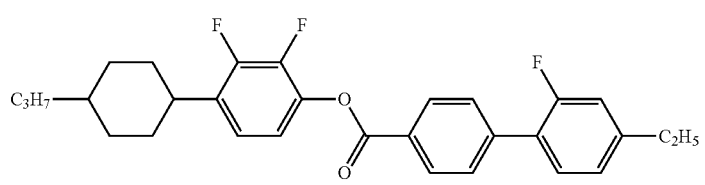 |
| 1897 | 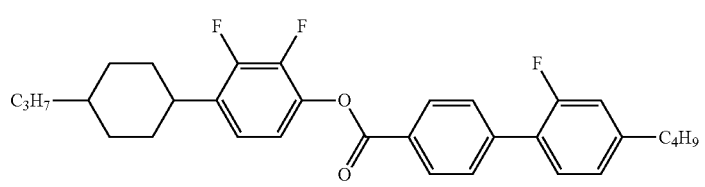 |
| 1898 | 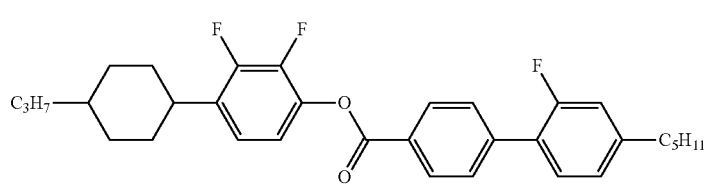 |
| 1899 | 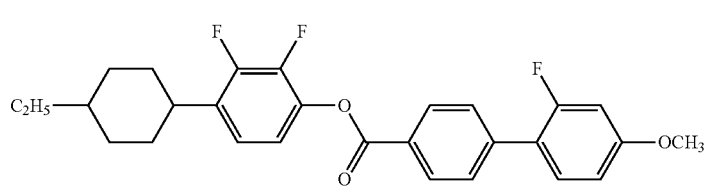 |

| No. | |
|---|---|
| 1900 | 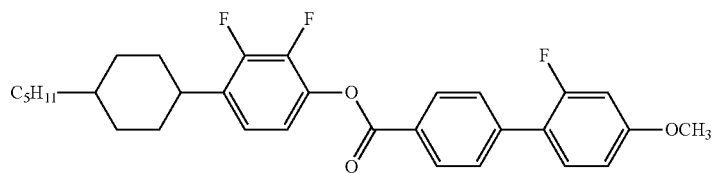 |
| 1901 | 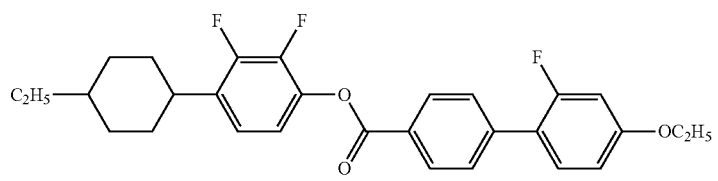 |
| 1902 | 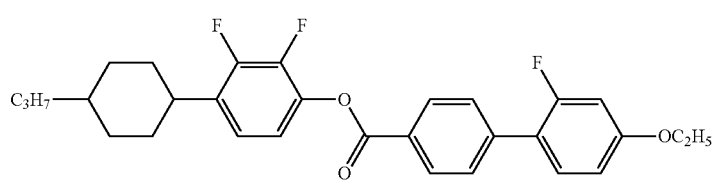 |
| 1903 | 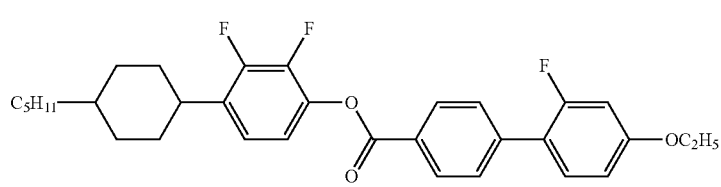 |
| 1904 | 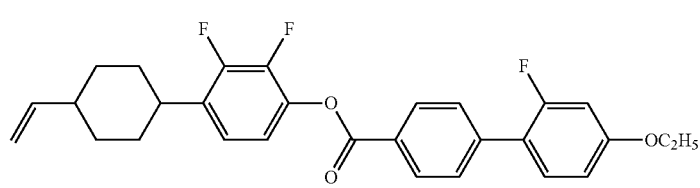 [SMILES: C=CC1CCC(c2ccc(OC(=O)c3ccc(-c4ccc(OCC)cc4F)cc3)c(F)c2F)CC1] |
| 1905 | 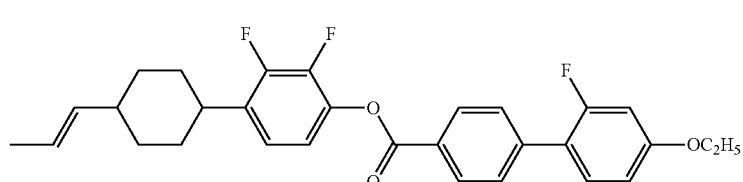 |
| 1906 | 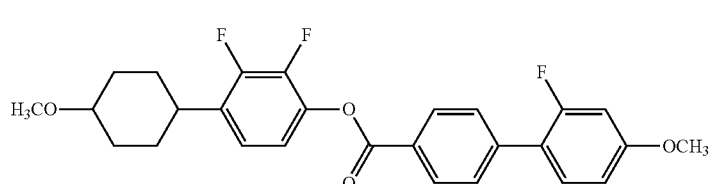 |
| 1907 | 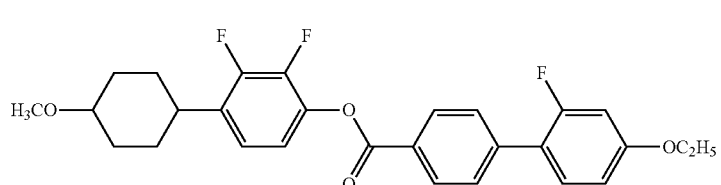 |

-continued
| No. | |
|---|---|
| 1908 | 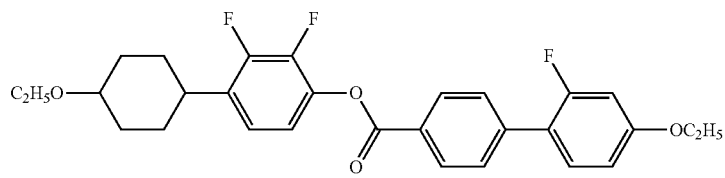 |
| 1909 | 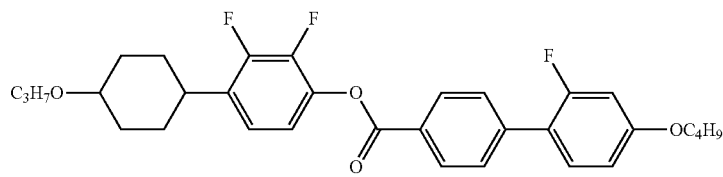 |
| 1910 | 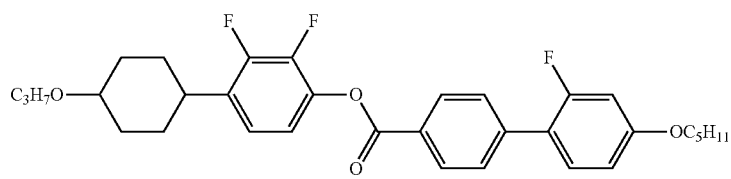 |
| 1911 | 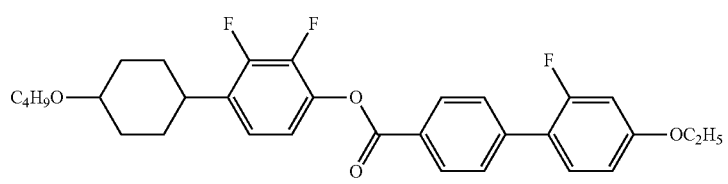 |
| 1912 | 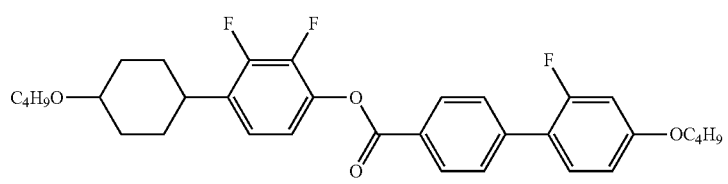 |
| 1913 | 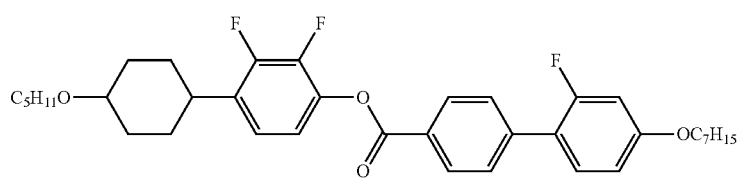 |
| 1914 | 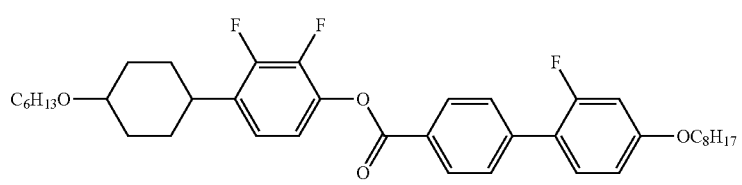 |
| 1915 | 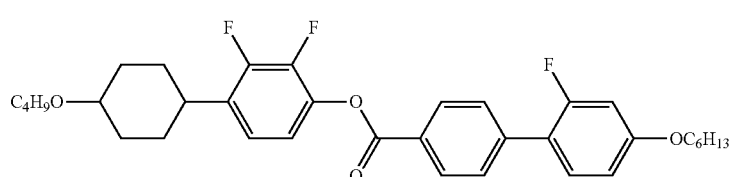 |

| No. | |
|---|---|
| 1916 | 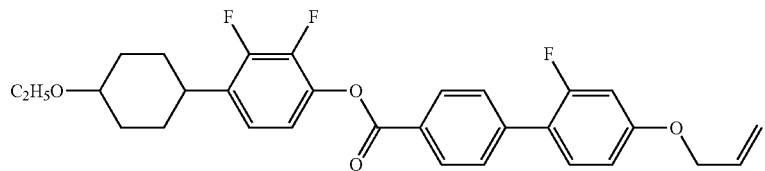 |
| 1917 | 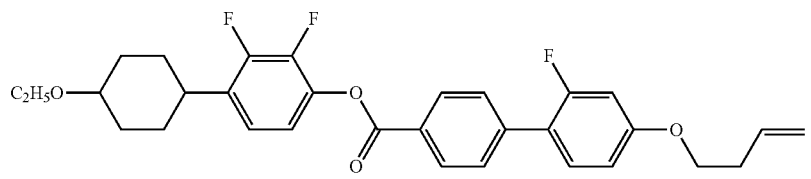 |
| 1918 | 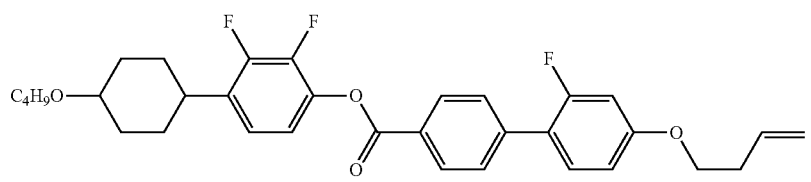 |
| 1919 | 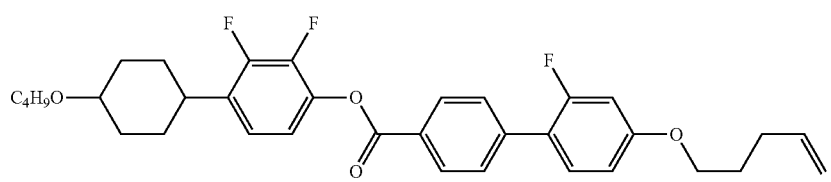 |
| 1920 | 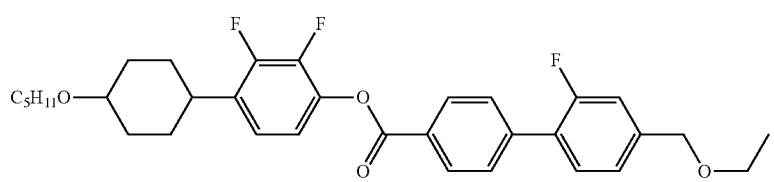 |
| 1921 | 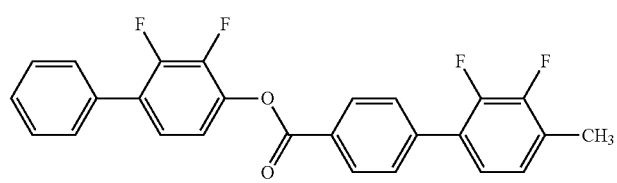 |
| 1922 | 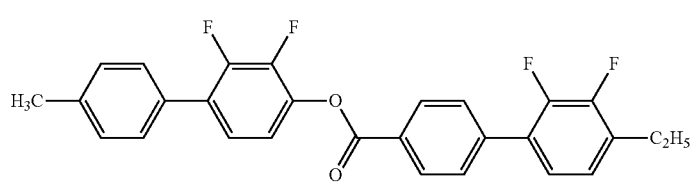 |
| 1923 | 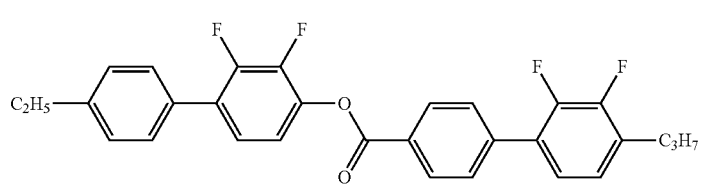 |

| No. | |
|---|---|
| 1924 | 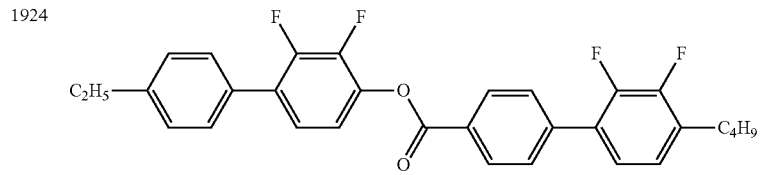 |
| 1925 | 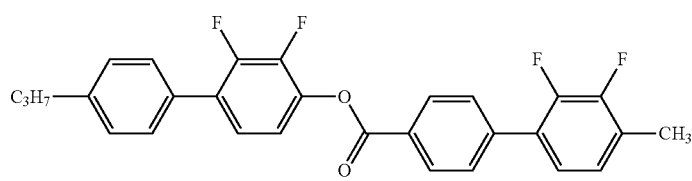 |
| 1926 | 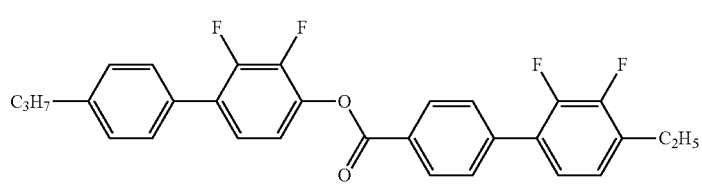 |
| 1927 | 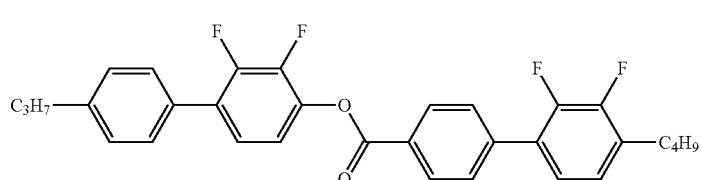 |
| 1928 | 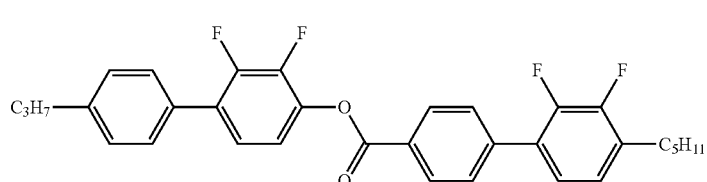 |
| 1929 | 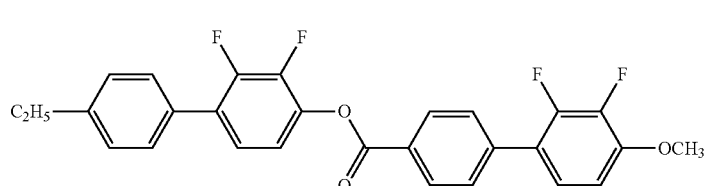 |
| 1930 | 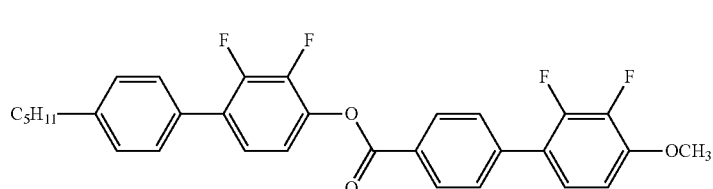 |
| 1931 | 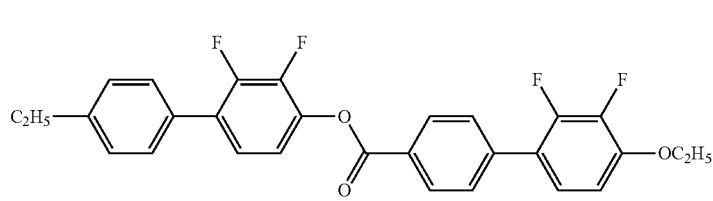 |

| No. | |
|---|---|
| 1932 | 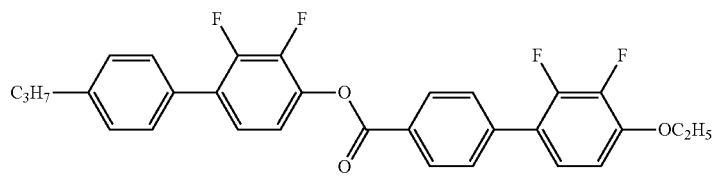 |
| 1933 | 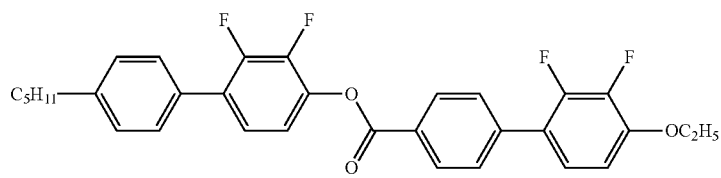 |
| 1934 | 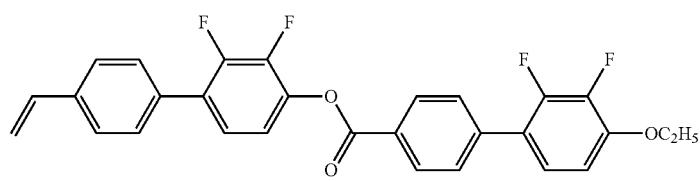 |
| 1935 | 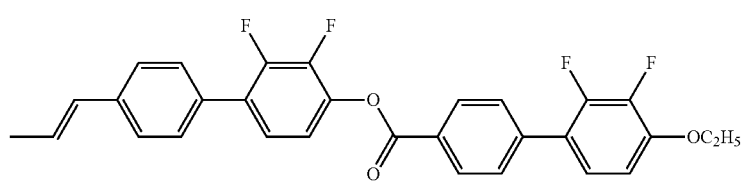 |
| 1936 | 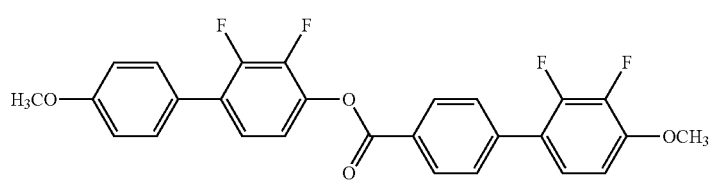 |
| 1937 | 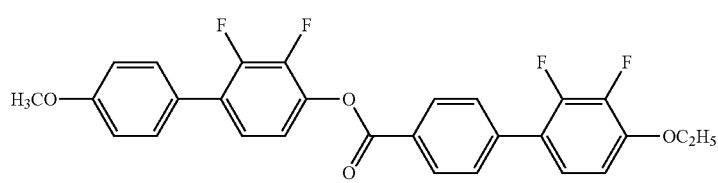 [SMILES: CCOc1ccc(-c2ccc(C(=O)Oc3ccc(-c4ccc(OC)cc4)c(F)c3F)cc2)c(F)c1F] |
| 1938 | 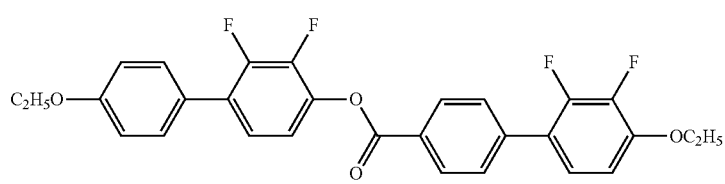 |
| 1939 | 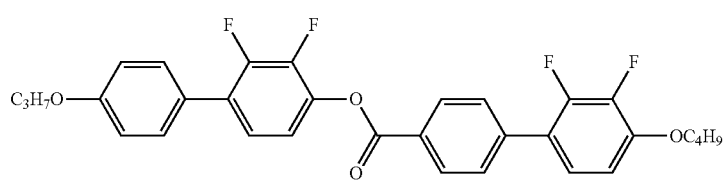 |

| No. | |
|---|---|
| 1940 | 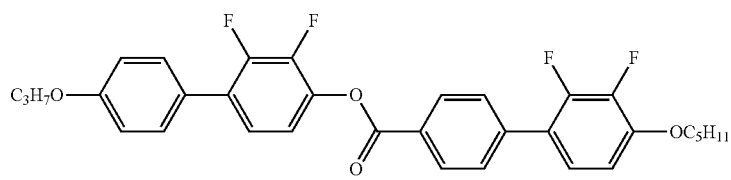 |
| 1941 | 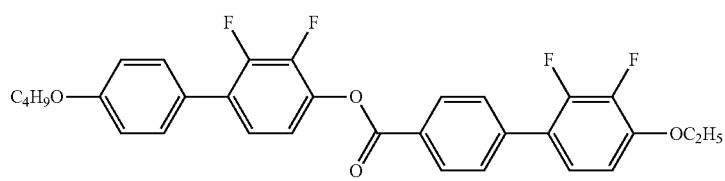 |
| 1942 | 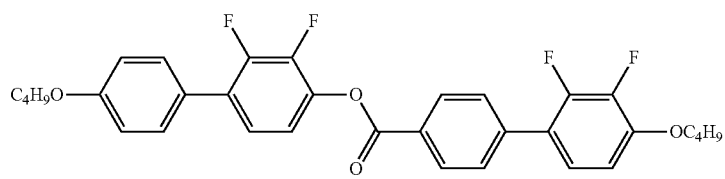 |
| 1943 | 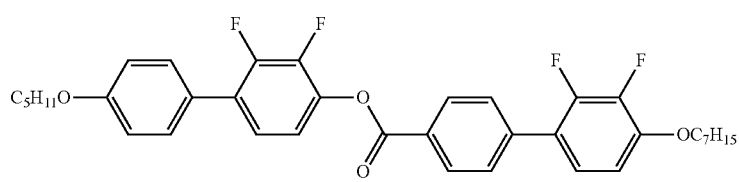 |
| 1944 | 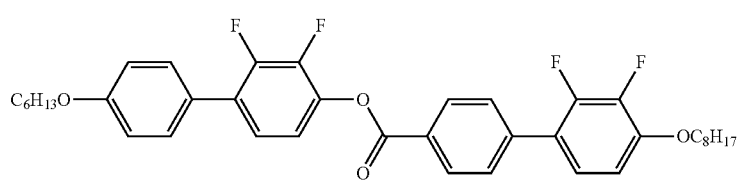 |
| 1945 | 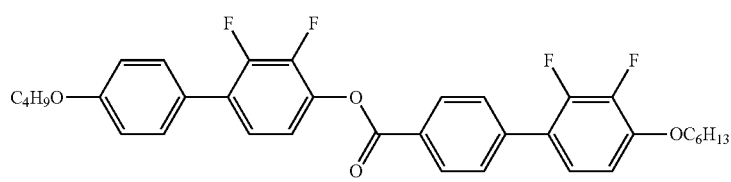 |
| 1946 | 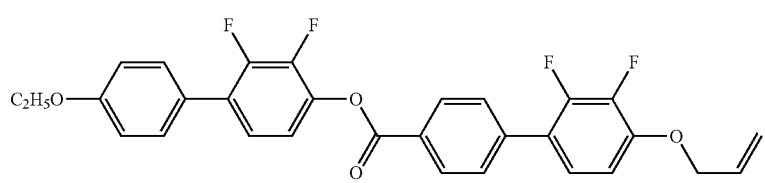 |
| 1947 | 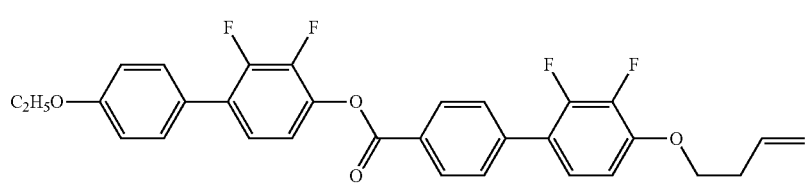 |

| No. | |
|---|---|
| 1948 | 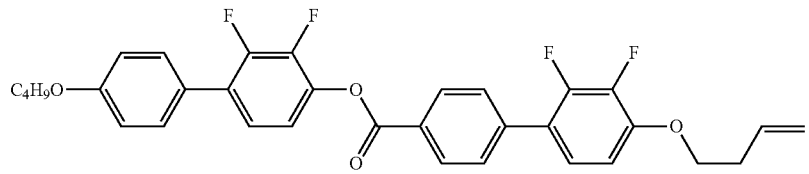 |
| 1949 | 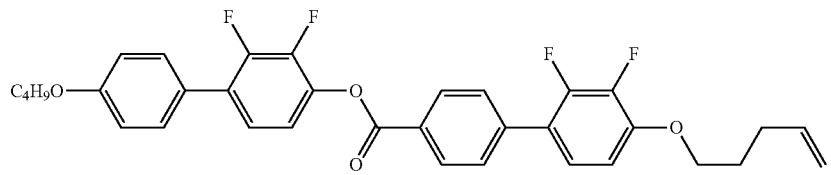 |
| 1950 | 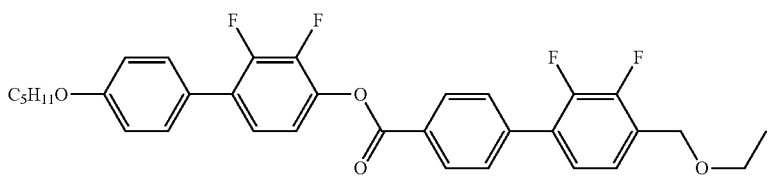 |
| 1951 | 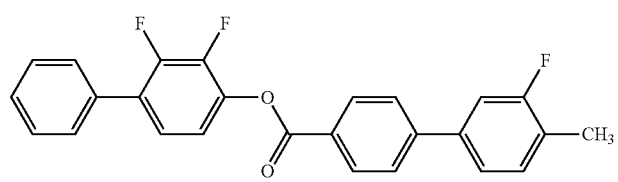 [SMILES: Cc1ccc(-c2ccc(C(=O)Oc3ccc(-c4ccccc4)c(F)c3F)cc2)cc1F] |
| 1952 | 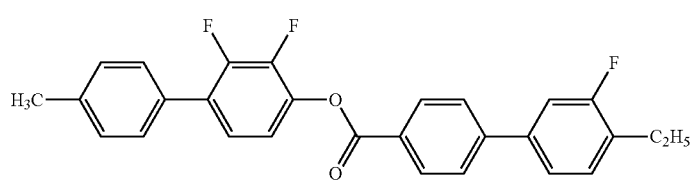 |
| 1953 | 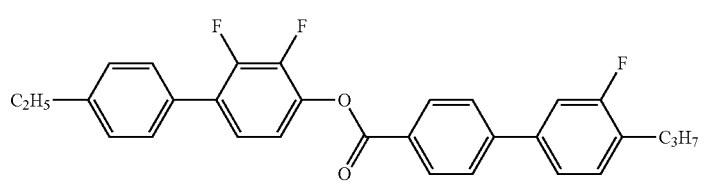 |
| 1954 | 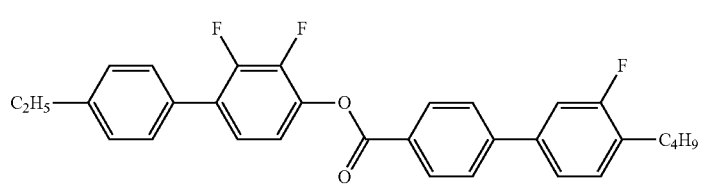 |
| 1955 | 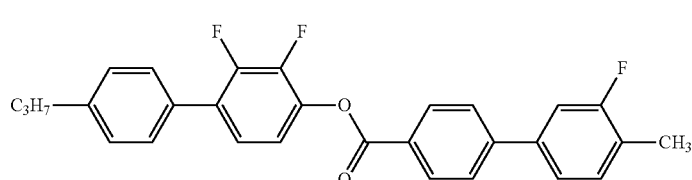 |

| No. | |
|---|---|
| 1956 | 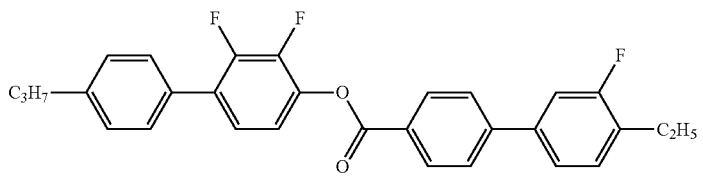 |
| 1957 | 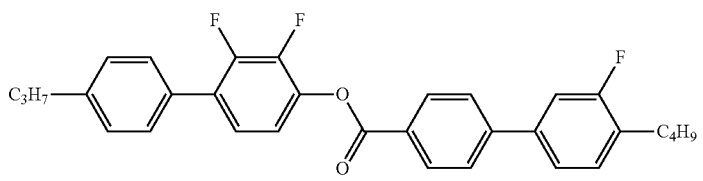 |
| 1958 | 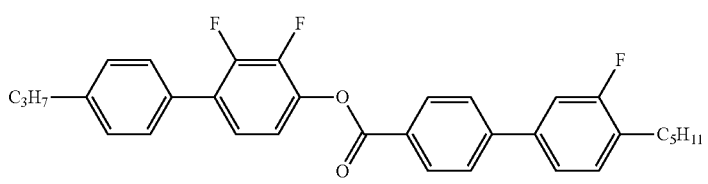 |
| 1959 | 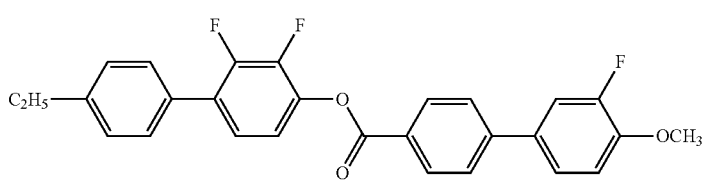 |
| 1960 | 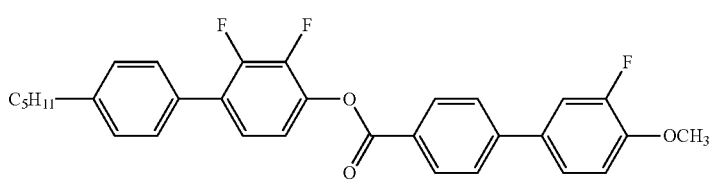 |
| 1961 | 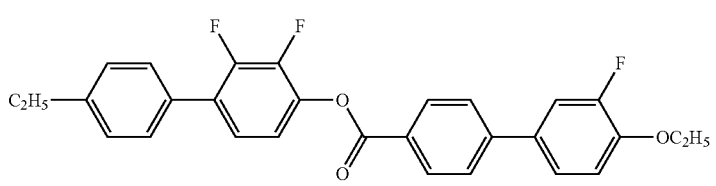 |
| 1962 | 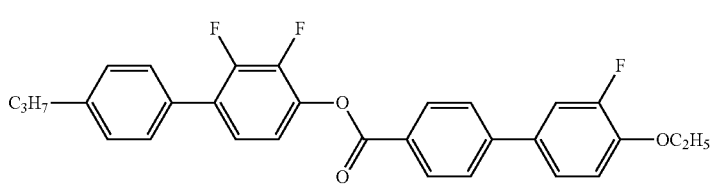 |
| 1663 | 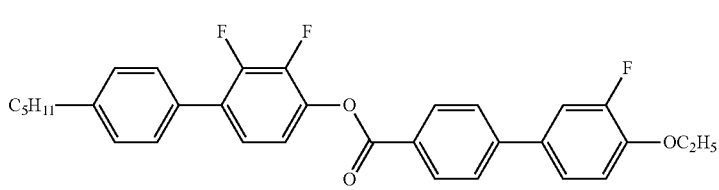 |

| No. | |
|---|---|
| 1964 | 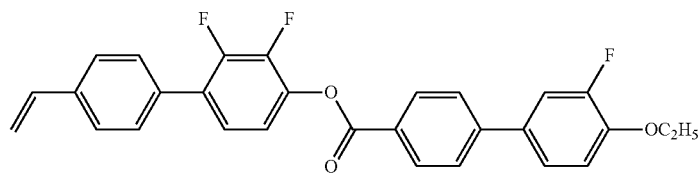 |
| 1965 | 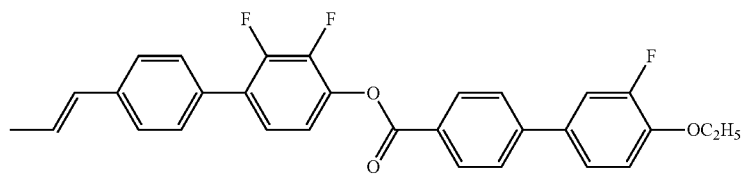 [SMILES: C/C=C/c1ccc(-c2ccc(OC(=O)c3ccc(-c4ccc(OCC)c(F)c4)cc3)c(F)c2F)cc1] |
| 1966 | 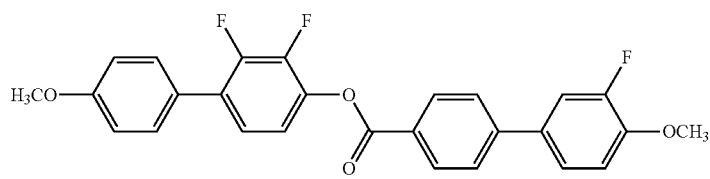 |
| 1967 | 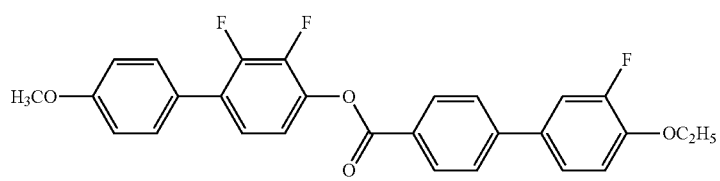 |
| 1968 | 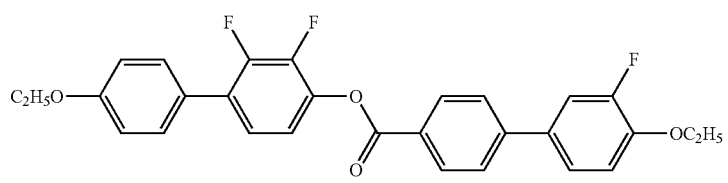 |
| 1969 | 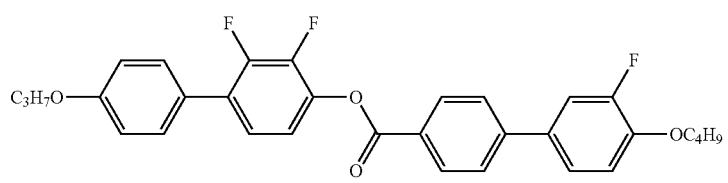 |
| 1970 | 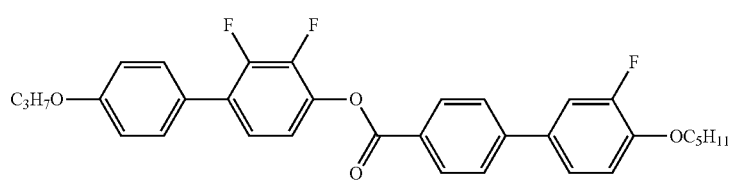 |
| 1971 | 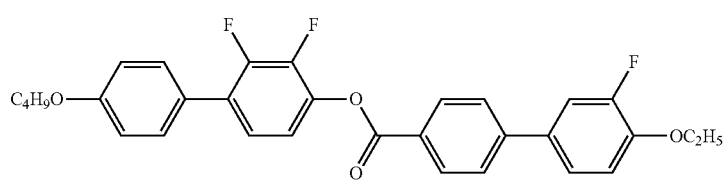 |

| No. | |
|---|---|
| 1972 | 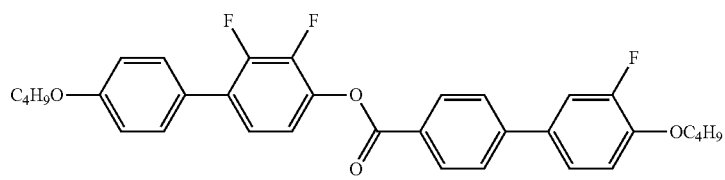 |
| 1973 | 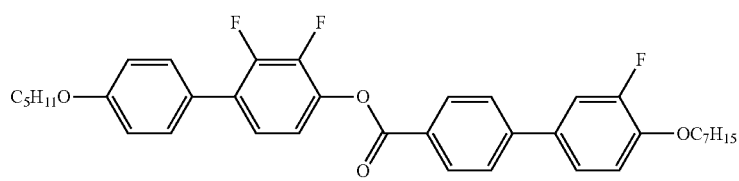 |
| 1974 | 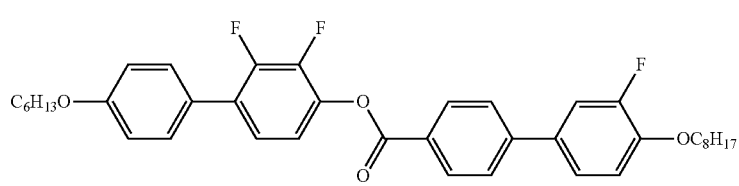 |
| 1975 | 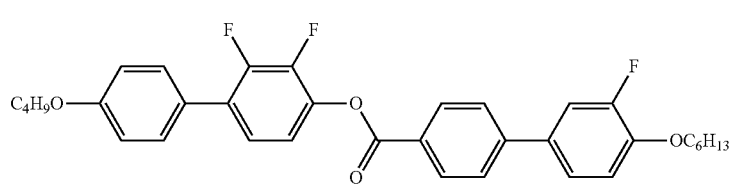 |
| 1976 | 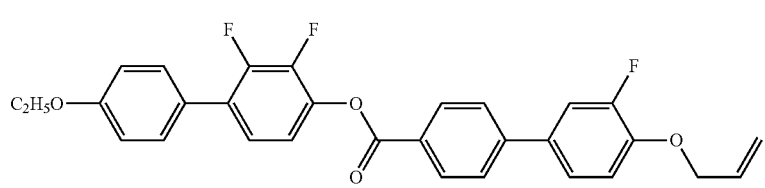 |
| 1977 | 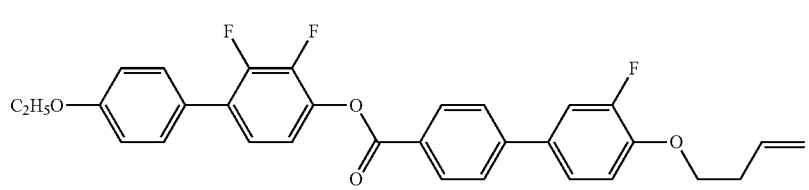 |
| 1978 | 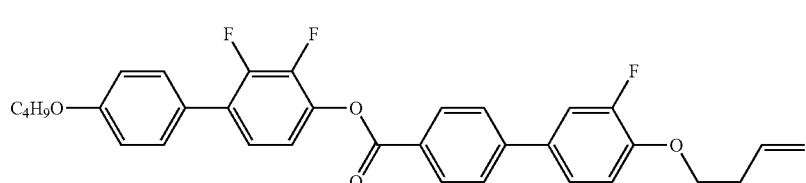 |
| 1979 | 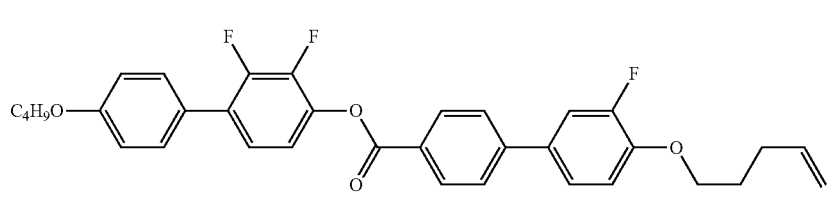 |

| No. |
|---|
| 1980 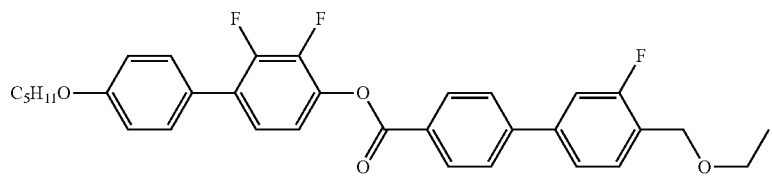 |
| 1981 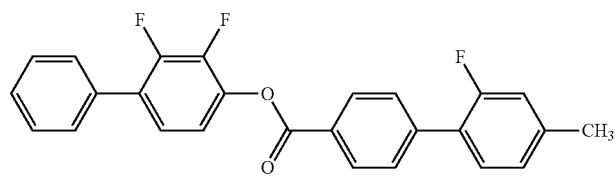 |
| 1982 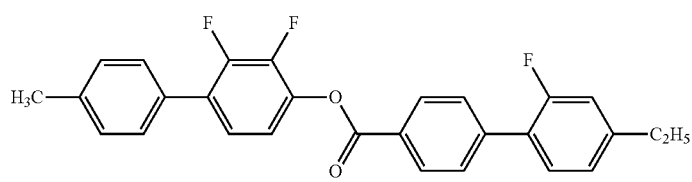 [SMILES: CCc1ccc(-c2ccc(C(=O)Oc3ccc(-c4ccc(C)cc4)c(F)c3F)cc2)c(F)c1] |
| 1983 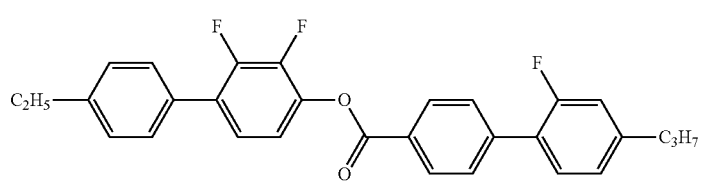 |
| 1984 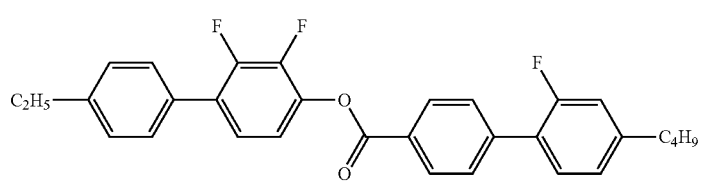 |
| 1985 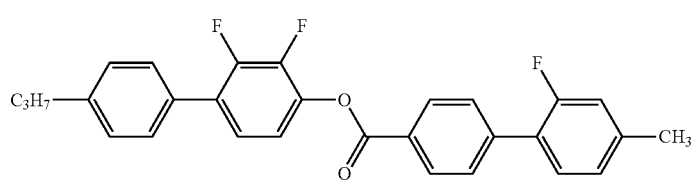 |
| 1986 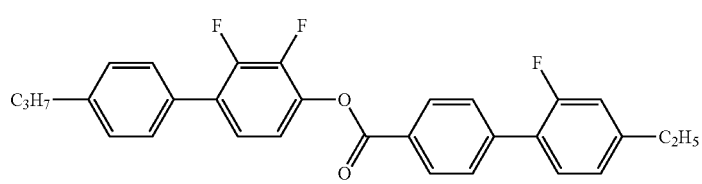 |
| 1987 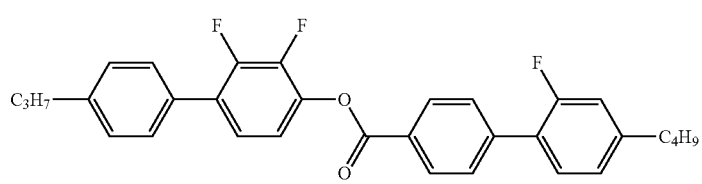 |

-continued
| No. | |
|---|---|
| 1988 | 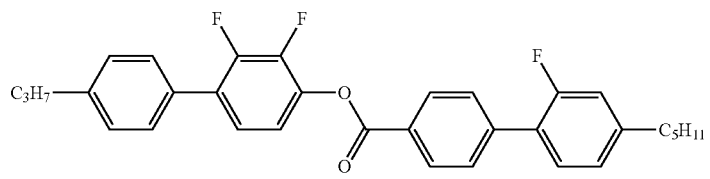 |
| 1989 | 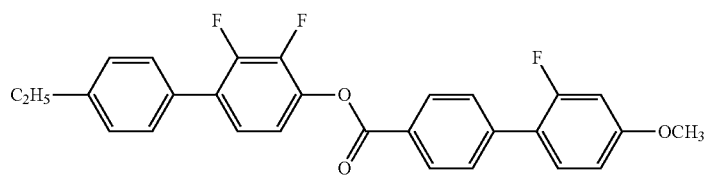 |
| 1990 | 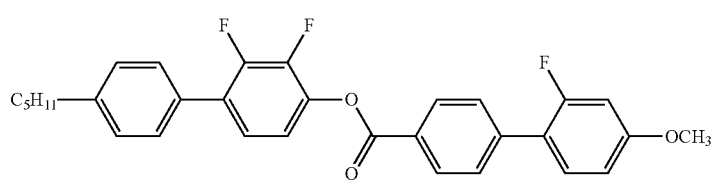 |
| 1991 | 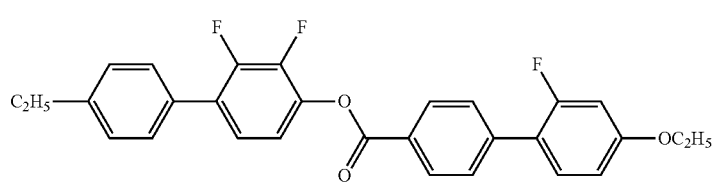 |
| 1992 | 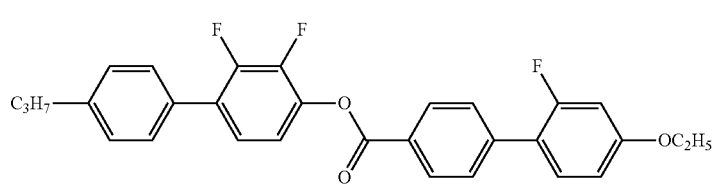 |
| 1993 | 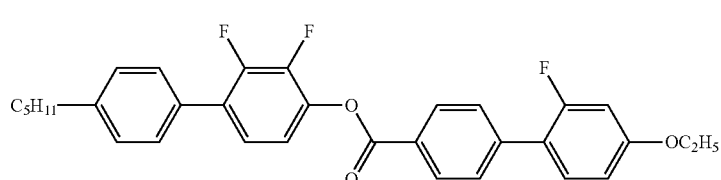 |
| 1994 | 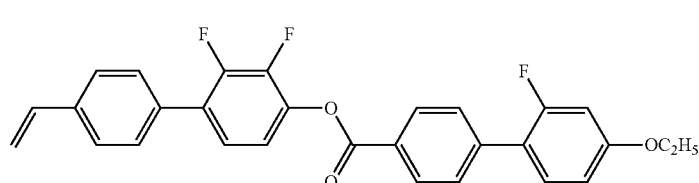 |
| 1995 | 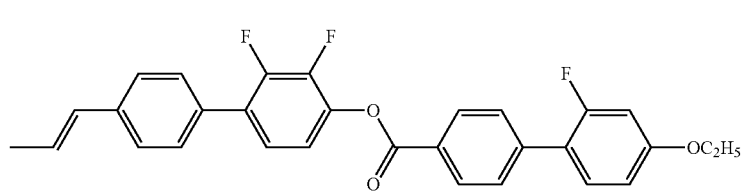 |

-continued
| No. |
|---|
| 1996 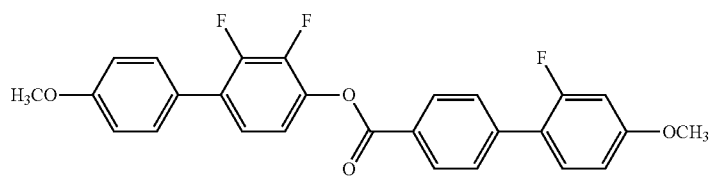 [SMILES: COc1ccc(-c2ccc(OC(=O)c3ccc(-c4ccc(OC)cc4F)cc3)c(F)c2F)cc1] |
| 1997 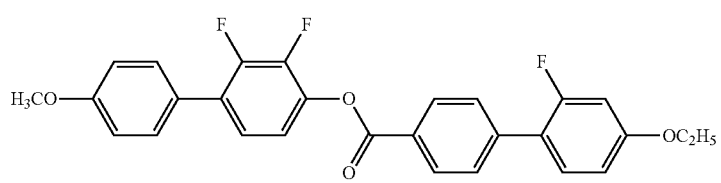 |
| 1998 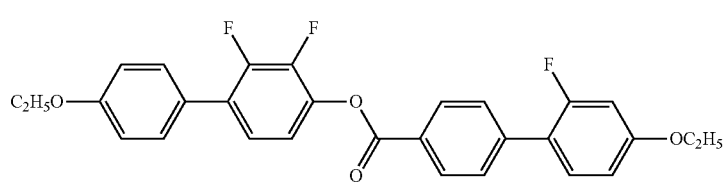 |
| 1999 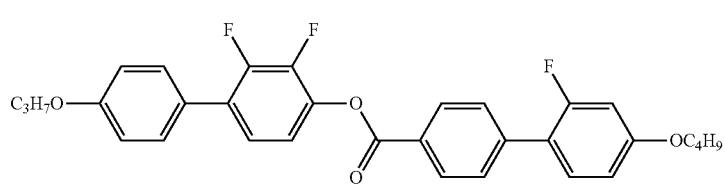 |
| 2000 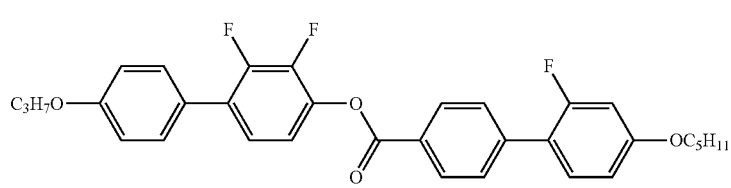 |
| 2001 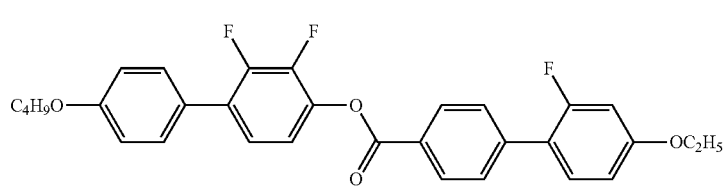 |
| 2002 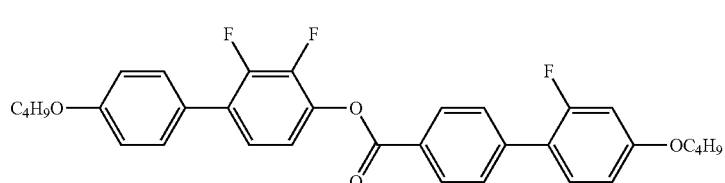 |
| 2003 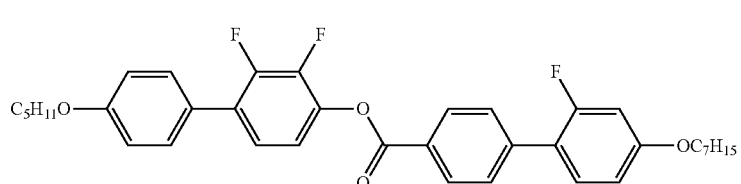 |

| No. | |
|---|---|
| 2004 | 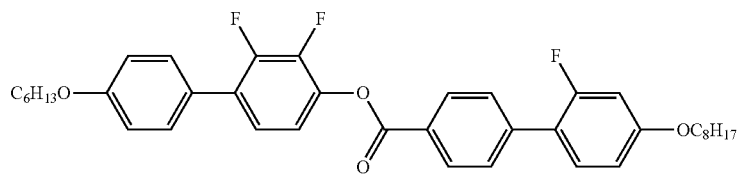 |
| 2005 | 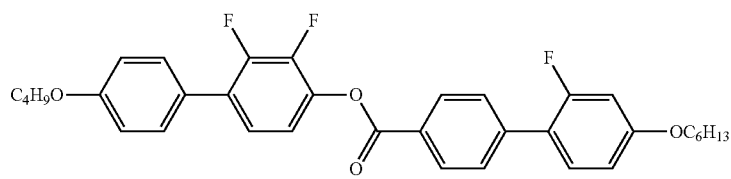 |
| 2006 | 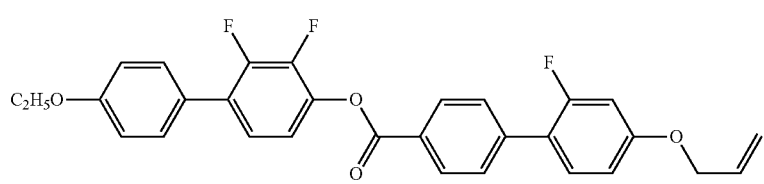 |
| 2007 | 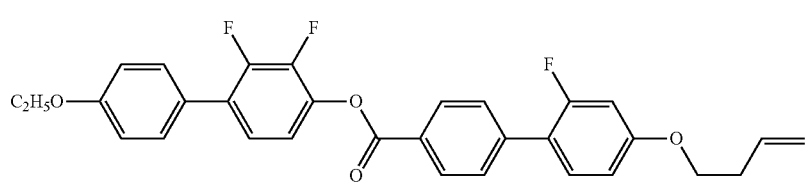 |
| 2008 | 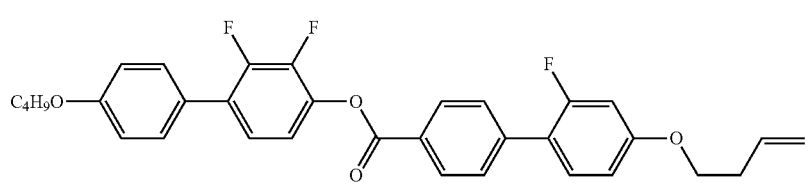 |
| 2009 | 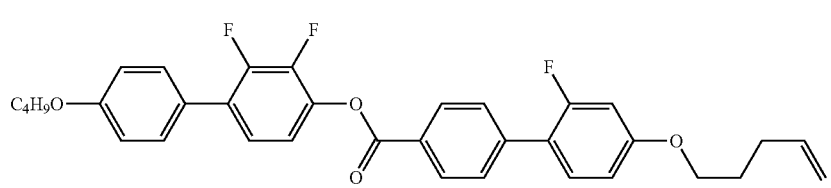 |
| 2010 | 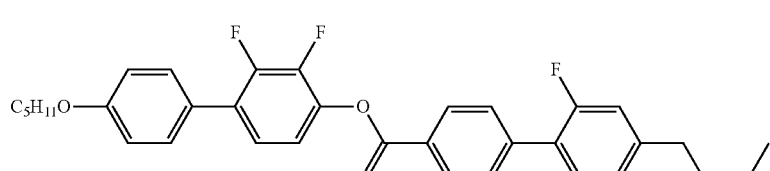 |
| 2011 | 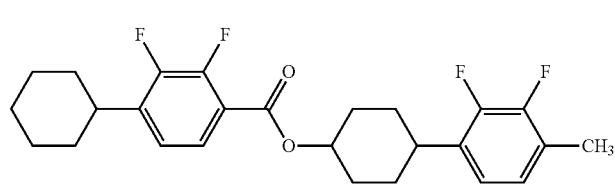 [SMILES: Cc1ccc(C2CCC(OC(=O)c3ccc(C4CCCCC4)c(F)c3F)CC2)c(F)c1F] |

-continued
| No. | |
|---|---|
| 2012 | 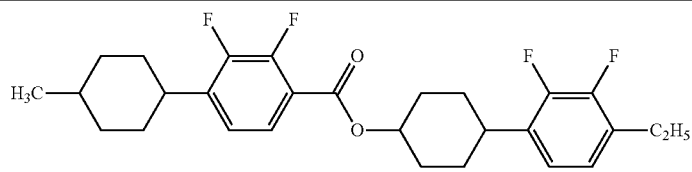 |
| 2013 | 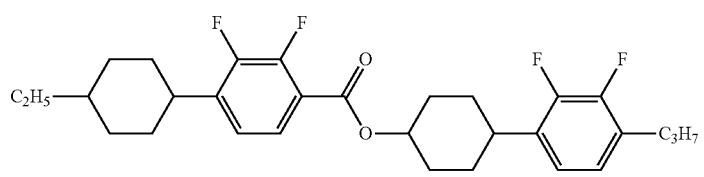 |
| 2014 | 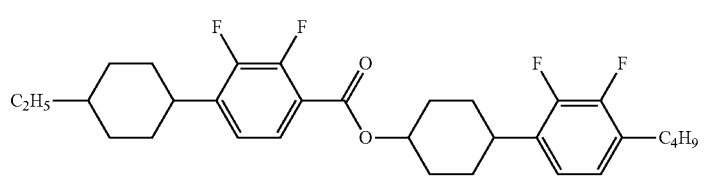 |
| 2015 | 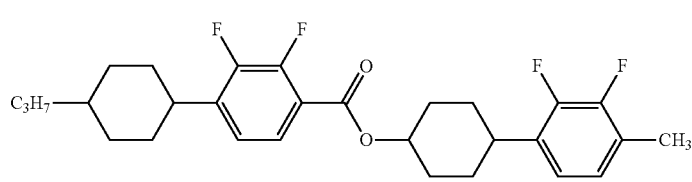 |
| 2016 | 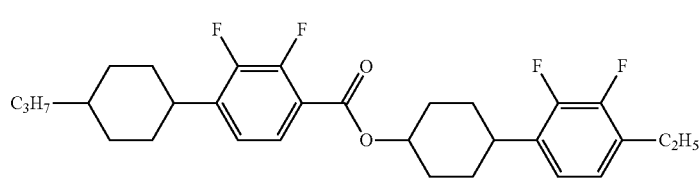 |
| 2017 | 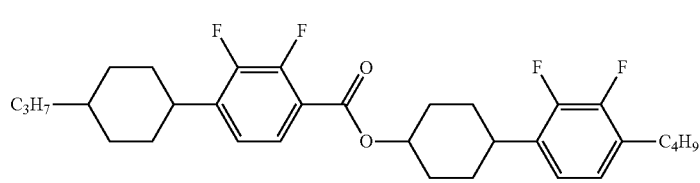 |
| 2018 | 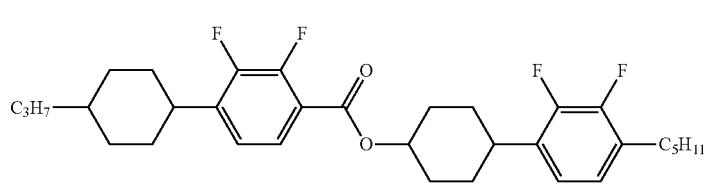 |
| 2019 | 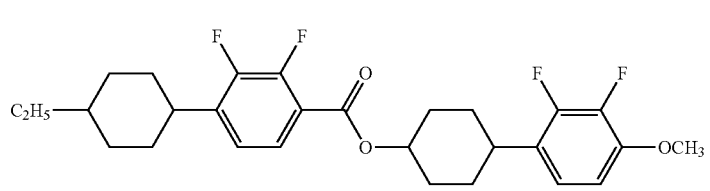 [SMILES: CCC1CCC(c2ccc(C(=O)OC3CCC(c4ccc(OC)c(F)c4F)CC3)c(F)c2F)CC1] |
| 2020 | 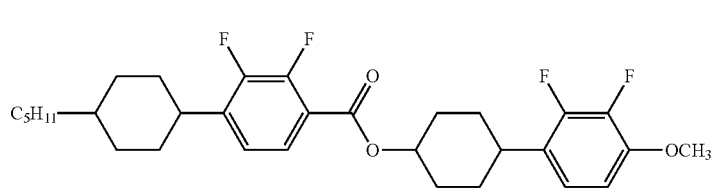 |

-continued
| No. | |
|---|---|
| 2021 | 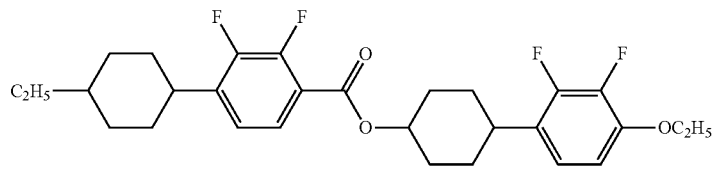 [SMILES: CCOc1ccc(C2CCC(OC(=O)c3ccc(C4CCC(CC)CC4)c(F)c3F)CC2)c(F)c1F] |
| 2022 | 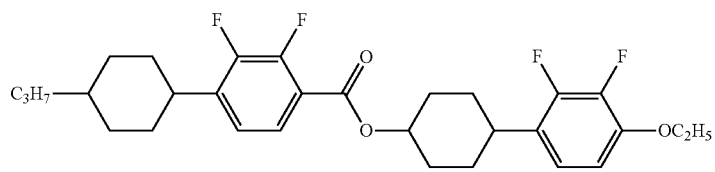 |
| 2023 | 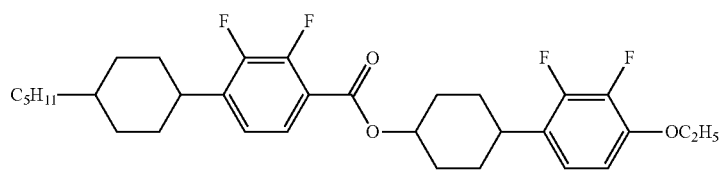 |
| 2024 | 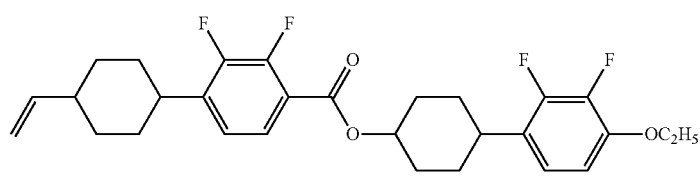 [SMILES: C=CC1CCC(c2ccc(C(=O)OC3CCC(c4ccc(OCC)c(F)c4F)CC3)c(F)c2F)CC1] |
| 2025 | 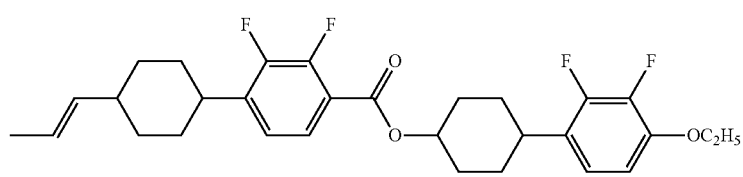 [SMILES: C/C=C/C1CCC(c2ccc(C(=O)OC3CCC(c4ccc(OCC)c(F)c4F)CC3)c(F)c2F)CC1] |
| 2026 | 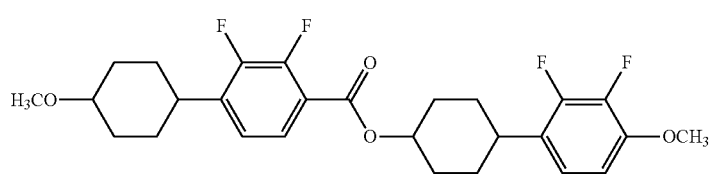 |
| 2027 | 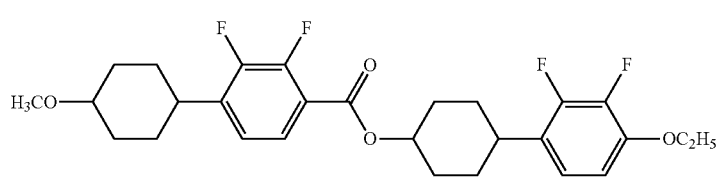 |
| 2028 | 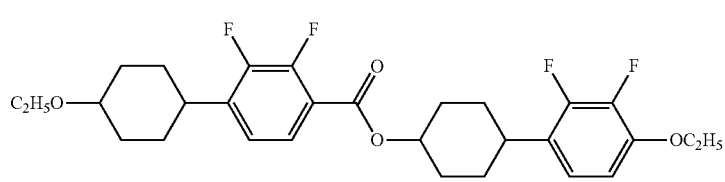 |

-continued
| No. | |
|---|---|
| 2029 | 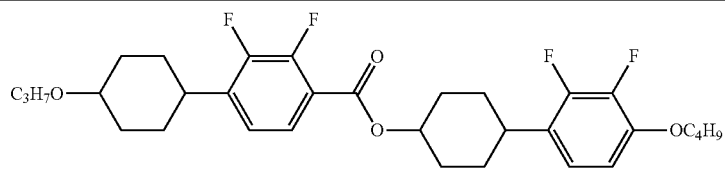 |
| 2030 | 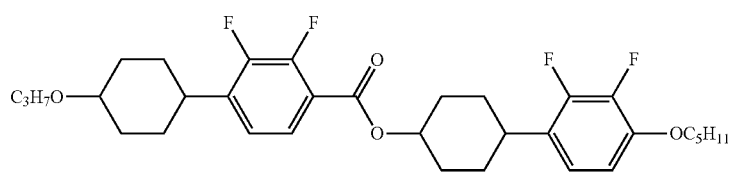 |
| 2031 | 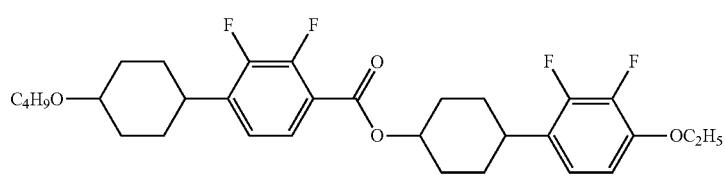 |
| 2032 | 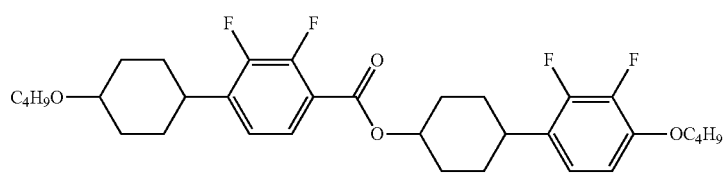 |
| 2033 | 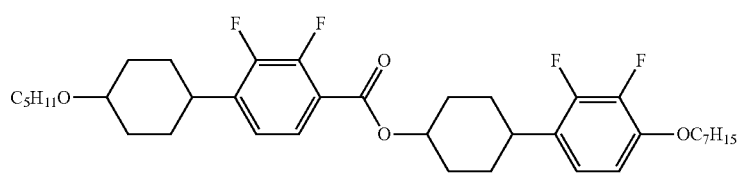 |
| 2034 | 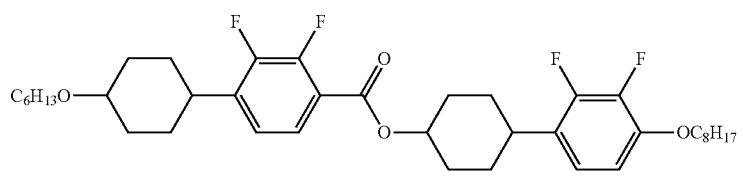 |
| 2035 | 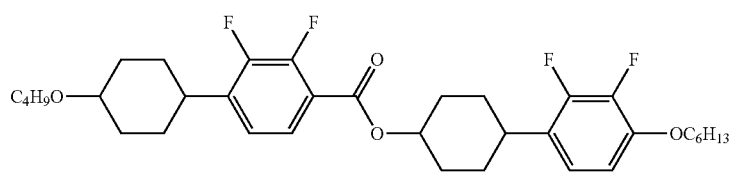 |
| 2036 | 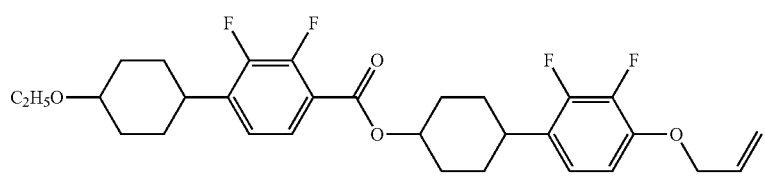 |
| 2037 | 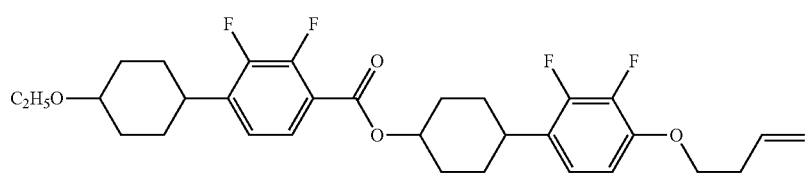 |

-continued
| No. |
|---|
2038 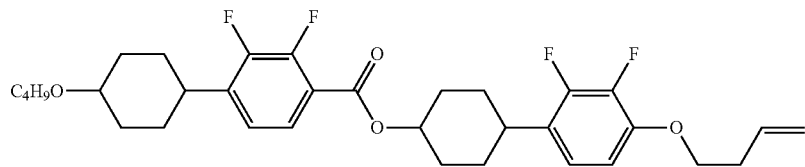
2039 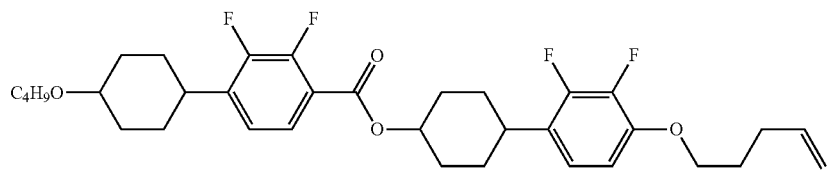
2040 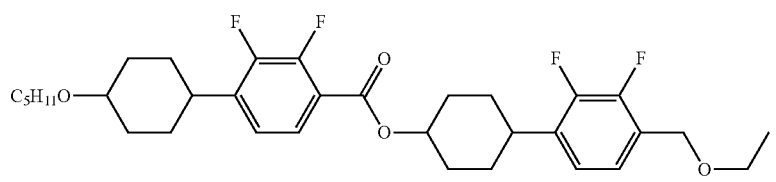
2041 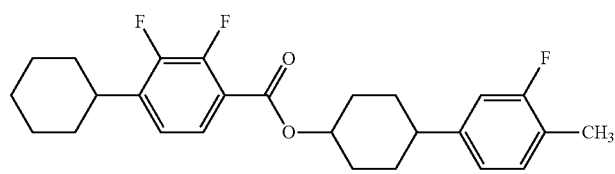 [SMILES: Cc1ccc(C2CCC(OC(=O)c3ccc(C4CCCCC4)c(F)c3F)CC2)cc1F]
2042 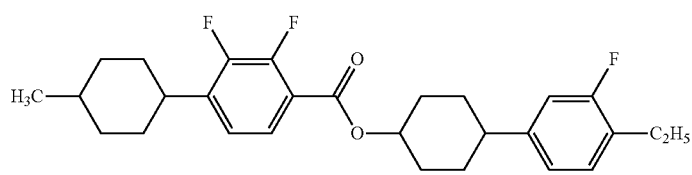 [SMILES: CCc1ccc(C2CCC(OC(=O)c3ccc(C4CCC(C)CC4)c(F)c3F)CC2)cc1F]
2043 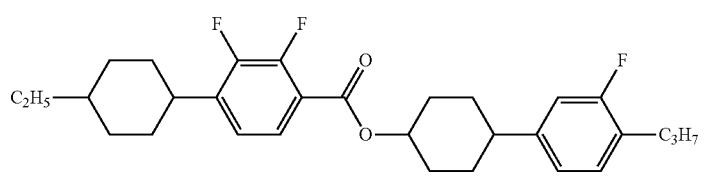
2044 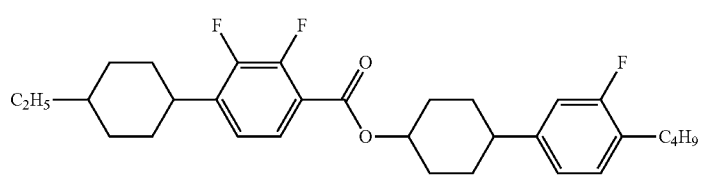
2045 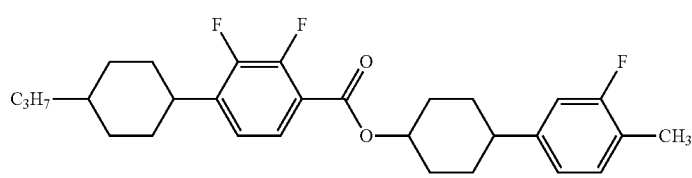

| No. | |
|---|---|
| 2046 | 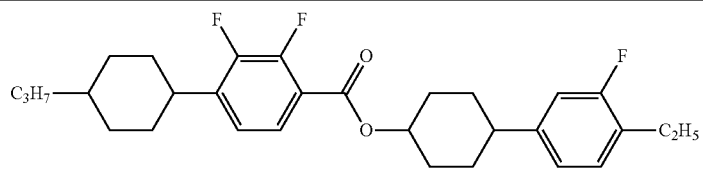 |
| 2047 | 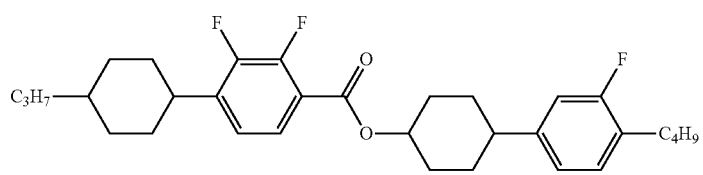 |
| 2048 | 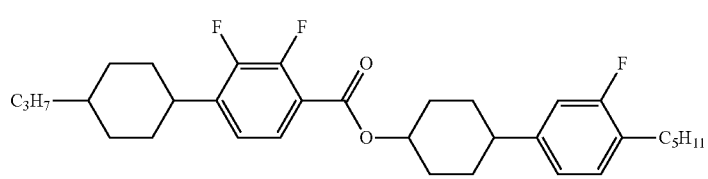 |
| 2049 | 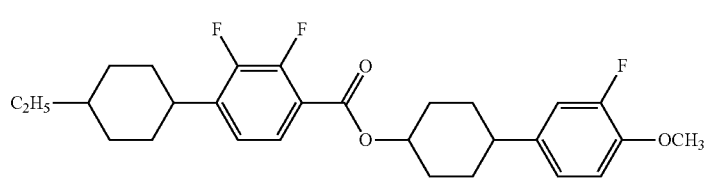 |
| 2050 | 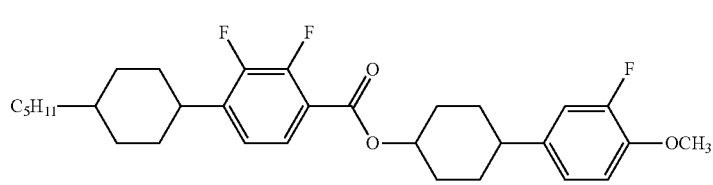 |
| 2051 | 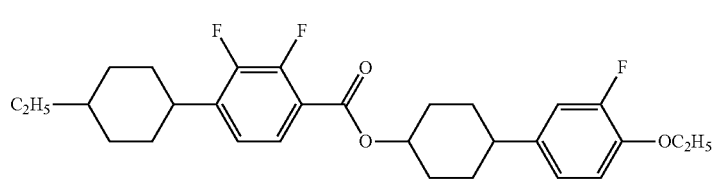 [SMILES: CCOc1ccc(C2CCC(OC(=O)c3ccc(C4CCC(CC)CC4)c(F)c3F)CC2)cc1F] |
| 2052 | 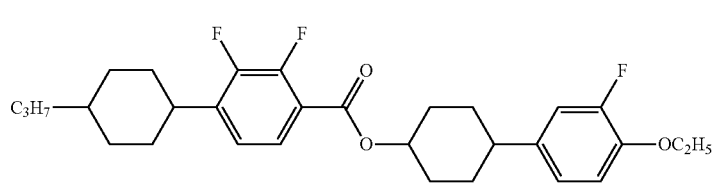 |
| 2053 | 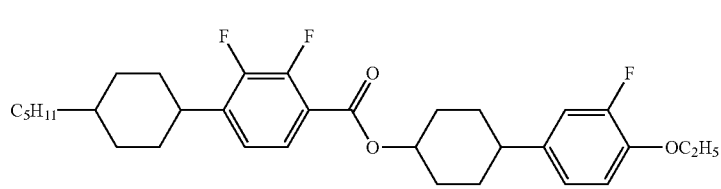 |
| 2054 | 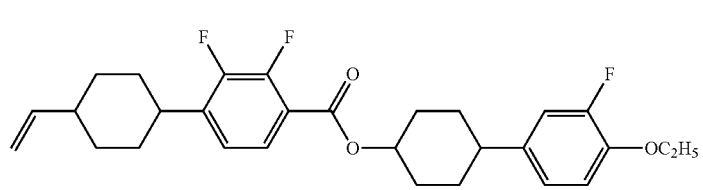 |

| No. | |
|---|---|
| 2055 | 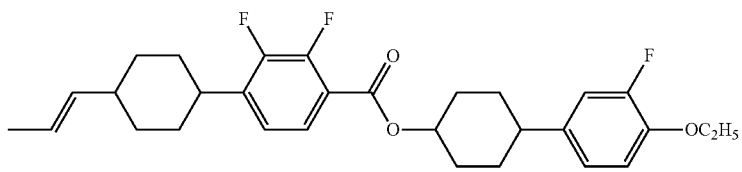 [SMILES: C/C=C/C1CCC(c2ccc(C(=O)OC3CCC(c4ccc(OCC)c(F)c4)CC3)c(F)c2F)CC1] |
| 2056 | 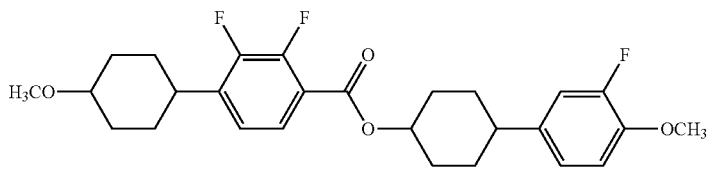 |
| 2057 | 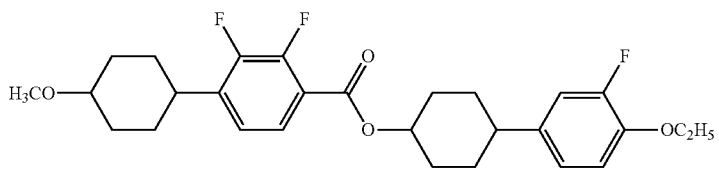 |
| 2058 | 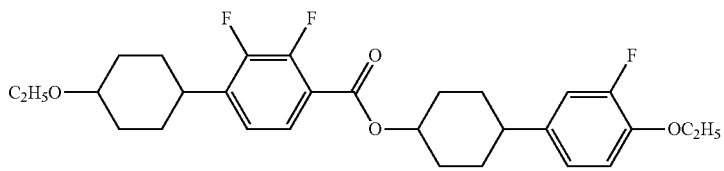 |
| 2059 | 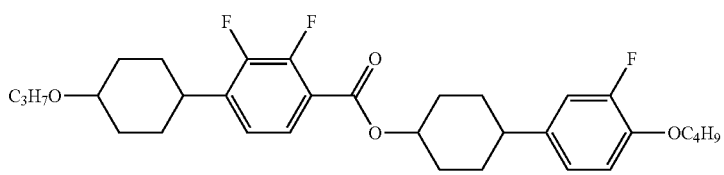 |
| 2060 | 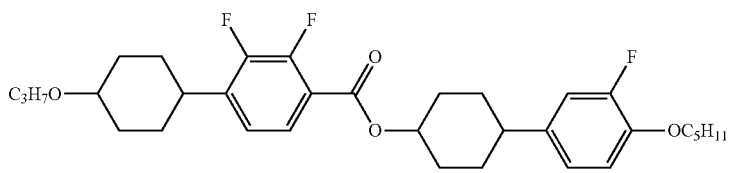 |
| 2061 | 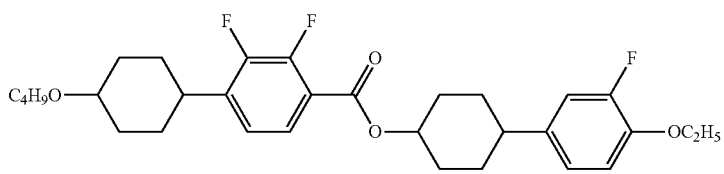 |
| 2062 | 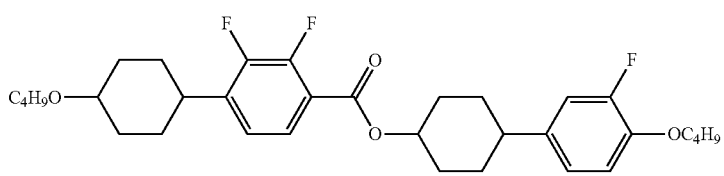 |

| No. |
|---|
| 2063 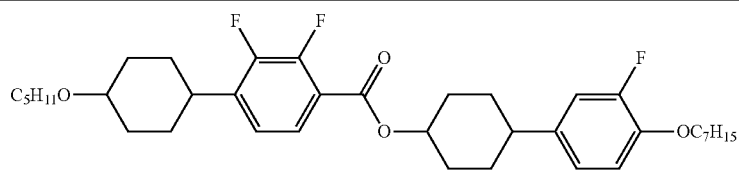 |
| 2064 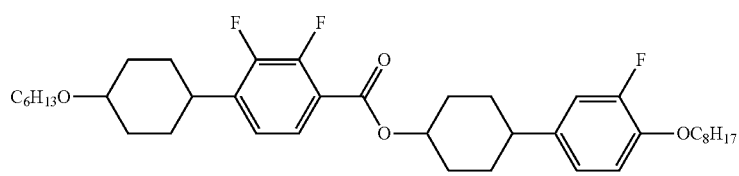 |
| 2065 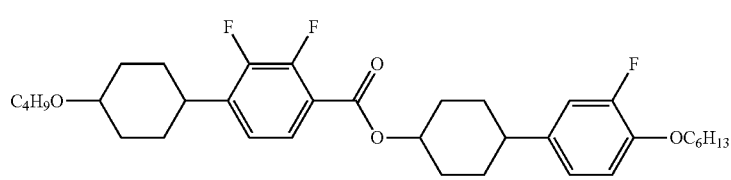 |
| 2066 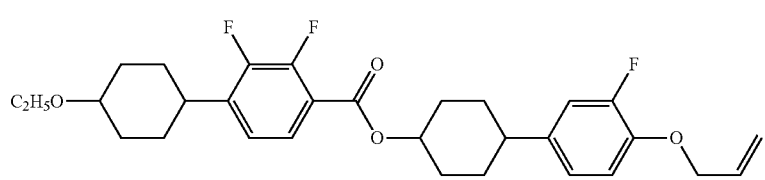 |
| 2067 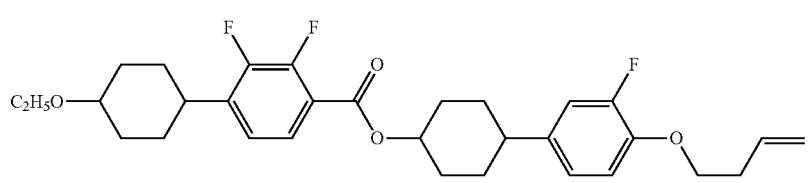 |
| 2068 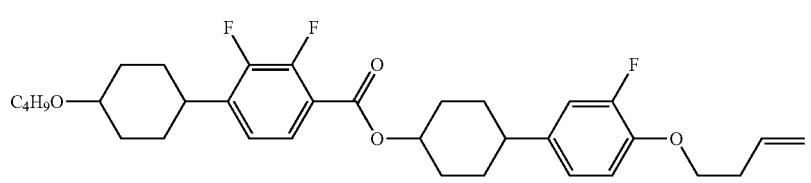 |
| 2069 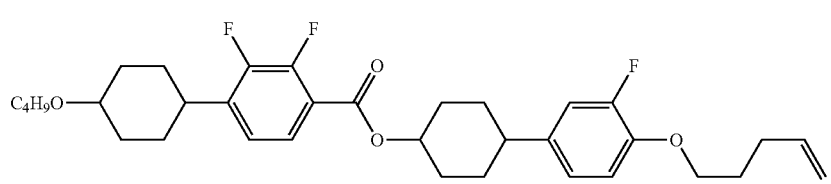 |
| 2070 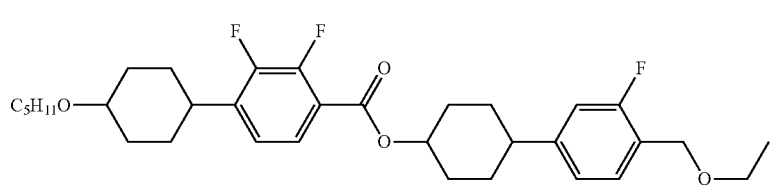 |
| 2071 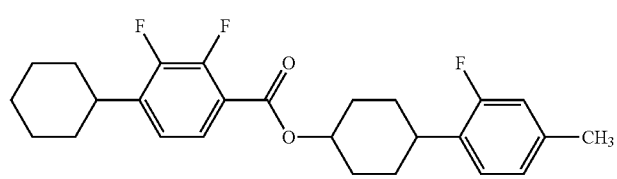 [SMILES: Cc1ccc(C2CCC(OC(=O)c3ccc(C4CCCCC4)c(F)c3F)CC2)c(F)c1] |

| No. | |
|---|---|
| 2072 | 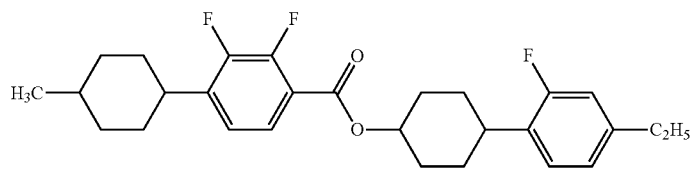 [SMILES: CCc1ccc(C2CCC(OC(=O)c3ccc(C4CCC(C)CC4)c(F)c3F)CC2)c(F)c1] |
| 2073 | 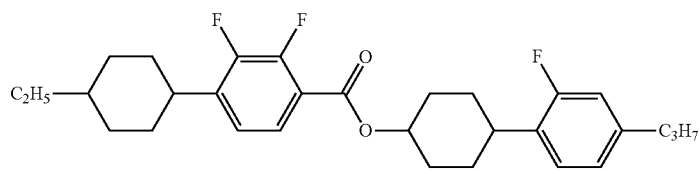 |
| 2074 | 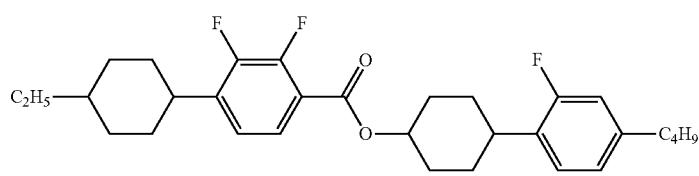 |
| 2075 | 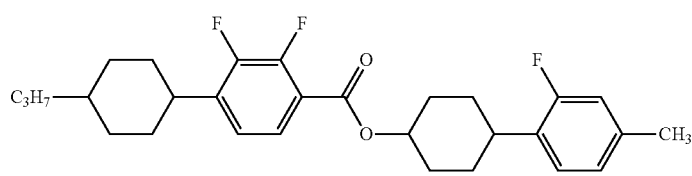 |
| 2076 | 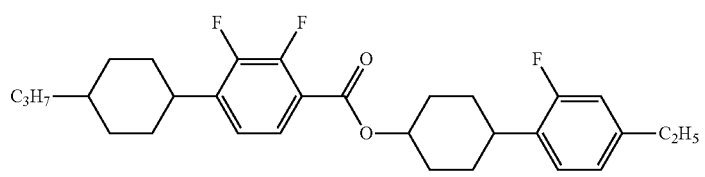 |
| 2077 | 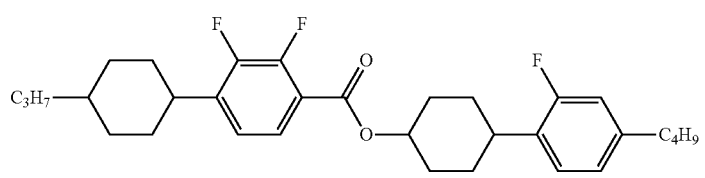 |
| 2078 | 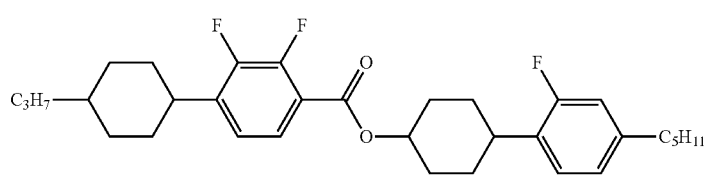 |
| 2079 | 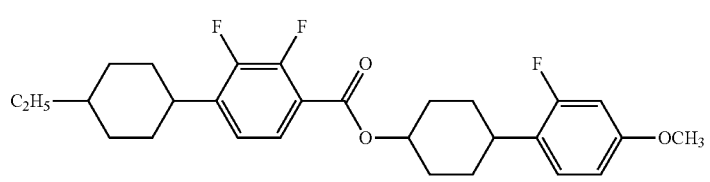 [SMILES: CCC1CCC(c2ccc(C(=O)OC3CCC(c4ccc(OC)cc4F)CC3)c(F)c2F)CC1] |

| No. |
|---|
| 2080 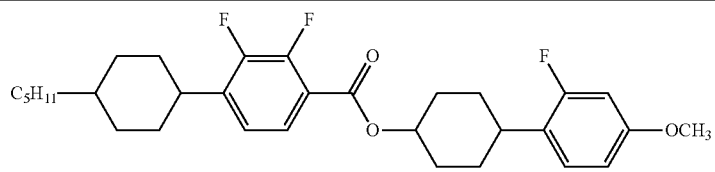 |
| 2081 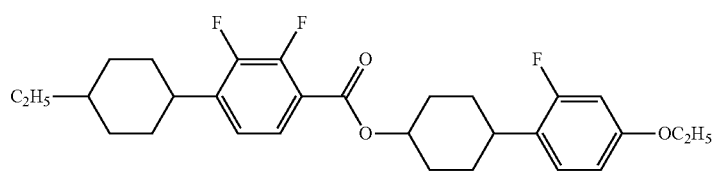 |
| 2082 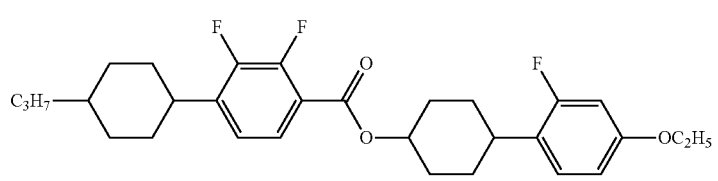 |
| 2083 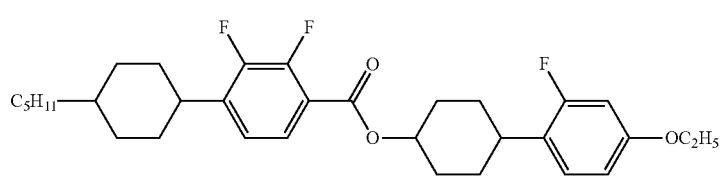 |
| 2084 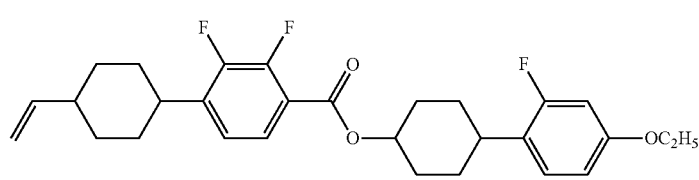 [SMILES: C=CC1CCC(c2ccc(C(=O)OC3CCC(c4ccc(OCC)cc4F)CC3)c(F)c2F)CC1] |
| 2085 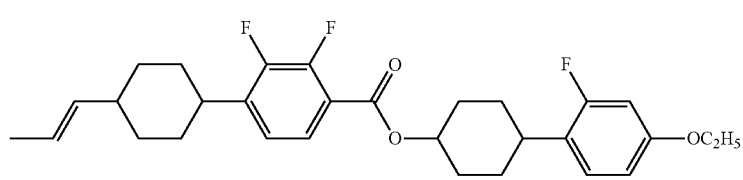 [SMILES: C/C=C/C1CCC(c2ccc(C(=O)OC3CCC(c4ccc(OCC)cc4F)CC3)c(F)c2F)CC1] |
| 2086 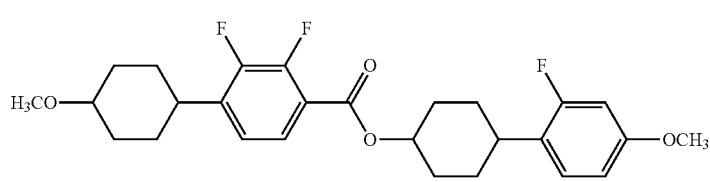 |
| 2087 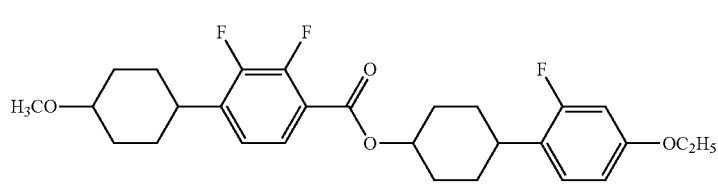 |
| 2088 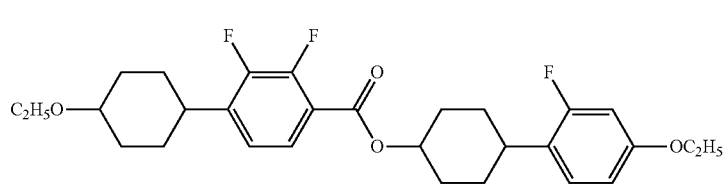 |

| No. | |
|---|---|
| 2089 | 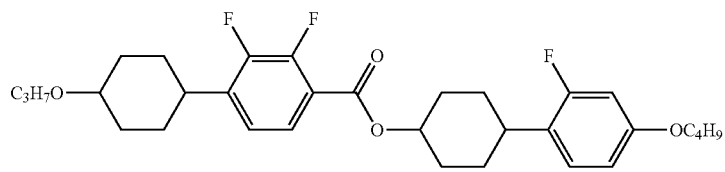 |
| 2090 | 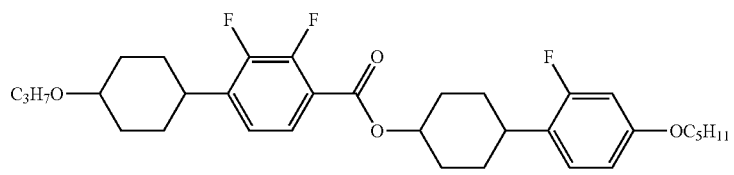 |
| 2091 | 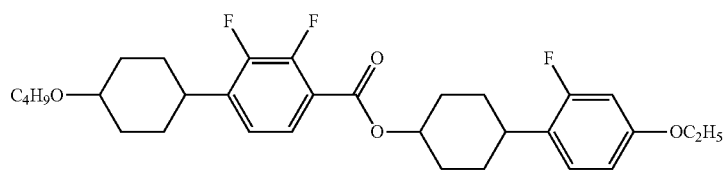 |
| 2092 | 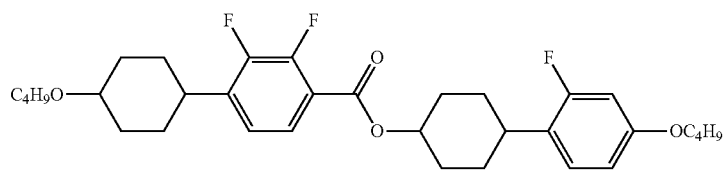 |
| 2093 | 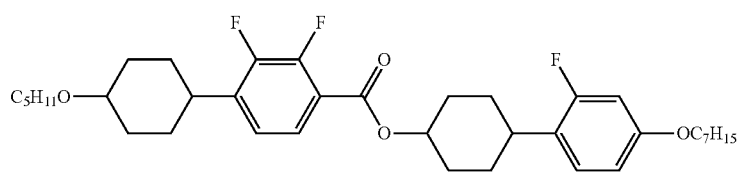 |
| 2094 | 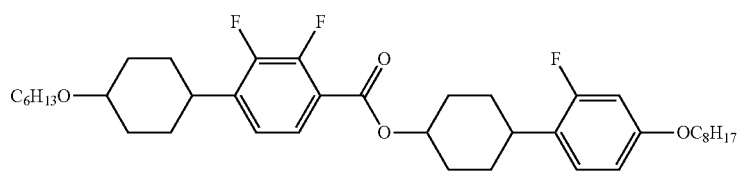 |
| 2095 | 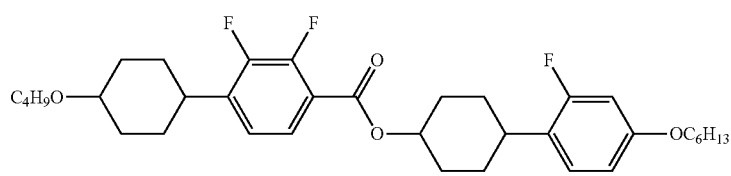 |
| 2096 | 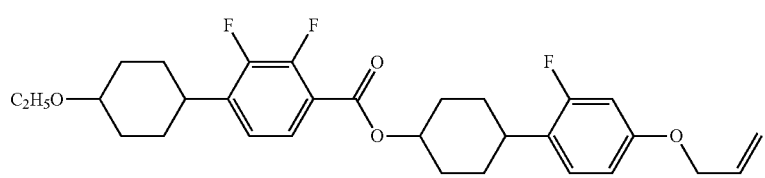 |

| No. | |
|---|---|
| 2097 | 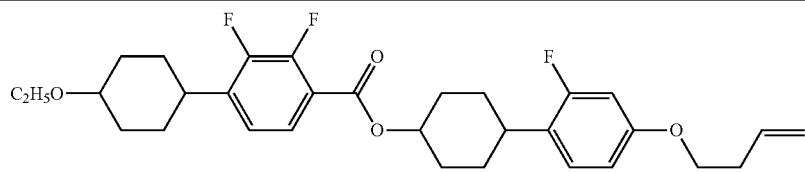 |
| 2098 | 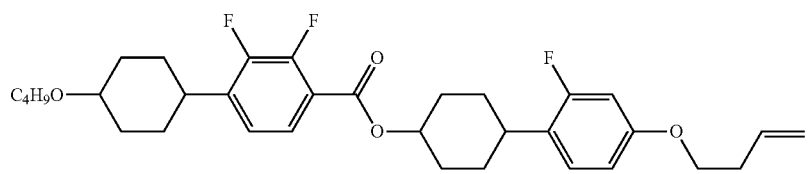 |
| 2099 | 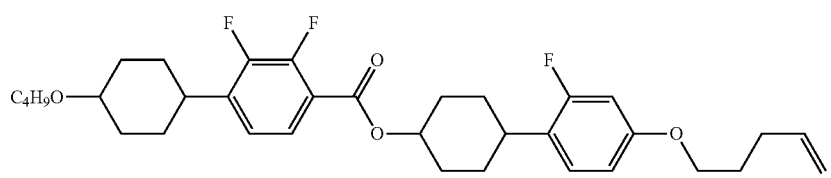 |
| 2100 | 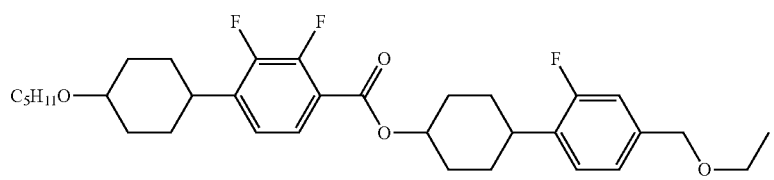 |
| 2101 | 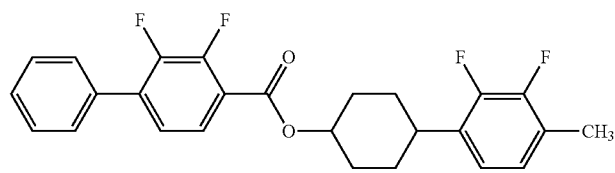 |
| 2102 | 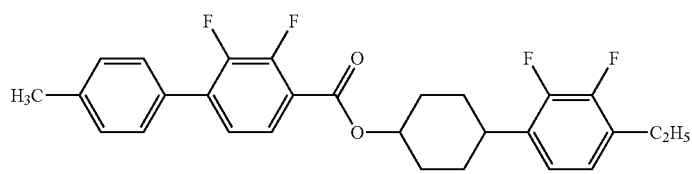 [SMILES: CCc1ccc(C2CCC(OC(=O)c3ccc(-c4ccc(C)cc4)c(F)c3F)CC2)c(F)c1F] |
| 2103 | 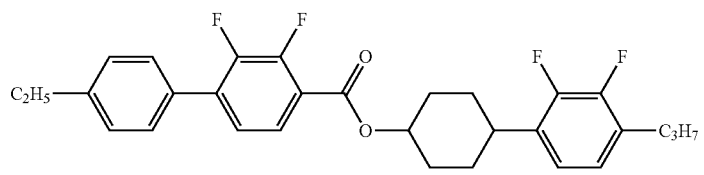 |
| 2104 | 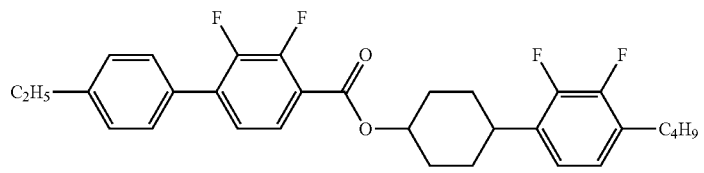 |
| 2105 | 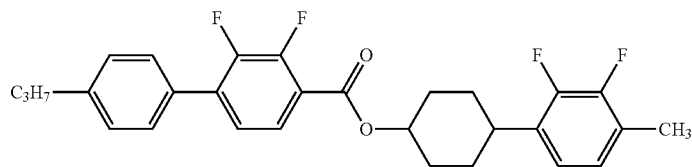 |

| No. |
|---|
| 2106 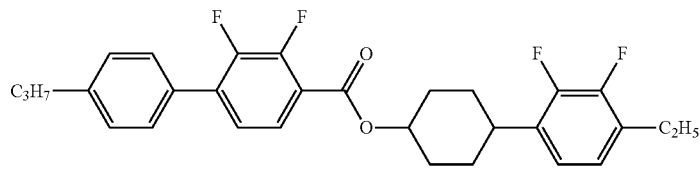 |
| 2107 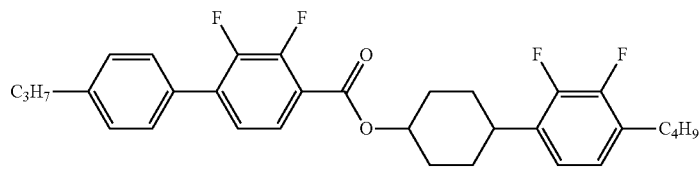 |
| 2108 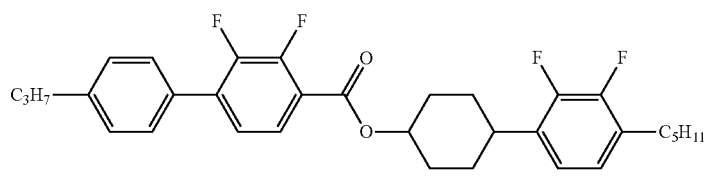 |
| 2109 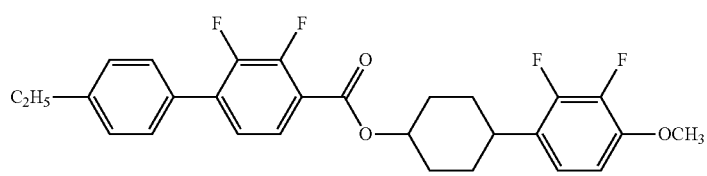 [SMILES: CCc1ccc(-c2ccc(C(=O)OC3CCC(c4ccc(OC)c(F)c4F)CC3)c(F)c2F)cc1] |
| 2110 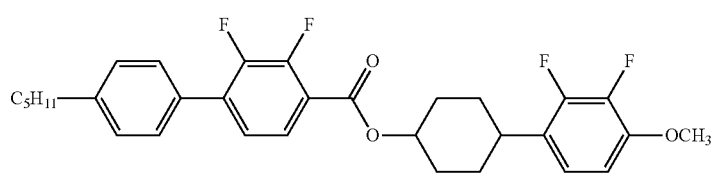 [SMILES: COc1ccc(-c2ccc(C(=O)OC3CCC(c4ccc(OC)c(F)c4F)CC3)c(F)c2F)cc1] |
| 2111 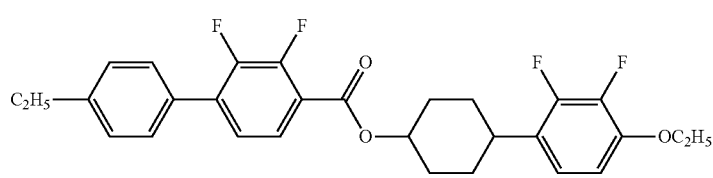 |
| 2112 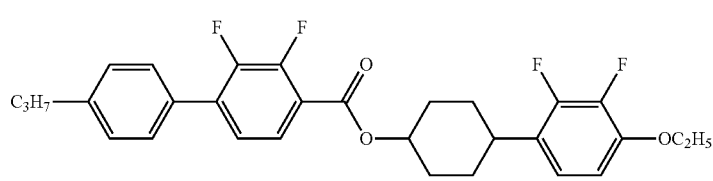 |
| 2113  |

| No. | |
|---|---|
| 2114 | 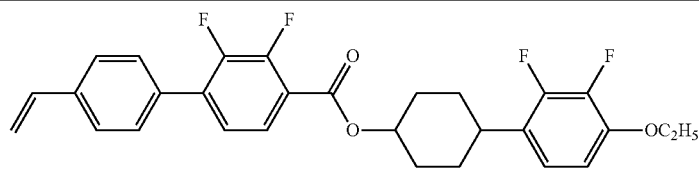 |
| 2115 | 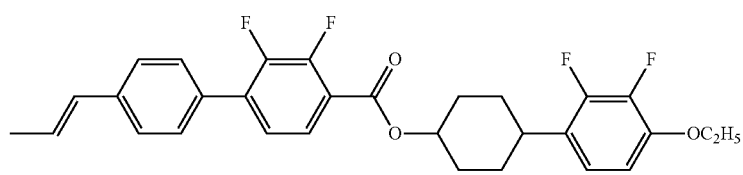 |
| 2116 | 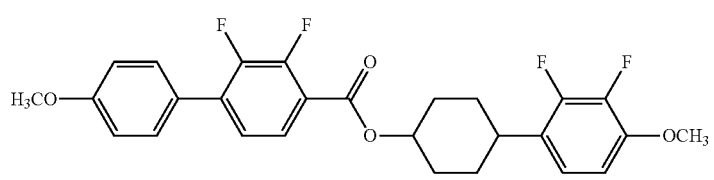 |
| 2117 | 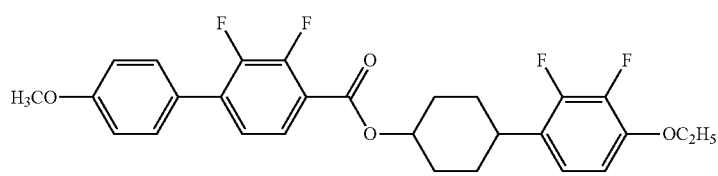 |
| 2118 | 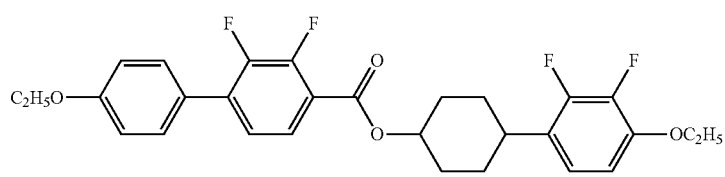 |
| 2119 | 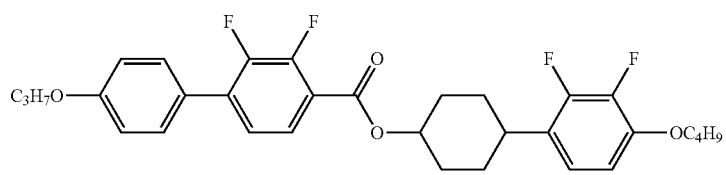 |
| 2120 | 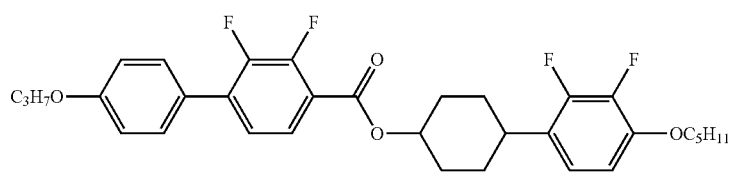 |
| 2121 | 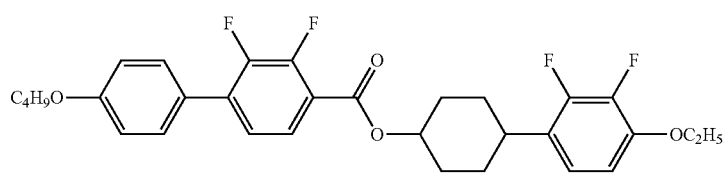 |
| 2122 | 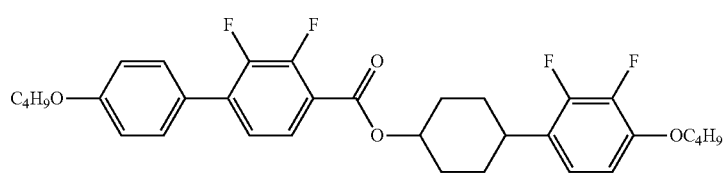 |

-continued
| No. | |
|---|---|
| 2123 | 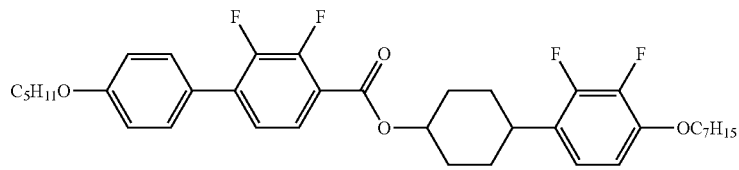 |
| 2124 | 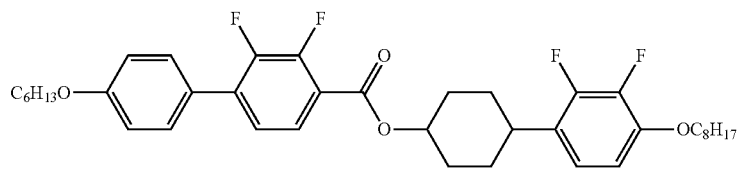 |
| 2125 | 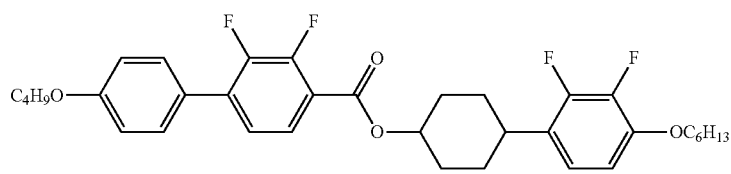 |
| 2126 | 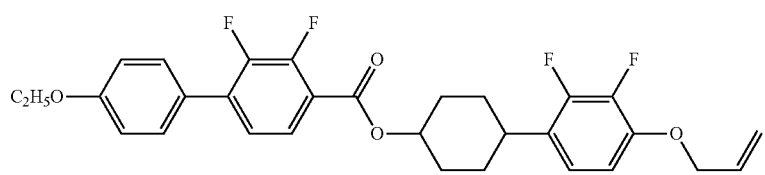 |
| 2127 | 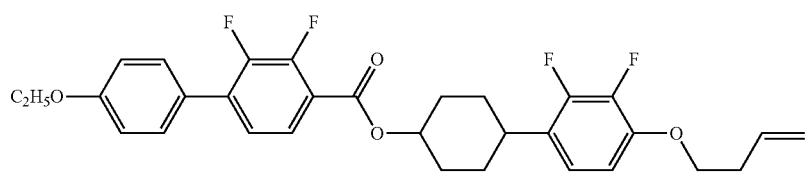 |
| 2128 | 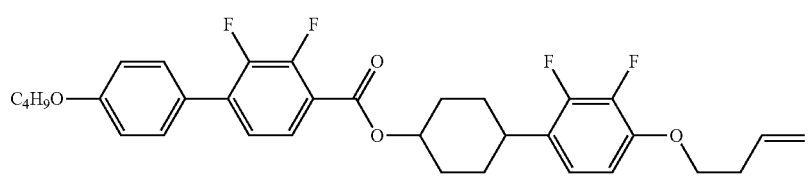 |
| 2129 | 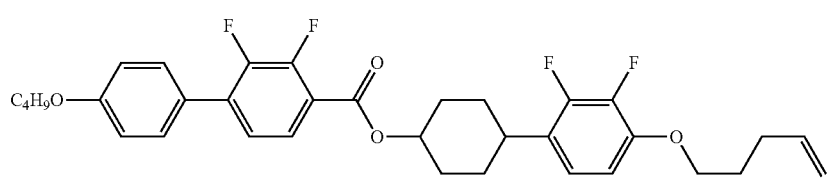 |
| 2130 | 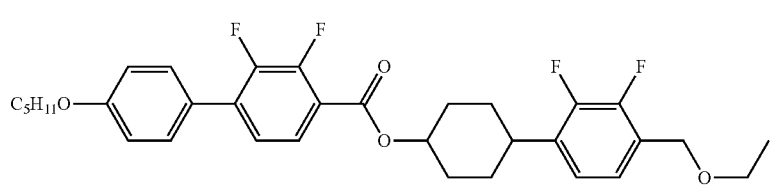 |

| No. | |
|---|---|
| 2131 | 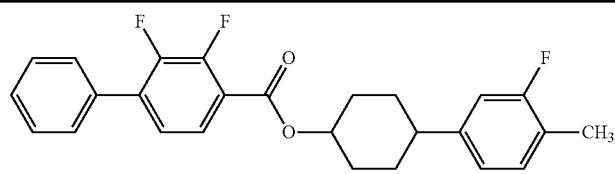 |
| 2132 | 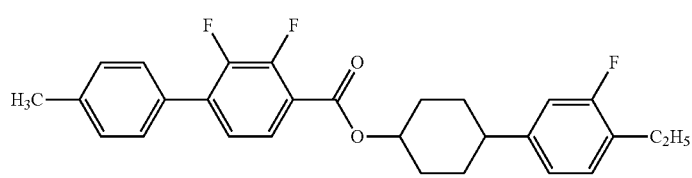 |
| 2133 | 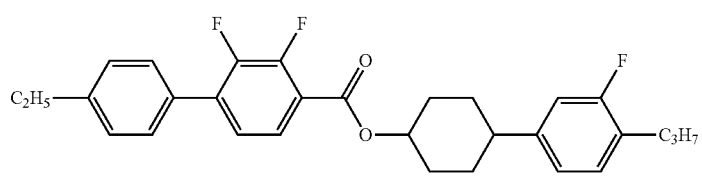 |
| 2134 | 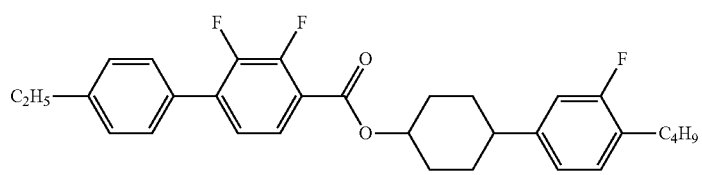 |
| 2135 | 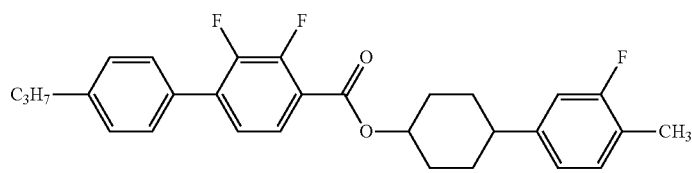 |
| 2136 | 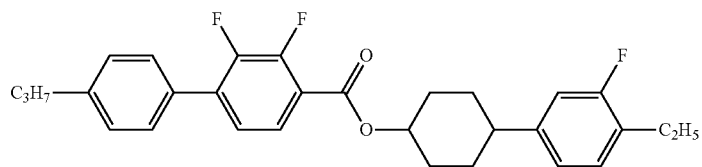 |
| 2137 | 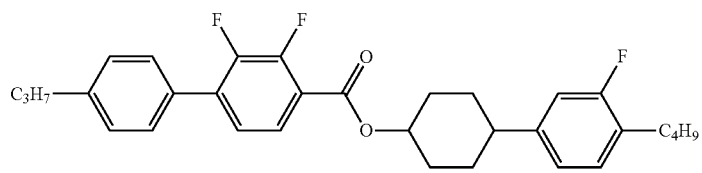 |
| 2138 | 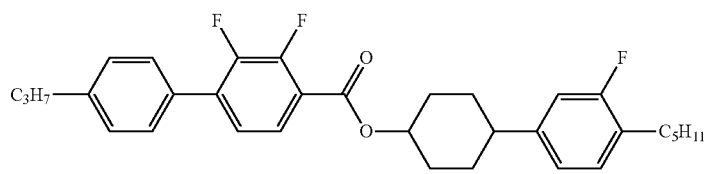 |
| 2139 | 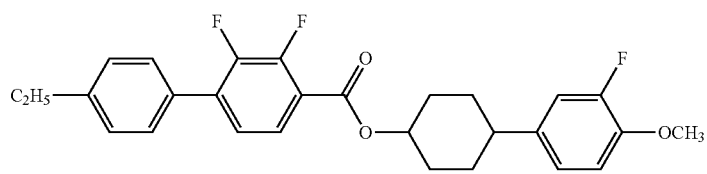 [SMILES: CCc1ccc(-c2ccc(C(=O)OC3CCC(c4ccc(OC)c(F)c4)CC3)c(F)c2F)cc1] |

| No. | |
|---|---|
| 2140 | 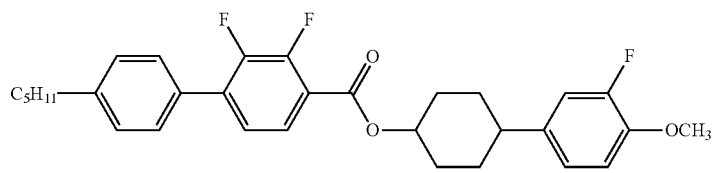 |
| 2141 | 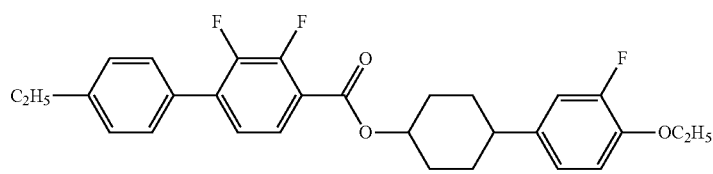 [SMILES: CCOc1ccc(C2CCC(OC(=O)c3ccc(-c4ccc(CC)cc4)c(F)c3F)CC2)cc1F] |
| 2142 | 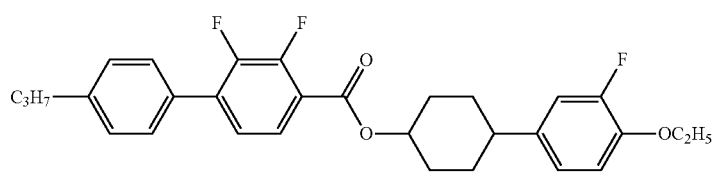 |
| 2143 | 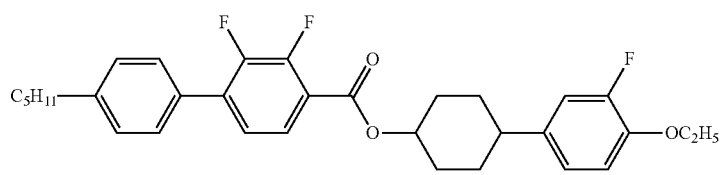 |
| 2144 | 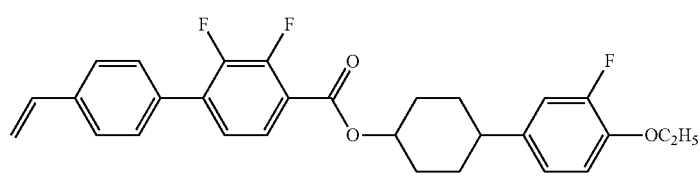 [SMILES: C=Cc1ccc(-c2ccc(C(=O)OC3CCC(c4ccc(OCC)c(F)c4)CC3)c(F)c2F)cc1] |
| 2145 | 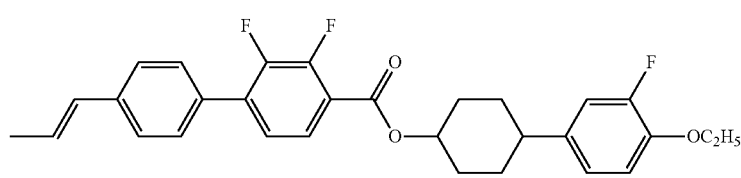 [SMILES: C/C=C/c1ccc(-c2ccc(C(=O)OC3CCC(c4ccc(OCC)c(F)c4)CC3)c(F)c2F)cc1] |
| 2146 | 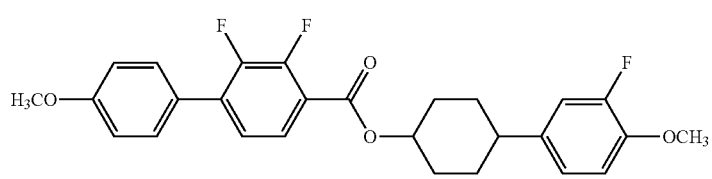 |
| 2147 | 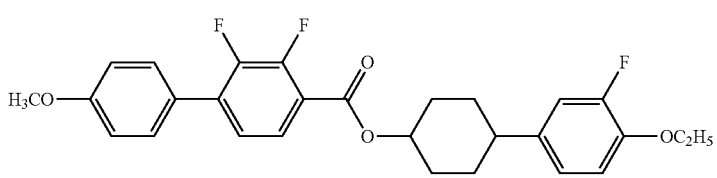 |

-continued
| No. | |
|---|---|
| 2148 | 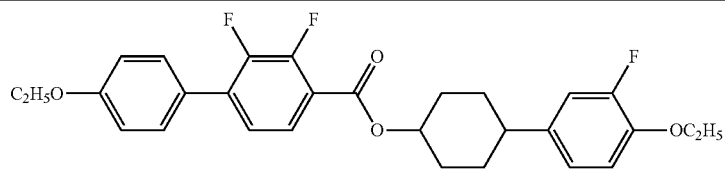 |
| 2149 | 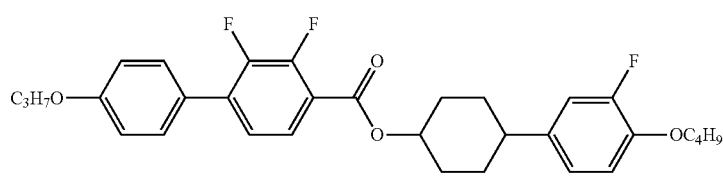 |
| 2150 | 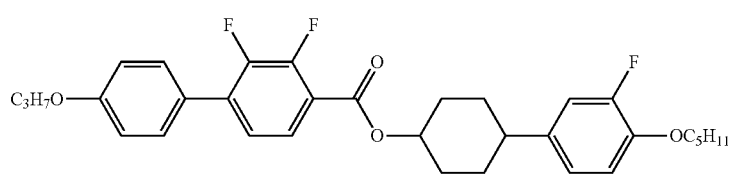 |
| 2151 | 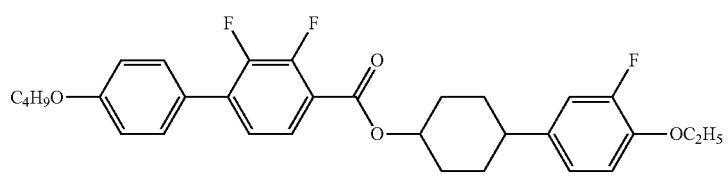 |
| 2152 | 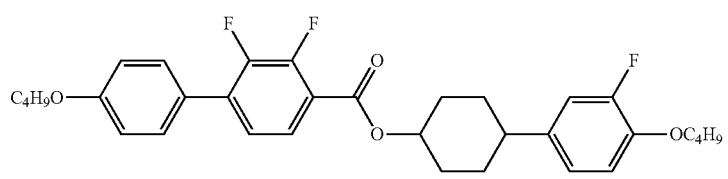 |
| 2153 | 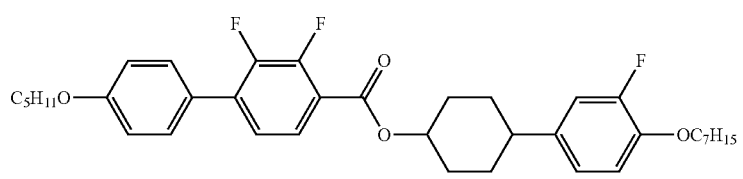 |
| 2154 | 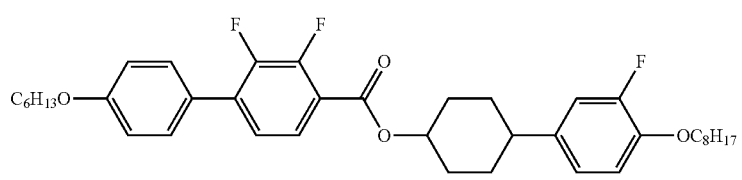 |
| 2155 | 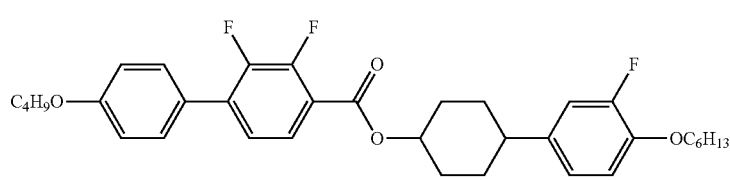 |
| 2156 | 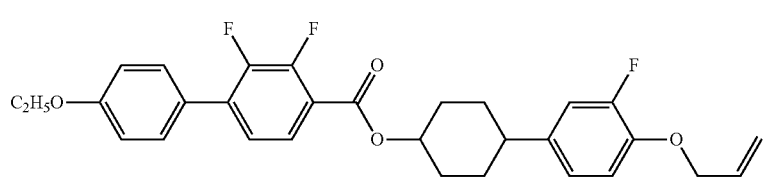 |

| No. | |
|---|---|
| 2157 | 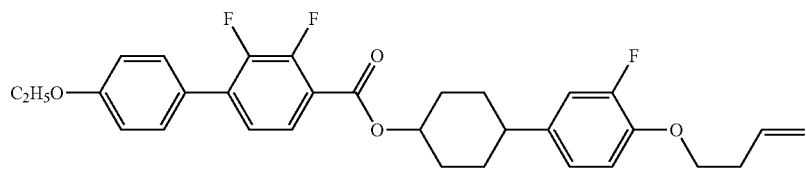 |
| 2158 | 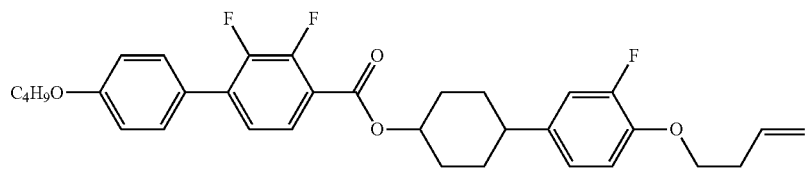 |
| 2159 | 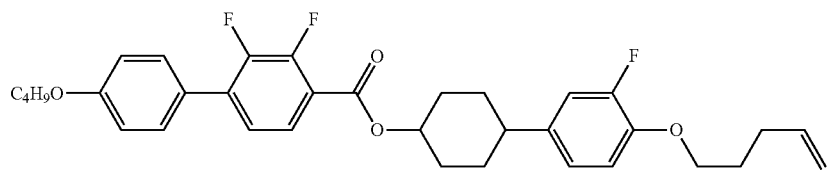 |
| 2160 | 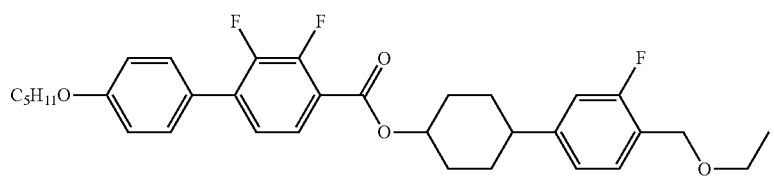 |
| 2161 | 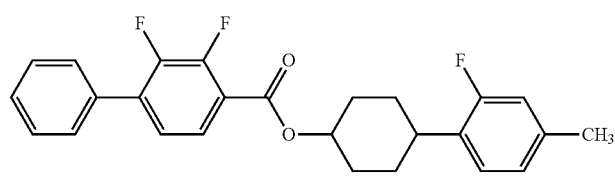 |
| 2162 | 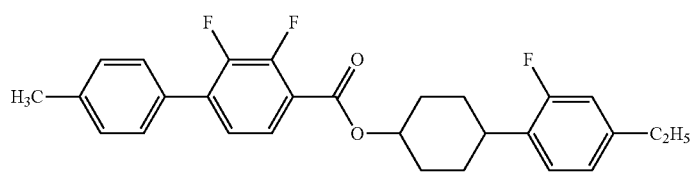 |
| 2163 | 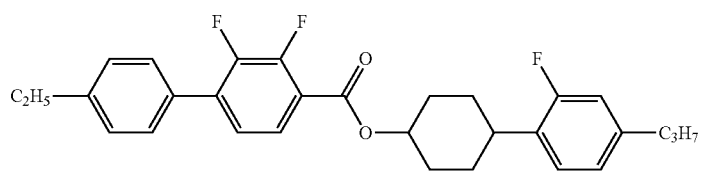 |
| 2164 | 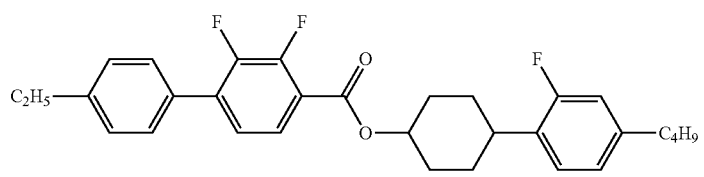 |

| No. | |
|---|---|
| 2165 | 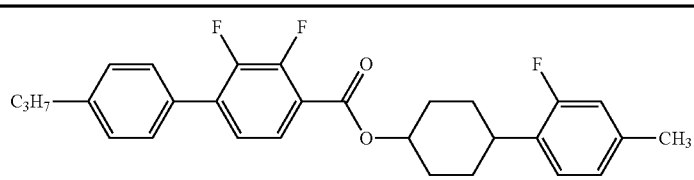 |
| 2166 | 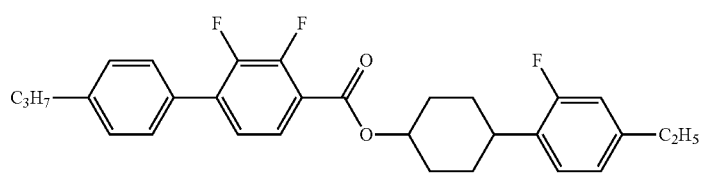 |
| 2167 | 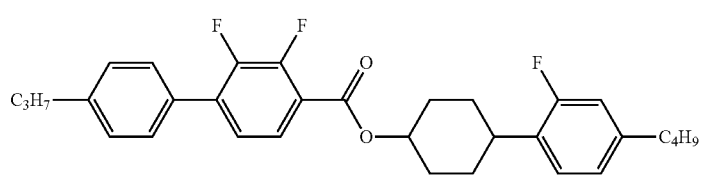 |
| 2168 | 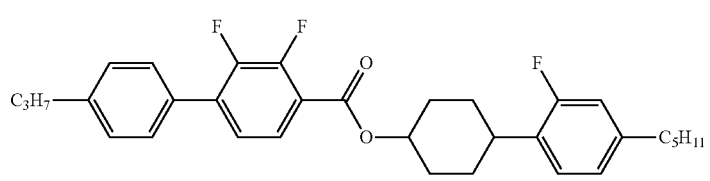 |
| 2169 | 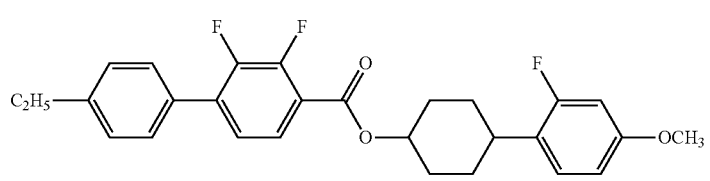 |
| 2170 | 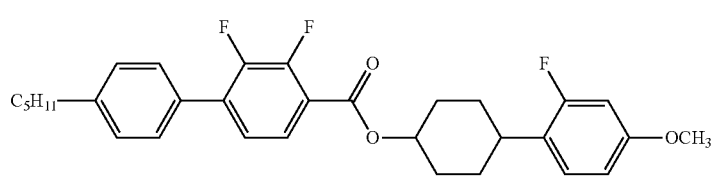 |
| 2171 | 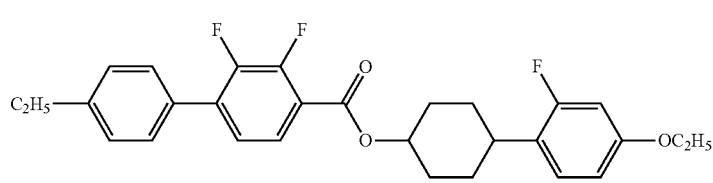 |
| 2172 | 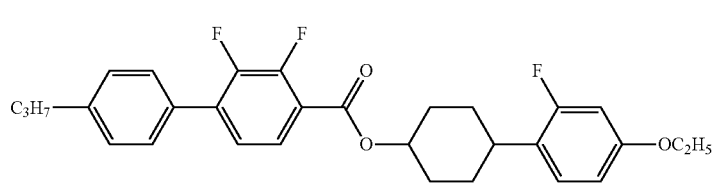 [SMILES: CCOc1ccc(C2CCC(OC(=O)c3ccc(-c4ccc(CC)cc4)c(F)c3F)CC2)c(F)c1] |
| 2173 | 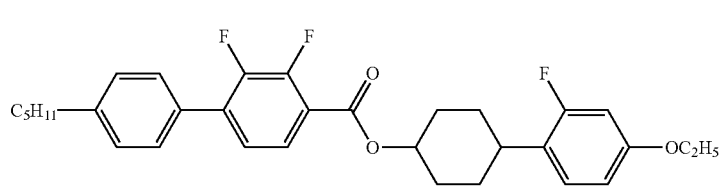 |

| No. | |
|---|---|
| 2174 | 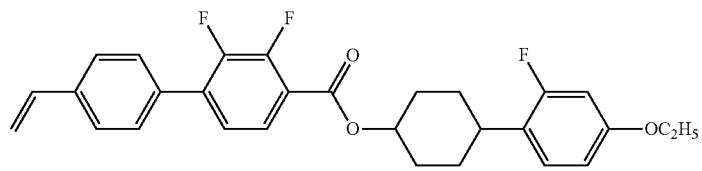 |
| 2175 | 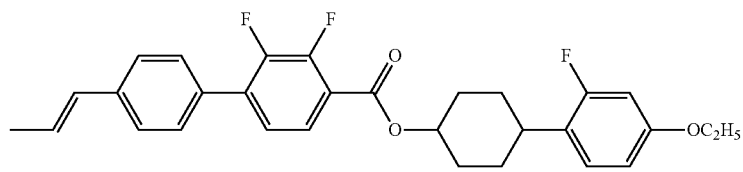 |
| 2176 | 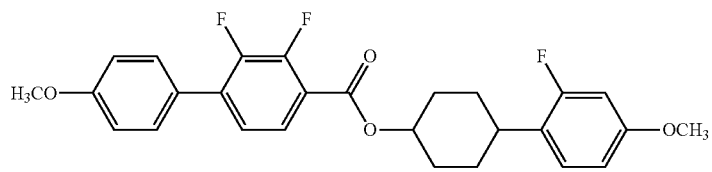 [SMILES: COc1ccc(-c2ccc(C(=O)OC3CCC(c4ccc(OC)cc4F)CC3)c(F)c2F)cc1] |
| 2177 | 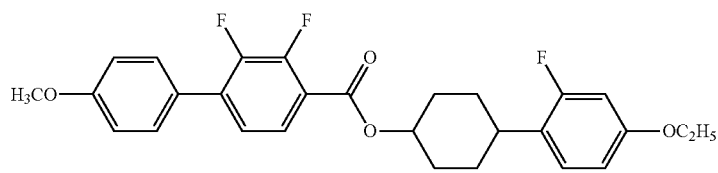 [SMILES: CCOc1ccc(C2CCC(OC(=O)c3ccc(-c4ccc(OC)cc4)c(F)c3F)CC2)c(F)c1] |
| 2178 | 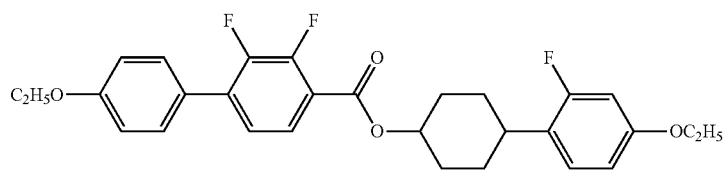 |
| 2179 | 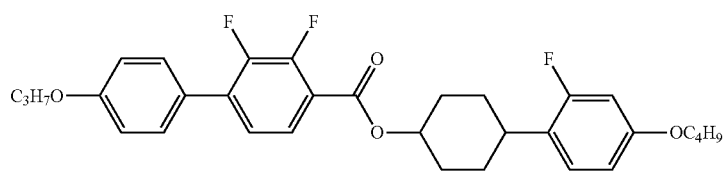 |
| 2180 | 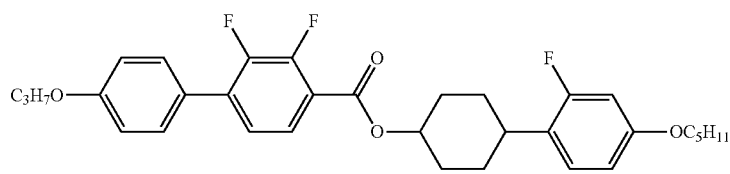 |
| 2181 | 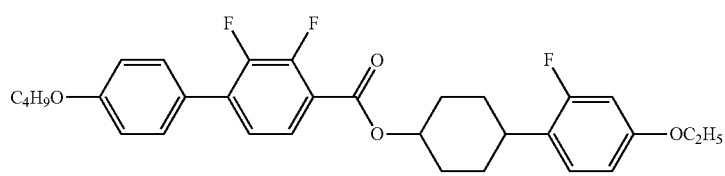 |

| No. | |
|---|---|
| 2182 | 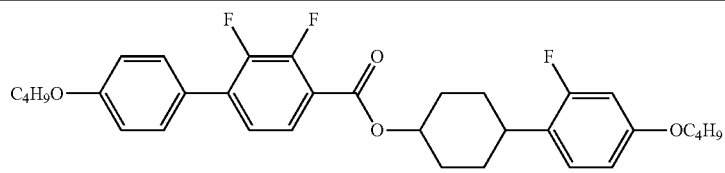 |
| 2183 | 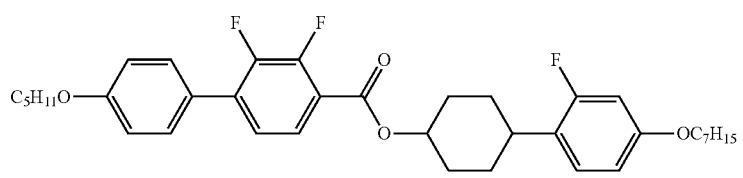 |
| 2184 | 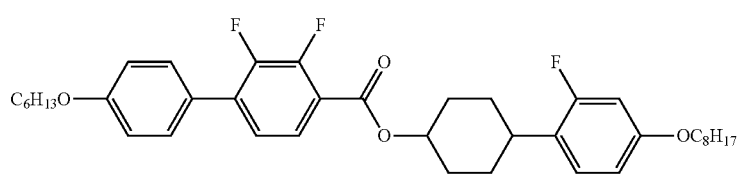 |
| 2185 | 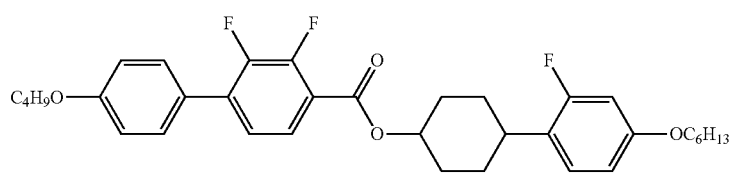 |
| 2186 | 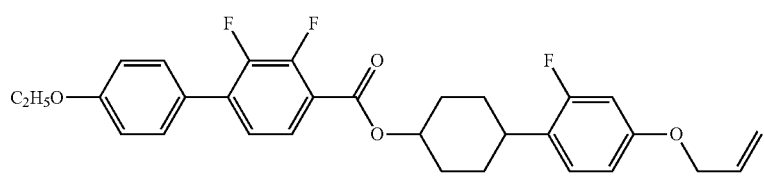 |
| 2187 | 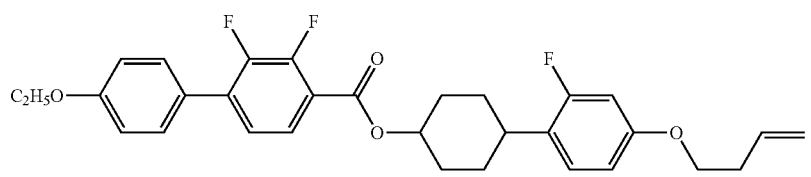 |
| 2188 | 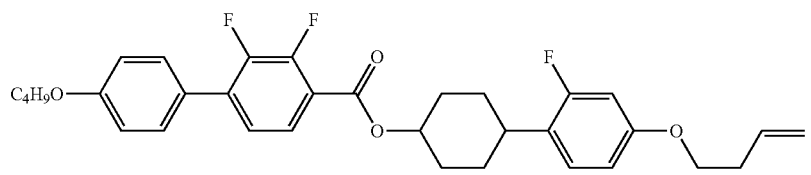 |
| 2189 | 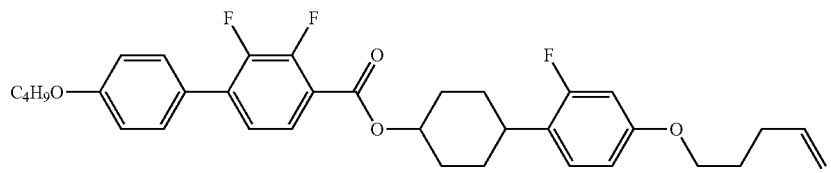 |
| 2190 | 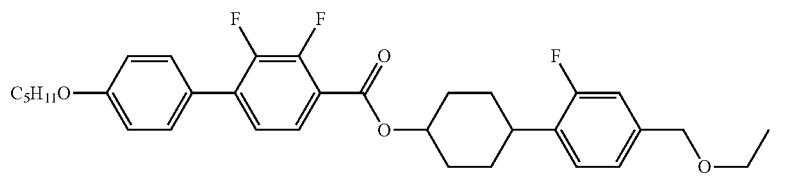 |

| No. | |
|---|---|
| 2191 | 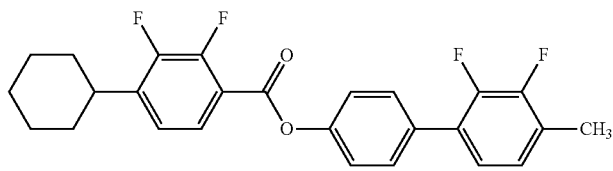 |
| 2192 | 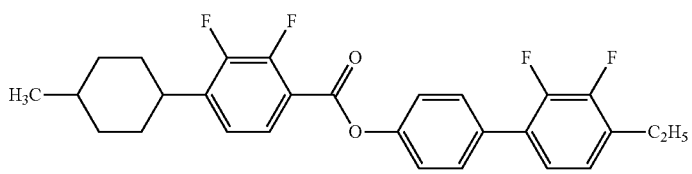 |
| 2193 | 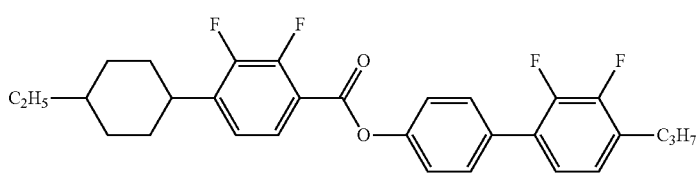 |
| 2194 | 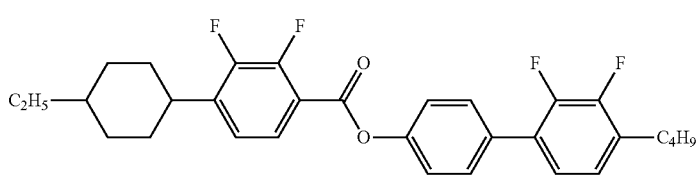 |
| 2195 | 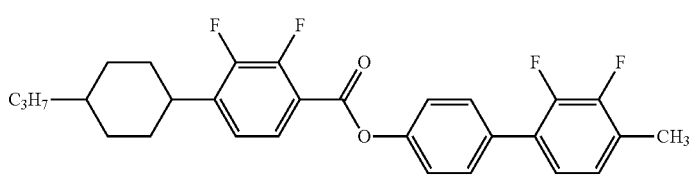 |
| 2196 | 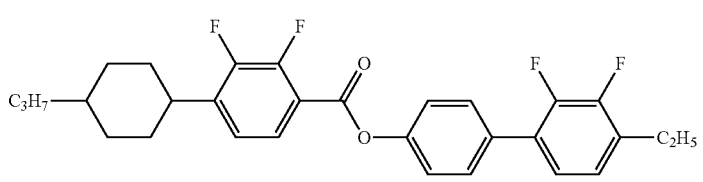 |
| 2197 | 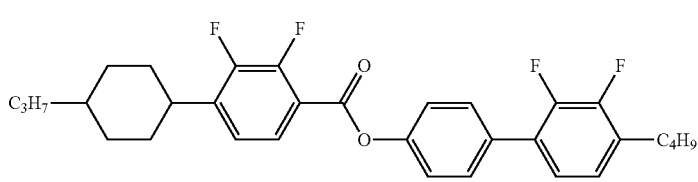 |
| 2198 | 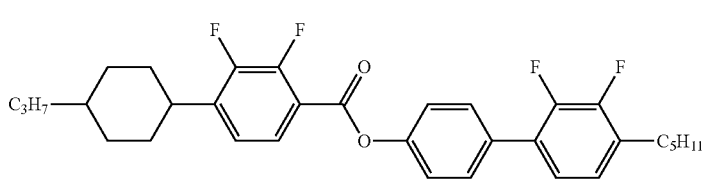 |

-continued
| No. | |
|---|---|
| 2199 | 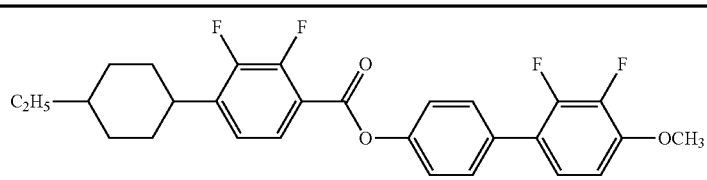 |
| 2200 | 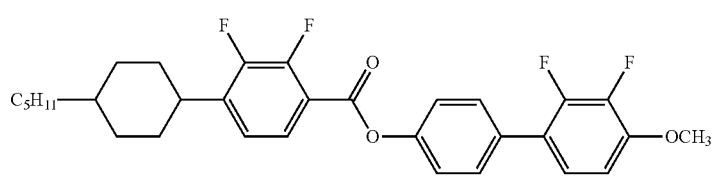 |
| 2201 | 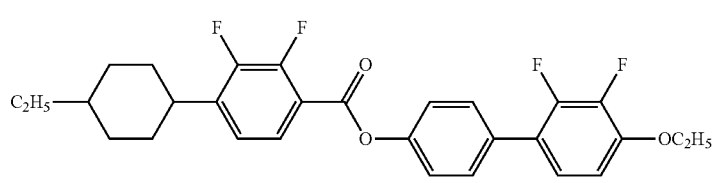 |
| 2202 | 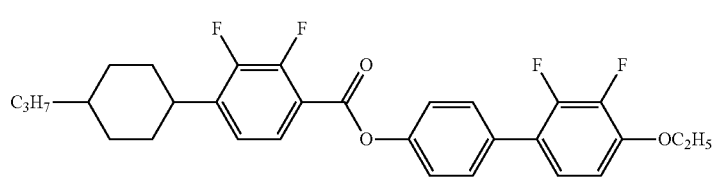 [SMILES: CCOc1ccc(-c2ccc(OC(=O)c3ccc(C4CCC(CC)CC4)c(F)c3F)cc2)c(F)c1F] |
| 2203 | 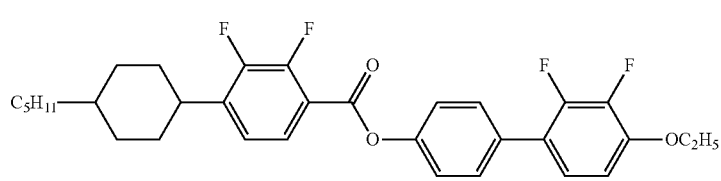 |
| 2204 | 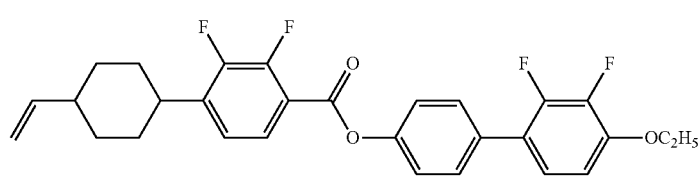 |
| 2205 | 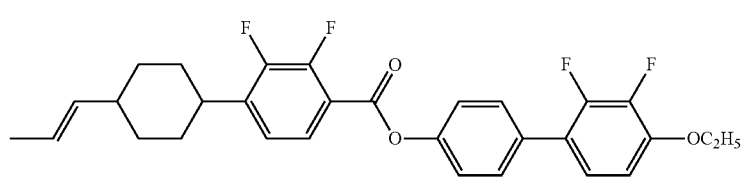 [SMILES: C/C=C/C1CCC(c2ccc(C(=O)Oc3ccc(-c4ccc(OCC)c(F)c4F)cc3)c(F)c2F)CC1] |
| 2206 | 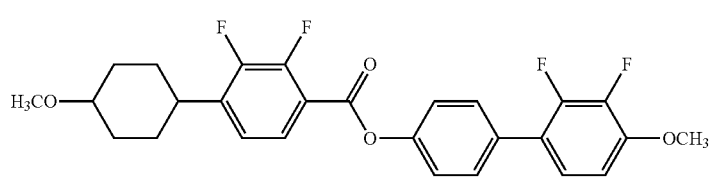 [SMILES: COc1ccc(-c2ccc(OC(=O)c3ccc(C4CCC(OC)CC4)c(F)c3F)cc2)c(F)c1F] |
| 2207 | 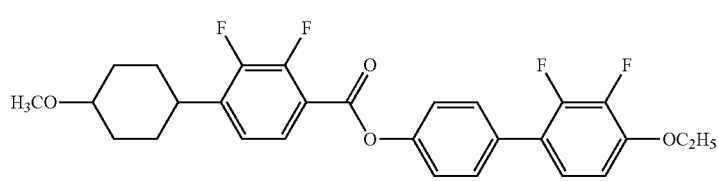 [SMILES: CCOc1ccc(-c2ccc(OC(=O)c3ccc(C4CCC(OC)CC4)c(F)c3F)cc2)c(F)c1F] |

| No. | |
|---|---|
| 2208 | 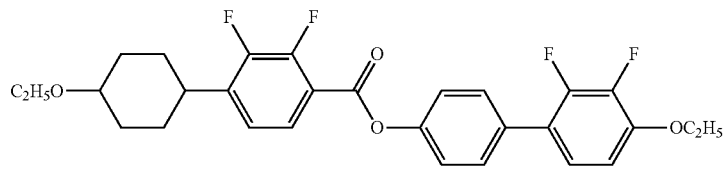 |
| 2209 | 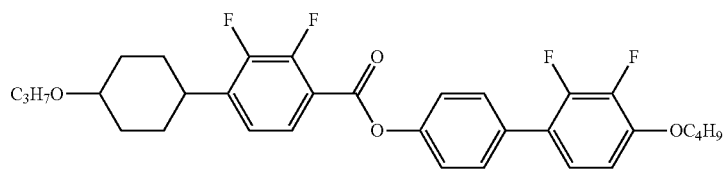 |
| 2210 | 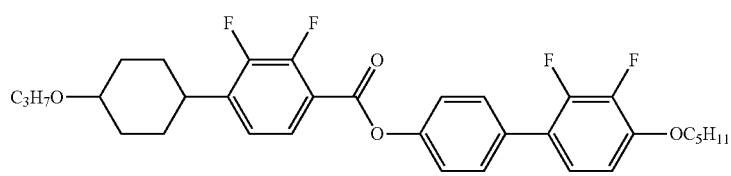 |
| 2211 | 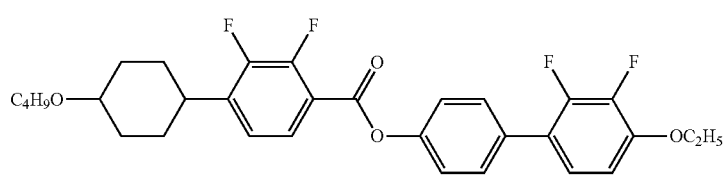 |
| 2212 | 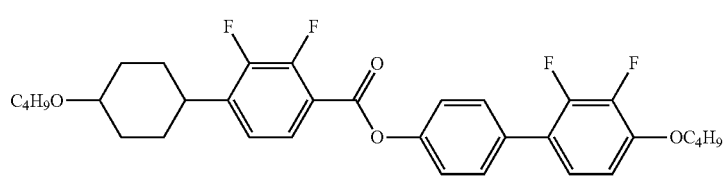 |
| 2213 | 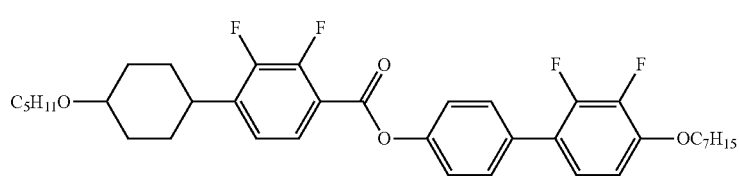 |
| 2214 | 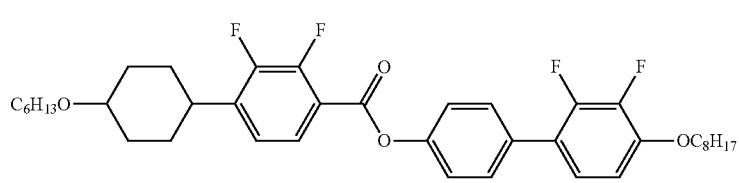 |
| 2215 | 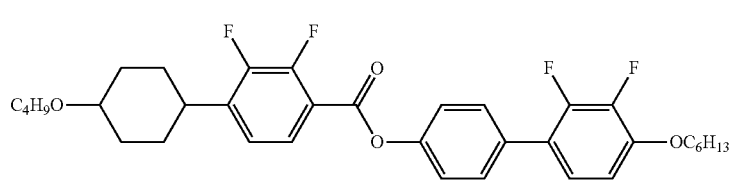 |

| No. | |
|---|---|
| 2216 | 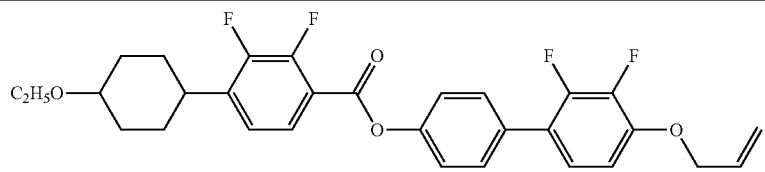 |
| 2217 | 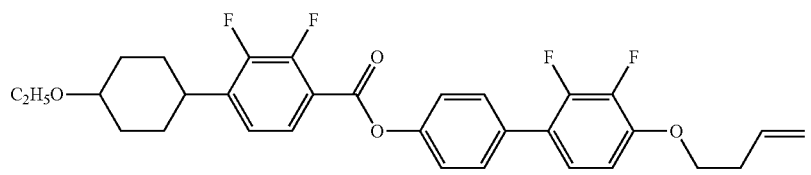 |
| 2218 | 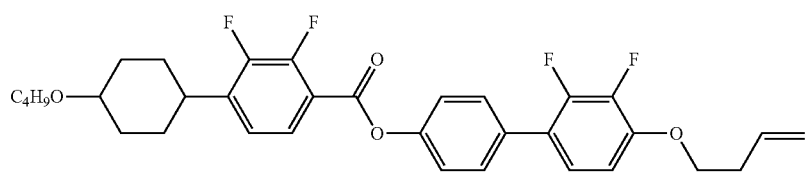 |
| 2219 | 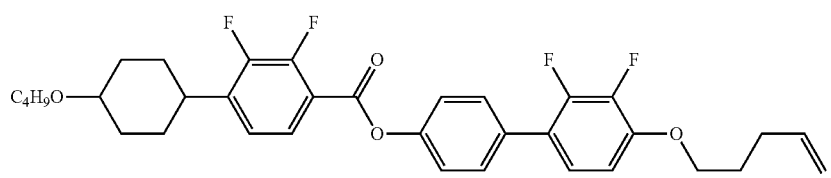 |
| 2220 | 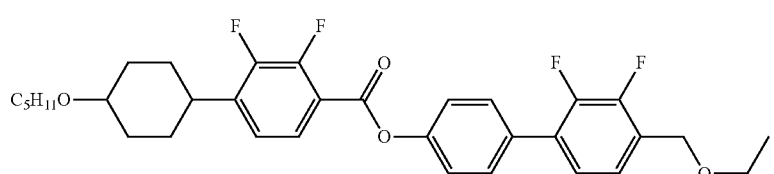 |
| 2221 | 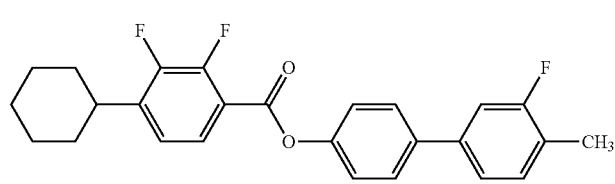 |
| 2222 | 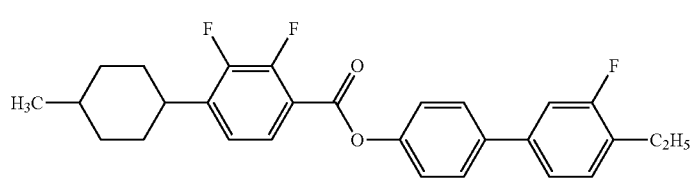 [SMILES: CCc1ccc(-c2ccc(OC(=O)c3ccc(C4CCC(C)CC4)c(F)c3F)cc2)cc1F] |
| 2223 | 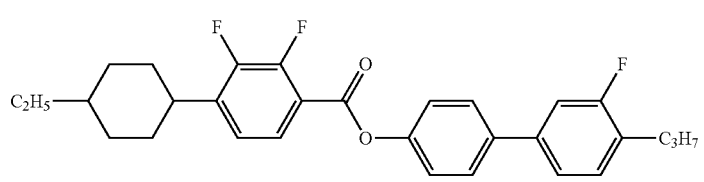 |
| 2224 | 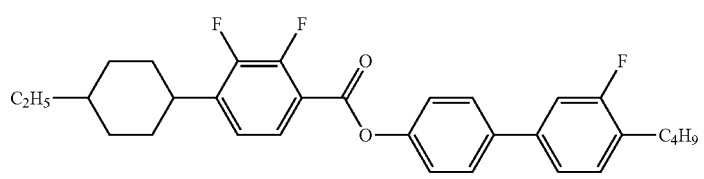 |

-continued
| No. | |
|---|---|
| 2225 | 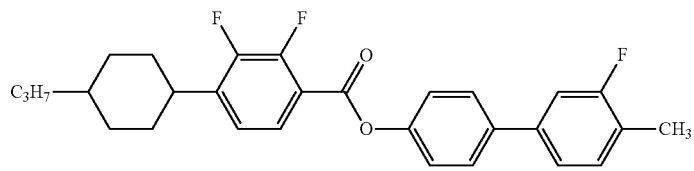 |
| 2226 | 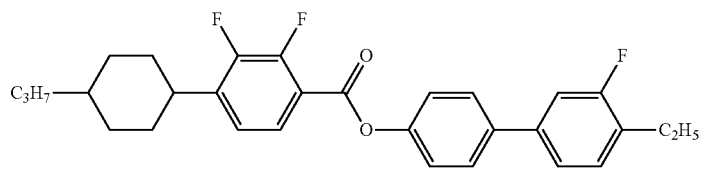 |
| 2227 | 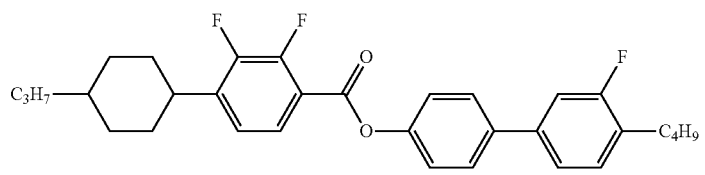 |
| 2228 | 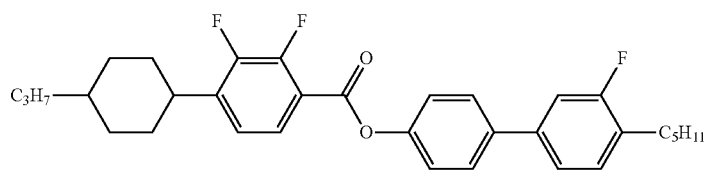 |
| 2229 | 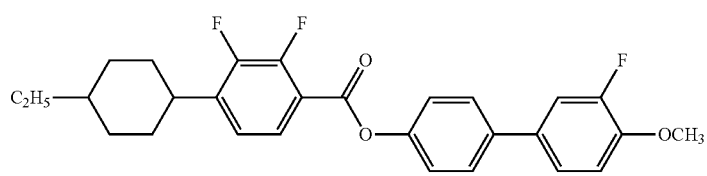 |
| 2230 | 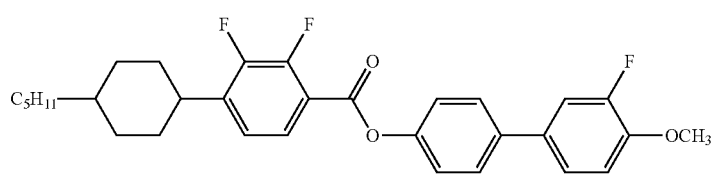 |
| 2231 | 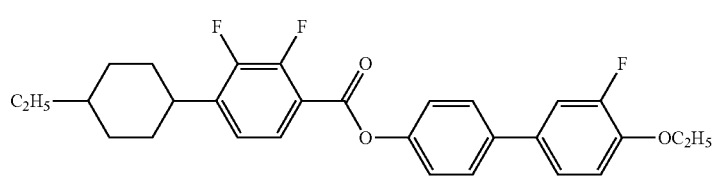 |
| 2232 | 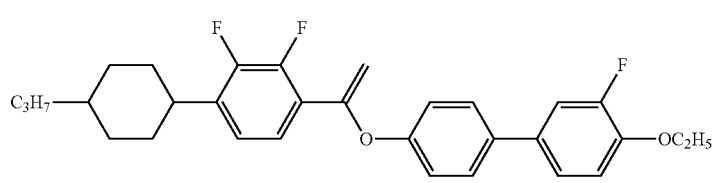 |

| No. | |
|---|---|
| 2223 | 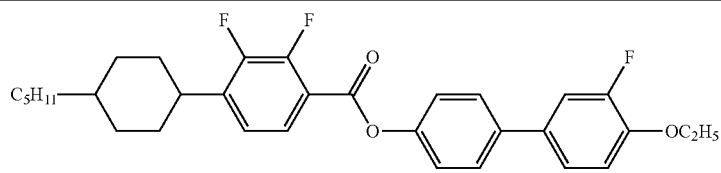 |
| 2224 | 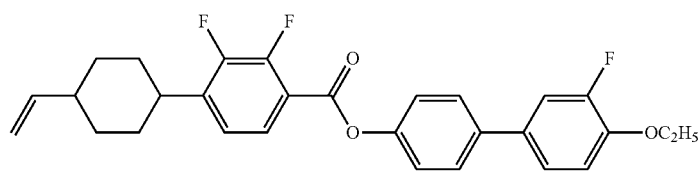 |
| 2225 | 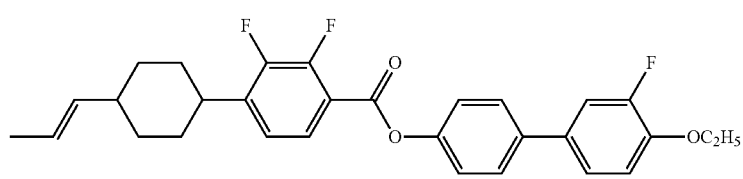 [SMILES: C/C=C/C1CCC(c2ccc(C(=O)Oc3ccc(-c4ccc(OCC)c(F)c4)cc3)c(F)c2F)CC1] |
| 2236 | 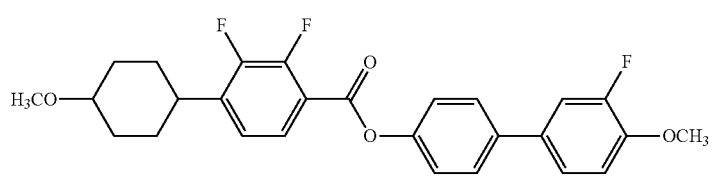 [SMILES: COc1ccc(-c2ccc(OC(=O)c3ccc(C4CCC(OC)CC4)c(F)c3F)cc2)cc1F] |
| 2237 | 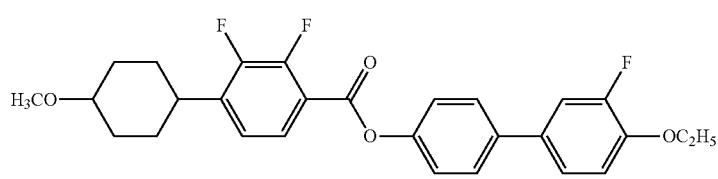 |
| 2238 | 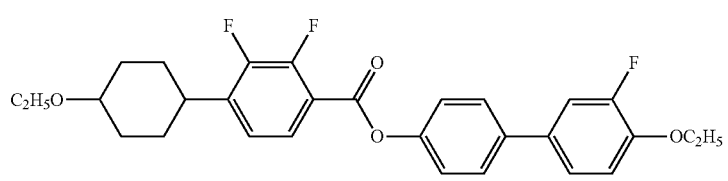 |
| 2239 | 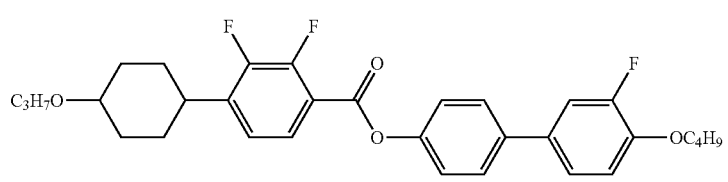 |
| 2240 | 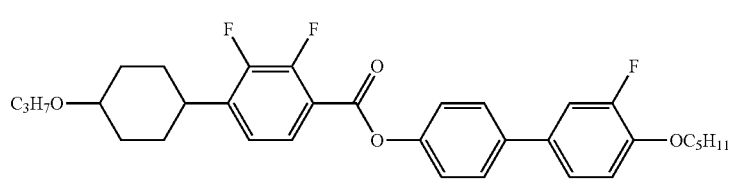 |
| 2241 | 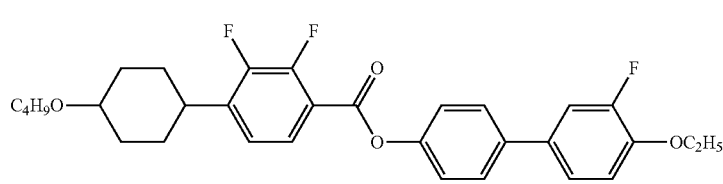 |

| No. | |
|---|---|
| 2242 | 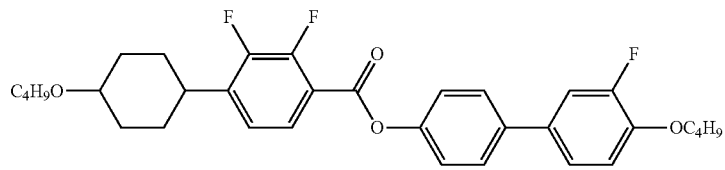 |
| 2243 | 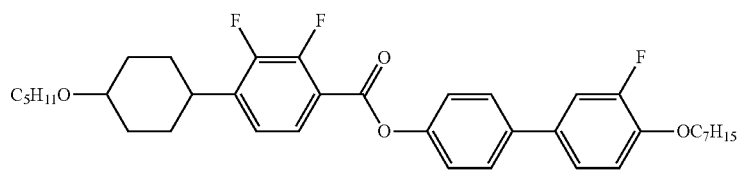 |
| 2244 | 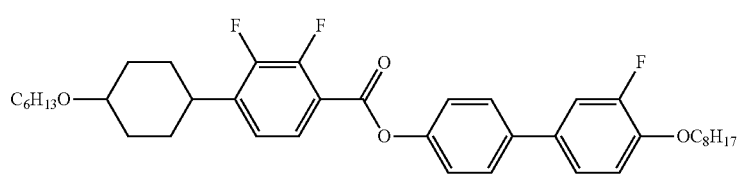 |
| 2245 | 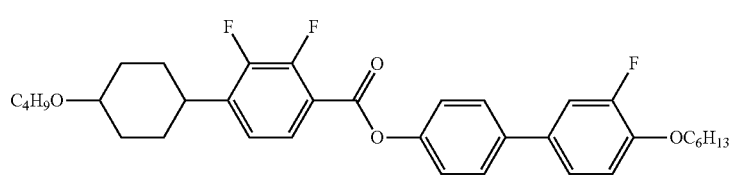 |
| 2246 | 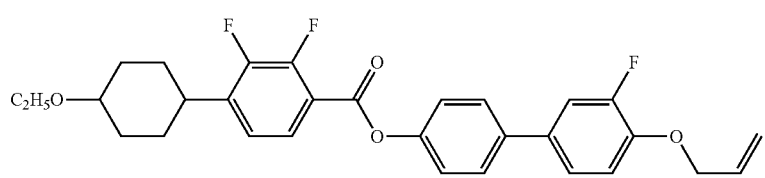 |
| 2247 | 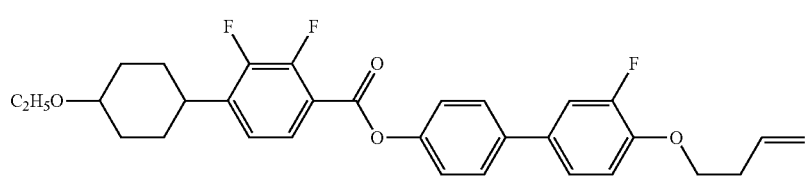 |
| 2248 | 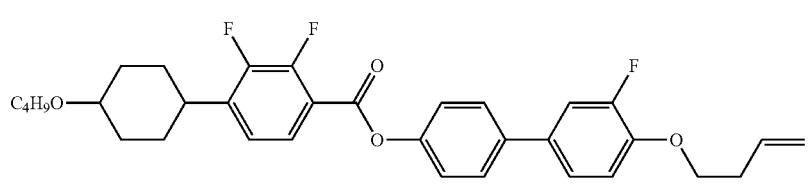 |
| 2249 | 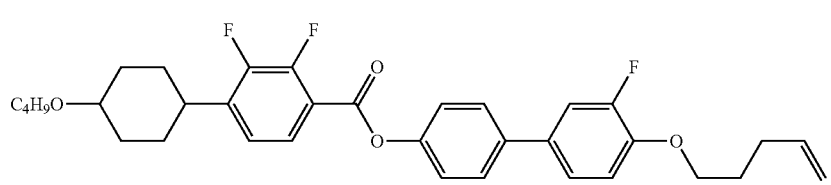 |

| No. | |
|---|---|
| 2250 | 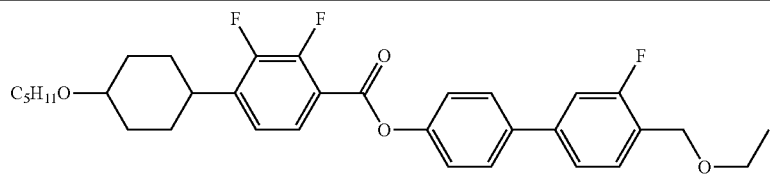 |
| 2251 | 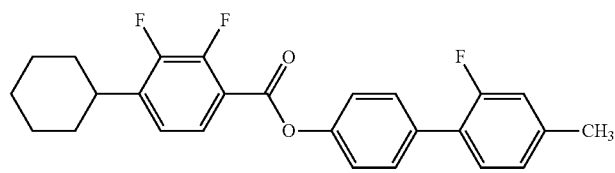 [SMILES: Cc1ccc(-c2ccc(OC(=O)c3ccc(C4CCCCC4)c(F)c3F)cc2)c(F)c1] |
| 2252 | 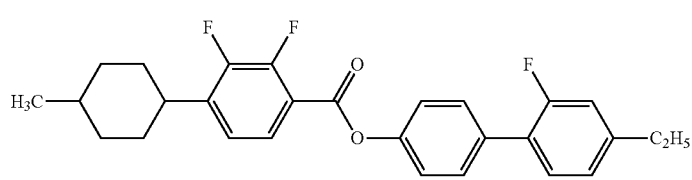 [SMILES: CCc1ccc(-c2ccc(OC(=O)c3ccc(C4CCC(C)CC4)c(F)c3F)cc2)c(F)c1] |
| 2253 | 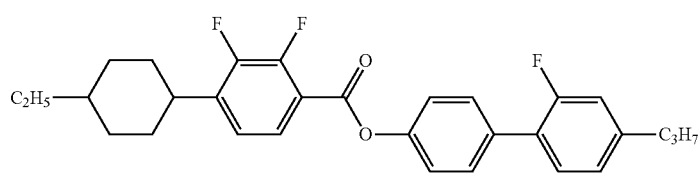 |
| 2254 | 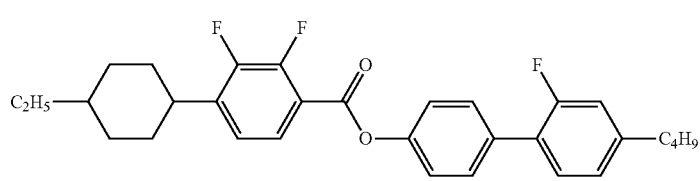 |
| 2255 | 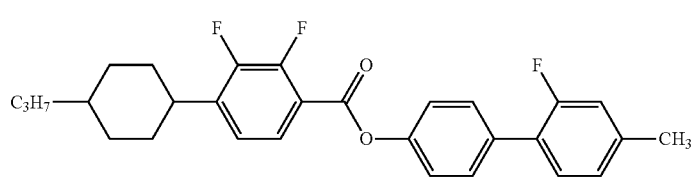 |
| 2256 | 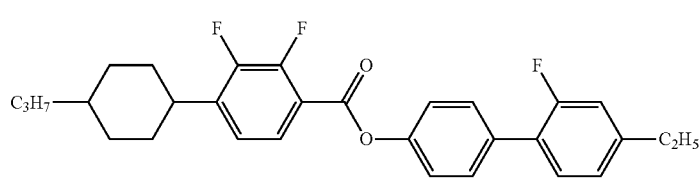 |
| 2257 | 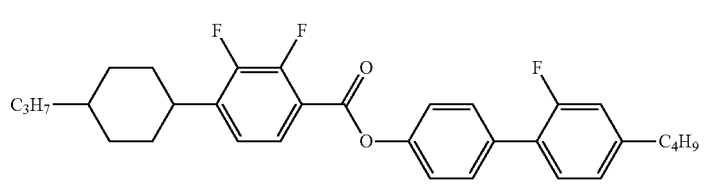 |
| 2258 | 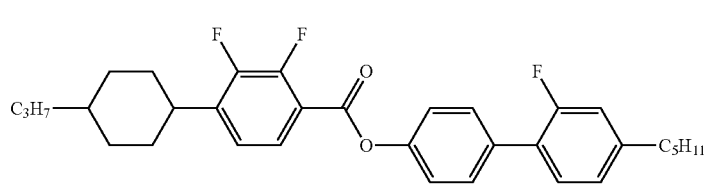 |

| No. |
|---|
| 2259 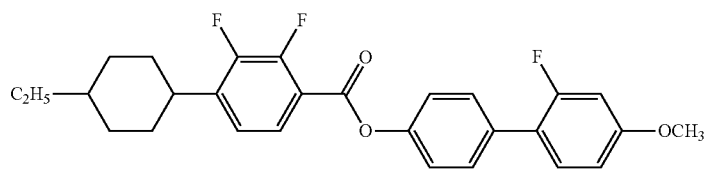 |
| 2260 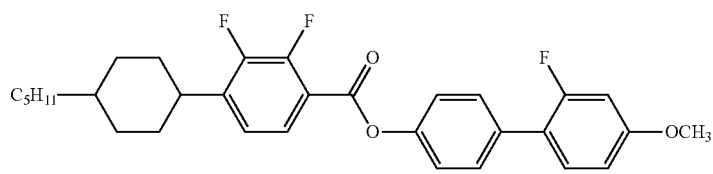 |
| 2261 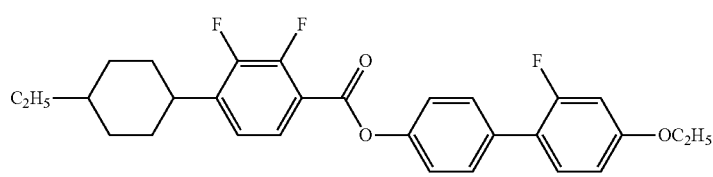 [SMILES: CCOc1ccc(-c2ccc(OC(=O)c3ccc(C4CCC(CC)CC4)c(F)c3F)cc2)c(F)c1] |
| 2262 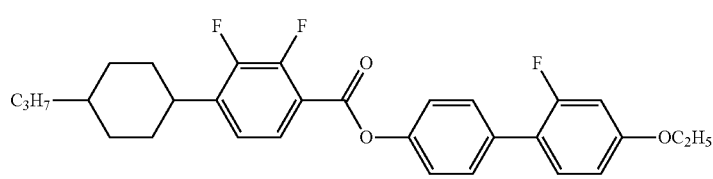 |
| 2263 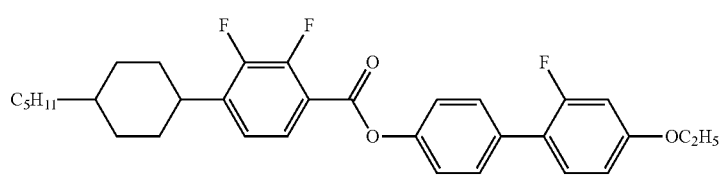 |
| 2264 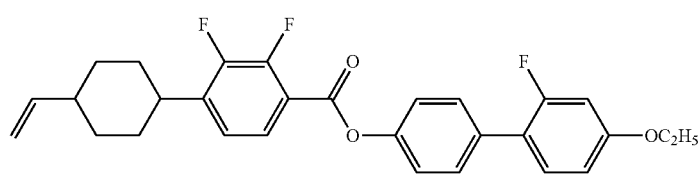 |
| 2265 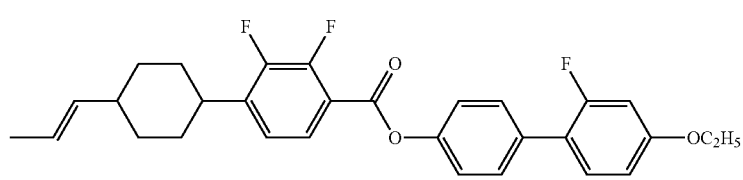 |
| 2266 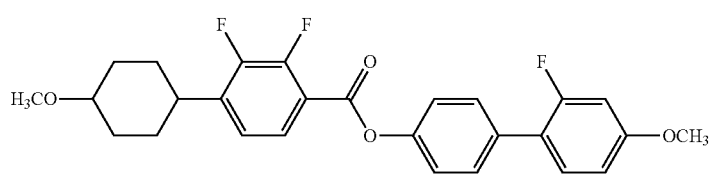 |

| No. | |
|---|---|
| 2267 | 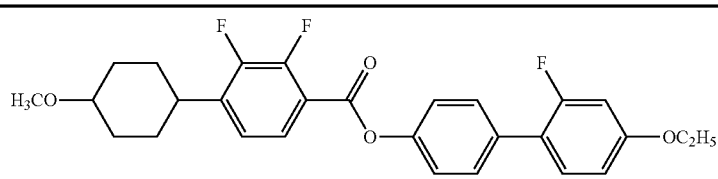 |
| 2268 | 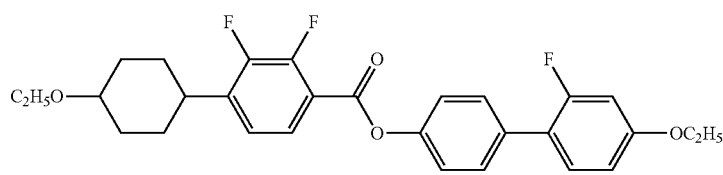 |
| 2269 | 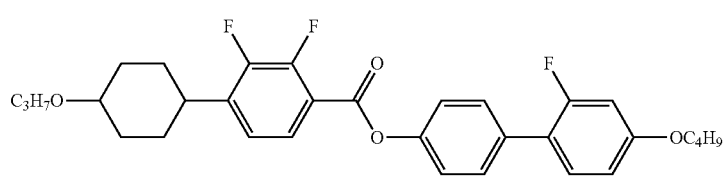 |
| 2270 | 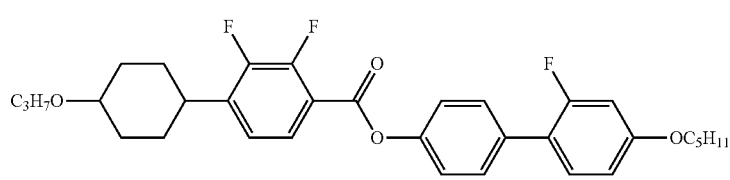 |
| 2271 | 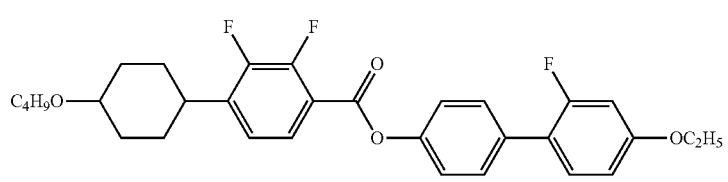 |
| 2272 | 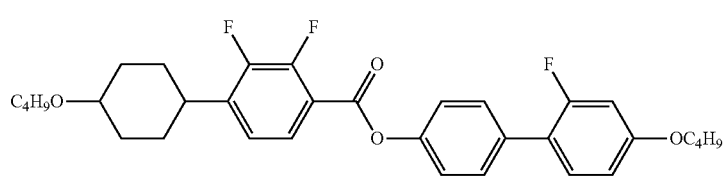 |
| 2273 | 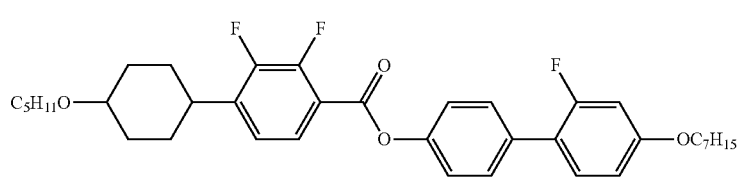 |
| 2274 | 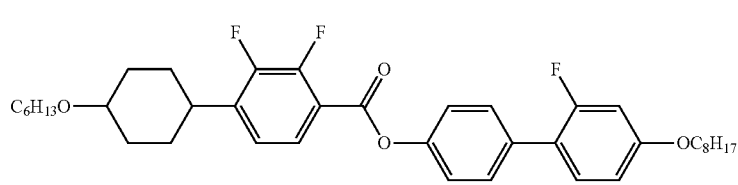 |
| 2275 | 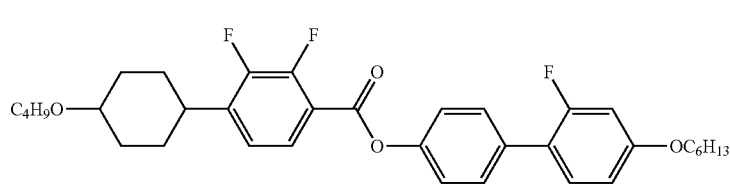 |

-continued
| No. | |
|---|---|
| 2276 | 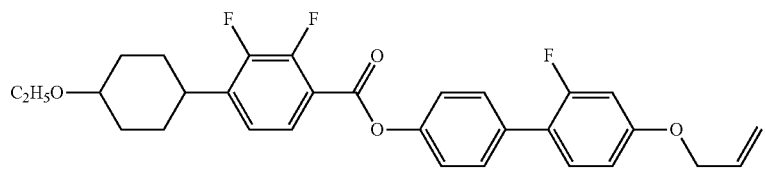 |
| 2277 | 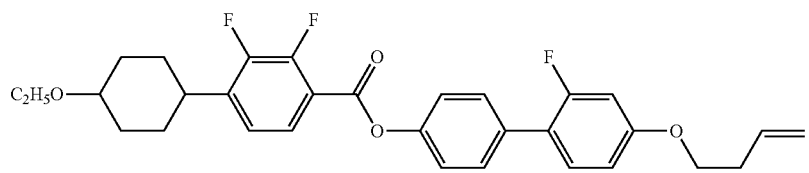 |
| 2278 | 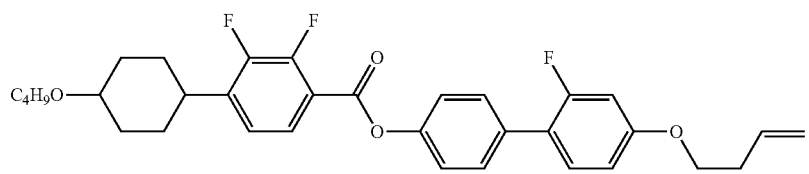 |
| 2279 | 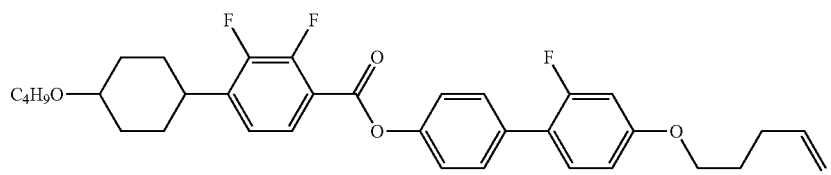 |
| 2280 | 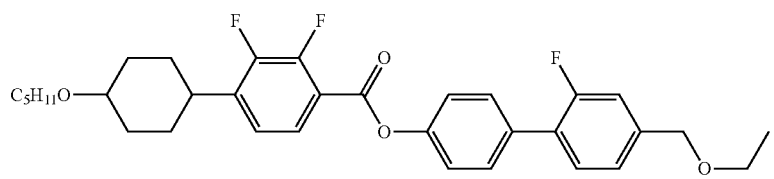 |
| 2281 | 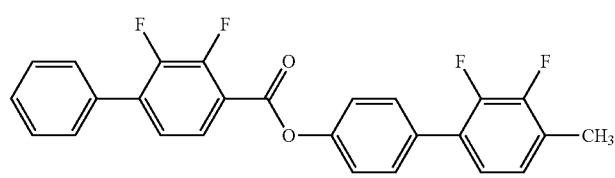 |
| 2282 | 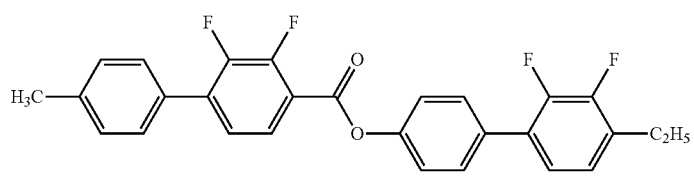 |
| 2283 | 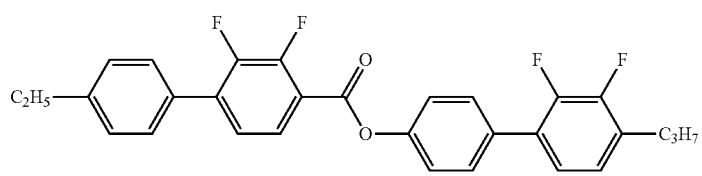 |

| No. | |
|---|---|
| 2284 | 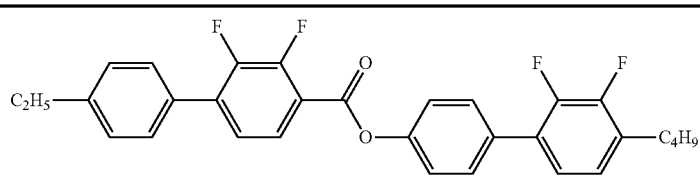 |
| 2285 | 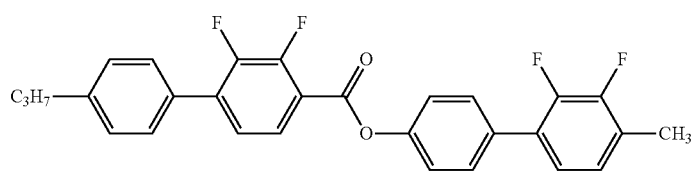 |
| 2286 | 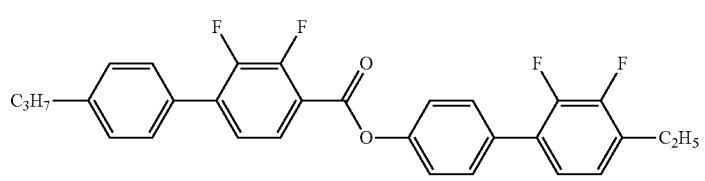 |
| 2287 | 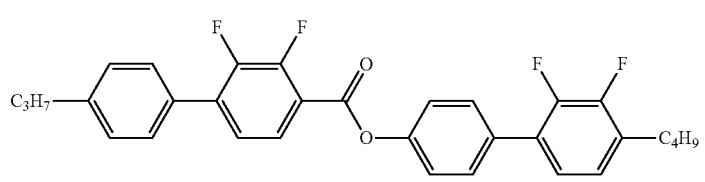 |
| 2288 | 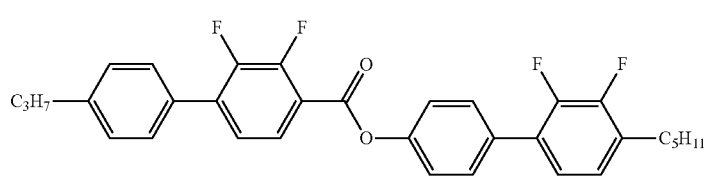 |
| 2289 | 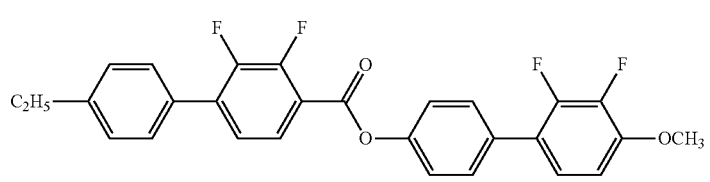 [SMILES: CCc1ccc(-c2ccc(C(=O)Oc3ccc(-c4ccc(OC)c(F)c4F)cc3)c(F)c2F)cc1] |
| 2290 | 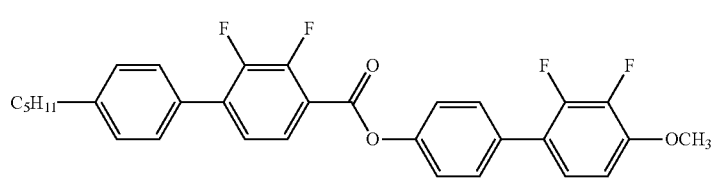 |
| 2291 | 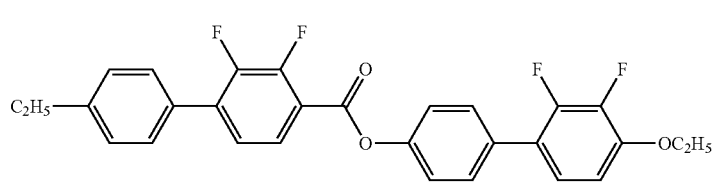 [SMILES: CCOc1ccc(-c2ccc(OC(=O)c3ccc(-c4ccc(CC)cc4)c(F)c3F)cc2)c(F)c1F] |
| 2292 | 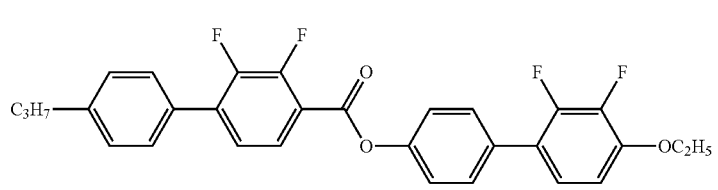 |

-continued
| No. | |
|---|---|
| 2293 | 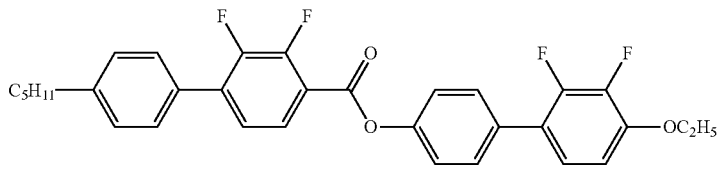 |
| 2294 | 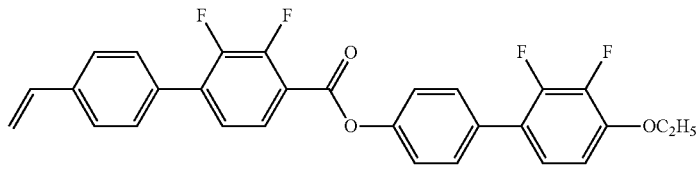 [SMILES: C=Cc1ccc(-c2ccc(C(=O)Oc3ccc(-c4ccc(OCC)c(F)c4F)cc3)c(F)c2F)cc1] |
| 2295 | 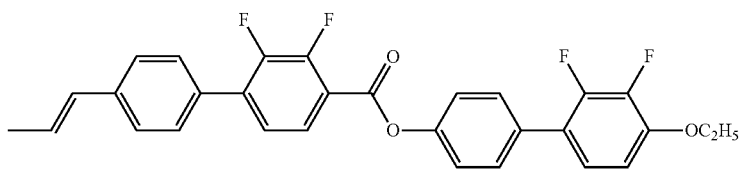 [SMILES: C/C=C/c1ccc(-c2ccc(C(=O)Oc3ccc(-c4ccc(OCC)c(F)c4F)cc3)c(F)c2F)cc1] |
| 2296 | 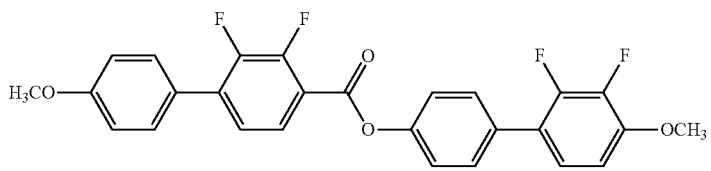 |
| 2297 | 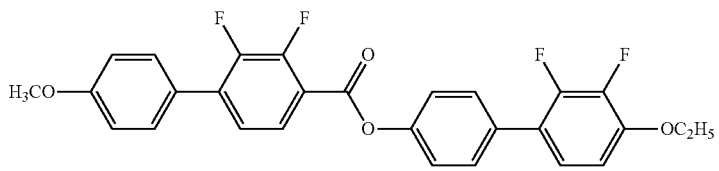 |
| 2298 | 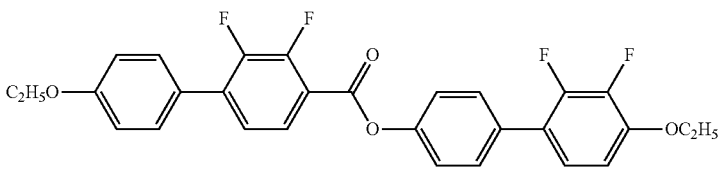 |
| 2299 | 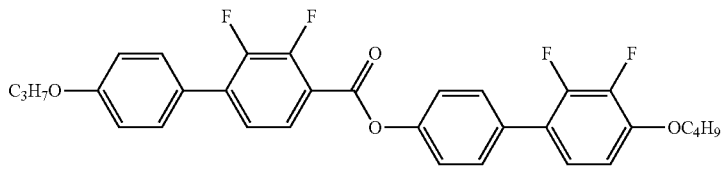 |
| 2300 | 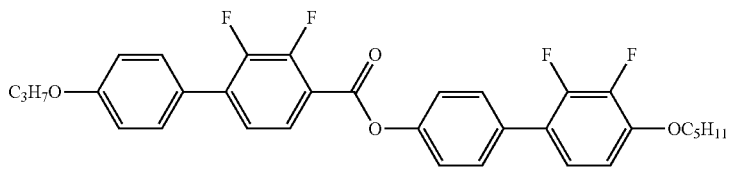 |

| No. | |
|---|---|
| 2301 | 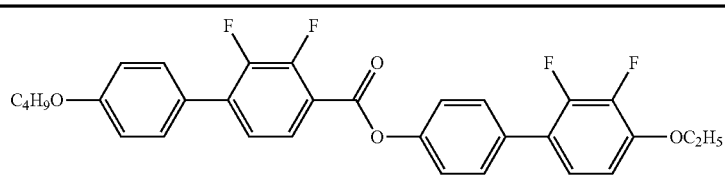 |
| 2302 | 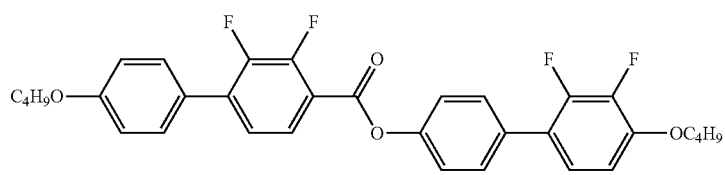 |
| 2303 | 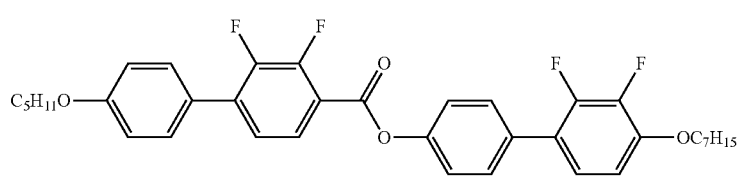 |
| 2304 | 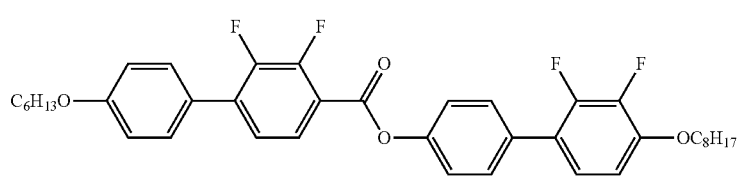 |
| 2305 | 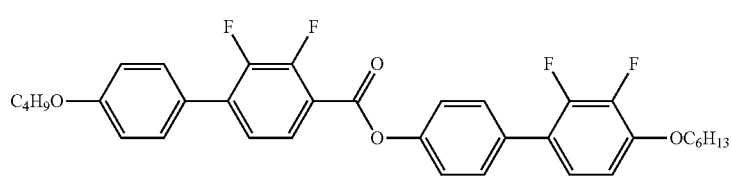 |
| 2306 | 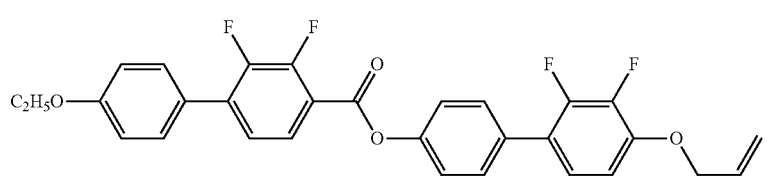 |
| 2307 | 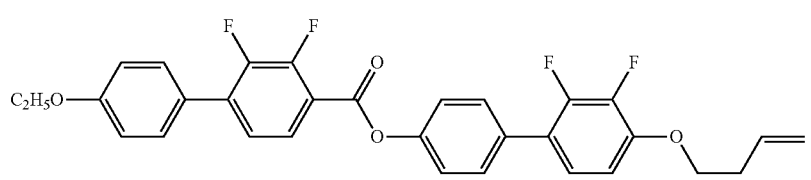 |
| 2308 | 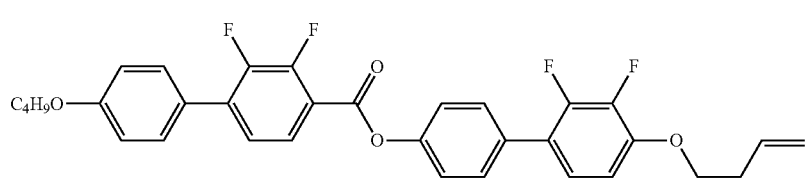 |
| 2309 | 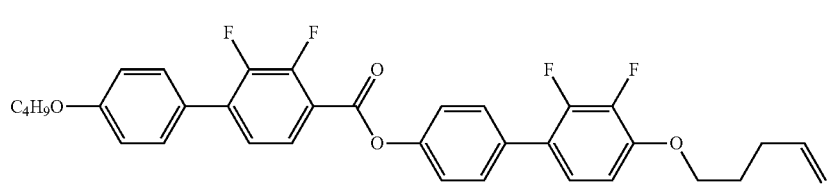 |

| No. | |
|---|---|
| 2310 | 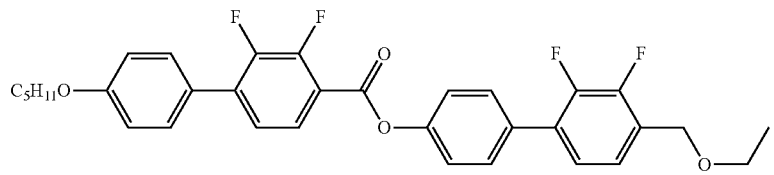 |
| 2311 | 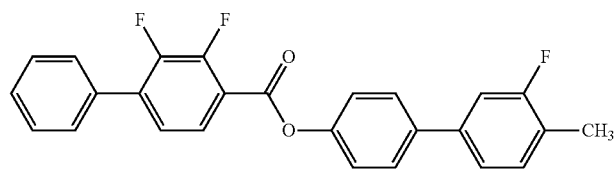 [SMILES: Cc1ccc(-c2ccc(OC(=O)c3ccc(-c4ccccc4)c(F)c3F)cc2)cc1F] |
| 2312 | 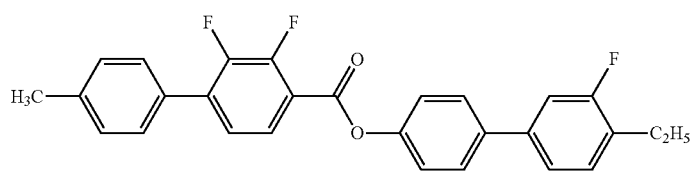 [SMILES: CCc1ccc(-c2ccc(OC(=O)c3ccc(-c4ccc(C)cc4)c(F)c3F)cc2)cc1F] |
| 2313 | 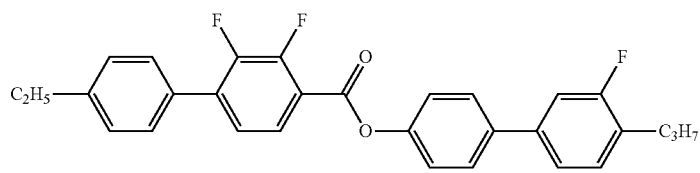 |
| 2314 | 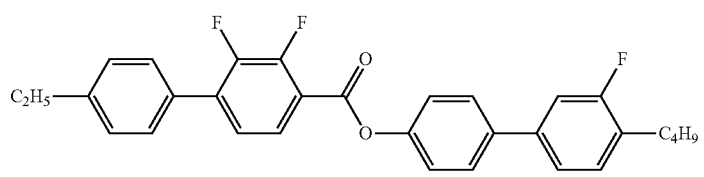 |
| 2315 | 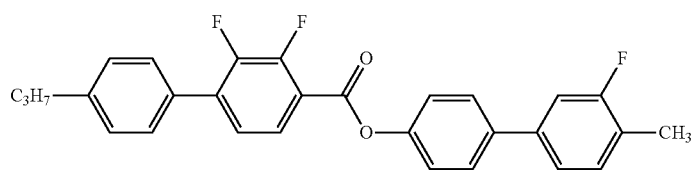 |
| 2316 | 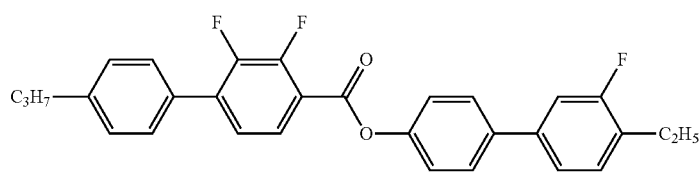 |
| 2317 | 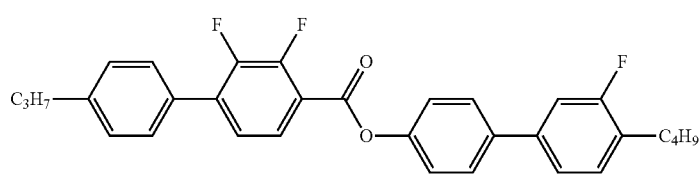 |

-continued
| No. | |
|---|---|
| 2318 | 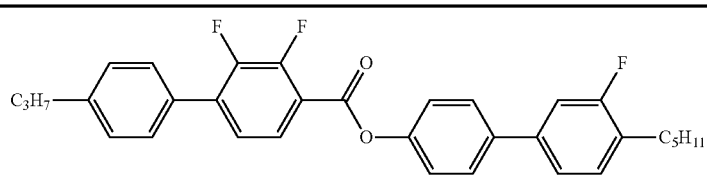 |
| 2319 | 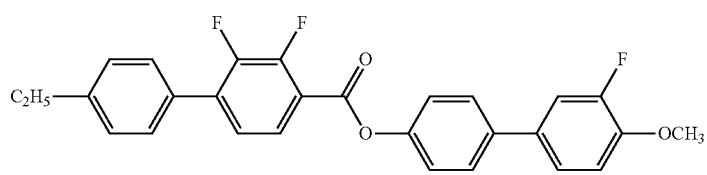 |
| 2320 | 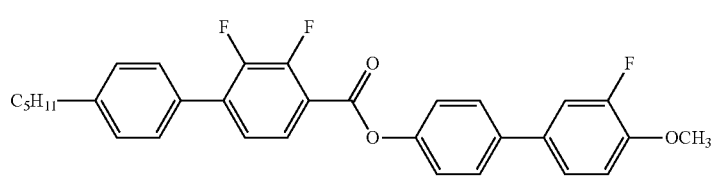 |
| 2321 | 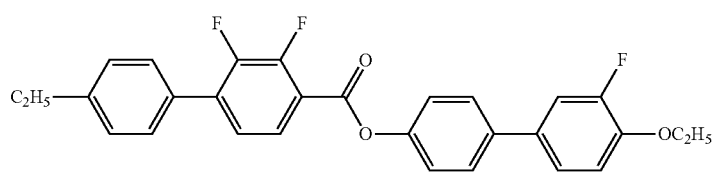 |
| 2322 | 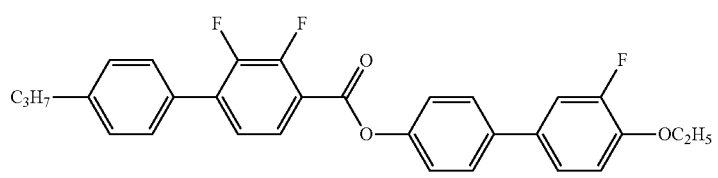 [SMILES: CCOc1ccc(-c2ccc(OC(=O)c3ccc(-c4ccc(CC)cc4)c(F)c3F)cc2)cc1F] |
| 2323 | 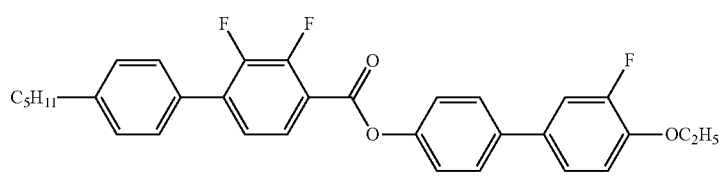 |
| 2324 | 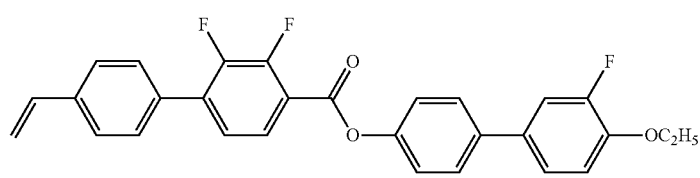 [SMILES: C=Cc1ccc(-c2ccc(C(=O)Oc3ccc(-c4ccc(OCC)c(F)c4)cc3)c(F)c2F)cc1] |
| 2325 | 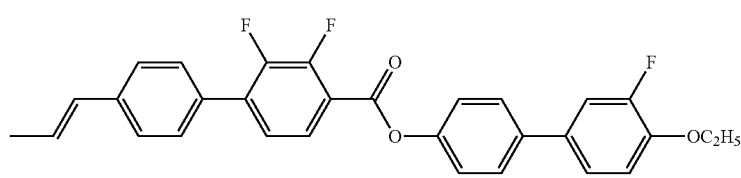 [SMILES: C/C=C/c1ccc(-c2ccc(C(=O)Oc3ccc(-c4ccc(OCC)c(F)c4)cc3)c(F)c2F)cc1] |
| 2326 | 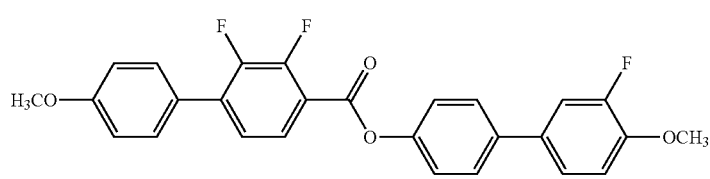 [SMILES: COc1ccc(-c2ccc(C(=O)Oc3ccc(-c4ccc(OC)c(F)c4)cc3)c(F)c2F)cc1] |

| No. | |
|---|---|
| 2327 | 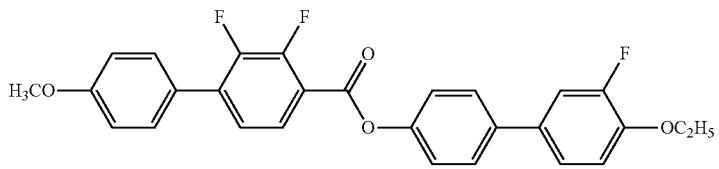 |
| 2328 | 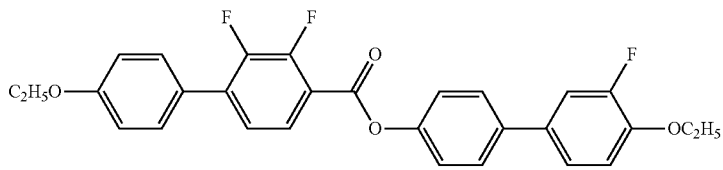 |
| 2329 | 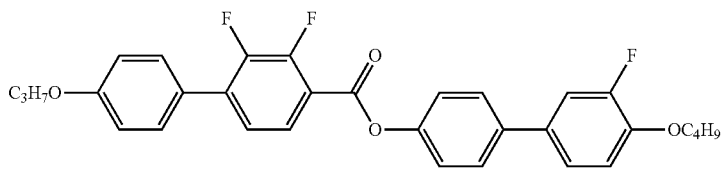 |
| 2330 | 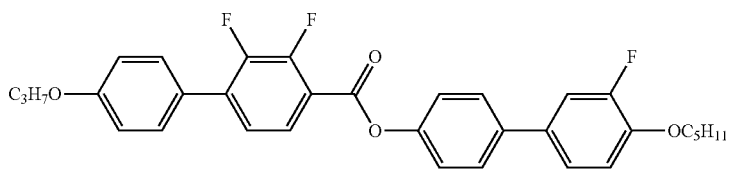 |
| 2331 | 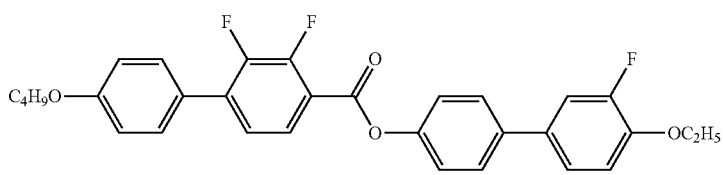 |
| 2332 | 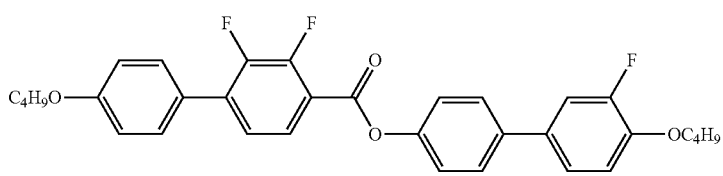 |
| 2333 | 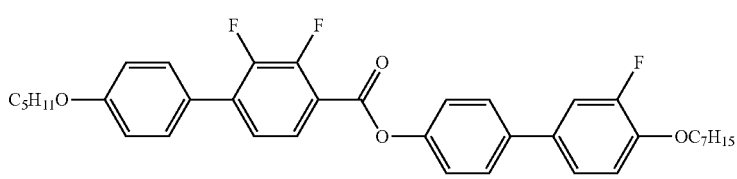 |
| 2334 | 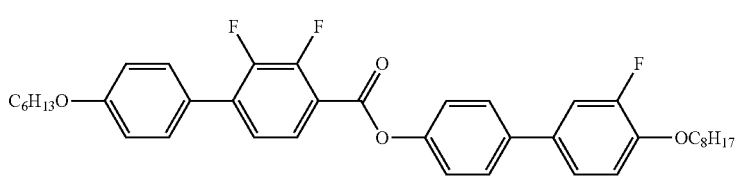 |

| No. | |
|---|---|
| 2335 | 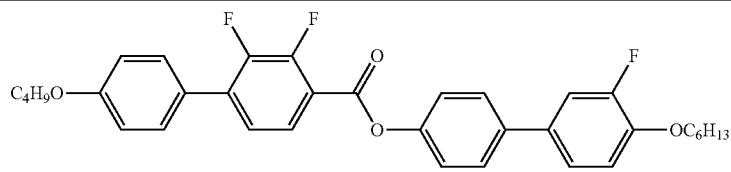 |
| 2336 | 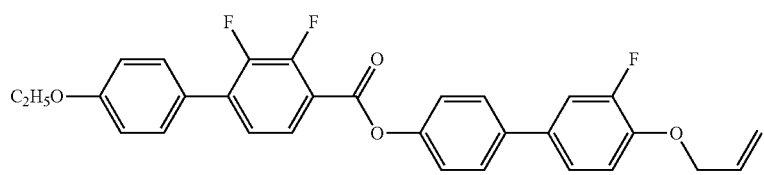 |
| 2337 | 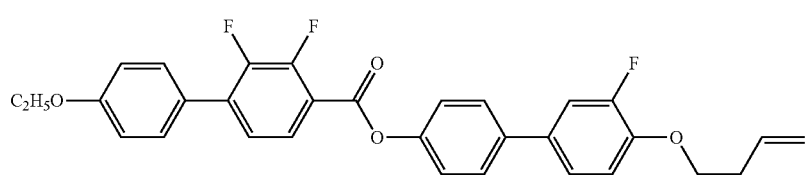 |
| 2338 | 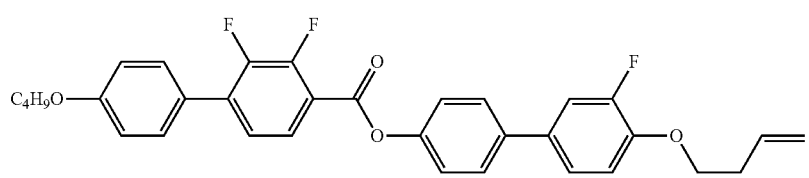 |
| 2339 | 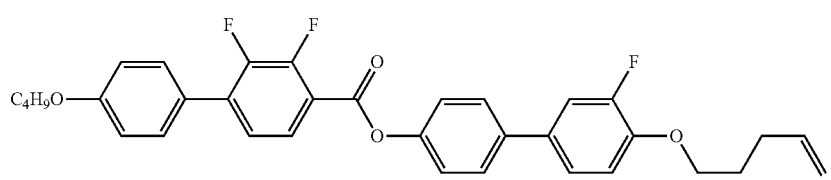 |
| 2340 | 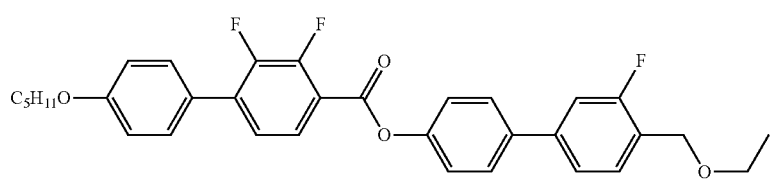 |
| 2341 | 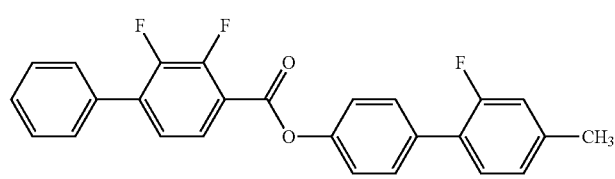 |
| 2342 | 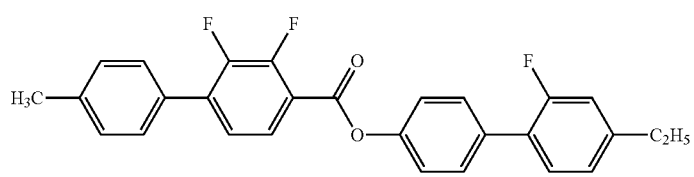 [SMILES: CCc1ccc(-c2ccc(OC(=O)c3ccc(-c4ccc(C)cc4)c(F)c3F)cc2)c(F)c1] |
| 2343 | 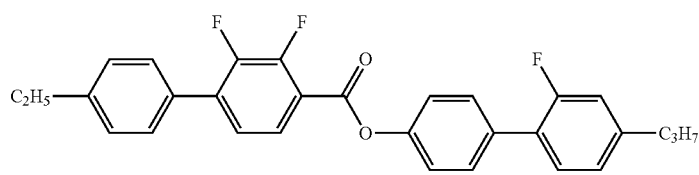 |

-continued
| No. | |
|---|---|
| 2344 | 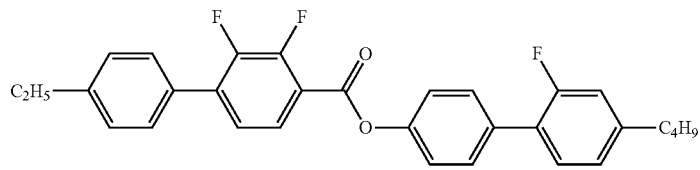 |
| 2345 | 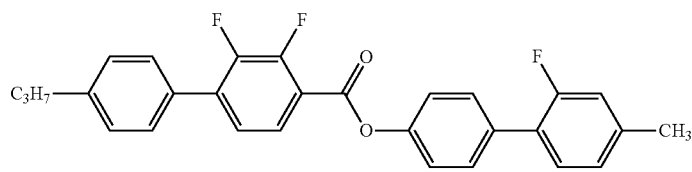 |
| 2346 | 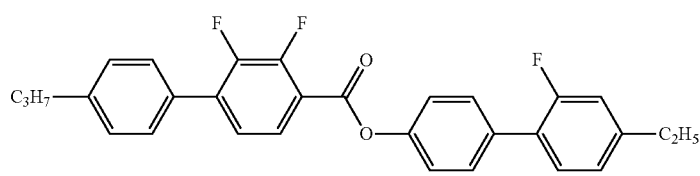 |
| 2347 | 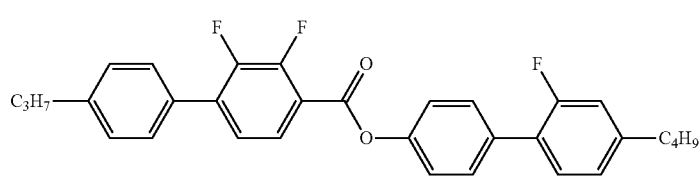 |
| 2348 | 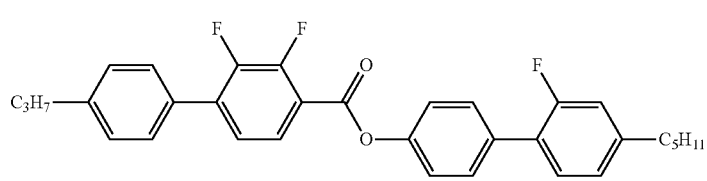 |
| 2349 | 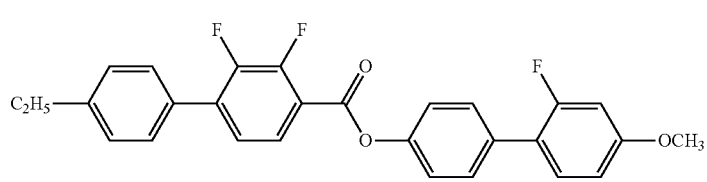 |
| 2350 | 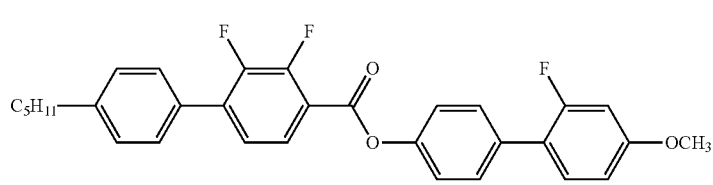 |
| 2351 | 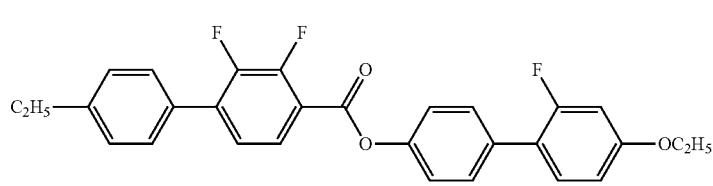 [SMILES: CCOc1ccc(-c2ccc(OC(=O)c3ccc(-c4ccc(CC)cc4)c(F)c3F)cc2)c(F)c1] |

| No. | |
|---|---|
| 2352 | 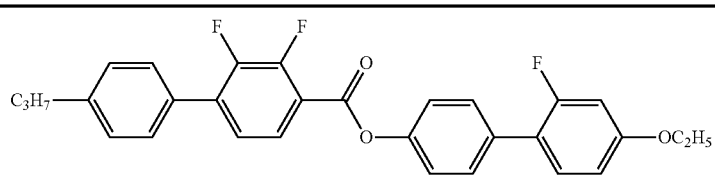 |
| 2353 | 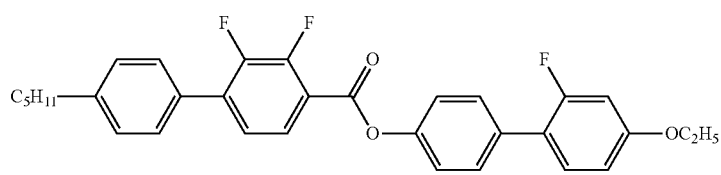 |
| 2354 | 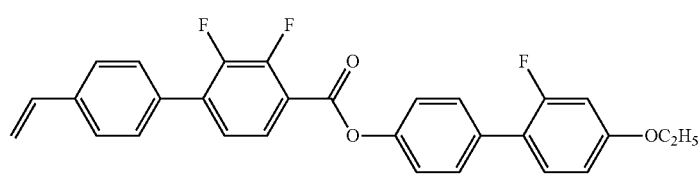 |
| 2355 | 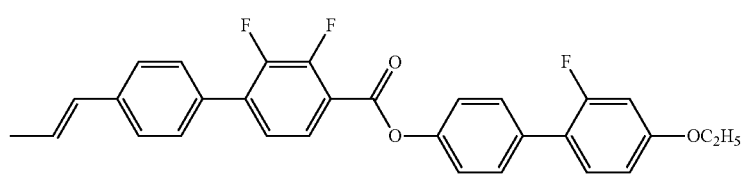 |
| 2356 | 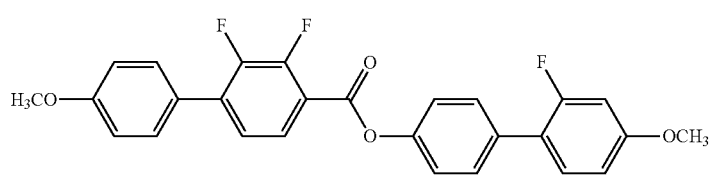 [SMILES: COc1ccc(-c2ccc(C(=O)Oc3ccc(-c4ccc(OC)cc4F)cc3)c(F)c2F)cc1] |
| 2357 | 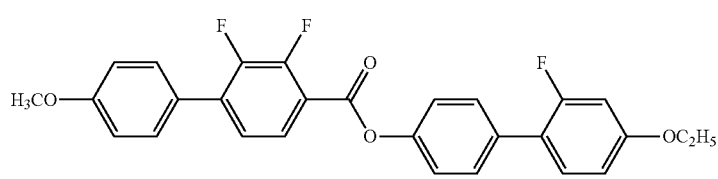 |
| 2358 | 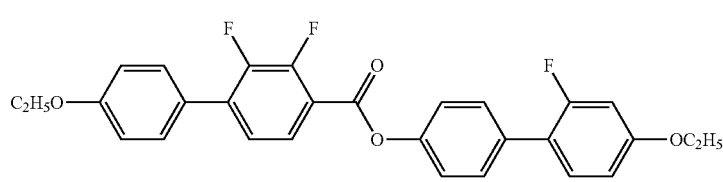 |
| 2359 | 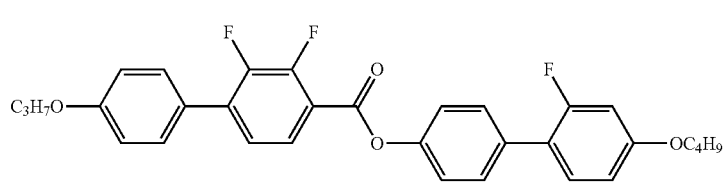 |
| 2360 | 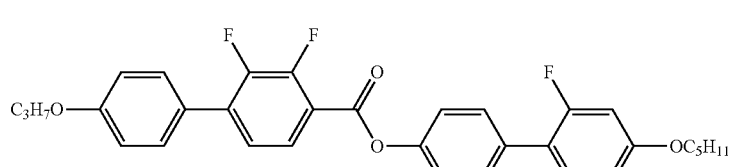 |

-continued
| No. | |
|---|---|
| 2361 | 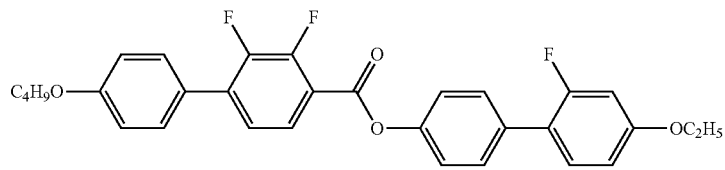 |
| 2362 | 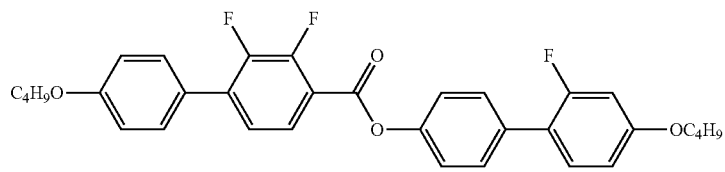 |
| 2363 | 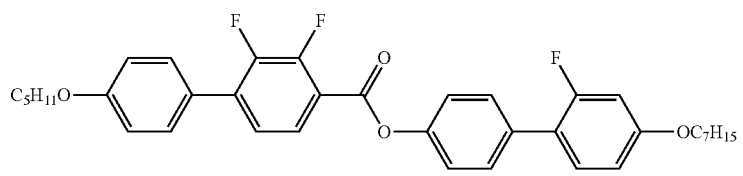 |
| 2364 | 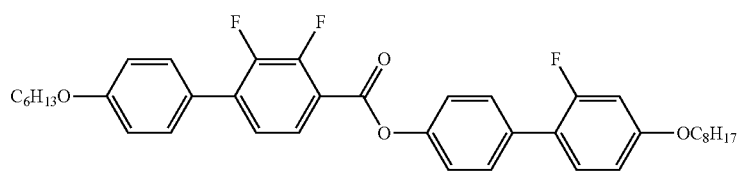 |
| 2365 | 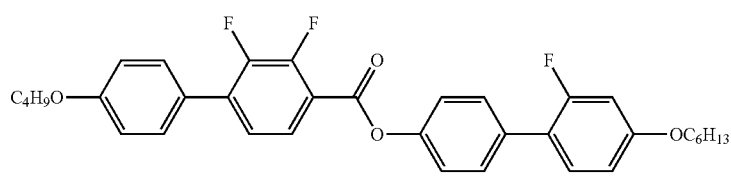 |
| 2366 | 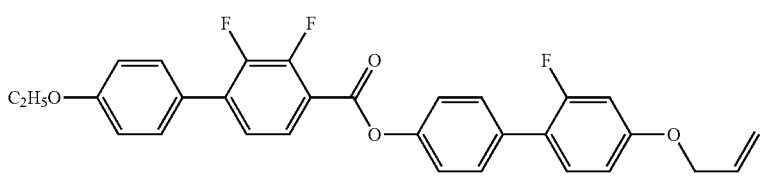 |
| 2367 | 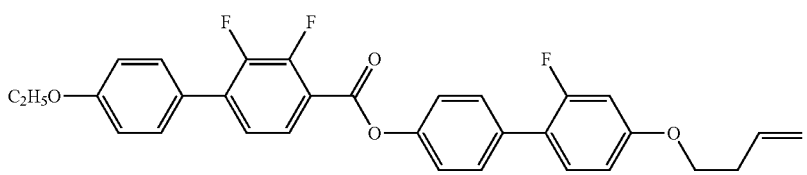 |
| 2368 | 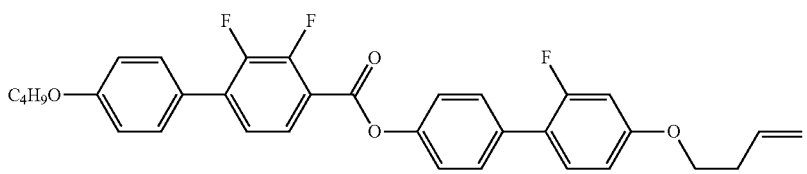 |

-continued
| No. |
|---|
| 2369 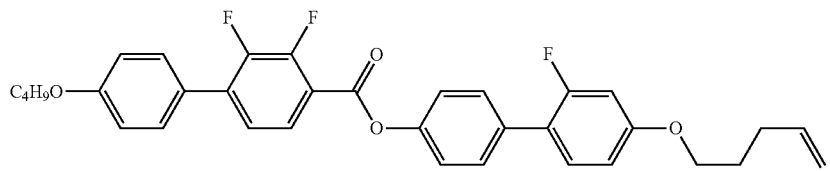 |
| 2370 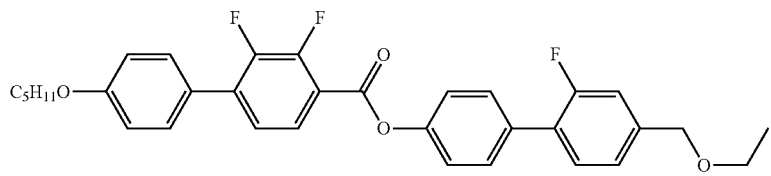 |
| 2371 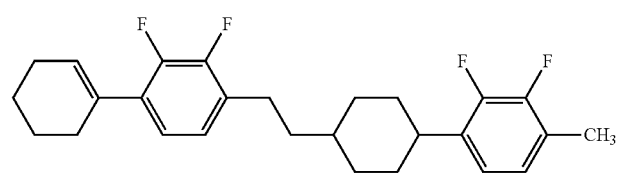 |
| 2372 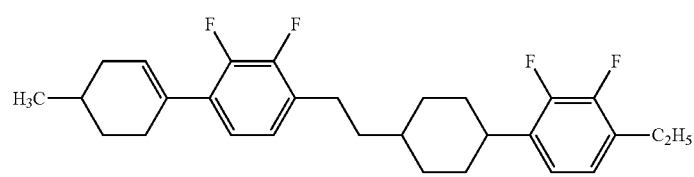 |
| 2373 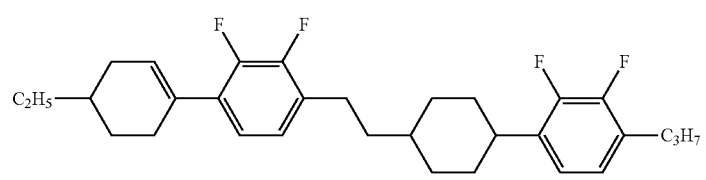 |
| 2374 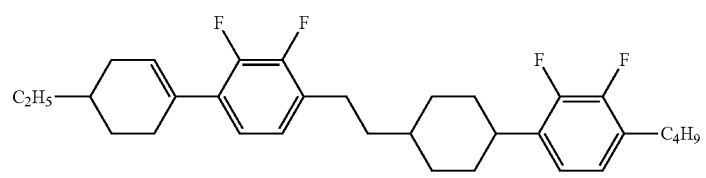 |
| 2375 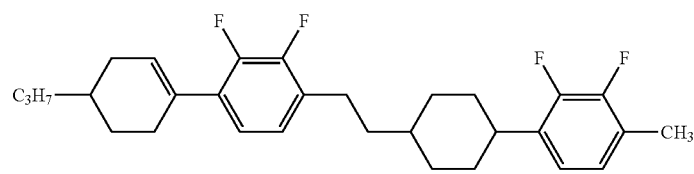 |
| 2376 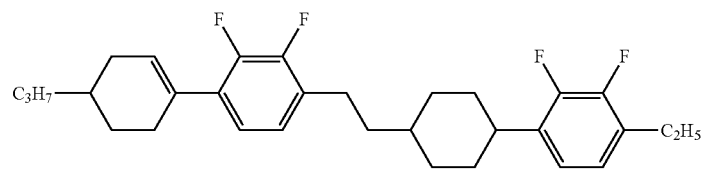 |
| 2377 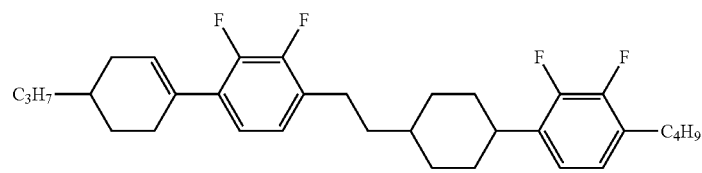 |

| No. |
|---|
| 2378 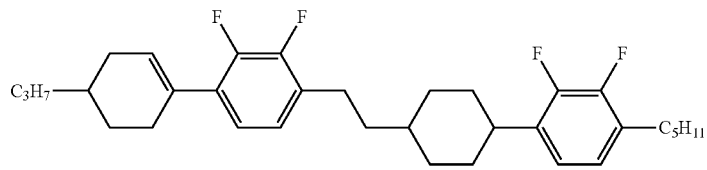 |
| 2379 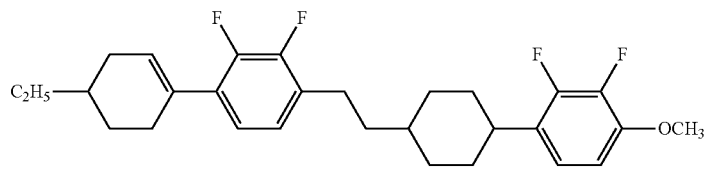 |
| 2380 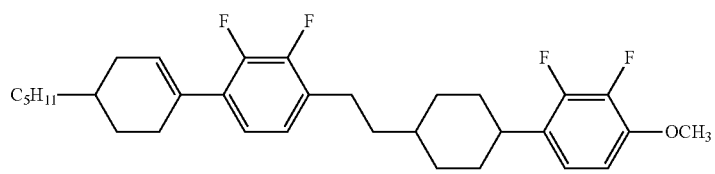 |
| 2381 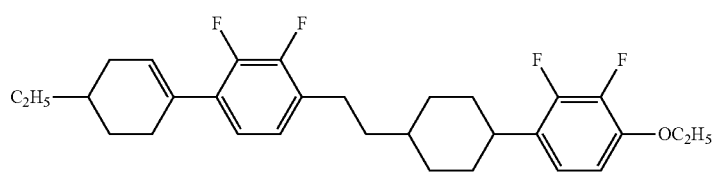 |
| 2382 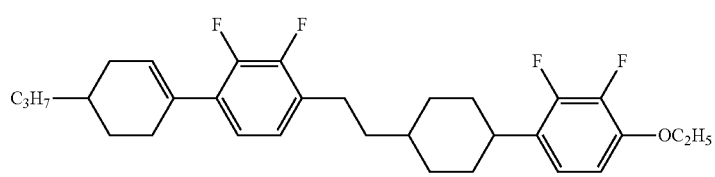 |
| 2383 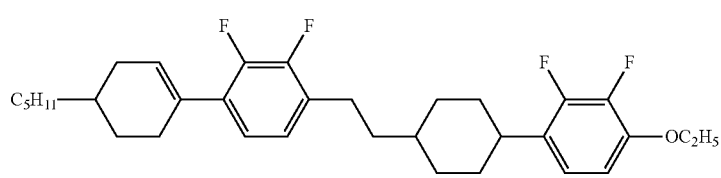 [SMILES: CCOc1ccc(C2CCC(CCc3ccc(C4=CCC(OC)CC4)c(F)c3F)CC2)c(F)c1F] |
| 2384 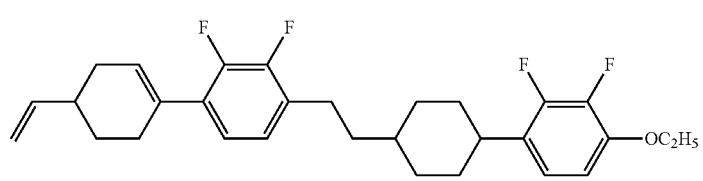 |
| 2385 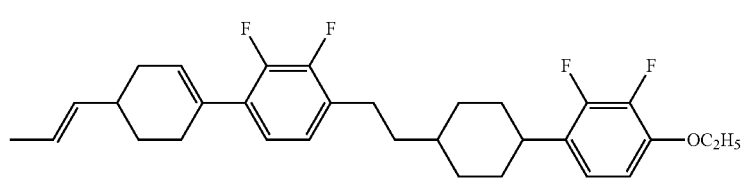 |

| No. |
|---|
| 2386 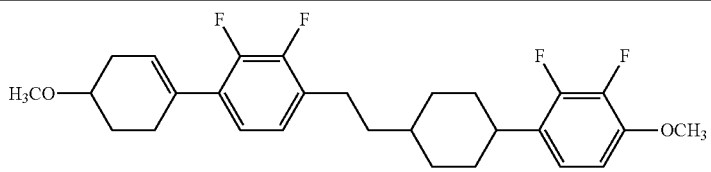 |
| 2387 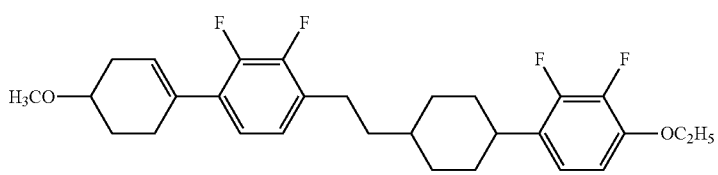 |
| 2388 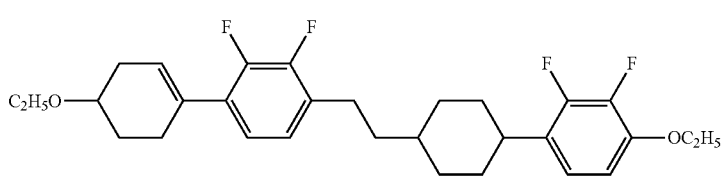 |
| 2389 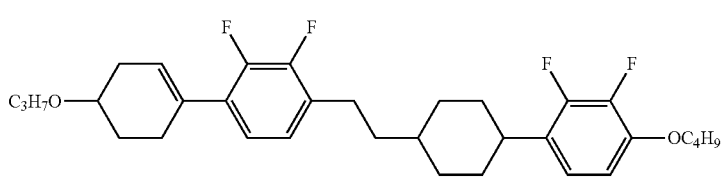 |
| 2390 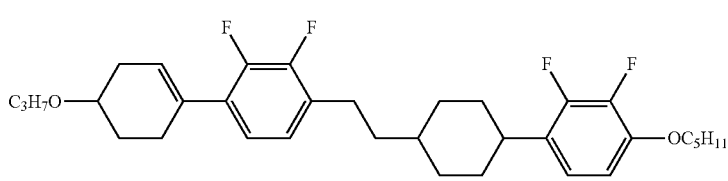 |
| 2391 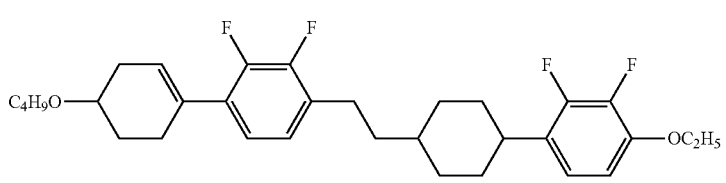 |
| 2392 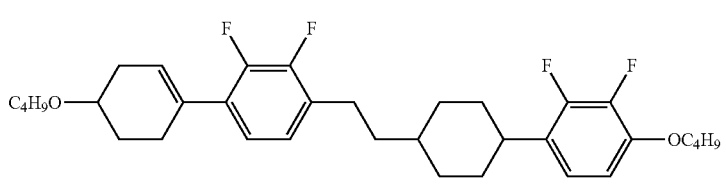 |
| 2393 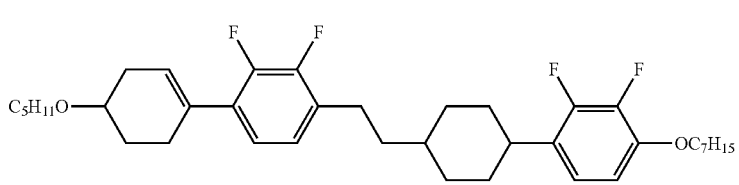 |
| 2394 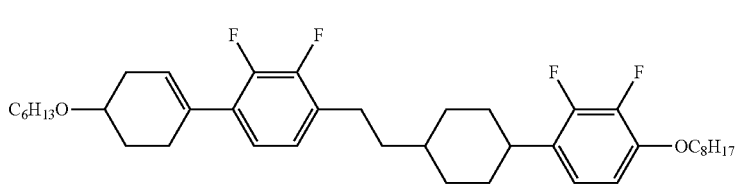 |

| No. |
|---|
| 2395 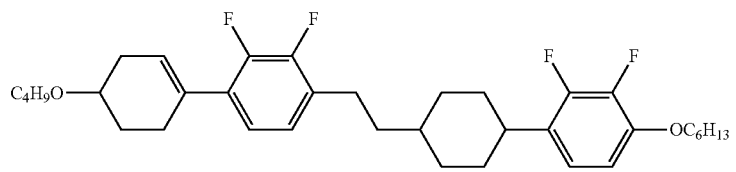 |
| 2396 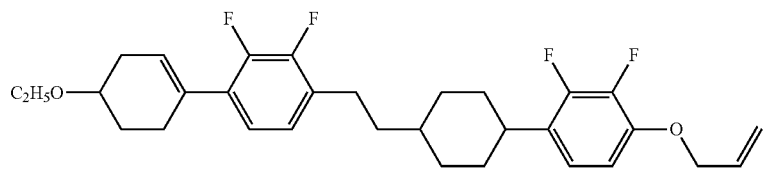 |
| 2397 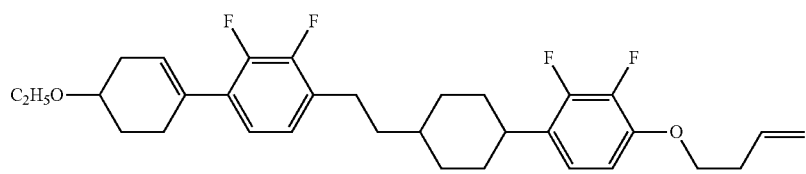 |
| 2398 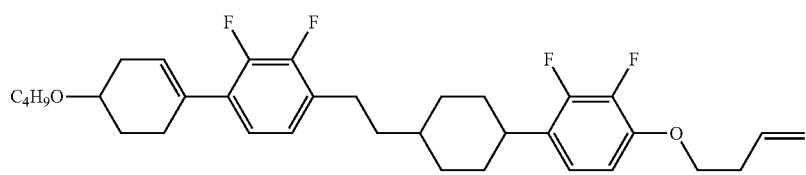 |
| 2399 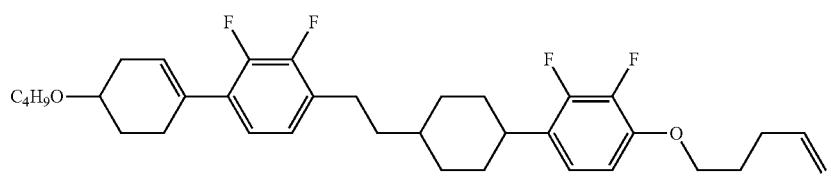 |
| 2400 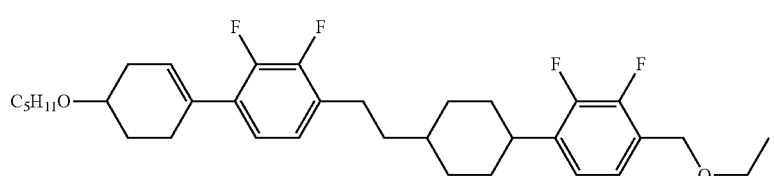 |
| 2401 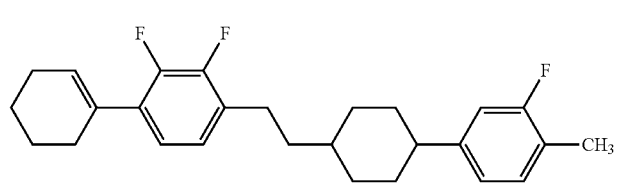 |
| 2402 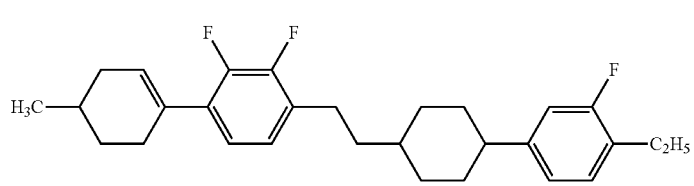 |

| No. | |
|---|---|
| 2403 | 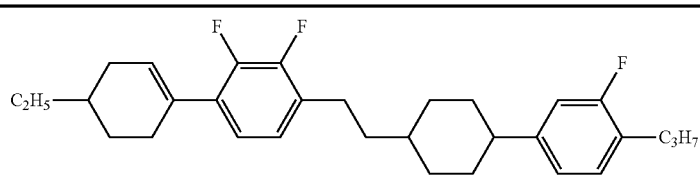 |
| 2404 | 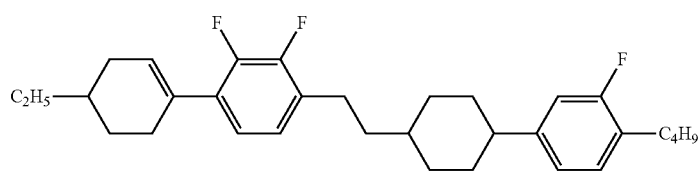 |
| 2405 | 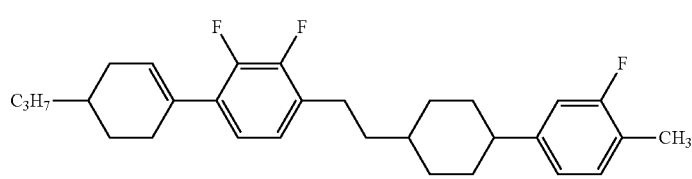 |
| 2406 | 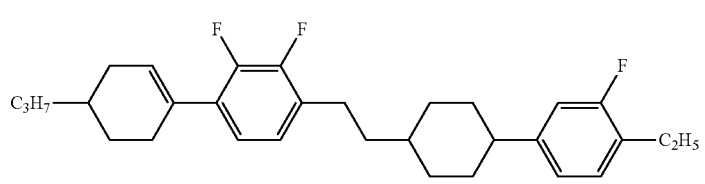 |
| 2407 | 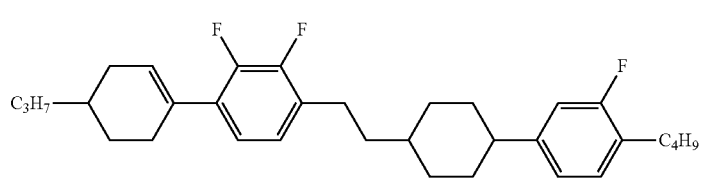 |
| 2408 | 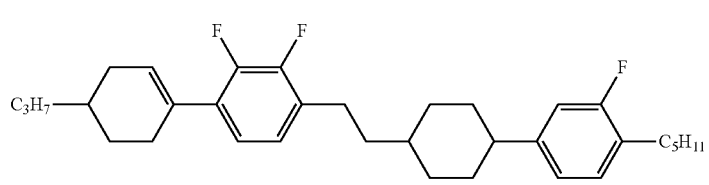 |
| 2409 | 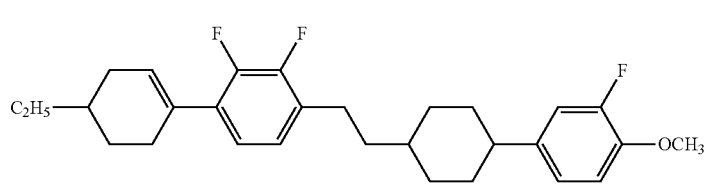 |
| 2410 | 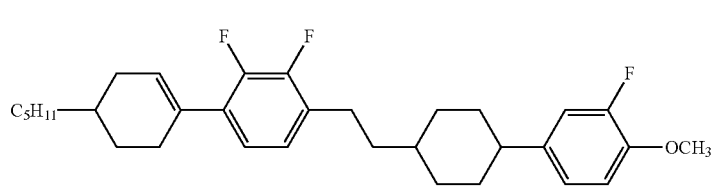 |
| 2411 | 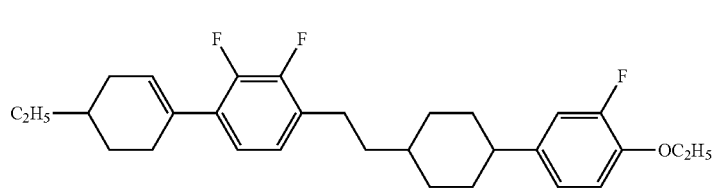 |

| No. | |
|---|---|
| 2412 | 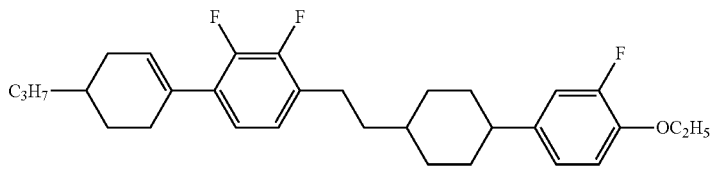 |
| 2413 | 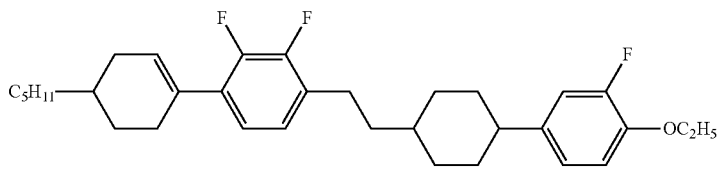 |
| 2414 | 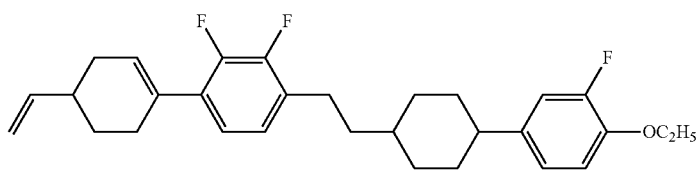 |
| 2415 | 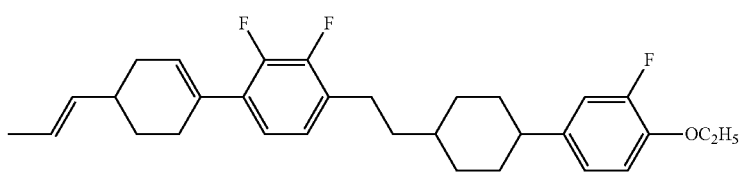 |
| 2416 | 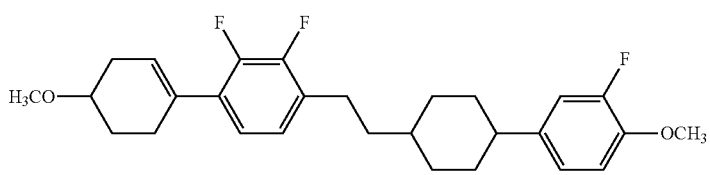 [SMILES: COc1ccc(C2CCC(CCc3ccc(C4=CCC(OC)CC4)c(F)c3F)CC2)cc1F] |
| 2417 | 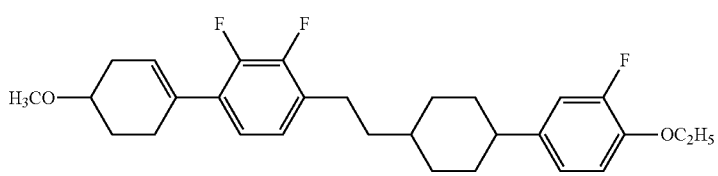 [SMILES: CCOc1ccc(C2CCC(CCc3ccc(C4=CCC(OC)CC4)c(F)c3F)CC2)cc1F] |
| 2418 | 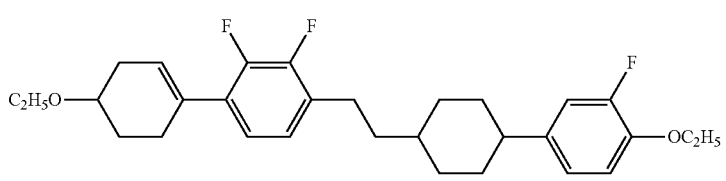 |
| 2419 | 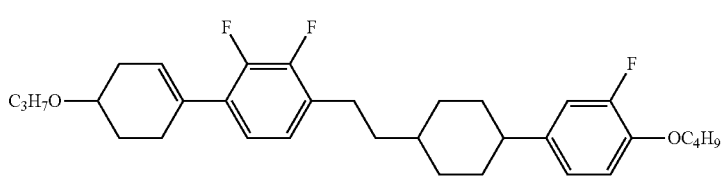 |

| No. |
|---|
| 2420 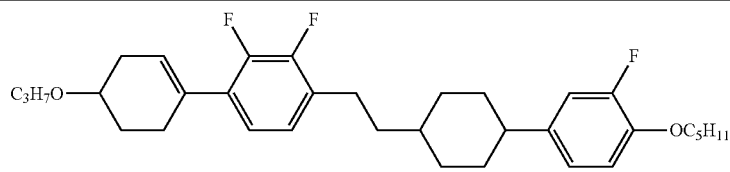 |
| 2421 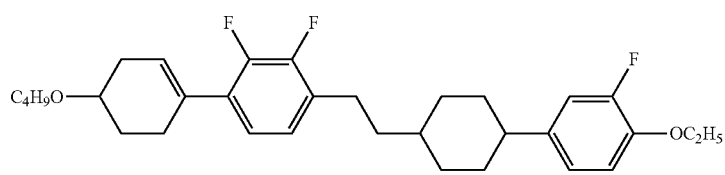 |
| 2422 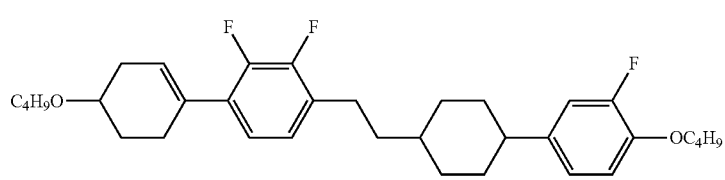 |
| 2423 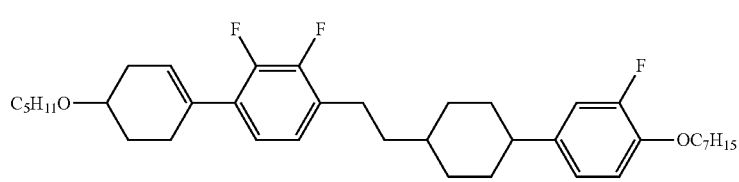 |
| 2424 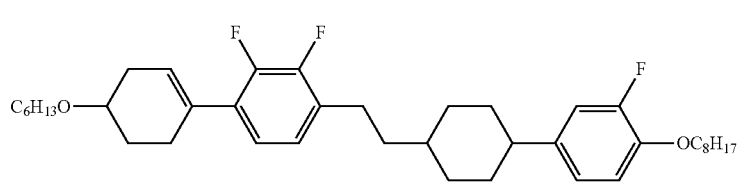 |
| 2425 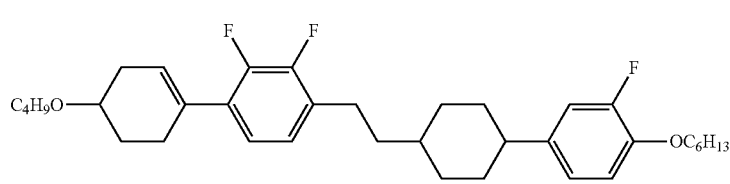 |
| 2426 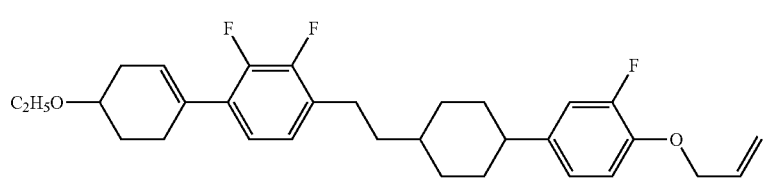 |
| 2427 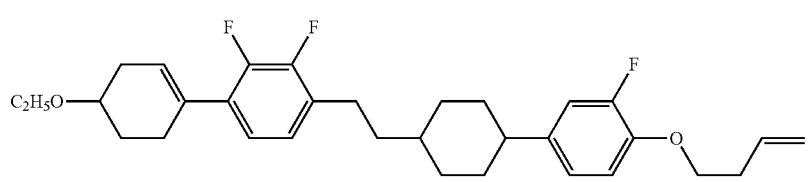 |
| 2428 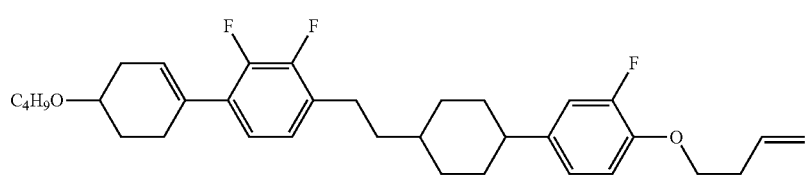 |

| No. | |
|---|---|
| 2429 | 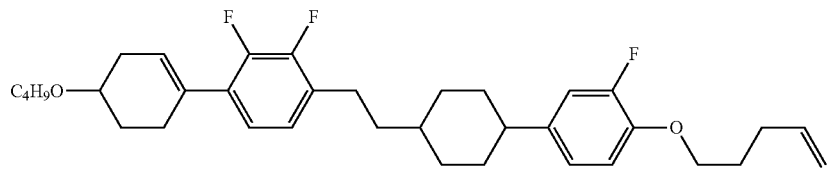 |
| 2430 | 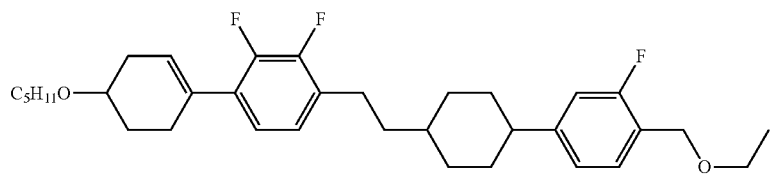 |
| 2431 | 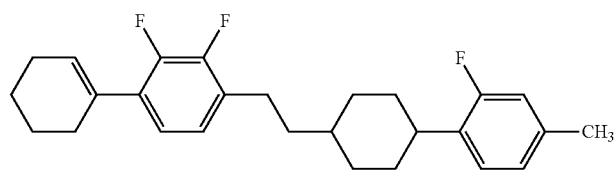 |
| 2432 | 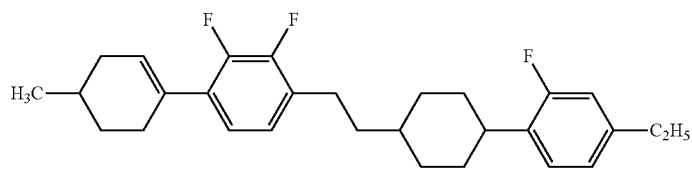 [SMILES: CCc1ccc(C2CCC(CCc3ccc(C4=CCC(C)CC4)c(F)c3F)CC2)c(F)c1] |
| 2433 | 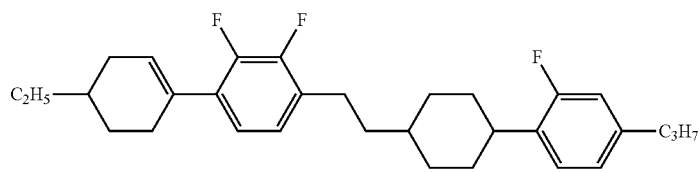 |
| 2434 | 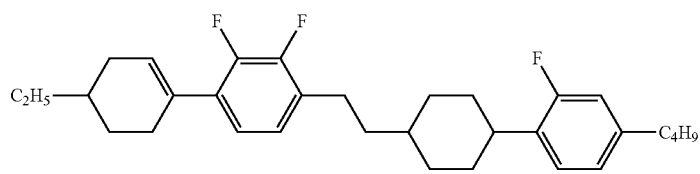 |
| 2435 | 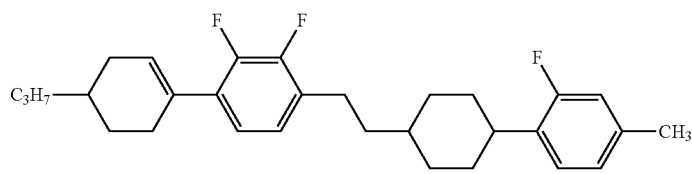 |
| 2436 | 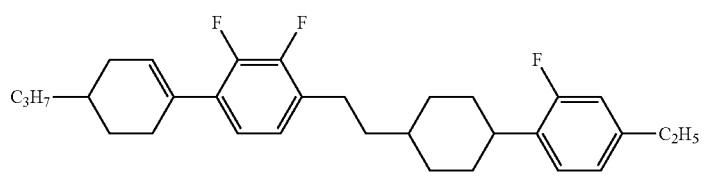 |

| No. | |
|---|---|
| 2437 | 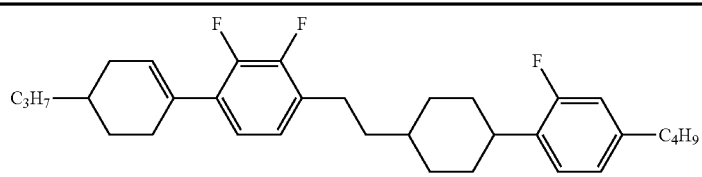 |
| 2438 | 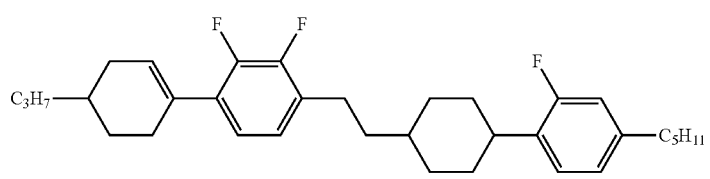 |
| 2439 | 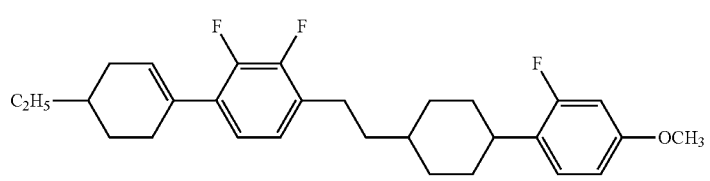 |
| 2440 | 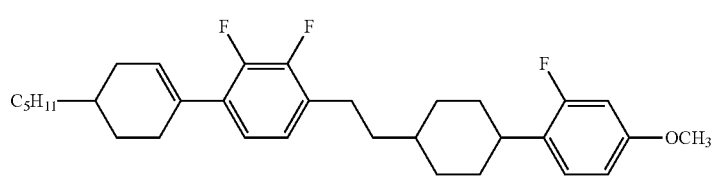 |
| 2441 | 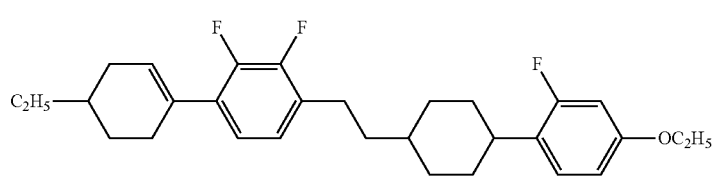 [SMILES: CCOc1ccc(C2CCC(CCc3ccc(C4=CCC(CC)CC4)c(F)c3F)CC2)c(F)c1] |
| 2442 | 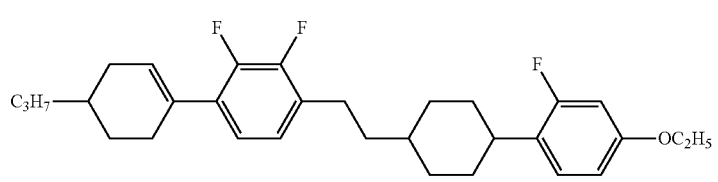 |
| 2443 | 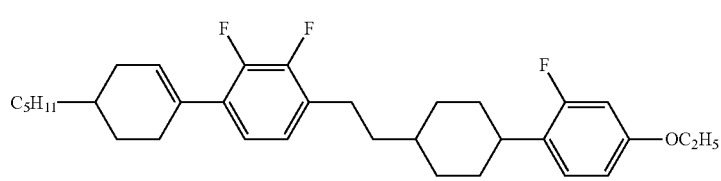 |
| 2444 | 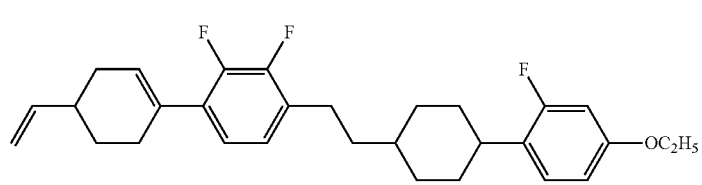 [SMILES: C=CC1CC=C(c2ccc(CCC3CCC(c4ccc(OCC)cc4F)CC3)c(F)c2F)CC1] |
| 2445 | 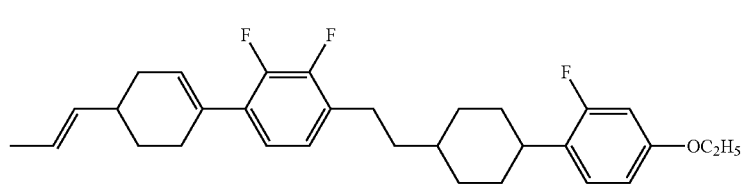 [SMILES: C/C=C/C1CC=C(c2ccc(CCC3CCC(c4ccc(OCC)cc4F)CC3)c(F)c2F)CC1] |

| No. |
|---|
| 2446 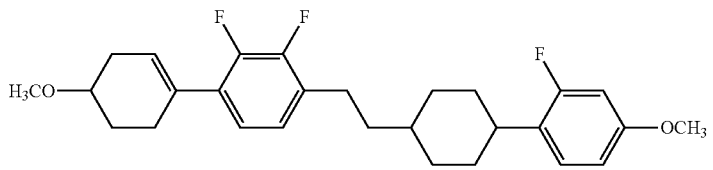 |
| 2447 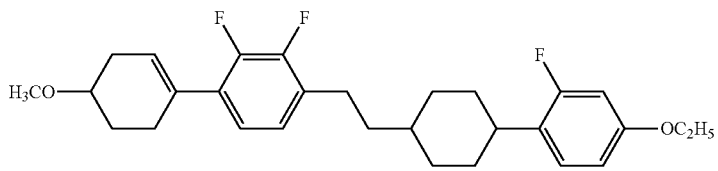 |
| 2448 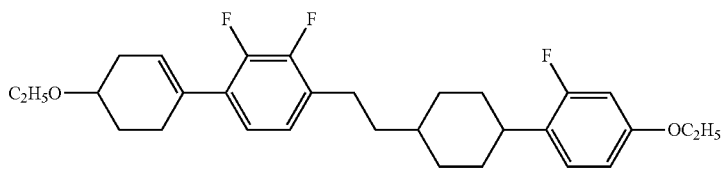 |
| 2449 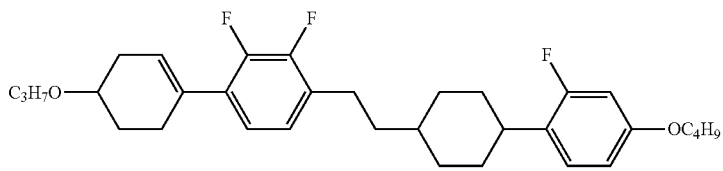 |
| 2450 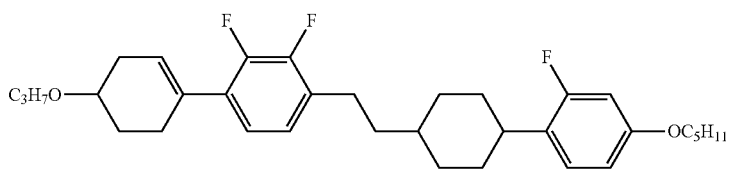 |
| 2451 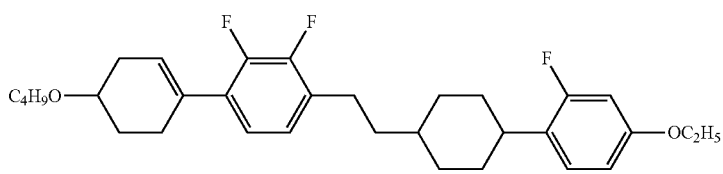 |
| 2452 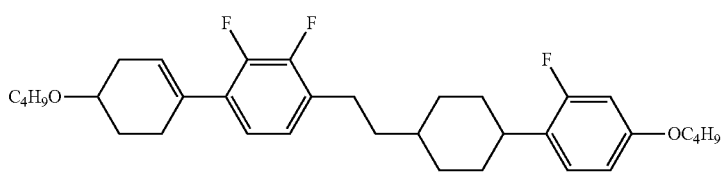 |
| 2453 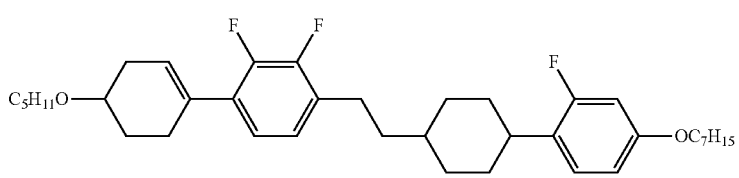 |

| No. | |
|---|---|
| 2454 | 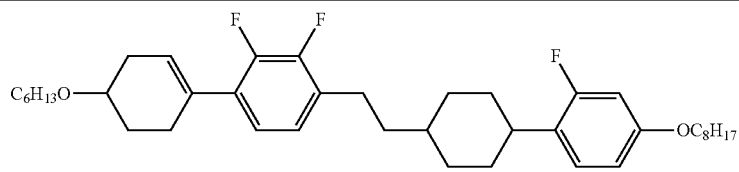 |
| 2455 | 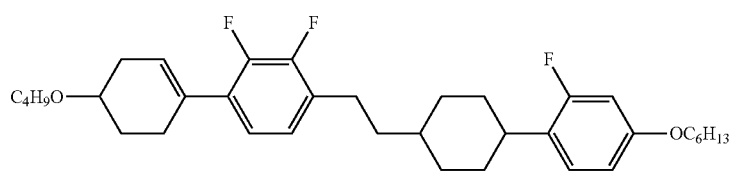 |
| 2456 | 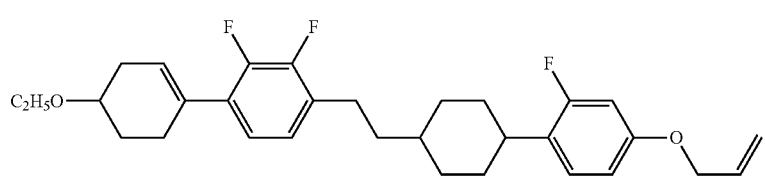 |
| 2457 | 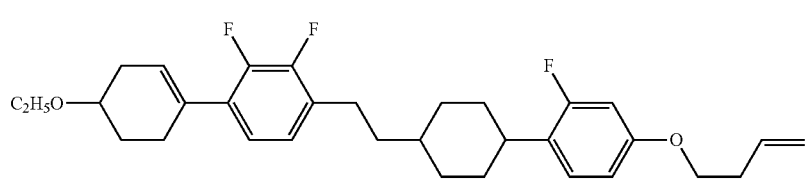 |
| 2458 | 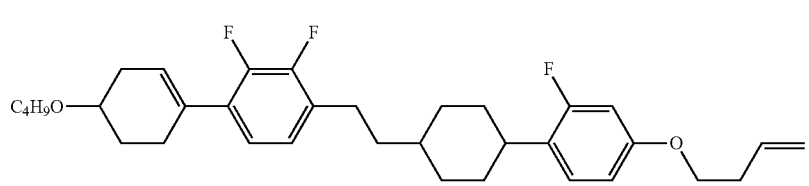 |
| 2459 | 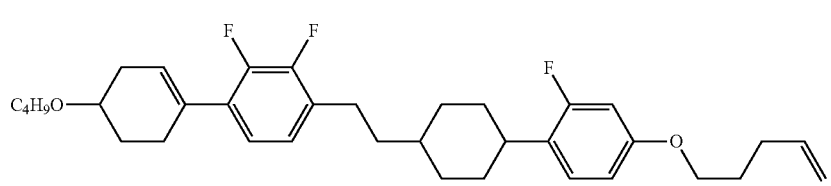 |
| 2460 | 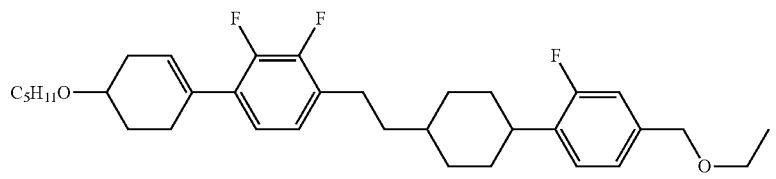 |
| 2461 | 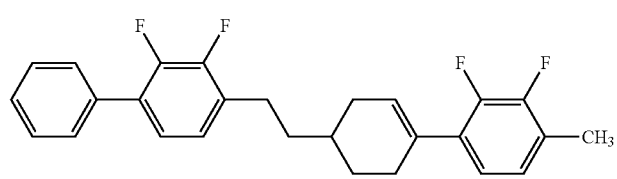 |
| 2462 | 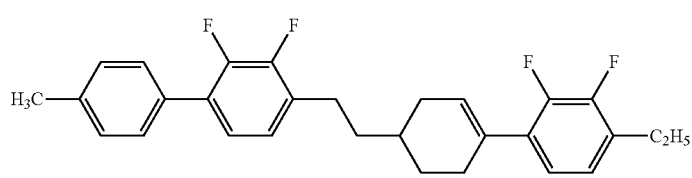 |

| No. | |
|---|---|
| 2463 | 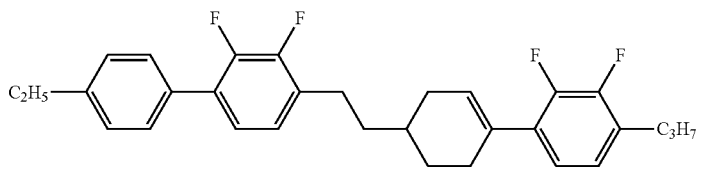 |
| 2464 | 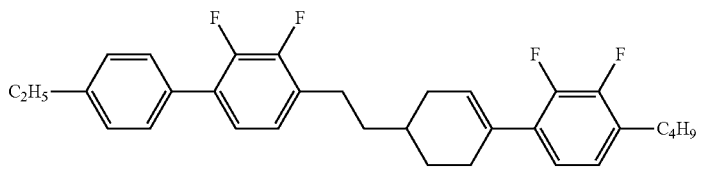 |
| 2465 | 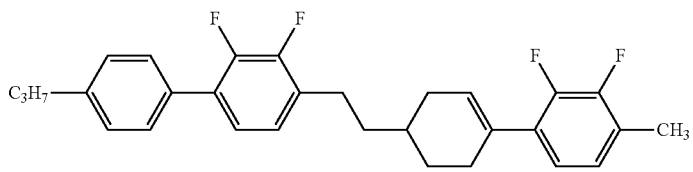 |
| 2466 | 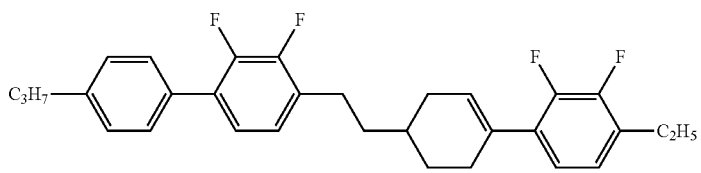 |
| 2467 | 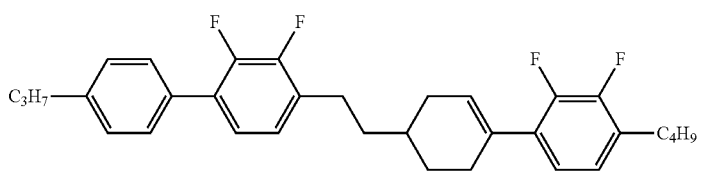 |
| 2468 | 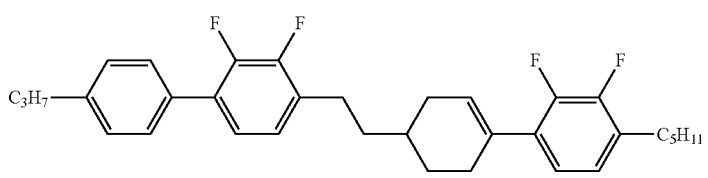 |
| 2469 | 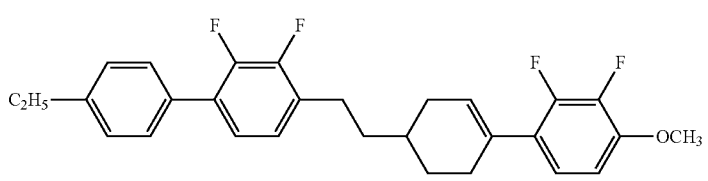 |
| 2470 | 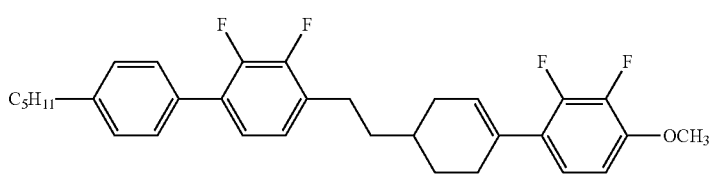 |

| No. | |
|---|---|
| 2471 | 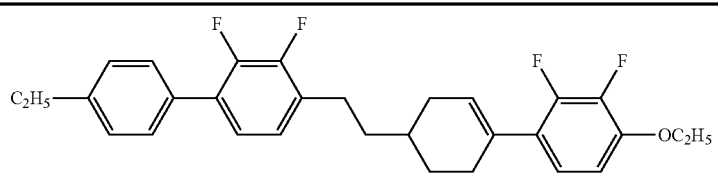 |
| 2472 | 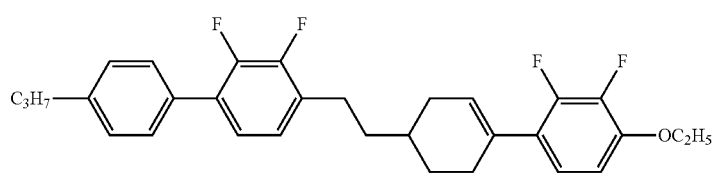 |
| 2473 | 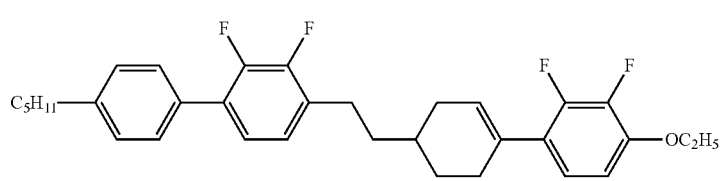 |
| 2474 | 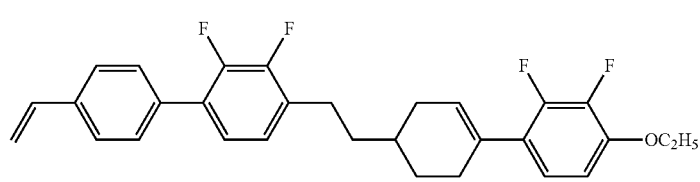 |
| 2475 | 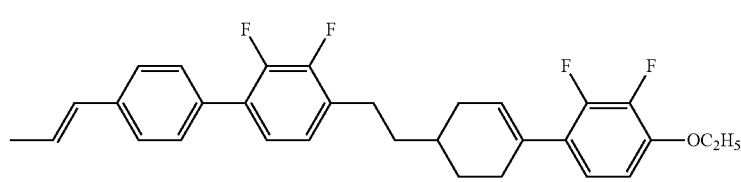 [SMILES: C/C=C/c1ccc(-c2ccc(CCC3CC=C(c4ccc(OCC)c(F)c4F)CC3)c(F)c2F)cc1] |
| 2476 | 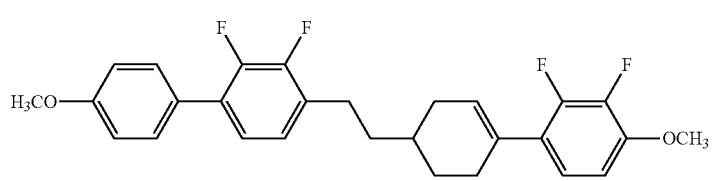 |
| 2477 | 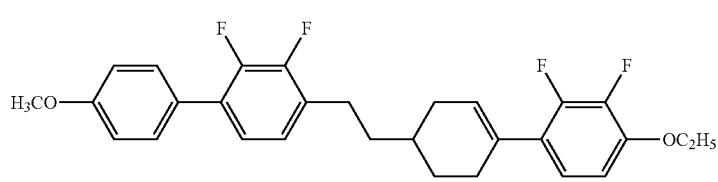 [SMILES: CCOc1ccc(C2=CCC(CCc3ccc(-c4ccc(OC)cc4)c(F)c3F)CC2)c(F)c1F] |
| 2478 | 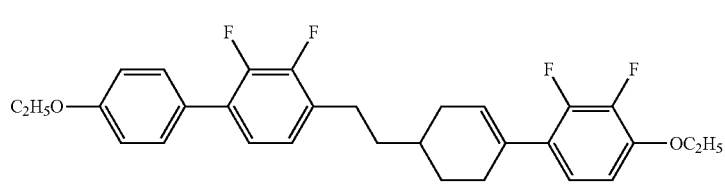 |
| 2479 | 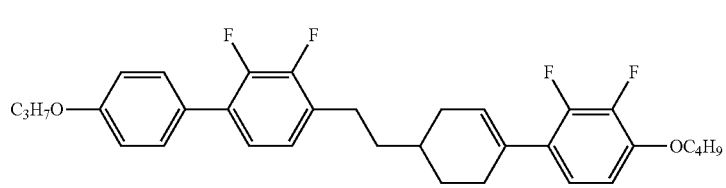 |

| No. | |
|---|---|
| 2480 | 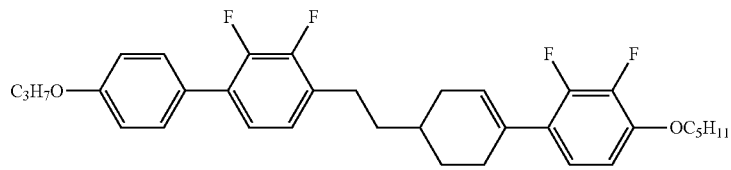 |
| 2481 | 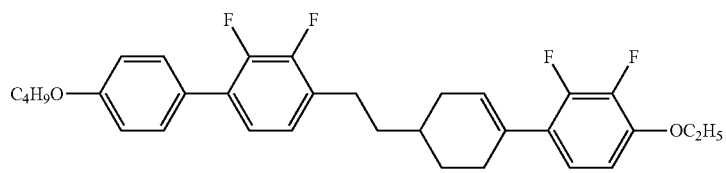 |
| 2482 | 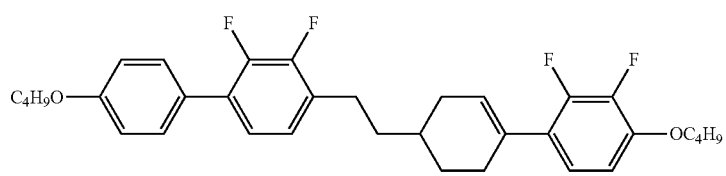 |
| 2483 | 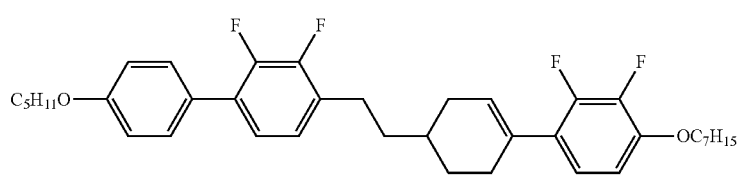 |
| 2484 | 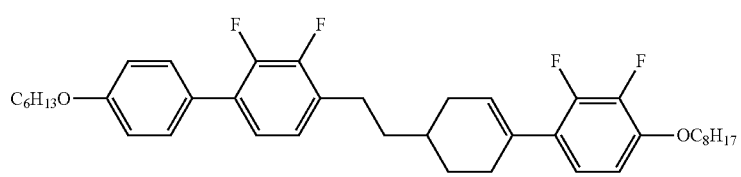 |
| 2485 | 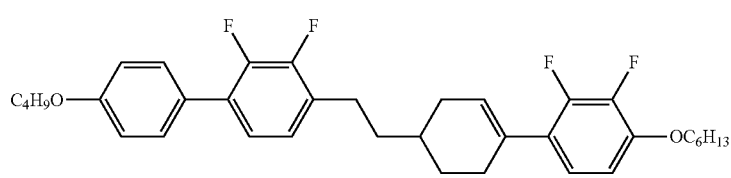 |
| 2486 | 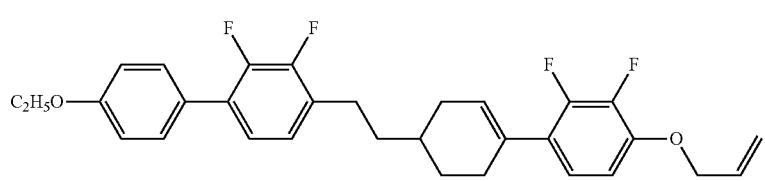 |
| 2487 | 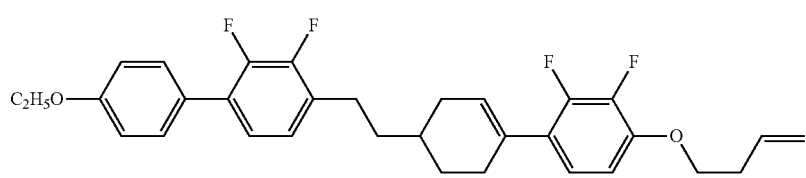 |

| No. | |
|---|---|
| 2488 | 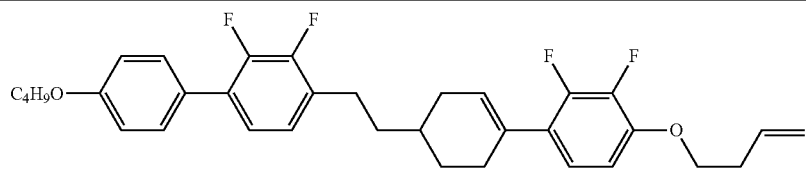 |
| 2489 | 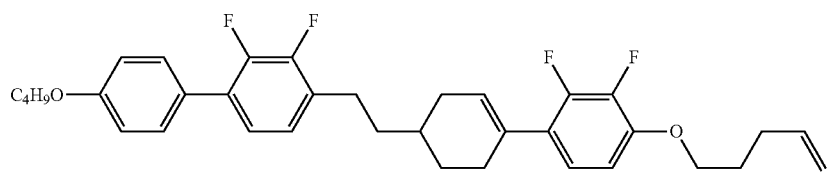 |
| 2490 | 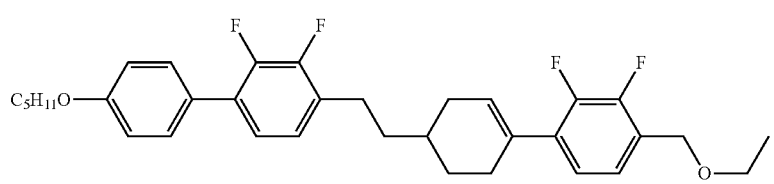 |
| 2491 | 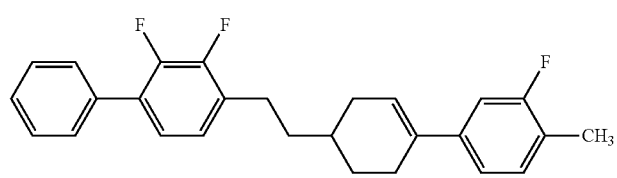 |
| 2492 | 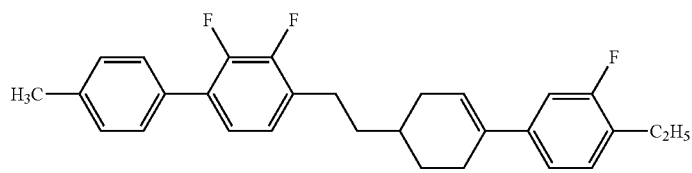 [SMILES: CCc1ccc(C2=CCC(CCc3ccc(-c4ccc(C)cc4)c(F)c3F)CC2)cc1F] |
| 2493 | 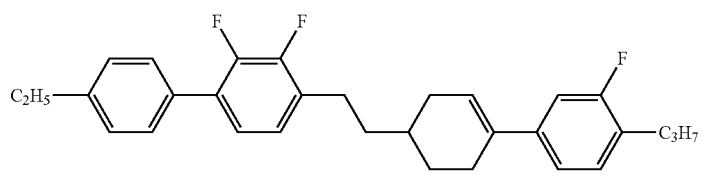 |
| 2494 | 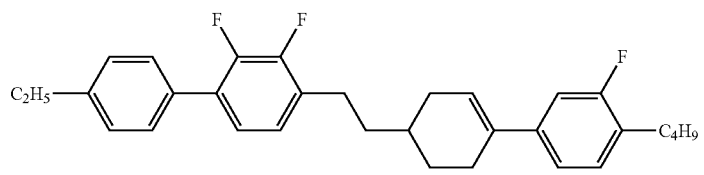 |
| 2495 | 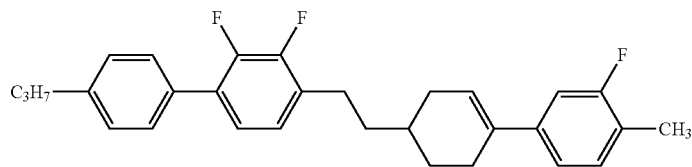 |
| 2496 | 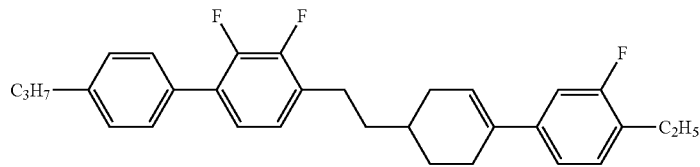 |

| No. | |
|---|---|
| 2497 | 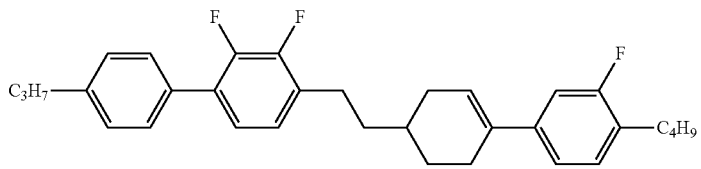 |
| 2498 | 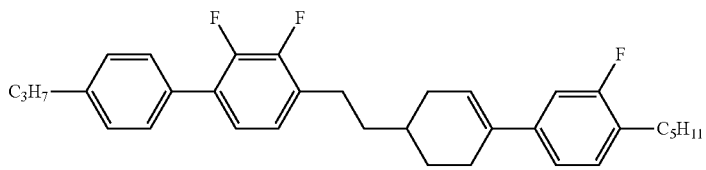 |
| 2499 | 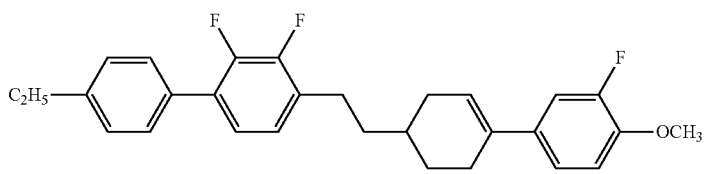 |
| 2500 | 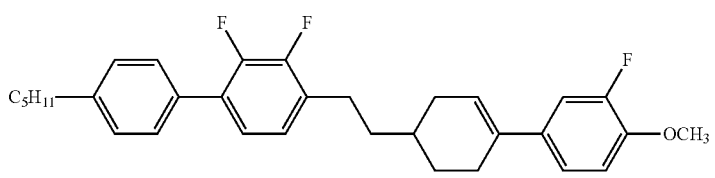 |
| 2501 | 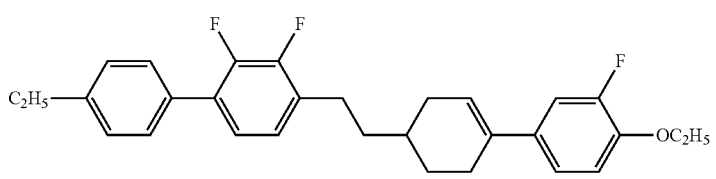 [SMILES: CCOc1ccc(C2=CCC(CCc3ccc(-c4ccc(CC)cc4)c(F)c3F)CC2)cc1F] |
| 2502 | 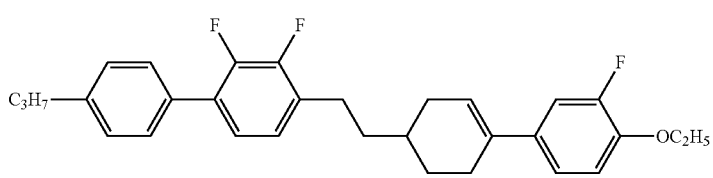 |
| 2503 | 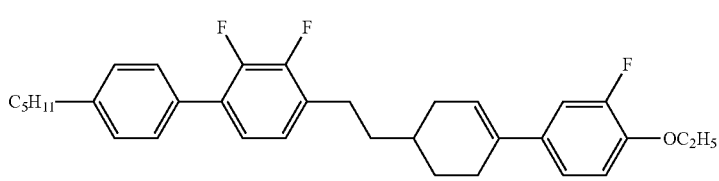 |
| 2504 | 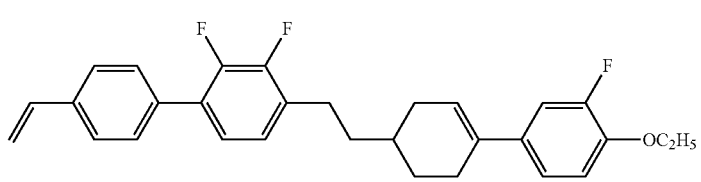 |

| No. | |
|---|---|
| 2505 | 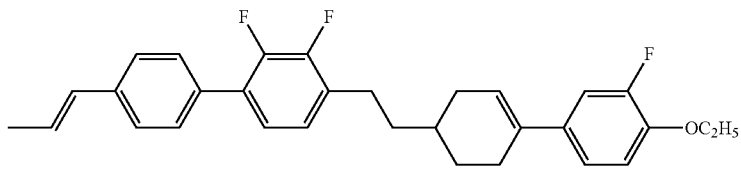 [SMILES: C/C=C/c1ccc(-c2ccc(CCC3CC=C(c4ccc(OCC)c(F)c4)CC3)c(F)c2F)cc1] |
| 2506 | 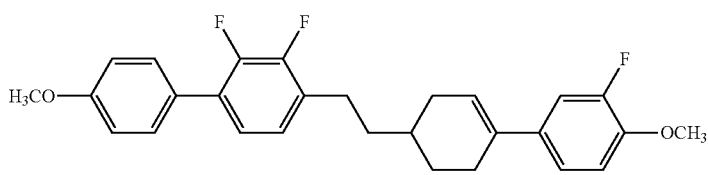 [SMILES: COc1ccc(-c2ccc(CCC3CC=C(c4ccc(OC)c(F)c4)CC3)c(F)c2F)cc1] |
| 2507 | 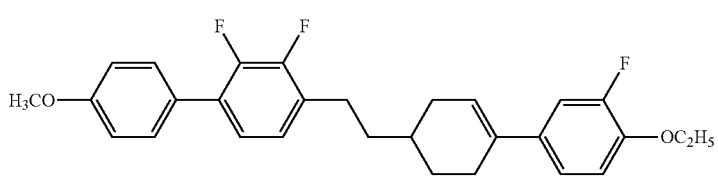 [SMILES: CCOc1ccc(C2=CCC(CCc3ccc(-c4ccc(OC)cc4)c(F)c3F)CC2)cc1F] |
| 2508 | 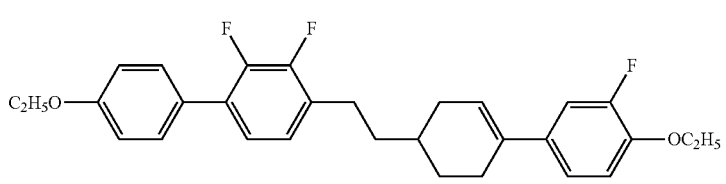 |
| 2509 | 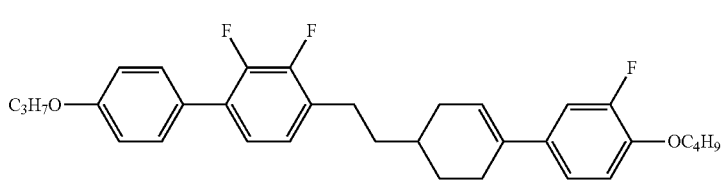 |
| 2510 | 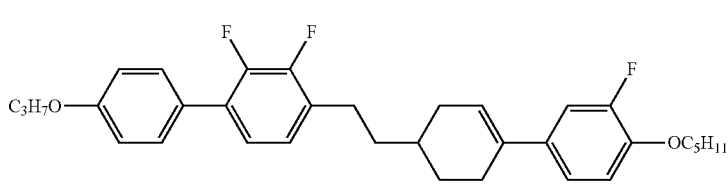 |
| 2511 | 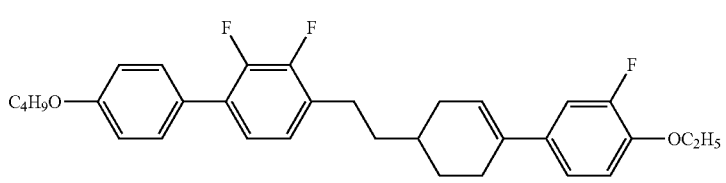 |
| 2512 | 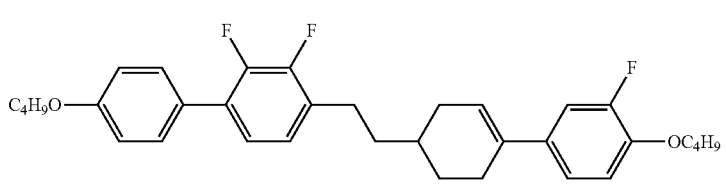 |
| 2513 | 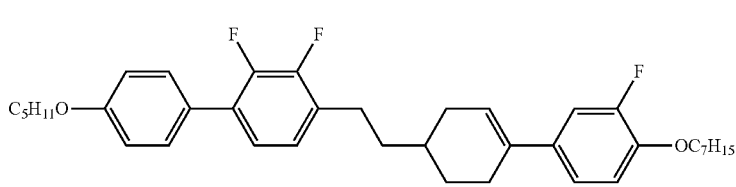 |

| No. | |
|---|---|
| 2514 | 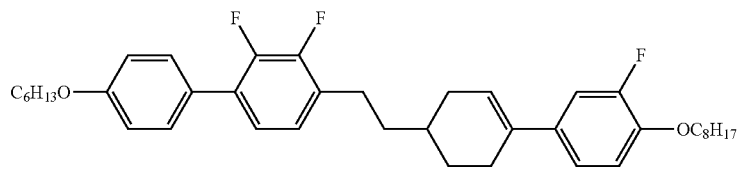 |
| 2515 | 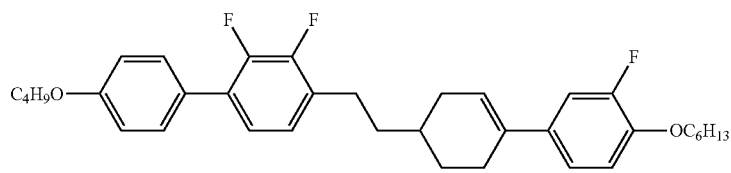 |
| 2516 | 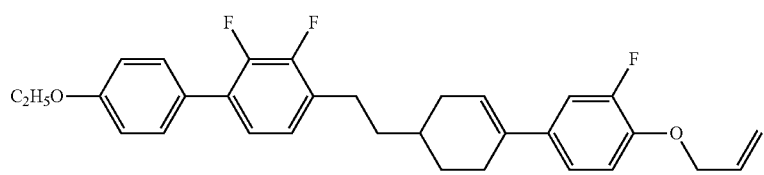 |
| 2517 | 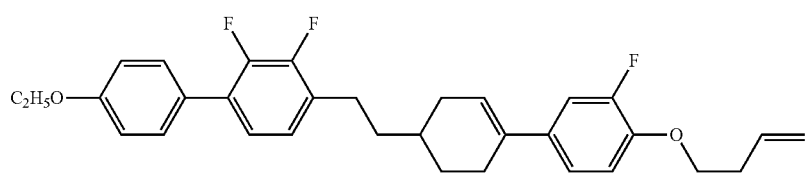 |
| 2518 | 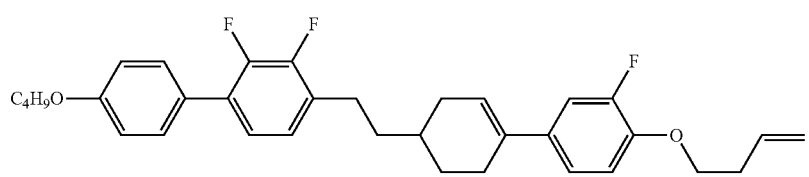 |
| 2519 | 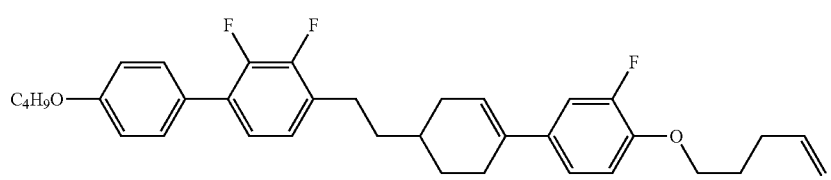 |
| 2520 | 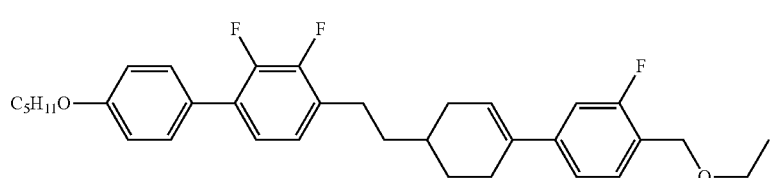 |
| 2521 | 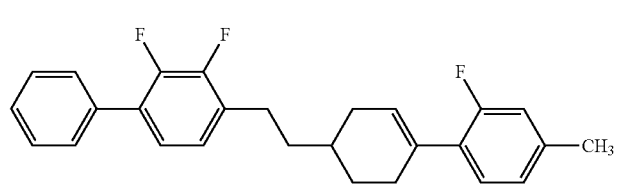 |

| No. | |
|---|---|
| 2522 | 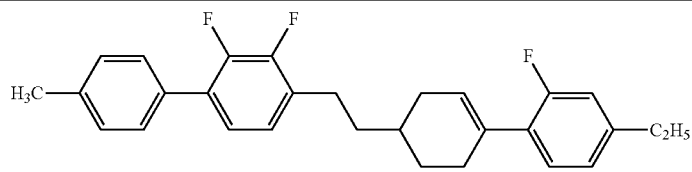 |
| 2523 | 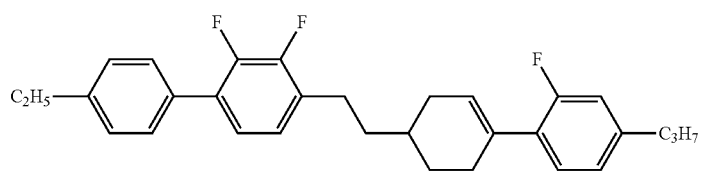 |
| 2524 | 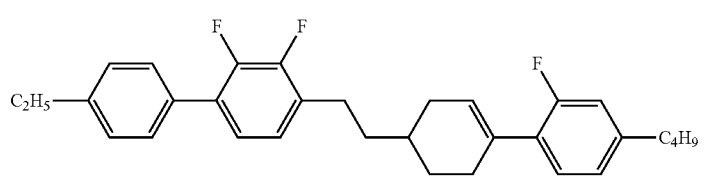 |
| 2525 | 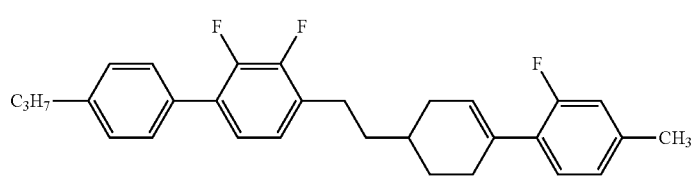 |
| 2526 | 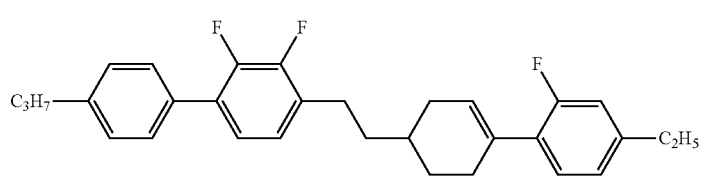 |
| 2527 | 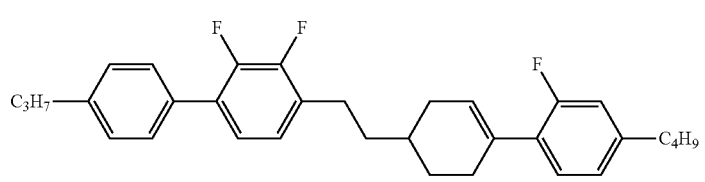 |
| 2528 | 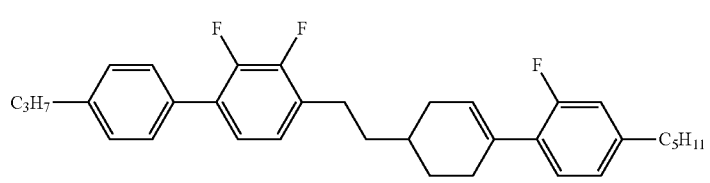 |
| 2529 | 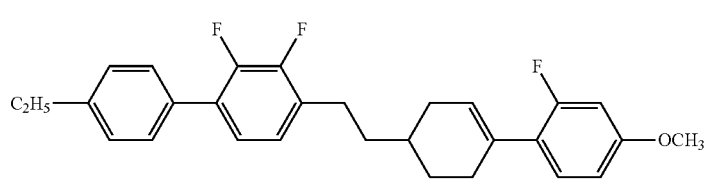 [SMILES: CCc1ccc(-c2ccc(CCC3CC=C(c4ccc(OC)cc4F)CC3)c(F)c2F)cc1] |
| 2530 | 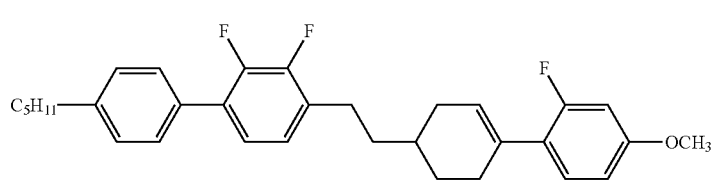 |

| No. |
| --- |
| 2531 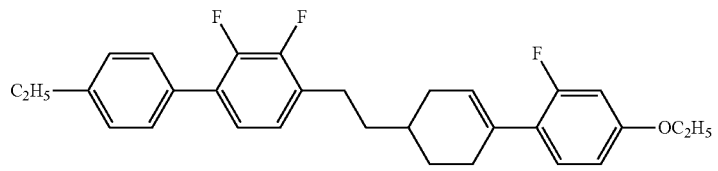 [SMILES: CCOc1ccc(C2=CCC(CCc3ccc(-c4ccc(CC)cc4)c(F)c3F)CC2)c(F)c1] |
| 2532 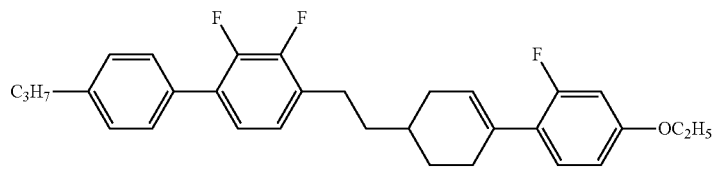 |
| 2533 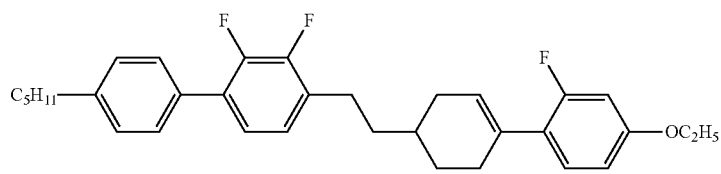 |
| 2534 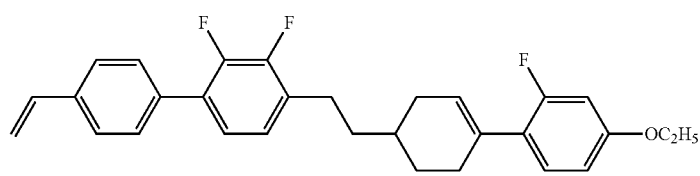 |
| 2535 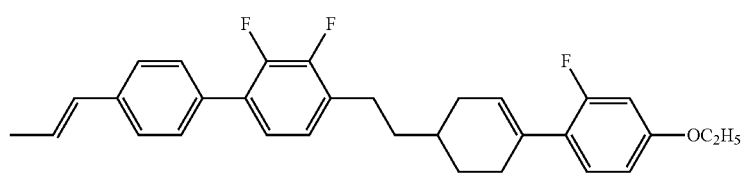 [SMILES: C/C=C/c1ccc(-c2ccc(CCC3CC=C(c4ccc(OCC)cc4F)CC3)c(F)c2F)cc1] |
| 2536 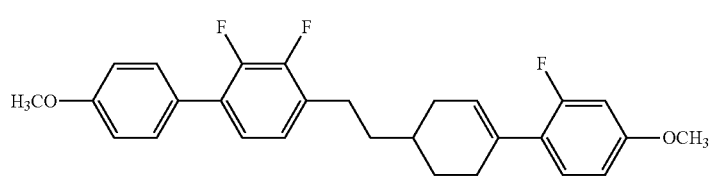 [SMILES: COc1ccc(-c2ccc(CCC3CC=C(c4ccc(OC)cc4F)CC3)c(F)c2F)cc1] |
| 2537 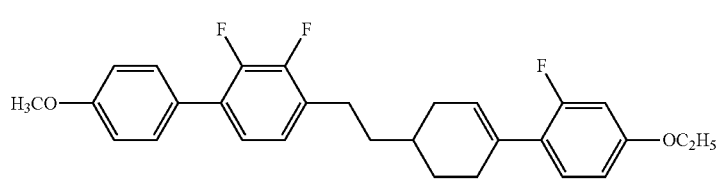 |
| 2538 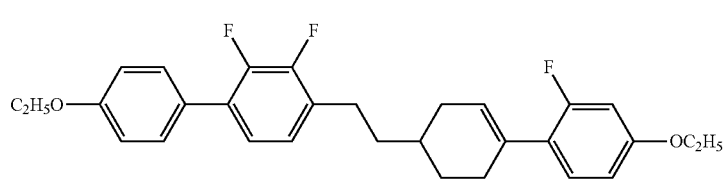 |

-continued
| No. | |
|---|---|
| 2539 | 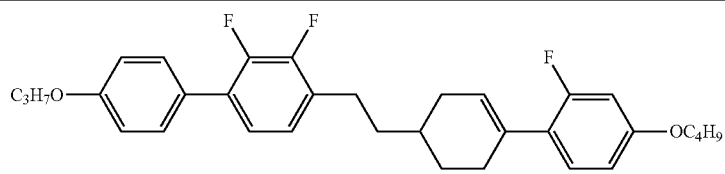 |
| 2540 | 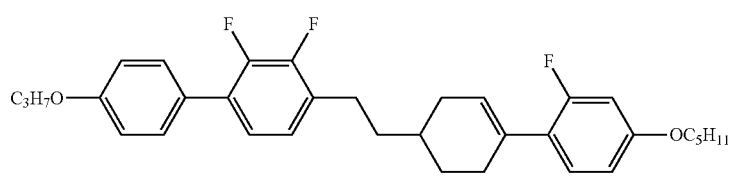 |
| 2541 | 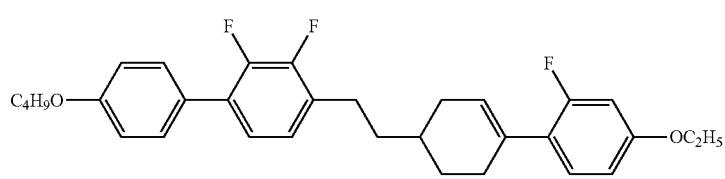 |
| 2542 | 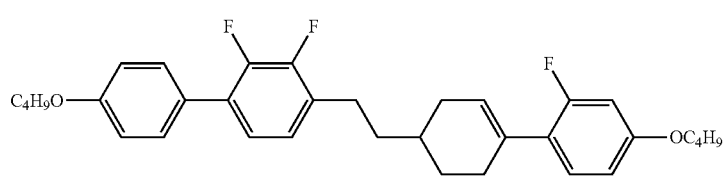 |
| 2543 | 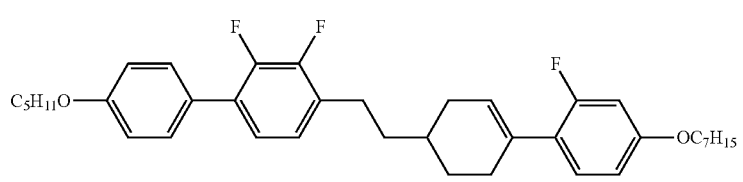 |
| 2544 | 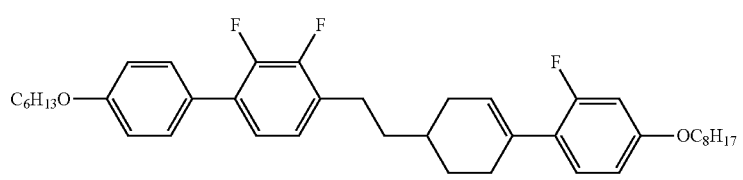 |
| 2545 | 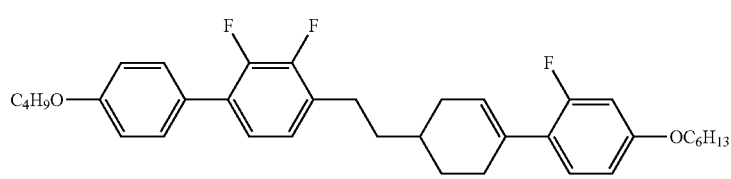 |
| 2546 | 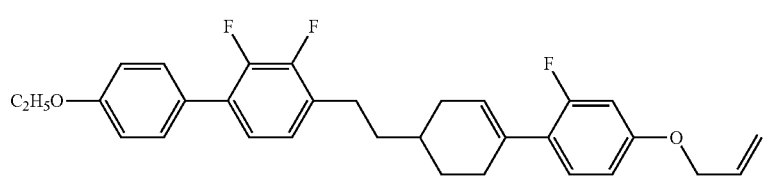 |
| 2547 | 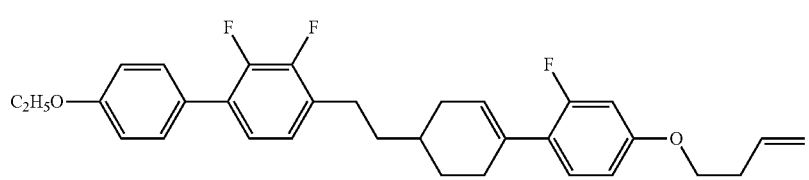 |

| No. | |
|---|---|
| 2548 | 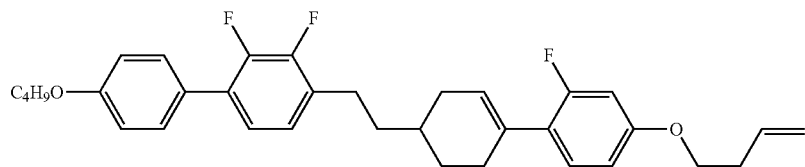 |
| 2549 | 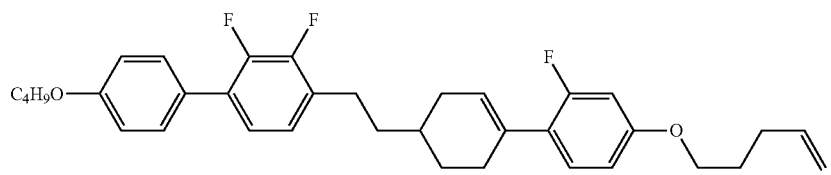 |
| 2550 | 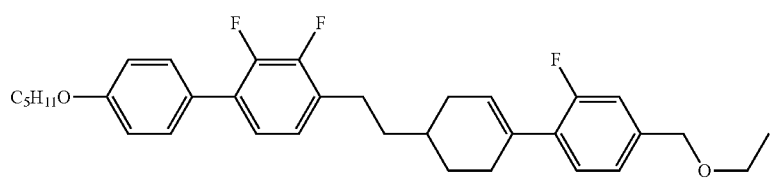 |
| 2551 | 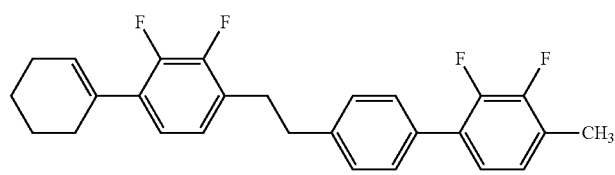 |
| 2552 | 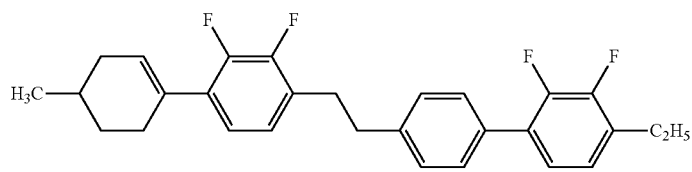 |
| 2553 | 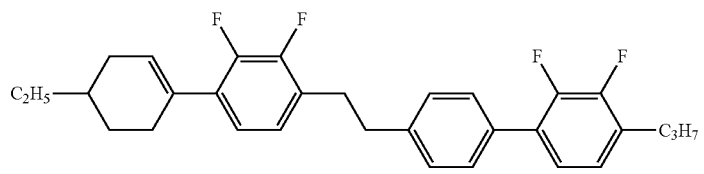 |
| 2554 | 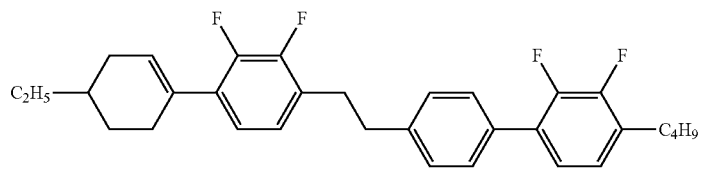 |
| 2555 | 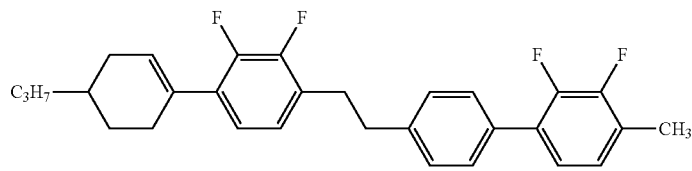 |

| No. | |
|---|---|
| 2556 | 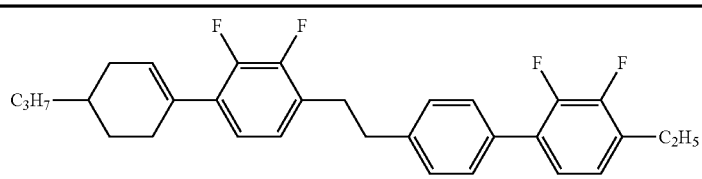 |
| 2557 | 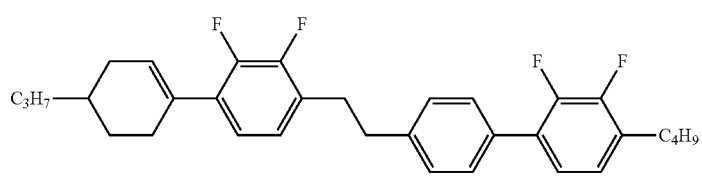 |
| 2558 | 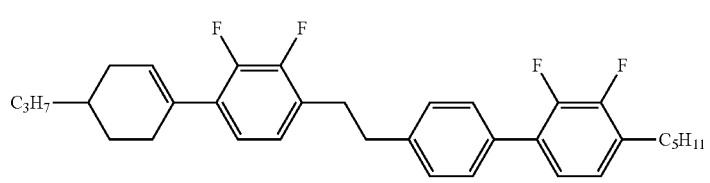 |
| 2559 | 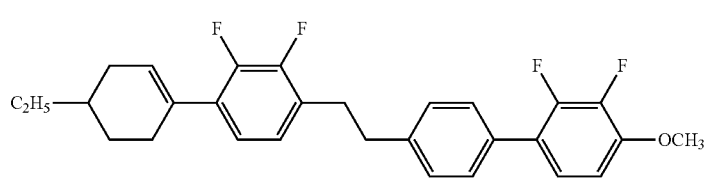 |
| 2560 | 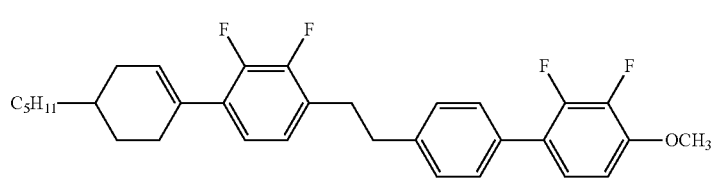 |
| 2561 | 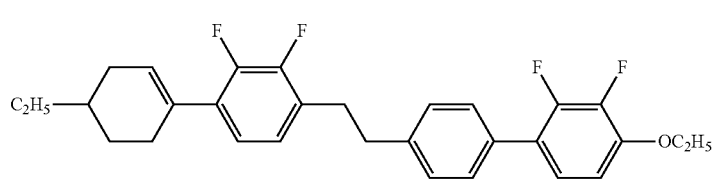 [SMILES: CCOc1ccc(-c2ccc(CCc3ccc(C4=CCC(CC)CC4)c(F)c3F)cc2)c(F)c1F] |
| 2562 | 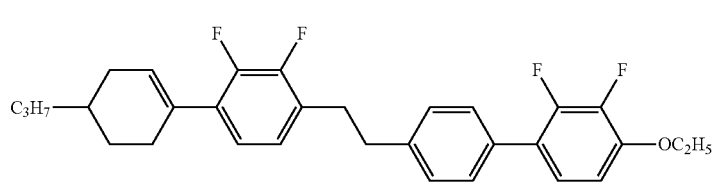 |
| 2563 | 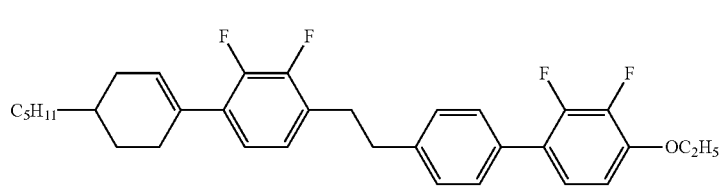 |
| 2564 | 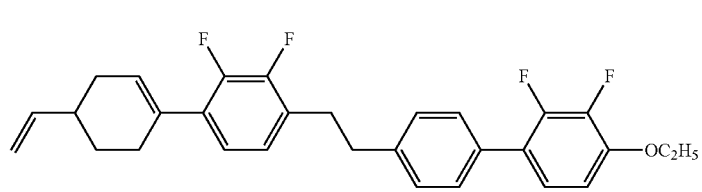 [SMILES: C=CC1CC=C(c2ccc(CCc3ccc(-c4ccc(OCC)c(F)c4F)cc3)c(F)c2F)CC1] |

| No. |
|---|
| 2565 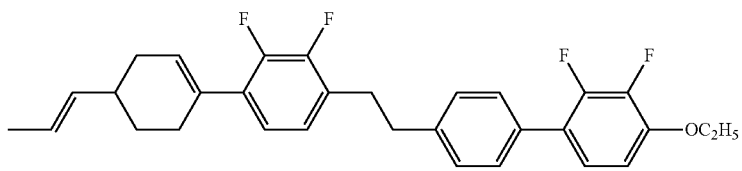 |
| 2566 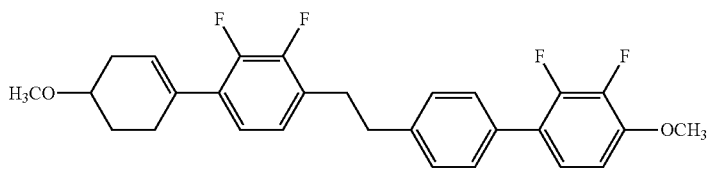 [SMILES: COc1ccc(-c2ccc(CCc3ccc(C4=CCC(OC)CC4)c(F)c3F)cc2)c(F)c1F] |
| 2567 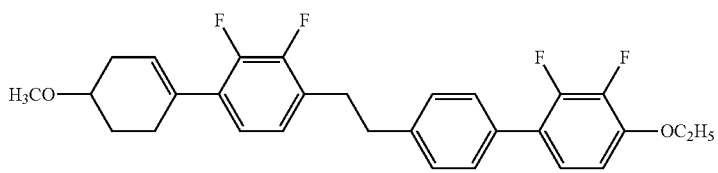 [SMILES: CCOc1ccc(-c2ccc(CCc3ccc(C4=CCC(OC)CC4)c(F)c3F)cc2)c(F)c1F] |
| 2568 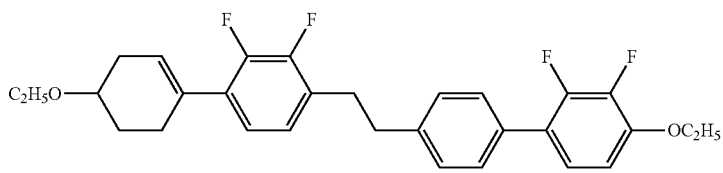 |
| 2569 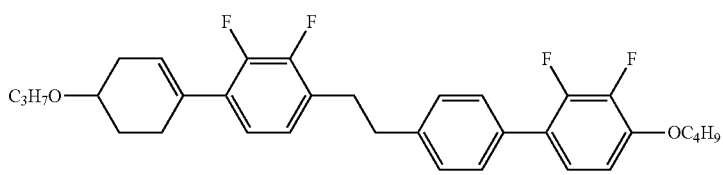 |
| 2570 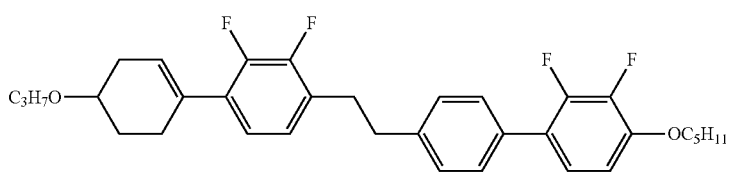 |
| 2571 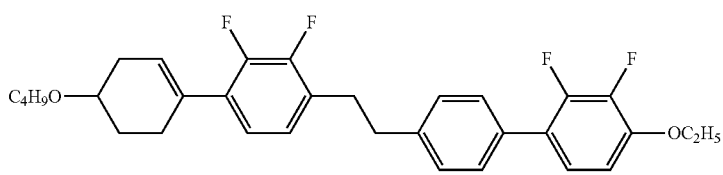 |
| 2572 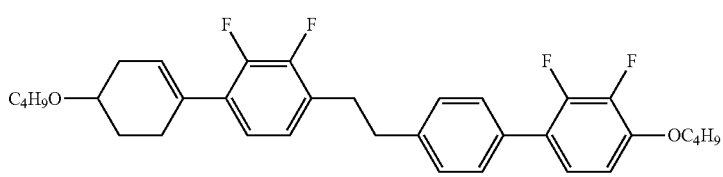 |

| No. | |
|---|---|
| 2573 | 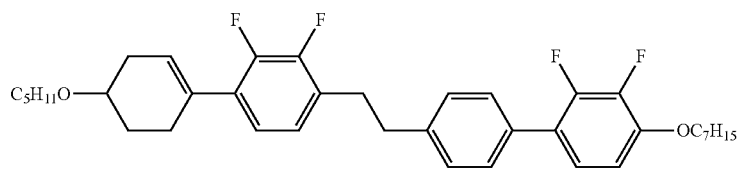 |
| 2574 | 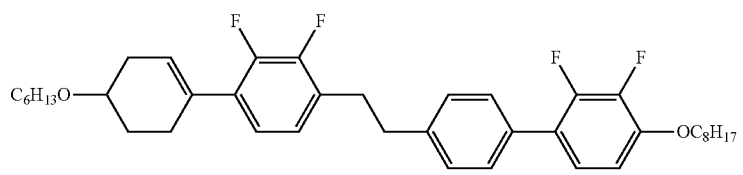 |
| 2575 | 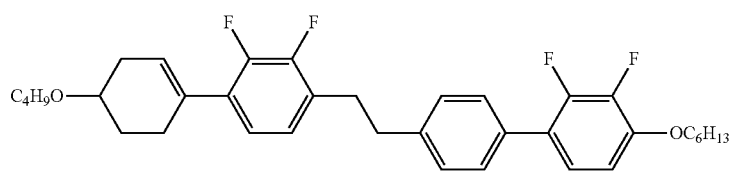 |
| 2576 | 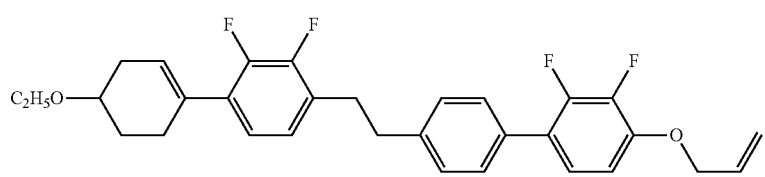 |
| 2577 | 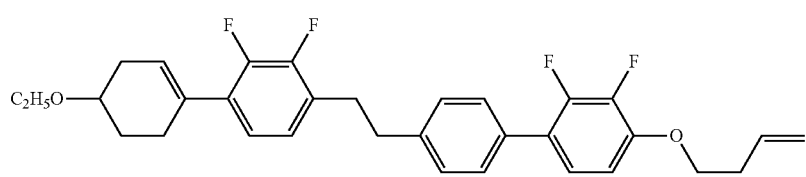 |
| 2578 | 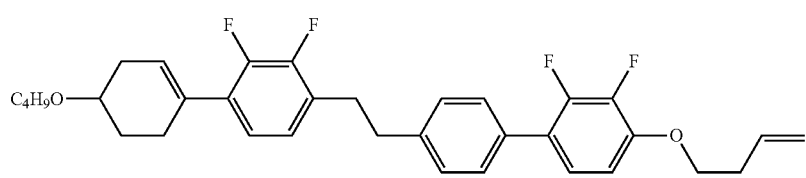 |
| 2579 | 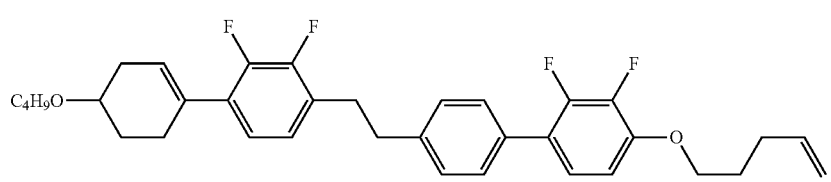 |
| 2580 | 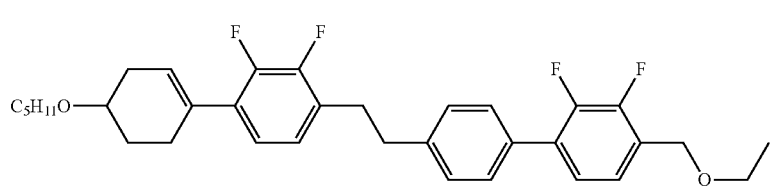 |

| No. | |
|---|---|
| 2581 | 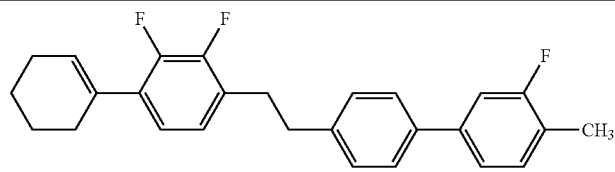 |
| 2582 | 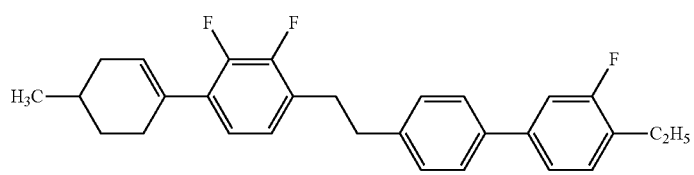 |
| 2583 | 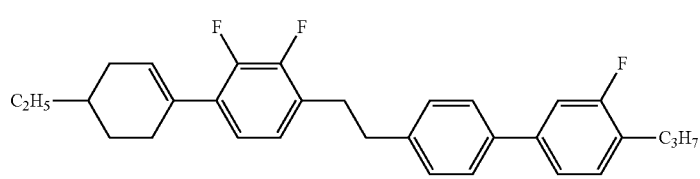 |
| 2584 | 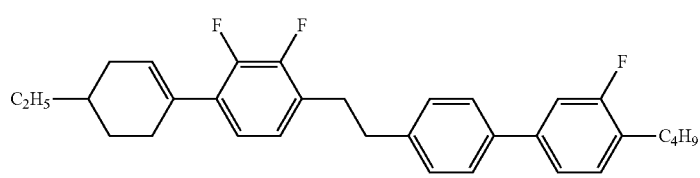 |
| 2585 | 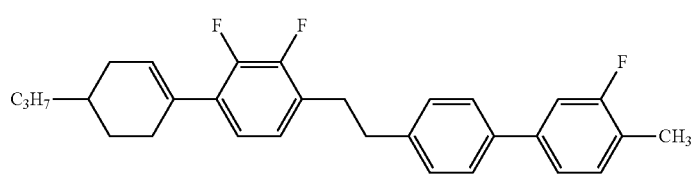 |
| 2586 | 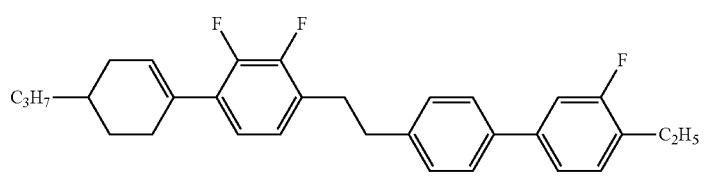 |
| 2587 | 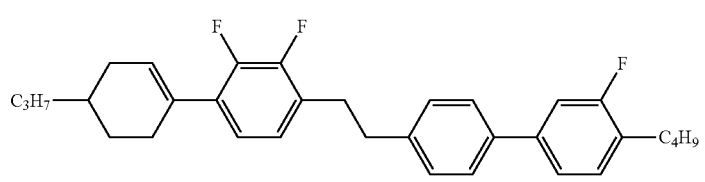 |
| 2588 | 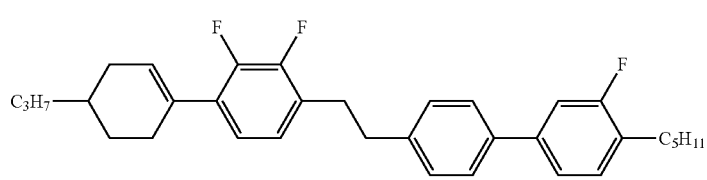 |
| 2589 | 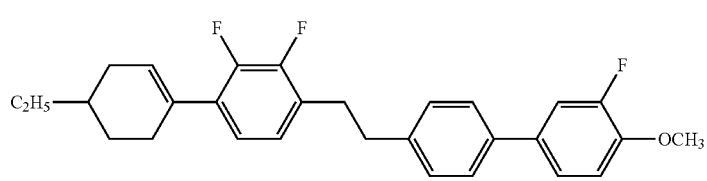 |

-continued
| No. | |
|---|---|
| 2590 | 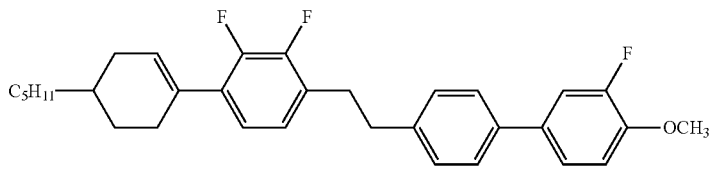 |
| 2591 | 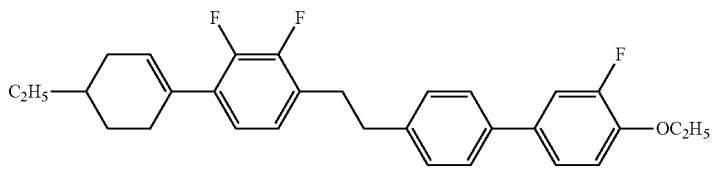 |
| 2592 | 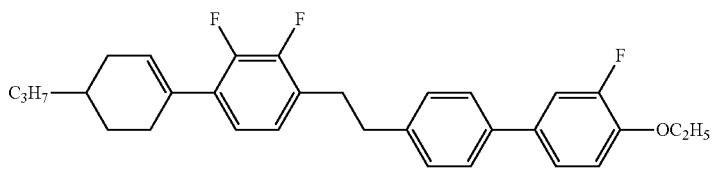 |
| 2593 | 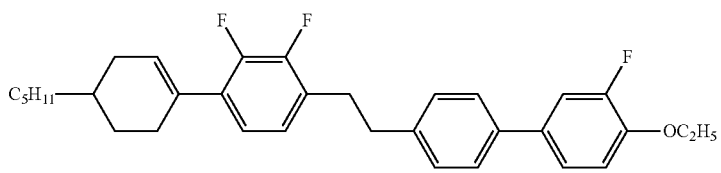 |
| 2594 | 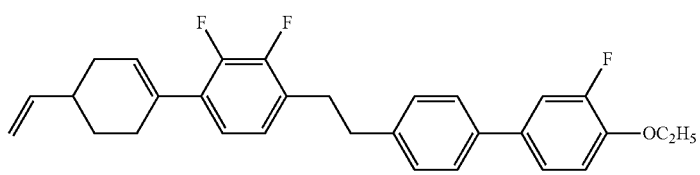 |
| 2595 | 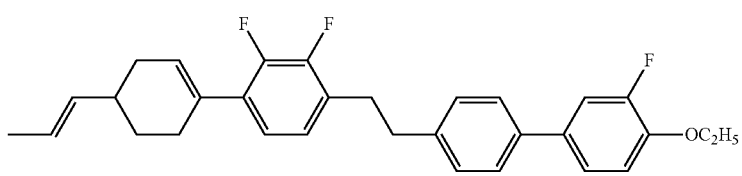 |
| 2596 | 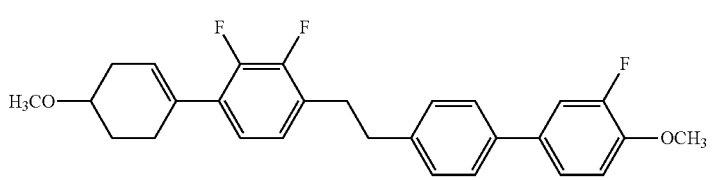 |
| 2597 | 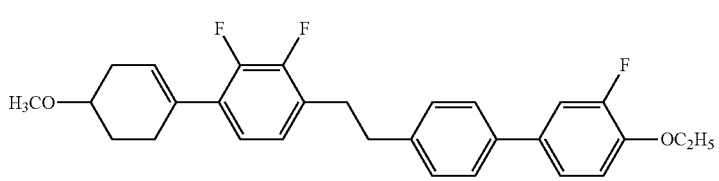 |

| No. | |
|---|---|
| 2598 | 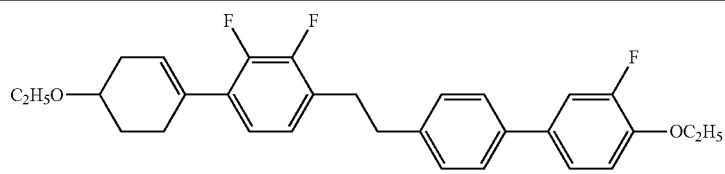 |
| 2599 | 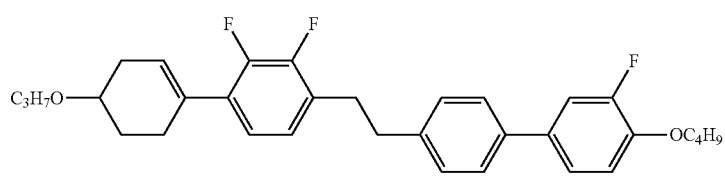 |
| 2600 | 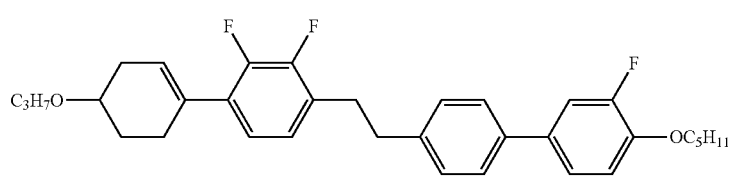 |
| 2601 | 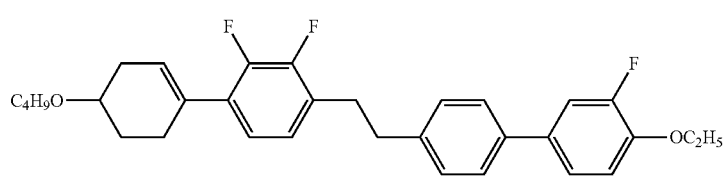 |
| 2602 | 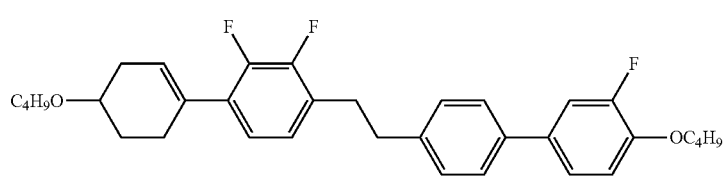 |
| 2603 | 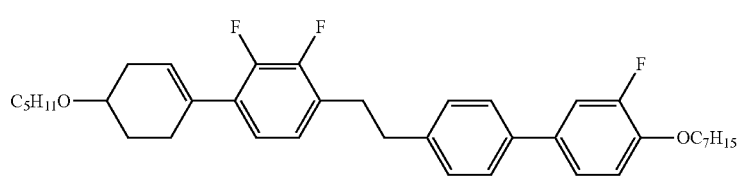 |
| 2604 | 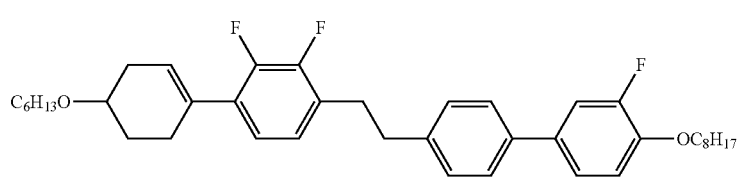 |
| 2605 | 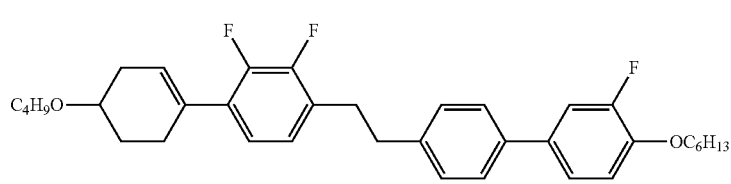 |
| 2606 | 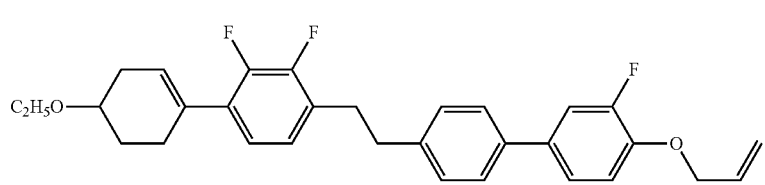 |

| No. |
|---|
| 2607 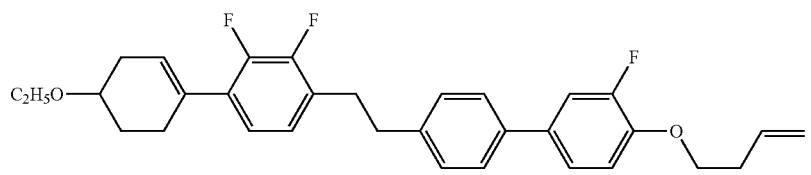 |
| 2608 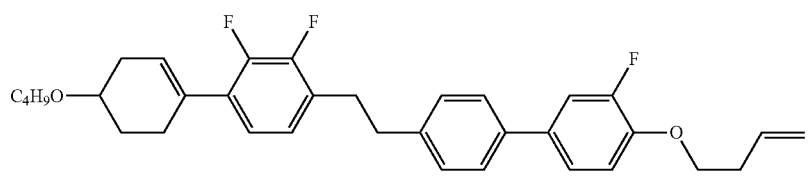 |
| 2609 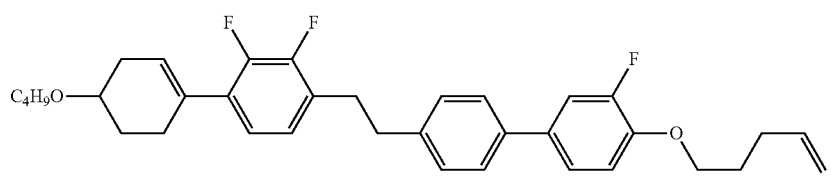 |
| 2610 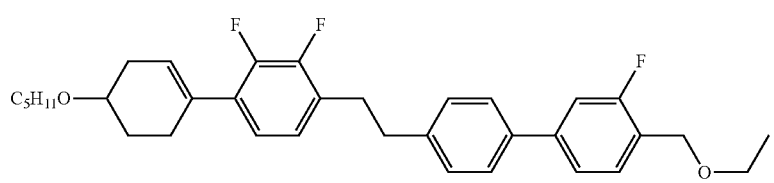 |
| 2611 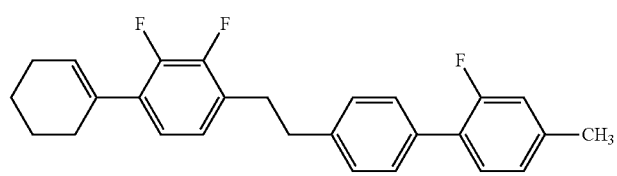 |
| 2612 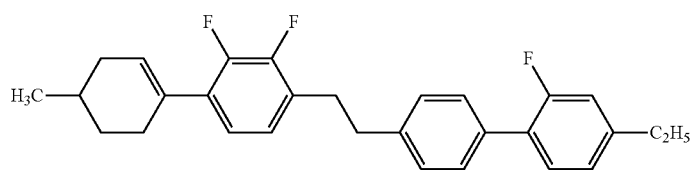 |
| 2613 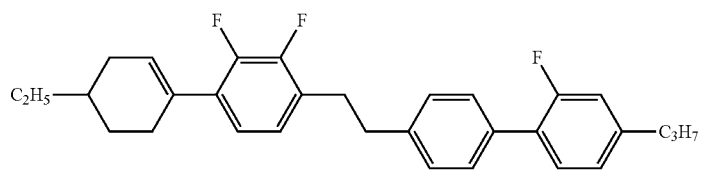 |
| 2614 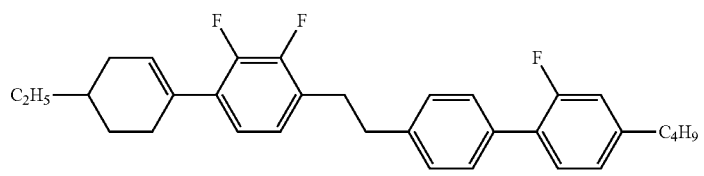 |

-continued
| No. |
|---|
| 2615 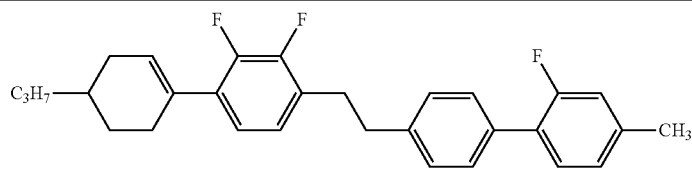 |
| 2616 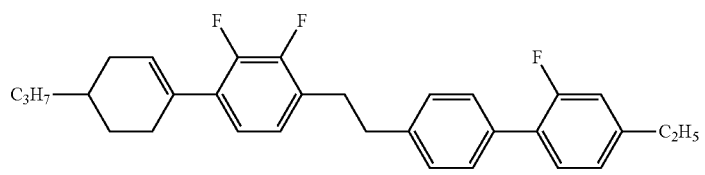 |
| 2617 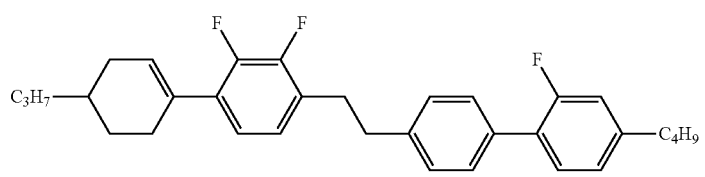 |
| 2618 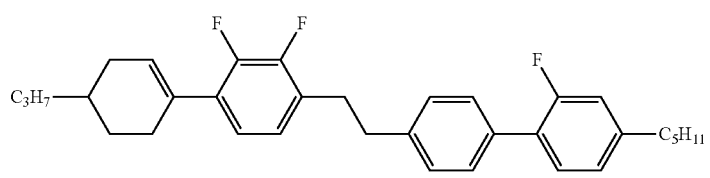 |
| 2619 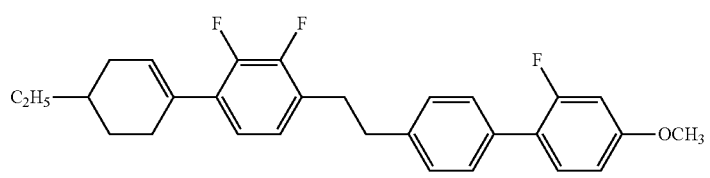 |
| 2620 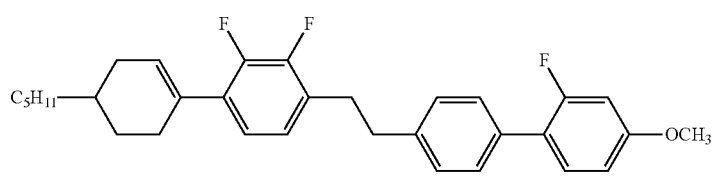 |
| 2621 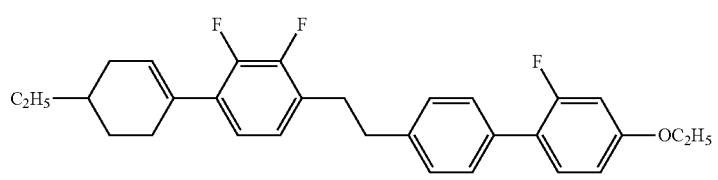 |
| 2622 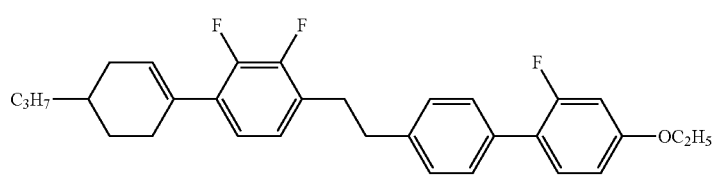 |
| 2623 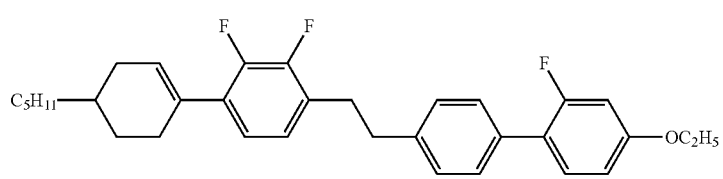 |

| No. | |
|---|---|
| 2624 | 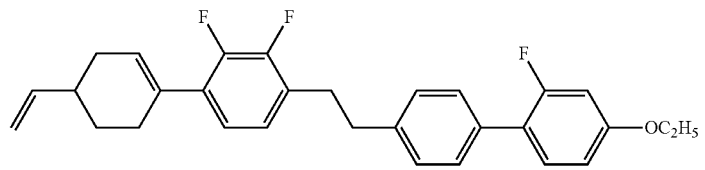 [SMILES: C=CC1CC=C(c2ccc(CCc3ccc(-c4ccc(OCC)cc4F)cc3)c(F)c2F)CC1] |
| 2625 | 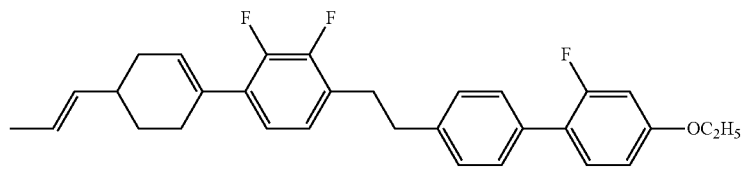 |
| 2626 | 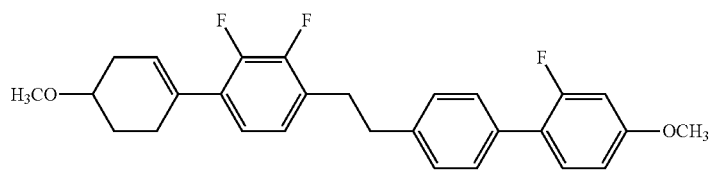 [SMILES: COc1ccc(-c2ccc(CCc3ccc(C4=CCC(OC)CC4)c(F)c3F)cc2)c(F)c1] |
| 2627 | 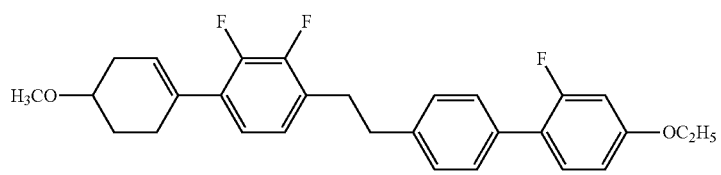 |
| 2628 | 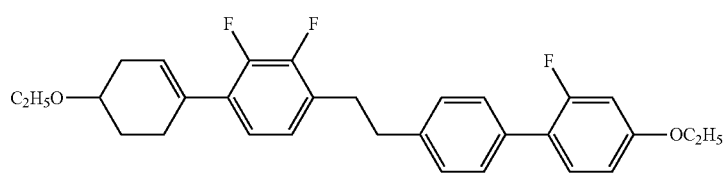 |
| 2629 | 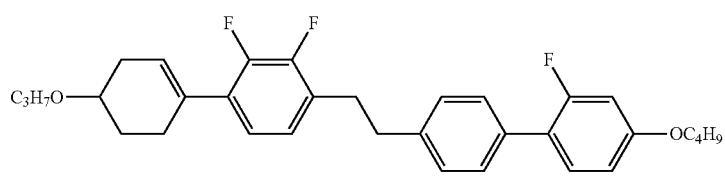 |
| 2630 | 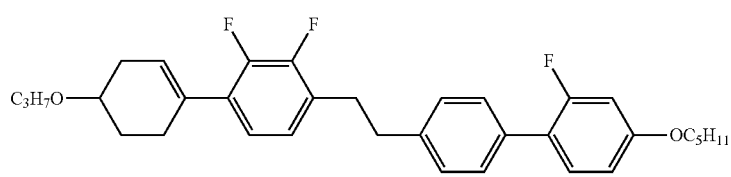 |
| 2631 | 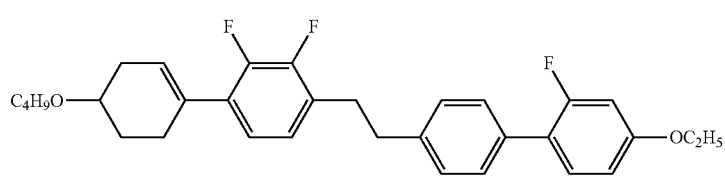 |

| No. | |
|---|---|
| 2632 | 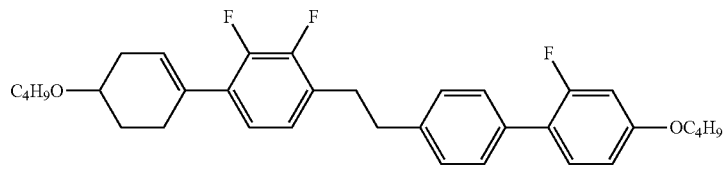 |
| 2633 | 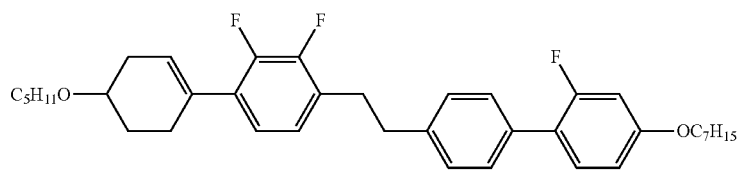 |
| 2634 | 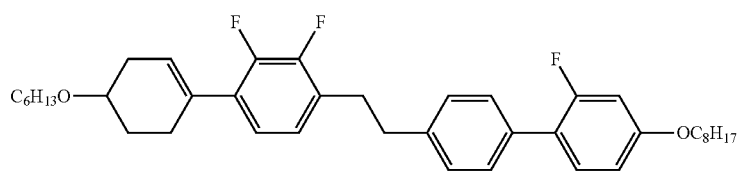 |
| 2635 | 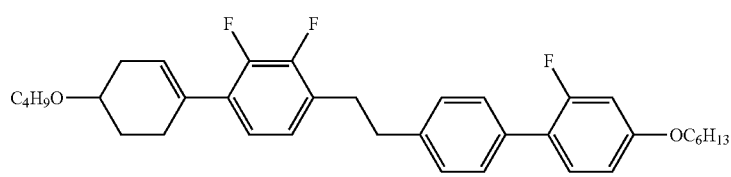 |
| 2636 | 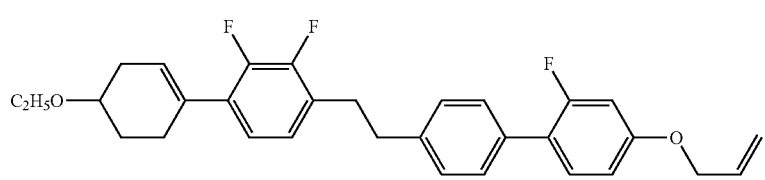 |
| 2637 | 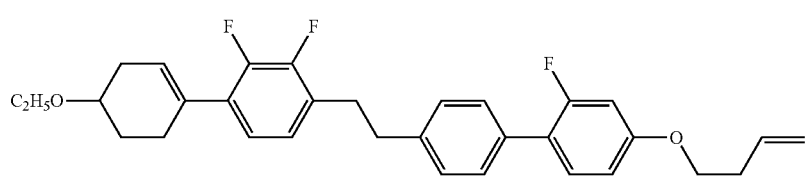 |
| 2638 | 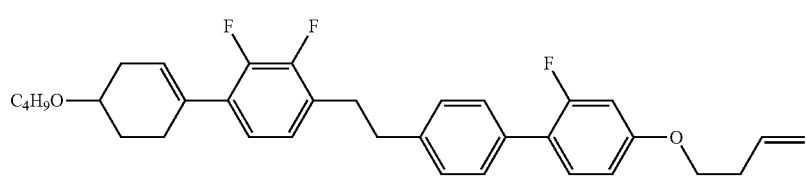 |
| 2639 | 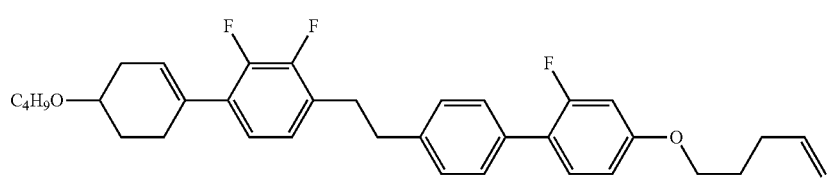 |

-continued
| No. |
|---|
| 2640 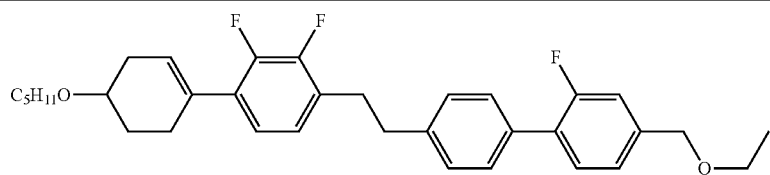 |
| 2641 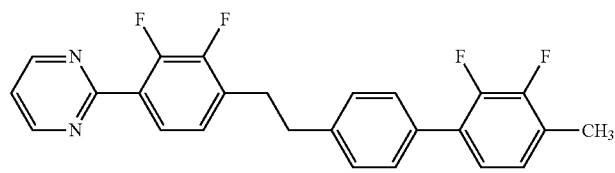 |
| 2642 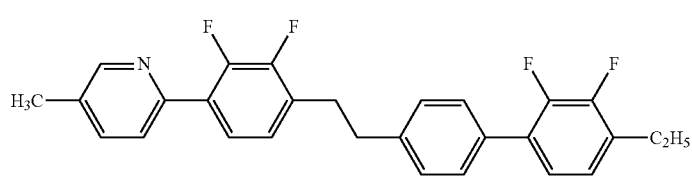 |
| 2643 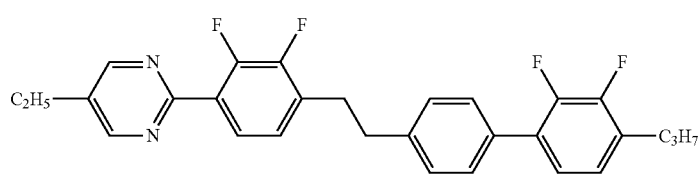 |
| 2644 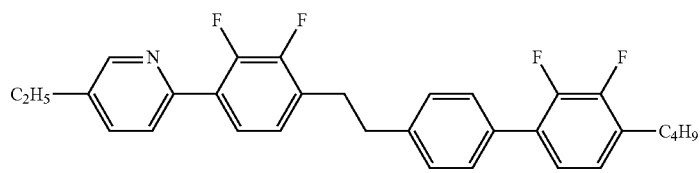 |
| 2645 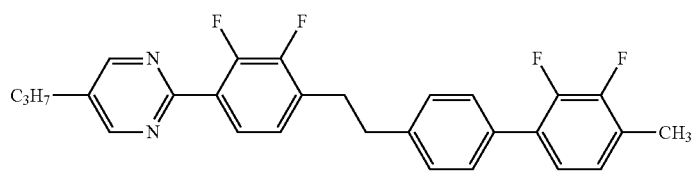 |
| 2646 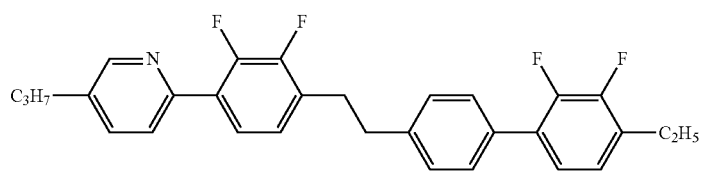 |
| 2647 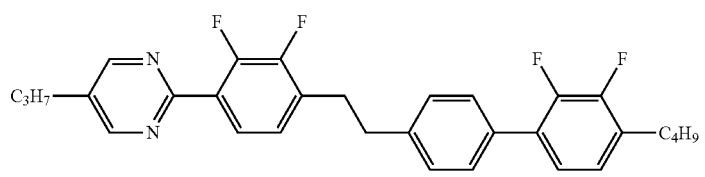 |
| 2648 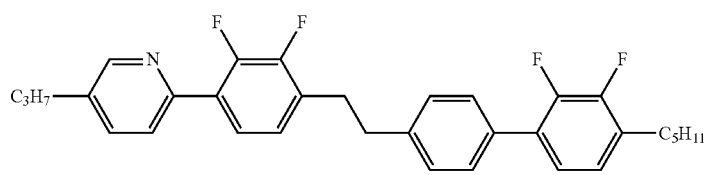 |

-continued
| No. | |
|---|---|
| 2649 | 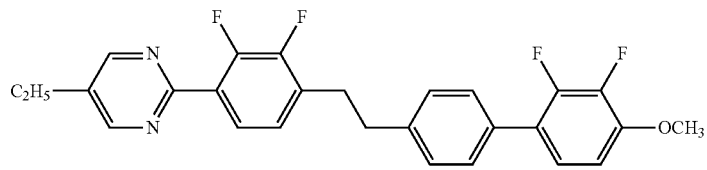 [SMILES: CCc1cnc(-c2ccc(CCc3ccc(-c4ccc(OC)c(F)c4F)cc3)c(F)c2F)nc1] |
| 2650 | 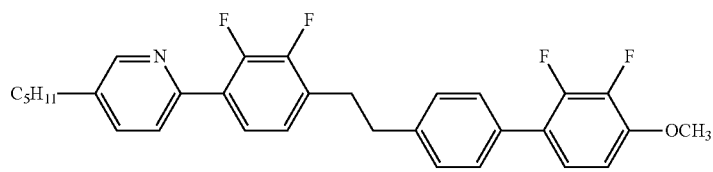 |
| 2651 | 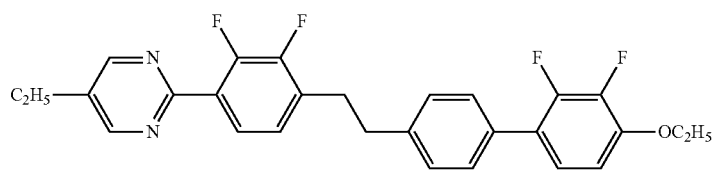 |
| 2652 | 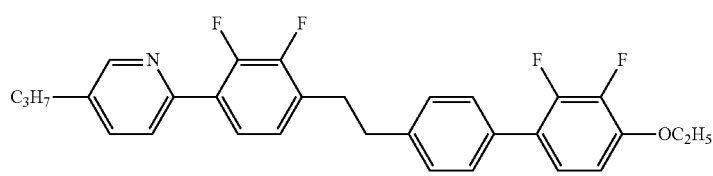 |
| 2653 | 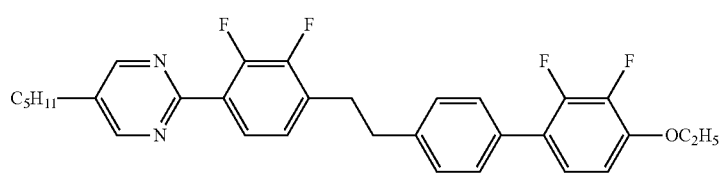 |
| 2654 | 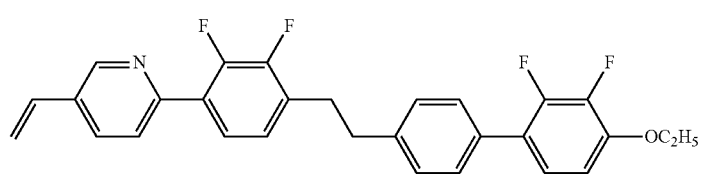 |
| 2655 | 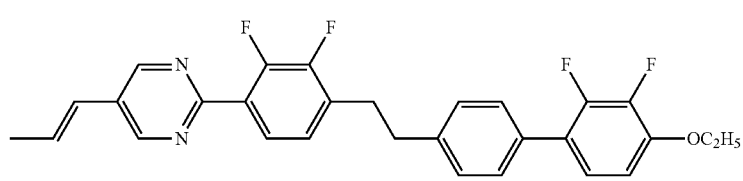 |
| 2656 | 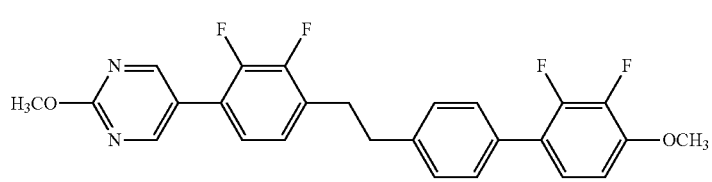 |

| No. | |
|---|---|
| 2657 | 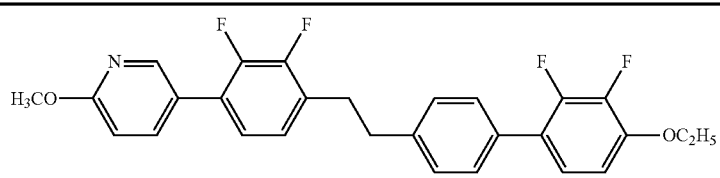 |
| 2658 | 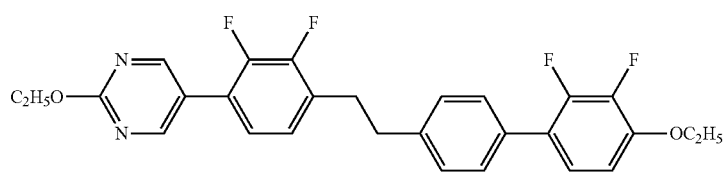 |
| 2659 | 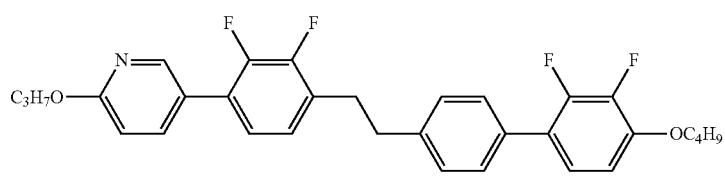 |
| 2660 | 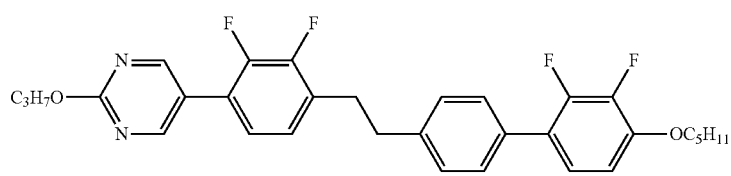 |
| 2661 | 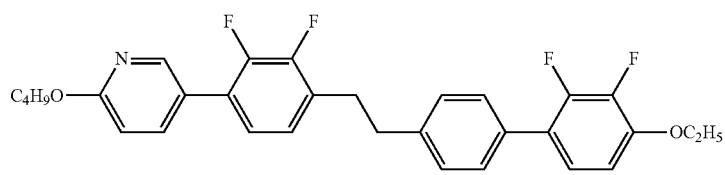 |
| 2662 | 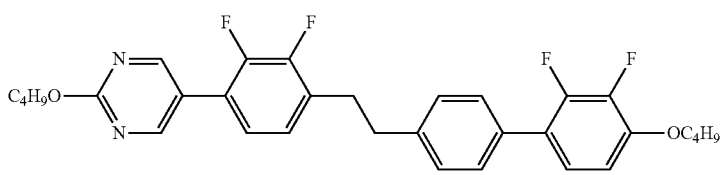 |
| 2663 | 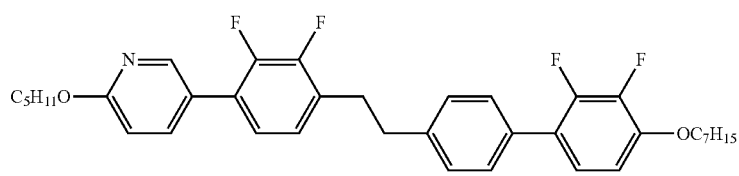 |
| 2664 | 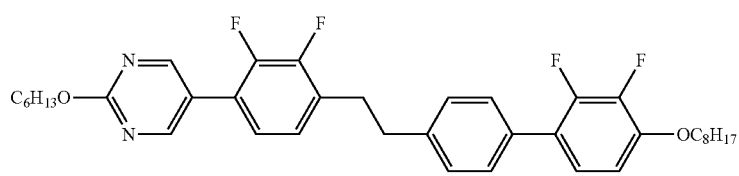 |
| 2665 | 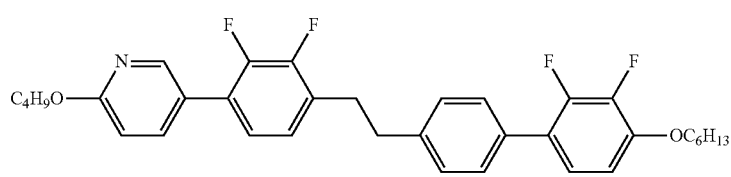 |

| No. |
|---|
| 2666 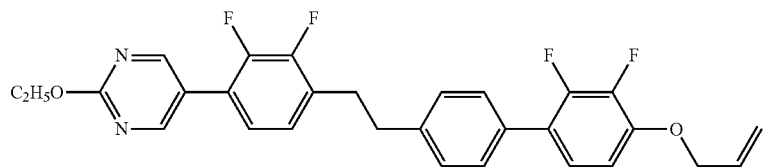 |
| 2667 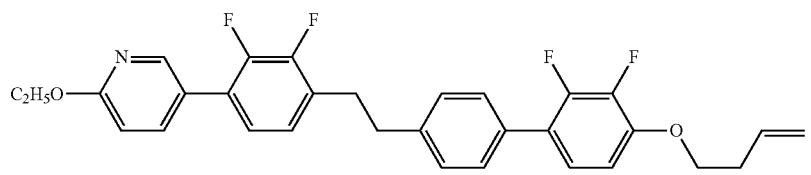 |
| 2668 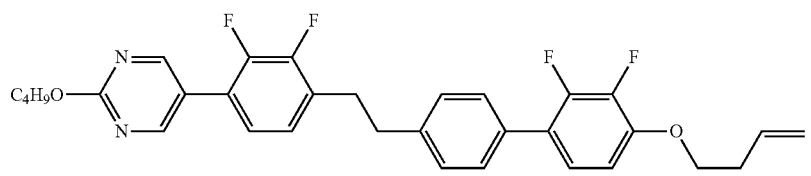 |
| 2669 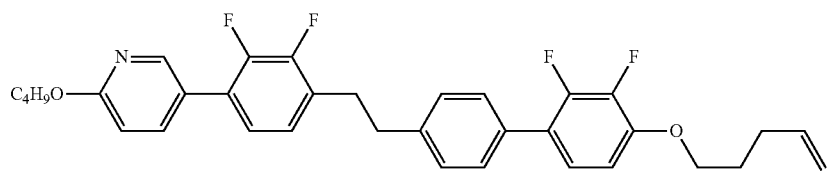 |
| 2670 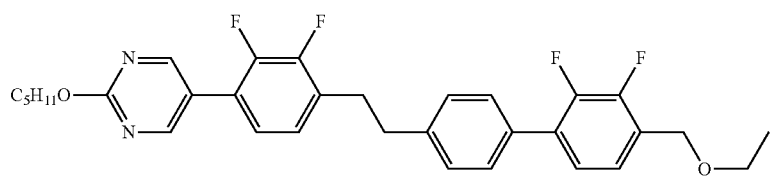 |
| 2671 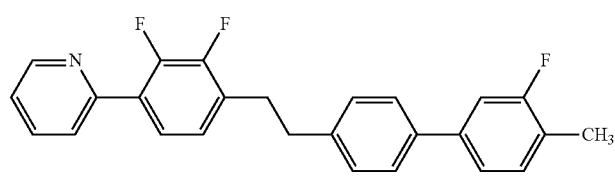 |
| 2672 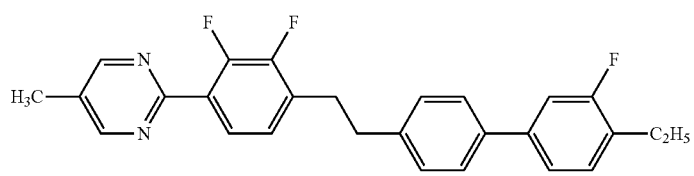 |
| 2673 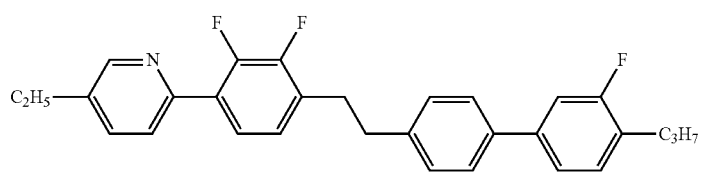 |

-continued
| No. |
|---|
2674 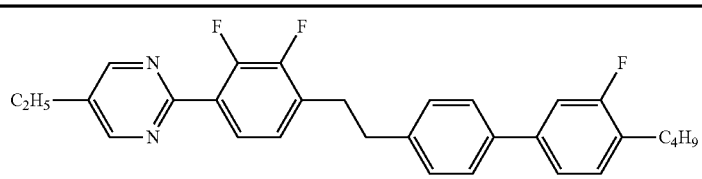
2675 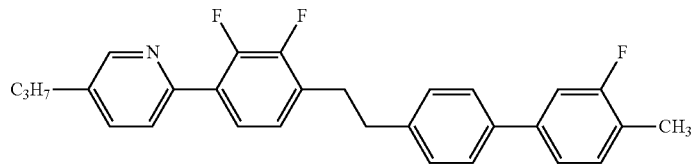
2676 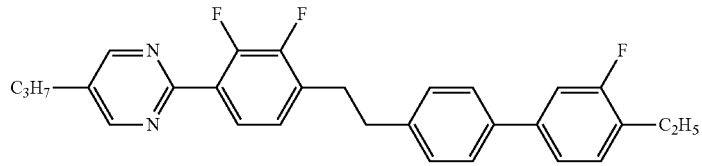
2677 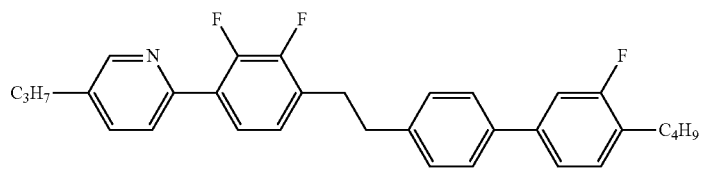
2678 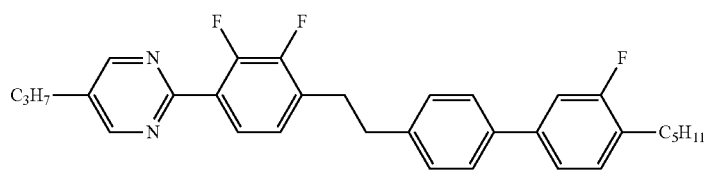
2679 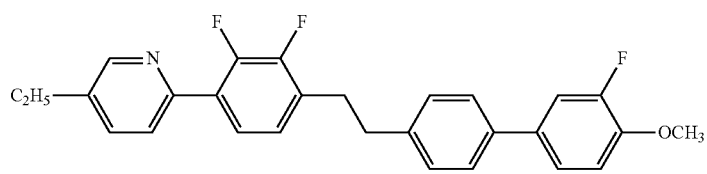
2680 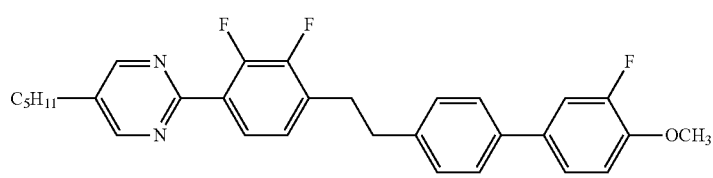
2681 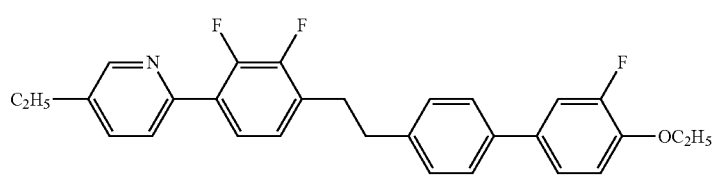
2682 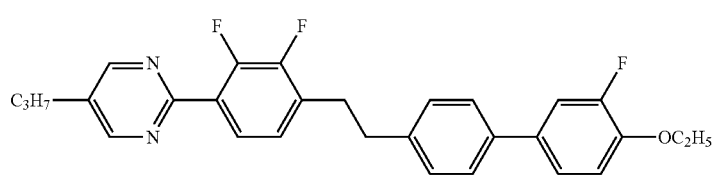

| No. | |
|---|---|
| 2683 | 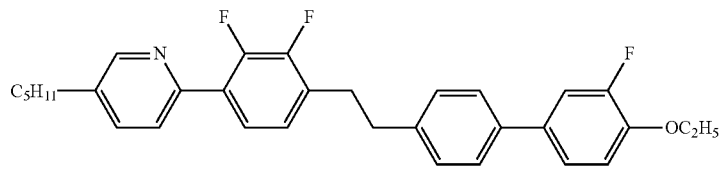 |
| 2684 | 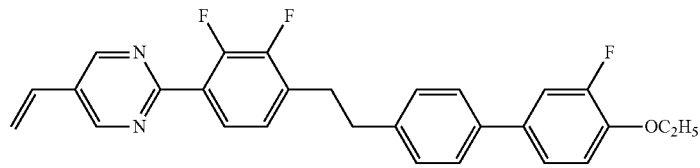 |
| 2685 | 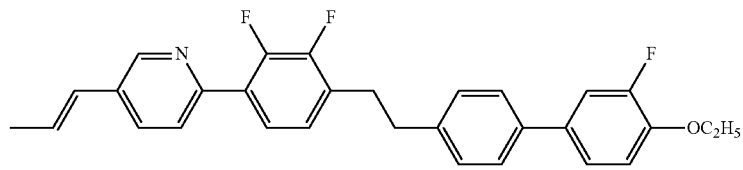 |
| 2686 | 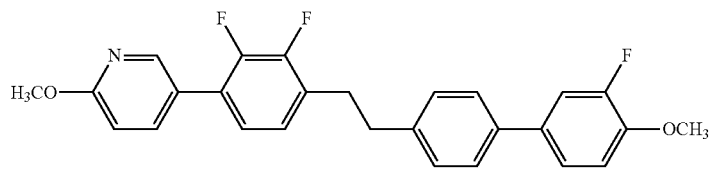 |
| 2687 | 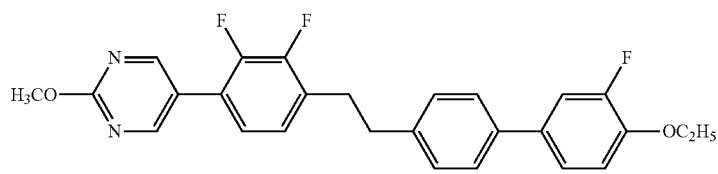 |
| 2688 | 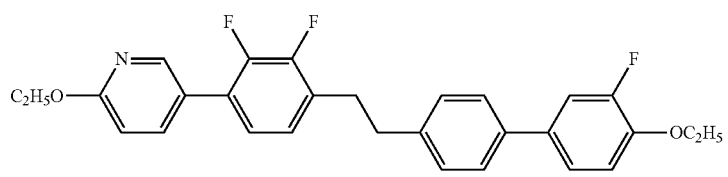 |
| 2689 | 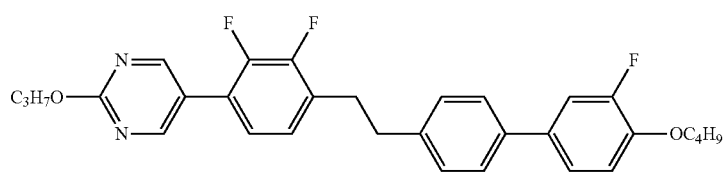 |
| 2690 | 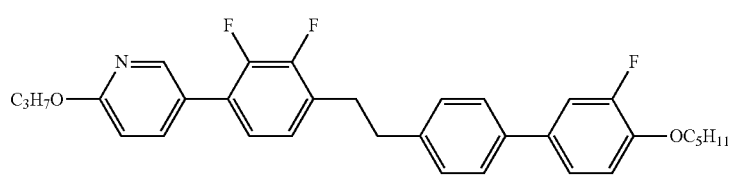 |

| No. | |
|---|---|
| 2691 | 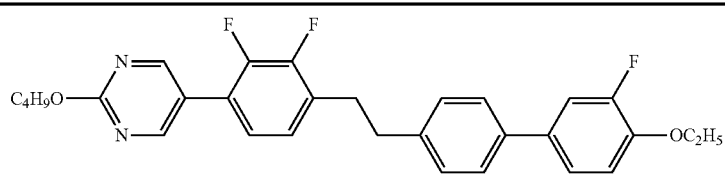 |
| 2692 | 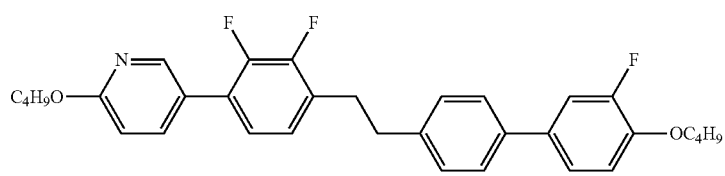 |
| 2693 | 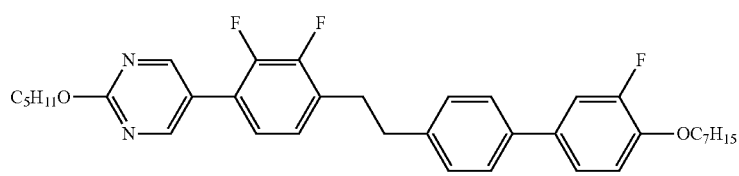 |
| 2694 | 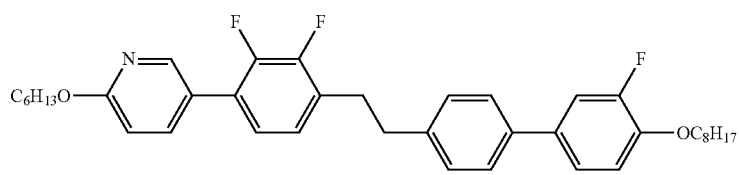 |
| 2695 | 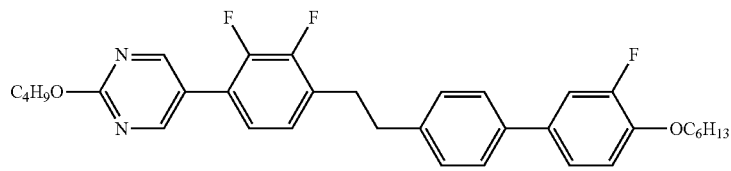 |
| 2696 | 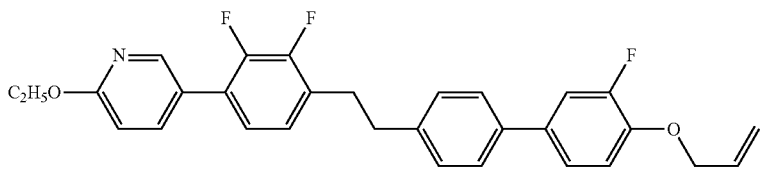 |
| 2697 | 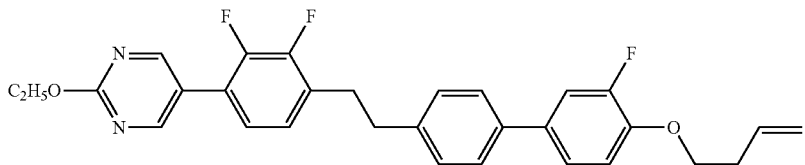 |
| 2698 | 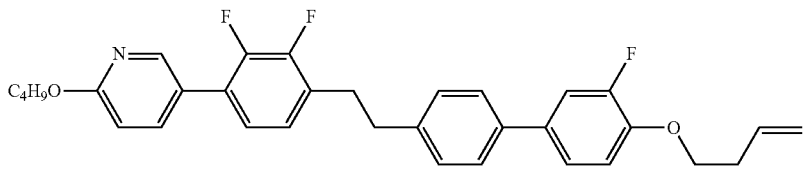 |
| 2699 | 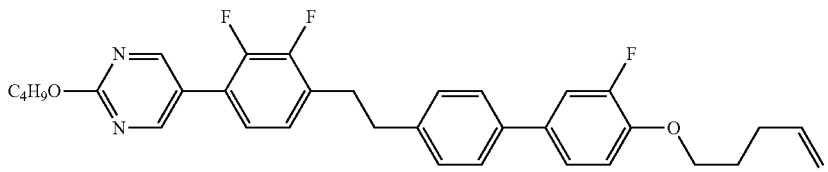 |

-continued
| No. | |
|---|---|
| 2700 | 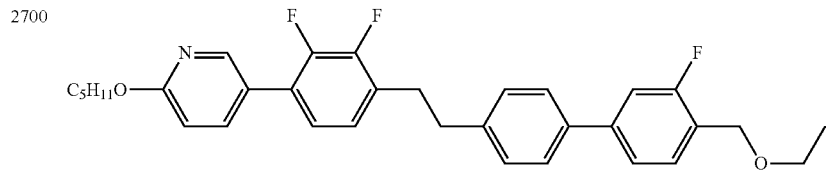 |
| 2701 | 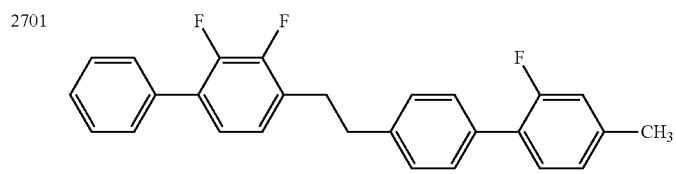 |
| 2702 | 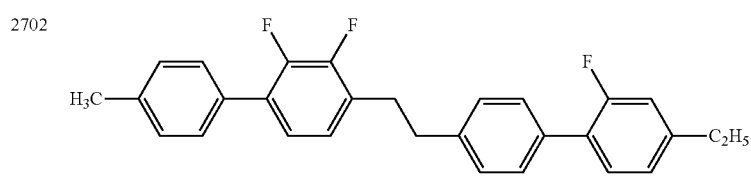 |
| 2703 | 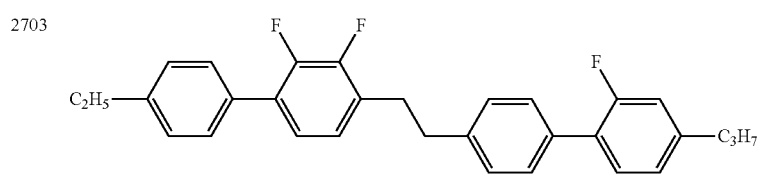 |
| 2704 | 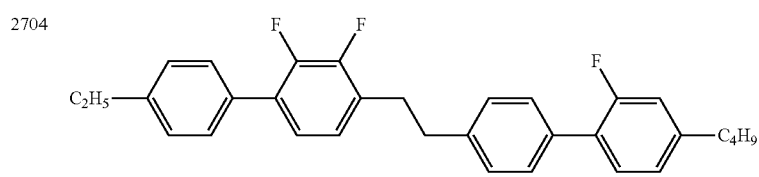 |
| 2705 | 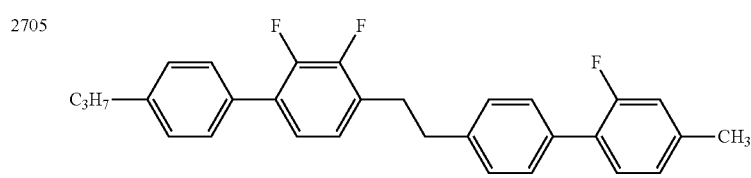 |
| 2706 | 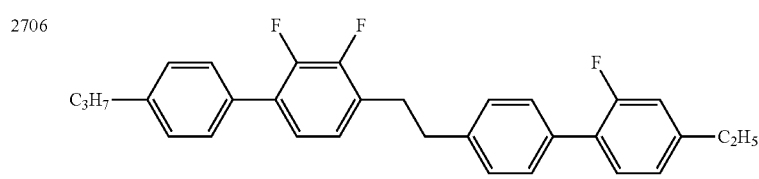 |
| 2707 | 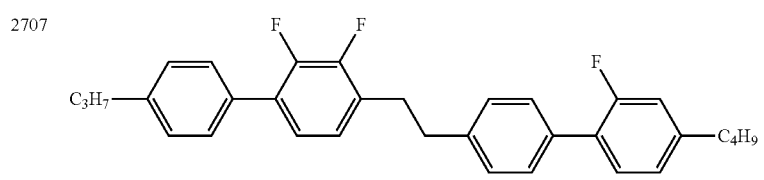 |

US 8,394,294 B2
723                                                                                                  724
-continued
| No. |
|---|
| 2708 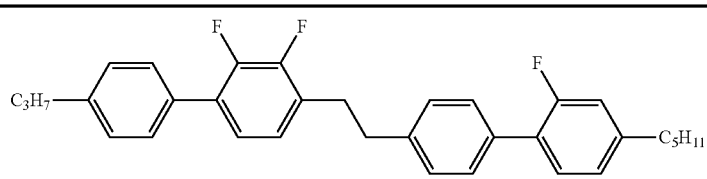 |
| 2709 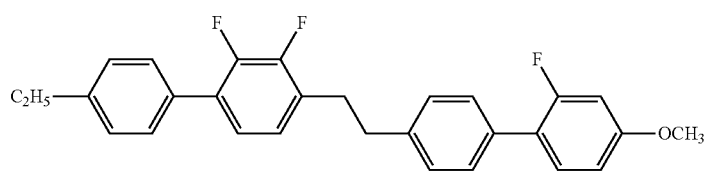 |
| 2710 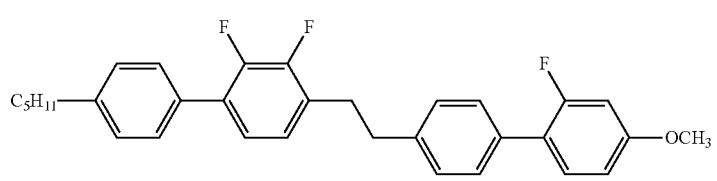 |
| 2711 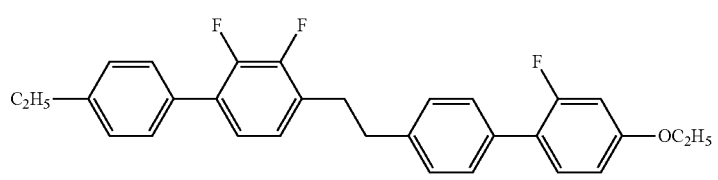 |
| 2712 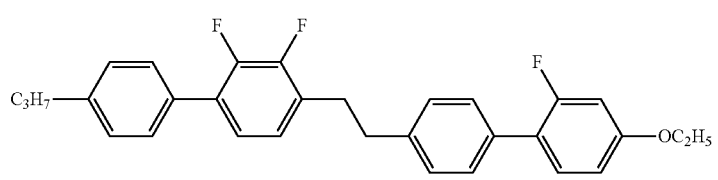 |
| 2713 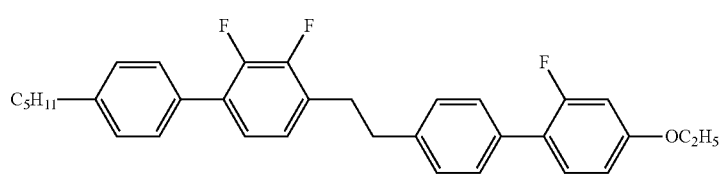 |
| 2714 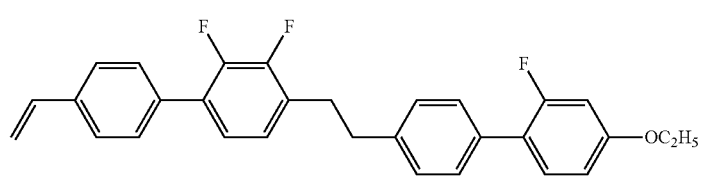 |
| 2715 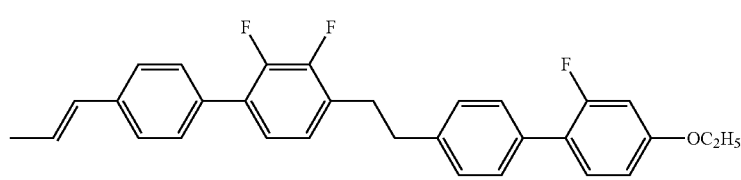 |
| 2716 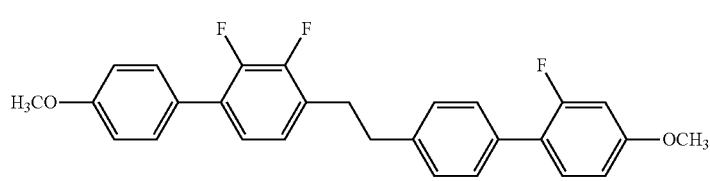 |

| No. | |
|---|---|
| 2717 | 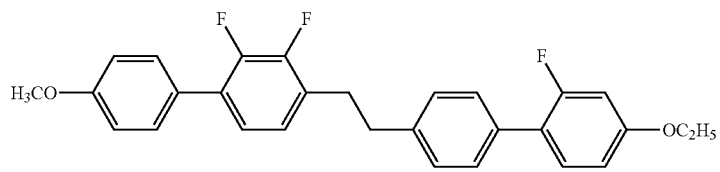 |
| 2718 | 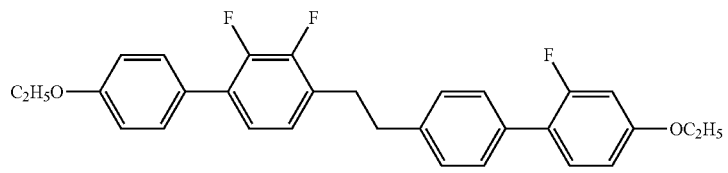 |
| 2719 | 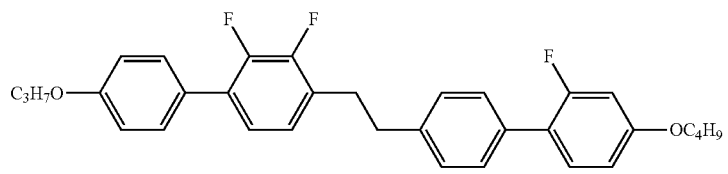 |
| 2720 | 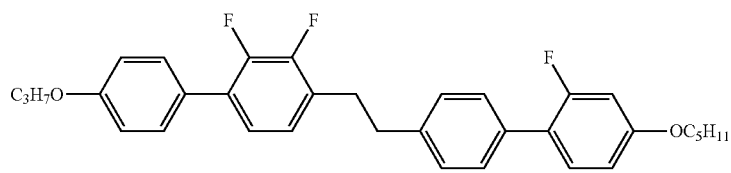 |
| 2721 | 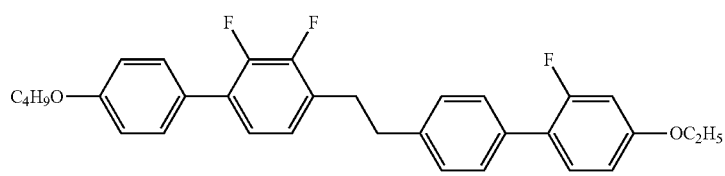 |
| 2722 | 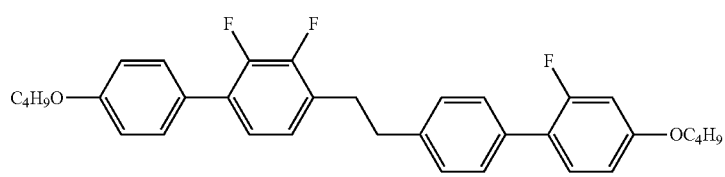 |
| 2723 | 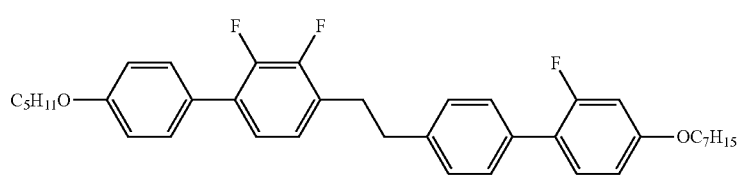 |
| 2724 | 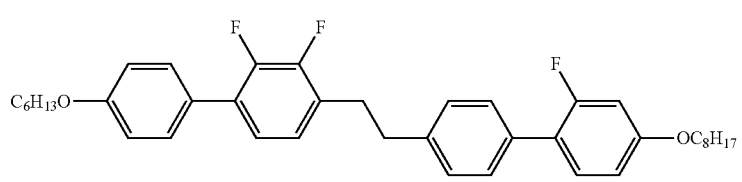 |

| No. | |
|---|---|
| 2725 | 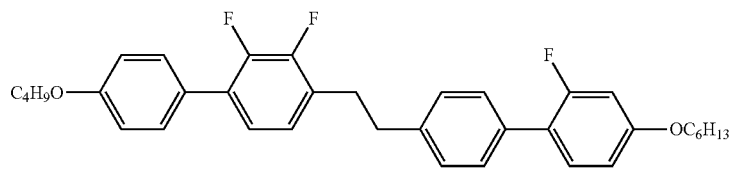 |
| 2726 | 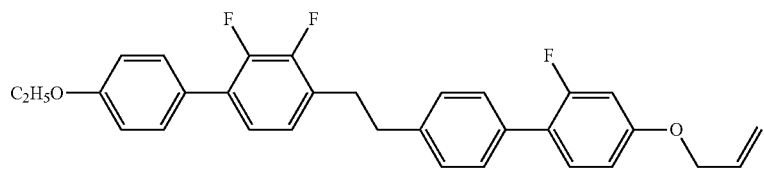 |
| 2727 | 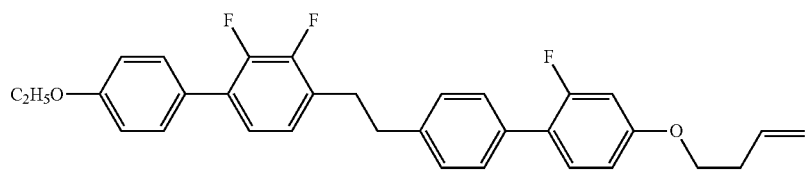 |
| 2728 | 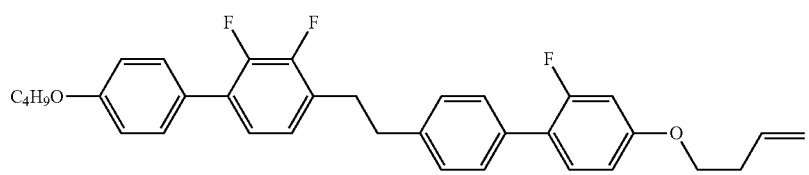 |
| 2729 | 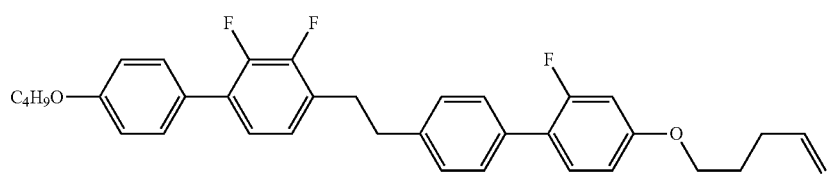 |
| 2730 | 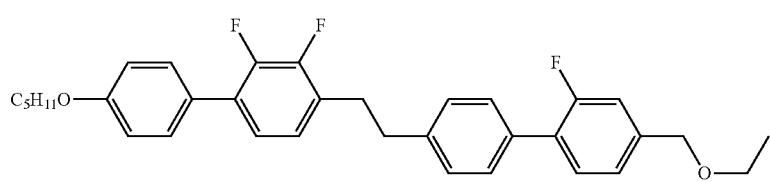 |
| 2731 | 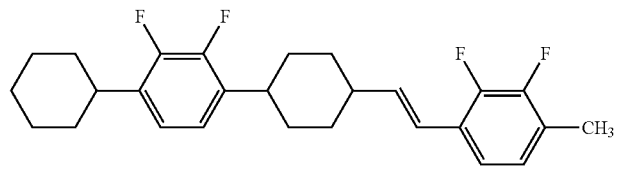 |
| 2732 | 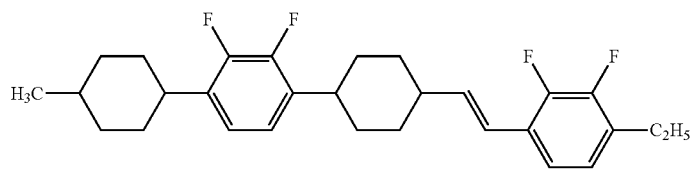 |

| No. | |
|---|---|
| 2733 | 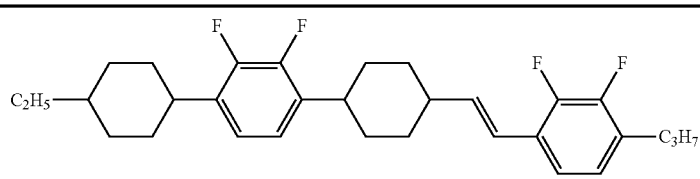 |
| 2734 | 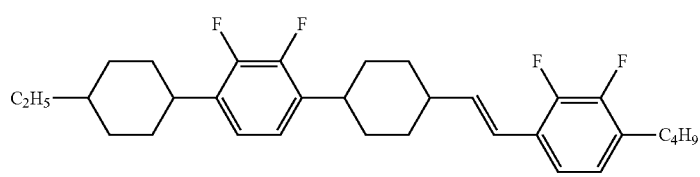 |
| 2735 | 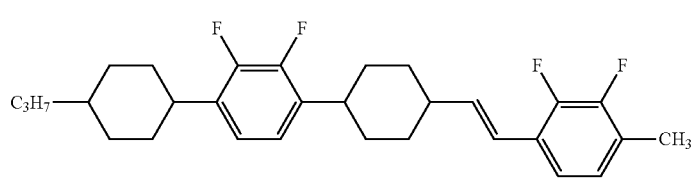 |
| 2736 | 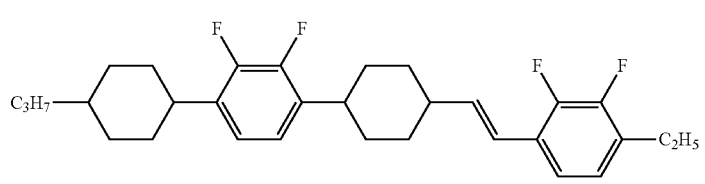 |
| 2737 | 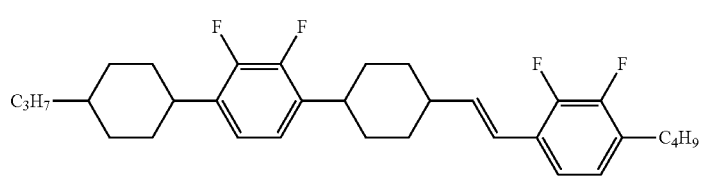 |
| 2738 | 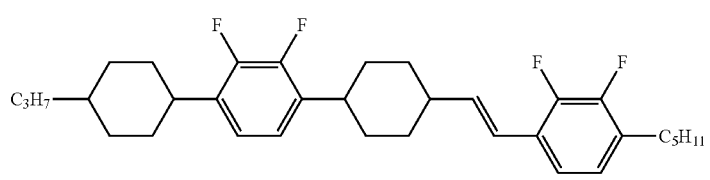 |
| 2739 | 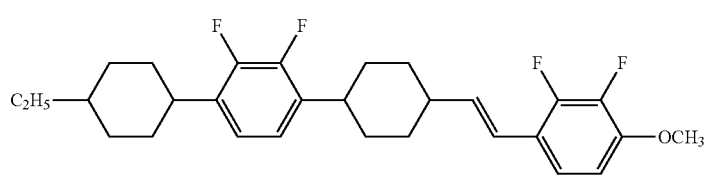 [SMILES: CCC1CCC(c2ccc(C3CCC(/C=C/c4ccc(OC)c(F)c4F)CC3)c(F)c2F)CC1] |
| 2740 | 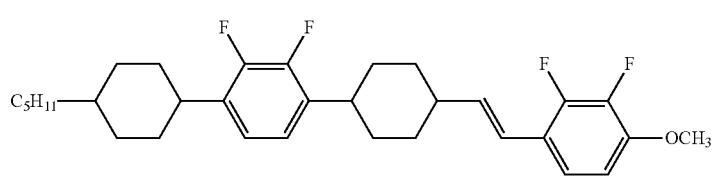 |
| 2741 | 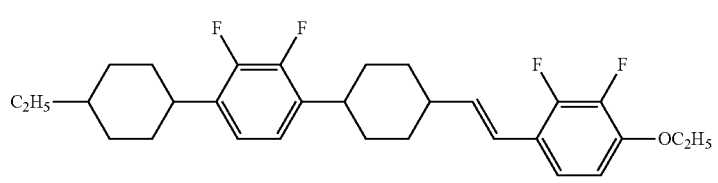 |

| No. | |
|---|---|
| 2742 | 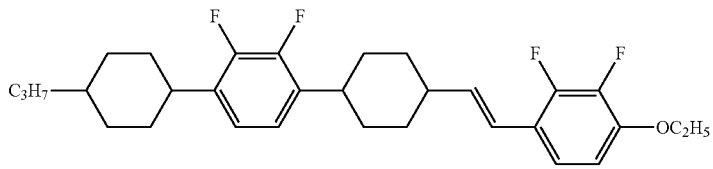 |
| 2743 | 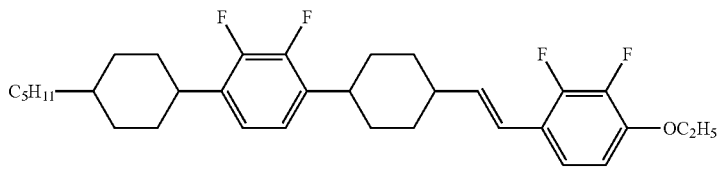 |
| 2744 | 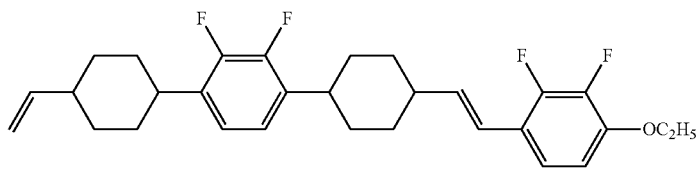 [SMILES: C=CC1CCC(c2ccc(C3CCC(/C=C/c4ccc(OCC)c(F)c4F)CC3)c(F)c2F)CC1] |
| 2745 | 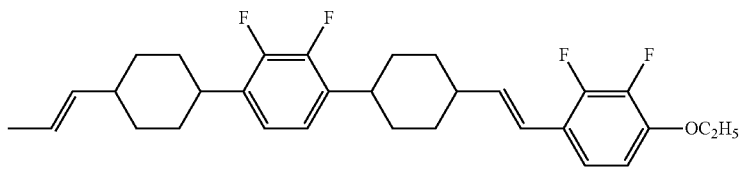 |
| 2746 | 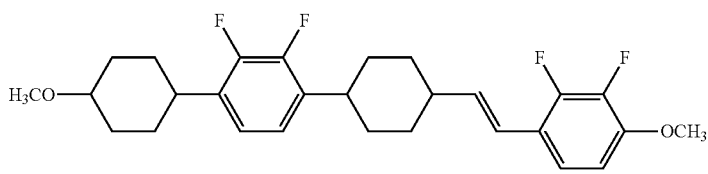 [SMILES: COc1ccc(/C=C/C2CCC(c3ccc(C4CCC(OC)CC4)c(F)c3F)CC2)c(F)c1F] |
| 2747 | 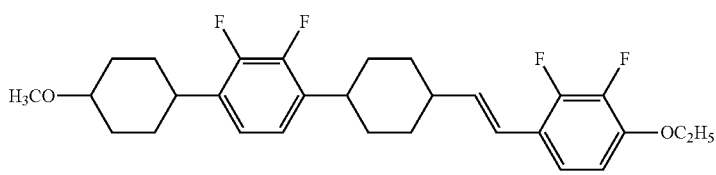 |
| 2748 | 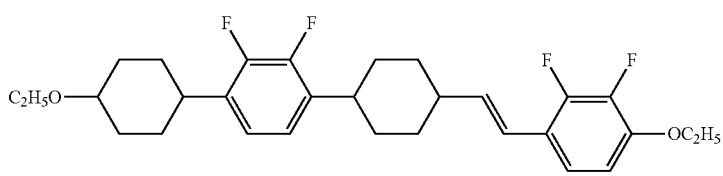 |
| 2749 | 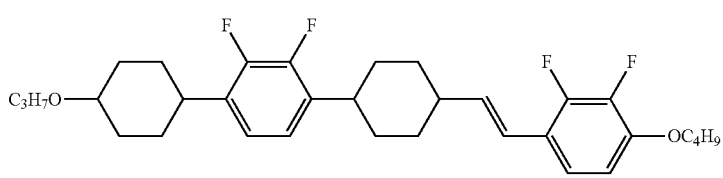 |

| No. | |
|---|---|
| 2750 | 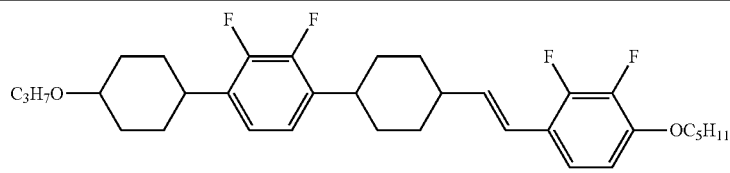 |
| 2751 | 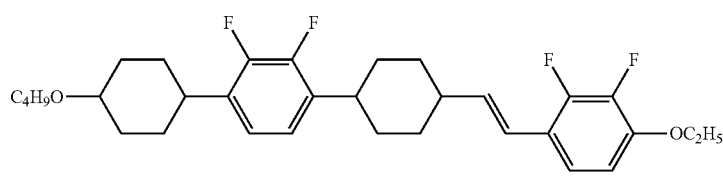 |
| 2752 | 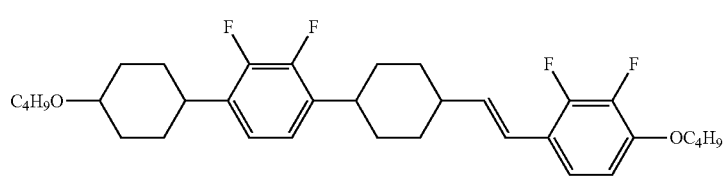 |
| 2753 | 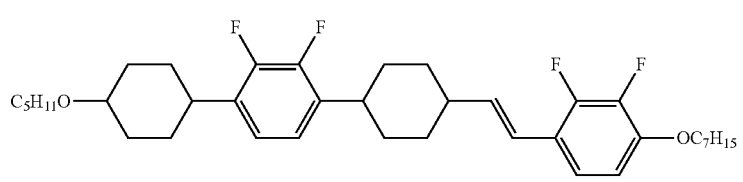 |
| 2754 | 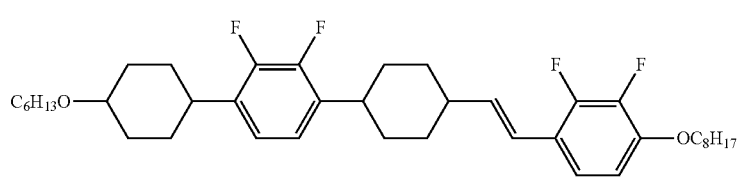 |
| 2755 | 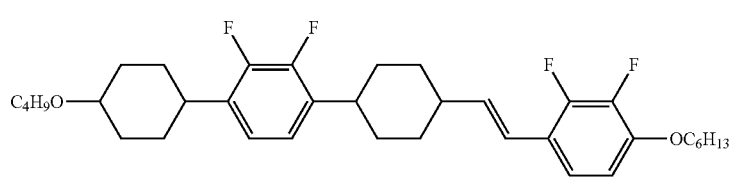 |
| 2756 | 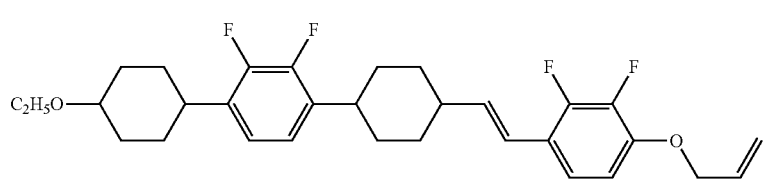 |
| 2757 | 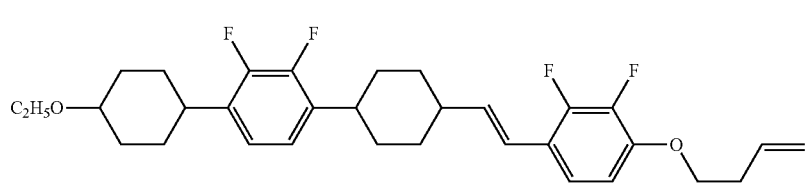 |
| 2758 | 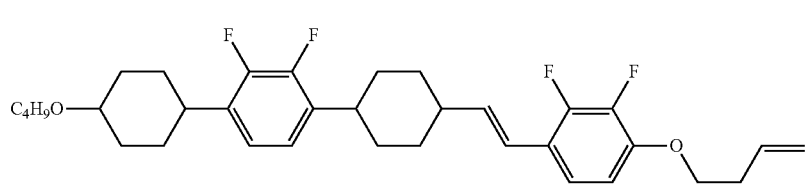 |

| No. | |
|---|---|
| 2759 | 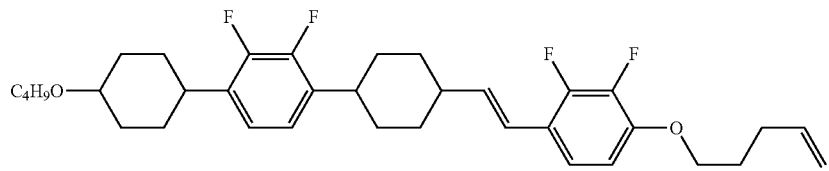 |
| 2760 | 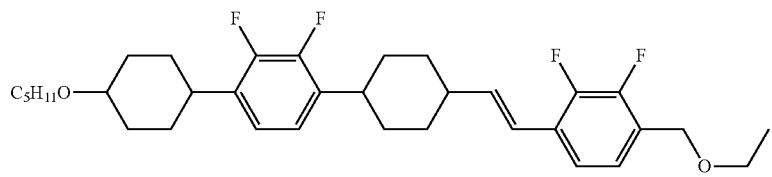 |
| 2761 | 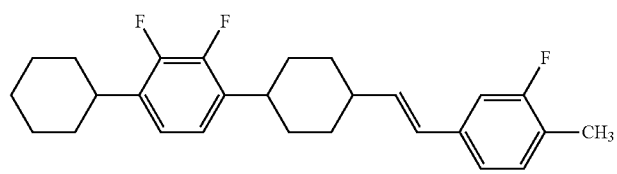 [SMILES: Cc1ccc(/C=C/C2CCC(c3ccc(C4CCCCC4)c(F)c3F)CC2)cc1F] |
| 2762 | 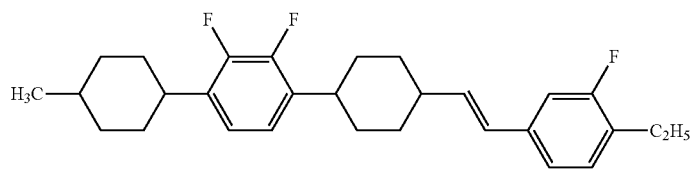 |
| 2763 | 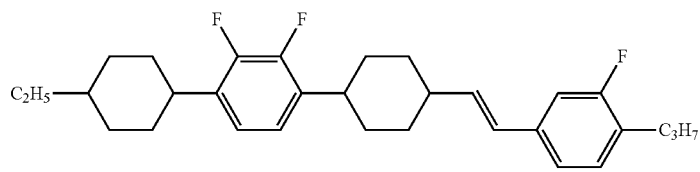 |
| 2764 | 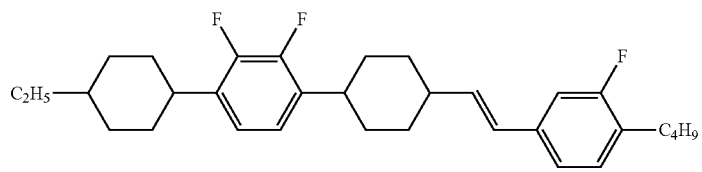 |
| 2765 | 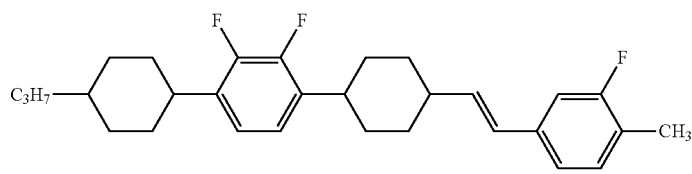 |
| 2766 | 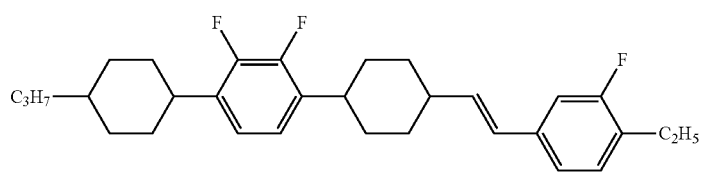 |

| No. |
|---|
| 2767 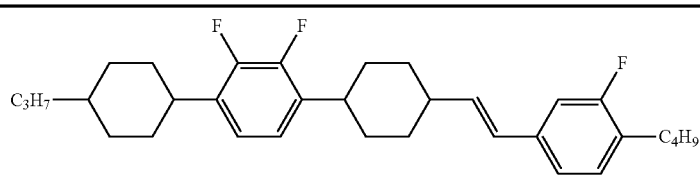 |
| 2768 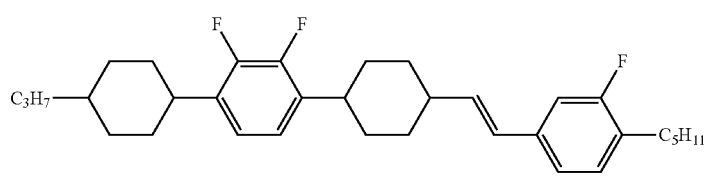 |
| 2769 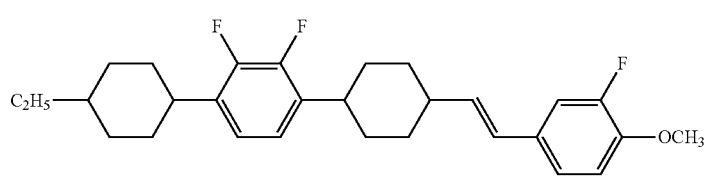 |
| 2770 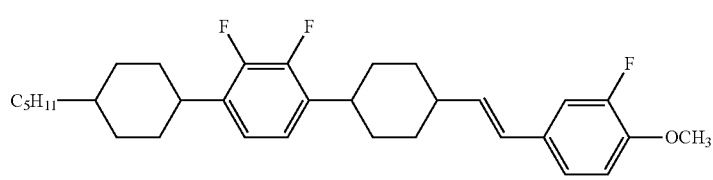 |
| 2771 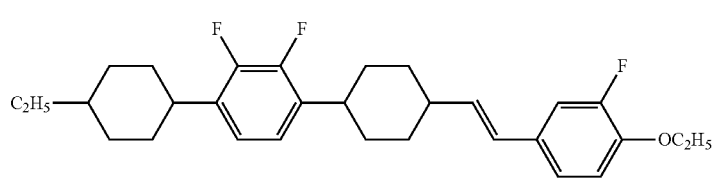 [SMILES: CCOc1ccc(/C=C/C2CCC(c3ccc(C4CCC(CC)CC4)c(F)c3F)CC2)cc1F] |
| 2772 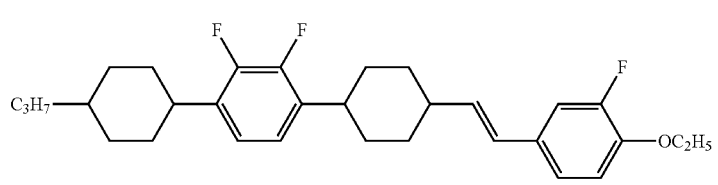 |
| 2773 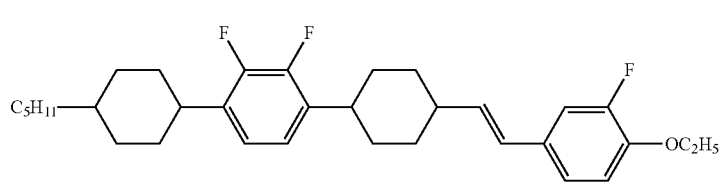 |
| 2774 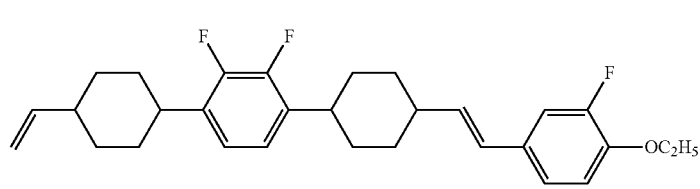 [SMILES: C=CC1CCC(c2ccc(C3CCC(/C=C/c4ccc(OCC)c(F)c4)CC3)c(F)c2F)CC1] |
| 2775 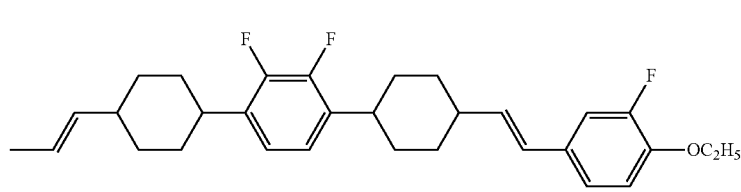 |

| No. | |
|---|---|
| 2776 | 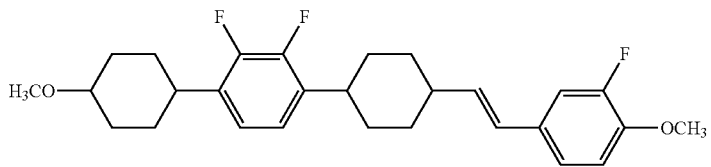 |
| 2777 | 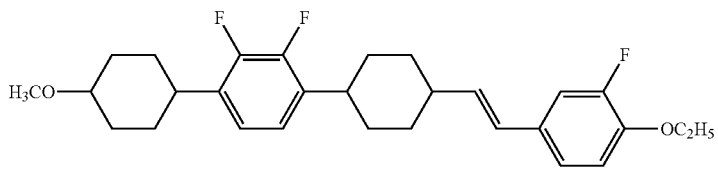 |
| 2778 | 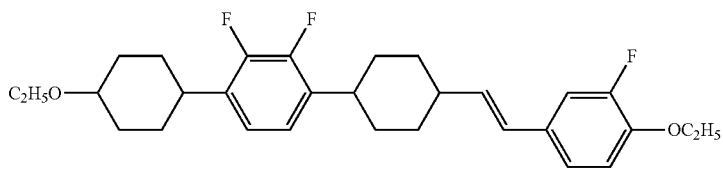 |
| 2779 | 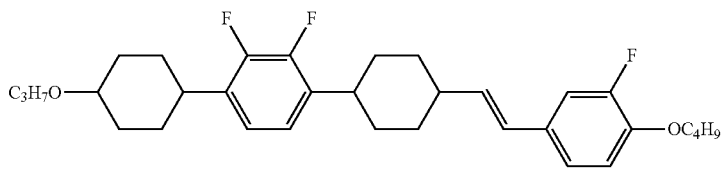 |
| 2780 | 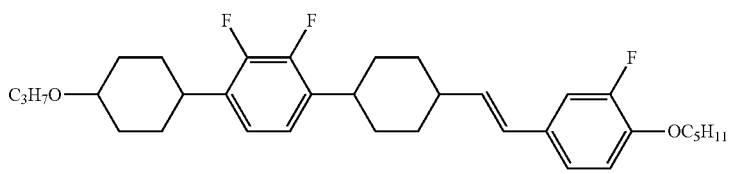 |
| 2781 | 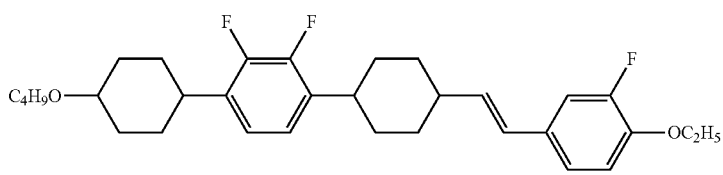 |
| 2782 | 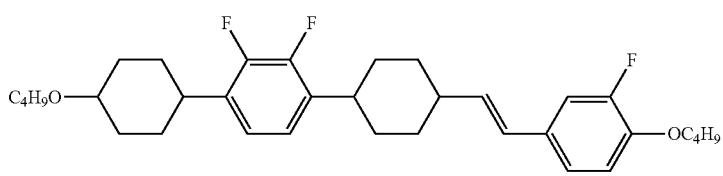 |
| 2783 | 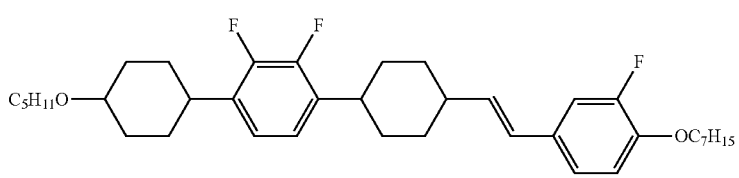 |

| No. | |
|---|---|
| 2784 | 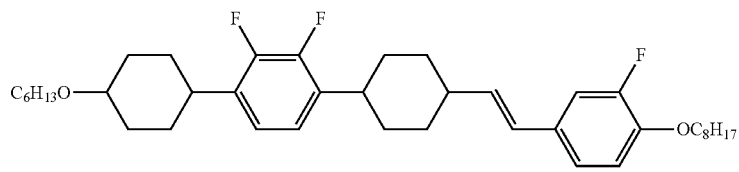 |
| 2785 | 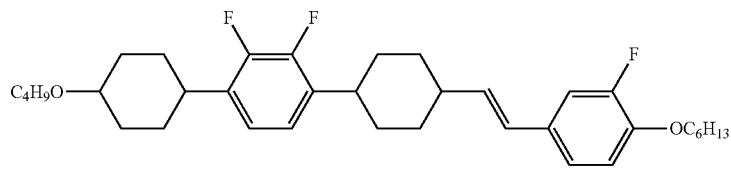 |
| 2786 | 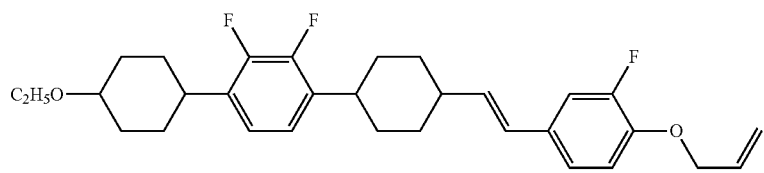 |
| 2787 | 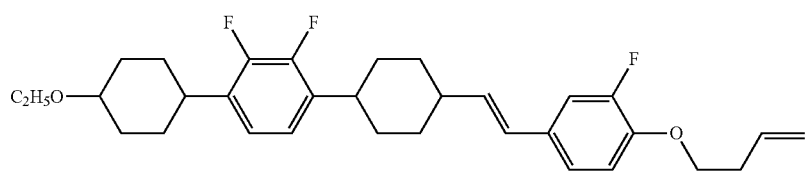 |
| 2788 | 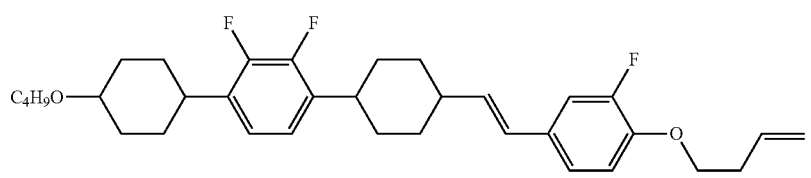 |
| 2789 | 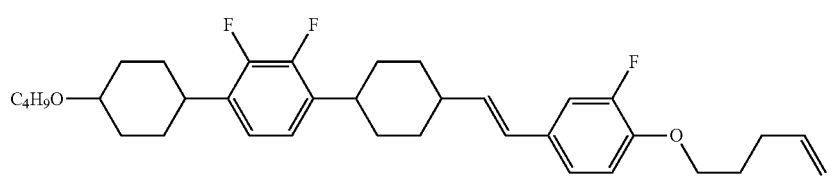 |
| 2790 | 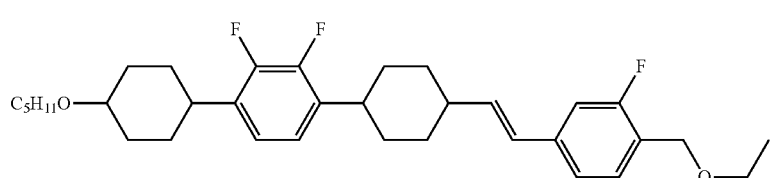 |
| 2791 | 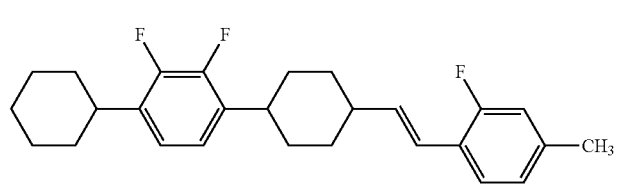 |

| No. | |
|---|---|
| 2792 | 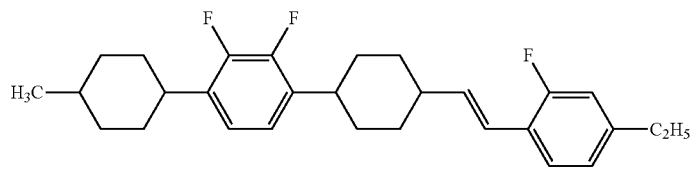 |
| 2793 | 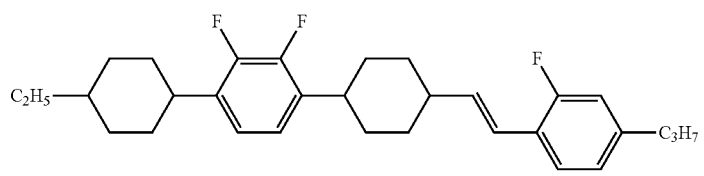 |
| 2794 | 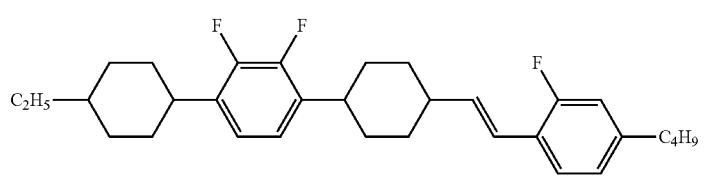 |
| 2795 | 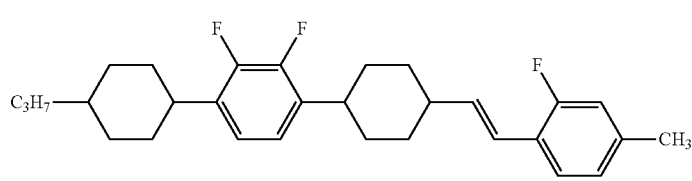 |
| 2796 | 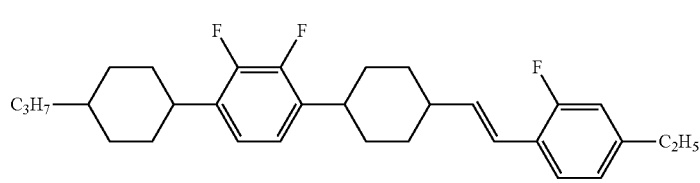 |
| 2797 | 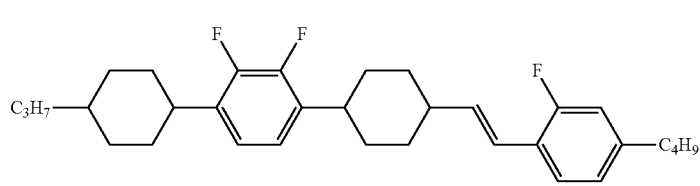 |
| 2798 | 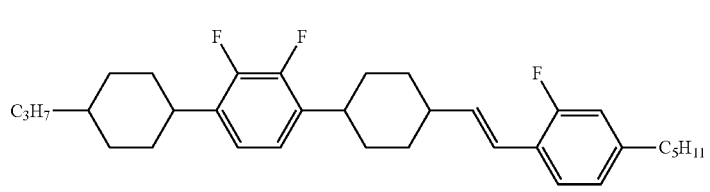 |
| 2799 | 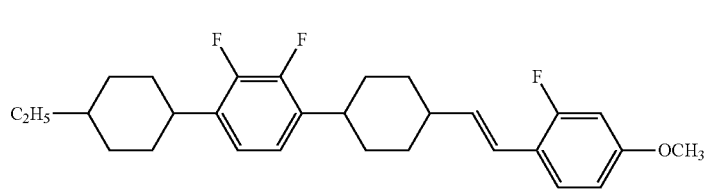 |
| 2800 | 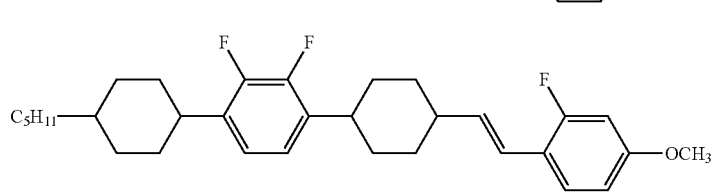 |

-continued
| No. | |
|---|---|
| 2801 | 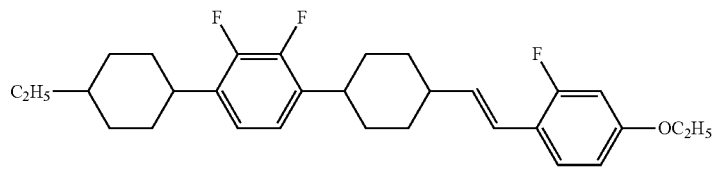 [SMILES: CCOc1ccc(/C=C/C2CCC(c3ccc(C4CCC(CC)CC4)c(F)c3F)CC2)c(F)c1] |
| 2802 | 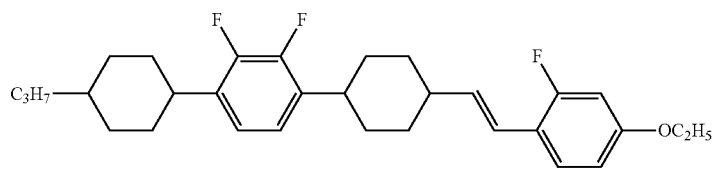 |
| 2803 | 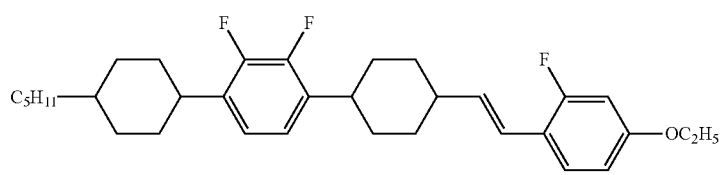 |
| 2804 | 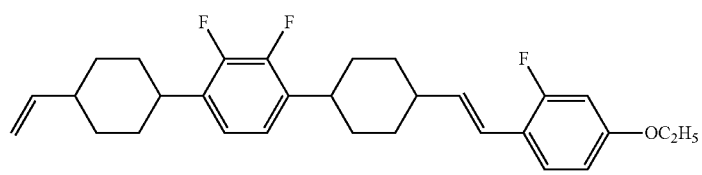 |
| 2805 | 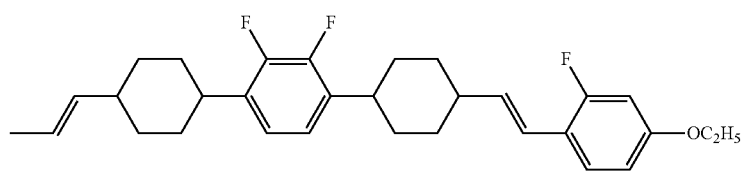 [SMILES: C/C=C/C1CCC(c2ccc(C3CCC(/C=C/c4ccc(OCC)cc4F)CC3)c(F)c2F)CC1] |
| 2806 | 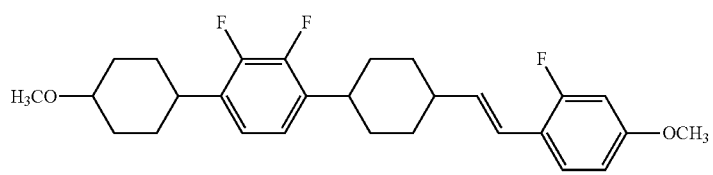 [SMILES: COc1ccc(/C=C/C2CCC(c3ccc(C4CCC(OC)CC4)c(F)c3F)CC2)c(F)c1] |
| 2807 | 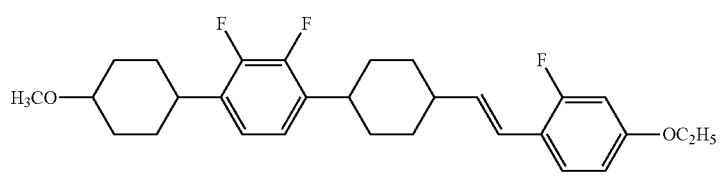 [SMILES: CCOc1ccc(/C=C/C2CCC(c3ccc(C4CCC(OC)CC4)c(F)c3F)CC2)c(F)c1] |
| 2808 | 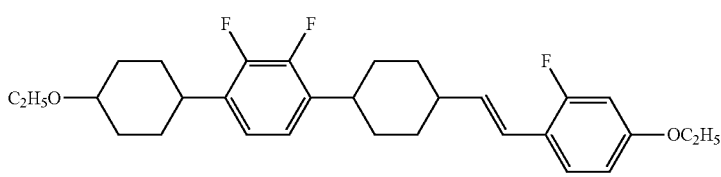 |

| No. | |
|---|---|
| 2809 | 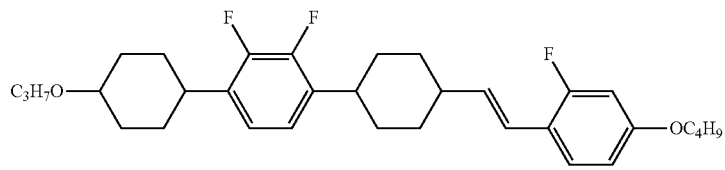 |
| 2810 | 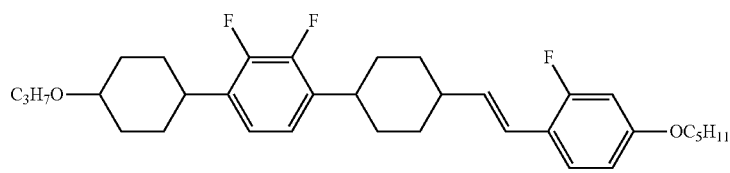 |
| 2811 | 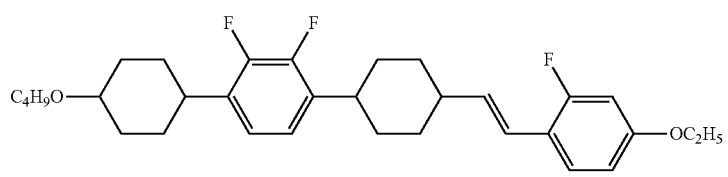 |
| 2812 | 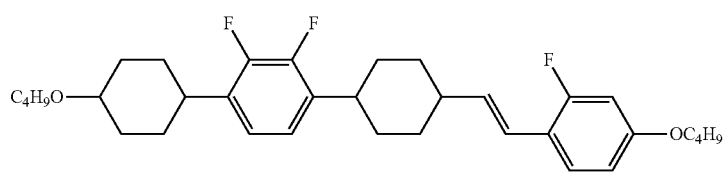 |
| 2813 | 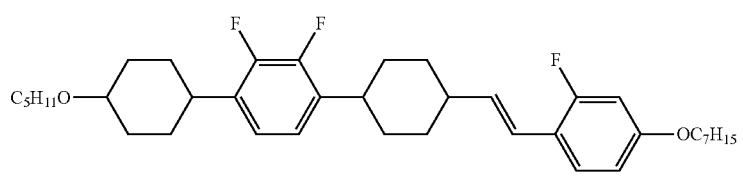 |
| 2814 | 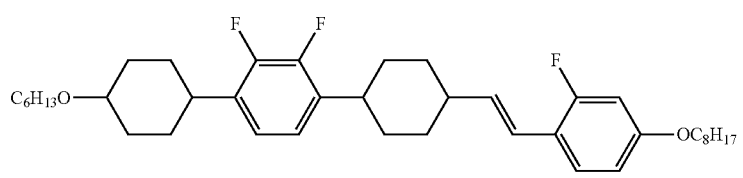 |
| 2815 | 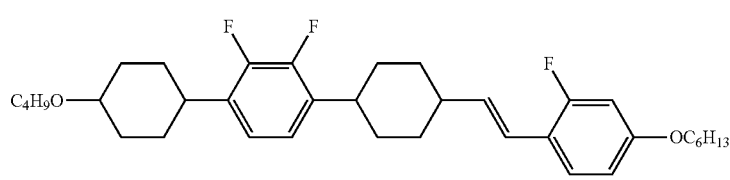 |
| 2816 | 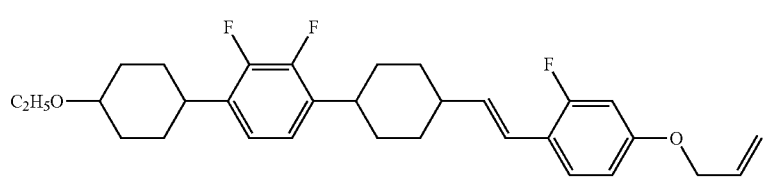 |
| 2817 | 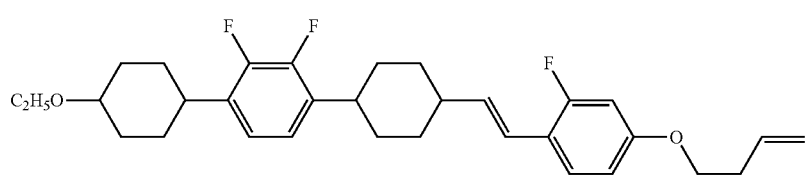 |

| No. | |
|---|---|
| 2818 | 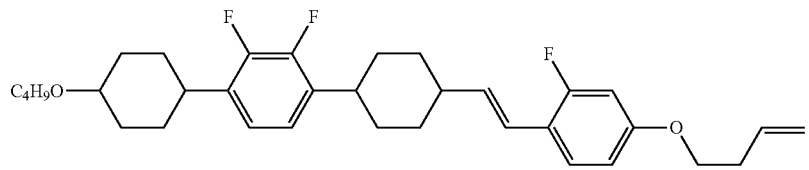 |
| 2819 | 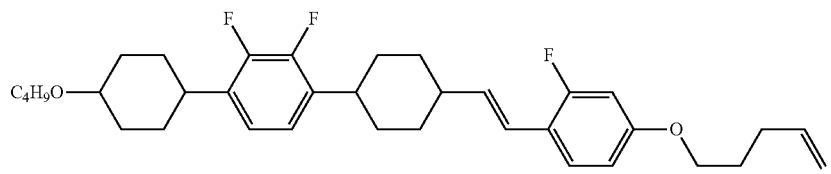 |
| 2820 | 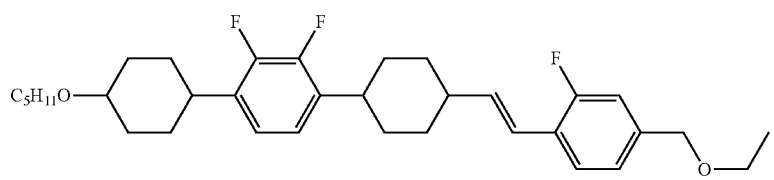 |
| 2821 | 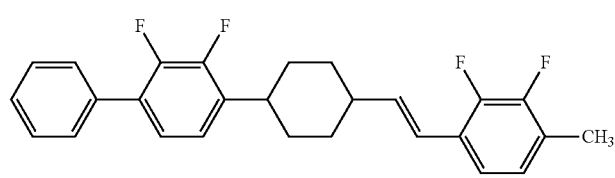 |
| 2822 | 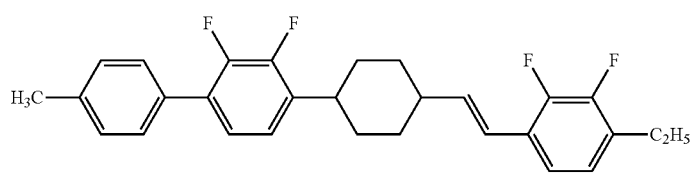 |
| 2823 | 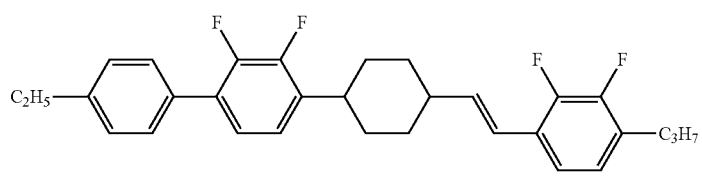 |
| 2824 | 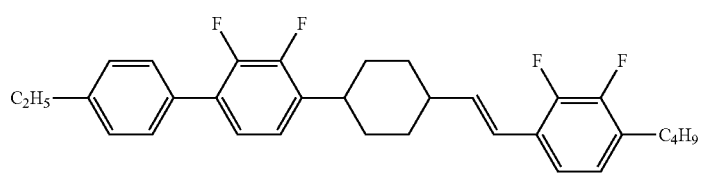 |
| 2825 | 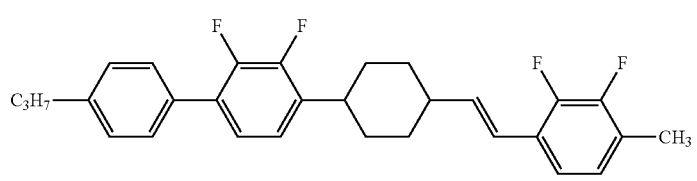 |

| No. |
|---|
| 2826 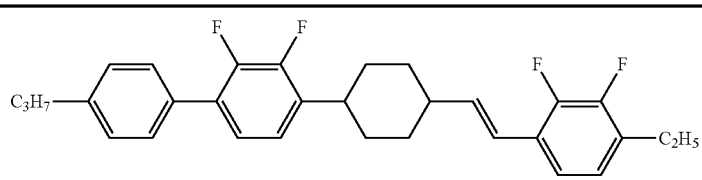 |
| 2827 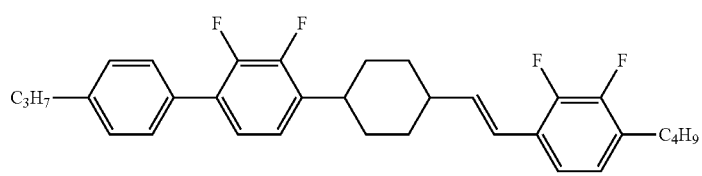 |
| 2828 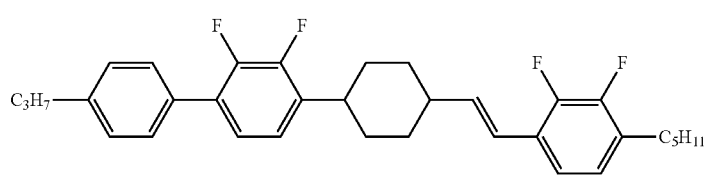 |
| 2829 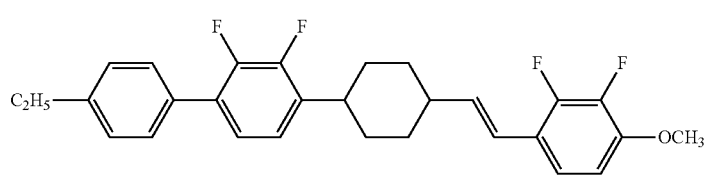 [SMILES: CCc1ccc(-c2ccc(C3CCC(/C=C/c4ccc(OC)c(F)c4F)CC3)c(F)c2F)cc1] |
| 2830 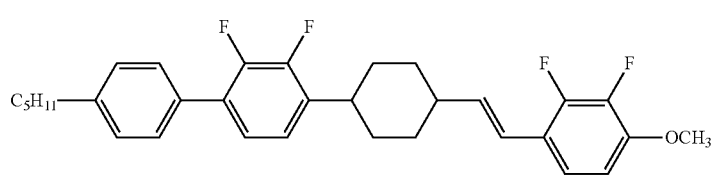 |
| 2831 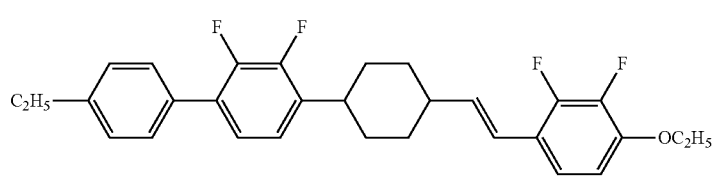 |
| 2832 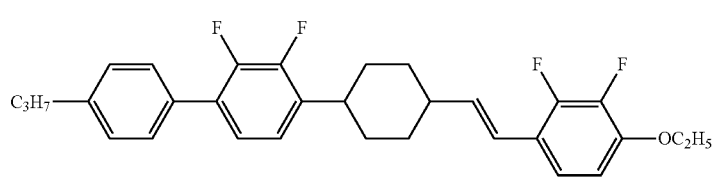 [SMILES: CCOc1ccc(/C=C/C2CCC(c3ccc(-c4ccc(CC)cc4)c(F)c3F)CC2)c(F)c1F] |
| 2833 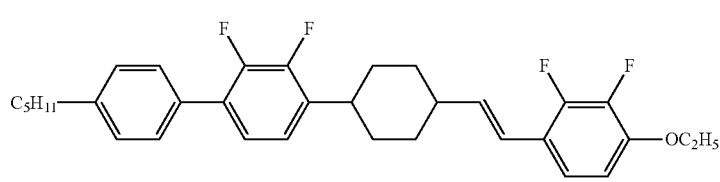 |
| 2834 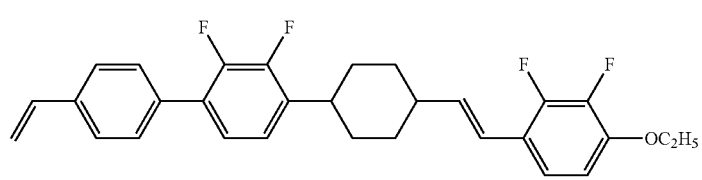 |

| No. |
|---|
| 2835 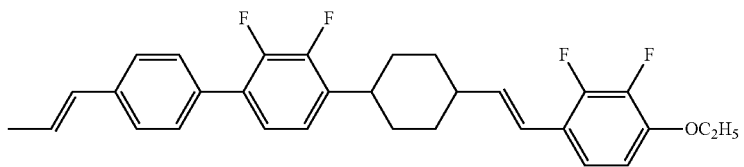 |
| 2836 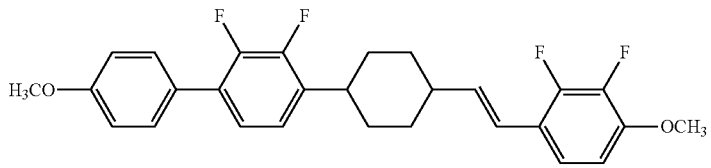 |
| 2837 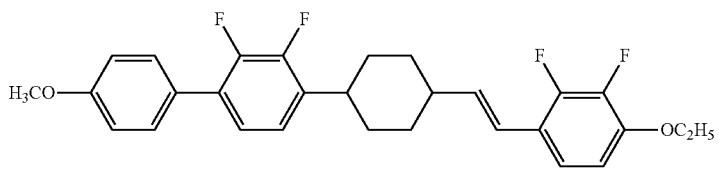 |
| 2838 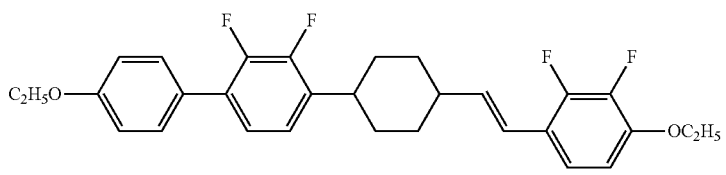 |
| 2839 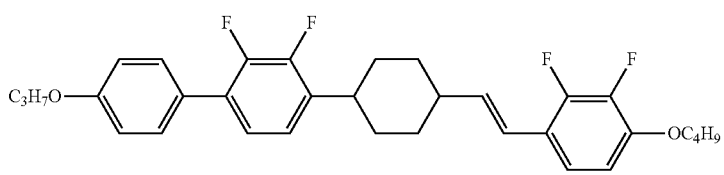 |
| 2840 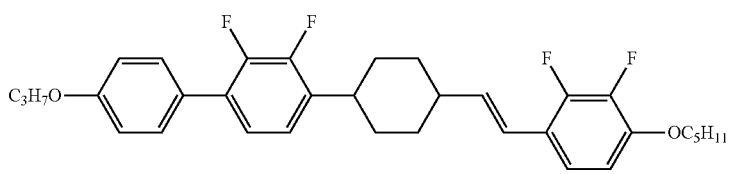 |
| 2841 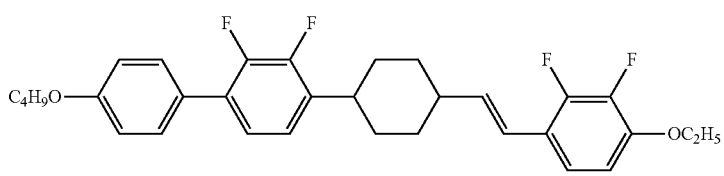 |
| 2842 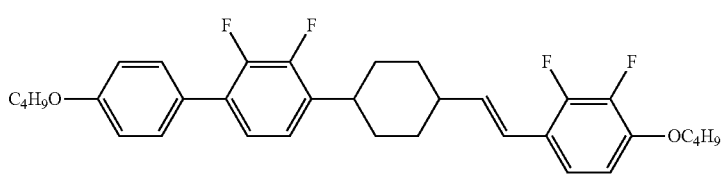 |

| No. |
|---|
| 2843 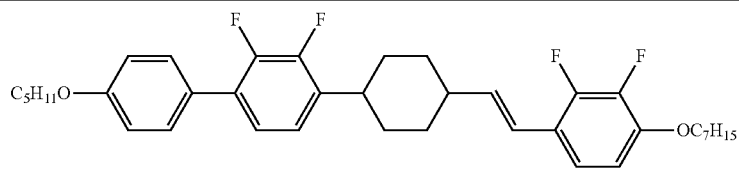 |
| 2844 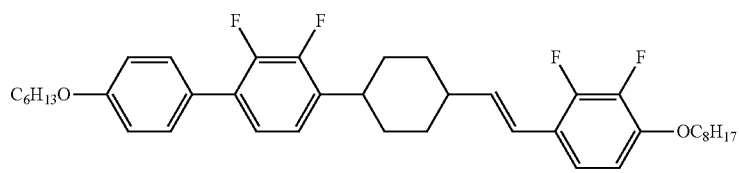 |
| 2845 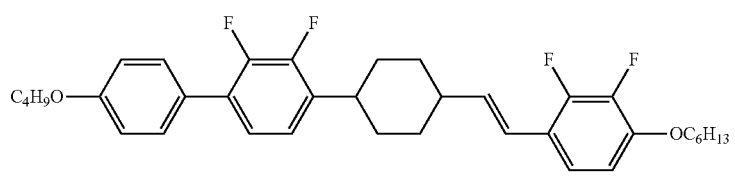 |
| 2846 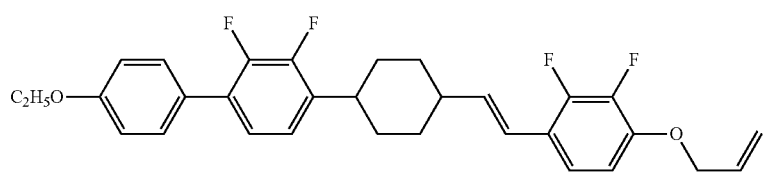 |
| 2847 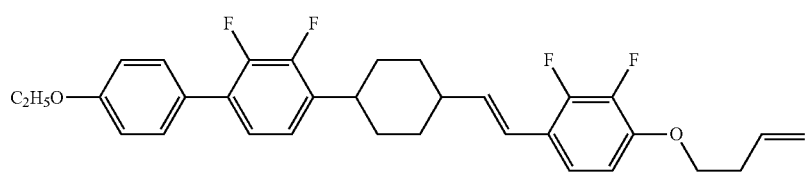 |
| 2848 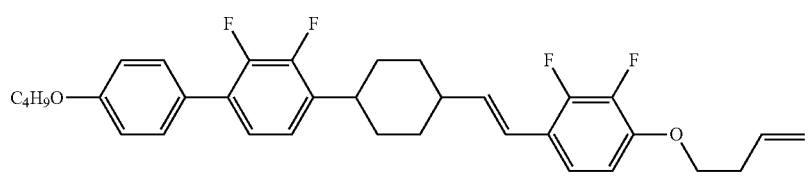 |
| 2849 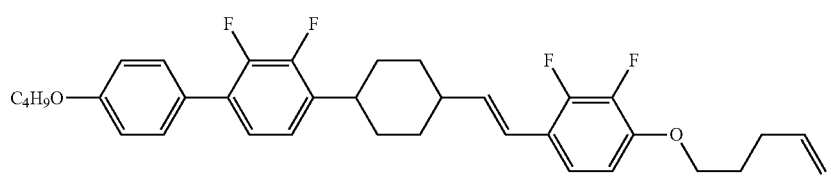 |
| 2850 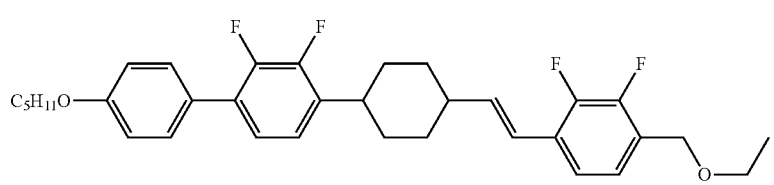 |
| 2851 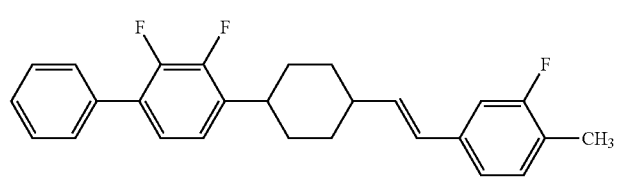 |

| No. | |
|---|---|
| 2852 | 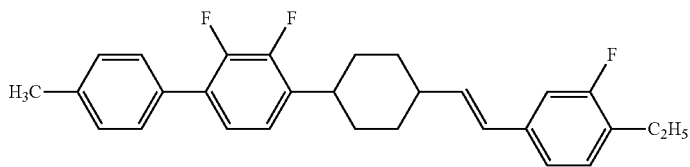 |
| 2853 | 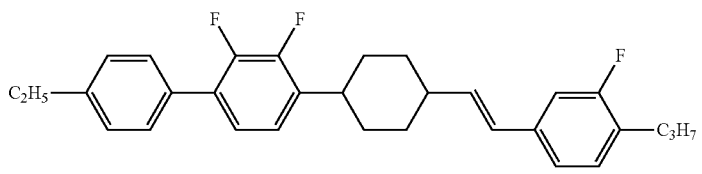 |
| 2854 | 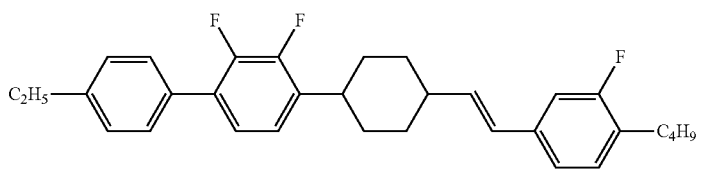 |
| 2855 | 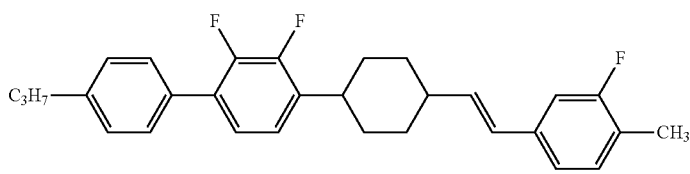 |
| 2856 | 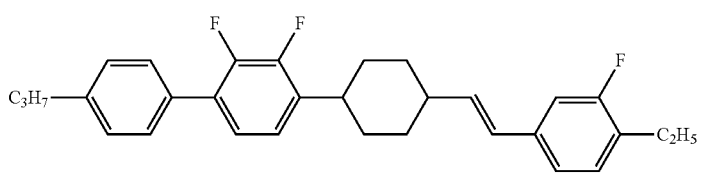 |
| 2857 | 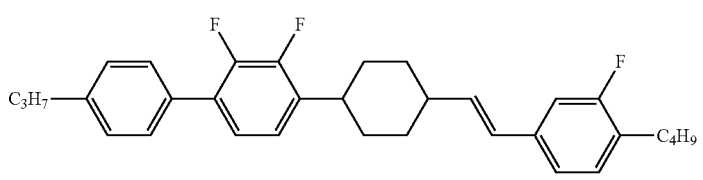 |
| 2858 | 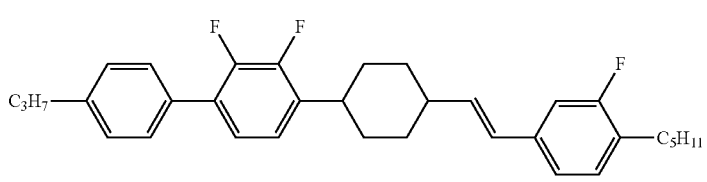 |
| 2859 | 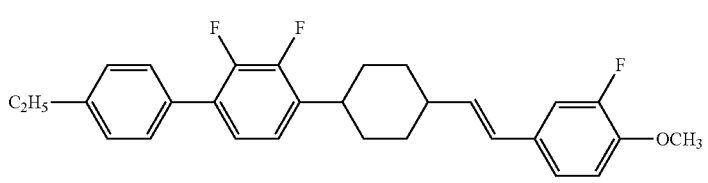 |

| No. |
| --- |
| 2860 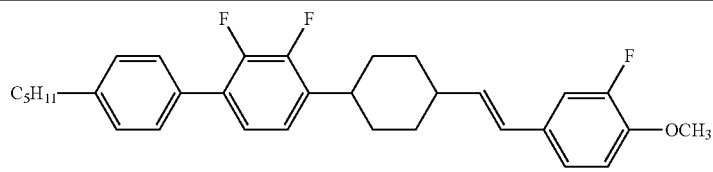 |
| 2861 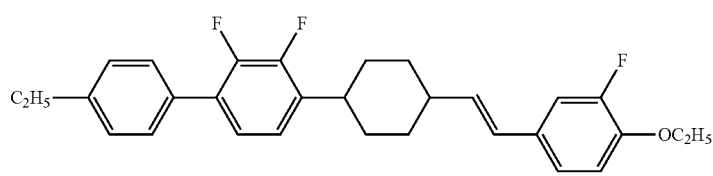 |
| 2862 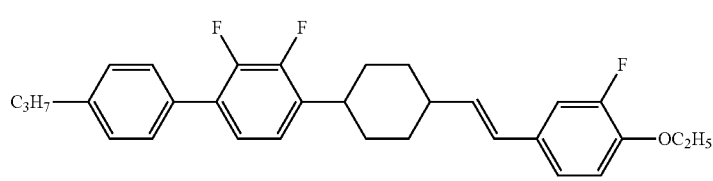 |
| 2863 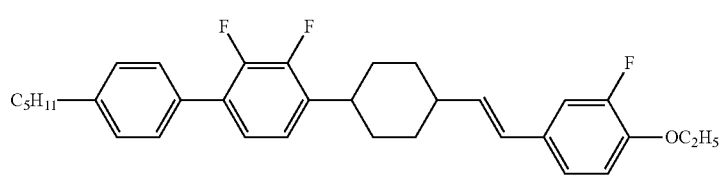 |
| 2864 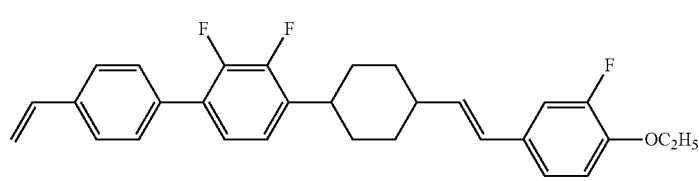 |
| 2865 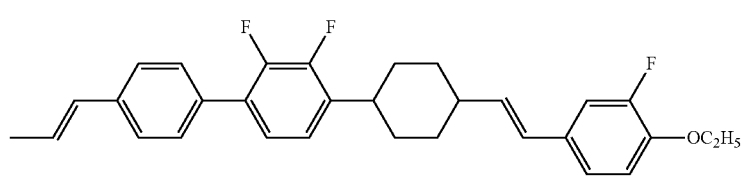 |
| 2866 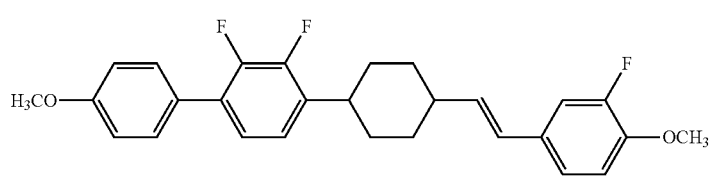 [SMILES: COc1ccc(-c2ccc(C3CCC(/C=C/c4ccc(OC)c(F)c4)CC3)c(F)c2F)cc1] |
| 2867 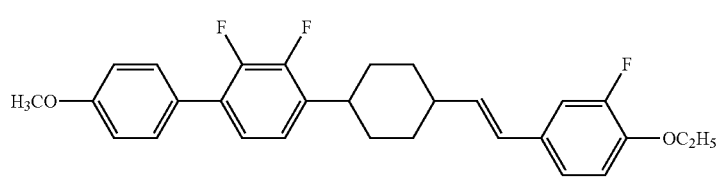 [SMILES: CCOc1ccc(/C=C/C2CCC(c3ccc(-c4ccc(OC)cc4)c(F)c3F)CC2)cc1F] |
| 2868 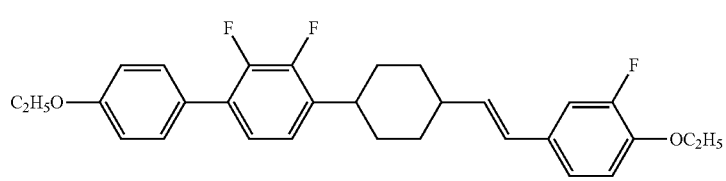 |

| No. | |
|---|---|
| 2869 | 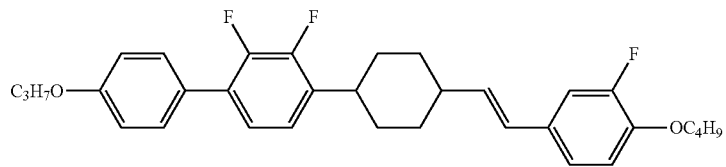 |
| 2870 | 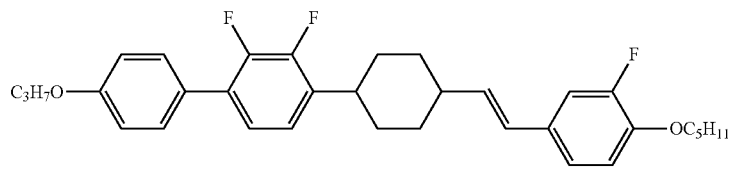 |
| 2871 | 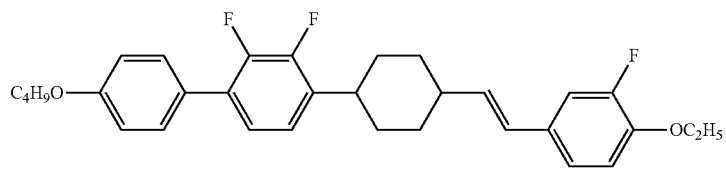 |
| 2872 | 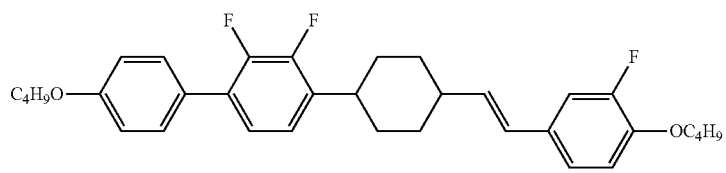 |
| 2873 | 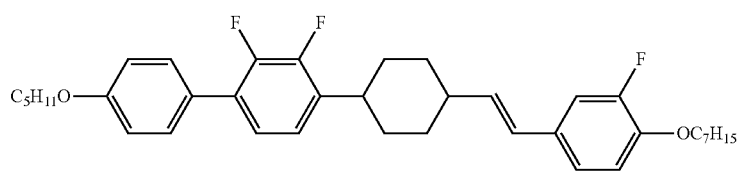 |
| 2874 | 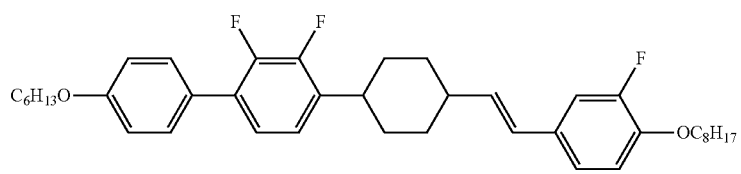 |
| 2875 | 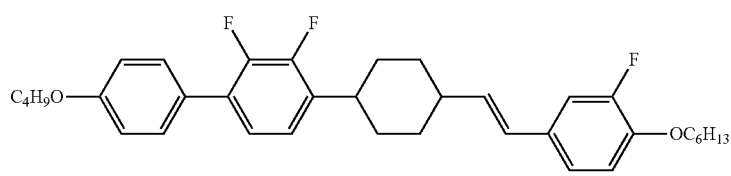 |
| 2776 | 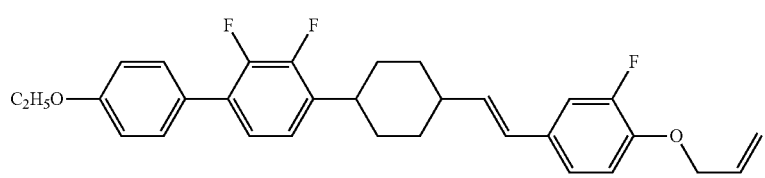 |

| No. | |
|---|---|
| 2877 | 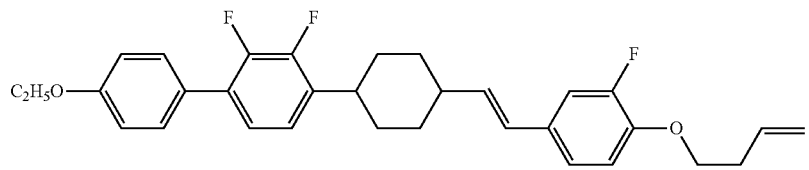 |
| 2878 | 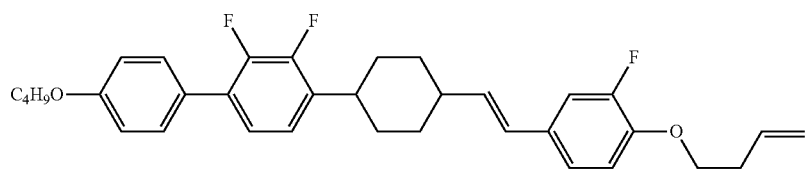 |
| 2879 | 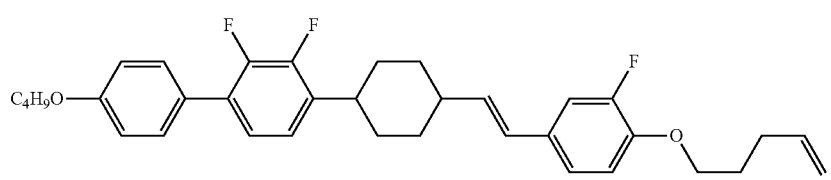 |
| 2880 | 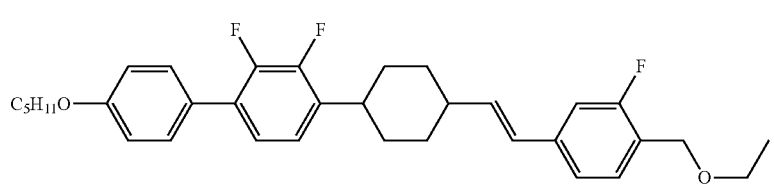 |
| 2881 | 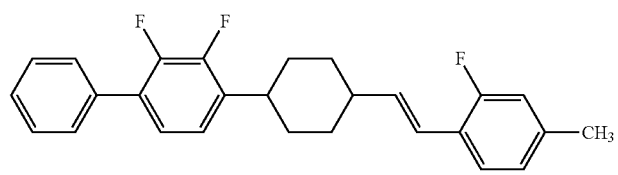 |
| 2882 | 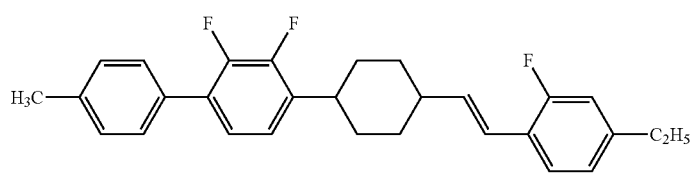 |
| 2883 | 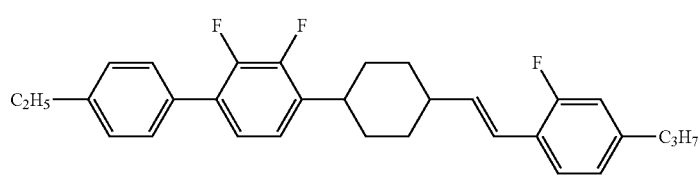 |
| 2884 | 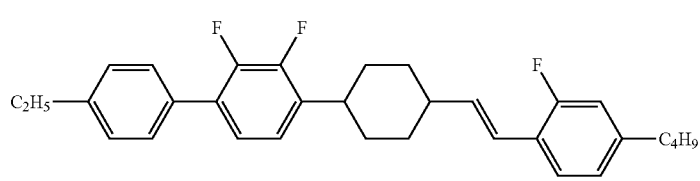 |
| 2885 | 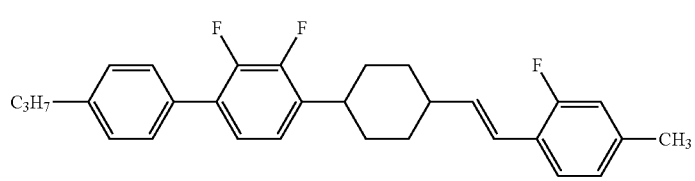 |

| No. |
|---|
| 2886 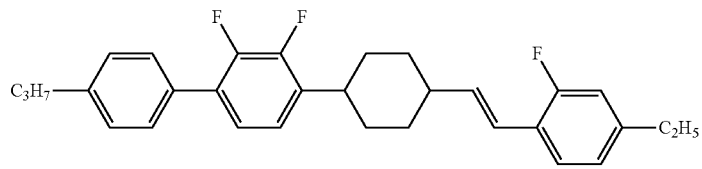 |
| 2887 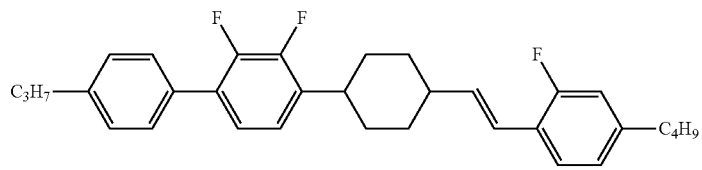 |
| 2888 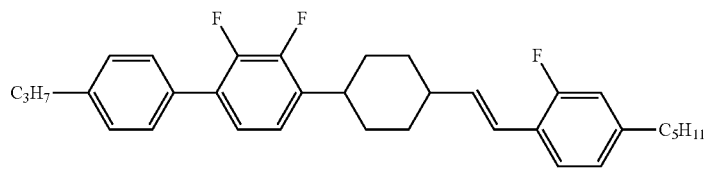 |
| 2889 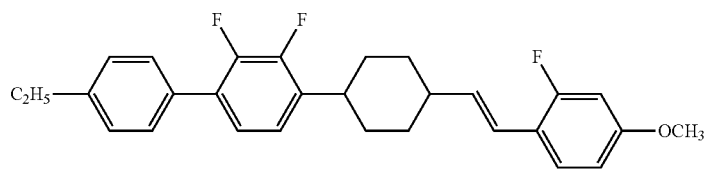 |
| 2890 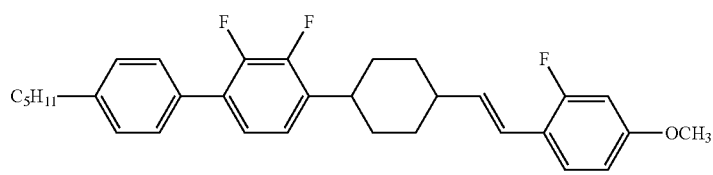 |
| 2891 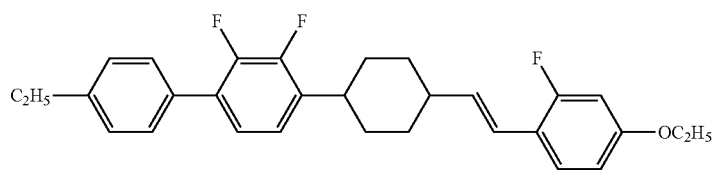 |
| 2892 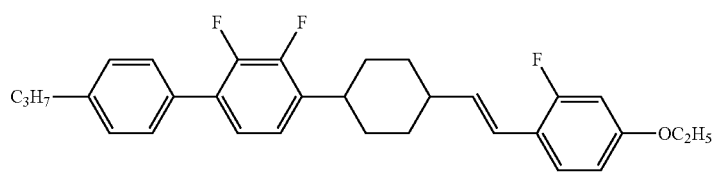 |
| 2893 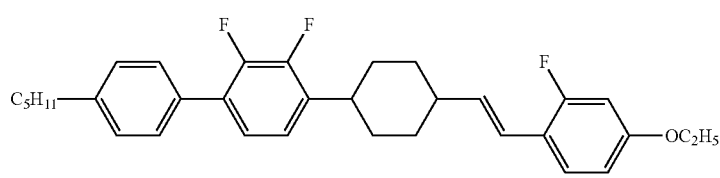 |

| No. | |
|---|---|
| 2894 | 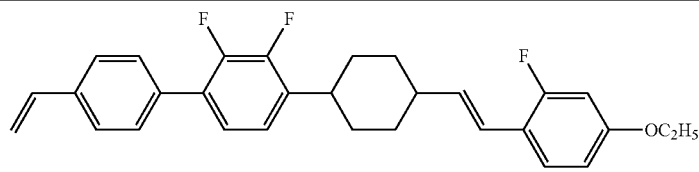 |
| 2895 | 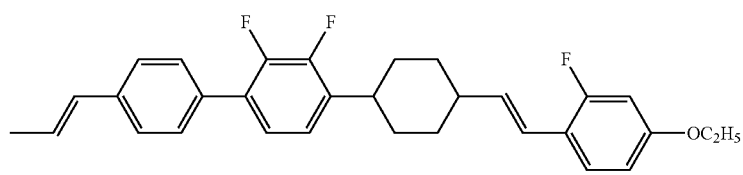 |
| 2896 | 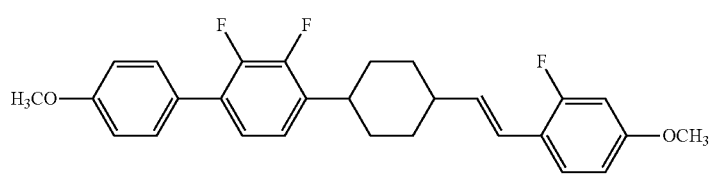 |
| 2897 | 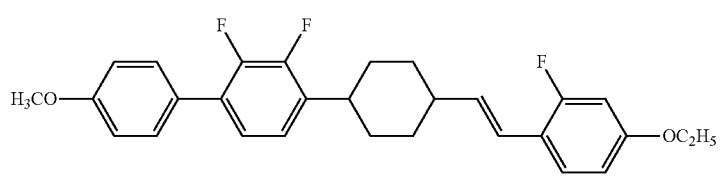 |
| 2898 | 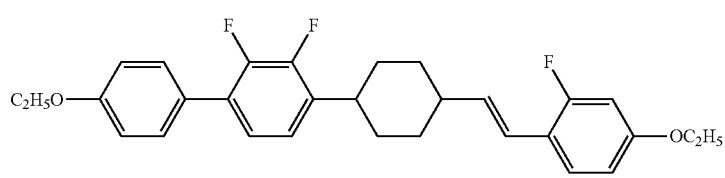 |
| 2899 | 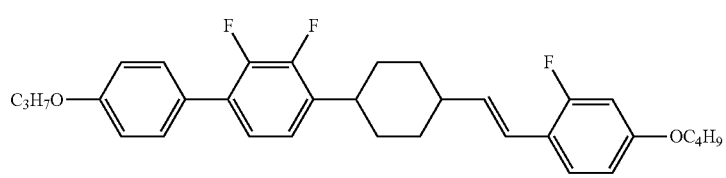 |
| 2900 | 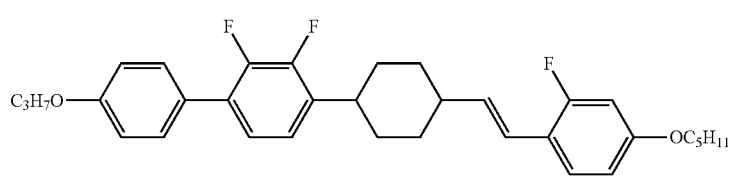 |
| 2901 | 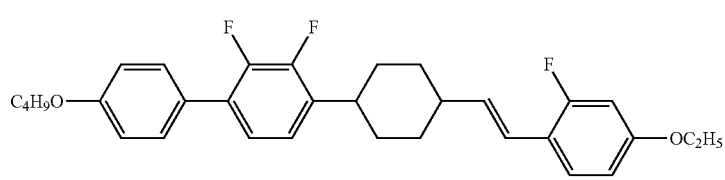 |
| 2902 | 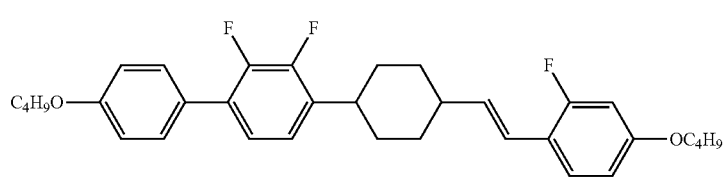 |

-continued
| No. | |
|---|---|
| 2903 | 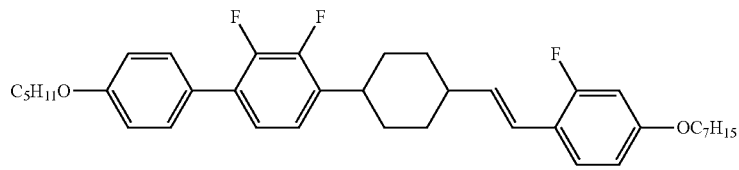 |
| 2904 | 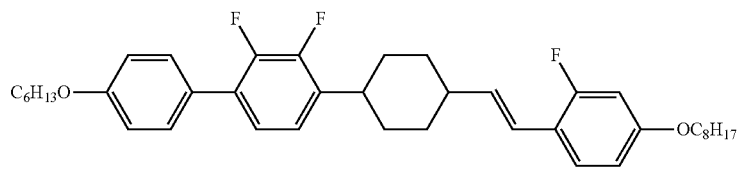 |
| 2905 | 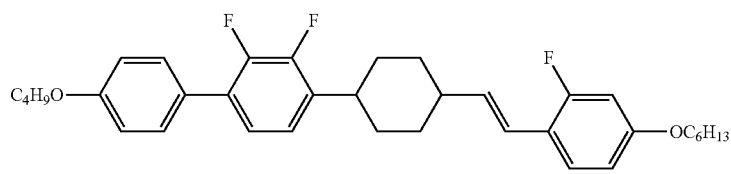 |
| 2906 | 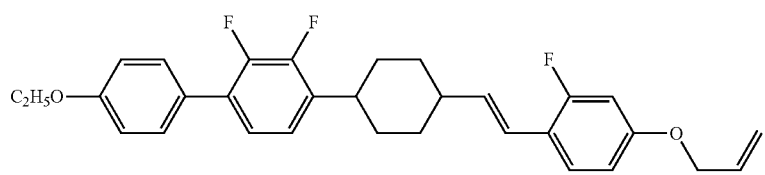 |
| 2907 | 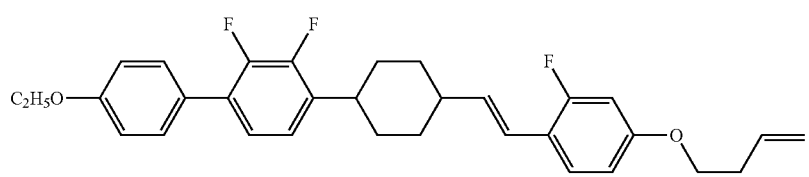 |
| 2908 | 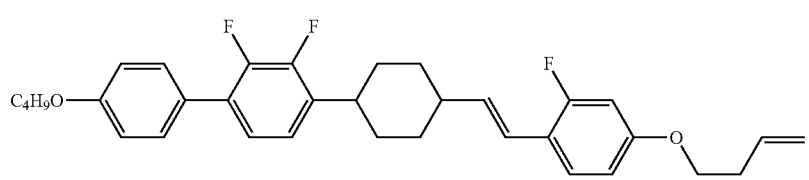 |
| 2909 | 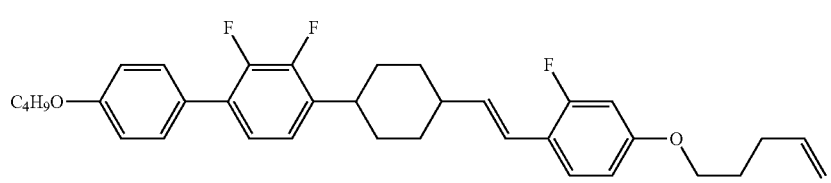 |
| 2910 | 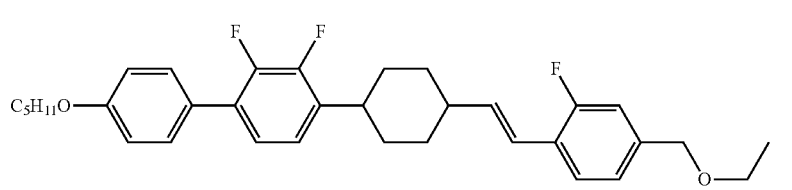 |

-continued
| No. | |
|---|---|
| 2911 | 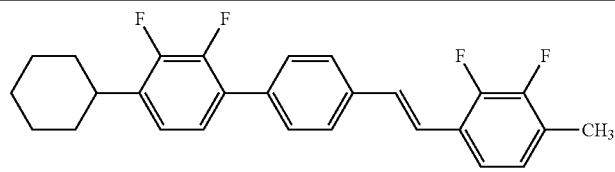 |
| 2912 | 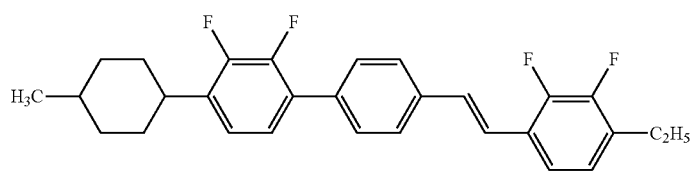 |
| 2913 | 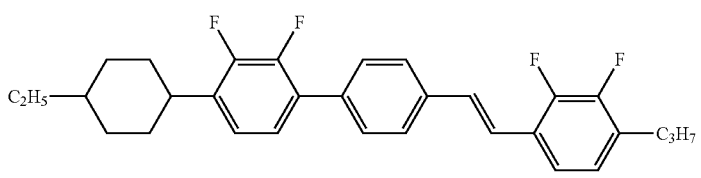 |
| 2914 | 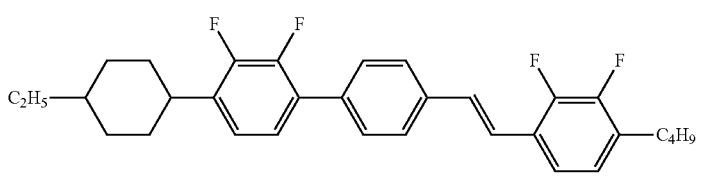 |
| 2915 | 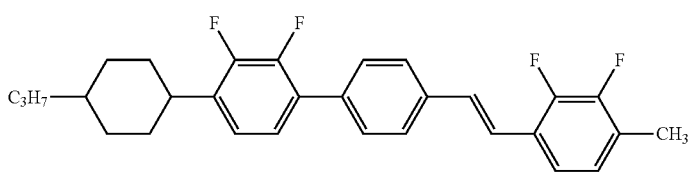 |
| 2916 | 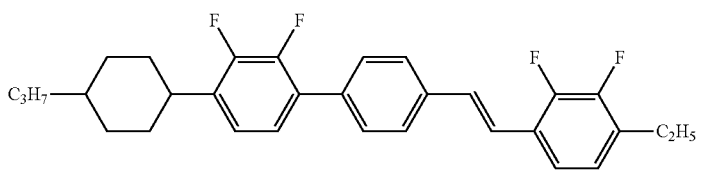 |
| 2917 | 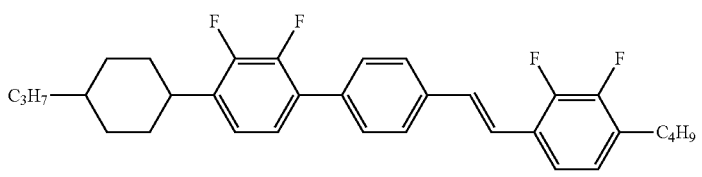 |
| 2918 | 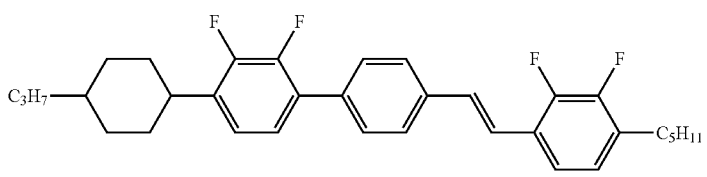 [SMILES: CCC1CCC(c2ccc(-c3ccc(/C=C/c4ccc(OC)c(F)c4F)cc3)c(F)c2F)CC1] |
| 2919 | 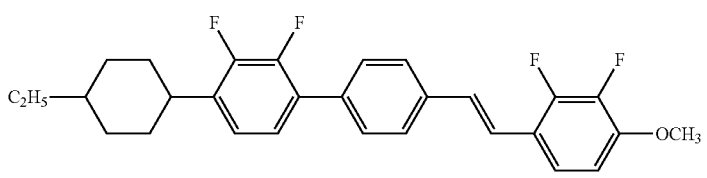 |

| No. |
|---|
| 2920 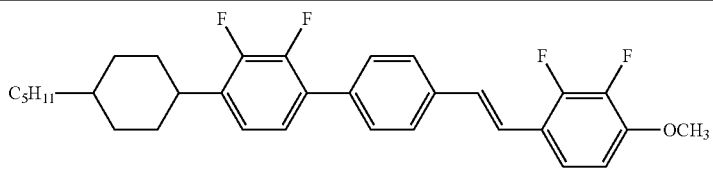 |
| 2921 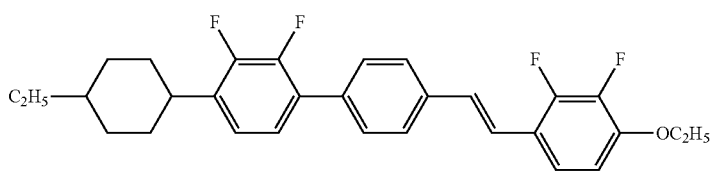 |
| 2922 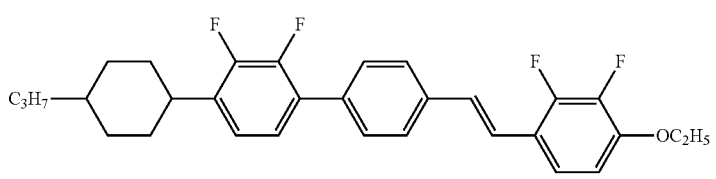 |
| 2923 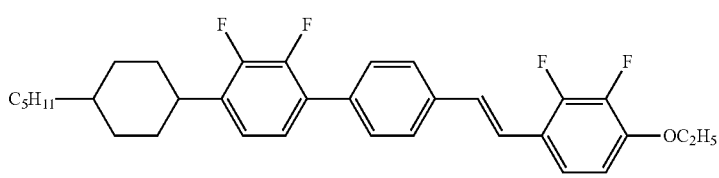 |
| 2924 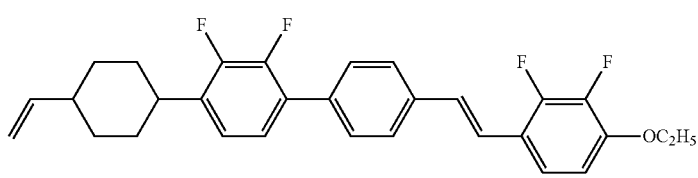 |
| 2925 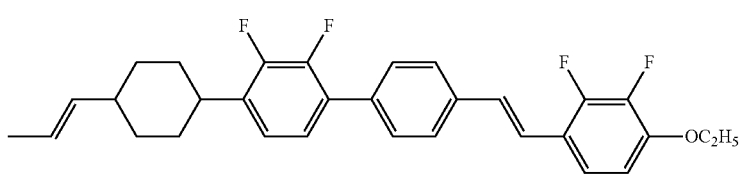 |
| 2926 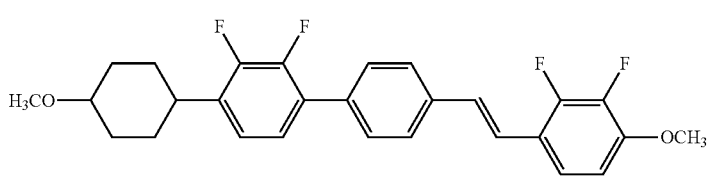 |
| 2927 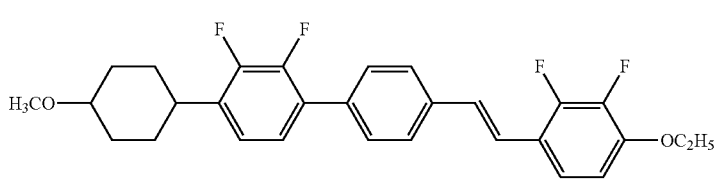 [SMILES: CCOc1ccc(/C=C/c2ccc(-c3ccc(C4CCC(OC)CC4)c(F)c3F)cc2)c(F)c1F] |
| 2928 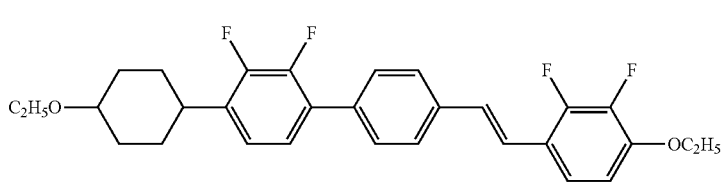 |

| No. | |
|---|---|
| 2929 | 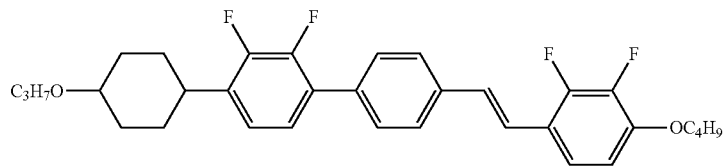 |
| 2930 | 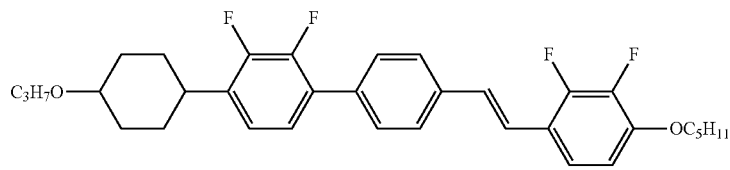 |
| 2931 | 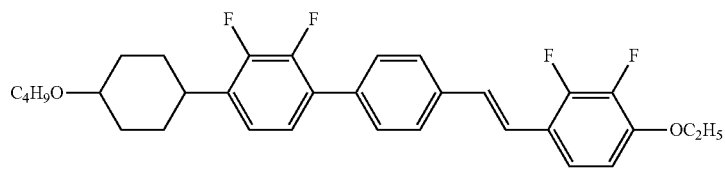 |
| 2932 | 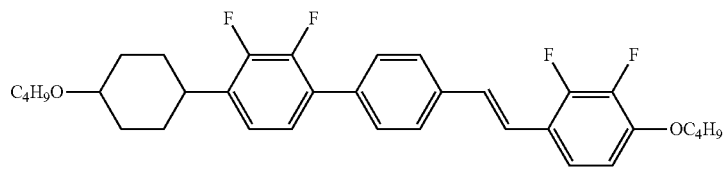 |
| 2933 | 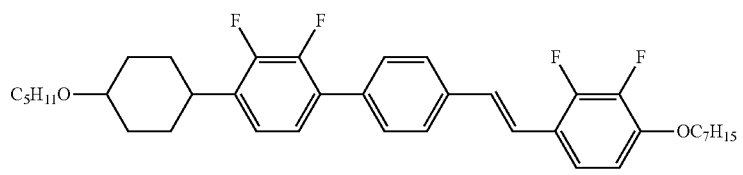 |
| 2934 | 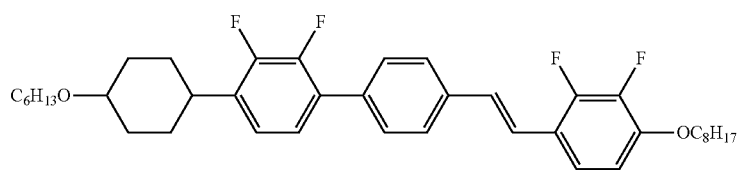 |
| 2935 | 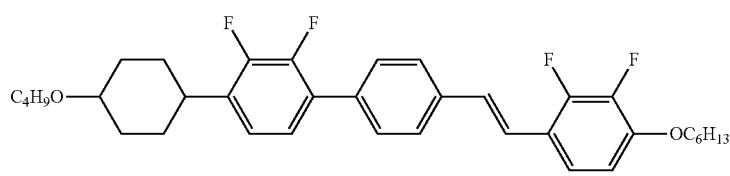 |
| 2936 | 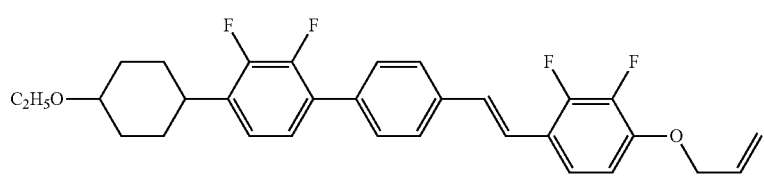 |

| No. | |
|---|---|
| 2937 | 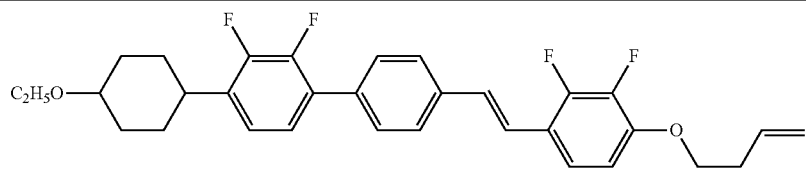 |
| 2938 | 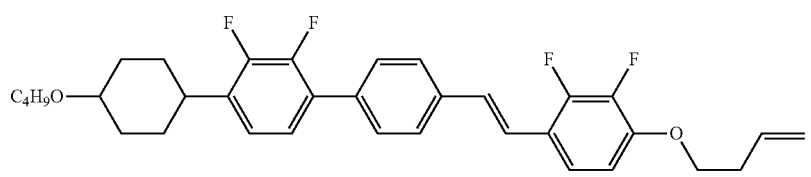 |
| 2939 | 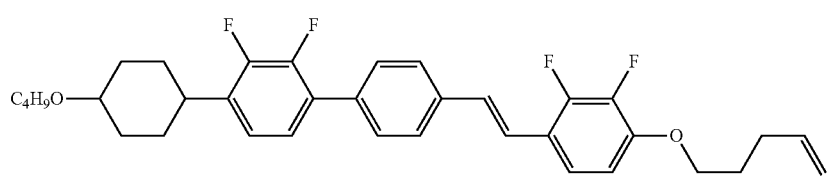 |
| 2940 | 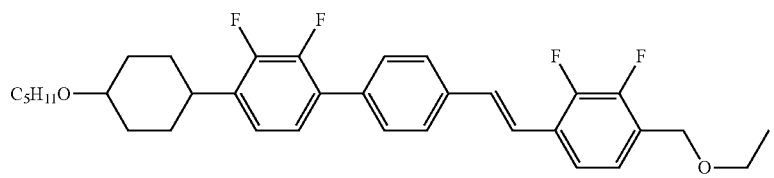 |
| 2941 | 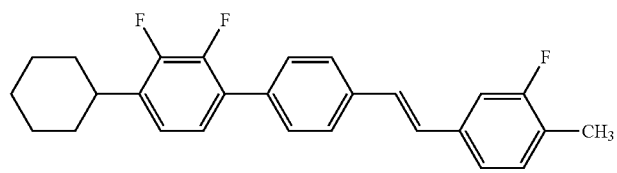 |
| 2942 | 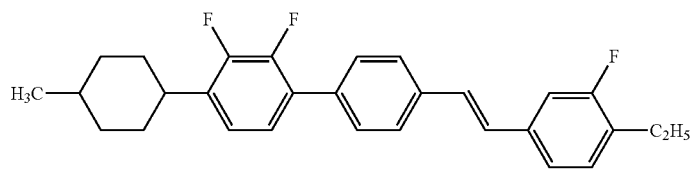 [SMILES: CCc1ccc(/C=C/c2ccc(-c3ccc(C4CCC(C)CC4)c(F)c3F)cc2)cc1F] |
| 2943 | 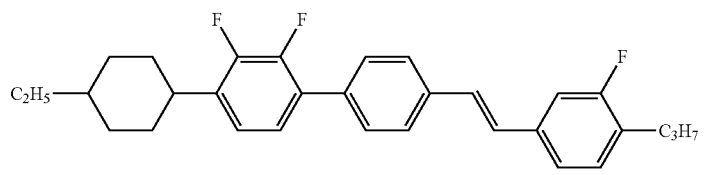 |
| 2944 | 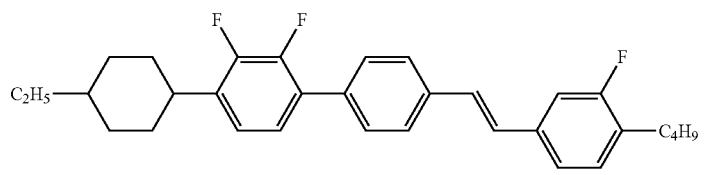 |
| 2945 | 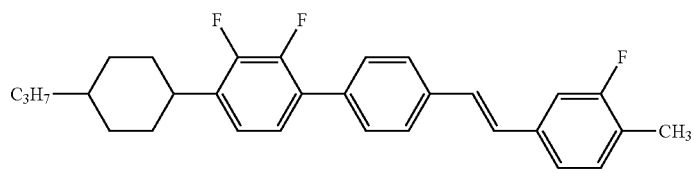 |

| No. | |
|---|---|
| 2946 | 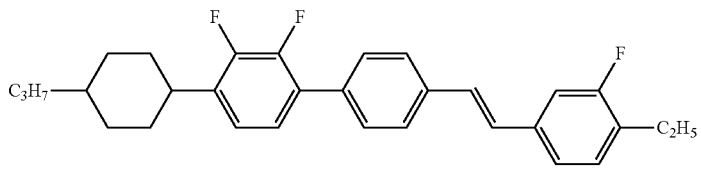 |
| 2947 | 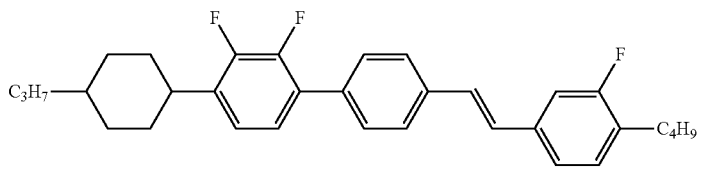 |
| 2948 | 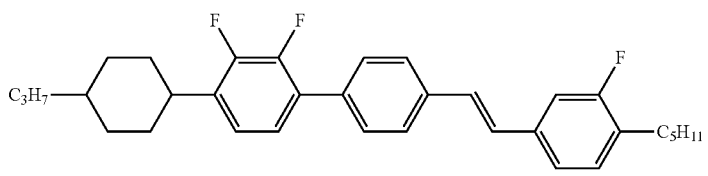 |
| 2949 | 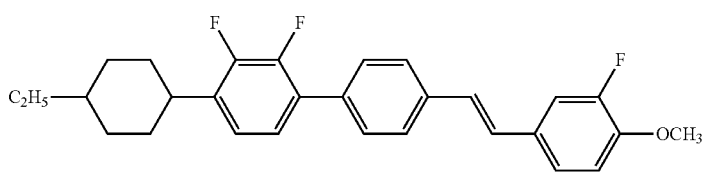 |
| 2950 | 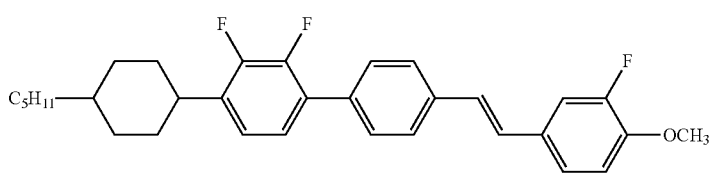 [SMILES: COc1ccc(/C=C/c2ccc(-c3ccc(C4CCC(OC)CC4)c(F)c3F)cc2)cc1F] |
| 2951 | 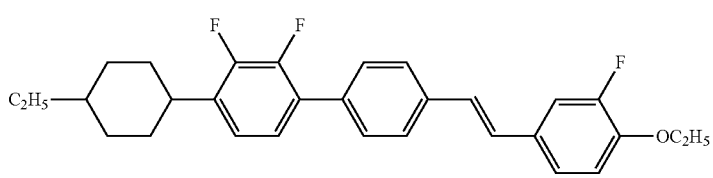 |
| 2952 | 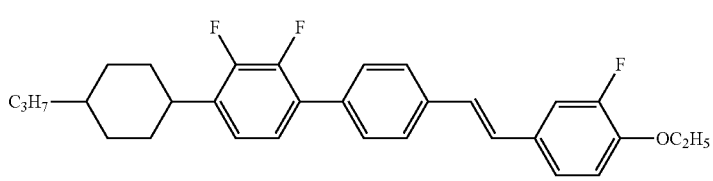 |
| 2953 | 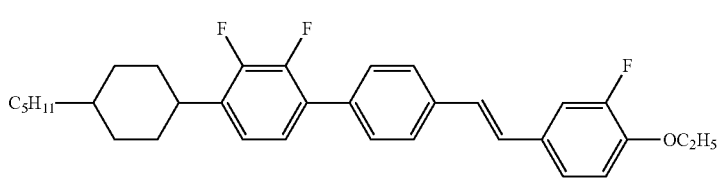 |

| No. | |
|---|---|
| 2954 | 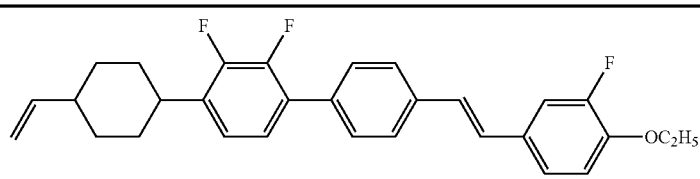 |
| 2955 | 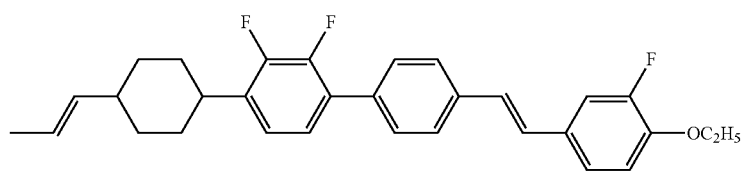 |
| 2956 | 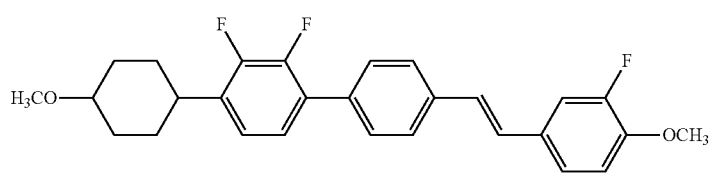 |
| 2957 | 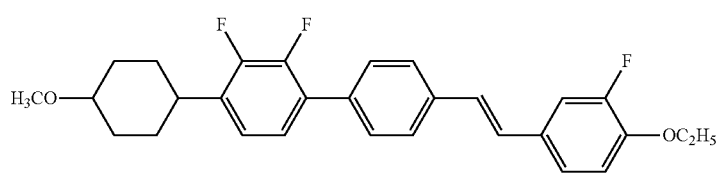 |
| 2958 | 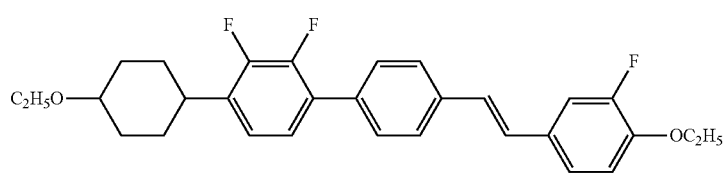 |
| 2959 | 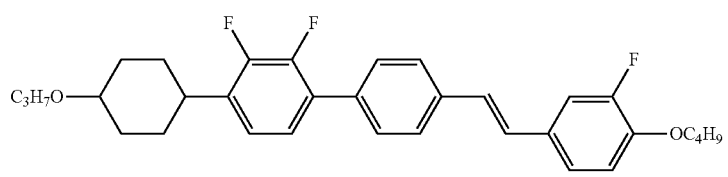 |
| 2960 | 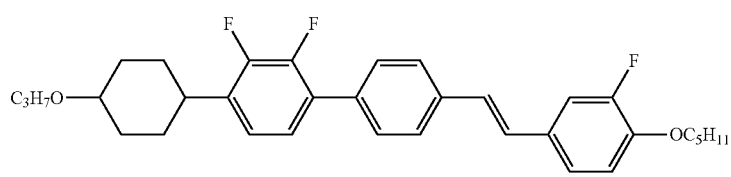 |
| 2961 | 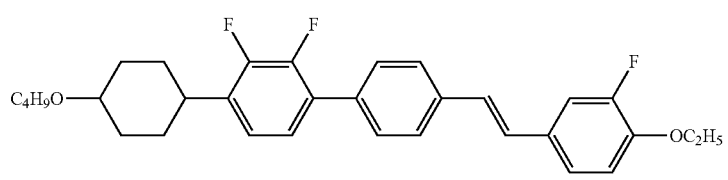 |
| 2962 | 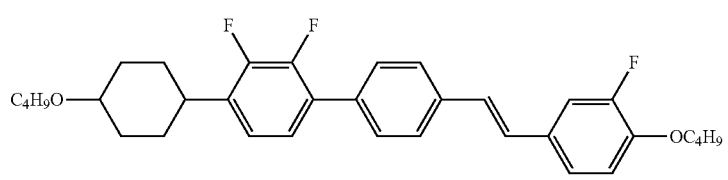 |

| No. | |
|---|---|
| 2963 | 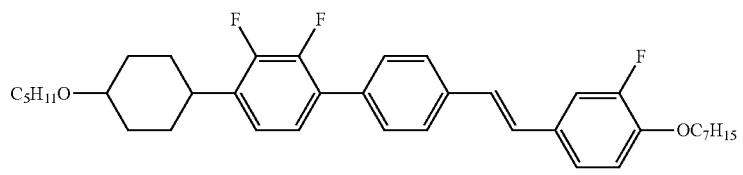 |
| 2964 | 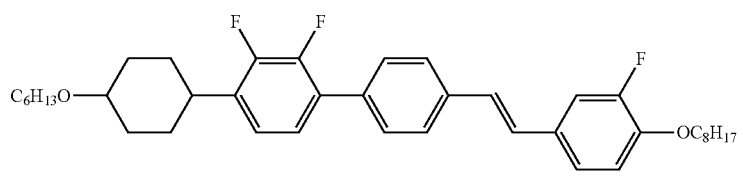 |
| 2965 | 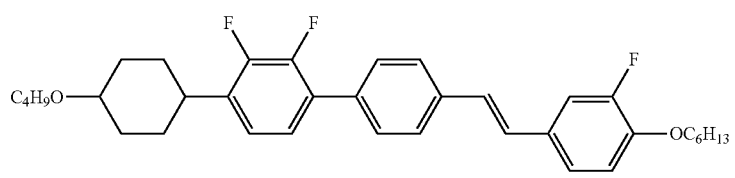 |
| 2966 | 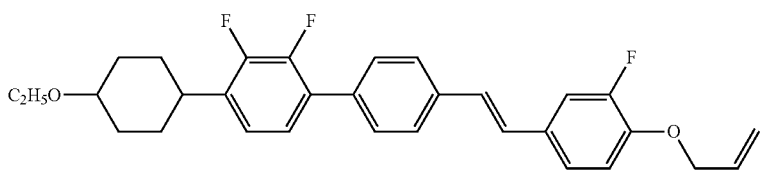 |
| 2967 | 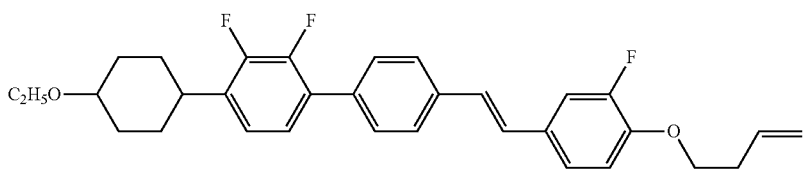 |
| 2968 | 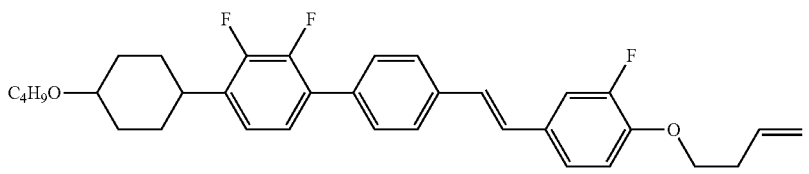 |
| 2969 | 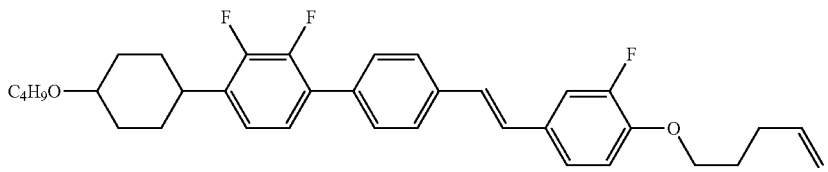 |
| 2970 | 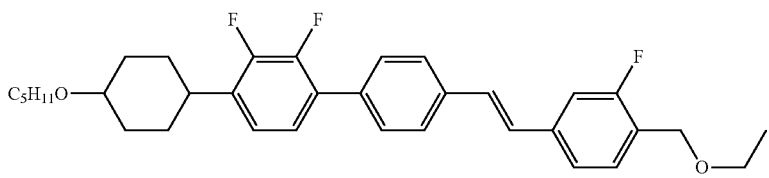 |

| No. | |
|---|---|
| 2971 | 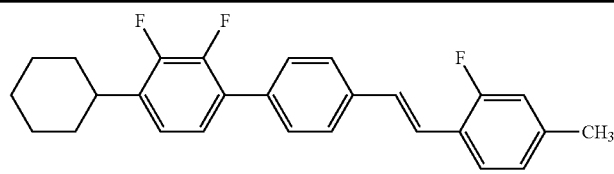 |
| 2972 | 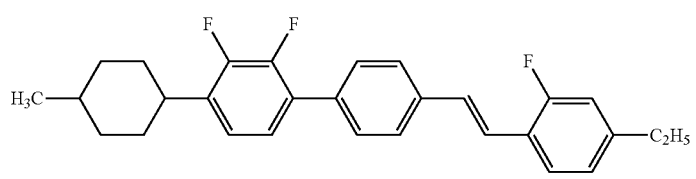 |
| 2973 | 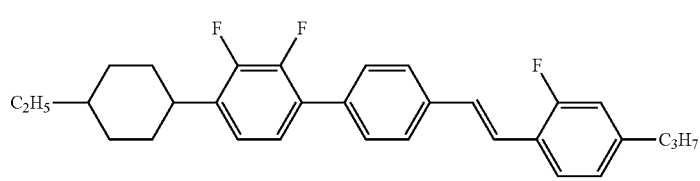 |
| 2794 | 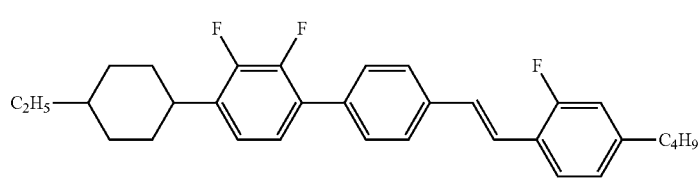 |
| 2975 | 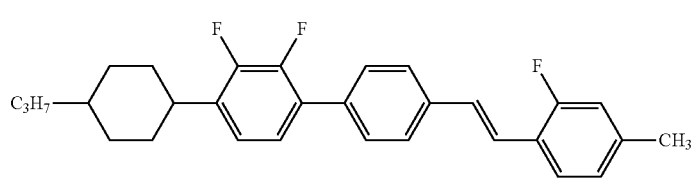 |
| 2976 | 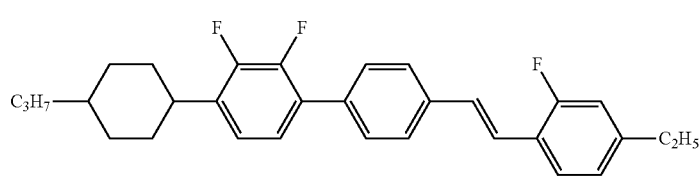 |
| 2977 | 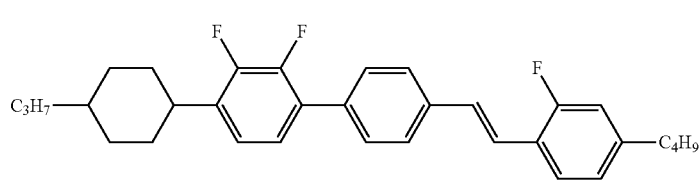 |
| 2978 | 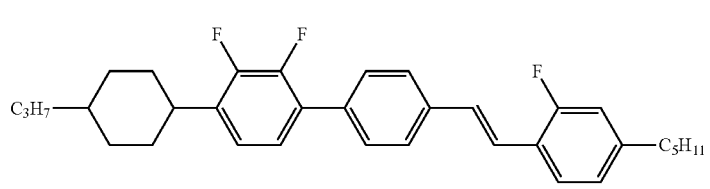 |
| 2979 | 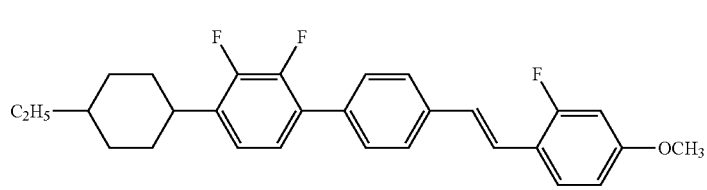 |

| No. | |
|---|---|
| 2980 | 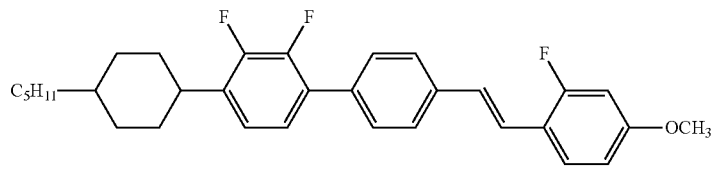 |
| 2981 | 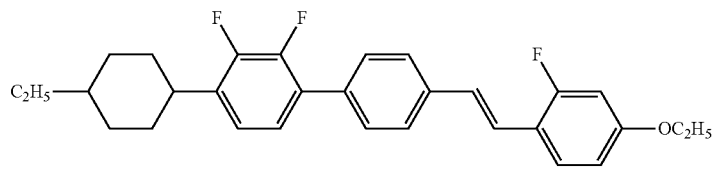 |
| 2982 | 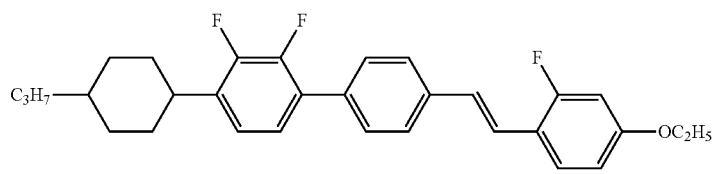 |
| 2983 | 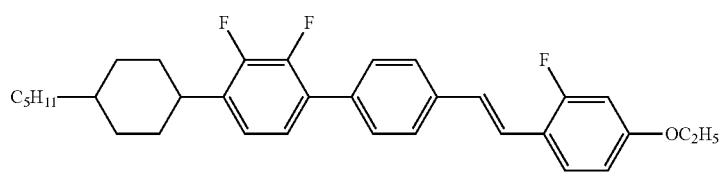 |
| 2984 | 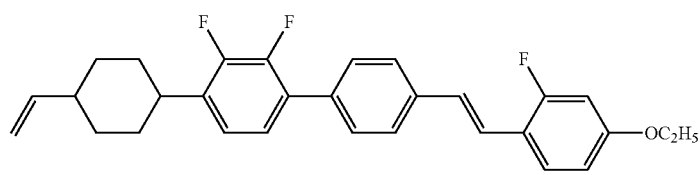 |
| 2985 | 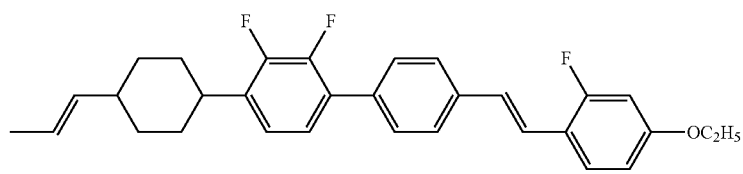 |
| 2986 | 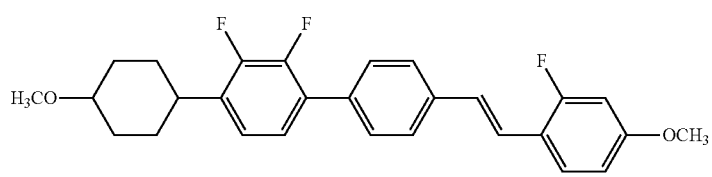 [SMILES: COc1ccc(/C=C/c2ccc(-c3ccc(C4CCC(OC)CC4)c(F)c3F)cc2)c(F)c1] |
| 2987 | 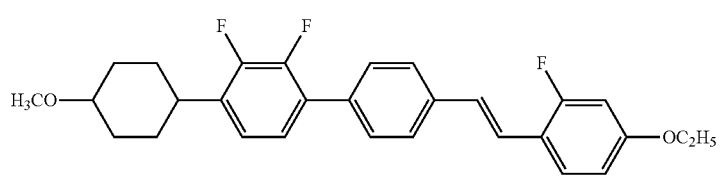 [SMILES: CCOc1ccc(/C=C/c2ccc(-c3ccc(C4CCC(OC)CC4)c(F)c3F)cc2)c(F)c1] |

| No. | |
|---|---|
| 2988 | 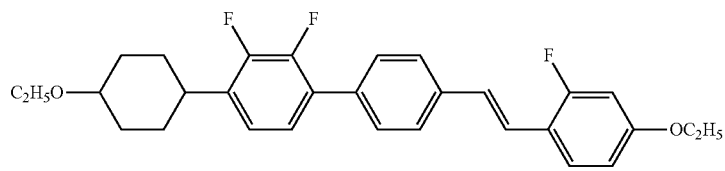 |
| 2989 | 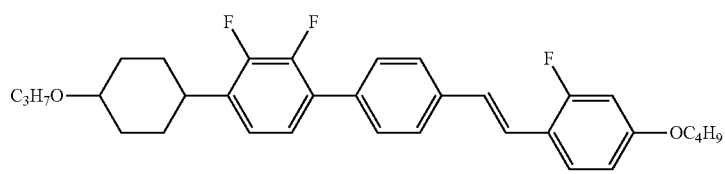 |
| 2990 | 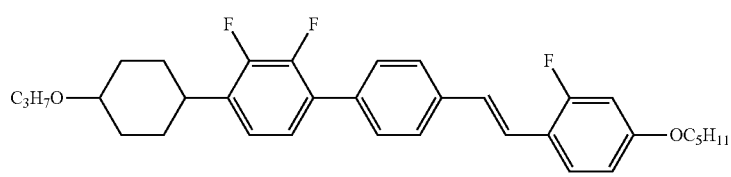 |
| 2991 | 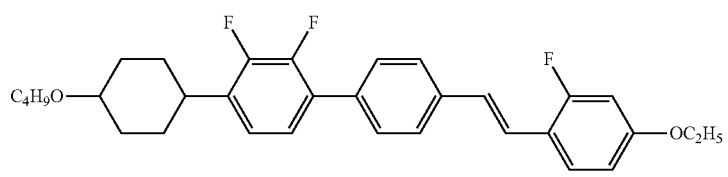 |
| 2992 | 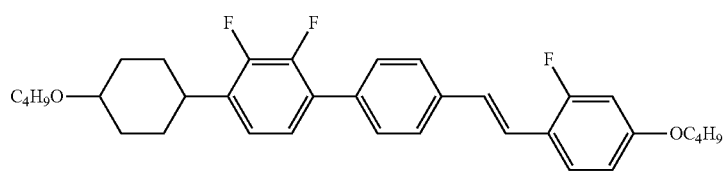 |
| 2993 | 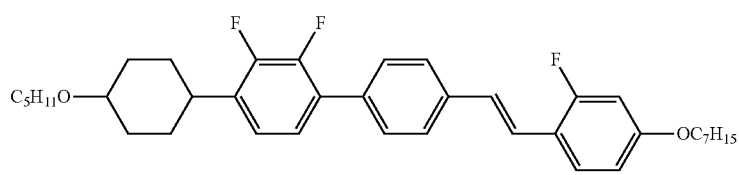 |
| 2994 | 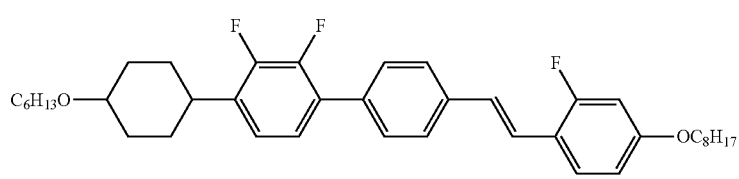 |
| 2995 | 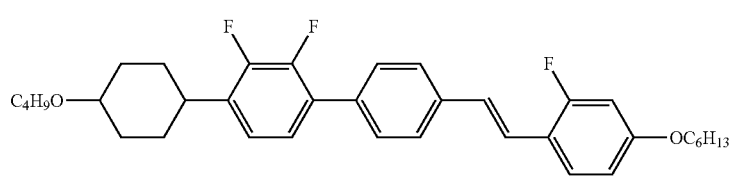 |
| 2996 | 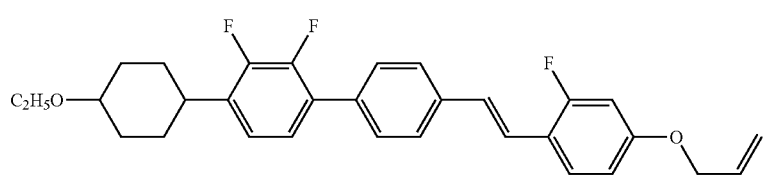 |

| No. | |
|---|---|
| 2997 | 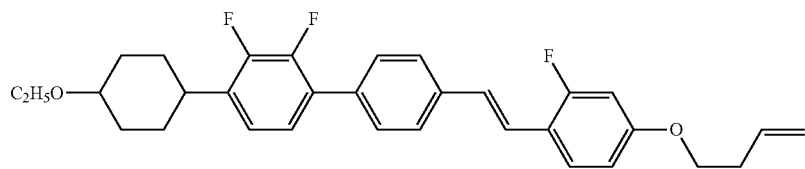 |
| 2998 | 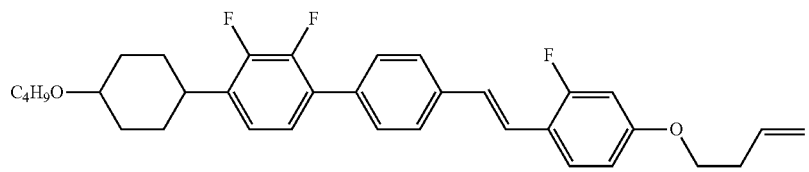 |
| 2999 | 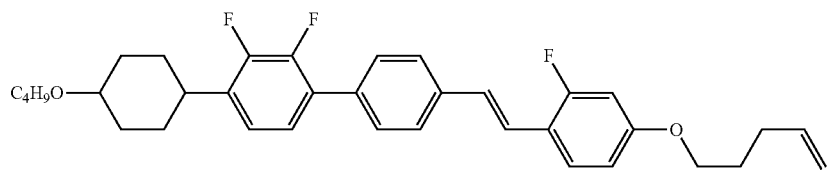 |
| 3000 | 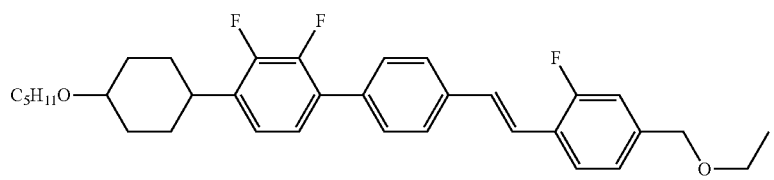 |
| 3001 |  |
| 3002 | 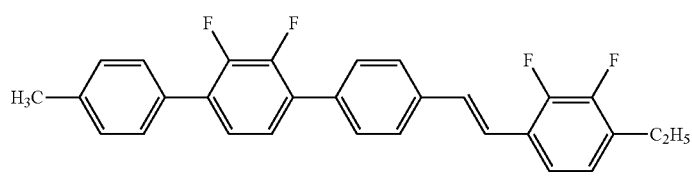 |
| 3003 | 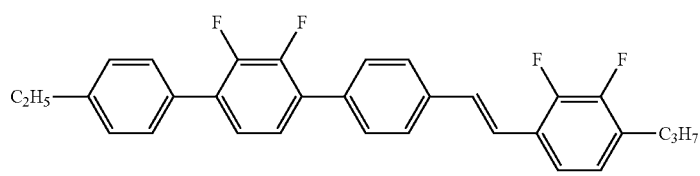 |
| 3004 | 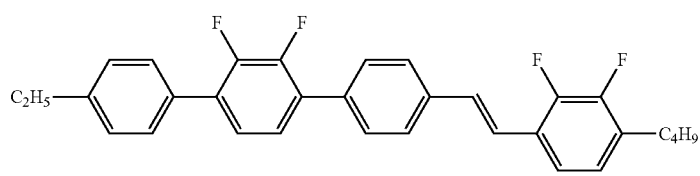 |

| No. | |
|---|---|
| 3005 | 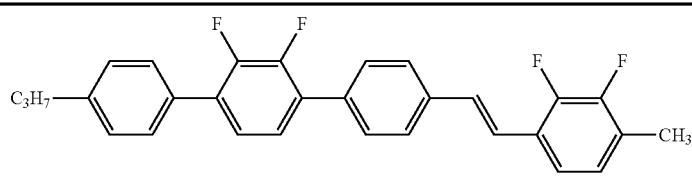 |
| 3006 | 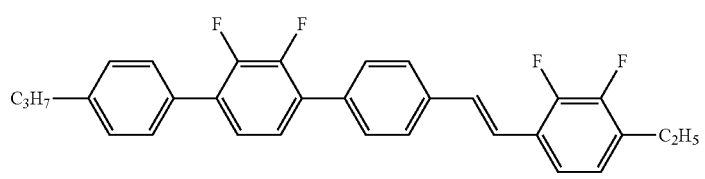 |
| 3007 | 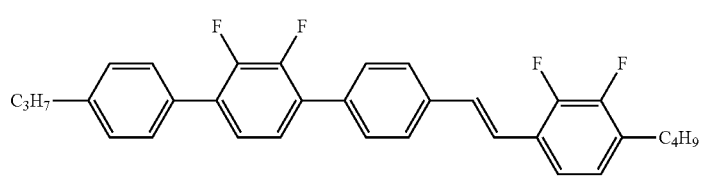 |
| 3008 | 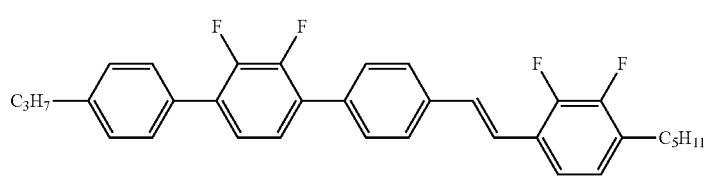 |
| 3009 | 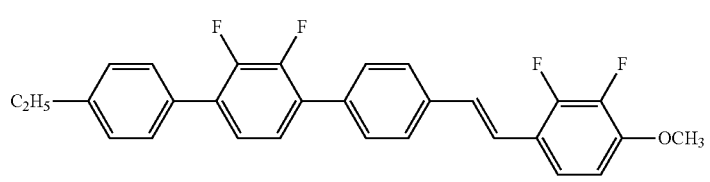 |
| 3010 | 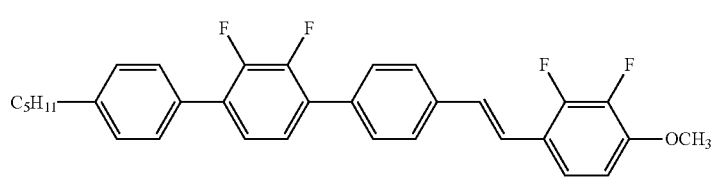 [SMILES: COc1ccc(-c2ccc(-c3ccc(/C=C/c4ccc(OC)c(F)c4F)cc3)c(F)c2F)cc1] |
| 3011 | 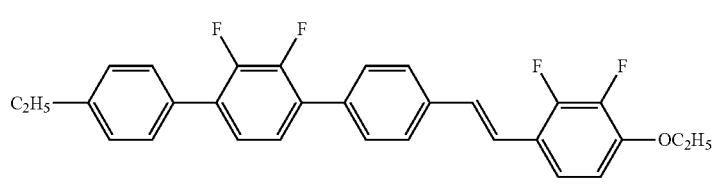 |
| 3012 | 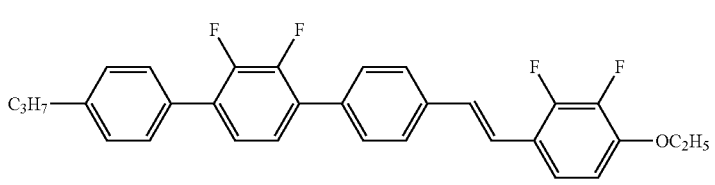 |
| 3013 | 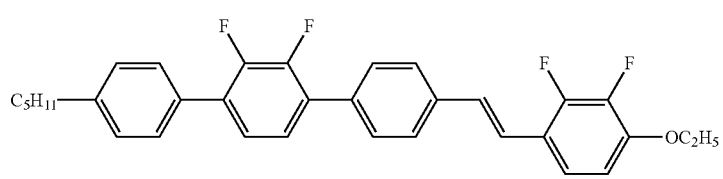 [SMILES: CCOc1ccc(/C=C/c2ccc(-c3ccc(-c4ccc(OC)cc4)c(F)c3F)cc2)c(F)c1F] |

| No. | |
|---|---|
| 3014 | 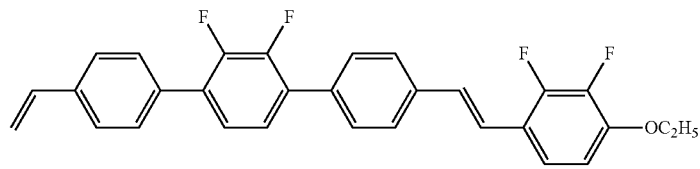 |
| 3015 | 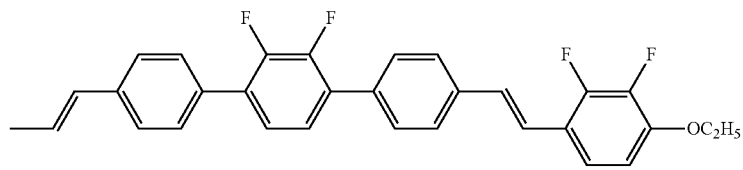 |
| 3016 | 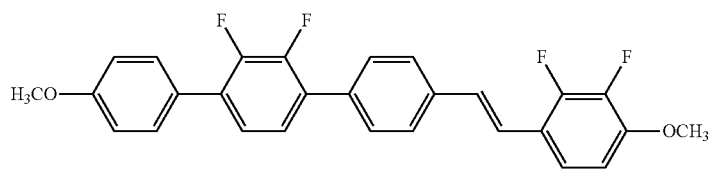 |
| 3017 | 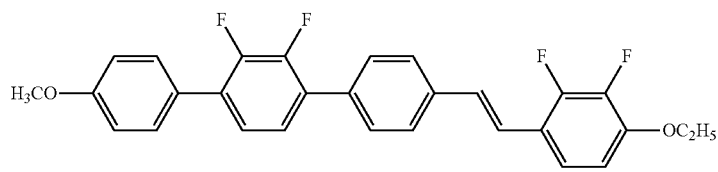 |
| 3018 |  |
| 3019 |  |
| 3020 | 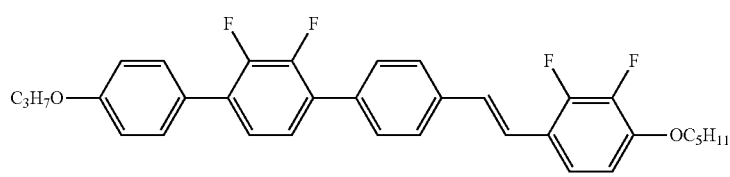 |
| 3021 | 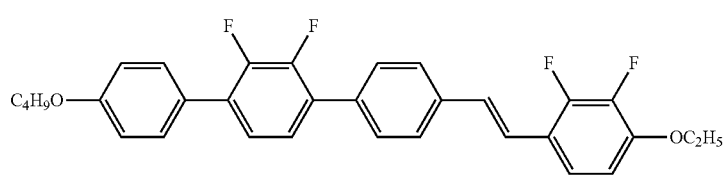 |

| No. |
|---|
| 3022 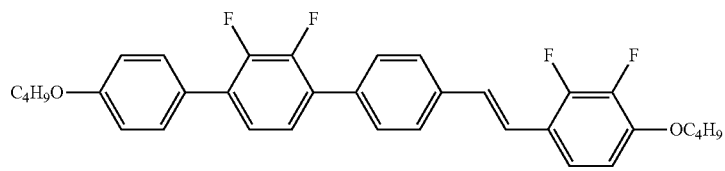 |
| 3023 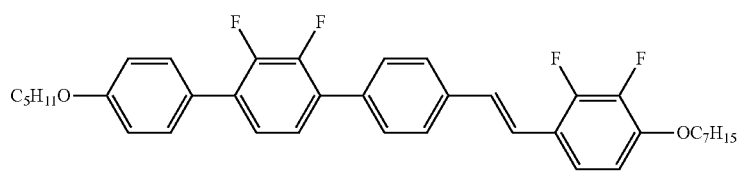 |
| 3024 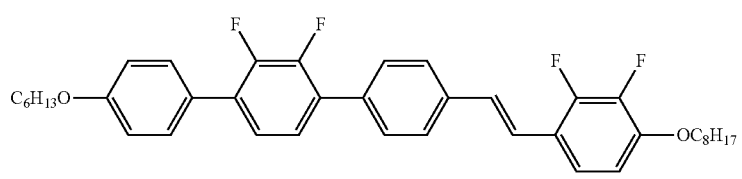 |
| 3025 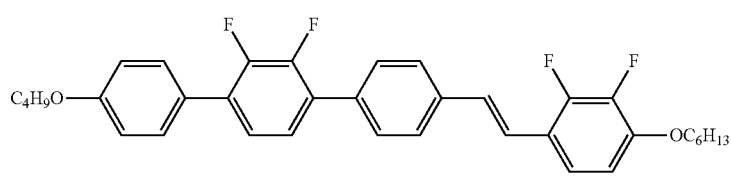 |
| 3026 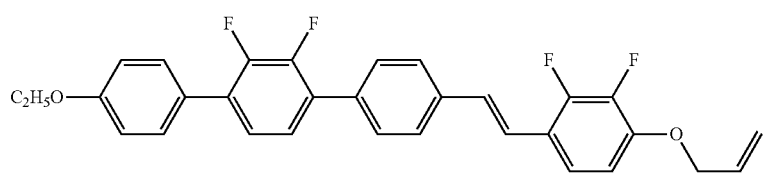 |
| 3027 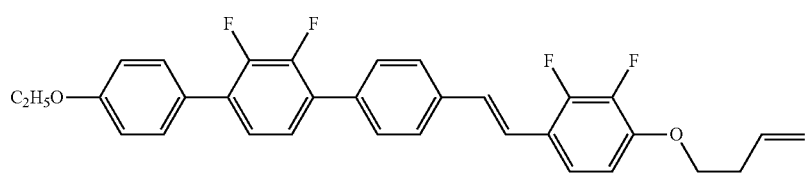 |
| 3028 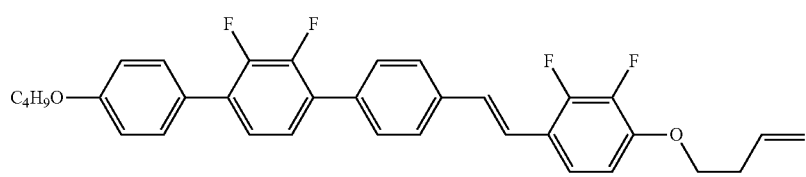 |
| 3029 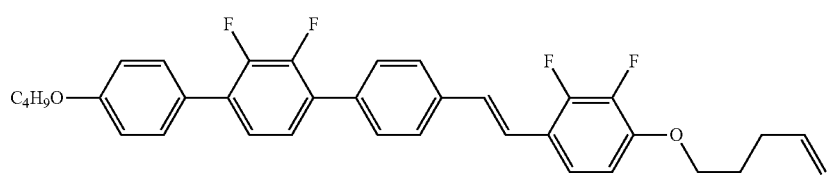 |
| 3030 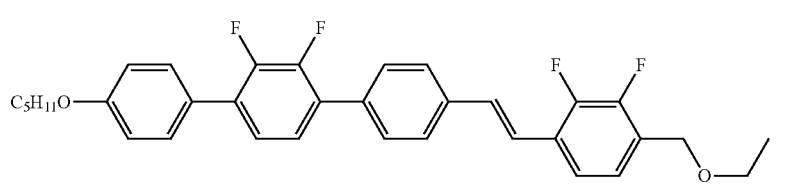 |

| No. | |
|---|---|
| 3031 | 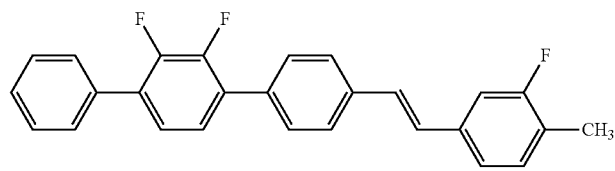 |
| 3032 | 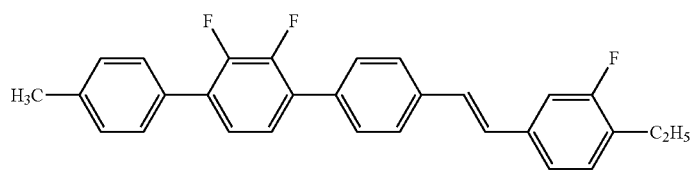 |
| 3033 | 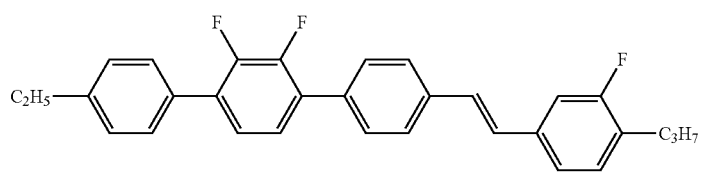 |
| 3034 | 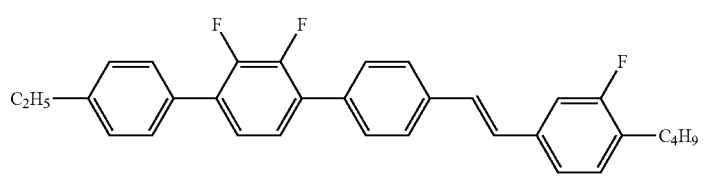 |
| 3035 | 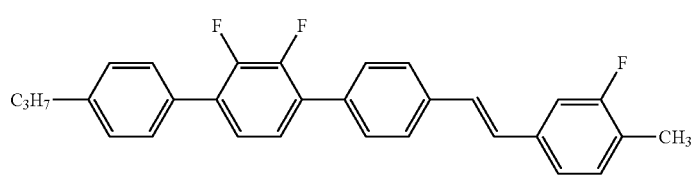 |
| 3036 | 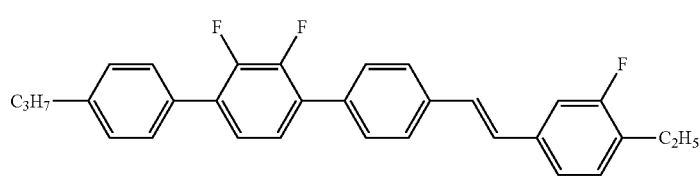 |
| 3037 | 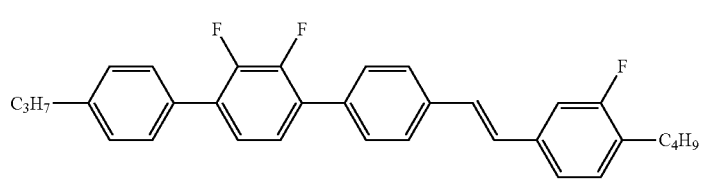 |
| 3038 | 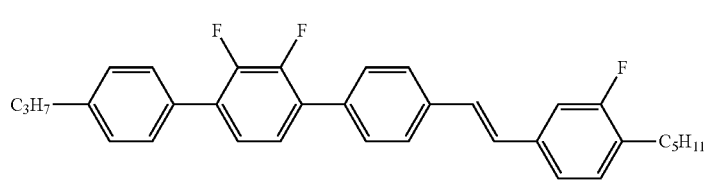 |

| No. | |
|---|---|
| 3039 | 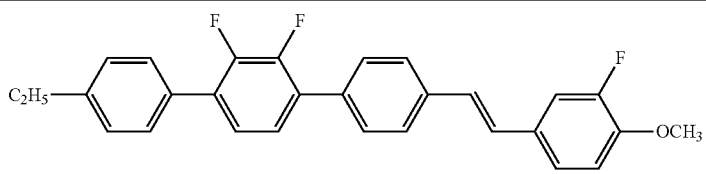 |
| 3040 | 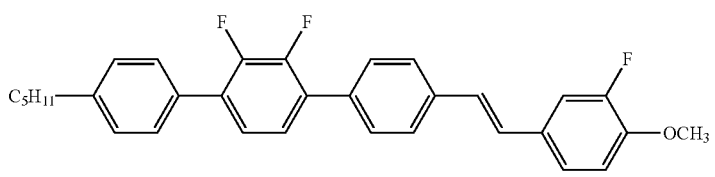 [SMILES: COc1ccc(-c2ccc(-c3ccc(/C=C/c4ccc(OC)c(F)c4)cc3)c(F)c2F)cc1] |
| 3041 | 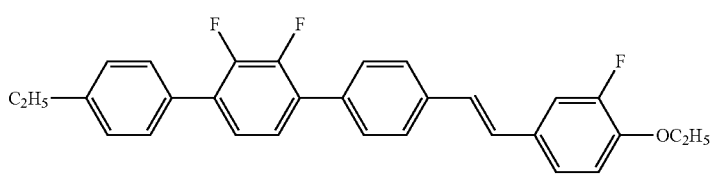 |
| 3042 | 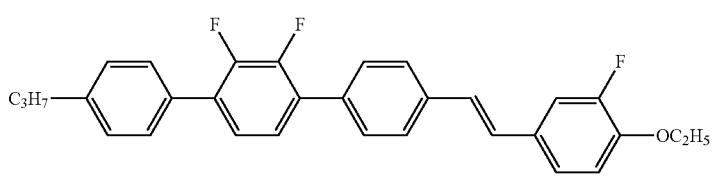 |
| 3043 | 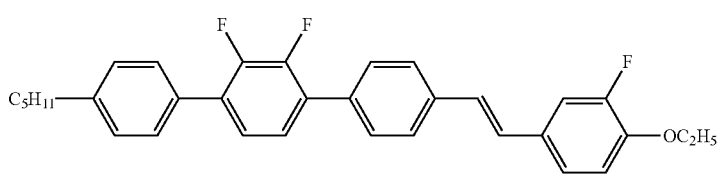 [SMILES: CCOc1ccc(/C=C/c2ccc(-c3ccc(-c4ccc(OC)cc4)c(F)c3F)cc2)cc1F] |
| 3044 | 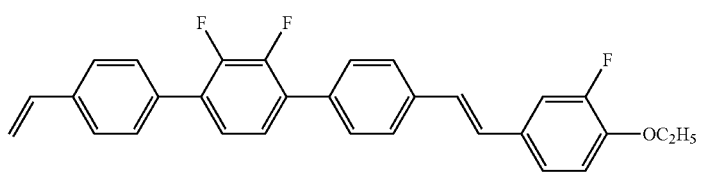 |
| 3045 | 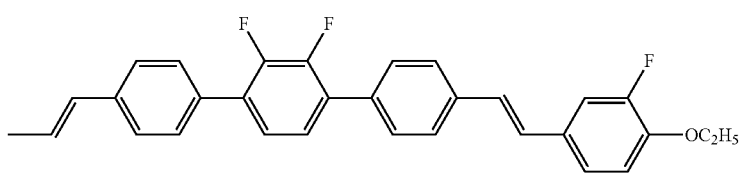 |
| 3046 | 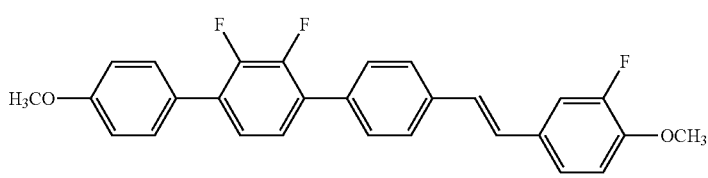 |
| 3047 | 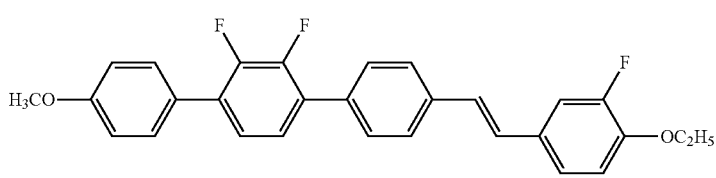 |

| No. |
|---|
| 3048 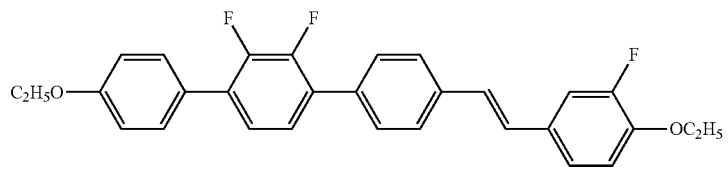 |
| 3049 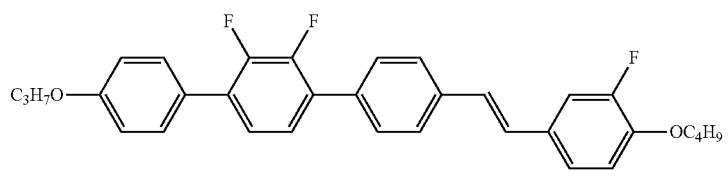 |
| 3050 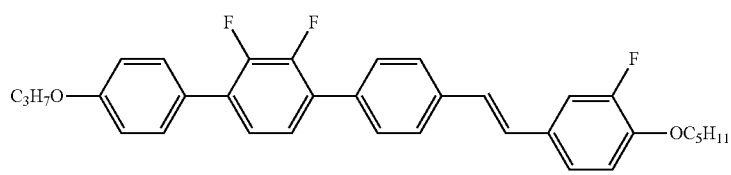 |
| 3051 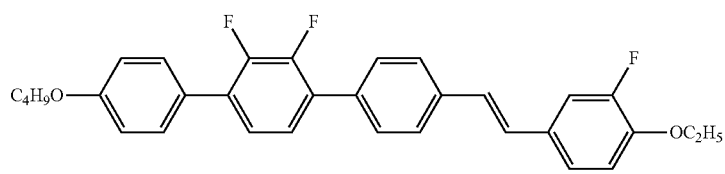 |
| 3052 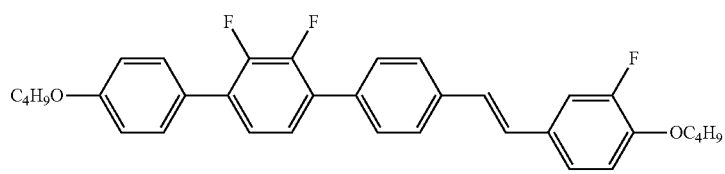 |
| 3053 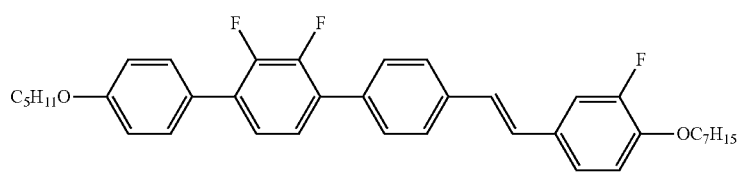 |
| 3054 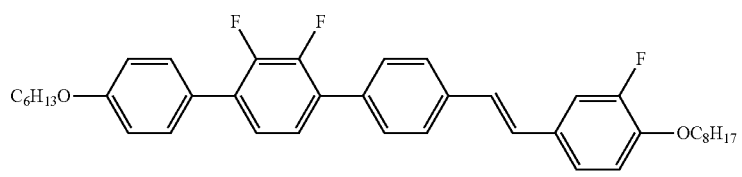 |
| 3055 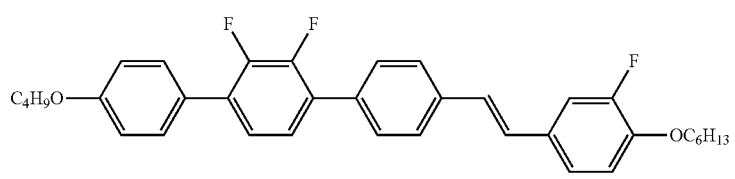 |

| No. | |
|---|---|
| 3056 | 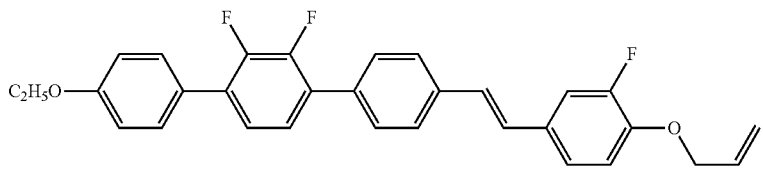 |
| 3057 | 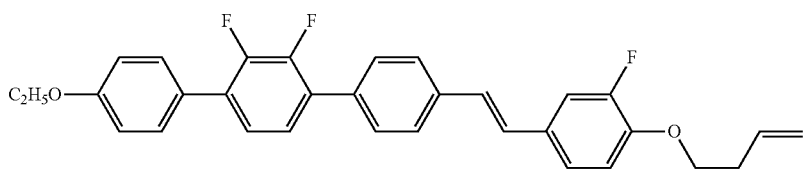 |
| 3058 | 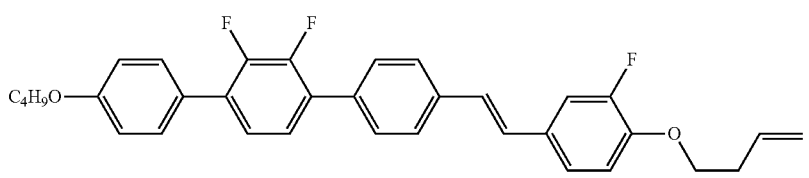 |
| 3059 | 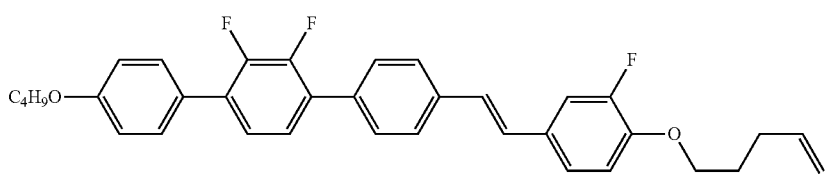 |
| 3060 | 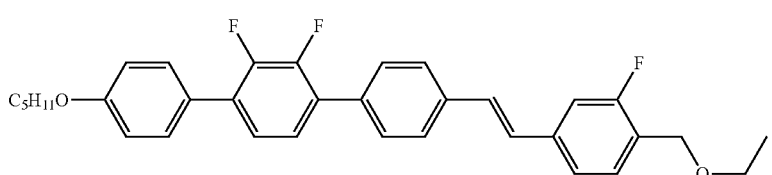 |
| 3061 | 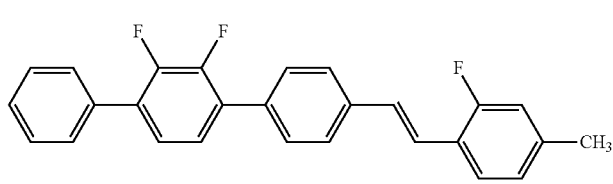 |
| 3062 | 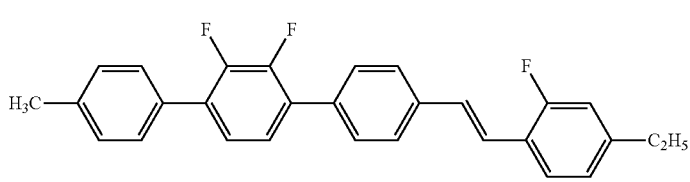 |
| 3063 | 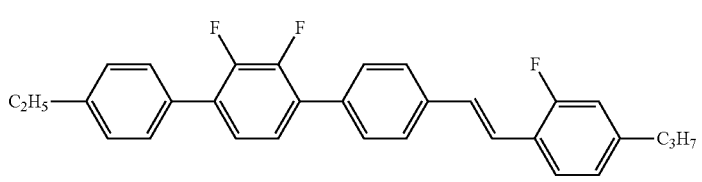 |
| 3064 | 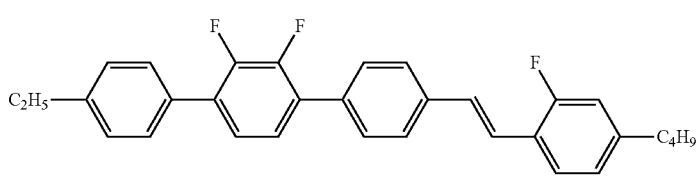 |

| No. |
|---|
| 3065 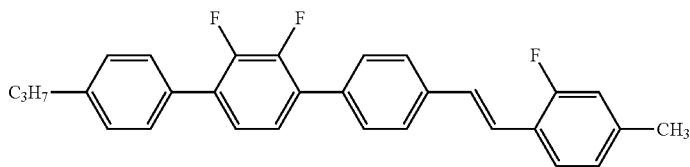 |
| 3066 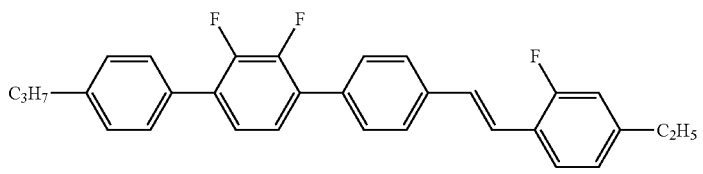 |
| 3067 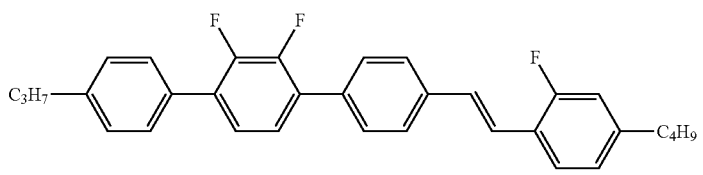 |
| 3068 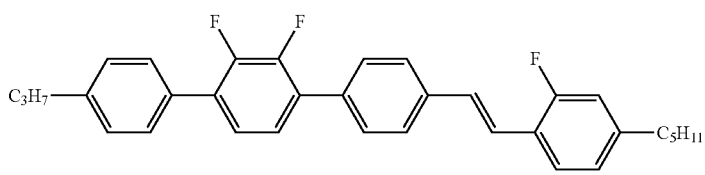 |
| 3069 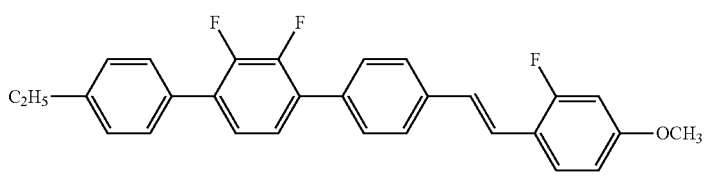 |
| 3070 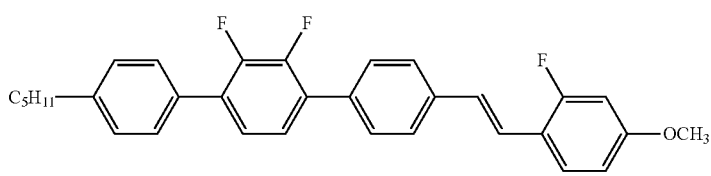 [SMILES: COc1ccc(-c2ccc(-c3ccc(/C=C/c4ccc(OC)cc4F)cc3)c(F)c2F)cc1] |
| 3071 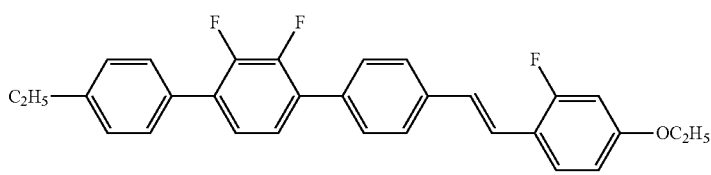 |
| 3072 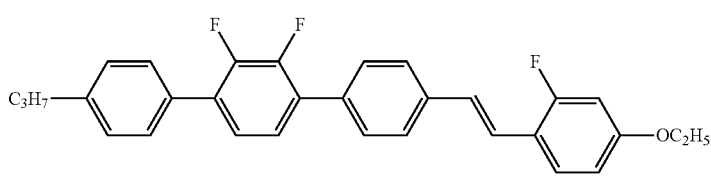 |

| No. |
|---|
| 3073 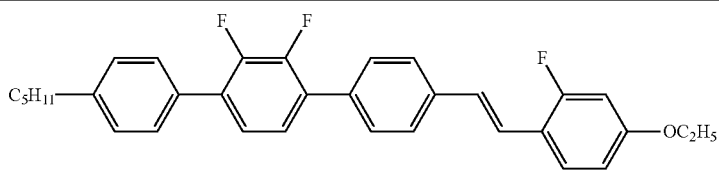 |
| 3074 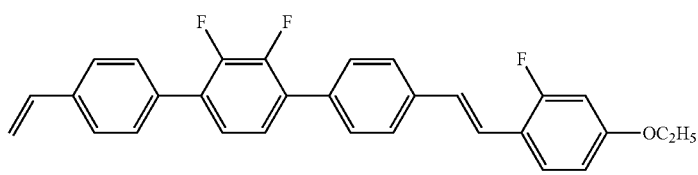 |
| 3075 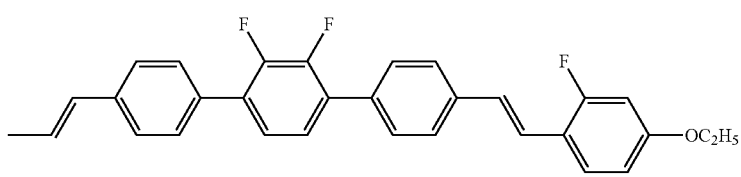 |
| 3076 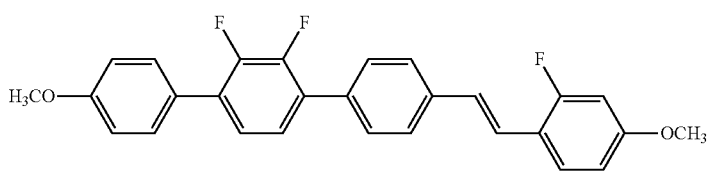 |
| 3077 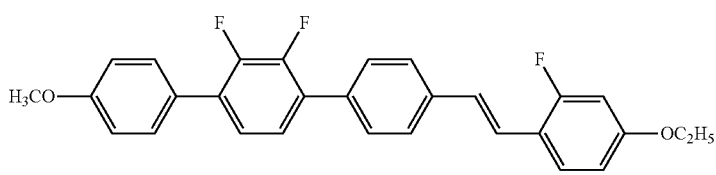 |
| 3078 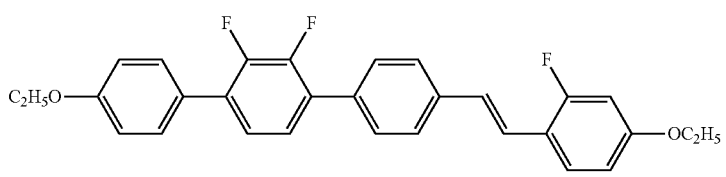 |
| 3079 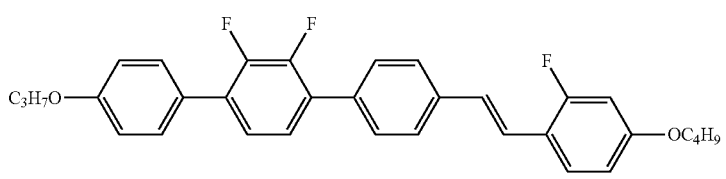 |
| 3080 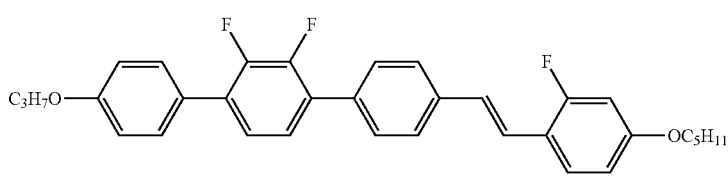 |
| 3081 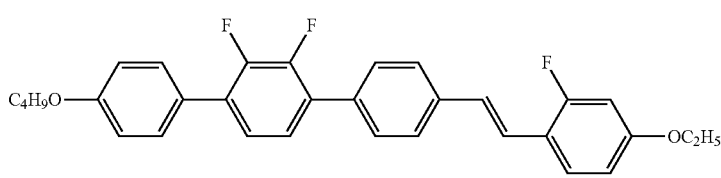 |

-continued
| No. |
|---|
3082 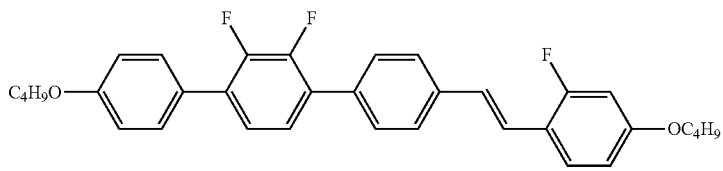
3083 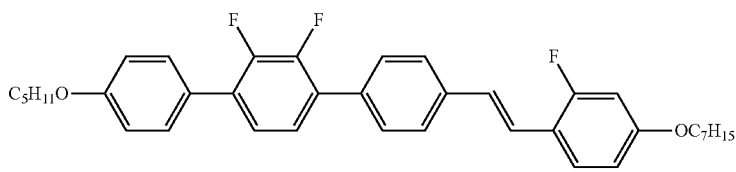
3084 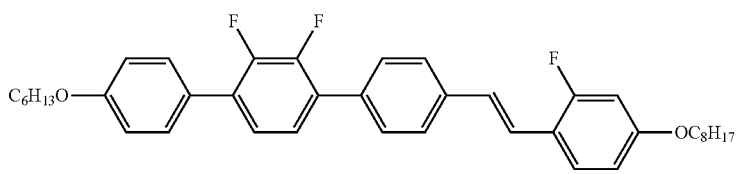
3085 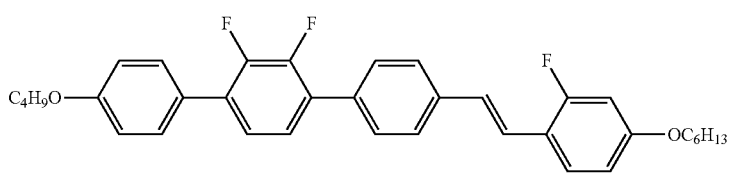
3086 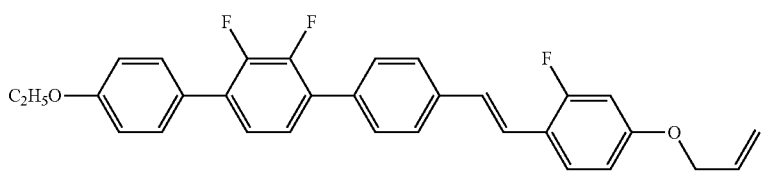
3087 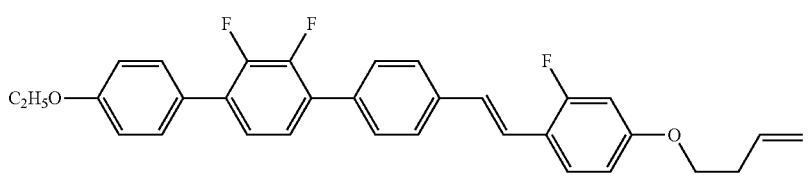
3088 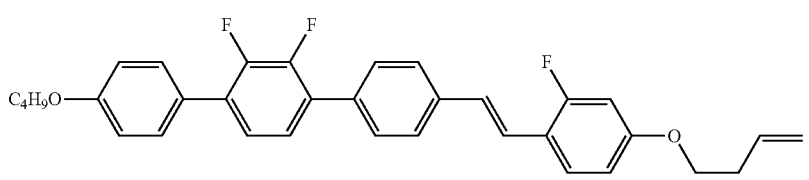
3089 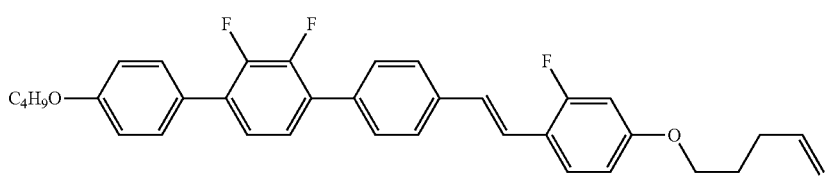

-continued
No.
3090 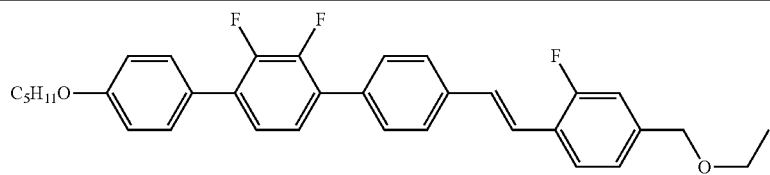
3091 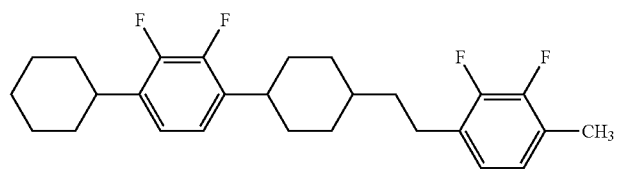
3092 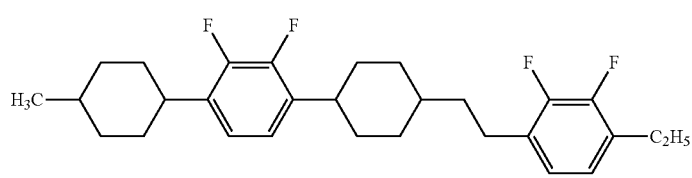
3093 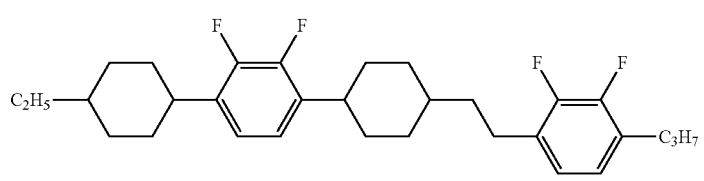
3094 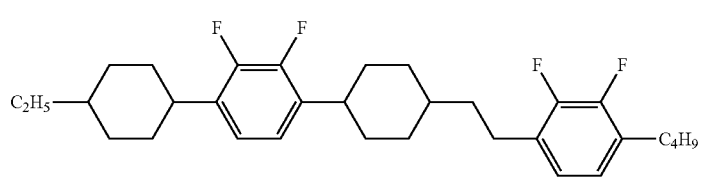
3095 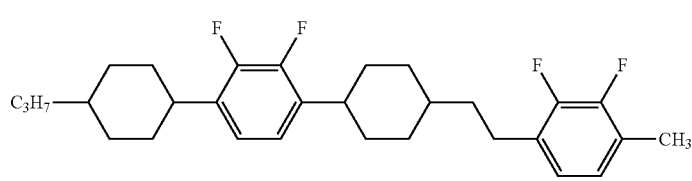
3096 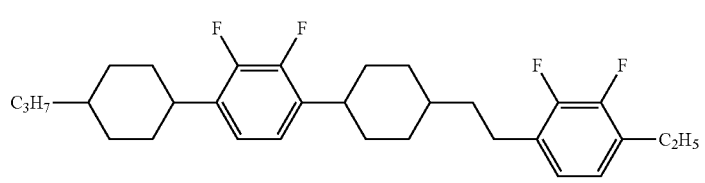
3097 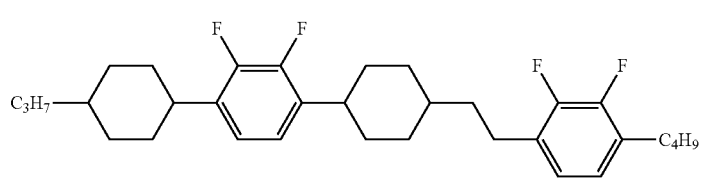
3098 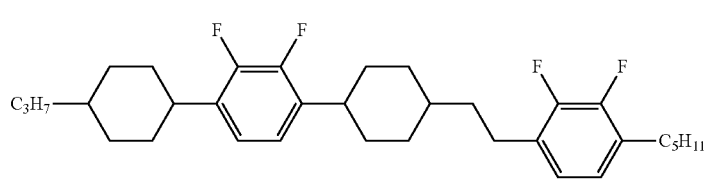

| No. | |
|---|---|
| 3099 | 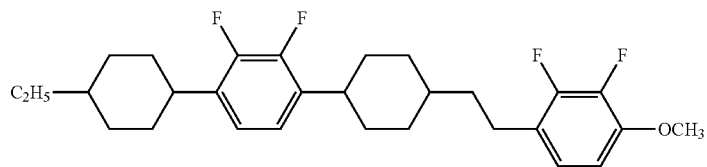 |
| 3100 | 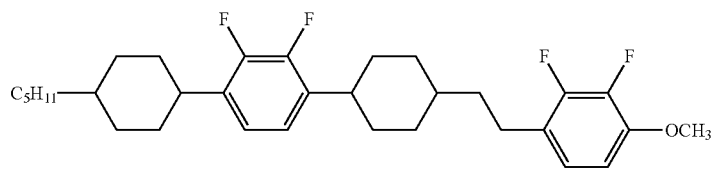 [SMILES: COc1ccc(CCC2CCC(c3ccc(C4CCC(OC)CC4)c(F)c3F)CC2)c(F)c1F] |
| 3101 | 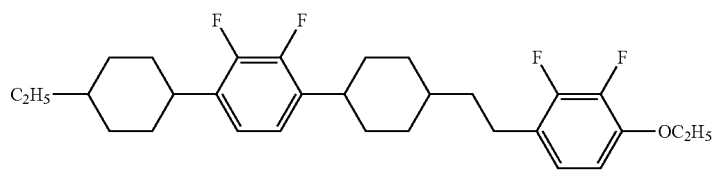 |
| 3102 | 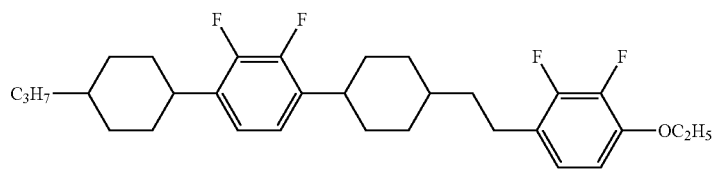 |
| 3103 | 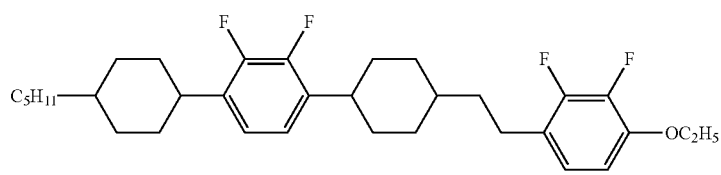 [SMILES: CCOc1ccc(CCC2CCC(c3ccc(C4CCC(OC)CC4)c(F)c3F)CC2)c(F)c1F] |
| 3104 | 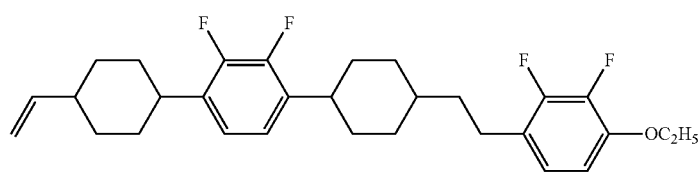 |
| 3105 | 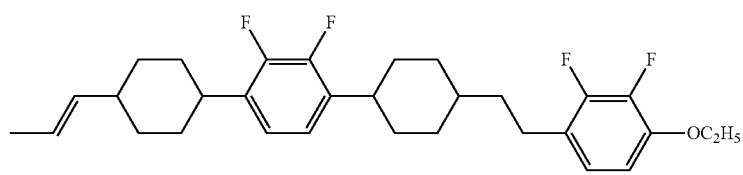 |
| 3106 | 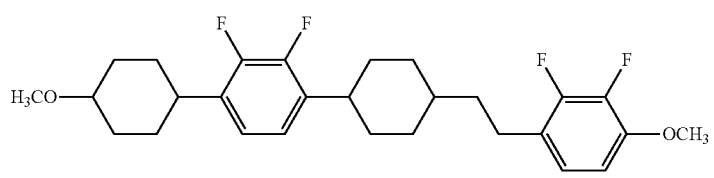 |

-continued
| No. | |
|---|---|
| 3107 | 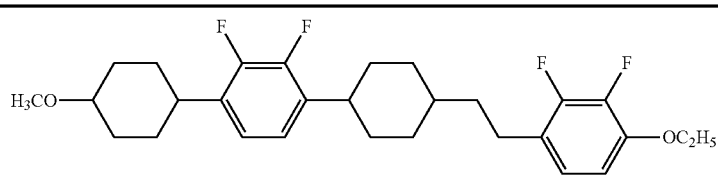 |
| 3108 | 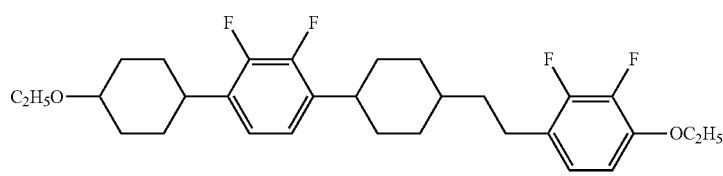 |
| 3109 | 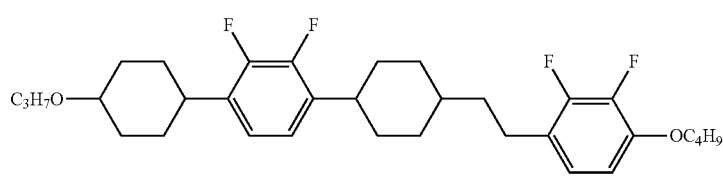 |
| 3110 | 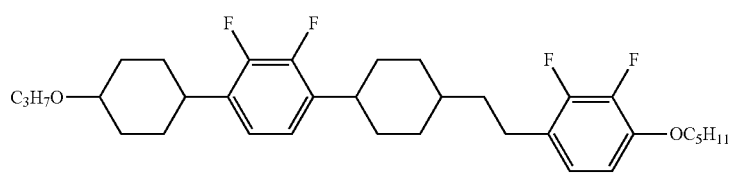 |
| 3111 | 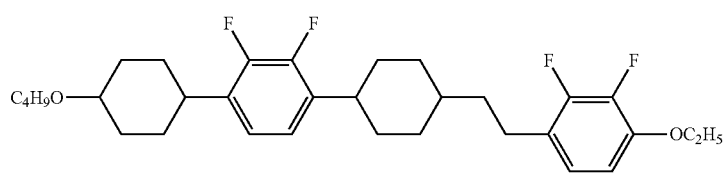 |
| 3112 | 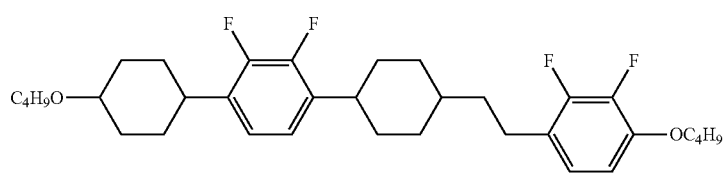 |
| 3113 | 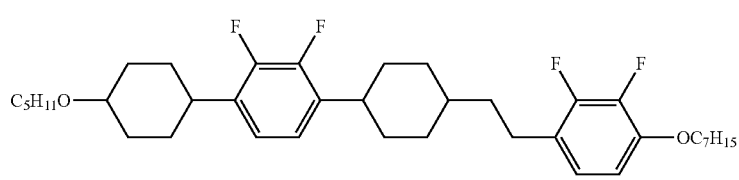 |
| 3114 | 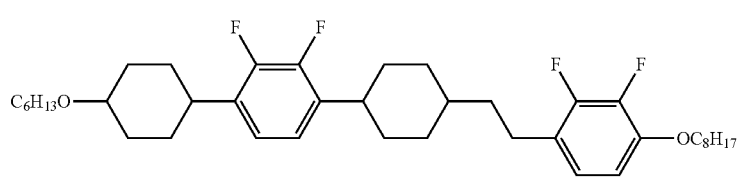 |
| 3115 | 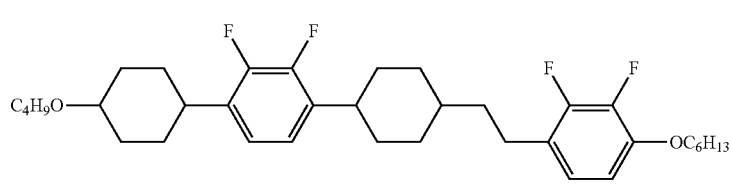 |

| No. |
|---|
| 3116 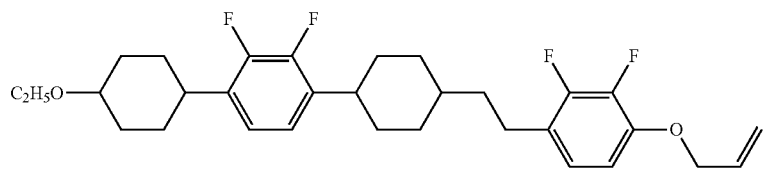 |
| 3117 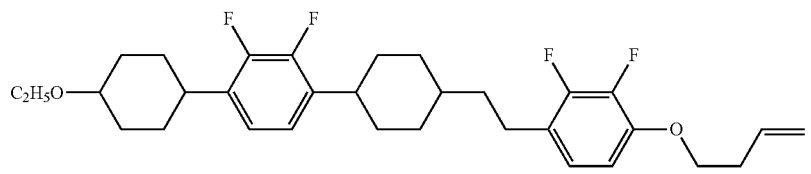 |
| 3118 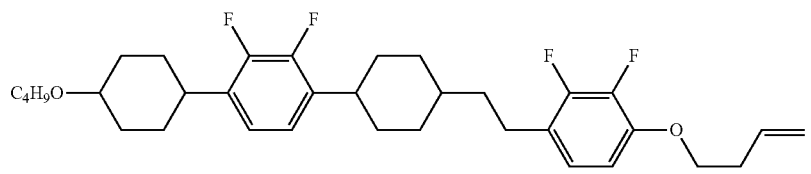 |
| 3119 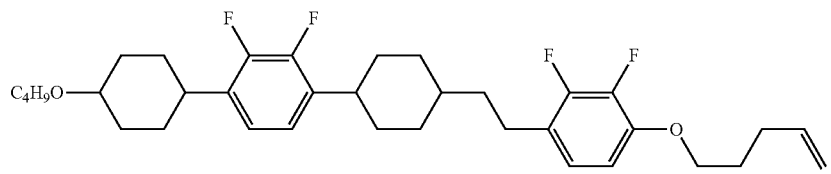 |
| 3120 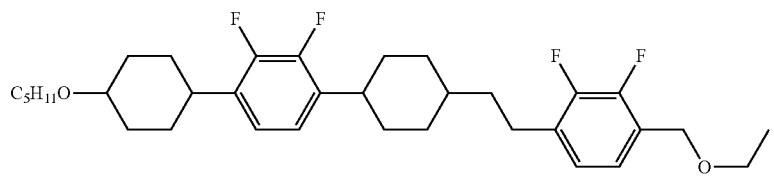 |
| 3121 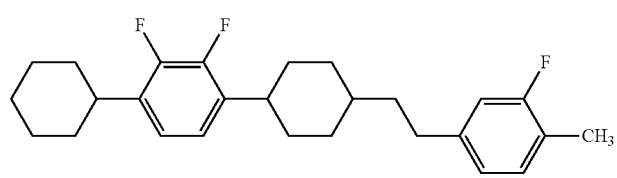 |
| 3122 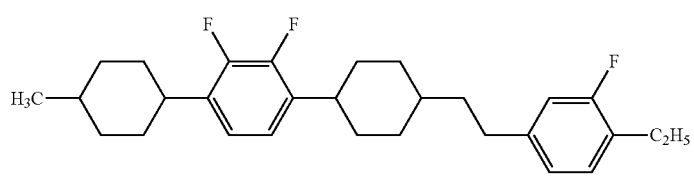 |
| 3123 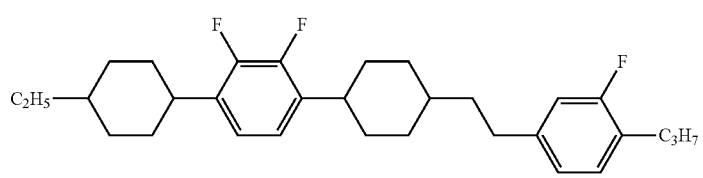 |

-continued
| No. | |
|---|---|
| 3124 | 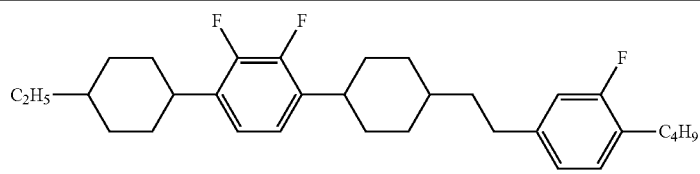 |
| 3125 | 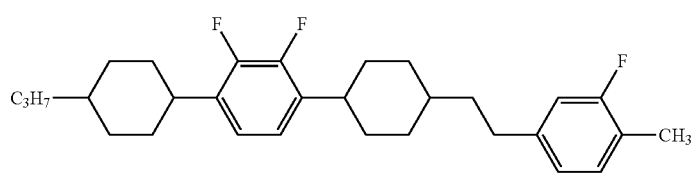 |
| 3126 | 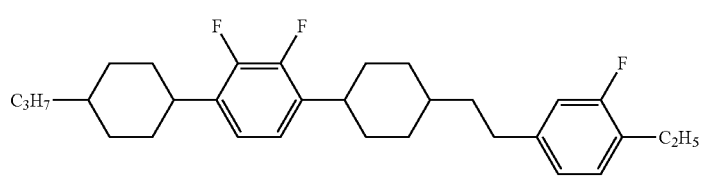 |
| 3127 | 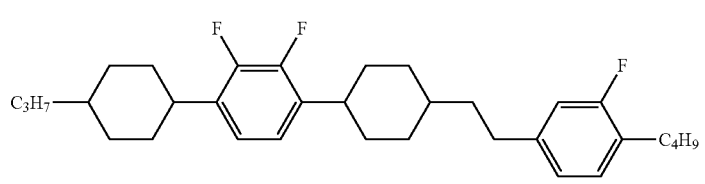 |
| 3128 | 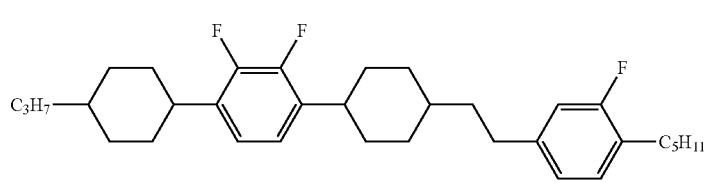 |
| 3129 | 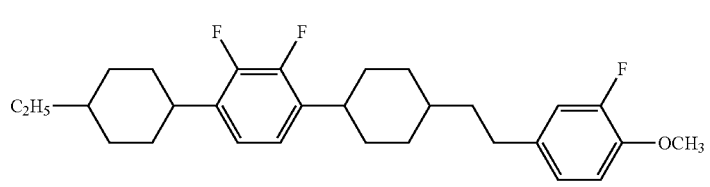 |
| 3130 | 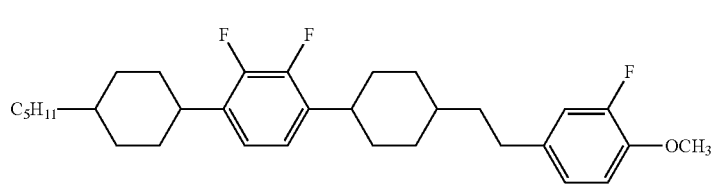 [SMILES: COc1ccc(CCC2CCC(c3ccc(C4CCC(OC)CC4)c(F)c3F)CC2)cc1F] |
| 3131 | 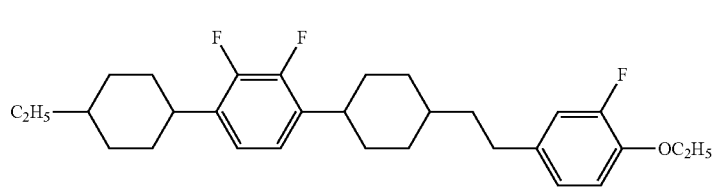 |
| 3132 |  |

| No. | |
|---|---|
| 3133 | 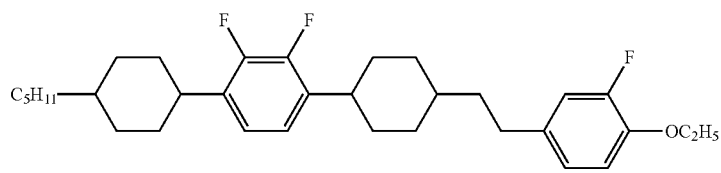 [SMILES: CCOc1ccc(CCC2CCC(c3ccc(C4CCC(OC)CC4)c(F)c3F)CC2)cc1F] |
| 3134 | 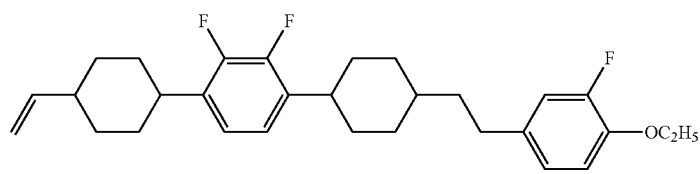 |
| 3135 | 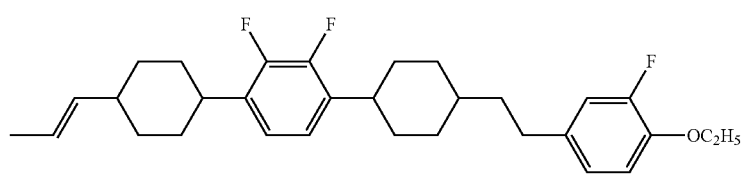 |
| 3136 | 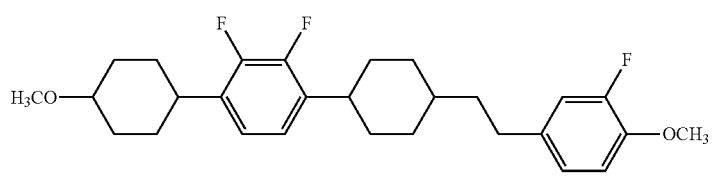 |
| 3137 | 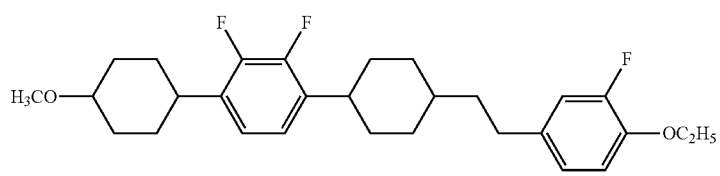 |
| 3138 | 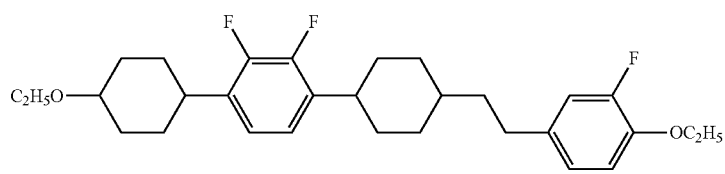 |
| 3139 | 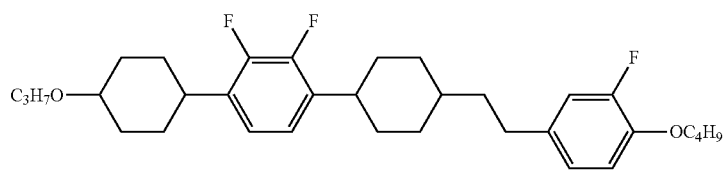 |
| 3140 | 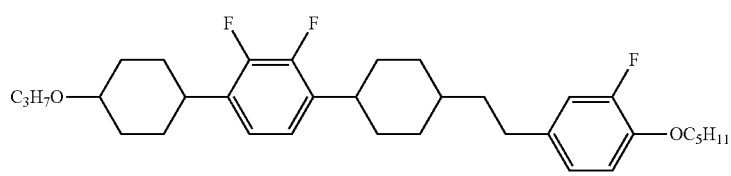 |

| No. | |
|---|---|
| 3141 | 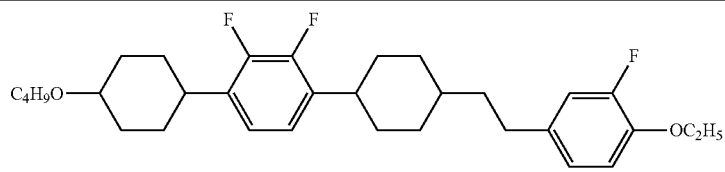 |
| 3142 | 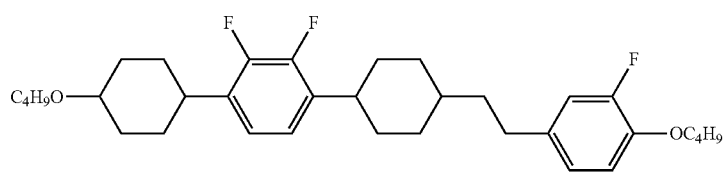 |
| 3143 | 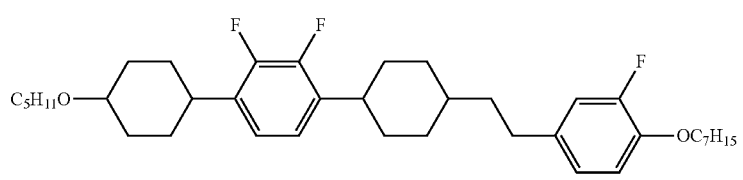 |
| 3144 | 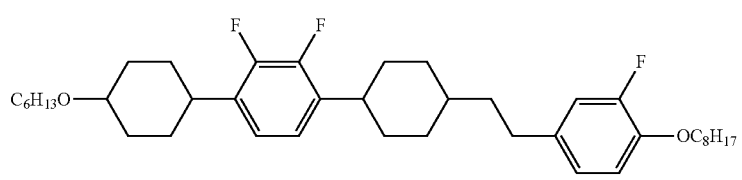 |
| 3145 | 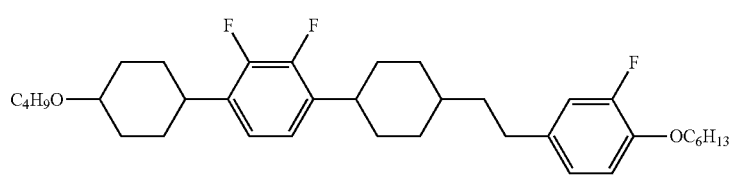 |
| 3146 | 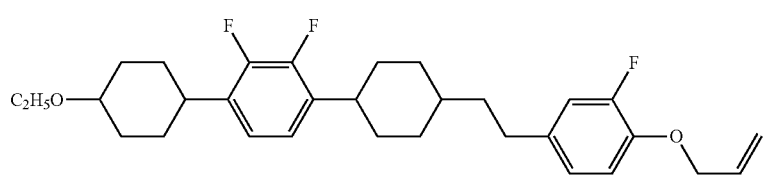 |
| 3147 | 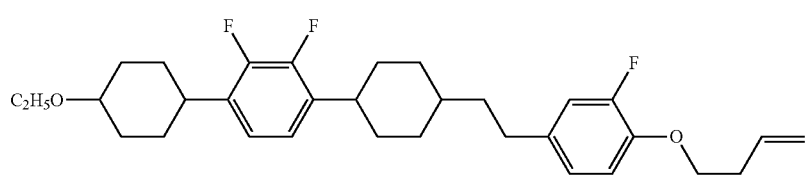 |
| 3148 | 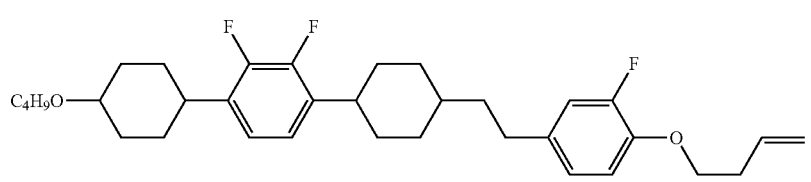 |
| 3149 | 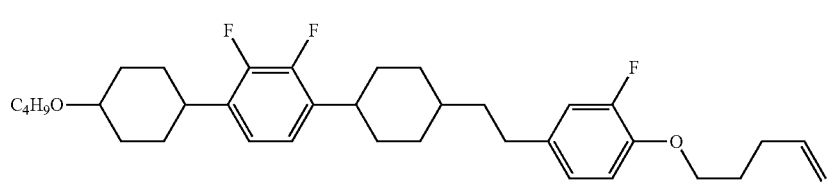 |

-continued
| No. | |
|---|---|
| 3150 | 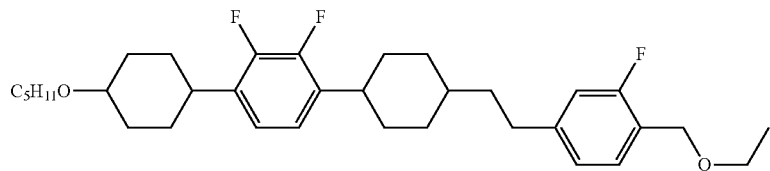 |
| 3151 | 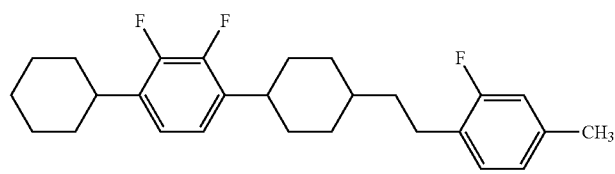 |
| 3152 | 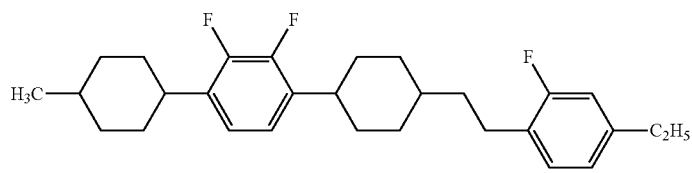 |
| 3153 | 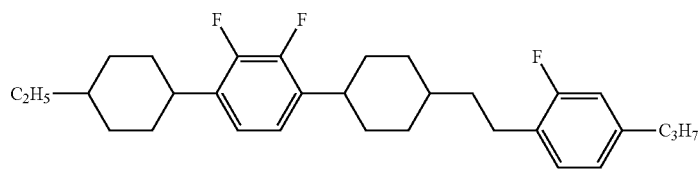 |
| 3154 | 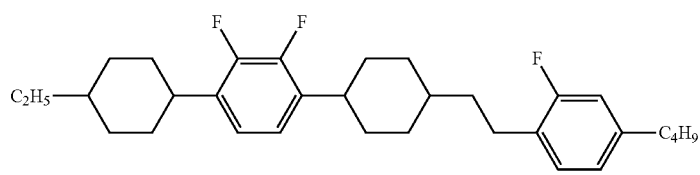 |
| 3155 | 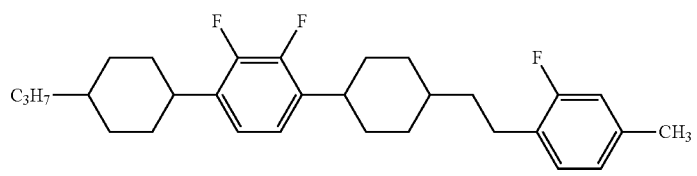 |
| 3156 | 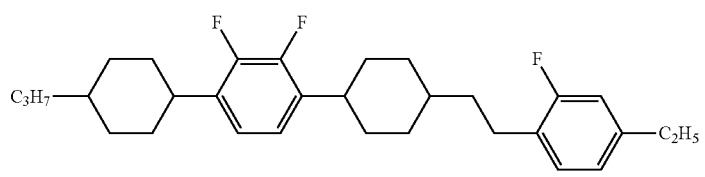 |
| 3157 | 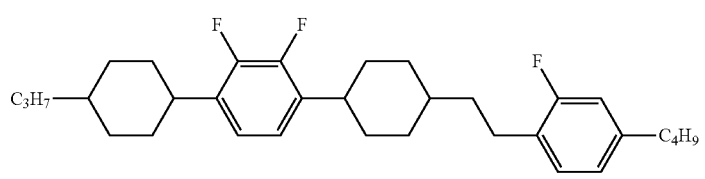 |

| No. | |
|---|---|
| 3158 | 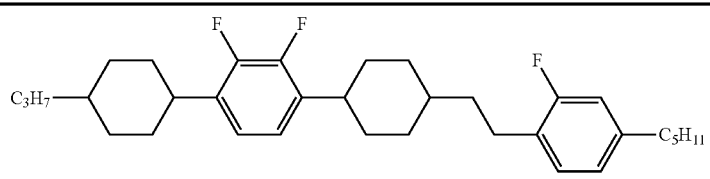 |
| 3159 | 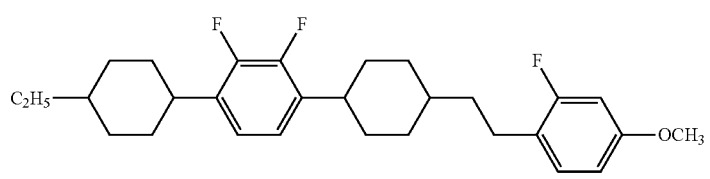 |
| 3160 | 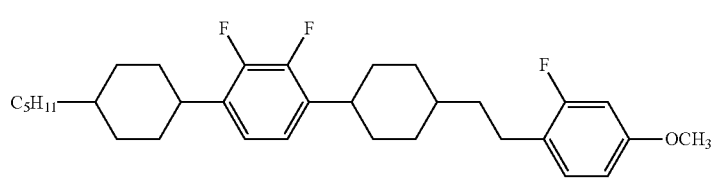 |
| 3161 | 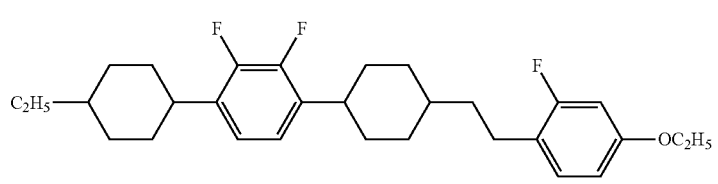 [SMILES: CCOc1ccc(CCC2CCC(c3ccc(C4CCC(CC)CC4)c(F)c3F)CC2)c(F)c1] |
| 3162 | 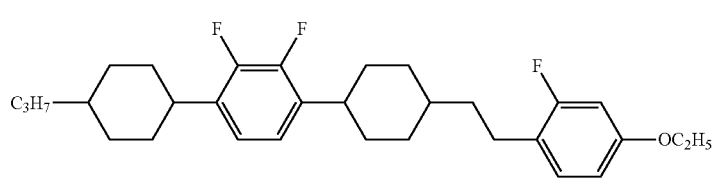 |
| 3163 | 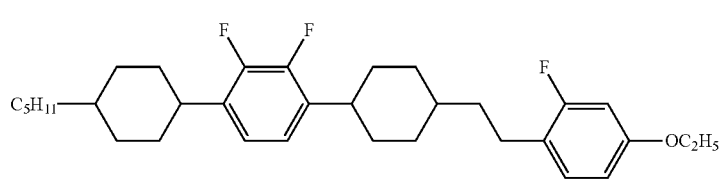 |
| 3164 | 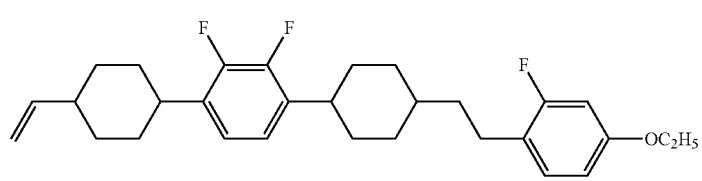 |
| 3165 | 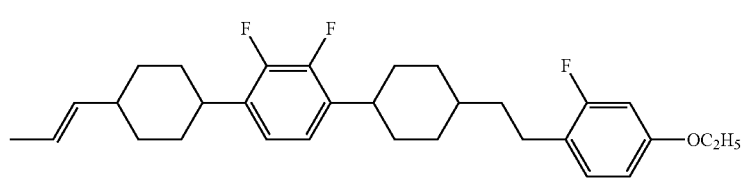 |
| 3166 | 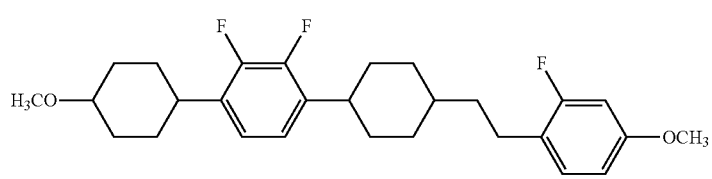 [SMILES: COc1ccc(CCC2CCC(c3ccc(C4CCC(OC)CC4)c(F)c3F)CC2)c(F)c1] |

| No. | |
|---|---|
| 3167 | 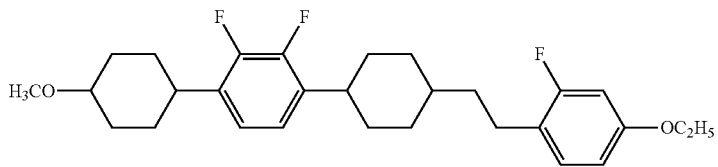 [SMILES: CCOc1ccc(CCC2CCC(c3ccc(C4CCC(OC)CC4)c(F)c3F)CC2)c(F)c1] |
| 3168 | 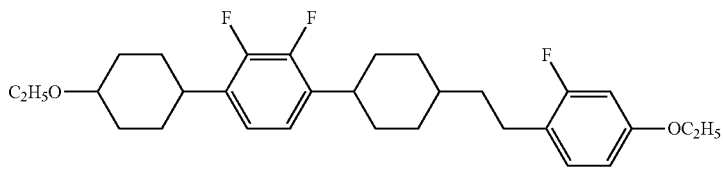 |
| 3169 | 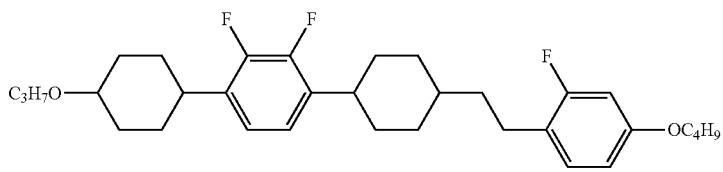 |
| 3170 | 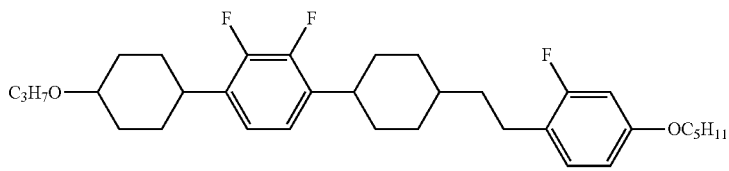 |
| 3171 | 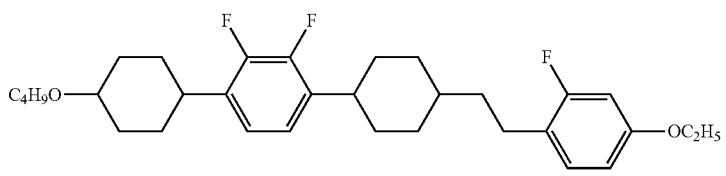 |
| 3172 | 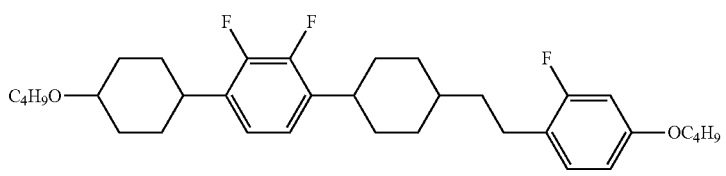 |
| 3173 | 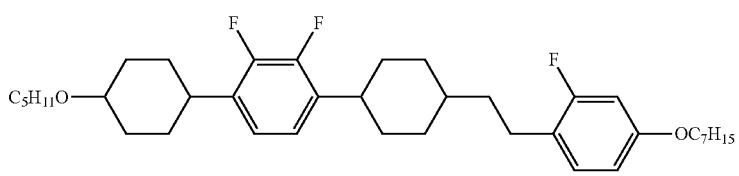 |
| 3174 | 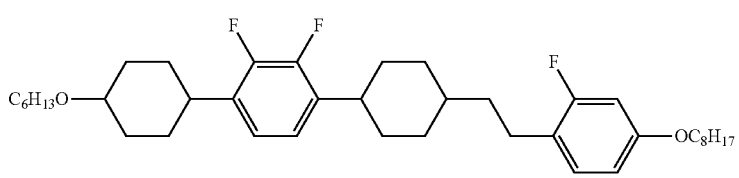 |

| No. | |
|---|---|
| 3175 | 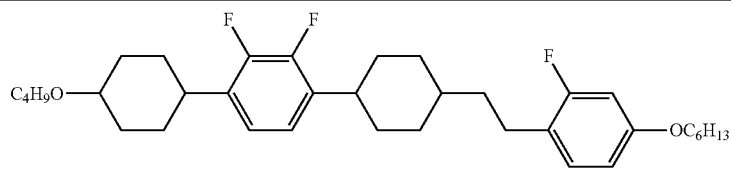 |
| 3176 | 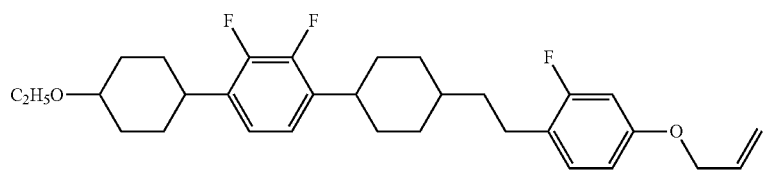 |
| 3177 | 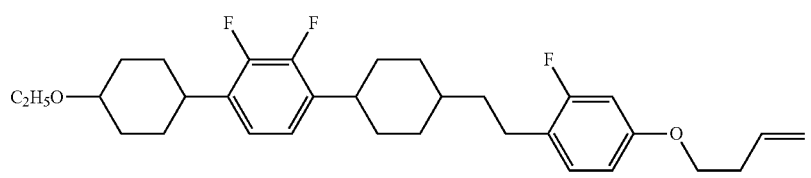 |
| 3178 | 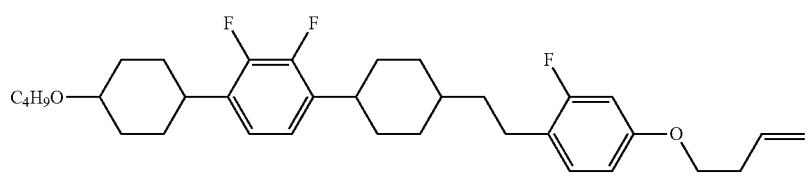 |
| 3179 | 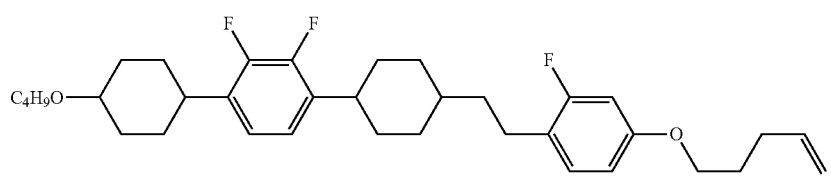 |
| 3180 | 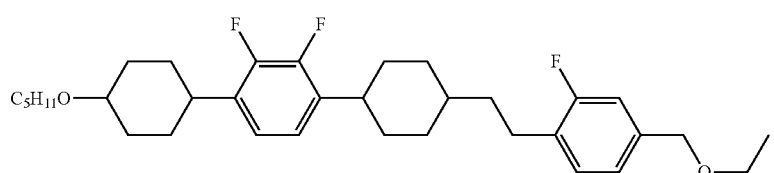 |
| 3181 | 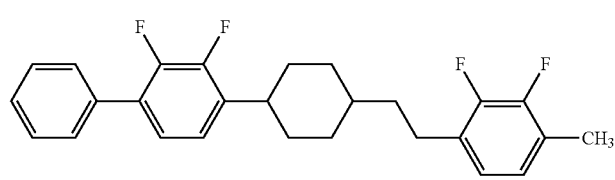 |
| 3182 | 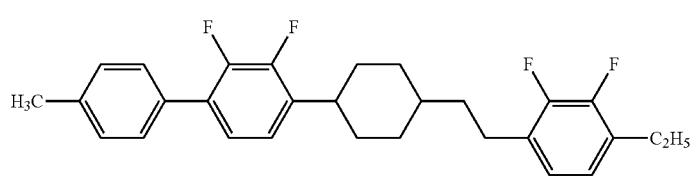 [SMILES: CCc1ccc(CCC2CCC(c3ccc(-c4ccc(C)cc4)c(F)c3F)CC2)c(F)c1F] |
| 3183 | 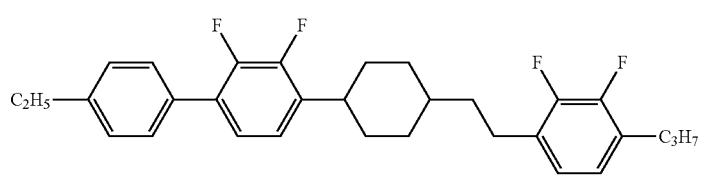 |

| No. | |
|---|---|
| 3184 | 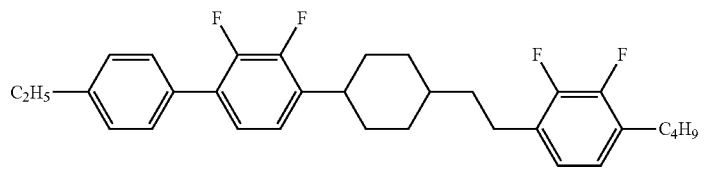 |
| 3185 | 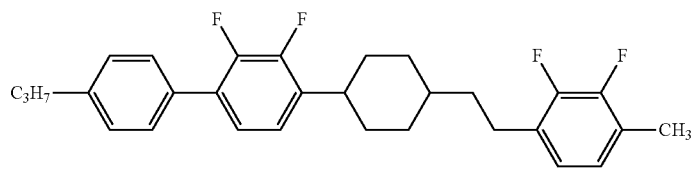 |
| 3186 | 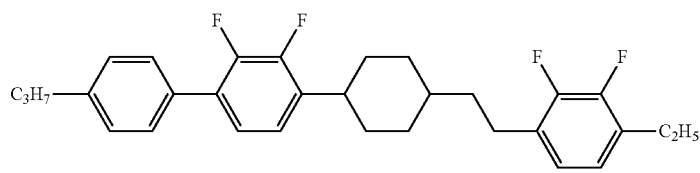 |
| 3187 | 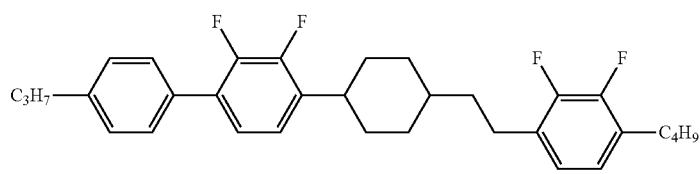 |
| 3188 | 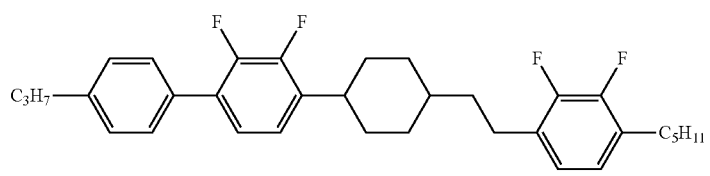 |
| 3189 |  |
| 3190 | 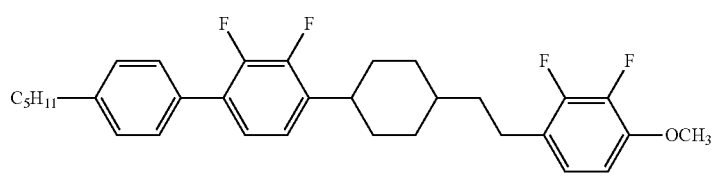 |
| 3191 | 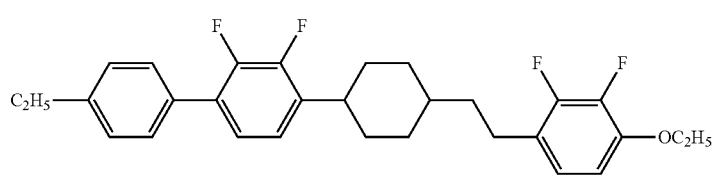 |

| No. |
|---|
| 3192 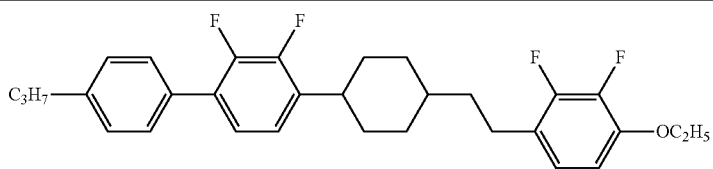 |
| 3193 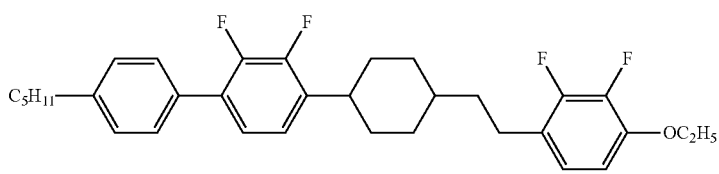 |
| 3194 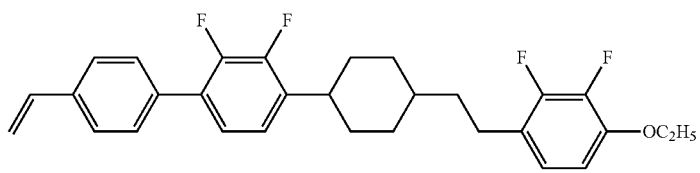 [SMILES: C=Cc1ccc(-c2ccc(C3CCC(CCc4ccc(OCC)c(F)c4F)CC3)c(F)c2F)cc1] |
| 3195 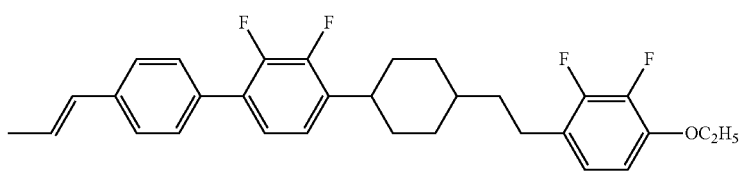 [SMILES: C/C=C/c1ccc(-c2ccc(C3CCC(CCc4ccc(OCC)c(F)c4F)CC3)c(F)c2F)cc1] |
| 3196 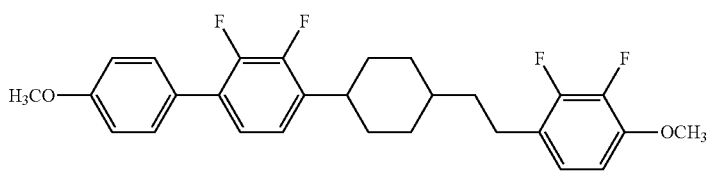 |
| 3197 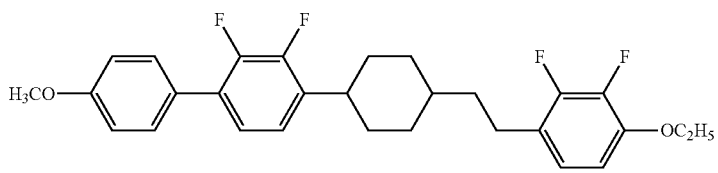 |
| 3198 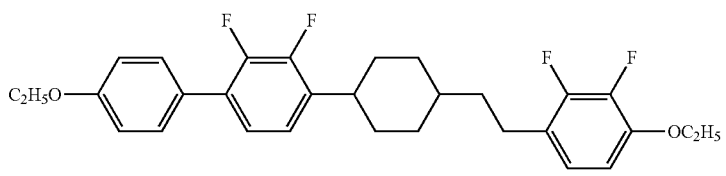 |
| 3199 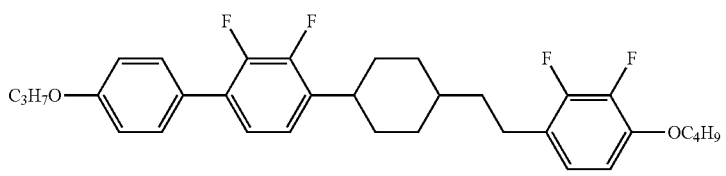 |
| 3200 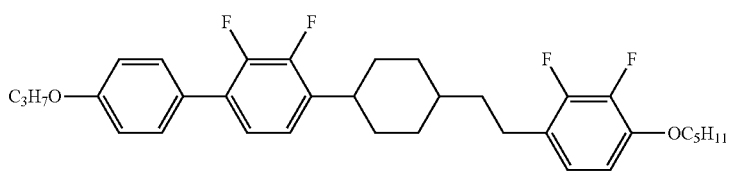 |

| No. | |
|---|---|
| 3201 | 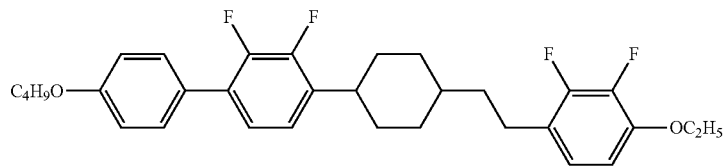 |
| 3202 | 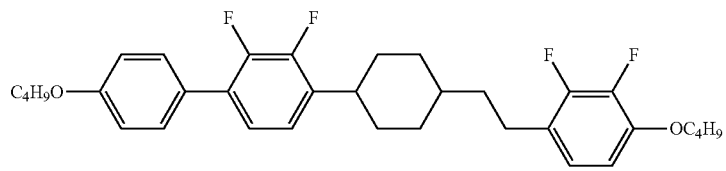 |
| 3203 | 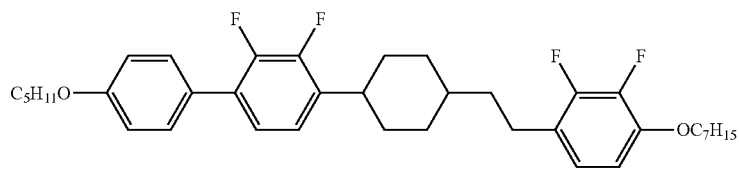 |
| 3204 | 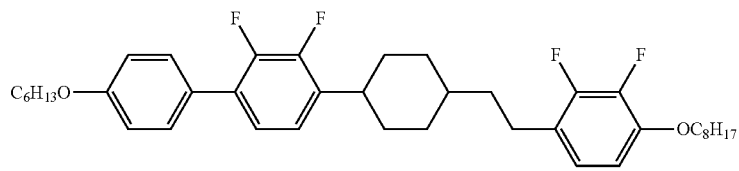 |
| 3205 | 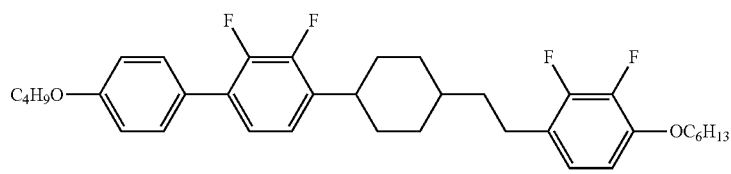 |
| 3206 | 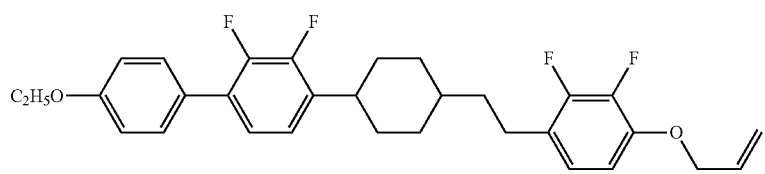 |
| 3207 | 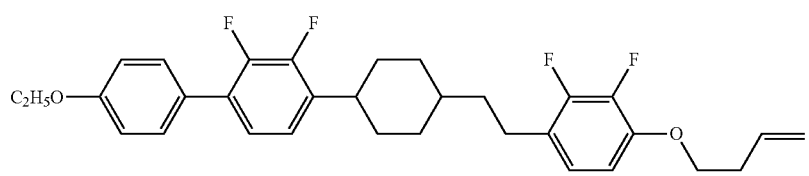 |
| 3208 | 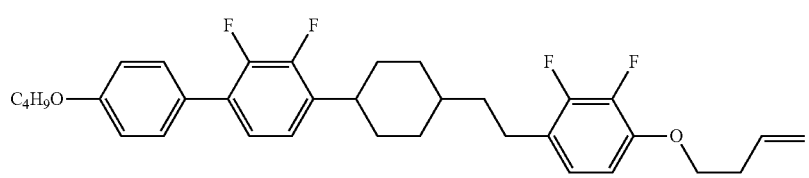 |

| No. | |
|---|---|
| 3209 | 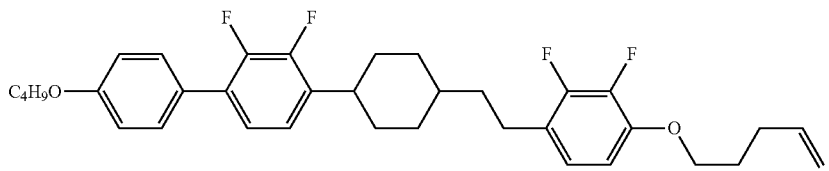 |
| 3210 | 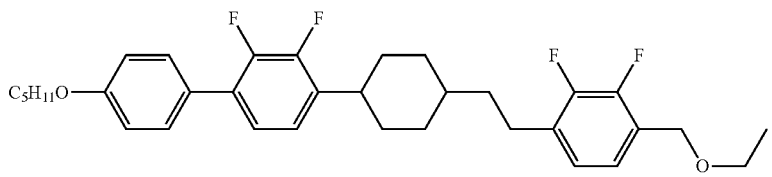 |
| 3211 | 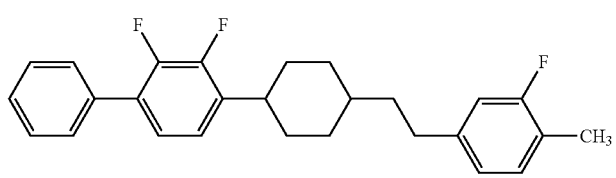 [SMILES: Cc1ccc(CCC2CCC(c3ccc(-c4ccccc4)c(F)c3F)CC2)cc1F] |
| 3212 | 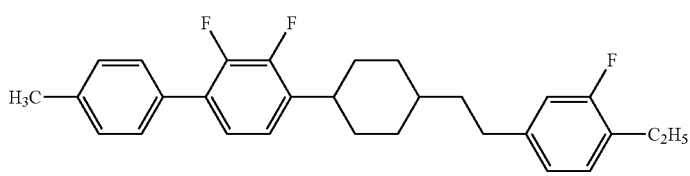 [SMILES: CCc1ccc(CCC2CCC(c3ccc(-c4ccc(C)cc4)c(F)c3F)CC2)cc1F] |
| 3213 | 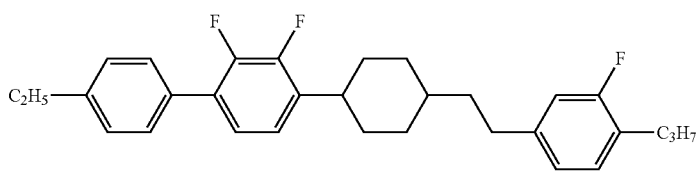 |
| 3124 | 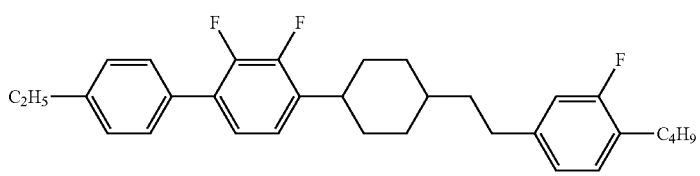 |
| 3215 | 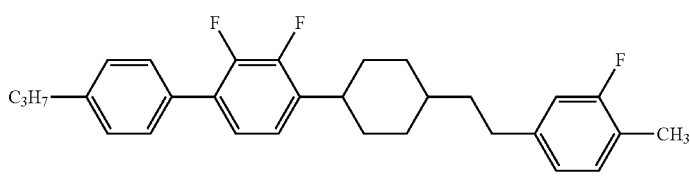 |
| 3216 | 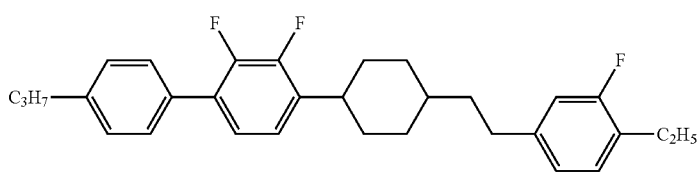 |
| 3217 | 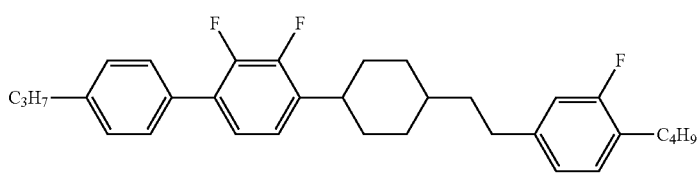 |

| No. |
|---|
| 3218 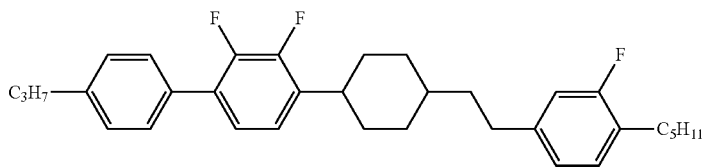 |
| 3219 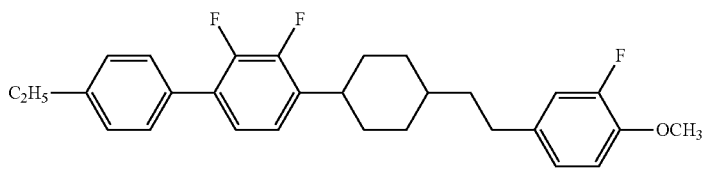 |
| 3220 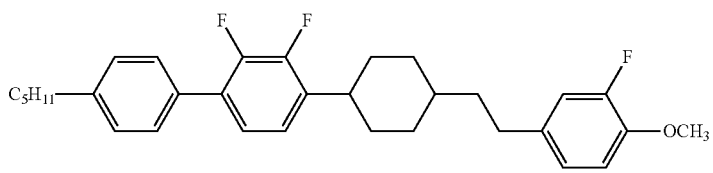 |
| 3221 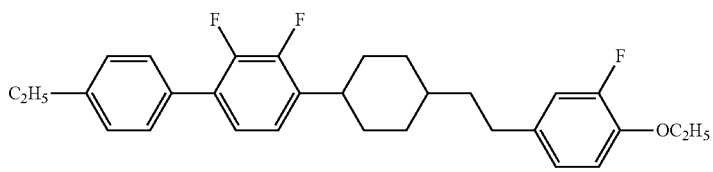 |
| 3222 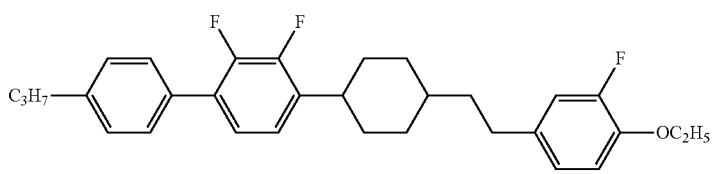 |
| 3223 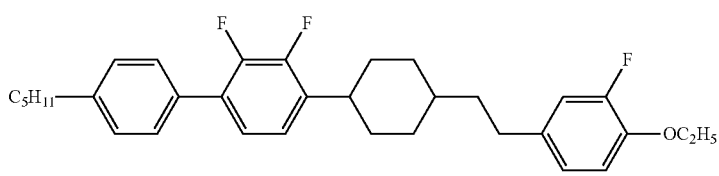 |
| 3224 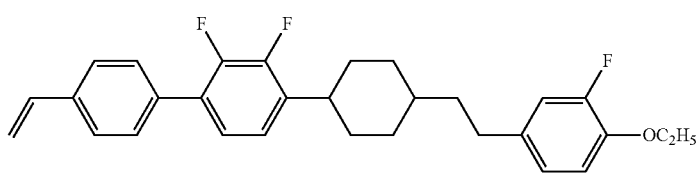 [SMILES: C=Cc1ccc(-c2ccc(C3CCC(CCc4ccc(OCC)c(F)c4)CC3)c(F)c2F)cc1] |
| 3225 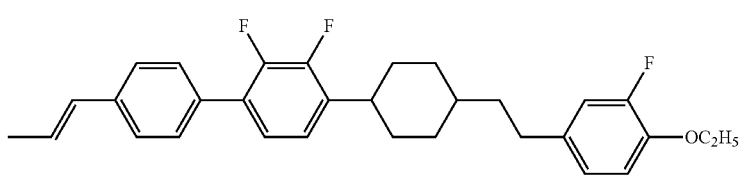 [SMILES: C/C=C/c1ccc(-c2ccc(C3CCC(CCc4ccc(OCC)c(F)c4)CC3)c(F)c2F)cc1] |

| No. | |
|---|---|
| 3226 | 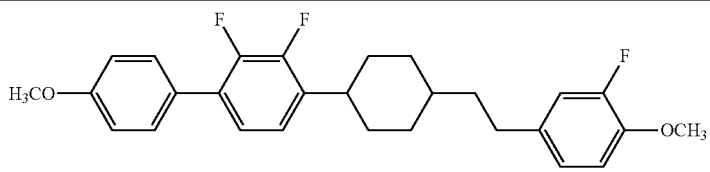 |
| 3227 | 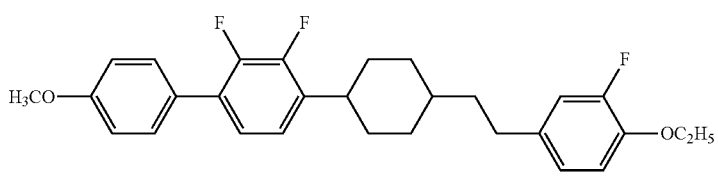 |
| 3228 | 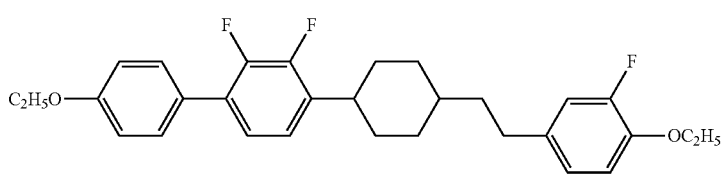 |
| 3229 | 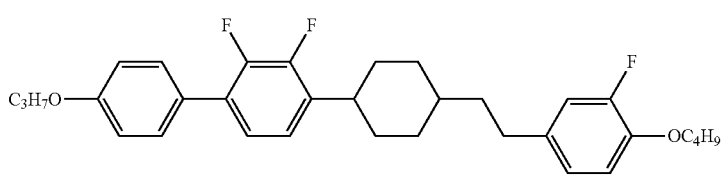 |
| 3230 | 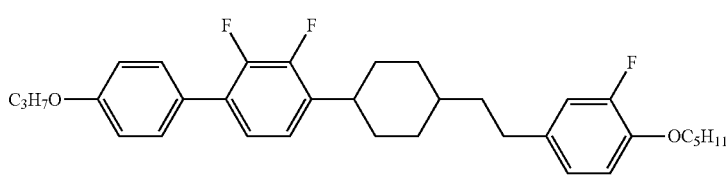 |
| 3231 | 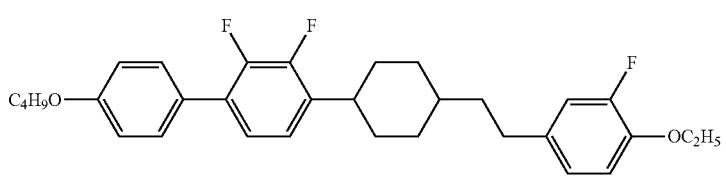 |
| 3232 | 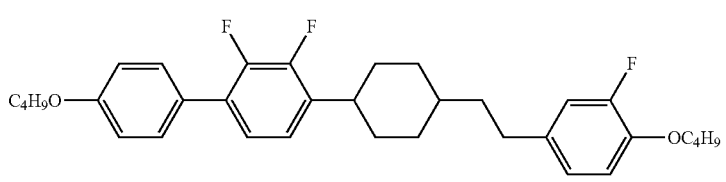 |
| 3233 | 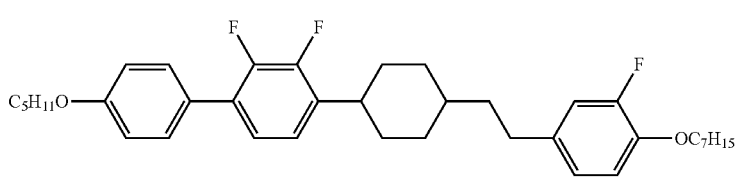 |
| 3234 | 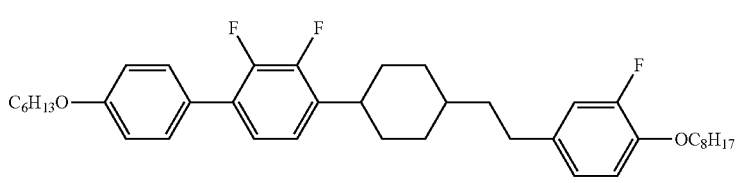 |

| No. | |
|---|---|
| 3235 | 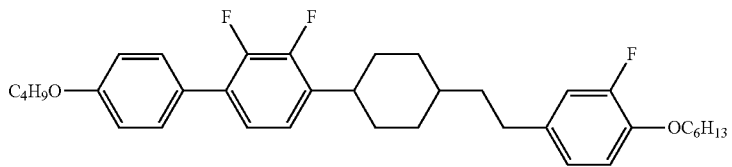 |
| 3236 | 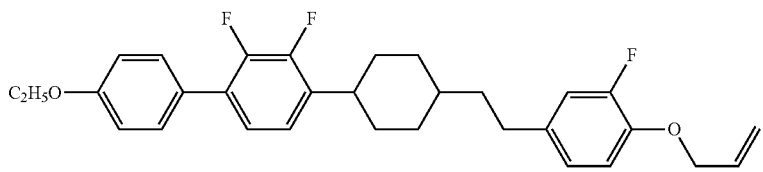 |
| 3237 | 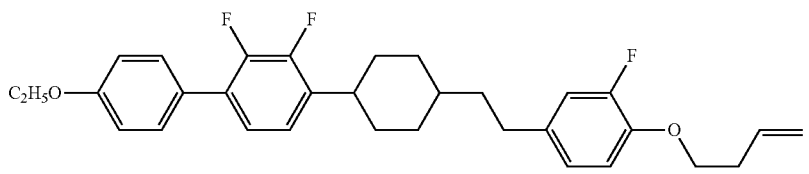 |
| 3238 | 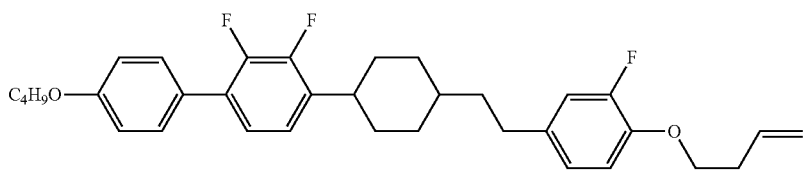 |
| 3239 | 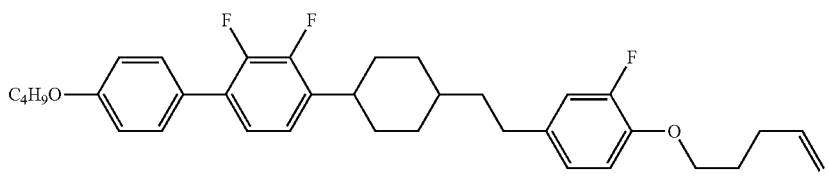 |
| 3240 | 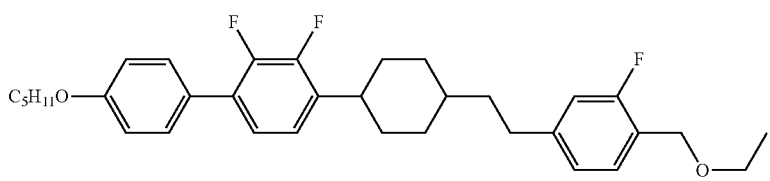 |
| 3241 | 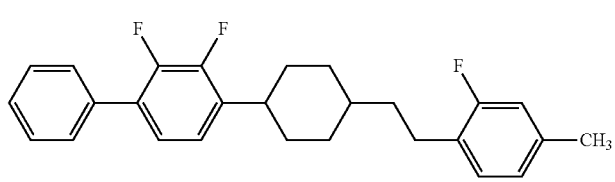 [SMILES: Cc1ccc(CCC2CCC(c3ccc(-c4ccccc4)c(F)c3F)CC2)c(F)c1] |
| 3242 | 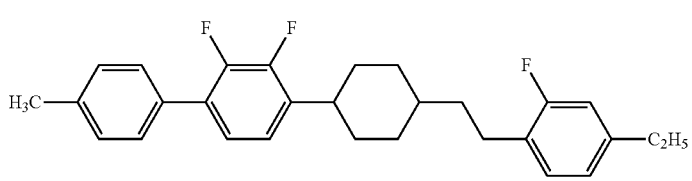 [SMILES: CCc1ccc(CCC2CCC(c3ccc(-c4ccc(C)cc4)c(F)c3F)CC2)c(F)c1] |

| No. | |
|---|---|
| 3243 | 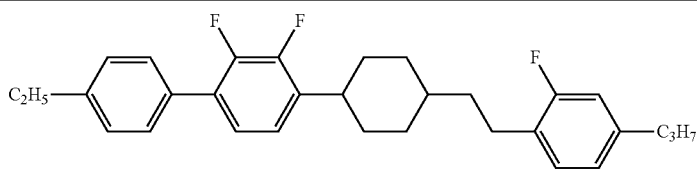 |
| 3244 | 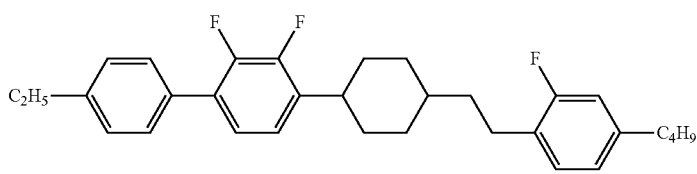 |
| 3245 | 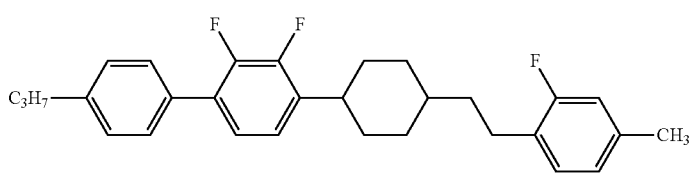 |
| 3246 | 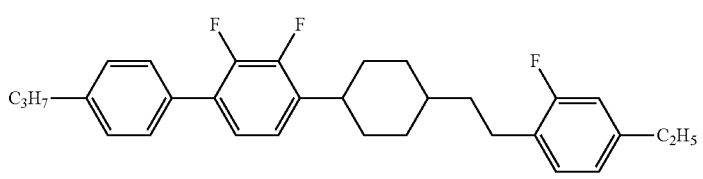 |
| 3247 | 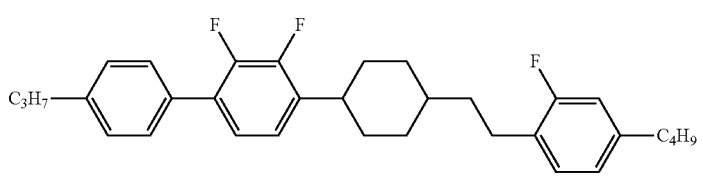 |
| 3248 | 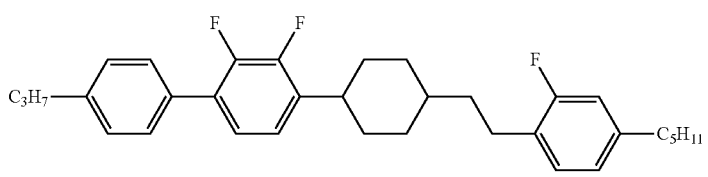 |
| 3249 | 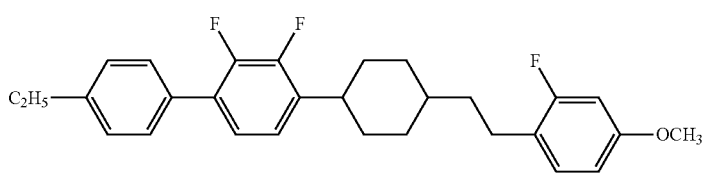 |
| 3250 | 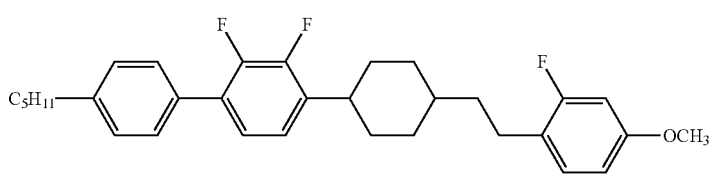 |
| 3251 | 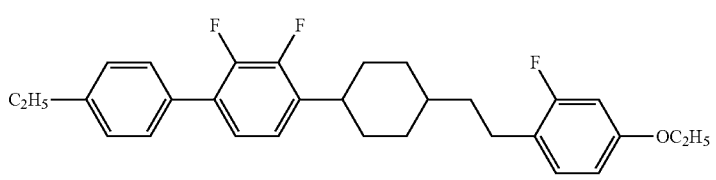 |

| No. |
|---|
| 3252 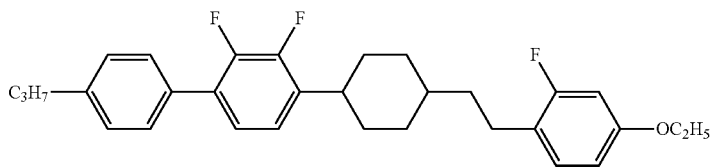 |
| 3253 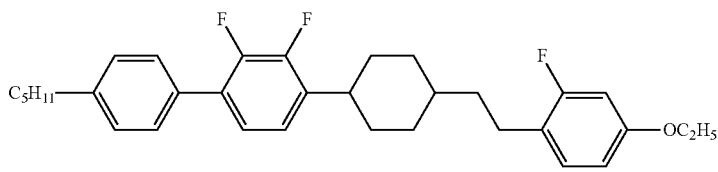 |
| 3254 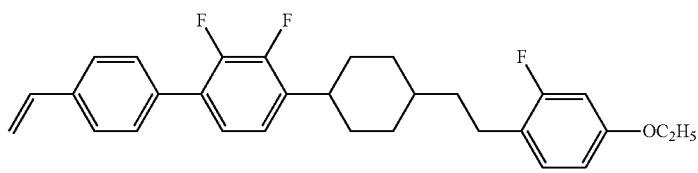 [SMILES: C=Cc1ccc(-c2ccc(C3CCC(CCc4ccc(OCC)cc4F)CC3)c(F)c2F)cc1] |
| 3255 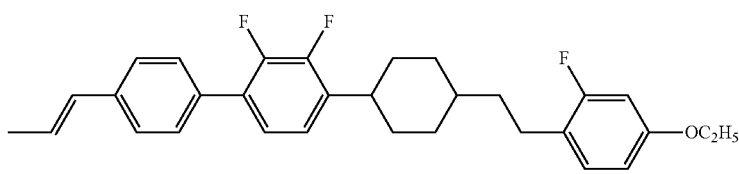 [SMILES: C/C=C/c1ccc(-c2ccc(C3CCC(CCc4ccc(OCC)cc4F)CC3)c(F)c2F)cc1] |
| 3256 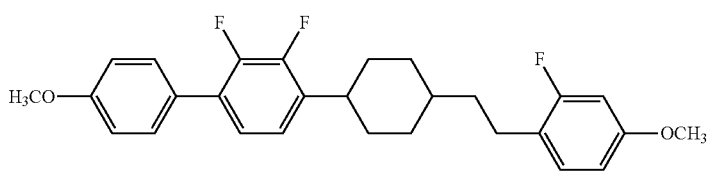 [SMILES: COc1ccc(-c2ccc(C3CCC(CCc4ccc(OC)cc4F)CC3)c(F)c2F)cc1] |
| 3257 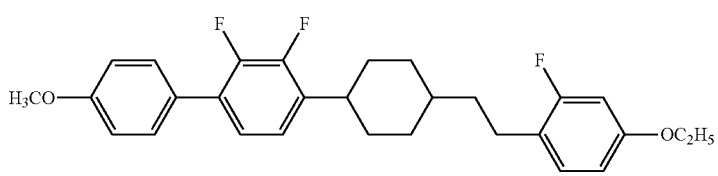 [SMILES: CCOc1ccc(CCC2CCC(c3ccc(-c4ccc(OC)cc4)c(F)c3F)CC2)c(F)c1] |
| 3258 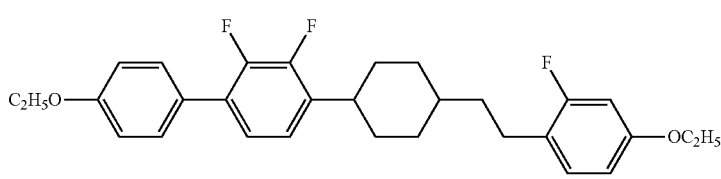 |
| 3259 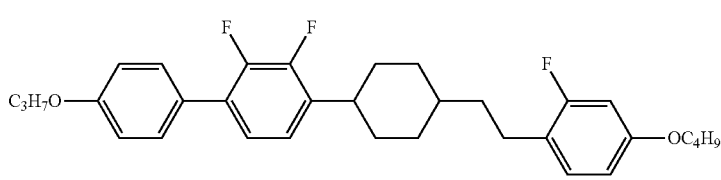 |

| No. |
|---|
| 3260 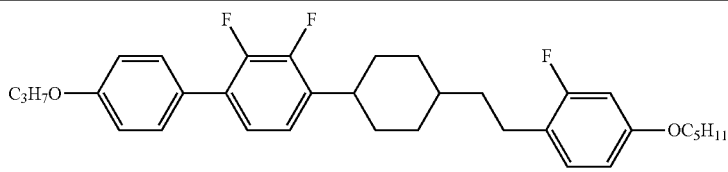 |
| 3261 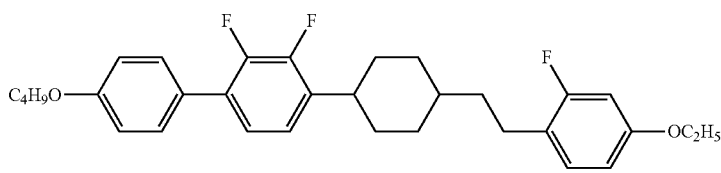 |
| 3262 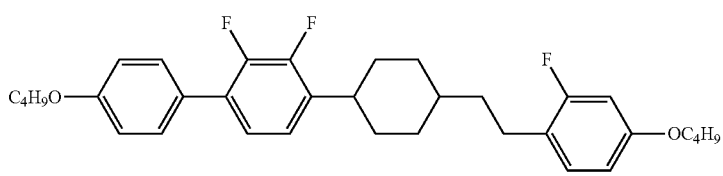 |
| 3263 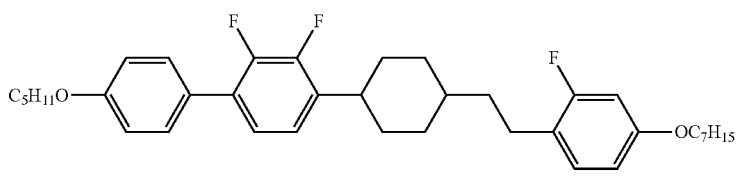 |
| 3264 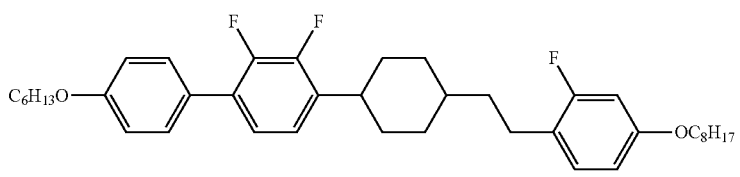 |
| 3265 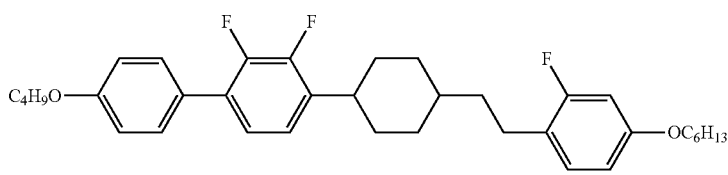 |
| 3266 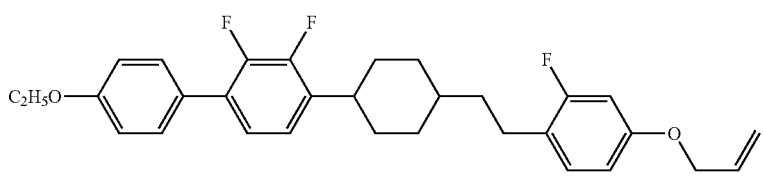 |
| 3267 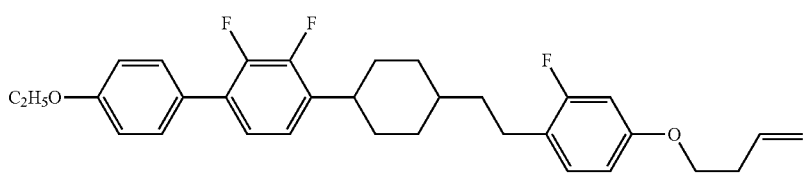 |
| 3268 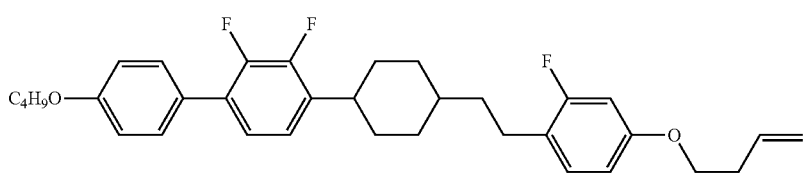 |

| No. |
|---|
| 3269 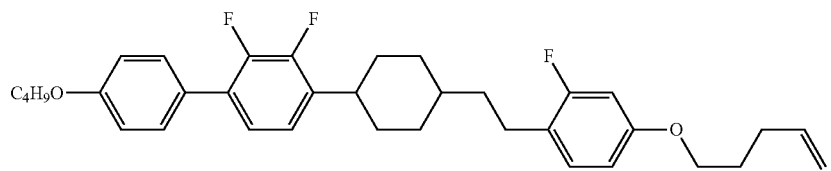 |
| 3270 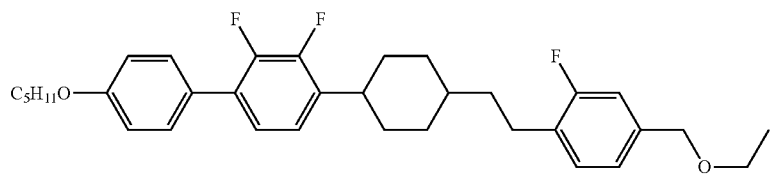 |
| 3271 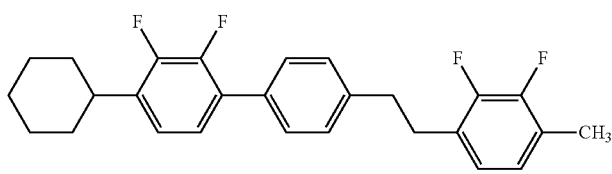 [SMILES: Cc1ccc(CCc2ccc(-c3ccc(C4CCCCC4)c(F)c3F)cc2)c(F)c1F] |
| 3272 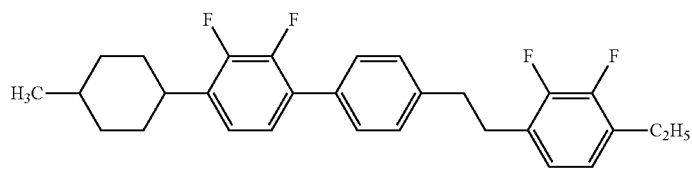 [SMILES: CCc1ccc(CCc2ccc(-c3ccc(C4CCC(C)CC4)c(F)c3F)cc2)c(F)c1F] |
| 3273 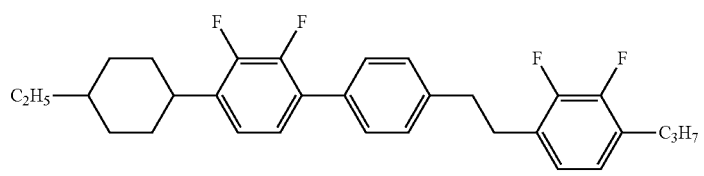 |
| 3274 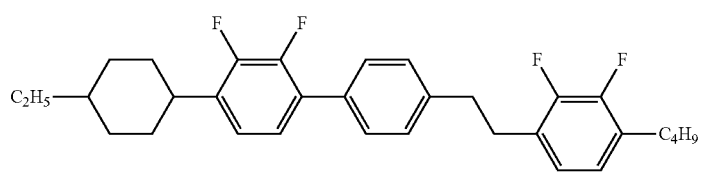 |
| 3275 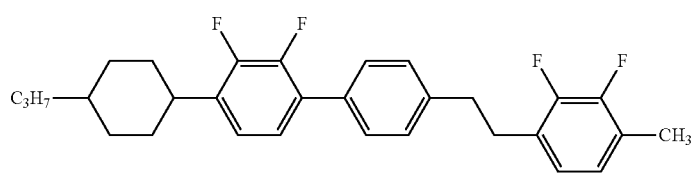 |
| 3276 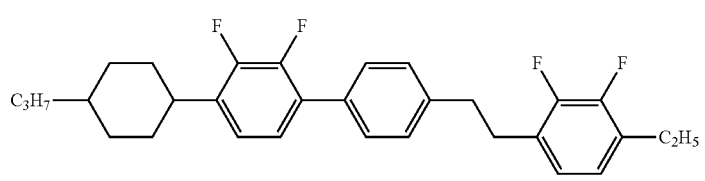 |

| No. | |
|---|---|
| 3277 | 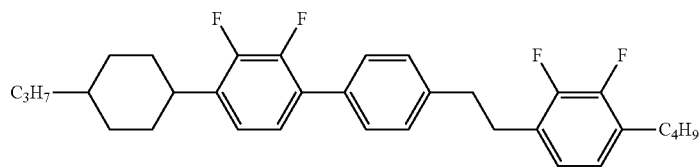 |
| 3278 | 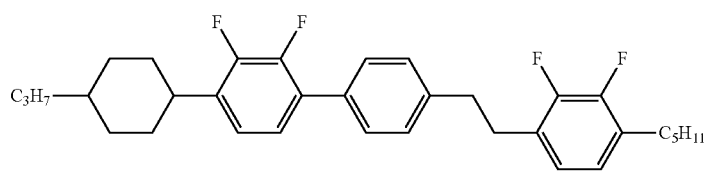 |
| 3279 | 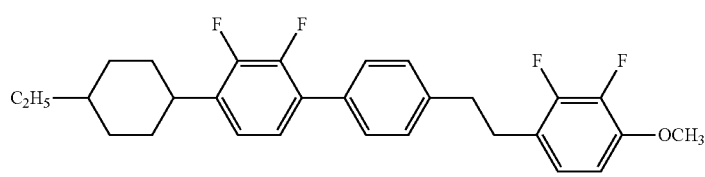 |
| 3280 | 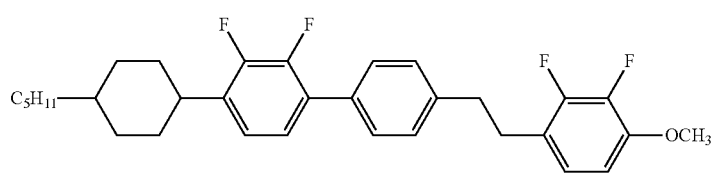 |
| 3281 | 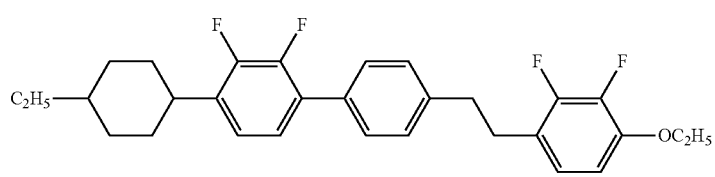 |
| 3282 | 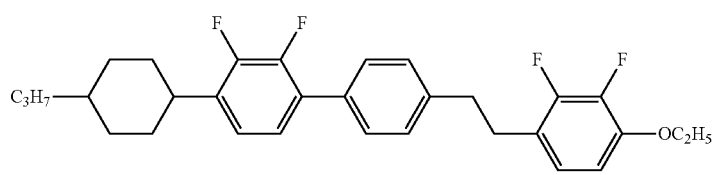 |
| 3283 | 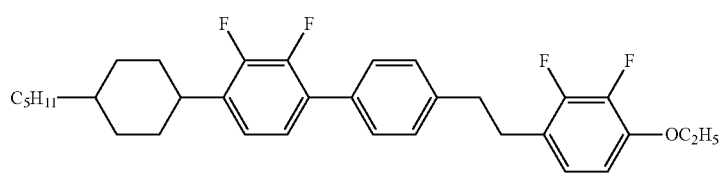 |
| 3284 | 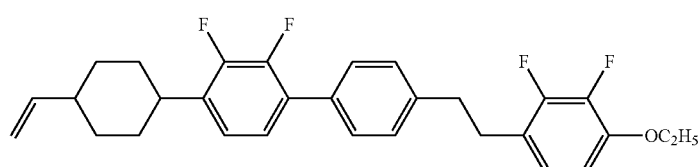 |
| 3285 | 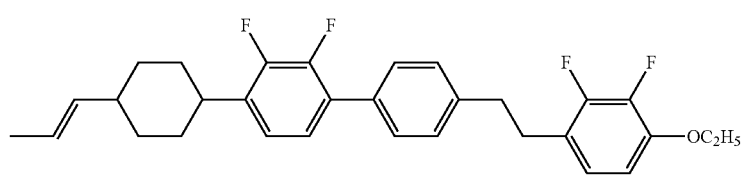 |

-continued
| No. |
|---|
| 3286 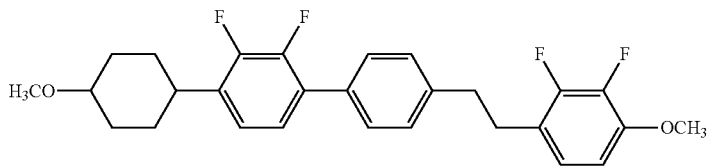 |
| 3287 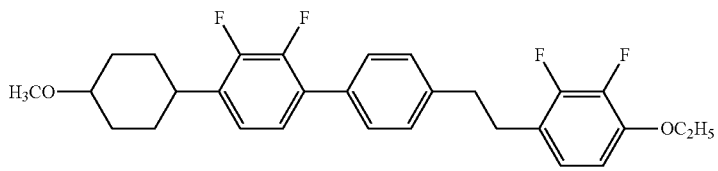 |
| 3288 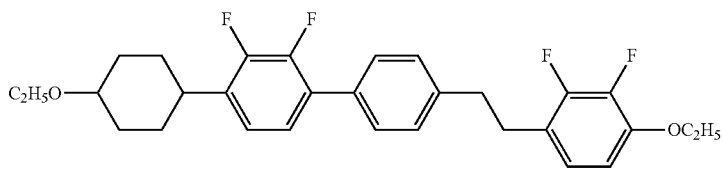 |
| 3289 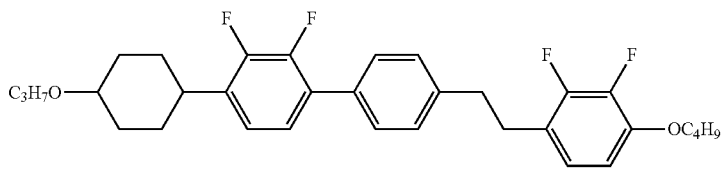 |
| 3290 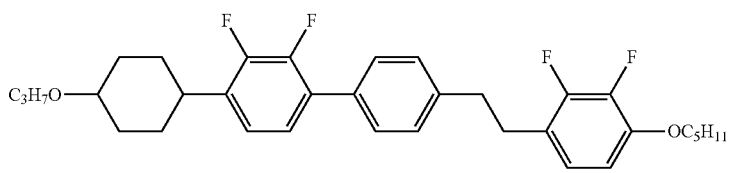 |
| 3291 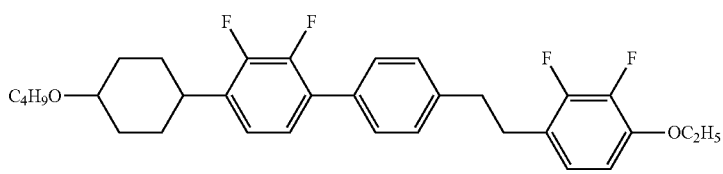 |
| 3292 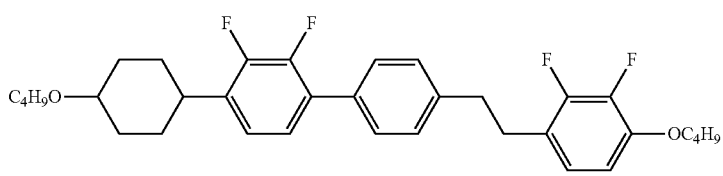 |
| 3293 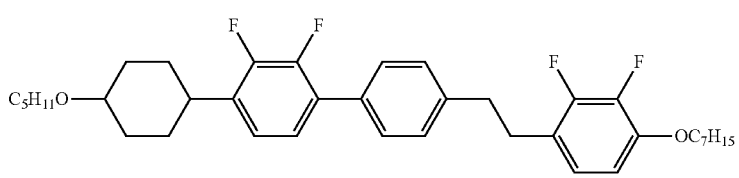 |

| No. | |
|---|---|
| 3294 | 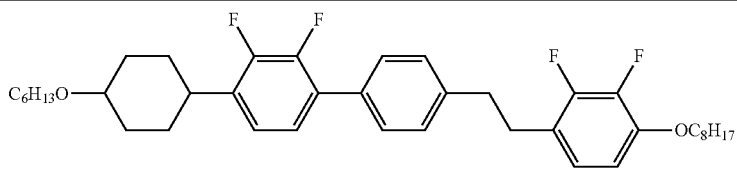 |
| 3295 | 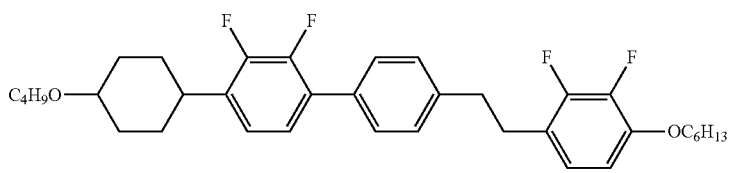 |
| 3296 | 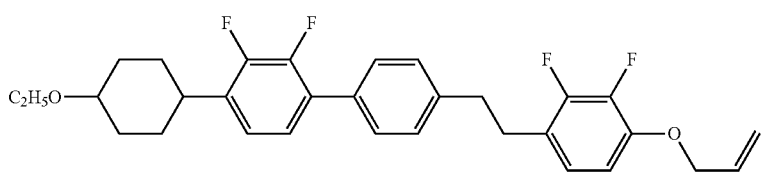 |
| 3297 | 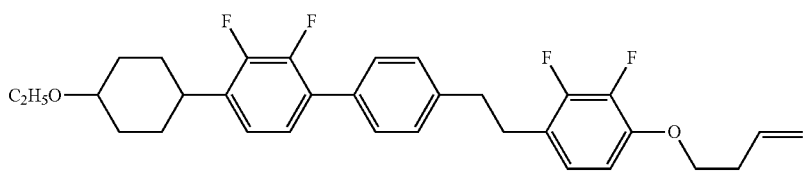 |
| 3298 | 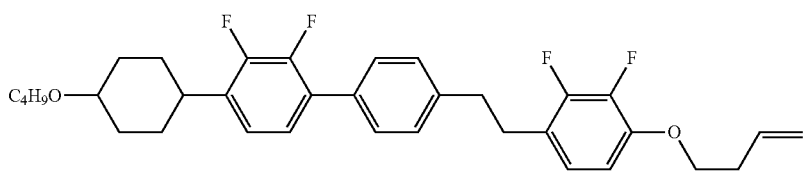 |
| 3299 | 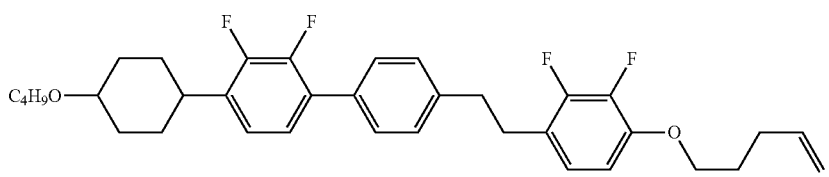 |
| 3300 | 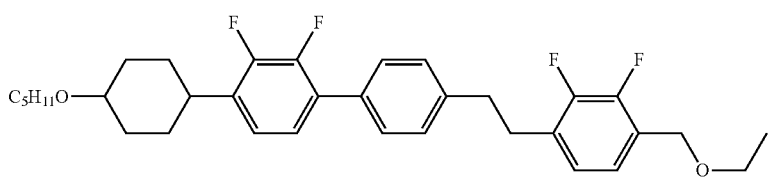 |
| 3301 | 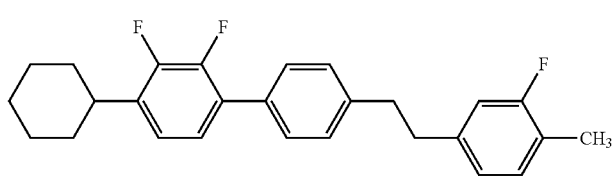 [SMILES: Cc1ccc(CCc2ccc(-c3ccc(C4CCCCC4)c(F)c3F)cc2)cc1F] |
| 3302 | 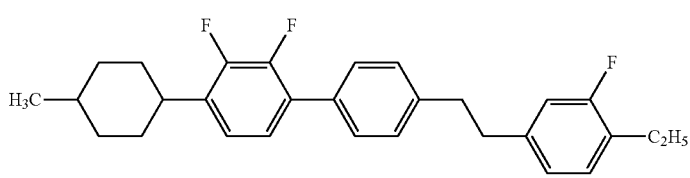 |

| No. | |
|---|---|
| 3303 | 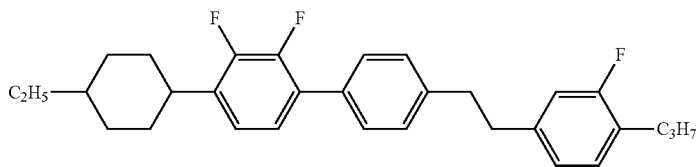 |
| 3304 | 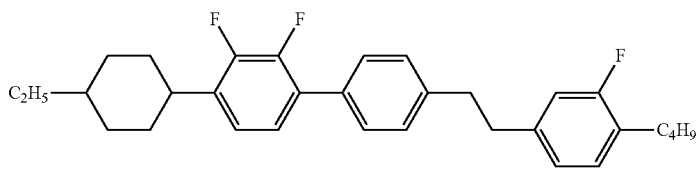 |
| 3305 | 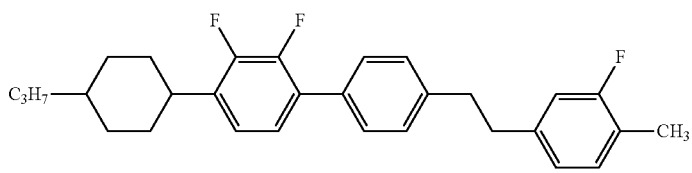 |
| 3306 | 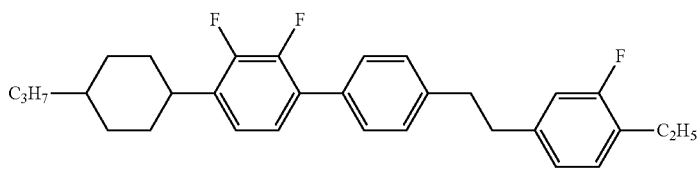 |
| 3307 | 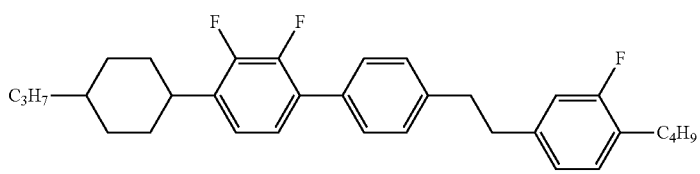 |
| 3308 | 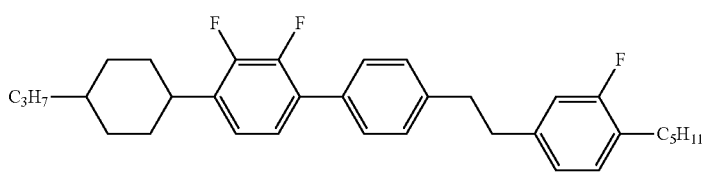 |
| 3309 | 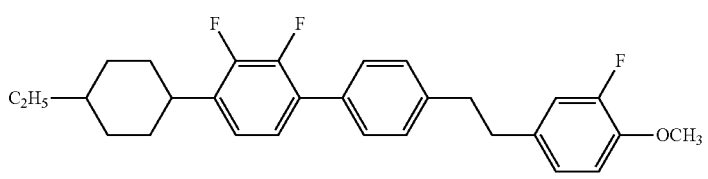 [SMILES: CCC1CCC(c2ccc(-c3ccc(CCc4ccc(OC)c(F)c4)cc3)c(F)c2F)CC1] |
| 3310 | 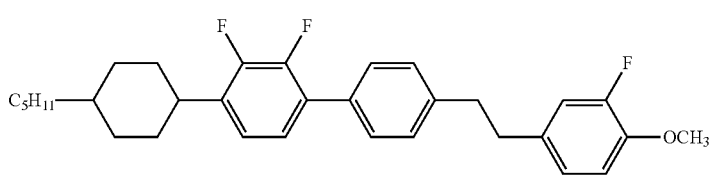 |

| No. | |
|---|---|
| 3311 | 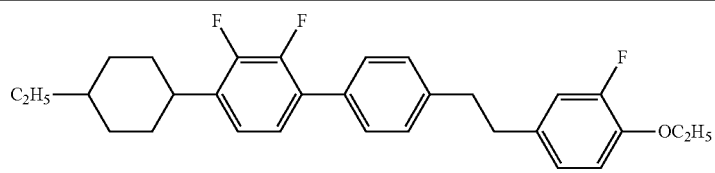 |
| 3312 | 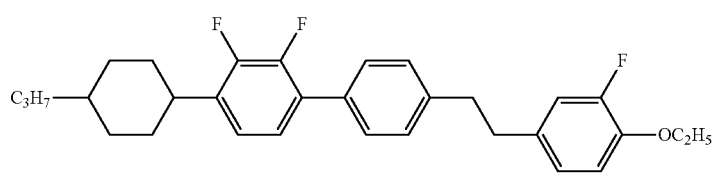 |
| 3313 | 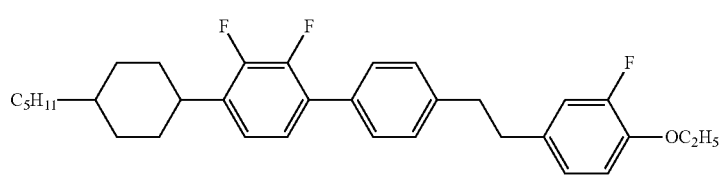 |
| 3314 | 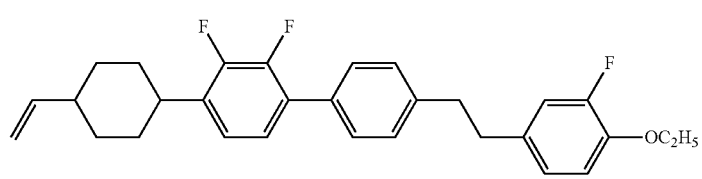 [SMILES: C=CC1CCC(c2ccc(-c3ccc(CCc4ccc(OCC)c(F)c4)cc3)c(F)c2F)CC1] |
| 3315 | 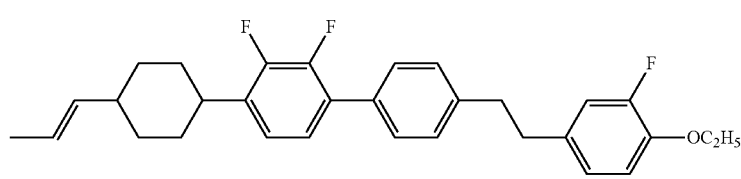 |
| 3316 | 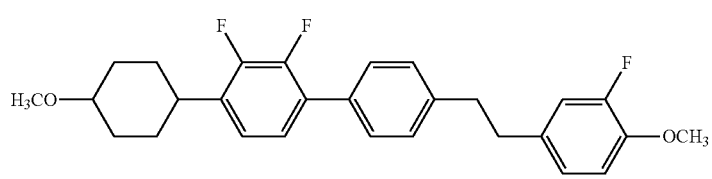 |
| 3317 | 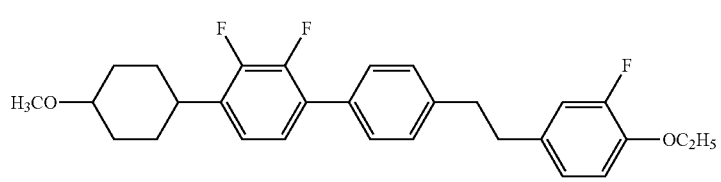 |
| 3318 | 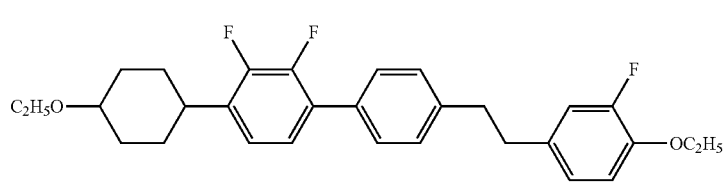 |
| 3319 | 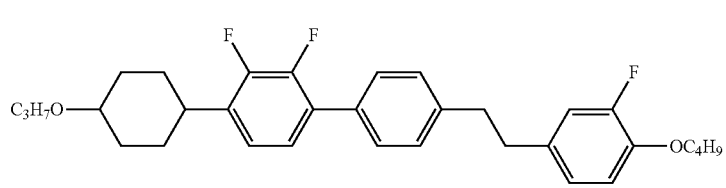 |

| No. | |
|---|---|
| 3320 | 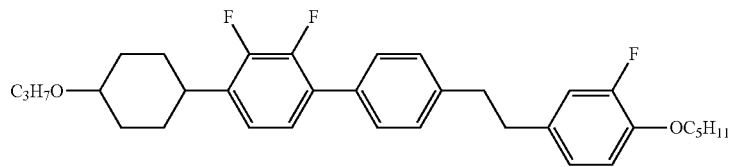 |
| 3321 | 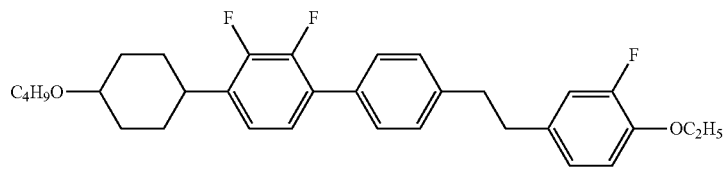 |
| 3322 | 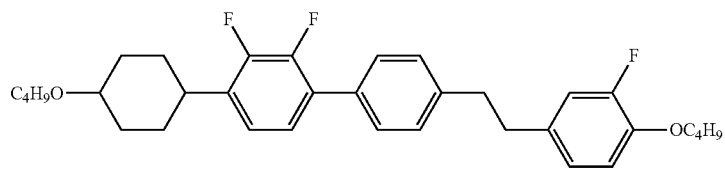 |
| 3323 | 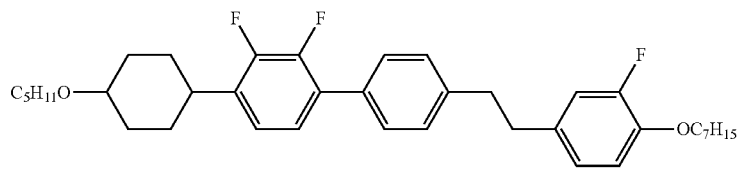 |
| 3324 | 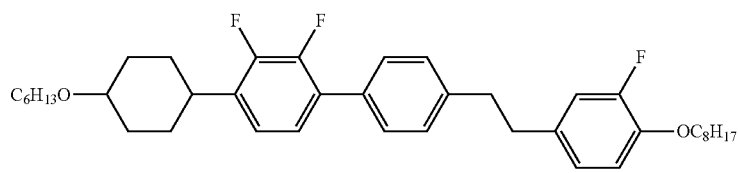 |
| 3325 | 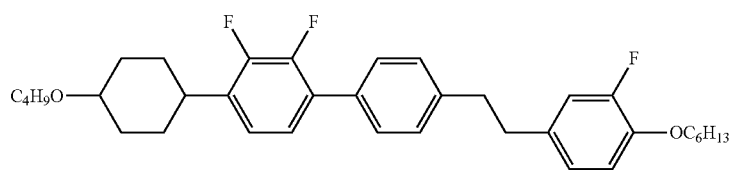 |
| 3326 | 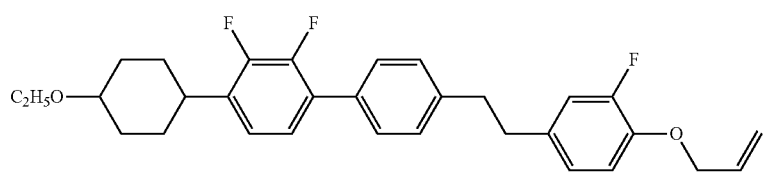 |
| 3327 | 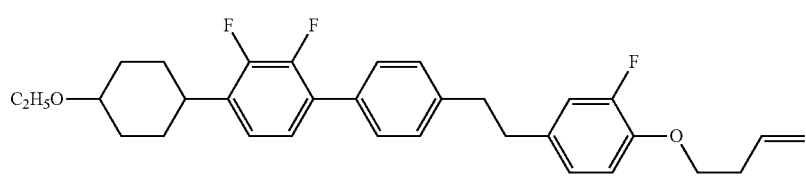 |

| No. | |
|---|---|
| 3328 | 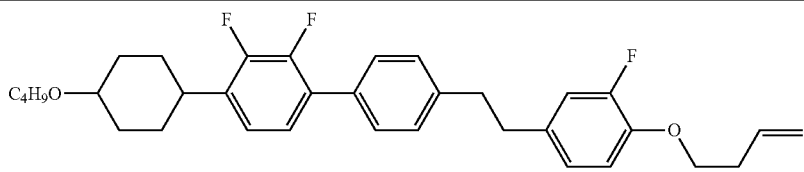 |
| 3329 | 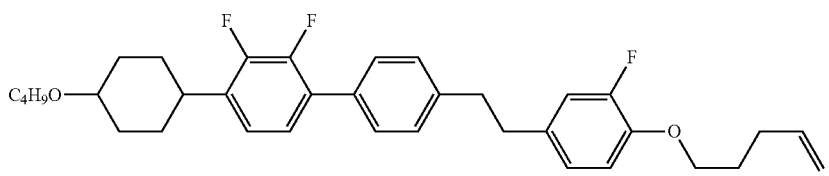 |
| 3330 | 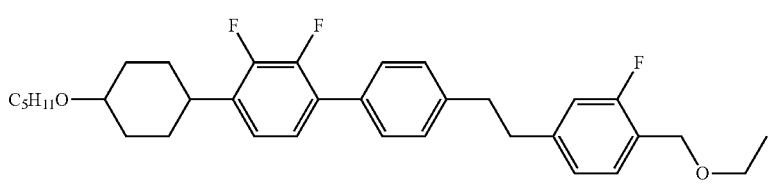 |
| 3331 | 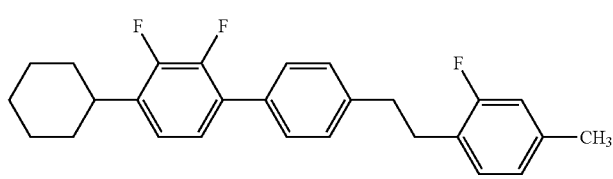 [SMILES: Cc1ccc(CCc2ccc(-c3ccc(C4CCCCC4)c(F)c3F)cc2)c(F)c1] |
| 3332 | 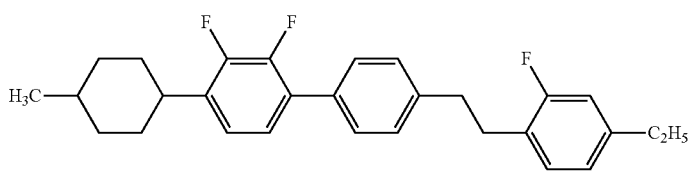 |
| 3333 | 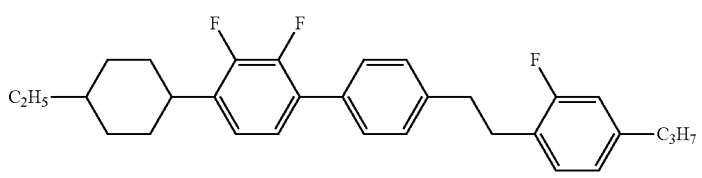 |
| 3334 | 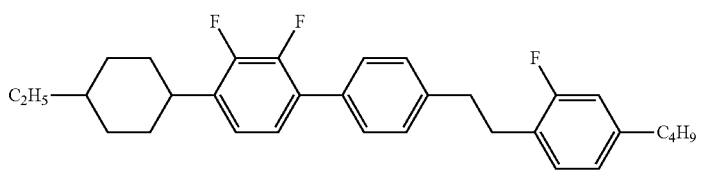 |
| 3335 | 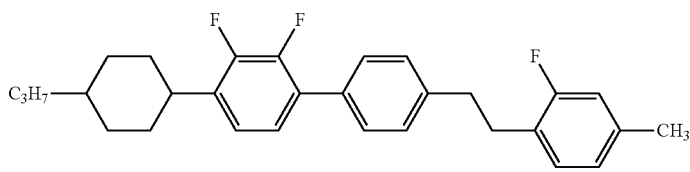 |
| 3336 | 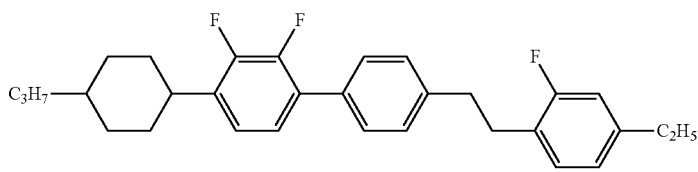 |

| No. | |
|---|---|
| 3337 | 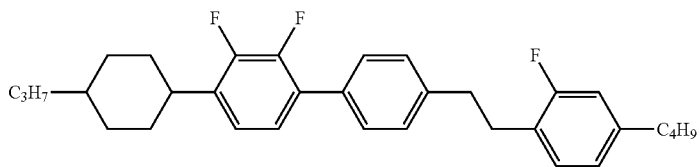 |
| 3338 | 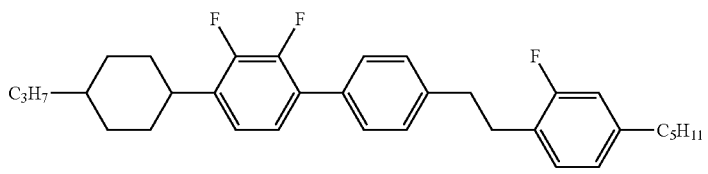 |
| 3339 | 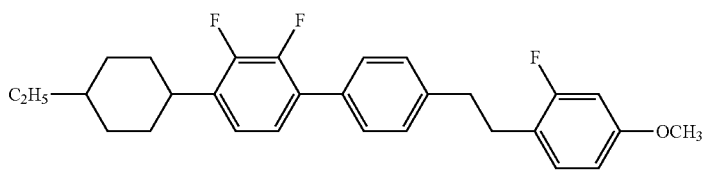 |
| 3340 | 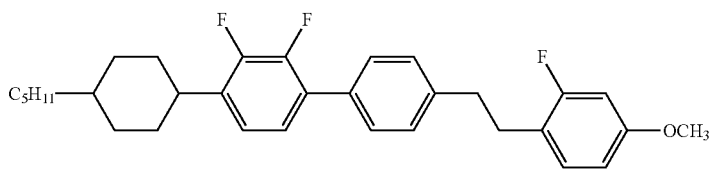 |
| 3341 | 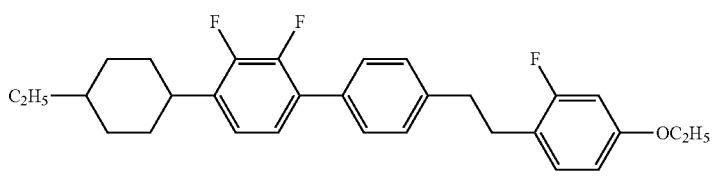 |
| 3342 | 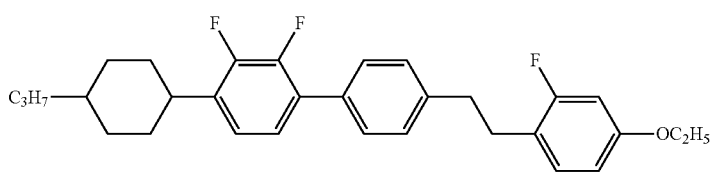 |
| 3343 | 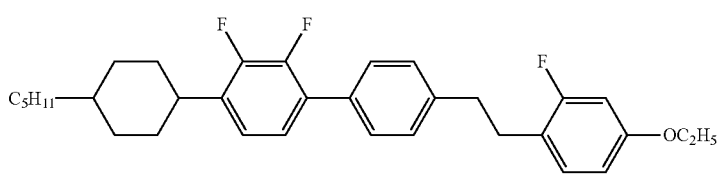 |
| 3344 | 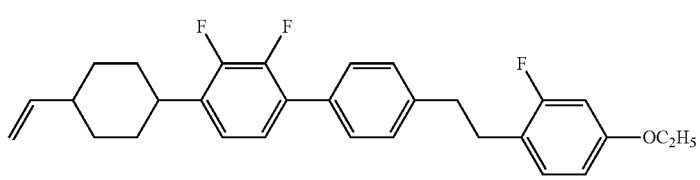 |

| No. | |
|---|---|
| 3345 | 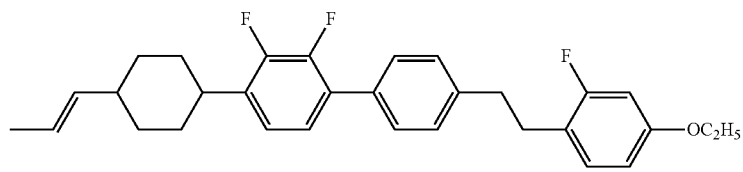 |
| 3346 | 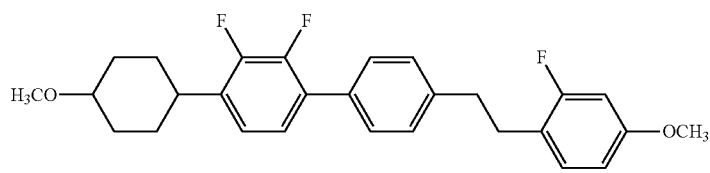 [SMILES: COc1ccc(CCc2ccc(-c3ccc(C4CCC(OC)CC4)c(F)c3F)cc2)c(F)c1] |
| 3347 | 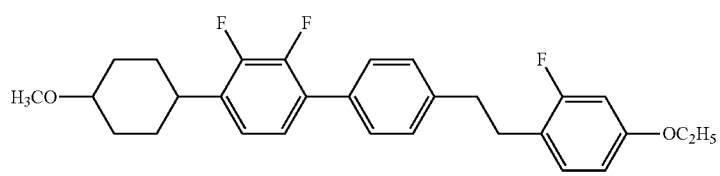 |
| 3348 | 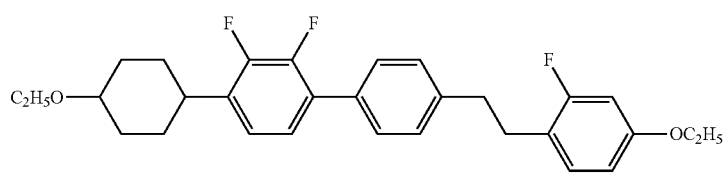 |
| 3349 | 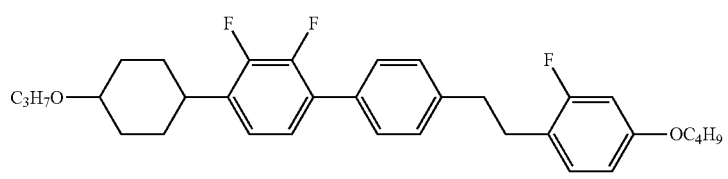 |
| 3350 | 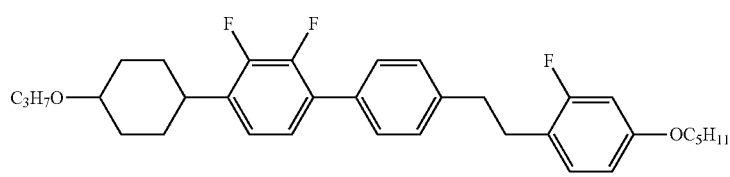 |
| 3351 | 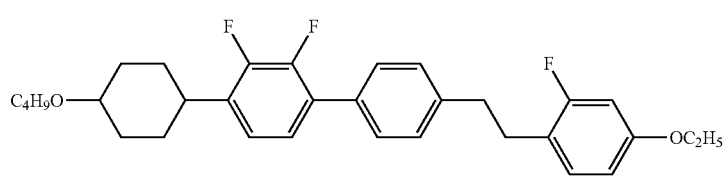 |
| 3352 | 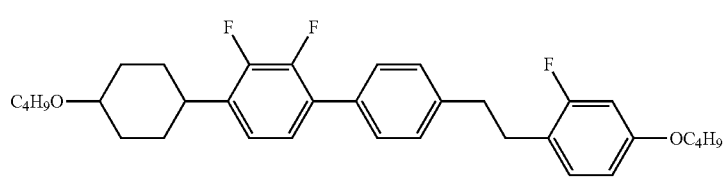 |
| 3353 | 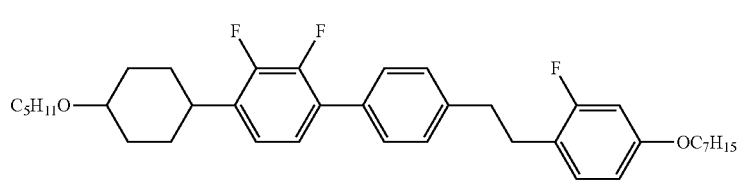 |

| No. | |
|---|---|
| 3354 | 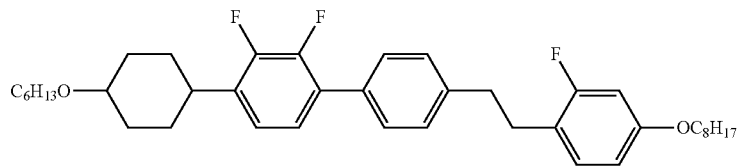 |
| 3355 | 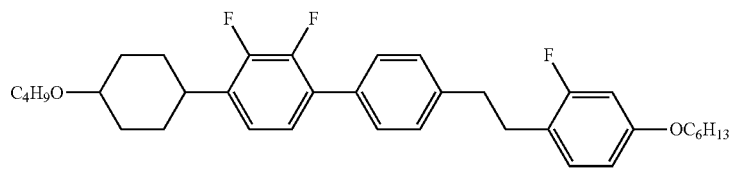 |
| 3356 | 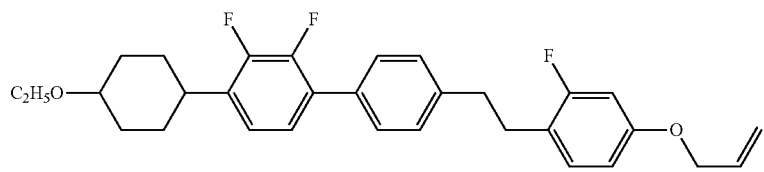 |
| 3357 | 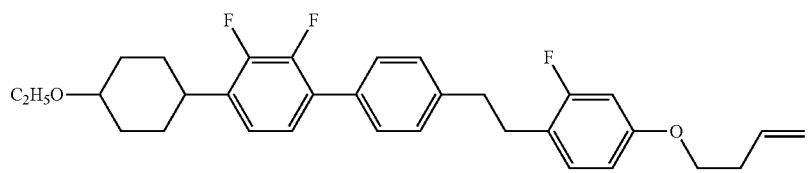 |
| 3358 | 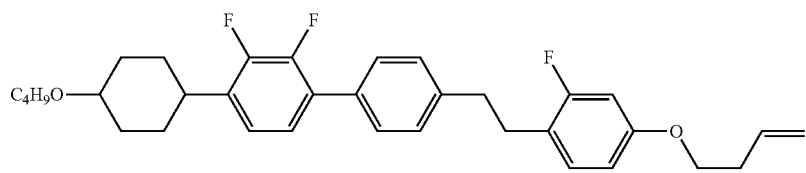 |
| 3359 | 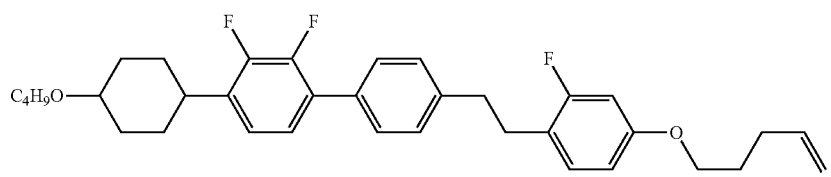 |
| 3360 | 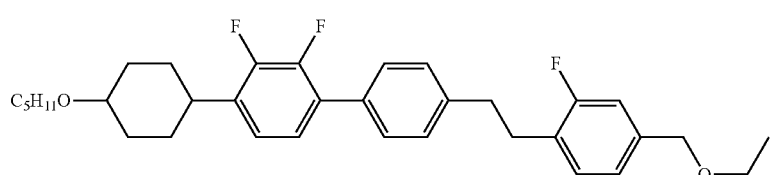 |
| 3361 | 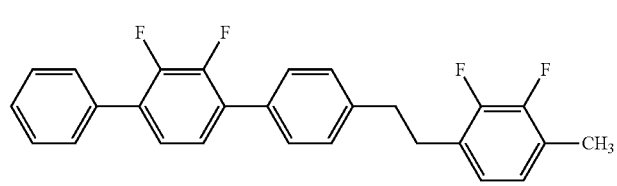 |

| No. | |
|---|---|
| 3362 | 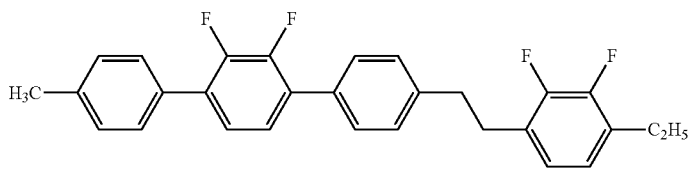 |
| 3363 | 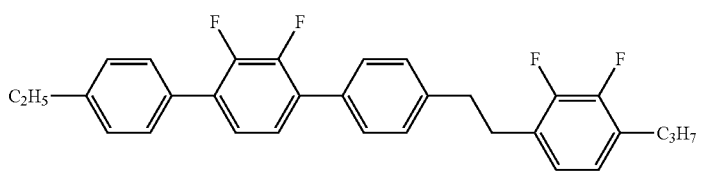 |
| 3364 | 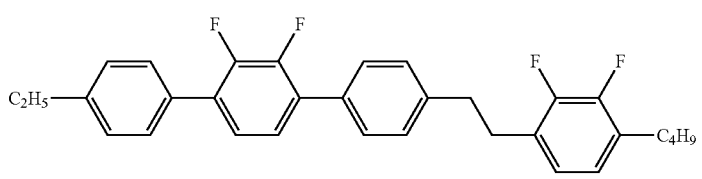 |
| 3365 | 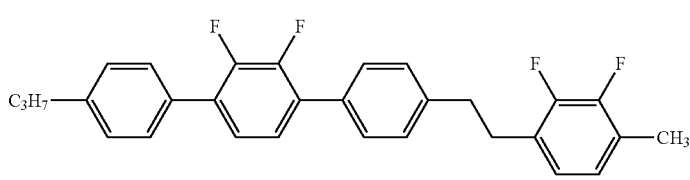 |
| 3366 | 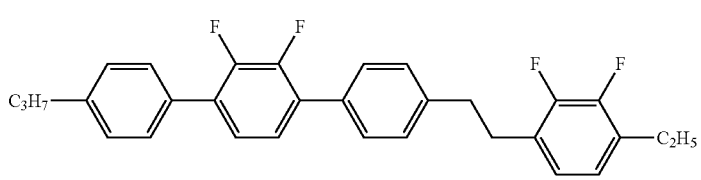 |
| 3367 | 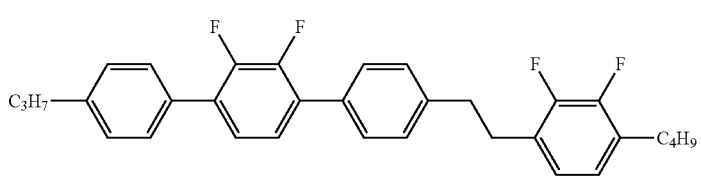 |
| 3368 | 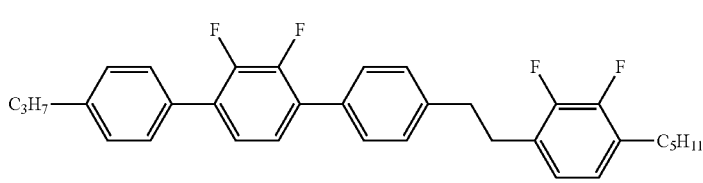 |
| 3369 | 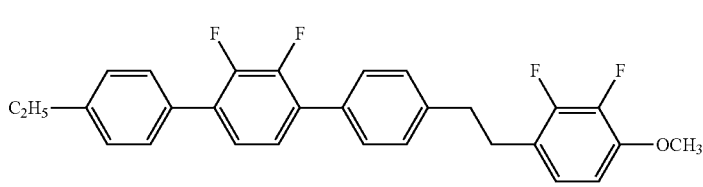 |
| 3370 | 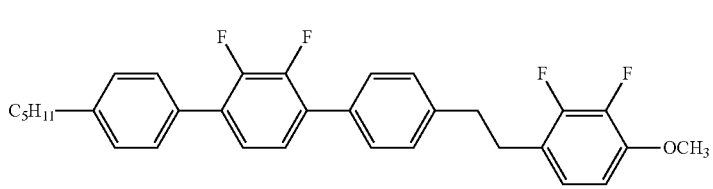 |

| No. | |
|---|---|
| 3371 | 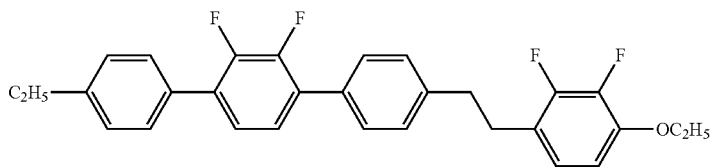 |
| 3372 | 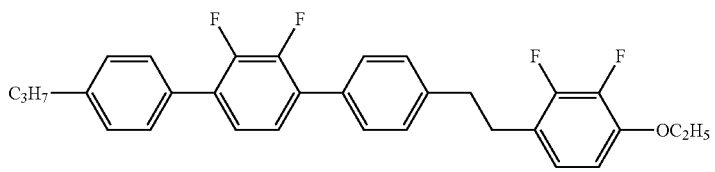 |
| 3373 | 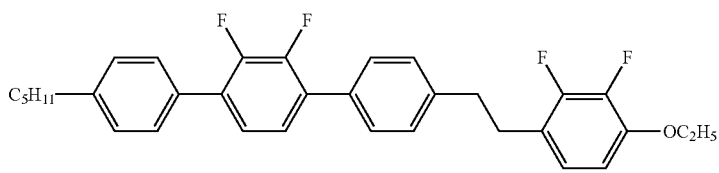 |
| 3374 | 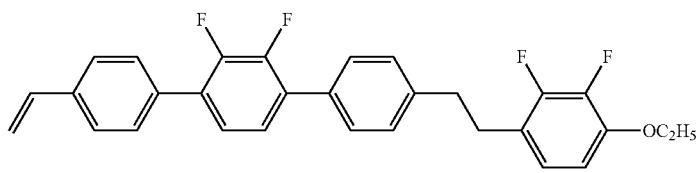 |
| 3375 | 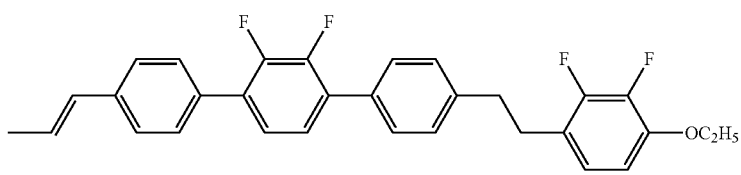 |
| 3376 | 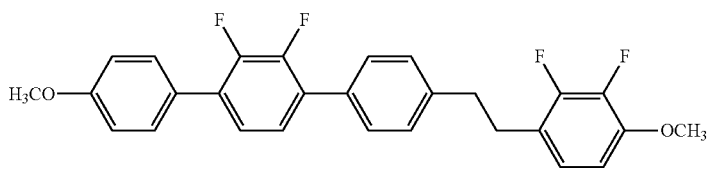 [SMILES: COc1ccc(-c2ccc(-c3ccc(CCc4ccc(OC)c(F)c4F)cc3)c(F)c2F)cc1] |
| 3377 | 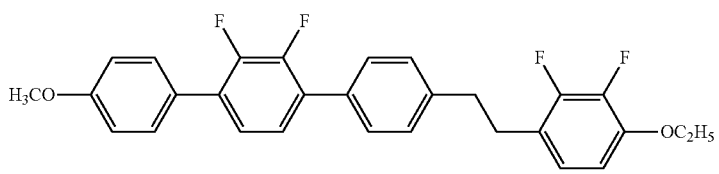 |
| 3378 | 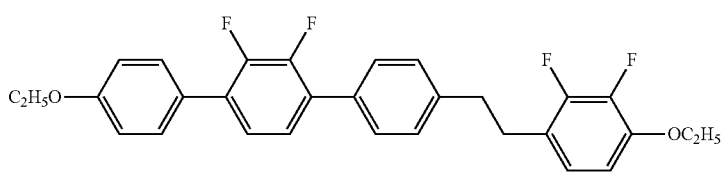 |

| No. | |
|---|---|
| 3379 | 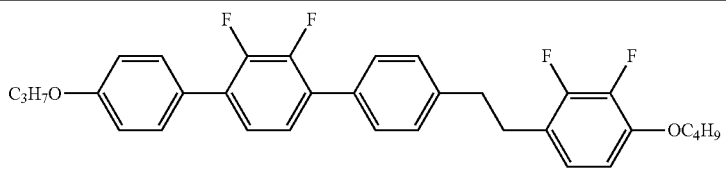 |
| 3380 | 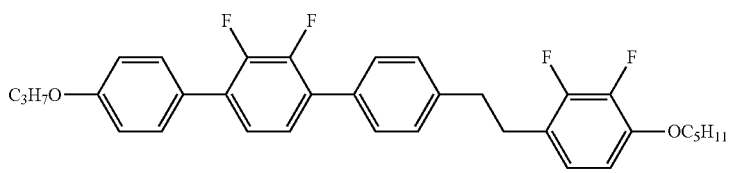 |
| 3381 |  |
| 3382 |  |
| 3383 | 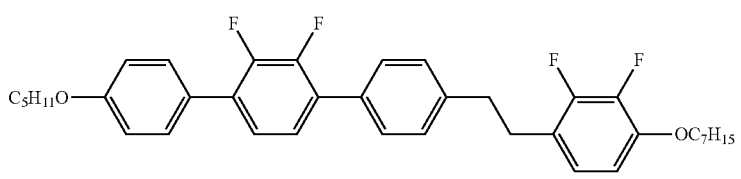 |
| 3384 | 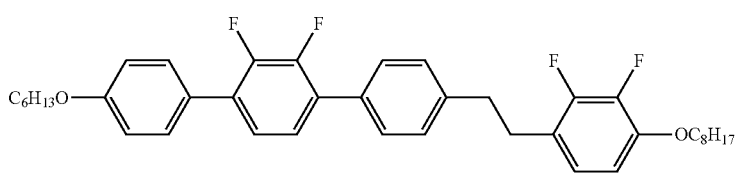 |
| 3385 | 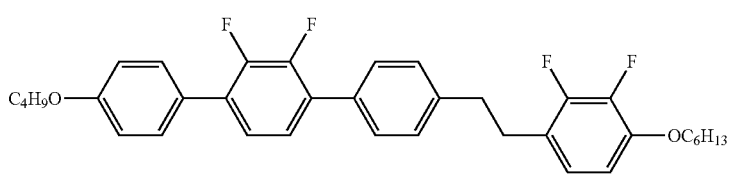 |
| 3386 | 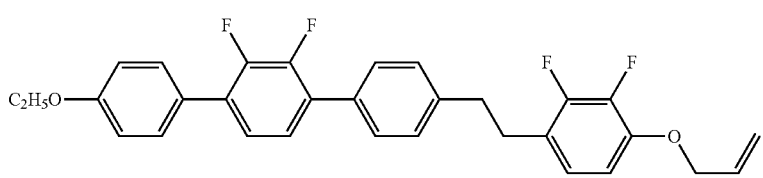 |
| 3387 | 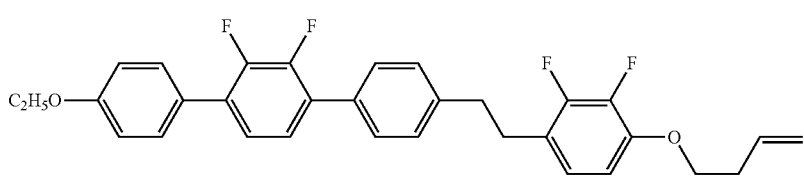 |

-continued
| No. | |
|---|---|
| 3388 | 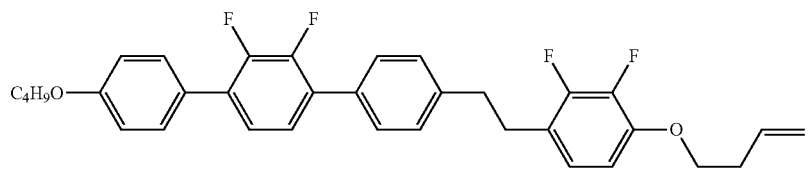 |
| 3389 | 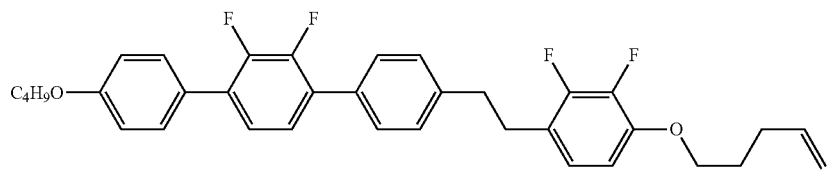 |
| 3390 | 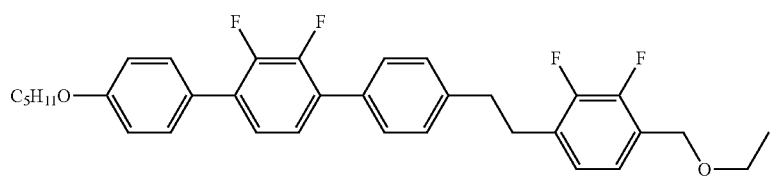 |
| 3391 | 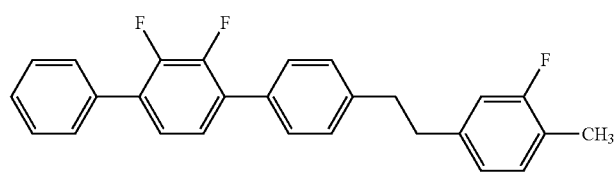 |
| 3392 | 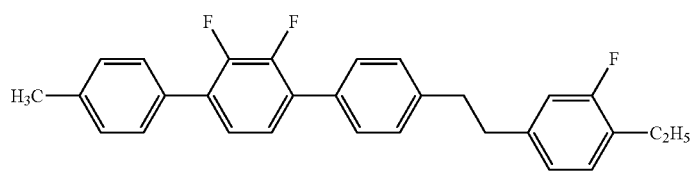 |
| 3393 | 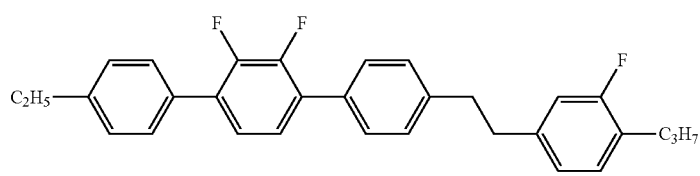 |
| 3394 | 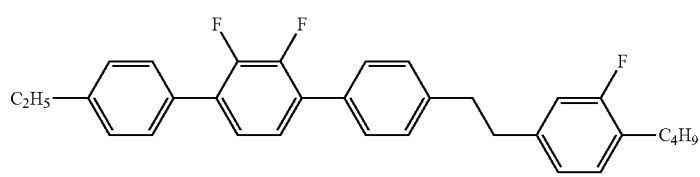 |
| 3395 | 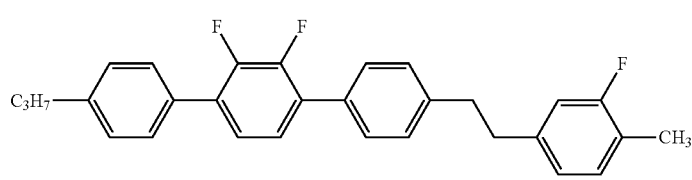 |

-continued
| No. | |
|---|---|
| 3396 | 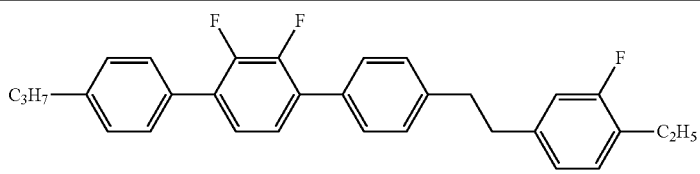 |
| 3397 | 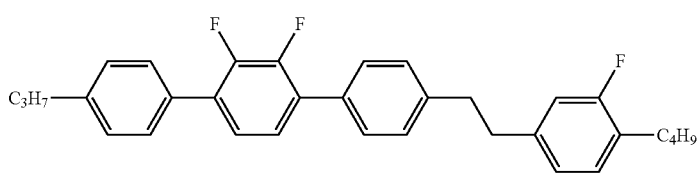 |
| 3398 | 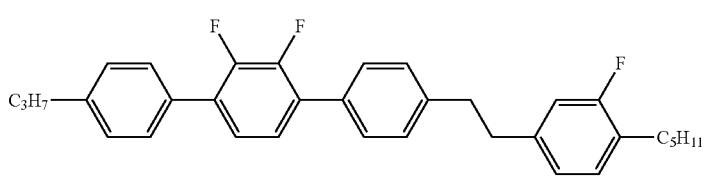 |
| 3399 | 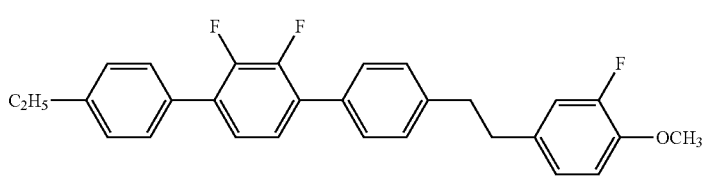 |
| 3400 | 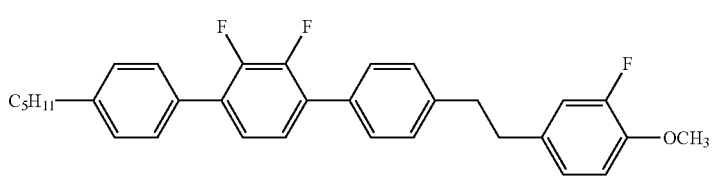 |
| 3401 | 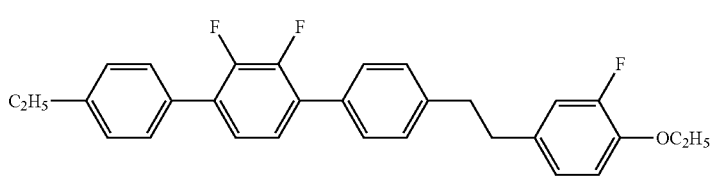 |
| 3402 | 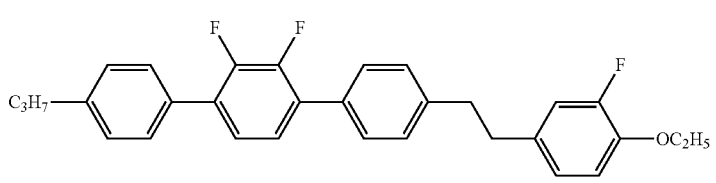 |
| 3403 | 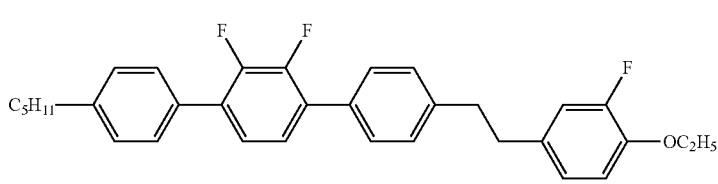 [SMILES: CCOc1ccc(CCc2ccc(-c3ccc(-c4ccc(OC)cc4)c(F)c3F)cc2)cc1F] |
| 3404 | 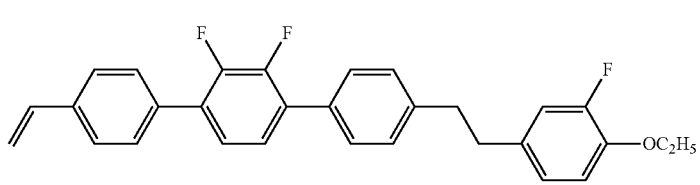 |

| No. |
|---|
| 3405 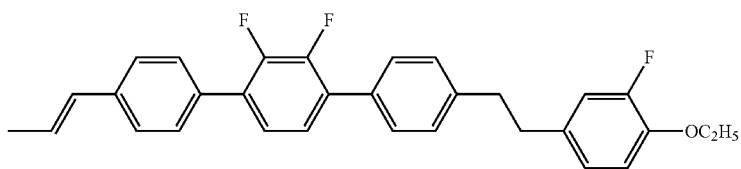 |
| 3406 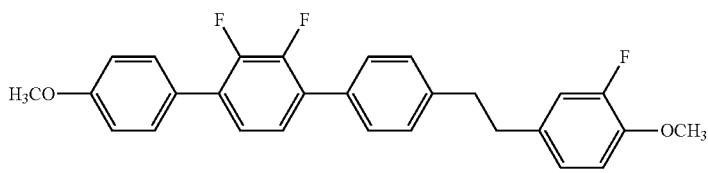 |
| 3407 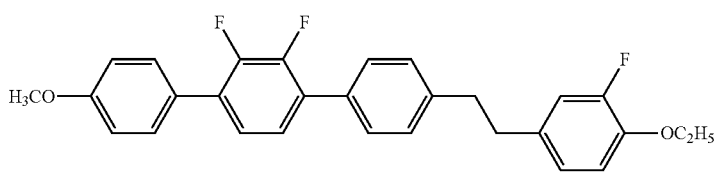 |
| 3408 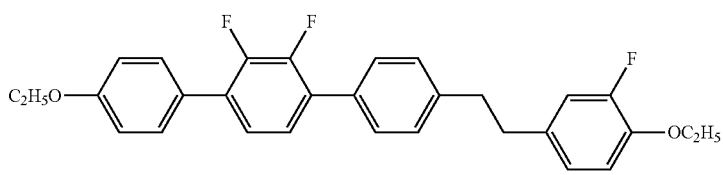 |
| 3409 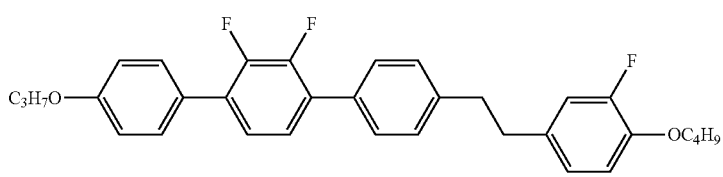 |
| 3410 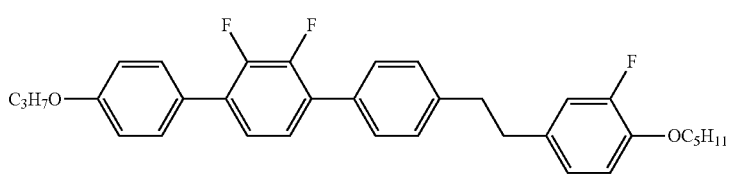 |
| 3411 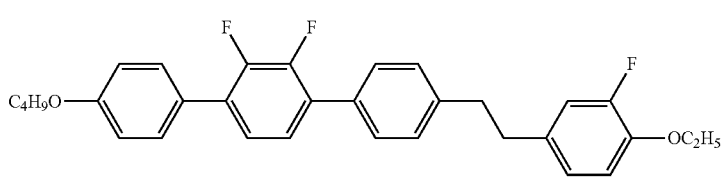 |
| 3412 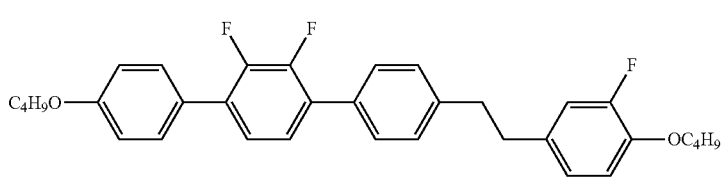 |

| No. |
|---|
| 3413 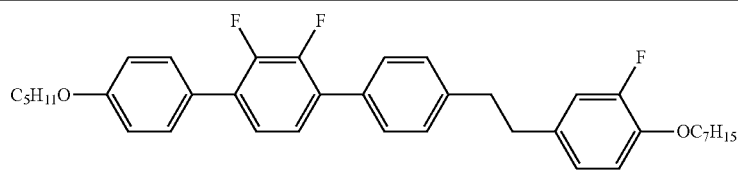 |
| 3414 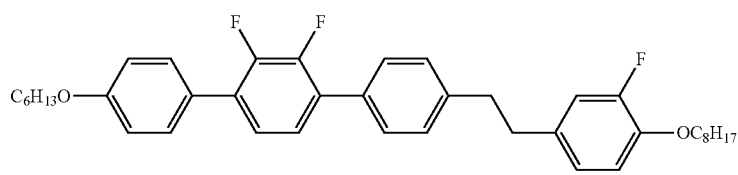 |
| 3415 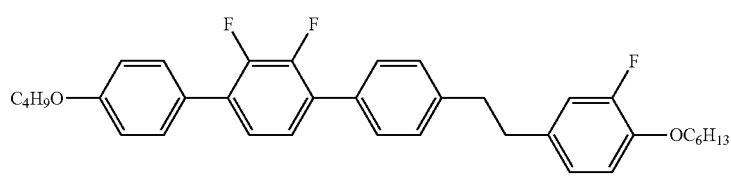 |
| 3416 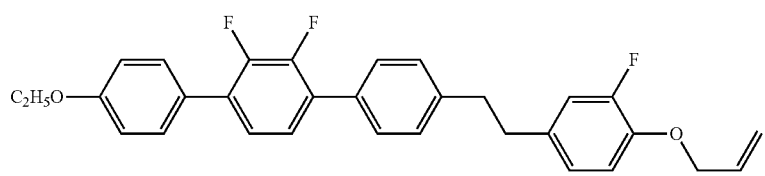 |
| 3417 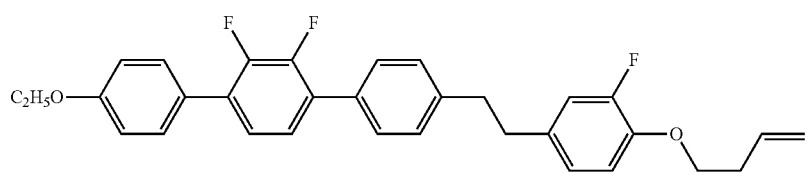 |
| 3418 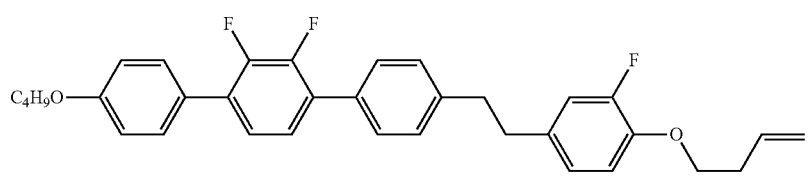 |
| 3419 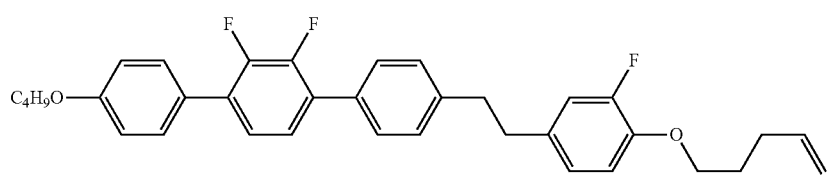 |
| 3420 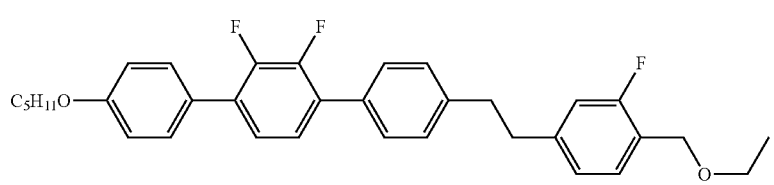 |
| 3421 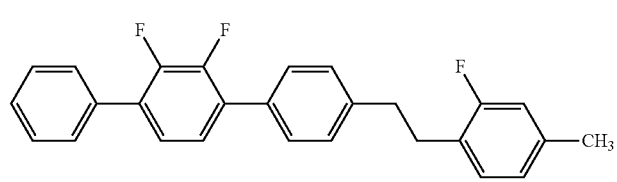 |

| No. | |
|---|---|
| 3422 | 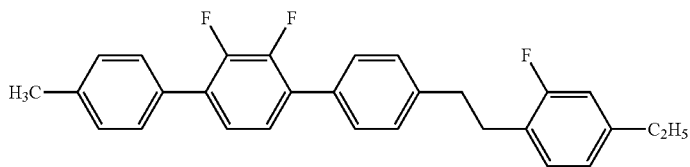 |
| 3423 | 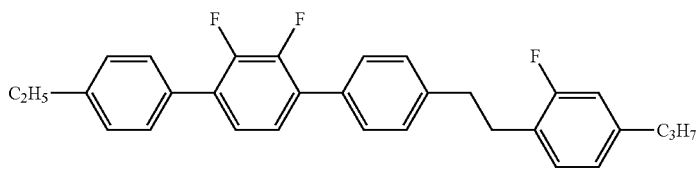 |
| 3424 | 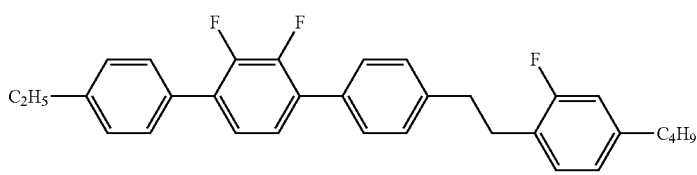 |
| 3425 | 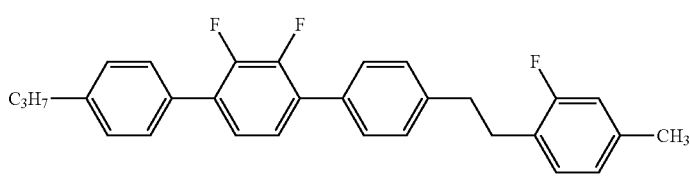 |
| 3426 | 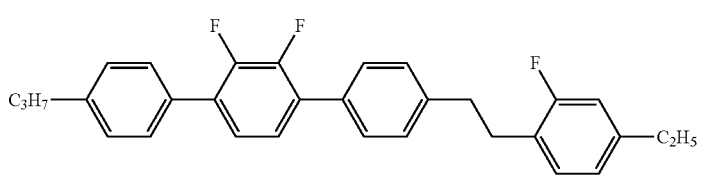 |
| 3427 | 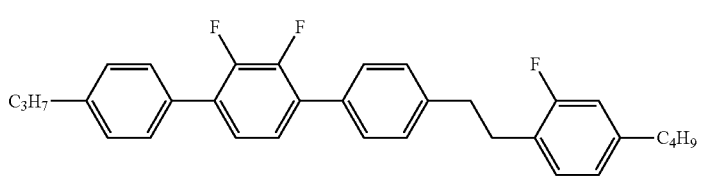 |
| 3428 | 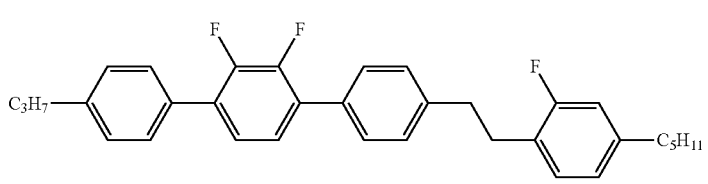 [SMILES: CCc1ccc(-c2ccc(-c3ccc(CCc4ccc(OC)cc4F)cc3)c(F)c2F)cc1] |
| 3429 | 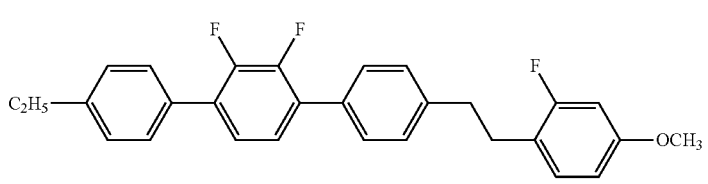 |

| No. | |
|---|---|
| 3430 | 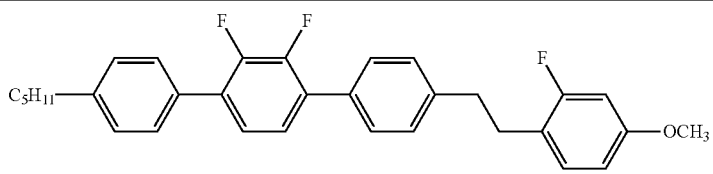 |
| 3431 | 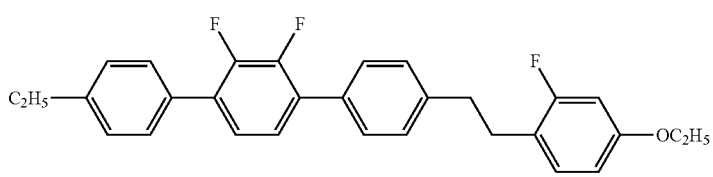 |
| 3432 | 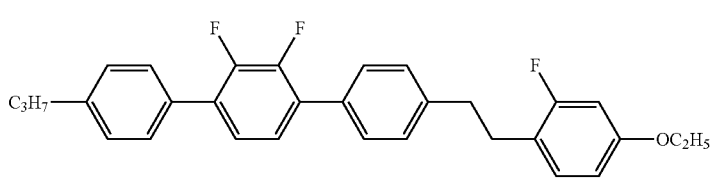 |
| 3433 | 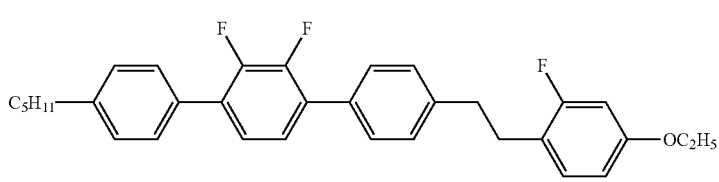 [SMILES: CCOc1ccc(CCc2ccc(-c3ccc(-c4ccc(OC)cc4)c(F)c3F)cc2)c(F)c1] |
| 3434 | 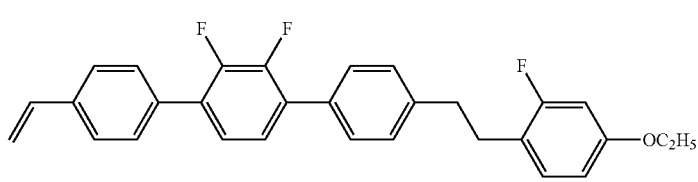 |
| 3435 | 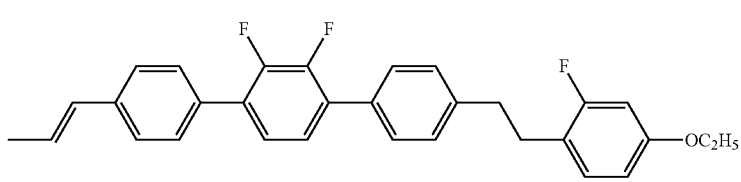 |
| 3436 | 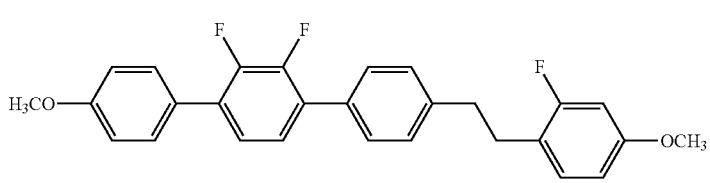 |
| 3437 | 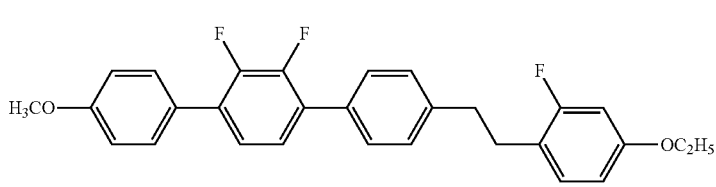 |
| 3438 | 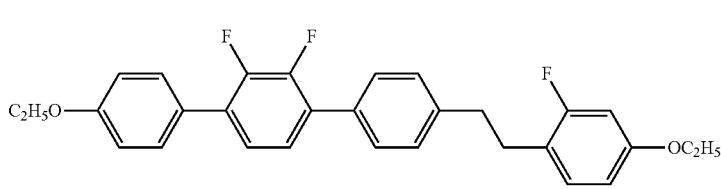 |

| No. | |
|---|---|
| 3439 | 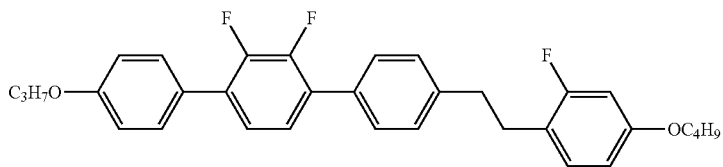 |
| 3440 | 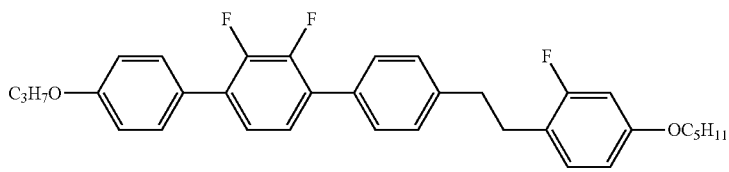 |
| 3441 | 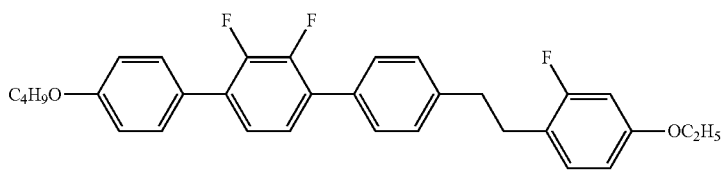 |
| 3442 | 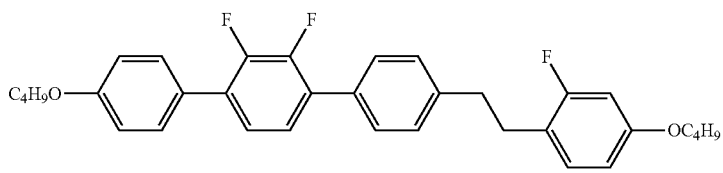 |
| 3443 | 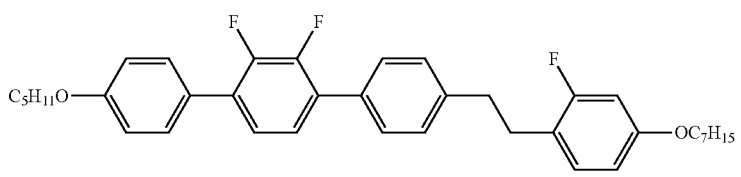 |
| 3444 | 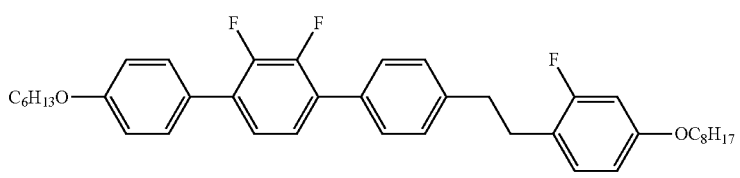 |
| 3445 | 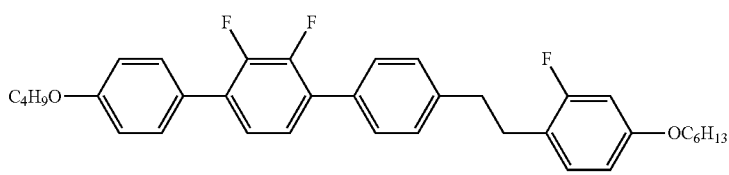 |
| 3446 | 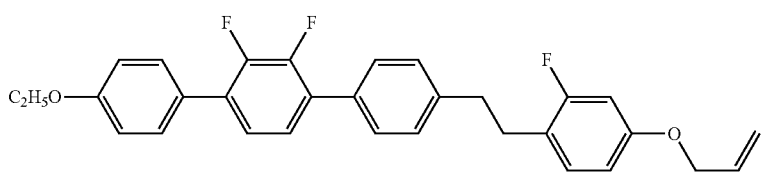 |

| No. |
|---|
| 3447 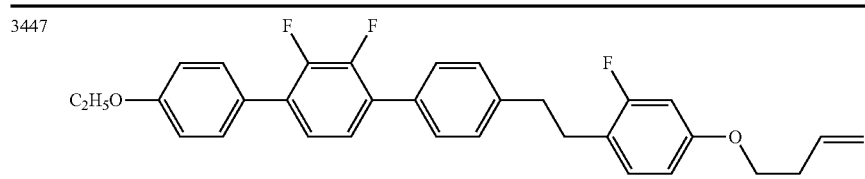 |
| 3448 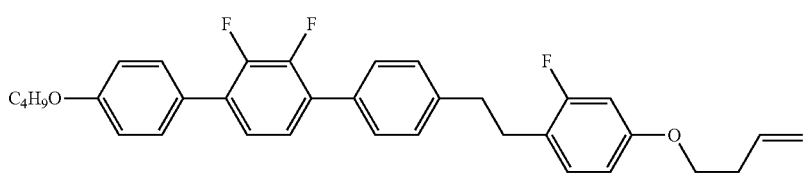 |
| 3449 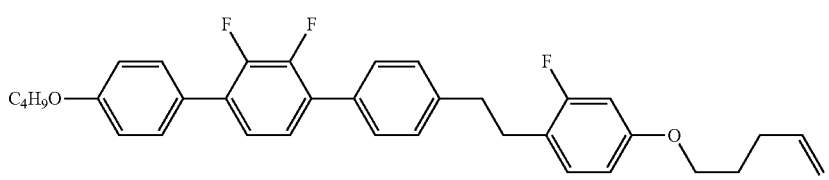 |
| 3450 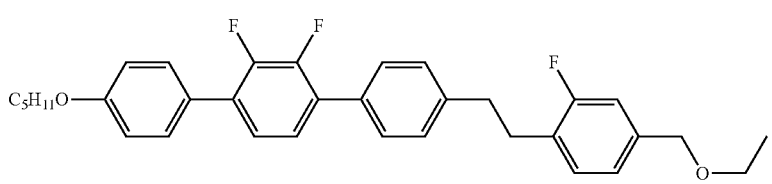 |
| 3451 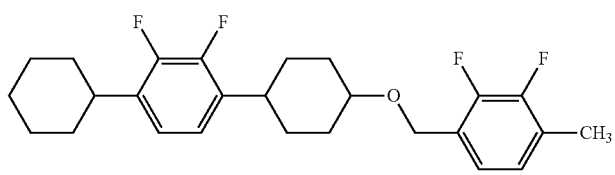 |
| 3452 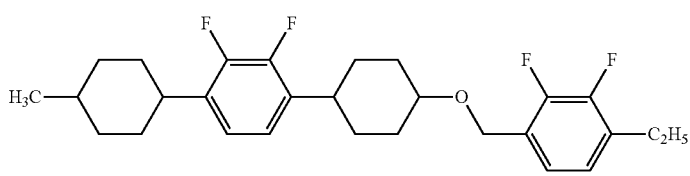 |
| 3453 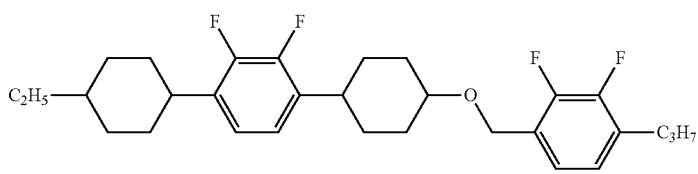 |
| 3454 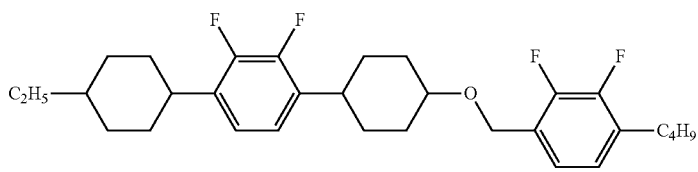 |
| 3455 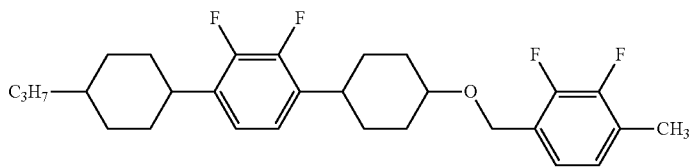 |

| No. | |
|---|---|
| 3456 | 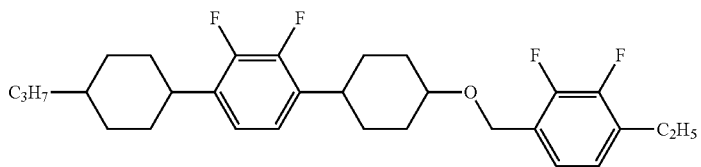 |
| 3457 | 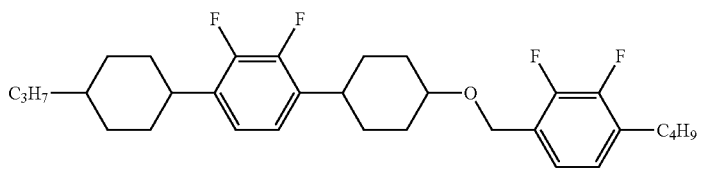 |
| 3458 | 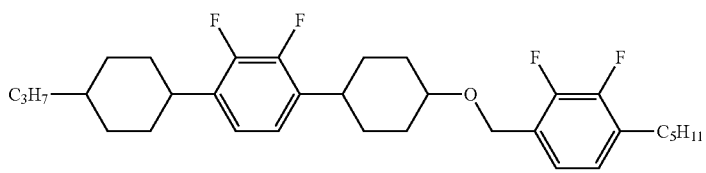 |
| 3459 | 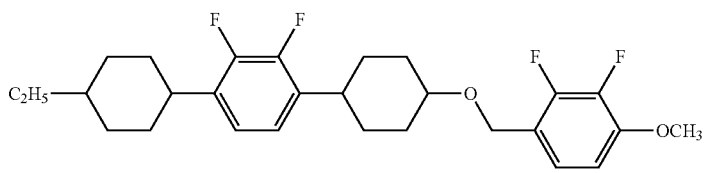 |
| 3460 | 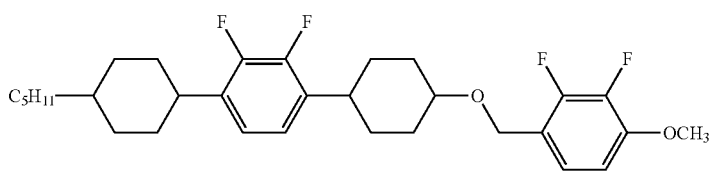 |
| 3461 | 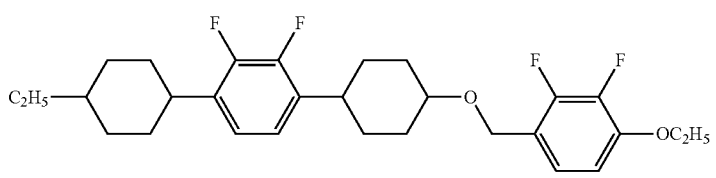 |
| 3462 | 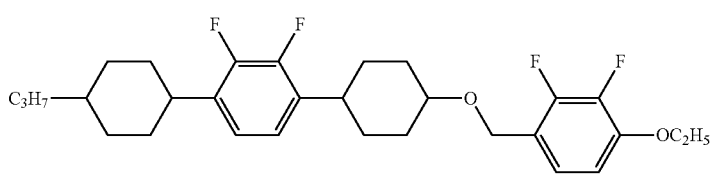 |
| 3463 | 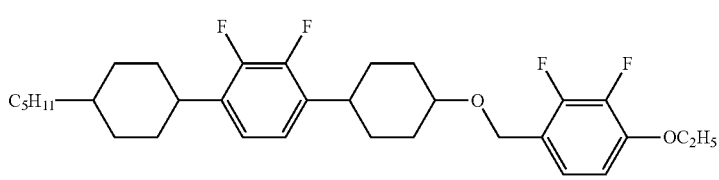 |

-continued
No.
3464 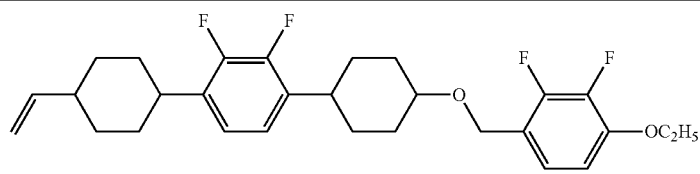
3465 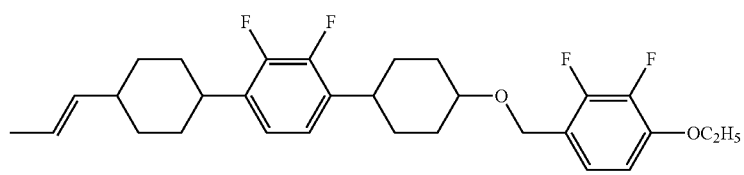
3466 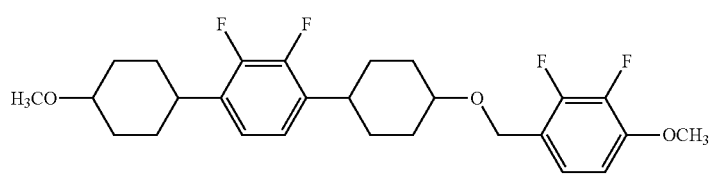
3467 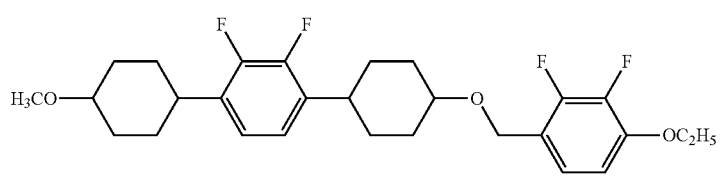 [SMILES: CCOc1ccc(COC2CCC(c3ccc(C4CCC(OC)CC4)c(F)c3F)CC2)c(F)c1F]
3468 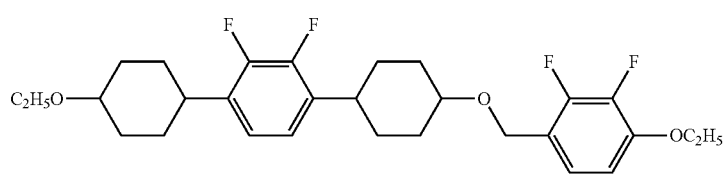
3469 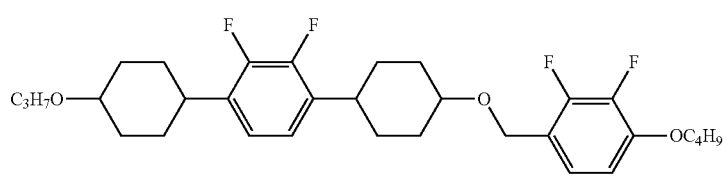
3470 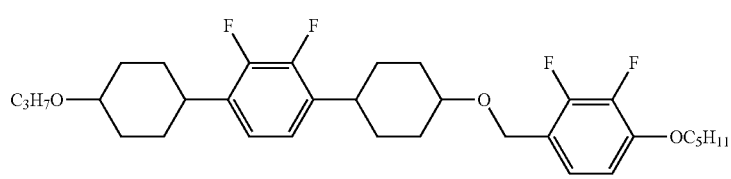
3471 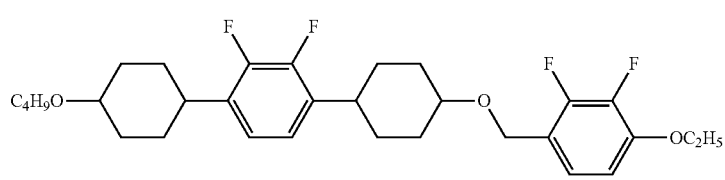
3472 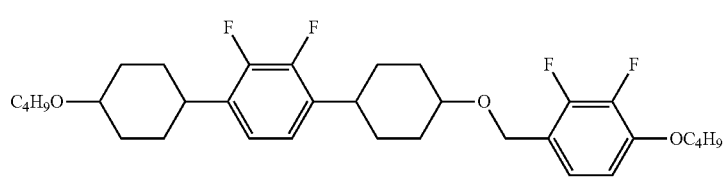

| No. |
|---|
| 3473 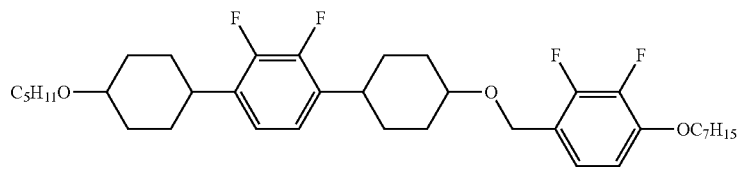 |
| 3474 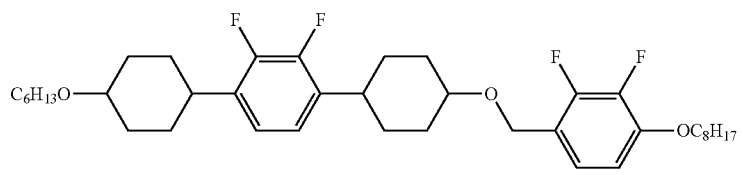 |
| 3475 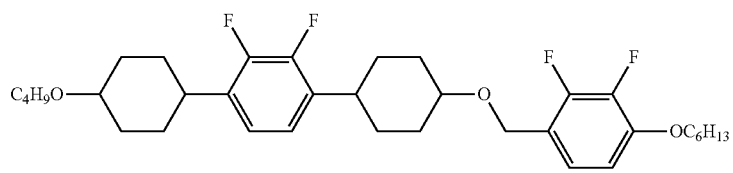 |
| 3476 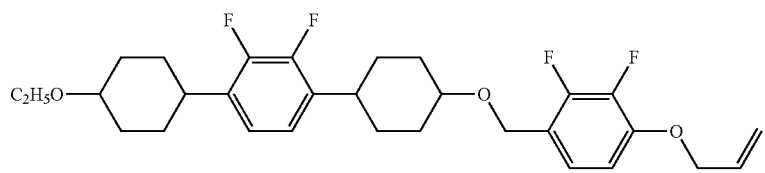 |
| 3477 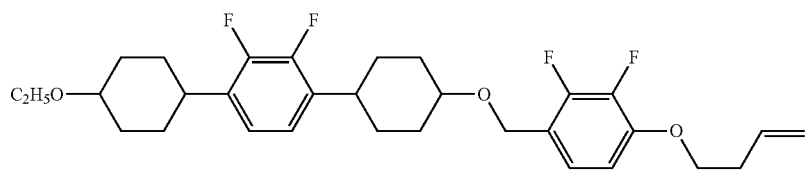 |
| 3478 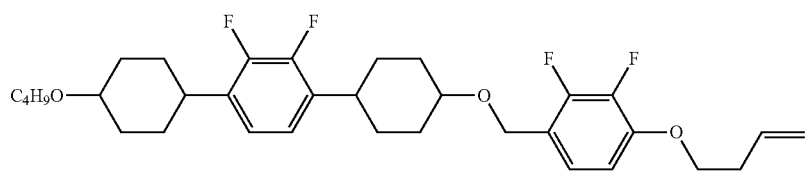 |
| 3479 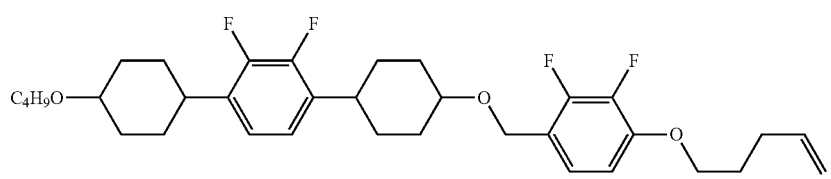 |
| 3480 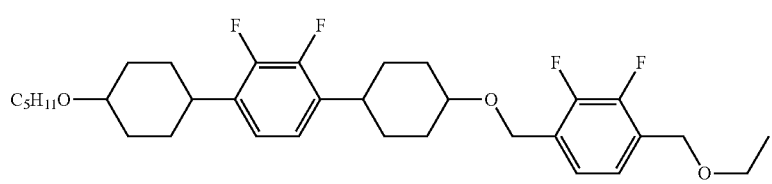 |

-continued
| No. | |
|---|---|
| 3481 | 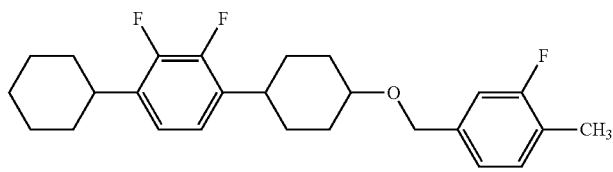 |
| 3482 | 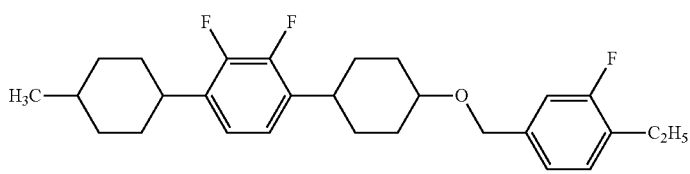 |
| 3483 | 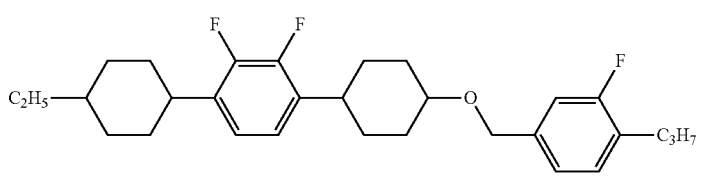 |
| 3484 | 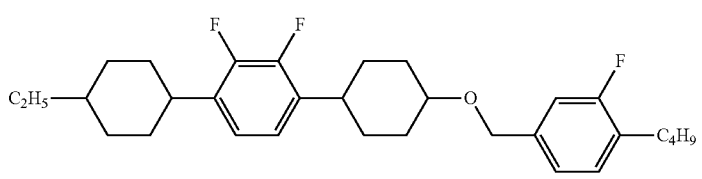 |
| 3485 | 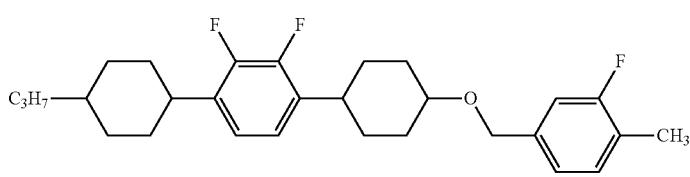 |
| 3486 | 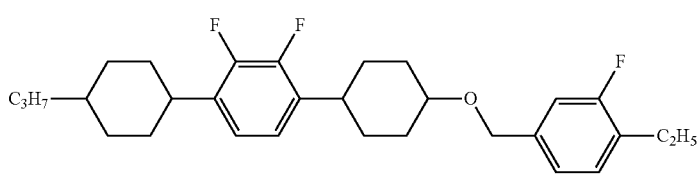 |
| 3487 | 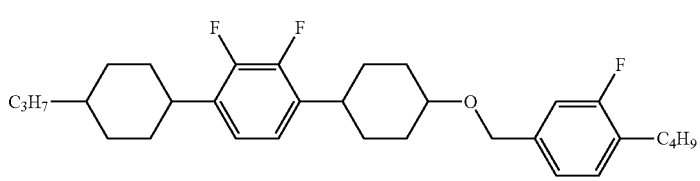 |
| 3488 | 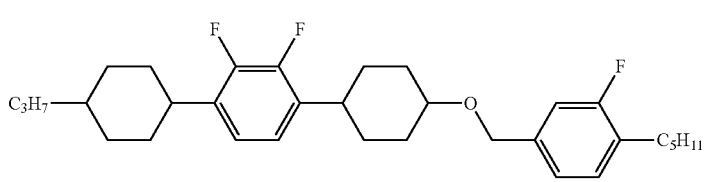 [SMILES: CCC1CCC(c2ccc(C3CCC(OCc4ccc(OC)c(F)c4)CC3)c(F)c2F)CC1] |
| 3489 | 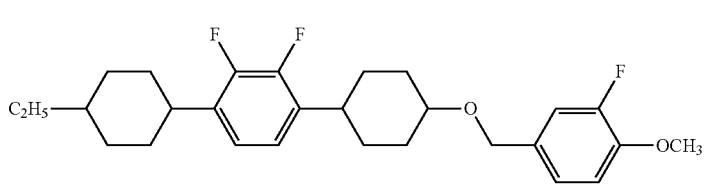 |

-continued
| No. | |
|---|---|
| 3490 | 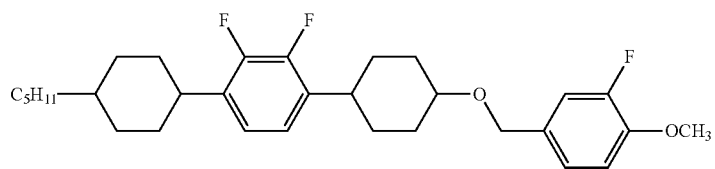 |
| 3491 | 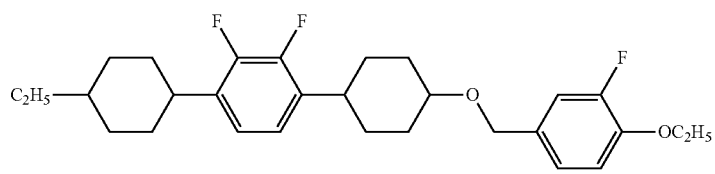 |
| 3492 | 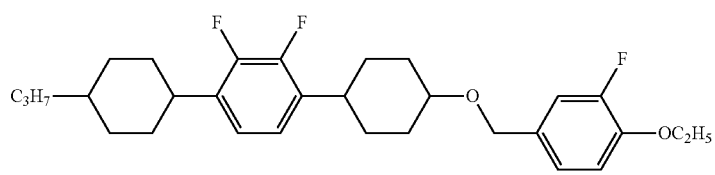 |
| 3493 | 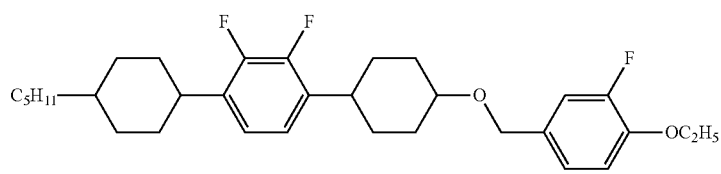 |
| 3494 | 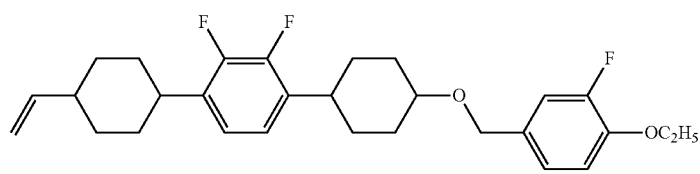 |
| 3495 | 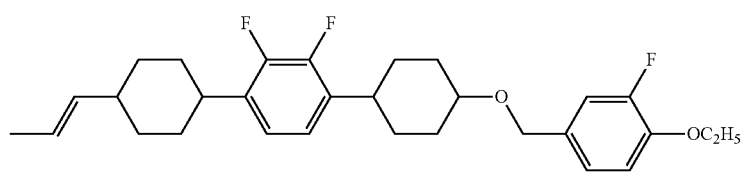 |
| 3496 | 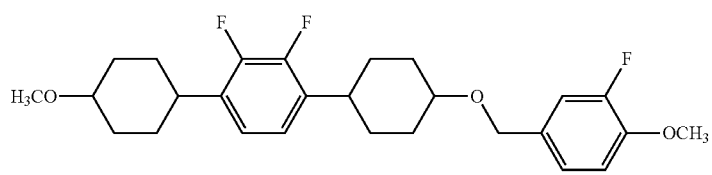 |
| 3497 | 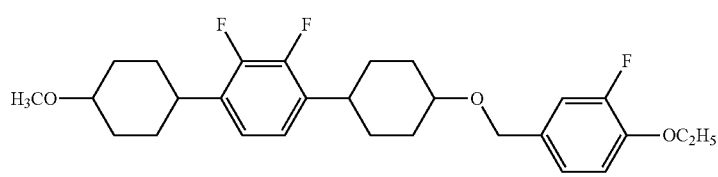 |

-continued
| No. | |
|---|---|
| 3498 | 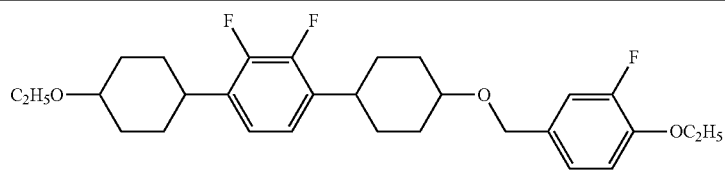 |
| 3499 | 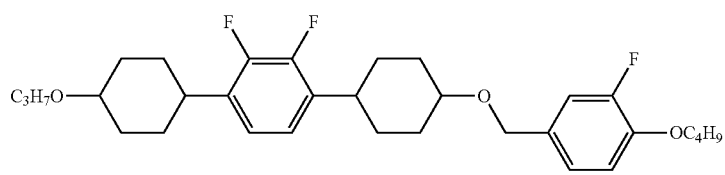 |
| 3500 | 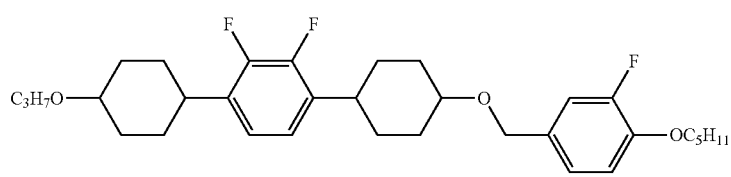 |
| 3501 | 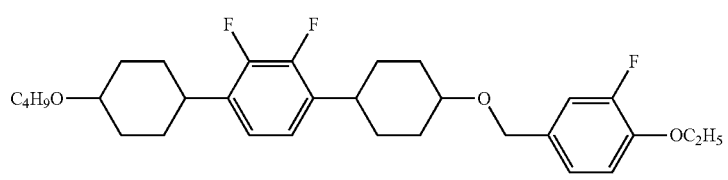 |
| 3502 | 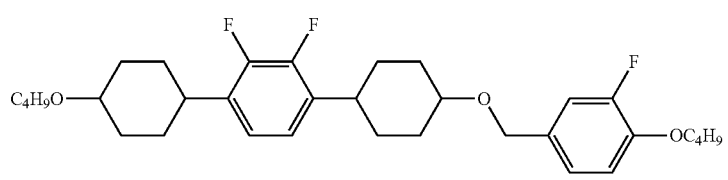 |
| 3503 | 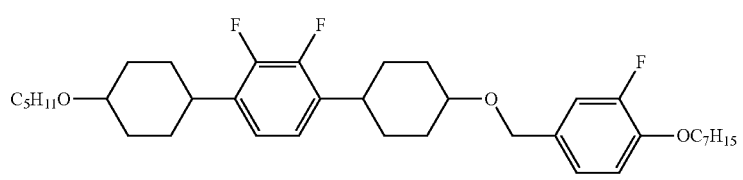 |
| 3504 | 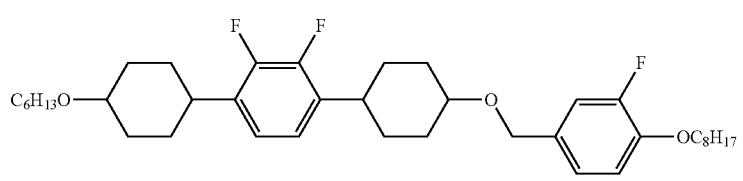 |
| 3505 | 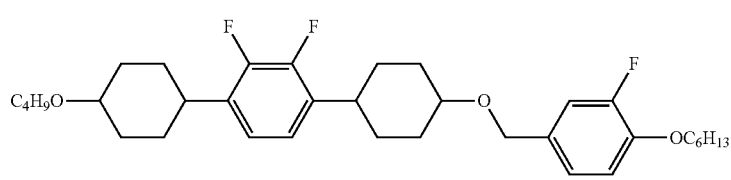 |
| 3506 | 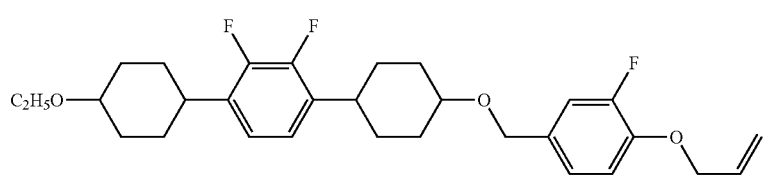 |

| No. | |
|---|---|
| 3507 | 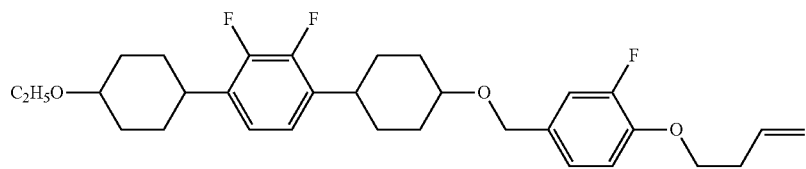 |
| 3508 | 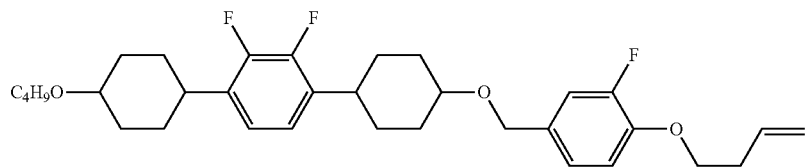 |
| 3509 | 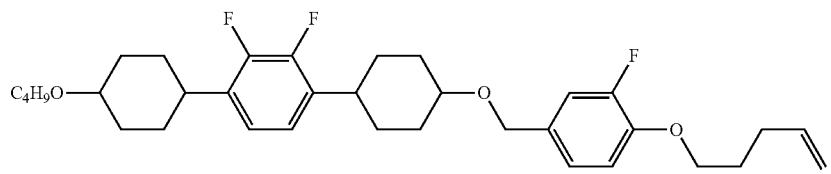 |
| 3510 | 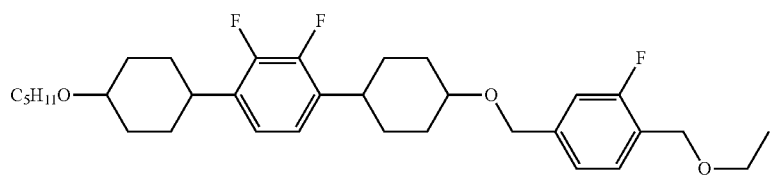 |
| 3511 | 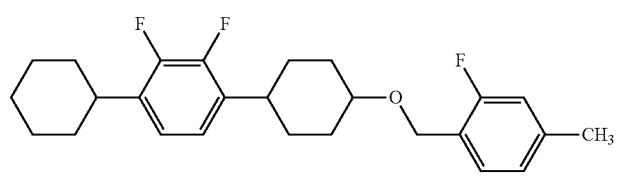 |
| 3512 | 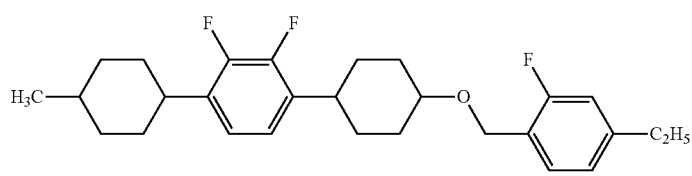 |
| 3513 | 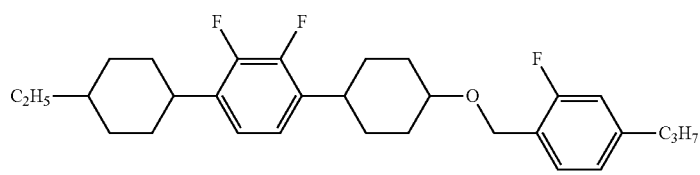 |
| 3514 | 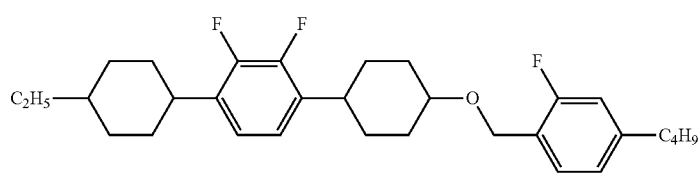 |

-continued
| No. |
|---|
| 3515 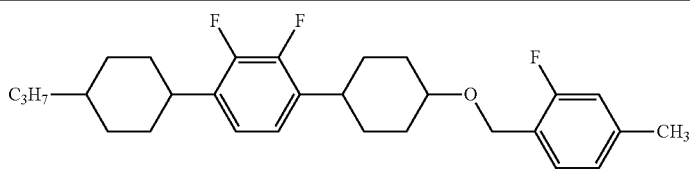 |
| 3516 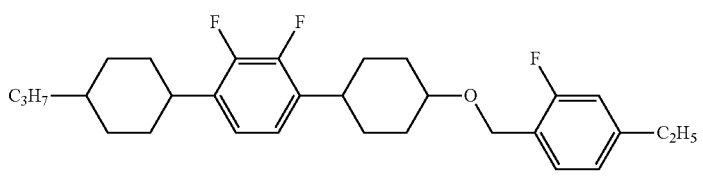 |
| 3517 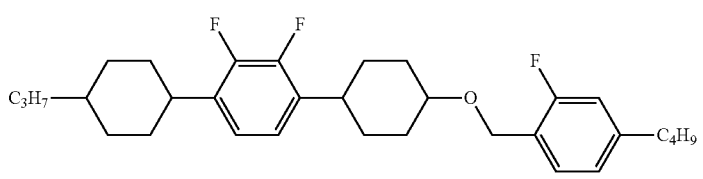 |
| 3518 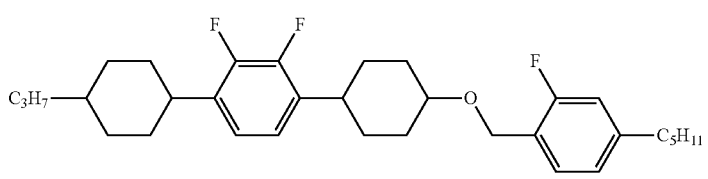 |
| 3519  |
| 3520 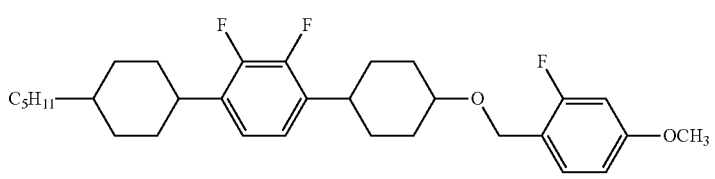 |
| 3521 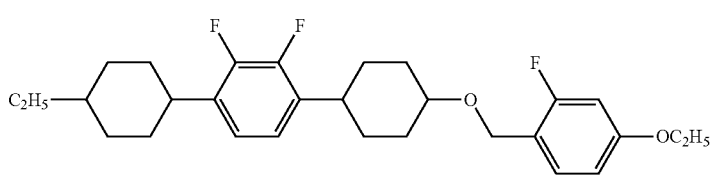 |
| 3522 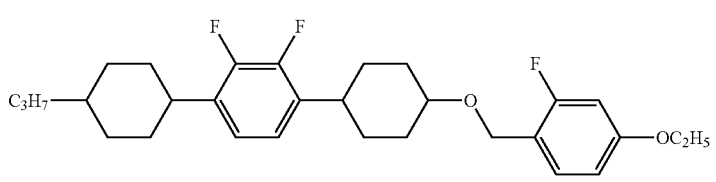 |
| 3523 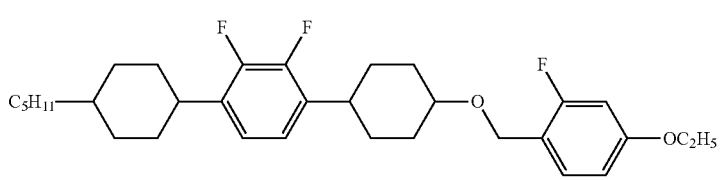 |

-continued
| No. | |
|---|---|
| 3524 | 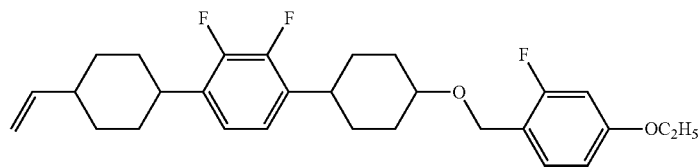 [SMILES: C=CC1CCC(c2ccc(C3CCC(OCc4ccc(OCC)cc4F)CC3)c(F)c2F)CC1] |
| 3525 | 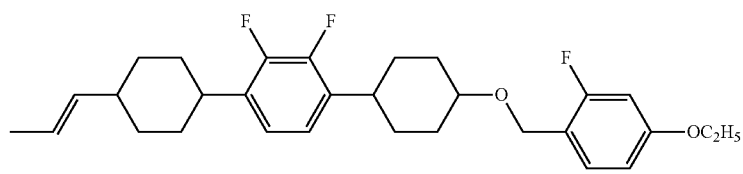 |
| 3526 | 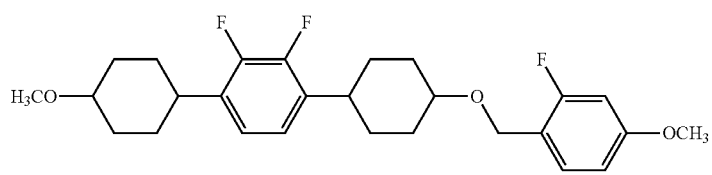 |
| 3527 | 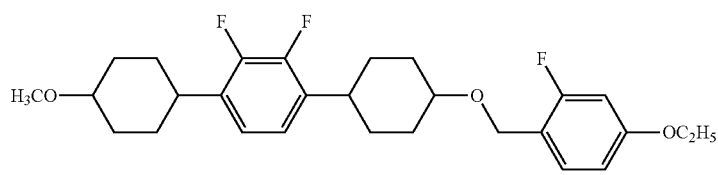 |
| 3528 | 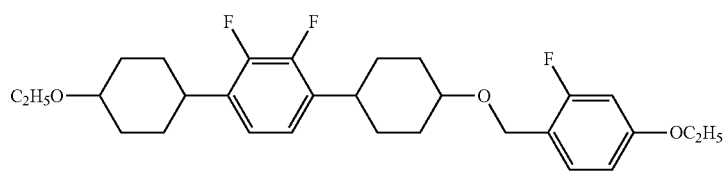 |
| 3529 | 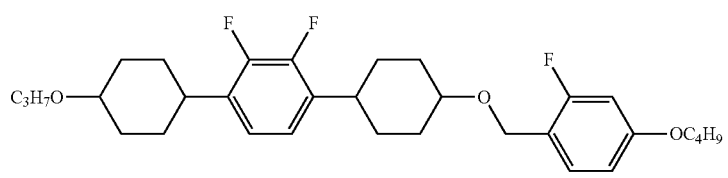 |
| 3530 | 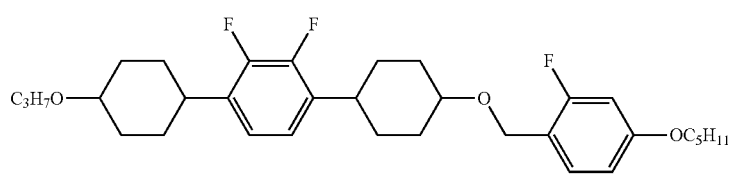 |
| 3531 | 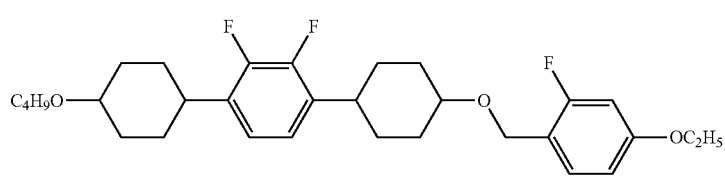 |

| No. |
|---|
| 3532 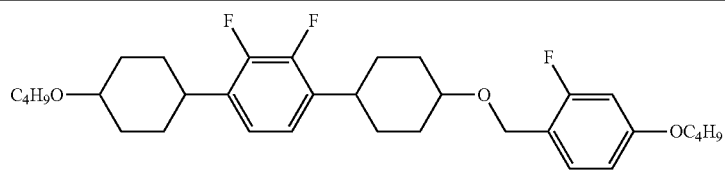 |
| 3533 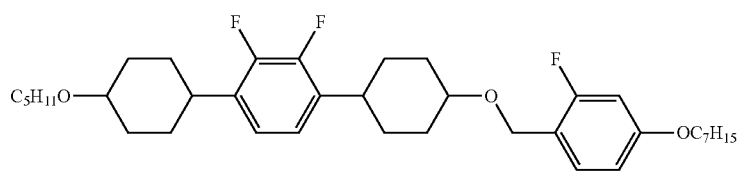 |
| 3534 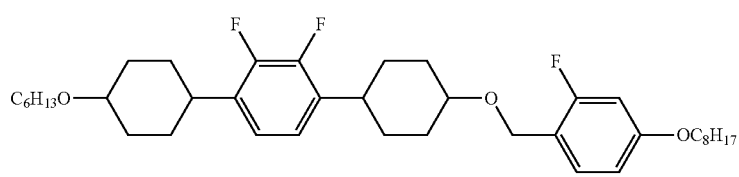 |
| 3535 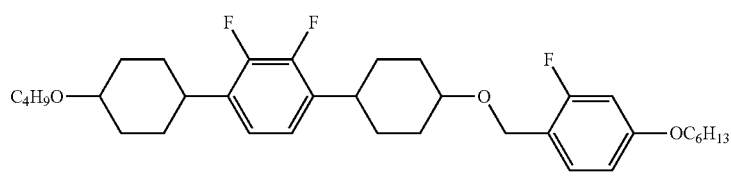 |
| 3536 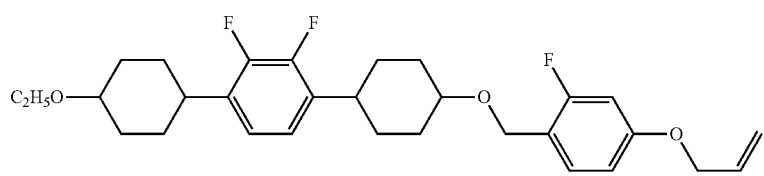 |
| 3537 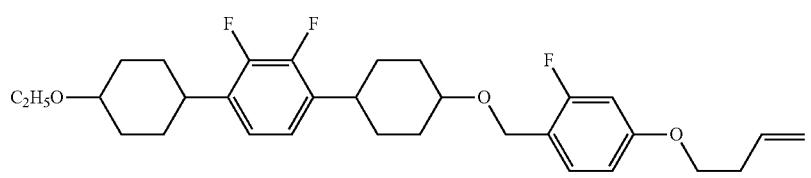 |
| 3538 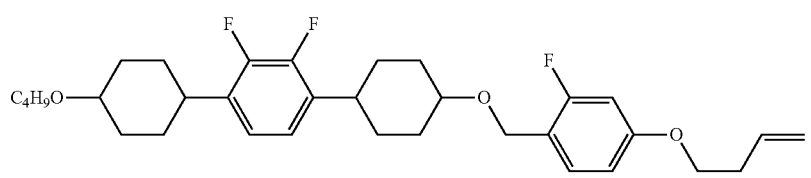 |
| 3539 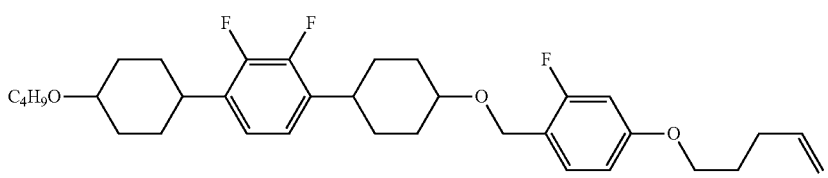 |
| 3540 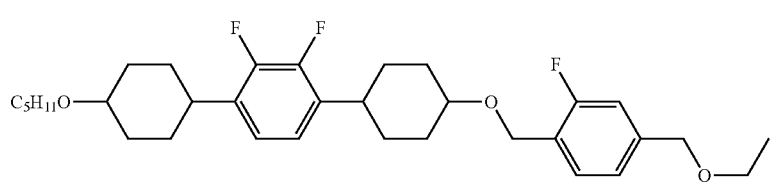 |

| No. | |
|---|---|
| 3541 | 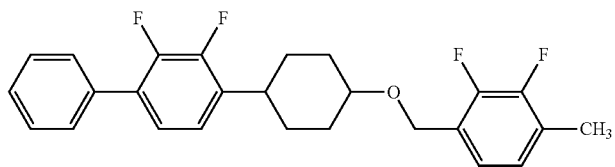 [SMILES: Cc1ccc(COC2CCC(c3ccc(-c4ccccc4)c(F)c3F)CC2)c(F)c1F] |
| 3542 | 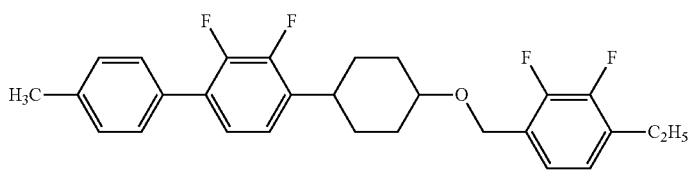 |
| 3543 | 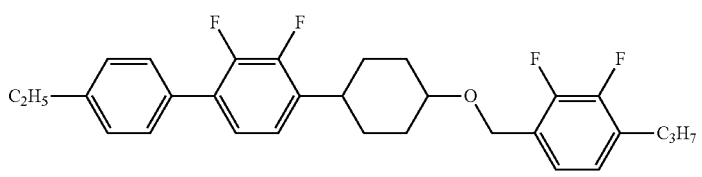 |
| 3544 | 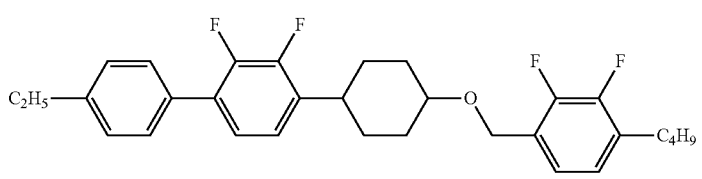 |
| 3545 | 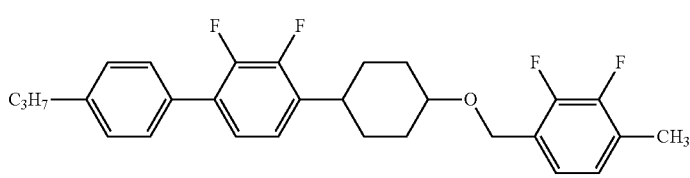 |
| 3546 | 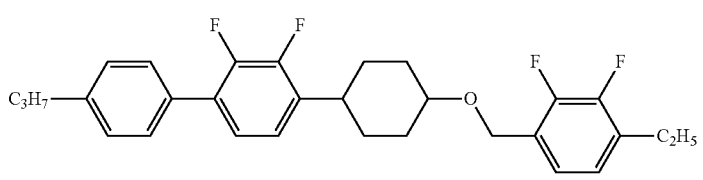 |
| 3547 | 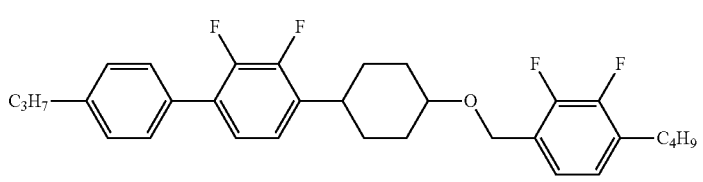 |
| 3548 | 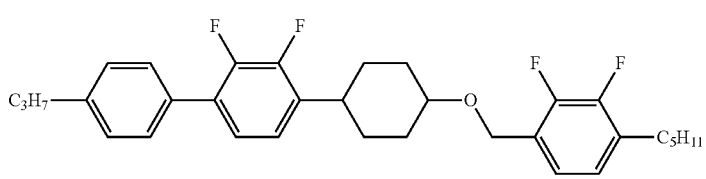 |

-continued
| No. | |
|---|---|
| 3549 | 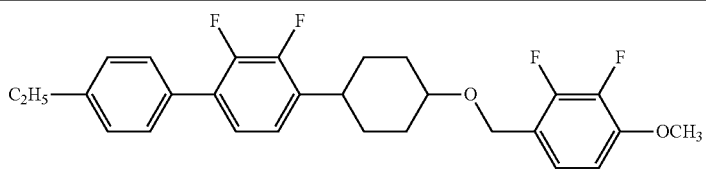 |
| 3550 | 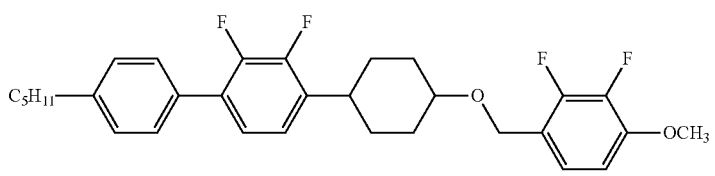 |
| 3551 | 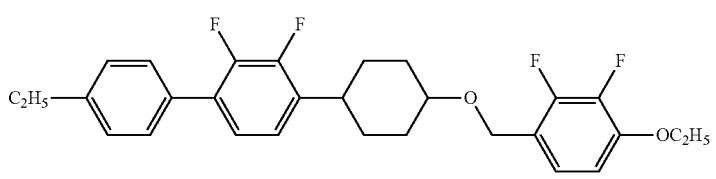 [SMILES: CCOc1ccc(COC2CCC(c3ccc(-c4ccc(CC)cc4)c(F)c3F)CC2)c(F)c1F] |
| 3552 | 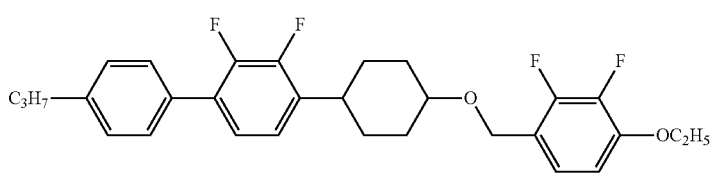 |
| 3553 | 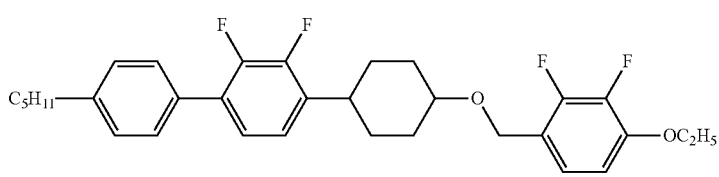 |
| 3554 | 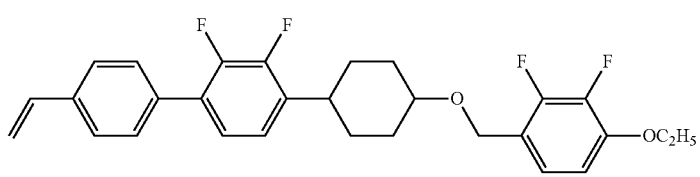 |
| 3555 | 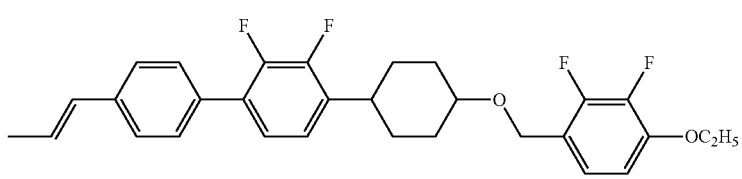 |
| 3556 | 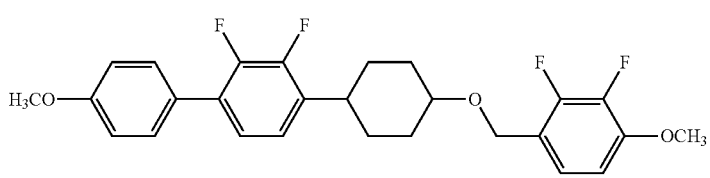 |
| 3557 | 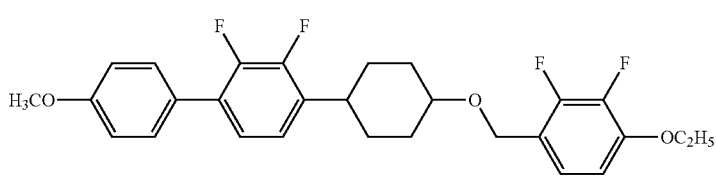 |

| No. | |
|---|---|
| 3558 | 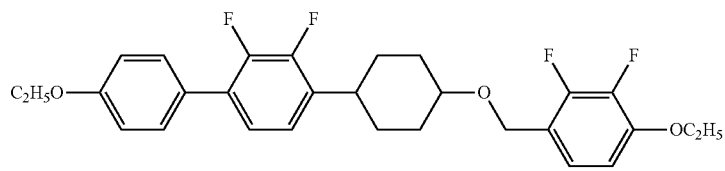 |
| 3559 | 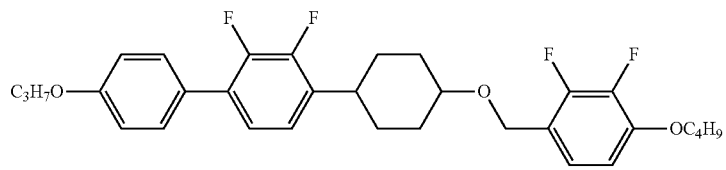 |
| 3560 | 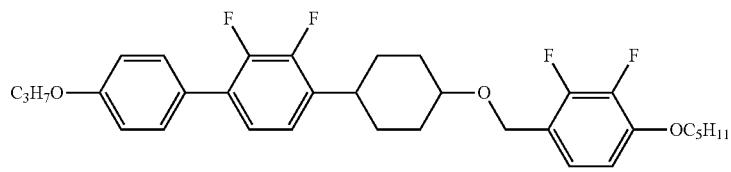 |
| 3561 | 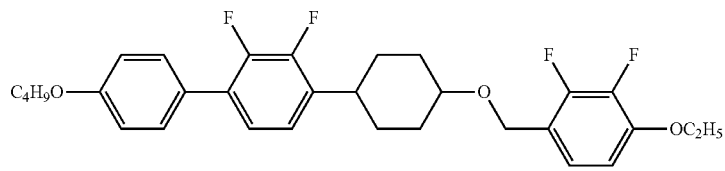 |
| 3562 | 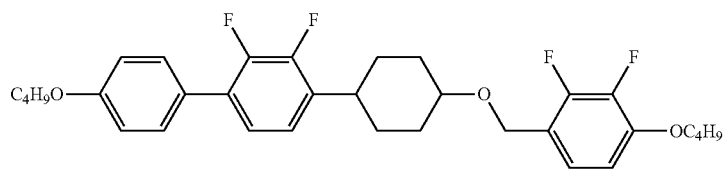 |
| 3563 | 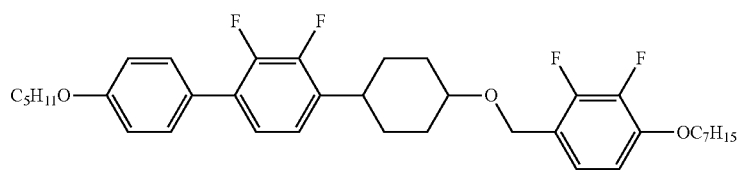 |
| 3564 | 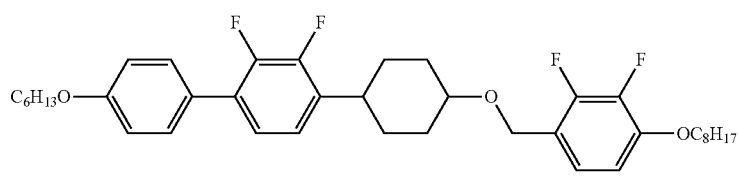 |
| 3565 | 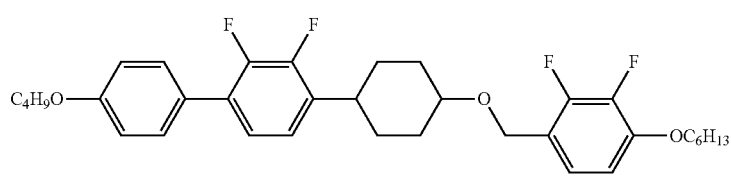 |

-continued
No.
3566 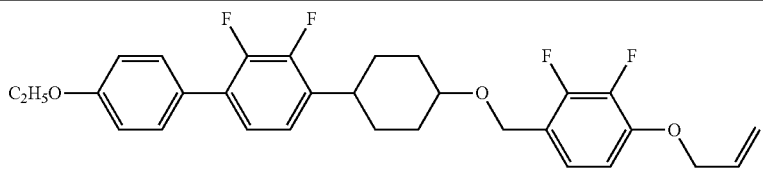
3567 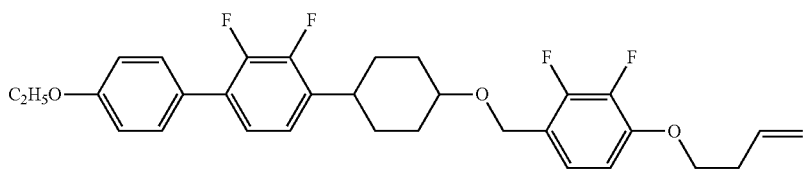
3568 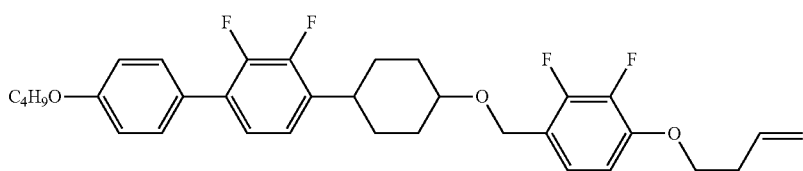
3569 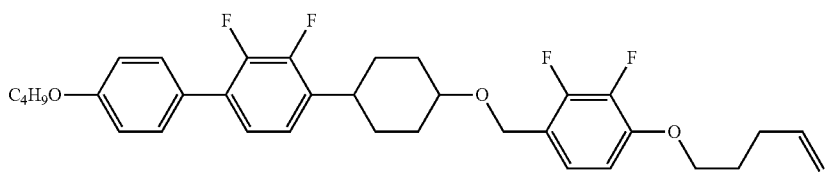
3570 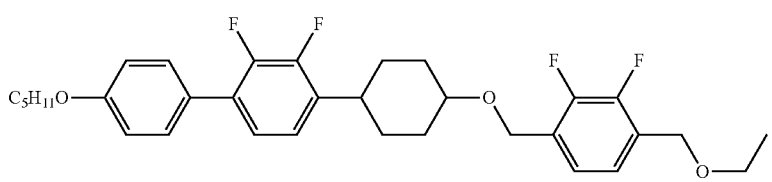
3571 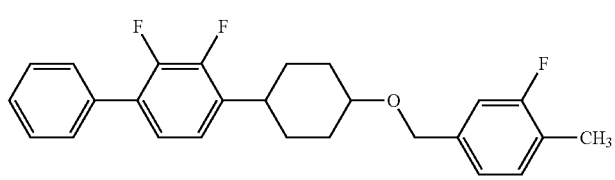
3572 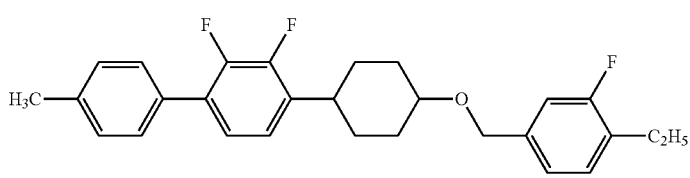 [SMILES: CCc1ccc(COC2CCC(c3ccc(-c4ccc(C)cc4)c(F)c3F)CC2)cc1F]
3573 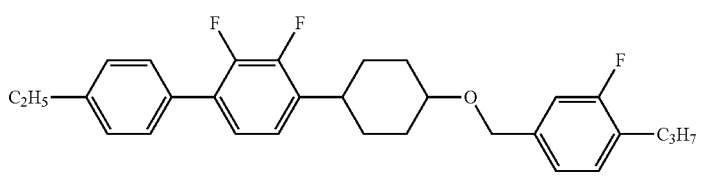
3574 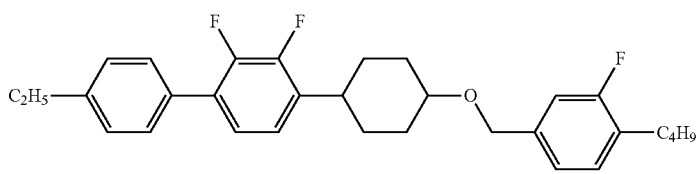

| No. | |
|---|---|
| 3575 | 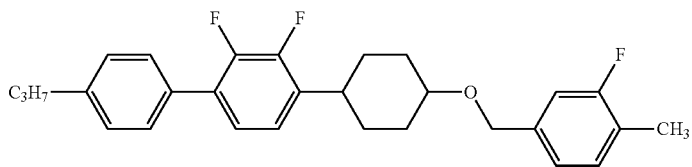 |
| 3576 | 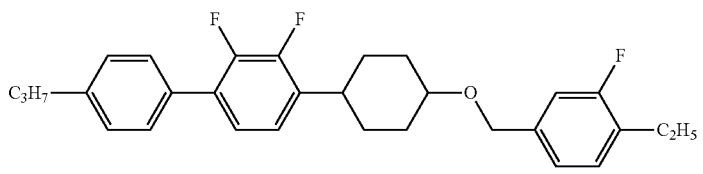 |
| 3577 | 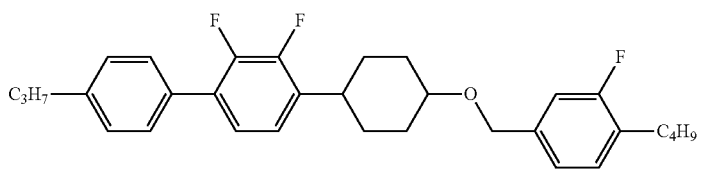 |
| 3578 | 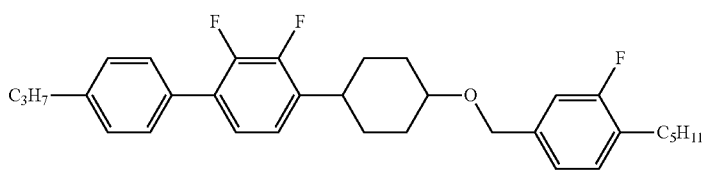 |
| 3579 | 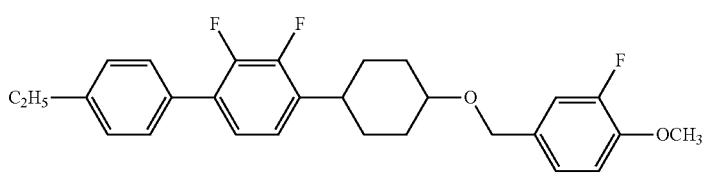 |
| 3580 | 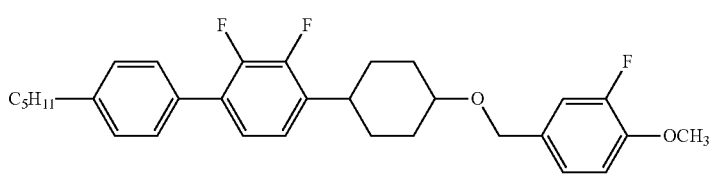 |
| 3581 | 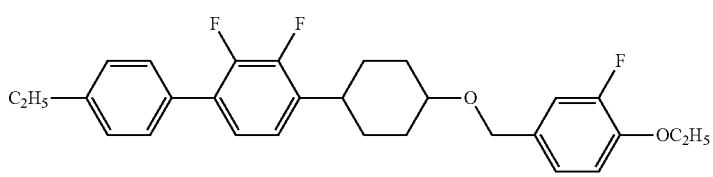 |
| 3582 | 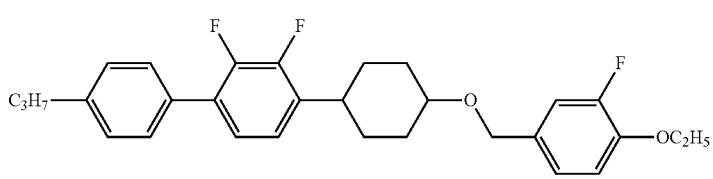 |

| No. | |
|---|---|
| 3583 | 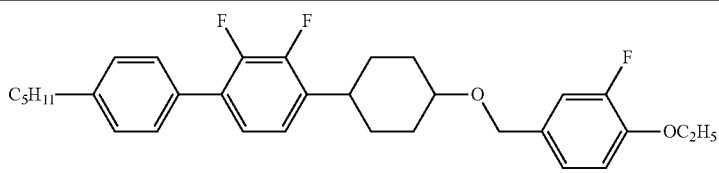 |
| 3584 | 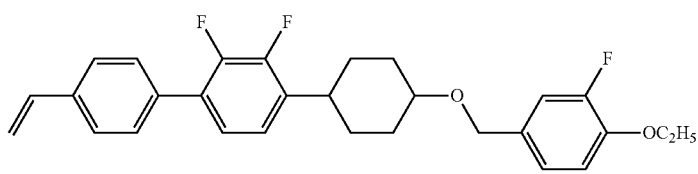 |
| 3585 | 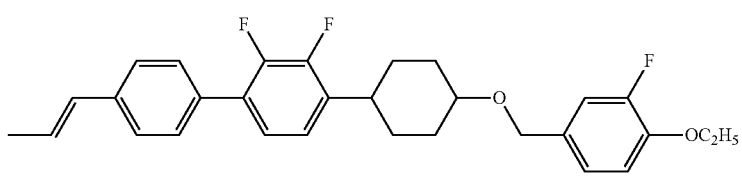 [SMILES: C/C=C/c1ccc(-c2ccc(C3CCC(OCc4ccc(OCC)c(F)c4)CC3)c(F)c2F)cc1] |
| 3586 | 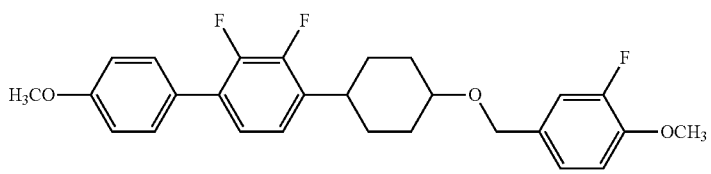 |
| 3587 | 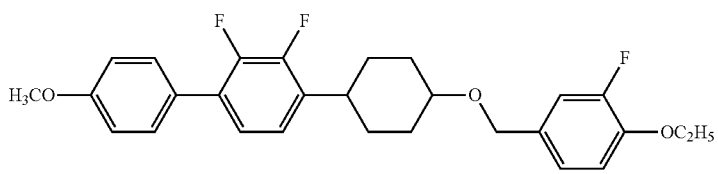 |
| 3588 | 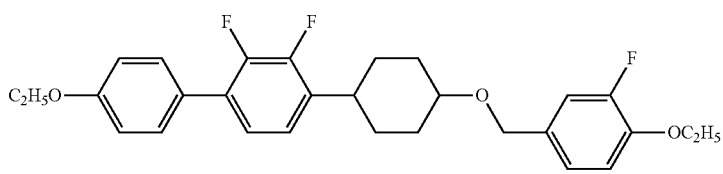 |
| 3589 | 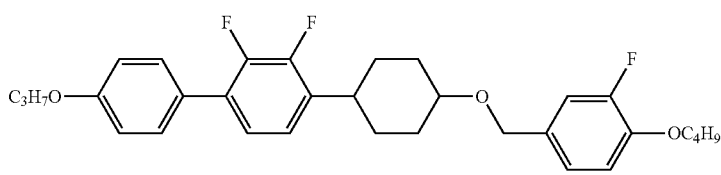 |
| 3590 | 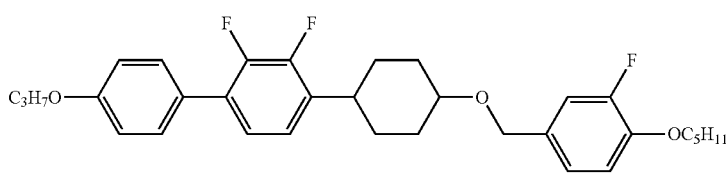 |
| 3591 | 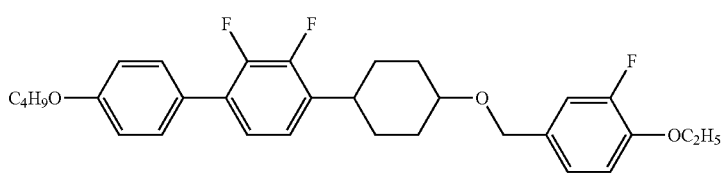 |

| No. |
|---|
| 3592 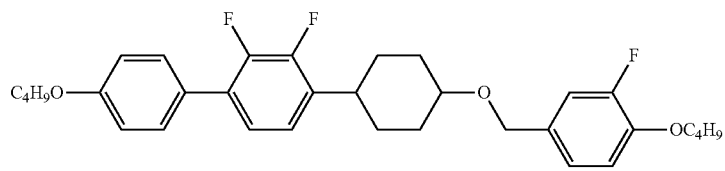 |
| 3593 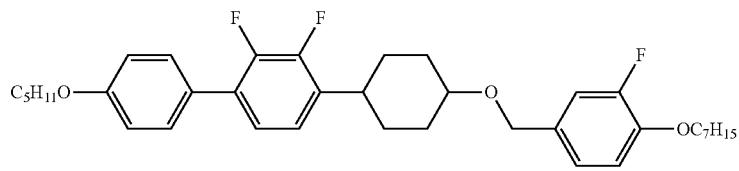 |
| 3594 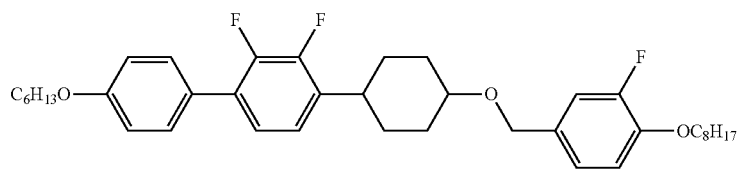 |
| 3595 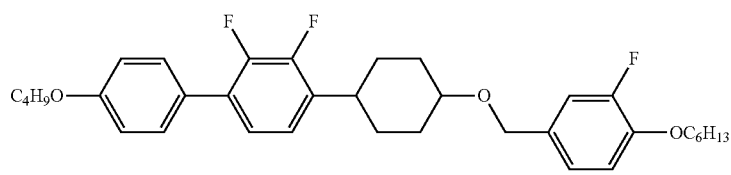 |
| 3596 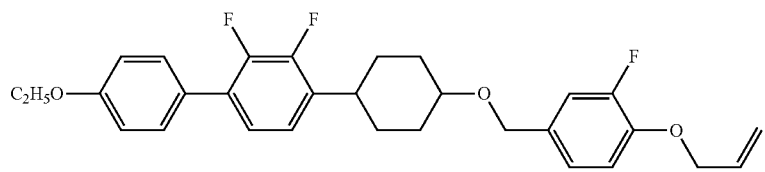 |
| 3597 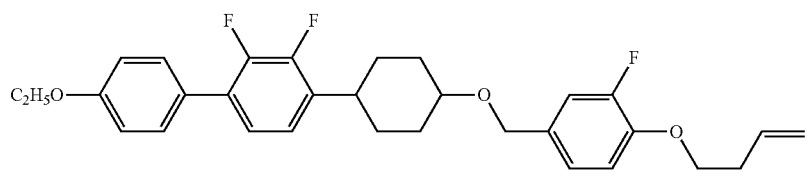 |
| 3598 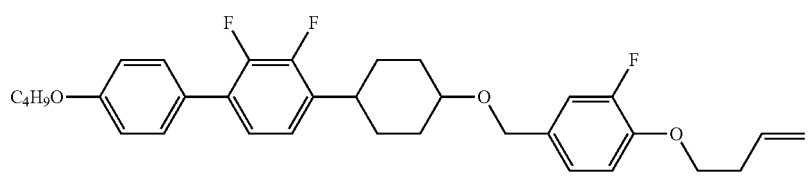 |
| 3599 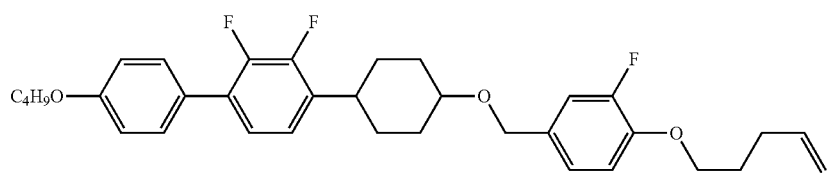 |

| No. |
|---|
| 3600 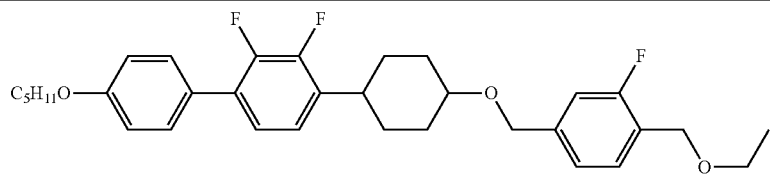 |
| 3601 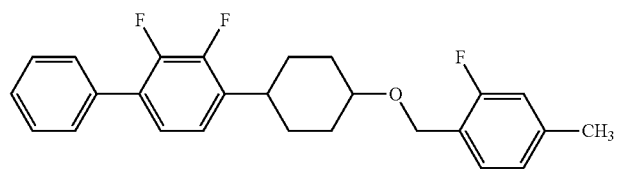 [SMILES: Cc1ccc(COC2CCC(c3ccc(-c4ccccc4)c(F)c3F)CC2)c(F)c1] |
| 3602 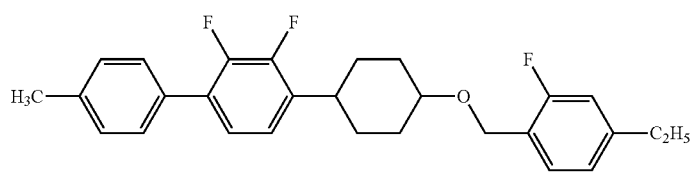 |
| 3603 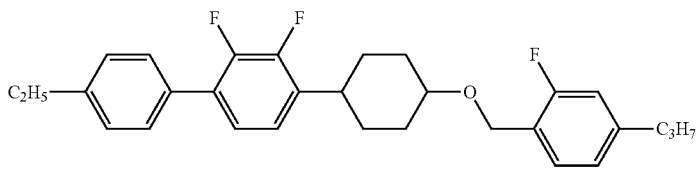 |
| 3604 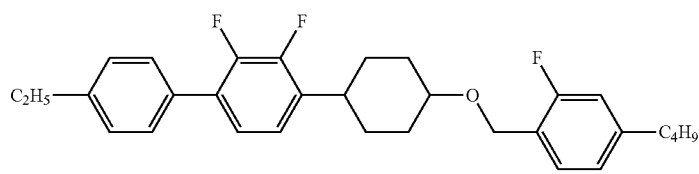 |
| 3605 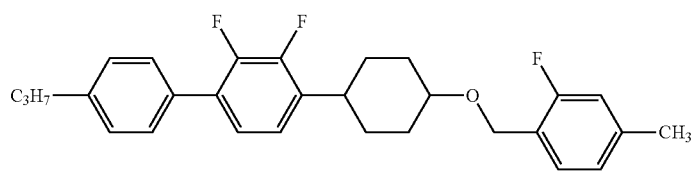 |
| 3606 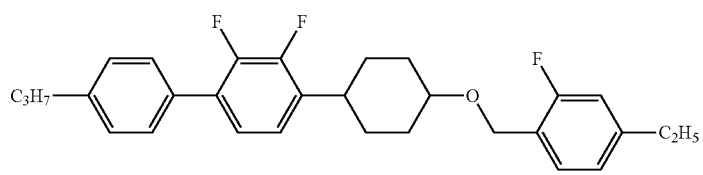 |
| 3607 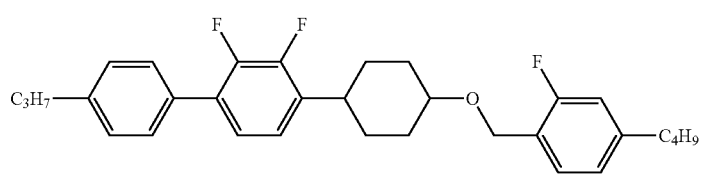 |
| 3608 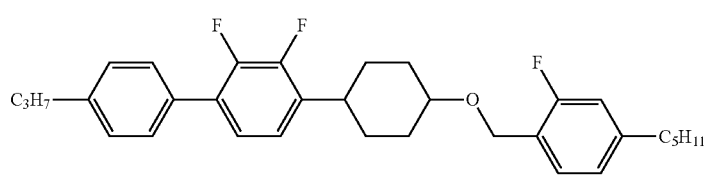 |

| No. | |
|---|---|
| 3609 | 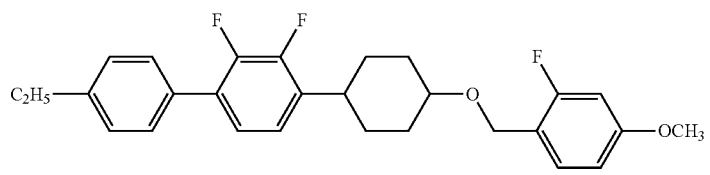 [SMILES: CCc1ccc(-c2ccc(C3CCC(OCc4ccc(OC)cc4F)CC3)c(F)c2F)cc1] |
| 3610 |  |
| 3611 | 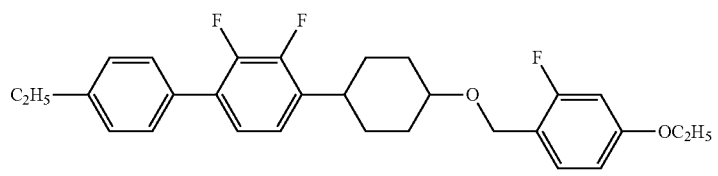 |
| 3612 | 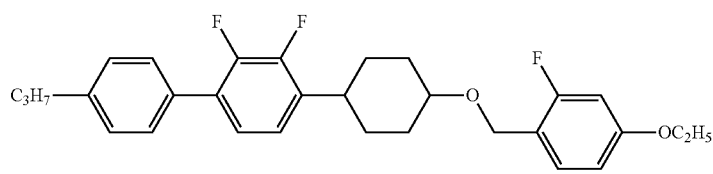 |
| 3613 | 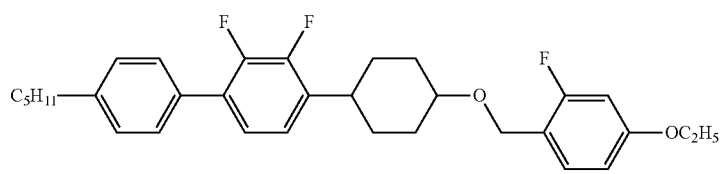 |
| 3614 | 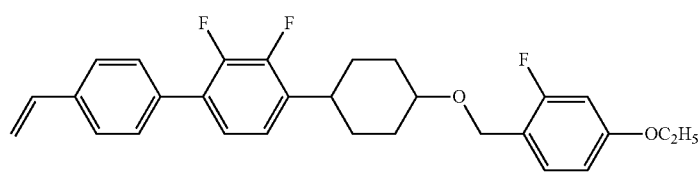 |
| 3615 | 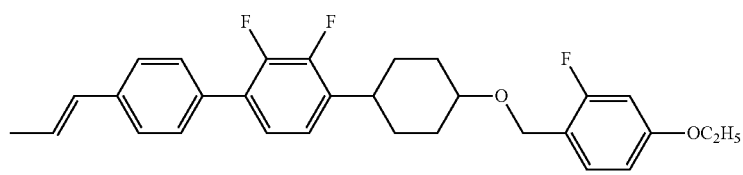 [SMILES: C/C=C/c1ccc(-c2ccc(C3CCC(OCc4ccc(OCC)cc4F)CC3)c(F)c2F)cc1] |
| 3616 | 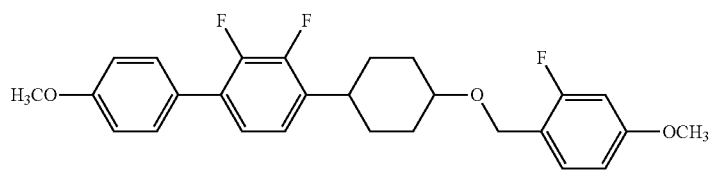 |

| No. |
|---|
| 3617 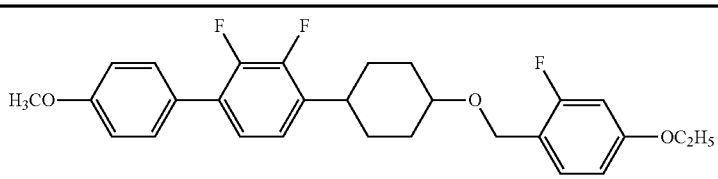 |
| 3618 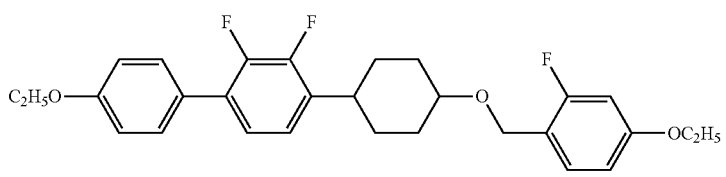 |
| 3619 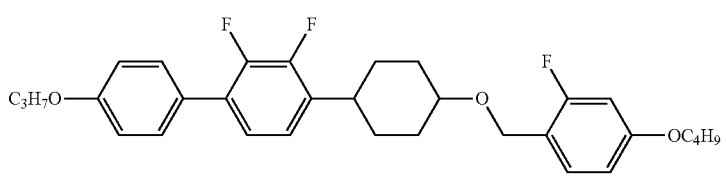 |
| 3620 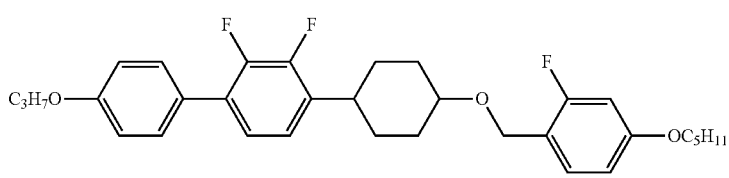 |
| 3621 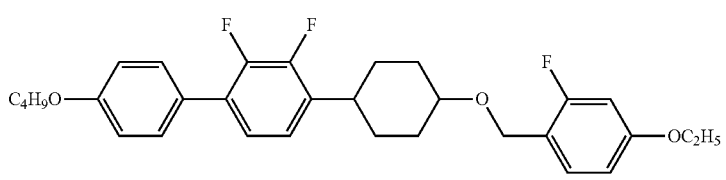 |
| 3622 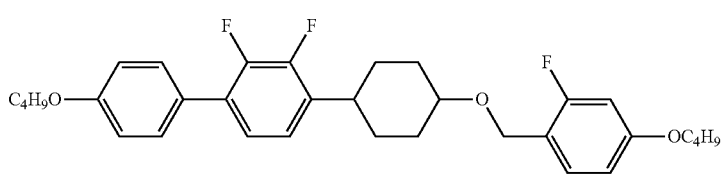 |
| 3623 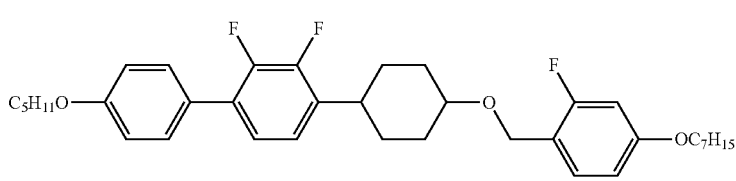 |
| 3624 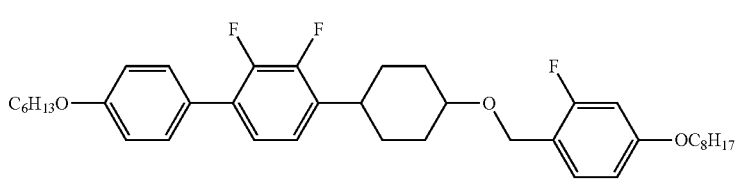 |
| 3625 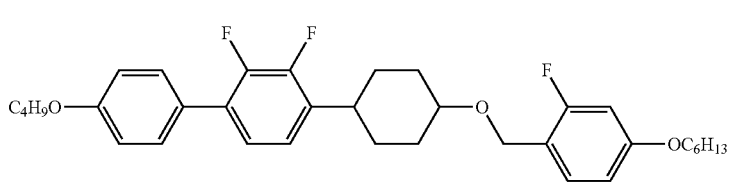 |

| No. |
|---|
| 3626 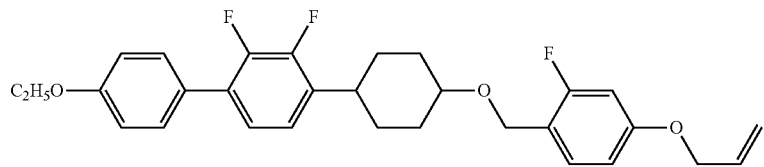 |
| 3627 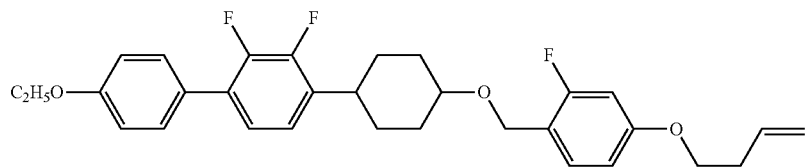 |
| 3628 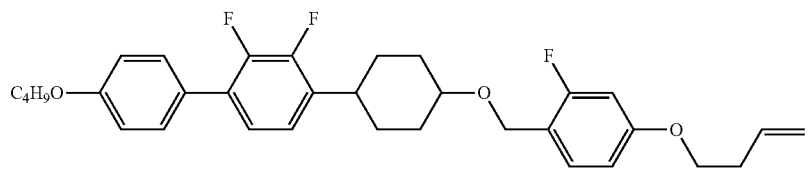 |
| 3629 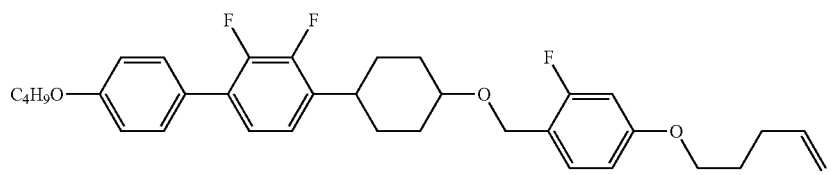 |
| 3630 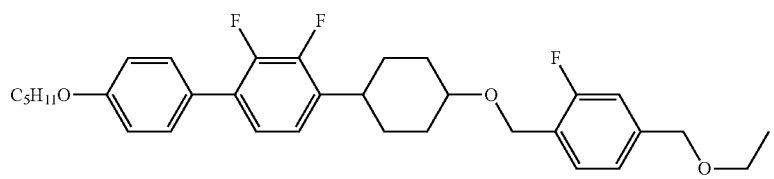 |
| 3631 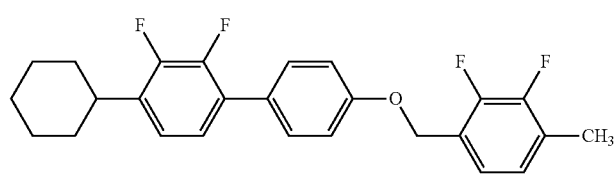 |
| 3632 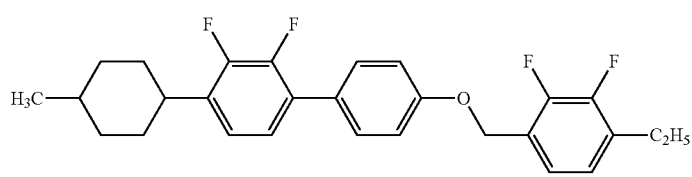 |
| 3633 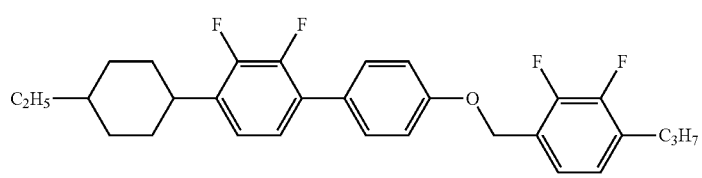 |

| No. |
|---|
| 3634 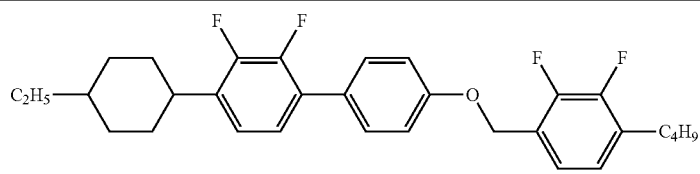 |
| 3635 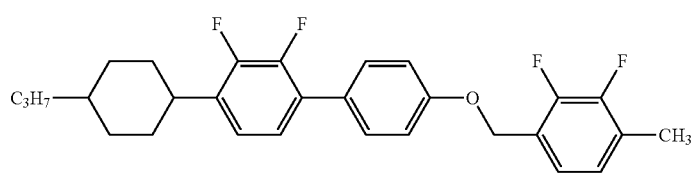 |
| 3636 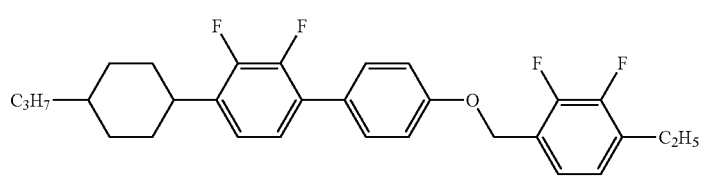 |
| 3637 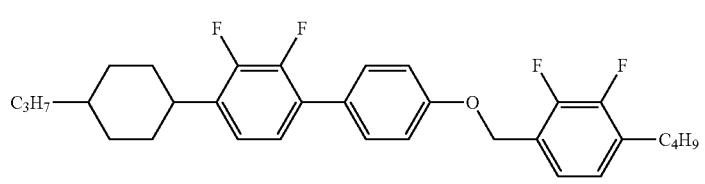 |
| 3638 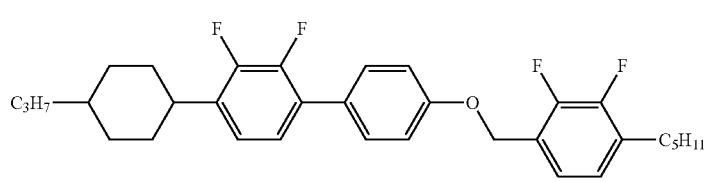 |
| 3639 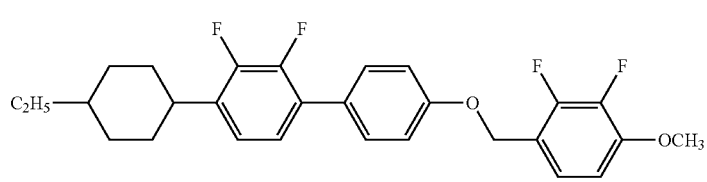 |
| 3640 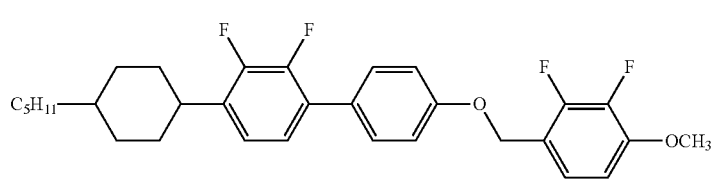 |
| 3641 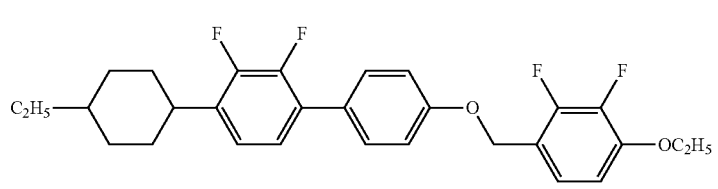 |
| 3642 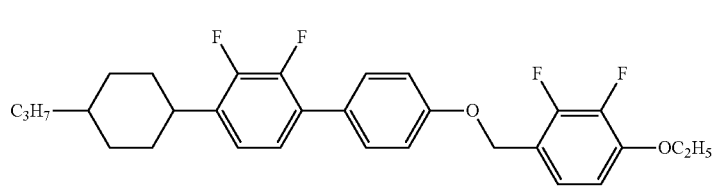 |

| No. |
|---|
| 3643 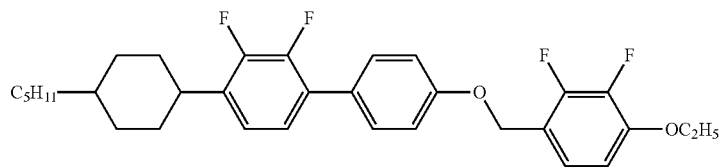 |
| 3644 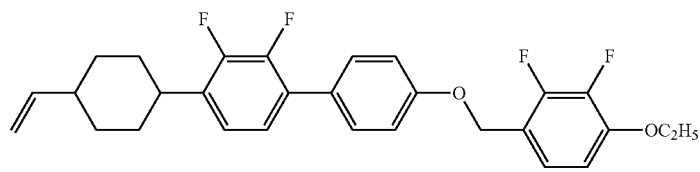 |
| 3645 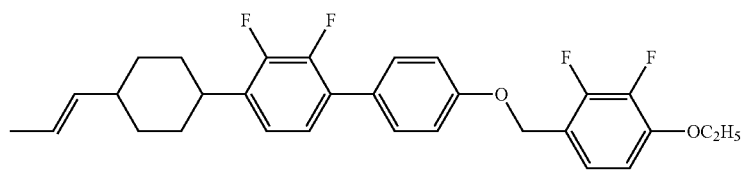 |
| 3646 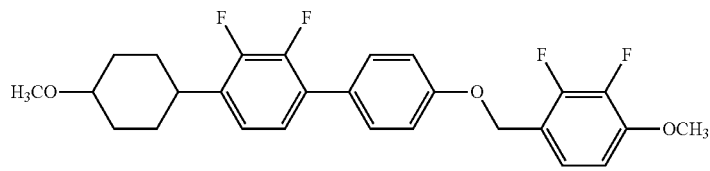 |
| 3647 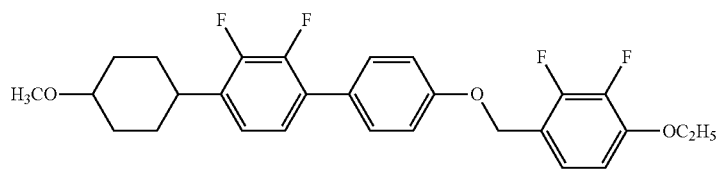 |
| 3648 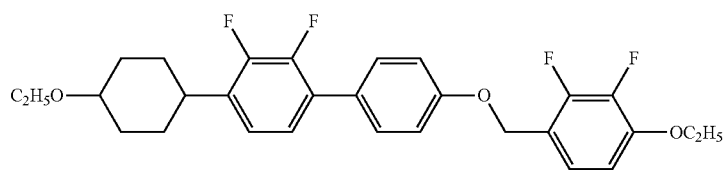 |
| 3649 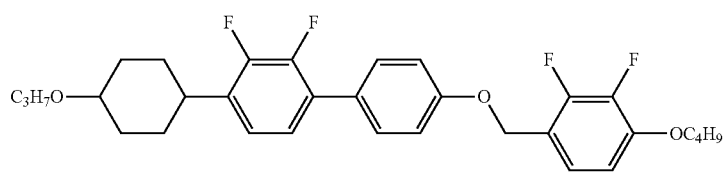 |
| 3650 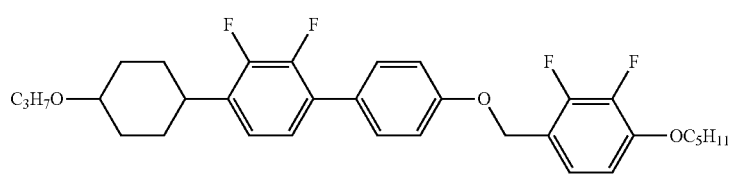 |

| No. | |
|---|---|
| 3651 | 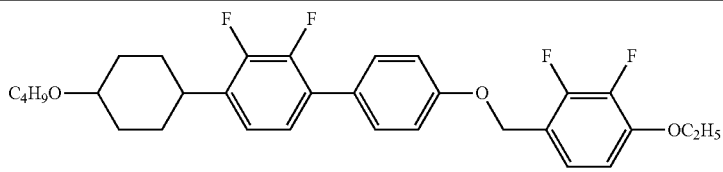 |
| 3652 | 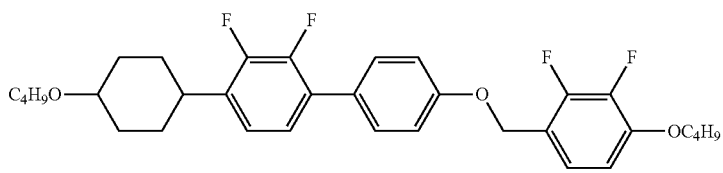 |
| 3653 | 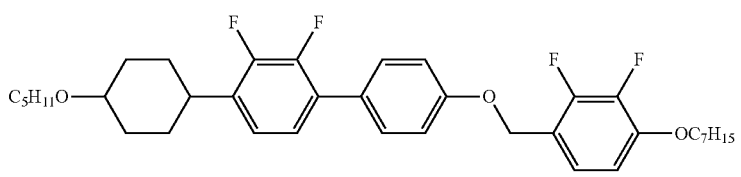 |
| 3654 | 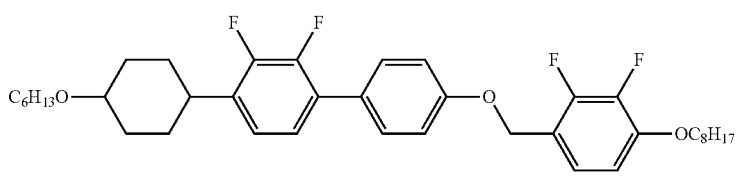 |
| 3655 | 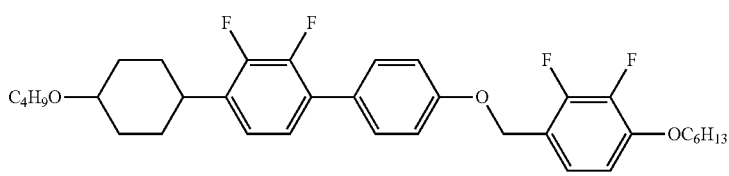 |
| 3656 | 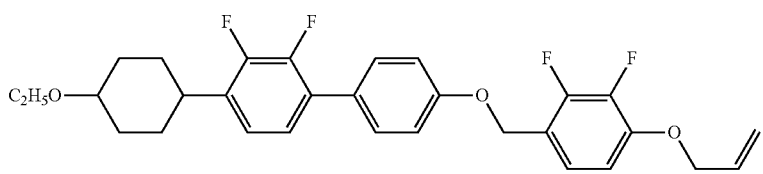 |
| 3657 | 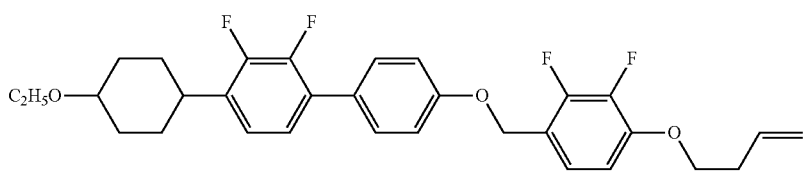 |
| 3658 | 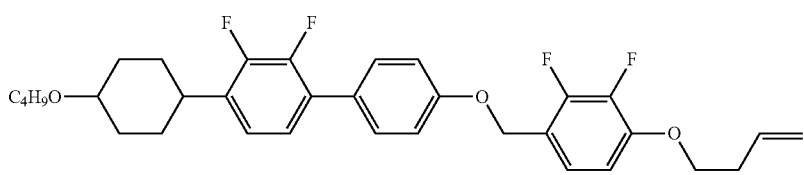 |
| 3659 | 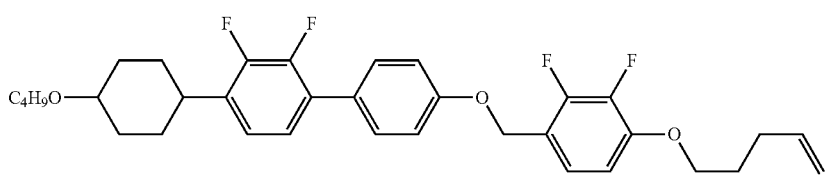 |

| No. | |
|---|---|
| 3660 | 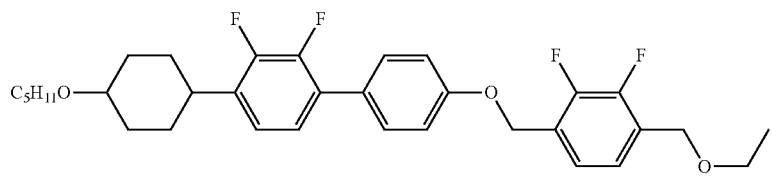 |
| 3661 | 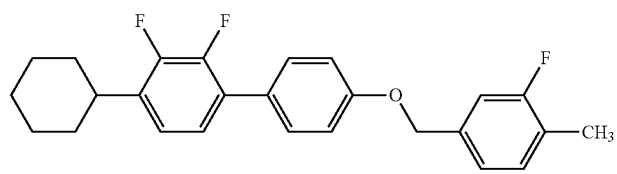 |
| 3662 | 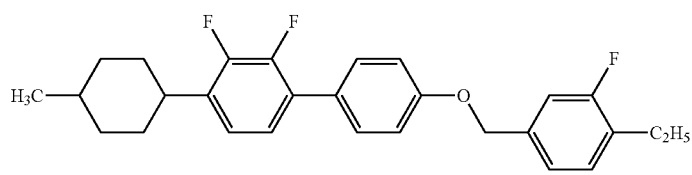 |
| 3663 | 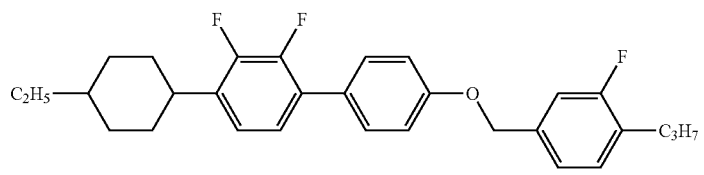 |
| 3664 | 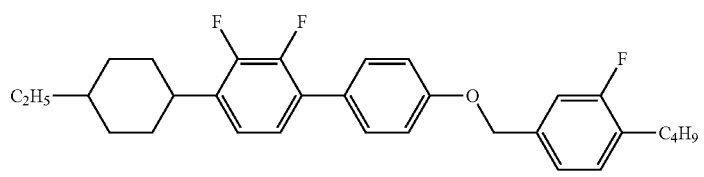 |
| 3665 | 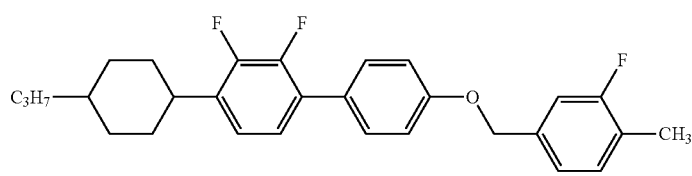 |
| 3666 | 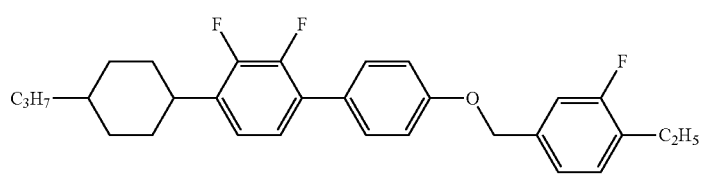 |
| 3667 | 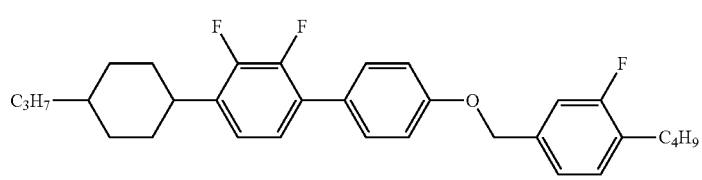 |

| No. |
|---|
| 3668 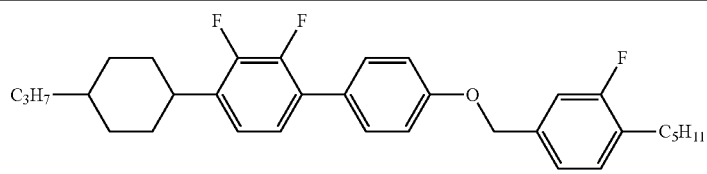 |
| 3669 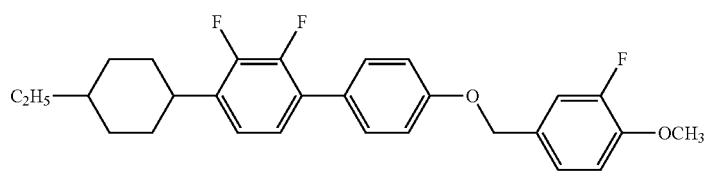 |
| 3670 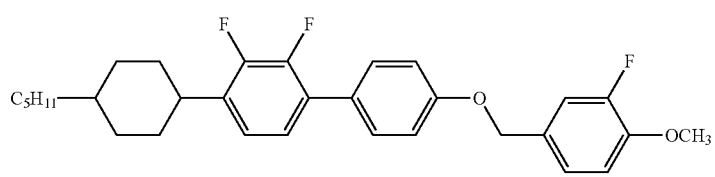 |
| 3671 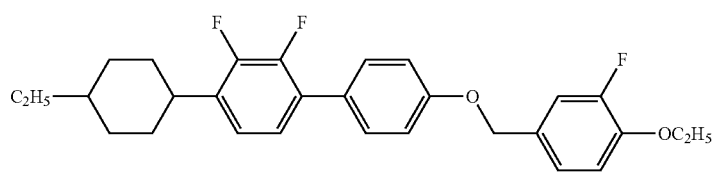 |
| 3672 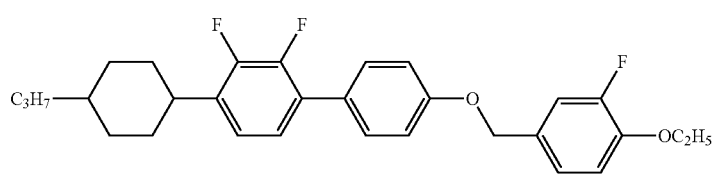 |
| 3673 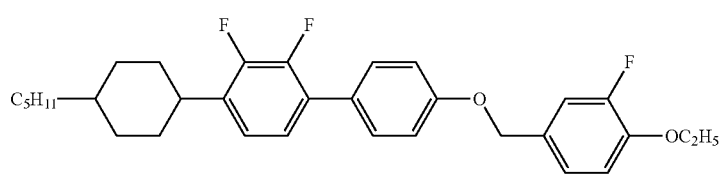 |
| 3674 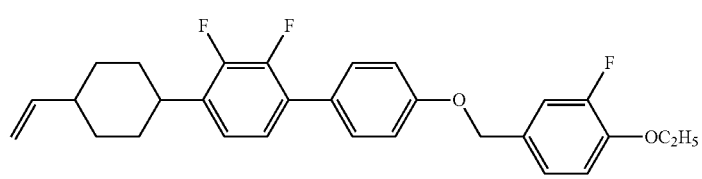 |
| 3675 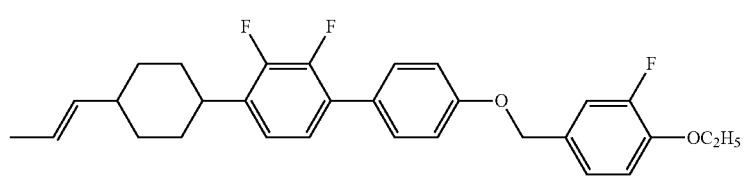 |
| 3676 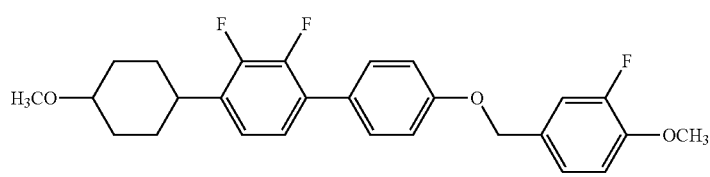 |

-continued
| No. | |
|---|---|
| 3677 | 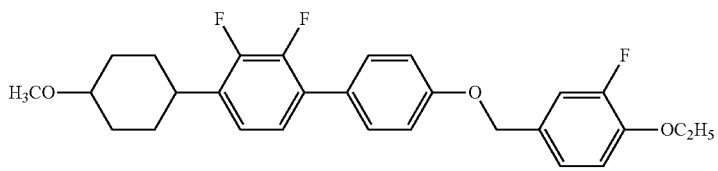 |
| 3678 | 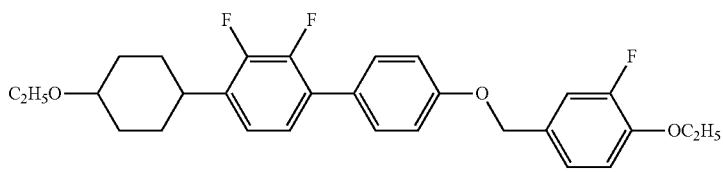 |
| 3679 | 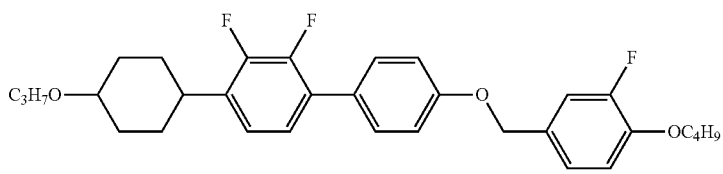 |
| 3680 | 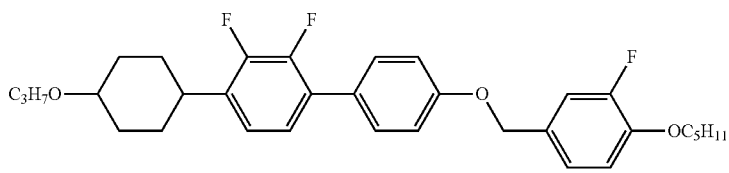 |
| 3681 | 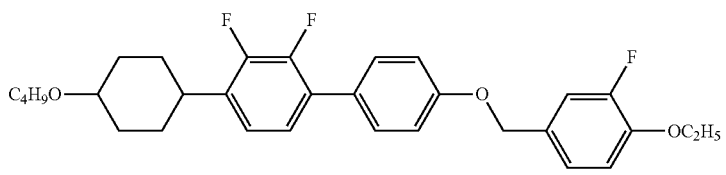 |
| 3682 | 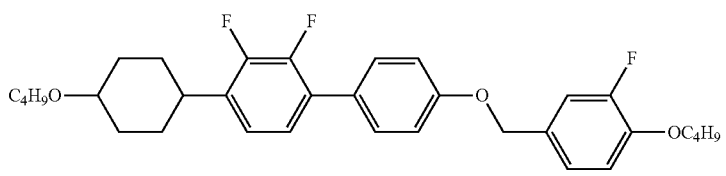 |
| 3683 | 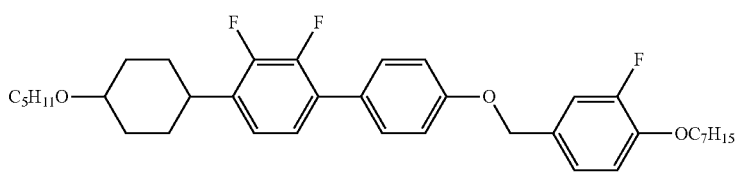 |
| 3684 | 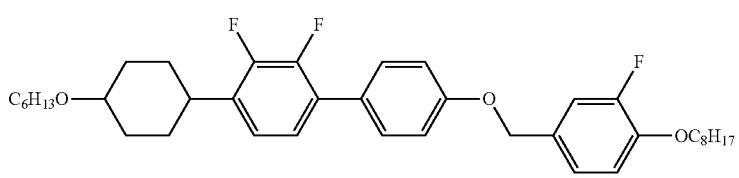 |

| No. | |
|---|---|
| 3685 | 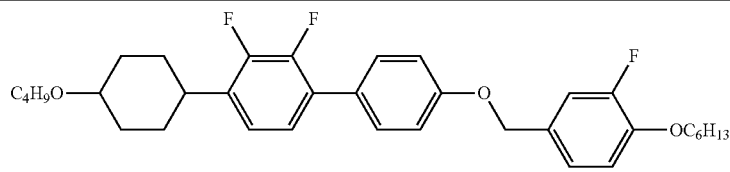 |
| 3686 | 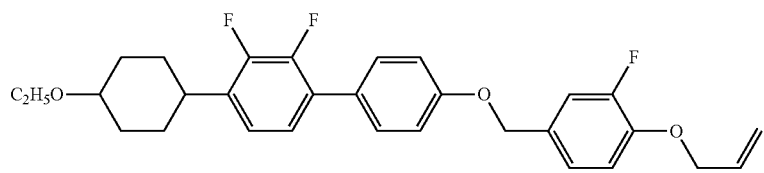 |
| 3687 | 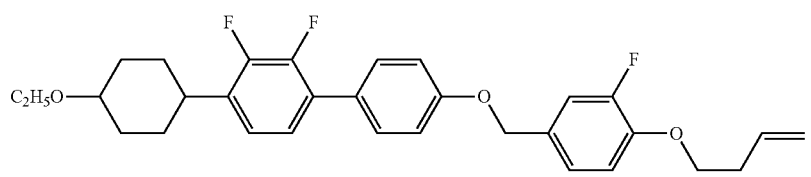 |
| 3688 | 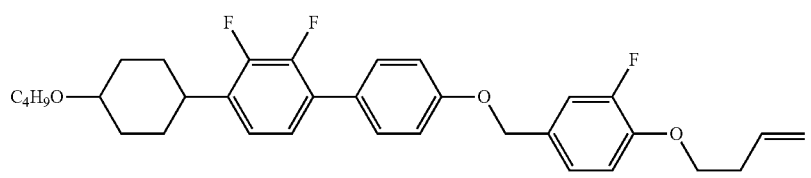 |
| 3689 | 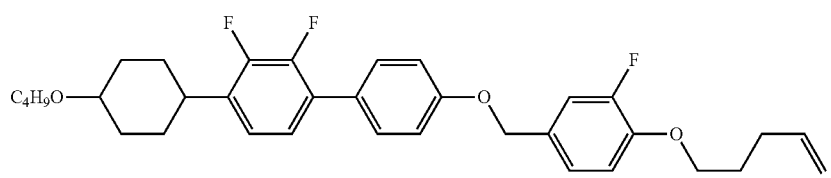 |
| 3690 | 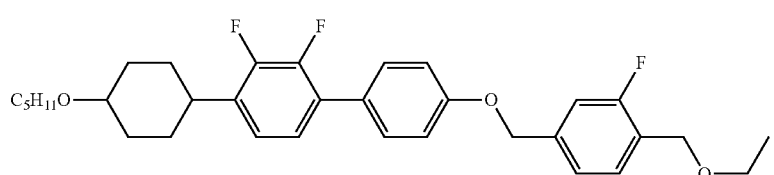 |
| 3691 | 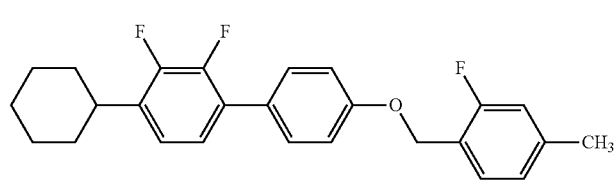 |
| 3692 | 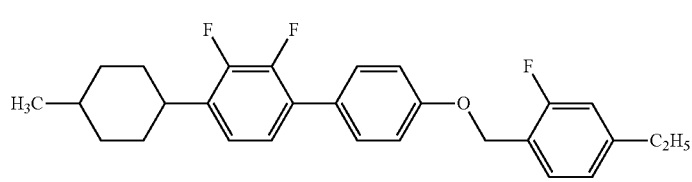 [SMILES: CCc1ccc(COc2ccc(-c3ccc(C4CCC(C)CC4)c(F)c3F)cc2)c(F)c1] |
| 3693 | 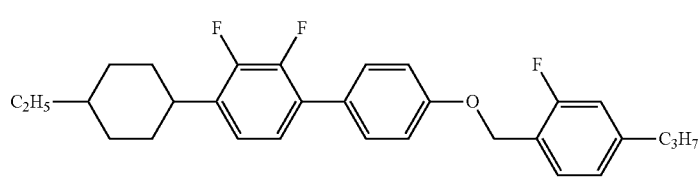 |

| No. | |
|---|---|
| 3694 | 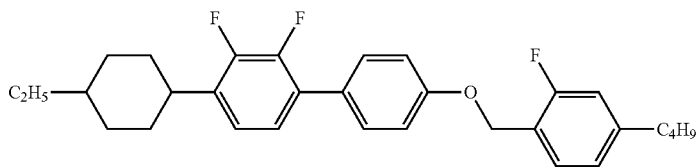 |
| 3695 | 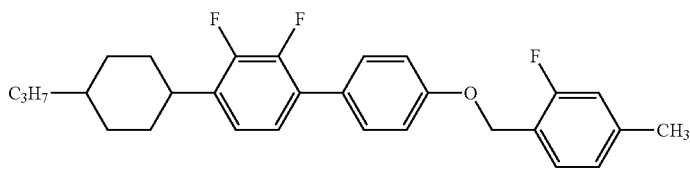 |
| 3696 | 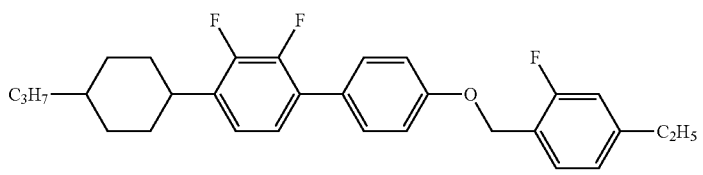 |
| 3697 | 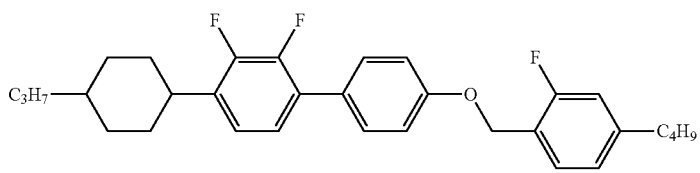 |
| 3698 | 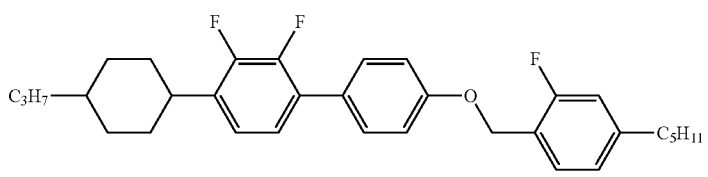 |
| 3699 |  |
| 3700 | 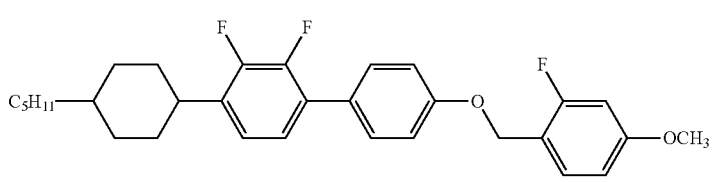 |
| 3701 | 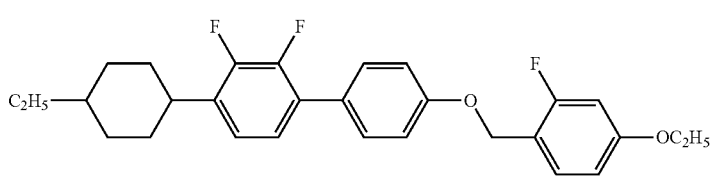 |

-continued
| No. |
|---|
| 3702 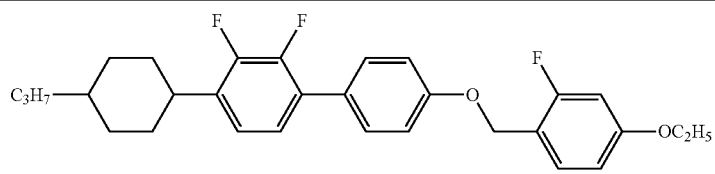 |
| 3703 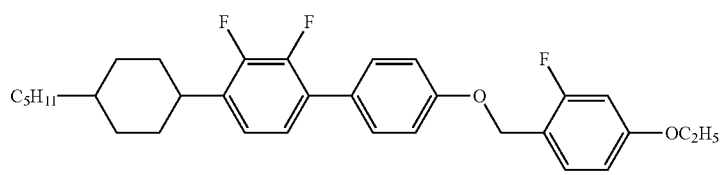 |
| 3704 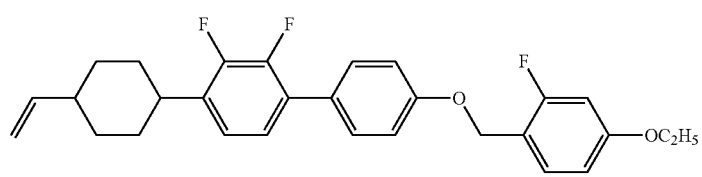 |
| 3705 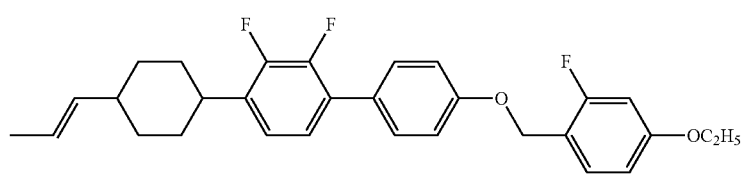 |
| 3706 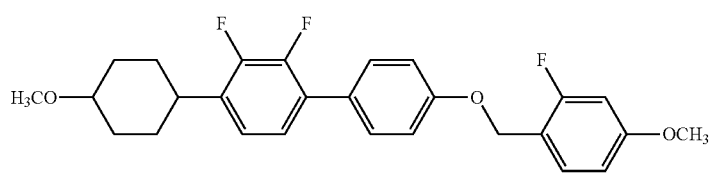 [SMILES: COc1ccc(COc2ccc(-c3ccc(C4CCC(OC)CC4)c(F)c3F)cc2)c(F)c1] |
| 3707 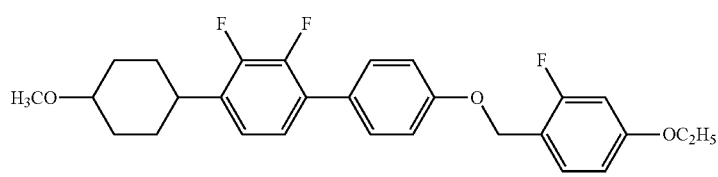 |
| 3708 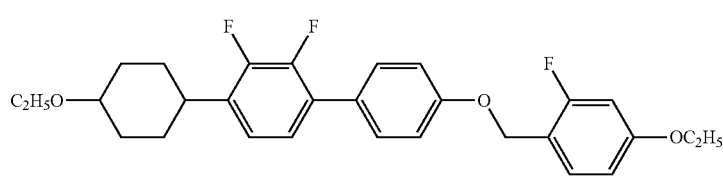 |
| 3709 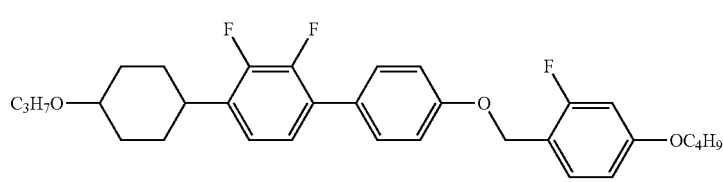 |
| 3710 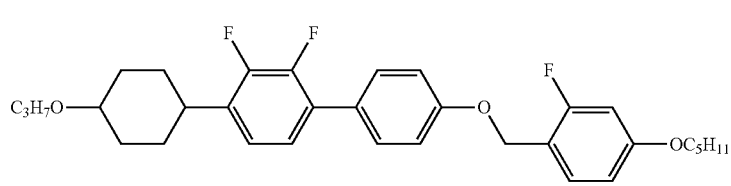 |

| No. | |
|---|---|
| 3711 | 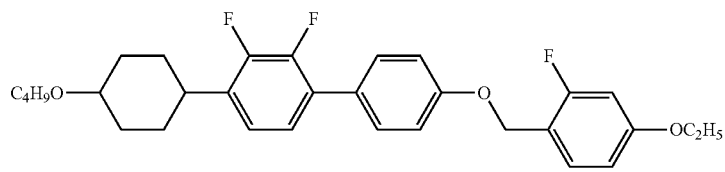 |
| 3712 | 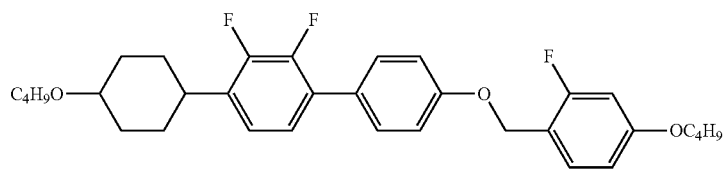 |
| 3713 | 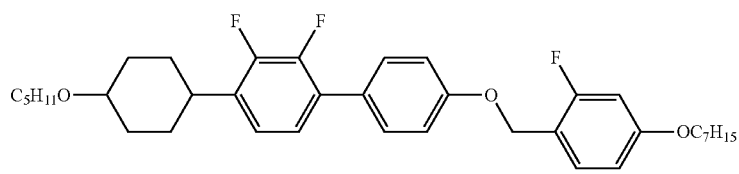 |
| 3714 | 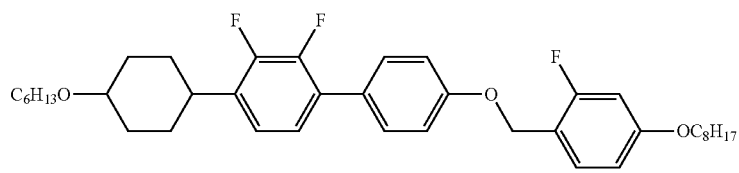 |
| 3715 | 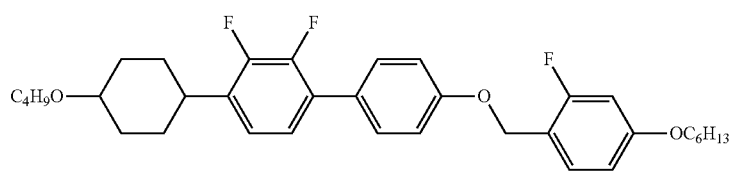 |
| 3716 | 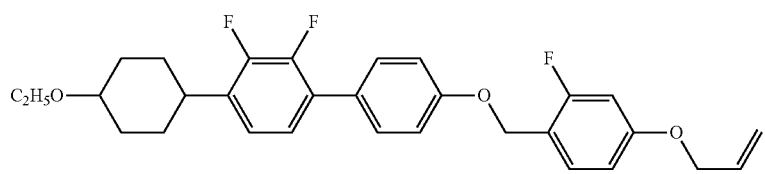 |
| 3717 | 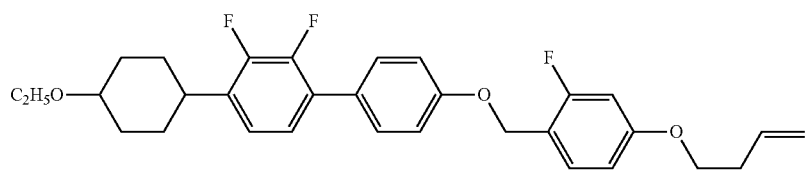 |
| 3718 | 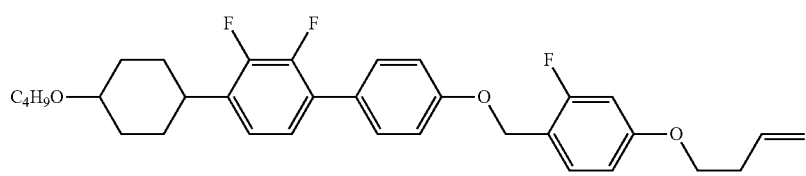 |

| No. | |
|---|---|
| 3719 | 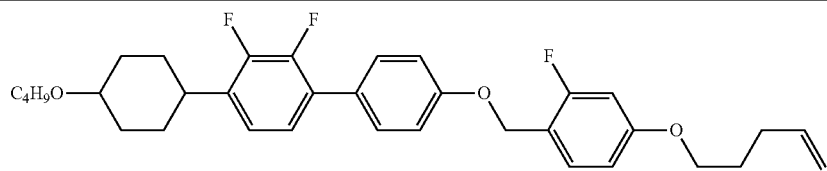 |
| 3720 | 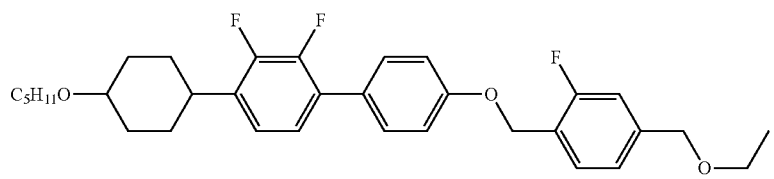 |
| 3721 | 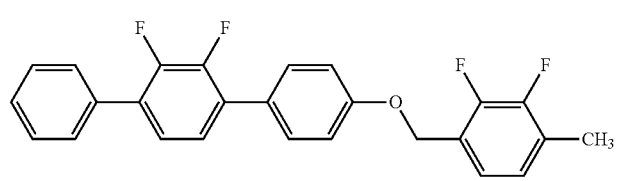 |
| 3722 | 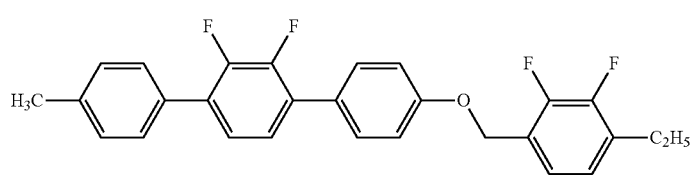 |
| 3723 | 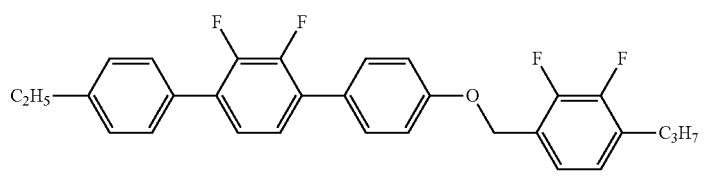 |
| 3724 | 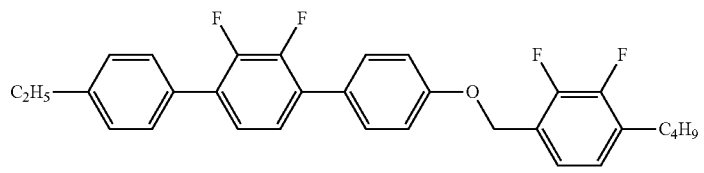 |
| 3725 | 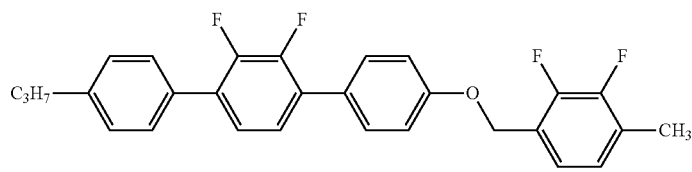 |
| 3726 |  |
| 3727 | 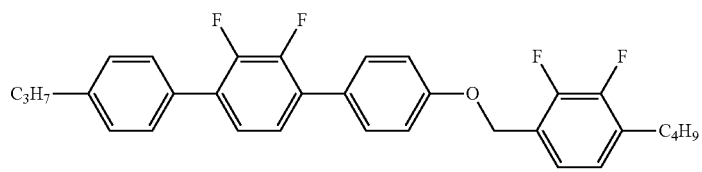 |

| No. |
|---|
| 3728 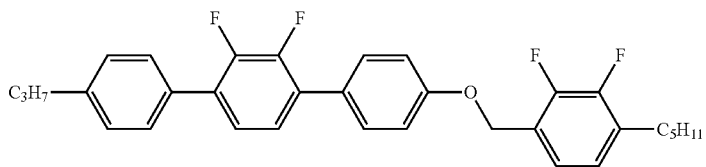 |
| 3729 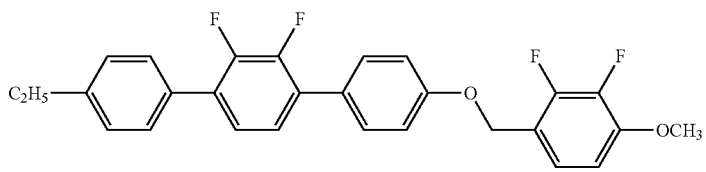 |
| 3730 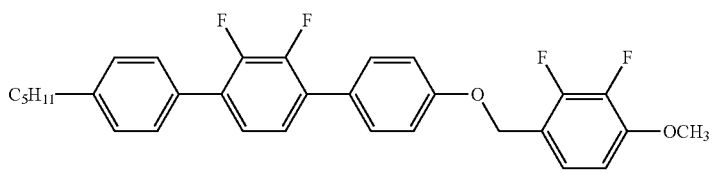 |
| 3731 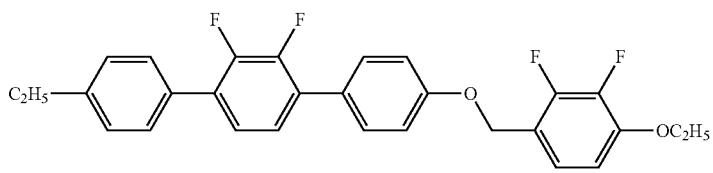 |
| 3732 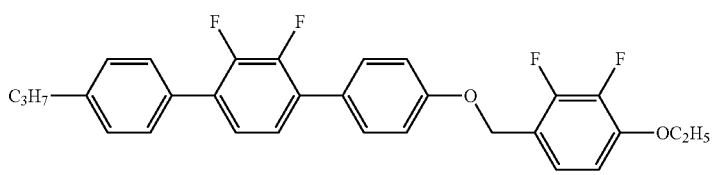 |
| 3733 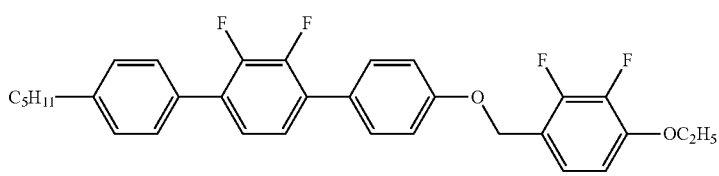 |
| 3734 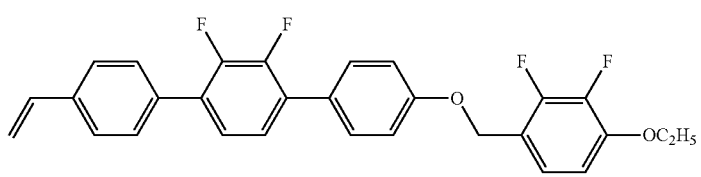 |
| 3735 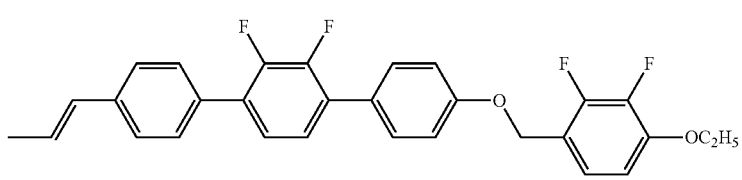 |

| No. |
|---|
| 3736 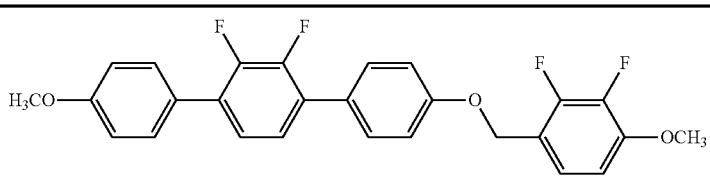 |
| 3737 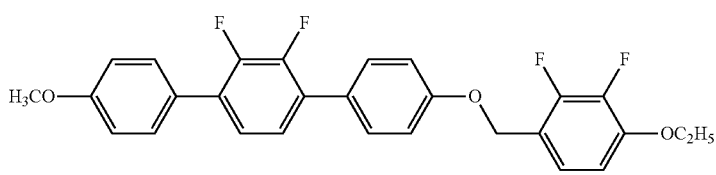 [SMILES: CCOc1ccc(COc2ccc(-c3ccc(-c4ccc(OC)cc4)c(F)c3F)cc2)c(F)c1F] |
| 3738 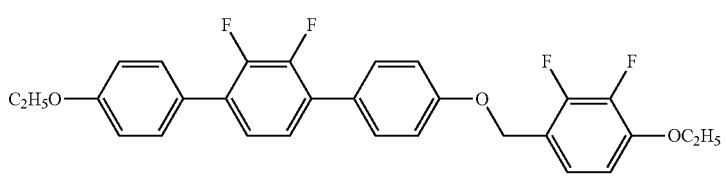 |
| 3739  |
| 3740 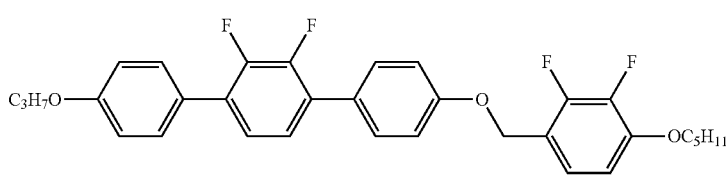 |
| 3741 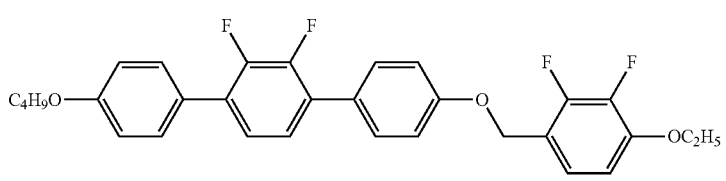 |
| 3742 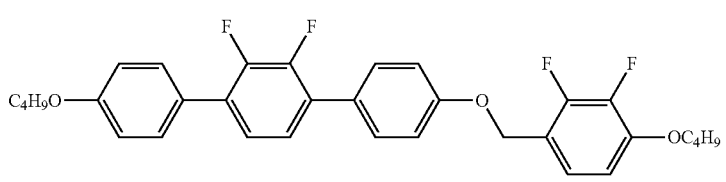 |
| 3743 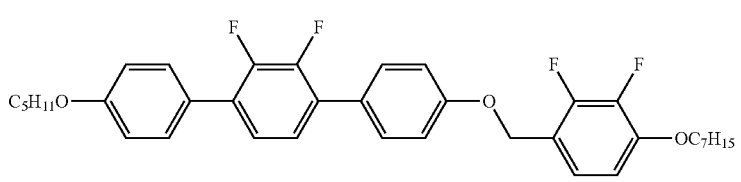 |
| 3744 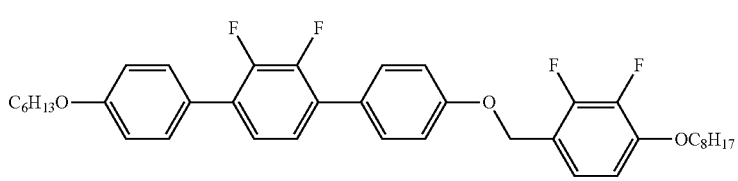 |

| No. |
|---|
3745 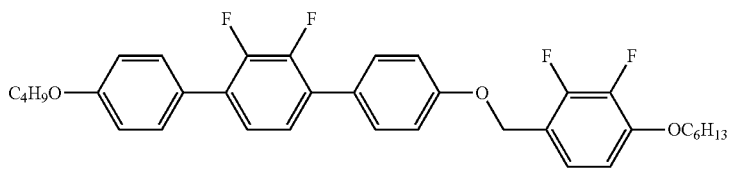
3746 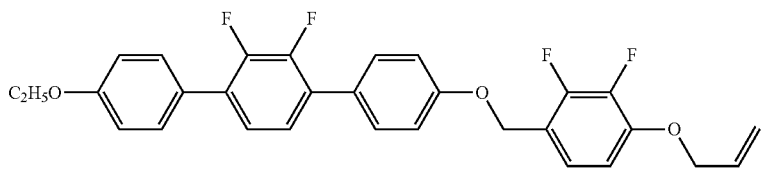
3747 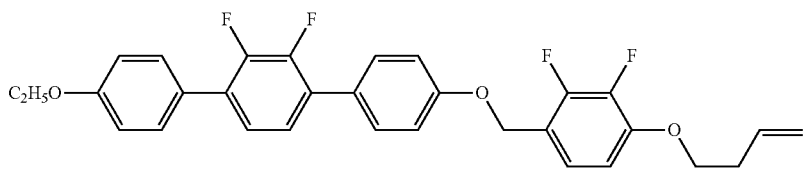
3748 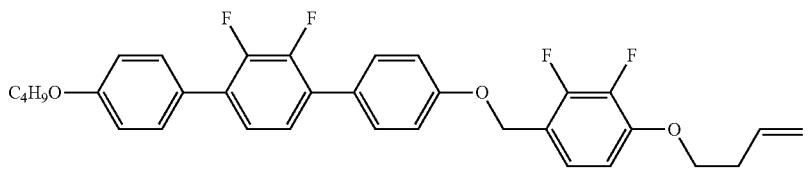
3749 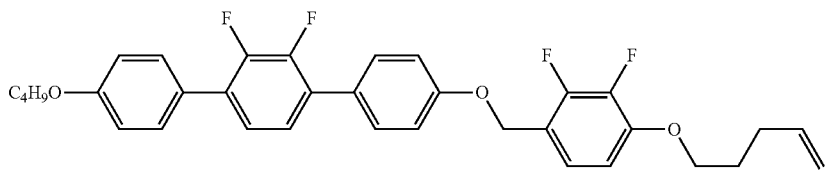
3750 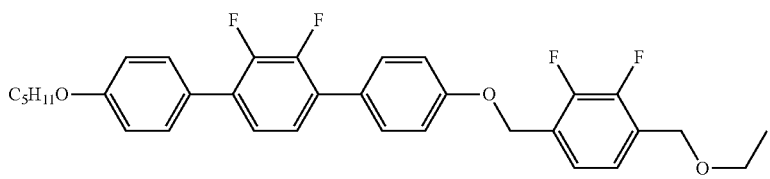
3751 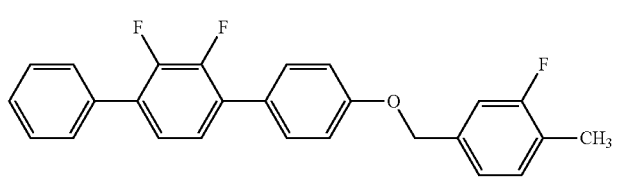
3752 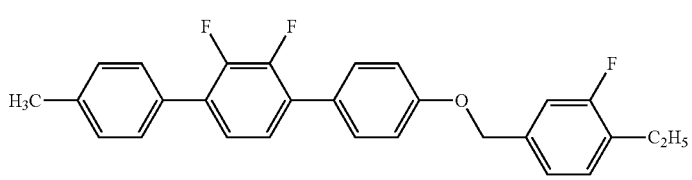

| No. | |
|---|---|
| 3753 | 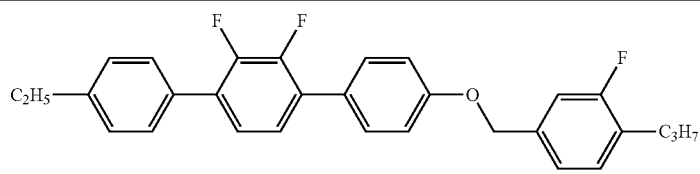 |
| 3754 | 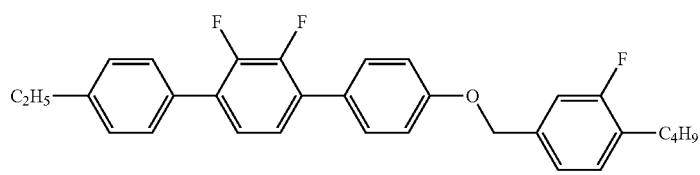 |
| 3755 | 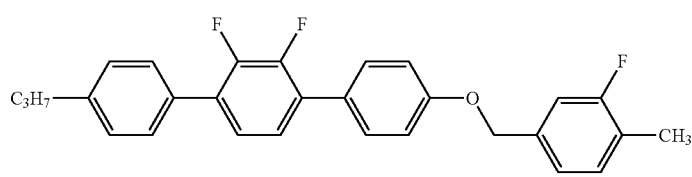 |
| 3756 | 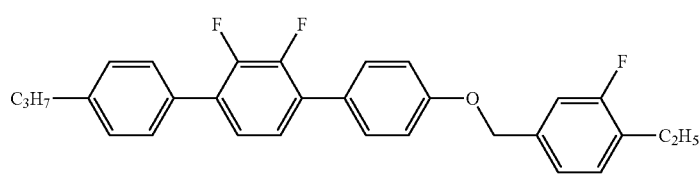 |
| 3757 | 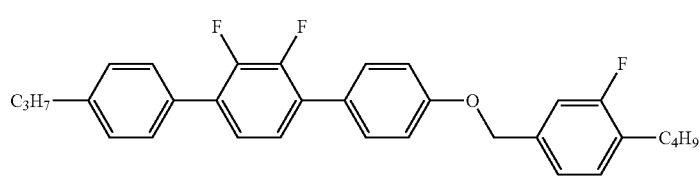 |
| 3758 | 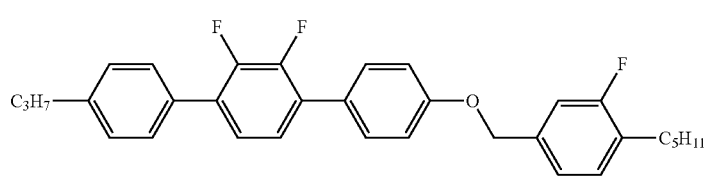 |
| 3759 | 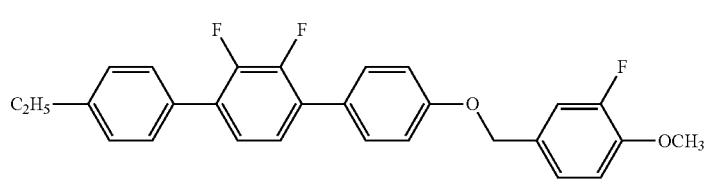 |
| 3760 | 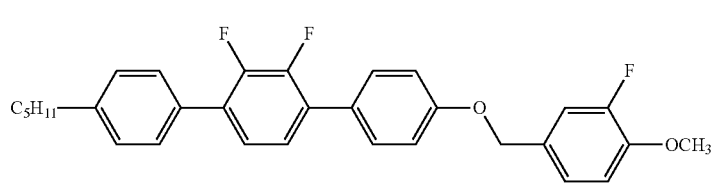 |
| 3761 | 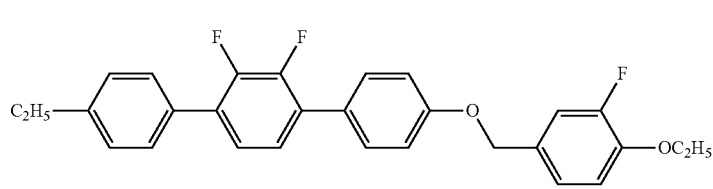 |

| No. |
|---|
| 3762 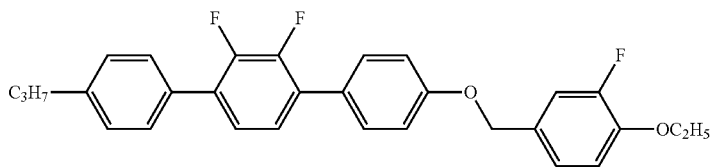 |
| 3763 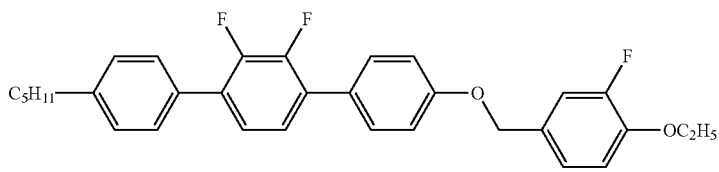 |
| 3764 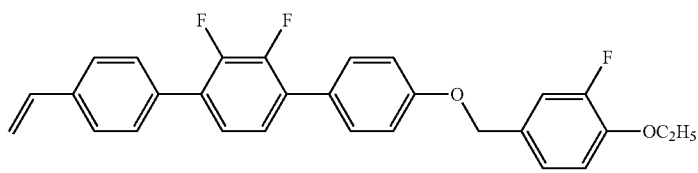 |
| 3765 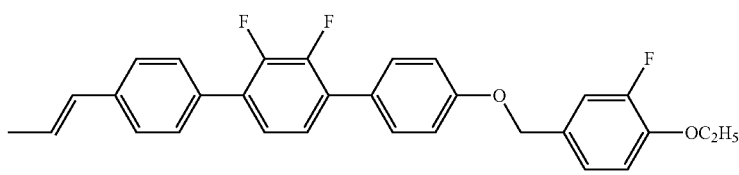 |
| 3766 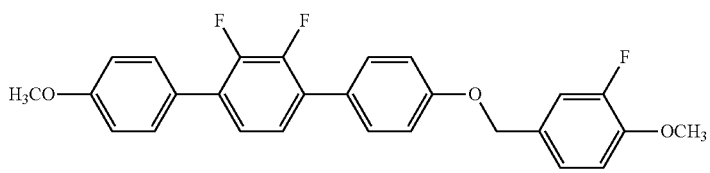 [SMILES: COc1ccc(-c2ccc(-c3ccc(OCc4ccc(OC)c(F)c4)cc3)c(F)c2F)cc1] |
| 3767 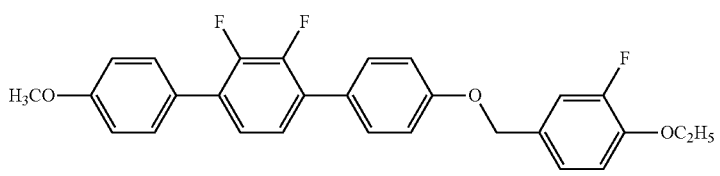 [SMILES: CCOc1ccc(COc2ccc(-c3ccc(-c4ccc(OC)cc4)c(F)c3F)cc2)cc1F] |
| 3768 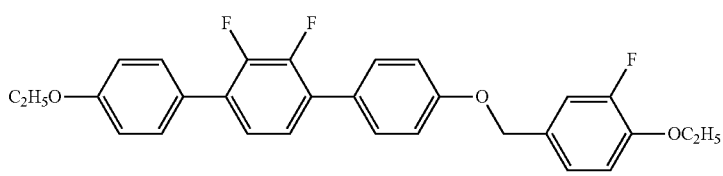 |
| 3769 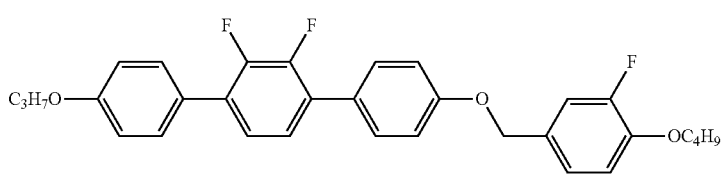 |

| No. |
|---|
| 3770 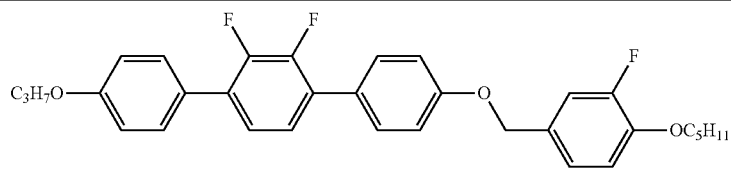 |
| 3771 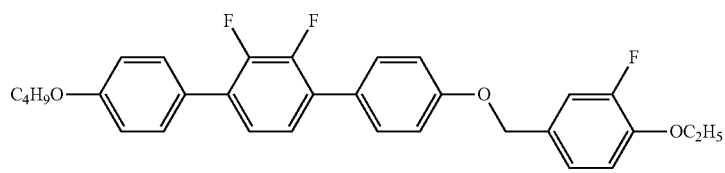 |
| 3772 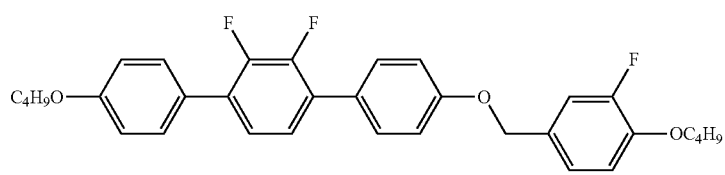 |
| 3773 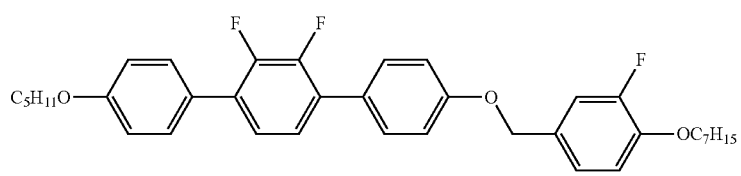 |
| 3774 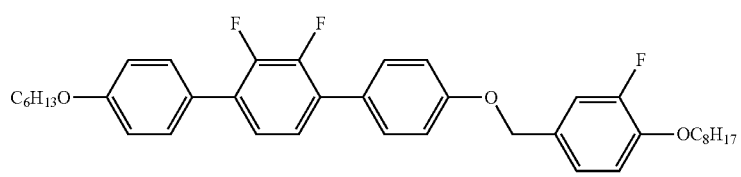 |
| 3775 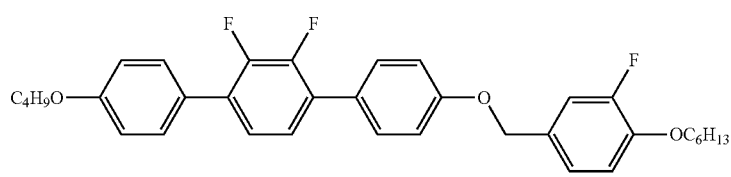 |
| 3776 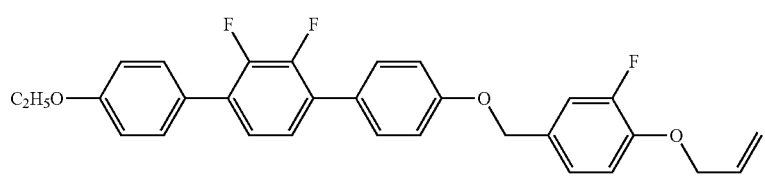 |
| 3777 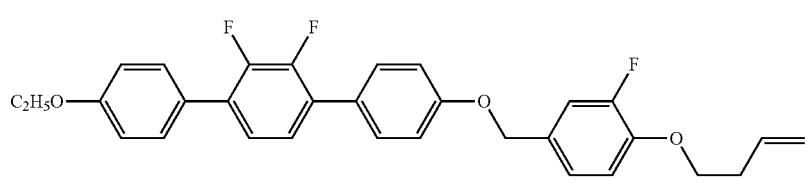 |
| 3778 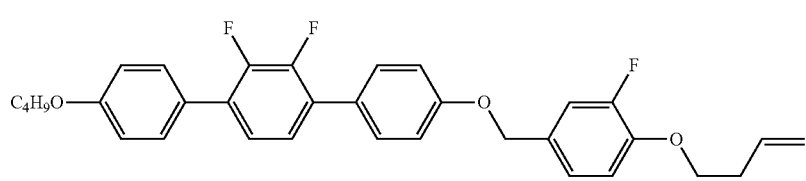 |

-continued
| No. | |
|---|---|
| 3779 | 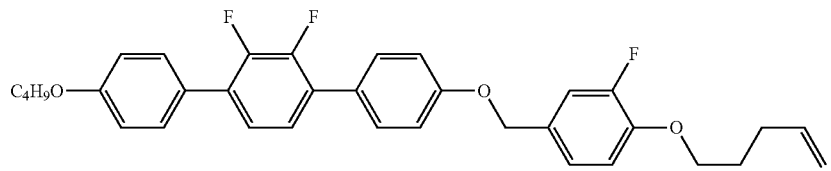 |
| 3780 | 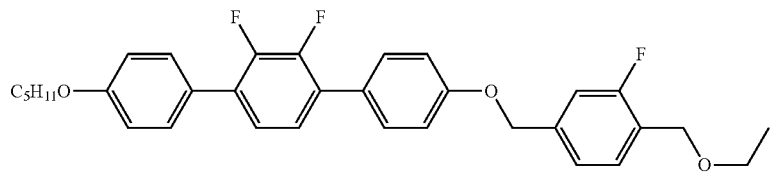 |
| 3781 | 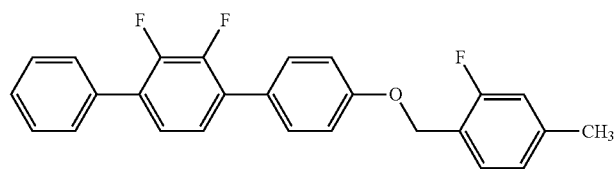 |
| 3782 | 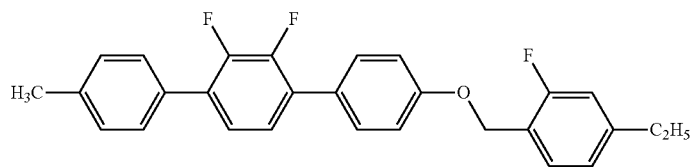 |
| 3783 | 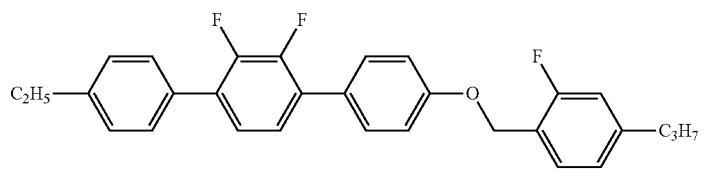 |
| 3784 | 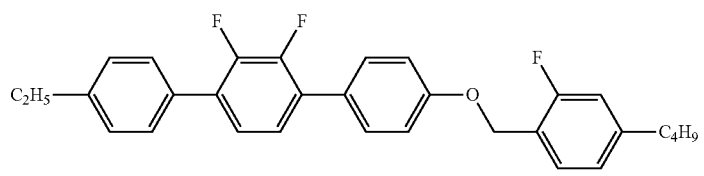 |
| 3785 | 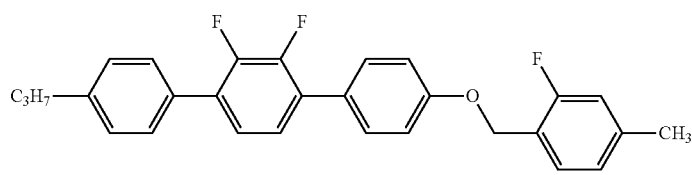 |
| 3786 | 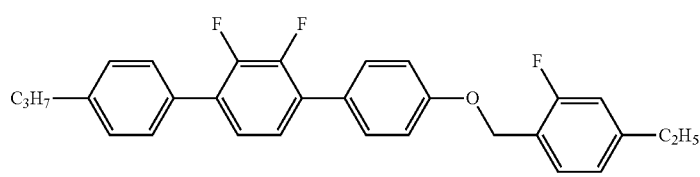 |

| No. |
|---|
| 3787 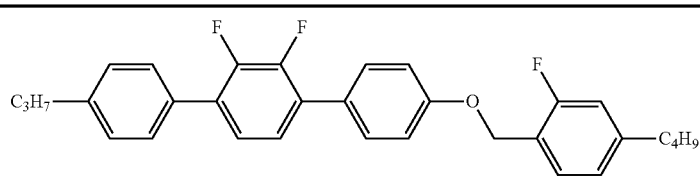 |
| 3788 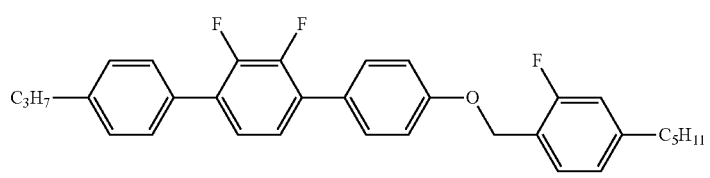 |
| 3789 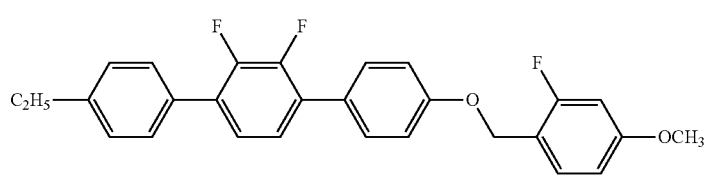 [SMILES: CCc1ccc(-c2ccc(-c3ccc(OCc4ccc(OC)cc4F)cc3)c(F)c2F)cc1] |
| 3790 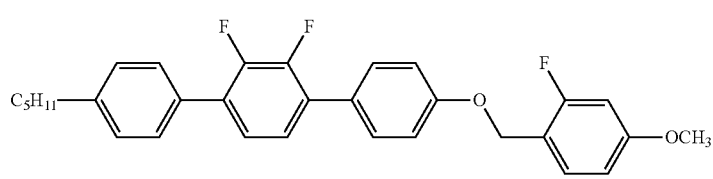 |
| 3791 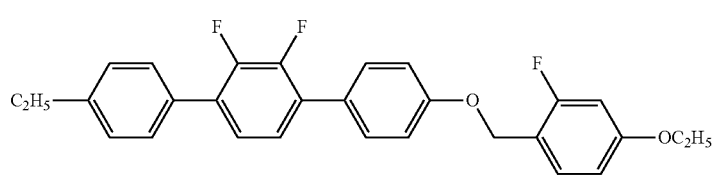 |
| 3792 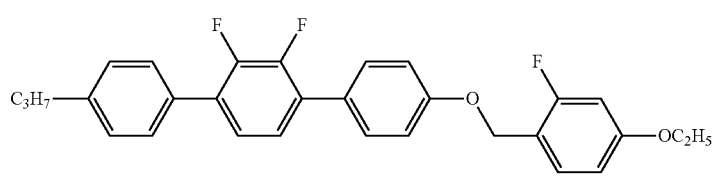 |
| 3793 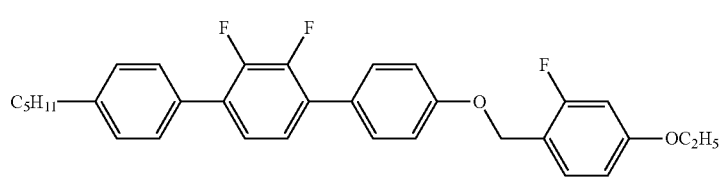 |
| 3794 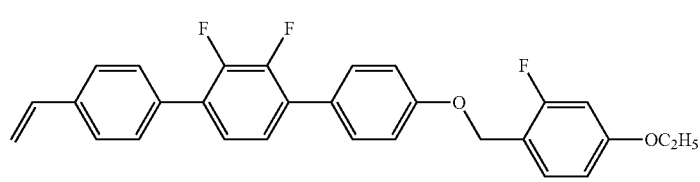 [SMILES: C=Cc1ccc(-c2ccc(-c3ccc(OCc4ccc(OCC)cc4F)cc3)c(F)c2F)cc1] |
| 3795 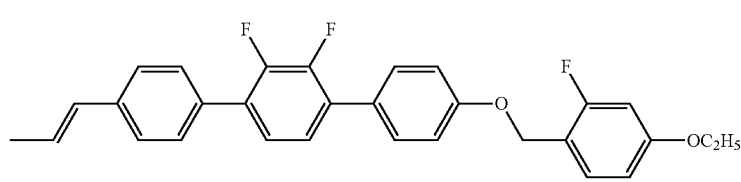 |

| No. |
|---|
| 3796 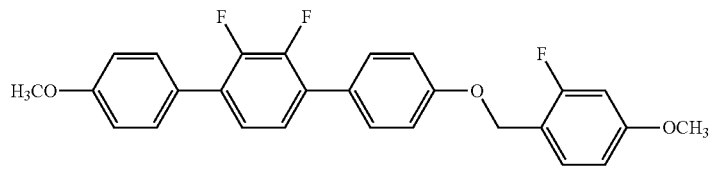 |
| 3797 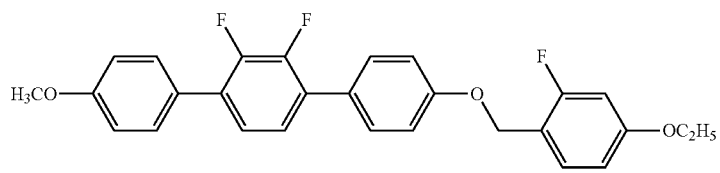 |
| 3798 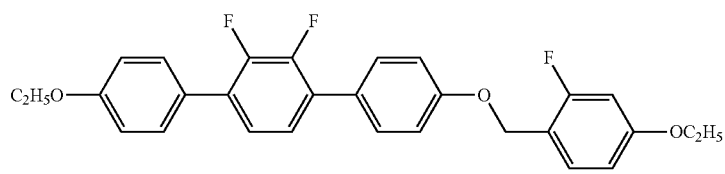 |
| 3799 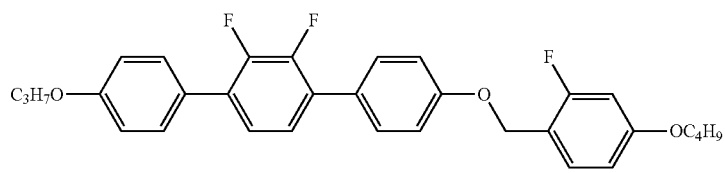 |
| 3800 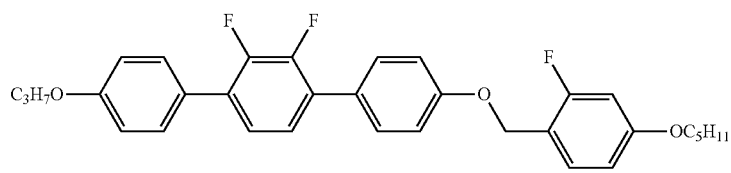 |
| 3801 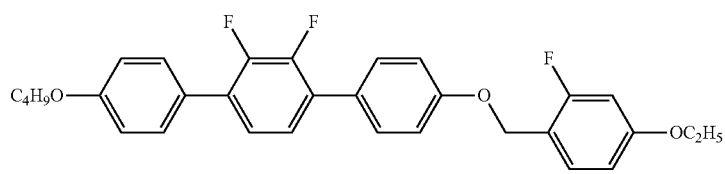 |
| 3802 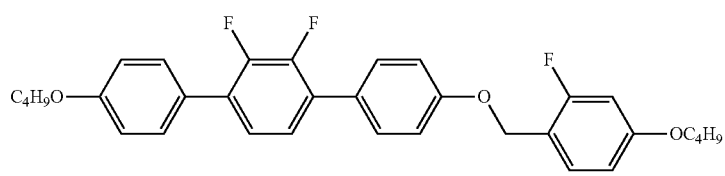 |
| 3803 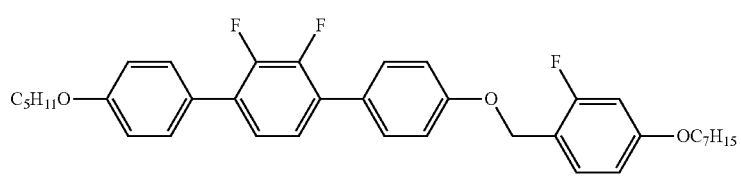 |

| No. |
|---|
| 3804 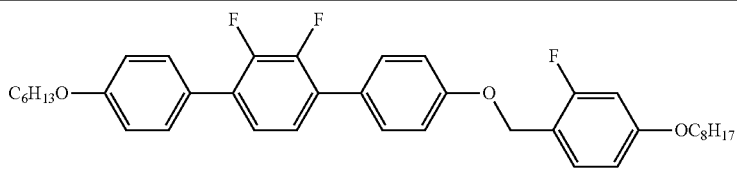 |
| 3805 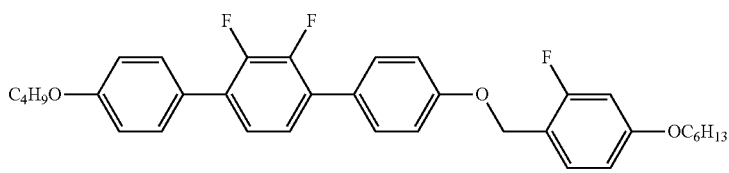 |
| 3806 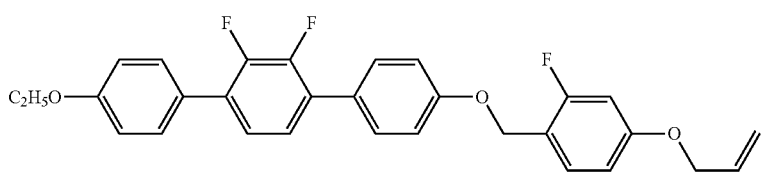 |
| 3807 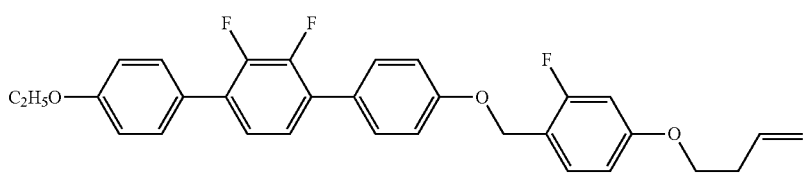 |
| 3808 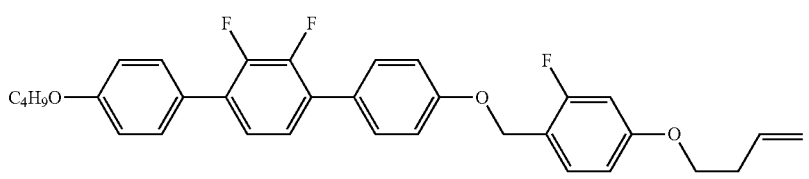 |
| 3809 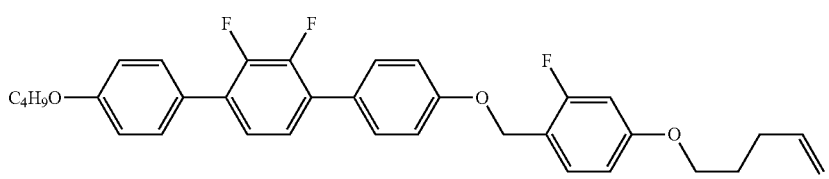 |
| 3810 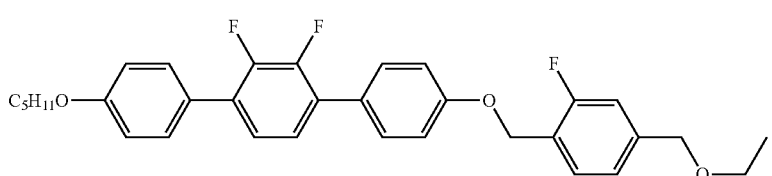 |
| 3811 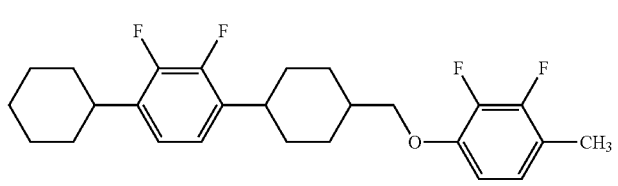 [SMILES: Cc1ccc(OCC2CCC(c3ccc(C4CCCCC4)c(F)c3F)CC2)c(F)c1F] |
| 3812 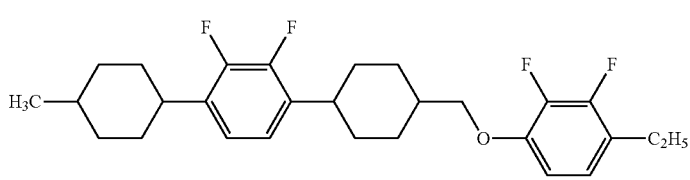 |

-continued
| No. | |
|---|---|
| 3813 | 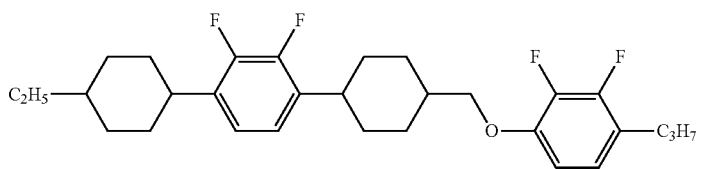 |
| 3814 | 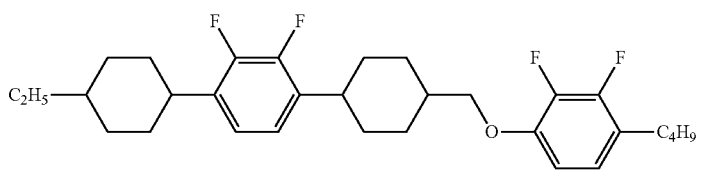 |
| 3815 | 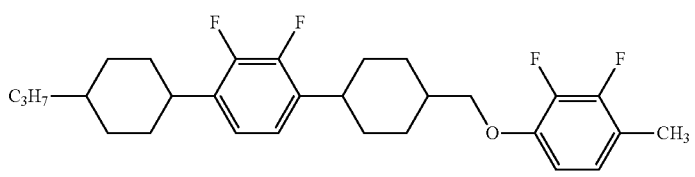 |
| 3816 | 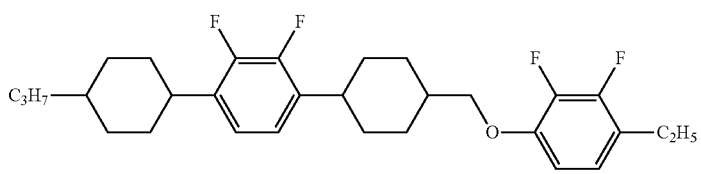 |
| 3817 | 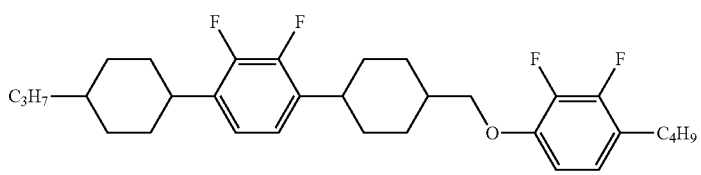 |
| 3818 | 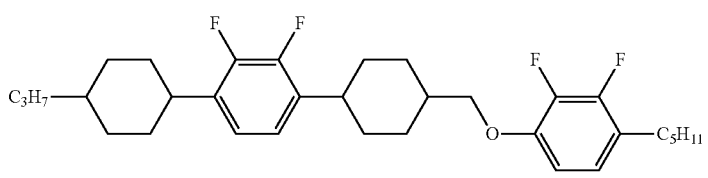 |
| 3819 | 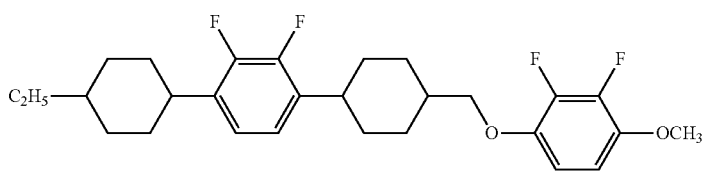 [SMILES: CCC1CCC(c2ccc(C3CCC(COc4ccc(OC)c(F)c4F)CC3)c(F)c2F)CC1] |
| 3820 | 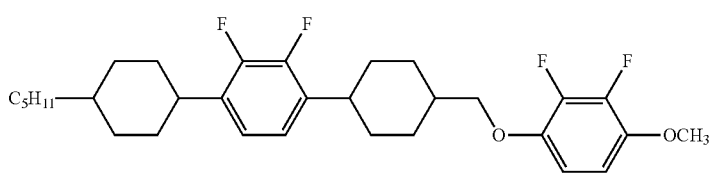 |

| No. |
|---|
| 3821 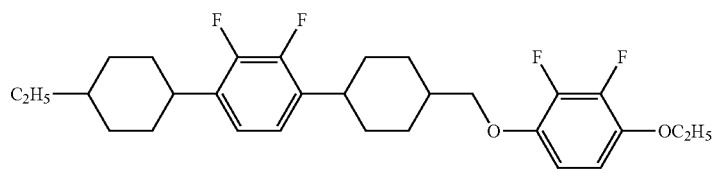 [SMILES: CCOc1ccc(OCC2CCC(c3ccc(C4CCC(CC)CC4)c(F)c3F)CC2)c(F)c1F] |
| 3822  |
| 3823 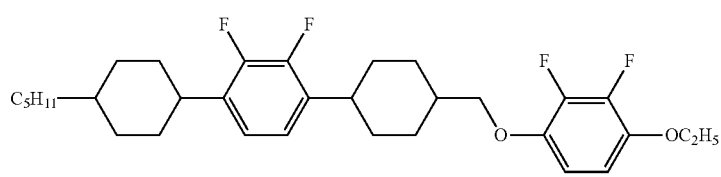 C₁ −33.1 C₂ 91.5 N 209.3 I<br>T$_{NI}$; 179.3° C., Δε; −6.10, Δn; 0.134 |
| 3824 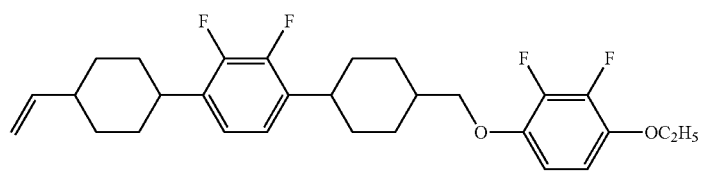 |
| 3825 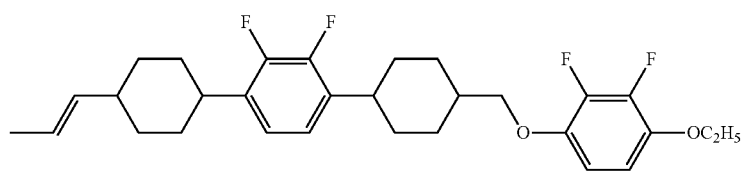 [SMILES: C/C=C/C1CCC(c2ccc(C3CCC(COc4ccc(OCC)c(F)c4F)CC3)c(F)c2F)CC1] |
| 3826 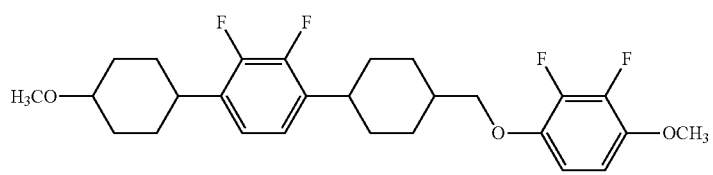 [SMILES: COc1ccc(OCC2CCC(c3ccc(C4CCC(OC)CC4)c(F)c3F)CC2)c(F)c1F] |
| 3827 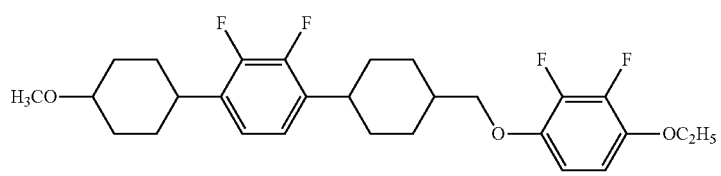 |
| 3828 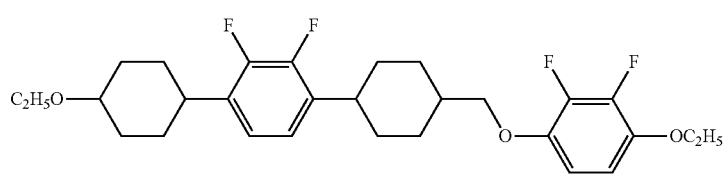 |

| No. |
|---|
| 3829 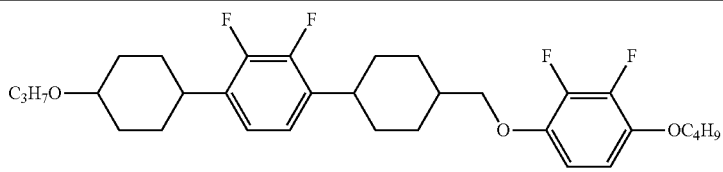 |
| 3830 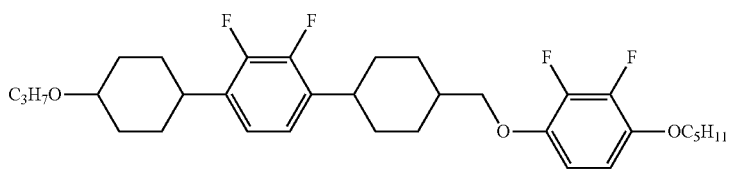 |
| 3831 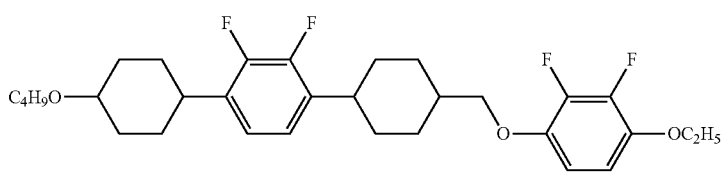 |
| 3832 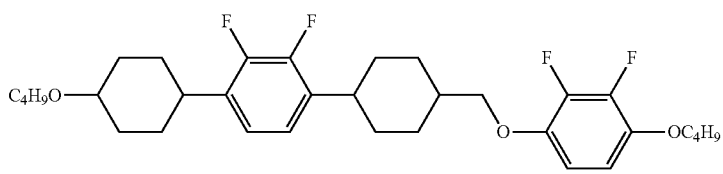 |
| 3833  |
| 3834 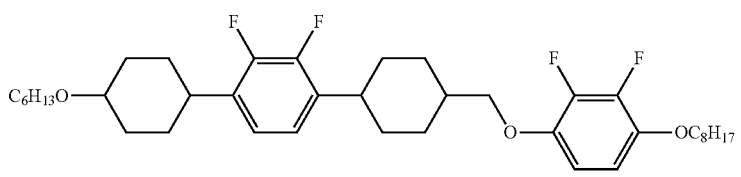 |
| 3835 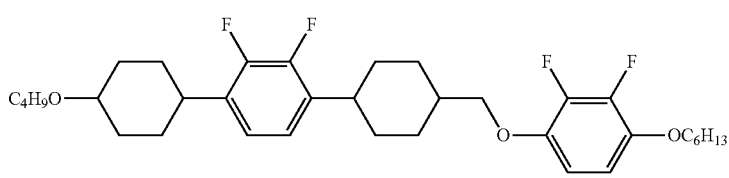 |
| 3836 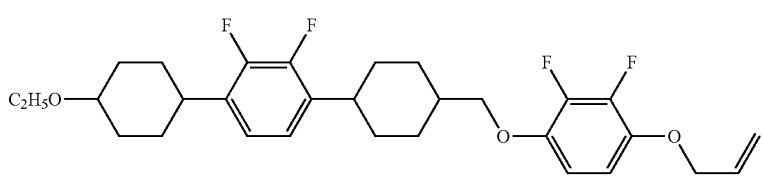 |
| 3837 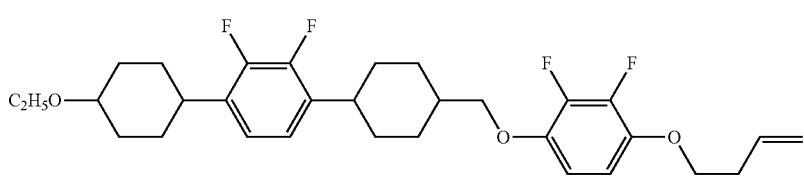 |

-continued
| No. | |
|---|---|
| 3838 | 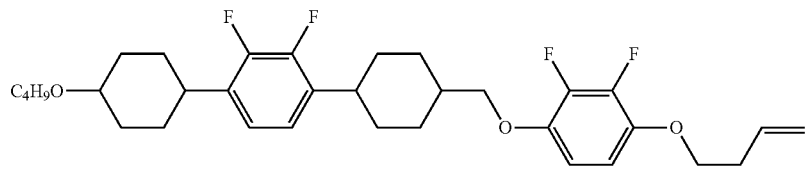 |
| 3839 | 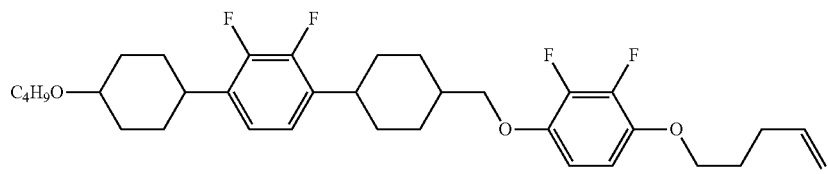 |
| 3840 | 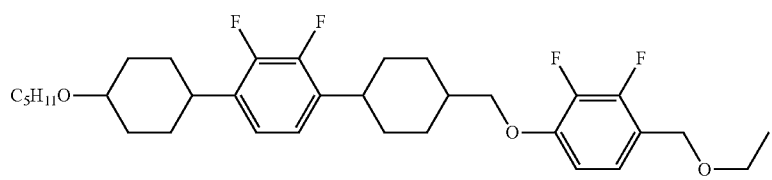 |
| 3841 | 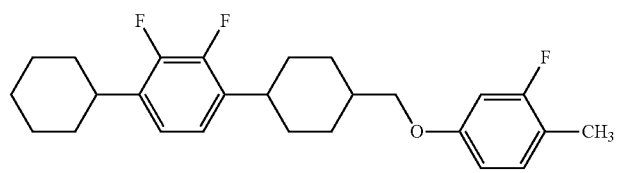 |
| 3842 | 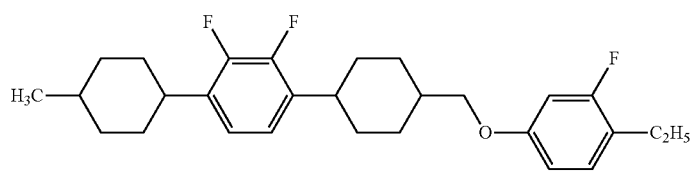 |
| 3843 | 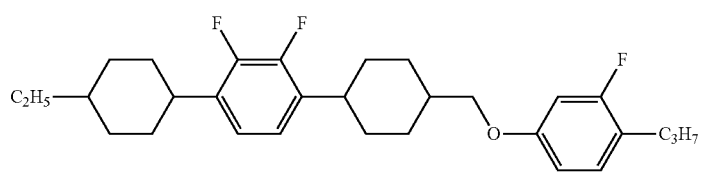 |
| 3844 | 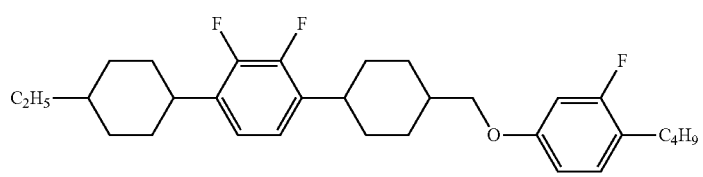 |
| 3845 | 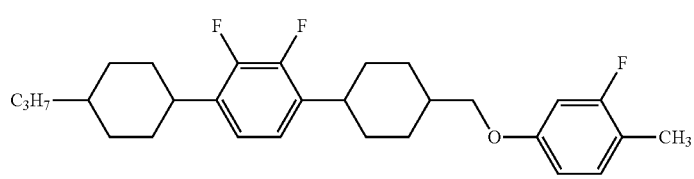 |

| No. | |
|---|---|
| 3846 | 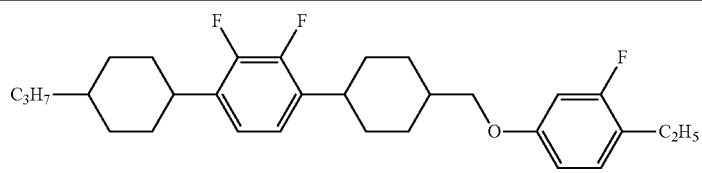 |
| 3847 | 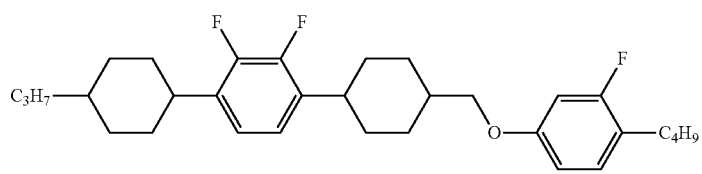 |
| 3848 | 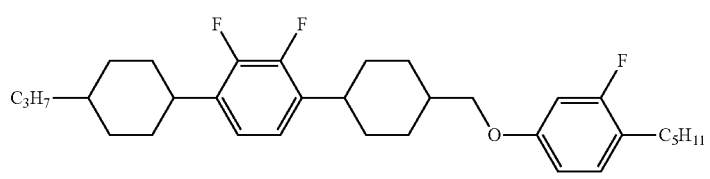 |
| 3849 | 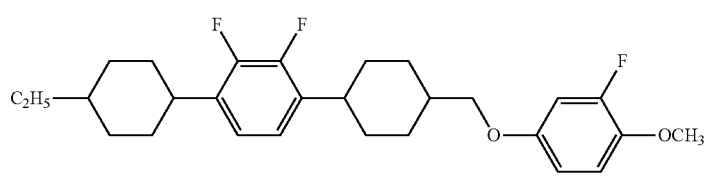 [SMILES: CCC1CCC(c2ccc(C3CCC(COc4ccc(OC)c(F)c4)CC3)c(F)c2F)CC1] |
| 3850 | 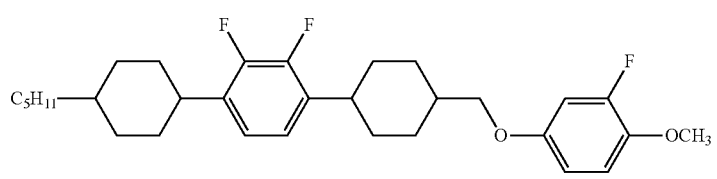 |
| 3851 | 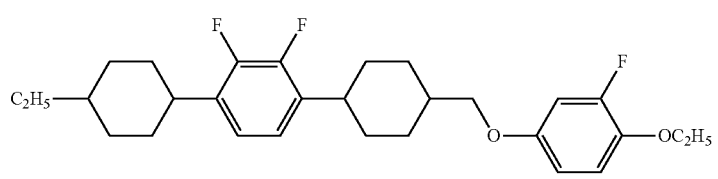 |
| 3852 | 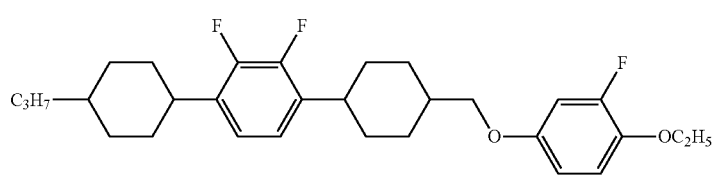 |
| 3853 | 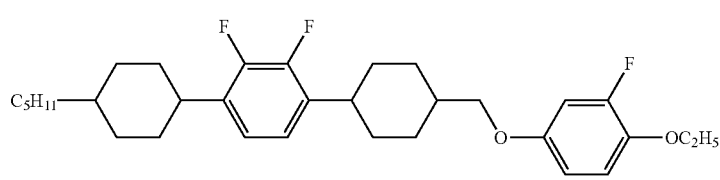 |
| 3854 | 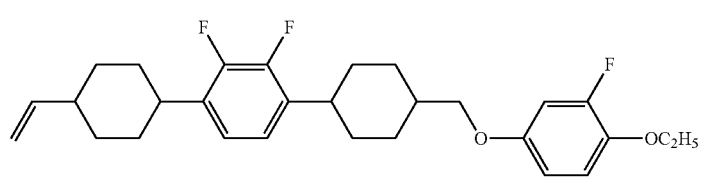 |

| No. | |
|---|---|
| 3855 | 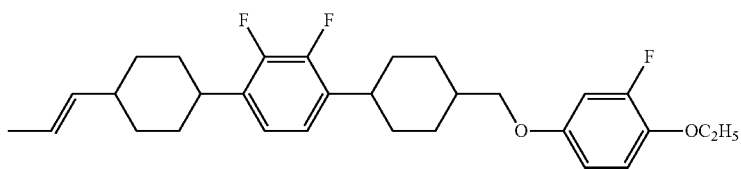 [SMILES: C/C=C/C1CCC(c2ccc(C3CCC(COc4ccc(OCC)c(F)c4)CC3)c(F)c2F)CC1] |
| 3856 | 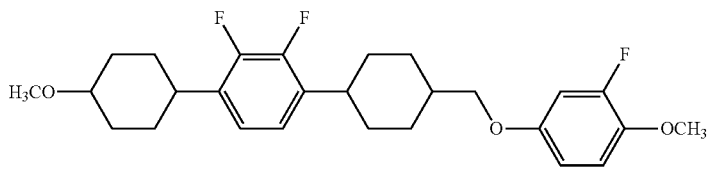 |
| 3857 | 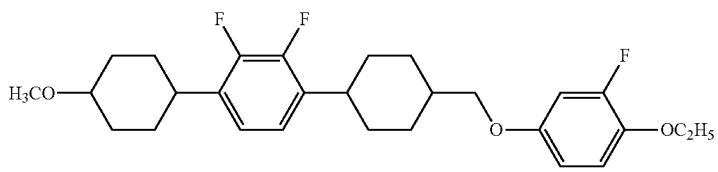 |
| 3858 | 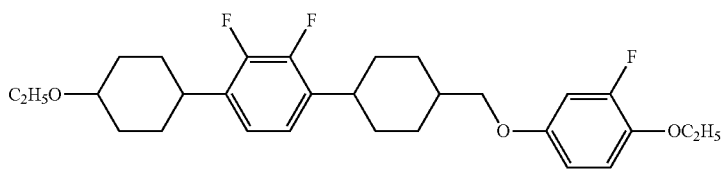 |
| 3859 | 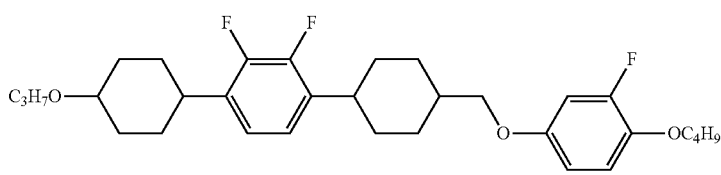 |
| 3860 | 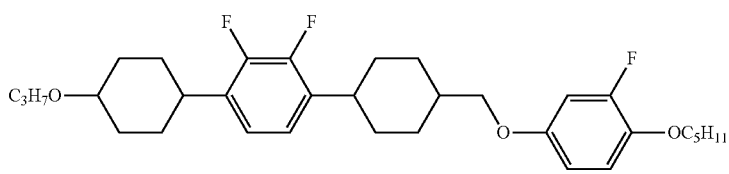 |
| 3861 | 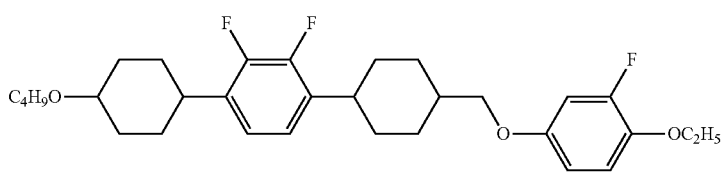 |
| 3862 | 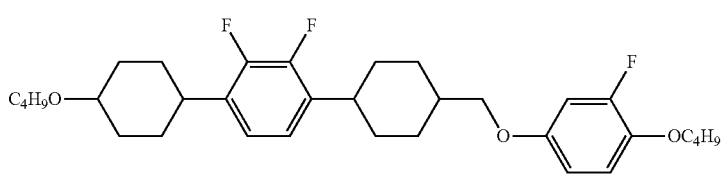 |

| No. | |
|---|---|
| 3863 | 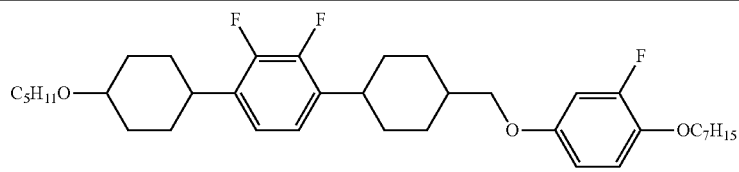 |
| 3864 | 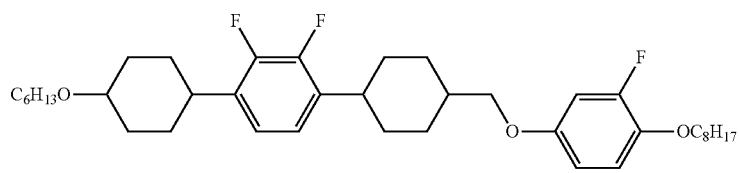 |
| 3865 | 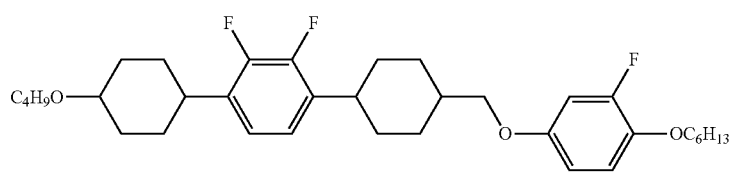 |
| 3866 | 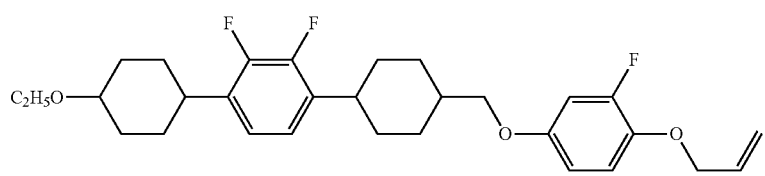 |
| 3867 | 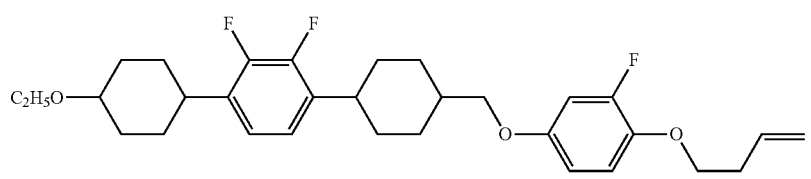 |
| 3868 | 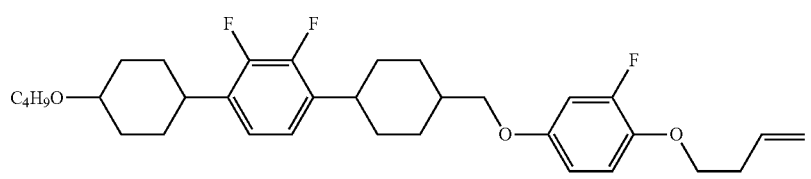 |
| 3869 | 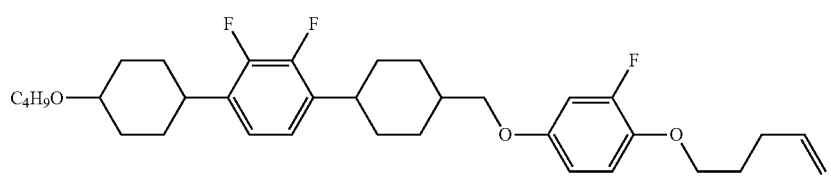 |
| 3870 | 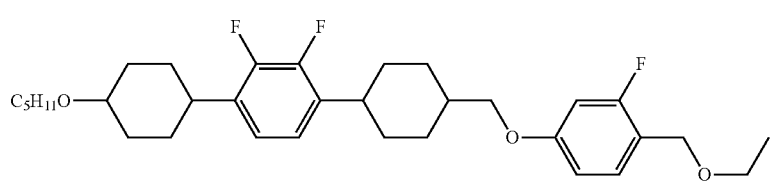 |
| 3871 | 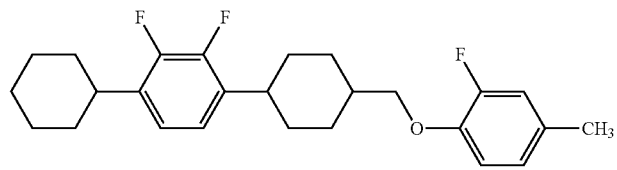 |

| No. | |
|---|---|
| 3872 | 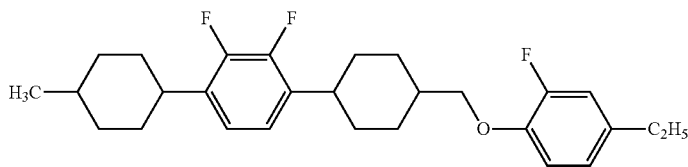 [SMILES: CCc1ccc(OCC2CCC(c3ccc(C4CCC(C)CC4)c(F)c3F)CC2)c(F)c1] |
| 3873 | 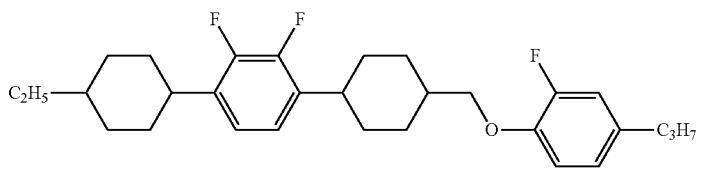 |
| 3874 | 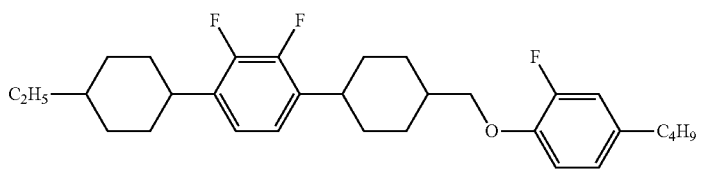 |
| 3875 | 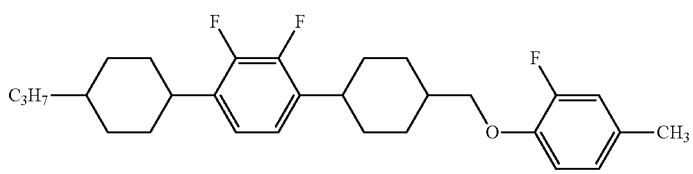 |
| 3876 | 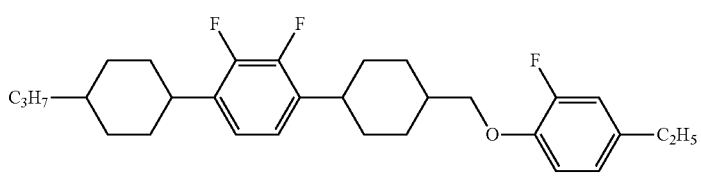 |
| 3877 | 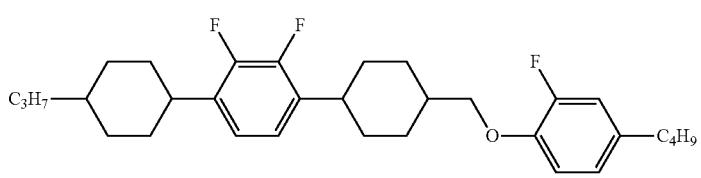 |
| 3878 | 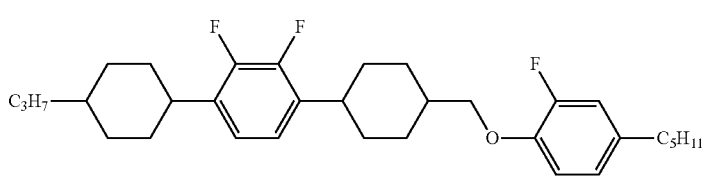 |
| 3879 | 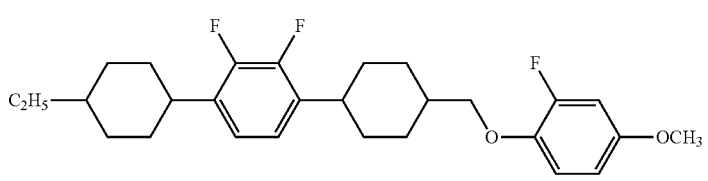 [SMILES: CCC1CCC(c2ccc(C3CCC(COc4ccc(OC)cc4F)CC3)c(F)c2F)CC1] |

| No. |
|---|
| 3880 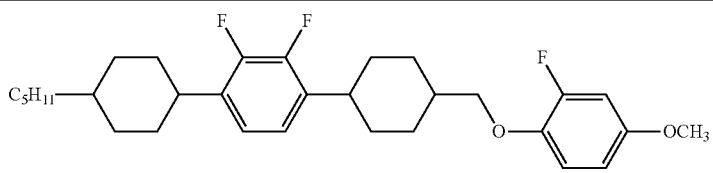 |
| 3881 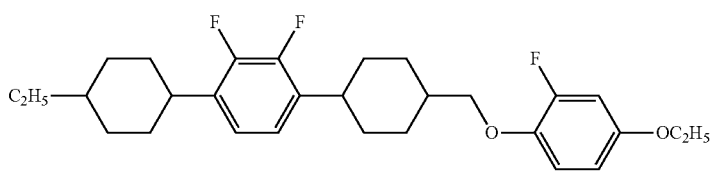 |
| 3882 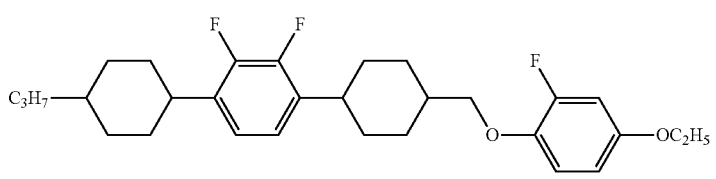 |
| 3883 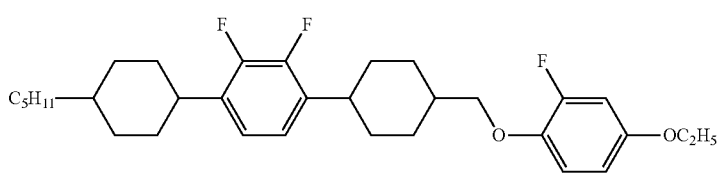 [SMILES: CCOc1ccc(OCC2CCC(c3ccc(C4CCC(OC)CC4)c(F)c3F)CC2)c(F)c1] |
| 3884 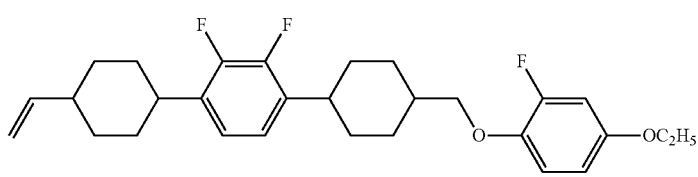 |
| 3885 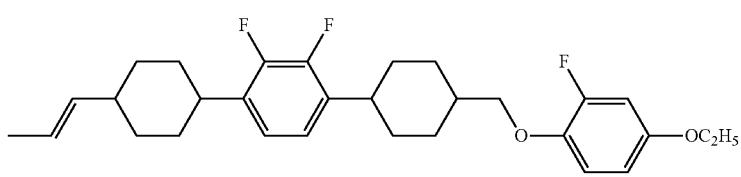 |
| 3886 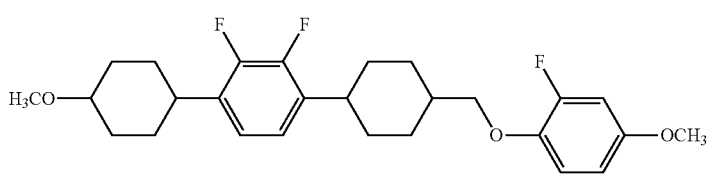 |
| 3887 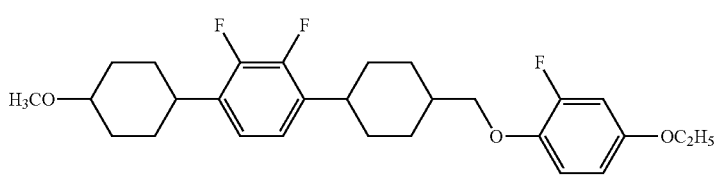 |
| 3888 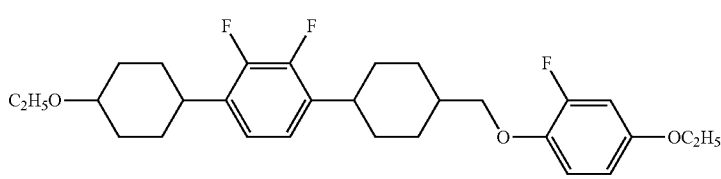 |

-continued
| No. | |
|---|---|
| 3889 | 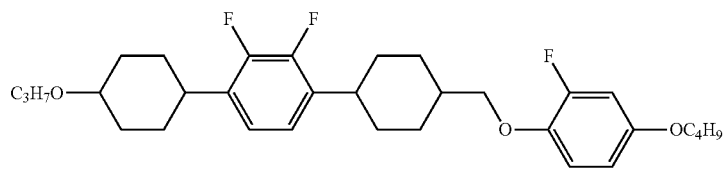 |
| 3890 | 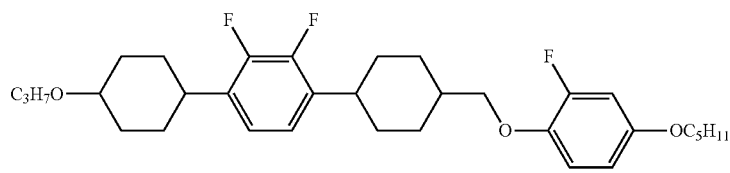 |
| 3891 | 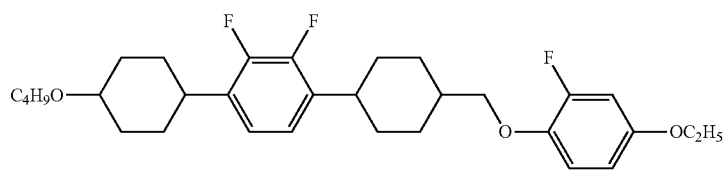 |
| 3892 | 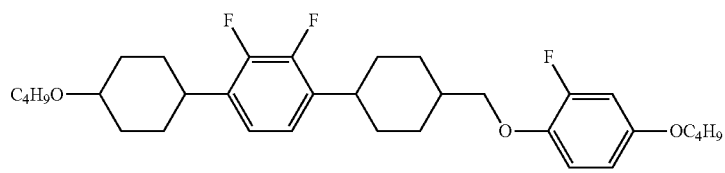 |
| 3893 | 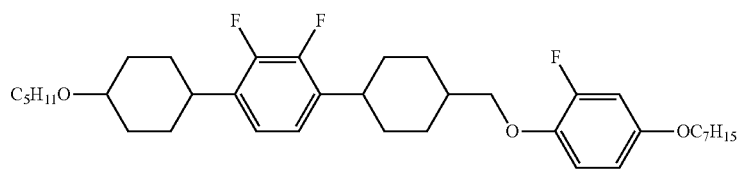 |
| 3894 | 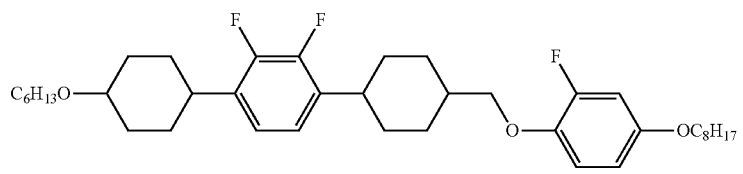 |
| 3895 | 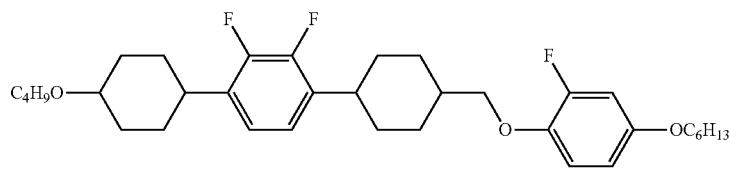 |
| 3896 | 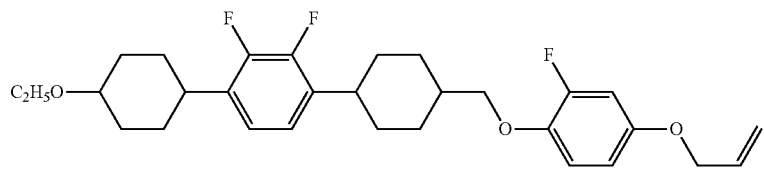 |

| No. | |
|---|---|
| 3897 | 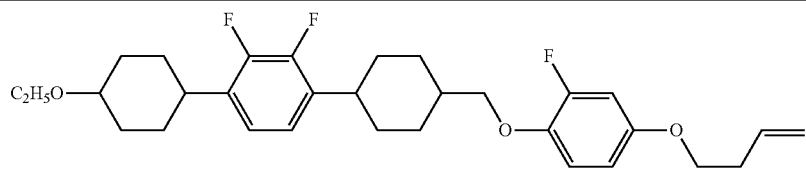 |
| 3898 | 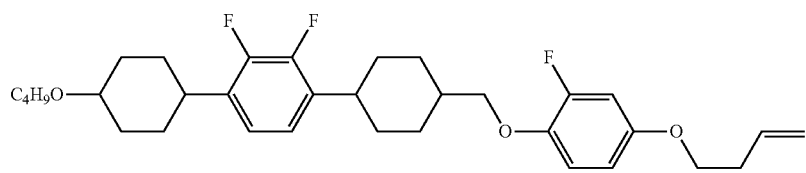 |
| 3899 | 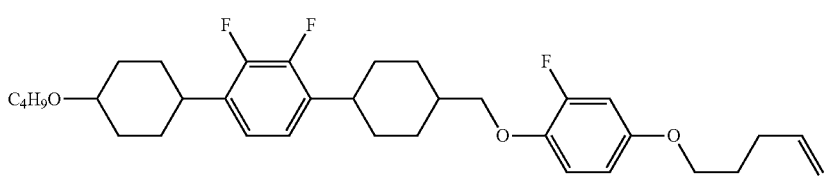 |
| 3900 | 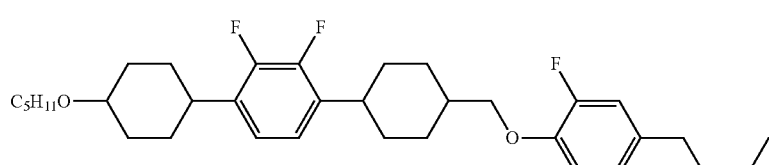 |
| 3901 | 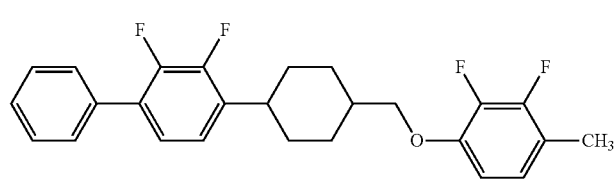 [SMILES: Cc1ccc(OCC2CCC(c3ccc(-c4ccccc4)c(F)c3F)CC2)c(F)c1F] |
| 3902 | 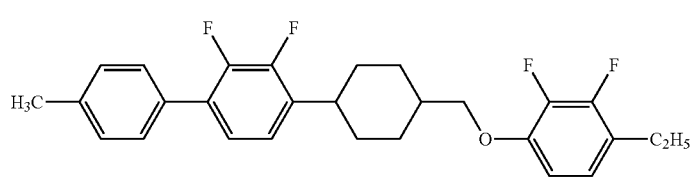 [SMILES: CCc1ccc(OCC2CCC(c3ccc(-c4ccc(C)cc4)c(F)c3F)CC2)c(F)c1F] |
| 3903 | 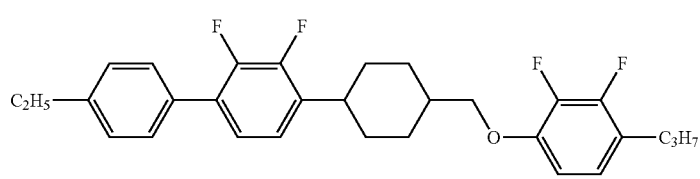 |
| 3904 | 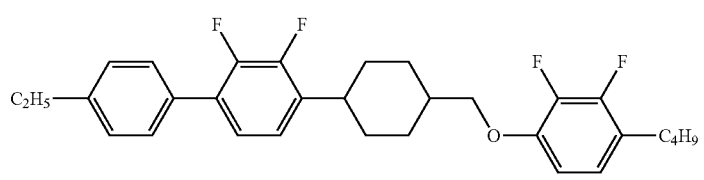 |
| 3905 | 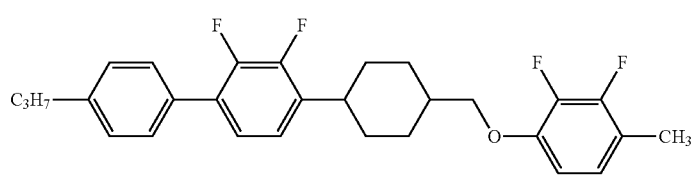 |

| No. | |
|---|---|
| 3906 | 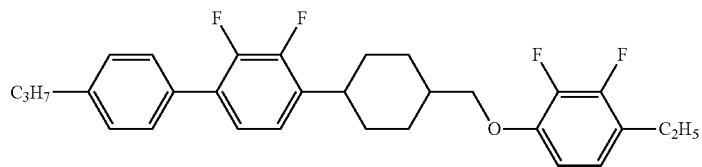 |
| 3907 | 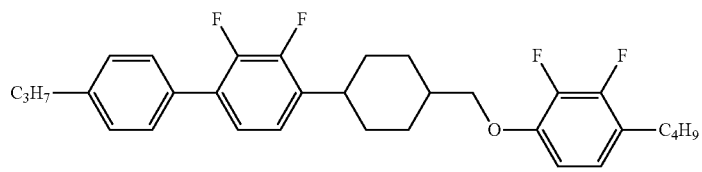 |
| 3908 | 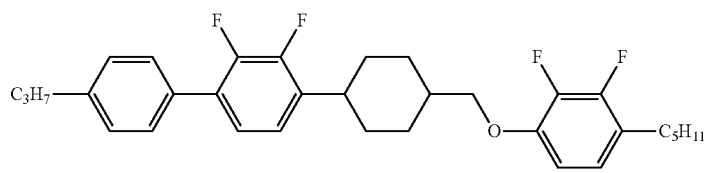 |
| 3909 | 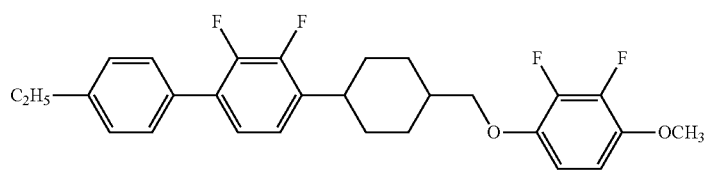 |
| 3910 | 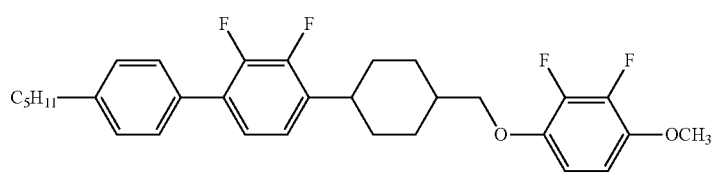 |
| 3911 |  |
| 3912 | 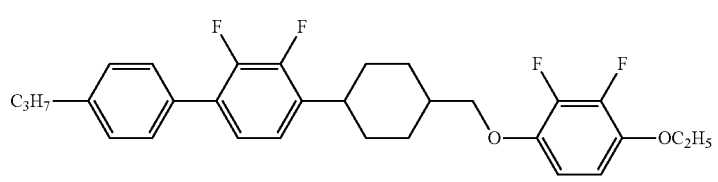 |
| 3913 | 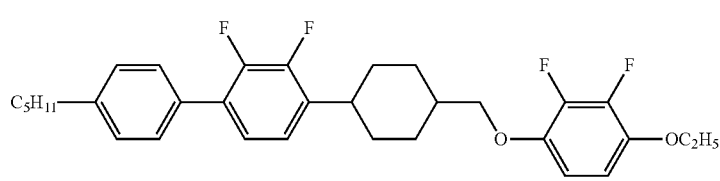 |

-continued
| No. | |
|---|---|
| 3914 | 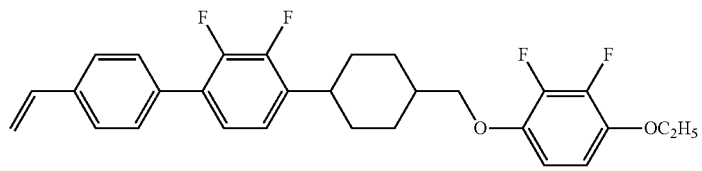 [SMILES: C=Cc1ccc(-c2ccc(C3CCC(COc4ccc(OCC)c(F)c4F)CC3)c(F)c2F)cc1] |
| 3915 | 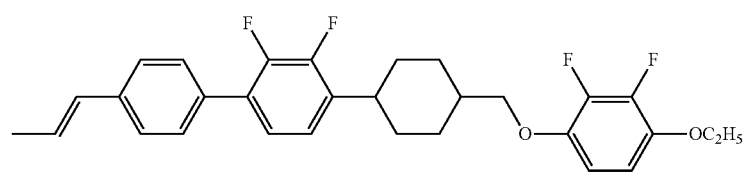 [SMILES: C/C=C/c1ccc(-c2ccc(C3CCC(COc4ccc(OCC)c(F)c4F)CC3)c(F)c2F)cc1] |
| 3916 | 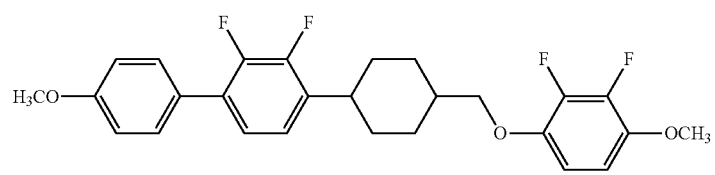 [SMILES: COc1ccc(-c2ccc(C3CCC(COc4ccc(OC)c(F)c4F)CC3)c(F)c2F)cc1] |
| 3917 | 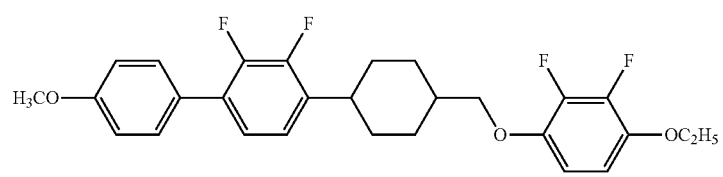 |
| 3918 | 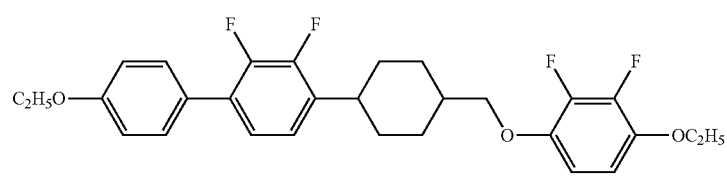 |
| 3919 | 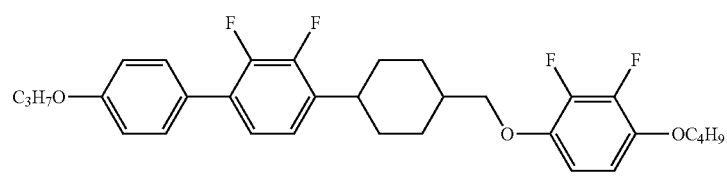 |
| 3920 | 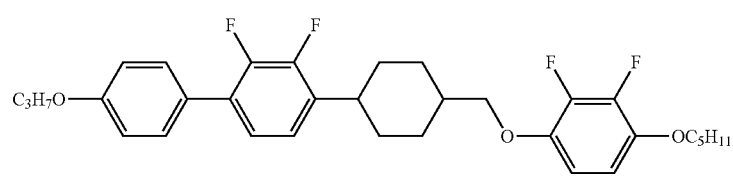 |
| 3921 | 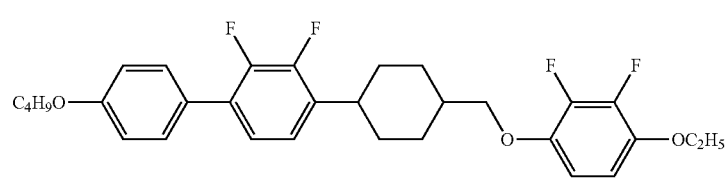 |
$C_1$ 85.4 $C_2$ 96.2 N 228.4 I
$T_{NI}$; 204.6° C., Δε; −6.93, Δn; 0.217

-continued
| No. |
|---|
| 3922 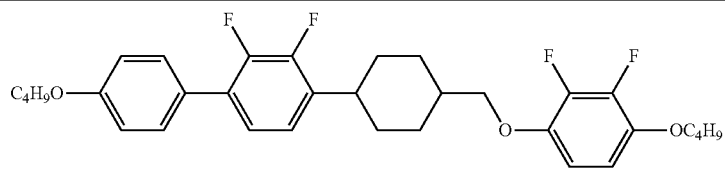 |
| 3923 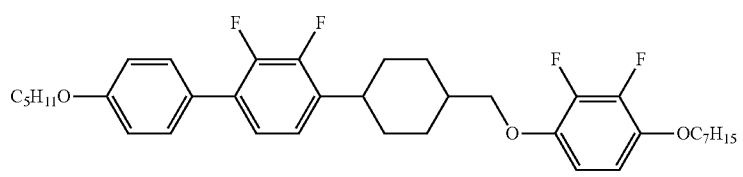 |
| 3924 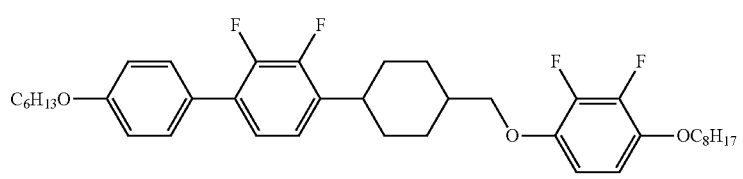 |
| 3925 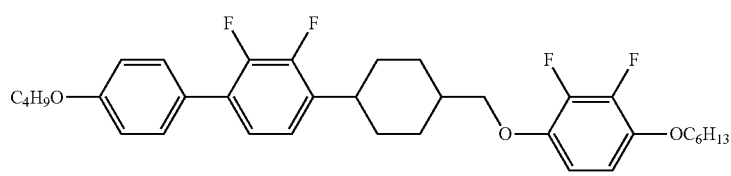 |
| 3926 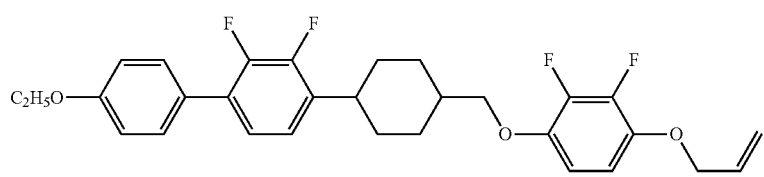 |
| 3927 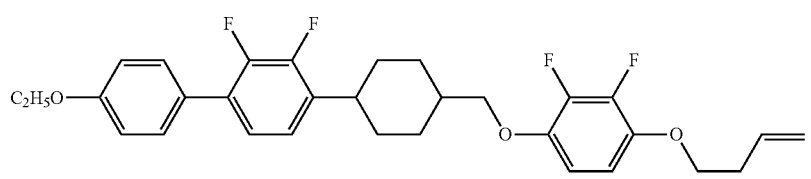 |
| 3928 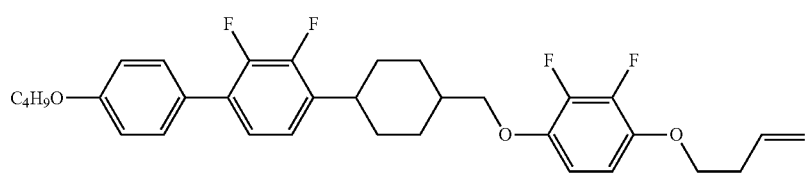 |
| 3929 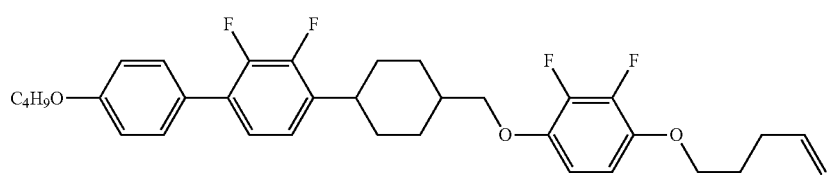 |
| 3930 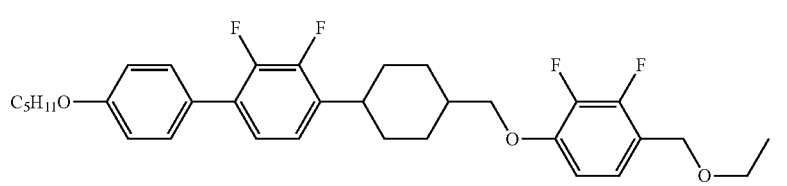 |

| No. | |
|---|---|
| 3931 | 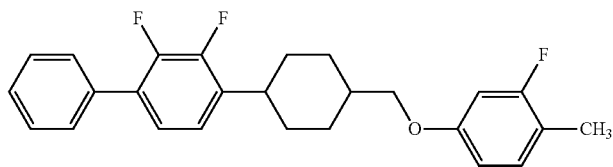 [SMILES: Cc1ccc(OCC2CCC(c3ccc(-c4ccccc4)c(F)c3F)CC2)cc1F] |
| 3932 | 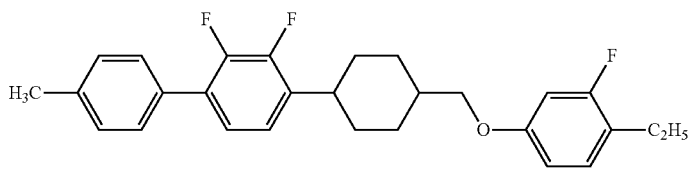 |
| 3933 | 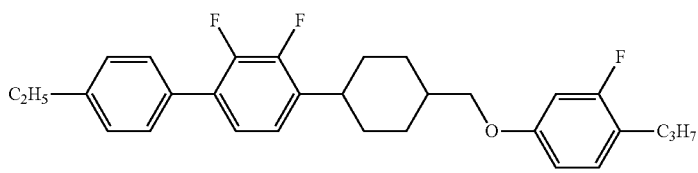 |
| 3934 | 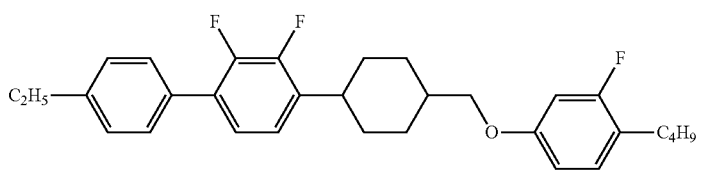 |
| 3935 | 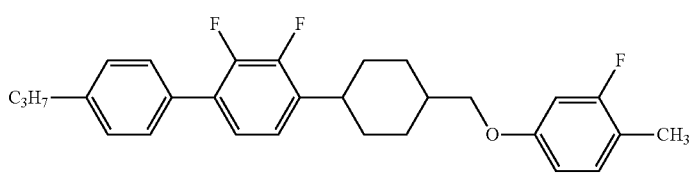 |
| 3936 | 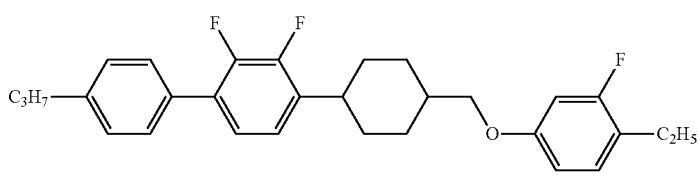 |
| 3937 | 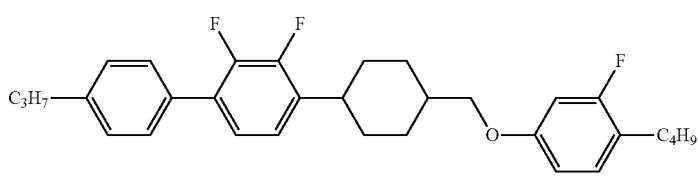 |
| 3938 | 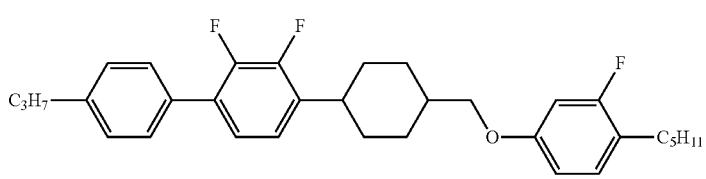 |

| No. | |
|---|---|
| 3939 | 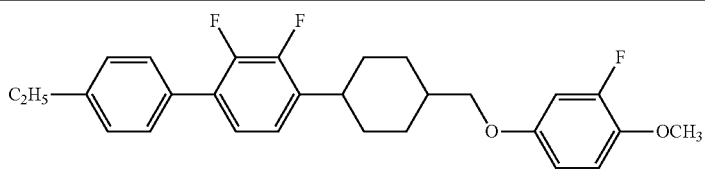 |
| 3940 | 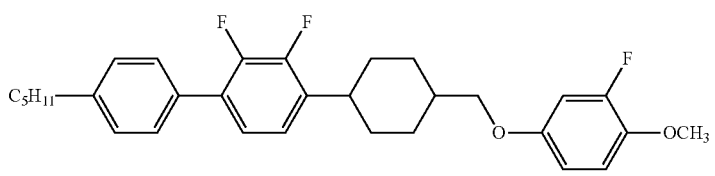 |
| 3941 | 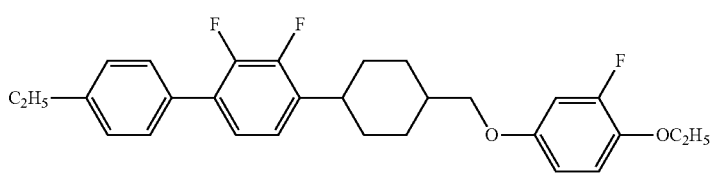 [SMILES: CCOc1ccc(OCC2CCC(c3ccc(-c4ccc(CC)cc4)c(F)c3F)CC2)cc1F] |
| 3942 | 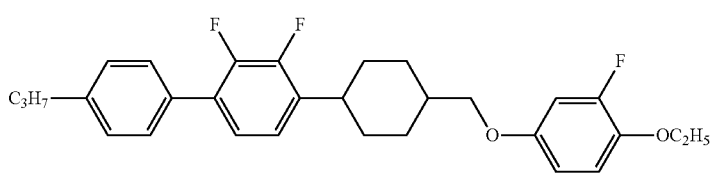 |
| 3943 | 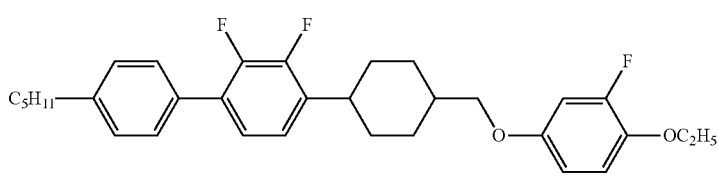 |
| 3944 | 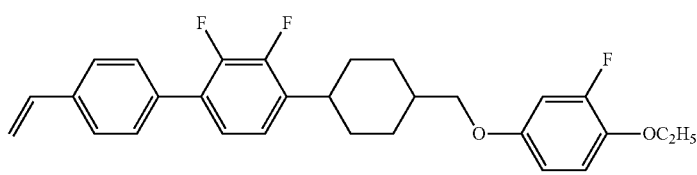 |
| 3945 | 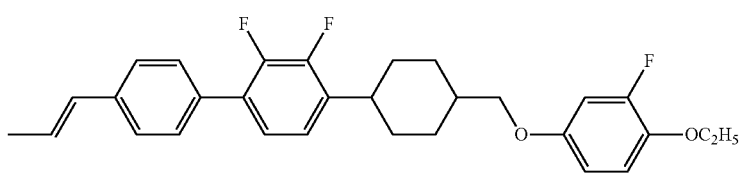 |
| 3946 | 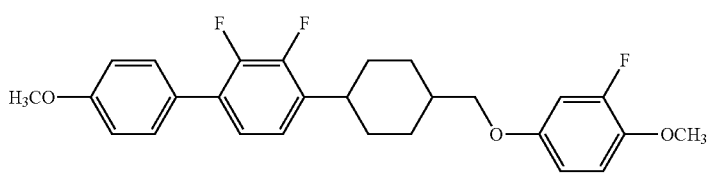 [SMILES: COc1ccc(-c2ccc(C3CCC(COc4ccc(OC)c(F)c4)CC3)c(F)c2F)cc1] |
| 3947 | 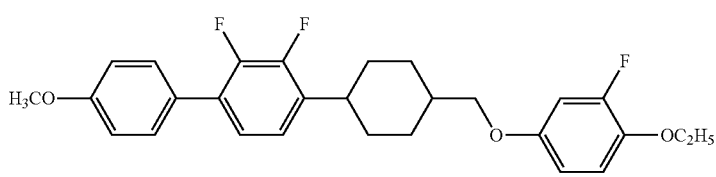 |

| No. |
|---|
| 3948 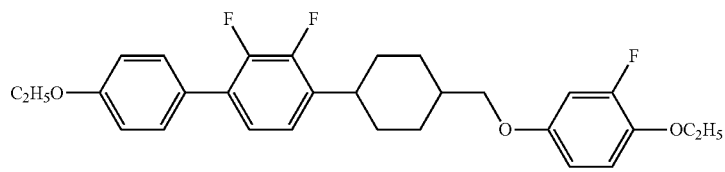 |
| 3949 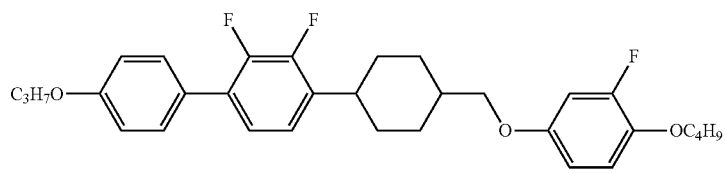 |
| 3950 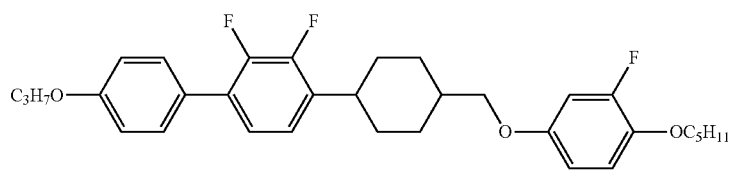 |
| 3951 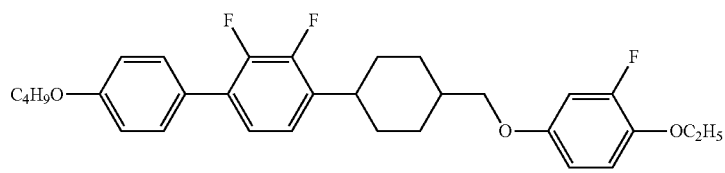 |
| 3952 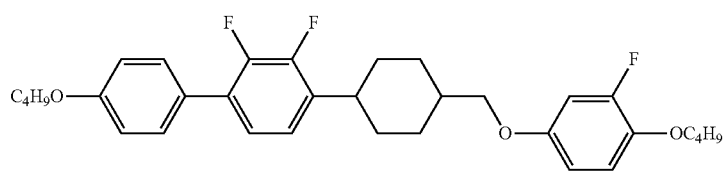 |
| 3953 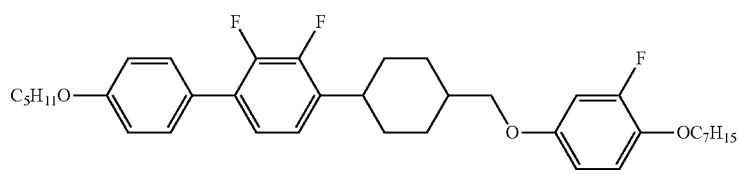 |
| 3954 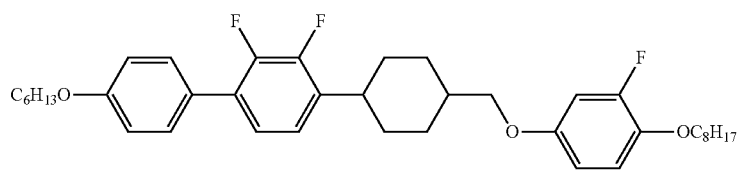 |
| 3955 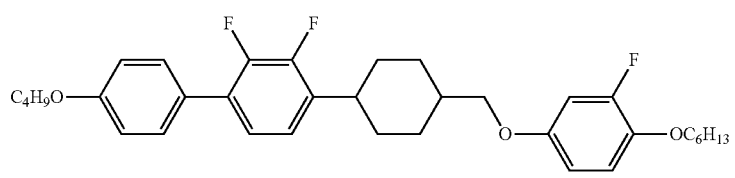 |

| No. | |
|---|---|
| 3956 | 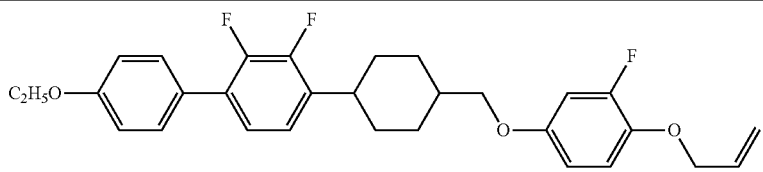 |
| 3957 | 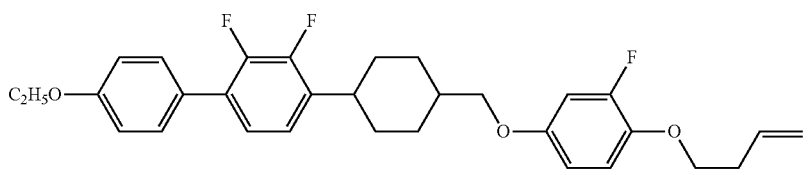 |
| 3958 | 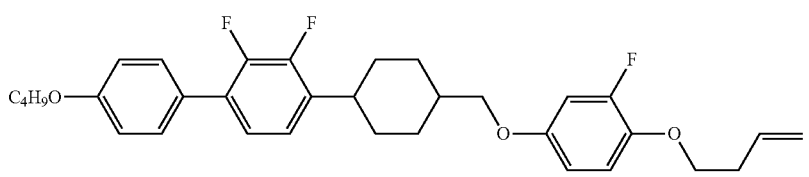 |
| 3959 | 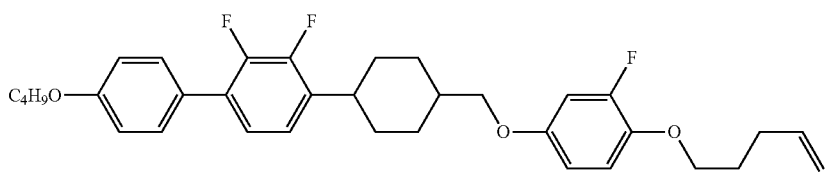 |
| 3960 | 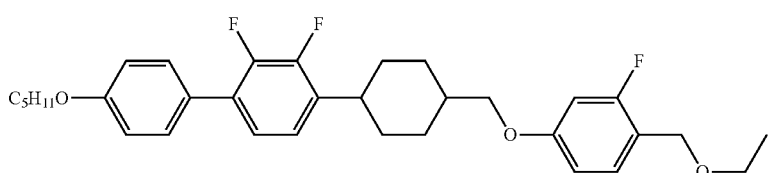 |
| 3961 | 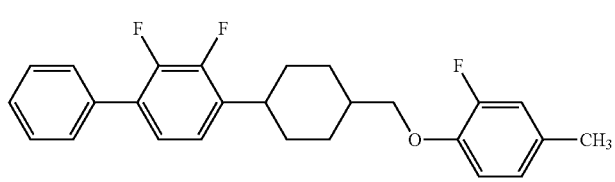 |
| 3962 | 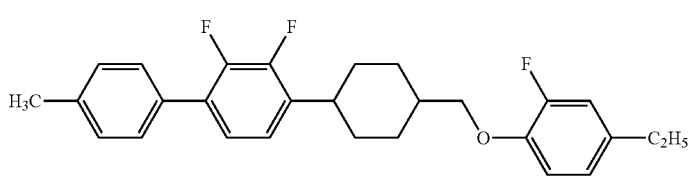 [SMILES: CCc1ccc(OCC2CCC(c3ccc(-c4ccc(C)cc4)c(F)c3F)CC2)c(F)c1] |
| 3963 | 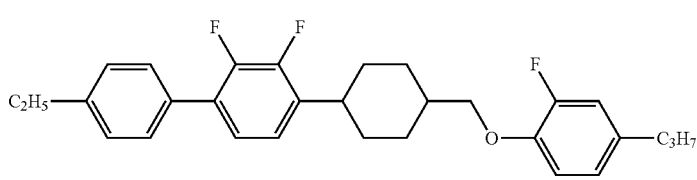 |
| 3964 | 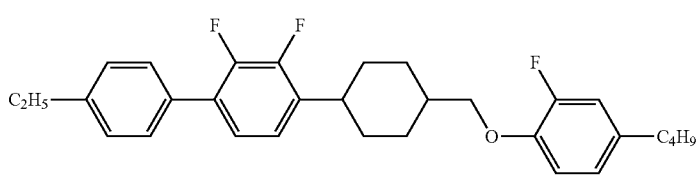 |

| No. | |
|---|---|
| 3965 | 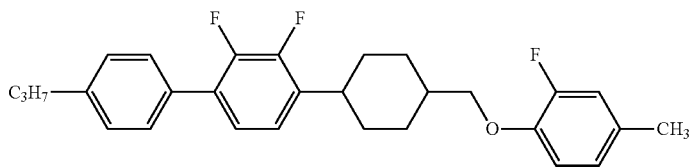 |
| 3966 |  |
| 3967 |  |
| 3968 | 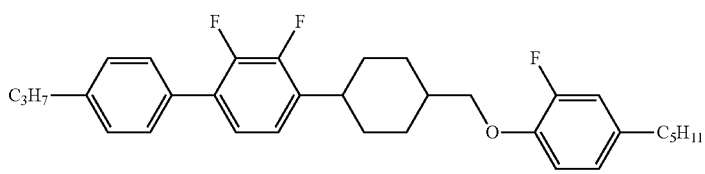 |
| 3969 | 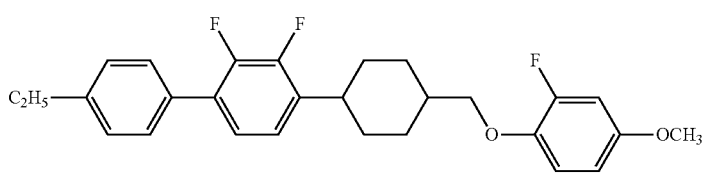 |
| 3970 | 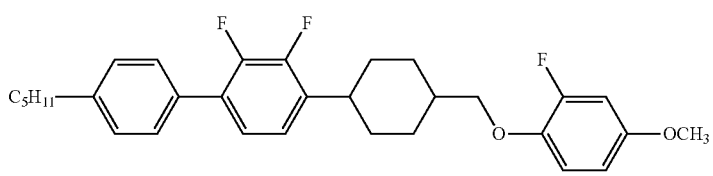 |
| 3971 | 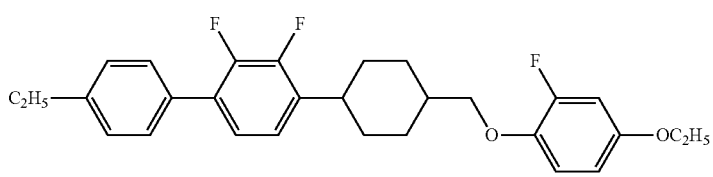 [SMILES: CCOc1ccc(OCC2CCC(c3ccc(-c4ccc(CC)cc4)c(F)c3F)CC2)c(F)c1] |
| 3972 | 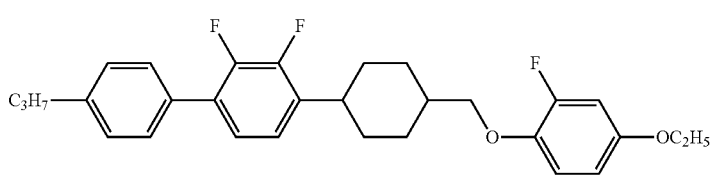 |

| No. | |
|---|---|
| 3973 | 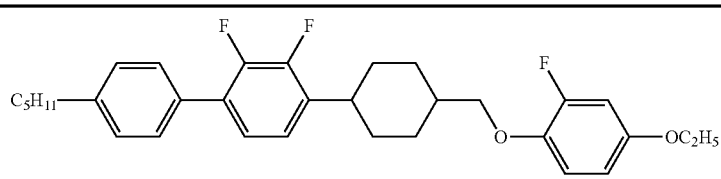 |
| 3974 | 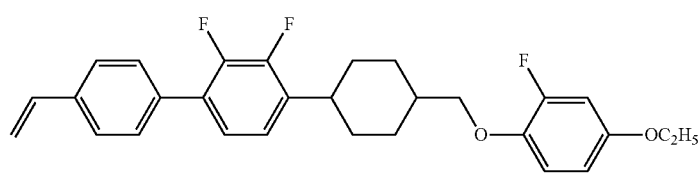 |
| 3975 | 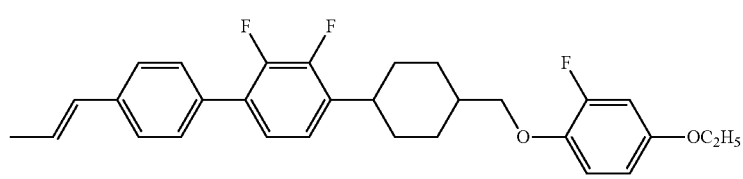 [SMILES: C/C=C/c1ccc(-c2ccc(C3CCC(COc4ccc(OCC)cc4F)CC3)c(F)c2F)cc1] |
| 3976 | 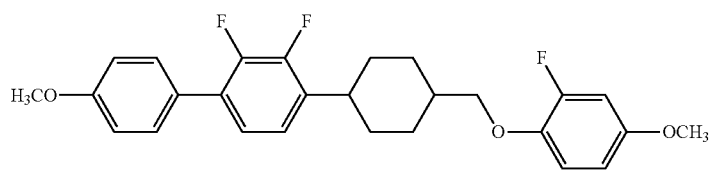 |
| 3977 | 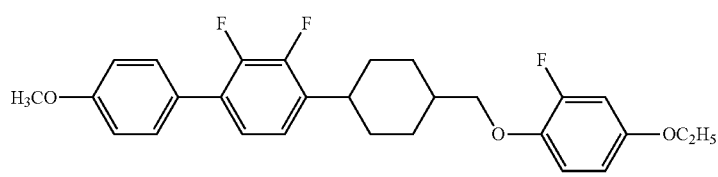 [SMILES: CCOc1ccc(OCC2CCC(c3ccc(-c4ccc(OC)cc4)c(F)c3F)CC2)c(F)c1] |
| 3978 | 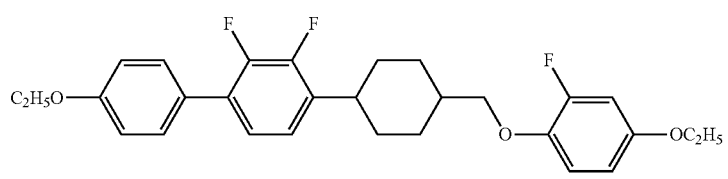 |
| 3979 | 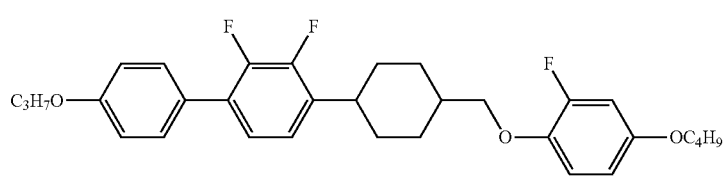 |
| 3980 | 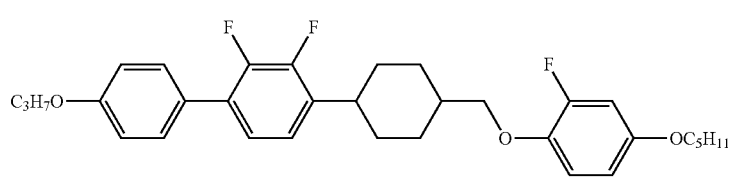 |
| 3981 | 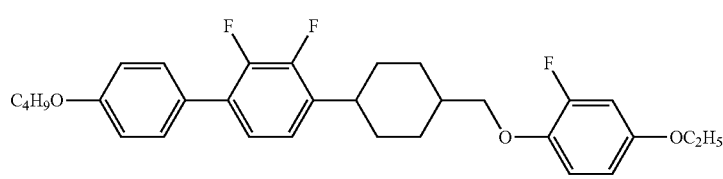 |

-continued
No.
3982
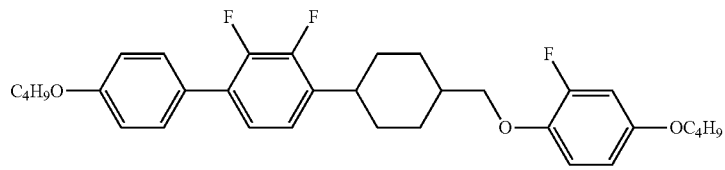
3983
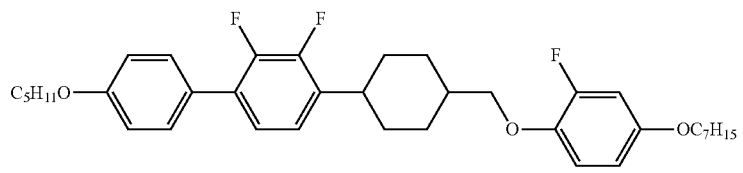
3984
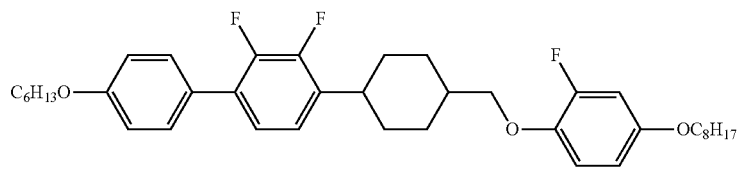
3985
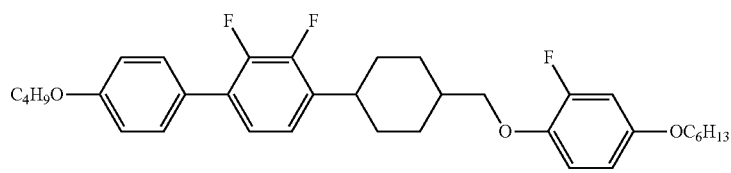
3986
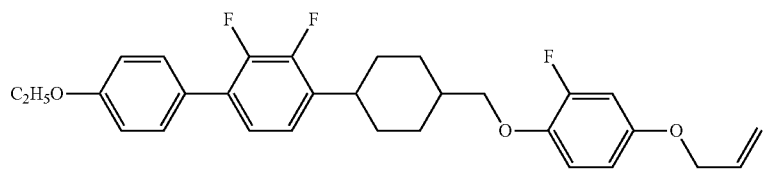
3987
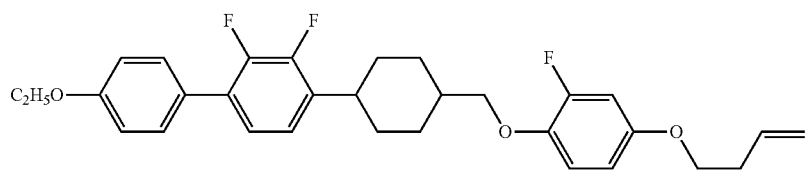
3988
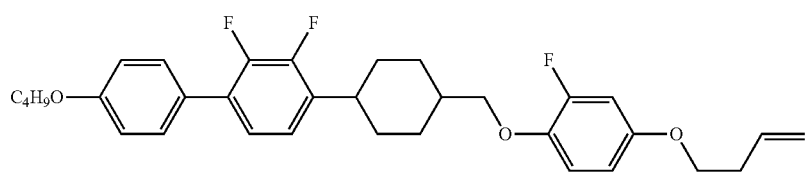
3989
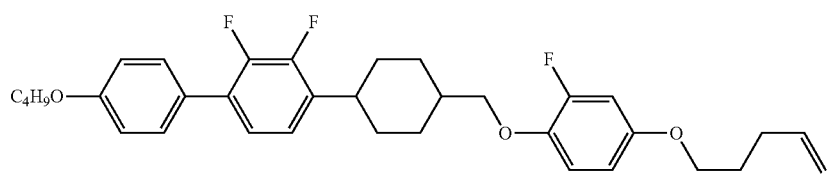

| No. | |
|---|---|
| 3990 | 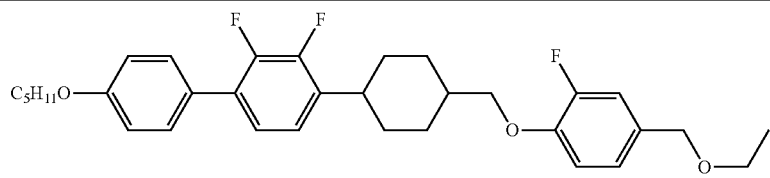 |
| 3991 | 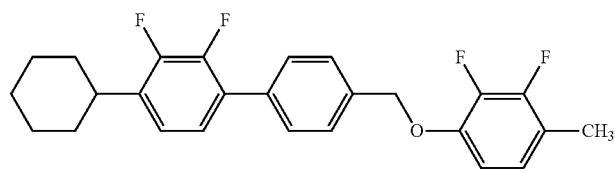 [SMILES: Cc1ccc(OCc2ccc(-c3ccc(C4CCCCC4)c(F)c3F)cc2)c(F)c1F] |
| 3992 | 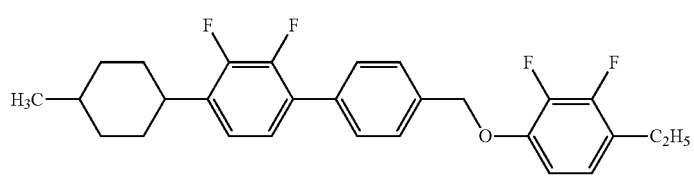 |
| 3993 |  |
| 3994 |  |
| 3995 | 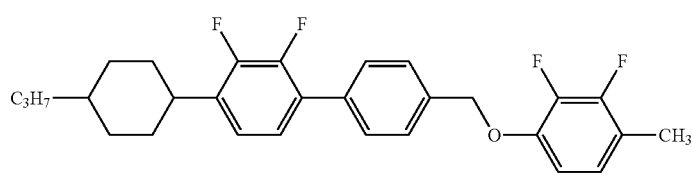 |
| 3996 |  |
| 3997 |  |
| 3998 | 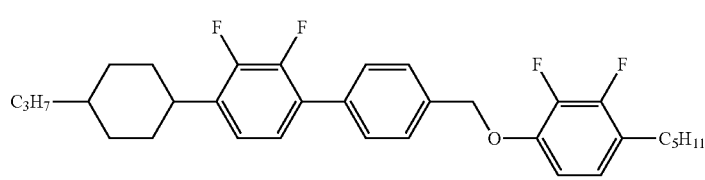 |

| No. | |
|---|---|
| 3999 | 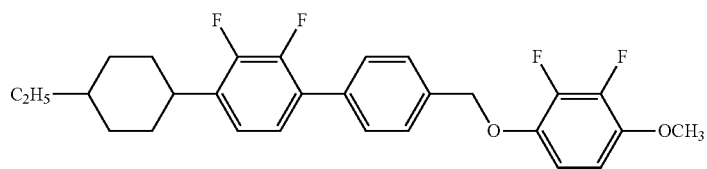 |
| 4000 |  |
| 4001 | 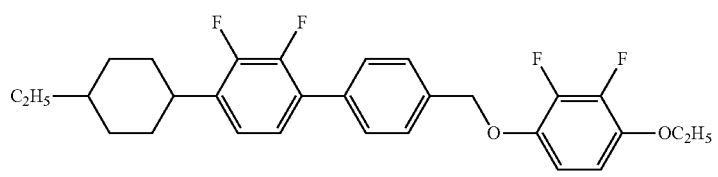 [SMILES: CCOc1ccc(OCc2ccc(-c3ccc(C4CCC(CC)CC4)c(F)c3F)cc2)c(F)c1F] |
| 4002 | 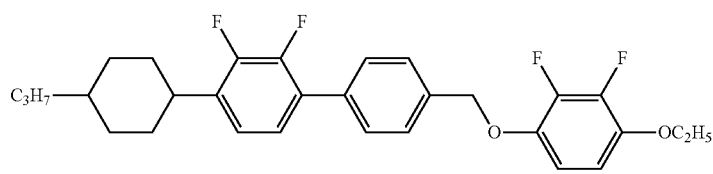 |
| 4003 | 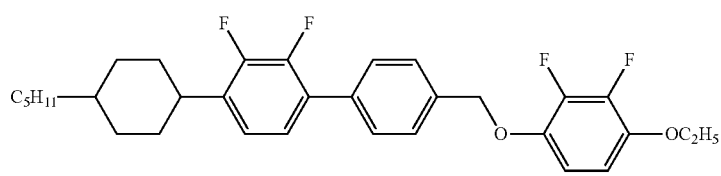 |
| 4004 | 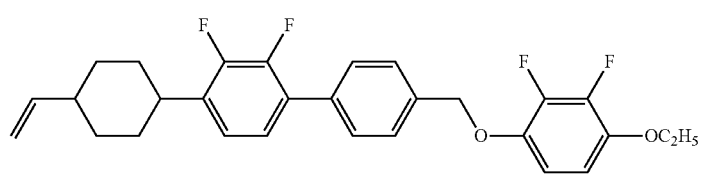 |
| 4005 | 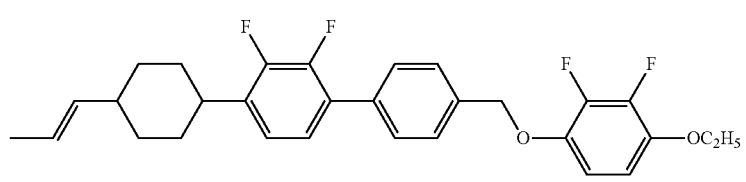 [SMILES: C/C=C/C1CCC(c2ccc(-c3ccc(COc4ccc(OCC)c(F)c4F)cc3)c(F)c2F)CC1] |
| 4006 | 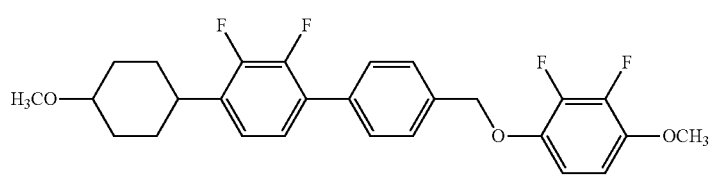 |

| No. | |
|---|---|
| 4007 | 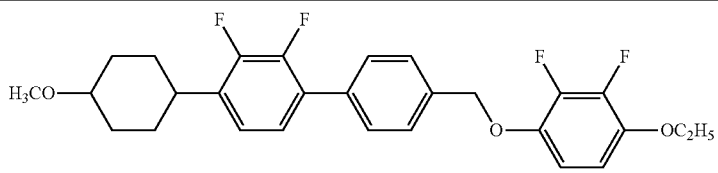 |
| 4008 |  |
| 4009 |  |
| 4010 | 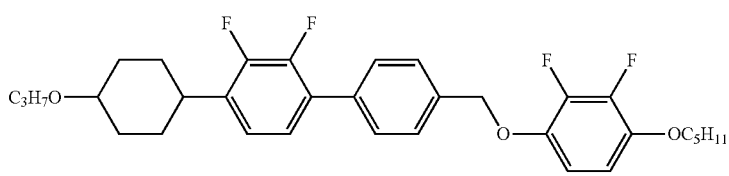 |
| 4011 |  |
| 4012 | 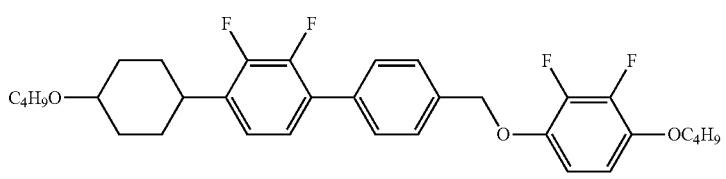 |
| 4013 | 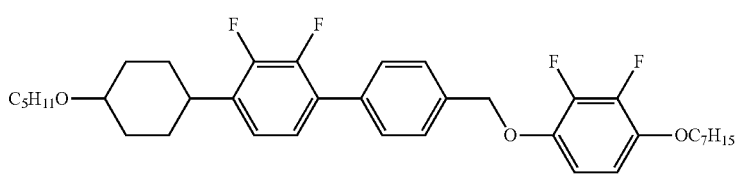 |
| 4014 | 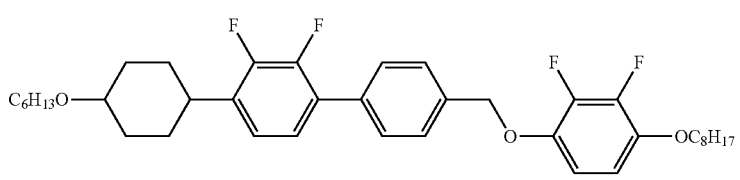 |
| 4015 | 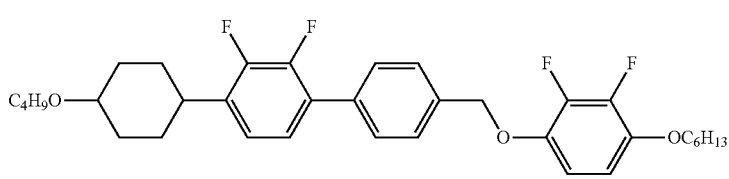 |

| No. | |
|---|---|
| 4016 | 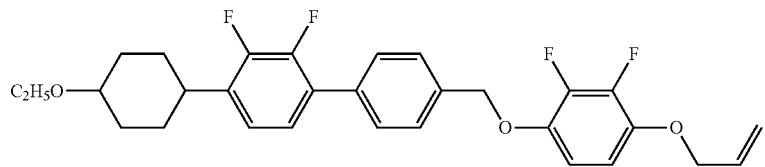 |
| 4017 | 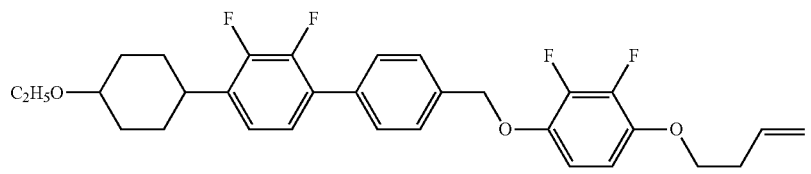 |
| 4018 | 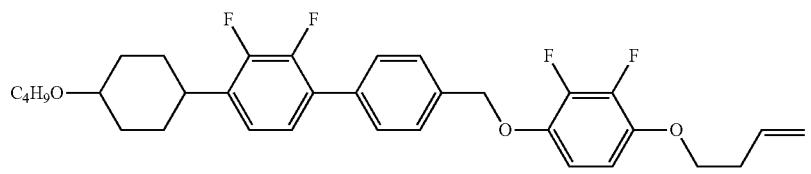 |
| 4019 | 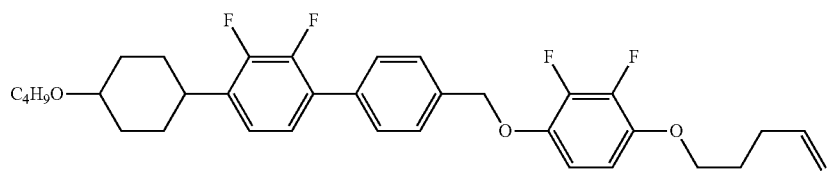 |
| 4020 | 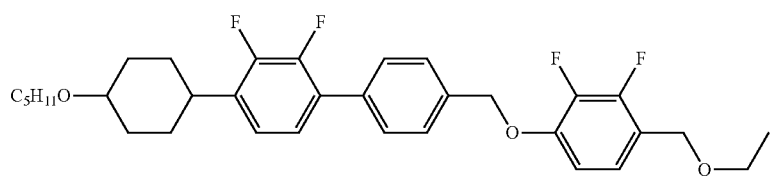 |
| 4021 | 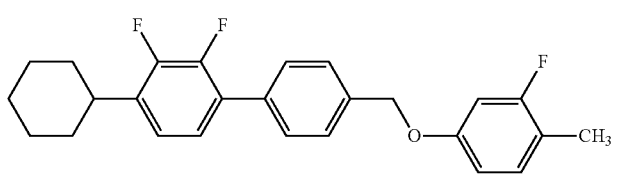 |
| 4022 | 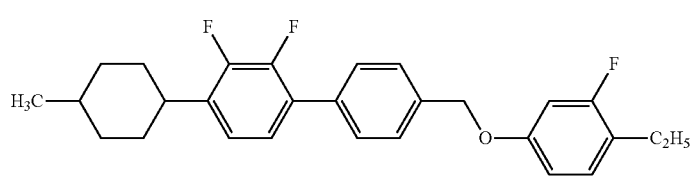 [SMILES: CCc1ccc(OCc2ccc(-c3ccc(C4CCC(C)CC4)c(F)c3F)cc2)cc1F] |
| 4023 | 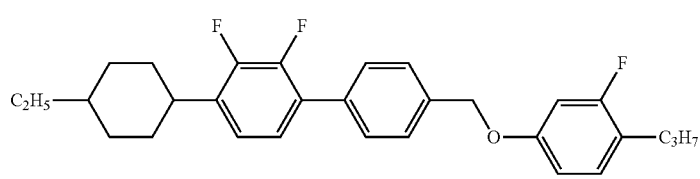 |

| No. | |
|---|---|
| 4024 | 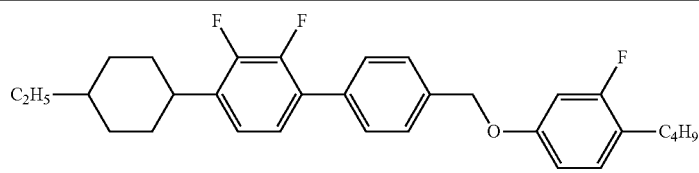 |
| 4025 | 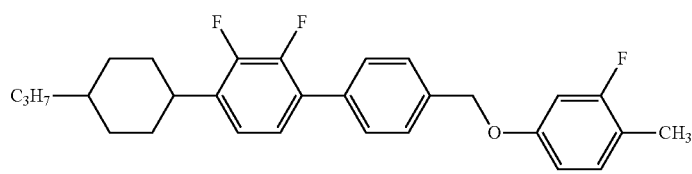 |
| 4026 | 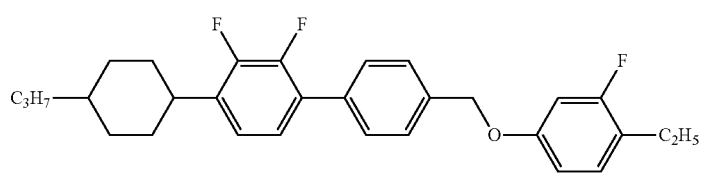 |
| 4027 | 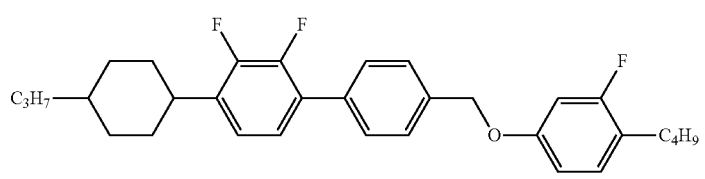 |
| 4028 | 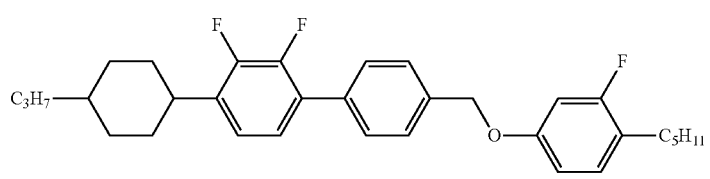 |
| 4029 | 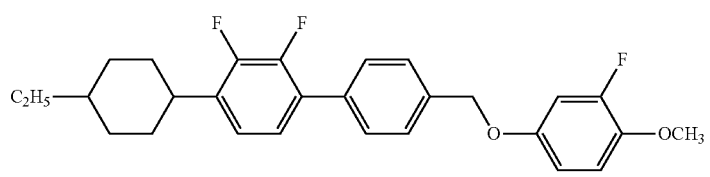 |
| 4030 | 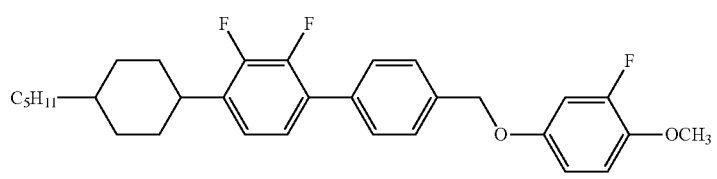 |
| 4031 | 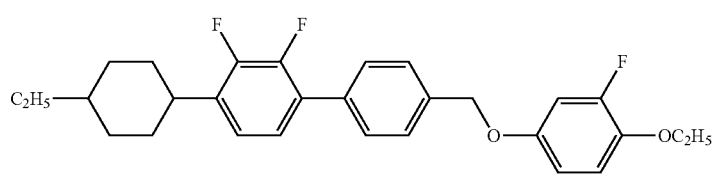 |
| 4032 | 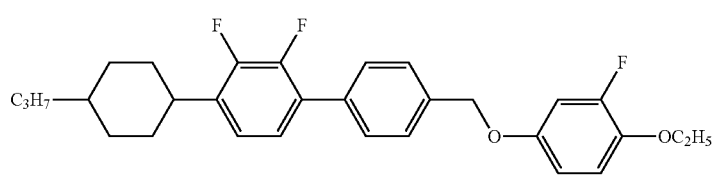 |

| No. | |
|---|---|
| 4033 | 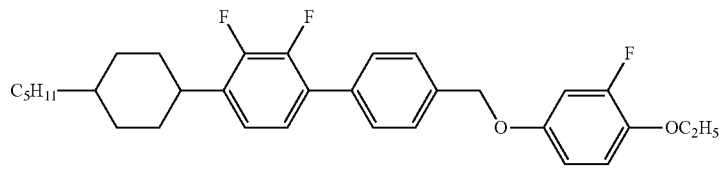 |
| 4034 | 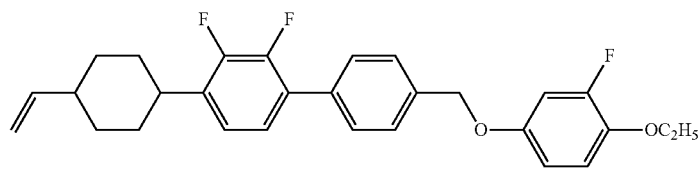 |
| 4035 | 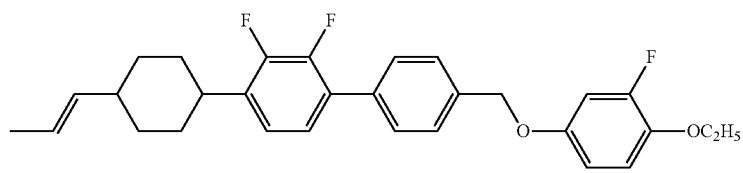 [SMILES: C/C=C/C1CCC(c2ccc(-c3ccc(COc4ccc(OCC)c(F)c4)cc3)c(F)c2F)CC1] |
| 4036 | 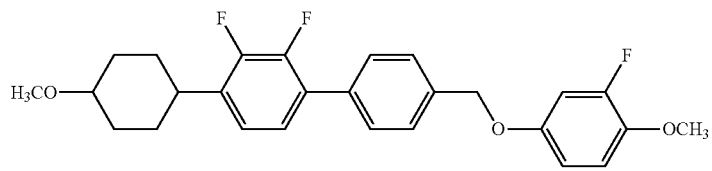 |
| 4037 | 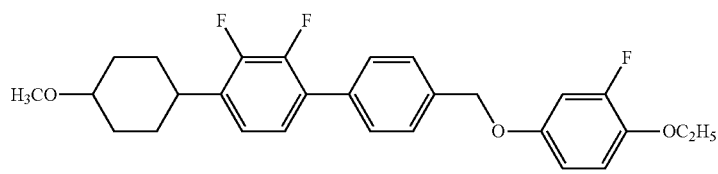 |
| 4038 | 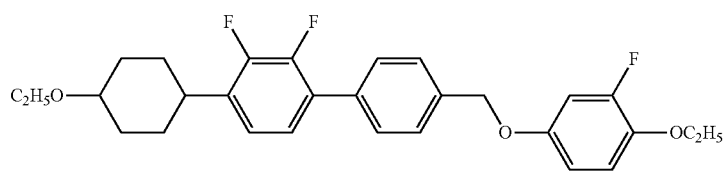 |
| 4039 | 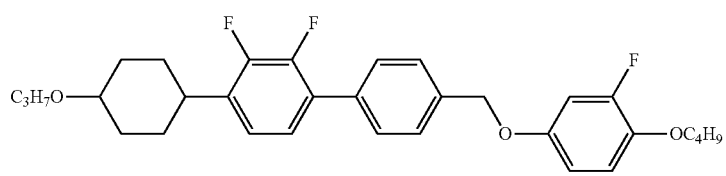 |
| 4040 | 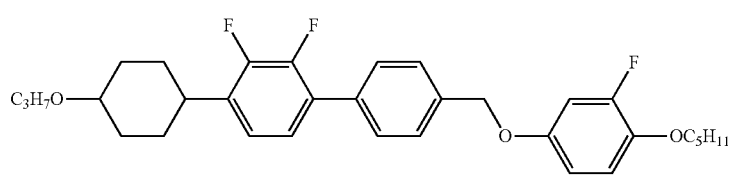 |

| No. | |
|---|---|
| 4041 | 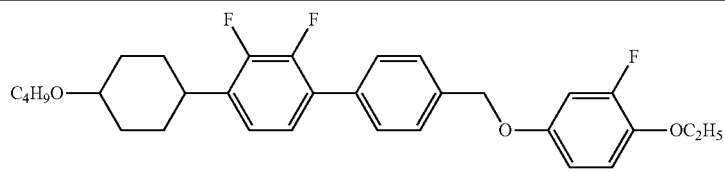 |
| 4042 | 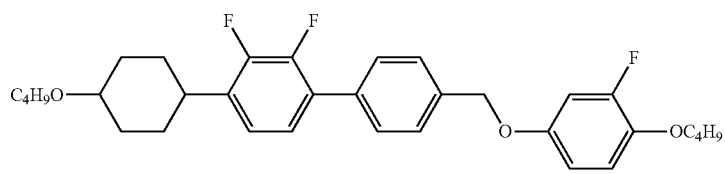 |
| 4043 | 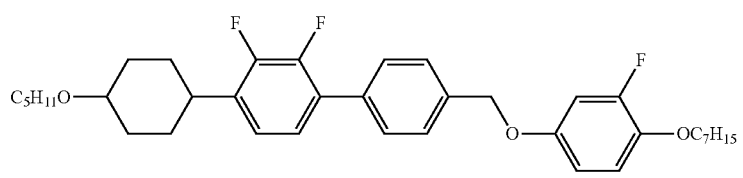 |
| 4044 | 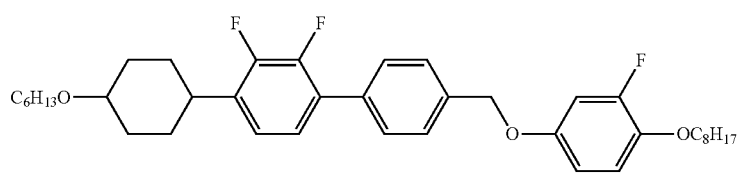 |
| 4045 | 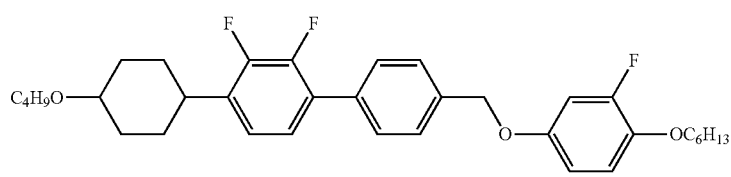 |
| 4046 | 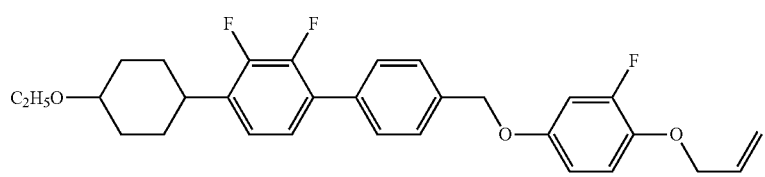 |
| 4047 | 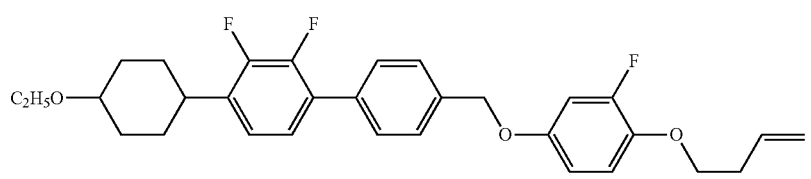 |
| 4048 | 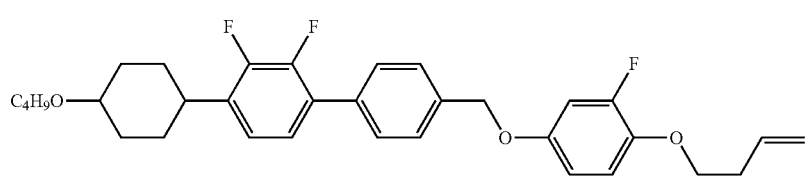 |
| 4049 | 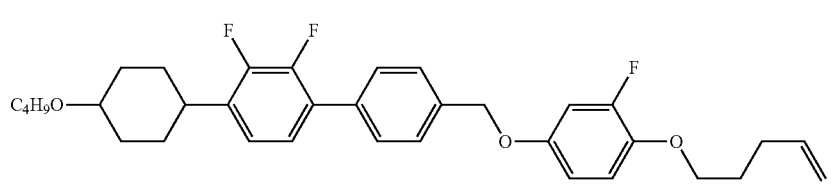 |

| No. | |
|---|---|
| 4050 | 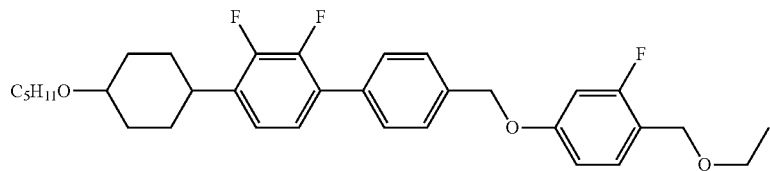 |
| 4051 | 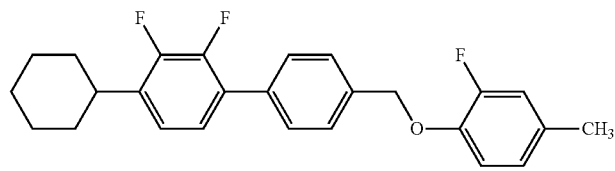 [SMILES: Cc1ccc(OCc2ccc(-c3ccc(C4CCCCC4)c(F)c3F)cc2)c(F)c1] |
| 4052 | 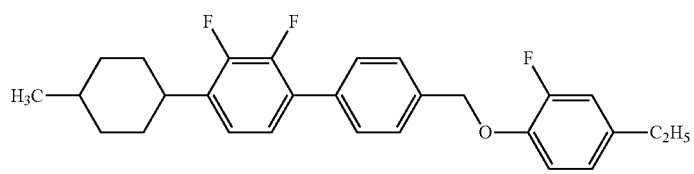 [SMILES: CCc1ccc(OCc2ccc(-c3ccc(C4CCC(C)CC4)c(F)c3F)cc2)c(F)c1] |
| 4043 | 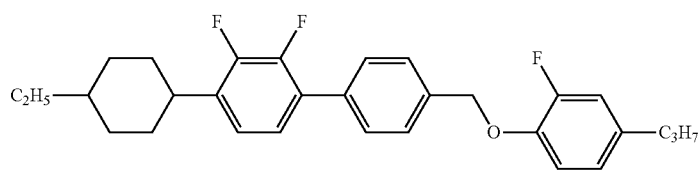 |
| 4054 | 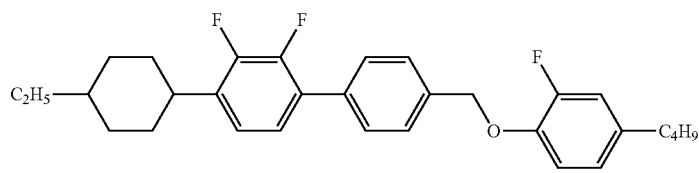 |
| 4055 | 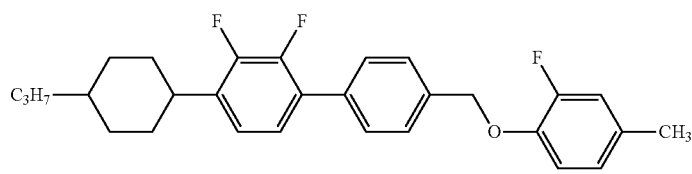 |
| 4056 | 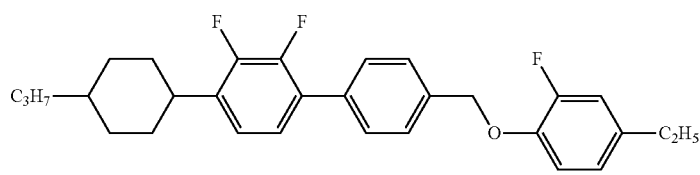 |
| 4057 | 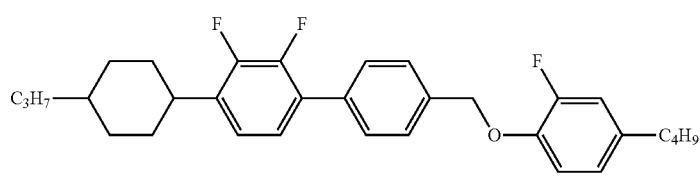 |

| No. | |
|---|---|
| 4058 | 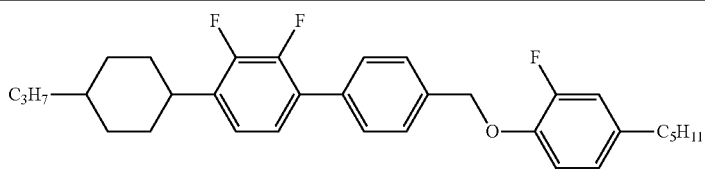 |
| 4059 | 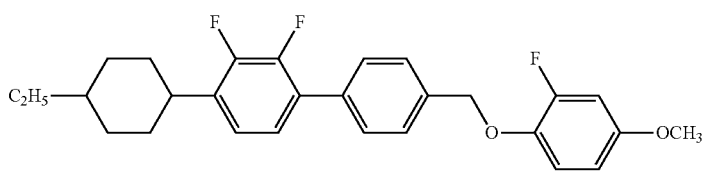 |
| 4060 | 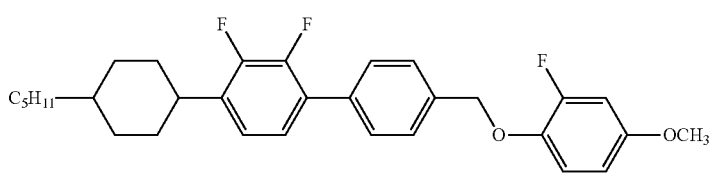 |
| 4061 | 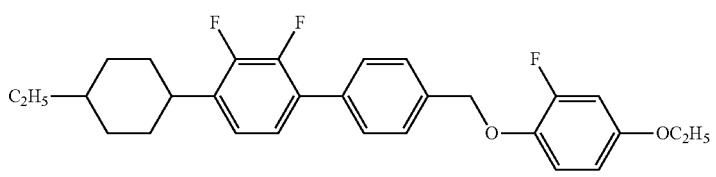 [SMILES: CCOc1ccc(OCc2ccc(-c3ccc(C4CCC(CC)CC4)c(F)c3F)cc2)c(F)c1] |
| 4062 | 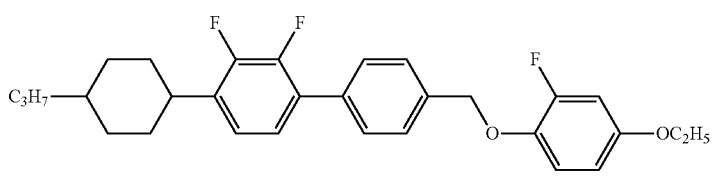 |
| 4063 | 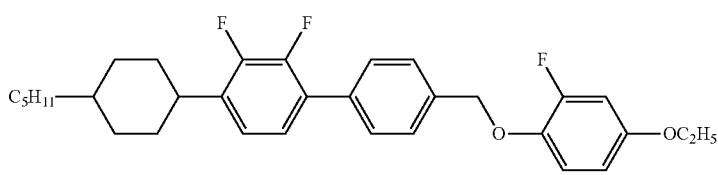 |
| 4064 | 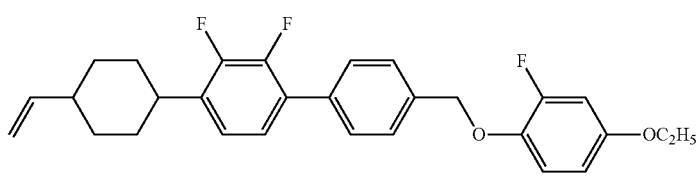 [SMILES: C=CC1CCC(c2ccc(-c3ccc(COc4ccc(OCC)cc4F)cc3)c(F)c2F)CC1] |
| 4065 | 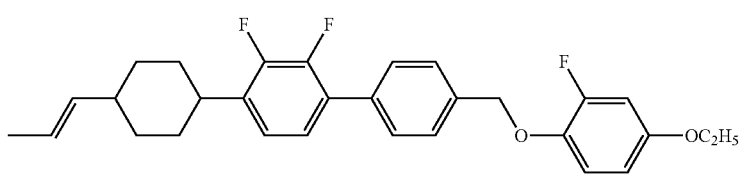 [SMILES: C/C=C/C1CCC(c2ccc(-c3ccc(COc4ccc(OCC)cc4F)cc3)c(F)c2F)CC1] |
| 4066 | 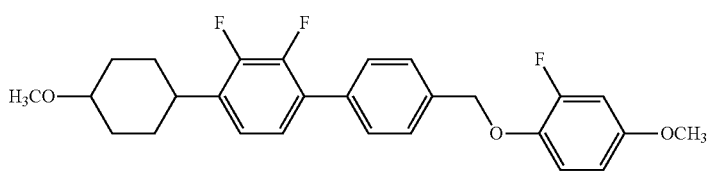 |

-continued
| No. | |
|---|---|
| 4067 | 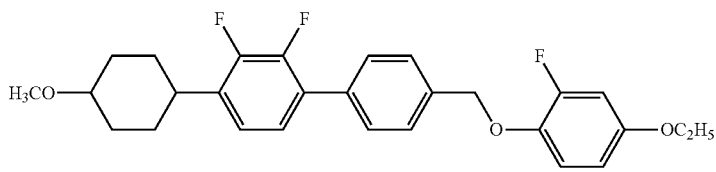 |
| 4068 | 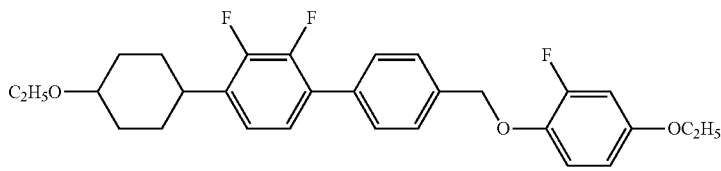 |
| 4069 | 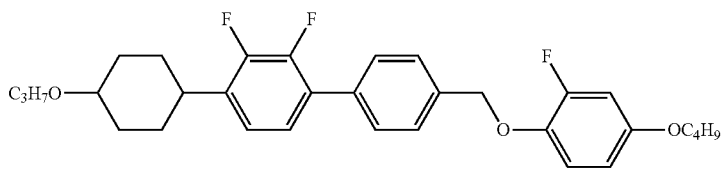 |
| 4070 | 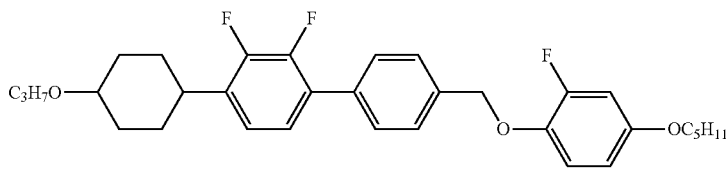 |
| 4071 | 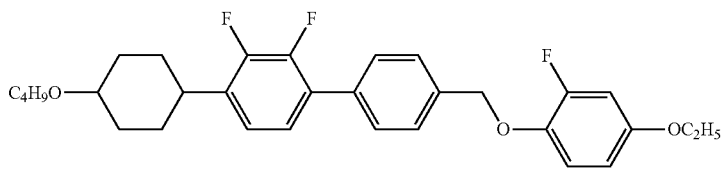 |
| 4072 | 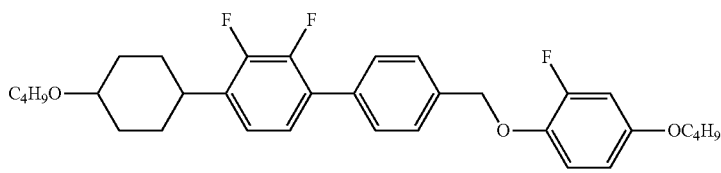 |
| 4073 | 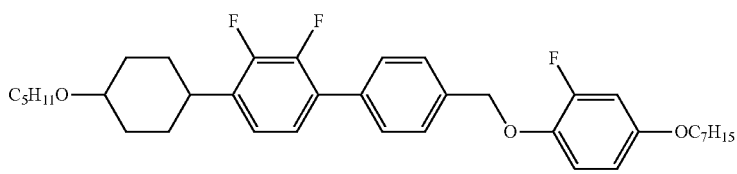 |
| 4074 | 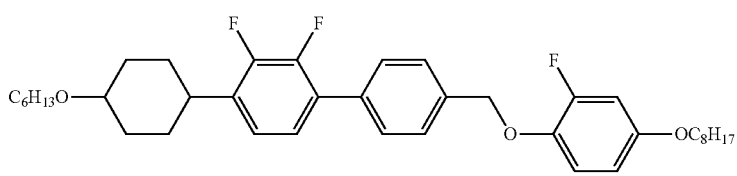 |

| No. |
|---|
| 4075 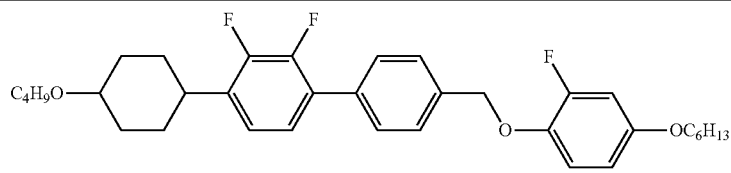 |
| 4076 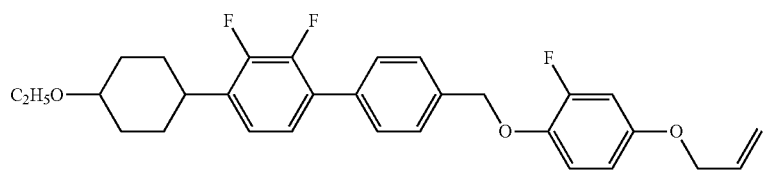 |
| 4077 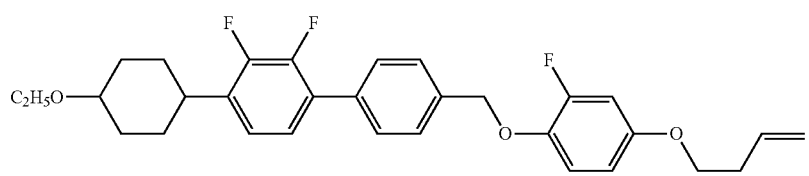 |
| 4078 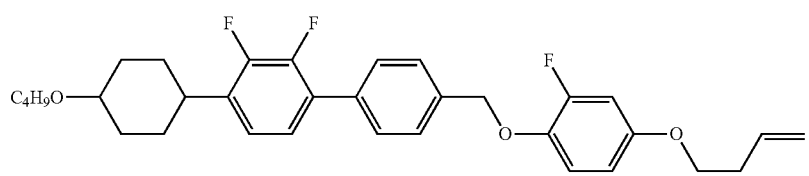 |
| 4079 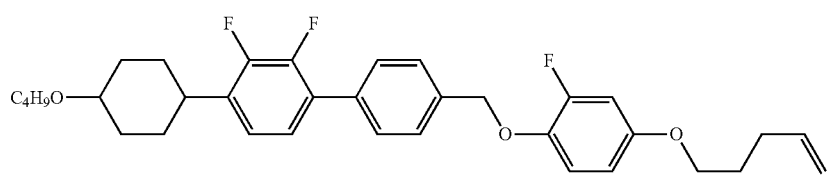 |
| 4080 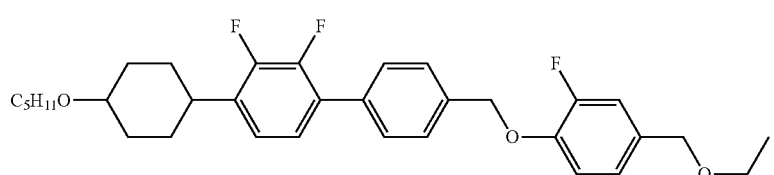 |
| 4081 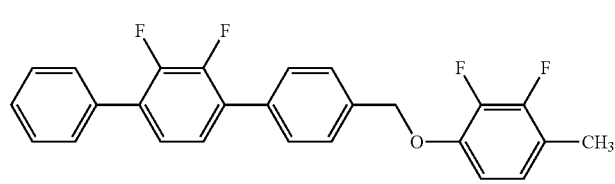 [SMILES: Cc1ccc(OCc2ccc(-c3ccc(-c4ccccc4)c(F)c3F)cc2)c(F)c1F] |
| 4082 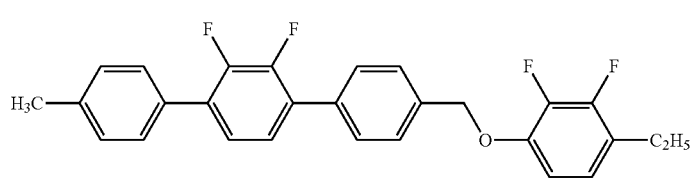 [SMILES: CCc1ccc(OCc2ccc(-c3ccc(-c4ccc(C)cc4)c(F)c3F)cc2)c(F)c1F] |
| 4083 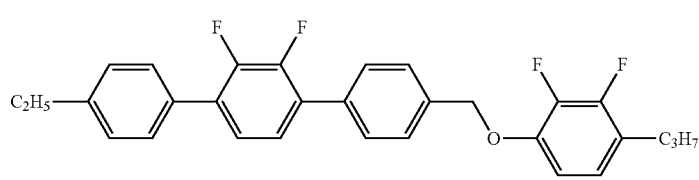 |

| No. |
|---|
| 4084 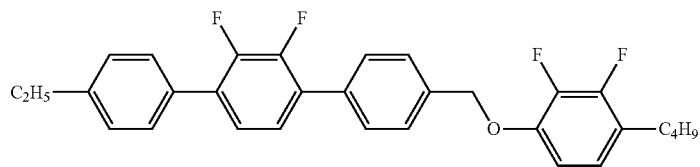 |
| 4085 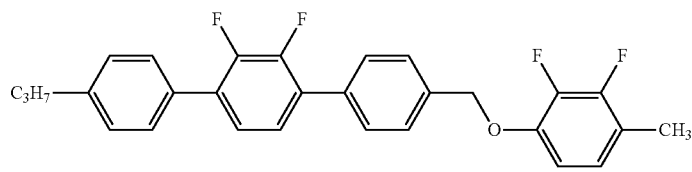 |
| 4086 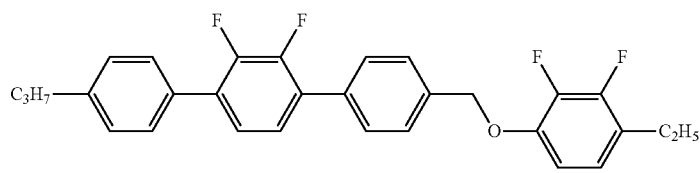 |
| 4087 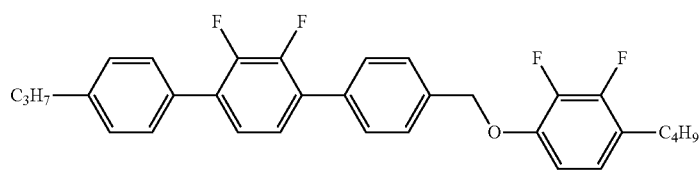 |
| 4088 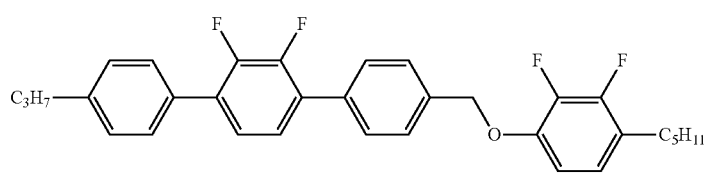 |
| 4089 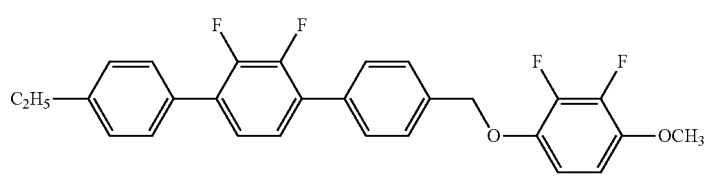 |
| 4090 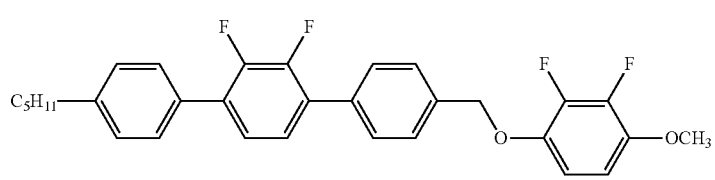 |
| 4091 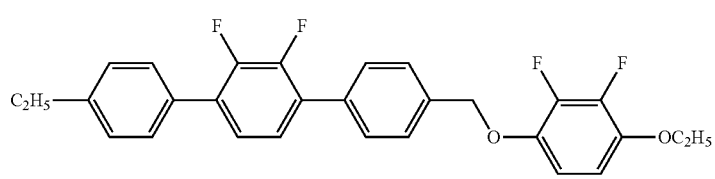 |

| No. |
|---|
| 4092 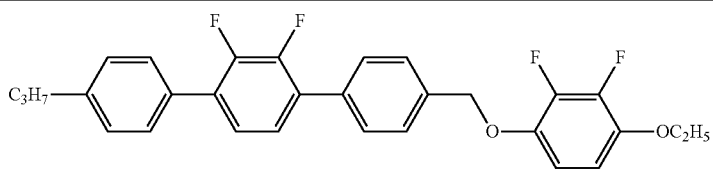 |
| 4093 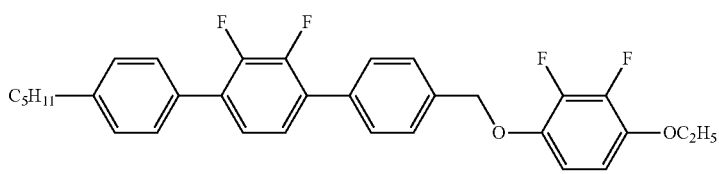 |
| 4094 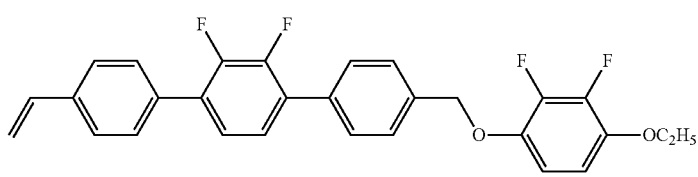 [SMILES: C=Cc1ccc(-c2ccc(-c3ccc(COc4ccc(OCC)c(F)c4F)cc3)c(F)c2F)cc1] |
| 4095 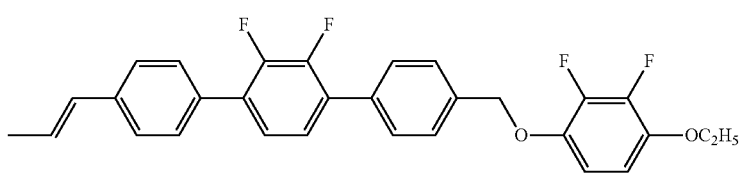 [SMILES: C/C=C/c1ccc(-c2ccc(-c3ccc(COc4ccc(OCC)c(F)c4F)cc3)c(F)c2F)cc1] |
| 4096 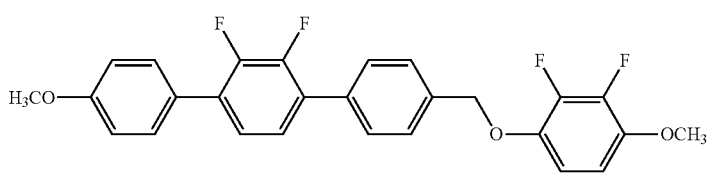 |
| 4097 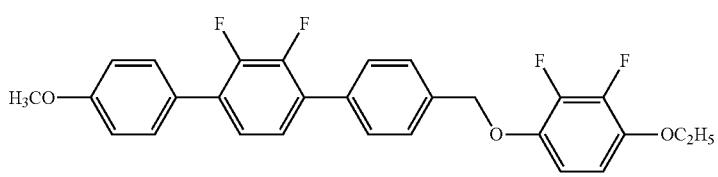 |
| 4098 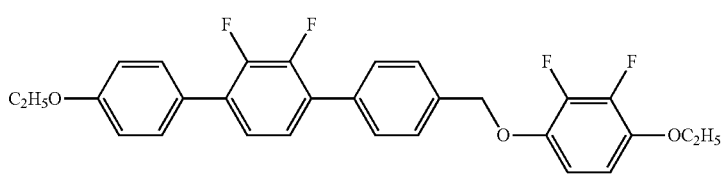 |
| 4099 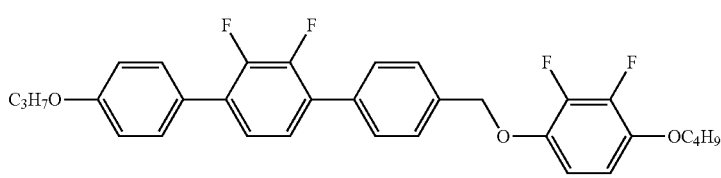 |
| 4100 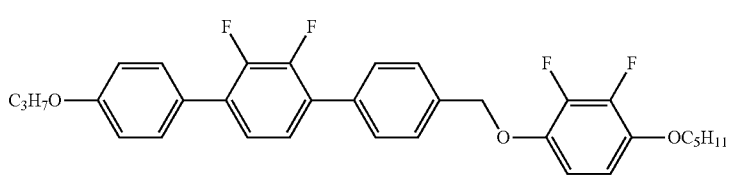 |

| No. | |
|---|---|
| 4101 | 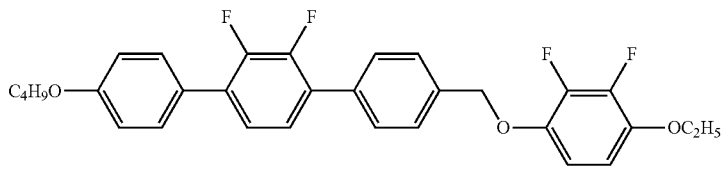 |
| 4102 | 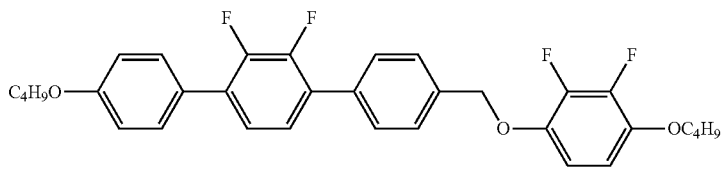 |
| 4103 | 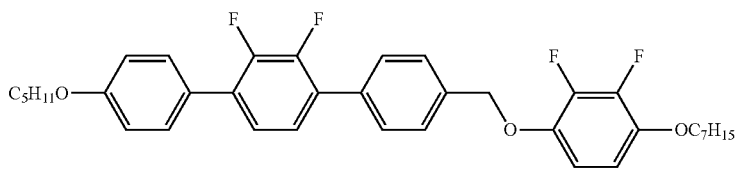 |
| 4104 | 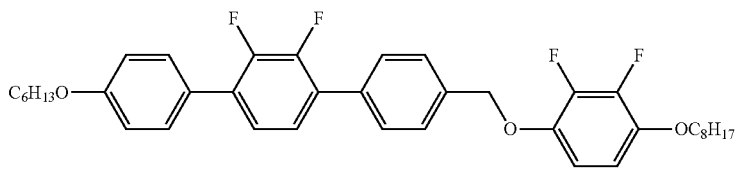 |
| 4105 | 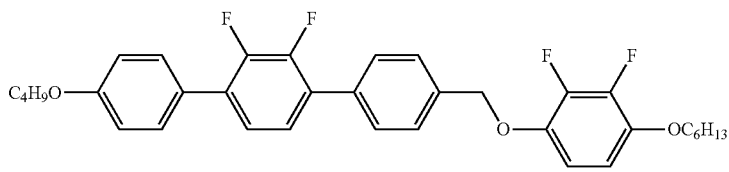 |
| 4106 | 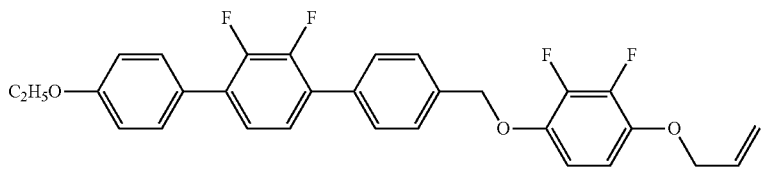 |
| 4107 | 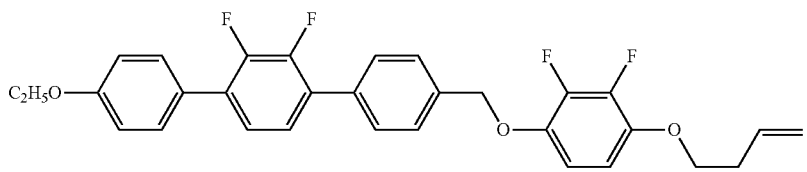 |
| 4108 | 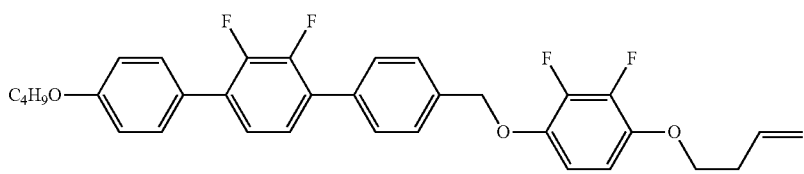 |

| No. | |
|---|---|
| 4109 | 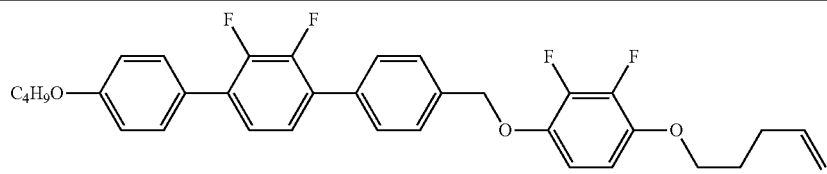 |
| 4110 | 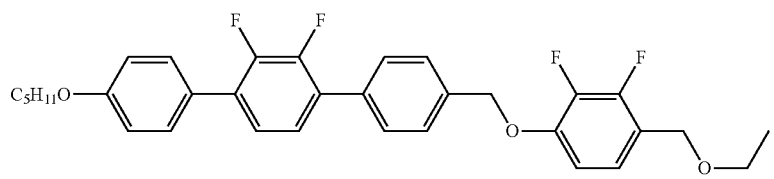 |
| 4111 | 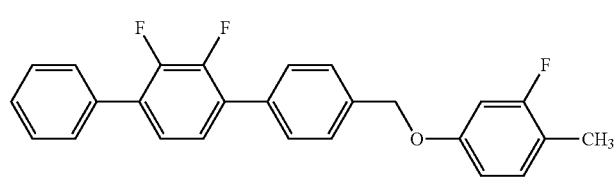 [SMILES: Cc1ccc(OCc2ccc(-c3ccc(-c4ccccc4)c(F)c3F)cc2)cc1F] |
| 4112 | 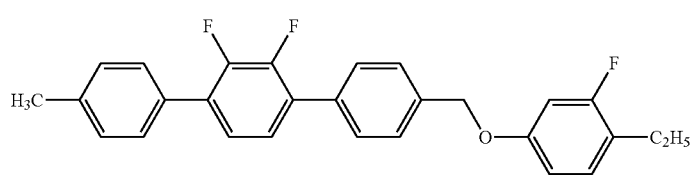 [SMILES: CCc1ccc(OCc2ccc(-c3ccc(-c4ccc(C)cc4)c(F)c3F)cc2)cc1F] |
| 4113 | 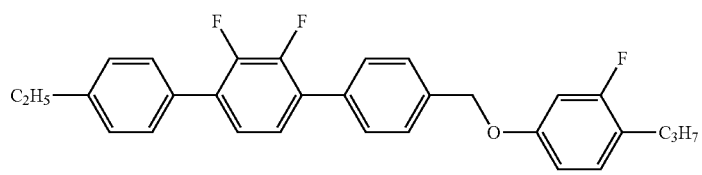 |
| 4114 | 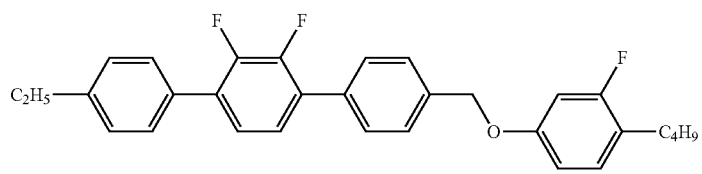 |
| 4115 | 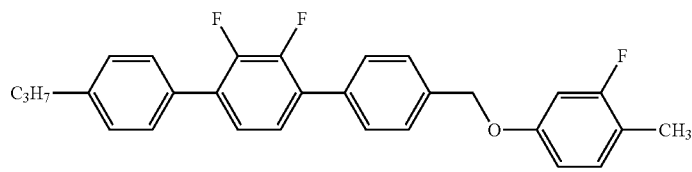 |
| 4116 | 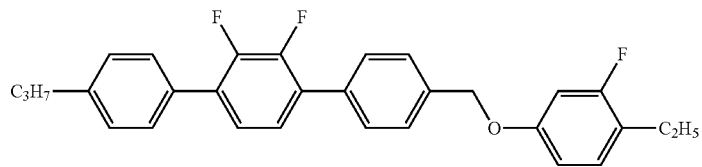 |
| 4117 | 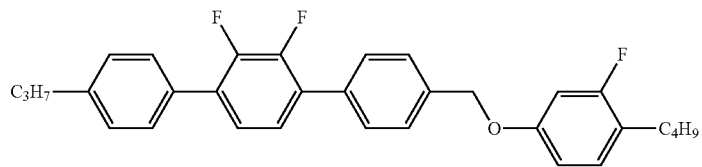 |

| No. | |
|---|---|
| 4118 | 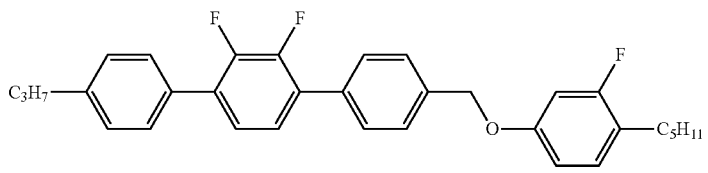 |
| 4119 | 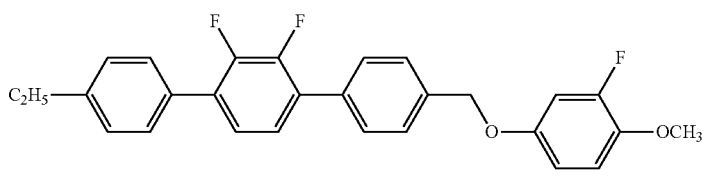 |
| 4120 | 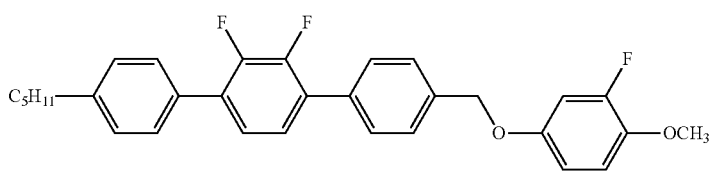 |
| 4121 | 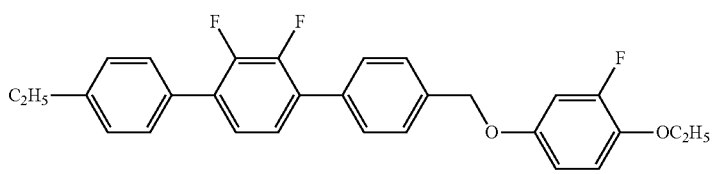 |
| 4122 | 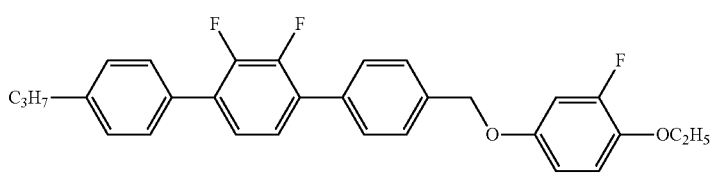 |
| 4123 | 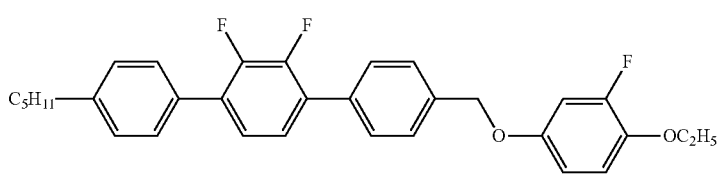 |
| 4124 | 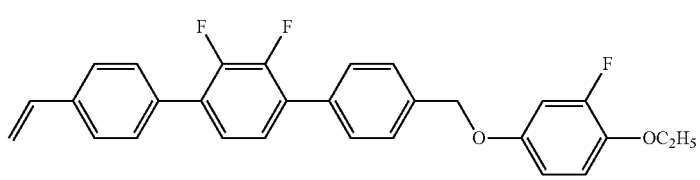 [SMILES: C=Cc1ccc(-c2ccc(-c3ccc(COc4ccc(OCC)c(F)c4)cc3)c(F)c2F)cc1] |
| 4125 | 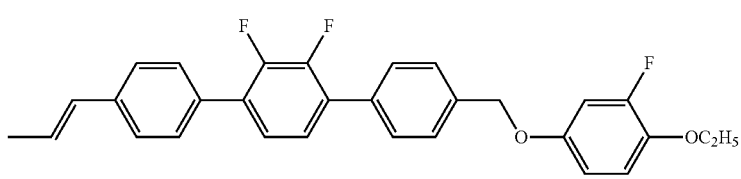 [SMILES: C/C=C/c1ccc(-c2ccc(-c3ccc(COc4ccc(OCC)c(F)c4)cc3)c(F)c2F)cc1] |

| No. | |
|---|---|
| 4126 | 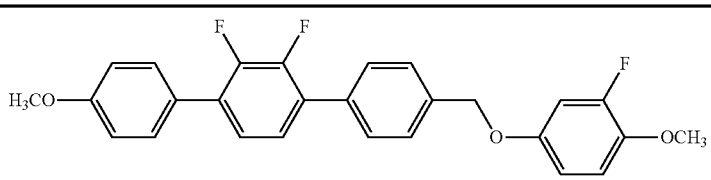 |
| 4127 | 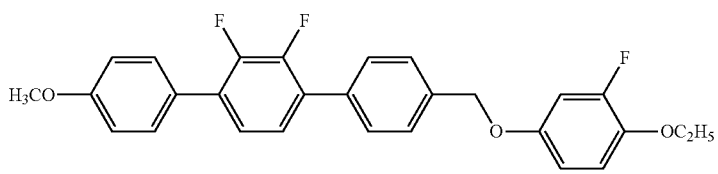 |
| 4128 | 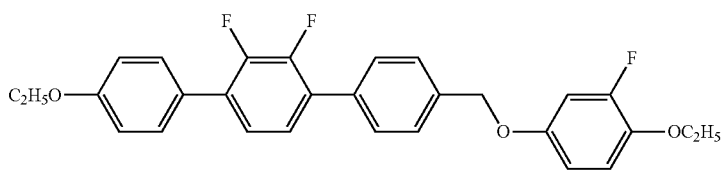 |
| 4129 | 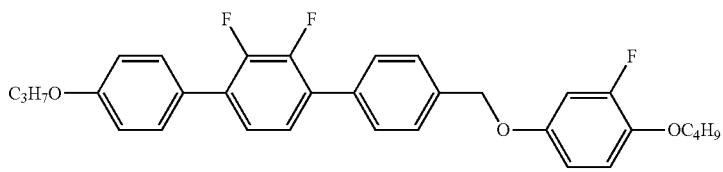 |
| 4130 | 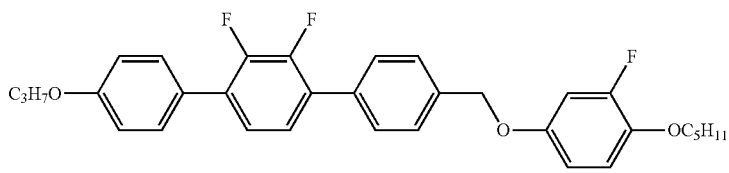 |
| 4131 | 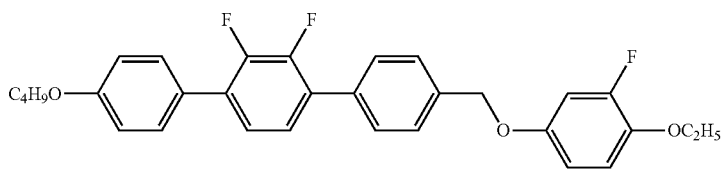 |
| 4132 | 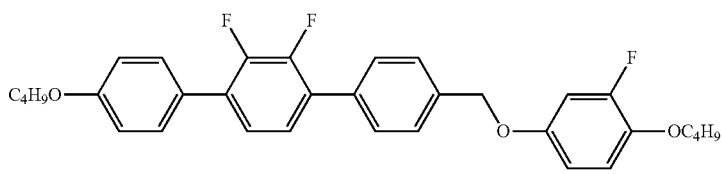 |
| 4133 | 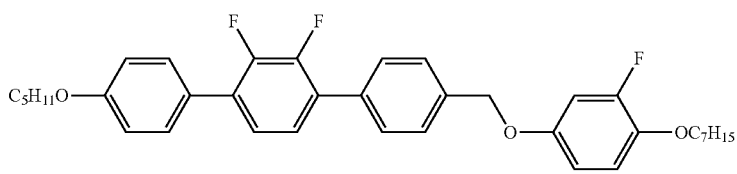 |
| 4134 | 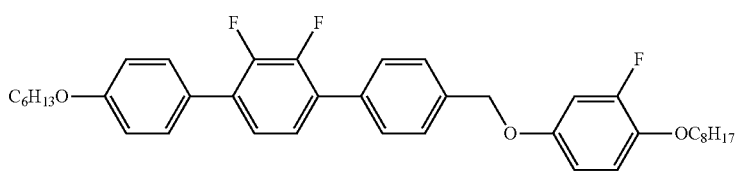 |

| No. | |
|---|---|
| 4135 | 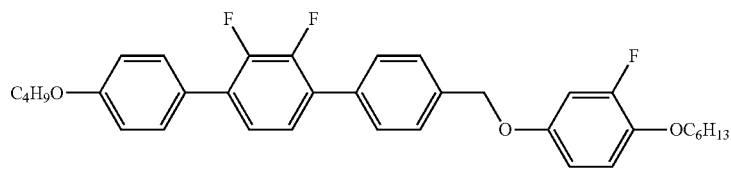 |
| 4136 | 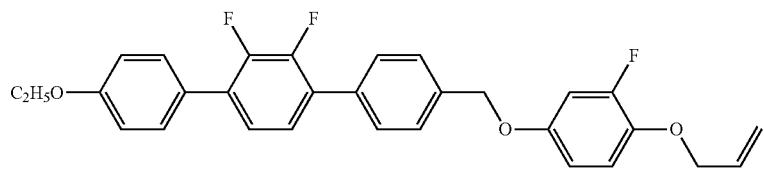 |
| 4137 | 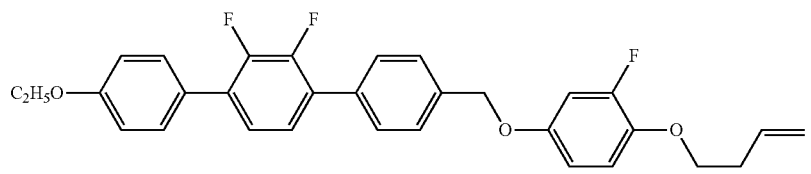 |
| 4138 | 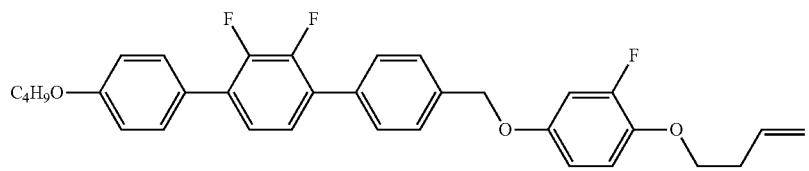 |
| 4139 | 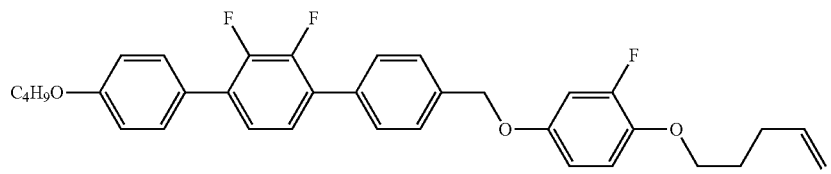 |
| 4140 | 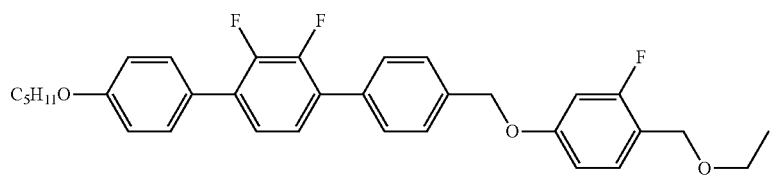 |
| 4141 | 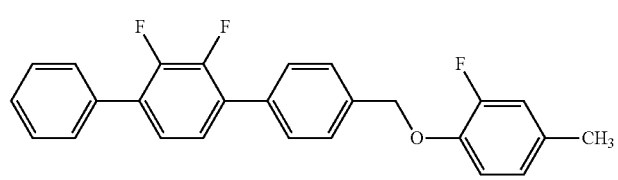 [SMILES: Cc1ccc(OCc2ccc(-c3ccc(-c4ccccc4)c(F)c3F)cc2)c(F)c1] |
| 4142 | 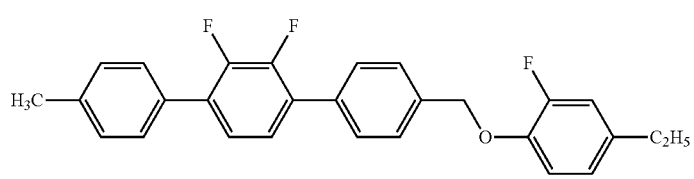 [SMILES: CCc1ccc(OCc2ccc(-c3ccc(-c4ccc(C)cc4)c(F)c3F)cc2)c(F)c1] |

| No. | |
|---|---|
| 4143 | 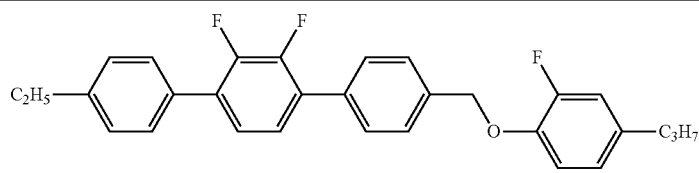 |
| 4144 | 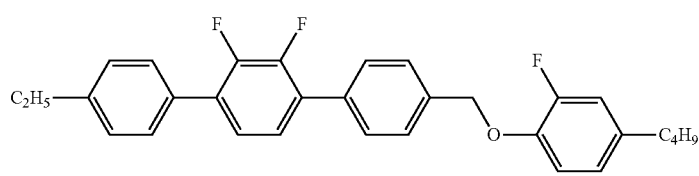 |
| 4145 | 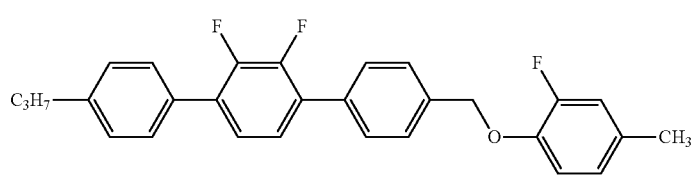 |
| 4146 | 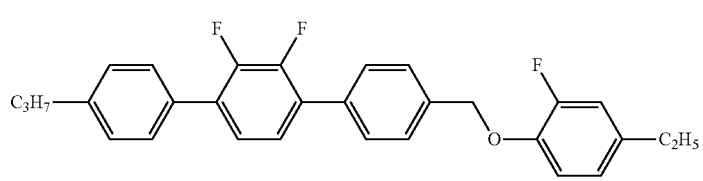 |
| 4147 | 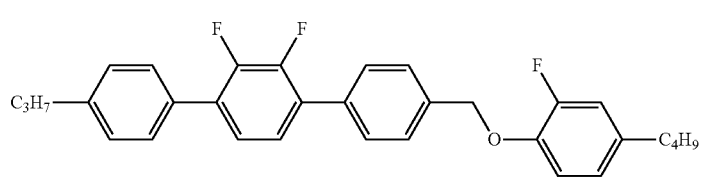 |
| 4148 | 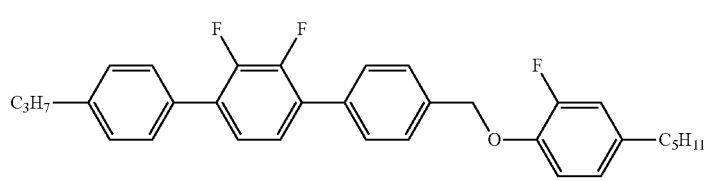 |
| 4149 | 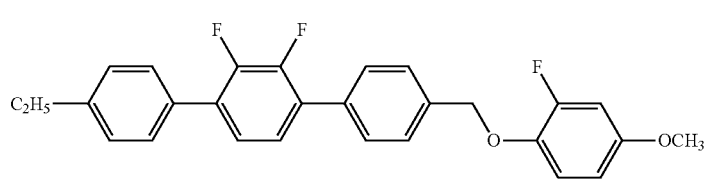 [SMILES: CCc1ccc(-c2ccc(-c3ccc(COc4ccc(OC)cc4F)cc3)c(F)c2F)cc1] |
| 4150 | 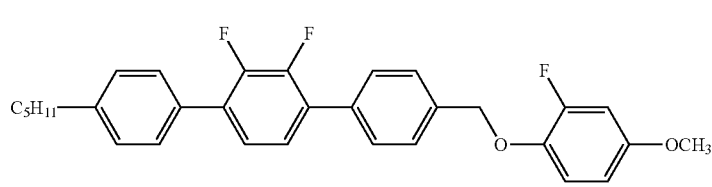 |
| 4151 | 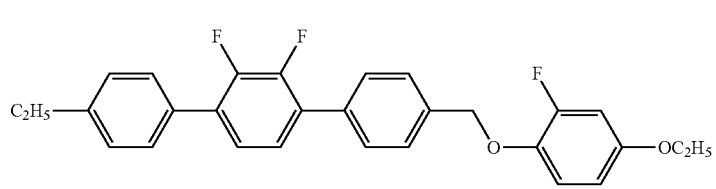 |

| No. | |
|---|---|
| 4152 | 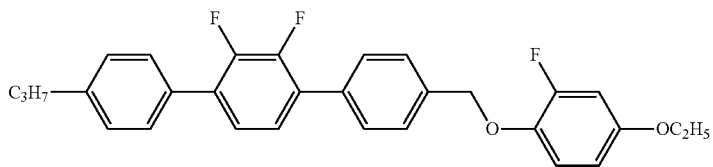 |
| 4153 | 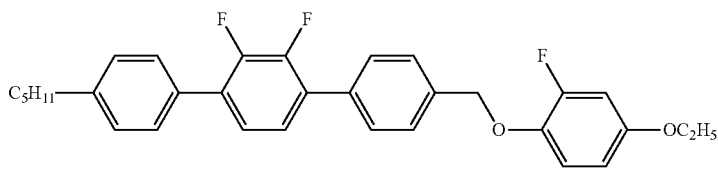 |
| 4154 | 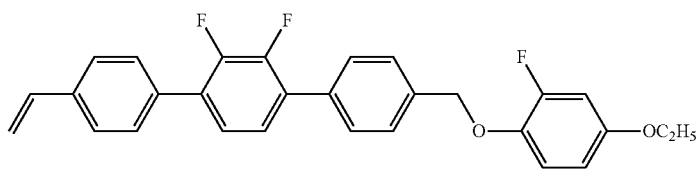 [SMILES: C=Cc1ccc(-c2ccc(-c3ccc(COc4ccc(OCC)cc4F)cc3)c(F)c2F)cc1] |
| 4155 | 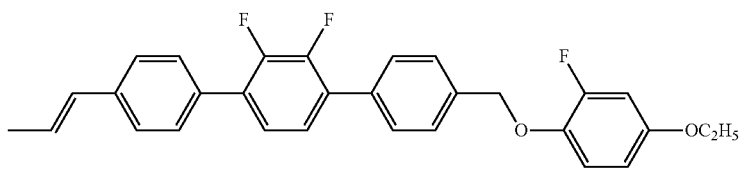 [SMILES: C/C=C/c1ccc(-c2ccc(-c3ccc(COc4ccc(OCC)cc4F)cc3)c(F)c2F)cc1] |
| 4156 | 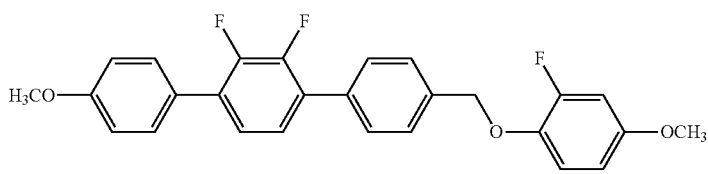 |
| 4157 | 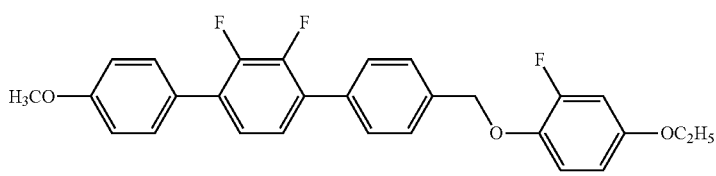 |
| 4158 | 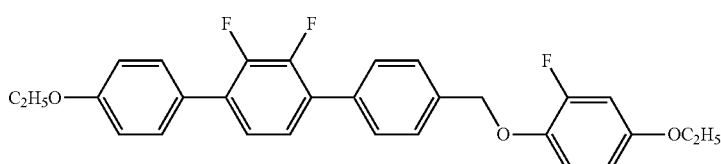 |
| 4159 | 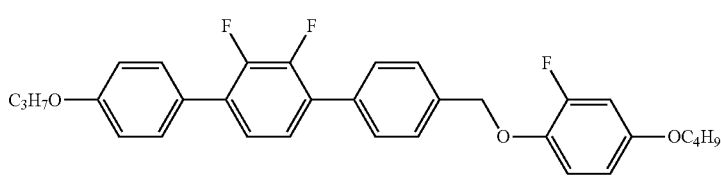 |

| No. | |
|---|---|
| 4160 | 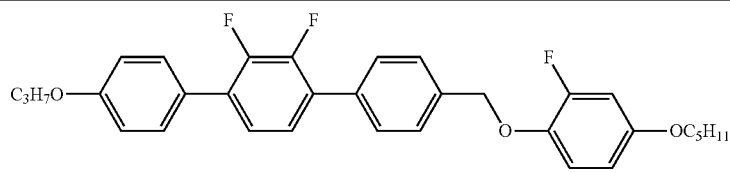 |
| 4161 | 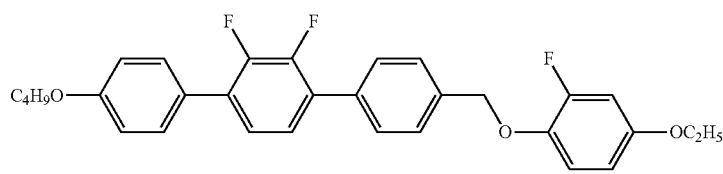 |
| 4162 | 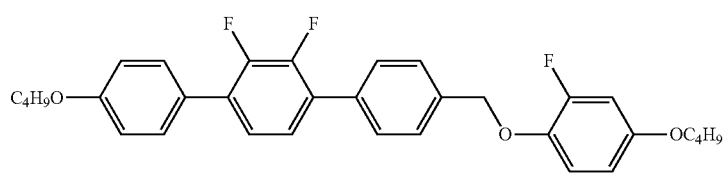 |
| 4163 | 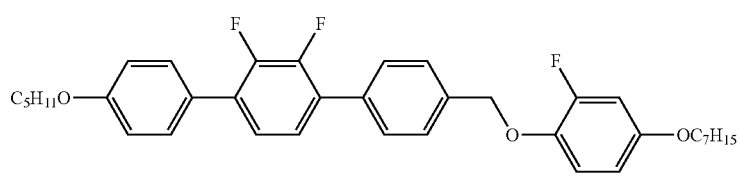 |
| 4164 | 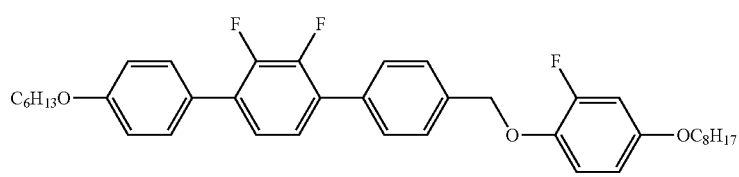 |
| 4165 | 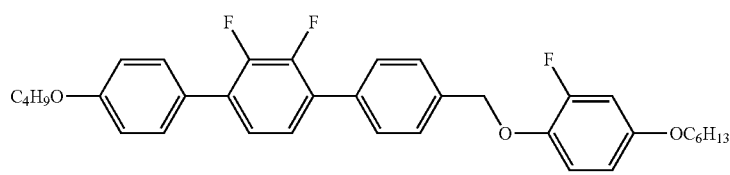 |
| 4166 | 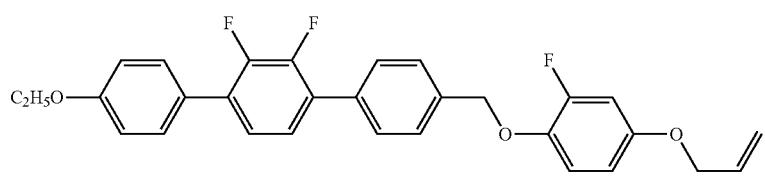 |
| 4167 | 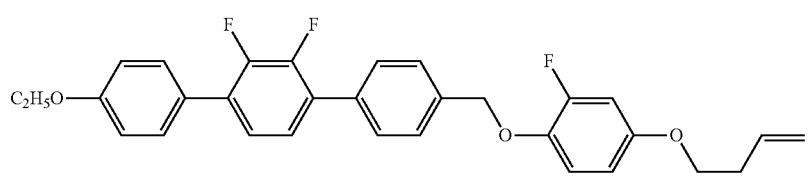 |
| 4168 | 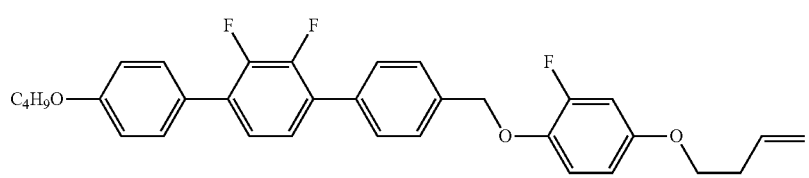 |

-continued
| No. |
|---|
| 4169 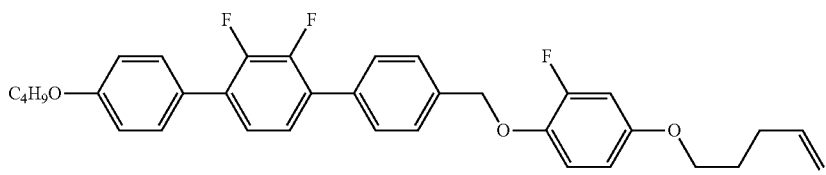 |
| 4170 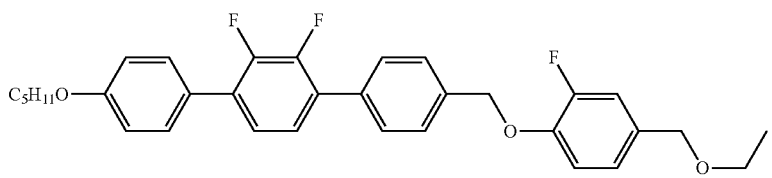 |
| 4171 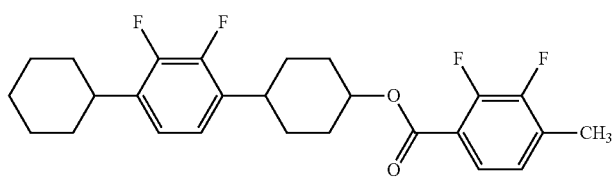 [SMILES: Cc1ccc(C(=O)OC2CCC(c3ccc(C4CCCCC4)c(F)c3F)CC2)c(F)c1F] |
| 4172 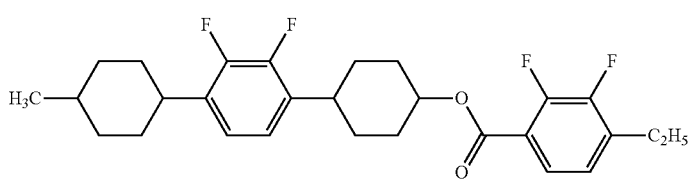 |
| 4173 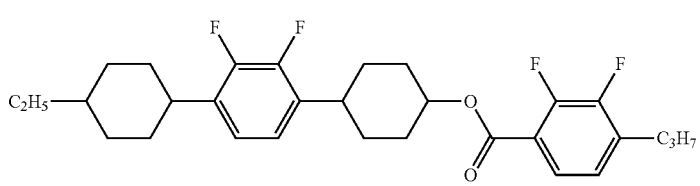 |
| 4174 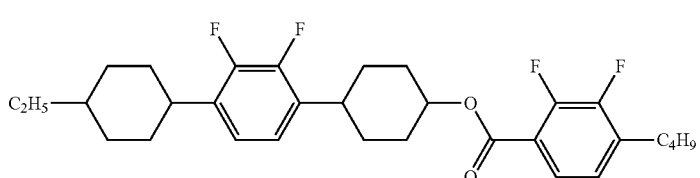 |
| 4175 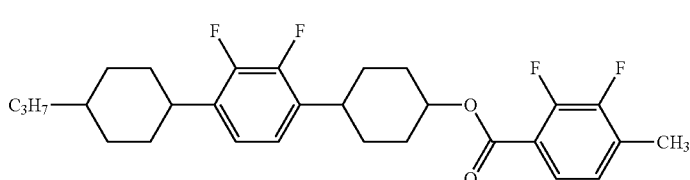 |
| 4176 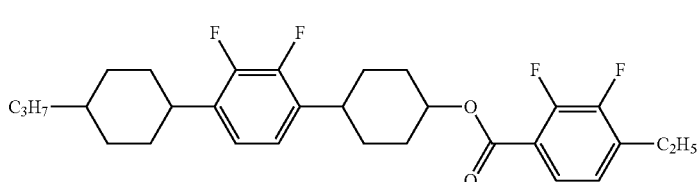 |

| No. | |
|---|---|
| 4177 | 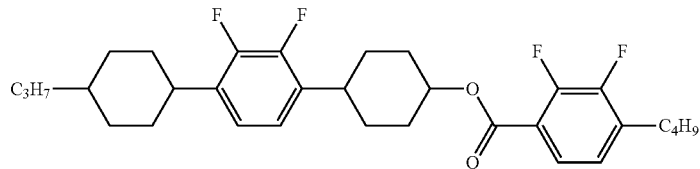 |
| 4178 | 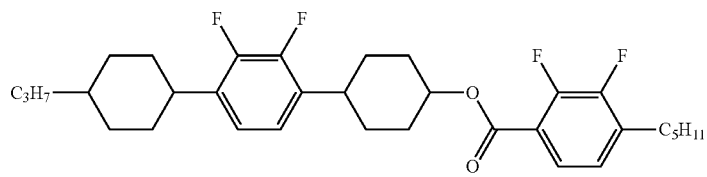 |
| 4179 | 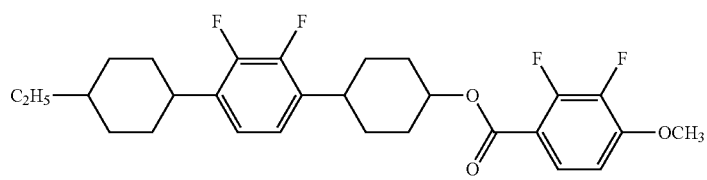 |
| 4180 | 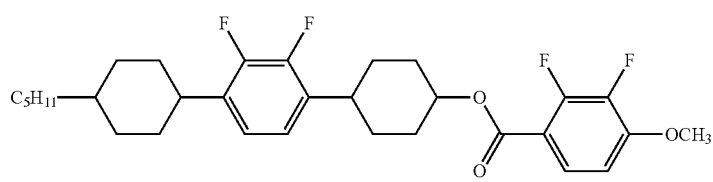 |
| 4181 | 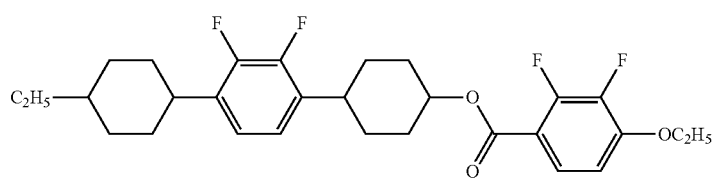 |
| 4182 | 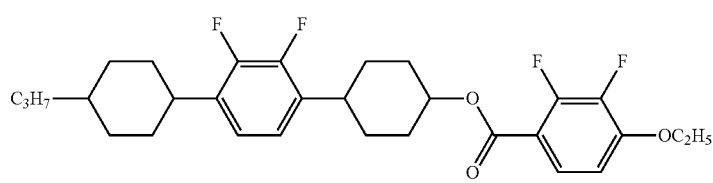 |
| 4183 | 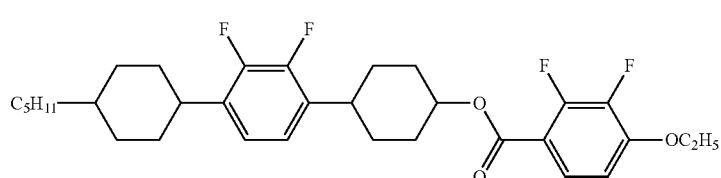 |
| 4184 | 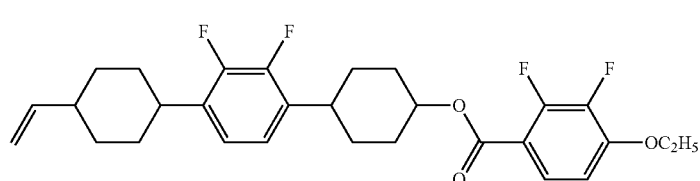 |

| No. |
|---|
| 4185 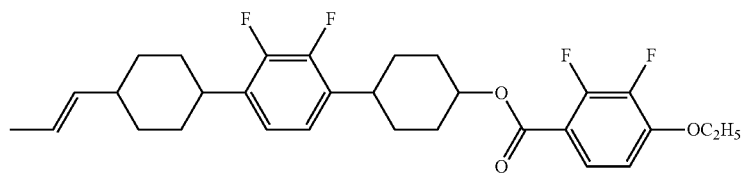 [SMILES: C/C=C/C1CCC(c2ccc(C3CCC(OC(=O)c4ccc(OCC)c(F)c4F)CC3)c(F)c2F)CC1] |
| 4186 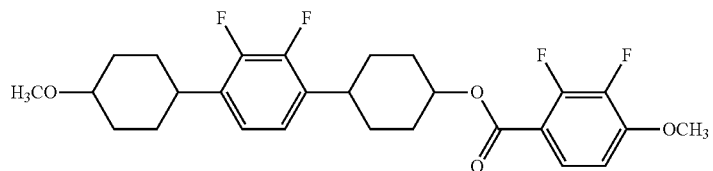 |
| 4187 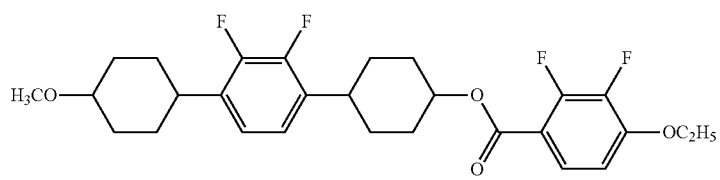 |
| 4188 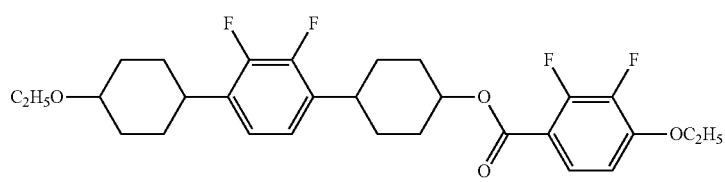 |
| 4189 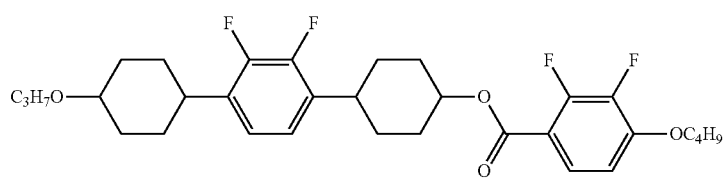 |
| 4190 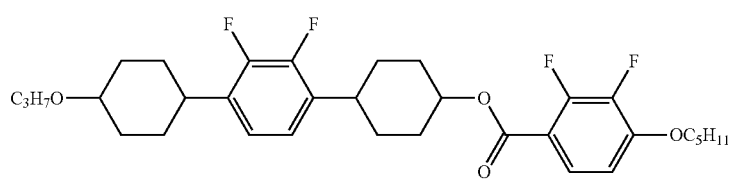 |
| 4191 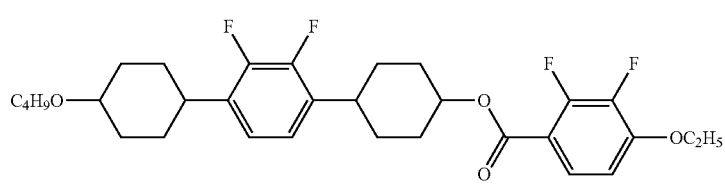 |
| 4192 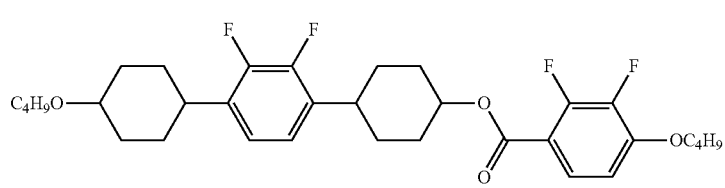 |

-continued
| No. | |
|---|---|
| 4193 | 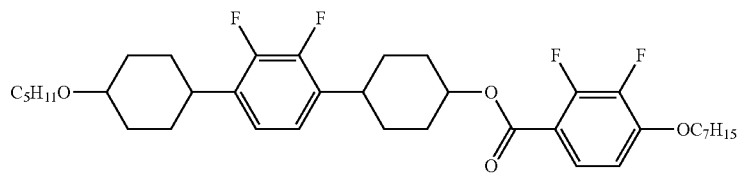 |
| 4194 | 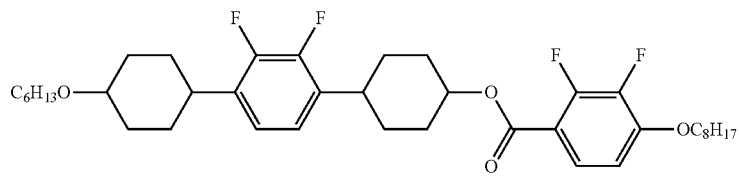 |
| 4195 | 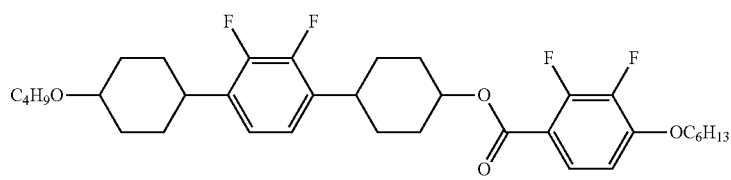 |
| 4196 | 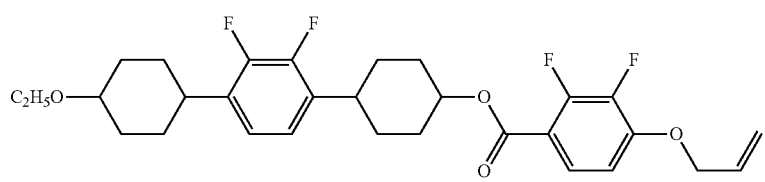 |
| 4197 | 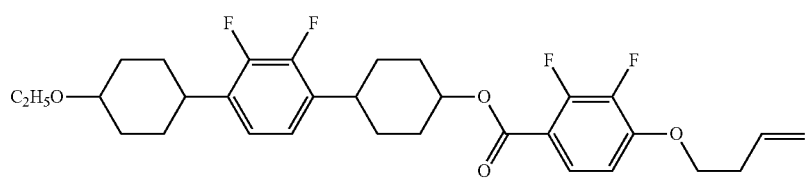 |
| 4198 | 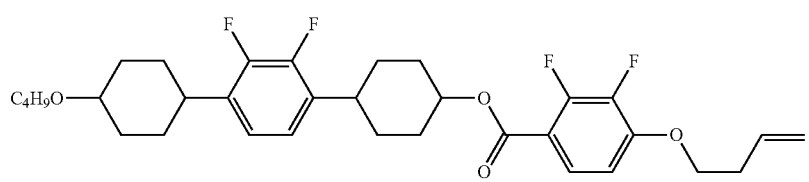 |
| 4199 | 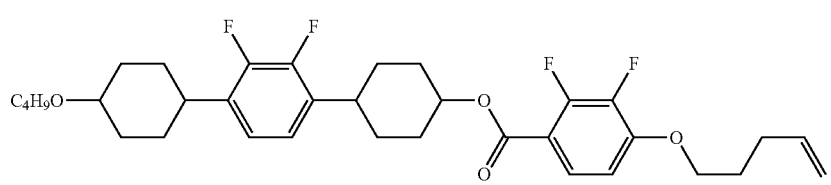 |
| 4200 | 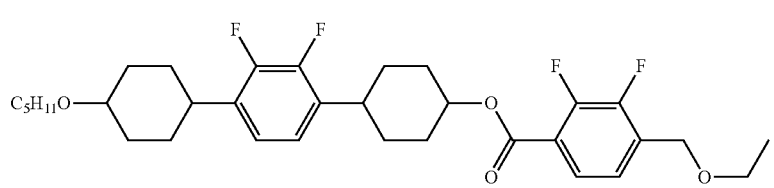 |

-continued
| No. | |
|---|---|
| 4201 | 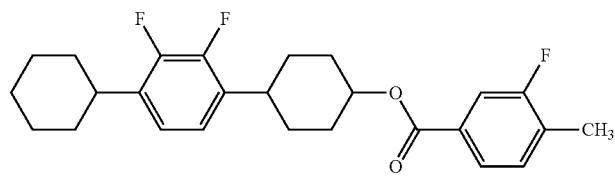 [SMILES: Cc1ccc(C(=O)OC2CCC(c3ccc(C4CCCCC4)c(F)c3F)CC2)cc1F] |
| 4202 | 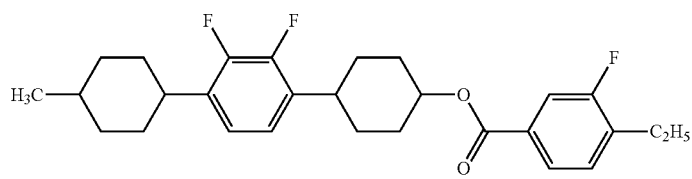 [SMILES: CCc1ccc(C(=O)OC2CCC(c3ccc(C4CCC(C)CC4)c(F)c3F)CC2)cc1F] |
| 4203 | 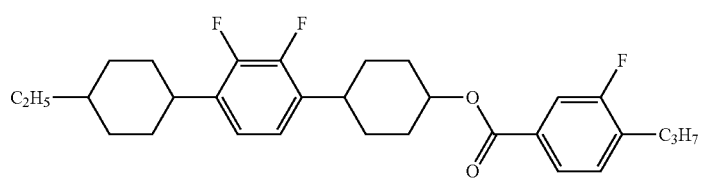 |
| 4204 | 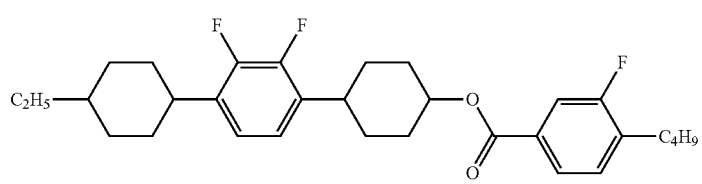 |
| 4205 | 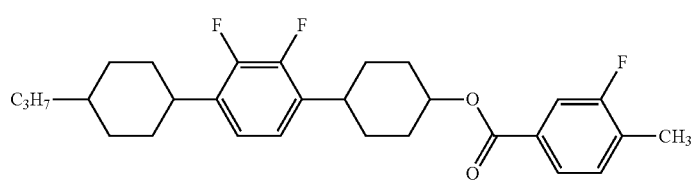 |
| 4206 | 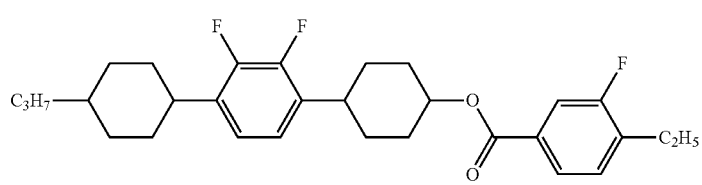 |
| 4207 | 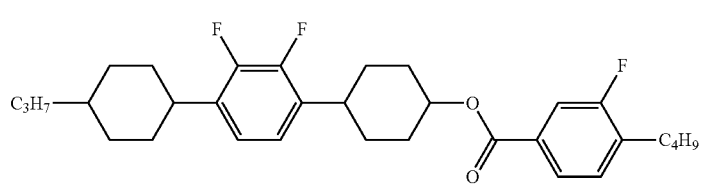 |
| 4208 | 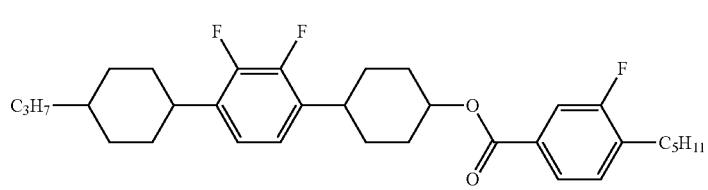 |

| No. | |
|---|---|
| 4209 | 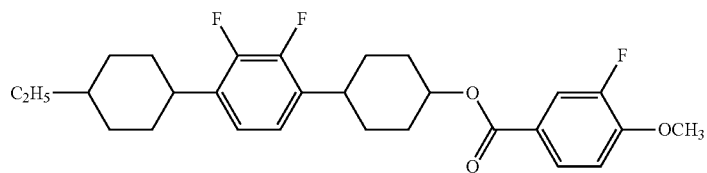 [SMILES: CCC1CCC(c2ccc(C3CCC(OC(=O)c4ccc(OC)c(F)c4)CC3)c(F)c2F)CC1] |
| 4210 | 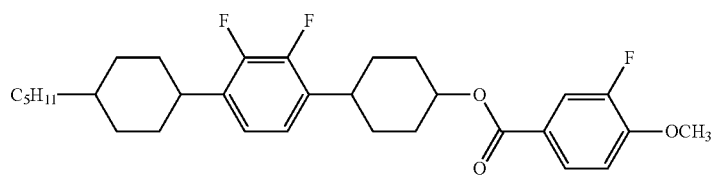 |
| 4211 | 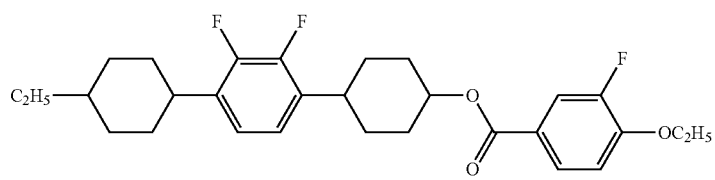 |
| 4212 | 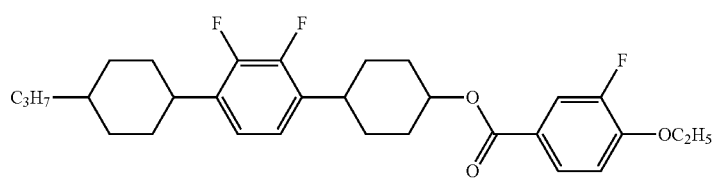 |
| 4213 | 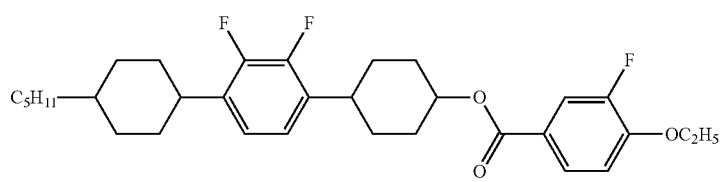 |
| 4214 | 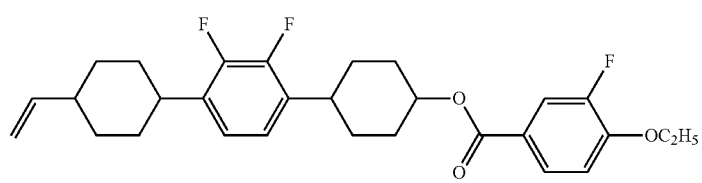 |
| 4215 | 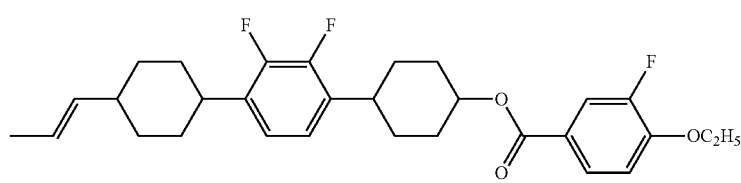 [SMILES: C/C=C/C1CCC(c2ccc(C3CCC(OC(=O)c4ccc(OCC)c(F)c4)CC3)c(F)c2F)CC1] |
| 4216 | 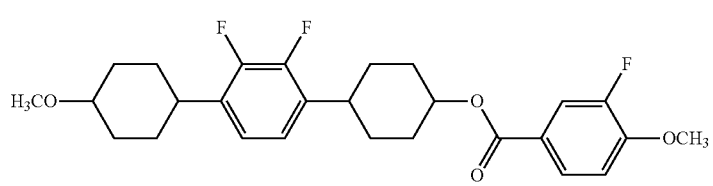 [SMILES: COc1ccc(C(=O)OC2CCC(c3ccc(C4CCC(OC)CC4)c(F)c3F)CC2)cc1F] |

| No. | |
|---|---|
| 4217 | 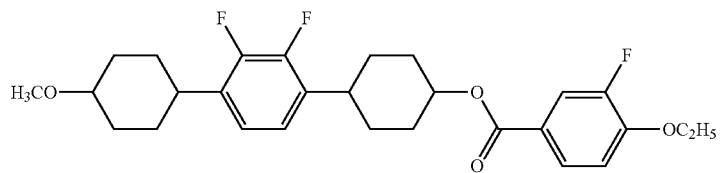 |
| 4218 | 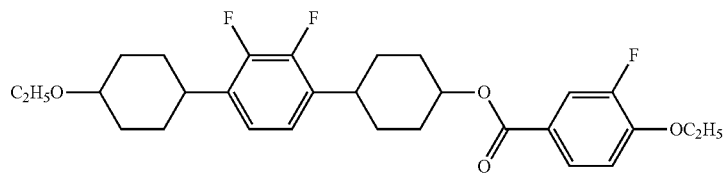 |
| 4219 | 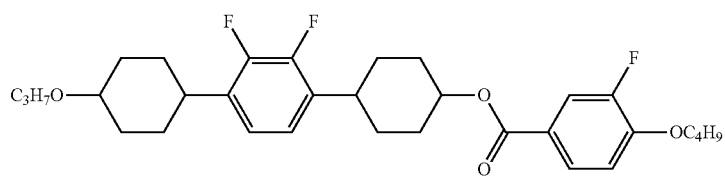 |
| 4220 | 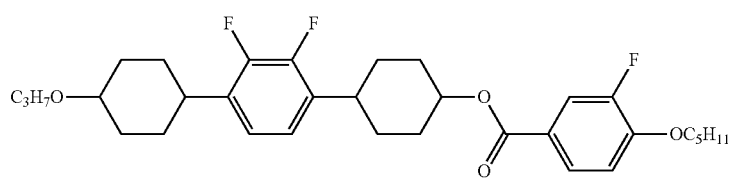 |
| 4221 | 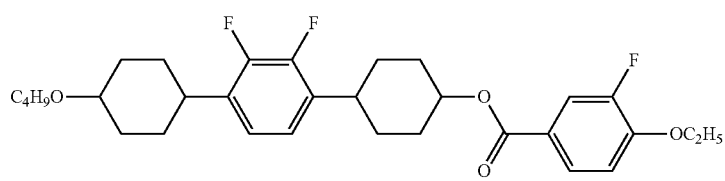 |
| 4222 | 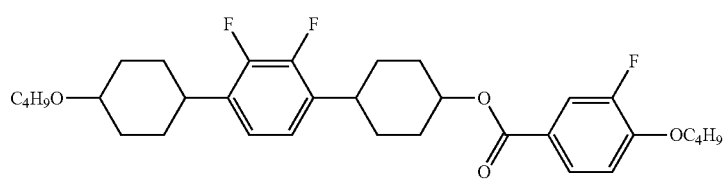 |
| 4223 | 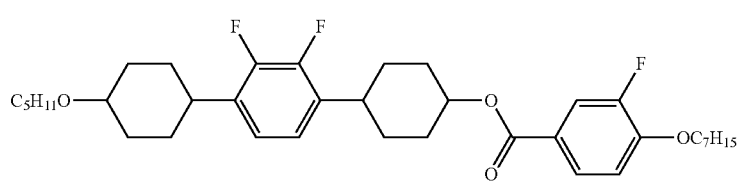 |
| 4224 | 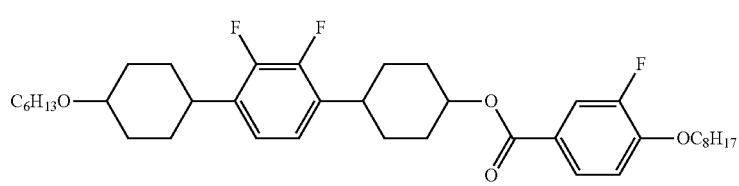 |

| No. | |
|---|---|
| 4225 | 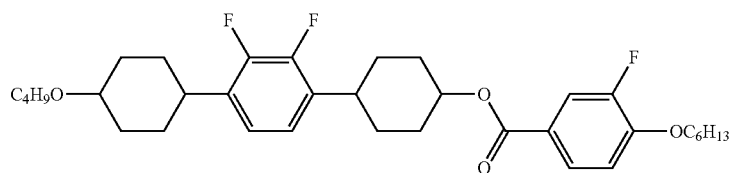 |
| 4226 | 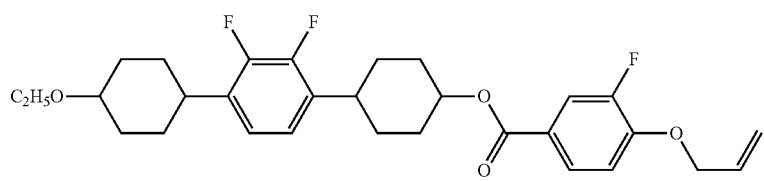 |
| 4227 | 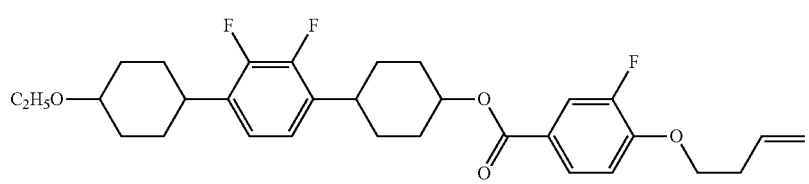 |
| 4228 | 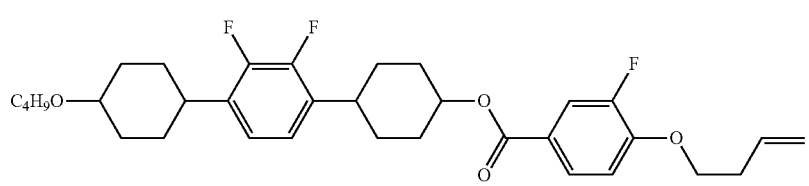 |
| 4229 | 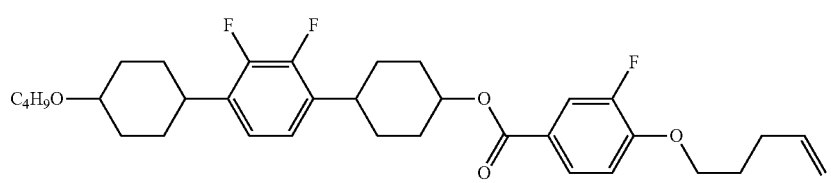 |
| 4230 | 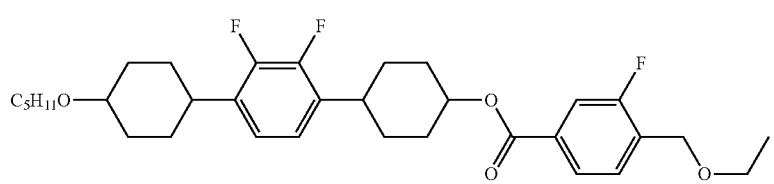 |
| 4231 | 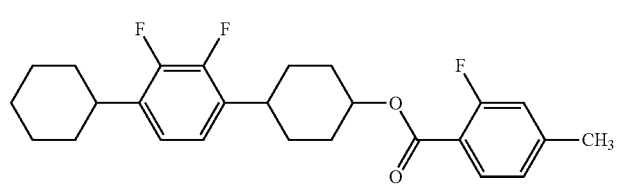 [SMILES: Cc1ccc(C(=O)OC2CCC(c3ccc(C4CCCCC4)c(F)c3F)CC2)c(F)c1] |
| 4232 | 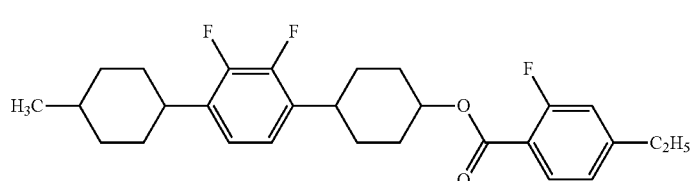 |

| No. |
|---|
| 4233 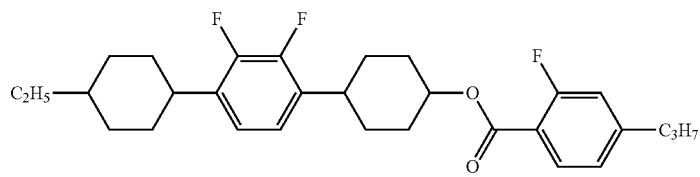 |
| 4234 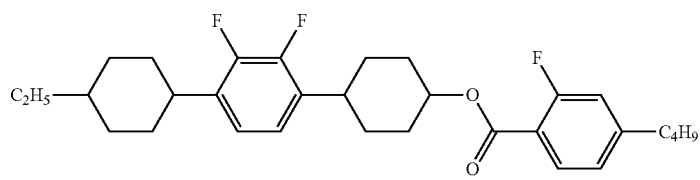 |
| 4235 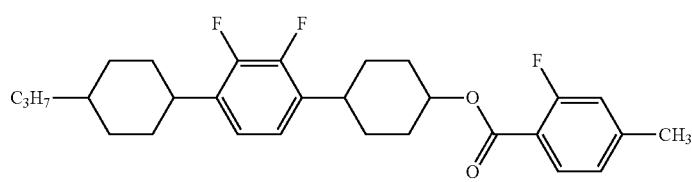 |
| 4236 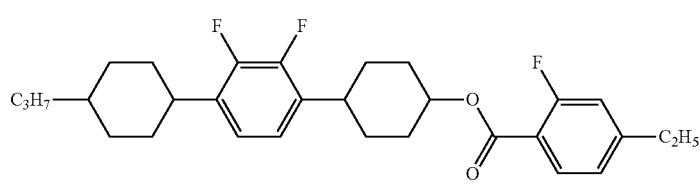 |
| 4237 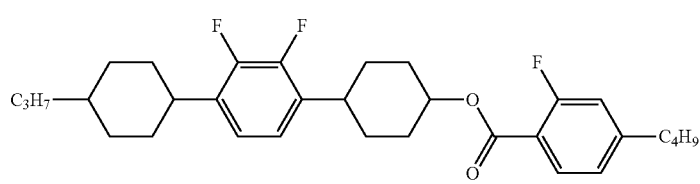 |
| 4238 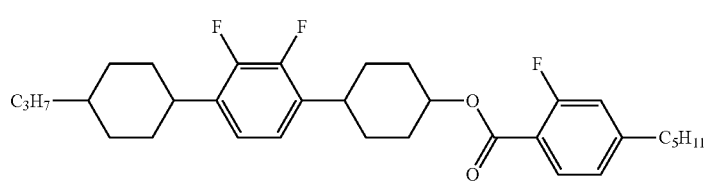 |
| 4239 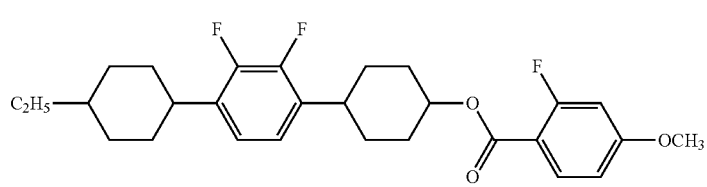 |
| 4240 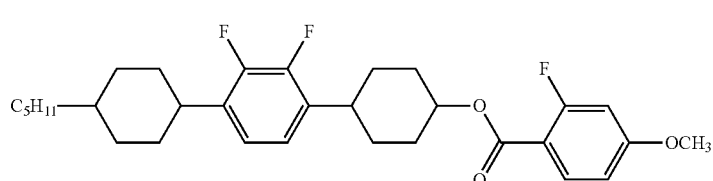 |

| No. |
|---|
| 4241 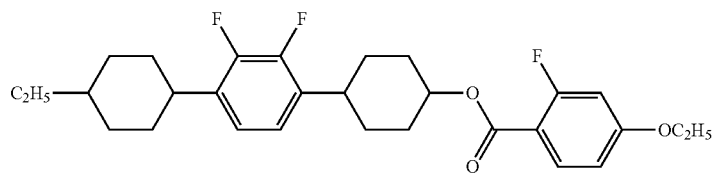 |
| 4242 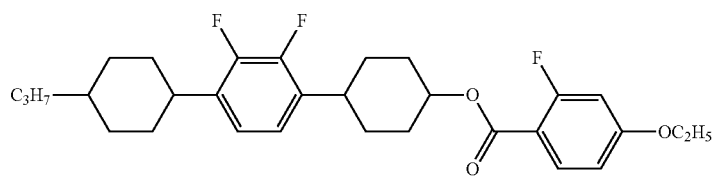 |
| 4243 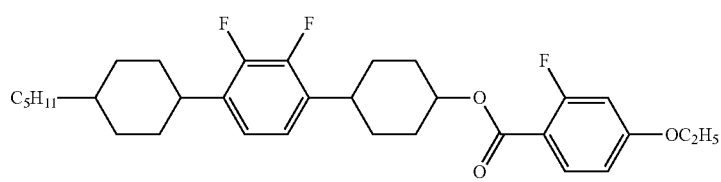 |
| 4244 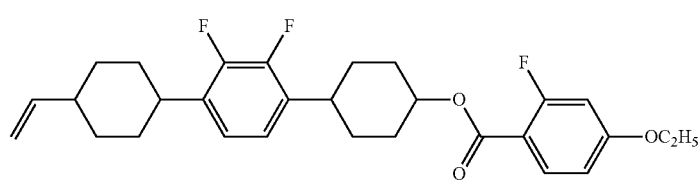 |
| 4245 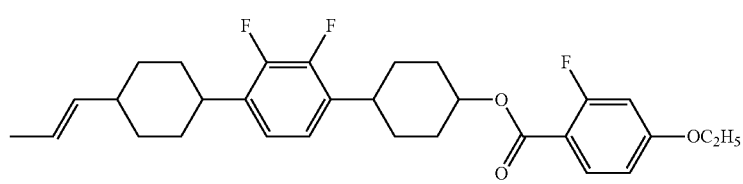 [SMILES: C/C=C/C1CCC(c2ccc(C3CCC(OC(=O)c4ccc(OCC)cc4F)CC3)c(F)c2F)CC1] |
| 4246 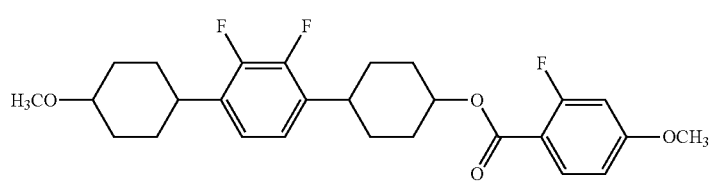 |
| 4247 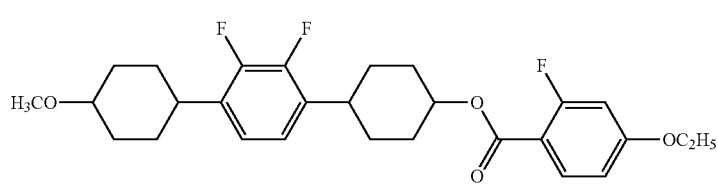 |
| 4248 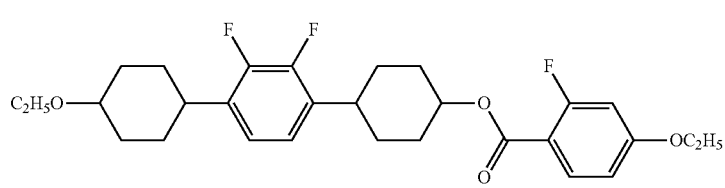 |

| No. | |
|---|---|
| 4249 | 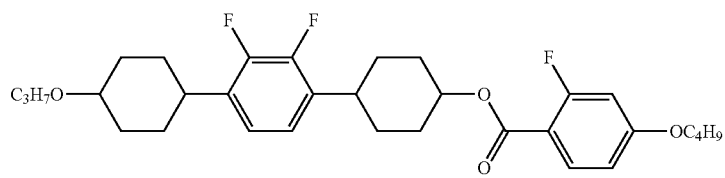 |
| 4250 | 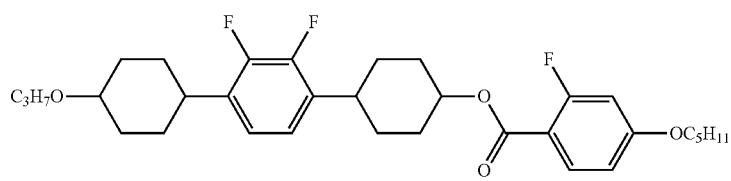 |
| 4251 | 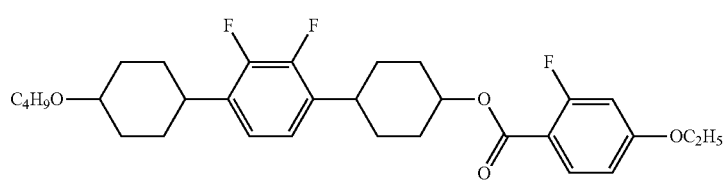 |
| 4252 | 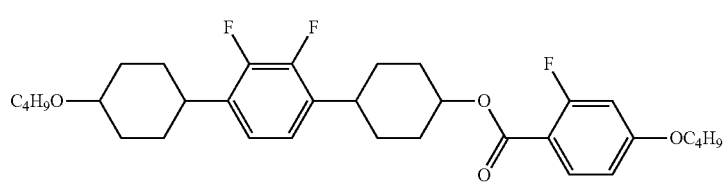 |
| 4253 | 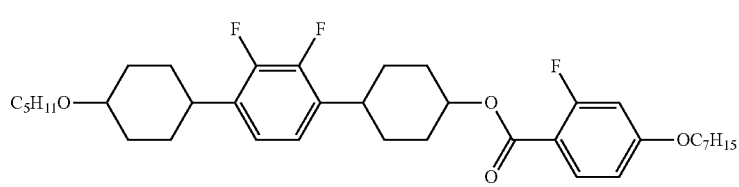 |
| 4254 | 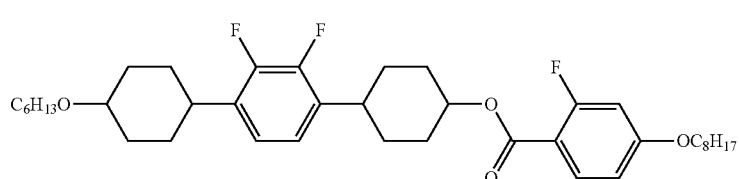 |
| 4255 | 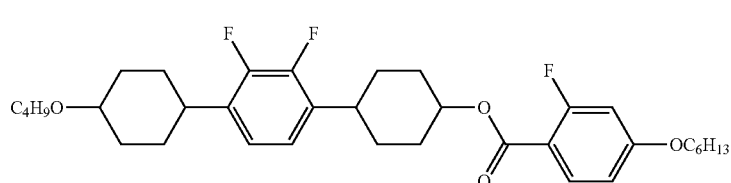 |
| 4256 | 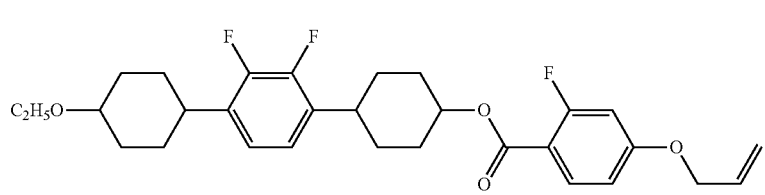 |

| No. |
| --- |
| 4257 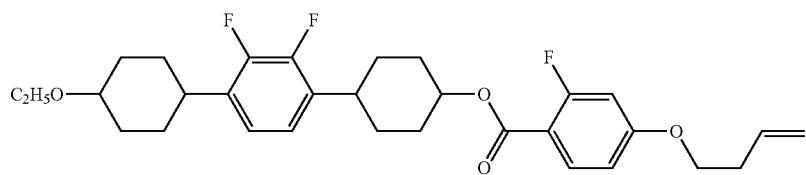 |
| 4258 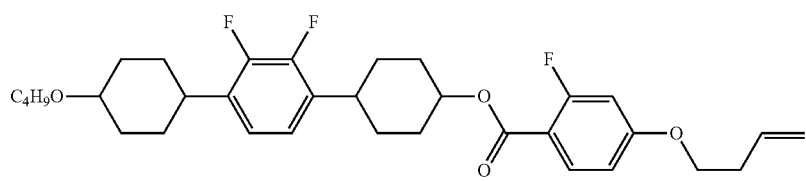 |
| 4259 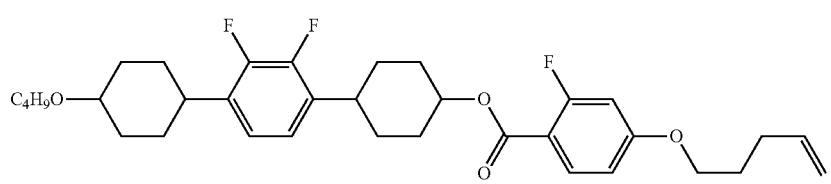 |
| 4260 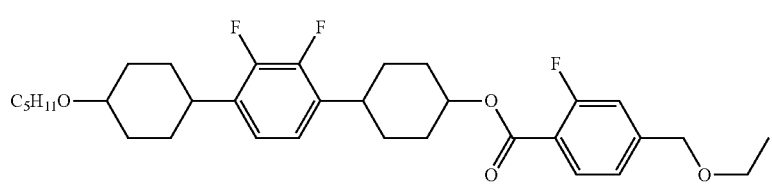 |
| 4261 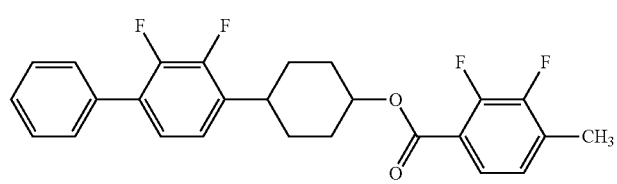 [SMILES: Cc1ccc(C(=O)OC2CCC(c3ccc(-c4ccccc4)c(F)c3F)CC2)c(F)c1F] |
| 4262 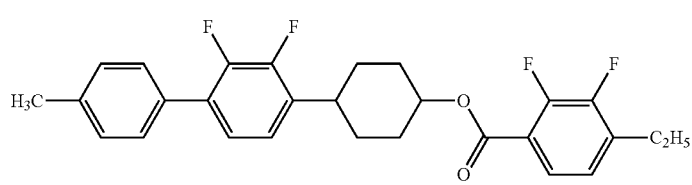 |
| 4263 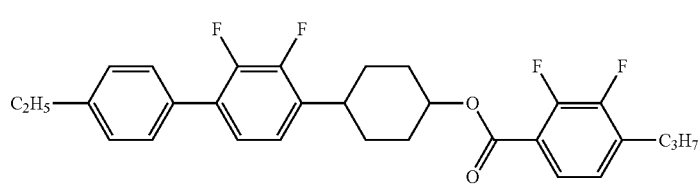 |
| 4264 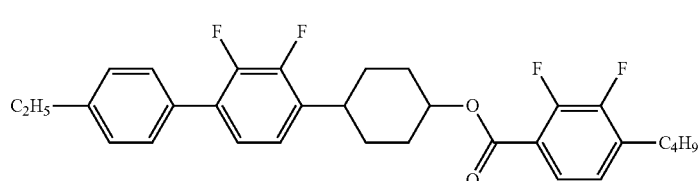 |

| No. | |
|---|---|
| 4265 | 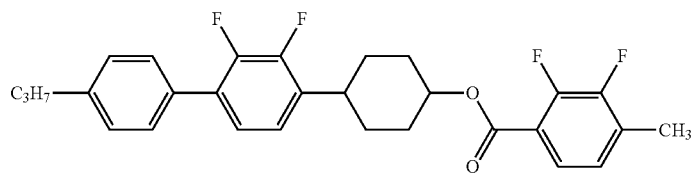 |
| 4266 | 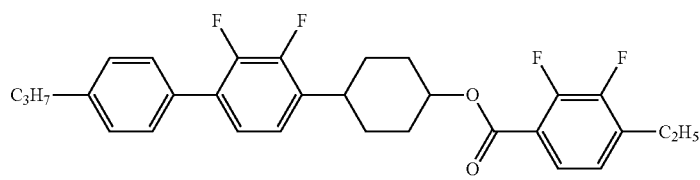 |
| 4267 | 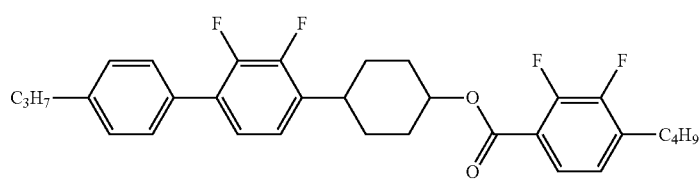 |
| 4268 | 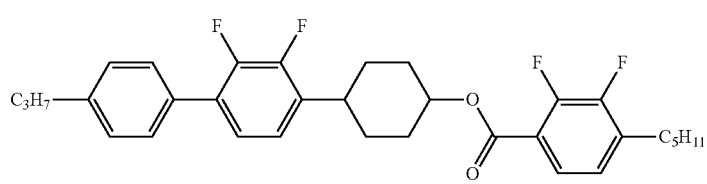 |
| 4269 | 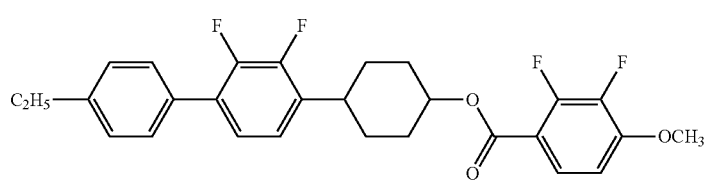 [SMILES: CCc1ccc(-c2ccc(C3CCC(OC(=O)c4ccc(OC)c(F)c4F)CC3)c(F)c2F)cc1] |
| 4270 | 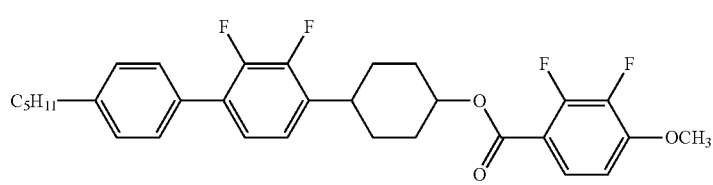 [SMILES: COc1ccc(-c2ccc(C3CCC(OC(=O)c4ccc(OC)c(F)c4F)CC3)c(F)c2F)cc1] |
| 4271 | 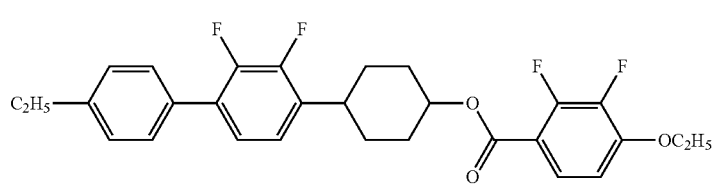 |
| 4272 | 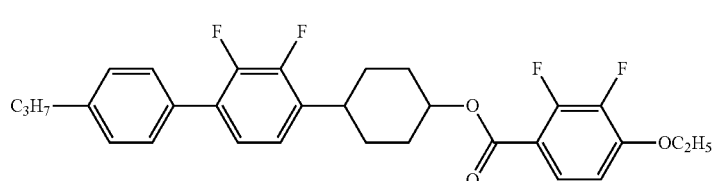 |

-continued
| No. | |
|---|---|
| 4273 | 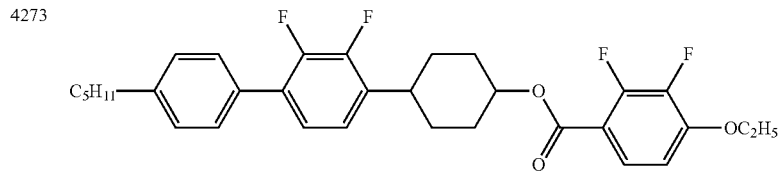 |
| 4274 | 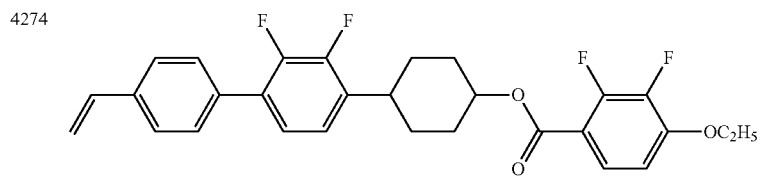 |
| 4275 | 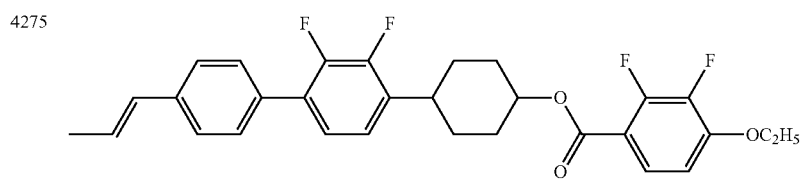 |
| 4276 | 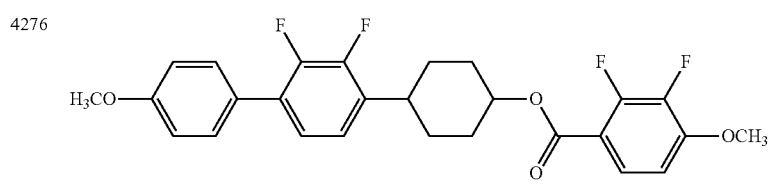 |
| 4277 | 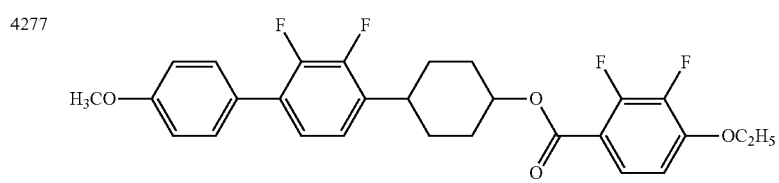 |
| 4278 | 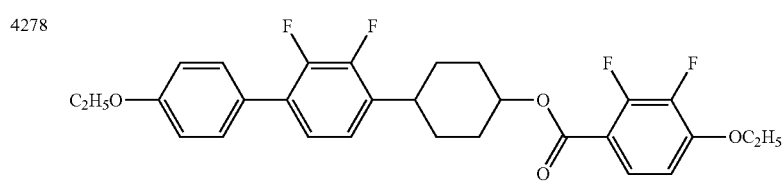 |
| 4279 | 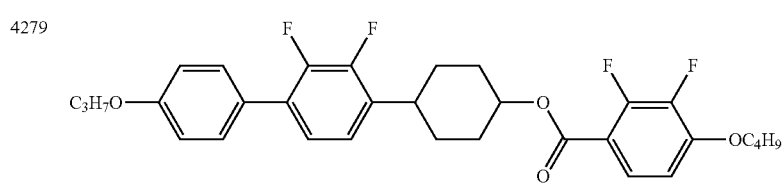 |
| 4280 | 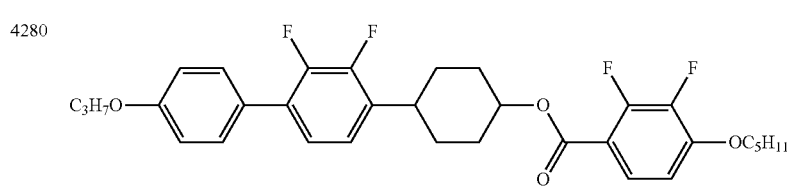 |

-continued
| No. | |
|---|---|
| 4281 | 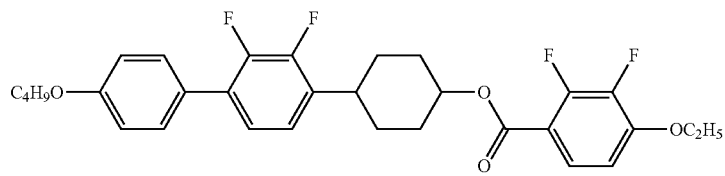 |
| 4282 | 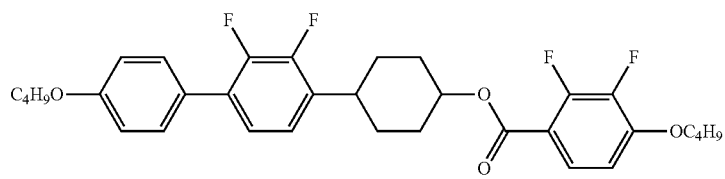 |
| 4283 | 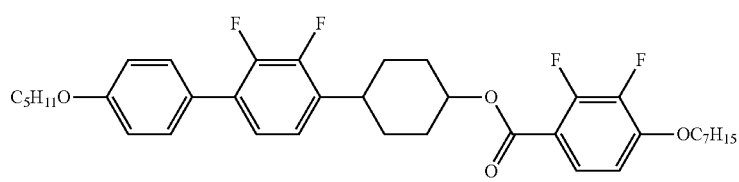 |
| 4284 | 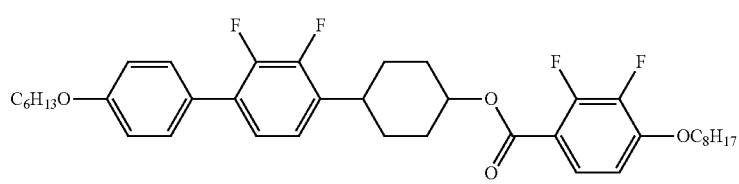 |
| 4285 | 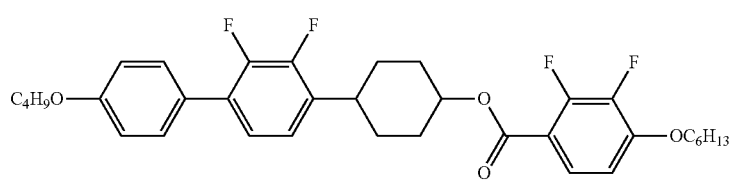 |
| 4286 | 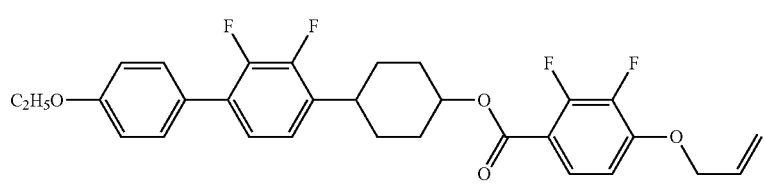 |
| 4287 | 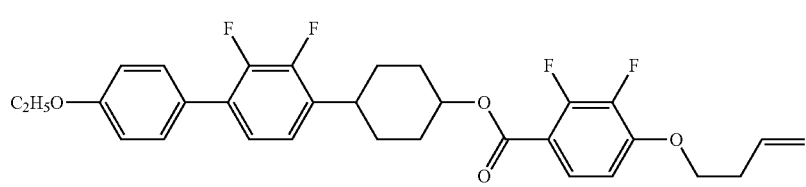 |
| 4288 | 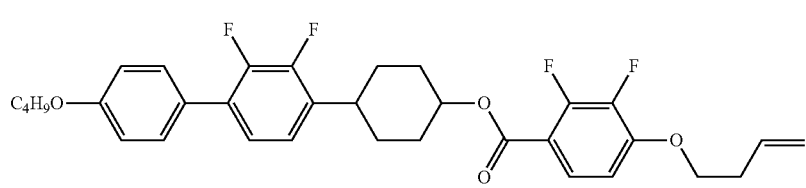 |

| No. |
|---|
| 4289 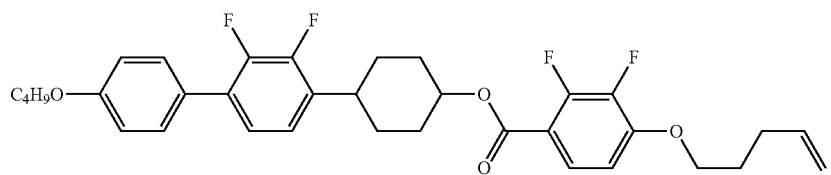 |
| 4290 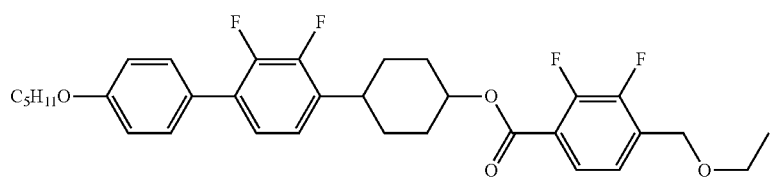 |
| 4291 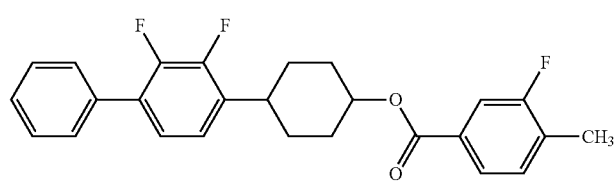 |
| 4292 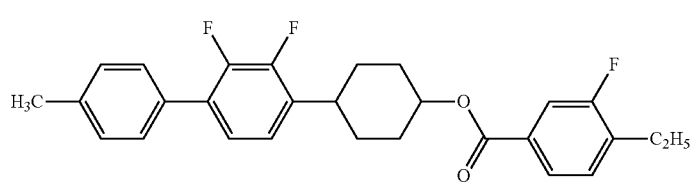 [SMILES: CCc1ccc(C(=O)OC2CCC(c3ccc(-c4ccc(C)cc4)c(F)c3F)CC2)cc1F] |
| 4293 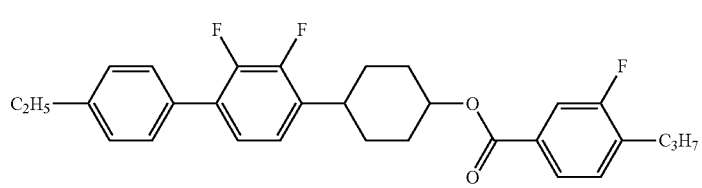 |
| 4294 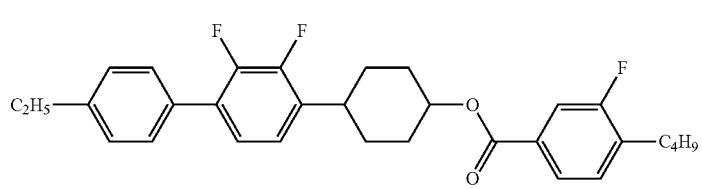 |
| 4295 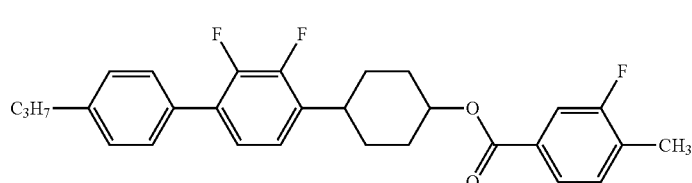 |
| 4296 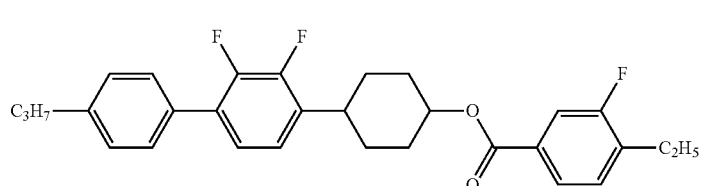 |

| No. | |
|---|---|
| 4297 | 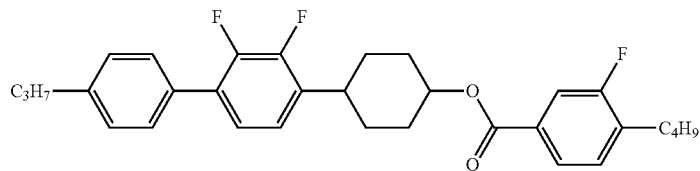 |
| 4298 | 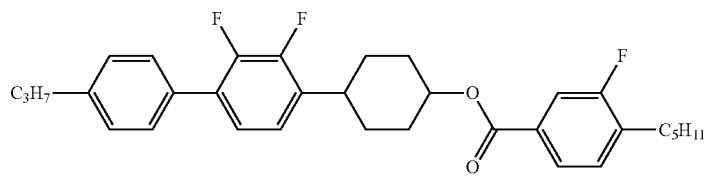 |
| 4299 | 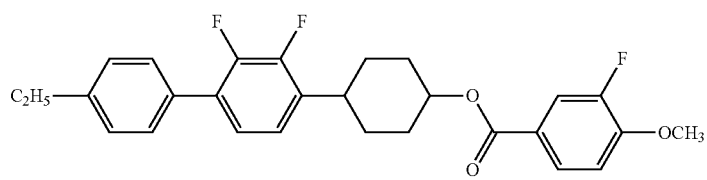 |
| 4300 | 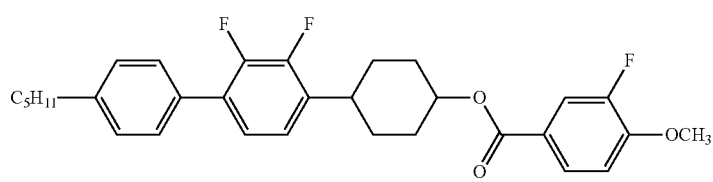 |
| 4301 | 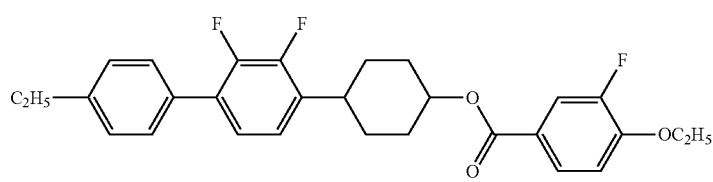 [SMILES: CCOc1ccc(C(=O)OC2CCC(c3ccc(-c4ccc(CC)cc4)c(F)c3F)CC2)cc1F] |
| 4302 | 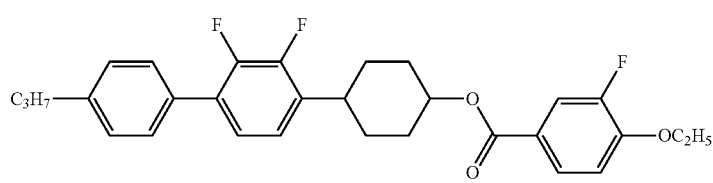 |
| 4303 | 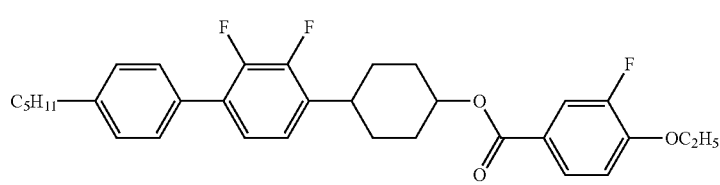 |
| 4304 | 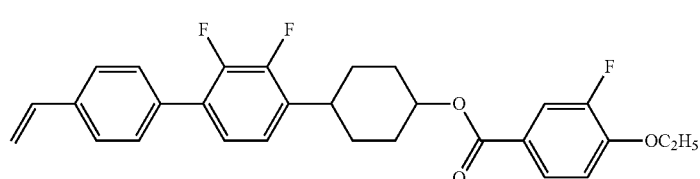 |

-continued
| No. | |
|---|---|
| 4305 | 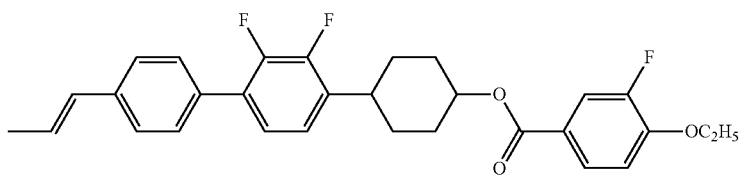 [SMILES: C/C=C/c1ccc(-c2ccc(C3CCC(OC(=O)c4ccc(OCC)c(F)c4)CC3)c(F)c2F)cc1] |
| 4306 | 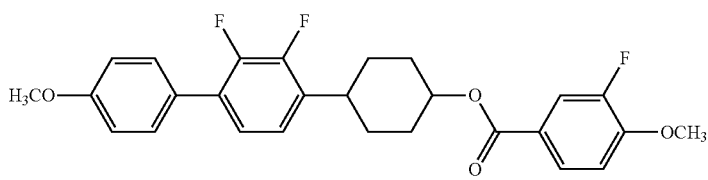 [SMILES: COc1ccc(-c2ccc(C3CCC(OC(=O)c4ccc(OC)c(F)c4)CC3)c(F)c2F)cc1] |
| 4307 | 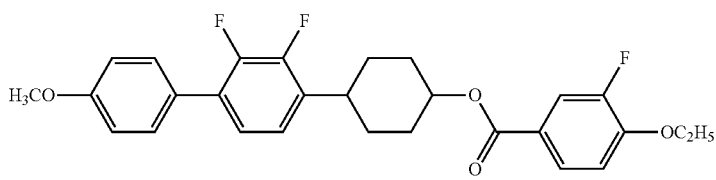 |
| 4308 | 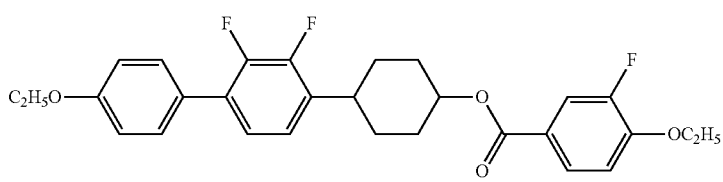 |
| 4309 | 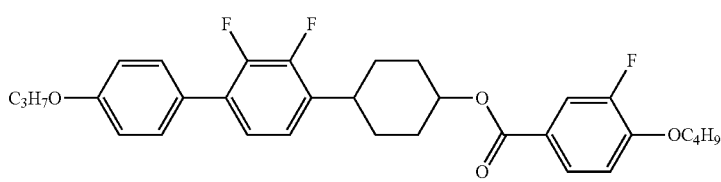 |
| 4310 | 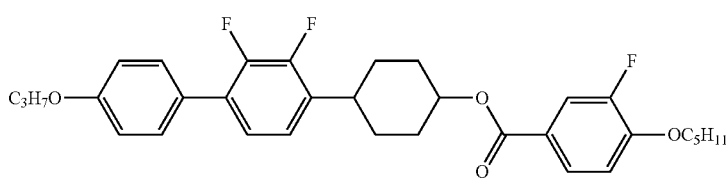 |
| 4311 | 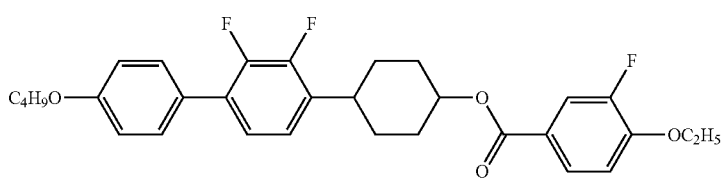 |
| 4312 | 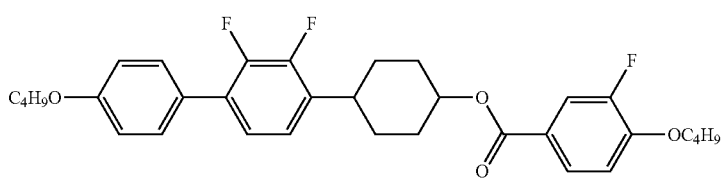 |

| No. |
|---|
| 4313 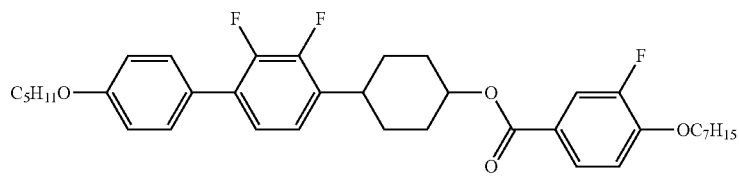 |
| 4314 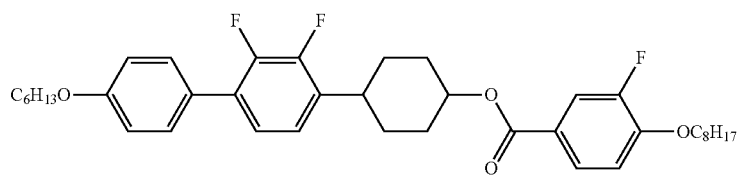 |
| 4315 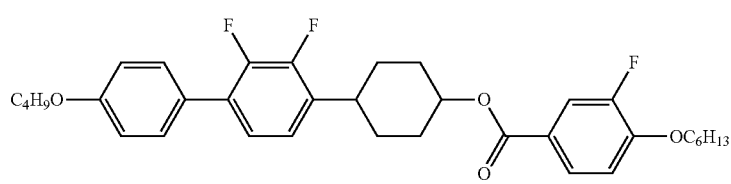 |
| 4316 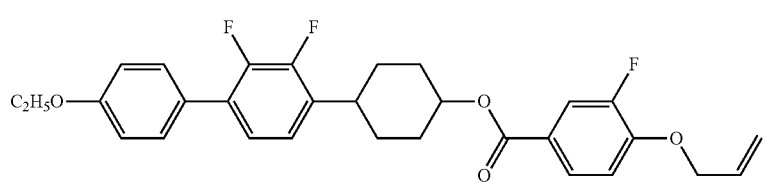 |
| 4317 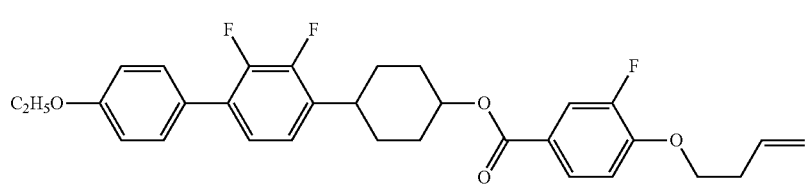 |
| 4318 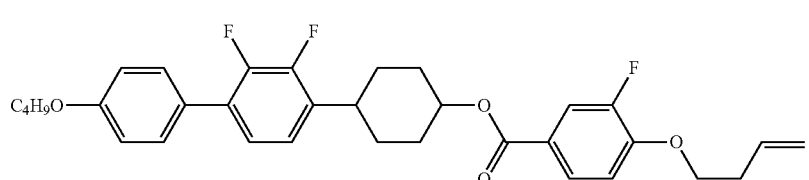 |
| 4319 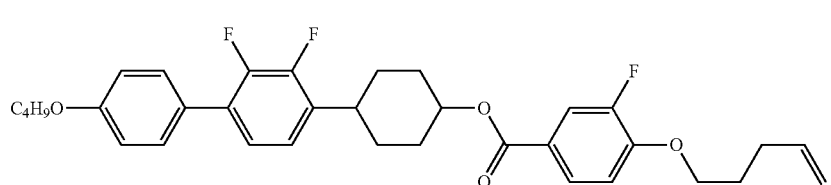 |
| 4320 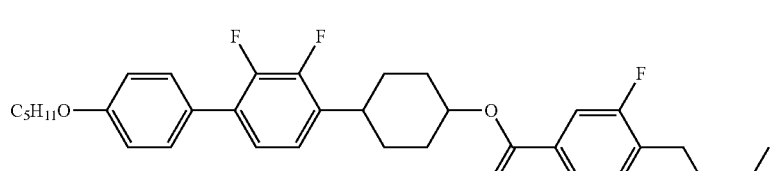 |

| No. | |
|---|---|
| 4321 | 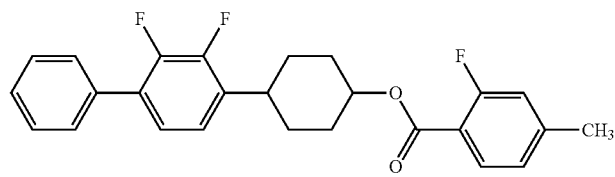 |
| 4322 | 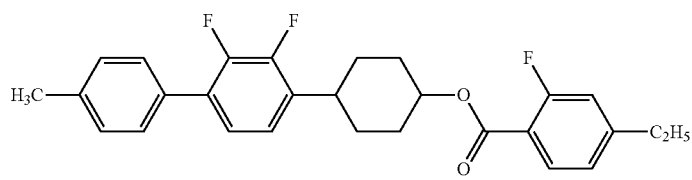 [SMILES: CCc1ccc(C(=O)OC2CCC(c3ccc(-c4ccc(C)cc4)c(F)c3F)CC2)c(F)c1] |
| 4323 | 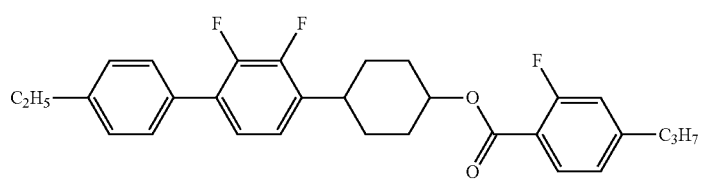 |
| 4324 | 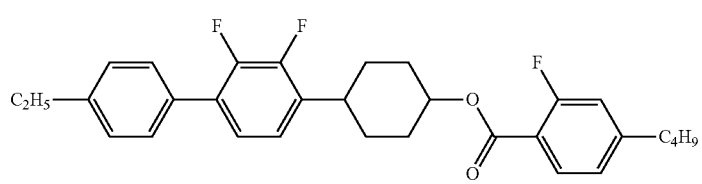 |
| 4325 | 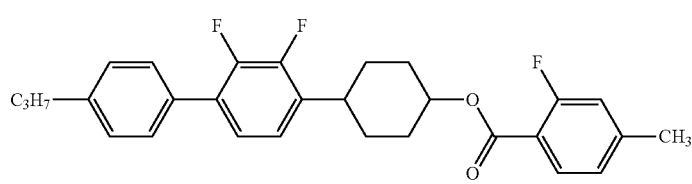 |
| 4326 | 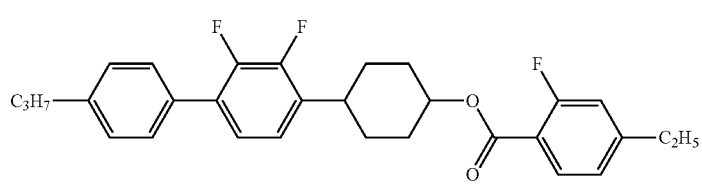 |
| 4327 | 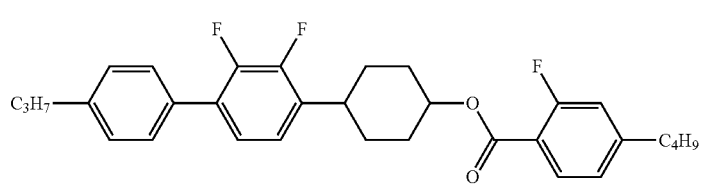 |
| 4328 | 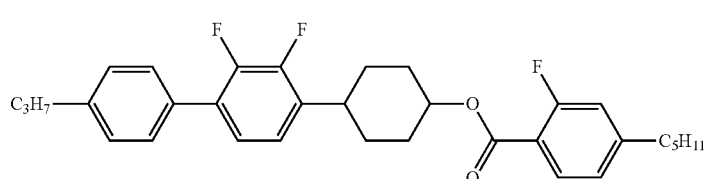 |

-continued
| No. | |
|---|---|
| 4329 | 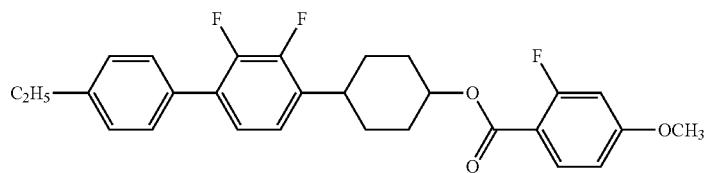 |
| 4330 | 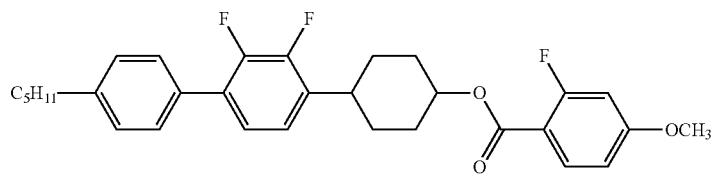 |
| 4331 | 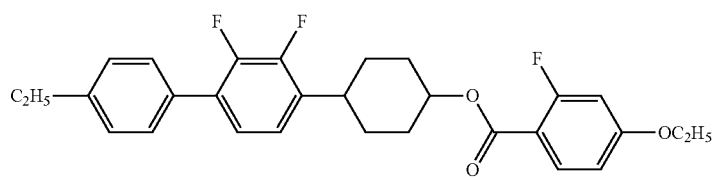 |
| 4332 | 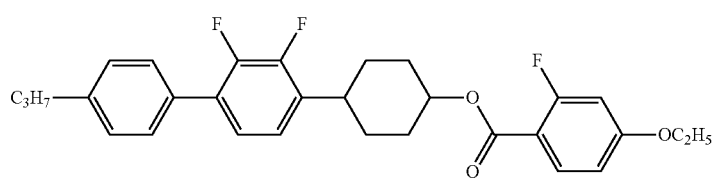 |
| 4333 | 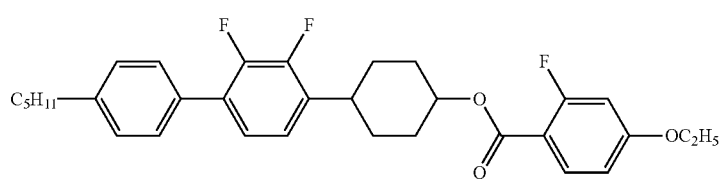 |
| 4334 | 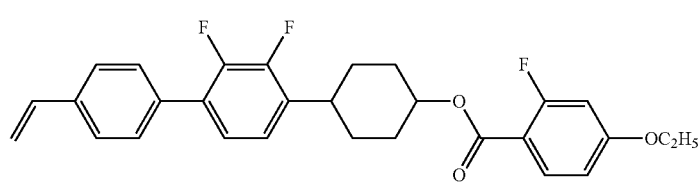 [SMILES: C=Cc1ccc(-c2ccc(C3CCC(OC(=O)c4ccc(OCC)cc4F)CC3)c(F)c2F)cc1] |
| 4335 | 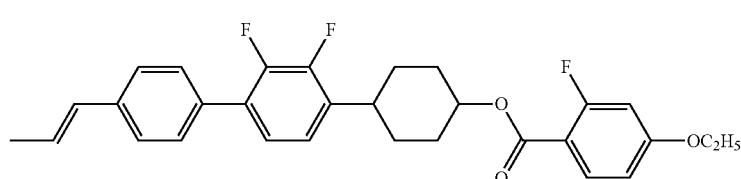 |
| 4336 | 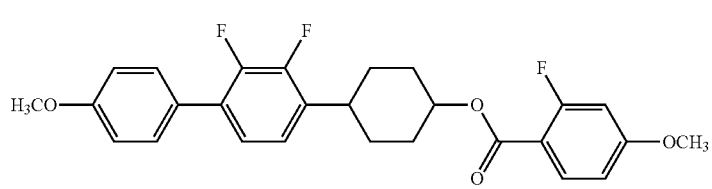 |

| No. | |
|---|---|
| 4337 | 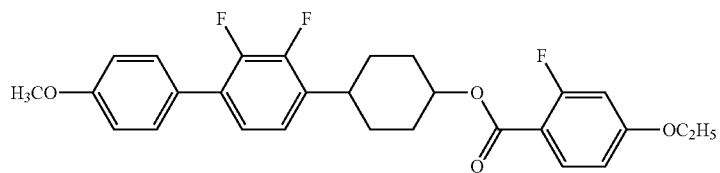 |
| 4338 | 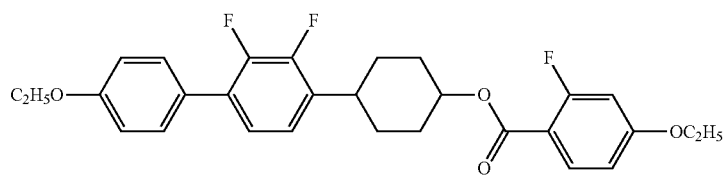 |
| 4339 | 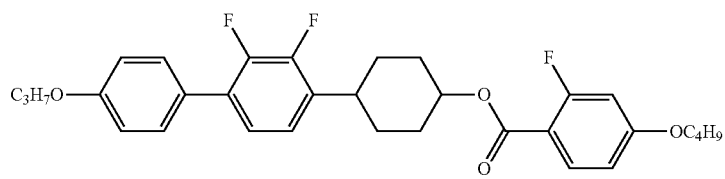 |
| 4340 | 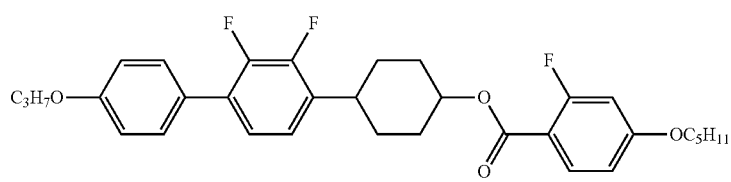 |
| 4341 | 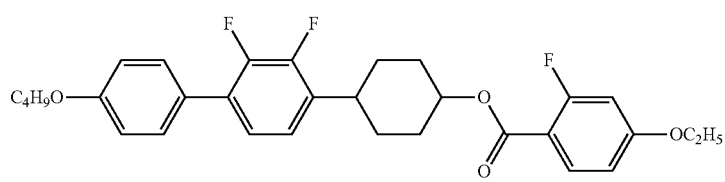 |
| 4342 | 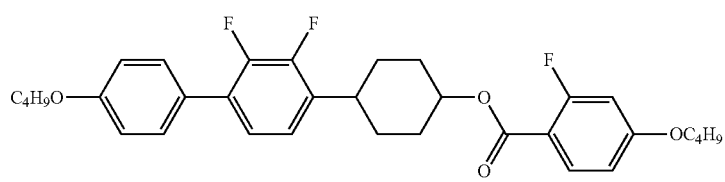 |
| 4343 | 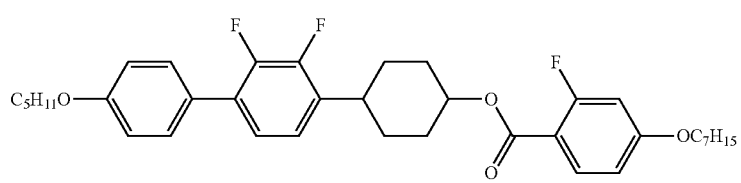 |
| 4344 | 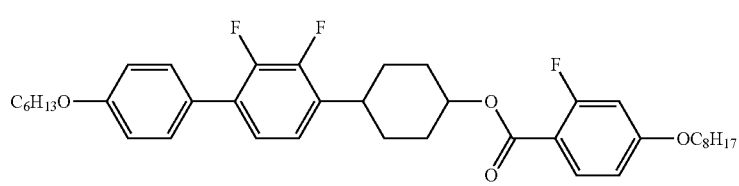 |

-continued
| No. | |
|---|---|
| 4345 | 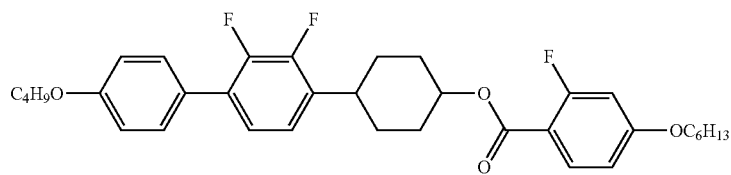 |
| 4346 | 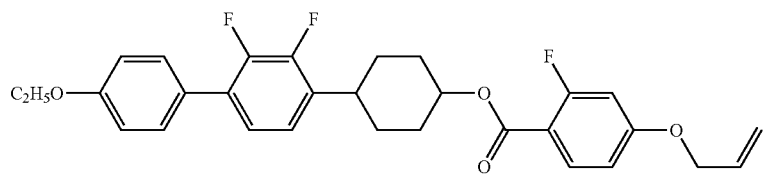 |
| 4347 | 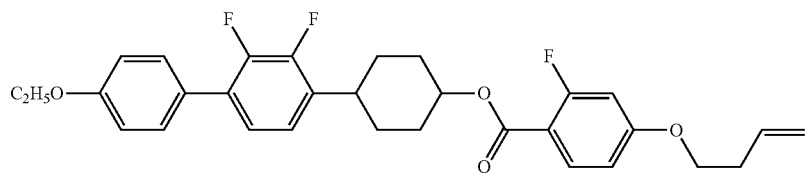 |
| 4348 | 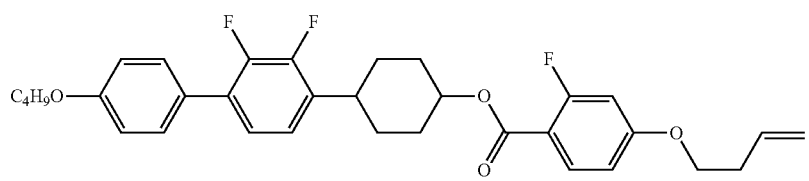 |
| 4349 | 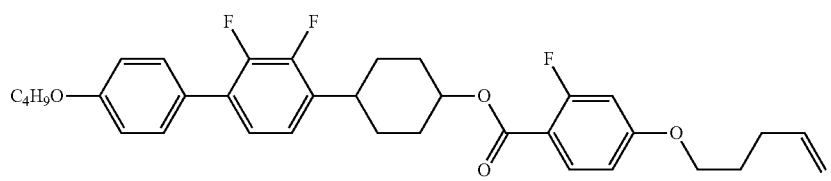 |
| 4350 | 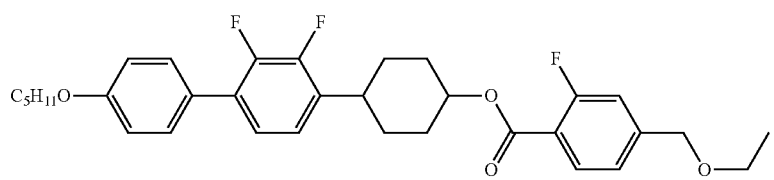 |
| 4351 | 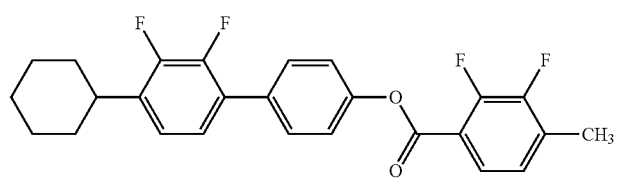 |
| 4352 | 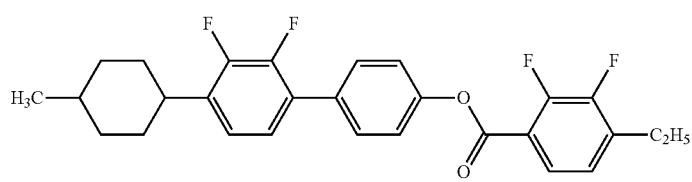 [SMILES: CCc1ccc(C(=O)Oc2ccc(-c3ccc(C4CCC(C)CC4)c(F)c3F)cc2)c(F)c1F] |

| No. | |
|---|---|
| 4353 | 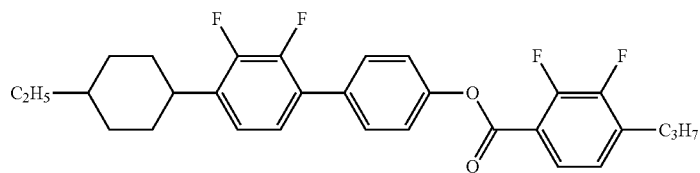 |
| 4354 | 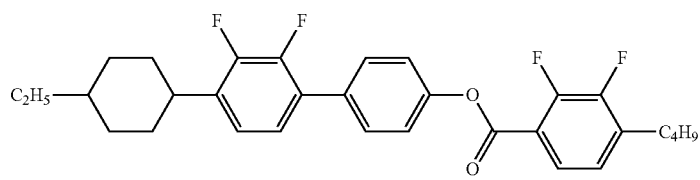 |
| 4355 | 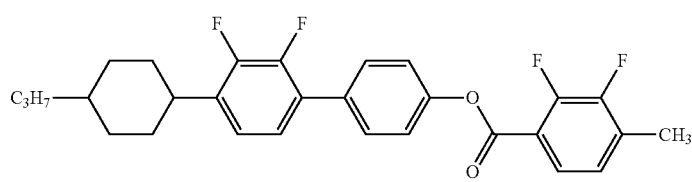 |
| 4356 | 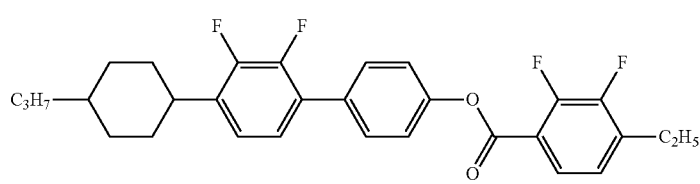 |
| 4357 | 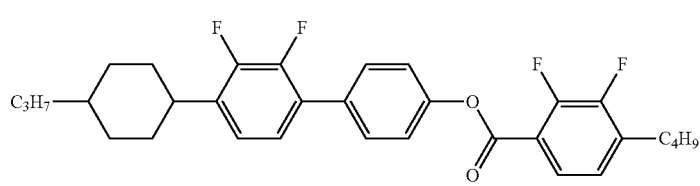 |
| 4358 | 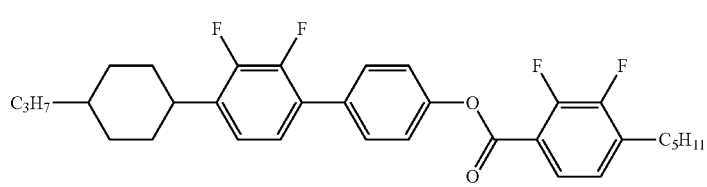 |
| 4359 | 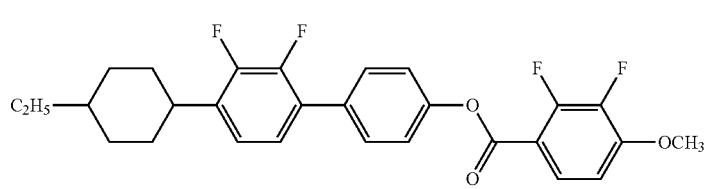 |
| 4360 | 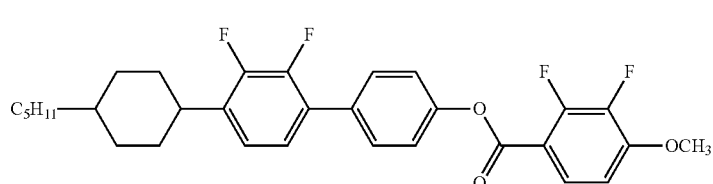 |

-continued
| No. | |
|---|---|
| 4361 | 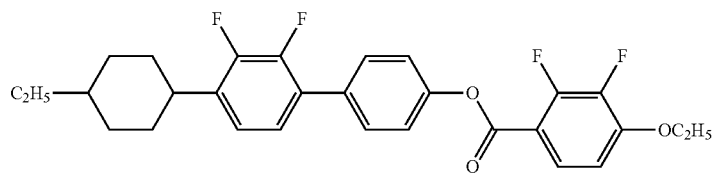 |
| 4362 | 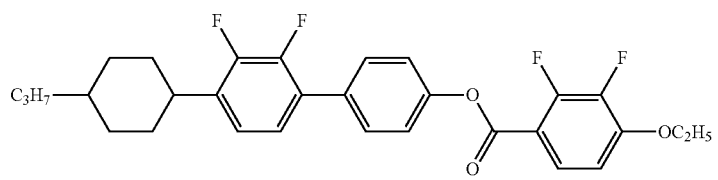 |
| 4363 | 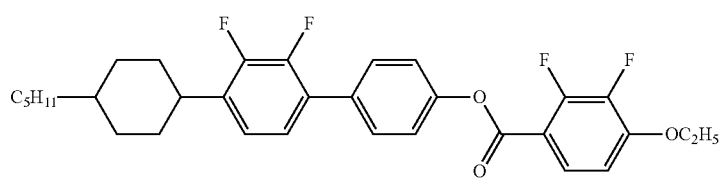 |
| 4364 | 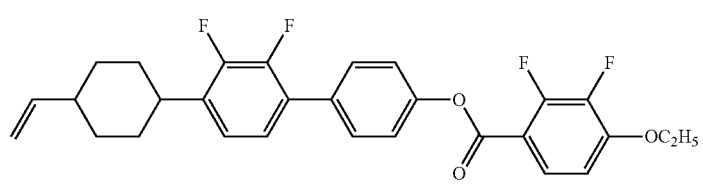 [SMILES: C=CC1CCC(c2ccc(-c3ccc(OC(=O)c4ccc(OCC)c(F)c4F)cc3)c(F)c2F)CC1] |
| 4365 | 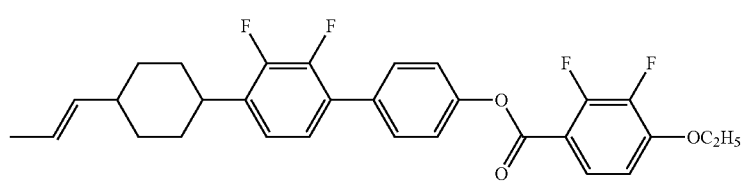 |
| 4366 | 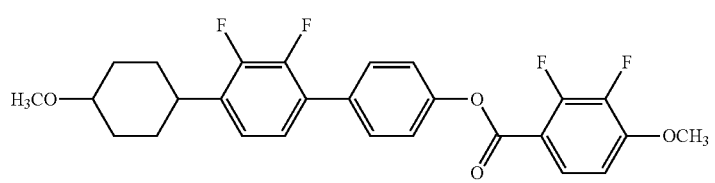 |
| 4367 | 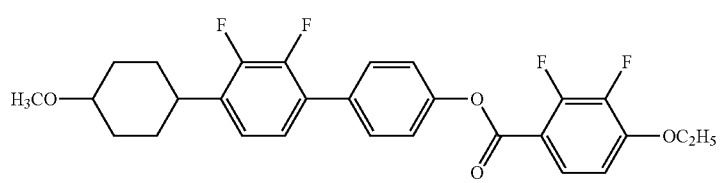 |
| 4368 | 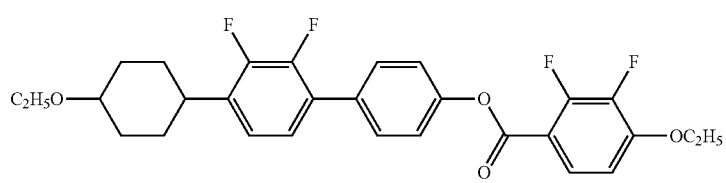 |

-continued
| No. |
|---|
| 4369 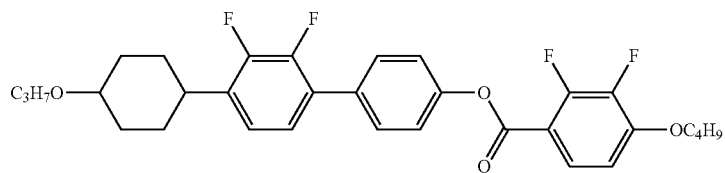 |
| 4370 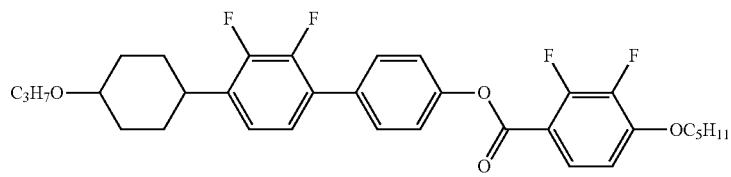 |
| 4371 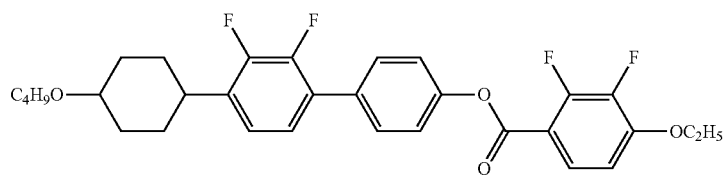 |
| 4372 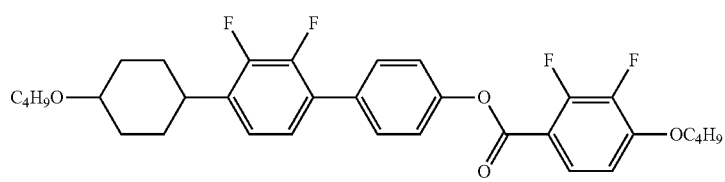 |
| 4373 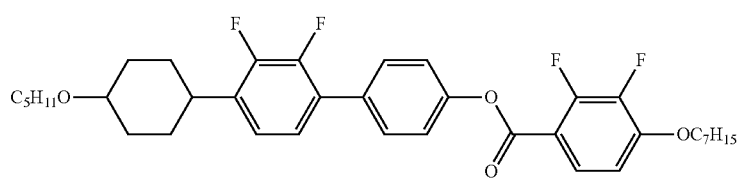 |
| 4374 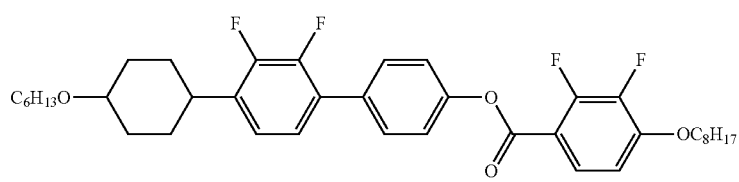 |
| 4375 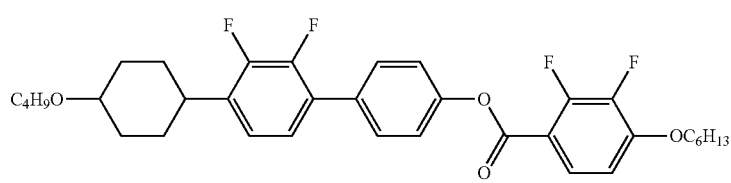 |
| 4376 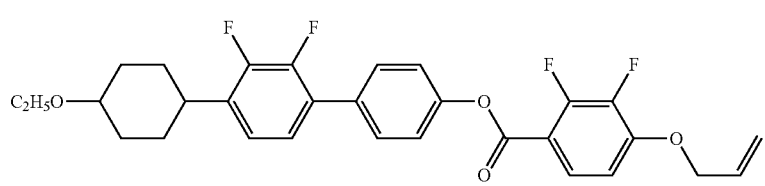 |

-continued
| No. | |
|---|---|
| 4377 | 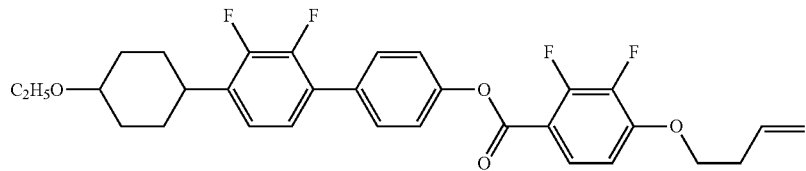 |
| 4378 | 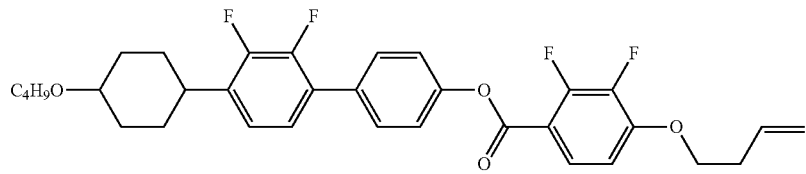 |
| 4379 | 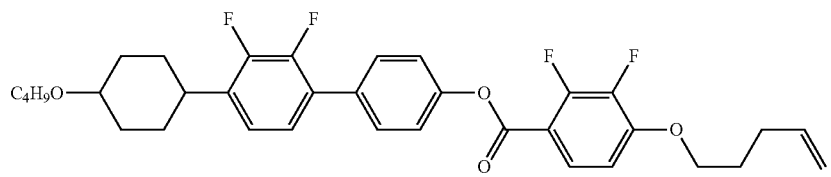 |
| 4380 | 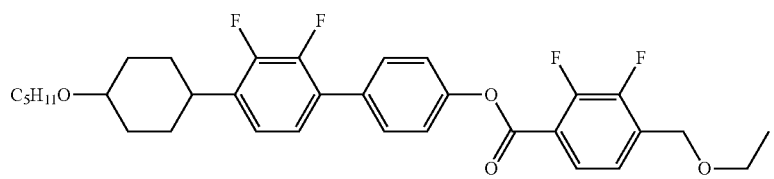 |
| 4381 | 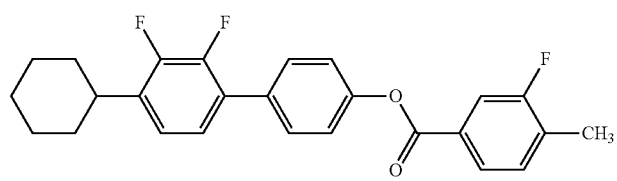 [SMILES: Cc1ccc(C(=O)Oc2ccc(-c3ccc(C4CCCCC4)c(F)c3F)cc2)cc1F] |
| 4382 | 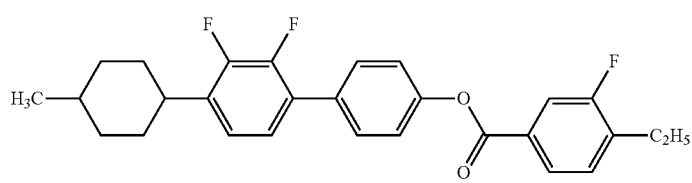 |
| 4383 | 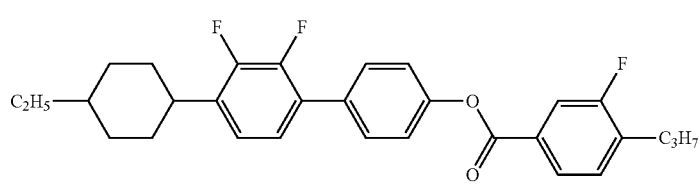 |
| 4384 | 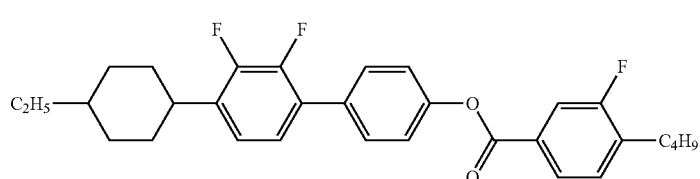 |

-continued
| No. | |
|---|---|
| 4385 | 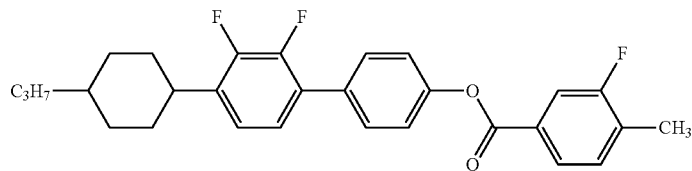 |
| 4386 | 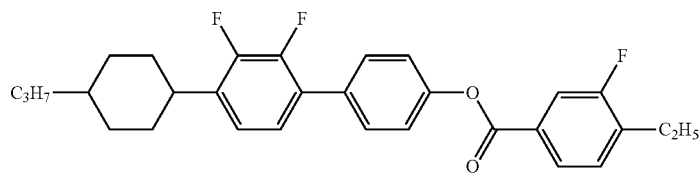 |
| 4387 | 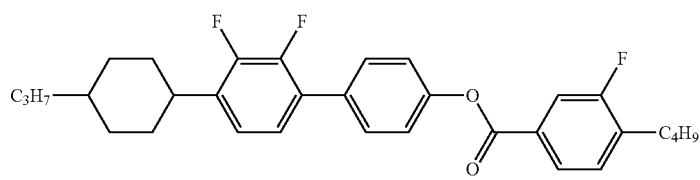 |
| 4388 | 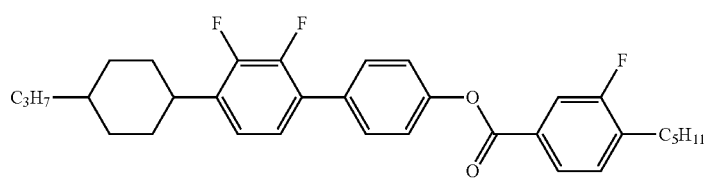 |
| 4389 | 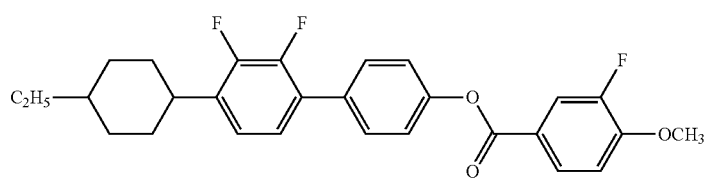 [SMILES: CCC1CCC(c2ccc(-c3ccc(OC(=O)c4ccc(OC)c(F)c4)cc3)c(F)c2F)CC1] |
| 4390 | 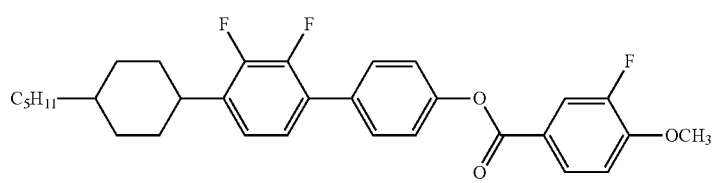 |
| 4391 | 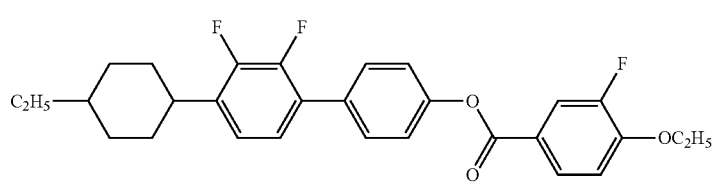 |
| 4392 | 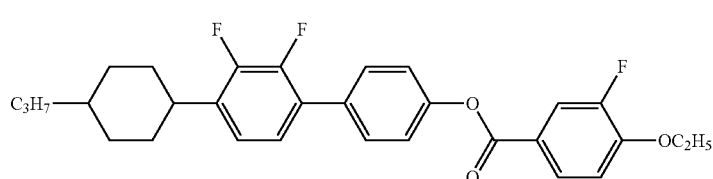 |

| No. |
|---|
| 4393 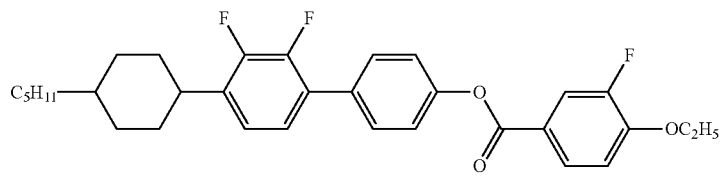 |
| 4394 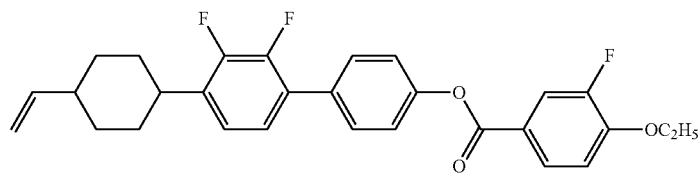 [SMILES: C=CC1CCC(c2ccc(-c3ccc(OC(=O)c4ccc(OCC)c(F)c4)cc3)c(F)c2F)CC1] |
| 4395 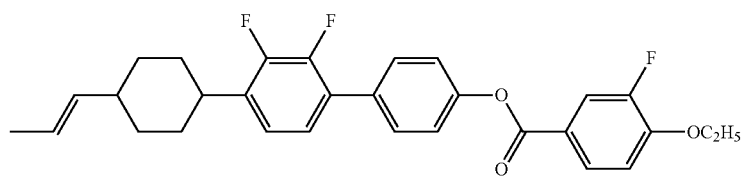 [SMILES: C/C=C/C1CCC(c2ccc(-c3ccc(OC(=O)c4ccc(OCC)c(F)c4)cc3)c(F)c2F)CC1] |
| 4396 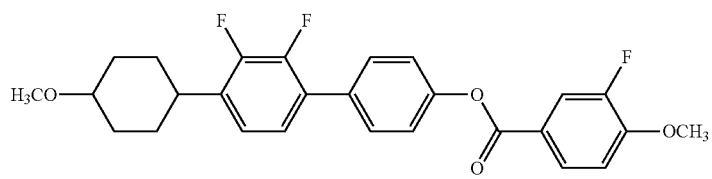 |
| 4397 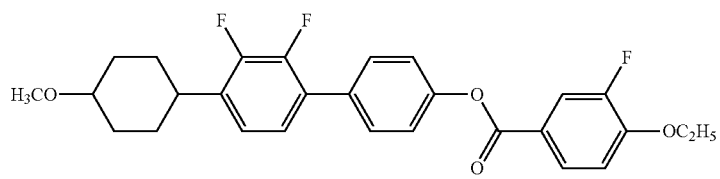 |
| 4398 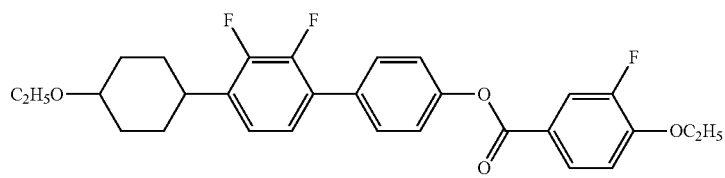 |
| 4399 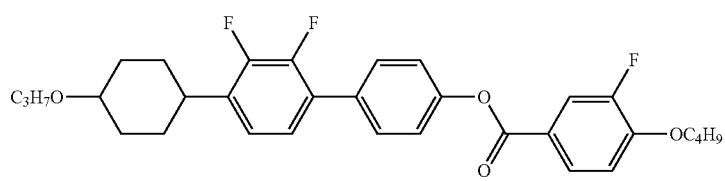 |
| 4400 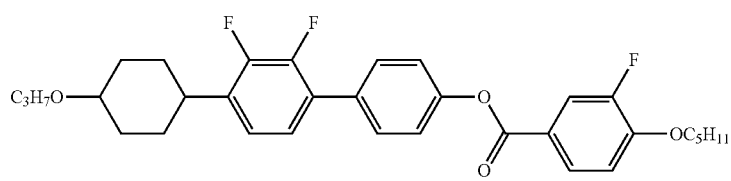 |

| No. | |
|---|---|
| 4401 | 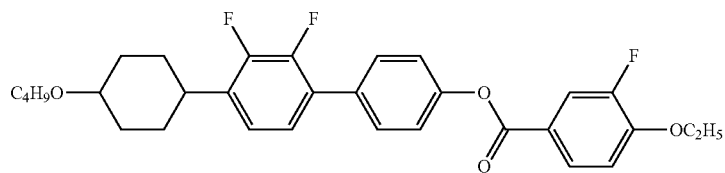 |
| 4402 | 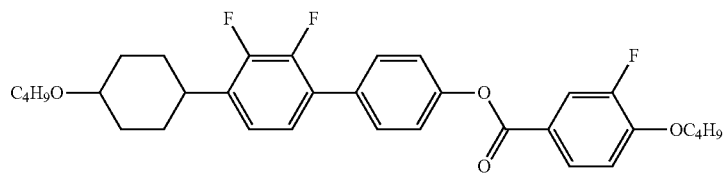 |
| 4403 | 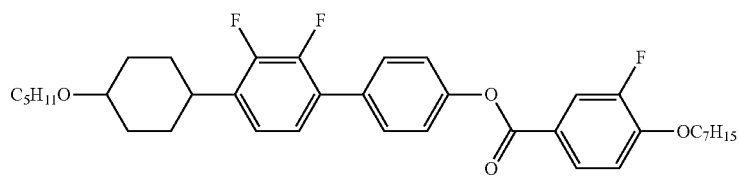 |
| 4404 | 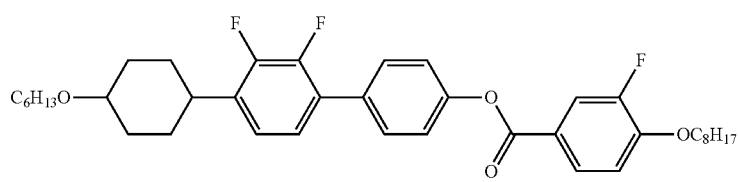 |
| 4405 | 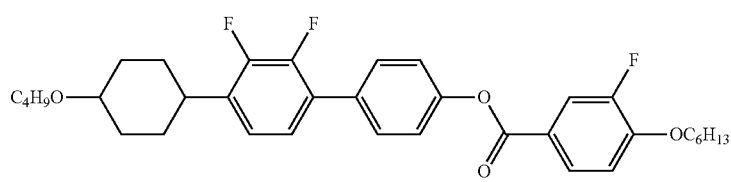 |
| 4406 | 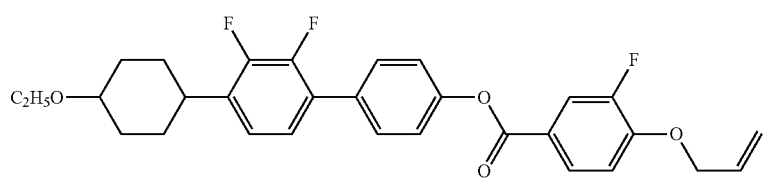 |
| 4407 | 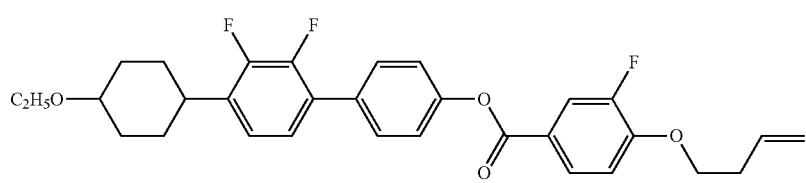 |
| 4408 | 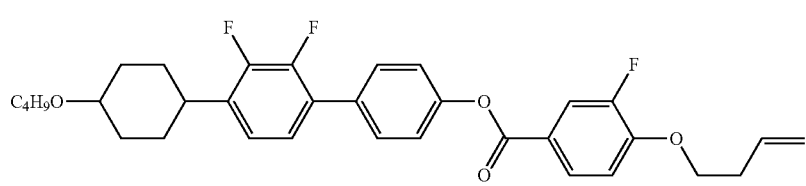 |

-continued
| No. | |
|---|---|
| 4409 | 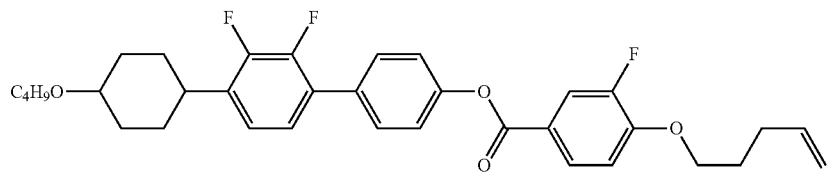 |
| 4410 | 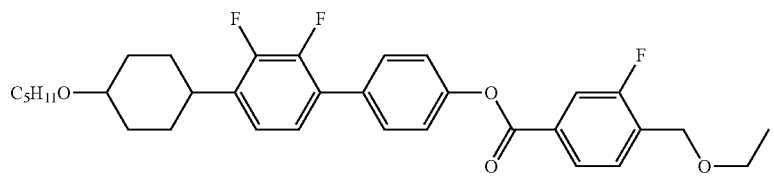 |
| 4411 | 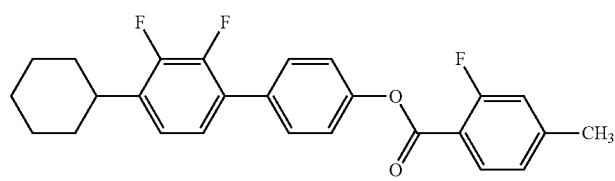 [SMILES: Cc1ccc(C(=O)Oc2ccc(-c3ccc(C4CCCCC4)c(F)c3F)cc2)c(F)c1] |
| 4412 | 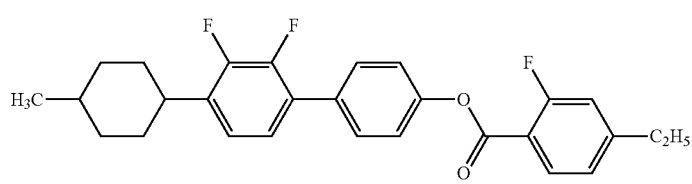 [SMILES: CCc1ccc(C(=O)Oc2ccc(-c3ccc(C4CCC(C)CC4)c(F)c3F)cc2)c(F)c1] |
| 4413 | 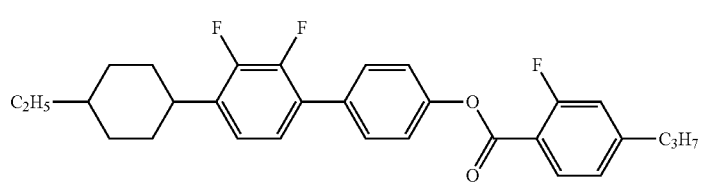 |
| 4414 | 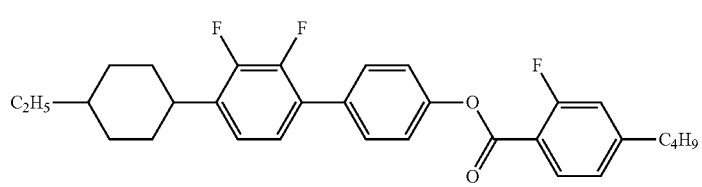 |
| 4415 | 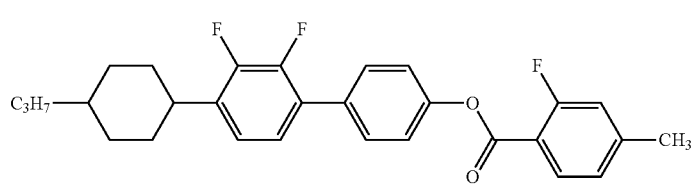 |
| 4416 | 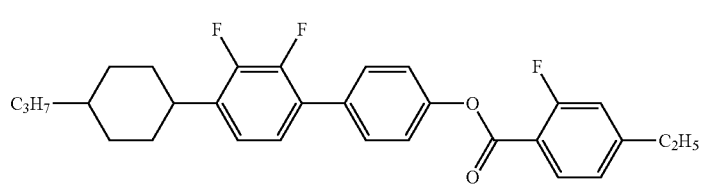 |

| No. | |
|---|---|
| 4417 | 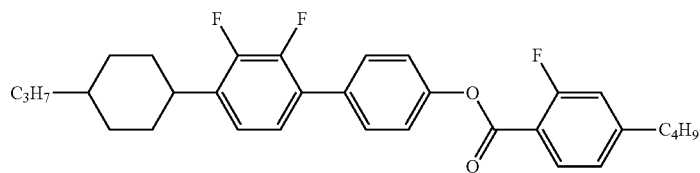 |
| 4418 | 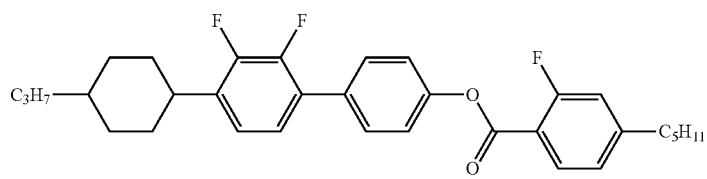 |
| 4419 | 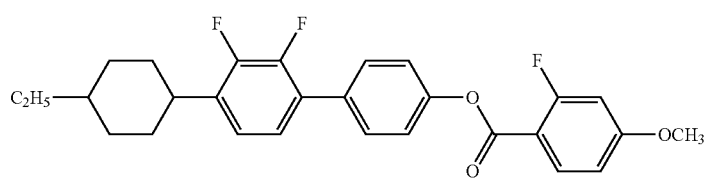 |
| 4420 | 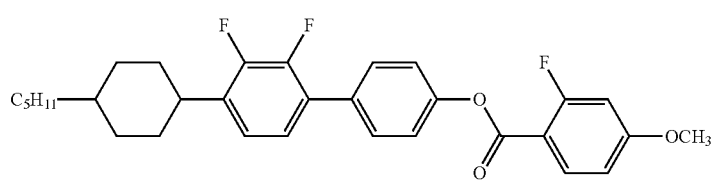 |
| 4421 | 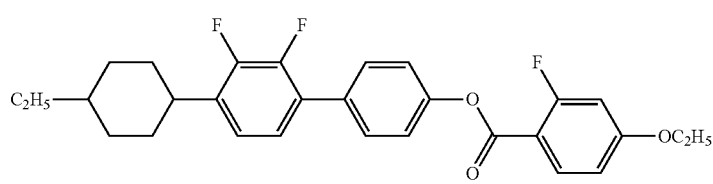 |
| 4422 | 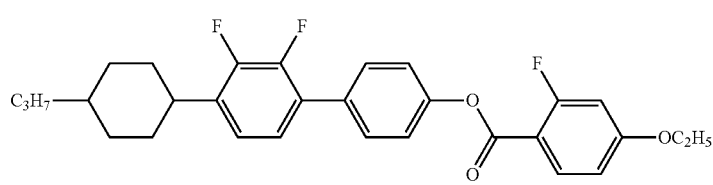 |
| 4423 | 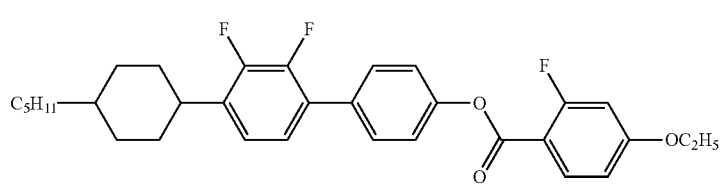 |
| 4424 | 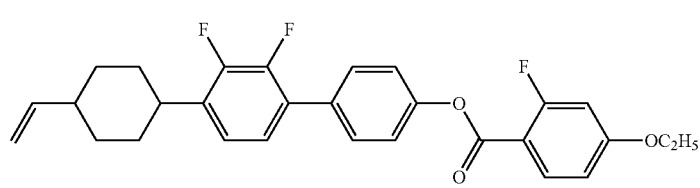 [SMILES: C=CC1CCC(c2ccc(-c3ccc(OC(=O)c4ccc(OCC)cc4F)cc3)c(F)c2F)CC1] |

| No. | |
|---|---|
| 4425 | 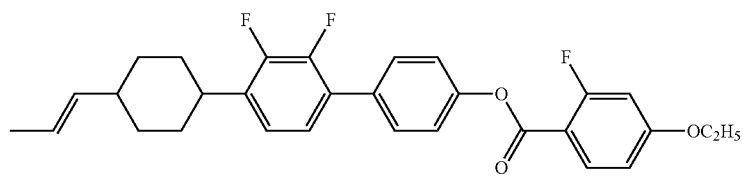 [SMILES: C/C=C/C1CCC(c2ccc(-c3ccc(OC(=O)c4ccc(OCC)cc4F)cc3)c(F)c2F)CC1] |
| 4426 | 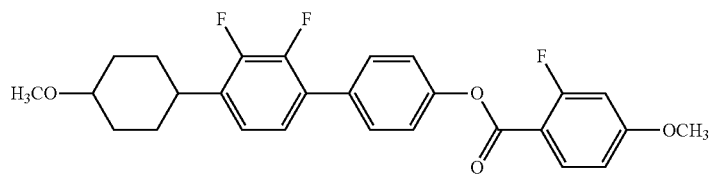 [SMILES: COc1ccc(C(=O)Oc2ccc(-c3ccc(C4CCC(OC)CC4)c(F)c3F)cc2)c(F)c1] |
| 4427 | 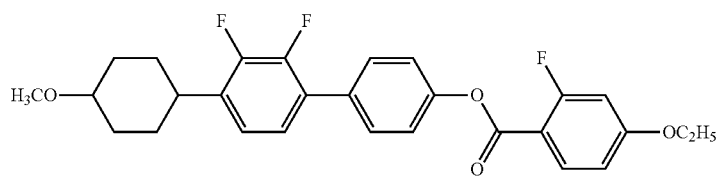 [SMILES: CCOc1ccc(C(=O)Oc2ccc(-c3ccc(C4CCC(OC)CC4)c(F)c3F)cc2)c(F)c1] |
| 4428 | 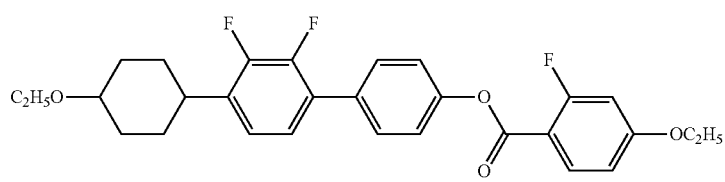 |
| 4429 | 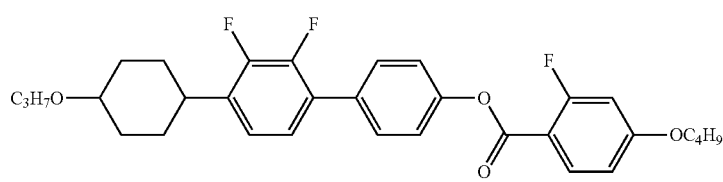 |
| 4430 | 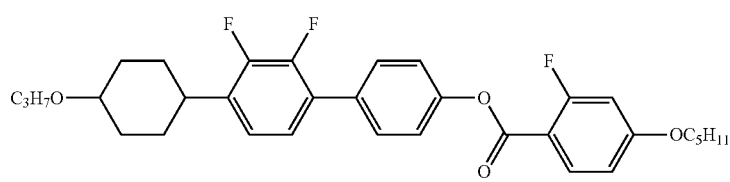 |
| 4431 | 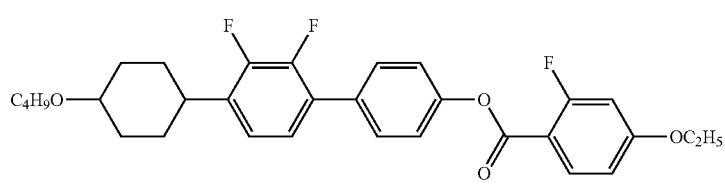 |
| 4432 | 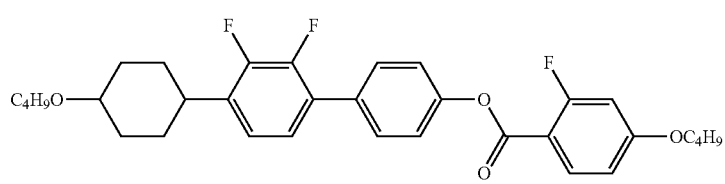 |

| No. | |
|---|---|
| 4433 | 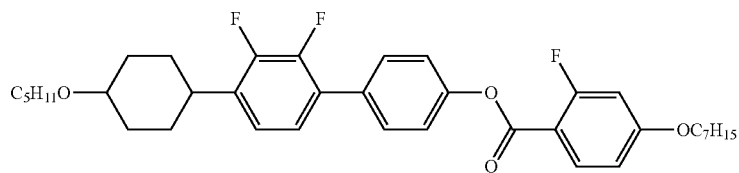 |
| 4434 | 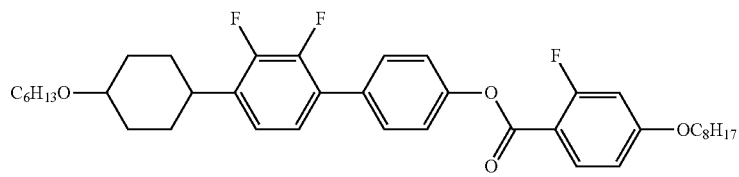 |
| 4435 | 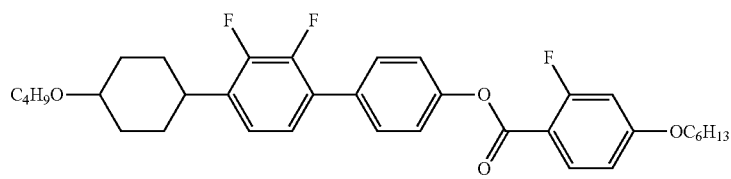 |
| 4436 | 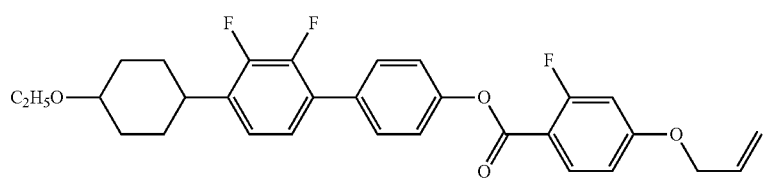 |
| 4437 | 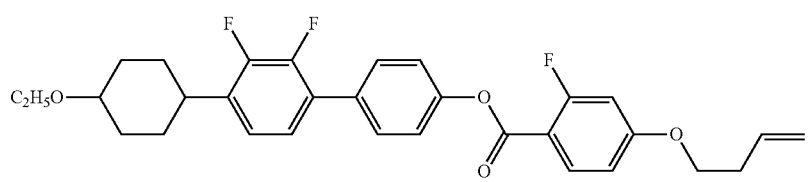 |
| 4438 | 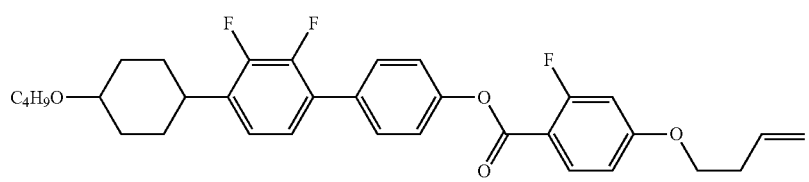 |
| 4439 | 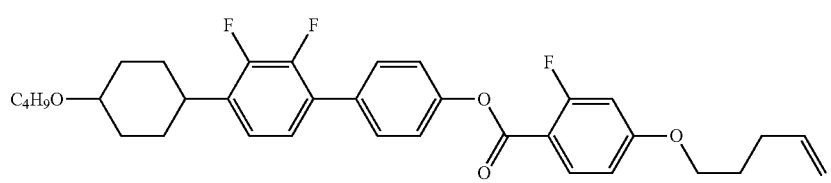 |
| 4440 | 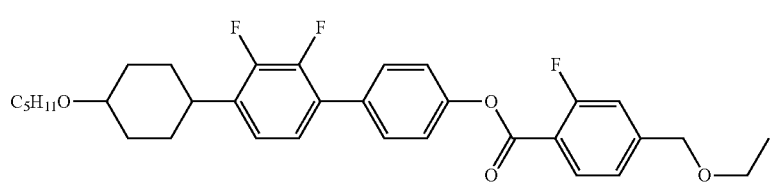 |

| No. | |
|---|---|
| 4441 | 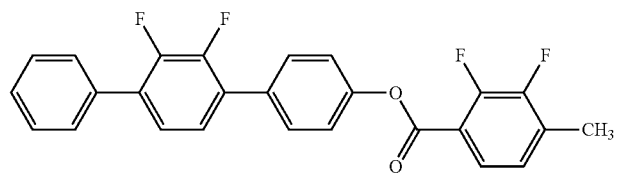 [SMILES: Cc1ccc(C(=O)Oc2ccc(-c3ccc(-c4ccccc4)c(F)c3F)cc2)c(F)c1F] |
| 4442 | 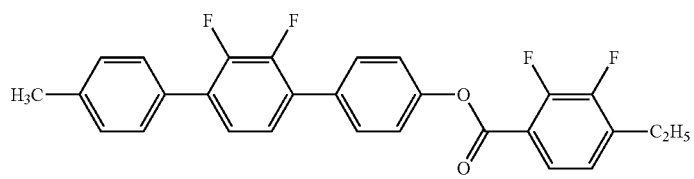 |
| 4443 | 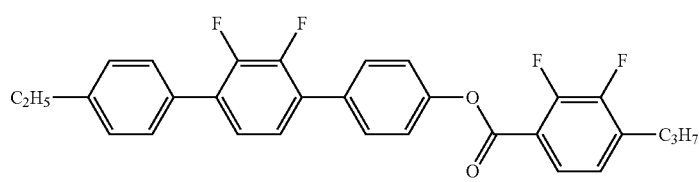 |
| 4444 | 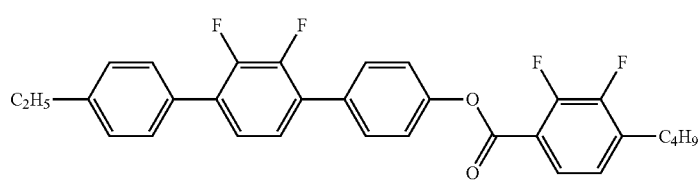 |
| 4445 | 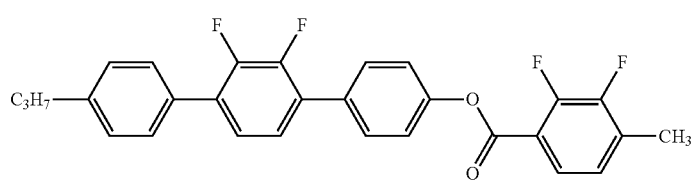 |
| 4446 | 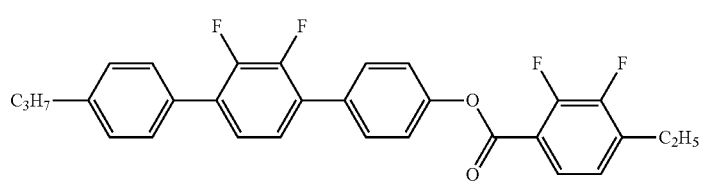 |
| 4447 | 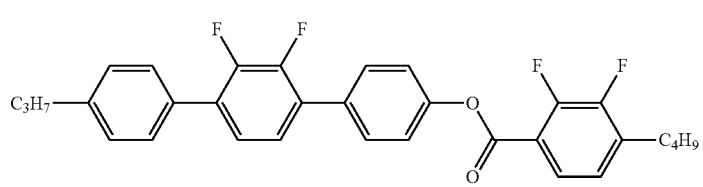 |
| 4448 | 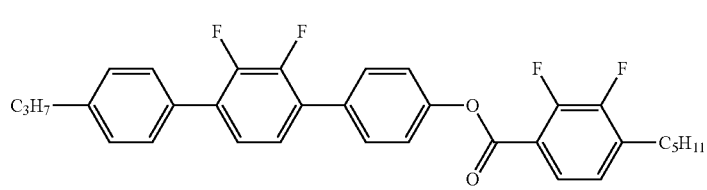 |

| No. | |
|---|---|
| 4449 | 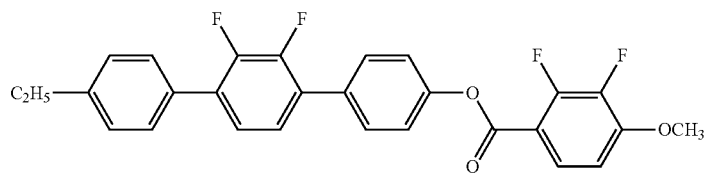 [SMILES: CCc1ccc(-c2ccc(-c3ccc(OC(=O)c4ccc(OC)c(F)c4F)cc3)c(F)c2F)cc1] |
| 4450 | 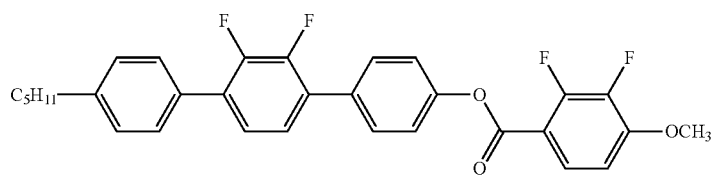 |
| 4451 | 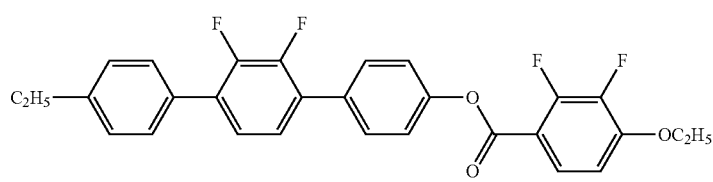 |
| 4452 | 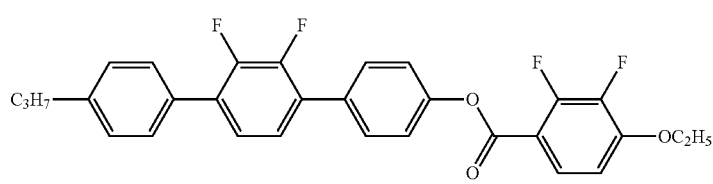 |
| 4453 | 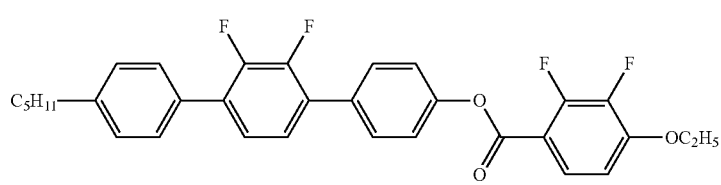 |
| 4454 | 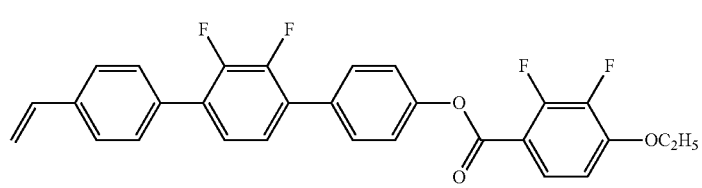 [SMILES: C=Cc1ccc(-c2ccc(-c3ccc(OC(=O)c4ccc(OCC)c(F)c4F)cc3)c(F)c2F)cc1] |
| 4455 | 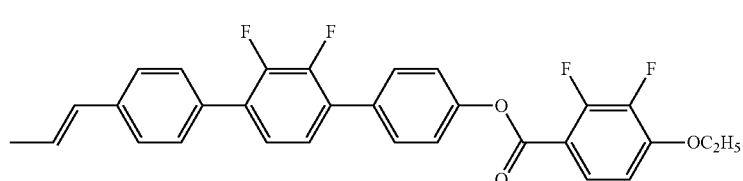 |
| 4456 | 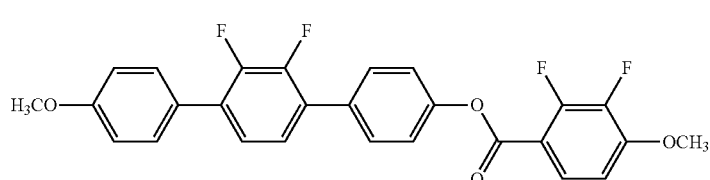 |

| No. | |
|---|---|
| 4457 | 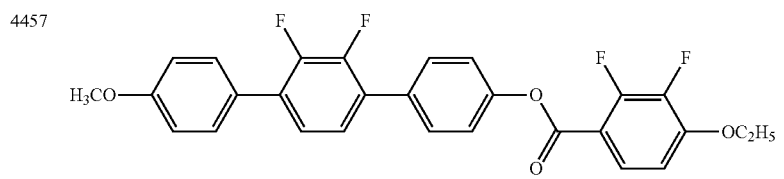 |
| 4458 | 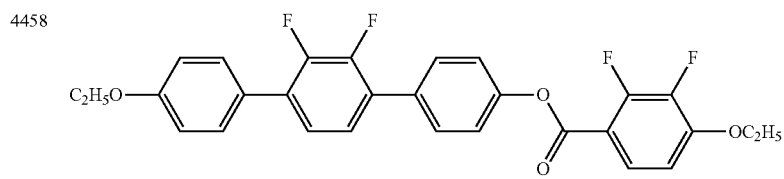 |
| 4459 | 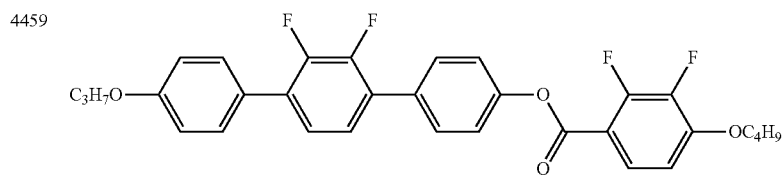 |
| 4460 | 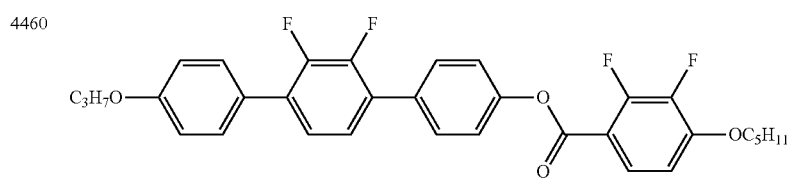 |
| 4461 | 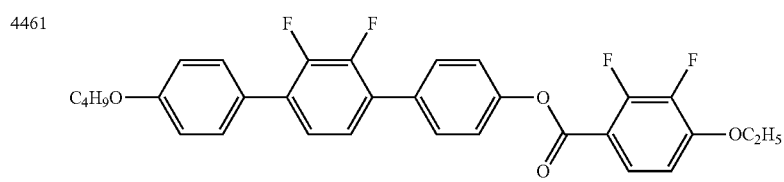 |
| 4462 | 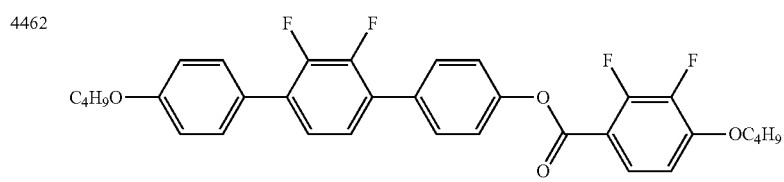 |
| 4463 | 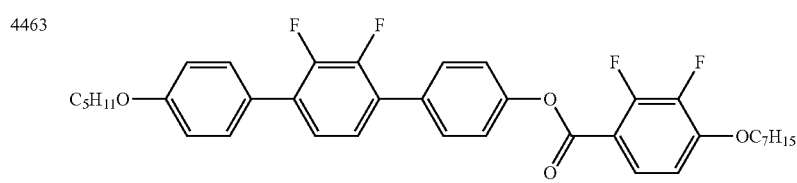 |
| 4464 | 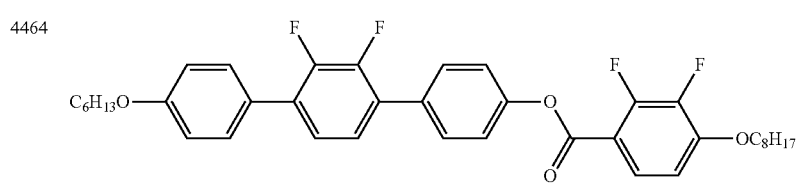 |

-continued
| No. | |
|---|---|
| 4465 | 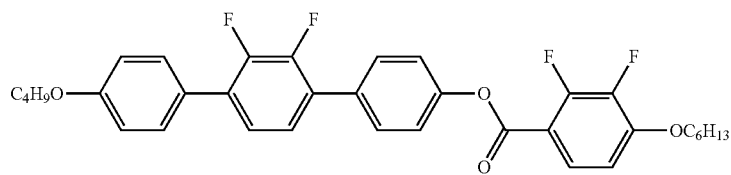 |
| 4466 | 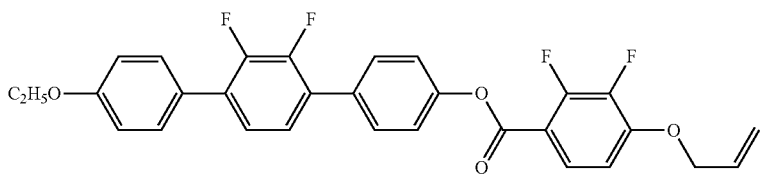 |
| 4467 | 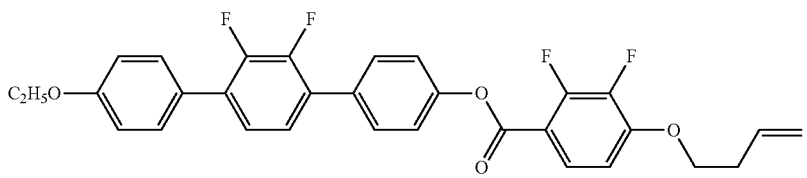 |
| 4468 | 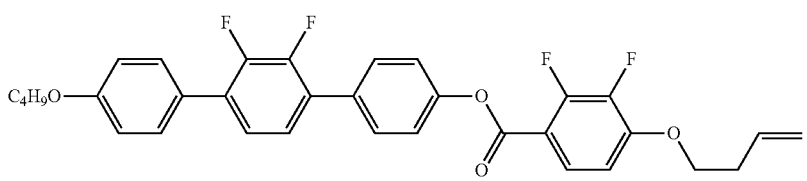 |
| 4469 | 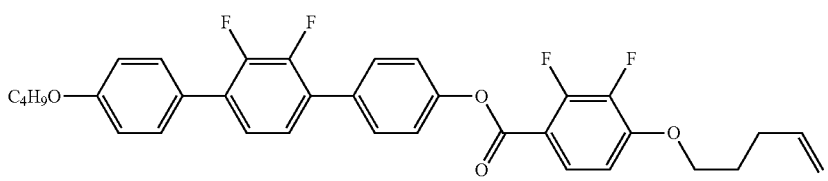 |
| 4470 | 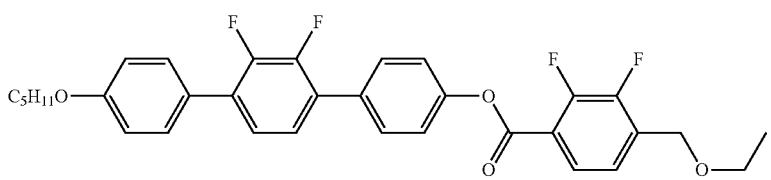 |
| 4471 | 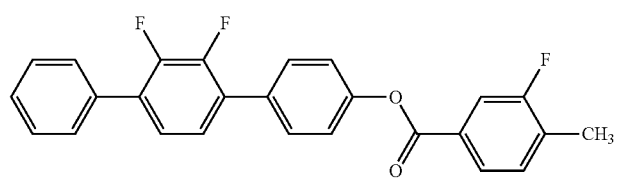 [SMILES: Cc1ccc(C(=O)Oc2ccc(-c3ccc(-c4ccccc4)c(F)c3F)cc2)cc1F] |
| 4472 | 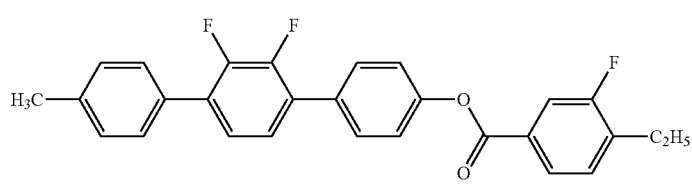 [SMILES: CCc1ccc(C(=O)Oc2ccc(-c3ccc(-c4ccc(C)cc4)c(F)c3F)cc2)cc1F] |

| No. | |
|---|---|
| 4473 | 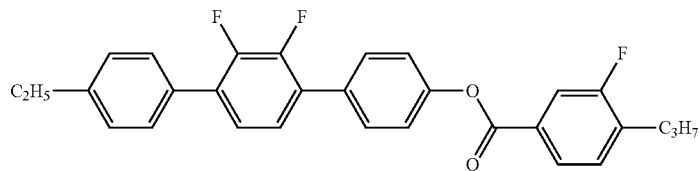 |
| 4474 | 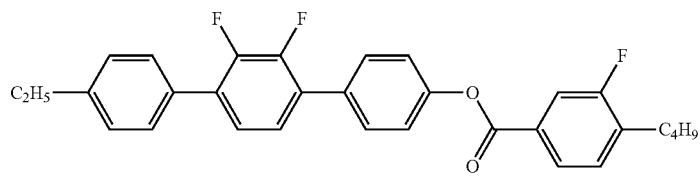 |
| 4475 | 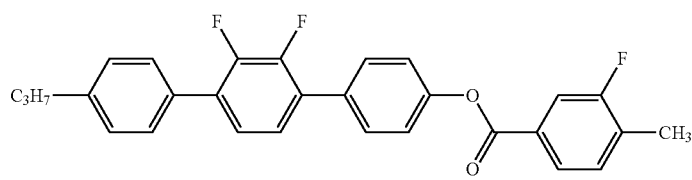 |
| 4476 | 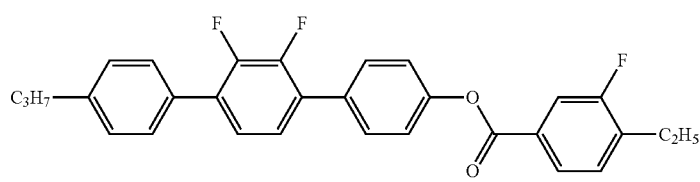 |
| 4477 | 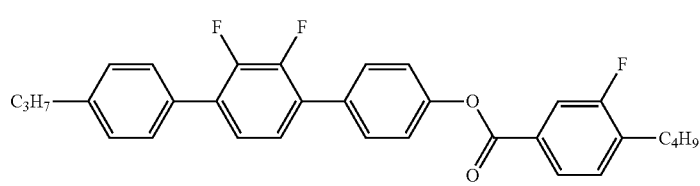 |
| 4478 | 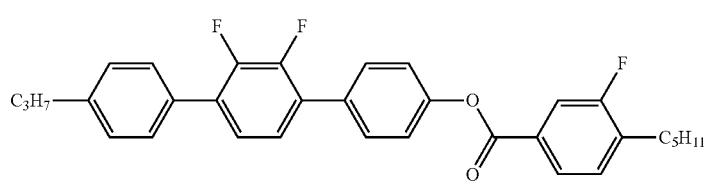 |
| 4479 | 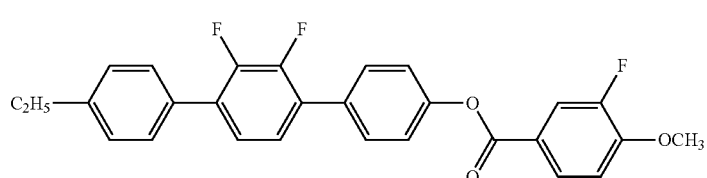 |
| 4480 | 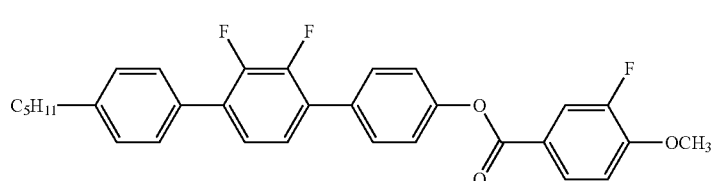 |

| No. |
|---|
| 4481 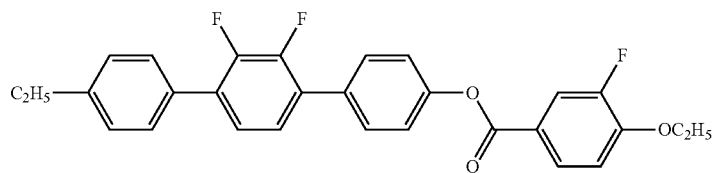 |
| 4482 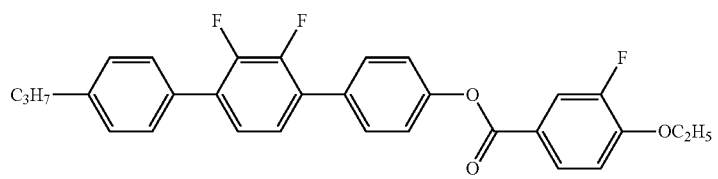 |
| 4483 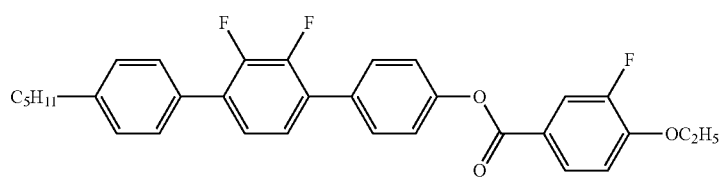 |
| 4484 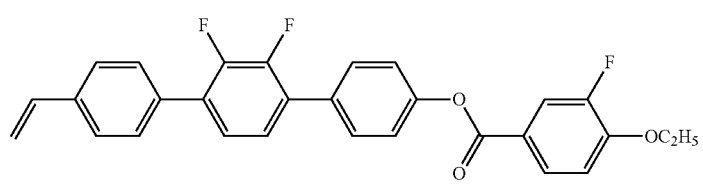 [SMILES: C=Cc1ccc(-c2ccc(-c3ccc(OC(=O)c4ccc(OCC)c(F)c4)cc3)c(F)c2F)cc1] |
| 4485 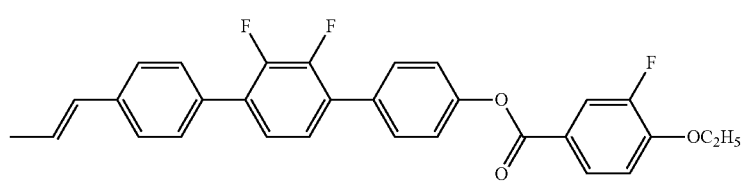 [SMILES: C/C=C/c1ccc(-c2ccc(-c3ccc(OC(=O)c4ccc(OCC)c(F)c4)cc3)c(F)c2F)cc1] |
| 4486 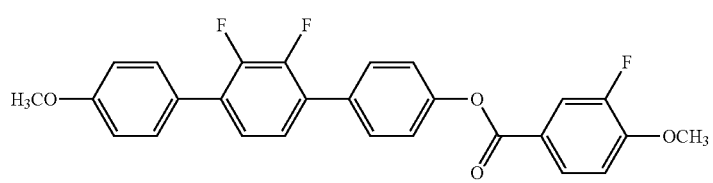 |
| 4487 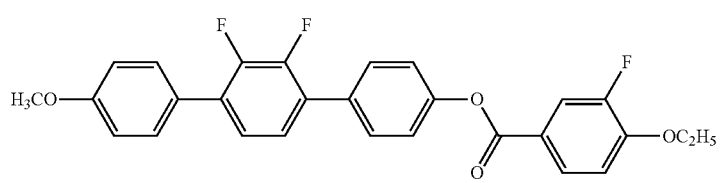 |
| 4488 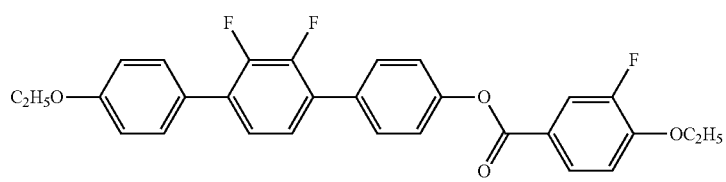 |

| No. | |
|---|---|
| 4489 | 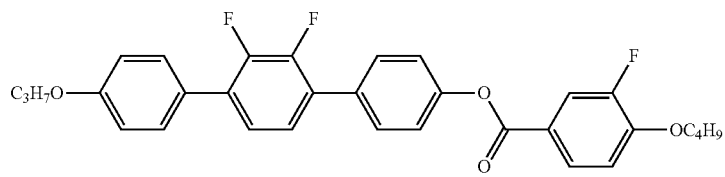 |
| 4490 | 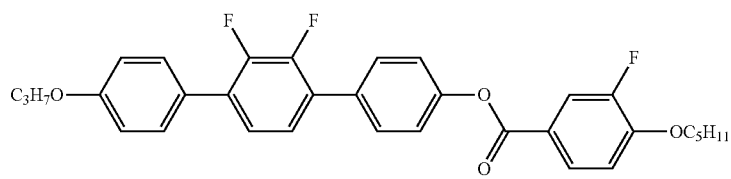 |
| 4491 | 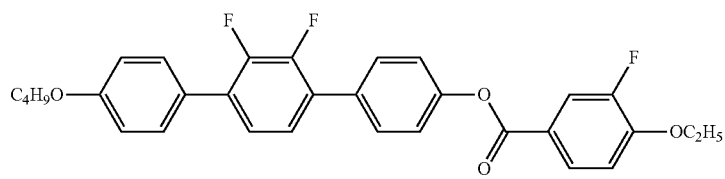 |
| 4492 | 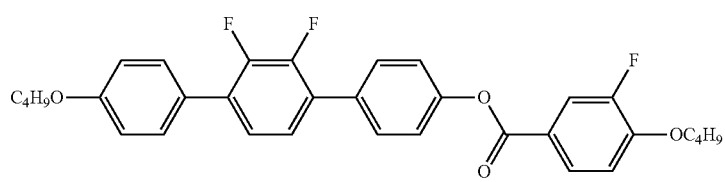 |
| 4493 | 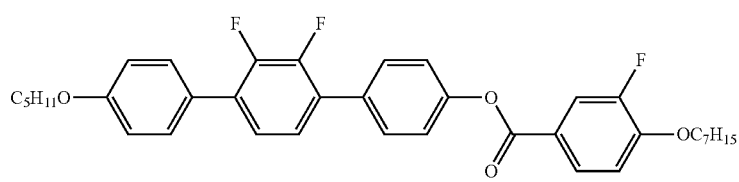 |
| 4494 | 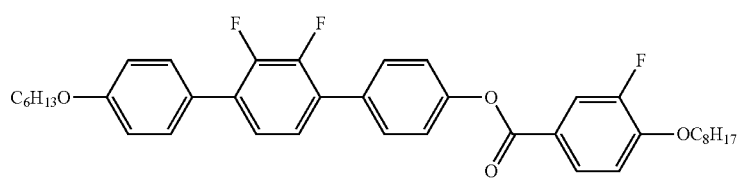 |
| 4495 | 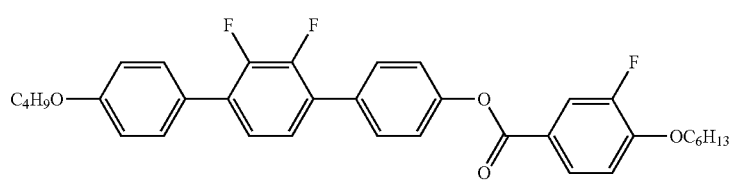 |
| 4496 | 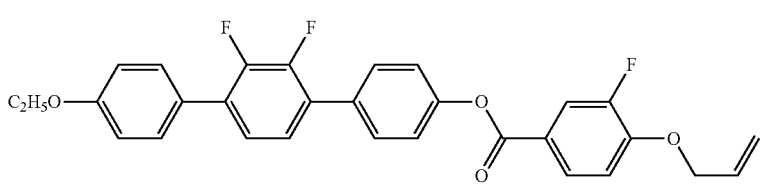 |

| No. | |
|---|---|
| 4497 | 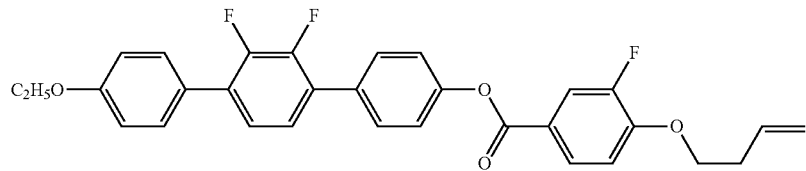 |
| 4498 | 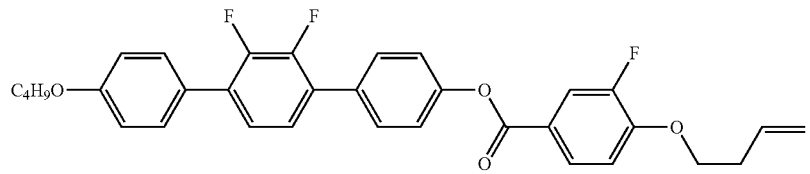 |
| 4499 | 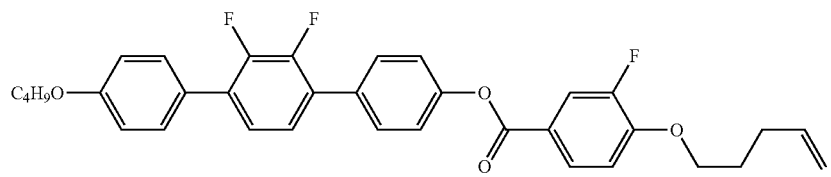 |
| 4500 | 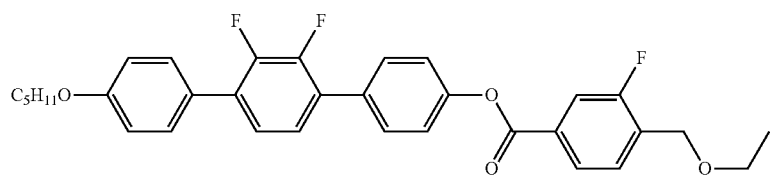 |
| 4501 | 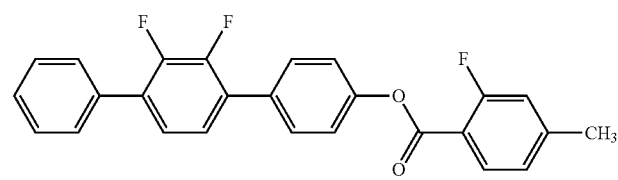 [SMILES: Cc1ccc(C(=O)Oc2ccc(-c3ccc(-c4ccccc4)c(F)c3F)cc2)c(F)c1] |
| 4502 | 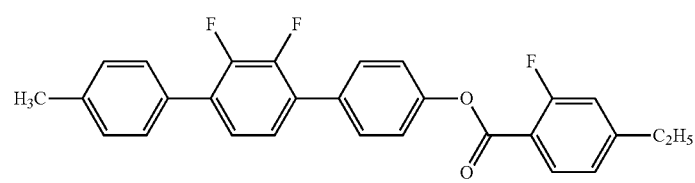 |
| 4503 | 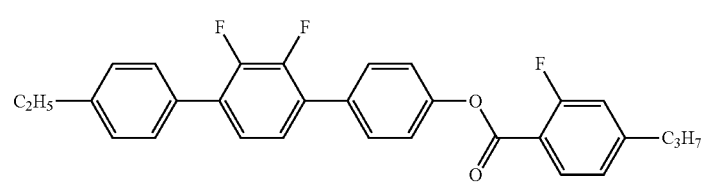 |
| 4504 | 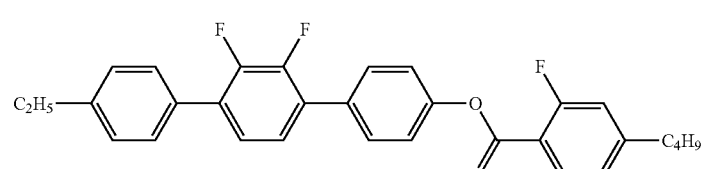 |

| No. |
|---|
| 4505 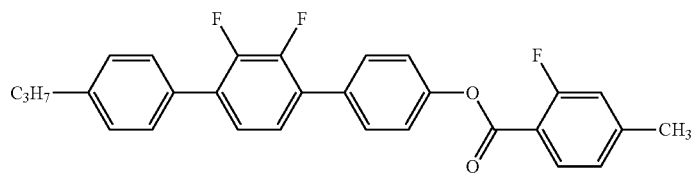 |
| 4506 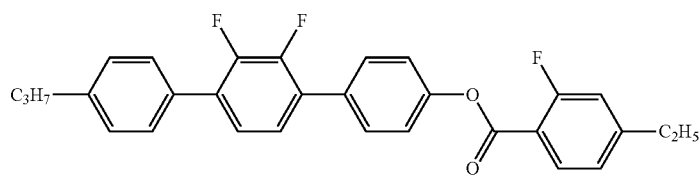 |
| 4507 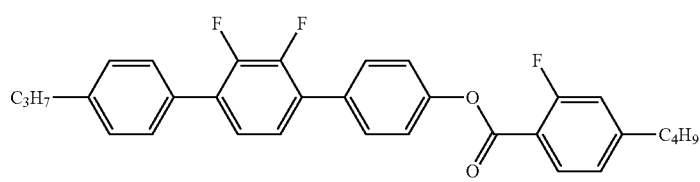 |
| 4508 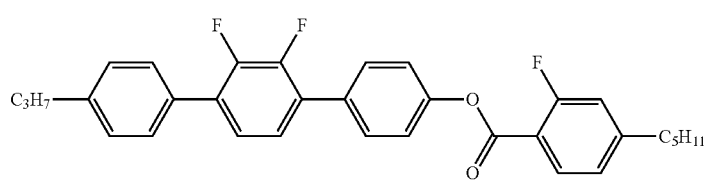 |
| 4509 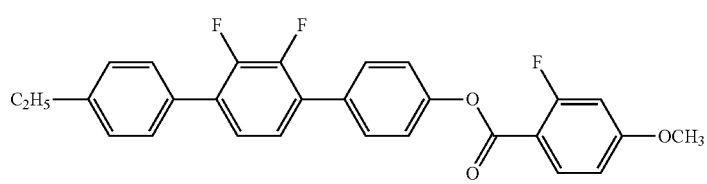 |
| 4510 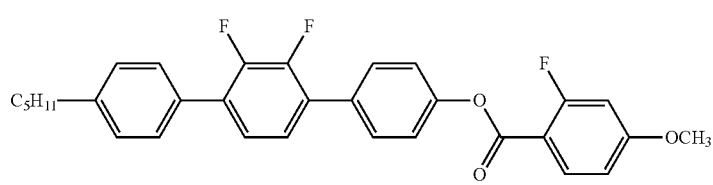 |
| 4511 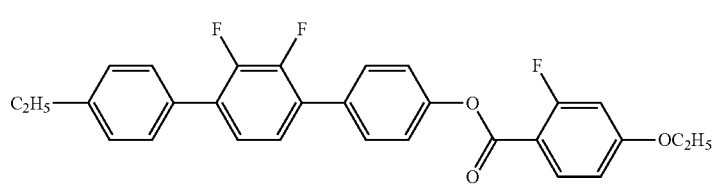 |
| 4512 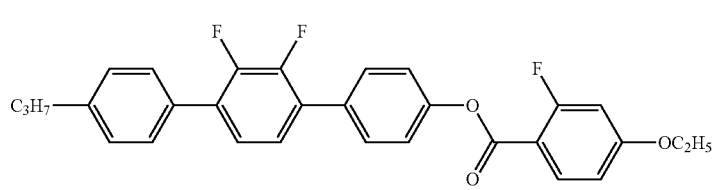 |

| No. |
|---|
| 4513 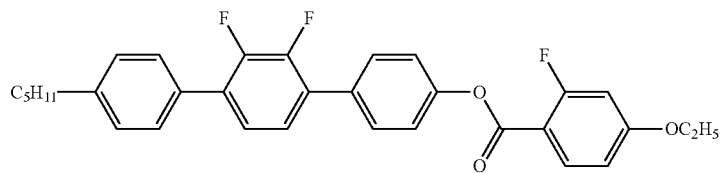 |
| 4514 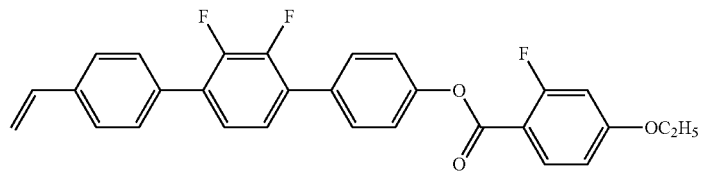 |
| 4515 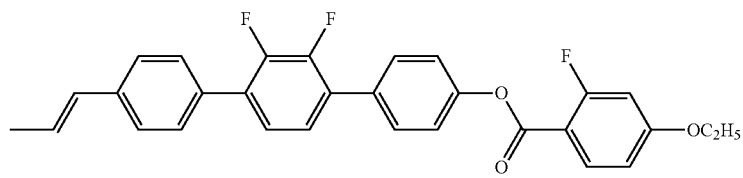 [SMILES: C/C=C/c1ccc(-c2ccc(-c3ccc(OC(=O)c4ccc(OCC)cc4F)cc3)c(F)c2F)cc1] |
| 4516 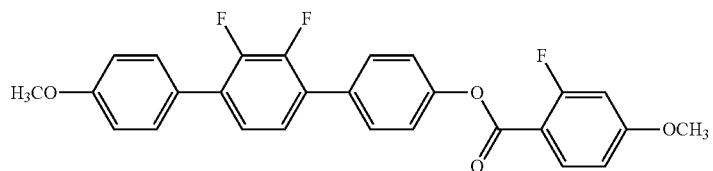 [SMILES: COc1ccc(-c2ccc(-c3ccc(OC(=O)c4ccc(OC)cc4F)cc3)c(F)c2F)cc1] |
| 4517 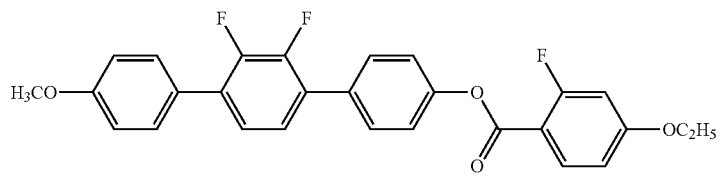 |
| 4518 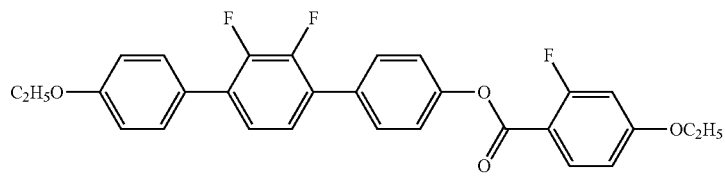 |
| 4519 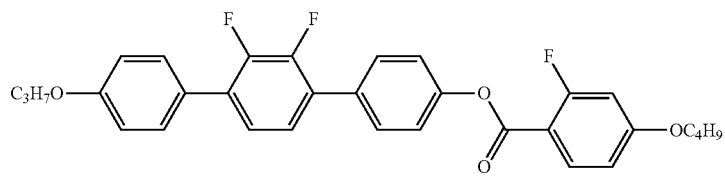 |
| 4520 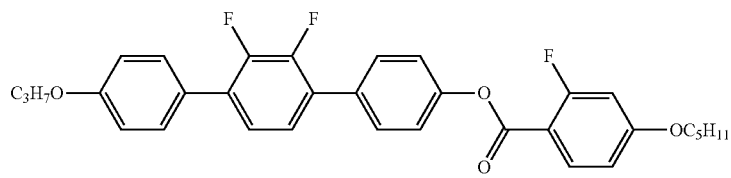 |

| No. | |
|---|---|
| 4521 | 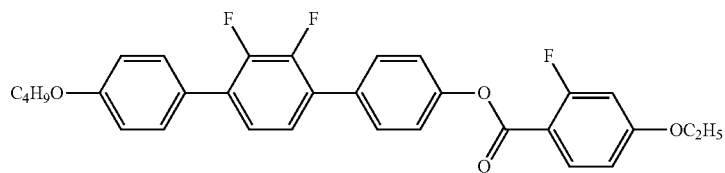 |
| 4522 | 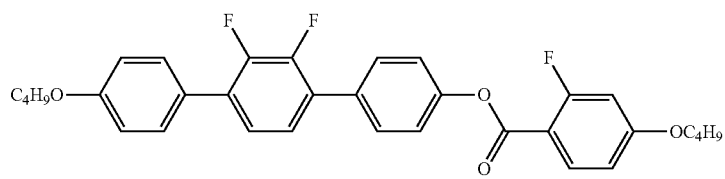 |
| 4523 | 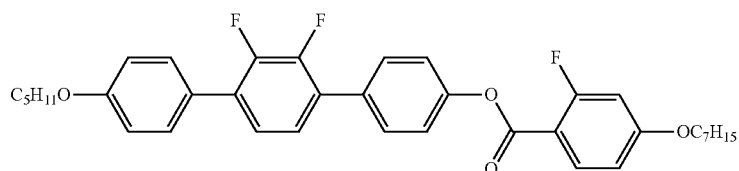 |
| 4524 | 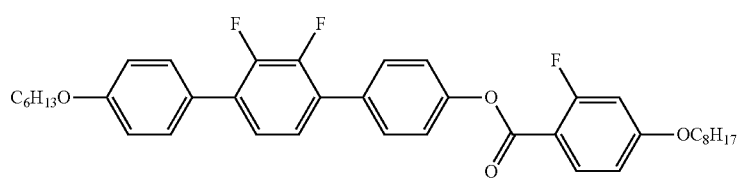 |
| 4525 | 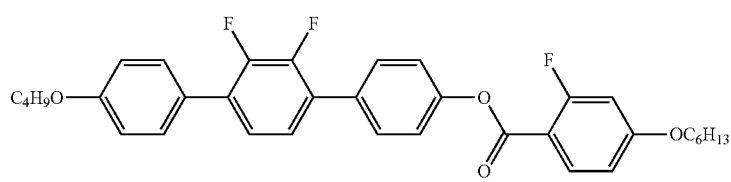 |
| 4526 | 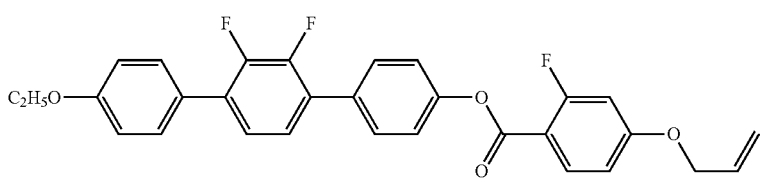 |
| 4527 | 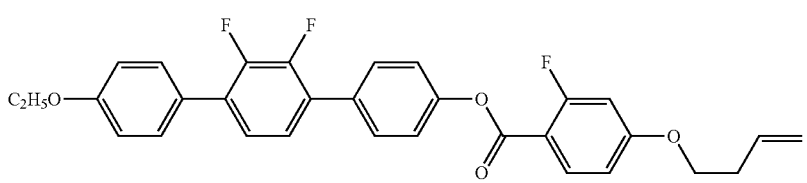 |
| 4528 | 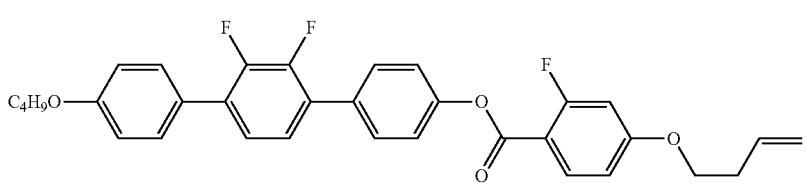 |

| No. | |
|---|---|
| 4529 | 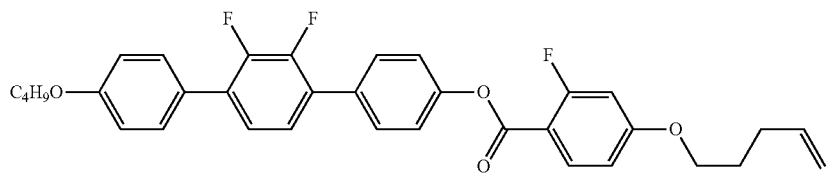 |
| 4530 | 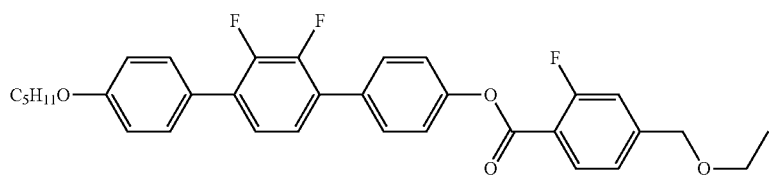 |
| 4531 | 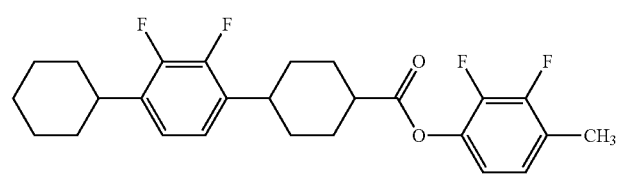 [SMILES: Cc1ccc(OC(=O)C2CCC(c3ccc(C4CCCCC4)c(F)c3F)CC2)c(F)c1F] |
| 4532 | 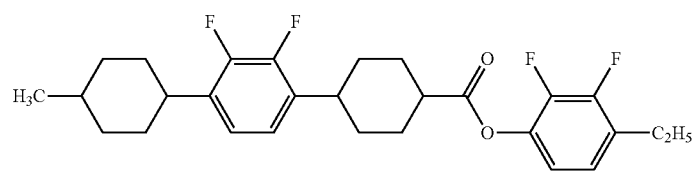 |
| 4533 | 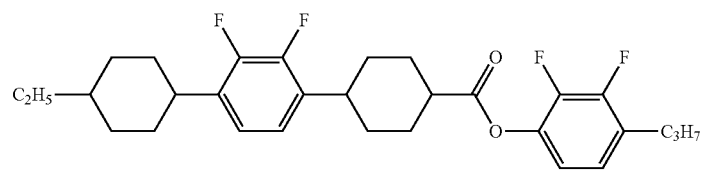 |
| 4534 | 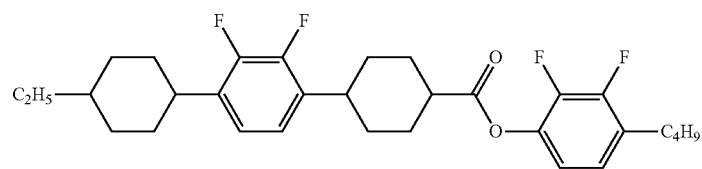 |
| 4535 | 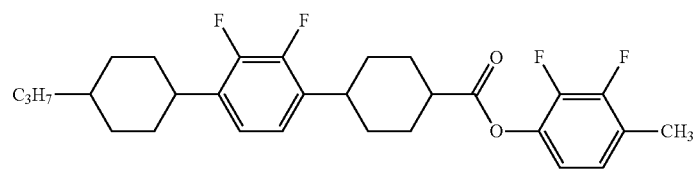 |
| 4536 | 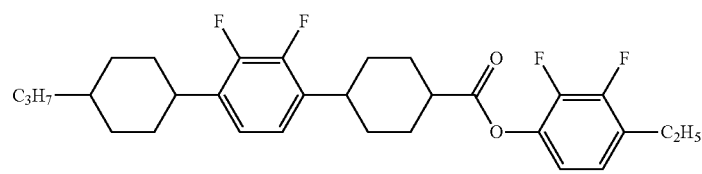 |

| No. | |
|---|---|
| 4537 | 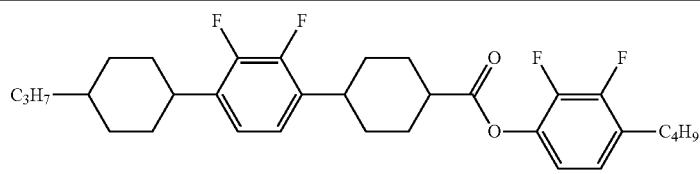 |
| 4538 | 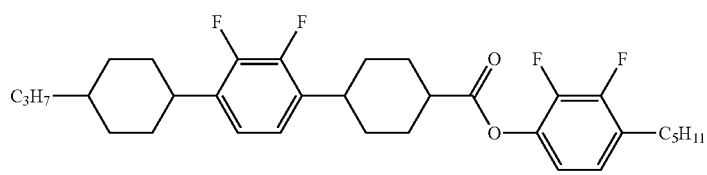 |
| 4539 | 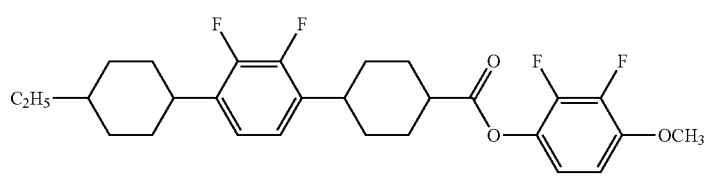 |
| 4540 | 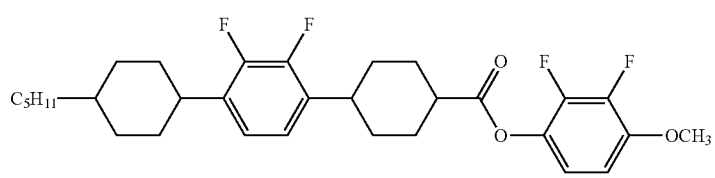 [SMILES: COc1ccc(OC(=O)C2CCC(c3ccc(C4CCC(OC)CC4)c(F)c3F)CC2)c(F)c1F] |
| 4541 | 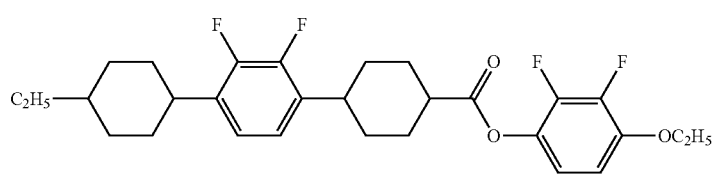 |
| 4542 | 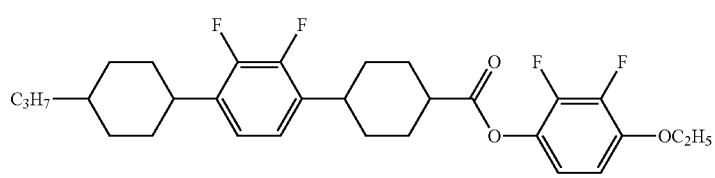 |
| 4543 | 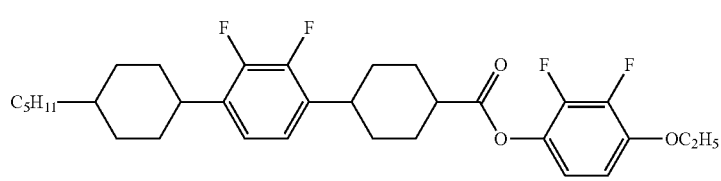 |
| 4544 | 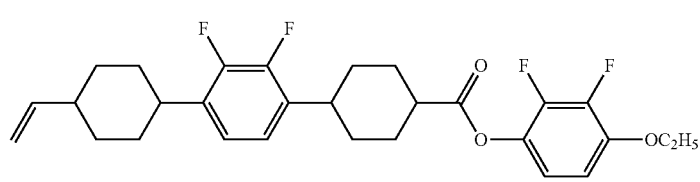 |
| 4545 | 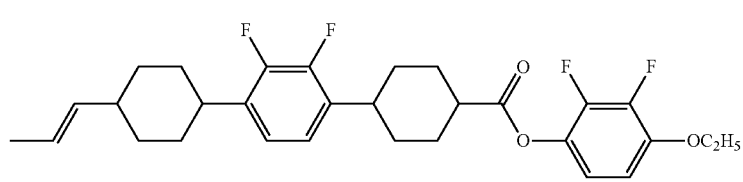 |

| No. |
|---|
| 4546 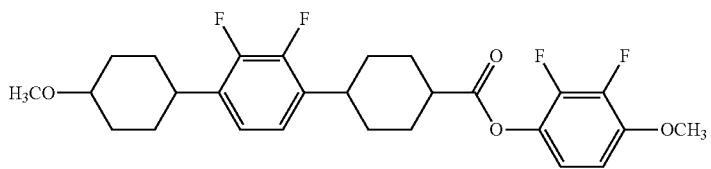 |
| 4547 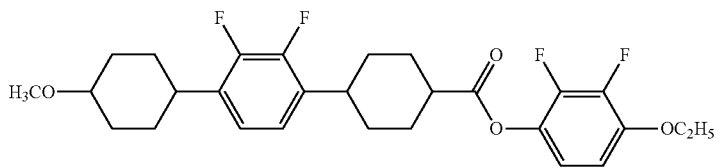 [SMILES: CCOc1ccc(OC(=O)C2CCC(c3ccc(C4CCC(OC)CC4)c(F)c3F)CC2)c(F)c1F] |
| 4548 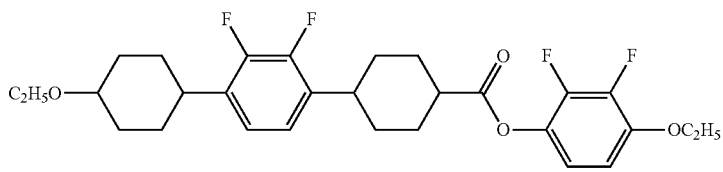 |
| 4549 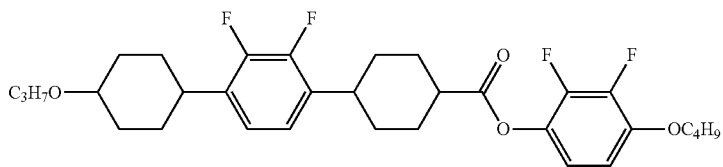 |
| 4550 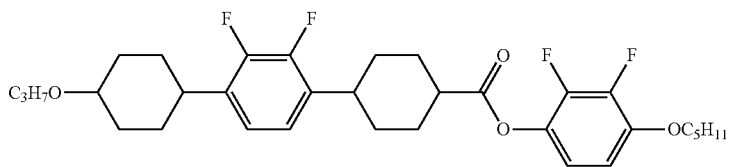 |
| 4551 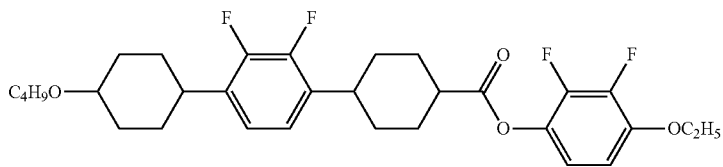 |
| 4552 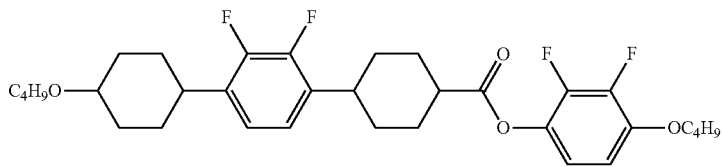 |
| 4553 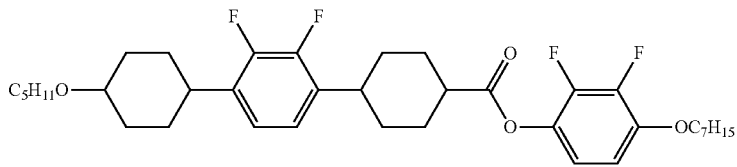 |

| No. |
|---|
| 4554 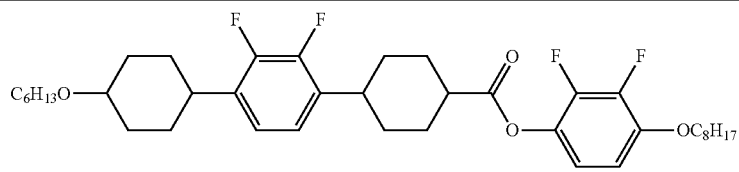 |
| 4555 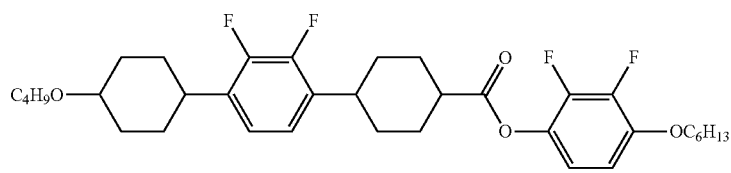 |
| 4556 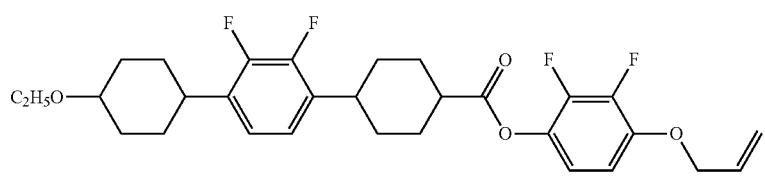 |
| 4557 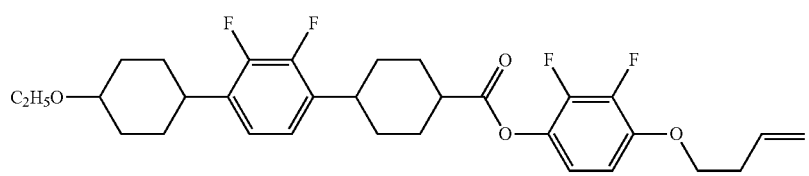 |
| 4558 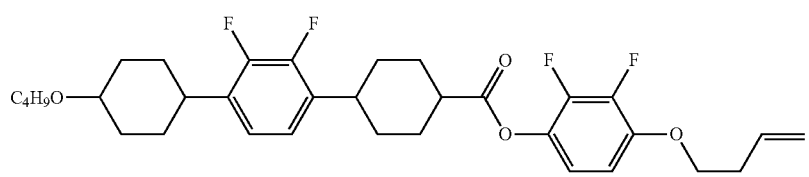 |
| 4559 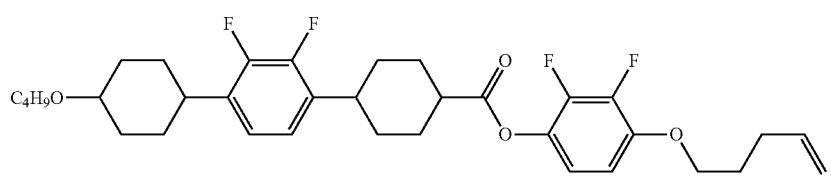 |
| 4560 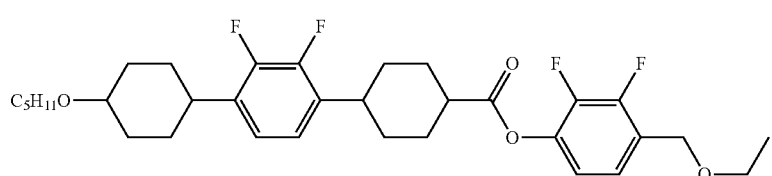 |
| 4561 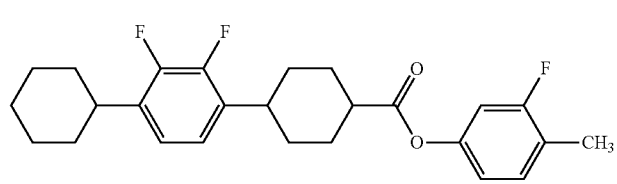 [SMILES: Cc1ccc(OC(=O)C2CCC(c3ccc(C4CCCCC4)c(F)c3F)CC2)cc1F] |
| 4562 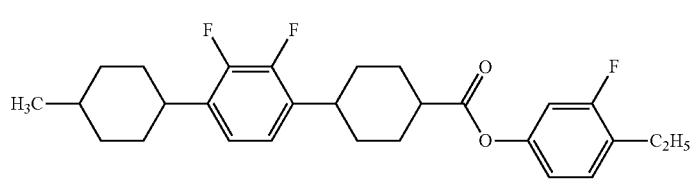 |

| No. | |
|---|---|
| 4563 | 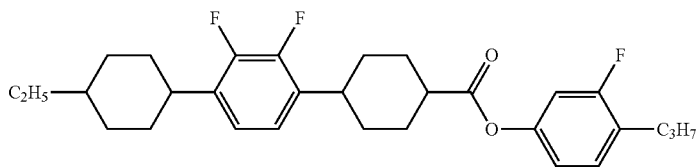 |
| 4564 | 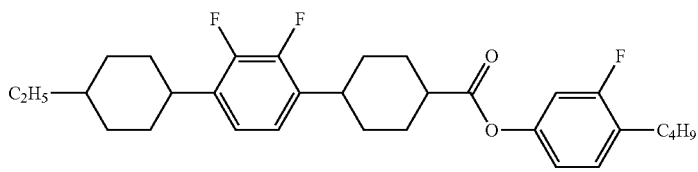 |
| 4565 | 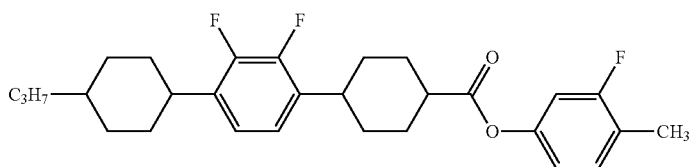 |
| 4566 | 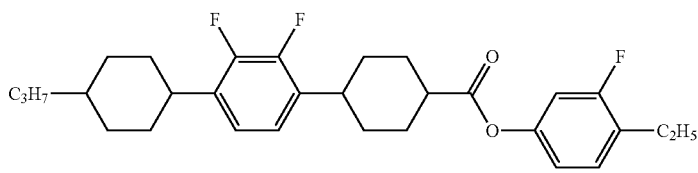 |
| 4567 | 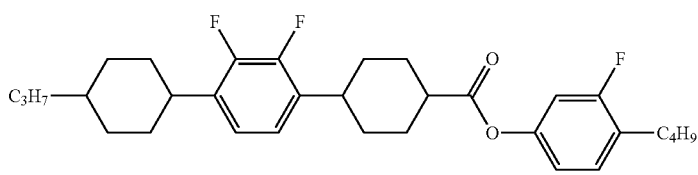 |
| 4568 | 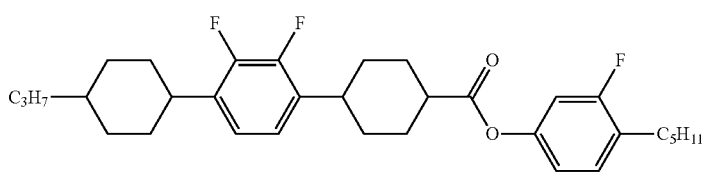 |
| 4569 | 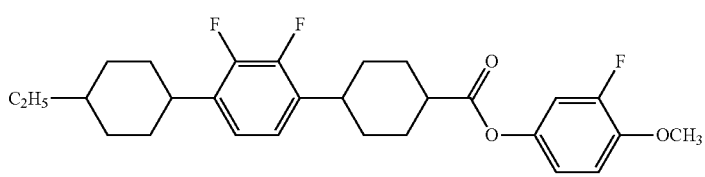 |
| 4570 | 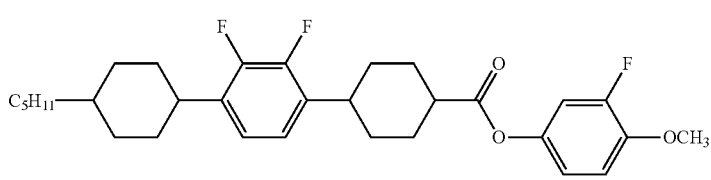 [SMILES: COc1ccc(OC(=O)C2CCC(c3ccc(C4CCC(OC)CC4)c(F)c3F)CC2)cc1F] |

| No. | |
|---|---|
| 4571 | 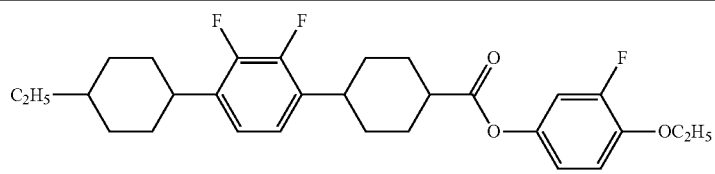 |
| 4572 | 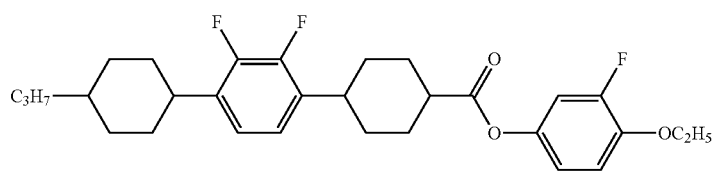 |
| 4573 | 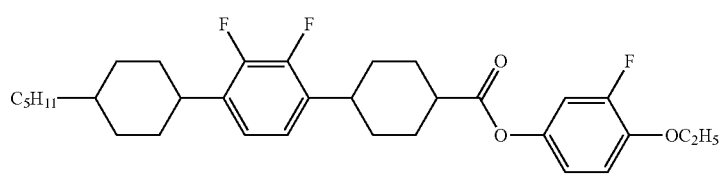 [SMILES: CCOc1ccc(OC(=O)C2CCC(c3ccc(C4CCC(OC)CC4)c(F)c3F)CC2)cc1F] |
| 4574 | 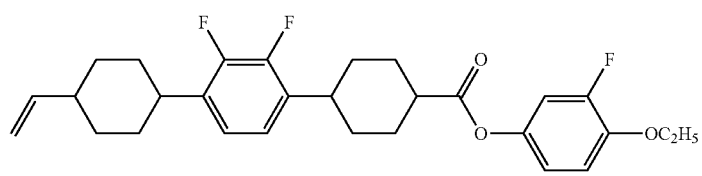 |
| 4575 | 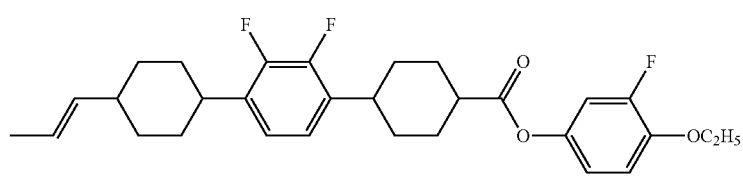 |
| 4576 | 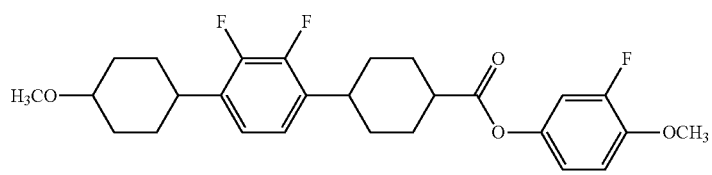 |
| 4577 | 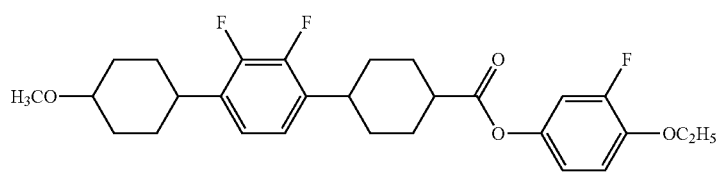 |
| 4578 | 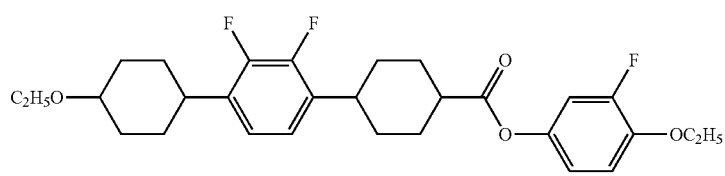 |
| 4579 | 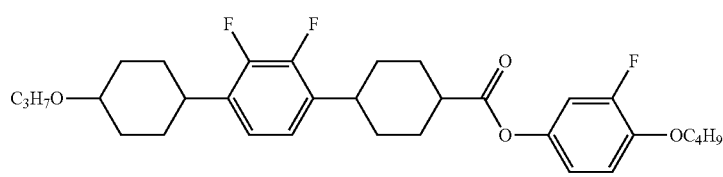 |

-continued
| No. | |
|---|---|
| 4580 | 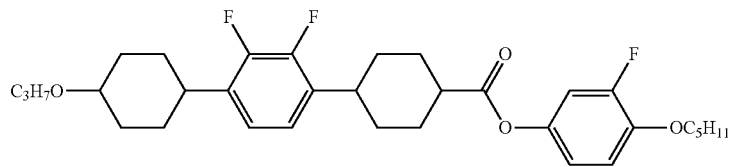 |
| 4581 | 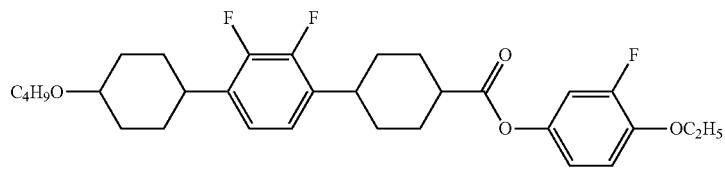 |
| 4582 | 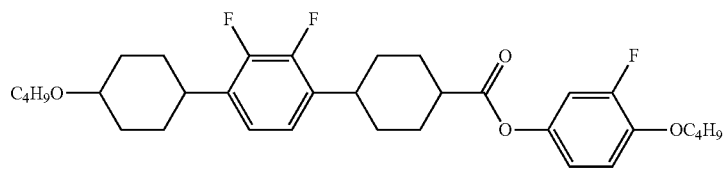 |
| 4583 | 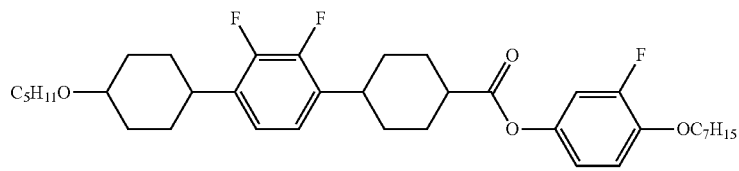 |
| 4584 | 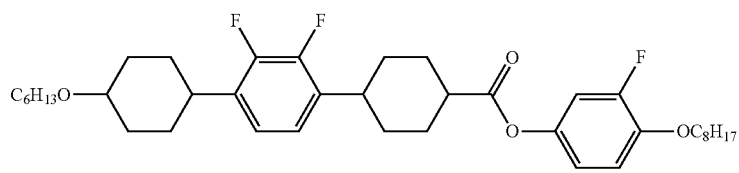 |
| 4585 | 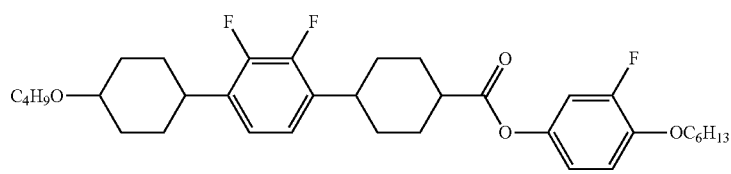 |
| 4586 | 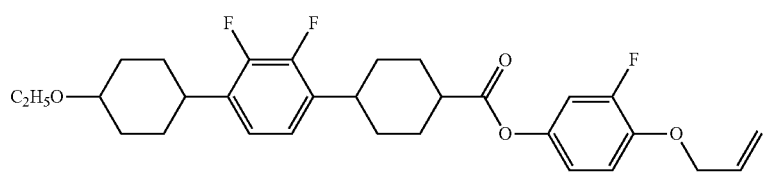 |
| 4587 | 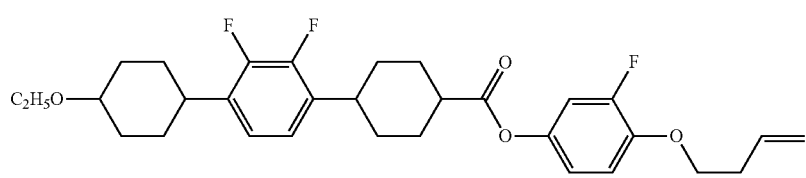 |

-continued
| No. | |
|---|---|
| 4588 | 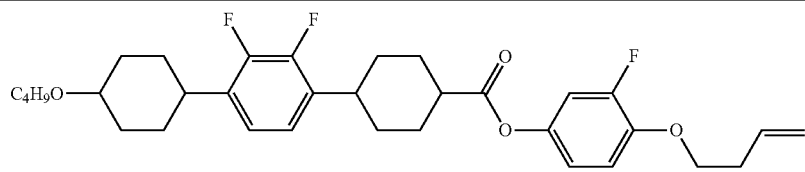 |
| 4589 | 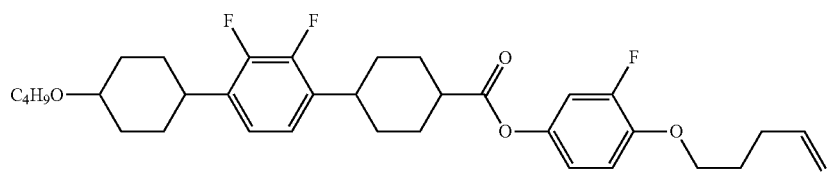 |
| 4590 | 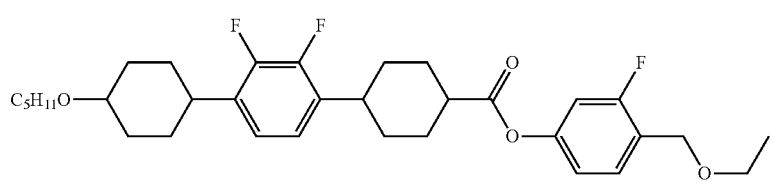 |
| 4591 | 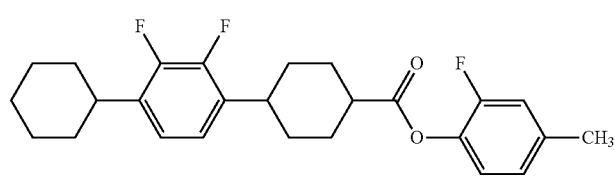 |
| 4592 | 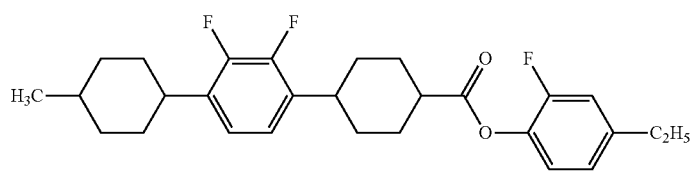 |
| 4593 | 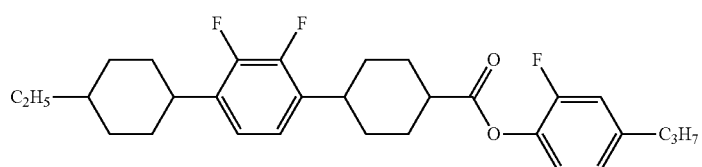 |
| 4594 | 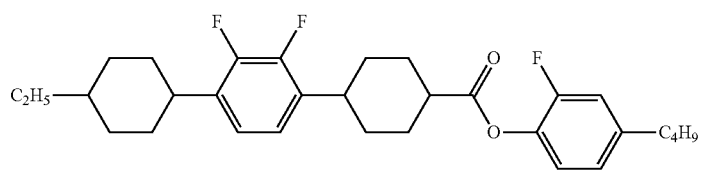 |
| 4595 | 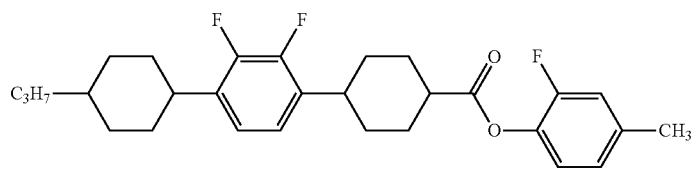 |
| 4596 | 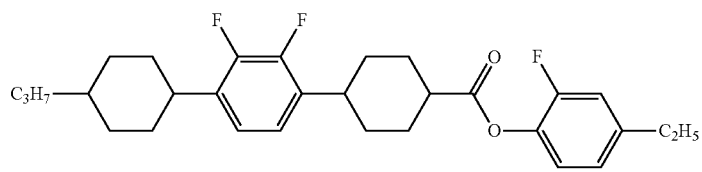 |

| No. | |
|---|---|
| 4597 | 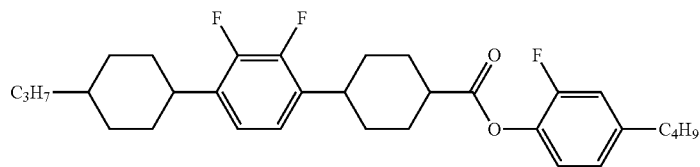 |
| 4598 | 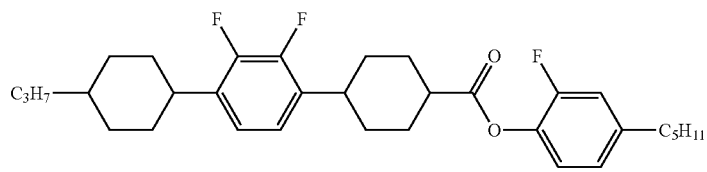 |
| 4599 | 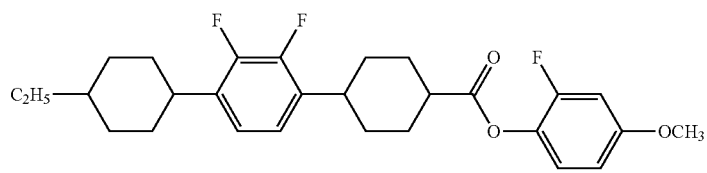 |
| 4600 | 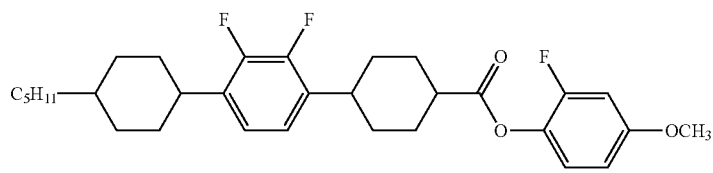 |
| 4601 | 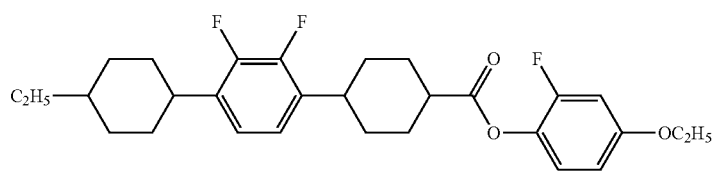 |
| 4602 | 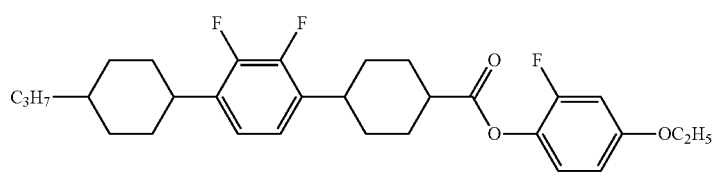 |
| 4603 | 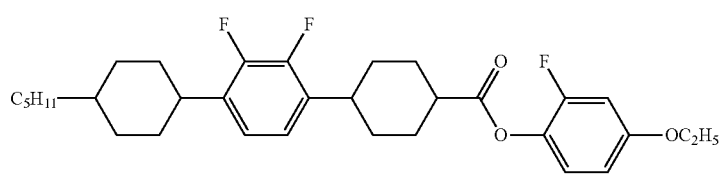 |
| 4604 | 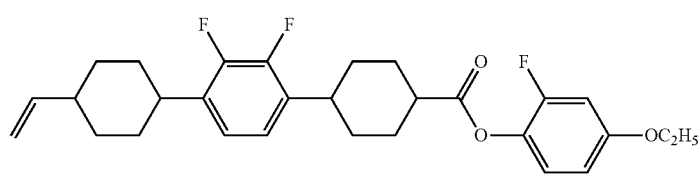 |

-continued
| No. | |
|---|---|
| 4605 | 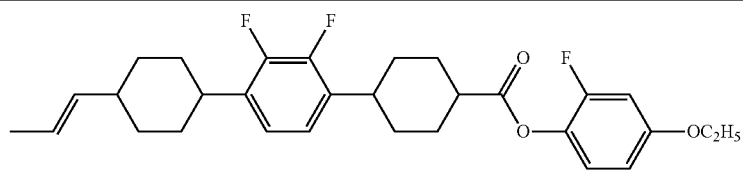 |
| 4606 | 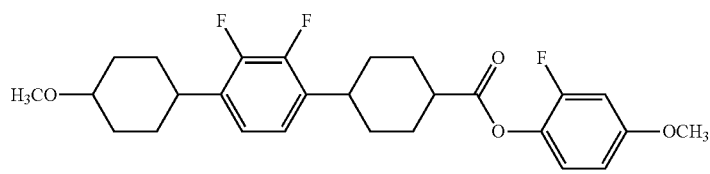 [SMILES: COc1ccc(OC(=O)C2CCC(c3ccc(C4CCC(OC)CC4)c(F)c3F)CC2)c(F)c1] |
| 4607 | 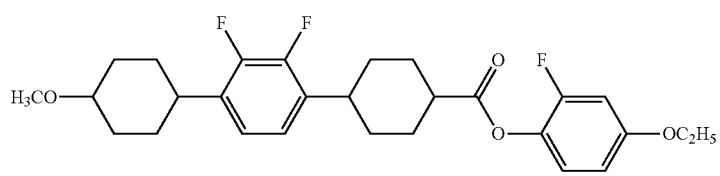 [SMILES: CCOc1ccc(OC(=O)C2CCC(c3ccc(C4CCC(OC)CC4)c(F)c3F)CC2)c(F)c1] |
| 4608 | 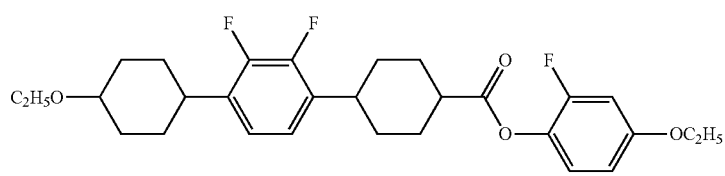 |
| 4609 | 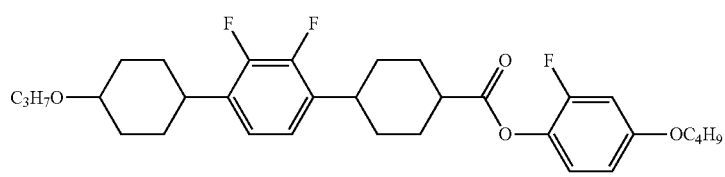 |
| 4610 | 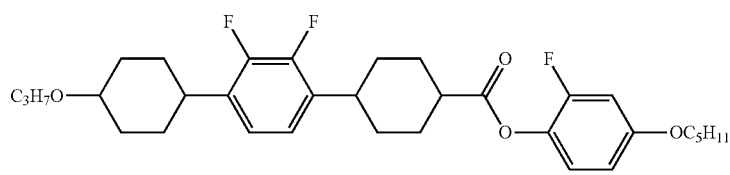 |
| 4611 | 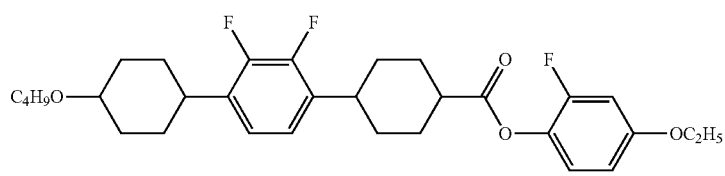 |
| 4612 | 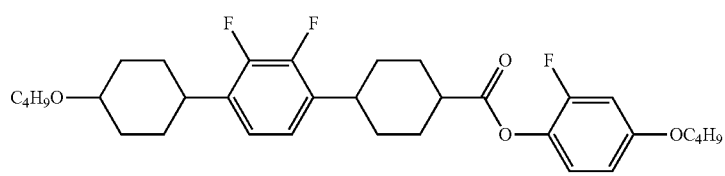 |
| 4613 | 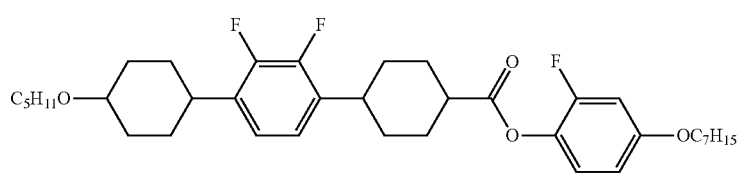 |

-continued
| No. | |
|---|---|
| 4614 | 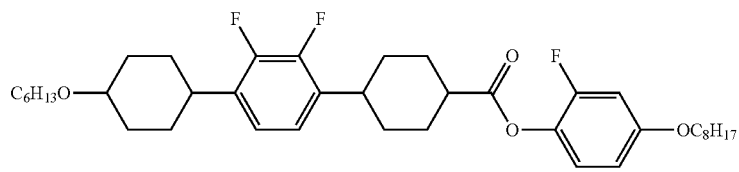 |
| 4615 | 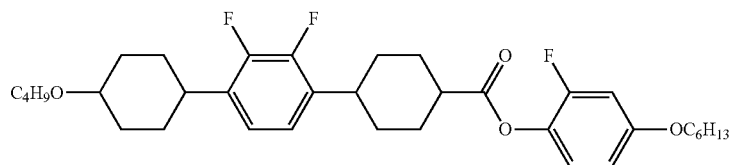 |
| 4616 | 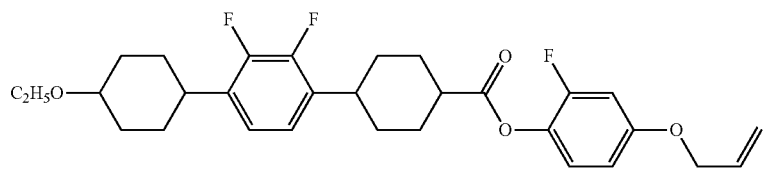 |
| 4617 | 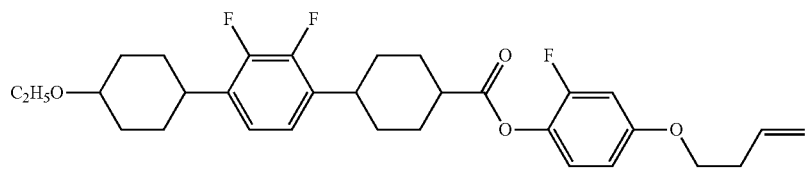 |
| 4618 | 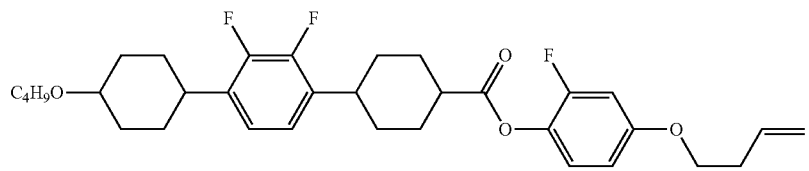 |
| 4619 | 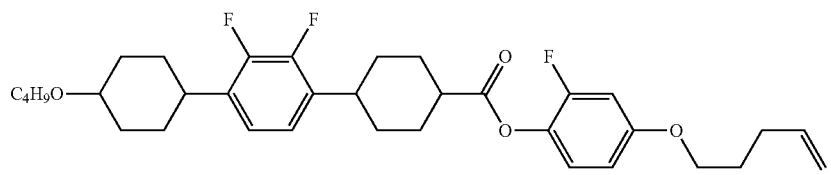 |
| 4620 | 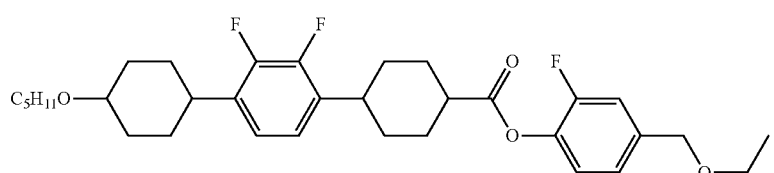 |
| 4621 | 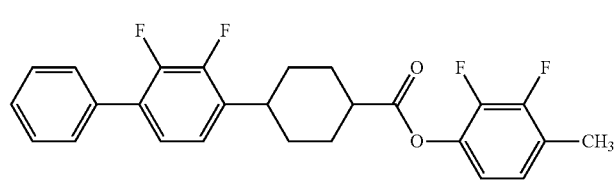 |

| No. | |
|---|---|
| 4622 | 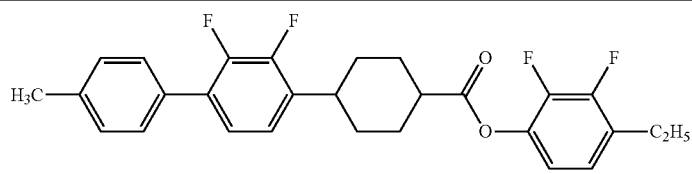 |
| 4623 | 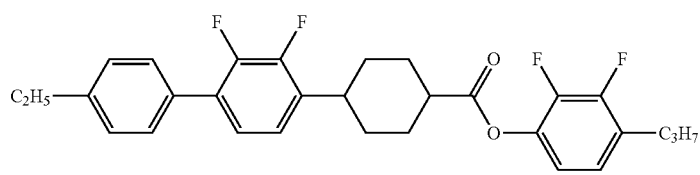 |
| 4624 | 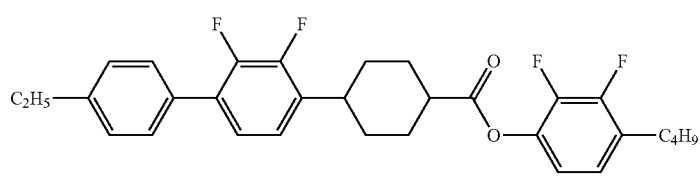 |
| 4625 | 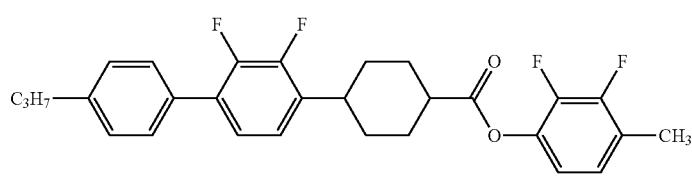 |
| 4626 | 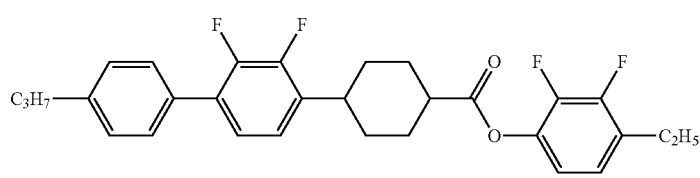 |
| 4627 | 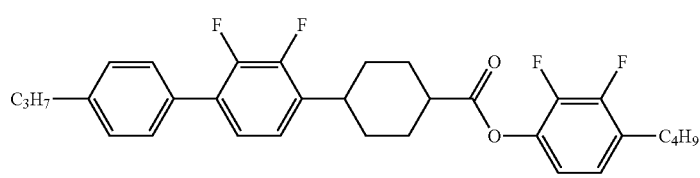 |
| 4628 | 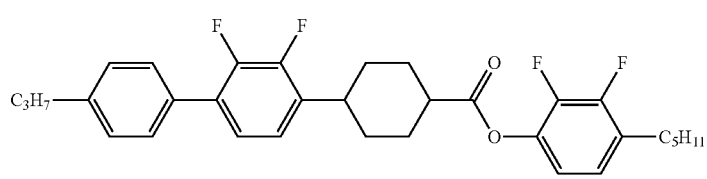 |
| 4629 | 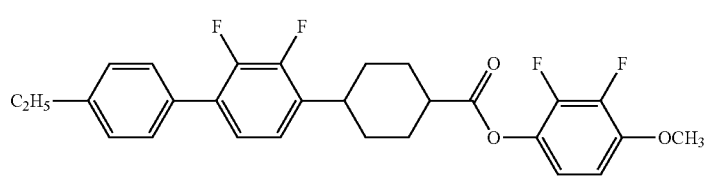 |
| 4630 | 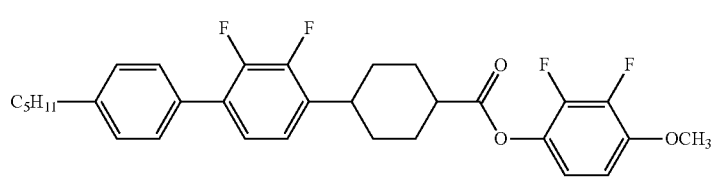 |

-continued
| No. | |
|---|---|
| 4631 | 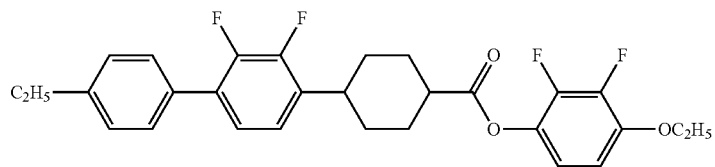 |
| 4632 | 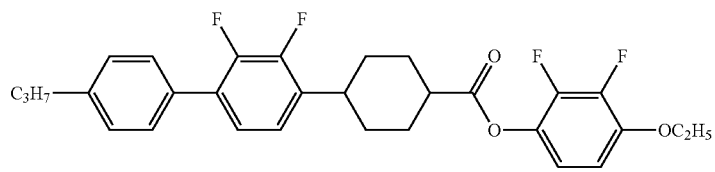 |
| 4633 | 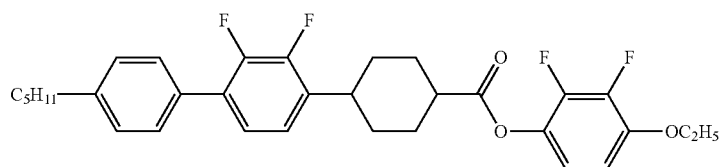 |
| 4634 | 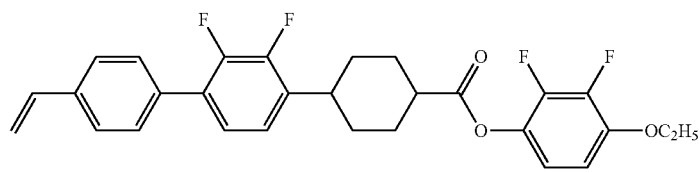 |
| 4635 | 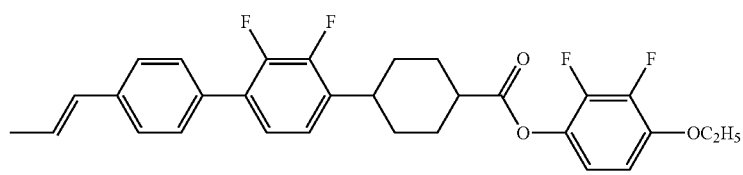 |
| 4636 | 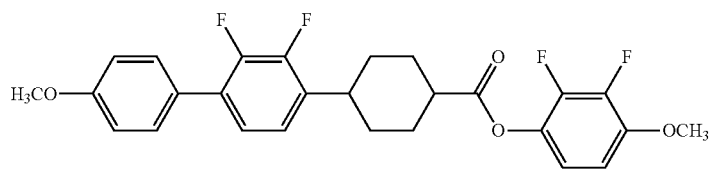 [SMILES: COc1ccc(-c2ccc(C3CCC(C(=O)Oc4ccc(OC)c(F)c4F)CC3)c(F)c2F)cc1] |
| 4637 | 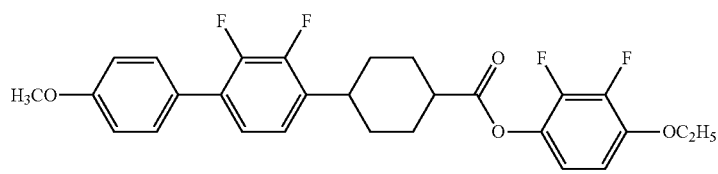 |
| 4638 | 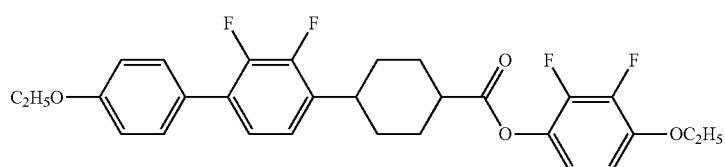 |

| No. | |
|---|---|
| 4639 | 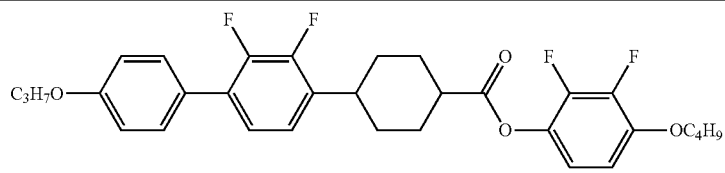 |
| 4640 | 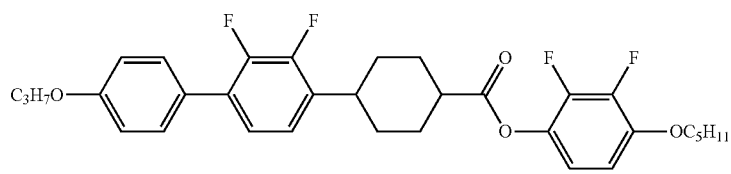 |
| 4641 | 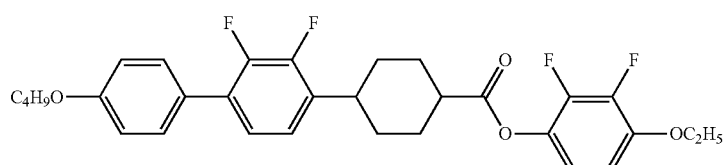 |
| 4642 | 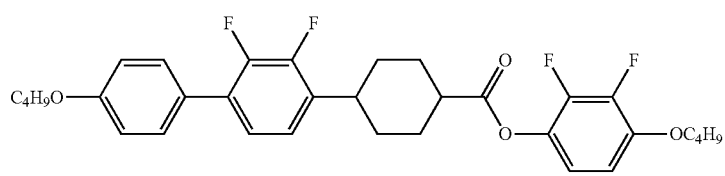 |
| 4643 | 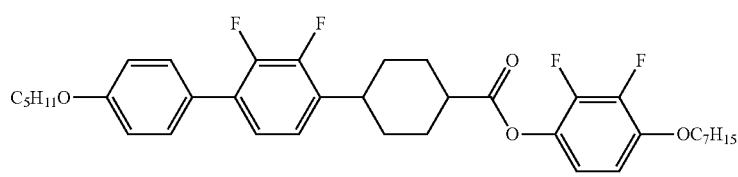 |
| 4644 | 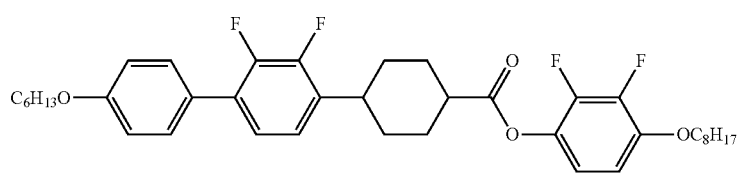 |
| 4645 | 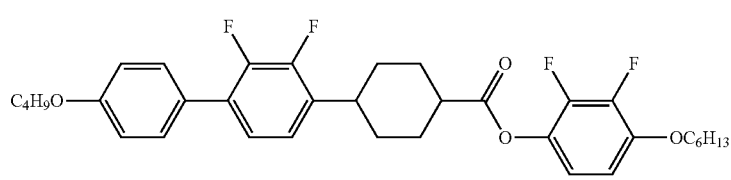 |
| 4646 | 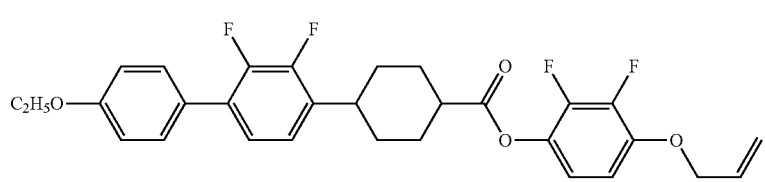 |
| 4647 | 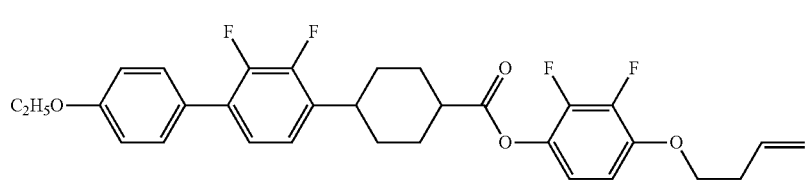 |

| No. | |
|---|---|
| 4648 | 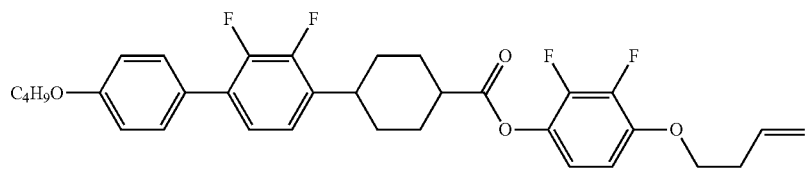 |
| 4649 | 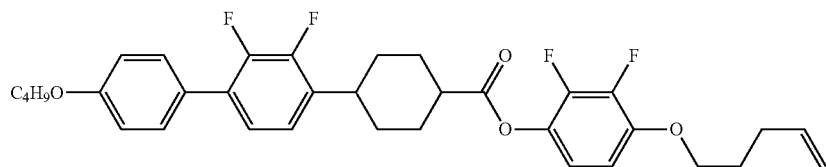 |
| 4650 | 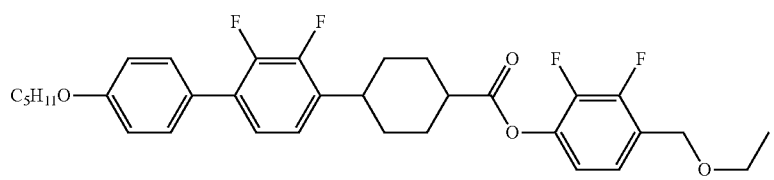 |
| 4651 | 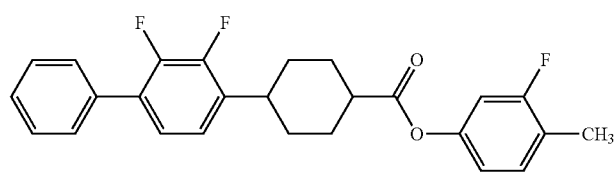 |
| 4652 | 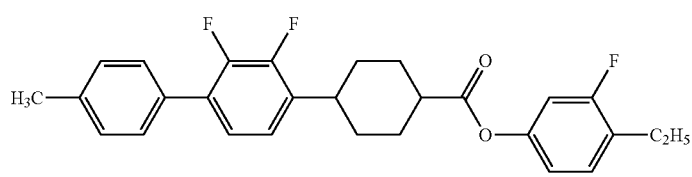 |
| 4653 | 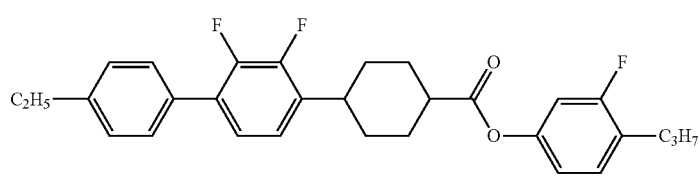 |
| 4654 | 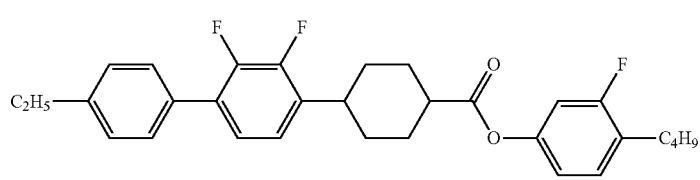 |
| 4655 | 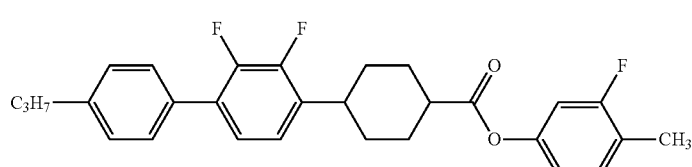 |

| No. | |
|---|---|
| 4656 | 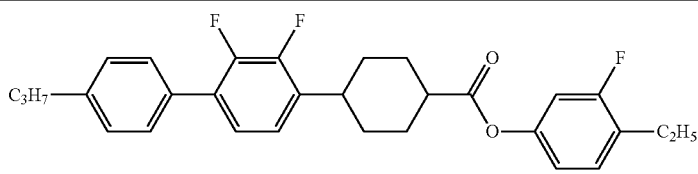 |
| 4657 | 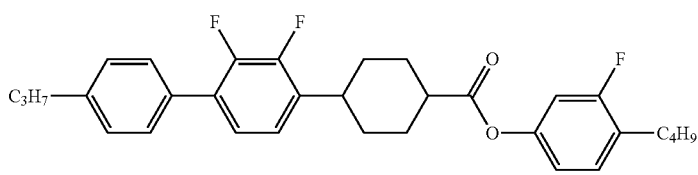 |
| 4658 | 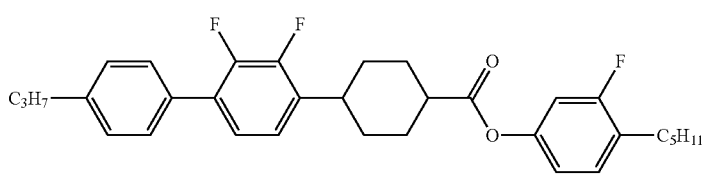 |
| 4659 | 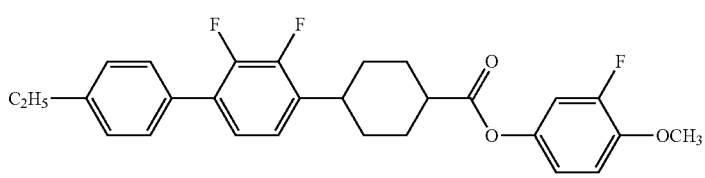 [SMILES: CCc1ccc(-c2ccc(C3CCC(C(=O)Oc4ccc(OC)cc4F)CC3)c(F)c2F)cc1] |
| 4660 | 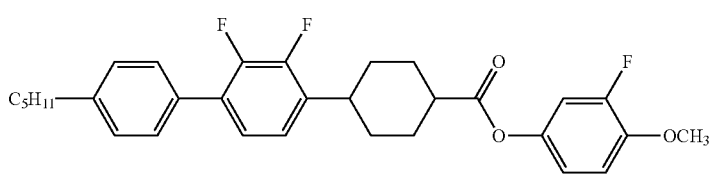 |
| 4661 | 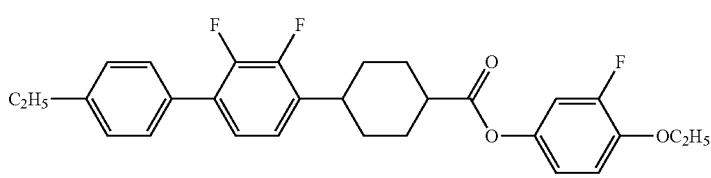 |
| 4662 | 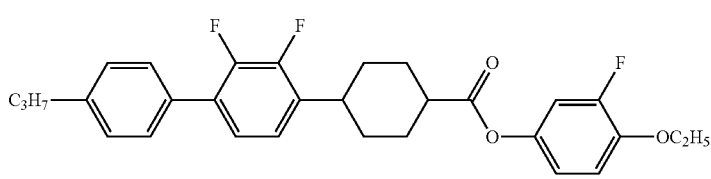 |
| 4663 | 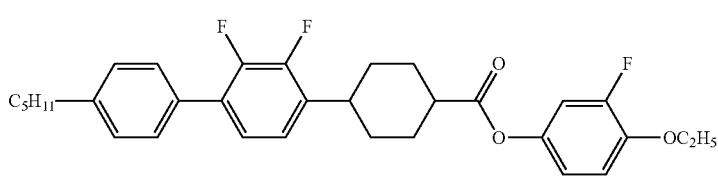 |
| 4664 | 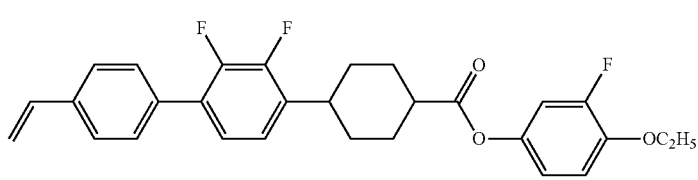 |

| No. |
|---|
| 4665 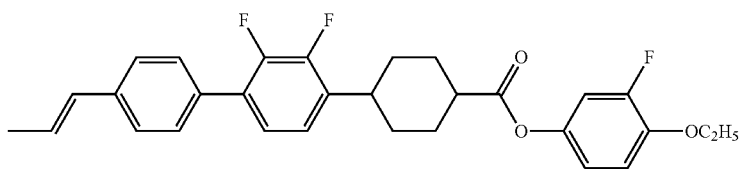 |
| 4666 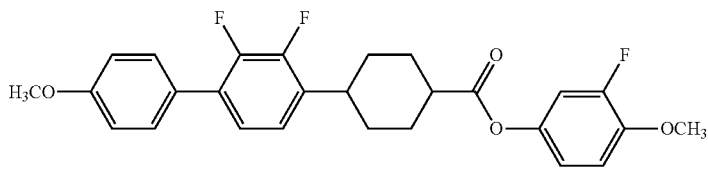 |
| 4667 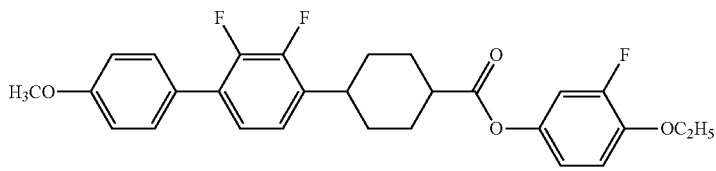 |
| 4668 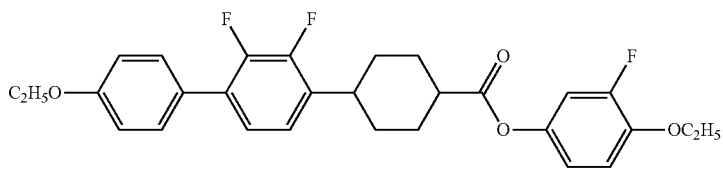 |
| 4669 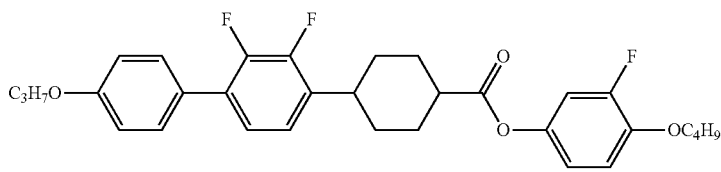 |
| 4670 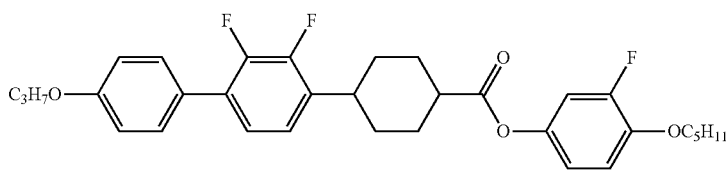 |
| 4671 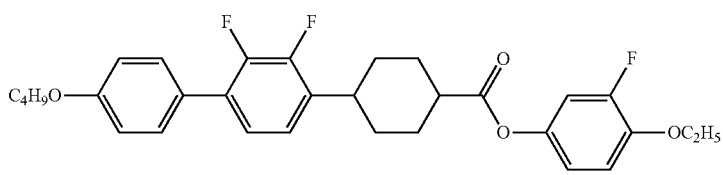 |
| 4672 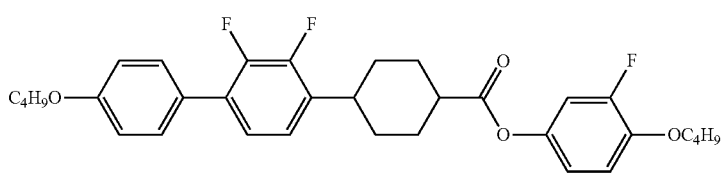 |

| No. | |
|---|---|
| 4673 | 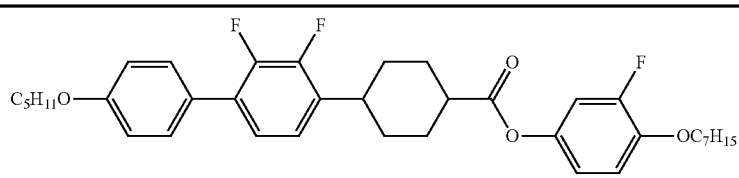 |
| 4674 | 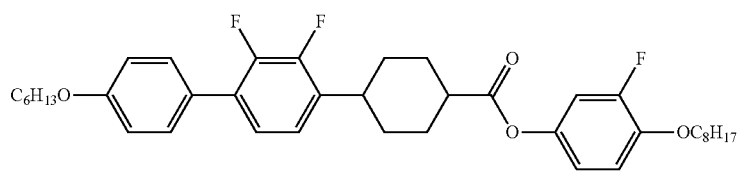 |
| 4675 | 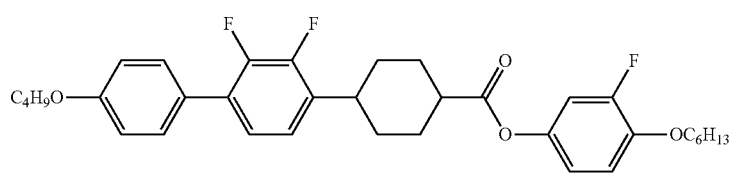 |
| 4676 | 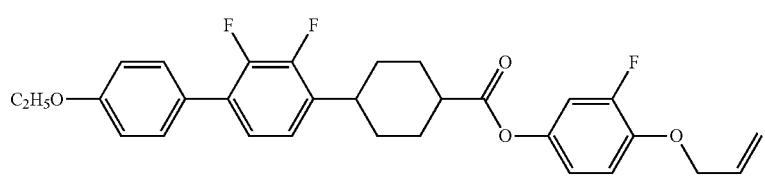 |
| 4677 | 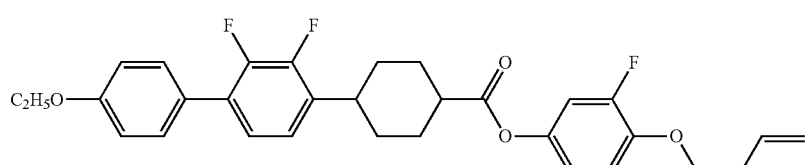 |
| 4678 | 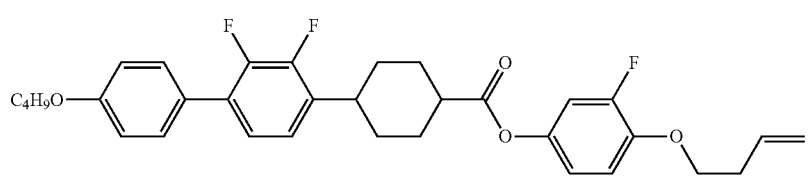 |
| 4679 | 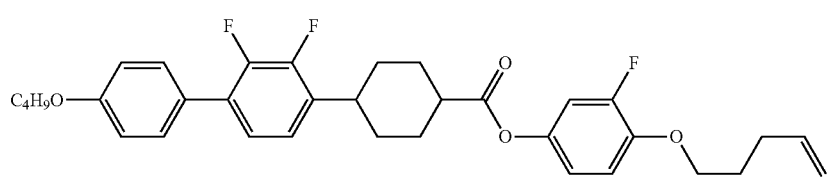 |
| 4680 | 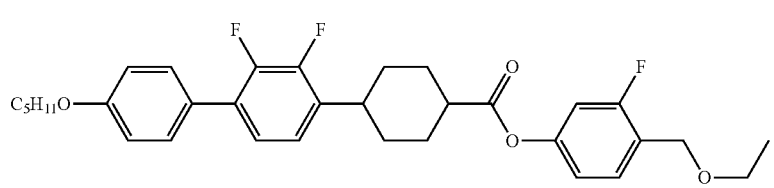 |
| 4681 | 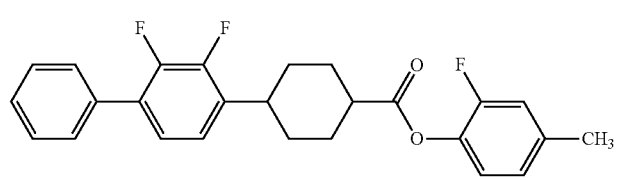 |

-continued
| No. | |
|---|---|
| 4682 | 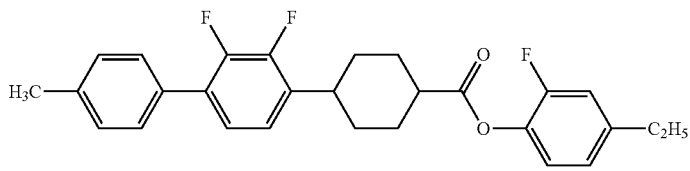 |
| 4683 | 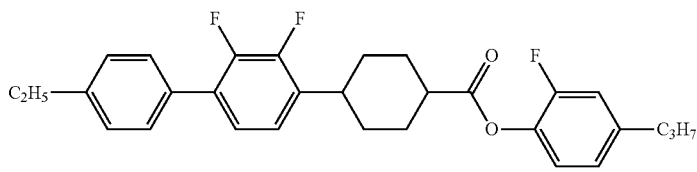 |
| 4684 | 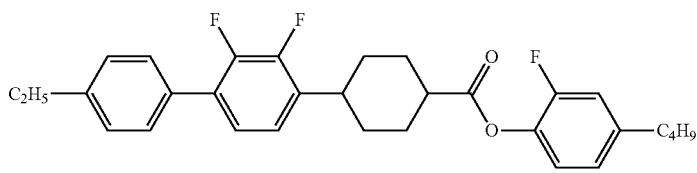 |
| 4685 | 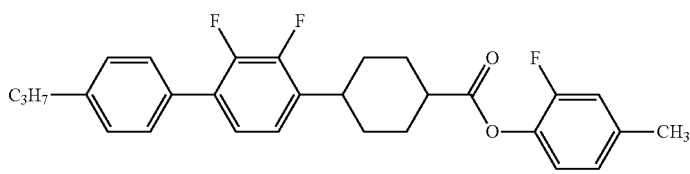 |
| 4686 | 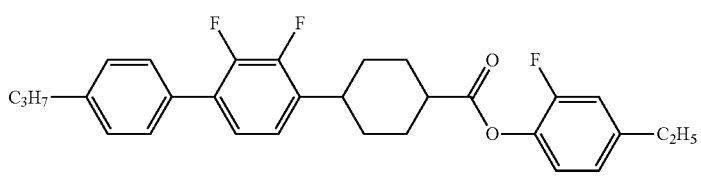 |
| 4687 | 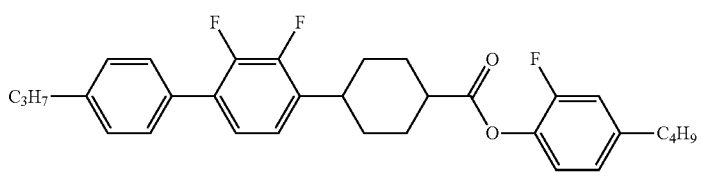 |
| 4688 | 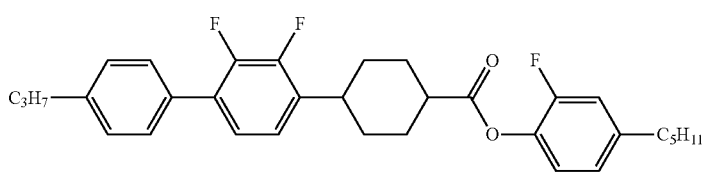 |
| 4689 | 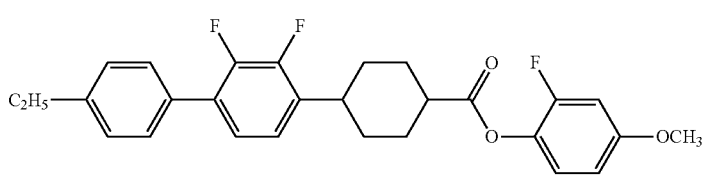 |

-continued
| No. | |
|---|---|
| 4690 | 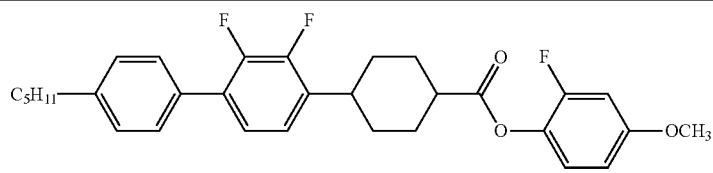 |
| 4691 | 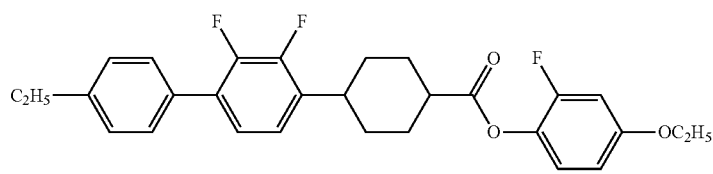 |
| 4692 | 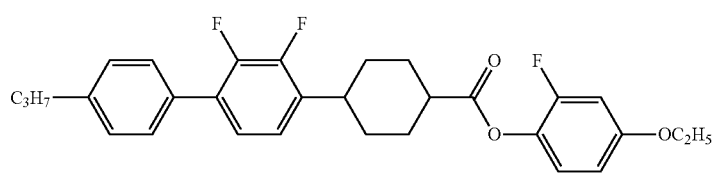 |
| 4693 | 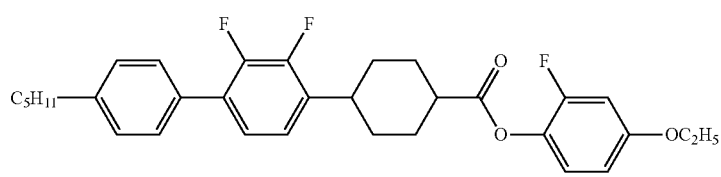 |
| 4694 | 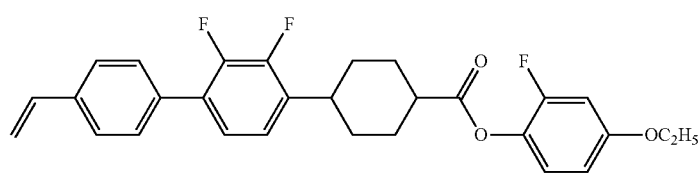 [SMILES: C=Cc1ccc(-c2ccc(C3CCC(C(=O)Oc4ccc(OCC)cc4F)CC3)c(F)c2F)cc1] |
| 4695 | 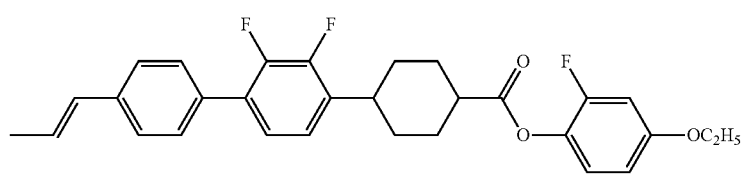 [SMILES: C/C=C/c1ccc(-c2ccc(C3CCC(C(=O)Oc4ccc(OCC)cc4F)CC3)c(F)c2F)cc1] |
| 4696 | 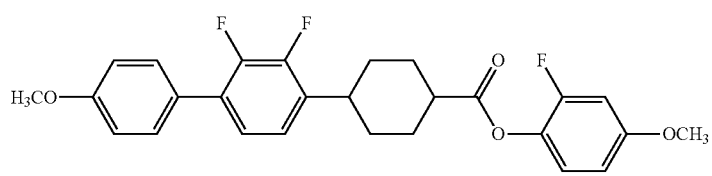 |
| 4697 | 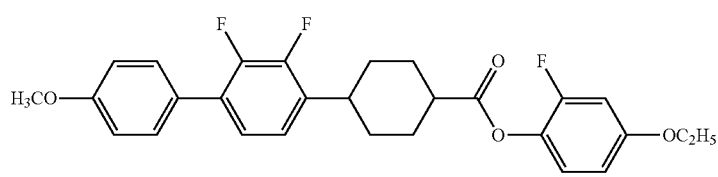 |
| 4698 | 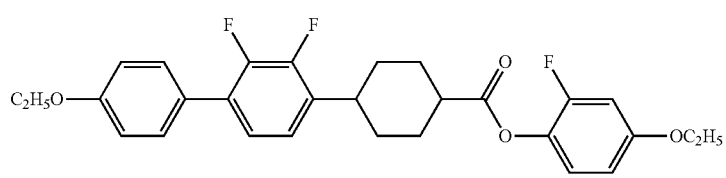 |

| No. | |
|---|---|
| 4699 | 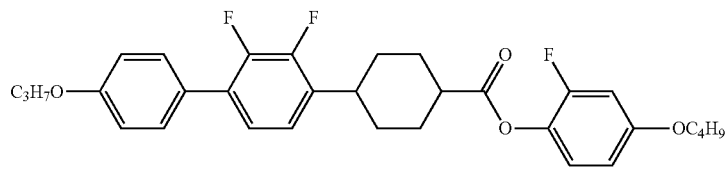 |
| 4700 | 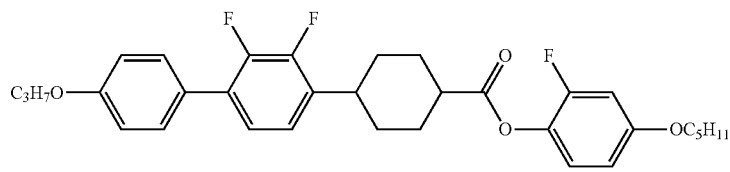 |
| 4701 | 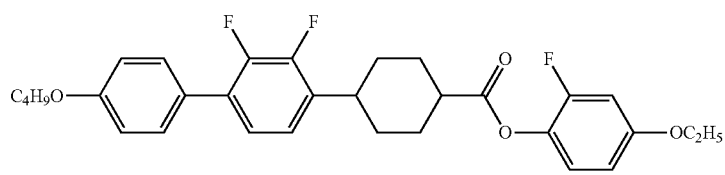 |
| 4702 | 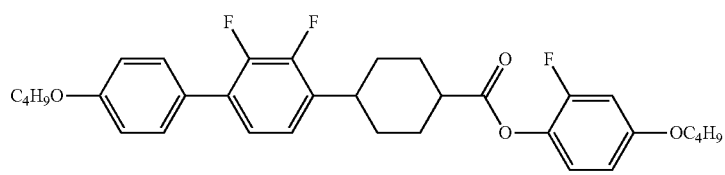 |
| 4703 | 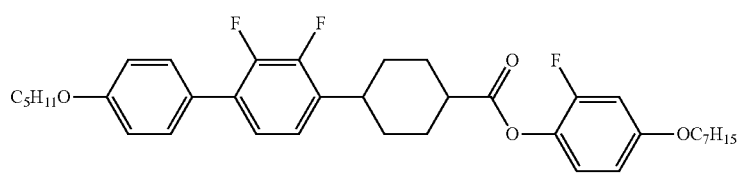 |
| 4704 | 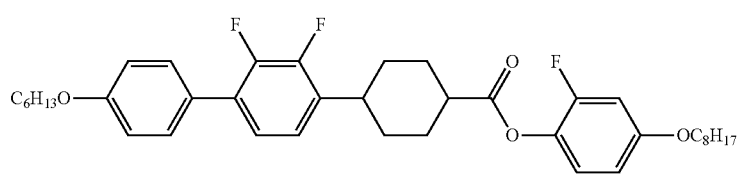 |
| 4705 | 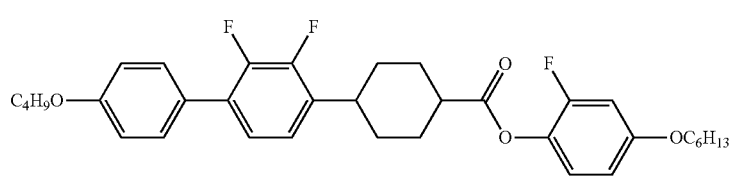 |
| 4706 | 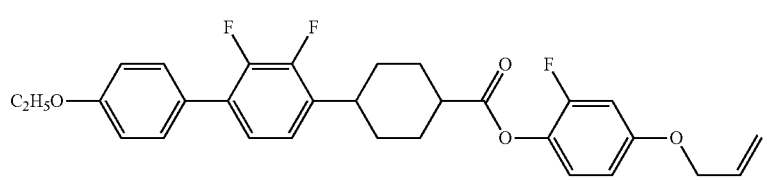 |

| No. | |
|---|---|
| 4707 | 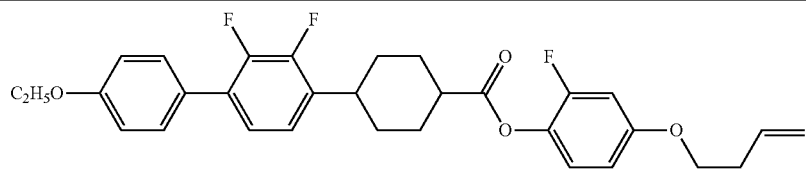 |
| 4708 | 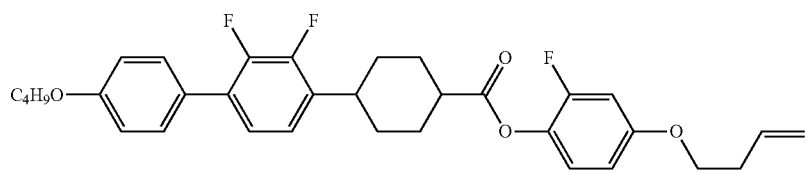 |
| 4709 | 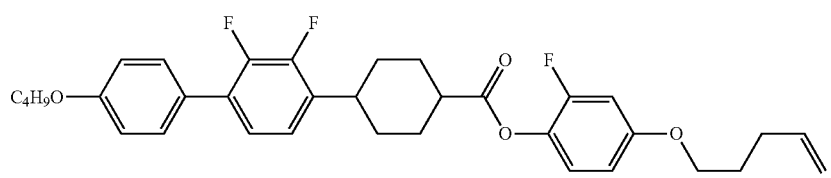 |
| 4710 | 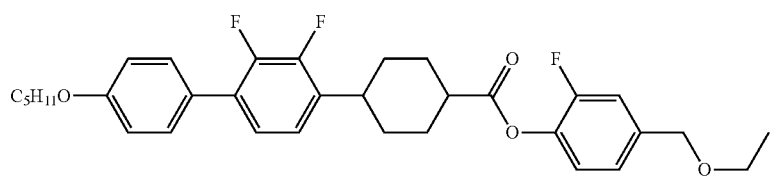 |
| 4711 | 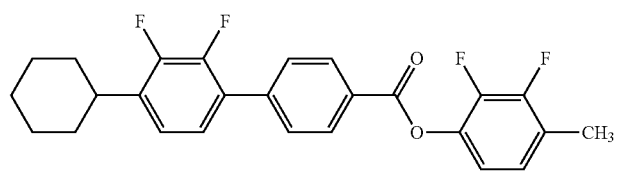 [SMILES: Cc1ccc(OC(=O)c2ccc(-c3ccc(C4CCCCC4)c(F)c3F)cc2)c(F)c1F] |
| 4712 | 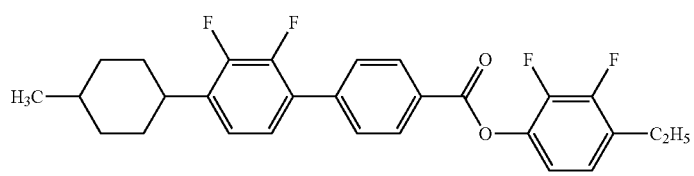 [SMILES: CCc1ccc(OC(=O)c2ccc(-c3ccc(C4CCC(C)CC4)c(F)c3F)cc2)c(F)c1F] |
| 4713 | 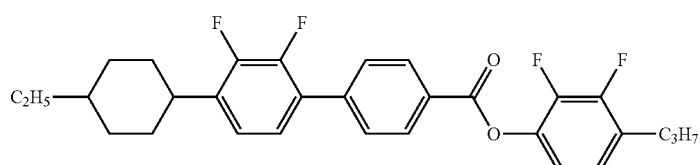 |
| 4714 | 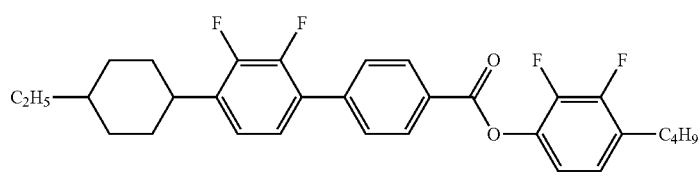 |
| 4715 | 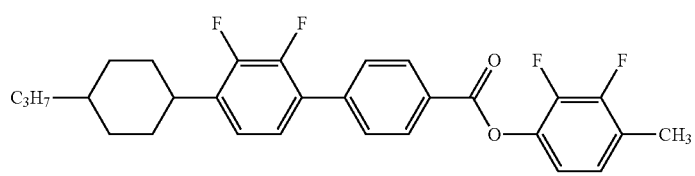 |

| No. |
|---|
| 4716 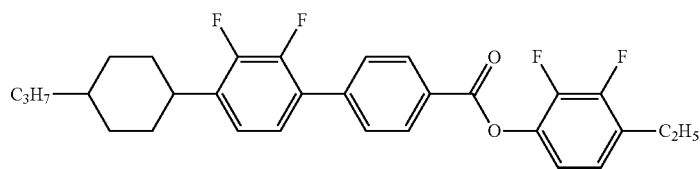 |
| 4717 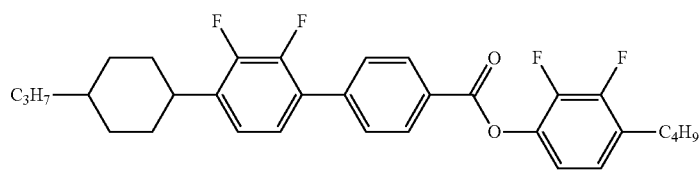 |
| 4718 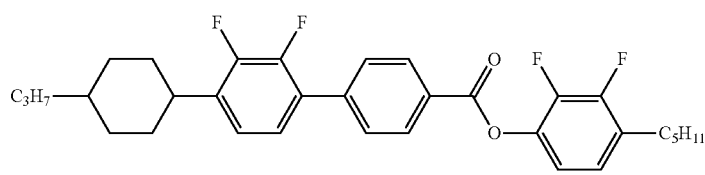 |
| 4719 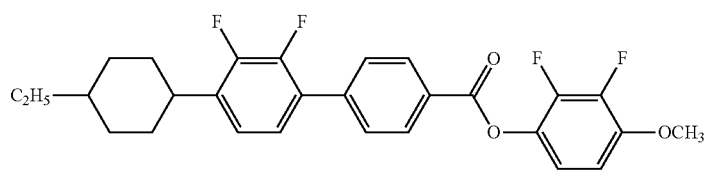 |
| 4720 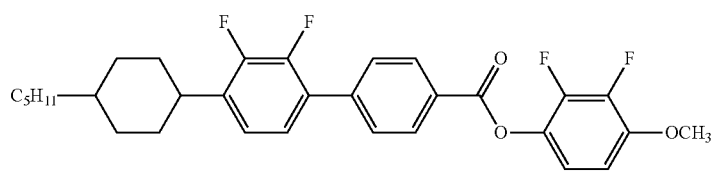 |
| 4721 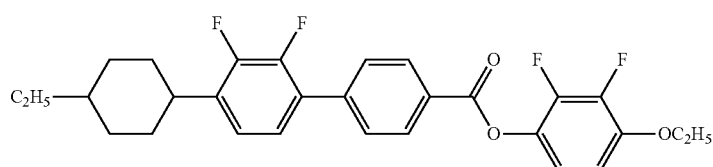 |
| 4722 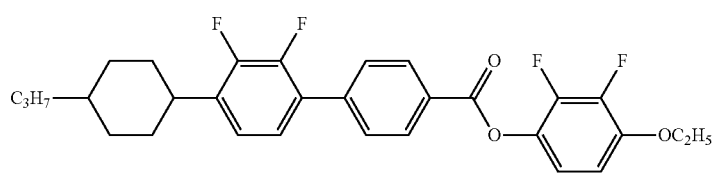 |
| 4723 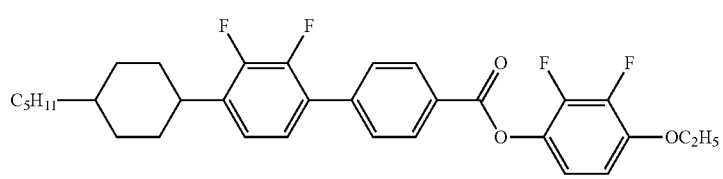 |

| No. | |
|---|---|
| 4724 | 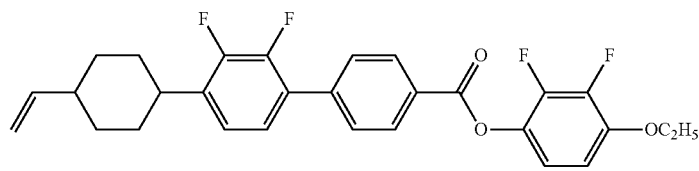 |
| 4725 | 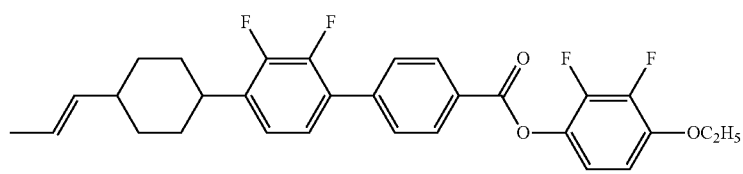 |
| 4726 | 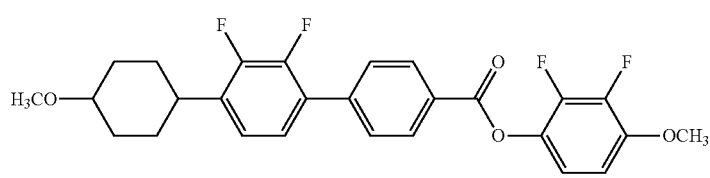 [SMILES: COc1ccc(OC(=O)c2ccc(-c3ccc(C4CCC(OC)CC4)c(F)c3F)cc2)c(F)c1F] |
| 4727 | 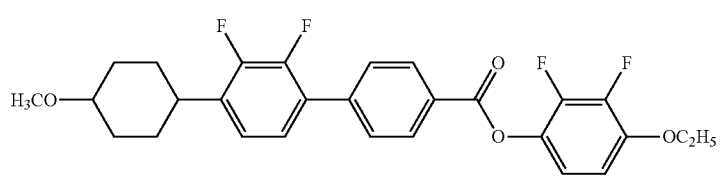 |
| 4728 | 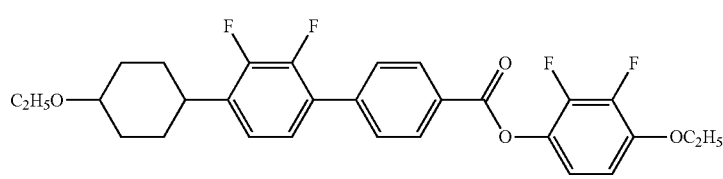 |
| 4729 | 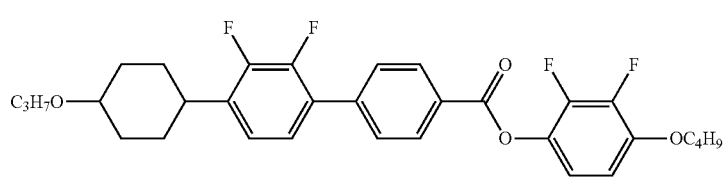 |
| 4730 | 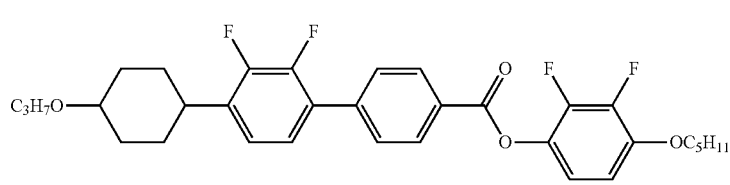 |
| 4731 | 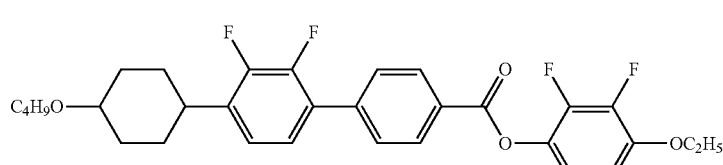 |
| 4732 | 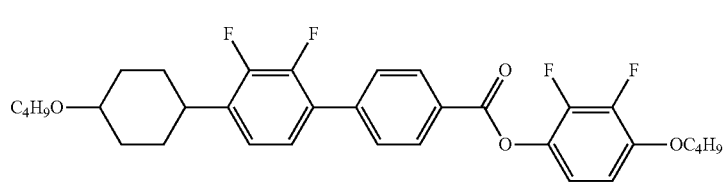 |

| No. | |
|---|---|
| 4733 | 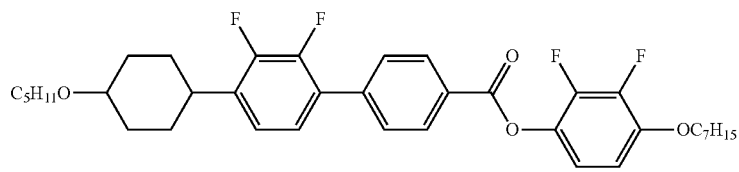 |
| 4734 | 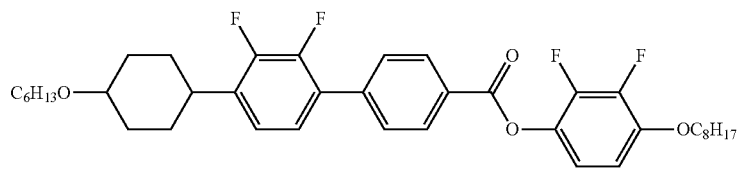 |
| 4735 | 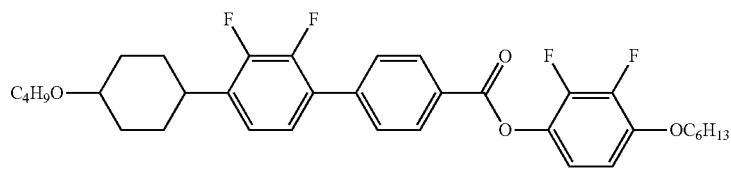 |
| 4736 | 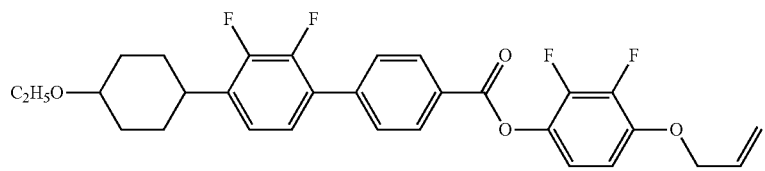 |
| 4737 | 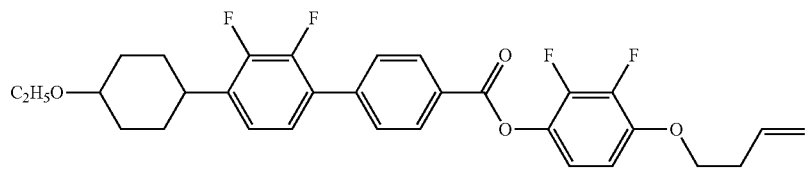 |
| 4738 | 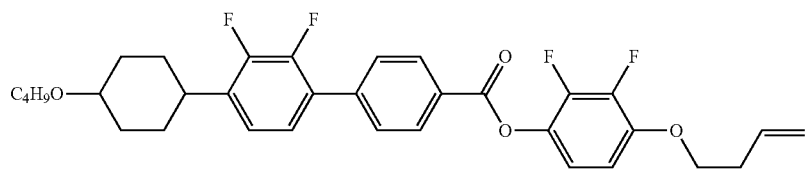 |
| 4739 | 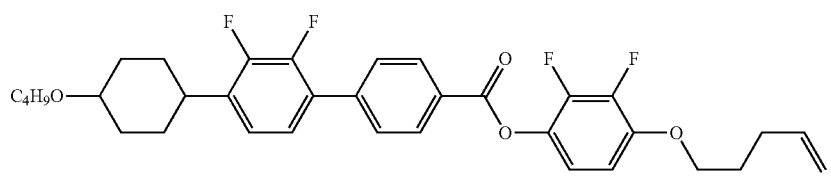 |
| 4740 | 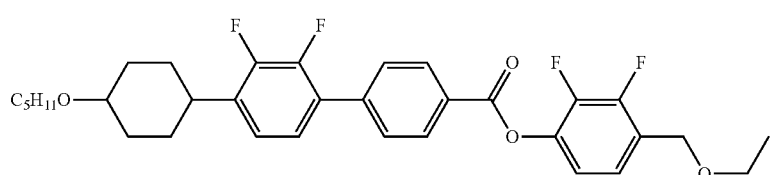 |

-continued
| No. | |
|---|---|
| 4741 | 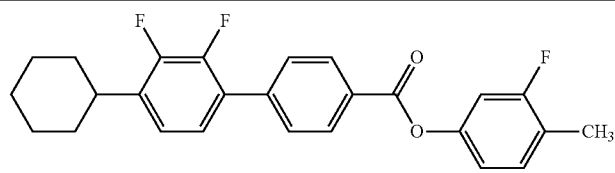 |
| 4742 | 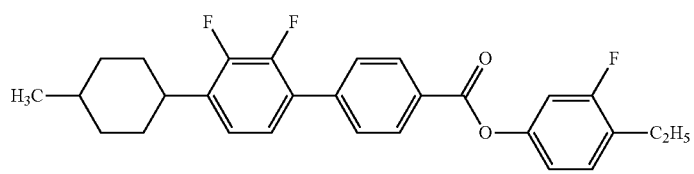 |
| 4743 | 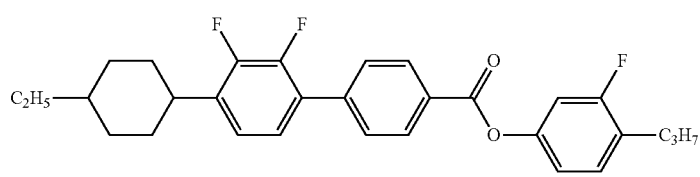 |
| 4744 | 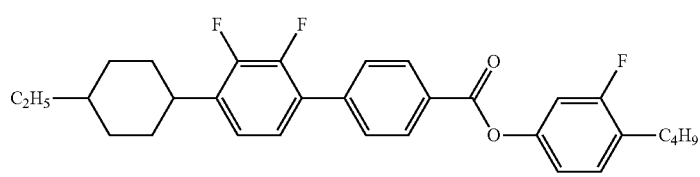 |
| 4745 | 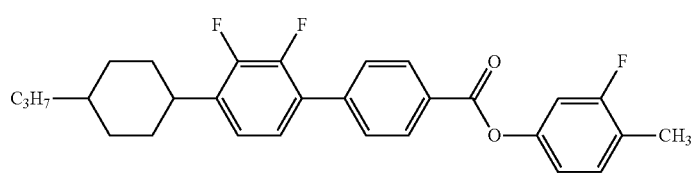 |
| 4746 | 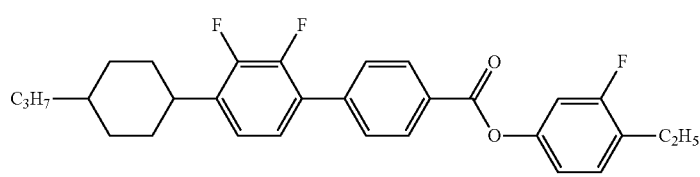 |
| 4747 | 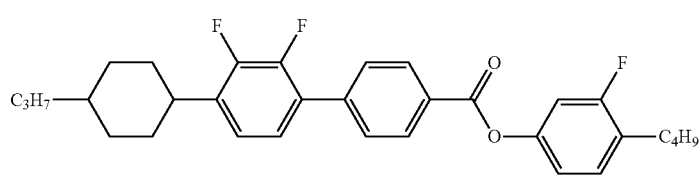 |
| 4748 | 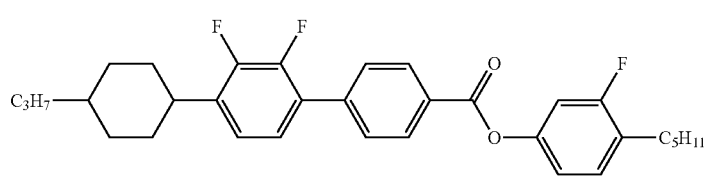 |
| 4749 | 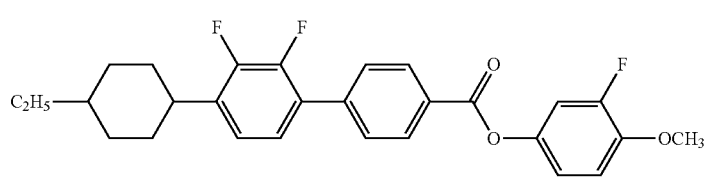 |

| No. | |
|---|---|
| 4750 | 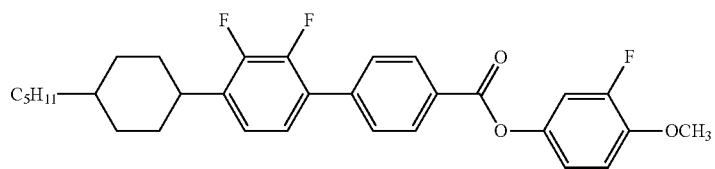 |
| 4751 | 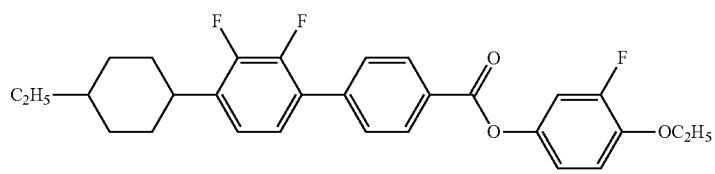 |
| 4752 | 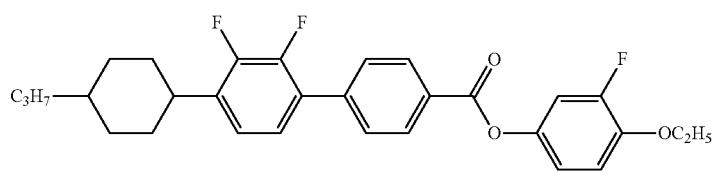 |
| 4753 | 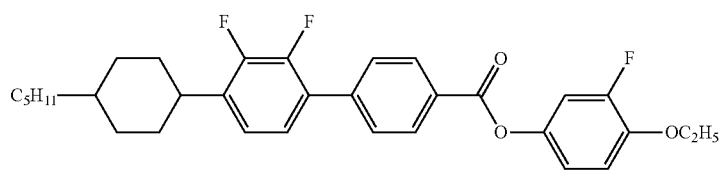 [SMILES: CCOc1ccc(OC(=O)c2ccc(-c3ccc(C4CCC(OC)CC4)c(F)c3F)cc2)cc1F] |
| 4754 | 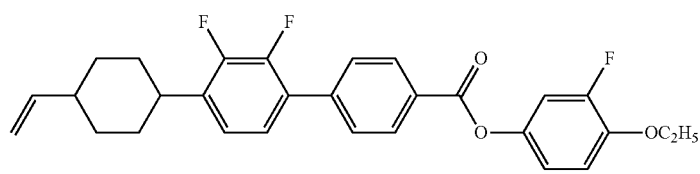 |
| 4755 | 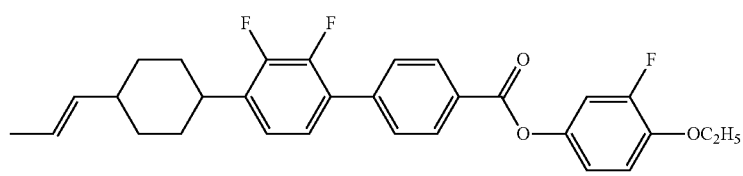 |
| 4756 | 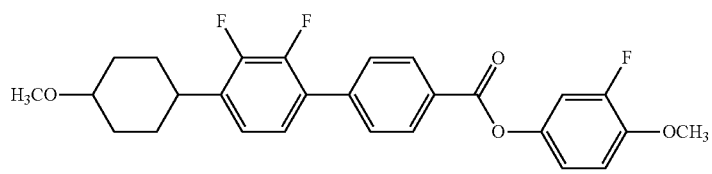 |
| 4757 | 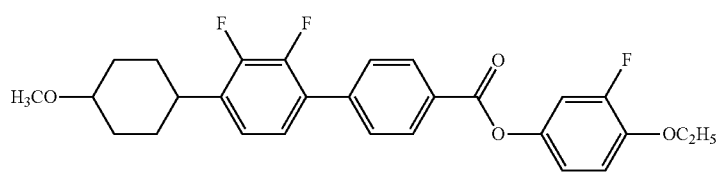 |

| No. | |
|---|---|
| 4758 | 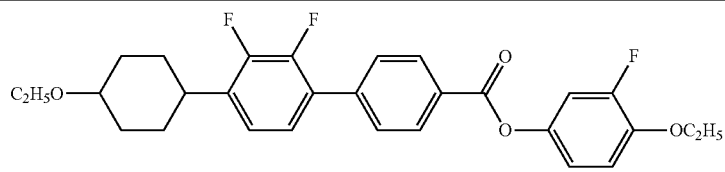 |
| 4759 | 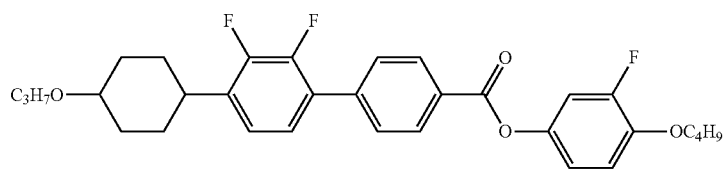 |
| 4760 | 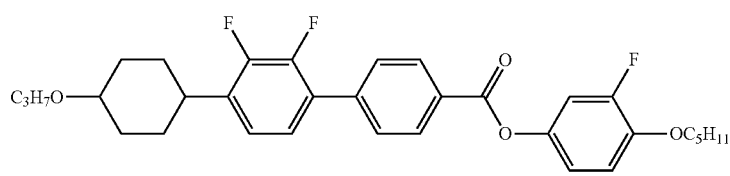 |
| 4761 | 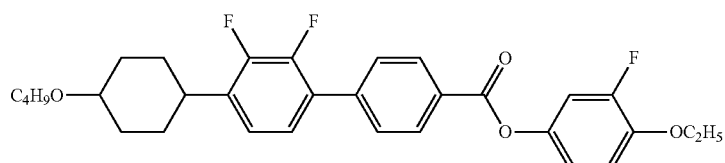 |
| 4762 | 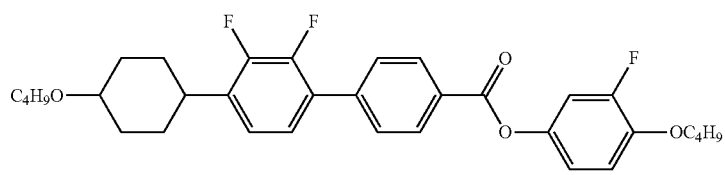 |
| 4763 | 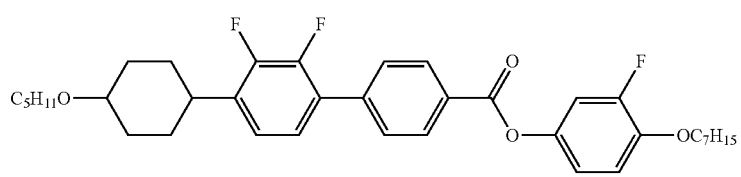 |
| 4764 | 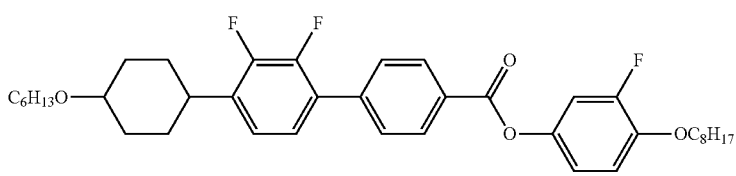 |
| 4765 | 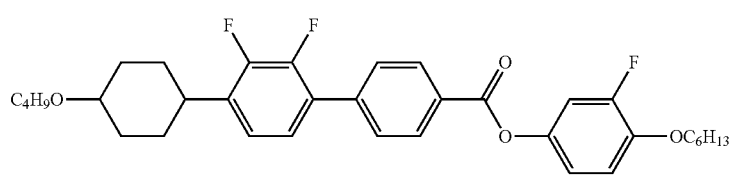 |
| 4766 | 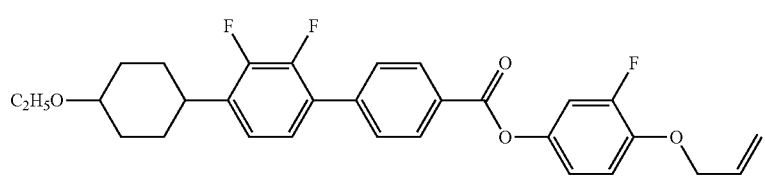 |

| No. | |
|---|---|
| 4767 | 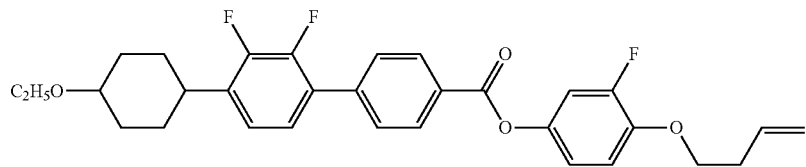 |
| 4768 | 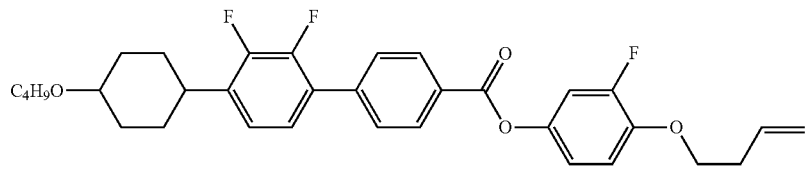 |
| 4769 | 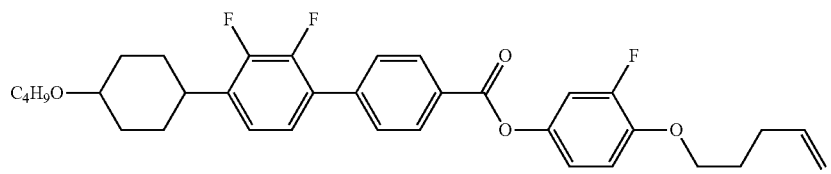 |
| 4770 | 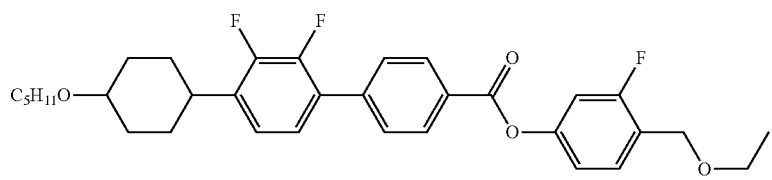 |
| 4771 | 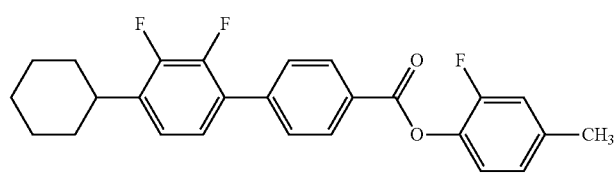 |
| 4772 | 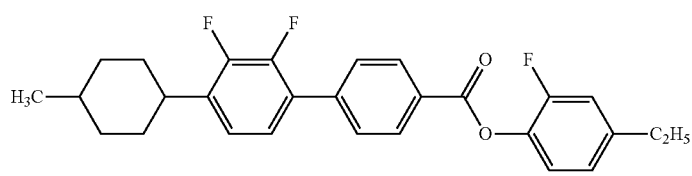 |
| 4773 | 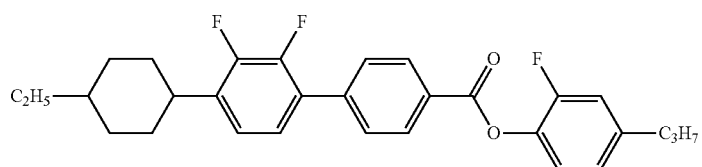 |
| 4774 | 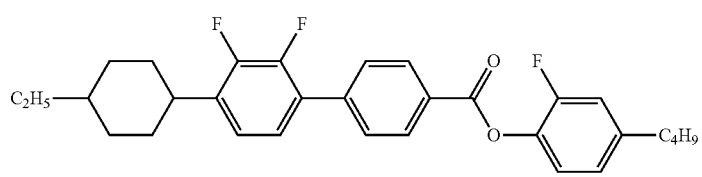 |

| No. | |
|---|---|
| 4775 | 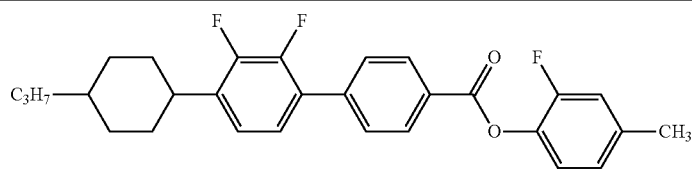 |
| 4776 | 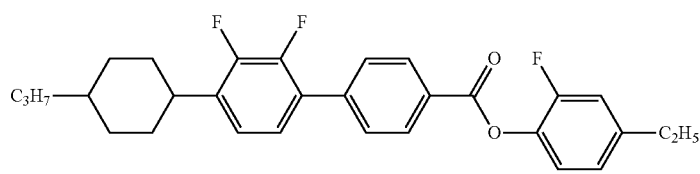 |
| 4777 | 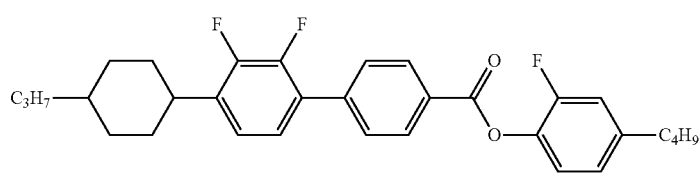 |
| 4778 | 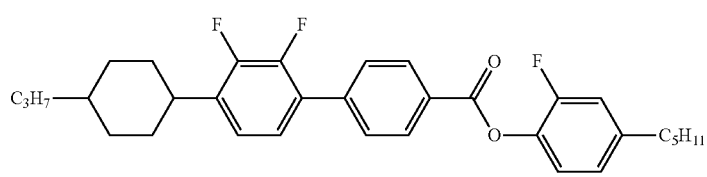 |
| 4779 | 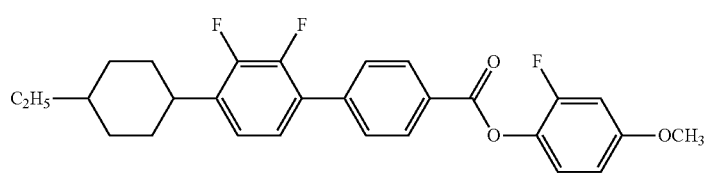 |
| 4780 | 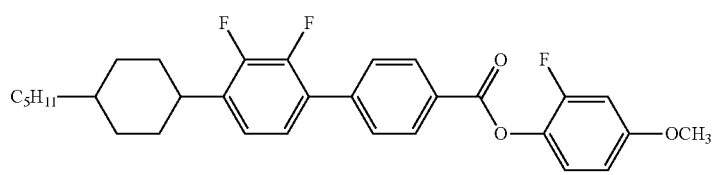 |
| 4781 | 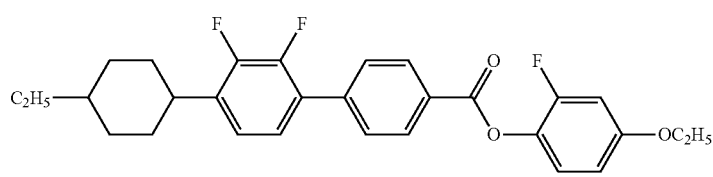 |
| 4782 | 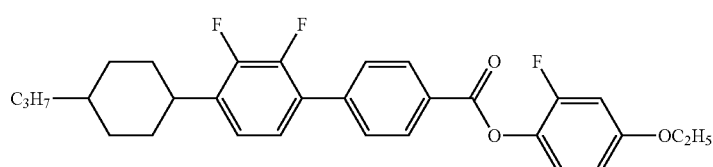 |
| 4783 | 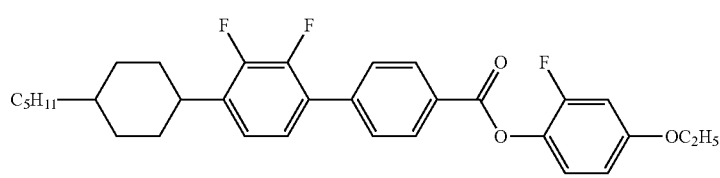 |

| No. | |
|---|---|
| 4784 | 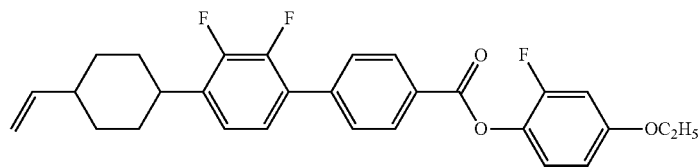 [SMILES: C=CC1CCC(c2ccc(-c3ccc(C(=O)Oc4ccc(OCC)cc4F)cc3)c(F)c2F)CC1] |
| 4785 | 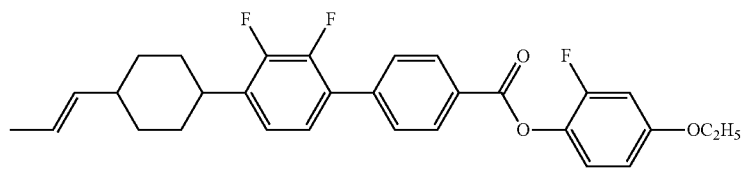 |
| 4786 | 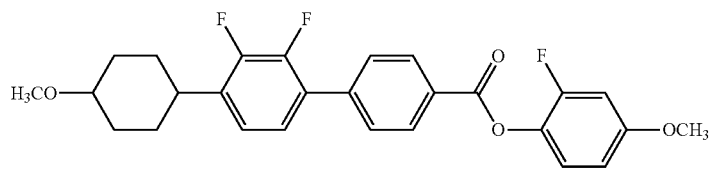 |
| 4787 | 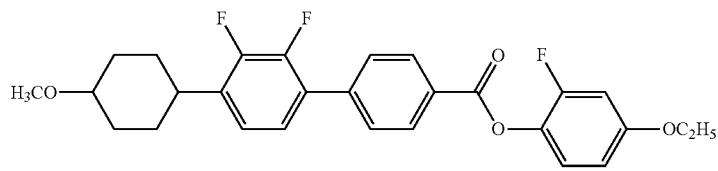 [SMILES: CCOc1ccc(OC(=O)c2ccc(-c3ccc(C4CCC(OC)CC4)c(F)c3F)cc2)c(F)c1] |
| 4788 | 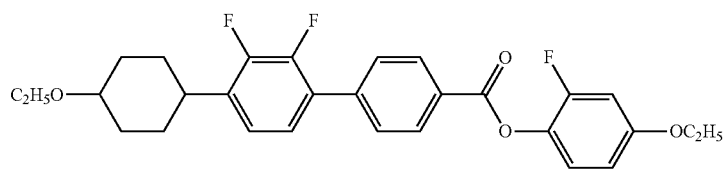 |
| 4789 | 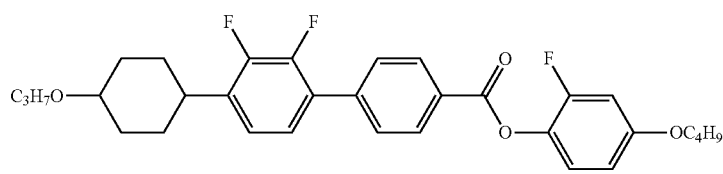 |
| 4790 | 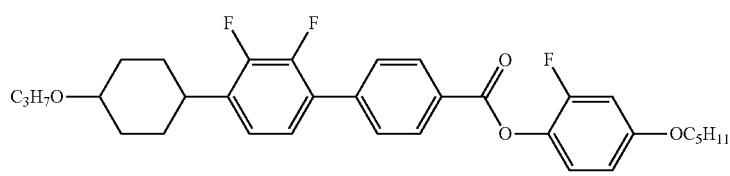 |
| 4791 | 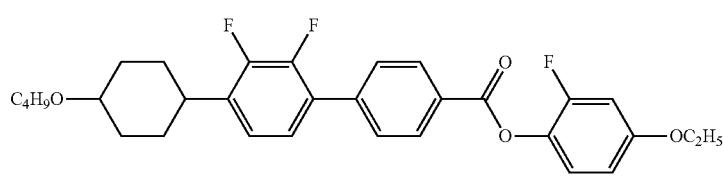 |

-continued
| No. | |
|---|---|
| 4792 | 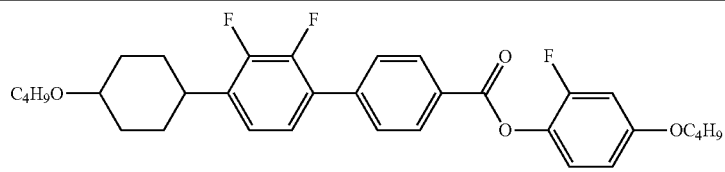 |
| 4793 | 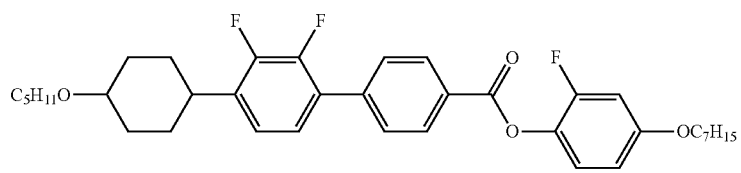 |
| 4794 | 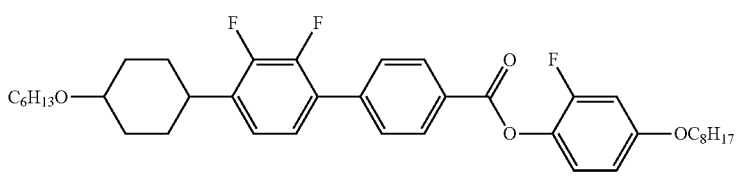 |
| 4795 | 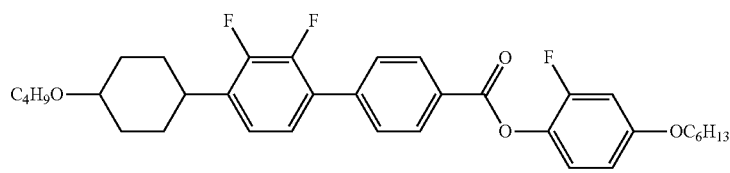 |
| 4796 | 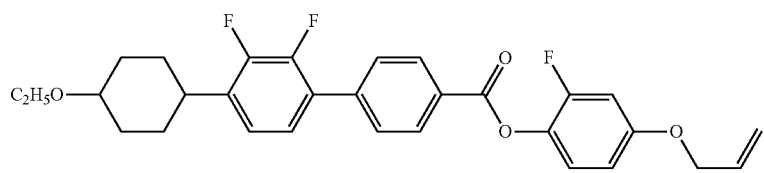 |
| 4797 | 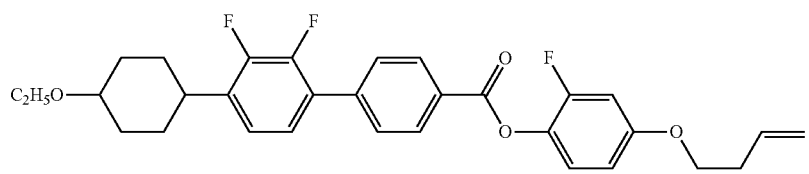 |
| 4798 | 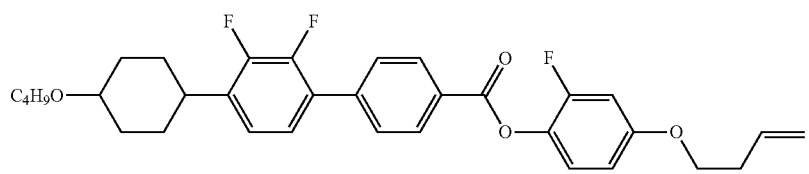 |
| 4799 | 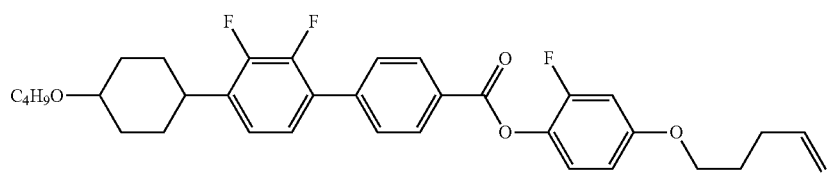 |
| 4800 | 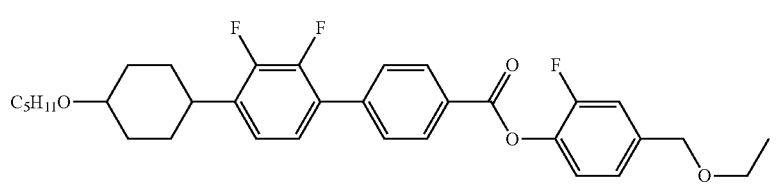 |

| No. | |
|---|---|
| 4801 | 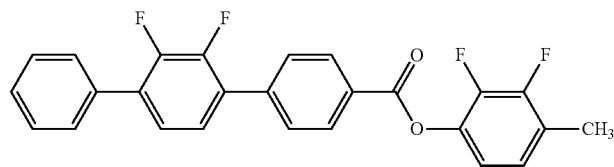 [SMILES: Cc1ccc(OC(=O)c2ccc(-c3ccc(-c4ccccc4)c(F)c3F)cc2)c(F)c1F] |
| 4802 | 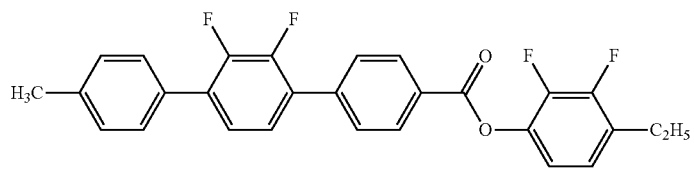 |
| 4803 | 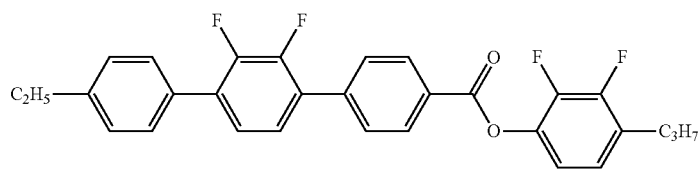 |
| 4804 | 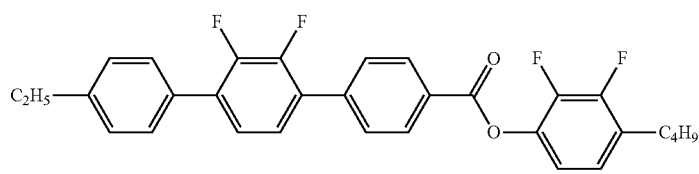 |
| 4805 | 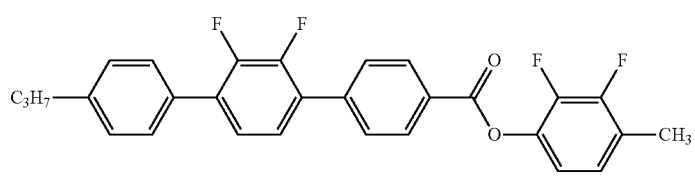 |
| 4806 | 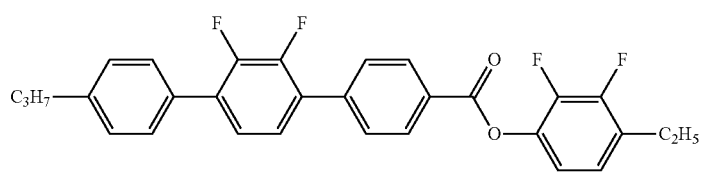 |
| 4807 | 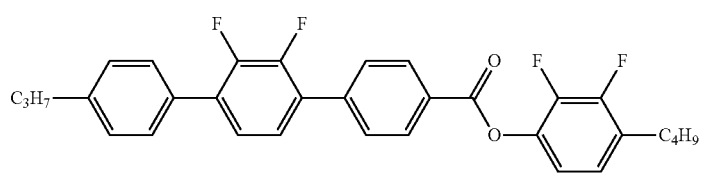 |
| 4808 | 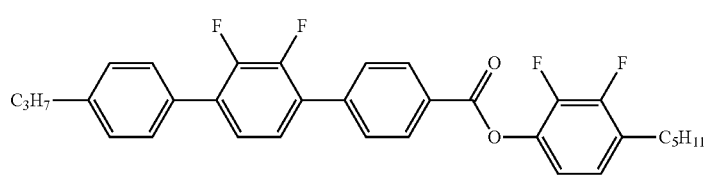 |

| No. | |
|---|---|
| 4809 | 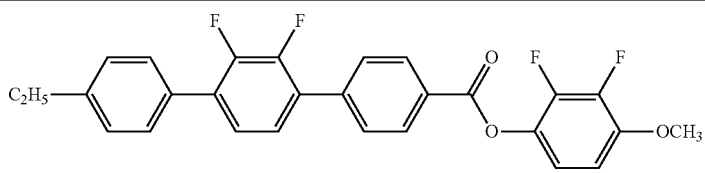 |
| 4810 | 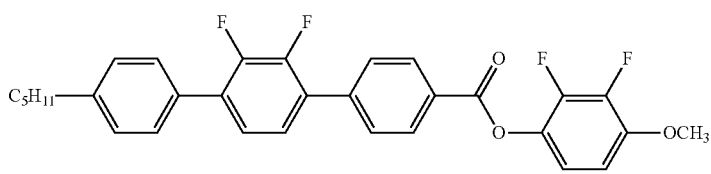 |
| 4811 | 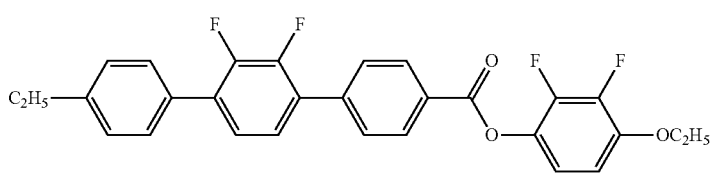 [SMILES: CCOc1ccc(OC(=O)c2ccc(-c3ccc(-c4ccc(CC)cc4)c(F)c3F)cc2)c(F)c1F] |
| 4812 | 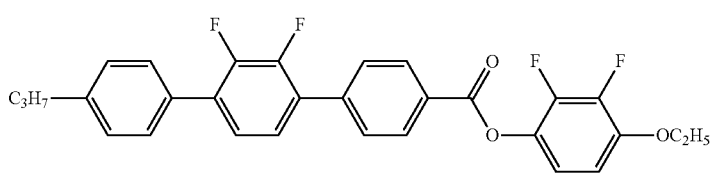 |
| 4813 | 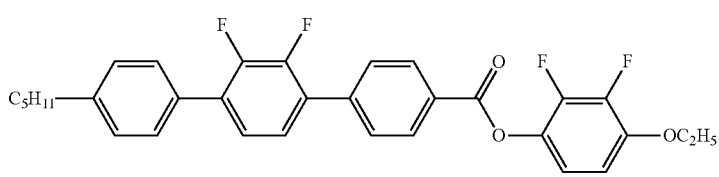 |
| 4814 | 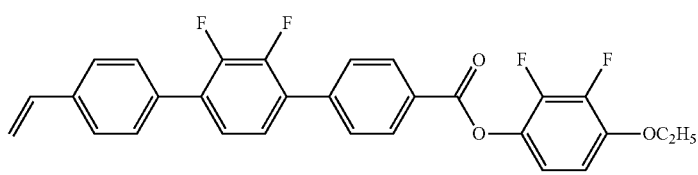 |
| 4815 | 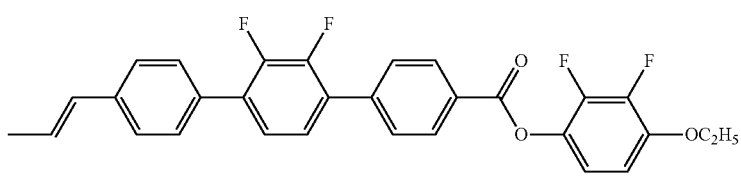 [SMILES: C/C=C/c1ccc(-c2ccc(-c3ccc(C(=O)Oc4ccc(OCC)c(F)c4F)cc3)c(F)c2F)cc1] |
| 4816 | 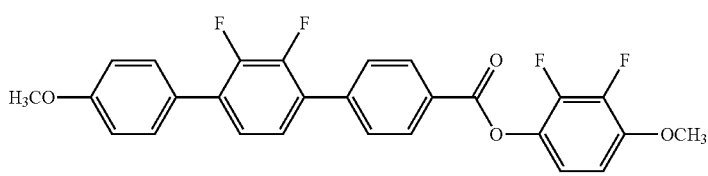 |
| 4817 | 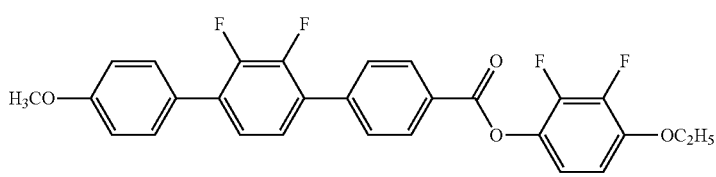 |

| No. |
|---|
| 4818 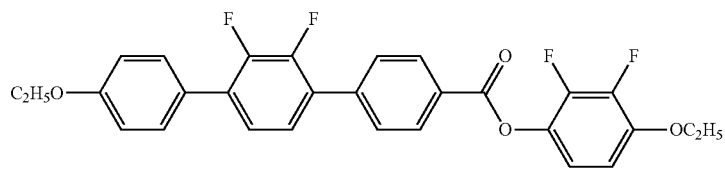 |
| 4819 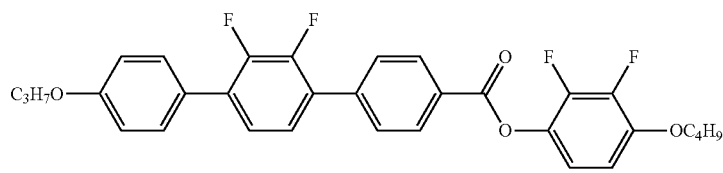 |
| 4820 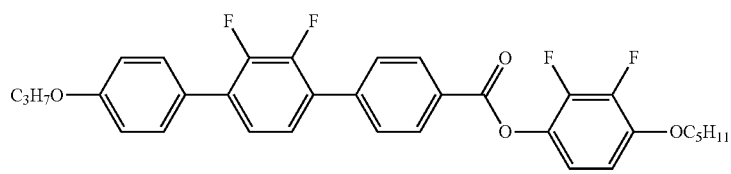 |
| 4821 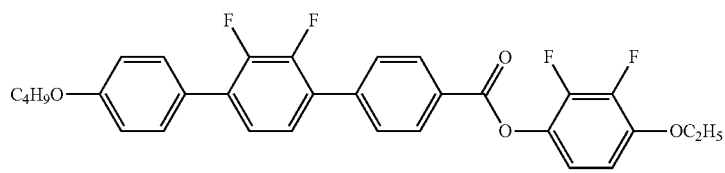 |
| 4822 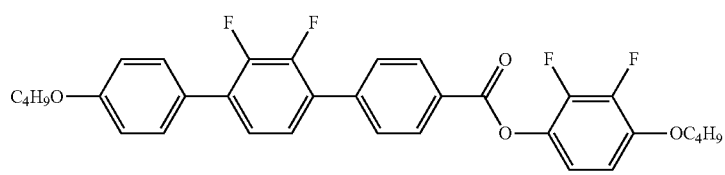 |
| 4823 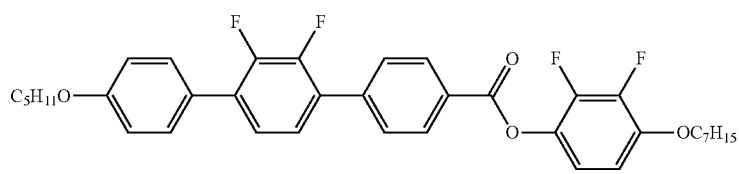 |
| 4824 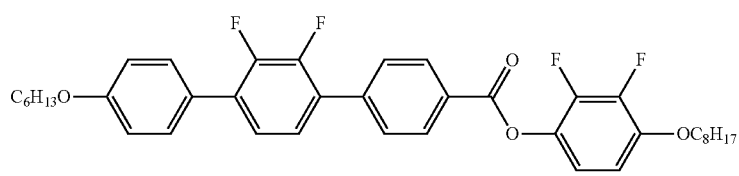 |
| 4825 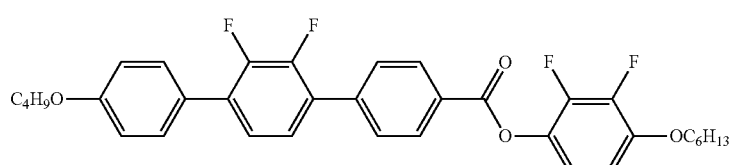 |

-continued
| No. | |
|---|---|
| 4826 | 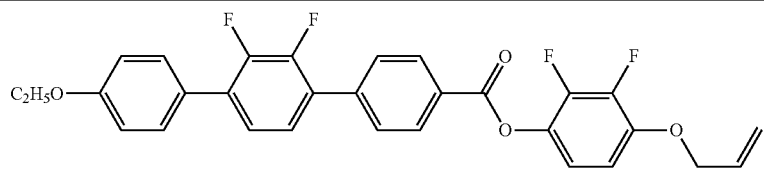 |
| 4827 | 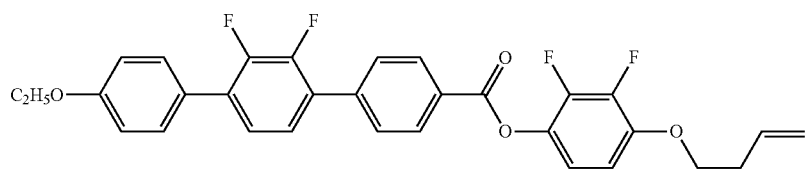 |
| 4828 | 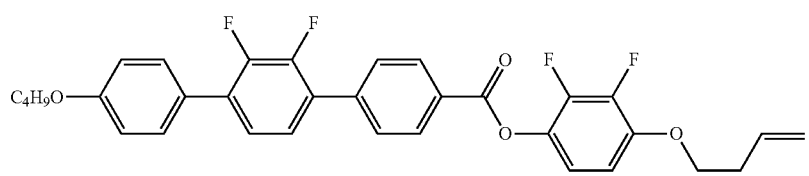 |
| 4829 | 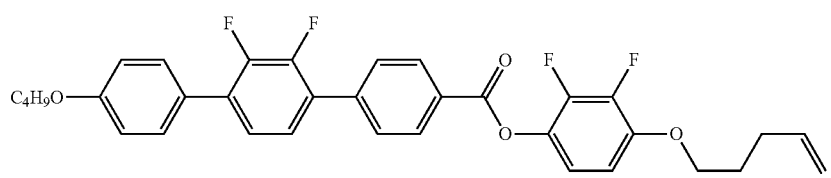 |
| 4830 | 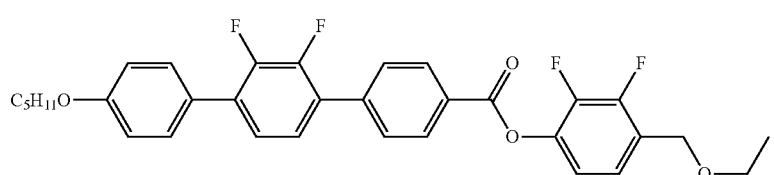 |
| 4831 | 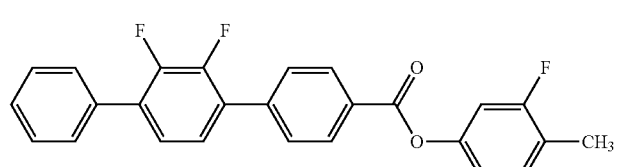 |
| 4832 | 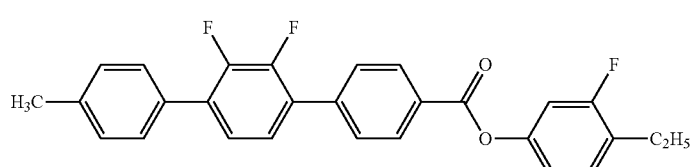 |
| 4833 | 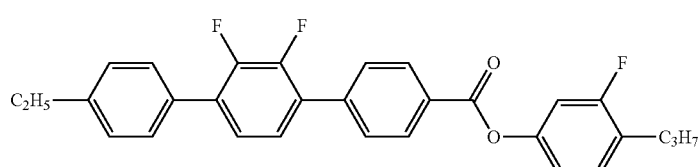 |
| 4834 | 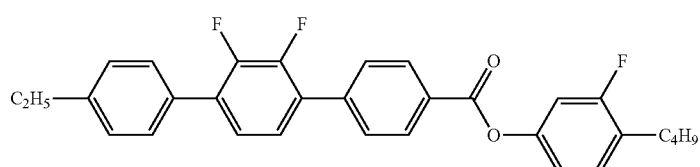 |

| No. | |
|---|---|
| 4835 | 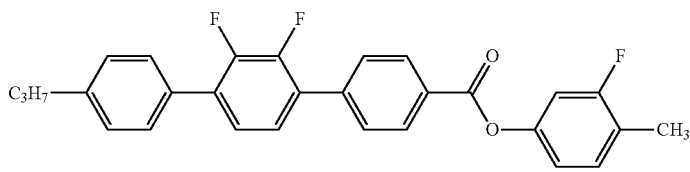 |
| 4836 | 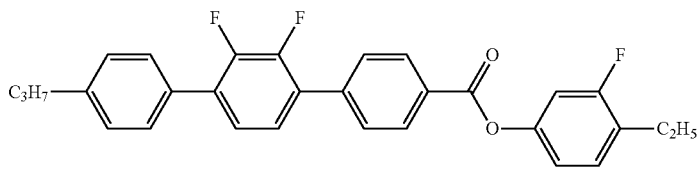 |
| 4837 | 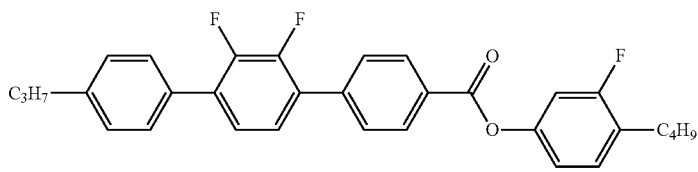 |
| 4838 | 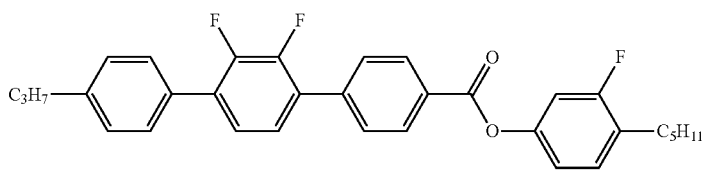 |
| 4839 | 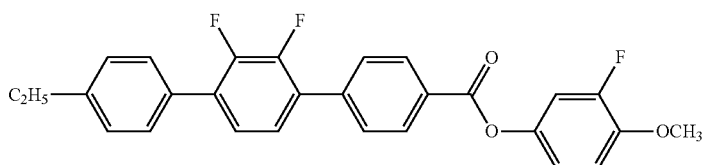 |
| 4840 | 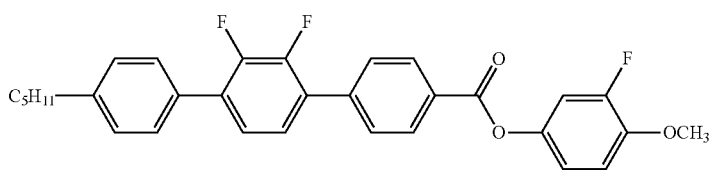 |
| 4841 | 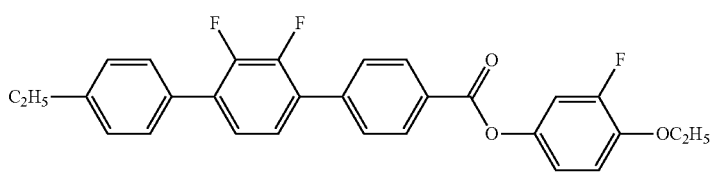 |
| 4842 | 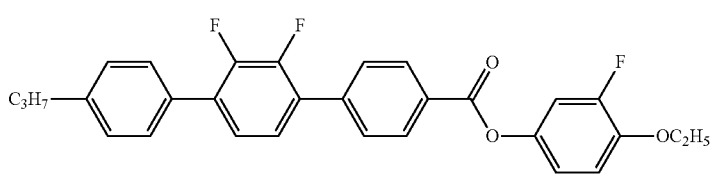 [SMILES: CCOc1ccc(OC(=O)c2ccc(-c3ccc(-c4ccc(CC)cc4)c(F)c3F)cc2)cc1F] |

| No. | |
|---|---|
| 4843 | 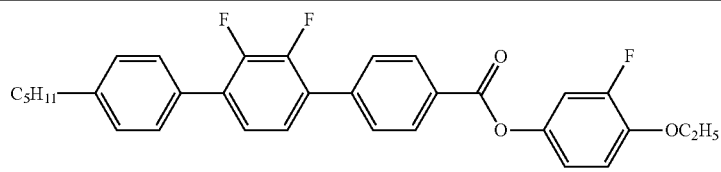 |
| 4844 | 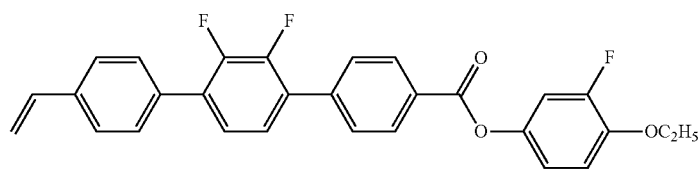 [SMILES: C=Cc1ccc(-c2ccc(-c3ccc(C(=O)Oc4ccc(OCC)c(F)c4)cc3)c(F)c2F)cc1] |
| 4845 | 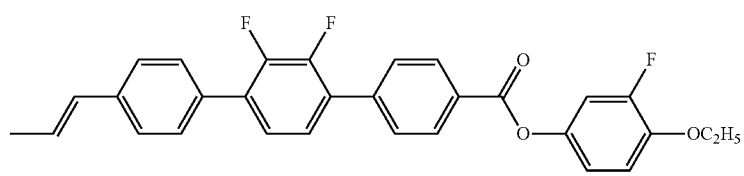 [SMILES: C/C=C/c1ccc(-c2ccc(-c3ccc(C(=O)Oc4ccc(OCC)c(F)c4)cc3)c(F)c2F)cc1] |
| 4846 | 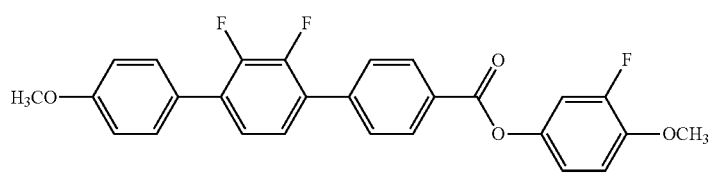 |
| 4847 | 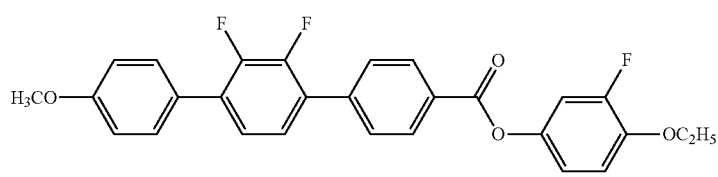 [SMILES: CCOc1ccc(OC(=O)c2ccc(-c3ccc(-c4ccc(OC)cc4)c(F)c3F)cc2)cc1F] |
| 4848 | 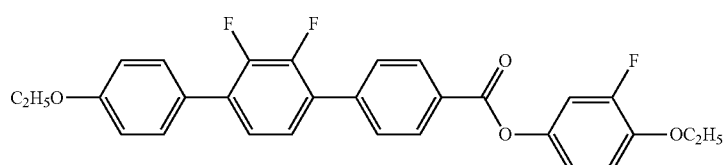 |
| 4849 | 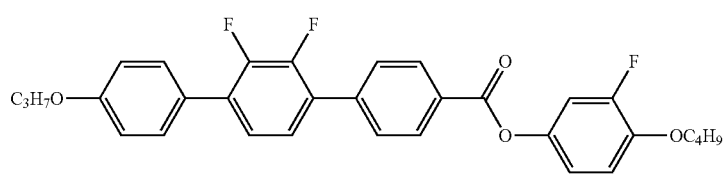 |
| 4850 | 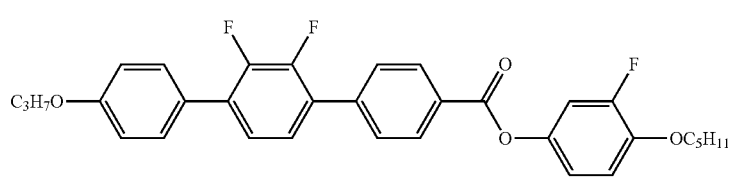 |
| 4851 | 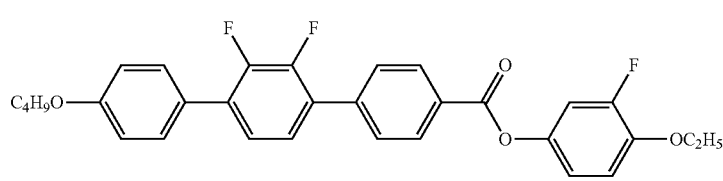 |

| No. | |
|---|---|
| 4852 | 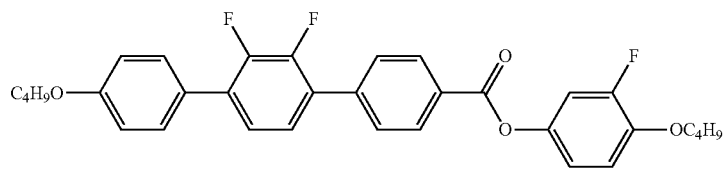 |
| 4853 | 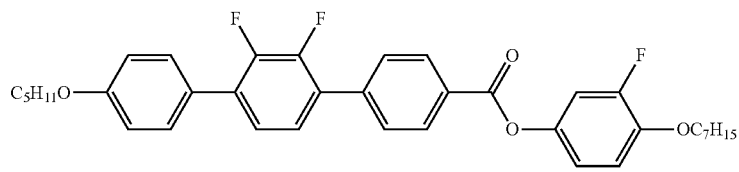 |
| 4854 | 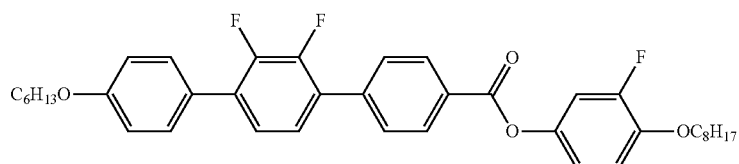 |
| 4855 | 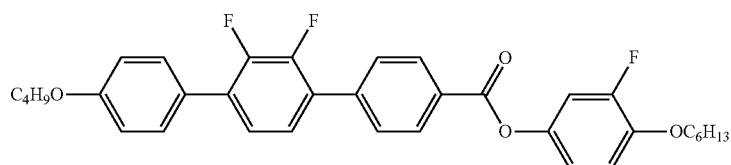 |
| 4856 | 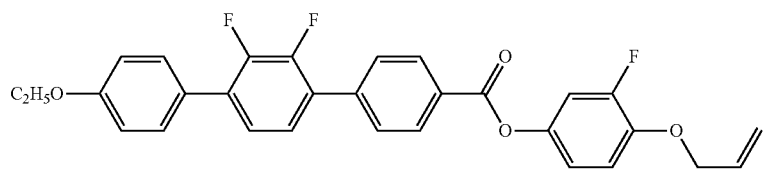 |
| 4857 | 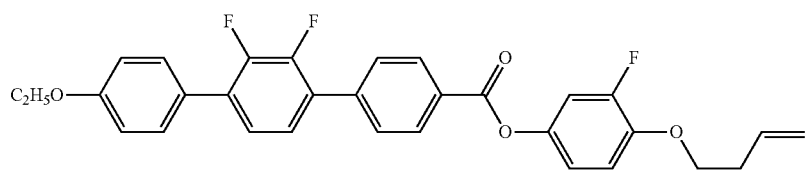 |
| 4858 | 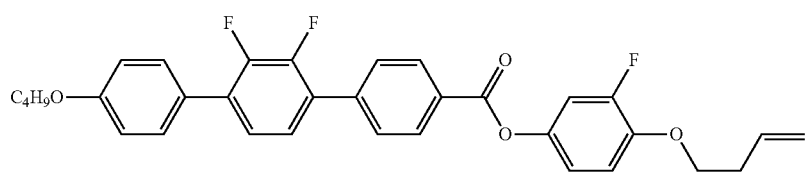 |
| 4859 | 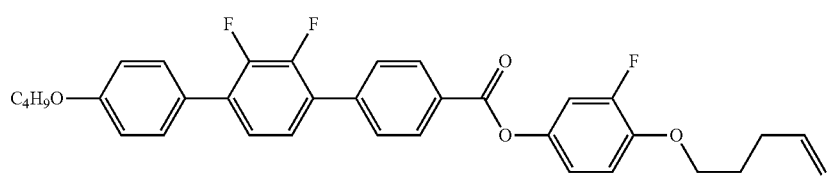 |

| No. | |
|---|---|
| 4860 | 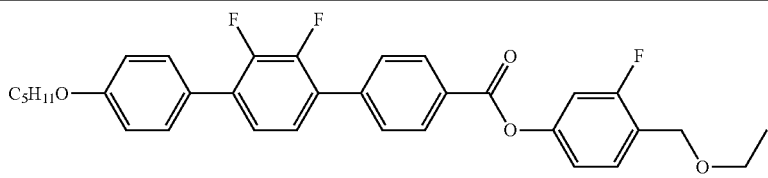 |
| 4861 | 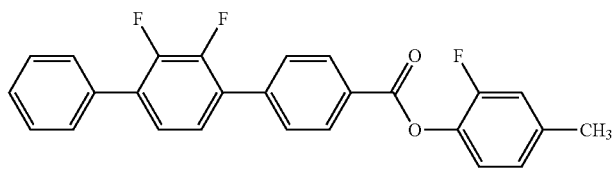 |
| 4862 | 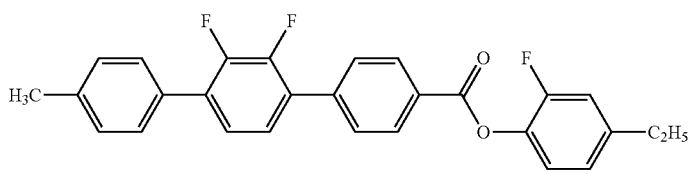 [SMILES: CCc1ccc(OC(=O)c2ccc(-c3ccc(-c4ccc(C)cc4)c(F)c3F)cc2)c(F)c1] |
| 4863 | 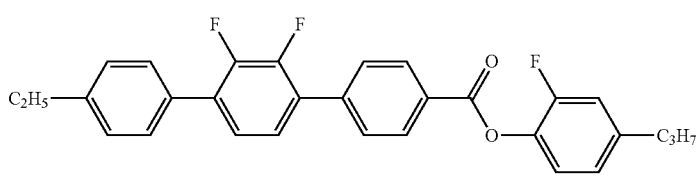 |
| 4864 | 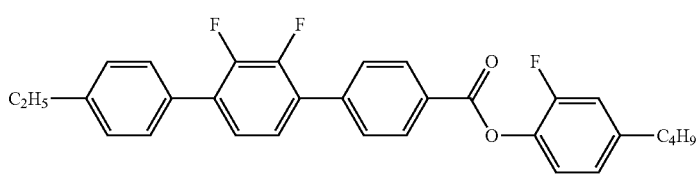 |
| 4865 | 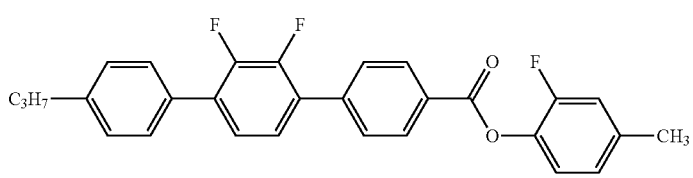 |
| 4866 | 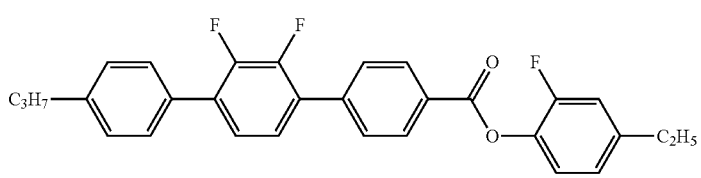 |
| 4867 | 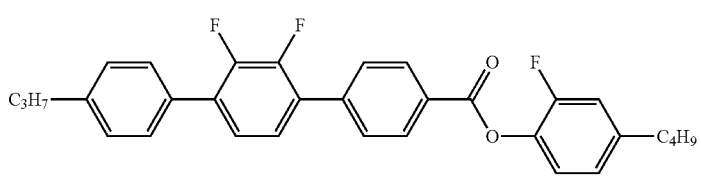 |
| 4868 | 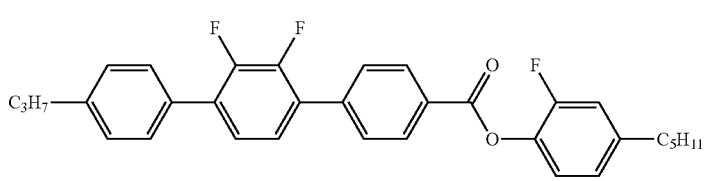 |

| No. | |
|---|---|
| 4869 | 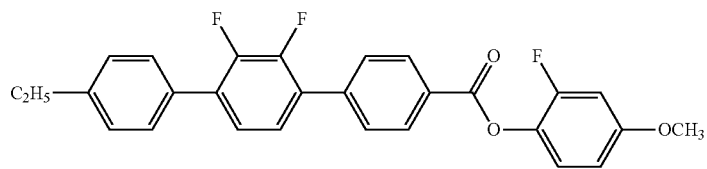 |
| 4870 | 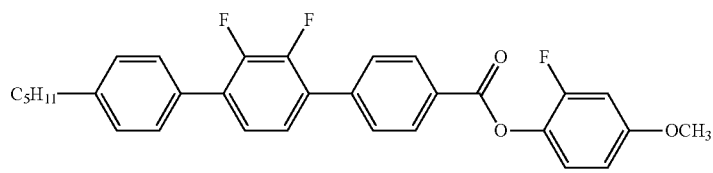 |
| 4871 | 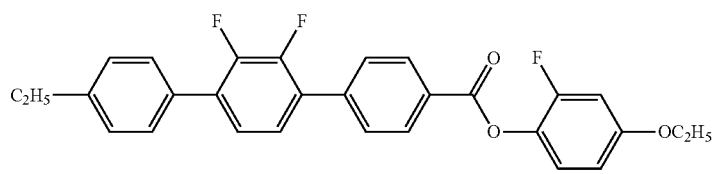 |
| 4872 | 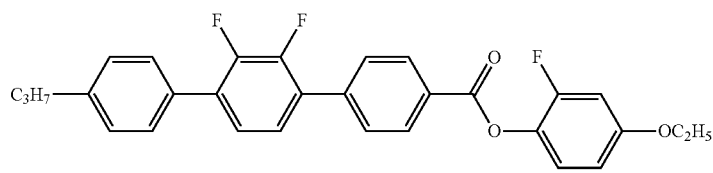 [SMILES: CCOc1ccc(OC(=O)c2ccc(-c3ccc(-c4ccc(CC)cc4)c(F)c3F)cc2)c(F)c1] |
| 4873 | 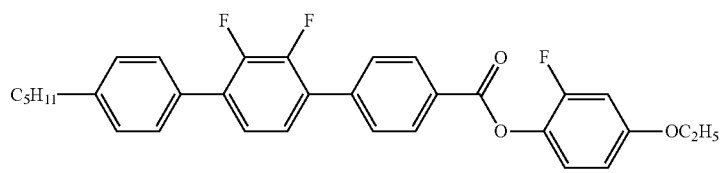 |
| 4874 | 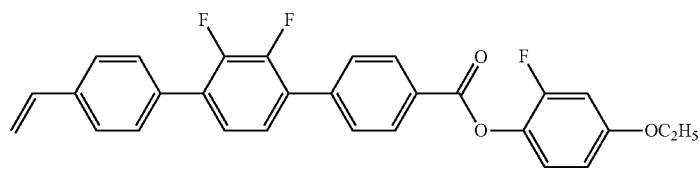 |
| 4875 | 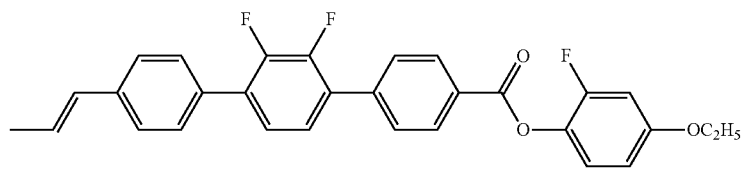 |
| 4876 | 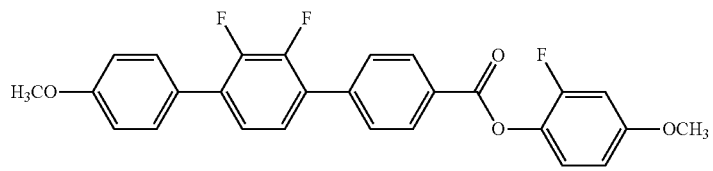 [SMILES: COc1ccc(-c2ccc(-c3ccc(C(=O)Oc4ccc(OC)cc4F)cc3)c(F)c2F)cc1] |

| No. | |
|---|---|
| 4877 | 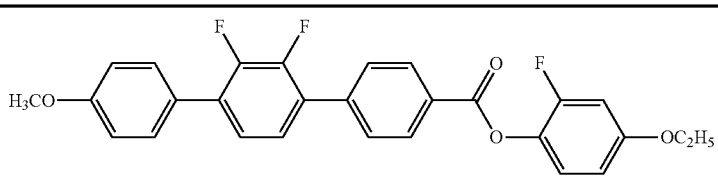 |
| 4878 | 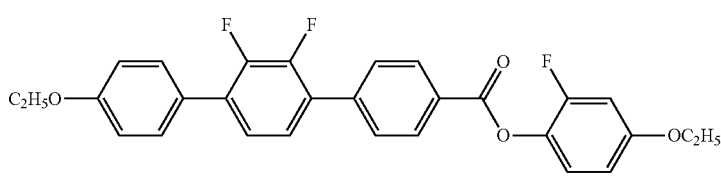 |
| 4879 | 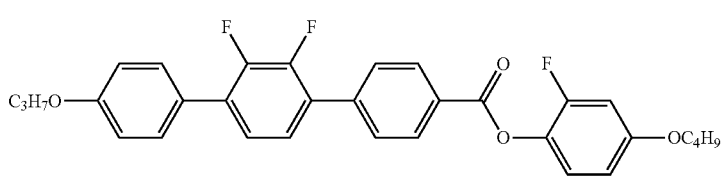 |
| 4880 | 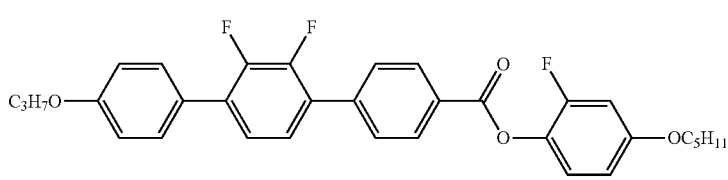 |
| 4881 | 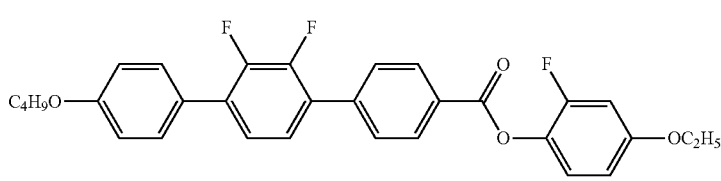 |
| 4882 | 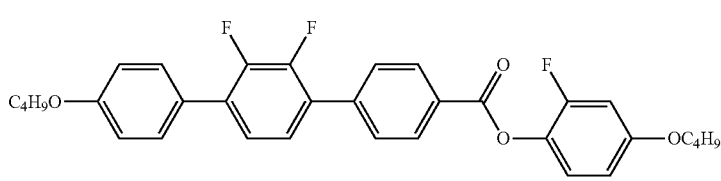 |
| 4883 | 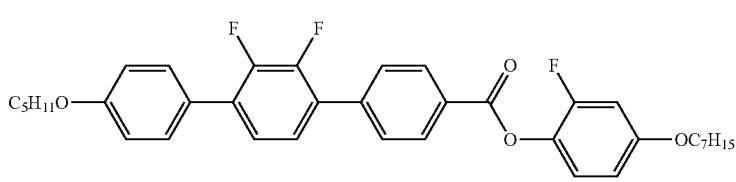 |
| 4884 | 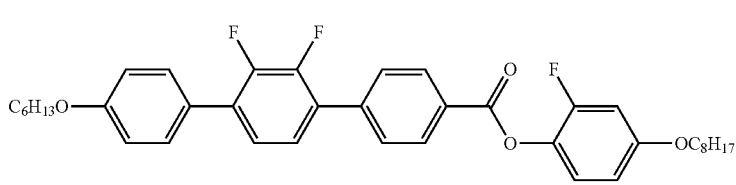 |
| 4885 | 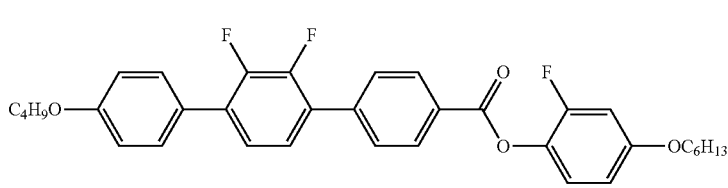 |

-continued

| No. | |
|---|---|
| 4886 | 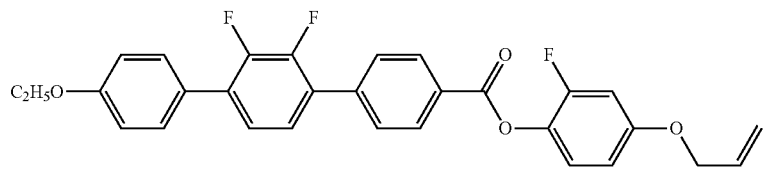 |
| 4887 | 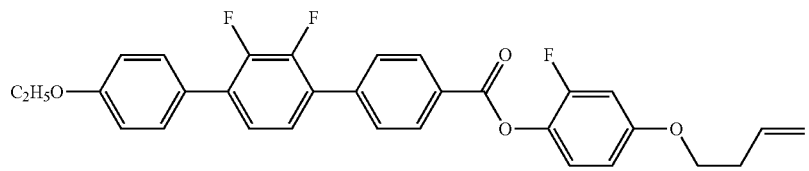 |
| 4888 | 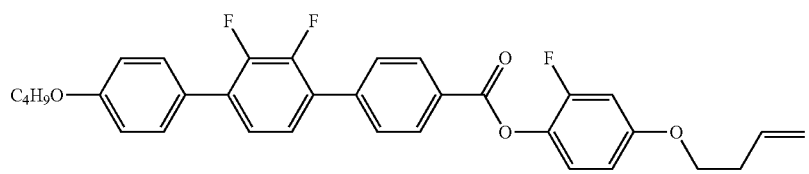 |
| 4889 | 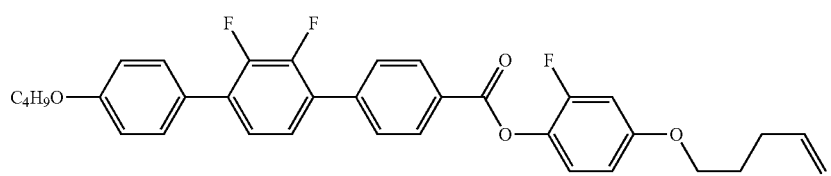 |
| 4890 | 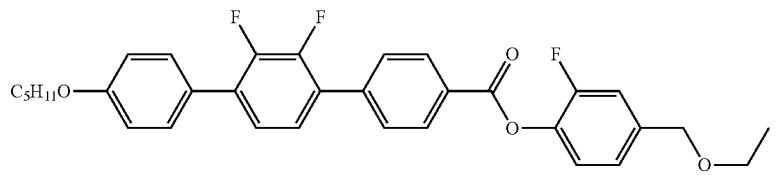 |

Comparative Example 1

As a comparative example, 4-(2,3-difluoro-4-ethoxy-1,1'-biphenylethyl)-trans-4-propyl-(2-fluorophenyl)cyclohexane (F) was synthesized.

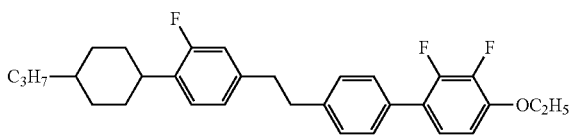

(F)

The chemical shift δ (ppm) of $^1$H-NMR analysis was as follows, and the obtained compound was identified as 4-(2,3-difluoro-4-ethoxy-1,1'-biphenylethyl)-trans-4-propyl-(2-fluorophenyl)cyclohexane (F). The solvent for measurement was $CDCl_3$.

Chemical shift δ (ppm); 7.43 (d, 2H), 7.26 (t, 3H), 7.14 (t, 1H), 7.09 (td, 1H), 6.93 (d, 1H), 6.86 (d, 1H), 6.79 (t, 1H), 4.15 (q, 2H), 2.93 (m, 4H), 2.79 (tt, 1H), 1.85 (m, 4H), 1.53-1.41 (m, 5H), 1.39-1.18 (m, 5H), 1.12-1.02 (m, 2H) and 0.90 (t, 3H).

The transition temperature of the compound (F) was as follows.

Transition temperature: C 81.5 N 209.5 I.

Five compounds referred to as the mother liquid crystals (i), which were described above, were mixed and the mother liquid crystals (i) having a nematic phase were prepared. The physical properties of the mother liquid crystals (i) were as follows.

Maximum temperature $(T_{NI})$=74.6° C.

Viscosity $(\eta_{20})$=18.9 mPa·s.

Optical anisotropy (Δn)=0.087.

Dielectric anisotropy (Δ∈)=−1.3.

The liquid crystal composition (ii) consisting of 85% by weight of the mother liquid crystals (i) and 15% by weight of 4-(2,3-difluoro-4-ethoxy-1,1'-biphenylethyl)-trans-4-propyl-(2-fluorophenyl)cyclohexane (F) was prepared. Extrapolated values on the physical properties of the comparative compound (E) were calculated on the basis of measurement on the physical properties of the liquid crystal composition (ii) obtained, and of the extrapolation of the measured values. The values were as follows.

Maximum temperature $(T_{NI})$=195.3° C.

Optical anisotropy (Δn)=0.207.

Dielectric anisotropy (Δ∈)=−4.76.

Example 10

Physical Properties of the Compound No. 1843

The liquid crystal composition (iii) consisting of 85% by weight of the mother liquid crystals (i) and 15% by weight of 4-ethoxy-2,3-difluoro-1,1'-biphenylbenzoic acid trans-4-pentylcyclohexyl-2,3-difluorophenyl ester (No. 1843) obtained in Example 7 was prepared. Physical property values of the compound (No. 1843) were calculated on the basis of measurement on the physical properties of the liquid crystal composition (iii) obtained and of the extrapolation of the measured values. The values were as follows.

Maximum temperature ($T_{NI}$)=247.9° C.
Optical anisotropy ($\Delta n$)=0.227.
Dielectric anisotropy ($\Delta \in$)=−5.82.

From these results, it was found the compound No. 1843 had a low melting point, a high maximum temperature ($T_{NI}$), a large optical anisotropy ($\Delta n$) and a large negative dielectric anisotropy ($\Delta \in$).

Moreover, the compound No. 1843 was found to have a higher maximum temperature ($T_{NI}$), a larger optical anisotropy ($\Delta n$) and a larger negative dielectric anisotropy ($\Delta \in$) as compared with those of the comparative compound (F).

Comparative Example 2

As a comparative example, 4-ethoxy-2,3-difluoro-4'-(4-pentylcyclohexylphenoxymethyl)-1,1'-biphenyl (G) was synthesized.

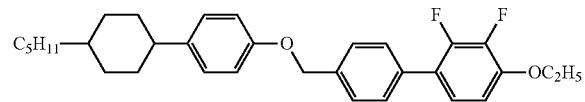

(G)

The chemical shift δ (ppm) of $^1$H-NMR analysis was as follows, and that the obtained compound was identified as 4-ethoxy-2,3-difluoro-4'-(4-pentylcyclohexylphenoxymethyl)-1,1'-biphenyl (G). The solvent for measurement was CDCl$_3$.

Chemical shift δ (ppm); 7.50 (q, 4H), 7.14 (d, 2H), 7.09 (td, 1H), 6.92 (d, 1H), 6.78 (t, 1H), 4.17 (q, 2H), 2.42 (tt, 1H), 1.86 (m, 4H), 1.53-1.17 (m, 13H), 1.08-0.98 (m, 2H), and 0.89 (t, 3H).

The transition temperature of the compound (G) was as follows.

Transition temperature: C 136.2 $S_A$ 164.4 N 219.7 I.

The liquid crystal composition (iv) consisting of 95% by weight of the mother liquid crystals (i) and 5% by weight of 4-ethoxy-2,3-difluoro-4'-(trans-4-pentylcyclohexylphenoxymethyl)-1,1'-biphenyl (G) synthesized was prepared. The physical property values of the comparative compound (G) were calculated on the basis of measurement on the physical properties of the liquid crystal composition (iv) obtained and of the extrapolation of the measured values. The values were as follows.

Optical anisotropy ($\Delta n$)=0.167.
Dielectric anisotropy ($\Delta \in$)=−4.33.
Viscosity (η)=139.3 mPa·s.
The elastic constant $K_{33}$ of the liquid crystal composition (v) was 14.37 pN.

Example 11

Physical Properties of the Compound No. 1123

The liquid crystal composition (v) consisting of 95% by weight of the mother liquid crystals (i) and 5% by weight of 4-ethoxy-2,3-difluoro-4'-[2,3-difluoro-4-(4-pentylcyclohexyl)phenoxymethyl]-1,1'-biphenyl (No. 1123) obtained in Example 1 was prepared. The physical property values of the compound No. 1123 were calculated on the basis of measurement on the physical properties of the liquid crystal composition (v) obtained and of the extrapolation of the measured values. The values were as follows.

Optical anisotropy ($\Delta n$)=0.207.
Dielectric anisotropy ($\Delta \in$)=−7.40.
Viscosity (η)=91.7 mPa·s.
The elastic constant $K_{33}$ of the liquid crystal composition (v) was 15.79 pN.

From these results, it was found the compound No. 1123 had a low melting point, a high maximum temperature ($T_{NI}$), a large optical anisotropy ($\Delta n$) and a large negative dielectric anisotropy ($\Delta \in$).

Moreover, the compound (No. 1123) was found to have a larger optical anisotropy ($\Delta n$), a larger negative dielectric anisotropy ($\Delta \in$), a lower melting point, a smaller viscosity (η) and a larger elastic constant $K_{33}$, as compared with those of the comparative compound (G).

Comparative Example 3

As a comparative example, 4-ethoxy-2,3,2",3"-tetrafluoro-4"-(4-pentylphenylethyl)-1,1"-terphenyl (H) similar to the compound (E) was synthesized.

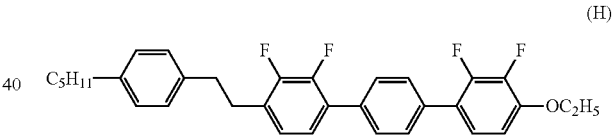

(H)

The chemical shift δ (ppm) of $^1$H-NMR analysis was as follows, and the compound obtained was identified as 4-ethoxy-2,3,2",3"-tetrafluoro-4"-(4-pentylphenylethyl)-1,1"-terphenyl (H). The solvent for measurement was CDCl$_3$.

Chemical shift δ (ppm); 7.60 (dd, 4H), 7.18-7.10 (m, 6H), 6.97 (t, 1H), 6.82 (td, 1H), 4.18 (q, 2H), 3.00 (m, 2H), 2.93 (m, 2H), 2.58 (t, 2H), 1.61 (m, 2H), 1.49 (t, 3H), 1.39-1.27 (m, 4H) and 0.89 (t, 3H).

The transition temperature of the compound (H) was as follows.

Transition temperature: C 146.1 N 209.0 I.

The liquid crystal composition (vi) consisting of 95% by weight of the mother liquid crystals (i) and 5% by weight of 4-ethoxy-2,3,2",3"-tetrafluoro-4"-(4-pentylphenylethyl)-1,1"-terphenyl (H) was prepared. The physical property values of the comparative compound (H) were calculated on the basis of measurement on the physical properties of the liquid crystal composition (vi) obtained and of the extrapolation of the measured values. The values were as follows.

Optical anisotropy ($\Delta n$)=0.167.
Dielectric anisotropy ($\Delta \in$)=−4.33.
Viscosity (η)=139.3 mPa·s.
The elastic constant $K_{33}$ of the liquid crystal composition (vi) was 14.37 pN.

Example 12

Physical Properties of the Compound No. 1041

The liquid crystal composition (vii) consisting of 95% by weight of the mother liquid crystals (i) and 5% by weight of trans-4-(2,3-difluoro-4-ethoxyphenyl)-4-[2,3-difluoro-4'-butoxy-1,1'-biphenoxymethyl]cyclohexane (No. 1041) obtained in Example 3 was prepared. The physical property values of the compound (No. 1041) were calculated on the basis of measurement on the physical properties of the liquid crystal composition (vii) obtained and of the extrapolation of the measured values. The values were as follows.

Maximum temperature $(T_{NI})$=202.6° C.;
Dielectric anisotropy $(\Delta\epsilon)$=−6.44.
Viscosity $(\eta)$=101.7 mPa·s.

From these results, it was found that the liquid crystal compound No. 1041 had a low melting point, a high maximum temperature $(T_{NI})$ and a large negative dielectric anisotropy $(\Delta\epsilon)$.

Moreover, the compound No. 1041 was found to have a higher maximum temperature $(T_{NI})$, a larger negative dielectric anisotropy $(\Delta\epsilon)$, a lower melting point and a smaller viscosity $(\eta)$, as compared with those of the comparative compound (H).

[Examples of Liquid Crystal Compositions]

Hereinafter, the liquid crystal compositions obtained by means of the invention will be explained in detail on the basis of examples. Compounds used in the examples are expressed as symbols according to the notations in the table below. In the table, 1,4-cyclohexylene has a trans-configuration. The ratio (percentage) of each compound means a weight percentage (% by weight) based on the total weight of the liquid crystal composition, unless otherwise indicated. Characteristic values of the liquid crystal composition obtained are shown in the last part of each example.

A number described next to the name of a compound in each example corresponds to that of the formula of the compound used for the first to third components of the invention described above. When the symbol "-" is only given instead of the number of a formula, it means another compound which is different from that of the components.

The notations using symbols for compounds are shown below.

TABLE

Method of Description of Compound using Symbols
R—(A$_1$)—Z$_1$— ... —Z$_n$—(A$_n$)—R'

| 1) Left Terminal Group R— | Symbol |
|---|---|
| $C_nH_{2n+1}$— | n— |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right Terminal Group —R' | Symbol |
|---|---|
| —$C_nH_{2n+1}$ | —n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | —nV |
| —CH=$CF_2$ | —VFF |
| —$COOCH_3$ | —EMe |

TABLE-continued

Method of Description of Compound using Symbols
R—(A$_1$)—Z$_1$— ... —Z$_n$—(A$_n$)—R'

| 3) Bonding Group —Z$_n$— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |

| 4) Ring Structure —A$_n$— | Symbol |
|---|---|
| (cyclohexane ring) | H |
| (cyclohexene ring) | Ch |
| (tetrahydropyran ring, O top-left) | Dh |
| (tetrahydropyran ring, O top-right) | dh |
| (dioxane ring, 1,3-dioxane) | G |
| (dioxane ring, alternate) | g |
| (benzene ring) | B |
| (2-fluoro benzene) | B(2F) |
| (3-fluoro benzene) | B(3F) |
| (2,3-difluoro benzene) | B(2F,3F) |
| (2-fluoro-3-chloro benzene) | B(2F,3Cl) |

TABLE-continued

Method of Description of Compound using Symbols
R—(A$_1$)—Z$_1$— ... —Z$_n$—(A$_n$)—R'

  B(2Cl,3F)

5) Example of Description

Example 1. 5-HB(2F,3F)O1HB(2F,3F)—O2

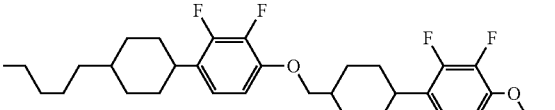

Example 2. 5-HB(2F,3F)O1BB(2F,3F)—O2

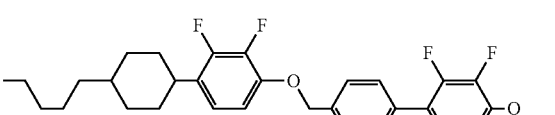

Example 3. 3-HHB-3

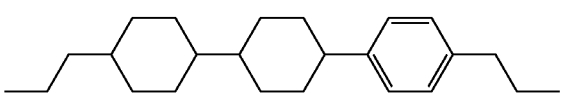

Example 4. 5-HBB(2F,3Cl)—O2

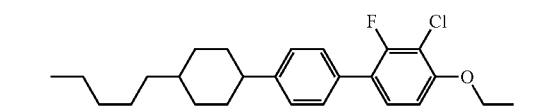

Characteristics were measured according to the following methods. Most methods are described in the Standard of Electric Industries Association of Japan, EIAJ•ED-2521 A or those with some modifications.

(1) Maximum Temperature of Nematic Phase (NI; ° C.)

A sample was placed on a hot plate in a melting point apparatus equipped with a polarizing microscope and was heated at the rate of 1° C. per minute. Temperature was measured when part of the sample began to change from a nematic phase to an isotropic liquid. Hereinafter, the maximum temperature of a nematic phase may be abbreviated to the "maximum temperature."

(2) Minimum Temperature of Nematic Phase (TC; ° C.)

Samples having a nematic phase were respectively kept in freezers at 0° C., −10° C., −20° C., −30° C. and −40° C. for ten days, and then liquid crystal phases were observed. For example, when the sample still remained to be a nematic phase at −20° C. and changed to crystals or a smectic phase at −30° C., Tc was expressed as ≦−20° C. Hereinafter, the minimum temperature of a nematic phase may be abbreviated to the "minimum temperature."

(3) Optical Anisotropy (Δn; measured at 25° C.)

The optical anisotropy was measured by use of an Abbe refractometer with a polarizing plate attached to the ocular, using light at a wavelength of 589 nm. The surface of the main prism was rubbed in one direction, and then a sample was dropped onto the main prism. A refractive index (n∥) when the direction of polarization was parallel to that of rubbing and a refractive index (n⊥) when the direction of polarization was perpendicular to that of rubbing were measured. The value (Δn) of optical anisotropy was calculated from the formula of Δn=n∥−n⊥.

(4) Viscosity (η; Measured at 20° C.; mPa·s)

Viscosity was measured by use of an E-type viscometer.

(5) Dielectric Anisotropy (Δ∈; Measured at 25° C.)

A solution of octadecyltriethoxysilane (0.16 mL) in ethanol (20 mL) was applied to a thoroughly cleaned glass substrate. The glass substrate was rotated with a spinner, and then heated at 150° C. for one hour. A VA device in which a distance (cell gap) was 20 μm was assembled from the two glass substrates.

A polyimide alignment film was prepared on glass substrates in a similar manner. After a rubbing-treatment to the alignment film obtained on the glass substrates, a TN device in which a distance between the two glass substrates was 9 μm and the twist angle was 80 degrees was assembled.

A sample (a liquid crystal composition, or a mixture of a compound and mother liquid crystals) was put in the VA device obtained, a voltage of 0.5 V (1 kHz, sine waves) was applied, and then a dielectric constant (∈∥) in a major axis direction of the liquid crystal molecules was measured.

The sample (the liquid crystal composition, or the mixture of the compound and the mother liquid crystals) was put in the TN device obtained, a voltage of 0.5 V (1 kHz, sine waves) was applied, and then the dielectric constant (∈⊥) in a minor axis direction of liquid crystal molecules was measured. The value of dielectric anisotropy was calculated from the equation of Δ∈=∈∥−∈⊥.

A composition in which this value is negative has negative dielectric anisotropy.

(6) Voltage Holding Ratio (VHR; Measured at 25° C. and 100° C.; %)

A sample was put in a cell having a polyimide alignment film in which the distance between two glass substrates (cell gap) was 6 μm, giving TN device. The TN device was charged at 25° C. by applying pulse voltage (60 microseconds at 5V). The waveforms of the voltage applied to the TN device were observed with a cathode ray oscilloscope and an area between a voltage curve and a horizontal axis in a unit period (16.7 milliseconds) was measured. An area was similarly measured based on the waveform of the applied voltage after the TN device had been removed. The value of the voltage holding ratio (%) was calculated from the equation: (voltage holding ratio)=(value of the area in the presence of a TN device)/(value of the area in the absence of TN device)×100.

The voltage holding ratio thus obtained was referred to as "VHR-1". Then, the TN device was heated at 100° C. for 250 hours. After the TN device had been allowed to come to 25° C., the voltage holding ratio was measured by a method similar to that described above. The voltage holding ratio obtained after the heating test was referred to as "VHR-2." The heating test means an acceleration test and was used as a test corresponding to a long-term durability test for the TN device.

Example 13

| | | |
|---|---|---|
| 5-HB(2F,3F)O1HB(2F,3F)-O2 | (No. 943) | 6% |
| 5-HB(2F,3F)O1BB(2F,3F)-O2 | (No. 1123) | 6% |
| 3-HH-4 | (2-1) | 5% |
| 3-HB(2F,3F)-O2 | (3-1) | 16% |
| 5-HB(2F,3F)-O2 | (3-1) | 21% |
| 2-HHB(2F,3F)-1 | (3-29) | 5% |

-continued

| | | |
|---|---|---|
| 3-HHB(2F,3F)-1 | (3-29) | 7% |
| 3-HHB(2F,3F)-O2 | (3-29) | 14% |
| 5-HHB(2F,3F)-O2 | (3-29) | 20% |

NI = 83.8° C.; Δn = 0.095; η = 34.4 mPa·s; Δε = −5.0.

Example 14

| | | |
|---|---|---|
| 4O-BB(2F,3F)O1HB(2F,3F)-O2 | (No. 1041) | 6% |
| 3-HB-O1 | (2-4) | 15% |
| 3-HH-4 | (2-1) | 5% |
| 3-HB(2F,3F)-O2 | (3-1) | 12% |
| 5-HB(2F,3F)-O2 | (3-1) | 12% |
| 2-HHB(2F,3F)-1 | (3-29) | 12% |
| 3-HHB(2F,3F)-1 | (3-29) | 6% |
| 3-HHB(2F,3F)-O2 | (3-29) | 13% |
| 5-HHB(2F,3F)-O2 | (3-29) | 13% |
| 3-HHB-1 | (2-25) | 6% |

NI = 91.2° C.; TC ≦ −20° C.; Δn = 0.094; η = 39.8 mPa·s.

Example 15

| | | |
|---|---|---|
| 4O-ChB(2F,3F)O1HB(2F,3F)-O2 | (No. 951) | 5% |
| 3-HB-O1 | (2-4) | 10% |
| 3-HH-4 | (2-1) | 5% |
| 3-HB(2F,3F)-O2 | (3-1) | 12% |
| 5-HB(2F,3F)-O2 | (3-1) | 12% |
| 2-HHB(2F,3F)-1 | (3-29) | 12% |
| 3-HHB(2F,3F)-1 | (3-29) | 12% |
| 3-HHB(2F,3F)-O2 | (3-29) | 13% |
| 5-HHB(2F,3F)-O2 | (3-29) | 13% |
| 6-HEB(2F,3F)-O2 | (3-29) | 6% |

NI = 88.7° C.; TC ≦ −20° C.; Δn = 0.091; η = 40.8 mPa·s; Δε = −4.0.

Example 16

| | | |
|---|---|---|
| 5-HB(2F,3F)H1OB(2F,3F)-O2 | (No. 3823) | 9% |
| 3-HH-4 | (2-1) | 8% |
| 3-H2B(2F,3F)-O2 | (3-3) | 22% |
| 5-H2B(2F,3F)-O2 | (3-3) | 22% |
| 2-HHB(2F,3Cl)-O2 | (3-59) | 2% |
| 3-HHB(2F,3Cl)-O2 | (3-59) | 3% |
| 4-HHB(2F,3Cl)-O2 | (3-59) | 2% |
| 5-HHB(2F,3Cl)-O2 | (3-59) | 2% |
| 3-HBB(2F,3Cl)-O2 | (3-93) | 9% |
| V-HHB-1 | (2-25) | 6% |
| 3-HHB-3 | (2-25) | 6% |
| 3-HHEBH-3 | (2-74) | 3% |
| 3-HHEBH-4 | (2-74) | 3% |
| 3-HHEBH-5 | (2-74) | 3% |

NI = 94.7° C.; TC ≦ −20° C.; Δn = 0.098; η = 30.0 mPa·s; Δε = −4.1.

Example 17

| | | |
|---|---|---|
| 5-HB(2F,3F)H1OB(2F,3F)-O2 | (No. 3823) | 3% |
| 4O-BB(2F,3F)H1OB(2F,3F)-O2 | (No. 3921) | 4% |
| 3-HH-4 | (2-1) | 15% |

-continued

| | | |
|---|---|---|
| 3-H2B(2F,3F)-O2 | (3-3) | 15% |
| 5-H2B(2F,3F)-O2 | (3-3) | 15% |
| 3-HHB(2F,3Cl)-O2 | (3-59) | 5% |
| 2-HBB(2F,3F)-O2 | (3-93) | 3% |
| 3-HBB(2F,3F)-O2 | (3-93) | 9% |
| 5-HBB(2F,3F)-O2 | (3-93) | 9% |
| 3-HHB-1 | (2-25) | 3% |
| 3-HHB-3 | (2-25) | 4% |
| 3-HHB-O1 | (2-25) | 3% |
| 3-HB-O2 | (2-4) | 12% |

NI = 89.3° C.; TC ≦ −20° C.; Δn = 0.106; η = 25.7 mPa·s; Δε = −4.5.

A pitch measured when 0.25 part of optically active compound (Op-5) was added to 100 parts of the above composition was 61.3 μm.

Example 18

| | | |
|---|---|---|
| 2O-B(2F,3F)BEB(2F,3F)H-5 | (No. 1843) | 3% |
| 2O-B(2F,3F)HEB(2F,3F)H-5 | (No. 1663) | 3% |
| 2-HH-3 | (2-1) | 5% |
| 3-HH-O1 | (2-1) | 4% |
| 3-HH-O3 | (2-1) | 5% |
| 5-HH-O1 | (2-1) | 4% |
| 3-HB(2F,3F)-O2 | (3-1) | 12% |
| 5-HB(2F,3F)-O2 | (3-1) | 11% |
| 3-HHB(2F,3F)-O2 | (3-59) | 14% |
| 5-HHB(2F,3F)-O2 | (3-59) | 15% |
| 3-HHB(2F,3F)-2 | (3-59) | 24% |

Example 19

| | | |
|---|---|---|
| 5-HB(2F,3F)O1HB(2F,3F)-O2 | (No. 943) | 5% |
| 5-HB(2F,3F)O1BB(2F,3F)-O2 | (No. 1123) | 5% |
| 3-HH-5 | (2-1) | 5% |
| 3-HH-4 | (2-1) | 5% |
| 3-HH-O1 | (2-1) | 6% |
| 3-HH-O3 | (2-1) | 6% |
| 3-HB-O1 | (2-4) | 5% |
| 3-HB-O2 | (2-4) | 5% |
| 3-HB(2F,3F)-O2 | (3-1) | 10% |
| 5-HB(2F,3F)-O2 | (3-1) | 10% |
| 3-HHB(2F,3F)-O2 | (3-59) | 12% |
| 5-HHB(2F,3F)-O2 | (3-59) | 13% |
| 3-HHB(2F,3F)-2 | (3-59) | 4% |
| 2-HHB(2F,3F)-1 | (3-59) | 4% |
| 3-HHEH-3 | (2-46) | 5% |

Example 20

| | | |
|---|---|---|
| 5-HB(2F,3F)O1HB(2F,3F)-O2 | (No. 943) | 6% |
| 5-HB(2F,3F)O1BB(2F,3F)-O2 | (No. 1123) | 6% |
| 2-H2H-3 | (2-2) | 5% |
| 3-H2H-V | (2-2) | 17% |
| 3-HBBH-5 | (2-69) | 3% |
| 1O1-HBBH-4 | (2-69) | 3% |
| 5-HBB(3F)B-2 | (2-73) | 3% |
| V-HB(2F,3F)-O2 | (3-1) | 7% |
| 5-HB(2F,3F)-O2 | (3-1) | 7% |
| 3-H2B(2F,3F)-O2 | (3-3) | 12% |
| 5-H2B(2F,3F)-O2 | (3-3) | 12% |
| 3-HBB(2F,3F)-O2 | (3-93) | 8% |

Example 21

| | | |
|---|---|---|
| 5-GB(2F,3F)O1HB(2F,3F)-O2 | (No. 940) | 3% |
| 4O-BB(2F,3F)H1OB(2F,3F)-O2 | (No. 3921) | 4% |
| 3-HH-4 | (2-1) | 15% |
| 3-H2B(2F,3F)-O2 | (3-3) | 15% |
| 5-H2B(2F,3F)-O2 | (3-3) | 15% |
| 3-HHB(2F,3Cl)-O2 | (3-59) | 5% |
| 2-HBB(2F,3F)-O2 | (3-93) | 3% |
| 3-HBB(2F,3F)-O2 | (3-93) | 9% |
| 5-HBB(2F,3F)-O2 | (3-93) | 9% |
| 3-HHB-1 | (2-25) | 3% |
| 3-HHB-3 | (2-25) | 4% |
| 3-HHB-O1 | (2-25) | 3% |
| 3-HB-O2 | (2-4) | 12% |

NI = 89.1° C.; Δn = 0.106; η = 26.6 mPa · s; Δε = −4.4.

Example 22

| | | |
|---|---|---|
| 5-HB(2F,3F)chB(2F,3F)-O2 | (No. 12) | 5% |
| 3-HB-O1 | (2-4) | 10% |
| 3-HH-4 | (2-1) | 5% |
| 3-HB(2F,3F)-O2 | (3-1) | 12% |
| 5-HB(2F,3F)-O2 | (3-1) | 12% |
| 2-HHB(2F,3F)-1 | (3-59) | 12% |
| 3-HHB(2F,3F)-1 | (3-59) | 12% |
| 3-HHB(2F,3F)-O2 | (3-59) | 13% |
| 5-HHB(2F,3F)-O2 | (3-59) | 13% |
| 6-HEB(2F,3F)-O2 | (3-29) | 6% |

NI = 90.5° C.; TC ≦ −20° C.; Δn = 0.091; η = 38.6 mPa · s; Δε = −4.0.

Example 23

| | | |
|---|---|---|
| 5-HB(2F,3F)chB(2F,3F)-O2 | (No. 12) | 3% |
| 5-HB(2F,3F)HB(2F,3F)-O2 | (No. 13) | 4% |
| 3-HH-4 | (2-1) | 15% |
| 3-H2B(2F,3F)-O2 | (3-3) | 15% |
| 5-H2B(2F,3F)-O2 | (3-3) | 15% |
| 3-HHB(2F,3Cl)-O2 | (3-59) | 5% |
| 2-HBB(2F,3F)-O2 | (3-93) | 3% |
| 3-HBB(2F,3F)-O2 | (3-93) | 9% |
| 5-HBB(2F,3F)-O2 | (3-93) | 9% |
| 3-HHB-1 | (2-25) | 3% |
| 3-HHB-3 | (2-25) | 4% |
| 3-HHB-O1 | (2-25) | 3% |
| 3-HB-O2 | (2-4) | 12% |

NI = 88.9° C.; Δn = 0.103; η = 25.5 mPa · s; Δε = −4.4.

Example 24

| | | |
|---|---|---|
| 5-HB(2F,3F)HB(2F,3F)-O2 | (No. 13) | 6% |
| 3-HB-O1 | (2-4) | 15% |
| 3-HH-4 | (2-1) | 5% |
| 3-HB(2F,3F)-O2 | (3-1) | 12% |
| 5-HB(2F,3F)-O2 | (3-1) | 12% |
| 2-HHB(2F,3F)-1 | (3-59) | 12% |
| 3-HHB(2F,3F)-1 | (3-59) | 6% |
| 3-HHB(2F,3F)-O2 | (3-59) | 13% |
| 5-HHB(2F,3F)-O2 | (3-59) | 13% |
| 3-HHB-1 | (2-25) | 6% |

NI = 90.6° C.; Δn = 0.092; η = 39.4 mPa · s; Δε = −3.5.

INDUSTRIAL APPLICABILITY

The liquid crystal compound of the invention has stability to heat, light and so forth, a nematic phase in a wide temperature range, a small viscosity, a large optical anisotropy and a suitable elastic constant $K_{33}$, and further has a suitable and negative dielectric anisotropy and an excellent compatibility with other liquid crystal compounds. A liquid crystal composition comprising this compound has stability to heat, light and so forth, a small viscosity, a large optical anisotropy, a suitable elastic constant $K_{33}$, a suitable and negative dielectric anisotropy and a low threshold voltage, and further has a high maximum temperature of a nematic phase and a low minimum temperature of the nematic phase. Since a liquid crystal display device containing this composition has a short response time, a low electric power consumption, a small driving voltage, a large contrast ratio and a wide temperature range in which the device can be used, it can be used for a liquid crystal display panel, a liquid crystal display module or the like.

What is claimed is:

1. A liquid crystal compound represented by formula (a):

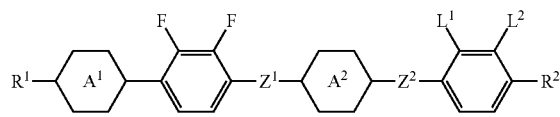

(a)

wherein, in formula (a), $R^1$ and $R^2$ are each independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ and ring $A^2$ are each independently 1,4-phenylene, trans-1,4-cyclohexylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl;

$L^1$ and $L^2$ are each independently hydrogen or fluorine, and at least one of $L^1$ and $L^2$ is fluorine;

when one of ring $A^1$ and ring $A^2$ is 1,4-phenylene, the other is trans-1,4-cyclohexylene, tetrahydropyran-2,5-diyl, tetrahydropyran-3,6-diyl, 1,3-dioxane-2,5-diyl, 1,3-dioxane-3,6-diyl, pyrimidine-2,5-diyl, pyrimidine-3,6-diyl, pyridine-2,5-diyl or pyridine-3,6-diyl; and $Z^1$ and $Z^2$ are each independently a single bond, $-(CH_2)_2-$, $-CH=CH-$, $-C\equiv C-$, $-CH_2O-$, $-OCH_2-$, $-COO-$ or $-OCO-$.-

2. The compound according to claim 1, wherein the compound is represented by formula (a-1) or (a-2):

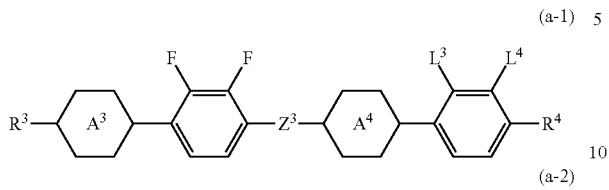

(a-1)

(a-2)

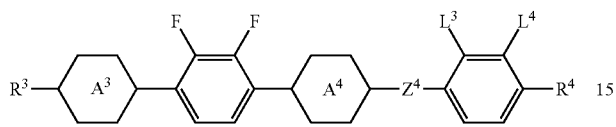

wherein, in formulas (a-1) and (a-2),
$R^3$ and $R^4$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^3$ and ring $A^4$ are each independently 1,4-phenylene, trans-1,4-cyclohexylene, tetrahydropyran-2,5-diyl or tetrahydropyran-3,6-diyl;
when one of ring $A^1$ and ring $A^2$ is 1,4-phenylene, the other is trans-1,4-cyclohexylene, tetrahydropyran-2,5-diyl or tetrahydropyran-3,6-diyl;
$L^3$ and $L^4$ are each independently hydrogen or fluorine, and at least one of $L^3$ and $L^4$ is fluorine; and
$Z^3$ and $Z^4$ are each independently —(CH$_2$)$_2$—, —CH=CH—, —CH$_2$O—, —OCH$_2$—, —COO— or —OCO—.

3. The compound according to claim 2, wherein the compound is represented by formula (a-11) or (a-14):

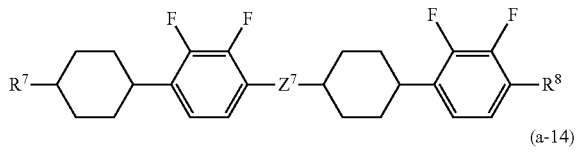

(a-11)

(a-14)

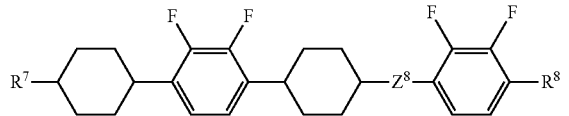

wherein, in formulas (a-11) and (a-14),
$R^7$ and $R^8$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and
$Z^7$ and $Z^8$ are each independently —(CH$_2$)$_2$—, —CH$_2$O—, —OCH$_2$—, —COO— or —OCO—.

4. The compound according to claim 2, wherein the compound is represented by any one of formulas (a-17), (a-20), (a-23), and (a-26):

(a-17)

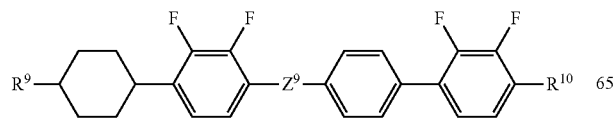

(a-23)

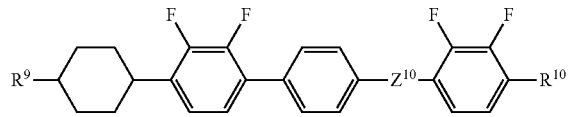

(a-20)

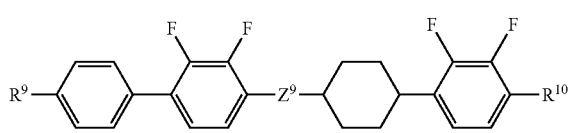

(a-26)

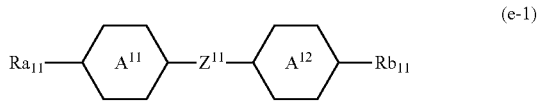

wherein, in formulas (a-17), (a-20), (a-23), and (a-26),
$R^9$ and $R^{10}$ are each independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and
$Z^9$ and $Z^{10}$ are each independently —(CH$_2$)$_2$—, —CH$_2$O—, —OCH$_2$—, —COO— or —OCO—.

5. The compound according to claim 3, wherein, in formulas (a-11) and (a-14), $Z^5$ and $Z^6$ are —CH$_2$O— or —OCH$_2$—.

6. The compound according to claim 3, wherein, in formulas (a-11) and (a-14), $Z^5$ and $Z^6$ are —COO— or —OCO—.

7. The compound according to claim 4, wherein, in formulas (a-17), (a-20), (a-23), and (a-26), $Z^7$ and $Z^8$ are —CH$_2$O— or —OCH$_2$—.

8. The compound according to claim 4, wherein, in formulas (a-17), (a-20), (a-23), and (a-26), $Z^7$ and $Z^8$ are —OCH$_2$—.

9. The compound according to claim 4, wherein, in formulas (a-17), (a-20), (a-23), and (a-26), $Z^7$ and $Z^8$ are —COO— or —OCO—.

10. A liquid crystal composition which has negative dielectric anisotropy, comprising a first component which is at least one compound selected from compounds according to claim 1, and a second component which is at least one compound selected from the group of compounds represented by formulas (e-1) to (e-3):

(e-1)

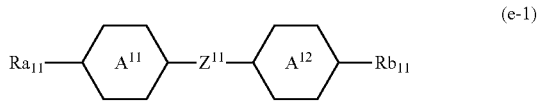

(e-2)

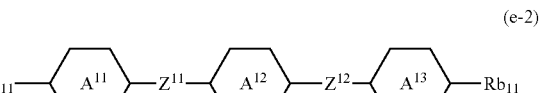

(e-3)

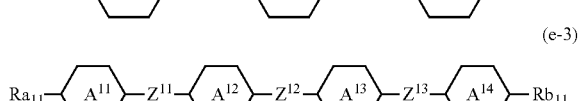

wherein, in formulas (e-1) to (e-3), $Ra_{11}$ and $Rb_{11}$ are each independently alkyl having 1 to 10 carbons, and in this alkyl, —$CH_2$— may be nonadjacently replaced by —O—, and —$(CH_2)_2$— may be nonadjacently replaced by —CH=CH—, and hydrogen may be replaced by fluorine;

ring $A^{11}$, ring $A^{12}$, ring $A^{13}$ and ring $A^{14}$ are each independently trans-1,4-cyclohexylene, 1,4-phenylene, 2-fluoro-1,4-phenylene, 3-fluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl; and $Z^{11}$, $Z^{12}$ and $Z^{13}$ are each independently a single bond, —$CH_2$—$CH_2$—, —CH=CH—, —C≡C—, —COO— or —$CH_2O$—.

11. A liquid crystal composition which has negative dielectric anisotropy, comprising a first component which is at least one compound selected from the group of compounds according to claim 2, and a second component which is at least one compound selected from the group of compounds represented by formulas (e-1) to (e-3):

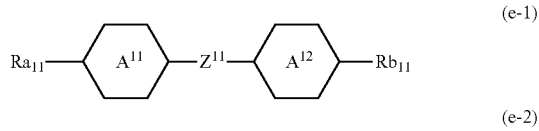
(e-1)

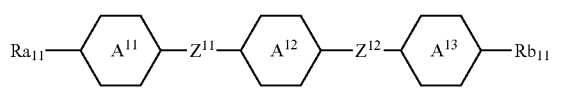
(e-2)

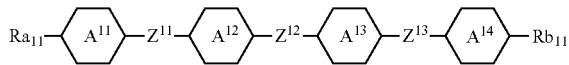
(e-3)

wherein, in formulas (e-1) to (e-3), $Ra_{11}$ and $Rb_{11}$ are each independently alkyl having 1 to 10 carbons, and in this alkyl, —$CH_2$— may be nonadjacently replaced by —O—, and —$(CH_2)_2$— may be nonadjacently replaced by —CH=CH—, and hydrogen may be replaced by fluorine;

ring $A^{11}$, ring $A^{12}$, ring $A^{13}$ and ring $A^{14}$ are each independently trans-1,4-cyclohexylene, 1,4-phenylene, 2-fluoro-1,4-phenylene, 3-fluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl; and $Z^{11}$, $Z^{12}$ and $Z^{13}$ are each independently a single bond, —$CH_2$—$CH_2$—, —CH=CH—, —C≡C—, —COO— or —$CH_2O$—.

12. The liquid crystal composition according to claim 11, wherein the content ratio of the first component is in the range of 5% to 60% by weight and the content ratio of the second component is in the range of 40% to 95% by weight, based on the total weight of the liquid crystal composition.

13. The liquid crystal composition according to claim 10, further comprising a third component which is at least one compound selected from the group of compounds represented by formulas (g-1) to (g-6), in addition to the first and second components:

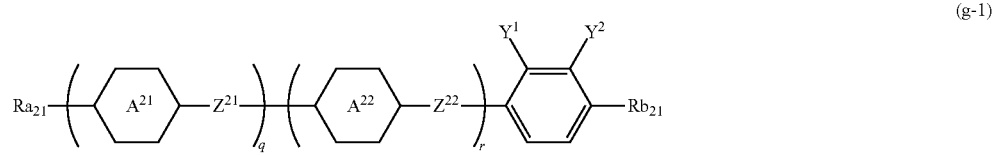
(g-1)

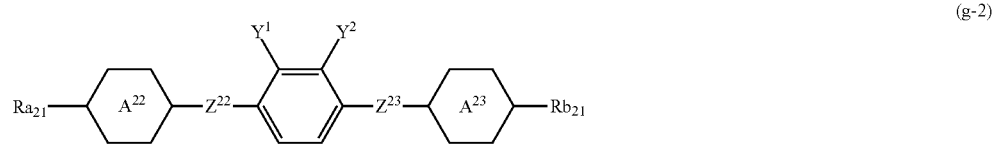
(g-2)

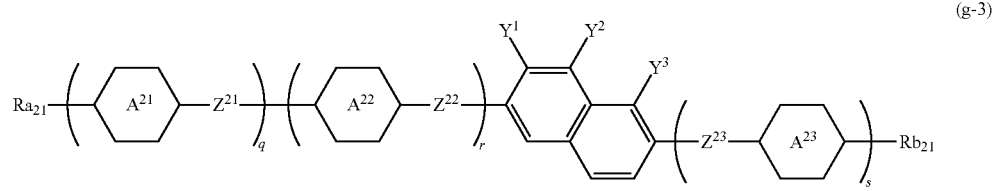
(g-3)

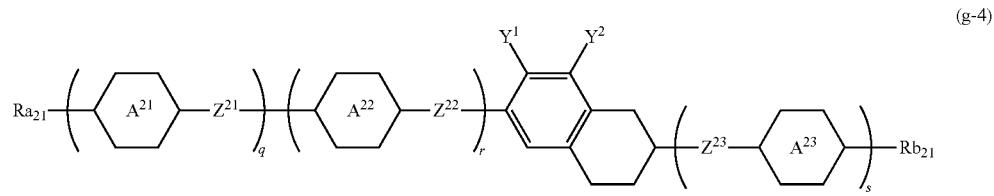
(g-4)

-continued

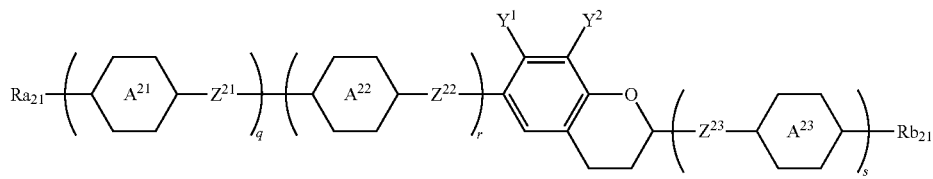
(g-5)

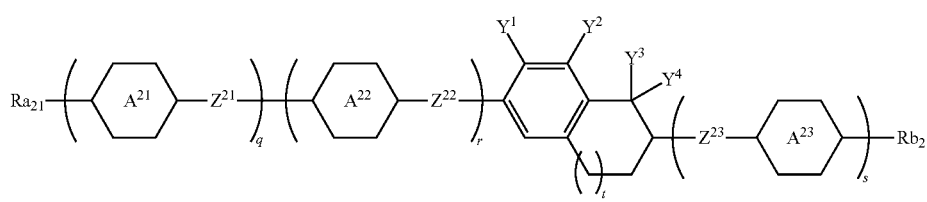
(g-6)

wherein, in formulas (g-1) to (g-6), $Ra_{21}$ and $Rb_{21}$ are each independently hydrogen or alkyl having 1 to 10 carbons, and in the alkyl, —$CH_2$— may be nonadjacently replaced by —O—, and —$(CH_2)_2$— may be nonadjacently replaced by —CH=CH—, and hydrogen may be replaced by fluorine;

ring $A^{21}$, ring $A^{22}$ and ring $A^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl;

$Z^{21}$, $Z^{22}$ and $Z^{23}$ are each independently a single bond, —$CH_2$—$CH_2$—, —CH=CH—, —C≡C—, —$OCF_2$—, —$CF_2O$—, —$OCF_2CH_2CH_2$—, —$CH_2CH_2CF_2O$—, —COO—, —OCO—, —$OCH_2$— or —$CH_2O$—;

$Y^1$, $Y^2$, $Y^3$ and $Y^4$ are each independently fluorine or chlorine;

q, r and s are each independently 0, 1 or 2, q+r is 1 or 2, and q+r+s is 1, 2 or 3; and t is 0, 1 or 2.

14. The liquid crystal composition according to claim 10, further comprising a third component which is at least one compound selected from the group of compounds represented by formulas (h-1) to (h-7), in addition to the first and second components:

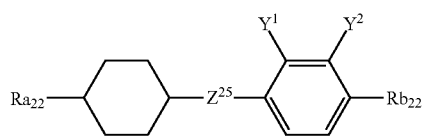
(h-1)

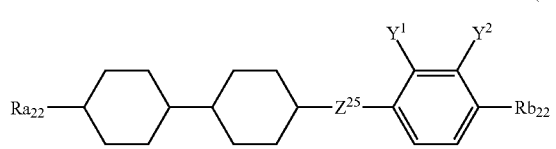
(h-2)

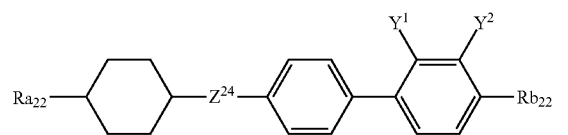
(h-3)

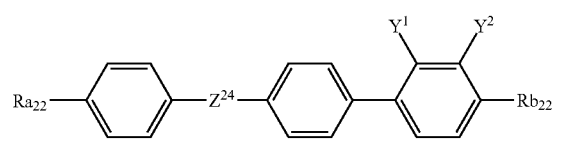
(h-4)

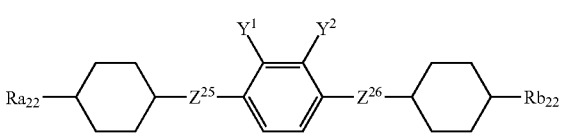
(h-5)

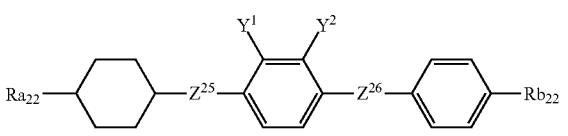
(h-6)

wherein, in formulas (h-1) to (h-7), $Ra_{22}$ and $Rb_{22}$ are each independently straight-chain alkyl having 1 to 8 carbons, straight-chain alkenyl having 2 to 8 carbons or alkoxy having 1 to 7 carbons;

$Z^{24}$, $Z^{25}$ and $Z^{26}$ are each independently a single bond, —$CH_2CH_2$—, —$CH_2O$— or —$OCH_2$—; and $Y^1$ and $Y^2$ are simultaneously fluorine, or one of $Y^1$ and $Y^2$ is fluorine and the other is chlorine.

15. A liquid crystal composition which has negative dielectric anisotropy, comprising a first component which is at least one compound selected from the compounds according to claim 2, a second component which is at least one compound selected from the group of compounds represented by formulas (e-1) to (e-3), and a third component which is at least one compound selected from the group of compounds represented by formulas (h-1) to (h-7):

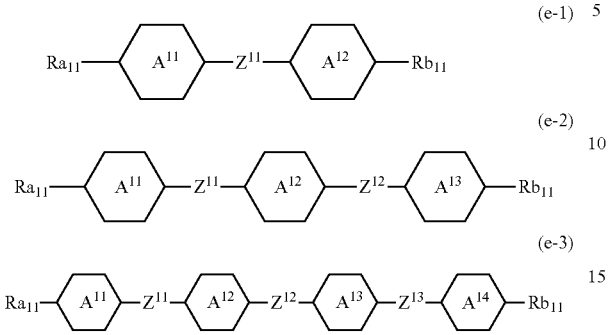

wherein, in formulas (e-1) to (e-3),

Ra$_{11}$ and Rb$_{11}$ are each independently alkyl having 1 to 10 carbons, and in this alkyl, —CH$_2$— may be nonadjacently replaced by —O—, and —(CH$_2$)$_2$— may be nonadjacently replaced by —CH═CH—, and hydrogen may be replaced by fluorine;

ring A$^{11}$, ring A$^{12}$, ring A$^{13}$ and ring A$^{14}$ are each independently trans-1,4-cyclohexylene, 1,4-phenylene, 2-fluoro-1,4-phenylene, 3-fluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl; and Z$^{11}$, Z$^{12}$ and Z$^{13}$ are each independently a single bond, —CH$_2$—CH$_2$—, —CH═CH—, —C≡C—, —COO— or —CH$_2$O—,

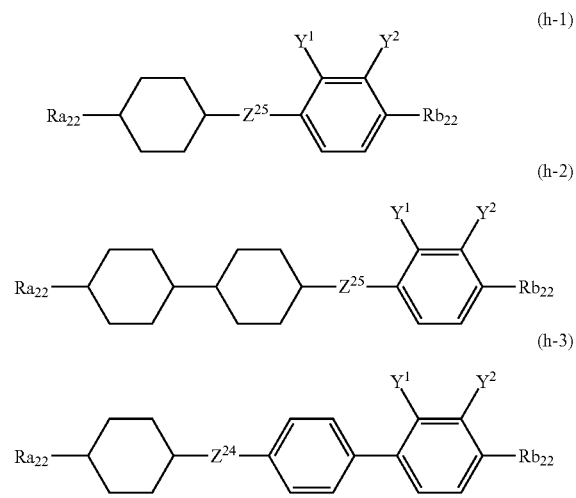

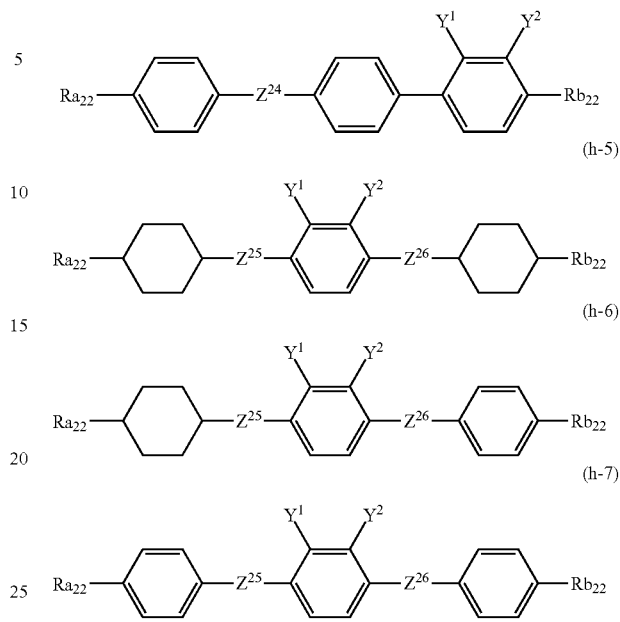

wherein, in formulas (h-1) to (h-7),

Ra$_{22}$ and Rb$_{22}$ are each independently straight-chain alkyl having 1 to 8 carbons, straight-chain alkenyl having 2 to 8 carbons or alkoxy having 1 to 7 carbons;

Z$^{24}$, Z$^{25}$ and Z$^{26}$ are each independently a single bond, —CH$_2$CH$_2$—, —CH$_2$O— or —OCH$_2$—; and Y$^1$ and Y$^2$ are simultaneously fluorine, or one of Y$^1$ and Y$^2$ is fluorine and the other is chlorine.

16. The liquid crystal composition according to claim 13, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

17. A liquid crystal display device containing the liquid crystal composition according to claim 10.

18. The liquid crystal display device according to claim 17, wherein the operating mode thereof is a VA mode, a PSA mode or an IPS mode, and the driving mode thereof is an active matrix mode.

19. The compound according to claim 3, wherein, in formulas (a-11) and (a-14), Z$^5$ and Z$^6$ are —(CH$_2$)$_2$—.

20. The compound according to claim 4, wherein, in formulas (a-17), (a-20), (a-23), and (a-26), Z$^7$ and Z$^8$ are —CH$_2$O—.

21. The liquid crystal composition according to claim 11, further comprising a third component which is at least one compound selected from the group of compounds represented by formulas (g-1) to (g-6), in addition to the first and second components:

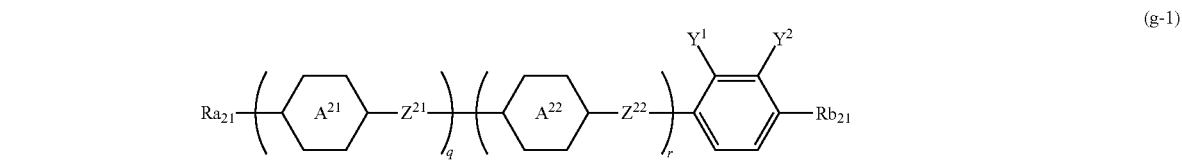

-continued

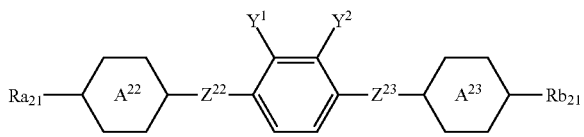
(g-2)

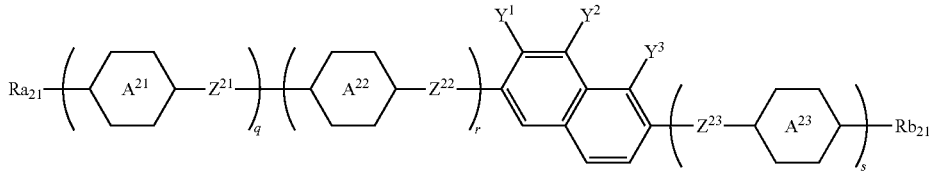
(g-3)

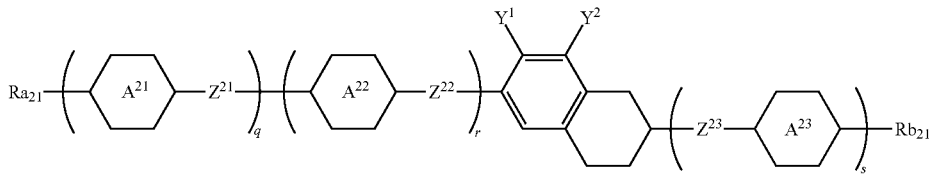
(g-4)

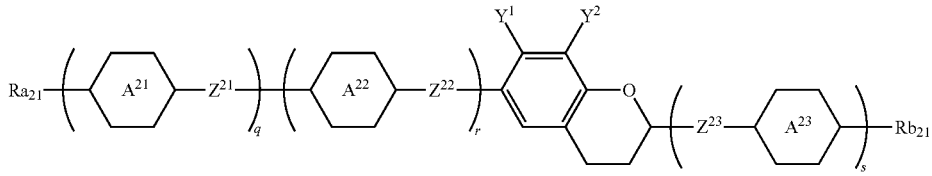
(g-5)

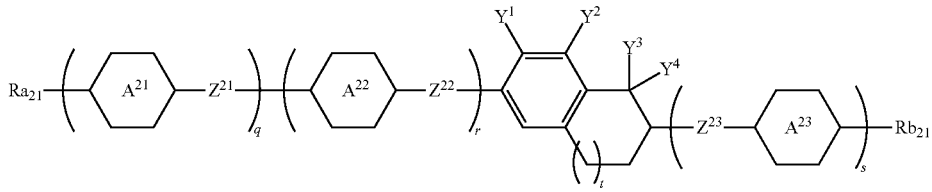
(g-6)

wherein, in formulas (g-1) to (g-6),

Ra$_{21}$ and Rb$_{21}$ are each independently hydrogen or alkyl having 1 to 10 carbons, and in the alkyl, —CH$_2$— may be nonadjacently replaced by —O—, and —(CH$_2$)$_2$— may be nonadjacently replaced by —CH=CH—, and hydrogen may be replaced by fluorine;

ring A$^{21}$, ring A$^{22}$ and ring A$^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, pyrimidine-3,6-diyl, 1,3-dioxane-2,5-diyl, 1,3-dioxane-3,6-diyl, tetrahydropyran-2,5-diyl or tetrahydropyran-3,6-diyl;

Z$^{21}$, Z$^{22}$ and Z$^{23}$ are each independently a single bond, —CH$_2$—CH$_2$—, —CH=CH—, —C≡C—, —OCF$_2$—, —CF$_2$O—, —OCF$_2$CH$_2$CH$_2$—, —CH$_2$CH$_2$CF$_2$O—, —COO—, —OCO—, —OCH$_2$— or —CH$_2$O—;

Y$^1$, Y$^2$, Y$^3$ and Y$^4$ are each independently fluorine or chlorine;

q, r and s are each independently 0, 1 or 2, q+r is 1 or 2, and q+r+s is 1, 2 or 3; and t is 0, 1 or 2.

22. The liquid crystal composition according to claim 11, further comprising a third component which is at least one compound selected from the group of compounds represented by formulas (h-1) to (h-7), in addition to the first and second components:

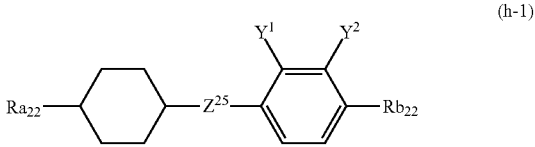
(h-1)

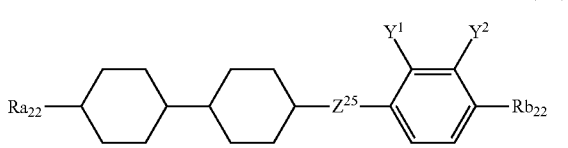
(h-2)

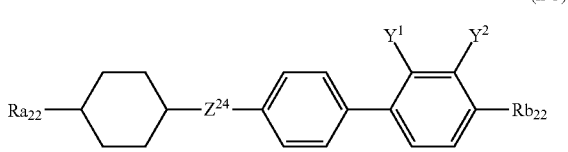
(h-3)

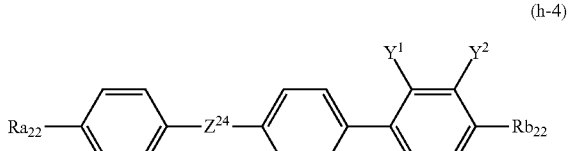
(h-4)

(h-5)
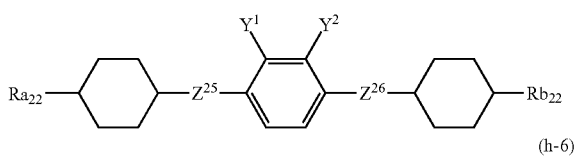

(h-6)
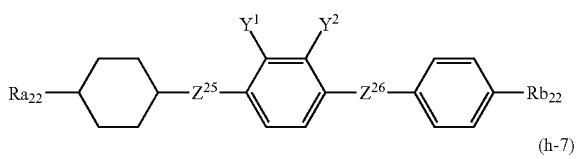

(h-7)
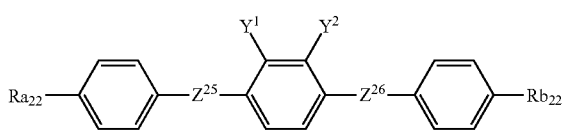

wherein, in formulas (h-1) to (h-7), $Ra_{22}$ and $Rb_{22}$ are each independently straight-chain alkyl having 1 to 8 carbons, straight-chain alkenyl having 2 to 8 carbons or alkoxy having 1 to 7 carbons;

$Z^{24}$, $Z^{25}$ and $Z^{26}$ are each independently a single bond, —$CH_2CH_2$—, —$CH_2O$— or —$OCH_2$—; and $Y^1$ and $Y^2$ are simultaneously fluorine, or one of $Y^1$ and $Y^2$ is fluorine and the other is chlorine.

23. The liquid crystal composition according to claim 14, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

24. The liquid crystal composition according to claim 15, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

25. The liquid crystal composition according to claim 21, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

26. The liquid crystal composition according to claim 22, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

* * * * *